(12) United States Patent
Du et al.

(10) Patent No.: US 8,906,880 B2
(45) Date of Patent: Dec. 9, 2014

(54) NUCLEOSIDE PHOSPHORAMIDATE PRODRUGS

(71) Applicant: Gilead Pharmasset LLC, Foster City, CA (US)

(72) Inventors: Jinfa Du, Redwood City, CA (US); Dhanapalan Nagarathnam, Bethany, CT (US); Michael Joseph Sofia, Doylestown, PA (US); Peiyuan Wang, Foster City, CA (US)

(73) Assignee: Gilead Pharmasset LLC, Foster City, CA (US)

( * ) Notice: Subject to any disclaimer, the term of this patent is extended or adjusted under 35 U.S.C. 154(b) by 0 days.

(21) Appl. No.: 14/255,833

(22) Filed: Apr. 17, 2014

(65) Prior Publication Data

US 2014/0315852 A1    Oct. 23, 2014

Related U.S. Application Data

(63) Continuation of application No. 14/057,675, filed on Oct. 18, 2013, now Pat. No. 8,735,372, which is a continuation of application No. 13/609,614, filed on Sep. 11, 2012, now Pat. No. 8,580,765, which is a continuation of application No. 13/099,671, filed on May 3, 2011, now Pat. No. 8,334,270, which is a continuation of application No. 12/053,015, filed on Mar. 21, 2008, now Pat. No. 7,964,580.

(60) Provisional application No. 60/982,309, filed on Oct. 24, 2007, provisional application No. 60/909,315, filed on Mar. 30, 2007.

(51) Int. Cl.
*A01N 43/04* (2006.01)
*A61K 31/70* (2006.01)
*C07H 19/10* (2006.01)
*A61K 31/7072* (2006.01)
*A61K 45/06* (2006.01)

(52) U.S. Cl.
CPC ............ *C07H 19/10* (2013.01); *A61K 31/7072* (2013.01); *A61K 45/06* (2013.01)
USPC .................... 514/51; 514/43; 514/49; 514/50

(58) Field of Classification Search
None
See application file for complete search history.

(56) References Cited

U.S. PATENT DOCUMENTS

| | | |
|---|---|---|
| 3,798,209 A | 3/1974 | Witkowski et al. |
| 3,852,267 A | 12/1974 | Meyer, Jr. et al. |
| RE29,835 E | 11/1978 | Witkowski et al. |
| 4,814,477 A | 3/1989 | Wijnberg et al. |
| 4,957,924 A | 9/1990 | Beauchamp |
| 5,026,687 A | 6/1991 | Yarchoan et al. |
| 5,118,820 A | 6/1992 | Hertel |
| 5,149,794 A | 9/1992 | Yatvin et al. |
| 5,157,027 A | 10/1992 | Biller et al. |
| 5,192,549 A | 3/1993 | Barenolz et al. |
| 5,194,654 A | 3/1993 | Hostetler et al. |
| 5,223,263 A | 6/1993 | Hostetler et al. |
| 5,256,641 A | 10/1993 | Yatvin et al. |
| 5,256,798 A | 10/1993 | Chou et al. |
| 5,372,808 A | 12/1994 | Blatt et al. |
| 5,376,380 A | 12/1994 | Kikuchi et al. |
| 5,405,598 A | 4/1995 | Schinazi et al. |
| 5,411,947 A | 5/1995 | Hostetler et al. |
| 5,420,266 A | 5/1995 | Britton et al. |
| 5,426,183 A | 6/1995 | Kjell |
| 5,453,499 A | 9/1995 | Chou et al. |
| 5,462,724 A | 10/1995 | Schinazi et al. |
| 5,463,092 A | 10/1995 | Hostetler et al. |
| 5,496,546 A | 3/1996 | Wang et al. |
| 5,538,865 A | 7/1996 | Reyes et al. |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,610,054 A | 3/1997 | Draper |
| 5,633,358 A | 5/1997 | Gruetzke et al. |
| 5,633,388 A | 5/1997 | Diana et al. |

(Continued)

FOREIGN PATENT DOCUMENTS

| | | |
|---|---|---|
| CN | 101108870 A | 1/2008 |
| DE | 199 14 474 A1 | 10/1999 |

(Continued)

OTHER PUBLICATIONS

McGuigan et al. FEBS Letters (1994), vol. 351, pp. 11-14.*
Gudmundsson, Kristjan S., et al., "Phosphoramidate Protides of Carbocyclic 2',3'-Dideoxy-2',3'-Didehydro-7-Deazaadenosine with Potent Activity Against HIV and HBV," Nucleosides, Nucleotides & Nucleic Acids (2004) 23(12):1929-1937.

(Continued)

*Primary Examiner* — Patrick Lewis
(74) *Attorney, Agent, or Firm* — Sheppard Mullin Richter & Hampton LLP

(57) ABSTRACT

Disclosed herein are phosphoramidate prodrugs of nucleoside derivatives for the treatment of viral infections in mammals, which is a compound, its stereoisomer, salt (acid or basic addition salt), hydrate, solvate, or crystalline form thereof, represented by the following structure:

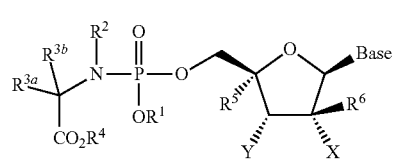

Also disclosed are methods of treatment, uses, and processes for preparing each of which utilize the compound represented by formula I.

11 Claims, No Drawings

(56) References Cited

U.S. PATENT DOCUMENTS

| | | |
|---|---|---|
| 5,676,942 A | 10/1997 | Testa et al. |
| 5,703,058 A | 12/1997 | Schinazi et al. |
| 5,711,944 A | 1/1998 | Gilbert et al. |
| 5,725,859 A | 3/1998 | Omer |
| 5,738,845 A | 4/1998 | Imakawa |
| 5,738,846 A | 4/1998 | Greenwald et al. |
| 5,747,646 A | 5/1998 | Hakimi et al. |
| 5,767,097 A | 6/1998 | Tam |
| 5,792,834 A | 8/1998 | Hakimi et al. |
| 5,830,455 A | 11/1998 | Valtuena et al. |
| 5,830,905 A | 11/1998 | Diana et al. |
| 5,834,594 A | 11/1998 | Hakimi et al. |
| 5,837,257 A | 11/1998 | Tsai et al. |
| 5,846,964 A | 12/1998 | Ozeki |
| 5,849,696 A | 12/1998 | Chretien et al. |
| 5,869,253 A | 2/1999 | Draper |
| 5,891,874 A | 4/1999 | Colacino et al. |
| 5,905,070 A | 5/1999 | Schinazi et al. |
| 5,908,621 A | 6/1999 | Glue et al. |
| 5,922,757 A | 7/1999 | Chojkier |
| 5,928,636 A | 7/1999 | Alber et al. |
| 5,942,223 A | 8/1999 | Bazer et al. |
| 5,980,884 A | 11/1999 | Blatt et al. |
| 5,990,276 A | 11/1999 | Zhang et al. |
| 6,004,933 A | 12/1999 | Spruce et al. |
| 6,034,134 A | 3/2000 | Gold et al. |
| 6,043,077 A | 3/2000 | Barber et al. |
| 6,056,961 A | 5/2000 | Lavie et al. |
| 6,060,080 A | 5/2000 | Kikuchi et al. |
| 6,090,932 A | 7/2000 | McGee et al. |
| 6,130,326 A | 10/2000 | Ramasamy et al. |
| 6,132,763 A | 10/2000 | Fisher |
| 6,156,501 A | 12/2000 | McGall et al. |
| 6,180,134 B1 | 1/2001 | Zalipsky et al. |
| 6,232,300 B1 | 5/2001 | Schinazi et al. |
| 6,239,159 B1 | 5/2001 | Brown et al. |
| 6,348,587 B1 | 2/2002 | Schinazi et al. |
| 6,372,883 B1 | 4/2002 | Attwood et al. |
| 6,391,859 B1 | 5/2002 | Schinazi et al. |
| 6,410,531 B1 | 6/2002 | Llinas-Brunet et al. |
| 6,420,380 B2 | 7/2002 | Llinas-Brunet et al. |
| 6,455,513 B1 | 9/2002 | McGuigan et al. |
| 6,455,690 B1 | 9/2002 | Tam et al. |
| 6,475,985 B1 | 11/2002 | Wagner et al. |
| 6,479,463 B1 | 11/2002 | Wang et al. |
| 6,495,677 B1 | 12/2002 | Ramasamy et al. |
| 6,509,320 B1 | 1/2003 | Wang et al. |
| 6,534,523 B1 | 3/2003 | Llinas-Brunet et al. |
| 6,552,183 B1 | 4/2003 | Ramasamy et al. |
| 6,555,677 B2 | 4/2003 | Petrillo et al. |
| 6,573,248 B2 | 6/2003 | Ramasamy et al. |
| 6,642,206 B2 | 11/2003 | Ramasamy et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,753,309 B2 | 6/2004 | Klecker et al. |
| 6,777,395 B2 | 8/2004 | Bhat et al. |
| 6,784,166 B2 | 8/2004 | Devos et al. |
| 6,787,305 B1 | 9/2004 | Li et al. |
| 6,787,526 B1 | 9/2004 | Bryant et al. |
| 6,815,542 B2 | 11/2004 | Hong et al. |
| 6,846,810 B2 | 1/2005 | Martin et al. |
| 6,897,201 B2 | 5/2005 | Boyer et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,962,991 B2 | 11/2005 | Dempcy et al. |
| 7,018,985 B1 | 3/2006 | Boyer et al. |
| 7,018,989 B2 | 3/2006 | McGuigan et al. |
| 7,081,449 B2 | 7/2006 | Pietrzkowski et al. |
| 7,105,499 B2 | 9/2006 | Carroll et al. |
| 7,148,206 B2 | 12/2006 | Sommadossi et al. |
| 7,163,929 B2 | 1/2007 | Sommadossi et al. |
| 7,202,224 B2 | 4/2007 | Eldrup et al. |
| 7,217,523 B2 | 5/2007 | Wagner |
| 7,268,119 B2 | 9/2007 | Cook et al. |
| 7,307,065 B2 | 12/2007 | Schinazi et al. |
| 7,365,057 B2 | 4/2008 | LaColla et al. |
| 7,390,791 B2 | 6/2008 | Becker et al. |
| 7,429,572 B2 | 9/2008 | Clark |
| 7,601,820 B2 | 10/2009 | Wang et al. |
| 7,879,815 B2 | 2/2011 | MacCoss et al. |
| 7,964,580 B2 | 6/2011 | Sofia et al. |
| 8,148,349 B2 | 4/2012 | Meppen et al. |
| 8,173,621 B2 | 5/2012 | Du et al. |
| 8,334,270 B2 | 12/2012 | Sofia et al. |
| 2001/0034440 A1 | 10/2001 | Shepard et al. |
| 2002/0058635 A1 | 5/2002 | Averett |
| 2002/0198173 A1 | 12/2002 | Schinazi et al. |
| 2003/0050229 A1 | 3/2003 | Sommadossi et al. |
| 2003/0060400 A1 | 3/2003 | LaColla et al. |
| 2003/0120071 A1 | 6/2003 | McGuigan et al. |
| 2003/0144502 A1 | 7/2003 | Pietrzkowski et al. |
| 2003/0153744 A1 | 8/2003 | Mekouar et al. |
| 2003/0187018 A1 | 10/2003 | Llinas-Brunet et al. |
| 2004/0006007 A1 | 1/2004 | Gosselin et al. |
| 2004/0014108 A1 | 1/2004 | Eldrup et al. |
| 2004/0023240 A1 | 2/2004 | Marliere et al. |
| 2004/0023901 A1 | 2/2004 | Cook et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0167140 A1 | 8/2004 | Schinazi et al. |
| 2004/0191824 A1 | 9/2004 | Dempcy et al. |
| 2004/0214844 A1 | 10/2004 | Otto et al. |
| 2004/0229839 A1 | 11/2004 | Babu et al. |
| 2004/0229840 A1 | 11/2004 | Bhat et al. |
| 2004/0248892 A1 | 12/2004 | Wang |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2004/0266996 A1 | 12/2004 | Rabi |
| 2005/0009737 A1 | 1/2005 | Clark |
| 2005/0020825 A1 | 1/2005 | Storer et al. |
| 2005/0026853 A1 | 2/2005 | Mekouar et al. |
| 2005/0031588 A1 | 2/2005 | Sommadossi et al. |
| 2005/0059632 A1 | 3/2005 | Storer et al. |
| 2005/0075309 A1 | 4/2005 | Storer et al. |
| 2005/0080034 A1 | 4/2005 | Standring et al. |
| 2005/0090660 A1 | 4/2005 | Watanabe et al. |
| 2005/0124532 A1 | 6/2005 | Sommadossi et al. |
| 2005/0130931 A1 | 6/2005 | Boyer et al. |
| 2005/0137161 A1 | 6/2005 | Sommadossi et al. |
| 2005/0148534 A1 | 7/2005 | Castellino et al. |
| 2005/0154056 A1 | 7/2005 | Yang et al. |
| 2005/0164960 A1 | 7/2005 | Olsen et al. |
| 2005/0215513 A1 | 9/2005 | Boojamra et al. |
| 2005/0227947 A1 | 10/2005 | Chen et al. |
| 2005/0261237 A1 | 11/2005 | Boojamra et al. |
| 2005/0267018 A1 | 12/2005 | Blatt et al. |
| 2006/0003951 A1 | 1/2006 | Mekouar et al. |
| 2006/0014943 A1 | 1/2006 | Dempcy et al. |
| 2006/0035866 A1 | 2/2006 | Cannizzaro et al. |
| 2006/0040890 A1 | 2/2006 | Martin et al. |
| 2006/0040927 A1 | 2/2006 | Blake et al. |
| 2006/0040944 A1 | 2/2006 | Gosselin et al. |
| 2006/0079478 A1 | 4/2006 | Boojamra et al. |
| 2006/0110727 A9 | 5/2006 | McGall et al. |
| 2006/0122146 A1 | 6/2006 | Chun et al. |
| 2006/0122154 A1 | 6/2006 | Olsen et al. |
| 2006/0142238 A1 | 6/2006 | McGuigan |
| 2006/0166964 A1 | 7/2006 | Hudyma et al. |
| 2006/0194749 A1 | 8/2006 | Keicher et al. |
| 2006/0199783 A1 | 9/2006 | Wang et al. |

(56) References Cited

U.S. PATENT DOCUMENTS

| | | |
|---|---|---|
| 2006/0241064 A1 | 10/2006 | Roberts et al. |
| 2006/0276511 A1 | 12/2006 | Serrano-Wu et al. |
| 2006/0293306 A1 | 12/2006 | Beaulieu et al. |
| 2007/0015905 A1 | 1/2007 | LaColla et al. |
| 2007/0037735 A1 | 2/2007 | Gosselin et al. |
| 2007/0037773 A1 | 2/2007 | Sommadossi et al. |
| 2007/0042939 A1 | 2/2007 | LaColla et al. |
| 2007/0042988 A1 | 2/2007 | Klumpp et al. |
| 2007/0042990 A1 | 2/2007 | Gosselin et al. |
| 2007/0049754 A1 | 3/2007 | Boojamra et al. |
| 2007/0060498 A1 | 3/2007 | Gosselin et al. |
| 2007/0060541 A1 | 3/2007 | Gosselin et al. |
| 2007/0087960 A1 | 4/2007 | Storer et al. |
| 2007/0197463 A1 | 8/2007 | Chun et al. |
| 2007/0225249 A1 | 9/2007 | Shi |
| 2007/0265222 A1 | 11/2007 | MacCoss et al. |
| 2007/0275912 A1 | 11/2007 | Bhat et al. |
| 2007/0275947 A1 | 11/2007 | Bergstrom |
| 2009/0137521 A1 | 5/2009 | Hamilton et al. |
| 2009/0176732 A1 | 7/2009 | Beigelman et al. |
| 2009/0233879 A1 | 9/2009 | Reddy et al. |
| 2009/0280084 A1 | 11/2009 | Schinazi et al. |
| 2009/0306007 A1 | 12/2009 | Wagner |
| 2010/0029008 A1 | 2/2010 | Rojas Stutz et al. |
| 2010/0035835 A1 | 2/2010 | Narjes et al. |
| 2010/0081628 A1 | 4/2010 | Du et al. |
| 2010/0137576 A1 | 6/2010 | Stec et al. |
| 2010/0152128 A1 | 6/2010 | Attenni et al. |
| 2010/0173863 A1 | 7/2010 | Schinazi et al. |
| 2010/0227801 A1 | 9/2010 | Hopkins et al. |
| 2010/0279973 A1 | 11/2010 | Chun et al. |
| 2010/0286083 A1 | 11/2010 | Bao et al. |
| 2010/0298257 A1 | 11/2010 | Ross et al. |
| 2010/0316594 A1 | 12/2010 | Sommadossi et al. |
| 2011/0015146 A1 | 1/2011 | Sofia et al. |
| 2011/0124592 A1 | 5/2011 | McGuigan et al. |
| 2011/0245484 A1 | 10/2011 | Ross et al. |
| 2011/0251152 A1 | 10/2011 | Ross et al. |
| 2012/0107278 A1 | 5/2012 | Berrey et al. |
| 2013/0109647 A1 | 5/2013 | Berrey |
| 2013/0136776 A1 | 5/2013 | Cleary |
| 2013/0288997 A1 | 10/2013 | Ross et al. |
| 2013/0310551 A1 | 11/2013 | Ross et al. |

FOREIGN PATENT DOCUMENTS

| | | |
|---|---|---|
| EP | 0 180 276 A1 | 5/1986 |
| EP | 0 350 287 A2 | 1/1990 |
| EP | 1 828 217 A2 | 9/2007 |
| EP | 1 881 001 A1 | 1/2008 |
| EP | 2 097 430 A1 | 9/2009 |
| EP | 2 124 555 A2 | 12/2009 |
| EP | 2 207 786 B1 | 3/2012 |
| JP | 5-238939 A | 9/1993 |
| WO | 89/02733 A1 | 4/1989 |
| WO | 90/00555 A1 | 1/1990 |
| WO | 91/16920 A1 | 11/1991 |
| WO | 91/18914 A1 | 12/1991 |
| WO | 91/19721 A1 | 12/1991 |
| WO | 93/00910 A1 | 1/1993 |
| WO | 94/26273 A1 | 11/1994 |
| WO | 95/13090 A1 | 5/1995 |
| WO | 95/24185 A1 | 9/1995 |
| WO | 96/15132 A1 | 5/1996 |
| WO | 96/32403 A2 | 10/1996 |
| WO | 97/12033 A1 | 4/1997 |
| WO | 97/36554 A1 | 10/1997 |
| WO | 98/16184 A2 | 4/1998 |
| WO | 98/17679 A1 | 4/1998 |
| WO | 98/22496 A2 | 5/1998 |
| WO | 99/07734 A2 | 2/1999 |
| WO | 99/15194 A1 | 4/1999 |
| WO | 99/32139 A1 | 7/1999 |
| WO | 99/32140 A1 | 7/1999 |
| WO | 99/43691 A1 | 9/1999 |
| WO | 99/59621 A1 | 11/1999 |
| WO | 99/64016 A1 | 12/1999 |
| WO | 00/06529 A1 | 2/2000 |
| WO | 00/09531 A2 | 2/2000 |
| WO | 00/37110 A2 | 6/2000 |
| WO | 01/09121 A2 | 2/2001 |
| WO | 01/32153 A2 | 5/2001 |
| WO | 01/60315 A2 | 8/2001 |
| WO | 01/79246 A2 | 10/2001 |
| WO | 01/81359 A1 | 11/2001 |
| WO | 01/90121 A2 | 11/2001 |
| WO | 01/91737 A2 | 12/2001 |
| WO | 01/92282 A2 | 12/2001 |
| WO | 01/96353 A2 | 12/2001 |
| WO | 02/08187 A1 | 1/2002 |
| WO | 02/08198 A2 | 1/2002 |
| WO | 02/08251 A2 | 1/2002 |
| WO | 02/08256 A2 | 1/2002 |
| WO | 02/18404 A2 | 3/2002 |
| WO | 02/32414 A2 | 4/2002 |
| WO | 02/32920 A2 | 4/2002 |
| WO | 02/48116 A2 | 6/2002 |
| WO | 02/48157 A2 | 6/2002 |
| WO | 02/48165 A2 | 6/2002 |
| WO | 02/48172 A2 | 6/2002 |
| WO | 02/057287 A2 | 7/2002 |
| WO | 02/057425 A2 | 7/2002 |
| WO | 02/060926 A2 | 8/2002 |
| WO | 02/100415 A2 | 12/2002 |
| WO | 03/000713 A1 | 1/2003 |
| WO | 03/006490 A1 | 1/2003 |
| WO | 03/010141 A2 | 2/2003 |
| WO | 03/024461 A1 | 3/2003 |
| WO | 03/026589 A2 | 4/2003 |
| WO | 03/037895 A1 | 5/2003 |
| WO | 03/051899 A1 | 6/2003 |
| WO | 03/053989 A1 | 7/2003 |
| WO | 03/061576 A2 | 7/2003 |
| WO | 03/062256 A1 | 7/2003 |
| WO | 03/064456 A1 | 8/2003 |
| WO | 03/068244 A1 | 8/2003 |
| WO | 03/101993 A1 | 12/2003 |
| WO | 03/104250 A1 | 12/2003 |
| WO | 03/105770 A2 | 12/2003 |
| WO | 03/106477 A1 | 12/2003 |
| WO | 04/000858 A2 | 12/2003 |
| WO | 2004/002422 A2 | 1/2004 |
| WO | 2004/002940 A1 | 1/2004 |
| WO | 2004/002944 A1 | 1/2004 |
| WO | 2004/002977 A1 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/009020 A2 | 1/2004 |
| WO | 2004/009610 A2 | 1/2004 |
| WO | 2004/011478 A2 | 2/2004 |
| WO | 2004/014313 A2 | 2/2004 |
| WO | 2004/014852 A2 | 2/2004 |
| WO | 2004/035571 A1 | 4/2004 |
| WO | 2004/041201 A2 | 5/2004 |
| WO | 2004/046331 A2 | 6/2004 |
| WO | 2004/065367 A1 | 8/2004 |
| WO | 2004/080466 A1 | 9/2004 |
| WO | 2004/094452 A2 | 11/2004 |
| WO | 2004/096210 A1 | 11/2004 |
| WO | 2004/096234 A2 | 11/2004 |
| WO | 2004/096235 A2 | 11/2004 |
| WO | 2004/096286 A2 | 11/2004 |
| WO | 2004/106356 A1 | 12/2004 |
| WO | 2005/002626 A2 | 1/2005 |
| WO | 2005/003147 A2 | 1/2005 |
| WO | 2005/007810 A2 | 1/2005 |
| WO | 2005/009418 A2 | 2/2005 |
| WO | 2005/012327 A2 | 2/2005 |
| WO | 2005/020884 A2 | 3/2005 |
| WO | 2005/021568 A2 | 3/2005 |
| WO | 2005/028502 A1 | 3/2005 |

(56) References Cited

FOREIGN PATENT DOCUMENTS

| | | | |
|---|---|---|---|
| WO | 2005/037214 | A2 | 4/2005 |
| WO | 2005/067900 | A2 | 7/2005 |
| WO | 2005/072361 | A2 | 8/2005 |
| WO | 2005/082144 | A1 | 9/2005 |
| WO | 2005/087788 | A2 | 9/2005 |
| WO | 2005/095403 | A2 | 10/2005 |
| WO | 2005/103045 | A1 | 11/2005 |
| WO | 2005/123087 | A2 | 12/2005 |
| WO | 2006/000922 | A2 | 1/2006 |
| WO | 2006/012078 | A2 | 2/2006 |
| WO | 2006/012440 | A2 | 2/2006 |
| WO | 2006/020082 | A1 | 2/2006 |
| WO | 2006/029081 | A2 | 3/2006 |
| WO | 2006/031725 | A2 | 3/2006 |
| WO | 2006/035061 | A1 | 4/2006 |
| WO | 2006/037028 | A2 | 4/2006 |
| WO | 2006/050161 | A2 | 5/2006 |
| WO | 2006/063149 | A1 | 6/2006 |
| WO | 2006/063717 | A2 | 6/2006 |
| WO | 2006/065335 | A2 | 6/2006 |
| WO | 2006/065590 | A2 | 6/2006 |
| WO | 2006/093801 | A1 | 9/2006 |
| WO | 2006/100310 | A1 | 9/2006 |
| WO | 2006/120251 | A1 | 11/2006 |
| WO | 2006/120252 | A2 | 11/2006 |
| WO | 2006/121820 | A1 | 11/2006 |
| WO | 2007/002602 | A2 | 1/2007 |
| WO | 2007/014920 | A1 | 2/2007 |
| WO | 2007/014921 | A1 | 2/2007 |
| WO | 2007/014922 | A1 | 2/2007 |
| WO | 2007/014925 | A1 | 2/2007 |
| WO | 2007/014926 | A1 | 2/2007 |
| WO | 2007/015824 | A2 | 2/2007 |
| WO | 2007/020193 | A2 | 2/2007 |
| WO | 2007/027248 | A2 | 3/2007 |
| WO | 2007/039142 | A1 | 4/2007 |
| WO | 2007/039145 | A1 | 4/2007 |
| WO | 2007/065829 | A1 | 6/2007 |
| WO | 2007/070556 | A2 | 6/2007 |
| WO | 2007/076034 | A2 | 7/2007 |
| WO | 2007/088148 | A1 | 8/2007 |
| WO | 2007/092000 | A1 | 8/2007 |
| WO | 2007/093901 | A1 | 8/2007 |
| WO | 2007/095269 | A2 | 8/2007 |
| WO | 2008/010921 | A2 | 1/2008 |
| WO | 2008/045419 | A1 | 4/2008 |
| WO | 2008/048128 | A1 | 4/2008 |
| WO | 2008/062206 | A2 | 5/2008 |
| WO | 2008/079206 | A1 | 7/2008 |
| WO | 2008/082601 | A2 | 7/2008 |
| WO | 2008/085508 | A2 | 7/2008 |
| WO | 2008/142055 | A2 | 11/2008 |
| WO | 2009/052287 | A1 | 4/2009 |
| WO | 2009/115893 | A2 | 9/2009 |
| WO | 2009/120878 | A2 | 10/2009 |
| WO | 2009/129120 | A2 | 10/2009 |
| WO | 2009/152095 | A2 | 12/2009 |
| WO | 2010/042834 | A1 | 4/2010 |
| WO | 2010/075554 | A1 | 7/2010 |
| WO | 2010/080878 | A1 | 7/2010 |

OTHER PUBLICATIONS

Siddiqui, Adam Q., et al., "The Presence of Substituents on the Aryl Moiety of the Aryl Phosphoramidate Derivatives of d4T Enhances Anti-HIV Efficacy in Cell Culture: A Structure-Activity Relationship," J. Med. Chem. (1999) 42:393-399.

Dumez, Darin, et al., "Large-Scale Synthesis and Formulation of GMP-Grade Stampidine, a New Anti-HIV Agent," Arzneim.-Forsch./Drug Res. (2006) 56(2a):136-151.

Gudmundsson, Kristjan S., et al., "Phosphoramidate Protides of 2',3'-Dideoxy-3'-fluoroadenosine and Related Nucleosides with Potent Activity Against HIV and HBV," Nucleosides, Nucleotides & Nucleic Acids (2003) 22 (10):1953-1961.

Nakayama, Kensaku, et al., "A Highly Enantioselective Synthesis of Phosphate Triesters," J. Am. Chem. Soc. (1990) 112:6936-6942.

Wozniak, Lucyna A., et al., "The stereospecific synthesis of P-chiral biophosphates and their analogues by the Stec reaction," Chem. Soc. Rev. (2003) 32:158-169.

Uchiyama, Mamoru, et al., "O-Selective Phosphorylation of Nucleosides without N-Protection," J. Org. Chem. (1993) 58:373-379.

Abraham et al., "Synthesis and Biological Activity of Aromatic Amino Acid Phosphoramidates of 5-fluoro-2'-deoxyuridine and 1-beta-Arabinofuranosylcytosine: Evidence of Phosphoramidase Activity," J. Med. Chem., vol. 39, No. 23, pp. 4569-4575, (1996).

Pogam et al., "No Evidence of R7128 Drug Resistance After Up to 4 Weeks Treatment of GT1, 2 and 3 Hepatitis C Virus Infected Individuals", 44th Annual Meeting of European Association for the Study of the Liver (EASL), Copenhagen, Denmark (Apr. 22-26, 2009).

Sofia et al., "beta-D-2'-Deoxy-2'-C-methyluridine Phosphoramidates: Potent and Selective Inhibitors of HCV RNA Replication", Poster #P-259, 14th International Symposium on Hepatitis C Virus and Related Viruses, Glasgow, Scotland, UK (Sep. 9 to 13, 2007).

Sofia, M.J., "beta-D-2'-Deoxy-2'-fluoro-2'-C-methyluridine Phosphoramidates: Potent and Selective Inhibitors of HCV RNA Replication", 2nd International Workshop on HCV—Resistance and New Compounds (Oct. 31, 2007).

Sofia et al., "beta-D-2'-Deoxy-2'-fluoro-2'-C-methyluridine Phosphoramidates: Potent and Selective Inhibitors of HCV RNA Replication", 2nd International Workshop on HCV, Poster #7 (Oct. 31, 2007).

Sofia, M.J., "R7128, A Potent and Selective Nucleoside Inhibitor of HCV NS5B Polymerase: An Overview of Clinical Efficacy and Progress Toward Second Generation Inhibitors", HCV Drug Discovery 2008, Chicago, IL (Apr. 28, 2008).

Response filed Oct. 25, 2010 at the EPO for European patent application No. EP08732818.3.

Abraham et al., "Synthesis, Biological Activity and Decomposition Studies of Amino Acid Phosphomonoester Amidates of Acyclovir," Nucleosides, Nucleotides and Nucleic Acids, vol. 16, No. 10, pp. 2079-2092 (1997).

Balzarini et al., "Mechanism of anti-HIV action of masked alaninyl d4t-MP derivatives," Proc. Natl. Acad. Sci., vol. 93, pp. 7295-7299 (1996).

Chang et al., "Amino Acid Phosphoramidate Monoesters of 3'-Azido-3'-deoxythymidine: Relationship between Antiviral Potency and Intracellular Metabolism," J. Med. Chem., vol. 44, No. 2, pp. 223-231 (2001).

Chen et al., "In Vivo Pharmacokinetics and Metabolism of Anti-Human Immunodeficiency Virus Agent D4t-5'-[P-Bromophenyl Methoxyalaninyl Phosphate] (Sampidine) in Mice," Drug Metabolism and Disposition, vol. 29, No. 7, pp. 1035-1041 (2001).

Chen et al., "Metabolism of Stavudine-5'-[P-Bromophenyl Methoxyalaninyl Phosphate], Stampidine, in Mice, Dogs, and Cats," Drug Metabolism and Disposition, vol. 30, No. 12, pp. 1523-1531 (2002).

Chou et al., "Evidence that Human Histidine Triad Nucleotide Binding Protein 3 (Hint3) is a Distinct Branch of the Histidine Triad (HIT) Superfamily," J. Mol. Biol., vol. 373, pp. 978-989 (2007).

Chou et al., "Phosphoramidate Pronucleotides: A Comparison of the Phosphoramidase Substrate Specificity of Human and Escherichia coli Histidine Triad Nucleotide Binding Proteins," Molecular Pharmaceutics, vol. 4, No. 2, pp. 208-217 (2006).

Cihlar et al. "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131," Antimicrobial Agents and Chemotherapy, vol. 52, No. 2, pp. 655-665 (2008).

Congiatu et al. "Molecular Modeling Studies on the Binding of Some Protides to the Putative Human Phosphoramidase Hint1," Nucleosides, Nucleotides and Nucleic Acids, vol. 26, pp. 1121-1124 (2007).

Congiatu et al., "Naphthyl Phosphoramidate Derivatives of BVdU as Potential Anticancer Agents: Design, Synthesis and Biological Evaluation," Nucleosides, Nucleotides, and Nucleic Acids, vol. 24, No. 5-7, pp. 485-489 (2005).

(56) References Cited

OTHER PUBLICATIONS

Curley et al., "Synthesis and anti-HIV evaluation of some phosphoramidate derivatives of AZT: studies on the effect of chain elongation on biological activity," Antiviral Research, vol. 14, pp. 345-356 (1990).
D'Cruz et al., "Stampidine: a selective oculo-genital microbicide," Journal of Antimicrobial Chemotherapy, vol. 56, pp. 10-19 (2005).
Drontle et al., "Designing a Pronucleotide Stratagem: Lessons from Amino Acid Phosphoramidates of Anticancer and Antiviral Pyrimidines," MiniReviews in Medicinal Chemistry, vol. 4, No. 4, pp. 409-419 (2004).
Egron et al., "S-Acyl-2-thioethyl Phosphoramidate Diester Derivatives as Mononucleotide Prodrugs" J. Med. Chem., vol. 46, No. 21, pp. 4564-4571 (2003).
Howes et al., "The Regiospecific One-Pot Phosphorylation of Either the 5'- or 2'-Hydroxyl in 3'-Deoxycytidines Without Protection: Critical Role of the Base," Nucleosides, Nucleotides, and Nucleic Acids, vol. 22, No. 5-8, pp. 687-689 (2003).
Iyer et al., "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)," J. Med. Chem., vol. 43, No. 11, pp. 2266-2274 (2000).
Kim et al., "Monitoring the Intracellular Metabolism of Nucleoside Phosphoramidate Pronucleotides by 31P NMR," Nucleosides, Nucleotides and Nucleic Acid, vol. 23, No. 1 & 2, pp. 483-493 (2004).
Lehsten et al., "An Improved Procedure for the Synthesis of Nucleoside Phosphoramidates," Organic Process Research and Development, vol. 6, pp. 819-822 (2002).
McGuigan et al., "Aryl phosphate derivatives of AZT retain activity against HIV1 in cell lines which are resistant to the action of AZT," Antiviral Research, vol 17, pp. 311-321 (1992).
McGuigan et al., "Application of Phosphoramidate ProTide Technology Significantly Improves Antiviral Potency of Carbocyclic Adenosine Derivatives," J. Med. Chem., vol. 49, No. 24, pp. 7215-7226 (2006).
McGuigan et al., "Application of Phosphoramidate Pronucleotides Technology to Abacavir Leads to a Significant Enhancement of Antiviral Potency," J. Med. Chem., vol. 48, No. 10, pp. 3504-3515 (2005).
McGuigan et al., "Aryl Phosphoramidate Derivatives of d4T Have Improved Anti-HIV Efficacy in Tissue Culture and May Act by the Generation of a Novel Intracellular Metabolite," J. Med. Chem., vol. 39, No. 8, pp. 1748-1753 (1996).
McGuigan et al., "Synthesis and anti-HIV activity of some novel chain-extended phosphoramidate derivatives of d4T (stavudine): esterase hydrolysis as a rapid predictive test for antiviral potency," Antiviral Chemistry and Chemotherapy, vol. 9, pp. 109-115 (1998).
McGuigan et al., "Synthesis and evaluation of some novel phosphoramidate derivatives of 3'-azido-3'-deoxythymidine (AZT) as anti-HIV compounds," Antiviral Chemistry and Chemotherapy, vol. 1, No. 2, pp. 107-113 (1990).
McIntee et al., "Probing the Mechanism of Action and Decomposition of Amino Acid Phosphomonoester Amidates of Antiviral Nucleoside Prodrugs," J. Med. Chem., vol. 40, No. 21, pp. 3323-3331 (1997).
Perrone et al., "First Example of Phosphoramidate Approach Applied to a 4'-Substituted Purine Nucleoside (4'-Azidoadenosine): Conversion of an Inactive Nucleoside to a Submicromolar Compound versus Hepatitis C Virus," J. Med. Chem., vol. 50, No. 22, pp. 5463-5470 (2007).
Perrone et al. "Application of the Phosphoramidate ProTide Approach to 4'-Azidouridine Confers Sub-micromolar Potency versus Hepatitis C Virus on an Inactive Nucleoside," J. Med. Chem., vol. 50, No. 8, 1840-1849 (2007).
Saboulard et al., "Characterization of the Activation Pathway of Phosphoramidate Triester Prodrugs of Stavudine and Zidovudine," Mol. Pharmacol., vol. 56, pp. 693-704 (1999).
Schultz, C., "Prodrugs of Biologically Active Phosphate Esters" Bioorg. and Med. Chem., vol. 11, pp. 885-898 (2003).
Siccardi et al., "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers," J. Pharmacol. and Exp. Ther., vol. 307, No. 3, pp. 1112-1119 (2003).
Siccardi et al., "Stereospecific chemical and enzymatic stability of phosphoramidate triester prodrugs of d4T in vitro," European Journal of Pharmaceutical Sciences, vol. 22, pp. 25-31 (2004).
Siddiqui et al., "Design and Synthesis of Lipophilic Phosphoramidate d4T-MP Prodrugs Expressing High Potency Against HIV in Cell Culture: Structural Determinants for in Vitro Activity and QSAR," J. Med. Chem., vol. 42, No. 20, pp. 4122-4128 (1999).
Siddiqui et al., "Enhancing the Aqueous Solubility of d4T-based Phosphoramidate Prodrugs," Bioorg. and Med. Chem. Lett., vol. 10, pp. 381-384 (2000).
Song et al., "Pharmacokinetics of Amino Acid Phosphoramidate Monoesters of Zidovudine in Rats," Antimicrobial Agents and Chemotherapy, vol. 46, No. 5, pp. 1357-1363 (2002).
Uckun et al., "In Vivo Pharmacokinetics and Toxicity Profile of the Anti-HIV Agent Stampidine in Dogs and Feline Immunodeficiency Virus-infected Cats," Arzneim.-Forsch./Drug Res., vol. 56, No. 2a, pp. 176-192 (2006).
Valette et al., "Decomposition Pathways and in Vitro HIV Inhibitory Effects of IsoddA Pronucleotides: Toward a Rational Approach for Intracellular Delivery of Nucleoside 5'-Monophosphates," J. Med. Chem., vol. 39, No. 10, pp. 1981-1990 (1996).
Venkatachalam et al., "Synthesis and metabolism of naphthyl substituted phosphoramidate derivatives of stavudine," Bioorg. and Med. Chem., vol. 14, pp. 5161-5177 (2006).
Venkatachalam et al., "Rational Drug Design of Multifunctional Phosphoramidate Substituted Nucleoside Analogs," Current Pharmaceutical Design, vol. 10, No. 15, pp. 1713-1726 (2004).
Wagner et al., "Antiviral Nucleoside Drug Delivery via Amino Acid Phosphoramidates," Nucleosides, Nucleotides and Nucleic Acids, vol. 18, No. 4 & 5, pp. 913-919 (1999).
Wu et al., "Synthesis and Biological Activity of a Gemcitabine Phosphoramidate Prodrug," J. Med. Chem., vol. 50, No. 15, pp. 3743-3746 (2007).
Gunic et al., "6-Hydrazinopurine 2'-methyl ribonucleosides and their 5'-monophosphate prodrugs as potent hepatitis C virus inhibitors," Bioorg. & Med. Chem. Lett., vol. 17, pp. 2456-2458 (2007).
International Search Report issued in International PCT application No. PCT/US2008/058183 mailed Mar. 31, 2010 (7 pages).
International Preliminary Examination Report along with Written Opinion of the International Searching Authority issued in International PCT application No. PCT/US2008/058183 issued Apr. 7, 2010 (17 pages).
Baschang et al., "Neue Derivate von Thymidin-3',5'-cyclophosphat," Angew. Chem., vol. 85, No. 1, pp. 44-45 (1973).
Broeders et al., "A 400- and 600-Mhz 'H NMR Confromational Study on Nucleoside Cyclic 3', 5' PV-TBP Systems. Conformational Transmission Induces Diequatorial Orientation of the 3', 5'-Dioxaphosphorinane Ring in a Nonchair Confirmation," J. Am. Chem. Soc., vol. 112, No. 21, pp. 7475-7482 (1990).
Engels et al., "Ctclophosphate, III. Synthese und Eignschaften von Uridin-3',5'-cyclophosphat-estern," Chemische Berichte, vol. 110, No. 6, pp. 2019-2027 (1977).
Lopez Aparicio et al., "Synthesis of Saccharinic Acid Derivatives," Carbohydrate Research, vol. 129, pp. 99-109 (1984).
Nelson et al., "The Question of Chair-twist Equilibria for the Phosphate Rings of Nucleoside Cyclic 3',5'Monophosphates. 1H NMR and X-ray Crystallographic Study of Diastereomers of Thymidine Phenyl Cyclic 3',5'-Monophosphate," J. Am. Chem. Soc., vol. 109, No. 13, pp. 4058-4064 (1987).
The Extended Search report includes the supplementary European search report issued in European Application No. 05775359.2 dated Sep. 15, 2010 (9 pages).
Gromova et al., "Optical Rotatory Dispersion and Circular Dichroism of Mono- and Oligonucleotide-Amino Acids (Amidates)," Biochim. Biophys. Acta., vol. 240, No. 1, pp. 1-11 (1971).

(56) References Cited

OTHER PUBLICATIONS

Harris et al., "Synthesis and antiviral evaluation of phosphoramidate derivatives of (E)-5-(2-bromovinyl)-2'deoxyuridine," Antiviral Chemistry & Chemotherapy, vol. 12, No. 5, pp. 293-300 (2001).
Juodka et al., "Oligonucleotides and Nucleotide-Peptides. XXXIV. Synthesis and Some Properties of Complex Nucleotidyl (Oligonucleotidyl)-(P-N)-Amino Acids (Peptides) and Their Ethyl Esters," J. Carbohydrates Nucleosides Nucleotides, vol. 6, No. 4, pp. 333-357 (1979).
Juodka et al., "Oligonucleotides and Nucleotide-Peptides. XXXV. Some Properties of Nucleotidyl-(5'-N)-Amino Acid Esters Differing in Amino Acid and Nucleotide Components," J. Carbohydrates Nucleosides Nucleotides, vol. 8, No. 1, pp. 19-39 (1981).
Juodka et al., "Oligonucleotides and Nucleotide-Peptides. XXXVII. On the Mechanism of Hydrolysis of Uridylyl-(5'-N)-Amino Acids. IntramolecuLar Catalysis by the alpha-Carboxyl Group of Amino Acids," J. Carbohydrates Nucleosides Nucleotides, vol. 8, No. 6, pp. 519-535 (1981).
Lackey et al., "Enzyme-catalyzed therapeutic agent (ECTA) design: activation of the antitumor ECTA compound NB1011 by thymidylate synthase," Biochemical Pharmacology, vol. 61, No. 2, pp. 179-189 (2001).
McIntee et al., "Amino Acid Phosphoramidate Nucleosides: Potential ADEPT/GDEPT Substrates," Bioorganic & Medicinal Chemistry Letters, vol. 11, No. 21, pp. 2803-2805 (2001).
Remy et al., "Studies on Flourinated Pyrimidines. XIV. The Synthesis of Derivatives of 5-Fluoro-2'-deoxyuridine 5'-Phosphate and Related Compounds," J. Org. Chem., vol. 27, No. 7, pp. 2491-2500 (1962).
Smirrnov et al., "A Fluorescent Study of Tryptophan Derivatives of Oligonucleotides and Their Helical Complexes with Polyuridylic," FEBS Letters, vol. 51. No. 1, pp. 211-214 (1975).
Yuodka et al., "Oligonucleotides and Polynucleotides. XXVI. Synthesis of Esters of Nucleotidyl- and Oligonucleotidyl(5'-N)-(Amino Acid)S and -Peptides," Soviet Journal of Bioorganic Chemistry, vol. 2, No. 11 pp. 1089-1094(1976) Translated from Russian.
U.S. Appl. No. 60/392,350, filed Jun. 28, 2002.
U.S. Appl. No. 60/392,351, filed Jun. 28, 2002.
Asif et al., "Pharmacokinetics of the Antiviral Agent B-D-2'-Deoxy-2'-Fluoro-2'-C-Methylcytidine in Rhesus Monkeys," Antimicrobial Agents and Chemotherapy, vol. 51, No. 8, pp. 2877-2882 (2007).
Banker et al., "Prodrugs," Modern Pharmaceutics, Third Edition, Revised and Expanded, pp. 451 and 596 (1996).
Battaglia et al., "Combination Therapy with Interferon and Ribavirin in the Treatment of Chronic Hepatitis C Infection," The Annals of Pharmacotherapy, vol. 34, No. 4, pp. 487-494 (2000).
Berenguer, M., "Hepatitis C virus in the transplant setting," Antiviral Therapy, vol. 3, Supplement 3, pp. 125-136 (1998).
Clark et al., "Design, Synthesis, and Antiviral Activity of 2'-Deoxy-2'-fluoro-2'-C-methylcytidine, a Potent Inhibitor of Hepatitis C Virus Replication," J. Med. Chem., vol. 48, No. 17, pp. 5504-5508 (2005).
Davis, G. L., "Current Therapy for Chronic Hepatitis C," Gastroenterology, vol. 118, No. 2, pp. S104-S114 (2000).
Eldrup et al., "Oral Session V: Hepatitis C Virus, Flaviviruses," Program and Abstracts, The Sixteenth International Conference on Antiviral Research, p. A75, Abstract 119 (Apr. 27 to May 1, 2003).
Eldrup et al., "Structure-Activity Relationship of Purine Ribonucleosides for Inhibition of Hepatitis C Virus RNA-Dependent RNA Polymerase," J. Med. Chem., vol. 47, No. 9, pp. 2283-2295 (2004).
Farquhar et al., "Synthesis and Biological Evaluation of Neutral Derivatives of 5-Fluoro-2'-deoxyuridine 5'-Phosphate," J. Med. Chem., vol. 26, No. 8, pp. 1153-1158 (1983).
Farquhar et al., "Synthesis of Biological Evaluation of 9-[5'-(2-Oxo-1,3,2-oxazaphosphorinan-2-yl)-beta-D-arabinosyl] adenine and 9[5'-(2-Oxo-1,3,2-dioxaphosphorinan-2-yl)-beta-D-arabinosyl]adenine: Potential Neutral Precursors of 9-[beta-D-Arabinofuranosyl]adenine 5'-Monophosphate," J. Med. Chem., vol. 28, No. 9, pp. 1358-1361 (1985).
Freed et al., "Evidence for acyloxymethyl esters of pyrimidine 5'-deoxyribonucleotides as extracellular sources of active 5'-deoxyribonucleotides in cultured cells," Biochemical Pharmacology, vol. 38, No. 19, pp. 3193-3198 (1989).
Hertel et al., "Synthesis of 2-Deoxy-2,2-difluoro-D-ribose and 2-Deoxy-2,2-difluoro-D-ribofuranosyl Nucleosides," J. Org. Chem., vol. 53, No. 11, pp. 2406-2409 (1988).
Hostetler et al., "Synthesis and Antiretroviral Activity of Phospholipid Analogs of Azidothymidine and Other Antiviral Nucleosides," J. Biol. Chem., vol. 265, No. 11, pp. 6112-6117 (1990).
Hunston et al., "Synthesis and Biological Properties of Some Cyclic Phosphotriesters Derived from 2'-Deoxy-5-fluorouridine," J. Med. Chem., vol. 27, No. 4, pp. 440-444 (1984).
International Search Report issued in International Application No. PCT/US2005/025916 mailed Jun. 15, 2006.
Jones et al., "Minireview: Nucleotide Prodrugs," Antiviral Research, vol. 27, No. 1-2pp. 1-17 (1995).
Khamnei et al., "Neighboring Group Catalysis in the Design of Nucleotide Prodrugs," J. Med. Chem., vol. 39, No. 20, pp. 4109-4115 (1996).
Kotra et al., "Structure-Activity Relationships of 2'-Deoxy-2',2'-difluoro-L-erythro-pentofuranosyl Nucleosides," J. Med. Chem., vol. 40, No. 22, pp. 3635-3644 (1997).
Kryuchkov et al., "Influence of Solvent on the Strength of Cyclic Oxygen-Containing Phosphorus Acids," Bulletin of the Academy of Sciences of the USSR. Division of Chemical Science, vol. 36, No. 6, Part 1, pp. 1145-1148 (1987) Translated from Russian.
Li et al., "Synthesis of the Phosphoramidite Derivative of 2'-Deoxy-2'-C-beta-methylcytidine", J. Org. Chem., vol. 68, No. 17, pp. 6799-6802 (2003).
Ma et al., "Characterization of the Metabolic Activation of Hepatitis C Virus Nucleoside Inhibitor B-D-2'-Deoxy-2-Fluoro-2'-C-Methylcytidine (PSI-6130) and Identification of a Novel Active 5'-Triphosphate Species," J. Biol. Chem., vol. 282, No. 41, pp. 29812-29820 (Oct. 12, 2007).
Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc. Perkin. Trans, 1, pp. 2345-2353 (1992).
Olsen et al., "2'-Modified Nucleoside Analogs as Inhibitors of Hepatitis C RNA Replication," Program and Abstracts, 16th International Conference on Antiviral Research, Abstract No. 121, p. A76 (Apr. 27-May 1, 2003).
Otto, M., "Evaluation of Nucleoside Analogs in the Hepatitis C Virus Replicon System," Framing the Knowledge of Therapeutics for Viral Hepatitis, IHL Press, First Edition, pp. 247-261 (2006).
Piantadosi et al., "Synthesis and Evaluation of Novel Ether Lipid Nucleoside Conjugates for Anti-HIV-1 Activity," J. Med. Chem., vol. 34, No. 4, pp. 1408-1414 (1991).
Pierra et al., "Synthesis and Pharmacokinetics of Valopicitabine (NM283), an Efficient Prodrug of the Potent Anti-HCV Agent 2'-C-Methylcytidine," J. Med. Chem., vol. 49, No. 22, pp. 6614-6620 (2006).
Starrett, Jr. et al., "Synthesis, Oral Bioavailability Determination, and in Vitro Evaluation of Prodrugs of the Antiviral Agent 9-[2-(Phosphonomethoxy)ethyl]adenine (PMEA)," J. Med. Chem., vol. 37, No. 12, pp. 1857-1864 (1994).
Stuyver et al., "Inhibition of hepatitis C replicon RNA synthesis by B-D-2'-deoxy-2'-fluoro-2'-C-methlcytidine: a specific inhibitor of hepatitis C virus replication," Antiviral Chemistry & Chemotherapy, vol. 17, No. 2, pp. 79-87 (2006).
Stuyver et al., "Dynamics of Subgenomic Hepatitis C Virus Replicon RNA Levels in Huh-7 Cells after Exposure to Nucleoside Antimetabolites," J. Virol., vol. 77, No. 19, pp. 10689-10694 (2003).
Stuyver et al., "Ribonucleoside Analogue that Blocks Replication of Bovine Viral Diarrhea and Hepatitis C Viruses in Culture," Antimicrobial Agents and Chemotherapy, vol. 47, No. 1, pp. 244-254 (2003).
Wolff, M.E., "Burger's Medicinal Chemistry and Drug Discovery," Fifth Edition, vol. 1, pp. 975-977 (1995).
Zon, G., "4 Cyclophosphoamide Analogues," Progress in Medicinal Chemistry, vol. 19, pp. 205-246 (1982).

(56) References Cited

OTHER PUBLICATIONS

Bhat et al., "Synthesis and Pharmacokinetic Properties of Nucleoside Analogues as Possible Inhibitors of HCV RNA Replication," (Oral Session V: Hepatitis C Virus, Flaviviruses), 16th International Conference on Antiviral Research, Abstract No. 120, p. A75 (Apr. 27-May 1, 2003).
Chu et al., "Isolation and Structure of SCH 351633: A Novel Hepatitis C Virus (HCV) NS3 Protease Inhibitor from the Fungus *Penicillium griseofulvum*," Bioorg. & Med. Chem. Lett., vol. 9, pp. 1949-1952 (1999).
Chu et al., "Structure of Sch 68631: A New Hepatitis C Virue Proteinase Inhibitor from *Streptomyces* sp." Tet. Lett., vol. 37, No. 40, pp. 7229-7232 (1996).
De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., vol. 37, No. 4, pp. 498-511 (1994).
Edmundson et al., "Cyclic Organophosphorus Compounds. Part 23. Configurational Assignments in the 4-Phenyl-1,3,2-dioxaphosphorinane Series. X-Ray Molecular Structure of cis-2-Benzylamino-4-phenyl-1,3,2- dioxaphosphorinane 2-oxide," J. Chem. Research (S), pp. 122-123 (1989).
Goekjian et al., "Synthesis of Fluorinated Marcocyclic Bis(indolyl)maleimides as Potential 19F NMR Probes for Protein Kinase C," J. Org. Chem. vol., 64., No. 12, pp. 4238-4246 (1999).
Hernandez et al., "Synthesis of Highly Functionalized Chiral Nitriles by Radical Fragmentation of beta-Hydroxy Azides. Convenient Transformation of Aldononitriles into 1,4- and 1,5-Iminoalditols," J. Org. Chem., vol. 69. No. 24, pp. 8437-8444 (2004).
Hostetler et al., "Greatly Enhanced Inhibition of Human Immunodeficiency Virus Type 1 Replication in CEM and HT4-6C Cells by 3'-Deoxythymidine Diphosphate Dimyristoylglycerol, a Lipid Prodrug of 3'-Deoxythymidine," Antimicrobial Agents and Chemotherapy, vol. 36, No. 9, pp. 2025-2029 (1992).
Kucera et al., "Novel Membrane-Interactive Ether Lipid Analogs That Inhibit Infectious HIV-1 Production and Induce Defective Virus Formation," Aids Research and Human Retroviruses, vol. 6, No. 4, pp. 491-501 (1990).
Meier et al., "Cyclic Saligenyl Phosphotriesters of 2',3'-Dideoxy-2',3'-didehydrothymidine (d4T)—A New Pro-Nucleotide Approach," Bioorg. & Med. Chem. Lett., vol. 7, No. 2, pp. 99-104, (1997).
Neidlein et al., "Mild Preparation of 1-Benzyloxyiminoalkylphosphonic Dichlorides: Application to the Synthesis of Cyclic Phosphonic Diesters and Cyclic Monoester Amides," Heterocycles, vol. 35, No. 2, pp. 1185-1203 (1993).
Nifantyev et al., "Synthesis and Structure of Some Stable Phospholane-Phospholanes," Phosphorus, Sulfur, and Silicon, vol. 113, pp. 1-13 (1996).
Novak, J. J. K., "Chiroptical Properties of 2-Methyl-1,4-Lactones; Revised Absolute Configuration of 2-Deoxy-2-C-Methyl-erythro-D-Pentono-1,4-Lactones," Collection Czechoslov. Chem. Commun., vol. 39, pp. 869-882 (1974).
Novak, J. J. K., "Nucleic Acid Components and Their Analogues CXLIII. Nucleosides Derived from 2-Deoxy-2(R)-C-Methyl-erythro-D-Pentose," Collection Czechoslov. Chem. Commun., vol. 36, pp. 3670-3677 (1971).
Oishi et al., "Asymmetric Dihydroxylation of Chiral Olefins. High Control of Diastereofacial Selection," Tet. Lett., vol. 34, No. 22, pp. 3573-3576 (1993).
Shih et al., "Preparation and Structures of 2-Dimethylamino-4-phenyl-1,3,2-dioxaphosphorinane-2-oxides," Bull. Inst. Chem., Acad. Sin., vol. 41, pp. 9-16, (Mar. 1994).
Stella, V. J., "Prodrugs as Therapeutics," Expert opinion on therapeutic patents, vol. 14, No. 3, pp. 277-280 (Mar. 2004).
Xiao-Ling et al., "Study on the Chirality of Sulfur in Ethyl (2S, 3R,4R)-4,5-O-Isopropylidene-2,3-sulfinyl-2,3,4,5-tetrahydroxy-pentanoate", Acta Chimica Sinica, vol. 55, pp. 600-604 (1997).
Xiao-Ling et al., "The Synthesis of (2S,3R)-Sphingosine from D-Mannitol", Acta Chimica Sinica, vol. 54, pp. 826-832 (1996).

International Search Report issued in International Application No. PCT/US2004/012472 mailed Dec. 30, 2004 (4 pages).
International Search Report issued in International Application No. PCT/US2005/025916 mailed Jun. 15, 2006 (2 pages).
International Search Report issued in International Application No. PCT/EP2006/069060 mailed Jan. 30, 2007 (4 pages).
International Search Report issued in International Application No. PCT/US2005/032406 mailed May 8, 2008 (3 pages).
Bartenschlager et al., "Nonstructural Protein 3 of the Hepatitis C Virus Encodes a Serine-Type Proteinase Required for Cleavage at the NS3/4 and NS4/5 Junctions," J. Virol., vol. 67, No. 7, pp. 3835-3844 (1993).
Bartenschlager et al., "Kinetic and Structural Analyses of Hepatitis C Virus Polyprotein Processing," J. Virol., vol. 68, No. 8, pp. 5045-5055 (1994).
Bazan et al., "Detection of a Trypsin-like Serine Protease Domain in Flaviviruses and Pestiviruses," Virology, vol. 171, pp. 637-639 (1989).
Beaulieu et al., "Inhibitors of the HCV NS5B polymerase: New hope for the treatment of hepatitis C infections," Current Opinion in Investigational Drugs, vol. 5, No. 8, pp. 838-850 (2004).
Behrens et al., "Identification and properties of the RNA-dependent RNA polymerase of hepatitis C virus," The EMBO Journal, vol. 15, No. 1, pp. 12-22 (1996).
Calisher et al., "Antigenic Relationships between Flaviviruses as Determined by Cross-neutralization Tests with Polyclonal Antisera," J. Gen. Virol., vol. 70, pp. 37-43 (1989).
Carroll et al., "Nucleoside Analog Inhibitors of Hepatitis C Virus Replication," Infectious Disorders—Drug Targets, vol. 6, No. 1, pp. 17-29 (2006).
Eckart et al., "The Hepatitis C Virus Encodes a Serine Protease Involved in Processing of the Putative Nonstructural Proteins from the Viral Polyprotein Precursor," Biochemical and Biophysical Research Communications, vol. 192, No. 2, pp. 399-406 (1993).
Failla et al., "Both NS3 and NS4A are Required for Proteolytic Processing of Hepatitis C Virus Nonstructural Proteins," J. Virol., vol. 68, No. 6, pp. 3753-3760 (1994).
Rice, C. M., "Flaviviridae: The Viruses and Their Replication," Fields Virology, 3rd Edition, vol. 1, pp. 931-959 (1996).
Gorbalenya et al., "A conserved NTP-motif in putative helicases," Nature, vol. 333, p. 22 (1988).
Gorbalenya et al., "N-terminal domains of putative helicases of flavi- and pestiviruses may be serine proteases," Nucleic Acids Research, vol. 17, No. 10, pp. 3889-3897 (1989).
Grakoui et al., "Characterization of the Hepatitis C Virus-Encoded Serine Proteinase: Determination of Proteinase-Dependent Polyprotein Clevage Sites," J. Virol., vol. 67, No. 5, pp. 2832-2843 (1993).
Grakoui et al., "A second hepatitis C virus-encoded proteinase," Proc. Natl. Acad. Sci., vol. 90, pp. 10583-10587 (1993).
Griffith et al., "HCV Anti-viral Agents," Annual Reports in Medicinal Chemistry, vol. 39, pp. 223-237 (2004).
Halstead, S. B., "Selective Primary Health Care: Strategies for Control of Disease in the Developing World. XI. Dengue," Review of Infectious Diseases, vol. 6, No. 2, pp. 251-263 (1984).
U.S. Appl. No. 12/553,483, Pending claims filed Feb. 22, 2010.
U.S. Appl. No. 12/645,710, filed Dec. 23, 2009.
U.S. Appl. No. 12/645,765, filed on Dec. 23, 2009.
U.S. Appl. No. 12/645,821, filed on Dec. 23, 2009.
U.S. Appl. No. 13/099,671, claims filed Sep. 4, 2012.
Halstead, S. B., "Pathogenesis of Dengue: Challenges to Molecular Biology," Science, vol. 239, pp. 476-481 (1988).
Hijikata et al., "Two Distinct Proteinase Activities required for the Processing of a Putative Nonstructural Precursor Protein of Hepatitis C Virus," J. Virol., vol. 67, No. 8, pp. 4665-4675 (1993).
Jin et al., "Expression, Isolation, and characterization of the Hepatitis C Virus ATPase/RNA Helicase," Archives of Biochemistry and Biophysics, vol. 323, No. 1, pp. 47-53 (1995).
Kim et al., "C-Terminal Domain of the Hepatitis C Virus NS3 Protein Contains an RNA Helicase Activity," Biochemical and Biophysical Research Communications, vol. 215, No. 1, pp. 160-166 (1995).
Koonin et al., "Evolution and Taxonomy of Positive-Strand RNA Viruses: Implications of Comparatives Analysis of Amino Acid

(56) References Cited

OTHER PUBLICATIONS

Sequences," Critical Reviews in Biochemistry and Molecular Biology, vol. 28, No. 5, pp. 375-430 (1993).
Lohmann et al., "Biochemical Properties of Hepatitis C Virus NS5B RNA-Dependent RNA Polymerase and Identification of Amino Acid Sequence Motifs Essential for Enzymatic Activity," J. Virol., vol. 71, No. 11, pp. 8416-8428 (1997).
Meyers et al., "Molecular Characterization of Pestiviruses," Advance in Virus Research, vol. 47, pp. 53-119 (1996).
Moennig et al., "The Pestiviruses," Advances in Virus Research, vol. 41, pp. 53-99 (1992).
Monath, T. P., M.D., "Japanese Encephalitis—A Plague of the Orient," N. Engl. J. Med., vol. 319, No. 10, pp. 641-643 (Sep. 8, 1988).
Ni et al., "Progress and development of small molecule HCV antivirals," Current Opinion in Drug Discovery & Development, vol. 7, No. 4, pp. 446-459 (2004).
Tan et al., "Hepatitis C Therapeutics: current Status and Emerging Strategies," Nature Reviews, vol. 1, pp. 867-881 (2002).
Tomei et al., "NS3 Is a Serine Protease Required for Processing of Hepatitis C Virus Polyprotein," J. Virol., vol. 67, No. 7, pp. 4017-4026 (1993).
Walker et al., "Promising candidates for the treatment of chronic hepatitis C," Expert Opin. Investig. Drugs, vol. 12, No. 8, pp. 1269-1280 (2003).
Warrener et al., "Pestivirus NS3 (p80) Protein Possesses RNA Helicase Activity," J. Virol., vol. 69, No. 3, pp. 1720-1726 (1995).
Wiskerchen et al., Pestivirus Gene Expression: Protein p80 of Bovine Viral Diarrhea Virus Is a Proteinase Involved in Polyprotein Processing, Virology, vol. 184, pp. 341-350 (1991).
Wu et al., "Targeting NS5B RNA-Dependent RNA Polymerase for Anti-HCV Chemotherapy," Current Drug Targets—Infectious Disorders, vol. 3, No. 3, pp. 207-219 (2003).
Xu et al., "Bovine Viral Diarrhea Virus NS3 Serine Proteinase: Polyprotein Cleavage Sites, Cofactor Requirements, and Molecular Model of an Enzyme Essential for Pestivirus Replication," J. Virol., vol. 71, No. 7, pp. 5312-5322 (1997).
Yuan et al., "Expression, Purification, and Partial Characterization of HCV RNA Polymerase," Biochemical and Biophysical Research Communications, vol. 232, No. 1, pp. 231-235 (1997).
Zhong et al., "Identification and characterization of an RNA-Dependent RNA Polymerase Activity within the Nonstructural Protein 5B Region of Bovine Viral Diarrhea Virus," J. Virol., vol. 72, No. 11, pp. 9365-9369 (1998).
Aquaro et al., "Activities of Masked 2',3'-Dideoxynucleoside Monophosphate Derivatives Against Human Immunodeficiency Virus in Resting Macrophages," Antimicrobial Agents and Chemotherapy, vol. 44, No. 1, pp. 173-177 (2000).
Chapman et al., "Purification of PMPA Amidate Prodrugs by SMB Chromatography and X-Ray Crystallography of the Diastereomerically Pure GS-7340," Nucleosides, Nucleotides & Nucleic Acids, vol. 20, No. 4-7, pp. 1085-1090 (2001).
Chapman et al., "Practical Synthesis, Separation, and Stereochemical Assignment of the PMPA Pro-Drug GS-7340," Nucleosides, Nucleotides & Nucleic Acids, vol. 20, No. 4-7, pp. 621-628 (2001).
Eisenberg et al., "Metabolism of GS-7340, A Novel Phenyl Monophosphoramidate Intracellular Prodrug of PMPA, in Blood," Nucleosides, Nucleotides & Nucleic Acids, vol. 20, No. 4-7, pp. 1091-1098 (2001).
Lee et al., "Selective Intracellular Activation of a Novel Prodrug of the Human Immunodeficiency Virus reverse Transcriptase Inhibitor Tenofovir Leads to Preferential Distribution and Accumulation in Lymphatic Tissue," Antimicrobial Agents and Chemotherapy, vol. 49, No. 5, pp. 1898-1906 (2005).
McGuigan et al., "Synthesis, anti-human immunodeficiency virus activity and esterase lability of some novel carboxylic ester-modified phosphoramidate derivatives of stavudine (d4T)," Antiviral Chemistry & Chemotherapy, vol. 9, pp. 473-479 (1998).
Murakami et al., "The Mechanism of Action of beta-D-2'-Deoxy-2'-Fluoro-2'-C-Methylcytidine Involves a Second Metabolic Pathway Leading to beta-D-2'-Deoxy-2'-Fluoro-2'-C-Methyluridine 5'-Triphosphate, a Potent Inhibitor of the Hepatitis C Virus RNA-Dependent RNA Polymerase," Antimicrobial Agents and Chemotherapy, vol. 52, No. 2, pp. 458-464 (2008).
Murakami et al., "Mechanism of Activation of beta-D-2'-Deoxy-2'-Fluoro-2'-C-Methylcytidine and Inhibition of hepatitis C Virus NS5B RNA Polymerase," Antimicrobial Agents and Chemotherapy, vol. 51, No. 2, pp. 503-509 (Feb. 2007).
Ray et al., "Intracellular Metabolism of the Nucleotide Prodrugs GS-9131, a Potent Anti-Human Immunodeficiency Virus Agent," Antimicrobial Agents and Chemotherapy, vol. 52, No. 2, pp. 648-654 (2008).
Stuyver et al., "Inhibition of the Subgenomic Hepatitis C Virus Replicon in Huh-7 Cells by 2'-Deoxy-2'-Fluorocytidine," Antimicrobial Agents and Chemotherapy, vol. 48, No. 2, pp. 651-654 (2004).
U.S. Appl. No. 10/828,753, Non-Final Office Action Rejection, mailed Mar. 30, 2007.
U.S. Appl. No. 10/828,753, Final Office Action Rejection, mailed Feb. 26, 2008.
U.S. Appl. No. 11/225,425, Non-Final Office Action Rejection, mailed Nov. 13, 2008.
U.S. Appl. No. 11/225,425, Non-Final Office Action Rejection, mailed Jul. 7, 2009.
Response to non-final Office Action dated Oct. 1, 2009 for U.S. Appl. No. 12/142,554.
U.S. Appl. No. 11/225,425, Final Office Action Rejection, mailed Feb. 18, 2010.
U.S. Appl. No. 11/353,597, Non-Final Office Action Rejection, mailed Oct. 2, 2007.
U.S. Appl. No. 11/353,597, Non-Final Office Action Rejection, mailed Jul. 17, 2008.
U.S. Appl. No. 11/353,597, Final Office Action Rejection, mailed Dec. 2, 2008.
U.S. Appl. No. 11/635,898, Non-Final Office Action Rejection, mailed Jul. 28, 2009.
U.S. Appl. No. 11/635,898, Pending claims filed Dec. 24, 2009.
U.S. Appl. No. 11/854,218, Pending claims filed Sep. 12, 2007.
U.S. Appl. No. 11/854,218, Non-Final Office Action Rejection, mailed Oct. 1, 2009.
U.S. Appl. No. 12/142,536, Pending claims filed Jun. 19, 2008.
U.S. Appl. No. 12/142,536, Non-Final Office Action Rejection, mailed Oct. 2, 2009.
U.S. Appl. No. 12/142,554, Non-Final Office Action Rejection, mailed Oct. 1, 2009.
U.S. Appl. No. 12/142,554, Pending claims filed Dec. 17, 2009.
U.S. Appl. No. 12/240,342, Pending claims filed Sep. 29, 2008.
U.S. Appl. No. 12/240,342, Non-Final Office Action Rejection, mailed Oct. 1, 2009.
U.S. Appl. No. 12/479,075, filed Jun. 5, 2009.
U.S. Appl. No. 12/553,483, Non-Final Office Action Rejection, mailed Dec. 17, 2009.
U.S. Appl. No. 14/013,237, filed Aug. 29, 2013.
Claims of U.S. Appl. No. 14/013,237 as amended Aug. 30, 2013.
U.S. Appl. No. 13/956,195, filed Jul. 31, 2013.
Claims of U.S. Appl. No. 13/956,195 as amended Oct. 21, 2013.
Codington, et al., "Nucleosides. XVIII. Synthesis of 2'-Fluorothymidine, 2'-Fluorodeoxyuridine, and Other 2'-Halogeno-2'-Deoxy Nucleosides[1,2]", The Division of Nucleoprotein Chemistry, Sloan-Kettering Institute for Cancer Research, Sloan-Kettering Division of Cornell University Medical Colleg, New York 21, New York, vol. 29, pp. 558-564, (1963).
Hrebabecky, et al.,"1-(3,5-0-alkylidene-2-deoxy-4-C-hydroxymethyl-alpha-L-*threo*-pentofuranosyl)uracils," Collect. Czhech. Chem. Commun., vol. 62, pp. 957-970, (1997).
Hrebabecky, et al., "Synthesis of 1-(3-azido-2,3-dideoxy-β-D-allofuranosyl)thymine, 1-(2,3-dideoxy-β-D-allofuranosyl)thymine, and 1-(2,3-dideoxy-β-D-*erythro*-hex-2-enofuranosyl)thymine," Carbohydrate Research, vol. 216, pp. 179-186, (1991).
Hrebabecky, et al., "Synthesis of 1-(3-azido-2,3-dideoxy-β-d-*ribo*-hexofuranosyl)-,1-(2,3-dideoxy-β-d-*erythro*-hexofuranosyl)- and 1-(2,3-dideoxy-β-d-*erythro*-hex-2-enofuranosyl)pyrimidine nucleosides," Collect. Czhech. Chem. Commun., vol. 59, pp. 412-420, (1993).

(56) References Cited

OTHER PUBLICATIONS

Hrebabecky, et al., "Synthesis of 1-(3-azido-2,3-dideoxy-4-C-hydroxymethyl-alpha-L-*threo*pentofuranosyl)thymine, 1-(2,3-dideoxy-4-C-hydroxy-methyl-alpha-L-*glycero*-pentofuranosyl)thymine and 1-(2,3-dideoxy-4-C-hydroxymethyl-alpha-L-*glycero*-pent-2-enofuranosyl)thymine," Collect Czech. Chem. Commun., vol. 58, pp. 409-420, (1992).

Lin, et al., "A stereospecific synthesis of 2',3'-dideoxy-β-L-cytidine (β-L-ddC), a potent inhibitor against human hepatitis B virus (HBV) and human immunodeficiency virus (HIV)," Tetrahedron Letters, vol. 35, No. 21, pp. 3477-3480, (1994).

Mourier, et al., "Enantioselective synthesis and biological evaluation of 5-*o*-carboranyl-pyrimidine-nucleosides," Bioorganic & Medicinal Chemistry, vol. 7, pp. 2759-2766, (1999).

Robins, et al., "Nucleic acid related compounds. 91. Biomimetic reactions are in harmony with loss of 2'-substituents as free radicals (not anions) during mechanism-based inactivation of ribonucleotide reductases. differential interactions of azide, halogen, and alkylthio groups with tributylstannane and triphenylsilane," Journal of the American Chemical Society, vol. 118, No. 46, pp. 11341-11348, (1996).

Saneyoshi, "Facile synthesis of 2'-*O*-cyanoethyluridine by ring-opening reaction of 2,2'-anhydrouridine with cyanoethyl trimethylsilyl ether in the presence of $BF_3$ $Et_2O$," Tetrahedron Letters, vol. 48, pp. 8554-8557, (2007).

Van Rompaey, et al., "*Mycobacterium tuberculosis* thymidine monophosphate kinase inhibitors; biological evaluation and conformational analysis of 2'-and 3'-modified thymidine analogues," Eur. J. Org. Chem., pp. 2911-2918, (2003).

Vanheusden, et al., "Synthesis and evaluation of thymidine-5'-*O*-monophosphate analogues as inhibitors of *Mycobacterium tuberculosis* thymidylate kinase," Bioorganic & Medicinal Chemistry Letters, vol. 12, pp. 2695-2698, (2002).

Vanheusden, et al., "Discovery of bicyclic thymidine analogues as selective and high-affinity inhibitors of *mycobacterium tuberculosis* thymidine monophosphate kinase," J. Med. Chem., vol. 47, pp. 6187-6194, (2004).

* cited by examiner

SEQUENCE LISTING

```
<160> NUMBER OF SEQ ID NOS: 3

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agccatggcg ttagtatgag tgt                                          23

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttccgcagac cactatgg                                                18

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 5'-FAM
<220> FEATURE:
<223> OTHER INFORMATION: 3'-TAMRA

<400> SEQUENCE: 3
cctccaggac cccccctccc                                              20
```

NUCLEOSIDE PHOSPHORAMIDATE PRODRUGS

CROSS-REFERENCE TO RELATED APPLICATIONS

This application is a continuation application of U.S. patent application Ser. No. 14/057,675, filed Oct. 18, 2013, which is a continuation application of U.S. patent application Ser. No. 13/609,614, filed Sep. 11, 2012, which issued as U.S. Pat. No. 8,580,765 on Nov. 12, 2013, which is a continuation of U.S. patent application Ser. No. 13/099,671, filed May 3, 2011, which issued as U.S. Pat. No. 8,334,270 on Dec. 18, 2012, which is a continuation of U.S. patent application Ser. No. 12/053,015, filed Mar. 21, 2008, which issued as U.S. Pat. No. 7,964,580 on Jun. 21, 2011, which claims the benefit of U.S. Provisional Application No. 60/982,309, filed Oct. 24, 2007, and U.S. Provisional Application No. 60/909,315, filed Mar. 30, 2007. The entire contents of the aforementioned applications are incorporated herein by reference in their entireties.

SEQUENCE LISTING

The instant application contains a Sequence Listing which has been submitted electronically in ASCII format and is hereby incorporated by reference in its entirety. Said ASCII copy, created on Jul. 7, 2014, is named PH3080.PC7-TRK1_SL.txt and is 1,253 bytes in size.

FIELD OF INVENTION

The present invention pertains to nucleoside phosphoramidates and their use as agents for treating viral diseases. These compounds are inhibitors of RNA-dependent RNA viral replication and are useful as inhibitors of HCV NS5B polymerase, as inhibitors of HCV replication and for treatment of hepatitis C infection in mammals. The invention provides novel chemical compounds, and the use of these compounds alone or in combination with other antiviral agents for treating HCV infection.

BACKGROUND

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 4.5 million infected people in the United States alone, according to the U.S. Center for Disease Control. According to the World Health Organization, there are more than 200 million infected individuals worldwide, with at least 3 to 4 million people being infected each year. Once infected, about 20% of people clear the virus, but the rest can harbor HCV the rest of their lives. Ten to twenty percent of chronically infected individuals eventually develop liver-destroying cirrhosis or cancer. The viral disease is transmitted parenterally by contaminated blood and blood products, contaminated needles, or sexually and vertically from infected mothers or carrier mothers to their offspring. Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection.

The HCV virion is an enveloped positive-strand RNA virus with a single oligoribonucleotide genomic sequence of about 9600 bases which encodes a polyprotein of about 3,010 amino acids. The protein products of the HCV gene consist of the structural proteins C, E1, and E2, and the non-structural proteins NS2, NS3, NS4A and NS4B, and NS5A and NS5B. The nonstructural (NS) proteins are believed to provide the catalytic machinery for viral replication. The NS3 protease releases NS5B, the RNA-dependent RNA polymerase from the polyprotein chain. HCV NS5B polymerase is required for the synthesis of a double-stranded RNA from a single-stranded viral RNA that serves as a template in the replication cycle of HCV. Therefore, NS5B polymerase is considered to be an essential component in the HCV replication complex (K. Ishi, et al, *Heptology*, 1999, 29; 1227-1235; V. Lohmann, et al., *Virology*, 1998, 249: 108-118). Inhibition of HCV NS5B polymerase prevents formation of the double-stranded HCV RNA and therefore constitutes an attractive approach to the development of HCV-specific antiviral therapies.

HCV belongs to a much larger family of viruses that share many common features.

Flaviviridae Viruses

The Flaviviridae family of viruses comprises at least three distinct genera: pestiviruses, which cause disease in cattle and pigs; flaviviruses, which are the primary cause of diseases such as dengue fever and yellow fever; and hepaciviruses, whose sole member is HCV. The flavivirus genus includes more than 68 members separated into groups on the basis of serological relatedness (Calisher et al., *J. Gen. Virol*, 1993, 70, 37-43). Clinical symptoms vary and include fever, encephalitis and hemorrhagic fever (*Fields Virology*, Editors: Fields, B. N., Knipe, D. M., and Howley, P. M., Lippincott-Raven Publishers, Philadelphia, Pa., 1996, Chapter 31, 931-959). Flaviviruses of global concern that are associated with human disease include the Dengue Hemorrhagic. Fever viruses (DHF), yellow fever virus, shock syndrome and Japanese encephalitis virus (Halstead, S. B., *Rev. Infect. Dis.*, 1984, 6, 251-264; Halstead, S. B., *Science*, 239:476-481, 1988; Monath, T. P., *New Eng. J. Med*, 1988, 319, 64 1-643).

The *pestivirus* genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53-98). *Pestivirus* infections of domesticated livestock (cattle, pigs and sheep) cause significant economic losses worldwide. BVDV causes mucosal disease in cattle and is of significant economic importance to the livestock industry (Meyers, G. and Thiel, H. J., Advances in Virus Research, 1996, 47, 53-118; Moennig V., et al, Adv. Vir. Res. 1992, 41, 53-98). Human pestiviruses have not been as extensively characterized as the animal pestiviruses. However, serological surveys indicate considerable *pestivirus* exposure in humans.

Pestiviruses and hepaciviruses are closely related virus groups within the Flaviviridae family. Other closely related viruses in this family include the GB virus A, GB virus A-like agents, GB virus-B and GB virus-C (also called hepatitis G virus, HGV). The *hepacivirus* group (hepatitis C virus; HCV) consists of a number of closely related but genotypically distinguishable viruses that infect humans. There are at least 6 HCV genotypes and more than 50 subtypes. Due to the similarities between pestiviruses and hepaciviruses, combined with the poor ability of hepaciviruses to grow efficiently in cell culture, bovine viral diarrhea virus (BVDV) is often used as a surrogate to study the HCV virus.

The genetic organization of pestiviruses and hepaciviruses is very similar. These positive stranded RNA viruses possess a single large open reading frame (ORF) encoding all the viral proteins necessary for virus replication. These proteins are expressed as a polyprotein that is co- and post-translationally processed by both cellular and virus-encoded proteinases to yield the mature viral proteins. The viral proteins responsible for the replication of the viral genome RNA are located within approximately the carboxy-terminal. Two-thirds of the ORF are termed nonstructural (NS) proteins. The genetic organization and polyprotein processing of the nonstructural protein portion of the ORF for pestiviruses and hepaciviruses is very similar. For both the pestiviruses and hepaciviruses, the mature nonstructural (NS) proteins, in sequential order from the amino-terminus of the nonstructural protein coding region to the carboxy-terminus of the ORF, consist of p7, NS2, NS3, NS4A, NS4B, NS5A, and NS5B.

The NS proteins of pestiviruses and hepaciviruses share sequence domains that are characteristic of specific protein functions. For example, the NS3 proteins of viruses in both groups possess amino acid sequence motifs characteristic of serine proteinases and of helicases (Gorbalenya et al., *Nature*, 1988, 333, 22; Bann and Fletterick *Virology*, 1989, 171, 637-639; Gorbalenya et al., *Nucleic Acid Res.* 1989, 17, 3889-3897). Similarly, the NS5B proteins of pestiviruses and hepaciviruses have the motifs characteristic of RNA-directed RNA polymerases (Koonin, E. V. and Dolja, V. V., *Crir. Rev. Biochem. Molec. Biol.* 1993, 28, 375-430).

The actual roles and functions of the NS proteins of pestiviruses and hepaciviruses in the lifecycle of the viruses are directly analogous. In both cases, the NS3 serine proteinase is responsible for all proteolytic processing of polyprotein precursors downstream of its position in the ORF (Wiskerchen and Collett, *Virology*, 1991, 184, 341-350; Bartenschlager et al., *J. Virol.* 1993, 67, 3835-3844; Eckart et al. *Biochem. Biophys. Res. Comm.* 1993, 192, 399-406; Grakoui et al., *J. Virol.* 1993, 67, 2832-2843; Grakoui et al., *Proc. Natl. Acad Sci. USA* 1993, 90, 10583-10587; Hijikata et al., *J. Virol.* 1993, 67, 4665-4675; Tome et al., *J. Virol.*, 1993, 67, 4017-4026). The NS4A protein, in both cases, acts as a cofactor with the NS3 serine protease (Bartenschlager et al., *J. Virol.* 1994, 68, 5045-5055; Failla et al., *J. Virol.* 1994, 68, 3753-3760; Xu et al., *J. Virol.*, 1997, 71:53 12-5322). The NS3 protein of both viruses also functions as a helicase (Kim et al., *Biochem. Biophys. Res. Comm.*, 1995, 215, 160-166; Jin and Peterson, *Arch. Biochem. Biophys.*, 1995, 323, 47-53; Warrener and Collett, *J. Virol.* 1995, 69, 1720-1726). Finally, the NS5B proteins of pestiviruses and hepaciviruses have the predicted RNA-directed RNA polymerases activity (Behrens et al., EMBO, 1996, 15, 12-22; Lechmann et al., *J. Virol.*, 1997, 71, 8416-8428; Yuan et al., *Biochem. Biophys. Res. Comm.* 1997, 232, 231-235; Hagedorn, PCT WO 97/12033; Zhong et al, *J. Virol.*, 1998, 72, 9365-9369).

Currently, there are limited treatment options for individuals infected with hepatitis C virus. The current approved therapeutic option is the use of immunotherapy with recombinant interferon-α alone or in combination with the nucleoside analog ribavirin. This therapy is limited in its clinical effectiveness and only 50% of treated patients respond to therapy. Therefore, there is significant need for more effective and novel therapies to address the unmet medical need posed by HCV infection.

A number of potential molecular targets for drug development of direct acting antivirals as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome and this enzyme has elicited significant interest among medicinal chemists.

Inhibitors of HCV NS5B as potential therapies for HCV infection have been reviewed: Tan, S.-L., et al., *Nature Rev. Drug Discov.*, 2002, 1, 867-881; Walker, M. P. et al., *Exp. Opin. Investigational Drugs*, 2003, 12, 1269-1280; Ni, Z-J., et al., *Current Opinion in Drug Discovery and Development*, 2004, 7, 446-459; Beaulieu, P. L., et al., *Current Opinion in Investigational Drugs.*, 2004, 5, 838-850; Wu, J., et al., *Current Drug Targets-Infectious Disorders*, 2003, 3, 207-219; Griffith, R. C., et al, *Annual Reports in Medicinal Chemistry*, 2004, 39, 223-237; Carrol, S., et al., *Infectious Disorders-Drug Targets*, 2006, 6, 17-29. The potential for the emergence of resistant HCV strains and the need to identify agents with broad genotype coverage supports the need for continuing efforts to identify novel and more effective nucleosides as HCV NS5B inhibitors.

Nucleoside inhibitors of NS5B polymerase can act either as a non-natural substrate that results in chain termination or as a competitive inhibitor which competes with nucleotide binding to the polymerase. To function as a chain terminator the nucleoside analog must be taken up by the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. Unfortunately, this limits the direct evaluation of nucleosides as inhibitors of HCV replication to cell-based assays capable of in situ phosphorylation.

In some cases, the biological activity of a nucleoside is hampered by its poor substrate characteristics for one or more of the kinases needed to convert it to the active triphosphate form. Formation of the monophosphate by a nucleoside kinase is generally viewed as the rate limiting step of the three phosphorylation events. To circumvent the need for the initial phosphorylation step in the metabolism of a nucleoside to the active triphosphate analog, the preparation of stable phosphate prodrugs has been reported. Nucleoside phosphoramidate prodrugs have been shown to be precursors of the active nucleoside triphosphate and to inhibit viral replication when administered to viral infected whole cells (McGuigan, C., et al., *J. Med. Chem.*, 1996, 39, 1748-1753; Valette, G., et al., *J. Med. Chem.*, 1996, 39, 1981-1990; Balzarini, J., et al., *Proc. National Acad Sci USA*, 1996, 93, 7295-7299; Siddiqui, A. Q., et al., *J. Med. Chem.*, 1999, 42, 4122-4128; Eisenberg, E. J., et al., *Nucleosides, Nucleosides and Nucleic Acids.* 2001, 20, 1091-1098; Lee, W. A., et al., *Antimicrobial Agents and Chemotherapy*, 2005, 49, 1898); US 2006/0241064; and WO 2007/095269.

Also limiting the utility of nucleosides as viable therapeutic agents is their sometimes poor physicochemical and pharmacokinetic properties. These poor properties can limit the intestinal absorption of an agent and limit uptake into the target tissue or cell. To improve on their properties prodrugs of nucleosides have been employed. It has been demonstrated that preparation of nucleoside phosphoramidates improves the systemic absorption of a nucleoside and furthermore, the phosphoramidate moiety of these "pronucleotides" is masked with neutral lipophilic groups to obtain a suitable partition coefficient to optimize uptake and transport into the cell dramatically enhancing the intracellular concentration of the nucleoside monophosphate analog relative to administering the parent nucleoside alone. Enzyme-mediated hydrolysis of the phosphate ester moiety produces a nucleoside monophosphate wherein the rate limiting initial phosphorylation is unnecessary.

SUMMARY OF THE INVENTION

The present invention is directed toward novel phosphoramidate prodrugs of nucleoside derivatives for the treatment of viral infections in mammals, which is a compound, its stereoisomers, salts (acid or basic addition salts), hydrates, solvates, or crystalline forms thereof, represented by the following structure:

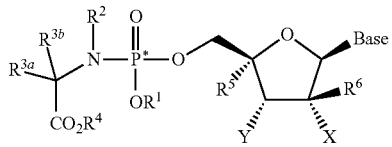

wherein (a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —N(R$^{1'}$)$_2$, $C_{1-6}$ acylamino, —NHSO$_2$C$_{1-6}$ alkyl, —SO$_2$N(R$^{1'}$)$_2$, COR$^{1''}$, and —SO$_2$C$_{1-6}$ alkyl; (R$^{1'}$ is independently hydrogen or alkyl, which includes, but is not limited to, $C_{1-20}$ alkyl, $C_{1-10}$ alkyl, or $C_{1-6}$ alkyl, R$^{1''}$ is —OR' or —N(R$^{1'}$)$_2$);

(b) $R^2$ is hydrogen, $C_{1-10}$ alkyl, $R^{3a}$ or $R^{3b}$ and $R^2$ together are $(CH_2)_n$ so as to form a cyclic ring that includes the adjoining N and C atoms, $C(O)CR^{3a}R^{3b}NHR^1$, where n is 2 to 4 and $R^1$, $R^{3a}$, and $R^{3b}$;

(c) $R^{3a}$ and $R^{3b}$ are (i) independently selected from hydrogen, $C_{1-10}$ alkyl, cycloalkyl, —(CH$_2$)$_c$(NR$^{3'}$)$_2$, $C_{1-6}$ hydroxyalkyl, —CH$_2$SH, —(CH$_2$)$_2$S(O)$_d$Me, —(CH$_2$)$_3$NHC(=NH)NH$_2$, (1H-indol-3-yl)methyl, (1H-imidazol-4-yl)methyl, —(CH$_2$)$_c$COR$^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_r$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where R$^{3'}$ is independently hydrogen or $C_{1-4}$ alkyl and R$^{3''}$ is —OR' or —N(R$^{3'}$)$_2$); (vi) $R^{3a}$ is H and $R^{3b}$ is H, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl; or (viii) $R^{3a}$ is CH$_3$, —CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and $R^{3b}$ is H, where R$^{3'}$ is independently hydrogen or alkyl, which includes, but is not limited to, $C_{1-20}$ alkyl, $C_{1-10}$ alkyl, or $C_{1-6}$ alkyl, R$^{3''}$ is —OR' or —N(R$^{3'}$)$_2$);

(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —(CH$_2$)$_p$OH, where p is 1-6, including hydroxylmethyl (CH$_2$OH), CH$_2$F, N$_3$, CH$_2$CN, CH$_2$NH$_2$, CH$_2$NHCH$_3$, CH$_2$N(CH$_3$)$_2$, alkyne (optionally substituted), or halogen, including. F, Cl, Br, or I, with the provisos that when X is OH, base is cytosine and $R^6$ is H, $R^5$ cannot be N$_3$ and when X is OH, $R^6$ is CH$_3$ or CH$_2$F and B is a purine base, $R^5$ cannot be H;

(f) $R^6$ is H, CH$_3$, CH$_2$F, CHF$_2$, CF$_3$, F, or CN;

(g) X is H, OH, F, OMe, halogen, NH$_2$, or N$_3$;

(h) Y is OH, H, $C_{1-4}$ alkyl, $C_{2-4}$ alkenyl, $C_{2-4}$ alkynyl, vinyl, N$_3$, CN, Cl, Br, F, I, NO$_2$, OC(O)O(C$_{1-4}$ alkyl), OC(O)O(C$_{1-4}$ alkyl), OC(O)O(C$_{2-4}$ alkynyl), OC(O)O(C$_{2-4}$ alkenyl), OC$_{1-10}$ haloalkyl, O(aminoacyl), O(C$_{1-10}$ acyl), O(C$_{1-4}$ alkyl), O(C$_{2-4}$ alkenyl), S(C$_{1-4}$ acyl), S(C$_{1-4}$ alkyl), S(C$_{2-4}$ alkynyl), S(C$_{2-4}$ alkenyl), SO(C$_{1-4}$ acyl), SO(C$_{1-4}$ alkyl), SO(C$_{2-4}$ alkynyl), SO(C$_{2-4}$ alkenyl), SO$_2$(C$_{1-4}$ acyl), SO$_2$(C$_{1-4}$ alkyl), SO$_2$(C$_{2-4}$ alkynyl), SO$_2$(C$_{2-4}$ alkenyl), OS(O)$_2$(C$_{1-4}$ acyl), OS(O)$_2$(C$_{1-4}$ alkyl), OS(O)$_2$(C$_{2-4}$ alkenyl), NH$_2$, NH(C$_{1-4}$ alkyl), NH(C$_{2-4}$ alkenyl), NH(C$_{2-4}$ alkynyl), NH(C$_{1-4}$ acyl), N(C$_{1-4}$ alkyl)$_2$, N(C$_{1-18}$ acyl)$_2$, wherein alkyl, alkynyl, alkenyl and vinyl are optionally substituted by N$_3$, CN, one to three halogen (Cl, Br, F, I), NO$_2$, C(O)O(C$_{1-4}$ alkyl), C(O)O(C$_{1-4}$ alkyl), C(O)O(C$_{2-4}$ alkynyl), C(O)O(C$_{2-4}$ alkenyl), O(C$_{1-4}$ acyl), O(C$_{1-4}$ alkyl), O(C$_{2-4}$ alkenyl), S(C$_{1-4}$ acyl), S(C$_{1-4}$ alkyl), S(C$_{2-4}$ alkynyl), S(C$_{2-4}$ alkenyl), SO(C$_{1-4}$ acyl), SO(C$_{1-4}$ alkyl), SO(C$_{2-4}$ alkynyl), SO(C$_{2-4}$ alkenyl), SO$_2$(C$_{1-4}$ acyl), SO$_2$(C$_{1-4}$ alkyl), SO$_2$(C$_{2-4}$ alkynyl), SO$_2$(C$_{2-4}$ alkenyl), OS(O)$_2$(C$_{1-4}$ acyl), OS(O)$_2$(C$_{1-4}$ alkyl), OS(O)$_2$(C$_{2-4}$ alkenyl), NH$_2$, NH(C$_{1-4}$ alkyl), NH(C$_{2-4}$ alkenyl), NH(C$_{2-4}$ alkynyl), NH(C$_{1-4}$ acyl), alkyl)$_2$, N(C$_{1-4}$ acyl)$_2$;

the base is a naturally occurring or modified purine or pyrimidine base represented by the following structures:

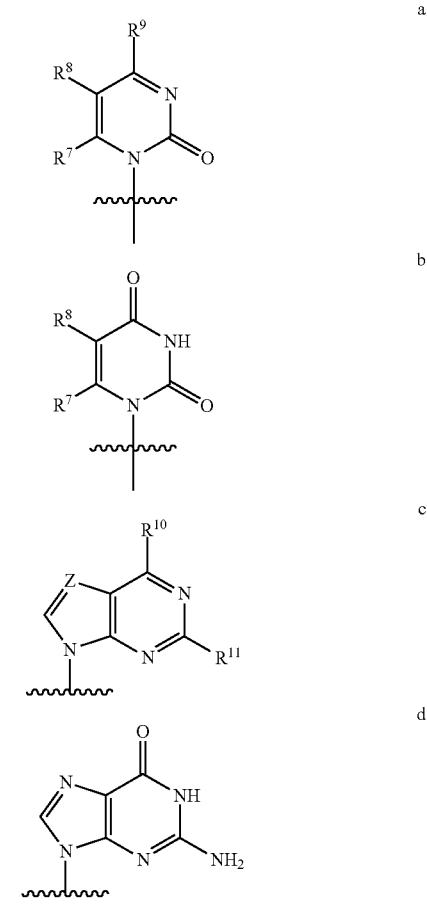

wherein

Z is N or CR$^{12}$;

R$^7$, R$^8$, R$^9$, R$^{10}$, and R$^{11}$ are independently H, F, Cl, Br, I, OH, OR', SH, SR', NH$_2$, NHR', NR'$_2$, lower alkyl of C$_1$-C$_6$, halogenated (F, Cl, Br, I) lower alkyl of C$_1$-C$_6$, lower alkenyl of C$_2$-C$_6$, halogenated (F, Cl, Br, I) lower alkenyl of C$_2$-C$_6$, lower alkynyl of C$_2$-C$_6$ such as C≡CH, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH=CHCO$_2$H, or CH=CHCO$_2$R', wherein R' is an optionally substituted alkyl, which includes, but is not limited to, an optionally substituted C$_{1-20}$ alkyl, an optionally substituted C$_{1-10}$ alkyl, an optionally substituted lower alkyl; an optionally substituted cycloalkyl; an optionally substituted alkynyl of C$_2$-C$_6$, an optionally substituted lower alkenyl of C$_2$-C$_6$, or optionally substituted acyl, which includes but is not limited to C(O) alkyl, C(O)(C$_{1-20}$ alkyl), C(O)(C$_{1-10}$ alkyl), or C(O)(lower alkyl) or alternatively, in the instance of NR'$_2$, each R' comprise at least one C atom that are joined to form a heterocycle comprising at least two carbon atoms; and R$^{12}$ is H, halogen (including F, Cl, Br, I), OH, OR', SH, SR', NH$_2$, NHR', NR'$_2$, NO$_2$ lower alkyl of C$_1$-C$_6$, halogenated (F, Cl, Br, I) lower alkyl of C$_1$-C$_6$, lower alkenyl of C$_2$-C$_6$, halogenated (F, Cl, Br, I) lower alkenyl of C$_2$-C$_6$, lower alkynyl of C$_2$-C$_6$, halogenated (F, Cl, Br, I) lower alkynyl of C$_2$-C$_6$, lower alkoxy of C$_1$-C$_6$, halogenated (F, Cl, Br, I) lower alkoxy of C$_1$-C$_6$, CO$_2$H, CO$_2$R', CONH$_2$, CONHR', CONR'$_2$, CH=CHCO$_2$H, or CH=CHCO$_2$R'; with the proviso that when base is represented by the structure c with R$^{11}$ being hydrogen, R$^{12}$ is not a: (i) —C≡C—H, (ii) —C=CH$_2$, or (iii) —NO$_2$.

DEFINITIONS

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the first definition provided in the Summary of the Invention.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "independently" is used herein to indicate that a variable is applied in any one instance without regard to the presence or absence of a variable having that same or a different definition within the same compound. Thus, in a compound in which R appears twice and is defined as "independently carbon or nitrogen", both R's can be carbon, both R's can be nitrogen, or one R' can be carbon and the other nitrogen.

The term "alkenyl" refers to an unsubstituted hydrocarbon chain radical having from 2 to 10 carbon atoms having one or two olefinic double bonds, preferably one olefinic double bond. The term "C$_{2-N}$ alkenyl" refers to an alkenyl comprising 2 to N carbon atoms, where N is an integer having the following values: 3, 4, 5, 6, 7, 8, 9, or 10. The term "C$_{2-10}$ alkenyl" refers to an alkenyl comprising 2 to 10 carbon atoms. The term "C$_{2-4}$ alkenyl" refers to an alkenyl comprising 2 to 4 carbon atoms. Examples include, but are not limited to, vinyl, 1-propenyl, 2-propenyl (allyl) or 2-butenyl (crotyl).

The term "halogenated alkenyl" refers to an alkenyl comprising at least one of F, Cl, Br, and I.

The term "alkyl" refers to an unbranded or branched chain, saturated, monovalent hydrocarbon residue containing 1 to 30 carbon atoms. The term "C$_{1-M}$ alkyl" refers to an alkyl comprising 1 to M carbon atoms, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. The term "C$_{1-4}$ alkyl" refers to an alkyl containing 1 to 4 carbon atoms. The term "lower alkyl" denotes a straight or branched chain hydrocarbon residue comprising 1 to 6 carbon atoms. "C$_{1-20}$ alkyl" as used herein refers to an alkyl comprising 1 to 20 carbon atoms. "C$_{1-10}$ alkyl" as used herein refers to an alkyl comprising 1 to 10 carbons. Examples of alkyl groups include, but are not limited to, lower alkyl groups include methyl, ethyl, propyl, i-propyl, n-butyl, i-butyl, i-butyl or pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

The term "cycloalkyl" refers to an unsubstituted or substituted carbocycle, in which the carbocycle contains 3 to 10 carbon atoms; preferably 3 to 8 carbon atoms; more preferably 3 to 6 carbon atoms (i.e., lower cycloalkyls). Examples of cycloalkyl groups include, but are not limited to, cyclopropyl, 2-methyl-cyclopropyl, cyclobutyl, cyclopentyl, and cyclohexyl.

The term "cycloalkyl alkyl" refers to an additionally unsubstituted or substituted alkyl substituted by a lower cycloalkyl. Examples of cycloalkyl alkyls include, but are not limited to, any one of methyl, ethyl, propyl, i-propyl, n-butyl, i-butyl, t-butyl or pentyl, isopentyl, neopentyl, hexyl, heptyl, and octyl that is substituted with cyclopropyl, 2-methyl-cyclopropyl, cyclobutyl, cyclopentyl, and cyclohexyl.

The term "cycloheteroalkyl" refers to an unsubstituted or substituted heterocycle, in which the heterocycle contains 2 to 9 carbon atoms; preferably 2 to 7 carbon atoms; more preferably 2 to 5 carbon atoms. Examples of cycloheteroalkyls include, but are not limited to, aziridin-2-yl, N—C$_{1-3}$-alkyl-aziridin-2-yl, azetidinyl, N—C$_{1-3}$-alkyl-azetidin-m'-yl, pyrrolidin-m'-yl, N—C$_{1-3}$-alkyl-pyrrolidin-m'-yl, piperidin-m'-yl, and N—C$_{1-3}$-alkyl-piperidin-m'-yl, where m' is 2, 3, or 4 depending on the cycloheteroalkyl. Specific examples of N—C$_{1-3}$-alkyl-cycloheteroalkyls include, but are not limited to, N-methyl-aziridin-2-yl, N-methyl-azetidin-3-yl, N-methyl-pyrrolidin-3-yl, N-methyl-pyrrolidin-4-yl, N-methyl-piperidin-2-yl, N-methyl-piperidin-3-yl, and N-methyl-piperidin-4-yl. In the instance of R$^4$, the point of attachment between the cycloheteroalkyl ring carbon and the oxygen occurs at any one of m'.

The term "heterocycle" refers to an unsubstituted or substituted heterocycle containing carbon, hydrogen, and at least one of N, O, and S, where the C and N can be trivalent or tetravalent, i.e., sp$^2$- or sp$^3$-hybridized. Examples of heterocycles include, but are not limited to, aziridine, azetidine, pyrrolidine, piperidine, imidazole, oxazole, piperazine, etc. In the instance of piperazine, as related to R$^{10}$ for NR'$_2$, the corresponding opposite nitrogen atom of the piperazinyl is substituted by a lower alkyl represented by the following structure:

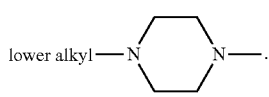

Preferably, the opposite nitrogen of the piperazinyl is substituted by a methyl group.

The term "halogenated alkyl" (or "haloalkyl") refers to an unbranched or branched chain alkyl comprising at least one of F, Cl, Br, and I. The term "$C_{1-M}$ haloalkyl" refers to an alkyl comprising 1 to M carbon atoms that comprises at least one of F, Cl, Br, and I, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. "$C_{1-3}$ haloalkyl" refers to a haloalkyl comprising 1 to 3 carbons and at least one of F, Cl, Br, and I. The term "halogenated lower alkyl" (or "lower haloalkyl") refers to a haloalkyl comprising 1 to 6 carbon atoms and at least one of F, Cl, Br, and I. Examples include, but are not limited to, fluoromethyl, chloromethyl, bromomethyl, iodomethyl, difluoromethyl, dichloromethyl, dibromomethyl, diiodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-difluoroethyl, 2,2-dichloroethyl, 2,2-dibromomethyl, 2-2-diiodomethyl, 3-fluoropropyl, 3-chloropropyl, 3-bromopropyl, 2,2,2-trifluoroethyl or 1,1,2,2,2-pentafluoroethyl.

The term "alkynyl" refers to an unbranched or branched hydrocarbon chain radical having from 2 to 10 carbon atoms, preferably 2 to 5 carbon atoms, and having one triple bond. The term "$C_{2-N}$ alkynyl" refers to an alkynyl comprising 2 to N carbon atoms, where N is an integer having the following values: 3, 4, 5, 6, 7, 8, 9, or 10. The term "$C_{2-4}$ alkynyl" refers to an alkynyl comprising 2 to 4 carbon atoms. The term "$C_{2-10}$ alkynyl" refers to an alkynyl comprising 2 to 10 carbons. Examples include, but are limited to, ethynyl, 1-propynyl, 2-propynyl, 1-butynyl, 2-butynyl or 3-butynyl.

The term "halogenated alkynyl" refers to an unbranched or branched hydrocarbon chain radical having from 2 to 10 carbon atoms, preferably 2 to 5 carbon atoms, and having one triple bond and at least one of F, Cl, Br, and I.

The term "cycloalkyl" refers to a saturated carbocyclic ring comprising 3 to 8 carbon atoms, i.e. cyclopropyl, cyclobutyl, cyclopentyl, cyclohexyl, cycloheptyl or cyclooctyl. The term "$C_{3-7}$ cycloalkyl" as used herein refers to a cycloalkyl comprising 3 to 7 carbons in the carbocyclic ring.

The term "alkoxy" refers to an —O-alkyl group or an —O-cycloalkyl group, wherein alkyl and cycloalkyl are as defined above. Examples of —O-alkyl groups include, but are not limited to, methoxy, ethoxy, n-propyloxy, i-propyloxy, n-butyloxy, i-butyloxy, t-butyloxy. "Lower alkoxy" as used herein denotes an alkoxy group with a "lower alkyl" group as previously defined. "$C_{1-10}$ alkoxy" refers to an —O-alkyl wherein alkyl is $C_{1-10}$. Examples of —O-cycloalkyl groups include, but are not limited to, —O-c-propyl, —O-c-butyl, —O-c-pentyl, and —O-c-hexyl.

The term "halogenated alkoxy" refers to an —O-alkyl group in which the alkyl group comprises at least one of F, Cl, Br, and I.

The term "halogenated lower alkoxy" refers to an —O-(lower alkyl) group in which the lower alkyl group comprises at least one of F, Cl, Br, and I.

The term "amino acid" includes naturally occurring and synthetic α, β γ or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a preferred embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isolecinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the esters of α, β γ or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations.

The term "aminoacyl" includes N,N-unsubstituted, N,N-monosubstituted, and N,N-disubstituted derivatives of naturally occurring and synthetic α, β γ or δ amino acyls, where the amino acyls are derived from amino acids. The amino-nitrogen can be substituted or unsubstituted. When the amino-nitrogen is substituted, the nitrogen is either mono- or di-substituted, where the substituent bound to the amino-nitrogen is a lower alkyl or an alkaryl. In the instance of its use for Y, the expression "O(aminoacyl)" is used. It is understood that the C3' carbon of the ribose is bound to the oxygen "O", which is then bound to the carbonyl carbon of the aminoacyl.

The terms "alkylamino" or "arylamino" refer to an amino group that has one or two alkyl or aryl substituents, respectively.

The term "protected," as used herein and unless otherwise defined, refers to a group that is added to an oxygen, nitrogen, or phosphorus atom to prevent its further reaction or for other purposes. A wide variety of oxygen and nitrogen protecting groups are known to those skilled in the art of organic synthesis. Non-limiting examples include: C(O)-alkyl, C(O)Ph, C(O)aryl, $CH_3$, $CH_2$-alkyl, $CH_2$-alkenyl, $CH_2$Ph, $CH_2$-aryl, $CH_2$O-alkyl, $CH_2$O-aryl, $SO_2$-alkyl, $SO_2$-aryl, tert-butyldimethylsilyl, tert-butyldiphenylsilyl, and 1,3-(1,1,3,3-tetraisopropyldisiloxanylidene).

The term "aryl," as used herein, and unless otherwise specified, refers to substituted or unsubstituted phenyl (Ph), biphenyl, or naphthyl, preferably the term aryl refers to substituted or unsubstituted phenyl. The aryl group can be substituted with one or more moieties selected from among hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The terms "alkaryl" or "alkylaryl" refer to an alkyl group with an aryl substituent, such as benzyl. The terms "aralkyl" or "arylalkyl" refer to an aryl group with an alkyl substituent.

The term "di(lower alkylamino-lower alkyl" refers to a lower alkyl substituted by an amino group that is itself substituted by two lower alkyl groups. Examples include, but are not limited to, $(CH_3)_2NCH_2$, $(CH_3)_2NCH_2CH_2$, $(CH_3)_2NCH_2CH_2CH_2$, etc. The examples above show lower alkyls substituted at the terminus carbon atom with an N,N-dimethyl-amino substituent. These are intended as examples only and are not intended to limit the meaning of the term "di (lower alkyl)amino-lower alkyl" so as to require the same. It is contemplated that the lower alkyl chain can be substituted with an N,N-di(lower alkyl)-amino at any point along the chain, e.g., CH₃CH(N-(lower alkyl)₂)CH₂CH₂.

The term "halo," as used herein, includes chloro, bromo, iodo and fluoro.

The term "acyl" refers to a substituent containing a carbonyl moiety and a non-carbonyl moiety. The carbonyl moiety contains a double-bond between the carbonyl carbon and a heteroatom, where the heteroatom is selected from among O, N and S. When the heteroatom is N, the N is substituted by a lower alkyl. The non-carbonyl moiety is selected from straight, branched, and cyclic alkyl, which includes, but is not limited to, a straight, branched, or cyclic $C_{1-20}$ alkyl, $C_{1-10}$ alkyl, or lower alkyl; alkoxyalkyl, including methoxymethyl; aralkyl, including benzyl; aryloxyalkyl, such as phenoxymethyl; or aryl, including phenyl optionally substituted with halogen (F, Cl, Br, I), hydroxyl, $C_1$ to $C_4$ alkyl, or $C_1$ to $C_4$ alkoxy, sulfonate esters, such as alkyl or aralkyl sulphonyl, including methanesulfonyl, the mono, di or triphosphate ester, trityl or monomethoxytrityl, substituted benzyl, trialkylsilyl (e.g. dimethyl-t-butylsilyl) or diphenylmethylsilyl. When at least one aryl group is present in the non-carbonyl moiety, it is preferred that the aryl group comprises a phenyl group.

The term "lower acyl" refers to an acyl group in which the non-carbonyl moiety is lower alkyl.

The term "purine" or "pyrimidine" base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-allylaminopurine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-iodopyrimidine, $C^6$-Iodo-pyrimidine, $C^5$—Br-vinyl pyrimidine, $C^6$—Br-vinyl pyrimidine, $C^5$-nitropyrimidine, $C^5$-amino-pyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term "tautomerism" and "tautomers" have their accepted plain meanings.

The term "P*" means that the phosphorous atom is chiral and that it has a corresponding Cahn-Ingold-Prelog designation of "R" or "S" which have their accepted plain meanings. It is contemplated that compounds of the formula I are racemic because the chirality at phosphorous. Applicants contemplate use of the racemate and/or the resolved enantiomers. In some instances, an asterisk does not appear next to the phosphoramidate phosphorous atom. In these instances, it is understood that the phosphorous atom is chiral and that one of ordinary skill understands this to be so unless the substituents bound to the phosphorous exclude the possibility of chirality at phosphorous, such as in P(O)Cl₃.

DETAILED DESCRIPTION OF THE INVENTION

An aspect of the invention is directed to a compound, its salts, hydrates, solvates, crystalline forms, and the like represented by formula I:

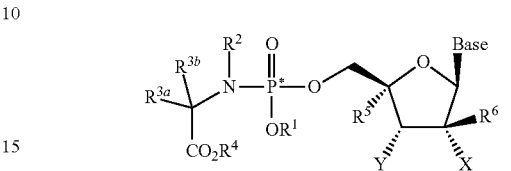

wherein (a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —N($R^{1'}$)₂, $C_{1-6}$ acylamino, —NHSO₂$C_{1-6}$ alkyl, —SO₂N($R^{1'}$)₂, COR$^{1''}$, and —SO₂$C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —N($R^{1'}$)₂);

(b) $R^2$ is hydrogen, $C_{1-10}$ alkyl, $R^{3a}$ or $R^{3b}$ and $R^2$ together are (CH₂)ₙ so as to form a cyclic ring that includes the adjoining N and C atoms, C(O)CR$^{3a}$R$^{3b}$NHR$^1$, where n is 2 to 4 and $R^1$, $R^{3a}$, and $R^{3b}$;

(c) $R^{3a}$ and $R^{3b}$ are (i) independently selected from hydrogen, $C_{1-10}$ alkyl, cycloalkyl, —(CH₂)$_c$(NR$^{3'}$)₂, $C_{1-6}$ hydroxyalkyl, —CH₂SH, —(CH₂)₂S(O)$_d$Me, —(CH₂)₃NHC(=NH)NH₂, (1H-indol-3-yl)methyl, (1H-imidazol-4-yl)methyl, —(CH₂)$_e$COR$^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are (CH₂)$_r$ so as to form a spiro ring; (iv) $R^{3a}$ is hydrogen and $R^{3b}$ and $R^2$ together are (CH₂)ₙ so as to form a cyclic ring that includes the adjoining N and C atoms (v) $R^{3b}$ is hydrogen and $R^{3a}$ and $R^2$ together are (CH₂)ₙ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is —OR' or —N($R^{3'}$)₂); (vi) $R^{3a}$ is H and $R^{3b}$ is H, CH₃, CH₂CH₃, CH(CH₃)₂, CH₂CH(CH₃)₂, CH(CH₃)CH₂CH₃, CH₂Ph, CH₂-indol-3-yl, —CH₂CH₂SCH₃, CH₂CO₂H, CH₂C(O)NH₂, CH₂CH₂COOH, CH₂CH₂C(O)NH₂, CH₂CH₂CH₂CH₂NH₂, —CH₂CH₂CH₂NHC(NH)NH₂, CH₂-imidazol-4-yl, CH₂OH, CH(OH)CH₃, CH₂((4'-OH)-Ph), CH₂SH, or lower cycloalkyl; or (viii) $R^{3a}$ is CH₃, —CH₂CH₃, CH(CH₃)₂, CH₂CH(CH₃)₂, CH(CH₃)CH₂CH₃, CH₂Ph, CH₂-indol-3-yl, —CH₂CH₂SCH₃, CH₂CO₂H, CH₂C(O)NH₂, CH₂CH₂COOH, CH₂CH₂C(O)NH₂, CH₂CH₂CH₂CH₂NH₂, —CH₂CH₂CH₂NHC(NH)NH₂, CH₂-imidazol-4-yl, CH₂OH, CH(OH)CH₃, CH₂((4'-OH)-Ph), CH₂SH, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —N($R^{3'}$)₂);

(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, alkyne (optionally substituted), or halogen, including F, Cl, Br, or I, with the provisos that when X is OH, base is cytosine and $R^6$ is H, $R^5$ cannot be $N_3$ and when X is OH, $R^6$ is $CH_3$ or $CH_2F$ and B is a purine base, $R^5$ cannot be H;

(f) $R^6$ is H, $CH_3$, $CH_2F$, $CHF_2$, $CF_3$, F, or CN;

(g) X is H, OH, F, OMe, halogen, $NH_2$, or $N_3$;

(h) Y is OH, H, $C_{1-4}$ alkyl, $C_{2-4}$ alkenyl, $C_{2-4}$ alkynyl, vinyl, $N_3$, CN, Cl, Br, F, I, $NO_2$, $OC(O)O(C_{1-4}$ alkyl), $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-10}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

the base is a naturally occurring or modified purine or pyrimidine base represented by the following structures:

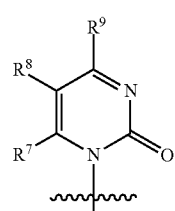

a

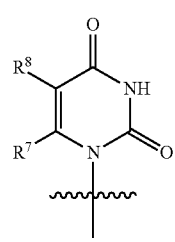

b

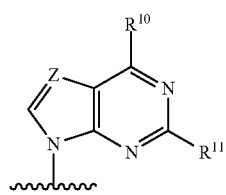

c

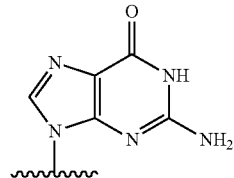

d wherein

Z is N or $CR^{12}$;

$R^7$, $R^8$, $R^9$, $R^{10}$, and $R^{11}$ are independently H, F, Cl, Br, I, OH, OR', SH, SR', $NH_2$, NHR', $NR'_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$, wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an optionally substituted alkynyl of $C_2$-$C_6$, an optionally substituted lower alkenyl of $C_2$-$C_6$, or optionally substituted acyl, which includes but is not limited to C(O) alkyl, $C(O)(C_{1-20}$ alkyl), $C(O)(C_{1-10}$ alkyl), or C(O)(lower alkyl) or alternatively, in the instance of $NR'_2$, each R' comprise at least one C atom that are joined to form a heterocycle comprising at least two carbon atoms; and $R^{12}$ is H, halogen (including F, Cl, Br, I), OH, OR', SH, SR', $NH_2$, NHR', $NR'_2$, $NO_2$ lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$; with the proviso that when base is represented by the structure c with $R^{11}$ being hydrogen, $R^{12}$ is not a: (i) —C≡C—H, (ii) —C=$CH_2$, or (iii) —$NO_2$.

As can be appreciated from the structure represented by formula I above, there are myriad ways to express the several embodiments and aspects of each embodiment of the present invention. As seen below, the inventors have disclosed certain embodiments directed to the compound of formula I, each having several aspects, based on the identity of the modified purine or pyrimidine base. This is not intended to be an explicit or implicit admission that the three embodiments are independent or distinct nor should it be interpreted as such. Rather, it is intended to convey information so that the full breadth of the present invention can be understood. Furthermore, the following embodiments, and aspects thereof, are not meant to be limiting on the full breadth of the invention as recited by the structure of formula I.

A first embodiment of the invention is directed to a compound represented by formula I-1:

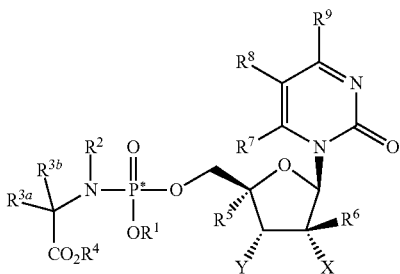

I-1 wherein (a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —$N(R^{1'})_2$, $C_{1-6}$ acylamino, —$NHSO_2C_{1-6}$ alkyl, —$SO_2N(R^{1'})_2$, $COR^{1''}$, and —$SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —$N(R^{1'})_2$);

(b) $R^2$ is hydrogen, $C_{1-10}$ alkyl, $R^{3a}$ or $R^{3b}$ and $R^2$ together are $(CH_2)_n$ so as to form a cyclic ring that includes the adjoining N and C atoms, $C(O)CR^{3a}R^{3b}NHR^1$, where n is 2 to 4 and $R^1$, $R^{3a}$, and $R^{3b}$;

(c) $R^{3a}$ and $R^{3b}$ are (i) independently selected from hydrogen, $C_{1-10}$ alkyl, cycloalkyl, —$(CH_2)_c(NR^{3'})_2$, $C_{1-6}$ hydroxyalkyl, —$CH_2SH$, —$(CH_2)_2S(O)_dMe$, —$(CH_2)_3NHC(=NH)NH_2$, (1H-indol-3-yl)methyl, (1H-imidazol-4-yl)methyl, —$(CH_2)COR^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_r$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is —OR' or —$N(R^{3'})_2$; (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, —$CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —$N(R^{3'})_2$);

(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, di(lower alkyl)-amino, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, alkyne (optionally substituted), or halogen, including F, Cl, Br, or I, with the provisos that when X is OH, base is cytosine and $R^6$ is H, $R^5$ cannot be $N_3$ and when X is OH, $R^6$ is $CH_3$ or $CH_2F$ and B is a purine base, $R^5$ cannot be H;

(f) $R^6$ is H, $CH_3$, $CH_2F$, $CHF_2$, $CF_3$, F or CN;

(g) X is H, OH, F, OMe, Cl, Br, I, $NH_2$, or $N_3$;

(h) Y is OH, H, $C_{1-4}$ alkyl, $C_{2-4}$ alkenyl, $C_{2-4}$ alkynyl, vinyl, $N_3$, CN, Cl, Br, F, I, $NO_2$, $OC(O)O(C_{1-4}$ alkyl), $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-10}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(i) $R^7$, $R^8$, $R^9$ are independently H, F, Cl, Br, I, OH, OR', SH, SR', $NH_2$, NHR', NR'$_2$, lower alkyl, halogenated (F, Cl, Br, I) lower alkyl, lower alkenyl of $C_2$-$C_6$, $CO_2H$, $CO_2R'$, $CONH_2$, CONHR', CONR'$_2$, wherein R' is a $C_{1-20}$ alkyl; a $C_{1-20}$ cycloalkyl; a $C_2$-$C_6$ alkenyl, a $C_2$-$C_6$ alkynyl.

A first aspect of the first embodiment is directed to a compound represented by formula I-1 wherein (a) $R^1$ is hydrogen, n-alkyl or aryl, which includes, but is not limited to, phenyl or naphthyl, where phenyl or naphthyl are optionally substituted with at least one of $C_{1-6}$ alkyl, $C_{1-6}$ alkoxy, F, Cl, Br, I, nitro, cyano, $C_{1-6}$ haloalkyl;

(b) $R^2$ is hydrogen or $CH_3$;

(c) $R^{3a}$ and $R^{3b}$ are independently (i) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 3 to 5, n is 2 to 4, and where $R^{3'}$ is independently hydrogen or $C_{1-6}$ alkyl and $R^{3''}$ is —OR' or —$N(R^{3'})_2$; (vi) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, or $CH_2SH$ and $R^{3b}$ is H;

(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl;

(e) $R^5$ is H, CN, $CH_3$, vinyl, $OCH_3$, $OCH_2CH_3$, $CH_2OH$, $CH_2$(halo), such as $CH_2F$, $N_3$, $CH_2CN$, $CH_2N_3$, $CH_2NH_2$, $CH_2NHCH_3$, $CH_2N(CH_3)_2$, halogen, including F, Cl, Br, or I, with the provisos that when X is OH, base is cytosine and $R^6$ is H, $R^5$ cannot be $N_3$;

(f) $R^6$ is H, $CH_3$, $CH_2F$, $CHF_2$, $CF_3$, F, or CN;

(g) X is H, OH, F, OMe, Cl, Br, I, $NH_2$, or $N_3$;

(h) Y is OH, H, $C_{1-4}$ alkyl, vinyl, $N_3$, CN, Cl, Br, F, I, $O(C_{1-6}$ acyl), $O(C_{1-4}$ alkyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl$)_2$, $N(C_{1-18}$ acyl$)_2$, wherein alkyl, alkynyl, alkenyl and vinyl are optionally substituted by $N_3$, CN, one to three halogen (Cl, Br, F, I), $NO_2$, $OC(O)O(C_{1-4}$ alkyl), $OC(O)O(C_{1-4}$ alkyl), $OC(O)O$ $(C_{2-4}$ alkynyl), $OC(O)O(C_{2-4}$ alkenyl), $OC_{1-4}$ haloalkyl, O(aminoacyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl$)_2$, or $N(C_{1-4}$ acyl$)_2$;

(i) $R^7$, $R^8$, $R^9$ are independently H, F, Cl, Br, I, OH, OR', SH, SR', $NH_2$, NHR', $NR'_2$, lower alkyl, halogenated (F, Cl, Br, I) lower alkyl, lower alkenyl of $C_2$-$C_6$, $CO_2H$, $CO_2R'$, $CONH_2$, CONHR', CONR'$_2$, wherein R' is a $C_{1-20}$ alkyl; a $C_{1-20}$ cycloalkyl; a $C_2$-$C_6$, alkenyl, a $C_2$-$C_6$ alkynyl.

A second aspect of the first embodiment is directed to a compound represented by formula I-1
wherein (a) $R^1$ is hydrogen, n-alkyl or a substituted or unsubstituted phenyl, where the substituent of the substituted phenyl is at least one of a $C_{1-3}$ alkyl, a $C_{1-3}$ alkoxy, F, Cl, Br, I, nitro, cyano, and a $C_{1-3}$ haloalkyl;

(b) $R^2$ is hydrogen or $CH_3$;

(c) $R^{3a}$ and $R^{3b}$ are independently (i) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 3 to 5, n is 2 to 4, and where $R^{3'}$ is independently hydrogen or $C_{1-6}$ alkyl and $R^{3''}$ is —OR' or —N($R^{3'}$)$_2$); (vi) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)$-Ph$)$, $CH_2SH$, or lower cycloalkyl; or (viii) $R^{3a}$ is $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)$-Ph$)$, or $CH_2SH$ and $R^{3b}$ is H;

(d) $R^4$ is hydrogen, $CH_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, di(lower alkyl)amino-lower alkyl, or aminoacyl;

(e) $R^5$ is H, CN, $CH_3$, $OCH_3$, $CH_2OH$, $CH_2$(halo), such as $CH_2F$, $N_3$, $CH_2CN$, $CH_2N_3$, $CH_2NH_2$, $CH_2NHCH_3$, $CH_2N(CH_3)_2$, halogen, including F, Cl, Br, or I, with the provisos that when X is OH, base is cytosine and $R^6$ is H, $R^5$ cannot be $N_3$;

(f) $R^6$ is H, $CH_3$, $CH_2F$, $CHF_2$, $CF_3$, F, or CN;

(g) X is H, OH, F, $OCH_3$, $NH_2$, or $N_3$;

(h) Y is OH, H, $CH_3$, vinyl, $N_3$, CN, Cl, Br, F, I, $OC(O)CH_3$, $OCH_3$, $NH_2$, $NHCH_3$, NH(vinyl), NH(acetyl), $NH(C(O)CH_3)$, $N(CH_3)_2$, $N(C(O)CH_3)_2$, or O(aminoacyl);

(i) $R^7$ and $R^8$ are independently H, F, Cl, Br, I, OH, $OCH_3$, SH, $SCH_3$, $NH_2$, $NHCH_3$, $N(CH_3)_2$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$; and (j) $R^9$ is selected from among OH, $OCH_3$, SH, $SCH_3$, $NH_2$, $NHCH_3$, $N(CH_3)_2$, OC(O)(C1-20 alkyl), which include but are not limited to $OC(O)(CH_2)_sCH_3$, NHC(O)(C1-20 alkyl), which include but are not limited to $NHC(O)(CH_2)_sCH_3$, and $N(C(O)(CH_2)_s)CH_3)_2$, which include but is not limited to $N(C(O)(CH_2)_sCH_3)_2$, where s is an integer selected from 0, 1, 2, 3, 4, 5, 6, 7, 8, 9, 10, 11, 12, 13, 14, 15, 16, 17, 18, and 19.

A third aspect of the first embodiment is directed to a compound represented by formula I-1
wherein (a) $R^1$ is hydrogen, n-alkyl or a substituted or unsubstituted phenyl, where the substituent of the substituted phenyl is at least one of a $CH_3$, $OCH_3$, F, Cl, Br, I, nitro, cyano, and a $CH_{3-q}X_q$, where X is F, Cl, Br, or and q is 1-3;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)$-Ph$)$, $CH_2SH$, or lower cycloalkyl or $R^{3a}$ is $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)$-Ph$)$, $CH_2SH$, or lower cycloalkyl and $R^{3b}$ is H;

(d) $R^4$ is hydrogen, $CH_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, lower haloalkyl, di(lower alkyl)amino-lower alkyl, or aminoacyl;

(e) $R^5$ is H, CN, $CH_3$, $OCH_3$, $CH_2OH$, $CH_2$(halo), such as $CH_2F$, $N_3$, $CH_2CN$, $CH_2N_3$, $CH_2NH_2$, $CH_2NHCH_3$, $CH_2N(CH_3)_2$, halogen, including F, Cl, Br, or I, with the provisos that when X is OH, base is cytosine and $R^6$ is H, $R^5$ cannot be $N_3$;

(f) $R^6$ is H, $CH_3$, $CH_2F$, $CHF_2$, $CF_3$, F, or CN;

(g) X is H, OH, F, $OCH_3$, $NH_2$, or $N_3$;

(h) Y is OH, H, $CH_3$, vinyl, $N_3$, CN, Cl, Br, F, 1, $OC(O)CH_3$, $OCH_3$, $NH_2$, $NHCH_3$, NH(vinyl), NH(acetyl), $NH(C(O)CH_3)$, $N(CH_3)_2$, $N(C(O)CH_3)_2$, or O(aminoacyl);

(i) $R^7$ and $R^8$ are independently H, F, Cl, Br, I, OH, $OCH_3$, SH, $SCH_3$, $NH_2$, $NHCH_3$, $N(CH_3)_2$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$, wherein R' is a $C_{1-20}$ alkyl; a $C_{1-20}$ cycloalkyl; a $C_2$-$C_6$ alkenyl, a $C_2$-$C_6$ alkynyl'; and (j) $R^9$ is selected from among OH, $OCH_3$, SH, $SCH_3$, $NH_2$, $NHCH_3$, $N(CH_3)_2$, OC(O)(C1-20 alkyl), which include but are not limited to $OC(O)(CH_2)_sCH_3$, NHC(O)(C1-20 alkyl), which include but are not limited to $NHC(O)(CH_2)_sCH_3$, and $N(C(O)(CH_2)_sCH_3)_2$, which include but is not limited to $N(C(O)(CH_2)_sCH_3)_2$, where s is an integer selected from 0, 1, 2, 3, 4, 5, 6, 7, 8, 9, 10, 11, 12, 13, 14, 15, 16, 17, 18, and 19.

A fourth aspect of the first embodiment is directed to a compound represented by formula I-2

I-2

[Chemical structure of formula I-2 showing a phosphoramidate nucleoside analog with substituents $R^1$, $R^2$, $R^{3a}$, $R^{3b}$, $R^4$, $R^5$, $R^6$, $R^7$, $R^8$, $R^9$, X, Y, and $CO_2R^4$, $OR^1$ groups]

wherein (a) $R^1$ is hydrogen, methyl, ethyl, n-propyl, i-propyl, or a substituted or unsubstituted phenyl, where the substituent of the substituted phenyl is at least one of a $CH_3$, $OCH_3$, F, Cl, Br, I, nitro, cyano, and a $CH_{3-q}X_q$, where X is F, Cl, Br, or I, and q is 1-3, (b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2(4'-OH)$-Ph), $CH_2SH$, or lower cycloalkyl or $R^{3a}$ is $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)$-Ph), $CH_2SH$, or lower cycloalkyl and $R^{3b}$ is H;

(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkylamino-lower alkyl, aryl, such as phenyl, heteroaryl, such as, pyridinyl, substituted aryl, or substituted heteroaryl;

(e) $R^5$ is H, CN, $CH_3$, $OCH_3$, $CH_2OH$, $CH_2F$, $N_3$, $CH_2CN$, $CH_2N_3$, $CH_2NH_2$, $CH_2NHCH_3$, $CH_2N(CH_3)_2$, halogen, including F, Cl, Br, or I, with the provisos that when X is OH, base is cytosine and $R^6$ is H, $R^5$ cannot be $N_3$;

(f) $R^6$ is H, $CH_3$, $CH_2F$, $CHF_2$, $CF_3$, F, or CN;

(g) X is H, OH, F, $OCH_3$, Cl, Br, I, $NH_2$, or $N_3$;

(h) Y is OH, H, $CH_3$, vinyl, $N_3$, CN, Cl, Br, F, I, $OC(O)CH_3$, $OCH_3$, $NH_2$, $NHCH_3$, NH(vinyl), NH(acetyl), $NH(C(O)CH_3)$, $N(CH_3)_2$, $N(C(O)CH_3)_2$, or O(aminoacyl);

(i) $R^7$ and $R^8$ are independently H, F, Cl, Br, I, OH, $OCH_3$, SH, $SCH_3$, $NH_2$, $NHCH_3$, $N(CH_3)_2$, $CH_3$, $CH_{3-q}X_q$, where X is F, Cl, Br, or I and q is 1 to 3, vinyl, $CO_2H$, $CO_2CH$, $CONH_2$, $CONHCH_3$, or $CON(CH)_2$, wherein R' is a $C_{1-20}$ alkyl; a $C_{1-20}$ cycloalkyl; a $C_2$-$C_6$ alkenyl, a $C_2$-$C_6$ alkynyl; and (j) $R^9$ is selected from among OH, $OCH_3$, SH, $SCH_3$, $NH_2$, $NHCH_3$, $N(CH_3)_2$, $OC(O)$(C1-20 alkyl), which include but are not limited to $OC(O)(CH_2)_sCH_3$, $NHC(O)$(C1-20 alkyl), which include but are not limited to $NHC(O)(CH_2)_sCH_3$, and $N(C(O)(CH_2)_sCH_3)_2$, which include but is not limited to $N(C(O)(CH_2)_sCH_3)_2$, where s is an integer selected from 0, 1, 2, 3, 4, 5, 6, 7, 8, 9, 10, 11, 12, 13, 14, 15, 16, 17, 18, and 19.

A fifth aspect of the first embodiment is directed to a compound represented by formula I-2 wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)$-Ph), $CH_2SH$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, lower haloalkyl, di(lower alkyl)amino-lower alkyl, or aminoacyl;

(e) $R^5$ is H, CN, $CH_3$, $OCH_3$, $CH_2OH$, $CH_2F$, halogen, including F, Cl, Br, or I;

(f) $R^6$ is H, $CH_3$, $CH_2F$, $CHF_2$, $CF_3$, F, or CN;

(g) X is H, OH, F, $OCH_3$, $NH_2$, or $N_3$;

(h) Y is OH, H, $CH_3$, vinyl, $N_3$, CN, Cl, Br, F, I, $OC(O)CH_3$, $OCH_3$, or O(aminoacyl);

(i) $R^7$ and $R^8$ are independently H, F, Cl, Br, I, OH, $OCH_3$, SH, $SCH_3$, $NH_2$, $NHCH_3$, $N(CH_3)_2$, $CH_3$, $CH_{3-q}X_q$, where X is F, Cl, Br, or I and q is 1 to 3, vinyl, $CO_2H$, $CO_2CH_3$, $CONH_2$, $CONHCH_3$, or $CON(CH_3)_2$, wherein R' is a $C_{1-20}$ alkyl; a $C_{1-20}$ cycloalkyl; a $C_2$-$C_6$ alkenyl, a $C_2$-$C_6$ alkynyl; and (j) $R^9$ is selected from among OH, $OCH_3$, SH, $SCH_3$, $NH_2$, $NHCH_3$, $N(CH_3)_2$, $OC(O)(C_{1-20}$ alkyl), which include but are not limited to $OC(O)(CH_2)_sCH_3$, $NHC(O)(C_{1-20}$ alkyl), which include but are not limited to $NHC(O)(CH_2)_sCH_3$, and $N(C(O)(CH_2)_sCH_3)_2$, which include but is not limited to $N(C(O)(CH_2)_sCH_3)_2$, where s is an integer selected from 0, 1, 2, 3, 4, 5, 6, 7, 8, 9, 10, 11, 12, 13, 14, 15, 16, 17, 18, and 19.

A sixth aspect of the first embodiment is directed to a compound represented by formula I-2 wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkyl)amino-lower alkyl, aryl, such as phenyl, heteroaryl, such as, pyridinyl, substituted aryl, or substituted heteroaryl;

(e) $R^5$ is H, OMe, CN, $CH_2F$, F, Cl, Br, or I;

(f) $R^6$ is H, $CH_3$, $CH_2F$, $CHF_2$, $CF_3$, or F;

(g) X is H, OH, F, $OCH_3$, F, Cl, Br, I, or $N_3$;

(h) Y is H, OH, $CH_3$, F, Cl, Br, I, or $N_3$, $OCH_3$, $OC(O)CH_3$, or O(aminoacyl);

(i) $R^7$ and $R^8$ are independently H, F, Br, $SCH_3$, $CH_3$, $CH_{3-q}X_q$, where X is F, Cl, Br, or I and q is 1 to 3, vinyl, $CO_2CH_3$, $CONH_2$, $CONHCH_3$, or $CON(CH_3)_2$; and (j) $R^9$ is selected from among OH, $OCH_3$, SH, $SCH_3$, $NH_2$, $NHCH_3$, $N(CH_3)_2$, $OC(O)(C_{1-20}$ alkyl), which include but are not limited to $OC(O)(CH_2)_sCH_3$, $NHC(O)(C_{1-20}$ alkyl), which include but are not limited to $NHC(O)(CH_2)_sCH_3$, and $N(C(O)(CH_2)_sCH_3)_2$, which include but is not limited to $N(C(O)(CH_2)_sCH_3)_2$, where s is an integer selected from 0, 1, 2, 3, 4, 5, 6, 7, 8, 9, 10, 11, 12, 13, 14, 15, 16, 17, 18, and 19.

A seventh aspect of the first embodiment is directed to a compound represented by formula I-2 wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H;

(f) $R^6$ is H, $CH_3$, $CH_2F$, $CHF_2$, $CF_3$, or F;

(g) X is H, OH, $OCH_3$, F, or $N_3$;

(h) Y is OH, $OCH_3$, $OC(O)CH_3$, or O(aminoacyl);

(i) $R^7$ and $R^8$ are independently H, F, Br, $SCH_3$, $CH_3$, $CH_{3-q}X_q$, where X is F, Cl, Br, or I and q is 1 to 3, vinyl, $CO_2CH_3$, $CONH_2$, $CONHCH_3$, or $CON(CH_3)_2$; and (j) $R^9$ is selected from among OH, $OCH_3$, $NH_2$, $NHCH_3$, $N(CH_3)_2$, $OC(O)(C_{1-20}$ alkyl), which include but are not limited to $OC(O)(CH_2)_sCH_3$, $NHC(O)(C_{1-20}$ alkyl), which include but are not limited to $NHC(O)(CH_2)_sCH_3$, and $N(C(O)(CH_2)_sCH_3)_2$, which include but are not limited to $N(C(O)(CH_2)_sCH_3)_2$, where s is an integer selected from among 0, 1, 2, 3, 4, 5, 6, 7, 8, 9, 10, 11, 12, 13, 14, 15, 16, 17, 18, and 19.

An eighth aspect of the first embodiment is directed to a compound represented by formula I-2 wherein (a) $R^1$ is hydrogen, methyl, phenyl, p-bromo-phenyl, p-chloro-phenyl, p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^nBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;

(e) $R^5$ is H;

(f) $R^6$ is H, $CH_3$, $CH_2F$, $CHF_2$, $CF_3$, or F;

(g) X is H, OH, $OCH_3$, F, or $N_3$;

(h) Y is OH, $OCH_3$, $OC(O)CH_3$, or O(aminoacyl);

(i) $R^7$ and $R^8$ are independently H, F, Br, $SCH_3$, $CH_3$, $CH_{3-q}X_q$, where X is F, Cl, Br, or I and q is 1 to 3, vinyl, $CO_2CH_3$, $CONH_2$, $CONHCH_3$, or $CON(CH_3)_2$;

(j) $R^9$ is selected from among OH, $OCH_3$, $NH_2$, $NHCH_3$, $N(CH_3)_2$, $OC(O)(C_{1-20}$ alkyl), which include but are not limited to $OC(O)(CH_2)_sCH_3$, $NHC(O)(C_{1-20}$ alkyl), which include but are not limited to $NHC(O)(CH_2)_sCH_3$, and $N(C(O)(CH_2)_sCH_3)_2$, which include but are not limited to $N(C(O)(CH_2)_sCH_3)_2$, where s is an integer selected from among 0, 1, 2, 3, 4, 5, 6, 7, 8, 9, 10, 11, 12, 13, 14, 15, 16, 17, 18, and 19.

A second embodiment of the invention is directed to a compound represented by formula I in which the base is a structure represented by formula b above, wherein $R^1$, $R^2$, $R^{3a}$, $R^{3b}$, $R^4$, $R^5$, $R^6$, X, Y, $R^7$, and $R^8$ are defined in the Summary of the invention section above.

A first aspect of the second embodiment is directed to a compound represented by formula I-3

I-3

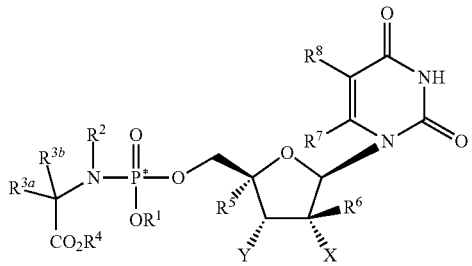

wherein (a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —$N(R^{1'})_2$, $C_{1-6}$ acylamino, —$NHSO_2C_{1-6}$ alkyl, —$SO_2N(R^{1'})_2$, $COR^{1''}$, and —$SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —$N(R^{1'})_2$);

(b) $R^2$ is hydrogen or $CH_3$;

(c) $R^3$ and $R^{3b}$ are (i) independently selected from hydrogen, $C_{1-10}$ alkyl, cycloalkyl, —$(CH_2)_c(NR^{3'})_2$, $C_{1-6}$ hydroxyalkyl, —$CH_2SH$, —$(CH_2)_2S(O)_dMe$, —$(CH_2)_3NHC(=NH)NH_2$, (1H-indol-3-yl)methyl, (1H-imidazol-4-yl)methyl, —$(CH_2)_eCOR^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano, (ii) $R^{3a}$ and $R^{3b}$ both are $C_{1-6}$ alkyl; (iii) $R^3$ and $R^{3b}$ together are $(CH_2)_r$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is —OR' or —$N(R^{3'})_2$); (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, —$CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —$N(R^{3'})_2$);

(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkylamino-lower alkyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, alkyne (optionally substituted), or halogen, including F, Cl, Br, or I, with the provisos that when X is OH, base is cytosine and $R^6$ is H, $R^5$ cannot be $N_3$ and when X is OH, $R^6$ is $CH_3$ or $CH_2F$ and B is a purine base, $R^5$ cannot be H;

(f) $R^6$ is H, $CH_3$, $CH_2F$, $CHF_2$, $CF_3$, F, or CN;

(g) X is H, OH, F, OH, OMe, Cl, Br, I, $NH_2$, or $N_3$;

(h) Y is OH, H, $C_{1-4}$ alkyl, $C_{2-4}$ alkenyl, $C_{2-4}$ alkynyl, vinyl, $N_3$, CN, Cl, Br, F, I, $NO_2$, $OC(O)O(C_{1-4}$ alkyl), $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-10}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}NH(C_{2-4}$ alkenyl), $NH(C_{2-4}$ alkynyl), $NH(C_{1-4}$ acyl), $N(C_{1-4}$ alkyl)$_2$, or $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, or $N(C_{1-4}$ acyl)$_2$;

(i) $R^7$ and $R^8$ are independently H, F, Cl, Br, I, OH, OR', SH, SR', $NH_2$, NHR', NR'$_2$, lower alkyl, halogenated (F, Cl, Br, I) lower alkyl, lower alkenyl of $C_2$-$C_6$, $CO_2H$, $CO_2R'$, $CONH_2$, CONHR', CONR'$_2$, wherein R' is a $C_{1-20}$ alkyl; a $C_{1-20}$ cycloalkyl; a $C_2$-$C_6$ alkenyl, a $C_2$-$C_6$ alkynyl.

The second aspect of the second embodiment is directed to a compound represented by formula I-3 wherein (a) $R^1$ is hydrogen, n-alkyl or aryl, which includes, but is not limited to, phenyl or naphthyl, where phenyl or naphthyl are optionally substituted with at least one of $C_{1-6}$ alkyl, $C_{1-6}$ alkoxy, F, Cl, Br, I, nitro, cyano, $C_{1-6}$ haloalkyl;

(b) $R^2$ is hydrogen or $CH_3$;

(c) $R^{3a}$ and $R^{3b}$ are independently (i) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 3 to 5, n is 2 to 4, and where $R^{3'}$ is independently hydrogen or $C_{1-6}$ alkyl and $R^{3''}$ is —OR' or —N(R$^{3'}$)$_2$); (vi) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, or $CH_2SH$ and $R^{3b}$ is H;

(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkylamino-lower alkyl, aryl, such as phenyl, heteroaryl, such as, pyridinyl, substituted aryl, or substituted heteroaryl;

(e) $R^5$ is H, CN, $CH_3$, vinyl, $OCH_3$, $OCH_2CH_3$, $CH_2OH$, $CH_2$(halo), such as $CH_2F$, $N_3$, $CH_2CN$, $CH_2N_3$, $CH_2NH_2$, $CH_2NHCH_3$, $CH_2N(CH_3)_2$, halogen, including F, Cl, Br, or I;

(f) $R^6$ is H, $CH_3$, $CH_2F$, $CHF_2$, $CF_3$, F, or CN;

(g) X is H, OH, F, OMe, halogen, $NH_2$, or $N_3$;

(h) Y is OH, H, $C_{1-4}$ alkyl, vinyl, $N_3$, CN, Cl, Br, F, I, $O(C_{1-6}$ acyl), $O(C_{1-4}$ alkyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $OC(O)O(C_{1-4}$ alkyl), $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(i) $R^7$ and $R^8$ are independently H, F, Cl, Br, I, OH, OR', SH, SR', $NH_2$, NHR', NR'$_2$, lower alkyl, halogenated (F, Cl, Br, I) lower alkyl, lower alkenyl of $C_2$-$C_6$, $CO_2H$, $CO_2R'$, $CONH_2$, CONHR', CONR'$_2$, wherein R' is a $C_{1-20}$ alkyl; a $C_{1-20}$ cycloalkyl; a $C_2$-$C_6$ alkenyl, a $C_2$-$C_6$ alkynyl.

The third aspect of the second embodiment is directed to a compound represented by formula I-3 wherein (a) $R^1$ is hydrogen, n-alkyl or a substituted or unsubstituted phenyl, where the substitutent of the substituted phenyl is at least one of a $C_{1-3}$ alkyl, a $C_{1-3}$ alkoxy, F, Cl, Br, I, nitro, cyano, and a $C_{1-3}$ haloalkyl;

(b) $R^2$ is hydrogen, $CH_3$, $R^{3a}$ or $R^{3b}$ and $R^2$ together are $(CH_2)_3$ so as to form a cyclic ring that includes the adjoining N and C atoms, $C(O)CR^{3a}R^{3b}NHR^1$, where n is 2 to 4 and $R^1$, $R^{3a}$, and $R^{3b}$ are as defined herein;

(c) $R^{3a}$ and $R^{3b}$ are independently (i) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 3 to 5, n is 2 to 4, and where $R^{3'}$ is independently hydrogen or $C_{1-6}$ alkyl and $R^{3''}$ is —OR' or —N(R$^{3'}$)$_2$); (vi) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;

(e) $R^5$ is H, CN, $CH_3$, $OCH_3$, $CH_2OH$, $CH_2$(halo), such as $CH_2F$, $N_3$, $CH_2CN$, $CH_2N_3$, $CH_2NH_2$, $CH_2NHCH_3$, $CH_2N(CH_3)_2$, halogen, including F, Cl, Br, or I;

(f) $R^6$ is H, $CH_3$, $CH_2F$, $CHF_2$, $CF_3$, F, or CN;

(g) X is H, OH, F, $OCH_3$, halogen, $NH_2$, or $N_3$ (h) Y is OH, H, $CH_3$, vinyl, $N_3$, CN, Cl, Br, F, I, $OC(O)CH_3$, $OCH_3$, $NH_2$, $NHCH_3$, NH(vinyl), NH(acetyl), $NH(C(O)CH_3)$, $N(CH_3)_2$, $N(C(O)CH_3)_2$;

(i) $R^7$ and $R^8$ are independently H, F, Cl, Br, I, OH, OCH$_3$, SH, SCH$_3$, NH$_2$, NHCH$_3$, N(CH$_3$)$_2$, CH$_3$, CH$_{3-q}$X$_q$, where X is F, Cl, Br, or I and q is 1 to 3, vinyl, CO$_2$H, CO$_2$CH$_3$, CONH$_2$, CONHCH$_3$, or CON(CH$_3$)$_2$.

The fourth aspect of the second embodiment is directed to a compound represented by formula I-3
wherein
(a) $R^1$ is hydrogen, n-alkyl or a substituted or unsubstituted phenyl, where the substitutent of the substituted phenyl is at least one of a CH$_3$, OCH$_3$, F, Cl, Br, I, nitro, cyano, and a CH$_{3-q}$X$_q$, where X is F, Cl, Br, or I, and q is 1-3;
(b) $R^2$ is hydrogen or CH$_3$;
(c) $R^{3a}$ is H and $R^{3b}$ is H, CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl or $R^{3a}$ is CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and $R^{3b}$ is H;
(d) $R^4$ is hydrogen, CH$_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, CN, CH$_3$, OCH$_3$, CH$_2$OH, CH$_2$(halo), such as CH$_2$F, N$_3$, CH$_2$CN, CH$_2$N$_3$, CH$_2$NH$_2$, CH$_2$NHCH$_3$, CH$_2$N(CH$_3$)$_2$, halogen, including F, Cl, Br, or I;
(f) $R^6$ is H, CH$_3$, CH$_2$F, CHF$_2$, CF$_3$, F, or CN;
(g) X is H, OH, F, OCH$_3$, NH$_2$, or N$_3$;
(h) Y is OH, H, CH$_3$, vinyl, N$_3$, CN, Cl, Br, F, I, OC(O)CH$_3$, OCH$_3$, NH$_2$, NHCH$_3$, NH(vinyl), NH(acetyl), NH(C(O)CH$_3$), N(CH$_3$)$_2$, N(C(O)CH$_3$)$_2$;
(i) $R^7$ and $R^8$ are independently H, F, Cl, Br, I, OH, OCH$_3$, SH, SCH$_3$, NH$_2$, NHCH$_3$, N(CH$_3$)$_2$, CH$_3$, CH$_{3-q}$X$_q$, where X is F, Cl, Br, or I and q is 1 to 3, vinyl, CO$_2$H, CO$_2$CH$_3$, CONH$_2$, CONHCH$_3$, or CON(CH$_3$)$_2$, wherein R' is a C$_{1-20}$ alkyl; a C$_{1-20}$ cycloalkyl; a C$_2$-C$_6$ alkenyl, a C$_2$-C$_6$ alkynyl.

The fifth aspect of the second embodiment is directed to a compound represented by formula I-4

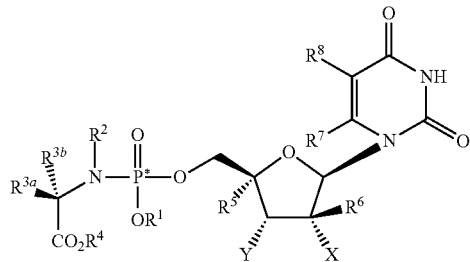

I-4 wherein
(a) $R^1$ is hydrogen, methyl, ethyl, n-propyl, i-propyl, or a substituted or unsubstituted phenyl, where the substitutent of the substituted phenyl is at least one of a CH$_3$, OCH$_3$, F, Cl, Br, I, nitro, cyano, and a CH$_{3-q}$X$_q$, where X is F, Cl, Br, or I, and q is 1-3;
(b) $R^2$ is hydrogen or CH$_3$;

(c) $R^{3a}$ is H and $R^{3b}$ is H, CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl or $R^{3a}$ is CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and $R^{3b}$ is H;
(d) $R^4$ is hydrogen, CH$_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, CN, CH$_3$, OCH$_3$, CH$_2$OH, CH$_2$F, N$_3$, CH$_3$CN, CH$_2$N$_3$, CH$_2$NH$_2$, CH$_2$NHCH$_3$, CH$_2$N(CH$_3$)$_2$, halogen, including F, Cl, Br, or I;
(f) $R^6$ is H, CH$_3$, CH$_2$F, CHF$_2$, CF$_3$, F, or CN;
(g) X is H, OH, F, OCH$_3$, Cl, Br, I, NH$_2$, or N$_3$;
(h) Y is OH, H, CH$_3$, vinyl, N$_3$, CN, Cl, Br, F, I, OC(O)CH$_3$, OCH$_3$, NH$_2$, NHCH$_3$, NH(vinyl), NH(acetyl), NH(C(O)CH$_3$), N(CH$_3$)$_2$, N(C(O)CH$_3$)$_2$;
(i) $R^7$ and $R^8$ are independently H, F, Cl, Br, I, OH, OCH$_3$, SH, SCH$_3$, NH$_2$, NHCH$_3$, N(CH$_3$)$_2$, CH$_3$, CH$_{3-q}$X$_q$, where X is F, Cl, Br, or I and q is 1 to 3, vinyl, CO$_2$H, CO$_2$CH$_3$, CONH$_2$, CONHCH$_3$, or CON(CH$_3$)$_2$, wherein R' is a C$_{1-20}$ alkyl; a C$_{1-20}$ cycloalkyl; a C$_2$-C$_6$ alkenyl, a C$_2$-C$_6$ alkynyl, The sixth aspect of the second embodiment is directed to a compound represented by formula I-4
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen or CH$_3$;
(c) $R^{3a}$ is H and $R^{3b}$ is H, CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl;
(d) $R^4$ is hydrogen, CH$_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower hatoalkyl, or di(lower alkylamino-lower alkyl;
(e) $R^5$ is H, CN, CH$_3$, OCH$_3$, CH$_2$OH, CH$_2$F, halogen, including. F, Cl, Br, or I;
(f) $R^6$ is H, CH$_3$, CH$_2$F, CHF$_2$, CF$_3$, F, or CN;
(g) X is H, OH, F, OCH$_3$, NH$_2$, or N$_3$;
(h) Y is OH, H, CH$_3$, vinyl, NH$_2$, N$_3$, CN, Cl, Br, F, I, OC(O)CH$_3$, OCH$_3$;
(i) $R^7$ and $R^8$ are independently H, F, Cl, Br, I, OH, OCH$_3$, SH, SCH$_3$, NH$_2$, NHCH$_3$, N(CH$_3$)$_2$, CH$_3$, CH$_{3-q}$X$_q$, where X is F, Cl, Br, or I and q is 1 to 3, vinyl, CO$_2$H, CO$_2$CH$_3$, CONH$_2$, CONHCH$_3$, or CON(CH$_3$)$_2$, wherein R' is a C$_{1-20}$ alkyl; a C$_{1-20}$ cycloalkyl; a C$_2$-C$_6$ alkenyl, a C$_2$-C$_6$ alkynyl.

The seventh aspect of the second embodiment is directed to a compound represented by formula I-4
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen or $CH_3$;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, OMe, CN, $CH_2F$, F, Cl, Br, or I;
(f) $R^6$ is H, $CH_3$, $CH_2F$, $CHF_2$, $CF_3$, or F;
(g) X is H, OH, F, $OCH_3$, F, Cl, Br, I, $NH_2$ or $N_3$;
(h) Y is H, OH, $CH_3$, F, Cl, Br, I, $NH_2$ or $N_3$, $OCH_3$, or $OC(O)CH_3$;
(i) $R^7$ and $R^8$ are independently H, F, Br, $SCH_3$, $CH_3$, $CH_{3-q}X^q$, where X is F, Cl, Br, or I and q is 1 to 3, vinyl, $CO_2CH_3$, $CONH_2$, $CONHCH_3$, or $CON(CH_3)_2$;

The eighth aspect of the second embodiment is directed to a compound represented by formula I-4
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;
(e) $R^5$ is H;
(f) $R^6$ is H, $CH_3$, $CH_2F$, $CHF_2$, $CF_3$, or F;
(g) X is H, OH, $OCH_3$, F, $NH_2$ or $N_3$;
(h) Y is OH, $NH_2$, $OCH_3$, or $OC(O)CH_3$;
(i) $R^7$ and $R^8$ are independently H, F, Br, $SCH_3$, $CH_3$, $CH_{3-q}X_q$, where X is F, Cl, Br, or I and q is 1 to 3, vinyl, $CO_2CH_3$, $CONH_2$, $CONHCH_3$, or $CON(CH_3)_2$.

The ninth aspect of the second embodiment is directed to a compound represented by formula I-4
wherein
(a) $R^1$ is hydrogen, methyl, phenyl, p-bromo-phenyl, p-chloro-phenyl, p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H;
(f) $R^6$ is H, $CH_3$, $CH_2F$, $CHF_2$, $CF_3$, or F;
(g) X is H, OH, $OCH_3$, F, or $N_3$;
(h) Y is OH, $OCH_3$, or $OC(O)CH_3$;
(i) $R^7$ and $R^8$ are independently H, F, Br, $SCH_3$, $CH_3$, $CH_{3-q}X_q$, where X is F, Cl, Br, or I and q is 1 to 3, vinyl, $CO_2CH_3$, $CONH_2$, $CONHCH_3$, or $CON(CH_3)_2$.

A third embodiment oldie invention is directed to a compound represented by formula I in which the base is a structure represented by formula c above, wherein $R^1$, $R^2$, $R^{3a}$, $R^{3b}$, $R^4$, $R^5$, $R^6$, X, Y, Z, $R^{10}$, $R^{11}$, and $R^{12}$ are defined in the Summary of the Invention section above; with the proviso that $R^{11}$ is not H.

A first aspect of the third embodiment is directed to a compound represented by formula I-5

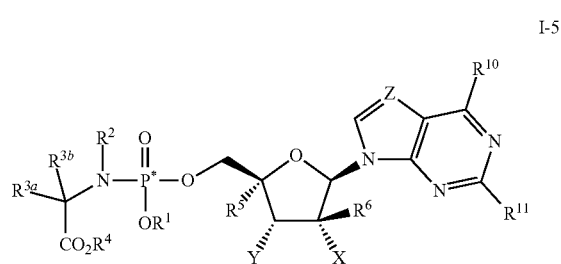

I-5 wherein
(a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, $-N(R^{1'})_2$, $C_{1-6}$ acylamino, $-NHSO_2C_{1-6}$ alkyl, $-SO_2N(R^{1'})_2$, $COR^{1''}$, and $-SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is $-OR'$ or $-N(R^{1'})_2$);
(b) $R^2$ is hydrogen or $CH_3$;
(c) $R^{3a}$ and $R^{3b}$ are (i) independently selected from hydrogen, $C_{1-10}$ alkyl, cycloalkyl, $-(CH_2)_c(NR^3)_2$, $C_{1-6}$ hydroxyalkyl, $-CH_2SH$, $-(CH_2)_2S(O)_dMe$, $-(CH_2)_3NHC(=NH)NH_2$, (1H-indol-3-yl)methyl, (1H-imidazol-4-yl)methyl, $-(CH_2)_eCOR^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_n$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is $-OR'$ or $-N(R^{3'})_2$); (vi) $R^{3a}$ is H and $R^{3b}$ is from H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, $-CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is $-OR'$ or $-N(R^{3'})_2$);
(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkyl)amino-lower alkyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, alkyne (optionally substituted), or halogen, including F, Cl, Br, or I, with the provisos that when X is OH, base is cytosine and $R^6$ is H, $R^5$ cannot be $N_3$ and when X is OH, $R^6$ is $CH_3$ or $CH_2F$ and B is a purine base, $R^5$ cannot be H;

(f) $R^6$ is H, $CH_3$, $CH_2F$, $CHF_2$, $CF_3$, F, or CN;

(g) X is H, OH, F, OMe, halogen, $NH_2$, or $N_3$;

(h) Y is OH, H, $C_{1-4}$ alkyl, $C_{2-4}$ alkenyl, $C_{2-4}$ alkynyl, vinyl, $N_3$, CN, Cl, Br, F, I, $NO_2$, $OC(O)O(C_{1-4}$ alkyl), $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-10}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(i) $R^{10}$ and $R^{11}$ are independently H, F, Cl, Br, I, OH, OR', SH, SR', $NH_2$, NHR', NR'$_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', CONR'$_2$, CH=CHCO$_2$H, or CH=CHCO$_2$R', with the proviso that when $R^{10}$ is OH and $R^{11}$ is not $NH_2$;

wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an optionally substituted alkynyl of $C_2$-$C_6$, an optionally substituted lower alkenyl of $C_2$-$C_6$, or optionally substituted acyl, which includes but is not limited to C(O) alkyl, $C(O)(C_{1-20}$ alkyl), $C(O)(C_{1-10}$ alkyl), or C(O)(lower alkyl) or alternatively, in the instance of NR'$_2$, each R' comprise at least one C atom that are joined to form a heterocycle comprising at least two carbon atoms; and (j) Z is N or $CR^{12}$; and $R^{12}$ is an H, halogen (including F, Cl, Br, I), OH, OR', SH, SR', $NH_2$, NHR', NR'$_2$, $NO_2$ lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', CONR'$_2$, CH=CHCO$_2$H, or CH=CHCO$_2$R'.

A second aspect of the third embodiment is directed to a compound represented by formula I-5
wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, lower haloalkyl, or di(lower alkyl)amino-lower alkyl;

(e) $R^5$ is H, CN, $CH_3$, $OCH_3$, $CH_2OH$, $CH_2F$, halogen, including F, Cl, Br, or I, with the provisos that when X is OH, $R^6$ is $CH_3$ or $CH_2F$, $R^5$ cannot be H.

(f) $R^6$ is H, $CH_3$, $CH_2F$, $CHF_2$, $CF_3$, F, or CN;

(g) X is H, OH, F, $OCH_3$, Cl, Br, I, $NH_2$, or N;

(h) Y is OH, H, $CH_3$, vinyl, $NH_2$, $N_3$, CN, Cl, Br, F, I, $OC(O)CH_3$, $OCH_3$;

(i) $R^{10}$ and $R^{11}$ are independently H, F, Br, I, OH, OR', $NH_2$, NHR', NR'$_2$, $CO_2R'$, $CONH_2$, CONHR', CONR'$_2$, CH=CHCO$_2$H, or CH=CHCO$_2$R', with the proviso that when $R^{10}$ is OH and $R^{11}$ is not $NH_2$;

wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or $CR^{12}$; and $R^{12}$ is an H, halogen (including F, Cl, Br, I), OR', $NH_2$, NHR', NR'$_2$, $NO_2$, lower alkyl of $C_1$-$C_6$, $CO_2R'$, $CONH_2$, CONHR', CONR'$_2$, CH=CHCO$_2$H, or CH=CHCO$_2$R'.

A third aspect of the third embodiment is directed to a compound represented by formula I-5
wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_2F$, F, Cl, Br, or I; with the proviso that X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, F, $OCH_3$, F, Cl, Br, I, $NH_2$ or $N_3$;

(h) Y is H, OH, $CH_3$, F, Cl, Br, I, $NH_2$ or $N_3$, $OCH_3$, or $OC(O)CH_3$;

(i) $R^{10}$ and $R^{11}$ are independently H, F, Br, I, OH, OR', $NH_2$, NHR', NR'$_2$, $CO_2R'$, $CONH_2$, CONHR', CONR'$_2$, CH=CHCO$_2$H, or CH=CHCO$_2$R', with the proviso that when $R^{10}$ is OH and $R^{11}$ is not $NH_2$;

wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or $CR^{12}$; and $R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, $CH=CHCO_2H$, or $CH=CHCO_2R'$.

A fourth aspect of the third embodiment is directed to a compound represented by formula I-5
wherein
(a) $R^1$ is hydrogen, methyl, ethyl, n-propyl, n-propyl, phenyl, p-tolyl, p-bromo-phenyl, p-chloro-phenyl, p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^3$ is H, with the provisos that when X is OH, $R^6$ is $CH_3$ or $CH_2F$, $R^5$ cannot be H;
(f) $R^6$ is H, $CH_3$, $CH_2F$, $CHF_2$, $CF_3$, or F;
(g) X is H, OH, $OCH_3$, F, $NH_2$ or $N_3$;
(h) Y is OH, $NH_2$, $OCH_3$, or $OC(O)CH_3$;
(i) $R^{10}$ and $R^{11}$ are independently H, F, Br, I, OH, OR', $NH_2$, NHR', $NR'_2$, $CO_2R'$, $CONH_2$, CONR', $CONR'_2$, $CH=CHCO_2H$, or $CH=CHCO_2R'$, with the proviso that when $R^{10}$ is OH and $R^{11}$ is not $NH_2$;
wherein R' is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and
(j) Z is N or $CR^{12}$; and
$R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, $CH=CHCO_2H$, or $CH=CHCO_2R'$.

A fifth aspect of the third embodiment is directed to a compound represented by formula I-5
wherein
(a) $R^1$ is hydrogen, methyl, phenyl, p-bromo-phenyl, p-chloro-phenyl, p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, with the provisos that when X is OH, $R^6$ is $CH_3$ or $CH_2F$, $R^5$ cannot be H;
(f) $R^6$ is H, $CH_3$, $CH_2F$, $CHF_2$, $CF_3$, or F;
(g) X is H, OH, $OCH_3$, F, $NH_2$ or $N_3$;
(h) Y is OH, $NH_2$, $OCH_3$, or $OC(O)CH_3$;
(i) $R^{10}$ and $R^{11}$ are independently H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$, with the proviso that when $R^{10}$ is OH and $R^{11}$ is not $NH_2$;
wherein R' is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and
(j) Z is N or $CR^{12}$; and
$R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, $CH=CHCO_2H$, or $CH=CHCO_2R'$.

A sixth aspect of the third embodiment is directed to a compound represented by formula I-5
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen or $CH_3$;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, CN, $CH_3$, $OCH_3$, $CH_2OH$, $CH_2F$, halogen, including F, Cl, Br, or I, with the provisos that when X is OH, $R^6$ is $CH_3$ or $CH_2F$, $R^5$ cannot be H.
$R^6$ is H, $CH_3$, $CH_2F$, $CHF_2$, $CF_3$, F, or CN;
(g) X is H, OH, F, $OCH_3$, Cl, Br, I, $NH_2$, or $N_3$,
(h) Y is OH, H, $CH_3$, vinyl, $NH_2$, $N_3$, CN, Cl, Br, F, I, $OC(O)CH_3$, $OCH_3$;
(i) $R^{10}$ is $NH_2$ and $R^{11}$ is H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$;
wherein R' is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and
(j) Z is N or $CR^{12}$; and
$R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, $CH=CHCO_2H$, or $CH=CHCO_2R'$.

A seventh aspect of the third embodiment is directed to a compound represented by formula I-5
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen or $CH_3$;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, CN, $CH_2F$, F, Cl, Br, or I; with the proviso that X is OH, $R^6$ is $CH_3$ or $CH_2F$, $R^5$ cannot be H;
(f) $R^6$ is H, $CH_3$, $CH_2F$, $CHF_2$, $CF_3$, or F;
(g) X is H, OH, F, $OCH_3$, F, Cl, Br, I, $NH_2$ or $N_3$;
(h) Y is H, OH, $CH_3$, F, Cl, Br, I, $NH_2$ or $N_3$, $OCH_3$, or $OC(O)CH_3$;
(i) $R^{10}$ is $NH_2$ and $R^{11}$ is H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$;
wherein R' is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and (j) Z is N or $CR^{12}$; and $R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, CH=$CHCO_2H$, or CH=$CHCO_2R'$.

An eighth aspect of the third embodiment is directed to a compound represented by formula I-5
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl;
(e) $R^5$ is H, with the provisos that when X is OH, $R^6$ is $CH_3$ or $CH_2F$, $R^5$ cannot be H;
(f) $R^6$ is H, $CH_3$, $CH_2F$, $CHF_2$, $CF_3$, or F;
(g) X is H, OH, $OCH_3$, F, $NH_2$ or $N_3$;
(h) Y is OH, $NH_2$, $OCH_3$, or $OC(O)CH_3$;
(i) $R^{10}$ is $NH_2$ and $R^{11}$ is H, F, Br, I, OH, OR', $NH_2$, NHR', $NR'_2$, $CO_2R'$, $CONH_2$, CONHR', $CONR'_2$, CH=$CHCO_2H$, or CH=$CHCO_2R'$;
wherein R' is a lower alkyl, a lower cycloalkyl, or C(O) (lower alkyl) or alternatively, in the instance of $NR'_2$, each R' comprise at least one C atom that are joined to form a heterocycle comprising at least two carbon atoms; and
(j) Z is N or $CR^{12}$; and
$R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, CH=$CHCO_2H$, or CH=$CHCO_2R'$.

A ninth aspect of the third embodiment is directed to a compound represented by formula I-5
wherein
(a) $R^1$ is hydrogen, methyl, phenyl, p-bromo-phenyl, p-chloro-phenyl, p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, or N-methyl-pyrrolidin-4-yl, lower haloalkyl, or di(lower alkylamino-lower alkyl;
(e) $R^5$ is H, with the provisos that when X is OH, $R^6$ is $CH_3$ or $CH_2F$, $R^5$ cannot be H;
(f) $R^6$ is H, $CH_3$, $CH_2F$, $CHF_2$, $CF_3$, or F;
(g) X is H, OH, $OCH_3$, F, $NH_2$ or $N_3$;
(h) Y is OH, $NH_2$, $OCH_3$, or $OC(O)CH_3$;
(i) $R^{10}$ is $NH_2$ and $R^{11}$ is H, F, Br, I, OH, OR', $NH_2$, NHR', $NR'_2$, $CO_2R'$, $CONH_2$, CONHR', $CONR'_2$, CH=$CHCO_2H$, or CH=$CHCO_2R'$;
wherein R' is a lower alkyl, a lower cycloalkyl, or C(O) (lower alkyl) or alternatively, in the instance of $NR'_2$, each R' comprise at least one C atom that are joined to form a heterocycle comprising at least two carbon atoms; and
(j) Z is N or $CR^{12}$; and
$R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, CH=$CHCO_2H$, or CH=$CHCO_2R'$.

A tenth aspect of the third embodiment is directed to a compound represented by formula I-6

I-6 wherein
(a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —$N(R^{1'})_2$, $C_{1-6}$ acylamino, —$NHSO_2C_{1-6}$ alkyl, —$SO_2N(R^{1'})_2$, $COR^{1''}$, and —$SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —$N(R^{1'})_2$);
(b) $R^2$ is hydrogen or $CH_3$;
(c) $R^{3a}$ and $R^{3b}$ are (i) independently selected from hydrogen, $C_{1-10}$ alkyl, cycloalkyl, —$(CH_2)_c(NR^{3'})_2$, $C_{1-6}$ hydroxyalkyl, —$CH_2SH$, —$(CH_2)_2S(O)_d$(Me, —$(CH_2)_3NHC$(=NH)$NH_2$, (1H-indol-3-yl)methyl, (1H-imidazol-4-yl)methyl, —$(CH_2)_eCOR^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_f$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is —OR' or —$N(R^{3'})_2$); (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)$-Ph), $CH_2SH$, or lower cycloalkyl; or (viii) $R^{3a}$ is $CH_3$, —$CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)$-Ph), $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —$N(R^{3'})_2$);
(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkyl)amino-lower alkyl, aryl, such as phenyl, heteroaryl, such as, pyridinyl, substituted aryl, or substituted heteroaryl;
(e) $R^5$ is H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $CH_2CN$, $CH_2NH_2$, $CH_2NHCH_3$, $CH_2N(CH_3)_2$, alkyne (optionally substituted), or halogen, including F, Cl, Br, or I, with the provisos that when X is OH, base is cytosine and $R^6$ is H, $R^5$ cannot be $N_3$ and when X is OH, $R^6$ is $CH_3$ or $CH_2F$ and B is a purine base, $R^5$ cannot be H;

(f) $R^6$ is H, $CH_3$, $CH_2F$, $CHF_2$, $CF_3$, F, or CN;

(g) X is H, OH, F, OMe, Cl, Br, I, $NH_2$, or $N_3$;

(h) Y is OH, H, $C_{1-4}$ alkyl, $C_{2-4}$ alkenyl, $C_{2-4}$ alkynyl, vinyl, $N_3$, CN, Cl, Br, F, I, $NO_2$, $OC(O)O(C_{1-4}$ alkyl), $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-10}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(i) $R^{10}$ and $R^{11}$ are independently H, F, Br, I, OH, OR', $NH_2$, NHR', NR'$_2$, $CO_2R'$, $CONH_2$, CONHR', CONR'$_2$, CH=CHCO$_2$H, or CH=CHCO$_2$R', with the proviso that when $R^{10}$ is OH and $R^{11}$ is not $NH_2$;

wherein is a lower alkyl, a lower cycloalkyl, or C(O)(lower alkyl) or alternatively, in the instance of NR'$_2$, each R' comprise at least one C atom that are joined to form a heterocycle comprising at least two carbon atoms; and (j) Z is N or $CR^{12}$; and $R^{12}$ is an H, halogen (including F, Cl, Br, I), OR', $NH_2$, NHR', NR'$_2$, $NO_2$, lower alkyl of $C_1$-$C_6$, $CO_2R'$, $CONH_2$, CONHR', CONR'$_2$, CH=CHCO$_2$H, or CH=CHCO$_2$R', An eleventh aspect of the third embodiment is directed to a compound represented by formula I-6
wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_3$, $OCH_3$, $CH_2OH$, $CH_2F$, halogen, including F, Cl, Br, or I, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, F, or CN;

(g) X is H, OH, F, OCH$_3$, Cl, Br, I, $NH_2$, or $N_3$;

(h) Y is OH, H, $CH_3$, vinyl, $NH_2$, $N_3$, CN, Cl, Br, F, I, $OC(O)CH_3$, $OCH_3$;

(i) $R^{10}$ and $R^{11}$ are independently H, F, Br, I, OH, OR', $NH_2$, NHR'$_2$, NR'$_2$, $CO_2R'$, $CONH_2$, CONHR', CONR'$_2$, CH=CHCO$_2$H, or CH=CHCO$_2$R', with the proviso that when $R^{10}$ is OH and $R^{11}$ is not $NH_2$;

wherein R' is a lower alkyl, a lower cycloalkyl, or C(O)(lower alkyl) or alternatively, in the instance of NR'$_2$, each comprise at least one C atom that are joined to form a heterocycle comprising at least two carbon atoms; and (j) Z is N or $CR^{12}$; and $R^{12}$ is an H, halogen (including F, Cl, Br, I), OR', $NH_2$, NHR', NR'$_2$, $NO_2$, lower alkyl of $C_1$-$C_6$, $CO_2R'$, $CONH_2$, CONHR', CONR'$_2$, CH=CHCO$_2$H, or CH=CHCO$_2$R'.

A twelfth aspect of the third embodiment is directed to a compound represented by formula I-6
wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_2F$, F, Cl, Br, or I, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, F, OCH$_3$, F, Cl, Br, I, $NH_2$ or $N_3$;

(h) Y is H, OH, $CH_3$, F, Cl, Br, I, $NH_2$ or $N_3$, $OCH_3$, or $OC(O)CH_3$;

(i) $R^{10}$ and $R^{11}$ are independently H, F, Br, I, OH, OR', $NH_2$, NHR', NR'$_2$, $CO_2R'$, $CONH_2$, CONHR', CONR'$_2$, CH=CHCO$_2$H, or CH=CHCO$_2$R', with the proviso that when $R^{10}$ is OH and $R^{11}$ is not $NH_2$;

wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or $CR^{12}$; and $R^{12}$ is a H, halogen (including F, Cl, Br, I), OR', $NH_2$, NHR', NR'$_2$, $NO_2$, lower alkyl of $C_1$-$C_6$, $CO_2R'$, $CONH_2$, CONHR', CONR'$_2$, CH=CHCO$_2$H, or CH=CHCO$_2$R'.

A thirteenth aspect of the third embodiment is directed to a compound represented by formula I-6
wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, OCH$_3$, F, $NH_2$ or $N_3$;

(h) Y is OH, $NH_2$, OCH$_3$, or $OC(O)CH_3$;

(i) $R^{10}$ and $R^{11}$ are independently H, F, Br, I, OH, OR', $NH_2$, NHR', NR'$_2$, $CO_2R'$, $CONH_2$, CONHR', CONR'$_2$, CH=CHCO$_2$H, or CH=CHCO$_2$R', with the proviso that when $R^{10}$ is OH and $R^{11}$ is not $NH_2$;

wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or CR$^{12}$; and R$^{12}$ is an H, halogen (including F, Cl, Br, I), OR', NH$_2$, NHR', NR'$_2$, NO$_2$, lower alkyl of C$_1$-C$_6$, CO$_2$R', CONH$_2$, CONHR', CONR'$_2$, CH=CHCO$_2$H, or CH=CHCO$_2$R'.

A fourteenth aspect of the third embodiment is directed to a compound represented by formula I-6 wherein (a) R$^1$ is hydrogen, methyl, phenyl, p-bromo-phenyl, p-chloro-phenyl, p-fluorophenyl;

(b) R$^2$ is hydrogen;

(c) R$^{3a}$ is H and R$^{3b}$ is CH$_3$, CH(CH$_3$)$_2$, CH$_2$CH(CH$_3$)$_2$, CH(CH$_3$)CH$_2$CH$_3$, CH$_2$Ph, or lower cycloalkyl;

(d) R$^4$ is hydrogen, CH$_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;

(e) R$^5$ is H, with the provisos that when X is OH, R$^6$ is CH$_3$ or CH$_2$F, R$^5$ cannot be H;

(f) R$^6$ is H, CH$_3$, CH$_2$F, CHF$_2$, CF$_3$, or F;

(g) X is H, OH, OCH$_3$, F, NH$_2$ or N$_3$;

(h) Y is OH, NH$_2$, OCH$_3$, or OC(O)CH$_3$;

(i) R$^{10}$ and R$^{11}$ are independently H, F, Br, I, OH, OR', NH$_2$, NHR', NR'$_2$, CO$_2$R', CONH$_2$, CONHR', CONR'$_2$, CH=CHCO$_2$H, or CH=CHCO$_2$R', with the proviso that when R$^{10}$ is OH and R$^{11}$ is not NH$_2$;

wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or CR$^{12}$; and R$^{12}$ is an H, halogen (including F, Cl, Br, I), OR', NH$_2$, NHR', NR'$_2$, NO$_2$, lower alkyl of C$_1$-C$_6$, CO$_2$R', CONH$_2$, CONHR', CONR'$_2$, CH=CHCO$_2$H, or CH=CHCO$_2$R'.

A fifteenth aspect of the third embodiment is directed to a compound represented by formula I-6 wherein (a) R$^1$ is hydrogen, n-alkyl: branched alkyl; cycloalkyl; or aryl, which includes, but is not limited to, phenyl or naphthyl, where phenyl or naphthyl are optionally substituted with at least one of C$_{1-6}$ alkyl, C$_{2-6}$ alkenyl, C$_{2-6}$ alkynyl, C$_{1-6}$ alkoxy, F, Cl, Br, I, nitro, cyano, C$_{1-6}$ haloalkyl, —N(R$^{1''}$)$_2$, acylamino, —NHSO$_2$C$_{1-6}$ alkyl, —SO$_2$N(R$^{1''}$)$_2$, COR$^{1''}$, and —SO$_2$C$_{1-6}$ alkyl; (R$^{1''}$ is independently hydrogen or alkyl, which includes, but is not limited to, C$_{1-20}$ alkyl, C$_{1-10}$ alkyl, or C$_{1-6}$ alkyl, R$^{1''}$ is —OR' or —N(R$^{1'}$)$_2$);

(b) R$^2$ is hydrogen or CH$_3$;

(c) R$^{3a}$ and R$^{3b}$ are (i) independently selected from hydrogen, C$_{1-10}$ alkyl, cycloalkyl, —(CH$_2$)$_c$(NR$^{3'}$)$_2$, C$_{1-6}$ hydroxyalkyl, —CH$_2$SH, —(CH$_2$)$_2$S(O)$_d$Me, —(CH$_2$)$_3$NHC(=NH)NH$_2$, (1H-indol-3-yl)methyl, (1H-imidazol-4-yl)methyl, —(CH$_2$)$_e$COR$^{3''}$, aryl and aryl C$_{1-3}$ alkyl, said aryl groups optionally substituted with a group selected from hydroxyl, C$_{1-10}$ alkyl, C$_{1-6}$ alkoxy, halogen, nitro and cyano; (ii) R$^{3a}$ and R$^{3b}$ both are C$_{1-6}$ alkyl; (iii) R$^{3a}$ and R$^{3b}$ together are (CH$_2$)$_f$ so as to form a spiro ring; (iv) R$^{3a}$ is hydrogen and R$^{3b}$ and R$^2$ together are (CH$_2$)$_n$ so as to form a cyclic ring that includes the adjoining N and C atoms (v) R$^{3b}$ is hydrogen and R$^{3a}$ and R$^2$ together are (CH$_2$)$_n$ so as to form a cyclic ring that includes the adjoining N and C atoms, where c is 1 to 6, d is 0 to 2, e is 0 to 3, f is 2 to 5, n is 2 to 4, and where R$^7$ is independently hydrogen or C$_{1-6}$ alkyl and R$^{3''}$ is —OR' or —N(R$^{3'}$)$_2$); (vi) R$^{3a}$ is H and R$^{3b}$ is H, CH$_3$, CH$_2$CH$_3$, CH(CH$_3$)$_2$, CH$_2$CH (CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl; or (viii) R$^{3a}$ is CH$_3$, —CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and R$^{3b}$ is H, where R$^{3'}$ is independently hydrogen or alkyl, which includes, but is not limited to, C$_{1-20}$ alkyl, C$_{1-10}$ alkyl, or C$_{1-6}$ alkyl, R$^{3''}$ is —OR' or —N(R$^{3'}$)$_2$);

(d) R$^4$ is hydrogen, C$_{1-10}$ alkyl, C$_{1-10}$ alkyl optionally substituted with a lower alkyl, alkoxy or halogen, C$_{1-10}$ haloalkyl, C$_{3-10}$ cycloalkyl, cycloalkyl alkyl, cycloheteroalkyl, aminoacyl, di(lower alkyl)amino-lower alkyl, aryl, such as phenyl, heteroaryl, such as, pyridinyl, substituted aryl, or substituted heteroaryl;

(e) R$^5$ is H, a lower alkyl, CN, vinyl, O-(lower alkyl), hydroxyl lower alkyl, i.e., —(CH$_2$)$_p$OH, where p is 1-6, including hydroxyl methyl (CH$_2$OH), CH$_2$F, N$_3$, CH$_2$CN, CH$_2$NH$_2$, CH$_2$NHCH$_3$, CH$_2$N(CH$_3$)$_2$, alkyne (optionally substituted), or halogen, including F, Cl, Br, or I, with the provisos that when X is OH, base is cytosine and R$^6$ is H, R$^5$ cannot be N$_3$ and when X is OH, R$^6$ is CH$_3$ or CH$_2$F and B is a purine base, R$^5$ cannot be H;

(f) R$^6$ is H, CH$_3$, CH$_2$F, CHF$_2$, CF$_3$, F, or CN;

(g) X is H, OH, F, OMe, halogen, NH$_2$, or N$_3$;

(h) Y is OH, H, C$_{1-4}$ alkyl, C$_{2-4}$ alkenyl, C$_{2-4}$ alkynyl, vinyl, N$_3$, CN, Cl, Br, F, I, NO$_2$, OC(O)O(C$_{1-4}$ alkyl), OC(O)O(C$_{1-4}$ alkyl), OC(O)O(C$_{2-4}$ alkynyl), OC(O)O(C$_{2-4}$ alkenyl), OC$_{1-10}$ haloalkyl, O(aminoacyl), O(C$_{1-10}$ acyl), O(C$_{1-4}$ alkyl), O(C$_{2-4}$ alkenyl), S(C$_{1-4}$ acyl), S(C$_{1-4}$ alkyl), S(C$_{2-4}$ alkynyl), S(C$_{2-4}$ alkenyl), SO(C$_{1-4}$ acyl), SO(C$_{1-4}$ alkyl), SO(C$_{2-4}$ alkynyl), SO(C$_{2-4}$ alkenyl), SO$_2$(C$_{1-4}$ acyl), SO$_2$(C$_{1-4}$ alkyl), SO$_2$(C$_{2-4}$ alkynyl), SO$_2$(C$_{2-4}$ alkenyl), OS(O)$_2$(C$_{1-4}$ acyl), OS(O)$_2$(C$_{1-4}$ alkyl), OS(O)$_2$(C$_{2-4}$ alkenyl), NH$_2$, NH(C$_{1-4}$ alkyl), NH(C$_{2-4}$ alkenyl), NH(C$_{2-4}$ alkynyl), NH(C$_{1-4}$ acyl), N(C$_{1-4}$ alkyl)$_2$, N(C$_{1-18}$ acyl)$_2$, wherein alkyl, alkynyl, alkenyl and vinyl are optionally substituted by N$_3$, CN, one to three halogen (Cl, Br, F, I), NO$_2$, C(O)O(C$_{1-4}$ alkyl), C(O)O(C$_{1-4}$ alkyl), C(O)O(C$_{2-4}$ alkynyl), C(O)O(C$_{2-4}$ alkenyl), O(C$_{1-4}$ acyl), O(C$_{1-4}$ alkyl), O(C$_{2-4}$ alkenyl), S(C$_{1-4}$ acyl), S(C$_{1-4}$ alkyl), S(C$_{2-4}$ alkynyl), S(C$_{2-4}$ alkenyl), SO(C$_{1-4}$ acyl), SO(C$_{1-4}$ alkyl), SO(C$_{2-4}$ alkynyl), SO(C$_{2-4}$ alkenyl), SO$_2$(C$_{1-4}$ acyl), SO$_2$(C$_{1-4}$ alkyl), SO$_2$(C$_{2-4}$ alkynyl), SO$_2$(C$_{2-4}$ alkenyl), OS(O)$_2$(C$_{1-4}$ acyl), OS(O)$_2$(C$_{1-4}$ alkyl), OS(O)$_2$(C$_{2-4}$ alkenyl), NH$_2$, NH(C$_{1-4}$ alkyl), NH(C$_{2-4}$ alkenyl), NH(C$_{2-4}$ alkynyl), NH(C$_{1-4}$ acyl), N(C$_{1-4}$ alkyl)$_2$, N(C$_{1-4}$ acyl);

(i) R$^{10}$ is NH$_2$ and R$^{11}$ is H, F, Br, I, OH, OR', NH$_2$, NHR', NR'$_2$, CO$_2$R', CONH$_2$, CONHR', CONR'$_2$, CH=CHCO$_2$H, or CH=CHCO$_2$R', wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or CR$^{12}$; and R$^{12}$ is an H, halogen (including F, Cl, Br, I), OR', NH$_2$, NHR', NR'$_2$, NO$_2$, lower alkyl of C$_1$-C$_6$, CO$_2$R', CONH$_2$, CONHR', CONR'$_2$, CH=CHCO$_2$H, or CH=CHCO$_2$R'.

An sixteenth aspect of the third embodiment is directed to a compound represented by formula I-6
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen or $CH_3$;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, CN, $CH_3$, $OCH_3$, $CH_2OH$, $CH_2F$, halogen, including F, Cl, Br, or I, with the provisos that when X is OH, $R^6$ is $CH_3$ or $CH_2F$, $R^5$ cannot be H;
(f) $R^6$ is H, $CH_3$, $CH_2F$, $CHF_2$, $CF_3$, F, or CN;
(g) X is H, OH, F, $OCH_3$, Cl, Br, I, $NH_2$, or $N_3$;
(h) Y is OH, H, $CH_3$, vinyl, $NH_2$, $N_3$, CN, Cl, Br, F, I, $OC(O)CH_3$, $OCH_3$;
(i) $R^{10}$ is $NH_2$ and $R^{11}$ is H, F, Br, I, OH, OR', $NH_2$, NHR', $NR'_2$, $CO_2R'$, $CONH_2$, CONHR', $CONR'_2$, CH=$CHCO_2H$, or CH=$CHCO_2R'$;
wherein R' is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and
(j) Z is N or $CR^{12}$; and
$R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, CH=$CHCO_2H$, or CH=$CHCO_2R'$.

A seventeenth aspect of the third embodiment is directed to a compound represented by formula I-6
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen or $CH_3$;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, CN, $CH_2F$, F, Cl, Br, or I, with the provisos that when X is OH, $R^6$ is $CH_3$ or $CH_2F$, $R^5$ cannot be H;
(f) $R^6$ is H, $CH_3$, $CH_2F$, $CHF_2$, $CF_3$, or F;
(g) X is H, OH, F, $OCH_3$, F, Cl, Br, I, $NH_2$ or $N_3$;
(h) Y is H, OH, $CH_3$, F, Cl, Br, I, $NH_2$ or $N_3$, $OCH_3$, or $OC(O)CH_3$;
(i) $R^{10}$ is $NH_2$ and $R^{11}$ is H, F, Br, I, OH, OR', $NH_2$, NHR', $NR'_2$, $CO_2R'$, $CONH_2$, CONHR', $CONR'_2$, CH=$CHCO_2H$, or CH=$CHCO_2R'$;
wherein is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and
(j) Z is N or $CR^{12}$; and $R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, CH=$CHCO_2H$, or CH=$CHCO_2R'$.

An eighteenth aspect of the third embodiment is directed to a compound represented by formula I-6
wherein
(a) $R^1$ is hydrogen, methyl, ethyl, n-propyl, i-propyl, phenyl, p-tolyl, p-bromo-phenyl, p-chloro-phenyl, p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-piperidin-4-yl, lower haloalkyl, or di(lower alkyl)amino-lower alkyl;
(e) $R^5$ is H, with the provisos that when X is OH, $R^6$ is $CH_3$ or $CH_2F$, $R^5$ cannot be H;
(f) $R^6$ is H, $CH_3$, $CH_2F$, $CHF_2$, $CF_3$, or F;
(g) X is H, OH, $OCH_3$, F, $NH_2$ or $N_3$;
(h) Y is OH, $NH_2$, $OCH_3$, or $OC(O)CH_3$;
(i) $R^{10}$ is $NH_2$ and $R^{11}$ is H, F, Br, I, OH, OR', $NH_2$, NHR', $NR'_2$, $CO_2R'$, $CONH_2$, CONHR', $CONR'_2$, CH=$CHCO_2H$, or CH=$CHCO_2R'$;
wherein R' is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and
(j) Z is N or $CR^{12}$; and
$R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, CH=$CHCO_2H$, or CH=$CHCO_2R'$, A nineteenth aspect of the third embodiment is directed to a compound represented by formula I-6
wherein
(a) $R^1$ is hydrogen, methyl, phenyl, p-bromo-phenyl, p-chloro-phenyl, p-fluorophenyl;
(b) $R^2$ is hydrogen;
(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;
(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;
(e) $R^5$ is H, with the provisos that when X is OH, $R^6$ is $CH_3$ or $CH_2F$, $R^5$ cannot be H;
(f) $R^6$ is H, $CH_3$, $CH_2F$, $CHF_2$, $CF_3$, or F;
(g) X is H, OH, $OCH_3$, F, $NH_2$ or $N_3$;
(h) Y is OH, $NH_2$, $OCH_3$, or $OC(O)CH_3$;
(i) $R^{10}$ is $NH_2$ and $R^{11}$ are independently H, F, Br, I, OH, OR', $NH_2$, NHR', $NR'_2$, $CO_2R'$, $CONH_2$, CONHR', $CONR'_2$, CH=$CHCO_2H$, or CH=$CHCO_2R'$;
wherein R' is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and
(j) is N or $CR^{12}$; and
$R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, CH=$CHCO_2H$, or CH=$CHCO_2R'$.

A fourth embodiment of the invention is directed to a compound represented by formula I in which the base is a structure represented by formula c above, where $R^{11}$ is H and $R^2$, $R^{3a}$, $R^{3b}$, $R^4$, $R^5$, $R^6$, X, and Y are defined in the Summary of the Invention section above.

A first aspect of the fourth embodiment is directed to a compound represented by formula I-7

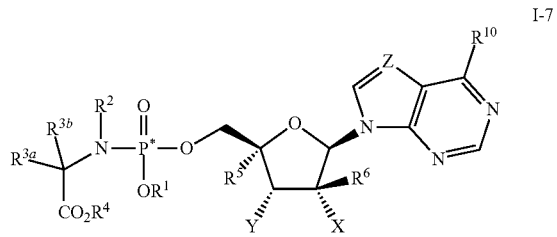

wherein (a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —$N(R^{1'})_2$, $C_{1-6}$ acylamino, —$NHSO_2C_{1-6}$ alkyl, —$SO_2N(R^{1'})_2$, $COR^{1''}$, and —$SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —$N(R^{1'})_2$);

(b) $R^2$ is hydrogen or $CH_3$;

(c) $R^{3a}$ and $R^{3b}$ are (i) independently selected from hydrogen, $C_{1-10}$ alkyl, cycloalkyl, —$(CH_2)_c(NR^{3'})_2$, $C_{1-6}$ hydroxyalkyl, —$CH_2SH$, —$(CH_2)_2S(O)_dMe$, —$(CH_2)_3NHC(=NH)NH_2$, (1H-indol-3-yl)methyl, (1H-imidazol-4-yl)methyl, —$(CH_2)_eCOR^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_f$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is —OR' or —$N(R^{3'})_2$); (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, —$CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —$N(R^{3'})_2$);

(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkylamino-lower alkyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, alkyne (optionally substituted), or halogen, including F, Cl, Br, or I, with the provisos that when X is OH, base is cytosine and $R^6$ is H, $R^5$ cannot be $N_3$ and when X is OH, $R^6$ is $CH_3$ or $CH_2F$ and B is a purine base, $R^5$ cannot be H;

(f) $R^6$ is H, $CH_3$, $CH_2F$, $CHF_2$, $CF_3$, F, or CN;

(g) X is H, OH, F, OMe, halogen, $NH_2$, or $N_3$;

(h) Y is OH, H, $C_{1-4}$ alkyl, $C_{2-4}$ alkenyl, $C_{2-4}$ alkynyl, vinyl, $N_3$, CN, Cl, Br, F, I, $NO_2$, $OC(O)O(C_{1-4}$ alkyl), $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-10}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), acyl, $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(i) $R^{10}$ is H, F, Cl, Br, I, OH, OR', SH, SR', $NH_2$, NHR', $NR'_2$, lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$ such as C≡CH, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$, wherein R' is an optionally substituted alkyl, which includes, but is not limited to, an optionally substituted $C_{1-20}$ alkyl, an optionally substituted $C_{1-10}$ alkyl, an optionally substituted lower alkyl; an optionally substituted cycloalkyl; an optionally substituted alkynyl of $C_2$-$C_6$, an optionally substituted lower alkenyl of $C_2$-$C_6$, or optionally substituted acyl, which includes but is not limited to C(O) alkyl, $C(O)(C_{1-20}$ alkyl), $C(O)(C_{1-10}$ alkyl), or C(O)(lower alkyl) or alternatively, in the instance of $NR'_2$, each R' comprise at least one C atom that are joined to form a heterocycle comprising at least two carbon atoms; and (i) Z is N or $CR^{12}$; and $R^{12}$ is H, halogen (including F, Cl, Br, I), OH, OR', SH, SR', $NH_2$, NHR', $NR'_2$, $NO_2$ lower alkyl of $C_1$-$C_6$, halogenated (F, Cl, Br, I) lower alkyl of $C_1$-$C_6$, lower alkenyl of $C_2$-$C_6$, halogenated (F, Cl, Br, I) lower alkenyl of $C_2$-$C_6$, lower alkynyl of $C_2$-$C_6$, halogenated (F, Cl, Br, I) lower alkynyl of $C_2$-$C_6$, lower alkoxy of $C_1$-$C_6$, halogenated (F, Cl, Br, I) lower alkoxy of $C_1$-$C_6$, $CO_2H$, $CO_2R'$, $CONH_2$, CONHR', $CONR'_2$, CH=$CHCO_2H$, or CH=$CHCO_2R'$; with the proviso that $R^{12}$ is not a: (i) —C≡C—H, (ii) —C=$CH_2$, or (iii) —$NO_2$.

A second aspect of the fourth embodiment is directed to a compound represented by formula I-7 wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

(d) $R^4$ is hydrogen, $CH_3$, Et, $^iPr$, $''Pr$, $''Bu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;

(e) $R^5$ is H, CN, $CH_3$, $OCH_3$, $CH_2OH$, $CH_2F$, halogen, including F, Cl, Br, or I, with the provisos that when X is OH, $R^6$ is $CH_3$ or $CH_2F$, $R^5$ cannot be H.

(f) $R^6$ is H, $CH_3$, $CH_2F$, $CHF_2$, $CF_3$, F, or CN;

(g) X is H, OH, F, $OCH_3$, halogen, $NH_2$, or $N_3$;

(h) Y is OH, H, $CH_3$, vinyl, $NH_2$, $N_3$, CN, Cl, Br, F, I, $OC(O)CH_3$, $OCH_3$;

(i) $R^{10}$ is H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$, wherein R' is a lower alkyl, a lower cycloalkyl, or C(O) (lower alkyl) or alternatively, in the instance of $NR'_2$, each R' comprise at least one C atom that are joined to form a heterocycle comprising at least two carbon atoms; and (j) Z is N or $CR^{12}$; and $R^{12}$ is H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONH_2$, $CH=CHCO_2H$, or $CH=CHCO_2R'$; with the proviso that $R^{12}$ is not a: (i) $-C{\equiv}C-H$, (ii) $-C=CH_2$, or (iii) $-NO_2$.

A third aspect of the third embodiment is directed to a compound represented by formula I-7 wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $''Pr$, $''Bu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_2F$, F, Cl, Br, or I; with the proviso that X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, F, $OCH_3$, F, Cl, Br, I, $NH_2$ or $N_3$;

(h) Y is H, OH, $CH_3$, F, Cl, Br, I, $NH_2$ or $N_3$, $OCH_3$, or $OC(O)CH_3$;

(i) $R^{10}$ is H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$, wherein R' is a lower alkyl, a lower cycloalkyl, or C(O) (lower alkyl) or alternatively, in the instance of $NR'_2$, each R' comprise at least one C atom that are joined to form a heterocycle comprising at least two carbon atoms; and (j) Z is N or $CR^{12}$; and $R^{12}$ is H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, $CH=CHCO_2H$, or $CH=CHCO_2R'$; with the proviso that $R^{12}$ is not a: (i) $-C{\equiv}C-H$, (ii) $-C=CH_2$, or (iii) $-NO_2$.

A fourth aspect of the fourth embodiment is directed to a compound represented by formula I-7 wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $''Pr$, $''Bu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, $OCH_3$, F, $NH_2$ or $N_3$;

(h) Y is OH, $NH_2$, $OCH_3$, or $OC(O)CH_3$;

(i) $R^{10}$ and $R^{11}$H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$, wherein R' is a lower alkyl, a lower cycloalkyl, or C(O) (lower alkyl) or alternatively, in the instance of $NR'_2$, each R' comprise at least one C atom that are joined to form a heterocycle comprising at least two carbon atoms; and (j) Z is N or $CR^{12}$; and $R^{12}$ is an H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, $CH=CHCO_2H$, or $CH=CHCO_2R'$; with the proviso that $R^{12}$ is not a: (i) $-C{\equiv}C-H$, (ii) $-C=CH_2$, or (iii) $-NO_2$.

A fifth aspect of the fourth embodiment is directed to a compound represented by formula I-7 wherein (a) $R^1$ is hydrogen, methyl, phenyl, p-bromo-phenyl, p-chloro-phenyl, p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $''Pr$, $''Bu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, $OCH_3$, F, $NH_2$ or $N_3$;

(h) Y is OH, $NH_2$, $OCH_3$, or $OC(O)CH_3$;

(i) $R^{10}$ is H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$, wherein R' is a lower alkyl, a lower cycloalkyl, or C(O) (lower alkyl) or alternatively, in the instance of $NR'_2$, each R' comprise at least one C atom that are joined to form a heterocycle comprising at least two carbon atoms; and (j) Z is N or $CR^{12}$; and $R^{12}$ is H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, $CH=CHCO_2H$, or $CH=CHCO_2R'$.

A sixth aspect of the fourth embodiment is directed to a compound represented by formula I-8

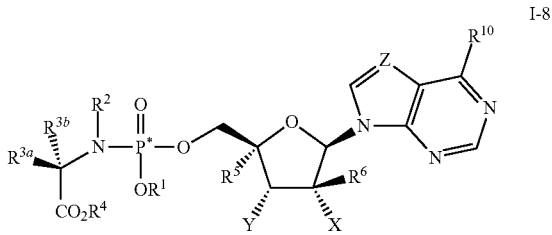

wherein (a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —$N(R^{1'})_2$, $C_{1-6}$ acylamino, —$NHSO_2C_{1-6}$ alkyl, —$SO_2N(R^{1'})_2$, $COR^{1'''}$, and —$SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —$N(R^{1'})_2$);

(b) $R^2$ is hydrogen or $CH_3$;

(c) $R^{3a}$ and $R^{3b}$ are (i) independently selected from hydrogen, $C_{1-10}$ alkyl, cycloalkyl, —$(CH_2)_c(NR^{3'})_2$, $C_{1-6}$ hydroxyalkyl, —$CH_2SH$, —$(CH_2)_2S(O)_dMe$, —$(CH_2)_3NHC(=NH)NH_2$, (1H-indol-3-yl)methyl, (1H-imidazol-4-yl)methyl, —$(CH_2)_eCOR^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_r$, so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is —OR' or —$N(R^{3'})_2$); (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, —$CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —$N(R^{3'})_2$);

(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkyl)amino-lower alkyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., —$(CH_2)_pOH$, where p is 1-6, including hydroxyl methyl ($CH_2OH$), $CH_2F$, $N_3$, $CH_2CN$, $CH_2NH_2$, $CH_2NHCH_3$, $CH_2N(CH_3)_2$, alkyne (optionally substituted), or halogen, including F, Cl, Br, or I, with the provisos that when X is OH, base is cytosine and $R^6$ is H, $R^5$ cannot be $N_3$ and when X is OH, $R^6$ is $CH_3$ or $CH_2F$ and B is a purine base, $R^5$ cannot be H;

(f) $R^6$ is H, $CH_3$, $CH_2F$, $CHF_2$, $CF_3$, F, or CN;

(g) X is H, OH, F, OMe, halogen, $NH_2$, or $N_3$;

(h) Y is OH, H, $C_{1-4}$ alkyl, $C_{2-4}$ alkenyl, $C_{2-4}$ alkynyl, vinyl, $N_3$, CN, Cl, Br, F, I, $NO_2$, $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-10}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$;

(i) $R^{10}$ is H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$, wherein R' is a lower alkyl, a lower cycloalkyl, or C(O)(lower alkyl) or alternatively, in the instance of $NR'_2$, each R' comprise at least one C atom that are joined to form a heterocycle comprising at least two carbon atoms; and (j) Z is N or $CR^{12}$; and $R^{12}$ is H, halogen (including F, Cl, Br, I), OR', $NH_2$, NHR', $NR'_2$, $NO_2$, lower alkyl of $C_1$-$C_6$, $CO_2R'$, $CONH_2$, CONHR', $CONR'_2$, $CH=CHCO_2H$, or $CH=CHCO_2R'$; with the proviso that when base is represented by the structure c with $R^{11}$ being hydrogen, $R^{12}$ is not a: (i) —C≡C—H, (ii) —C=$CH_2$, or (iii) —$NO_2$.

A seventh aspect of the fourth embodiment is directed to a compound represented by formula I-8 wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_3$, $OCH_3$, $CH_2OH$, $CH_2F$, halogen, including F, Cl, Br, or I, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, F, or CN;

(g) X is H, OH, F, $OCH_3$, halogen, $NH_2$, or $N_3$;

(h) Y is OH, H, $CH_3$, vinyl, $NH_2$, $N_3$, CN, Cl, Br, F, I, $OC(O)CH_3$, $OCH_3$;

(i) $R^{10}$ is H, F, Br, I, OH, OR', $NH_2$, NHR', $NR'_2$, $CO_2R'$, $CONH_2$, CONHR', $CONR'_2$, $CH=CHCO_2H$, or $CH=CHCO_2R'$, wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) N or CR$^{12}$; and R$^{12}$ is an H, halogen (including F, Cl, Br, I), OR', NH$_2$, NHR', NR'$_2$, NO$_2$, lower alkyl of C$_1$-C$_6$, CO$_2$R', CONH$_2$, CONHR', CONR'$_2$, CH=CHCO$_2$H, or CH=CHCO$_2$R'; with the proviso that R$^{12}$ is not a: (i) —C≡C—H, (ii) —C=CH$_2$, or (iii) —NO$_2$.

An eighth aspect of the fourth embodiment is directed to a compound represented by formula I-8 wherein (a) R$^1$ is hydrogen, methyl, ethyl, n-propyl, i-propyl, phenyl, p-tolyl, p-bromo-phenyl, p-chloro-phenyl, p-fluorophenyl;

(b) R$^2$ is hydrogen or CH$_3$;

(c) R$^{3a}$ is H and R$^{3b}$ is H, CH$_3$, CH(CH$_3$)$_2$, CH$_2$CH(CH$_3$)$_2$, CH(CH$_3$)CH$_2$CH$_3$, CH$_2$Ph, or lower cycloalkyl;

(d) R$^4$ is hydrogen, CH$_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;

(e) R$^5$ is H, CN, CH$_2$F, F, Cl, Br, or I, with the provisos that when X is OH, R$^6$ is CH$_3$ or CH$_2$F, R$^5$ cannot be H;

(f) R$^6$ is H, CH$_3$, CH$_2$F, CHF$_2$, CF$_3$, or F;

(g) X is H, OH, F, OCH$_3$, F, Cl, Br, I, NH$_2$ or N$_3$;

(h) Y is H, OH, CH$_3$, F, Cl, Br, I, NH$_2$ or N3, OCH$_3$, or OC(O)CH$_3$;

(i) R$^{10}$ is H, F, Br, I, OH, OR', NH$_2$, NHR', NR'$_2$, CO$_2$R', CONH$_2$, CONHR', CONR'$_2$, CH=CHCO$_2$H, or CH=CHCO$_2$R', wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or CR$^{12}$; and R$^{12}$ is an H, halogen (including F, Cl, Br, I), OR', NH$_2$, NHR', NR'$_2$, NO$_2$, lower alkyl of C$_1$-C$_6$, CO$_2$R', CONH$_2$, CONHR', CONR'$_2$, CH=CHCO$_2$H, or CH=CHCO$_2$R'; with the proviso that R$^{12}$ is not a: (i) —C≡C—H, (ii) —C=CH$_2$, or (iii) —NO$_2$.

A ninth aspect of the fourth embodiment is directed to a compound represented by formula I-8 wherein (a) R$^1$ is hydrogen, methyl, ethyl, n-propyl, i-propyl, phenyl, p-tolyl, p-bromo-phenyl, p-chloro-phenyl, p-fluorophenyl;

(b) R$^2$ is hydrogen;

(c) R$^{3a}$ is H and R$^{3b}$ is H, CH$_3$, CH(CH$_3$)$_2$, CH$_2$CH(CH$_3$)$_2$, CH(CH$_3$)CH$_2$CH$_3$, CH$_2$Ph, or lower cycloalkyl;

(d) R$^4$ is hydrogen, CH$_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) R$^5$ is H, with the provisos that when X is OH, R$^6$ is CH$_3$ or CH$_2$F, R$^5$ cannot be H;

(f) R$^6$ is H, CH$_3$, CH$_2$F, CHF$_2$, CF$_3$, or F;

(g) X is H, OH, OCH$_3$, F, NH$_2$ or N$_3$;

(h) Y is OH, NH$_2$, OCH$_3$, or OC(O)CH$_3$;

(i) R$^{10}$ is H, F, Br, I, OH, OR', NH$_2$, NHR', NR'$_2$, CO$_2$R', CONH$_2$, CONHR', CONR'$_2$, CH=CHCO$_2$H, or CH=CHCO$_2$R', wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or CR$^{12}$; and R$^{12}$ is an H, halogen (including F, Cl, Br, I), OR', NH$_2$, NHR', NR'$_2$, NO$_2$, lower alkyl of C$_1$-C$_6$, CO$_2$R', CONH$_2$, CONHR', CONR'$_2$, CH=CHCO$_2$H, or CH=CHCO$_2$R'; with the proviso that R$^{12}$ is not a: (i) —C≡C—H, (ii) —C=CH$_2$, or (iii) —NO$_2$.

A tenth aspect of the fourth embodiment is directed to a compound represented by formula I-8 wherein (a) R$^1$ is hydrogen, methyl, phenyl, p-bromo-phenyl, p-chloro-phenyl, p-fluorophenyl;

(b) R$^2$ is hydrogen;

(c) R$^{3a}$ is H and R$^{3b}$ is H, CH$_3$, CH(CH$_3$)$_2$, CH$_2$CH(CH$_3$)$_2$, CH(CH$_3$)CH$_2$CH$_3$, CH$_2$Ph, or lower cycloalkyl;

(d) R$^4$ is hydrogen, CH$_3$, Et, $^i$Pr, $^n$Pr, $^n$Bu, 2-butyl, $^t$Bu, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) R$^5$ is H, with the provisos that when X is OH, R$^6$ is CH$_3$ or CH$_2$F, R$^5$ cannot be H;

(f) R$^6$ is H, CH$_3$, CH$_2$F, CHF$_2$, CF$_3$, or F;

(g) X is H, OH, OCH$_3$, F, NH$_2$ or N$_3$;

(h) Y is OH, NH$_2$, OCH$_3$, or OC(O)CH$_3$;

(i) R$^{10}$ is H, F, Br, I, OH, OR', NH$_2$, NHR', NR'$_2$, CO$_2$R', CONH$_2$, CONHR', CONR'$_2$, CH=CHCO$_2$H, or CH=CHCO$_2$R', wherein R' is a lower alkyl, a lower cycloalkyl, or C(O) (lower alkyl) or alternatively, in the instance of NR'$_2$, each R' comprise at least one C atom that are joined to form a heterocycle comprising at least two carbon atoms; and (j) Z is N or CR$^{12}$; and R$^{12}$ is an H, halogen (including F, Cl, Br, I), OR', NH$_2$, NHR', NR'$_2$, NO$_2$, lower alkyl of C$_1$-C$_6$, CO$_2$R', CONH$_2$, CONHR', CONR'$_2$, CH=CHCO$_2$H, or CH=CHCO$_2$R'; with the proviso that R$^{12}$ is not a: (i) —C≡C—H, (ii) —C=CH$_2$, or (iii) —NO$_2$.

A fifth embodiment of the invention is directed to a compound represented by formula I in which the base is a structure represented by formula d above, wherein R$^1$, R$^2$, R$^{3a}$, R$^{3b}$, R$^4$, R$^5$, R$^6$, X, and Y are defined in the Summary of the Invention section above.

The first aspect of the fifth embodiment is directed to a compound represented by formula I-9

I-9 wherein (a) R$^1$ is hydrogen, n-alkyl; branched alkyl; cycloalkyl; or aryl, which includes, but is not limited to, phenyl or naphthyl, where phenyl or naphthyl are optionally substituted with at least one of C$_{1-6}$ alkyl, C$_{2-6}$ alkenyl, C$_{2-6}$ alkynyl, C$_{1-6}$ alkoxy, F, Cl, Br, I, nitro, cyano, $C_{1-6}$ haloalkyl, $-N(R^{1'})_2$, acylamino, $-NHSO_2C_{1-6}$ alkyl, $-SO_2N(R^{1'})_2$, $COR^{1''}$, and $-SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is $-OR'$ or $-N(R^{1'})_2$);

(b) $R^2$ is hydrogen or $CH_3$;

(c) $R^{3a}$ and $R^{3b}$ are (i) independently selected from hydrogen, $C_{1-10}$ alkyl, cycloalkyl, $-(CH_2)_c(NR^{3'})_2$, $C_{1-6}$ hydroxyalkyl, $-CH_2SH$, $-(CH_2)_2S(O)_dMe$, $-(CH_2)_3NHC(=NH)NH_2$, (1H-indol-3-yl)methyl, (1H-imidazol-4-yl)methyl, $-(CH_2)_eCOR^3$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_r$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^{3'}$ is independently hydrogen or $C_{1-6}$ alkyl and $R^{3''}$ is $-OR'$ or $-N(R^{3'})_2$); (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, $-CH_2CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, $CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is $-OR'$ or $-N(R^{3'})_2$);

(d) $R^4$ is hydrogen, $C_{1-10}$ alkyl, $C_{1-10}$ alkyl optionally substituted with a lower alkyl, alkoxy or halogen, $C_{1-10}$ haloalkyl, $C_{3-10}$ cycloalkyl, cycloalkyl alkyl, cycloheteroalkyl, aminoacyl, di(lower alkyl)amino-lower alkyl, aryl, such as phenyl, heteroaryl, such as, pyridinyl, substituted aryl, or substituted heteroaryl;

(e) $R^5$ is H, a lower alkyl, CN, vinyl, O-(lower alkyl), hydroxyl lower alkyl, i.e., $-(CH_2)_pOH$, where p is 1-6, including hydroxyl methyl $(CH_2OH)$, $CH_2F$, $N_3$, $CH_2CN$, $CH_2NH_2$, $CH_2NHCH_3$, $CH_2N(CH_3)_2$, alkyne (optionally substituted), or halogen, including F, Cl, Br, or I, with the provisos that when X is OH, base is cytosine and $R^6$ is H, $R^5$ cannot be $N_3$ and when X is OH, $R^6$ is $CH_3$ or $CH_2F$ and B is a purine base, $R^5$ cannot be H;

(f) $R^6$ is H, $CH_3$, $CH_2F$, $CHF_2$, $CF_3$, F, or CN;

(g) X is H, OH, F, OMe, halogen, $NH_2$, or $N_3$;

(h) Y is OH, H, $C_{1-4}$ alkyl, $C_{2-4}$ alkenyl, $C_{2-4}$ alkynyl, vinyl, $N_3$, CN, Cl, Br, F, I, $NO_2$, $OC(O)O(C_{1-4}$ alkyl), $OC(O)O(C_{1-4}$ alkyl), $OC(O)O(C_{2-4}$ alkynyl), $OC(O)O(C_{2-4}$ alkenyl), $OC_{1-10}$ haloalkyl, O(aminoacyl), $O(C_{1-10}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-18}$ acyl)$_2$, wherein alkyl, alkynyl, alkenyl and vinyl are optionally substituted by $N_3$, CN, one to three halogen (Cl, Br, F, I), $NO_2$, $C(O)O(C_{1-4}$ alkyl), $C(O)O(C_{1-4}$ alkyl), $C(O)O(C_{2-4}$ alkynyl), $C(O)O(C_{2-4}$ alkenyl), $O(C_{1-4}$ acyl), $O(C_{1-4}$ alkyl), $O(C_{2-4}$ alkenyl), $S(C_{1-4}$ acyl), $S(C_{1-4}$ alkyl), $S(C_{2-4}$ alkynyl), $S(C_{2-4}$ alkenyl), $SO(C_{1-4}$ acyl), $SO(C_{1-4}$ alkyl), $SO(C_{2-4}$ alkynyl), $SO(C_{2-4}$ alkenyl), $SO_2(C_{1-4}$ acyl), $SO_2(C_{1-4}$ alkyl), $SO_2(C_{2-4}$ alkynyl), $SO_2(C_{2-4}$ alkenyl), $OS(O)_2(C_{1-4}$ acyl), $OS(O)_2(C_{1-4}$ alkyl), $OS(O)_2(C_{2-4}$ alkenyl), $NH_2$, $NH(C_{1-4}$ alkyl), $NH(C_{2-4}$ alkenyl), $NH(C_{2-4}$ alkynyl), $NH(C_{1-4}$ acyl), $N(C_{1-4}$ alkyl)$_2$, $N(C_{1-4}$ acyl)$_2$.

A second aspect of the fifth embodiment is directed to a compound represented by formula I-9
wherein
(a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) R is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, $-CH_2CH_2SCH_3$, $CH_2CO_2H$, $CH_2C(O)NH_2$, $CH_2CH_2COOH$, $CH_2CH_2C(O)NH_2$, $CH_2CH_2CH_2NH_2$, $-CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_3$, $OCH_3$, $CH_2OH$, $CH_2F$, halogen, including F, Cl, Br, or I, with the provisos that when X is OH, $R^6$ is $CH_3$ or $CH_2F$, $R^5$ cannot be H.

(f) $R^6$ is H, $CH_3$, $CH_2F$, $CHF_2$, $CF_3$, F, or CN;

(g) X is H, OH, F, $OCH_3$, halogen, $NH_2$, or $N_3$;

(h) Y is OH, H, $CH_3$, vinyl, $NH_2$, $N_3$, CN, Cl, Br, F, 1, $OC(O)CH_3$, $OCH_3$;

A third aspect of the fifth embodiment is directed to a compound represented by formula I-9
wherein
(a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_2F$, F, Cl, Br, or I; with the proviso that X is OH, $R^6$ is $CH_3$ or $CH_2F$, $R^3$ cannot be H;

(f) $R^6$ is H, $CH_3$, $CH_2F$, $CHF_2$, $CF_3$, or F;

(g) X is H, OH, F, $OCH_3$, F, Cl, Br, I, $NH_2$ or $N_3$;

(h) Y is H, OH, $CH_3$, F, Cl, Br, I, $NH_2N_3$, $OCH_3$, or $OC(O)CH_3$;

A fourth aspect of the fifth embodiment is directed to a compound represented by formula I-9
wherein
(a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methylpyrrolidin-3-yl, N-methyl-pyrrolidin-4-yl, N-methyl-piperidin-4-yl, lower haloalkyl, or di(lower alkylamino-lower alkyl;

(e) $R^5$ is H, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, $OCH_3$, F, $NH_2$ or $N_3$;

(h) Y is OH, $NH_2$, $OCH_3$, or $OC(O)CH_3$;

A fifth aspect of the fifth embodiment is directed to a compound represented by formula I-9
wherein (a) $R^1$ is hydrogen, methyl, phenyl, p-bromo-phenyl, p-chloro-phenyl, p-fluorophenyl, (b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;

(e) $R^5$ is H, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, $OCH_3$, F, $NH_2$ or $N_3$;

(h) Y is OH, $NH_2$, $OCH_3$, or $OC(O)CH_3$;

A sixth aspect of the fifth embodiment is directed to a compound represented by formula I-10

I-10

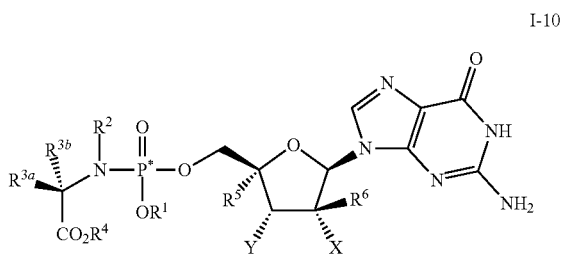

wherein (a) $R^1$ is hydrogen, methyl, ethyl, n-propyl, i-propyl, or a substituted or unsubstituted phenyl, where the substituent of the substituted phenyl is at least one of a $CH_3$, $OCH_3$, F, Cl, Br, I, nitro, cyano, and a $CH_{3-q}X_q$, where X is F, Cl, Br, or I, and q is 1-3;

(b) $R^2$ is hydrogen or $CH_3$;

$R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl or $R^{3a}$ is $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, CN, $CH_3$, $OCH_3$, $CH_2OH$, $CH_2F$, $N_3$, $CH_2CN$ $CH_2N_3$, $CH_2NH_2$, $CH_2NHCH_3$, $CH_2N(CH_3)_2$, halogen, including F, Cl, Br, or I, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, F, or CN;

(g) X is H, OH, F, $OCH_3$, Cl, Br, I, $NH_2$, or $N_3$, (h) Y is OH, H, $CH_3$, vinyl, $N_3$, CN, Cl, Br, F, I, $OC(O)CH_3$, $OCH_3$, $NH_2$, $NHCH_3$, NH(vinyl), NH(acetyl), NH(C(O)$CH_3$), $N(CH_3)_2$, $N(C(O)CH_3)_2$;

A seventh aspect of the fifth embodiment is directed to a compound represented by formula I-10
wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;

(e) $R^5$ is H, CN, $CH_3$, $OCH_3$, $CH_2OH$, $CH_2F$, halogen, including F, Cl, Br, or I, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, F, or CN;

(g) X is H, OH, F, $OCH_3$, Cl, Br, I, $NH_2$, or $N_3$; and (h) Y is OH, H, $CH_3$, vinyl, $NH_2$, $N_3$, CN, Cl, Br, F, I, $OC(O)CH_3$, $OCH_3$.

An eighth aspect of the fifth embodiment is directed to a compound represented by formula I-10
wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen or $CH_3$;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkylamino-lower alkyl;

(e) $R^5$ is H, CN, $CH_2F$, F, Cl, Br, or I, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, F, $OCH_3$, F, Cl, Br, I, $NH_2$ or $N_3$;

(h) Y is OH, H, $CH_3$, F, Cl, Br, I, $NH_2$ or $N_3$, $OCH_3$, or $OC(O)CH_3$;

A ninth aspect of the fifth embodiment is directed to a compound represented by formula I-10
wherein (a) $R^1$ is hydrogen, methyl, ethyl, n-propyl, i-propyl, phenyl, p-tolyl, p-bromo-phenyl, p-chloro-phenyl, p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-piperidin-4-yl, lower haloalkyl, or di(lower alkyl)amino-lower alkyl;

(e) $R^5$ is H, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, $OCH_3$, F, $NH_2$ or $N_3$;

(h) Y is OH, $NH_2$, OCH or $OC(O)CH_3$;

A tenth aspect of the fifth embodiment is directed to a compound represented by formula I-10
wherein (a) $R^1$ is hydrogen, methyl, phenyl, p-bromo-phenyl, p-chloro-phenyl, p-fluorophenyl;

(b) $R^2$ is hydrogen;

(c) $R^{3a}$ is H and $R^{3b}$ is H, $CH_3$, $CH(CH_3)_2$, $CH_2CH(CH_3)_2$, $CH(CH_3)CH_2CH_3$, $CH_2Ph$, or lower cycloalkyl;

(d) $R^4$ is hydrogen, $CH_3$, Et, $^iPr$, $^nPr$, $^nBu$, 2-butyl, $^tBu$, benzyl, cyclopropyl, cyclobutyl, cyclopentyl, cyclohexyl, N-methyl-aziridin-2-yl, N-methyl-azetidin-3-yl, N-methyl-pyrrolidin-3-yl, N-methyl-pyrrolidin-4-yl, N-methyl-piperidin-4-yl, lower haloalkyl, or di(lower alkyl)amino-lower alkyl;

(e) $R^5$ is H, with the provisos that when X is OH, $R^6$ is $CH_3$ or $CH_2F$, $R^5$ cannot be H;

(f) $R^6$ is H, $CH_3$, $CH_2F$, $CHF_2$, $CF_3$, or F;

(g) X is H, OH, $OCH_3$, F, $NH_2$ or $N_3$;

(h) Y is OH, $NH_2$, $OCH_3$, or $OC(O)CH_3$.

The following tables contain numeric identifiers associated with various substituent designators that should be viewed in light of the accompanying structure. These structures are contemplated species of the various aspects of the disclosed embodiments and are not intended to be limiting on full breadth of the contemplated compound represented by the structure of formula I. However, it is contemplated that any one of the exemplified nucleoside bases can be used in combination with any one of contemplated species that specify a particular combination of $R^1$, $R^2$, $R^{3a}$, $R^{3b}$, $R^4$, $R^5$, $R^6$, X, and Y. In each of the presented tables, the phosphoramidate substituent containing the substituents $R^{3a}$ and $R^{3b}$ are depicted without reference to stereochemical structure (cf. structures I-1, I-3, I-5, I-7, and I-9 above). It is contemplated that the compounds recited below embody compounds in which R projects toward the viewer while $R^{3b}$ projects away from the viewer (cf. structures I-2, I-4, I-6, I-8, and I-10). Moreover, it is contemplated that the compounds recited below also embody compounds in which $R^{3a}$ projects away from the viewer while $R^{3b}$ projects towards the viewer. Not meant to be limiting, however, it is contemplated that preferred compounds are those in which $R^{3a}$ projects towards the viewer and $R^{3b}$ projects away from the viewer such that the natural L-amino acid (S)-configuration is presented. Additionally, the inventors recognize that the phosphorus atom of the phosphoramidate moiety is another source of chirality. Although the structures below do not specifically depict chirality at phosphorus, the inventors recognize that stereochemical configurations are possible such that in a staggered (or zig-zag) line structure the oxo-substituent projects towards the viewer while the $OR^1$ substitutent projects away from the viewer, and vice versa, i.e., where the Cahn-Ingold-Prelog stereochemical designation of phosphorous is either R or S. Therefore, the structures below include all possible stereochemical configurations possible for phosphorus.

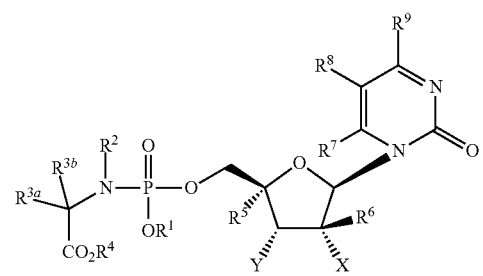

II

TABLE II-1

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-1-1 | $CH_3$ | H | H | H | $CH_3$ | H | $CH_3$ | OH | OH | H | H | $NH_2$ |
| II-1-2 | $CH_3$ | H | H | $CH_3$ | $CH_3$ | H | $CH_3$ | OH | OH | H | H | $NH_2$ |
| II-1-3 | $CH_3$ | H | H | $CH(CH_3)_2$ | $CH_3$ | H | $CH_3$ | OH | OH | H | H | $NH_2$ |
| II-1-4 | $CH_3$ | H | H | $CH_2CH(CH_3)_2$ | $CH_3$ | H | $CH_3$ | OH | OH | H | H | $NH_2$ |
| II-1-5 | $CH_3$ | H | H | $CH_2Ph$ | $CH_3$ | H | $CH_3$ | OH | OH | H | H | $NH_2$ |
| II-1-6 | $CH_3$ | H | H | $CH_2$-indol-3-yl | $CH_3$ | H | $CH_3$ | OH | OH | H | H | $NH_2$ |
| II-1-7 | $CH_3$ | H | H | $CH_2CH_2SCH_3$ | $CH_3$ | H | $CH_3$ | OH | OH | H | H | $NH_2$ |
| II-1-8 | $CH_3$ | * | H | * | $CH_3$ | H | $CH_3$ | OH | OH | H | H | $NH_2$ |

*$R^2$ and $R^{3b}$ joined together by $(CH_2)_3$ to form five-membered ring.

TABLE II-2

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-2-1 | Et | H | H | H | $CH_3$ | H | $CH_3$ | OH | OH | H | H | $NH_2$ |
| II-2-2 | Et | H | H | $CH_3$ | $CH_3$ | H | $CH_3$ | OH | OH | H | H | $NH_2$ |
| II-2-3 | Et | H | H | $CH(CH_3)_2$ | $CH_3$ | H | $CH_3$ | OH | OH | H | H | $NH_2$ |
| II-2-4 | Et | H | H | $CH_2CH(CH_3)_2$ | $CH_3$ | H | $CH_3$ | OH | OH | H | H | $NH_2$ |
| II-2-5 | Et | H | H | $CH_2Ph$ | $CH_3$ | H | $CH_3$ | OH | OH | H | H | $NH_2$ |
| II-2-6 | Et | H | H | $CH_2$-indol-3-yl | $CH_3$ | H | $CH_3$ | OH | OH | H | H | $NH_2$ |
| II-2-7 | Et | H | H | $CH_2CH_2SCH_3$ | $CH_3$ | H | $CH_3$ | OH | OH | H | H | $NH_2$ |
| II-2-8 | Et | * | H | * | $CH_3$ | H | $CH_3$ | OH | OH | H | H | $NH_2$ |

*$R^2$ and $R^{3b}$ joined together by $(CH_2)_3$ to form five-membered ring.

TABLE II-3

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-3-1 | ⁱPr | H | H | H | CH₃ | H | CH₃ | OH | OH | H | H | NH₂ |
| II-3-2 | ⁱPr | H | H | CH₃ | CH₃ | H | CH₃ | OH | OH | H | H | NH₂ |
| II-3-3 | ⁱPr | H | H | CH(CH₃)₂ | CH₃ | H | CH₃ | OH | OH | H | H | NH₂ |
| II-3-4 | ⁱPr | H | H | CH₂CH(CH₃)₂ | CH₃ | H | CH₃ | OH | OH | H | H | NH₂ |
| II-3-5 | ⁱPr | H | H | CH₂Ph | CH₃ | H | CH₃ | OH | OH | H | H | NH₂ |
| II-3-6 | ⁱPr | H | H | CH₂-indol-3-yl | CH₃ | H | CH₃ | OH | OH | H | H | NH₂ |
| II-3-7 | ⁱPr | H | H | CH₂CH₂SCH₃ | CH₃ | H | CH₃ | OH | OH | H | H | NH₂ |
| II-3-8 | ⁱPr | * | H | * | CH₃ | H | CH₃ | OH | OH | H | H | NH₂ |

*R² and R³ᵇ joined together by (CH₂)₃ to form five-membered ring.

TABLE II-4

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-4-1 | ᵗBu | H | H | H | CH₃ | H | CH₃ | OH | OH | H | H | NH₂ |
| II-4-2 | ᵗBu | H | H | CH₃ | CH₃ | H | CH₃ | OH | OH | H | H | NH₂ |
| II-4-3 | ᵗBu | H | H | CH(CH₃)₂ | CH₃ | H | CH₃ | OH | OH | H | H | NH₂ |
| II-4-4 | ᵗBu | H | H | CH₂CH(CH₃)₂ | CH₃ | H | CH₃ | OH | OH | H | H | NH₂ |
| II-4-5 | ᵗBu | H | H | CH₂Ph | CH₃ | H | CH₃ | OH | OH | H | H | NH₂ |
| II-4-6 | ᵗBu | H | H | CH₂-indol-3-yl | CH₃ | H | CH₃ | OH | OH | H | H | NH₂ |
| II-4-7 | ᵗBu | H | H | CH₂CH₂SCH₃ | CH₃ | H | CH₃ | OH | OH | H | H | NH₂ |
| II-4-8 | ᵗBu | * | H | * | CH₃ | H | CH₃ | OH | OH | H | H | NH₂ |

*R² and R³ᵇ joined together by (CH₂)₃ to form five-membered ring.

TABLE II-5

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-5-1 | Ph | H | H | H | CH₃ | H | CH₃ | OH | OH | H | H | NH₂ |
| II-5-2 | Ph | H | H | CH₃ | CH₃ | H | CH₃ | OH | OH | H | H | NH₂ |
| II-5-3 | Ph | H | H | CH(CH₃)₂ | CH₃ | H | CH₃ | OH | OH | H | H | NH₂ |
| II-5-4 | Ph | H | H | CH₂CH(CH₃)₂ | CH₃ | H | CH₃ | OH | OH | H | H | NH₂ |
| II-5-5 | Ph | H | H | CH₂Ph | CH₃ | H | CH₃ | OH | OH | H | H | NH₂ |
| II-5-6 | Ph | H | H | CH₂-indol-3-yl | CH₃ | H | CH₃ | OH | OH | H | H | NH₂ |
| II-5-7 | Ph | H | H | CH₂CH₂SCH₃ | CH₃ | H | CH₃ | OH | OH | H | H | NH₂ |
| II-5-8 | Ph | * | H | * | CH₃ | H | CH₃ | OH | OH | H | H | NH₂ |

*R² and R³ᵇ joined together by (CH₂)₃ to form five-membered ring.

TABLE II-6

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-6-1 | p-Me—Ph | H | H | H | CH₃ | H | CH₃ | OH | OH | H | H | NH₂ |
| II-6-2 | p-Me—Ph | H | H | CH₃ | CH₃ | H | CH₃ | OH | OH | H | H | NH₂ |
| II-6-3 | p-Me—Ph | H | H | CH(CH₃)₂ | CH₃ | H | CH₃ | OH | OH | H | H | NH₂ |
| II-6-4 | p-Me—Ph | H | H | CH₂CH(CH₃)₂ | CH₃ | H | CH₃ | OH | OH | H | H | NH₂ |
| II-6-5 | p-Me—Ph | H | H | CH₂Ph | CH₃ | H | CH₃ | OH | OH | H | H | NH₂ |
| II-6-6 | p-Me—Ph | H | H | CH₂-indol-3-yl | CH₃ | H | CH₃ | OH | OH | H | H | NH₂ |
| II-6-7 | p-Me—Ph | H | H | CH₂CH₂SCH₃ | CH₃ | H | CH₃ | OH | OH | H | H | NH₂ |
| II-6-8 | p-Me—Ph | * | H | * | CH₃ | H | CH₃ | OH | OH | H | H | NH₂ |

*R² and R³ᵇ joined together by (CH₂)₃ to form five-membered ring.

TABLE II-7

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-7-1 | p-F—Ph | H | H | H | CH₃ | H | CH₃ | OH | OH | H | H | NH₂ |
| II-7-2 | p-F—Ph | H | H | CH₃ | CH₃ | H | CH₃ | OH | OH | H | H | NH₂ |
| II-7-3 | p-F—Ph | H | H | CH(CH₃)₂ | CH₃ | H | CH₃ | OH | OH | H | H | NH₂ |

TABLE II-7-continued

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-7-4 | p-F—Ph | H | H | $CH_2CH(CH_3)_2$ | $CH_3$ | H | $CH_3$ | OH | OH | H | H | $NH_2$ |
| II-7-6 | p-F—Ph | H | H | $CH_2Ph$ | $CH_3$ | H | $CH_3$ | OH | OH | H | H | $NH_2$ |
| II-7-7 | p-F—Ph | H | H | $CH_2$-indol-3-yl | $CH_3$ | H | $CH_3$ | OH | OH | H | H | $NH_2$ |
| II-7-8 | p-F—Ph | H | H | $CH_2CH_2SCH_3$ | $CH_3$ | H | $CH_3$ | OH | OH | H | H | $NH_2$ |
| II-7-20 | p-F—Ph | * | H | * | $CH_3$ | H | $CH_3$ | OH | OH | H | H | $NH_2$ |

*$R^2$ and $R^{3b}$ joined together by $(CH_2)_3$ to form five-membered ring.

TABLE II-8

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-8-1 | p-Cl—Ph | H | H | H | $CH_3$ | H | $CH_3$ | OH | OH | H | H | $NH_2$ |
| II-8-2 | p-Cl—Ph | H | H | $CH_3$ | $CH_3$ | H | $CH_3$ | OH | OH | H | H | $NH_2$ |
| II-8-3 | p-Cl—Ph | H | H | $CH(CH_3)_2$ | $CH_3$ | H | $CH_3$ | OH | OH | H | H | $NH_2$ |
| II-8-4 | p-Cl—Ph | H | H | $CH_2CH(CH_3)_2$ | $CH_3$ | H | $CH_3$ | OH | OH | H | H | $NH_2$ |
| II-8-5 | p-Cl—Ph | H | H | $CH_2Ph$ | $CH_3$ | H | $CH_3$ | OH | OH | H | H | $NH_2$ |
| II-8-6 | p-Cl—Ph | H | H | $CH_2$-indol-3-yl | $CH_3$ | H | $CH_3$ | OH | OH | H | H | $NH_2$ |
| II-8-7 | p-Cl—Ph | H | H | $CH_2CH_2SCH_3$ | $CH_3$ | H | $CH_3$ | OH | OH | H | H | $NH_2$ |
| II-8-8 | p-Cl—Ph | * | H | * | $CH_3$ | H | $CH_3$ | OH | OH | H | H | $NH_2$ |

*$R^2$ and $R^{3b}$ joined together by $(CH_2)_3$ to form five-membered ring.

TABLE II-9

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-9-1 | p-Br—Ph | H | H | H | $CH_3$ | H | $CH_3$ | OH | OH | H | H | $NH_2$ |
| II-9-2 | p-Br—Ph | H | H | $CH_3$ | $CH_3$ | H | $CH_3$ | OH | OH | H | H | $NH_2$ |
| II-9-3 | p-Br—Ph | H | H | $CH(CH_3)_2$ | $CH_3$ | H | $CH_3$ | OH | OH | H | H | $NH_2$ |
| II-9-4 | p-Br—Ph | H | H | $CH_2CH(CH_3)_2$ | $CH_3$ | H | $CH_3$ | OH | OH | H | H | $NH_2$ |
| II-9-6 | p-Br—Ph | H | H | $CH_2Ph$ | $CH_3$ | H | $CH_3$ | OH | OH | H | H | $NH_2$ |
| II-9-7 | p-Br—Ph | H | H | $CH_2$-indol-3-yl | $CH_3$ | H | $CH_3$ | OH | OH | H | H | $NH_2$ |
| II-9-8 | p-Br—Ph | H | H | $CH_2CH_2SCH_3$ | $CH_3$ | H | $CH_3$ | OH | OH | H | H | $NH_2$ |
| II-9-20 | p-Br—Ph | * | H | * | $CH_3$ | H | $CH_3$ | OH | OH | H | H | $NH_2$ |

*$R^2$ and $R^{3b}$ joined together by $(CH_2)_3$ to form five-membered ring.

TABLE II-10

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-10-1 | p-I—Ph | H | H | H | $CH_3$ | H | $CH_3$ | OH | OH | H | H | $NH_2$ |
| II-10-2 | p-I—Ph | H | H | $CH_3$ | $CH_3$ | H | $CH_3$ | OH | OH | H | H | $NH_2$ |
| II-10-3 | p-I—Ph | H | H | $CH(CH_3)_2$ | $CH_3$ | H | $CH_3$ | OH | OH | H | H | $NH_2$ |
| II-10-4 | p-I—Ph | H | H | $CH_2CH(CH_3)_2$ | $CH_3$ | H | $CH_3$ | OH | OH | H | H | $NH_2$ |
| II-10-5 | p-I—Ph | H | H | $CH_2Ph$ | $CH_3$ | H | $CH_3$ | OH | OH | H | H | $NH_2$ |
| II-10-6 | p-I—Ph | H | H | $CH_2$-indol-3-yl | $CH_3$ | H | $CH_3$ | OH | OH | H | H | $NH_2$ |
| II-10-7 | p-I—Ph | H | H | $CH_2CH_2SCH_3$ | $CH_3$ | H | $CH_3$ | OH | OH | H | H | $NH_2$ |
| II-10-8 | p-I—Ph | * | H | * | $CH_3$ | H | $CH_3$ | OH | OH | H | H | $NH_2$ |

*$R^2$ and $R^{3b}$ joined together by $(CH_2)_3$ to form five-membered ring.

TABLE II-11

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-11-1 | $CH_3$ | H | H | H | Et | H | $CH_3$ | OH | OH | H | H | $NH_2$ |
| II-11-2 | $CH_3$ | H | H | $CH_3$ | Et | H | $CH_3$ | OH | OH | H | H | $NH_2$ |
| II-11-3 | $CH_3$ | H | H | $CH(CH_3)_2$ | Et | H | $CH_3$ | OH | OH | H | H | $NH_2$ |
| II-11-4 | $CH_3$ | H | H | $CH_2CH(CH_3)_2$ | Et | H | $CH_3$ | OH | OH | H | H | $NH_2$ |
| II-11-5 | $CH_3$ | H | H | $CH_2Ph$ | Et | H | $CH_3$ | OH | OH | H | H | $NH_2$ |
| II-11-6 | $CH_3$ | H | H | $CH_2$-indol-3-yl | Et | H | $CH_3$ | OH | OH | H | H | $NH_2$ |
| II-11-7 | $CH_3$ | H | H | $CH_2CH_2SCH_3$ | Et | H | $CH_3$ | OH | OH | H | H | $NH_2$ |
| II-11-8 | $CH_3$ | * | H | * | Et | H | $CH_3$ | OH | OH | H | H | $NH_2$ |

*$R^2$ and $R^{3b}$ joined together by $(CH_2)_3$ to form five-membered ring.

TABLE II-12

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-12-1 | Et | H | H | H | Et | H | $CH_3$ | OH | OH | H | H | $NH_2$ |
| II-12-2 | Et | H | H | $CH_3$ | Et | H | $CH_3$ | OH | OH | H | H | $NH_2$ |
| II-12-3 | Et | H | H | $CH(CH_3)_2$ | Et | H | $CH_3$ | OH | OH | H | H | $NH_2$ |
| II-12-4 | Et | H | H | $CH_2CH(CH_3)_2$ | Et | H | $CH_3$ | OH | OH | H | H | $NH_2$ |
| II-12-5 | Et | H | H | $CH_2Ph$ | Et | H | $CH_3$ | OH | OH | H | H | $NH_2$ |
| II-12-6 | Et | H | H | $CH_2$-indol-3-yl | Et | H | $CH_3$ | OH | OH | H | H | $NH_2$ |
| II-12-7 | Et | H | H | $CH_2CH_2SCH_3$ | Et | H | $CH_3$ | OH | OH | H | H | $NH_2$ |
| II-12-8 | Et | * | H | * | Et | H | $CH_3$ | OH | OH | H | H | $NH_2$ |

*$R^2$ and $R^{3b}$ joined together by $(CH_2)_3$ to form five-membered ring.

TABLE II-13

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-13-1 | $^i$Pr | H | H | H | Et | H | $CH_3$ | OH | OH | H | H | $NH_2$ |
| II-13-2 | $^i$Pr | H | H | $CH_3$ | Et | H | $CH_3$ | OH | OH | H | H | $NH_2$ |
| II-13-3 | $^i$Pr | H | H | $CH(CH_3)_2$ | Et | H | $CH_3$ | OH | OH | H | H | $NH_2$ |
| II-13-4 | $^i$Pr | H | H | $CH_2CH(CH_3)_2$ | Et | H | $CH_3$ | OH | OH | H | H | $NH_2$ |
| II-13-5 | $^i$Pr | H | H | $CH_2Ph$ | Et | H | $CH_3$ | OH | OH | H | H | $NH_2$ |
| II-13-6 | $^i$Pr | H | H | $CH_2$-indol-3-yl | Et | H | $CH_3$ | OH | OH | H | H | $NH_2$ |
| II-13-7 | $^i$Pr | H | H | $CH_2CH_2SCH_3$ | Et | H | $CH_3$ | OH | OH | H | H | $NH_2$ |
| II-13-8 | $^i$Pr | * | H | * | Et | H | $CH_3$ | OH | OH | H | H | $NH_2$ |

*$R^2$ and $R^{3b}$ joined together by $(CH_2)_3$ to form five-membered ring.

TABLE II-14

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-14-1 | $^t$Bu | H | H | H | Et | H | $CH_3$ | OH | OH | H | H | $NH_2$ |
| II-14-2 | $^t$Bu | H | H | $CH_3$ | Et | H | $CH_3$ | OH | OH | H | H | $NH_2$ |
| II-14-3 | $^t$Bu | H | H | $CH(CH_3)_2$ | Et | H | $CH_3$ | OH | OH | H | H | $NH_2$ |
| II-14-4 | $^t$Bu | H | H | $CH_2CH(CH_3)_2$ | Et | H | $CH_3$ | OH | OH | H | H | $NH_2$ |
| II-14-5 | $^t$Bu | H | H | $CH_2Ph$ | Et | H | $CH_3$ | OH | OH | H | H | $NH_2$ |
| II-14-6 | $^t$Bu | H | H | $CH_2$-indol-3-yl | Et | H | $CH_3$ | OH | OH | H | H | $NH_2$ |
| II-14-7 | $^t$Bu | H | H | $CH_2CH_2SCH_3$ | Et | H | $CH_3$ | OH | OH | H | H | $NH_2$ |
| II-14-8 | $^t$Bu | * | H | * | Et | H | $CH_3$ | OH | OH | H | H | $NH_2$ |

*$R^2$ and $R^{3b}$ joined together by $(CH_2)_3$ to form five-membered ring.

TABLE II-15

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-15-1 | Ph | H | H | H | Et | H | $CH_3$ | OH | OH | H | H | $NH_2$ |
| II-15-2 | Ph | H | H | $CH_3$ | Et | H | $CH_3$ | OH | OH | H | H | $NH_2$ |
| II-15-3 | Ph | H | H | $CH(CH_3)_2$ | Et | H | $CH_3$ | OH | OH | H | H | $NH_2$ |
| II-15-4 | Ph | H | H | $CH_2CH(CH_3)_2$ | Et | H | $CH_3$ | OH | OH | H | H | $NH_2$ |
| II-15-5 | Ph | H | H | $CH_2Ph$ | Et | H | $CH_3$ | OH | OH | H | H | $NH_2$ |
| II-15-6 | Ph | H | H | $CH_2$-indol-3-yl | Et | H | $CH_3$ | OH | OH | H | H | $NH_2$ |
| II-15-7 | Ph | H | H | $CH_2CH_2SCH_3$ | Et | H | $CH_3$ | OH | OH | H | H | $NH_2$ |
| II-15-8 | Ph | * | H | * | Et | H | $CH_3$ | OH | OH | H | H | $NH_2$ |

*$R^2$ and $R^{3b}$ joined together by $(CH_2)_3$ to form five-membered ring.

TABLE II-16

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-16-1 | p-Me—Ph | H | H | H | Et | H | $CH_3$ | OH | OH | H | H | $NH_2$ |
| II-16-2 | p-Me—Ph | H | H | $CH_3$ | Et | H | $CH_3$ | OH | OH | H | H | $NH_2$ |
| II-16-3 | p-Me—Ph | H | H | $CH(CH_3)_2$ | Et | H | $CH_3$ | OH | OH | H | H | $NH_2$ |

TABLE II-16-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-16-4 | p-Me—Ph | H | H | CH$_2$CH(CH$_3$)$_2$ | Et | H | CH$_3$ | OH | OH | H | H | NH$_2$ |
| II-16-5 | p-Me—Ph | H | H | CH$_2$Ph | Et | H | CH$_3$ | OH | OH | H | H | NH$_2$ |
| II-16-6 | p-Me—Ph | H | H | CH$_2$-indol-3-yl | Et | H | CH$_3$ | OH | OH | H | H | NH$_2$ |
| II-16-7 | p-Me—Ph | H | H | CH$_2$CH$_2$SCH$_3$ | Et | H | CH$_3$ | OH | OH | H | H | NH$_2$ |
| II-16-8 | p-Me—Ph | * | H | * | Et | H | CH$_3$ | OH | OH | H | H | NH$_2$ |

*R² and R³ᵇ joined together by (CH$_2$)$_3$ to form five-membered ring.

TABLE II-17

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-17-1 | p-F—Ph | H | H | H | Et | H | CH$_3$ | OH | OH | H | H | NH$_2$ |
| II-17-2 | p-F—Ph | H | H | CH$_3$ | Et | H | CH$_3$ | OH | OH | H | H | NH$_2$ |
| II-17-3 | p-F—Ph | H | H | CH(CH$_3$)$_2$ | Et | H | CH$_3$ | OH | OH | H | H | NH$_2$ |
| II-17-4 | p-F—Ph | H | H | CH$_2$CH(CH$_3$)$_2$ | Et | H | CH$_3$ | OH | OH | H | H | NH$_2$ |
| II-17-5 | p-F—Ph | H | H | CH$_2$Ph | Et | H | CH$_3$ | OH | OH | H | H | NH$_2$ |
| II-17-6 | p-F—Ph | H | H | CH$_2$-indol-3-yl | Et | H | CH$_3$ | OH | OH | H | H | NH$_2$ |
| II-17-7 | p-F—Ph | H | H | CH$_2$CH$_2$SCH$_3$ | Et | H | CH$_3$ | OH | OH | H | H | NH$_2$ |
| II-17-8 | p-F—Ph | * | H | * | Et | H | CH$_3$ | OH | OH | H | H | NH$_2$ |

*R² and R³ᵇ joined together by (CH$_2$)$_3$ to form five-membered ring.

TABLE II-18

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-18-1 | p-Cl—Ph | H | H | H | Et | H | CH$_3$ | OH | OH | H | H | NH$_2$ |
| II-18-2 | p-Cl—Ph | H | H | CH$_3$ | Et | H | CH$_3$ | OH | OH | H | H | NH$_2$ |
| II-18-3 | p-Cl—Ph | H | H | CH(CH$_3$)$_2$ | Et | H | CH$_3$ | OH | OH | H | H | NH$_2$ |
| II-18-4 | p-Cl—Ph | H | H | CH$_2$CH(CH$_3$)$_2$ | Et | H | CH$_3$ | OH | OH | H | H | NH$_2$ |
| II-18-5 | p-Cl—Ph | H | H | CH$_2$Ph | Et | H | CH$_3$ | OH | OH | H | H | NH$_2$ |
| II-18-6 | p-Cl—Ph | H | H | CH$_2$-indol-3-yl | Et | H | CH$_3$ | OH | OH | H | H | NH$_2$ |
| II-18-7 | p-Cl—Ph | H | H | CH$_2$CH$_2$SCH$_3$ | Et | H | CH$_3$ | OH | OH | H | H | NH$_2$ |
| II-18-8 | p-Cl—Ph | * | H | * | Et | H | CH$_3$ | OH | OH | H | H | NH$_2$ |

*R² and R³ᵇ joined together by (CH$_2$)$_3$ to form five-membered ring.

TABLE II-19

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-19-1 | p-Br—Ph | H | H | H | Et | H | CH$_3$ | OH | OH | H | H | NH$_2$ |
| II-19-2 | p-Br—Ph | H | H | CH$_3$ | Et | H | CH$_3$ | OH | OH | H | H | NH$_2$ |
| II-19-3 | p-Br—Ph | H | H | CH(CH$_3$)$_2$ | Et | H | CH$_3$ | OH | OH | H | H | NH$_2$ |
| II-19-4 | p-Br—Ph | H | H | CH$_2$CH(CH$_3$)$_2$ | Et | H | CH$_3$ | OH | OH | H | H | NH$_2$ |
| II-19-5 | p-Br—Ph | H | H | CH$_2$Ph | Et | H | CH$_3$ | OH | OH | H | H | NH$_2$ |
| II-19-6 | p-Br—Ph | H | H | CH$_2$-indol-3-yl | Et | H | CH$_3$ | OH | OH | H | H | NH$_2$ |
| II-19-7 | p-Br—Ph | H | H | CH$_2$CH$_2$SCH$_3$ | Et | H | CH$_3$ | OH | OH | H | H | NH$_2$ |
| II-19-8 | p-Br—Ph | * | H | * | Et | H | CH$_3$ | OH | OH | H | H | NH$_2$ |

*R² and R³ᵇ joined together by (CH$_2$)$_3$ to form five-membered ring.

TABLE II-20

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-20-1 | p-I—Ph | H | H | H | Et | H | CH$_3$ | OH | OH | H | H | NH$_2$ |
| II-20-2 | p-I—Ph | H | H | CH$_3$ | Et | H | CH$_3$ | OH | OH | H | H | NH$_2$ |
| II-20-3 | p-I—Ph | H | H | CH(CH$_3$)$_2$ | Et | H | CH$_3$ | OH | OH | H | H | NH$_2$ |
| II-20-4 | p-I—Ph | H | H | CH$_2$CH(CH$_3$)$_2$ | Et | H | CH$_3$ | OH | OH | H | H | NH$_2$ |
| II-20-5 | p-I—Ph | H | H | CH$_2$Ph | Et | H | CH$_3$ | OH | OH | H | H | NH$_2$ |
| II-20-6 | p-I—Ph | H | H | CH$_2$-indol-3-yl | Et | H | CH$_3$ | OH | OH | H | H | NH$_2$ |
| II-20-7 | p-I—Ph | H | H | CH$_2$CH$_2$SCH$_3$ | Et | H | CH$_3$ | OH | OH | H | H | NH$_2$ |
| II-20-8 | p-I—Ph | * | H | * | Et | H | CH$_3$ | OH | OH | H | H | NH$_2$ |

*R² and R³ᵇ joined together by (CH$_2$)$_3$ to form five-membered ring.

TABLE II-21

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-21-1 | $CH_3$ | H | H | H | $^iPr$ | H | $CH_3$ | OH | OH | H | H | $NH_2$ |
| II-21-2 | $CH_3$ | H | H | $CH_3$ | $^iPr$ | H | $CH_3$ | OH | OH | H | H | $NH_2$ |
| II-21-3 | $CH_3$ | H | H | $CH(CH_3)_2$ | $^iPr$ | H | $CH_3$ | OH | OH | H | H | $NH_2$ |
| II-21-4 | $CH_3$ | H | H | $CH_2CH(CH_3)_2$ | $^iPr$ | H | $CH_3$ | OH | OH | H | H | $NH_2$ |
| II-21-5 | $CH_3$ | H | H | $CH_2Ph$ | $^iPr$ | H | $CH_3$ | OH | OH | H | H | $NH_2$ |
| II-21-6 | $CH_3$ | H | H | $CH_2$-indol-3-yl | $^iPr$ | H | $CH_3$ | OH | OH | H | H | $NH_2$ |
| II-21-7 | $CH_3$ | H | H | $CH_2CH_2SCH_3$ | $^iPr$ | H | $CH_3$ | OH | OH | H | H | $NH_2$ |
| II-21-8 | $CH_3$ | * | H | * | $^iPr$ | H | $CH_3$ | OH | OH | H | H | $NH_2$ |

*$R^2$ and $R^{3b}$ joined together by $(CH_2)_3$ to form five-membered ring.

TABLE II-22

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-22-1 | Et | H | H | H | $^iPr$ | H | $CH_3$ | OH | OH | H | H | $NH_2$ |
| II-22-2 | Et | H | H | $CH_3$ | $^iPr$ | H | $CH_3$ | OH | OH | H | H | $NH_2$ |
| II-22-3 | Et | H | H | $CH(CH_3)_2$ | $^iPr$ | H | $CH_3$ | OH | OH | H | H | $NH_2$ |
| II-22-4 | Et | H | H | $CH_2CH(CH_3)_2$ | $^iPr$ | H | $CH_3$ | OH | OH | H | H | $NH_2$ |
| II-22-5 | Et | H | H | $CH_2Ph$ | $^iPr$ | H | $CH_3$ | OH | OH | H | H | $NH_2$ |
| II-22-6 | Et | H | H | $CH_2$-indol-3-yl | $^iPr$ | H | $CH_3$ | OH | OH | H | H | $NH_2$ |
| II-22-7 | Et | H | H | $CH_2CH_2SCH_3$ | $^iPr$ | H | $CH_3$ | OH | OH | H | H | $NH_2$ |
| II-22-8 | Et | * | H | * | $^iPr$ | H | $CH_3$ | OH | OH | H | H | $NH_2$ |

*$R^2$ and $R^{3b}$ joined together by $(CH_2)_3$ to form five-membered ring.

TABLE II-23

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-23-1 | $^iPr$ | H | H | H | $^iPr$ | H | $CH_3$ | OH | OH | H | H | $NH_2$ |
| II-23-2 | $^iPr$ | H | H | $CH_3$ | $^iPr$ | H | $CH_3$ | OH | OH | H | H | $NH_2$ |
| II-23-3 | $^iPr$ | H | H | $CH(CH_3)_2$ | $^iPr$ | H | $CH_3$ | OH | OH | H | H | $NH_2$ |
| II-23-4 | $^iPr$ | H | H | $CH_2CH(CH_3)_2$ | $^iPr$ | H | $CH_3$ | OH | OH | H | H | $NH_2$ |
| II-23-5 | $^iPr$ | H | H | $CH_2Ph$ | $^iPr$ | H | $CH_3$ | OH | OH | H | H | $NH_2$ |
| II-23-6 | $^iPr$ | H | H | $CH_2$-indol-3-yl | $^iPr$ | H | $CH_3$ | OH | OH | H | H | $NH_2$ |
| II-23-7 | $^iPr$ | H | H | $CH_2CH_2SCH_3$ | $^iPr$ | H | $CH_3$ | OH | OH | H | H | $NH_2$ |
| II-23-8 | $^iPr$ | * | H | * | $^iPr$ | H | $CH_3$ | OH | OH | H | H | $NH_2$ |

*$R^2$ and $R^{3b}$ joined together by $(CH_2)_3$ to form five-membered ring.

TABLE II-24

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-24-1 | $^tBu$ | H | H | H | $^iPr$ | H | $CH_3$ | OH | OH | H | H | $NH_2$ |
| II-24-2 | $^tBu$ | H | H | $CH_3$ | $^iPr$ | H | $CH_3$ | OH | OH | H | H | $NH_2$ |
| II-24-3 | $^tBu$ | H | H | $CH(CH_3)_2$ | $^iPr$ | H | $CH_3$ | OH | OH | H | H | $NH_2$ |
| II-24-4 | $^tBu$ | H | H | $CH_2CH(CH_3)_2$ | $^iPr$ | H | $CH_3$ | OH | OH | H | H | $NH_2$ |
| II-24-5 | $^tBu$ | H | H | $CH_2Ph$ | $^iPr$ | H | $CH_3$ | OH | OH | H | H | $NH_2$ |
| II-24-6 | $^tBu$ | H | H | $CH_2$-indol-3-yl | $^iPr$ | H | $CH_3$ | OH | OH | H | H | $NH_2$ |
| II-24-7 | $^tBu$ | H | H | $CH_2CH_2SCH_3$ | $^iPr$ | H | $CH_3$ | OH | OH | H | H | $NH_2$ |
| II-24-8 | $^tBu$ | * | H | * | $^iPr$ | H | $CH_3$ | OH | OH | H | H | $NH_2$ |

*$R^2$ and $R^{3b}$ joined together by $(CH_2)_3$ to form five-membered ring.

TABLE II-25

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-25-1 | Ph | H | H | H | $^iPr$ | H | $CH_3$ | OH | OH | H | H | $NH_2$ |
| II-25-2 | Ph | H | H | $CH_3$ | $^iPr$ | H | $CH_3$ | OH | OH | H | H | $NH_2$ |
| II-25-3 | Ph | H | H | $CH(CH_3)_2$ | $^iPr$ | H | $CH_3$ | OH | OH | H | H | $NH_2$ |

TABLE II-25-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-25-4 | Ph | H | H | CH₂CH(CH₃)₂ | $^i$Pr | H | CH₃ | OH | OH | H | H | NH₂ |
| II-25-5 | Ph | H | H | CH₂Ph | $^i$Pr | H | CH₃ | OH | OH | H | H | NH₂ |
| II-25-6 | Ph | H | H | CH₂-indol-3-yl | $^i$Pr | H | CH₃ | OH | OH | H | H | NH₂ |
| II-25-7 | Ph | H | H | CH₂CH₂SCH₃ | $^i$Pr | H | CH₃ | OH | OH | H | H | NH₂ |
| II-25-8 | Ph | * | H | * | $^i$Pr | H | CH₃ | OH | OH | H | H | NH₂ |

*R² and R³ᵇ joined together by (CH₂)₃ to form five-membered ring.

TABLE II-26

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-26-1 | p-Me—Ph | H | H | H | $^i$Pr | H | CH₃ | OH | OH | H | H | NH₂ |
| II-26-2 | p-Me—Ph | H | H | CH₃ | $^i$Pr | H | CH₃ | OH | OH | H | H | NH₂ |
| II-26-3 | p-Me—Ph | H | H | CH(CH₃)₂ | $^i$Pr | H | CH₃ | OH | OH | H | H | NH₂ |
| II-26-4 | p-Me—Ph | H | H | CH₂CH(CH₃)₂ | $^i$Pr | H | CH₃ | OH | OH | H | H | NH₂ |
| II-26-5 | p-Me—Ph | H | H | CH₂Ph | $^i$Pr | H | CH₃ | OH | OH | H | H | NH₂ |
| II-26-6 | p-Me—Ph | H | H | CH₂-indol-3-yl | $^i$Pr | H | CH₃ | OH | OH | H | H | NH₂ |
| II-26-7 | p-Me—Ph | H | H | CH₂CH₂SCH₃ | $^i$Pr | H | CH₃ | OH | OH | H | H | NH₂ |
| II-26-8 | p-Me—Ph | * | H | * | $^i$Pr | H | CH₃ | OH | OH | H | H | NH₂ |

*R² and R³ᵇ joined together by (CH₂)₃ to form five-membered ring.

TABLE II-27

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-27-1 | p-F—Ph | H | H | H | $^i$Pr | H | CH₃ | OH | OH | H | H | NH₂ |
| II-27-2 | p-F—Ph | H | H | CH₃ | $^i$Pr | H | CH₃ | OH | OH | H | H | NH₂ |
| II-27-3 | p-F—Ph | H | H | CH(CH₃)₂ | $^i$Pr | H | CH₃ | OH | OH | H | H | NH₂ |
| II-27-4 | p-F—Ph | H | H | CH₂CH(CH₃)₂ | $^i$Pr | H | CH₃ | OH | OH | H | H | NH₂ |
| II-27-5 | p-F—Ph | H | H | CH₂Ph | $^i$Pr | H | CH₃ | OH | OH | H | H | NH₂ |
| II-27-6 | p-F—Ph | H | H | CH₂-indol-3-yl | $^i$Pr | H | CH₃ | OH | OH | H | H | NH₂ |
| II-27-7 | p-F—Ph | H | H | CH₂CH₂SCH₃ | $^i$Pr | H | CH₃ | OH | OH | H | H | NH₂ |
| II-27-8 | p-F—Ph | * | H | * | $^i$Pr | H | CH₃ | OH | OH | H | H | NH₂ |

*R² and R³ᵇ joined together by (CH₂)₃ to form five-membered ring.

TABLE II-28

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-28-1 | p-Cl—Ph | H | H | H | $^i$Pr | H | CH₃ | OH | OH | H | H | NH₂ |
| II-28-2 | p-Cl—Ph | H | H | CH₃ | $^i$Pr | H | CH₃ | OH | OH | H | H | NH₂ |
| II-28-3 | p-Cl—Ph | H | H | CH(CH₃)₂ | $^i$Pr | H | CH₃ | OH | OH | H | H | NH₂ |
| II-28-4 | p-Cl—Ph | H | H | CH₂CH(CH₃)₂ | $^i$Pr | H | CH₃ | OH | OH | H | H | NH₂ |
| II-28-5 | p-Cl—Ph | H | H | CH₂Ph | $^i$Pr | H | CH₃ | OH | OH | H | H | NH₂ |
| II-28-6 | p-Cl—Ph | H | H | CH₂-indol-3-yl | $^i$Pr | H | CH₃ | OH | OH | H | H | NH₂ |
| II-28-7 | p-Cl—Ph | H | H | CH₂CH₂SCH₃ | $^i$Pr | H | CH₃ | OH | OH | H | H | NH₂ |
| II-28-8 | p-Cl—Ph | * | H | * | $^i$Pr | H | CH₃ | OH | OH | H | H | NH₂ |

*R² and R³ᵇ joined together by (CH₂)₃ to form five-membered ring.

TABLE II-29

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-29-1 | p-Br—Ph | H | H | H | $^i$Pr | H | CH₃ | OH | OH | H | H | NH₂ |
| II-29-2 | p-Br—Ph | H | H | CH₃ | $^i$Pr | H | CH₃ | OH | OH | H | H | NH₂ |
| II-29-3 | p-Br—Ph | H | H | CH(CH₃)₂ | $^i$Pr | H | CH₃ | OH | OH | H | H | NH₂ |
| II-29-4 | p-Br—Ph | H | H | CH₂CH(CH₃)₂ | $^i$Pr | H | CH₃ | OH | OH | H | H | NH₂ |
| II-29-5 | p-Br—Ph | H | H | CH₂Ph | $^i$Pr | H | CH₃ | OH | OH | H | H | NH₂ |
| II-29-6 | p-Br—Ph | H | H | CH₂-indol-3-yl | $^i$Pr | H | CH₃ | OH | OH | H | H | NH₂ |
| II-29-7 | p-Br—Ph | H | H | CH₂CH₂SCH₃ | $^i$Pr | H | CH₃ | OH | OH | H | H | NH₂ |
| II-29-8 | p-Br—Ph | * | H | * | $^i$Pr | H | CH₃ | OH | OH | H | H | NH₂ |

*R² and R³ᵇ joined together by (CH₂)₃ to form five-membered ring.

TABLE II-30

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-30-1 | p-I—Ph | H | H | H | $^i$Pr | H | CH$_3$ | OH | OH | H | H | NH$_2$ |
| II-30-2 | p-I—Ph | H | H | CH$_3$ | $^i$Pr | H | CH$_3$ | OH | OH | H | H | NH$_2$ |
| II-30-3 | p-I—Ph | H | H | CH(CH$_3$)$_2$ | $^i$Pr | H | CH$_3$ | OH | OH | H | H | NH$_2$ |
| II-30-4 | p-I—Ph | H | H | CH$_2$CH(CH$_3$)$_2$ | $^i$Pr | H | CH$_3$ | OH | OH | H | H | NH$_2$ |
| II-30-5 | p-I—Ph | H | H | CH$_2$Ph | $^i$Pr | H | CH$_3$ | OH | OH | H | H | NH$_2$ |
| II-30-6 | p-I—Ph | H | H | CH$_2$-indol-3-yl | $^i$Pr | H | CH$_3$ | OH | OH | H | H | NH$_2$ |
| II-30-7 | p-I—Ph | H | H | CH$_2$CH$_2$SCH$_3$ | $^i$Pr | H | CH$_3$ | OH | OH | H | H | NH$_2$ |
| II-30-8 | p-I—Ph | * | H | * | $^i$Pr | H | CH$_3$ | OH | OH | H | H | NH$_2$ |

*R² and R³ᵇ joined together by (CH$_2$)$_3$ to form five-membered ring.

TABLE II-31

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-31-1 | CH$_3$ | H | H | H | $^n$Bu | H | CH$_3$ | OH | OH | H | H | NH$_2$ |
| II-31-2 | CH$_3$ | H | H | CH$_3$ | $^n$Bu | H | CH$_3$ | OH | OH | H | H | NH$_2$ |
| II-31-3 | CH$_3$ | H | H | CH(CH$_3$)$_2$ | $^n$Bu | H | CH$_3$ | OH | OH | H | H | NH$_2$ |
| II-31-4 | CH$_3$ | H | H | CH$_2$CH(CH$_3$)$_2$ | $^n$Bu | H | CH$_3$ | OH | OH | H | H | NH$_2$ |
| II-31-5 | CH$_3$ | H | H | CH$_2$Ph | $^n$Bu | H | CH$_3$ | OH | OH | H | H | NH$_2$ |
| II-31-6 | CH$_3$ | H | H | CH$_2$-indol-3-yl | $^n$Bu | H | CH$_3$ | OH | OH | H | H | NH$_2$ |
| II-31-7 | CH$_3$ | H | H | CH$_2$CH$_2$SCH$_3$ | $^n$Bu | H | CH$_3$ | OH | OH | H | H | NH$_2$ |
| II-31-8 | CH$_3$ | * | H | * | $^n$Bu | H | CH$_3$ | OH | OH | H | H | NH$_2$ |

*R² and R³ᵇ joined together by (CH$_2$)$_3$ to form five-membered ring.

TABLE II-32

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-32-1 | Et | H | H | H | $^n$Bu | H | CH$_3$ | OH | OH | H | H | NH$_2$ |
| II-32-2 | Et | H | H | CH$_3$ | $^n$Bu | H | CH$_3$ | OH | OH | H | H | NH$_2$ |
| II-32-3 | Et | H | H | CH(CH$_3$)$_2$ | $^n$Bu | H | CH$_3$ | OH | OH | H | H | NH$_2$ |
| II-32-4 | Et | H | H | CH$_2$CH(CH$_3$)$_2$ | $^n$Bu | H | CH$_3$ | OH | OH | H | H | NH$_2$ |
| II-32-5 | Et | H | H | CH$_2$Ph | $^n$Bu | H | CH$_3$ | OH | OH | H | H | NH$_2$ |
| II-32-6 | Et | H | H | CH$_2$-indol-3-yl | $^n$Bu | H | CH$_3$ | OH | OH | H | H | NH$_2$ |
| II-32-7 | Et | H | H | CH$_2$CH$_2$SCH$_3$ | $^n$Bu | H | CH$_3$ | OH | OH | H | H | NH$_2$ |
| II-32-8 | Et | * | H | * | $^n$Bu | H | CH$_3$ | OH | OH | H | H | NH$_2$ |

*R² and R³ᵇ joined together by (CH$_2$)$_3$ to form five-membered ring.

TABLE II-33

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-33-1 | $^i$Pr | H | H | H | $^n$Bu | H | CH$_3$ | OH | OH | H | H | NH$_2$ |
| II-33-2 | $^i$Pr | H | H | CH$_3$ | $^n$Bu | H | CH$_3$ | OH | OH | H | H | NH$_2$ |
| II-33-3 | $^i$Pr | H | H | CH(CH$_3$)$_2$ | $^n$Bu | H | CH$_3$ | OH | OH | H | H | NH$_2$ |
| II-33-4 | $^i$Pr | H | H | CH$_2$CH(CH$_3$)$_2$ | $^n$Bu | H | CH$_3$ | OH | OH | H | H | NH$_2$ |
| II-33-5 | $^i$Pr | H | H | CH$_2$Ph | $^n$Bu | H | CH$_3$ | OH | OH | H | H | NH$_2$ |
| II-33-6 | $^i$Pr | H | H | CH$_2$-indol-3-yl | $^n$Bu | H | CH$_3$ | OH | OH | H | H | NH$_2$ |
| II-33-7 | $^i$Pr | H | H | CH$_2$CH$_2$SCH$_3$ | $^n$Bu | H | CH$_3$ | OH | OH | H | H | NH$_2$ |
| II-33-8 | $^i$Pr | * | H | * | $^n$Bu | H | CH$_3$ | OH | OH | H | H | NH$_2$ |

*R² and R³ᵇ joined together by (CH$_2$)$_3$ to form five-membered ring.

TABLE II-34

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-34-1 | $^t$Bu | H | H | H | $^n$Bu | H | CH$_3$ | OH | OH | H | H | NH$_2$ |
| II-34-2 | $^t$Bu | H | H | CH$_3$ | $^n$Bu | H | CH$_3$ | OH | OH | H | H | NH$_2$ |
| II-34-3 | $^t$Bu | H | H | CH(CH$_3$)$_2$ | $^n$Bu | H | CH$_3$ | OH | OH | H | H | NH$_2$ |
| II-34-4 | $^t$Bu | H | H | CH$_2$CH(CH$_3$)$_2$ | $^n$Bu | H | CH$_3$ | OH | OH | H | H | NH$_2$ |
| II-34-5 | $^t$Bu | H | H | CH$_2$Ph | $^n$Bu | H | CH$_3$ | OH | OH | H | H | NH$_2$ |

TABLE II-34-continued

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| II-34-6 | $^t$Bu | H | H | CH$_2$-indol-3-yl | $^n$Bu | H | CH$_3$ | OH | OH | H | H | NH$_2$ |
| II-34-7 | $^t$Bu | H | H | CH$_2$CH$_2$SCH$_3$ | $^n$Bu | H | CH$_3$ | OH | OH | H | H | NH$_2$ |
| II-34-8 | $^t$Bu | * | H | * | $^n$Bu | H | CH$_3$ | OH | OH | H | H | NH$_2$ |

*R$^2$ and R$^{3b}$ joined together by (CH$_2$)$_3$ to form five-membered ring.

TABLE II-35

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| II-35-1 | Ph | H | H | H | $^n$Bu | H | CH$_3$ | OH | OH | H | H | NH$_2$ |
| II-35-2 | Ph | H | H | CH$_3$ | $^n$Bu | H | CH$_3$ | OH | OH | H | H | NH$_2$ |
| II-35-3 | Ph | H | H | CH(CH$_3$)$_2$ | $^n$Bu | H | CH$_3$ | OH | OH | H | H | NH$_2$ |
| II-35-4 | Ph | H | H | CH$_2$CH(CH$_3$)$_2$ | $^n$Bu | H | CH$_3$ | OH | OH | H | H | NH$_2$ |
| II-35-5 | Ph | H | H | CH$_2$Ph | $^n$Bu | H | CH$_3$ | OH | OH | H | H | NH$_2$ |
| II-35-6 | Ph | H | H | CH$_2$-indol-3-yl | $^n$Bu | H | CH$_3$ | OH | OH | H | H | NH$_2$ |
| II-35-7 | Ph | H | H | CH$_2$CH$_2$SCH$_3$ | $^n$Bu | H | CH$_3$ | OH | OH | H | H | NH$_2$ |
| II-35-8 | Ph | * | H | * | $^n$Bu | H | CH$_3$ | OH | OH | H | H | NH$_2$ |

*R$^2$ and R$^{3b}$ joined together by (CH$_2$)$_3$ to form five-membered ring.

TABLE II-36

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| II-36-1 | p-Me—Ph | H | H | H | $^n$Bu | H | CH$_3$ | OH | OH | H | H | NH$_2$ |
| II-36-2 | p-Me—Ph | H | H | CH$_3$ | $^n$Bu | H | CH$_3$ | OH | OH | H | H | NH$_2$ |
| II-36-3 | p-Me—Ph | H | H | CH(CH$_3$)$_2$ | $^n$Bu | H | CH$_3$ | OH | OH | H | H | NH$_2$ |
| II-36-4 | p-Me—Ph | H | H | CH$_2$CH(CH$_3$)$_2$ | $^n$Bu | H | CH$_3$ | OH | OH | H | H | NH$_2$ |
| II-36-5 | p-Me—Ph | H | H | CH$_2$Ph | $^n$Bu | H | CH$_3$ | OH | OH | H | H | NH$_2$ |
| II-36-6 | p-Me—Ph | H | H | CH$_2$-indol-3-yl | $^n$Bu | H | CH$_3$ | OH | OH | H | H | NH$_2$ |
| II-36-7 | p-Me—Ph | H | H | CH$_2$CH$_2$SCH$_3$ | $^n$Bu | H | CH$_3$ | OH | OH | H | H | NH$_2$ |
| II-36-8 | p-Me—Ph | * | H | * | $^n$Bu | H | CH$_3$ | OH | OH | H | H | NH$_2$ |

*R$^2$ and R$^{3b}$ joined together by (CH$_2$)$_3$ to form five-membered ring.

TABLE II-37

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| II-37-1 | p-F—Ph | H | H | H | $^n$Bu | H | CH$_3$ | OH | OH | H | H | NH$_2$ |
| II-37-2 | p-F—Ph | H | H | CH$_3$ | $^n$Bu | H | CH$_3$ | OH | OH | H | H | NH$_2$ |
| II-37-3 | p-F—Ph | H | H | CH(CH$_3$)$_2$ | $^n$Bu | H | CH$_3$ | OH | OH | H | H | NH$_2$ |
| II-37-4 | p-F—Ph | H | H | CH$_2$CH(CH$_3$)$_2$ | $^n$Bu | H | CH$_3$ | OH | OH | H | H | NH$_2$ |
| II-37-5 | p-F—Ph | H | H | CH$_2$Ph | $^n$Bu | H | CH$_3$ | OH | OH | H | H | NH$_2$ |
| II-37-6 | p-F—Ph | H | H | CH$_2$-indol-3-yl | $^n$Bu | H | CH$_3$ | OH | OH | H | H | NH$_2$ |
| II-37-7 | p-F—Ph | H | H | CH$_2$CH$_2$SCH$_3$ | $^n$Bu | H | CH$_3$ | OH | OH | H | H | NH$_2$ |
| II-37-8 | p-F—Ph | * | H | * | $^n$Bu | H | CH$_3$ | OH | OH | H | H | NH$_2$ |

*R$^2$ and R$^{3b}$ joined together by (CH$_2$)$_3$ to form five-membered ring.

TABLE II-38

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| II-38-1 | p-Cl—Ph | H | H | H | $^n$Bu | H | CH$_3$ | OH | OH | H | H | NH$_2$ |
| II-38-2 | p-Cl—Ph | H | H | CH$_3$ | $^n$Bu | H | CH$_3$ | OH | OH | H | H | NH$_2$ |
| II-38-3 | p-Cl—Ph | H | H | CH(CH$_3$)$_2$ | $^n$Bu | H | CH$_3$ | OH | OH | H | H | NH$_2$ |
| II-38-4 | p-Cl—Ph | H | H | CH$_2$CH(CH$_3$)$_2$ | $^n$Bu | H | CH$_3$ | OH | OH | H | H | NH$_2$ |
| II-38-5 | p-Cl—Ph | H | H | CH$_2$Ph | $^n$Bu | H | CH$_3$ | OH | OH | H | H | NH$_2$ |
| II-38-6 | p-Cl—Ph | H | H | CH$_2$-indol-3-yl | $^n$Bu | H | CH$_3$ | OH | OH | H | H | NH$_2$ |
| II-38-7 | p-Cl—Ph | H | H | CH$_2$CH$_2$SCH$_3$ | $^n$Bu | H | CH$_3$ | OH | OH | H | H | NH$_2$ |
| II-38-8 | p-Cl—Ph | * | H | * | $^n$Bu | H | CH$_3$ | OH | OH | H | H | NH$_2$ |

*R$^2$ and R$^{3b}$ joined together by (CH$_2$)$_3$ to form five-membered ring.

TABLE II-39

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-39-1 | p-Br—Ph | H | H | H | ⁿBu | H | CH₃ | OH | OH | H | H | NH₂ |
| II-39-2 | p-Br—Ph | H | H | CH₃ | ⁿBu | H | CH₃ | OH | OH | H | H | NH₂ |
| II-39-3 | p-Br—Ph | H | H | CH(CH₃)₂ | ⁿBu | H | CH₃ | OH | OH | H | H | NH₂ |
| II-39-4 | p-Br—Ph | H | H | CH₂CH(CH₃)₂ | ⁿBu | H | CH₃ | OH | OH | H | H | NH₂ |
| II-39-5 | p-Br—Ph | H | H | CH₂Ph | ⁿBu | H | CH₃ | OH | OH | H | H | NH₂ |
| II-39-6 | p-Br—Ph | H | H | CH₂-indol-3-yl | ⁿBu | H | CH₃ | OH | OH | H | H | NH₂ |
| II-39-7 | p-Br—Ph | H | H | CH₂CH₂SCH₃ | ⁿBu | H | CH₃ | OH | OH | H | H | NH₂ |
| II-39-8 | p-Br—Ph | * | H | * | ⁿBu | H | CH₃ | OH | OH | H | H | NH₂ |

*R² and R³ᵇ joined together by (CH₂)₃ to form five-membered ring.

TABLE II-40

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-40-1 | p-I—Ph | H | H | H | ⁿBu | H | CH₃ | OH | OH | H | H | NH₂ |
| II-40-2 | p-I—Ph | H | H | CH₃ | ⁿBu | H | CH₃ | OH | OH | H | H | NH₂ |
| II-40-3 | p-I—Ph | H | H | CH(CH₃)₂ | ⁿBu | H | CH₃ | OH | OH | H | H | NH₂ |
| II-40-4 | p-I—Ph | H | H | CH₂CH(CH₃)₂ | ⁿBu | H | CH₃ | OH | OH | H | H | NH₂ |
| II-40-5 | p-I—Ph | H | H | CH₂Ph | ⁿBu | H | CH₃ | OH | OH | H | H | NH₂ |
| II-40-6 | p-I—Ph | H | H | CH₂-indol-3-yl | ⁿBu | H | CH₃ | OH | OH | H | H | NH₂ |
| II-40-7 | p-I—Ph | H | H | CH₂CH₂SCH₃ | ⁿBu | H | CH₃ | OH | OH | H | H | NH₂ |
| II-40-8 | p-I—Ph | * | H | * | ⁿBu | H | CH₃ | OH | OH | H | H | NH₂ |

*R² and R³ᵇ joined together by (CH₂)₃ to form five-membered ring.

TABLE II-41

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-41-1 | CH₃ | H | H | H | Bz | H | CH₃ | OH | OH | H | H | NH₂ |
| II-41-2 | CH₃ | H | H | CH₃ | Bz | H | CH₃ | OH | OH | H | H | NH₂ |
| II-41-3 | CH₃ | H | H | CH(CH₃)₂ | Bz | H | CH₃ | OH | OH | H | H | NH₂ |
| II-41-4 | CH₃ | H | H | CH₂CH(CH₃)₂ | Bz | H | CH₃ | OH | OH | H | H | NH₂ |
| II-41-5 | CH₃ | H | H | CH₂Ph | Bz | H | CH₃ | OH | OH | H | H | NH₂ |
| II-41-6 | CH₃ | H | H | CH₂-indol-3-yl | Bz | H | CH₃ | OH | OH | H | H | NH₂ |
| II-41-7 | CH₃ | H | H | CH₂CH₂SCH₃ | Bz | H | CH₃ | OH | OH | H | H | NH₂ |
| II-41-8 | CH₃ | * | H | * | Bz | H | CH₃ | OH | OH | H | H | NH₂ |

*R² and R³ᵇ joined together by (CH₂)₃ to form five-membered ring.

TABLE II-42

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-42-1 | Et | H | H | H | Bz | H | CH₃ | OH | OH | H | H | NH₂ |
| II-42-2 | Et | H | H | CH₃ | Bz | H | CH₃ | OH | OH | H | H | NH₂ |
| II-42-3 | Et | H | H | CH(CH₃)₂ | Bz | H | CH₃ | OH | OH | H | H | NH₂ |
| II-42-4 | Et | H | H | CH₂CH(CH₃)₂ | Bz | H | CH₃ | OH | OH | H | H | NH₂ |
| II-42-5 | Et | H | H | CH₂Ph | Bz | H | CH₃ | OH | OH | H | H | NH₂ |
| II-42-6 | Et | H | H | CH₂-indol-3-yl | Bz | H | CH₃ | OH | OH | H | H | NH₂ |
| II-42-7 | Et | H | H | CH₂CH₂SCH₃ | Bz | H | CH₃ | OH | OH | H | H | NH₂ |
| II-42-8 | Et | * | H | * | Bz | H | CH₃ | OH | OH | H | H | NH₂ |

*R² and R³ᵇ joined together by (CH₂)₃ to form five-membered ring.

TABLE II-43

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-43-1 | $^i$Pr | H | H | H | Bz | H | CH₃ | OH | OH | H | H | NH₂ |
| II-43-2 | $^i$Pr | H | H | CH₃ | Bz | H | CH₃ | OH | OH | H | H | NH₂ |
| II-43-3 | $^i$Pr | H | H | CH(CH₃)₂ | Bz | H | CH₃ | OH | OH | H | H | NH₂ |
| II-43-4 | $^i$Pr | H | H | CH₂CH(CH₃)₂ | Bz | H | CH₃ | OH | OH | H | H | NH₂ |
| II-43-5 | $^i$Pr | H | H | CH₂Ph | Bz | H | CH₃ | OH | OH | H | H | NH₂ |

TABLE II-43-continued

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-43-6 | $^i$Pr | H | H | $CH_2$-indol-3-yl | Bz | H | $CH_3$ | OH | OH | H | H | $NH_2$ |
| II-43-7 | $^i$Pr | H | H | $CH_2CH_2SCH_3$ | Bz | H | $CH_3$ | OH | OH | H | H | $NH_2$ |
| II-43-8 | $^i$Pr | * | H | * | Bz | H | $CH_3$ | OH | OH | H | H | $NH_2$ |

*$R^2$ and $R^{3b}$ joined together by $(CH_2)_3$ to form five-membered ring.

TABLE II-44

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-44-1 | $^t$Bu | H | H | H | Bz | H | $CH_3$ | OH | OH | H | H | $NH_2$ |
| II-44-2 | $^t$Bu | H | H | $CH_3$ | Bz | H | $CH_3$ | OH | OH | H | H | $NH_2$ |
| II-44-3 | $^t$Bu | H | H | $CH(CH_3)_2$ | Bz | H | $CH_3$ | OH | OH | H | H | $NH_2$ |
| II-44-4 | $^t$Bu | H | H | $CH_2CH(CH_3)_2$ | Bz | H | $CH_3$ | OH | OH | H | H | $NH_2$ |
| II-44-5 | $^t$Bu | H | H | $CH_2Ph$ | Bz | H | $CH_3$ | OH | OH | H | H | $NH_2$ |
| II-44-6 | $^t$Bu | H | H | $CH_2$-indol-3-yl | Bz | H | $CH_3$ | OH | OH | H | H | $NH_2$ |
| II-44-7 | $^t$Bu | H | H | $CH_2CH_2SCH_3$ | Bz | H | $CH_3$ | OH | OH | H | H | $NH_2$ |
| II-44-8 | $^t$Bu | * | H | * | Bz | H | $CH_3$ | OH | OH | H | H | $NH_2$ |

*$R^2$ and $R^{3b}$ joined together by $(CH_2)_3$ to form five-membered ring.

TABLE II-45

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-45-1 | Ph | H | H | H | Bz | H | $CH_3$ | OH | OH | H | H | $NH_2$ |
| II-45-2 | Ph | H | H | $CH_3$ | Bz | H | $CH_3$ | OH | OH | H | H | $NH_2$ |
| II-45-3 | Ph | H | H | $CH(CH_3)_2$ | Bz | H | $CH_3$ | OH | OH | H | H | $NH_2$ |
| II-45-4 | Ph | H | H | $CH_2CH(CH_3)_2$ | Bz | H | $CH_3$ | OH | OH | H | H | $NH_2$ |
| II-45-5 | Ph | H | H | $CH_2Ph$ | Bz | H | $CH_3$ | OH | OH | H | H | $NH_2$ |
| II-45-6 | Ph | H | H | $CH_2$-indol-3-yl | Bz | H | $CH_3$ | OH | OH | H | H | $NH_2$ |
| II-45-7 | Ph | H | H | $CH_2CH_2SCH_3$ | Bz | H | $CH_3$ | OH | OH | H | H | $NH_2$ |
| II-45-8 | Ph | * | H | * | Bz | H | $CH_3$ | OH | OH | H | H | $NH_2$ |

*$R^2$ and $R^{3b}$ joined together by $(CH_2)_3$ to form five-membered ring.

TABLE II-46

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-46-1 | p-Me—Ph | H | H | H | Bz | H | $CH_3$ | OH | OH | H | H | $NH_2$ |
| II-46-2 | p-Me—Ph | H | H | $CH_3$ | Bz | H | $CH_3$ | OH | OH | H | H | $NH_2$ |
| II-46-3 | p-Me—Ph | H | H | $CH(CH_3)_2$ | Bz | H | $CH_3$ | OH | OH | H | H | $NH_2$ |
| II-46-4 | p-Me—Ph | H | H | $CH_2CH(CH_3)_2$ | Bz | H | $CH_3$ | OH | OH | H | H | $NH_2$ |
| II-46-5 | p-Me—Ph | H | H | $CH_2Ph$ | Bz | H | $CH_3$ | OH | OH | H | H | $NH_2$ |
| II-46-6 | p-Me—Ph | H | H | $CH_2$-indol-3-yl | Bz | H | $CH_3$ | OH | OH | H | H | $NH_2$ |
| II-46-7 | p-Me—Ph | H | H | $CH_2CH_2SCH_3$ | Bz | H | $CH_3$ | OH | OH | H | H | $NH_2$ |
| II-46-8 | p-Me—Ph | * | H | * | Bz | H | $CH_3$ | OH | OH | H | H | $NH_2$ |

*$R^2$ and $R^{3b}$ joined together by $(CH_2)_3$ to form five-membered ring.

TABLE II-47

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| II-47-1 | p-F—Ph | H | H | H | Bz | H | $CH_3$ | OH | OH | H | H | $NH_2$ |
| II-47-2 | p-F—Ph | H | H | $CH_3$ | Bz | H | $CH_3$ | OH | OH | H | H | $NH_2$ |
| II-47-3 | p-F—Ph | H | H | $CH(CH_3)_2$ | Bz | H | $CH_3$ | OH | OH | H | H | $NH_2$ |
| II-47-4 | p-F—Ph | H | H | $CH_2CH(CH_3)_2$ | Bz | H | $CH_3$ | OH | OH | H | H | $NH_2$ |
| II-47-5 | p-F—Ph | H | H | $CH_2Ph$ | Bz | H | $CH_3$ | OH | OH | H | H | $NH_2$ |
| II-47-6 | p-F—Ph | H | H | $CH_2$-indol-3-yl | Bz | H | $CH_3$ | OH | OH | H | H | $NH_2$ |
| II-47-7 | p-F—Ph | H | H | $CH_2CH_2SCH_3$ | Bz | H | $CH_3$ | OH | OH | H | H | $NH_2$ |
| II-47-8 | p-F—Ph | * | H | * | Bz | H | $CH_3$ | OH | OH | H | H | $NH_2$ |

*$R^2$ and $R^{3b}$ joined together by $(CH_2)_3$ to form five-membered ring.

TABLE II-48

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-48-1 | p-Cl—Ph | H | H | H | Bz | H | $CH_3$ | OH | OH | H | H | $NH_2$ |
| II-48-2 | p-Cl—Ph | H | H | $CH_3$ | Bz | H | $CH_3$ | OH | OH | H | H | $NH_2$ |
| II-48-3 | p-Cl—Ph | H | H | $CH(CH_3)_2$ | Bz | H | $CH_3$ | OH | OH | H | H | $NH_2$ |
| II-48-4 | p-Cl—Ph | H | H | $CH_2CH(CH_3)_2$ | Bz | H | $CH_3$ | OH | OH | H | H | $NH_2$ |
| II-48-5 | p-Cl—Ph | H | H | $CH_2Ph$ | Bz | H | $CH_3$ | OH | OH | H | H | $NH_2$ |
| II-48-6 | p-Cl—Ph | H | H | $CH_2$-indol-3-yl | Bz | H | $CH_3$ | OH | OH | H | H | $NH_2$ |
| II-48-7 | p-Cl—Ph | H | H | $CH_2CH_2SCH_3$ | Bz | H | $CH_3$ | OH | OH | H | H | $NH_2$ |
| II-48-8 | p-Cl—Ph | * | H | * | Bz | H | $CH_3$ | OH | OH | H | H | $NH_2$ |

*R² and R³ᵇ joined together by $(CH_2)_3$ to form five-membered ring.

TABLE II-49

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-49-1 | p-Br—Ph | H | H | H | Bz | H | $CH_3$ | OH | OH | H | H | $NH_2$ |
| II-49-2 | p-Br—Ph | H | H | $CH_3$ | Bz | H | $CH_3$ | OH | OH | H | H | $NH_2$ |
| II-49-3 | p-Br—Ph | H | H | $CH(CH_3)_2$ | Bz | H | $CH_3$ | OH | OH | H | H | $NH_2$ |
| II-49-4 | p-Br—Ph | H | H | $CH_2CH(CH_3)_2$ | Bz | H | $CH_3$ | OH | OH | H | H | $NH_2$ |
| II-49-5 | p-Br—Ph | H | H | $CH_2Ph$ | Bz | H | $CH_3$ | OH | OH | H | H | $NH_2$ |
| II-49-6 | p-Br—Ph | H | H | $CH_2$-indol-3-yl | Bz | H | $CH_3$ | OH | OH | H | H | $NH_2$ |
| II-49-7 | p-Br—Ph | H | H | $CH_2CH_2SCH_3$ | Bz | H | $CH_3$ | OH | OH | H | H | $NH_2$ |
| II-49-8 | p-Br—Ph | * | H | * | Bz | H | $CH_3$ | OH | OH | H | H | $NH_2$ |

*R² and R³ᵇ joined together by $(CH_2)_3$ to form five-membered ring.

TABLE II-50

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| II-50-1 | p-I—Ph | H | H | H | Bz | H | $CH_3$ | OH | OH | H | H | $NH_2$ |
| II-50-2 | p-I—Ph | H | H | $CH_3$ | Bz | H | $CH_3$ | OH | OH | H | H | $NH_2$ |
| II-50-3 | p-I—Ph | H | H | $CH(CH_3)_2$ | Bz | H | $CH_3$ | OH | OH | H | H | $NH_2$ |
| II-50-4 | p-I—Ph | H | H | $CH_2CH(CH_3)_2$ | Bz | H | $CH_3$ | OH | OH | H | H | $NH_2$ |
| II-50-5 | p-I—Ph | H | H | $CH_2Ph$ | Bz | H | $CH_3$ | OH | OH | H | H | $NH_2$ |
| II-50-6 | p-I—Ph | H | H | $CH_2$-indol-3-yl | Bz | H | $CH_3$ | OH | OH | H | H | $NH_2$ |
| II-50-7 | p-I—Ph | H | H | $CH_2CH_2SCH_3$ | Bz | H | $CH_3$ | OH | OH | H | H | $NH_2$ |
| II-50-8 | p-I—Ph | * | H | * | Bz | H | $CH_3$ | OH | OH | H | H | $NH_2$ |

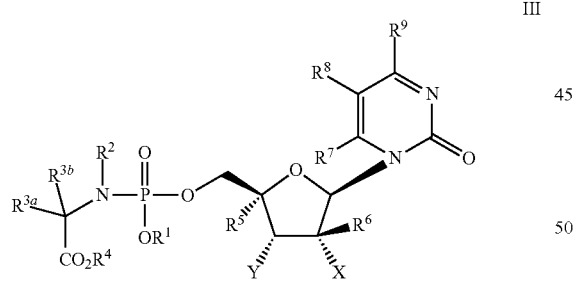

III

TABLE III-1

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-1-1 | $CH_3$ | H | H | H | $CH_3$ | H | $CH_3$ | F | OH | H | H | $NH_2$ |
| III-1-2 | $CH_3$ | H | H | $CH_3$ | $CH_3$ | H | $CH_3$ | F | OH | H | H | $NH_2$ |
| III-1-3 | $CH_3$ | H | H | $CH(CH_3)_2$ | $CH_3$ | H | $CH_3$ | F | OH | H | H | $NH_2$ |
| III-1-4 | $CH_3$ | H | H | $CH_2CH(CH_3)_2$ | $CH_3$ | H | $CH_3$ | F | OH | H | H | $NH_2$ |
| III-1-5 | $CH_3$ | H | H | $CH_2Ph$ | $CH_3$ | H | $CH_3$ | F | OH | H | H | $NH_2$ |
| III-1-6 | $CH_3$ | H | H | $CH_2$-indol-3-yl | $CH_3$ | H | $CH_3$ | F | OH | H | H | $NH_2$ |
| III-1-7 | $CH_3$ | H | H | $CH_2CH_2SCH_3$ | $CH_3$ | H | $CH_3$ | F | OH | H | H | $NH_2$ |
| III-1-8 | $CH_3$ | * | H | * | $CH_3$ | H | $CH_3$ | F | OH | H | H | $NH_2$ |

*R² and R³ᵇ joined together by $(CH_2)_3$ to form five-membered ring.

TABLE III-2

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-2-1 | Et | H | H | H | CH₃ | H | CH₃ | F | OH | H | H | NH₂ |
| III-2-2 | Et | H | H | CH₃ | CH₃ | H | CH₃ | F | OH | H | H | NH₂ |
| III-2-3 | Et | H | H | CH(CH₃)₂ | CH₃ | H | CH₃ | F | OH | H | H | NH₂ |
| III-2-4 | Et | H | H | CH₂CH(CH₃)₂ | CH₃ | H | CH₃ | F | OH | H | H | NH₂ |
| III-2-5 | Et | H | H | CH₂Ph | CH₃ | H | CH₃ | F | OH | H | H | NH₂ |
| III-2-6 | Et | H | H | CH₂-indol-3-yl | CH₃ | H | CH₃ | F | OH | H | H | NH₂ |
| III-2-7 | Et | H | H | CH₂CH₂SCH₃ | CH₃ | H | CH₃ | F | OH | H | H | NH₂ |
| III-2-8 | Et | * | H | * | CH₃ | H | CH₃ | F | OH | H | H | NH₂ |

*R² and R³ᵇ joined together by (CH₂)₃ to form five-membered ring.

TABLE III-3

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-3-1 | ⁱPr | H | H | H | CH₃ | H | CH₃ | F | OH | H | H | NH₂ |
| III-3-2 | ⁱPr | H | H | CH₃ | CH₃ | H | CH₃ | F | OH | H | H | NH₂ |
| III-3-3 | ⁱPr | H | H | CH(CH₃)₂ | CH₃ | H | CH₃ | F | OH | H | H | NH₂ |
| III-3-4 | ⁱPr | H | H | CH₂CH(CH₃)₂ | CH₃ | H | CH₃ | F | OH | H | H | NH₂ |
| III-3-5 | ⁱPr | H | H | CH₂Ph | CH₃ | H | CH₃ | F | OH | H | H | NH₂ |
| III-3-6 | ⁱPr | H | H | CH₂-indol-3-yl | CH₃ | H | CH₃ | F | OH | H | H | NH₂ |
| III-3-7 | ⁱPr | H | H | CH₂CH₂SCH₃ | CH₃ | H | CH₃ | F | OH | H | H | NH₂ |
| III-3-8 | ⁱPr | * | H | * | CH₃ | H | CH₃ | F | OH | H | H | NH₂ |

*R² and R³ᵇ joined together by (CH₂)₃ to form five-membered ring.

TABLE III-4

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-4-1 | ᵗBu | H | H | H | CH₃ | H | CH₃ | F | OH | H | H | NH₂ |
| III-4-2 | ᵗBu | H | H | CH₃ | CH₃ | H | CH₃ | F | OH | H | H | NH₂ |
| III-4-3 | ᵗBu | H | H | CH(CH₃)₂ | CH₃ | H | CH₃ | F | OH | H | H | NH₂ |
| III-4-4 | ᵗBu | H | H | CH₂CH(CH₃)₂ | CH₃ | H | CH₃ | F | OH | H | H | NH₂ |
| III-4-5 | ᵗBu | H | H | CH₂Ph | CH₃ | H | CH₃ | F | OH | H | H | NH₂ |
| III-4-6 | ᵗBu | H | H | CH₂-indol-3-yl | CH₃ | H | CH₃ | F | OH | H | H | NH₂ |
| III-4-7 | ᵗBu | H | H | CH₂CH₂SCH₃ | CH₃ | H | CH₃ | F | OH | H | H | NH₂ |
| III-4-8 | ᵗBu | * | H | * | CH₃ | H | CH₃ | F | OH | H | H | NH₂ |

*R² and R³ᵇ joined together by (CH₂)₃ to form five-membered ring.

TABLE III-5

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-5-1 | Ph | H | H | H | CH₃ | H | CH₃ | F | OH | H | H | NH₂ |
| III-5-2 | Ph | H | H | CH₃ | CH₃ | H | CH₃ | F | OH | H | H | NH₂ |
| III-5-3 | Ph | H | H | CH(CH₃)₂ | CH₃ | H | CH₃ | F | OH | H | H | NH₂ |
| III-5-4 | Ph | H | H | CH₂CH(CH₃)₂ | CH₃ | H | CH₃ | F | OH | H | H | NH₂ |
| III-5-5 | Ph | H | H | CH₂Ph | CH₃ | H | CH₃ | F | OH | H | H | NH₂ |
| III-5-6 | Ph | H | H | CH₂-indol-3-yl | CH₃ | H | CH₃ | F | OH | H | H | NH₂ |
| III-5-7 | Ph | H | H | CH₂CH₂SCH₃ | CH₃ | H | CH₃ | F | OH | H | H | NH₂ |
| III-5-8 | Ph | * | H | * | CH₃ | H | CH₃ | F | OH | H | H | NH₂ |

*R² and R³ᵇ joined together by (CH₂)₃ to form five-membered ring.

TABLE III-6

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-6-1 | p-Me—Ph | H | H | H | CH₃ | H | CH₃ | F | OH | H | H | NH₂ |
| III-6-2 | p-Me—Ph | H | H | CH₃ | CH₃ | H | CH₃ | F | OH | H | H | NH₂ |
| III-6-3 | p-Me—Ph | H | H | CH(CH₃)₂ | CH₃ | H | CH₃ | F | OH | H | H | NH₂ |

TABLE III-6-continued

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-6-4 | p-Me—Ph | H | H | CH$_2$CH(CH$_3$)$_2$ | CH$_3$ | H | CH$_3$ | F | OH | H | H | NH$_2$ |
| III-6-5 | p-Me—Ph | H | H | CH$_2$Ph | CH$_3$ | H | CH$_3$ | F | OH | H | H | NH$_2$ |
| III-6-6 | p-Me—Ph | H | H | CH$_2$-indol-3-yl | CH$_3$ | H | CH$_3$ | F | OH | H | H | NH$_2$ |
| III-6-7 | p-Me—Ph | H | H | CH$_2$CH$_2$SCH$_3$ | CH$_3$ | H | CH$_3$ | F | OH | H | H | NH$_2$ |
| III-6-8 | p-Me—Ph | * | H | * | CH$_3$ | H | CH$_3$ | F | OH | H | H | NH$_2$ |

*R$^2$ and R$^{3b}$ joined together by (CH$_2$)$_3$ to form five-membered ring.

TABLE III-7

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-7-1 | p-F—Ph | H | H | H | CH$_3$ | H | CH$_3$ | F | OH | H | H | NH$_2$ |
| III-7-2 | p-F—Ph | H | H | CH$_3$ | CH$_3$ | H | CH$_3$ | F | OH | H | H | NH$_2$ |
| III-7-3 | p-F—Ph | H | H | CH(CH$_3$)$_2$ | CH$_3$ | H | CH$_3$ | F | OH | H | H | NH$_2$ |
| III-7-4 | p-F—Ph | H | H | CH$_2$CH(CH$_3$)$_2$ | CH$_3$ | H | CH$_3$ | F | OH | H | H | NH$_2$ |
| III-7-6 | p-F—Ph | H | H | CH$_2$Ph | CH$_3$ | H | CH$_3$ | F | OH | H | H | NH$_2$ |
| III-7-7 | p-F—Ph | H | H | CH$_2$-indol-3-yl | CH$_3$ | H | CH$_3$ | F | OH | H | H | NH$_2$ |
| III-7-8 | p-F—Ph | H | H | CH$_2$CH$_2$SCH$_3$ | CH$_3$ | H | CH$_3$ | F | OH | H | H | NH$_2$ |
| III-7-20 | p-F—Ph | * | H | * | CH$_3$ | H | CH$_3$ | F | OH | H | H | NH$_2$ |

*R$^2$ and R$^{3b}$ joined together by (CH$_2$)$_3$ to form five-membered ring.

TABLE III-8

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-8-1 | p-Cl—Ph | H | H | H | CH$_3$ | H | CH$_3$ | F | OH | H | H | NH$_2$ |
| III-8-2 | p-Cl—Ph | H | H | CH$_3$ | CH$_3$ | H | CH$_3$ | F | OH | H | H | NH$_2$ |
| III-8-3 | p-Cl—Ph | H | H | CH(CH$_3$)$_2$ | CH$_3$ | H | CH$_3$ | F | OH | H | H | NH$_2$ |
| III-8-4 | p-Cl—Ph | H | H | CH$_2$CH(CH$_3$)$_2$ | CH$_3$ | H | CH$_3$ | F | OH | H | H | NH$_2$ |
| III-8-5 | p-Cl—Ph | H | H | CH$_2$Ph | CH$_3$ | H | CH$_3$ | F | OH | H | H | NH$_2$ |
| III-8-6 | p-Cl—Ph | H | H | CH$_2$-indol-3-yl | CH$_3$ | H | CH$_3$ | F | OH | H | H | NH$_2$ |
| III-8-7 | p-Cl—Ph | H | H | CH$_2$CH$_2$SCH$_3$ | CH$_3$ | H | CH$_3$ | F | OH | H | H | NH$_2$ |
| III-8-8 | p-Cl—Ph | * | H | * | CH$_3$ | H | CH$_3$ | F | OH | H | H | NH$_2$ |

*R$^2$ and R$^{3b}$ joined together by (CH$_2$)$_3$ to form five-membered ring.

TABLE III-9

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-9-1 | p-Br—Ph | H | H | H | CH$_3$ | H | CH$_3$ | F | OH | H | H | NH$_2$ |
| III-9-2 | p-Br—Ph | H | H | CH$_3$ | CH$_3$ | H | CH$_3$ | F | OH | H | H | NH$_2$ |
| III-9-3 | p-Br—Ph | H | H | CH(CH$_3$)$_2$ | CH$_3$ | H | CH$_3$ | F | OH | H | H | NH$_2$ |
| III-9-4 | p-Br—Ph | H | H | CH$_2$CH(CH$_3$)$_2$ | CH$_3$ | H | CH$_3$ | F | OH | H | H | NH$_2$ |
| III-9-6 | p-Br—Ph | H | H | CH$_2$Ph | CH$_3$ | H | CH$_3$ | F | OH | H | H | NH$_2$ |
| III-9-7 | p-Br—Ph | H | H | CH$_2$-indol-3-yl | CH$_3$ | H | CH$_3$ | F | OH | H | H | NH$_2$ |
| III-9-8 | p-Br—Ph | H | H | CH$_2$CH$_2$SCH$_3$ | CH$_3$ | H | CH$_3$ | F | OH | H | H | NH$_2$ |
| III-9-20 | p-Br—Ph | * | H | * | CH$_3$ | H | CH$_3$ | F | OH | H | H | NH$_2$ |

*R$^2$ and R$^{3b}$ joined together by (CH$_2$)$_3$ to form five-membered ring.

TABLE III-10

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-10-1 | p-I—Ph | H | H | H | CH$_3$ | H | CH$_3$ | F | OH | H | H | NH$_2$ |
| III-10-2 | p-I—Ph | H | H | CH$_3$ | CH$_3$ | H | CH$_3$ | F | OH | H | H | NH$_2$ |
| III-10-3 | p-I—Ph | H | H | CH(CH$_3$)$_2$ | CH$_3$ | H | CH$_3$ | F | OH | H | H | NH$_2$ |
| III-10-4 | p-I—Ph | H | H | CH$_2$CH(CH$_3$)$_2$ | CH$_3$ | H | CH$_3$ | F | OH | H | H | NH$_2$ |
| III-10-5 | p-I—Ph | H | H | CH$_2$Ph | CH$_3$ | H | CH$_3$ | F | OH | H | H | NH$_2$ |
| III-10-6 | p-I—Ph | H | H | CH$_2$-indol-3-yl | CH$_3$ | H | CH$_3$ | F | OH | H | H | NH$_2$ |
| III-10-7 | p-I—Ph | H | H | CH$_2$CH$_2$SCH$_3$ | CH$_3$ | H | CH$_3$ | F | OH | H | H | NH$_2$ |
| III-10-8 | p-I—Ph | * | H | * | CH$_3$ | H | CH$_3$ | F | OH | H | H | NH$_2$ |

*R$^2$ and R$^{3b}$ joined together by (CH$_2$)$_3$ to form five-membered ring.

TABLE III-11

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-11-1 | CH₃ | H | H | H | Et | H | CH₃ | F | OH | H | H | NH₂ |
| III-11-2 | CH₃ | H | H | CH₃ | Et | H | CH₃ | F | OH | H | H | NH₂ |
| III-11-3 | CH₃ | H | H | CH(CH₃)₂ | Et | H | CH₃ | F | OH | H | H | NH₂ |
| III-11-4 | CH₃ | H | H | CH₂CH(CH₃)₂ | Et | H | CH₃ | F | OH | H | H | NH₂ |
| III-11-5 | CH₃ | H | H | CH₂Ph | Et | H | CH₃ | F | OH | H | H | NH₂ |
| III-11-6 | CH₃ | H | H | CH₂-indol-3-yl | Et | H | CH₃ | F | OH | H | H | NH₂ |
| III-11-7 | CH₃ | H | H | CH₂CH₂SCH₃ | Et | H | CH₃ | F | OH | H | H | NH₂ |
| III-11-8 | CH₃ | * | H | * | Et | H | CH₃ | F | OH | H | H | NH₂ |

*R² and R³ᵇ joined together by (CH₂)₃ to form five-membered ring.

TABLE III-12

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-12-1 | Et | H | H | H | Et | H | CH₃ | F | OH | H | H | NH₂ |
| III-12-2 | Et | H | H | CH₃ | Et | H | CH₃ | F | OH | H | H | NH₂ |
| III-12-3 | Et | H | H | CH(CH₃)₂ | Et | H | CH₃ | F | OH | H | H | NH₂ |
| III-12-4 | Et | H | H | CH₂CH(CH₃)₂ | Et | H | CH₃ | F | OH | H | H | NH₂ |
| III-12-5 | Et | H | H | CH₂Ph | Et | H | CH₃ | F | OH | H | H | NH₂ |
| III-12-6 | Et | H | H | CH₂-indol-3-yl | Et | H | CH₃ | F | OH | H | H | NH₂ |
| III-12-7 | Et | H | H | CH₂CH₂SCH₃ | Et | H | CH₃ | F | OH | H | H | NH₂ |
| III-12-8 | Et | * | H | * | Et | H | CH₃ | F | OH | H | H | NH₂ |

*R² and R³ᵇ joined together by (CH₂)₃ to form five-membered ring.

TABLE III-13

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-13-1 | ⁱPr | H | H | H | Et | H | CH₃ | F | OH | H | H | NH₂ |
| III-13-2 | ⁱPr | H | H | CH₃ | Et | H | CH₃ | F | OH | H | H | NH₂ |
| III-13-3 | ⁱPr | H | H | CH(CH₃)₂ | Et | H | CH₃ | F | OH | H | H | NH₂ |
| III-13-4 | ⁱPr | H | H | CH₂CH(CH₃)₂ | Et | H | CH₃ | F | OH | H | H | NH₂ |
| III-13-5 | ⁱPr | H | H | CH₂Ph | Et | H | CH₃ | F | OH | H | H | NH₂ |
| III-13-6 | ⁱPr | H | H | CH₂-indol-3-yl | Et | H | CH₃ | F | OH | H | H | NH₂ |
| III-13-7 | ⁱPr | H | H | CH₂CH₂SCH₃ | Et | H | CH₃ | F | OH | H | H | NH₂ |
| III-13-8 | ⁱPr | * | H | * | Et | H | CH₃ | F | OH | H | H | NH₂ |

*R² and R³ᵇ joined together by (CH₂)₃ to form five-membered ring.

TABLE III-14

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-14-1 | ᵗBu | H | H | H | Et | H | CH₃ | F | OH | H | H | NH₂ |
| III-14-2 | ᵗBu | H | H | CH₃ | Et | H | CH₃ | F | OH | H | H | NH₂ |
| III-14-3 | ᵗBu | H | H | CH(CH₃)₂ | Et | H | CH₃ | F | OH | H | H | NH₂ |
| III-14-4 | ᵗBu | H | H | CH₂CH(CH₃)₂ | Et | H | CH₃ | F | OH | H | H | NH₂ |
| III-14-5 | ᵗBu | H | H | CH₂Ph | Et | H | CH₃ | F | OH | H | H | NH₂ |
| III-14-6 | ᵗBu | H | H | CH₂-indol-3-yl | Et | H | CH₃ | F | OH | H | H | NH₂ |
| III-14-7 | ᵗBu | H | H | CH₂CH₂SCH₃ | Et | H | CH₃ | F | OH | H | H | NH₂ |
| III-14-8 | ᵗBu | * | H | * | Et | H | CH₃ | F | OH | H | H | NH₂ |

*R² and R³ᵇ joined together by (CH₂)₃ to form five-membered ring.

TABLE III-15

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-15-1 | Ph | H | H | H | Et | H | CH₃ | F | OH | H | H | NH₂ |
| III-15-2 | Ph | H | H | CH₃ | Et | H | CH₃ | F | OH | H | H | NH₂ |
| III-15-3 | Ph | H | H | CH(CH₃)₂ | Et | H | CH₃ | F | OH | H | H | NH₂ |
| III-15-4 | Ph | H | H | CH₂CH(CH₃)₂ | Et | H | CH₃ | F | OH | H | H | NH₂ |
| III-15-5 | Ph | H | H | CH₂Ph | Et | H | CH₃ | F | OH | H | H | NH₂ |

TABLE III-15-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-15-6 | Ph | H | H | CH₂-indol-3-yl | Et | H | CH₃ | F | OH | H | H | NH₂ |
| III-15-7 | Ph | H | H | CH₂CH₂SCH₃ | Et | H | CH₃ | F | OH | H | H | NH₂ |
| III-15-8 | Ph | * | H | * | Et | H | CH₃ | F | OH | H | H | NH₂ |

*R² and R³ᵇ joined together by (CH₂)₃ to form five-membered ring.

TABLE III-16

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-16-1 | p-Me—Ph | H | H | H | Et | H | CH₃ | F | OH | H | H | NH₂ |
| III-16-2 | p-Me—Ph | H | H | CH₃ | Et | H | CH₃ | F | OH | H | H | NH₂ |
| III-16-3 | p-Me—Ph | H | H | CH(CH₃)₂ | Et | H | CH₃ | F | OH | H | H | NH₂ |
| III-16-4 | p-Me—Ph | H | H | CH₂CH(CH₃)₂ | Et | H | CH₃ | F | OH | H | H | NH₂ |
| III-16-5 | p-Me—Ph | H | H | CH₂Ph | Et | H | CH₃ | F | OH | H | H | NH₂ |
| III-16-6 | p-Me—Ph | H | H | CH₂-indol-3-yl | Et | H | CH₃ | F | OH | H | H | NH₂ |
| III-16-7 | p-Me—Ph | H | H | CH₂CH₂SCH₃ | Et | H | CH₃ | F | OH | H | H | NH₂ |
| III-16-8 | p-Me—Ph | * | H | * | Et | H | CH₃ | F | OH | H | H | NH₂ |

*R² and R³ᵇ joined together by (CH₂)₃ to form five-membered ring.

TABLE III-17

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-17-1 | p-F—Ph | H | H | H | Et | H | CH₃ | F | OH | H | H | NH₂ |
| III-17-2 | p-F—Ph | H | H | CH₃ | Et | H | CH₃ | F | OH | H | H | NH₂ |
| III-17-3 | p-F—Ph | H | H | CH(CH₃)₂ | Et | H | CH₃ | F | OH | H | H | NH₂ |
| III-17-4 | p-F—Ph | H | H | CH₂CH(CH₃)₂ | Et | H | CH₃ | F | OH | H | H | NH₂ |
| III-17-5 | p-F—Ph | H | H | CH₂Ph | Et | H | CH₃ | F | OH | H | H | NH₂ |
| III-17-6 | p-F—Ph | H | H | CH₂-indol-3-yl | Et | H | CH₃ | F | OH | H | H | NH₂ |
| III-17-7 | p-F—Ph | H | H | CH₂CH₂SCH₃ | Et | H | CH₃ | F | OH | H | H | NH₂ |
| III-17-8 | p-F—Ph | * | H | * | Et | H | CH₃ | F | OH | H | H | NH₂ |

*R² and R³ᵇ joined together by (CH₂)₃ to form five-membered ring.

TABLE III-18

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-18-1 | p-Cl—Ph | H | H | H | Et | H | CH₃ | F | OH | H | H | NH₂ |
| III-18-2 | p-Cl—Ph | H | H | CH₃ | Et | H | CH₃ | F | OH | H | H | NH₂ |
| III-18-3 | p-Cl—Ph | H | H | CH(CH₃)₂ | Et | H | CH₃ | F | OH | H | H | NH₂ |
| III-18-4 | p-Cl—Ph | H | H | CH₂CH(CH₃)₂ | Et | H | CH₃ | F | OH | H | H | NH₂ |
| III-18-5 | p-Cl—Ph | H | H | CH₂Ph | Et | H | CH₃ | F | OH | H | H | NH₂ |
| III-18-6 | p-Cl—Ph | H | H | CH₂-indol-3-yl | Et | H | CH₃ | F | OH | H | H | NH₂ |
| III-18-7 | p-Cl—Ph | H | H | CH₂CH₂SCH₃ | Et | H | CH₃ | F | OH | H | H | NH₂ |
| III-18-8 | p-Cl—Ph | * | H | * | Et | H | CH₃ | F | OH | H | H | NH₂ |

*R² and R³ᵇ joined together by (CH₂)₃ to form five-membered ring.

TABLE III-19

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-19-1 | p-Br—Ph | H | H | H | Et | H | CH₃ | F | OH | H | H | NH₂ |
| III-19-2 | p-Br—Ph | H | H | CH₃ | Et | H | CH₃ | F | OH | H | H | NH₂ |
| III-19-3 | p-Br—Ph | H | H | CH(CH₃)₂ | Et | H | CH₃ | F | OH | H | H | NH₂ |
| III-19-4 | p-Br—Ph | H | H | CH₂CH(CH₃)₂ | Et | H | CH₃ | F | OH | H | H | NH₂ |
| III-19-5 | p-Br—Ph | H | H | CH₂Ph | Et | H | CH₃ | F | OH | H | H | NH₂ |
| III-19-6 | p-Br—Ph | H | H | CH₂-indol-3-yl | Et | H | CH₃ | F | OH | H | H | NH₂ |
| III-19-7 | p-Br—Ph | H | H | CH₂CH₂SCH₃ | Et | H | CH₃ | F | OH | H | H | NH₂ |
| III-19-8 | p-Br—Ph | * | H | * | Et | H | CH₃ | F | OH | H | H | NH₂ |

*R² and R³ᵇ joined together by (CH₂)₃ to form five-membered ring.

TABLE III-20

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-20-1 | p-I—Ph | H | H | H | Et | H | $CH_3$ | F | OH | H | H | $NH_2$ |
| III-20-2 | p-I—Ph | H | H | $CH_3$ | Et | H | $CH_3$ | F | OH | H | H | $NH_2$ |
| III-20-3 | p-I—Ph | H | H | $CH(CH_3)_2$ | Et | H | $CH_3$ | F | OH | H | H | $NH_2$ |
| III-20-4 | p-I—Ph | H | H | $CH_2CH(CH_3)_2$ | Et | H | $CH_3$ | F | OH | H | H | $NH_2$ |
| III-20-5 | p-I—Ph | H | H | $CH_2Ph$ | Et | H | $CH_3$ | F | OH | H | H | $NH_2$ |
| III-20-6 | p-I—Ph | H | H | $CH_2$-indol-3-yl | Et | H | $CH_3$ | F | OH | H | H | $NH_2$ |
| III-20-7 | p-I—Ph | H | H | $CH_2CH_2SCH_3$ | Et | H | $CH_3$ | F | OH | H | H | $NH_2$ |
| III-20-8 | p-I—Ph | * | H | * | Et | H | $CH_3$ | F | OH | H | H | $NH_2$ |

*$R^2$ and $R^{3b}$ joined together by $(CH_2)_3$ to form five-membered ring.

TABLE III-21

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-21-1 | $CH_3$ | H | H | H | $^iPr$ | H | $CH_3$ | F | OH | H | H | $NH_2$ |
| III-21-2 | $CH_3$ | H | H | $CH_3$ | $^iPr$ | H | $CH_3$ | F | OH | H | H | $NH_2$ |
| III-21-3 | $CH_3$ | H | H | $CH(CH_3)_2$ | $^iPr$ | H | $CH_3$ | F | OH | H | H | $NH_2$ |
| III-21-4 | $CH_3$ | H | H | $CH_2CH(CH_3)_2$ | $^iPr$ | H | $CH_3$ | F | OH | H | H | $NH_2$ |
| III-21-5 | $CH_3$ | H | H | $CH_2Ph$ | $^iPr$ | H | $CH_3$ | F | OH | H | H | $NH_2$ |
| III-21-6 | $CH_3$ | H | H | $CH_2$-indol-3-yl | $^iPr$ | H | $CH_3$ | F | OH | H | H | $NH_2$ |
| III-21-7 | $CH_3$ | H | H | $CH_2CH_2SCH_3$ | $^iPr$ | H | $CH_3$ | F | OH | H | H | $NH_2$ |
| III-21-8 | $CH_3$ | * | H | * | $^iPr$ | H | $CH_3$ | F | OH | H | H | $NH_2$ |

*$R^2$ and $R^{3b}$ joined together by $(CH_2)_3$ to form five-membered ring.

TABLE III-22

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-22-1 | Et | H | H | H | $^iPr$ | H | $CH_3$ | F | OH | H | H | $NH_2$ |
| III-22-2 | Et | H | H | $CH_3$ | $^iPr$ | H | $CH_3$ | F | OH | H | H | $NH_2$ |
| III-22-3 | Et | H | H | $CH(CH_3)_2$ | $^iPr$ | H | $CH_3$ | F | OH | H | H | $NH_2$ |
| III-22-4 | Et | H | H | $CH_2CH(CH_3)_2$ | $^iPr$ | H | $CH_3$ | F | OH | H | H | $NH_2$ |
| III-22-5 | Et | H | H | $CH_2Ph$ | $^iPr$ | H | $CH_3$ | F | OH | H | H | $NH_2$ |
| III-22-6 | Et | H | H | $CH_2$-indol-3-yl | $^iPr$ | H | $CH_3$ | F | OH | H | H | $NH_2$ |
| III-22-7 | Et | H | H | $CH_2CH_2SCH_3$ | $^iPr$ | H | $CH_3$ | F | OH | H | H | $NH_2$ |
| III-22-8 | Et | * | H | * | $^iPr$ | H | $CH_3$ | F | OH | H | H | $NH_2$ |

*$R^2$ and $R^{3b}$ joined together by $(CH_2)_3$ to form five-membered ring.

TABLE III-23

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-23-1 | $^iPr$ | H | H | H | $^iPr$ | H | $CH_3$ | F | OH | H | H | $NH_2$ |
| III-23-2 | $^iPr$ | H | H | $CH_3$ | $^iPr$ | H | $CH_3$ | F | OH | H | H | $NH_2$ |
| III-23-3 | $^iPr$ | H | H | $CH(CH_3)_2$ | $^iPr$ | H | $CH_3$ | F | OH | H | H | $NH_2$ |
| III-23-4 | $^iPr$ | H | H | $CH_2CH(CH_3)_2$ | $^iPr$ | H | $CH_3$ | F | OH | H | H | $NH_2$ |
| III-23-5 | $^iPr$ | H | H | $CH_2Ph$ | $^iPr$ | H | $CH_3$ | F | OH | H | H | $NH_2$ |
| III-23-6 | $^iPr$ | H | H | $CH_2$-indol-3-yl | $^iPr$ | H | $CH_3$ | F | OH | H | H | $NH_2$ |
| III-23-7 | $^iPr$ | H | H | $CH_2CH_2SCH_3$ | $^iPr$ | H | $CH_3$ | F | OH | H | H | $NH_2$ |
| III-23-8 | $^iPr$ | * | H | * | $^iPr$ | H | $CH_3$ | F | OH | H | H | $NH_2$ |

*$R^2$ and $R^{3b}$ joined together by $(CH_2)_3$ to form five-membered ring.

TABLE III-24

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-24-1 | $^tBu$ | H | H | H | $^iPr$ | H | $CH_3$ | F | OH | H | H | $NH_2$ |
| III-24-2 | $^tBu$ | H | H | $CH_3$ | $^iPr$ | H | $CH_3$ | F | OH | H | H | $NH_2$ |
| III-24-3 | $^tBu$ | H | H | $CH(CH_3)_2$ | $^iPr$ | H | $CH_3$ | F | OH | H | H | $NH_2$ |
| III-24-4 | $^tBu$ | H | H | $CH_2CH(CH_3)_2$ | $^iPr$ | H | $CH_3$ | F | OH | H | H | $NH_2$ |
| III-24-5 | $^tBu$ | H | H | $CH_2Ph$ | $^iPr$ | H | $CH_3$ | F | OH | H | H | $NH_2$ |

TABLE III-24-continued

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-24-6 | $^t$Bu | H | H | CH$_2$-indol-3-yl | $^i$Pr | H | CH$_3$ | F | OH | H | H | NH$_2$ |
| III-24-7 | $^t$Bu | H | H | CH$_2$CH$_2$SCH$_3$ | $^i$Pr | H | CH$_3$ | F | OH | H | H | NH$_2$ |
| III-24-8 | $^t$Bu | * | H | * | $^i$Pr | H | CH$_3$ | F | OH | H | H | NH$_2$ |

*R$^2$ and R$^{3b}$ joined together by (CH$_2$)$_3$ to form five-membered ring.

TABLE III-25

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-25-1 | Ph | H | H | H | $^i$Pr | H | CH$_3$ | F | OH | H | H | NH$_2$ |
| III-25-2 | Ph | H | H | CH$_3$ | $^i$Pr | H | CH$_3$ | F | OH | H | H | NH$_2$ |
| III-25-3 | Ph | H | H | CH(CH$_3$)$_2$ | $^i$Pr | H | CH$_3$ | F | OH | H | H | NH$_2$ |
| III-25-4 | Ph | H | H | CH$_2$CH(CH$_3$)$_2$ | $^i$Pr | H | CH$_3$ | F | OH | H | H | NH$_2$ |
| III-25-5 | Ph | H | H | CH$_2$Ph | $^i$Pr | H | CH$_3$ | F | OH | H | H | NH$_2$ |
| III-25-6 | Ph | H | H | CH$_2$-indol-3-yl | $^i$Pr | H | CH$_3$ | F | OH | H | H | NH$_2$ |
| III-25-7 | Ph | H | H | CH$_2$CH$_2$SCH$_3$ | $^i$Pr | H | CH$_3$ | F | OH | H | H | NH$_2$ |
| III-25-8 | Ph | * | H | * | $^i$Pr | H | CH$_3$ | F | OH | H | H | NH$_2$ |

*R$^2$ and R$^{3b}$ joined together by (CH$_2$)$_3$ to form five-membered ring.

TABLE III-26

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-26-1 | p-Me—Ph | H | H | H | $^i$Pr | H | CH$_3$ | F | OH | H | H | NH$_2$ |
| III-26-2 | p-Me—Ph | H | H | CH$_3$ | $^i$Pr | H | CH$_3$ | F | OH | H | H | NH$_2$ |
| III-26-3 | p-Me—Ph | H | H | CH(CH$_3$)$_2$ | $^i$Pr | H | CH$_3$ | F | OH | H | H | NH$_2$ |
| III-26-4 | p-Me—Ph | H | H | CH$_2$CH(CH$_3$)$_2$ | $^i$Pr | H | CH$_3$ | F | OH | H | H | NH$_2$ |
| III-26-5 | p-Me—Ph | H | H | CH$_2$Ph | $^i$Pr | H | CH$_3$ | F | OH | H | H | NH$_2$ |
| III-26-6 | p-Me—Ph | H | H | CH$_2$-indol-3-yl | $^i$Pr | H | CH$_3$ | F | OH | H | H | NH$_2$ |
| III-26-7 | p-Me—Ph | H | H | CH$_2$CH$_2$SCH$_3$ | $^i$Pr | H | CH$_3$ | F | OH | H | H | NH$_2$ |
| III-26-8 | p-Me—Ph | * | H | * | $^i$Pr | H | CH$_3$ | F | OH | H | H | NH$_2$ |

*R$^2$ and R$^{3b}$ joined together by (CH$_2$)$_3$ to form five-membered ring.

TABLE III-27

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-27-1 | p-F—Ph | H | H | H | $^i$Pr | H | CH$_3$ | F | OH | H | H | NH$_2$ |
| III-27-2 | p-F—Ph | H | H | CH$_3$ | $^i$Pr | H | CH$_3$ | F | OH | H | H | NH$_2$ |
| III-27-3 | p-F—Ph | H | H | CH(CH$_3$)$_2$ | $^i$Pr | H | CH$_3$ | F | OH | H | H | NH$_2$ |
| III-27-4 | p-F—Ph | H | H | CH$_2$CH(CH$_3$)$_2$ | $^i$Pr | H | CH$_3$ | F | OH | H | H | NH$_2$ |
| III-27-5 | p-F—Ph | H | H | CH$_2$Ph | $^i$Pr | H | CH$_3$ | F | OH | H | H | NH$_2$ |
| III-27-6 | p-F—Ph | H | H | CH$_2$-indol-3-yl | $^i$Pr | H | CH$_3$ | F | OH | H | H | NH$_2$ |
| III-27-7 | p-F—Ph | H | H | CH$_2$CH$_2$SCH$_3$ | $^i$Pr | H | CH$_3$ | F | OH | H | H | NH$_2$ |
| III-27-8 | p-F—Ph | * | H | * | $^i$Pr | H | CH$_3$ | F | OH | H | H | NH$_2$ |

*R$^2$ and R$^{3b}$ joined together by (CH$_2$)$_3$ to form five-membered ring.

TABLE III-28

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| III-28-1 | p-Cl—Ph | H | H | H | $^i$Pr | H | CH$_3$ | F | OH | H | H | NH$_2$ |
| III-28-2 | p-Cl—Ph | H | H | CH$_3$ | $^i$Pr | H | CH$_3$ | F | OH | H | H | NH$_2$ |
| III-28-3 | p-Cl—Ph | H | H | CH(CH$_3$)$_2$ | $^i$Pr | H | CH$_3$ | F | OH | H | H | NH$_2$ |
| III-28-4 | p-Cl—Ph | H | H | CH$_2$CH(CH$_3$)$_2$ | $^i$Pr | H | CH$_3$ | F | OH | H | H | NH$_2$ |
| III-28-5 | p-Cl—Ph | H | H | CH$_2$Ph | $^i$Pr | H | CH$_3$ | F | OH | H | H | NH$_2$ |
| III-28-6 | p-Cl—Ph | H | H | CH$_2$-indol-3-yl | $^i$Pr | H | CH$_3$ | F | OH | H | H | NH$_2$ |
| III-28-7 | p-Cl—Ph | H | H | CH$_2$CH$_2$SCH$_3$ | $^i$Pr | H | CH$_3$ | F | OH | H | H | NH$_2$ |
| III-28-8 | p-Cl—Ph | * | H | * | $^i$Pr | H | CH$_3$ | F | OH | H | H | NH$_2$ |

*R$^2$ and R$^{3b}$ joined together by (CH$_2$)$_3$ to form five-membered ring.

TABLE III-29

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-29-1 | p-Br—Ph | H | H | H | $^i$Pr | H | CH$_3$ | F | OH | H | H | NH$_2$ |
| III-29-2 | p-Br—Ph | H | H | CH$_3$ | $^i$Pr | H | CH$_3$ | F | OH | H | H | NH$_2$ |
| III-29-3 | p-Br—Ph | H | H | CH(CH$_3$)$_2$ | $^i$Pr | H | CH$_3$ | F | OH | H | H | NH$_2$ |
| III-29-4 | p-Br—Ph | H | H | CH$_2$CH(CH$_3$)$_2$ | $^i$Pr | H | CH$_3$ | F | OH | H | H | NH$_2$ |
| III-29-5 | p-Br—Ph | H | H | CH$_2$Ph | $^i$Pr | H | CH$_3$ | F | OH | H | H | NH$_2$ |
| III-29-6 | p-Br—Ph | H | H | CH$_2$-indol-3-yl | $^i$Pr | H | CH$_3$ | F | OH | H | H | NH$_2$ |
| III-29-7 | p-Br—Ph | H | H | CH$_2$CH$_2$SCH$_3$ | $^i$Pr | H | CH$_3$ | F | OH | H | H | NH$_2$ |
| III-29-8 | p-Br—Ph | * | H | * | $^i$Pr | H | CH$_3$ | F | OH | H | H | NH$_2$ |

*$R^2$ and $R^{3b}$ joined together by (CH$_2$)$_3$ to form five-membered ring.

TABLE III-30

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-30-1 | p-I—Ph | H | H | H | $^i$Pr | H | CH$_3$ | F | OH | H | H | NH$_2$ |
| III-30-2 | p-I—Ph | H | H | CH$_3$ | $^i$Pr | H | CH$_3$ | F | OH | H | H | NH$_2$ |
| III-30-3 | p-I—Ph | H | H | CH(CH$_3$)$_2$ | $^i$Pr | H | CH$_3$ | F | OH | H | H | NH$_2$ |
| III-30-4 | p-I—Ph | H | H | CH$_2$CH(CH$_3$)$_2$ | $^i$Pr | H | CH$_3$ | F | OH | H | H | NH$_2$ |
| III-30-5 | p-I—Ph | H | H | CH$_2$Ph | $^i$Pr | H | CH$_3$ | F | OH | H | H | NH$_2$ |
| III-30-6 | p-I—Ph | H | H | CH$_2$-indol-3-yl | $^i$Pr | H | CH$_3$ | F | OH | H | H | NH$_2$ |
| III-30-7 | p-I—Ph | H | H | CH$_2$CH$_2$SCH$_3$ | $^i$Pr | H | CH$_3$ | F | OH | H | H | NH$_2$ |
| III-30-8 | p-I—Ph | * | H | * | $^i$Pr | H | CH$_3$ | F | OH | H | H | NH$_2$ |

*$R^2$ and $R^{3b}$ joined together by (CH$_2$)$_3$ to form five-membered ring.

TABLE III-31

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-31-1 | CH$_3$ | H | H | H | $^n$Bu | H | CH$_3$ | F | OH | H | H | NH$_2$ |
| III-31-2 | CH$_3$ | H | H | CH$_3$ | $^n$Bu | H | CH$_3$ | F | OH | H | H | NH$_2$ |
| III-31-3 | CH$_3$ | H | H | CH(CH$_3$)$_2$ | $^n$Bu | H | CH$_3$ | F | OH | H | H | NH$_2$ |
| III-31-4 | CH$_3$ | H | H | CH$_2$CH(CH$_3$)$_2$ | $^n$Bu | H | CH$_3$ | F | OH | H | H | NH$_2$ |
| III-31-5 | CH$_3$ | H | H | CH$_2$Ph | $^n$Bu | H | CH$_3$ | F | OH | H | H | NH$_2$ |
| III-31-6 | CH$_3$ | H | H | CH$_2$-indol-3-yl | $^n$Bu | H | CH$_3$ | F | OH | H | H | NH$_2$ |
| III-31-7 | CH$_3$ | H | H | CH$_2$CH$_2$SCH$_3$ | $^n$Bu | H | CH$_3$ | F | OH | H | H | NH$_2$ |
| III-31-8 | CH$_3$ | * | H | * | $^n$Bu | H | CH$_3$ | F | OH | H | H | NH$_2$ |

*$R^2$ and $R^{3b}$ joined together by (CH$_2$)$_3$ to form five-membered ring.

TABLE III-32

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-32-1 | Et | H | H | H | $^n$Bu | H | CH$_3$ | F | OH | H | H | NH$_2$ |
| III-32-2 | Et | H | H | CH$_3$ | $^n$Bu | H | CH$_3$ | F | OH | H | H | NH$_2$ |
| III-32-3 | Et | H | H | CH(CH$_3$)$_2$ | $^n$Bu | H | CH$_3$ | F | OH | H | H | NH$_2$ |
| III-32-4 | Et | H | H | CH$_2$CH(CH$_3$)$_2$ | $^n$Bu | H | CH$_3$ | F | OH | H | H | NH$_2$ |
| III-32-5 | Et | H | H | CH$_2$Ph | $^n$Bu | H | CH$_3$ | F | OH | H | H | NH$_2$ |
| III-32-6 | Et | H | H | CH$_2$-indol-3-yl | $^n$Bu | H | CH$_3$ | F | OH | H | H | NH$_2$ |
| III-32-7 | Et | H | H | CH$_2$CH$_2$SCH$_3$ | $^n$Bu | H | CH$_3$ | F | OH | H | H | NH$_2$ |
| III-32-8 | Et | * | H | * | $^n$Bu | H | CH$_3$ | F | OH | H | H | NH$_2$ |

*$R^2$ and $R^{3b}$ joined together by (CH$_2$)$_3$ to form five-membered ring.

TABLE III-33

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-33-1 | $^i$Pr | H | H | H | $^n$Bu | H | CH$_3$ | F | OH | H | H | NH$_2$ |
| III-33-2 | $^i$Pr | H | H | CH$_3$ | $^n$Bu | H | CH$_3$ | F | OH | H | H | NH$_2$ |
| III-33-3 | $^i$Pr | H | H | CH(CH$_3$)$_2$ | $^n$Bu | H | CH$_3$ | F | OH | H | H | NH$_2$ |
| III-33-4 | $^i$Pr | H | H | CH$_2$CH(CH$_3$)$_2$ | $^n$Bu | H | CH$_3$ | F | OH | H | H | NH$_2$ |
| III-33-5 | $^i$Pr | H | H | CH$_2$Ph | $^n$Bu | H | CH$_3$ | F | OH | H | H | NH$_2$ |

TABLE III-33-continued

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-33-6 | $^i$Pr | H | H | $CH_2$-indol-3-yl | $^n$Bu | H | $CH_3$ | F | OH | H | H | $NH_2$ |
| III-33-7 | $^i$Pr | H | H | $CH_2CH_2SCH_3$ | $^n$Bu | H | $CH_3$ | F | OH | H | H | $NH_2$ |
| III-33-8 | $^i$Pr | * | H | * | $^n$Bu | H | $CH_3$ | F | OH | H | H | $NH_2$ |

*$R^2$ and $R^{3b}$ joined together by $(CH_2)_3$ to form five-membered ring.

TABLE III-34

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-34-1 | $^t$Bu | H | H | H | $^n$Bu | H | $CH_3$ | F | OH | H | H | $NH_2$ |
| III-34-2 | $^t$Bu | H | H | $CH_3$ | $^n$Bu | H | $CH_3$ | F | OH | H | H | $NH_2$ |
| III-34-3 | $^t$Bu | H | H | $CH(CH_3)_2$ | $^n$Bu | H | $CH_3$ | F | OH | H | H | $NH_2$ |
| III-34-4 | $^t$Bu | H | H | $CH_2CH(CH_3)_2$ | $^n$Bu | H | $CH_3$ | F | OH | H | H | $NH_2$ |
| III-34-5 | $^t$Bu | H | H | $CH_2Ph$ | $^n$Bu | H | $CH_3$ | F | OH | H | H | $NH_2$ |
| III-34-6 | $^t$Bu | H | H | $CH_2$-indol-3-yl | $^n$Bu | H | $CH_3$ | F | OH | H | H | $NH_2$ |
| III-34-7 | $^t$Bu | H | H | $CH_2CH_2SCH_3$ | $^n$Bu | H | $CH_3$ | F | OH | H | H | $NH_2$ |
| III-34-8 | $^t$Bu | * | H | * | $^n$Bu | H | $CH_3$ | F | OH | H | H | $NH_2$ |

*$R^2$ and $R^{3b}$ joined together by $(CH_2)_3$ to form five-membered ring.

TABLE III-35

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-35-1 | Ph | H | H | H | $^n$Bu | H | $CH_3$ | F | OH | H | H | $NH_2$ |
| III-35-2 | Ph | H | H | $CH_3$ | $^n$Bu | H | $CH_3$ | F | OH | H | H | $NH_2$ |
| III-35-3 | Ph | H | H | $CH(CH_3)_2$ | $^n$Bu | H | $CH_3$ | F | OH | H | H | $NH_2$ |
| III-35-4 | Ph | H | H | $CH_2CH(CH_3)_2$ | $^n$Bu | H | $CH_3$ | F | OH | H | H | $NH_2$ |
| III-35-5 | Ph | H | H | $CH_2Ph$ | $^n$Bu | H | $CH_3$ | F | OH | H | H | $NH_2$ |
| III-35-6 | Ph | H | H | $CH_2$-indol-3-yl | $^n$Bu | H | $CH_3$ | F | OH | H | H | $NH_2$ |
| III-35-7 | Ph | H | H | $CH_2CH_2SCH_3$ | $^n$Bu | H | $CH_3$ | F | OH | H | H | $NH_2$ |
| III-35-8 | Ph | * | H | * | $^n$Bu | H | $CH_3$ | F | OH | H | H | $NH_2$ |

*$R^2$ and $R^{3b}$ joined together by $(CH_2)_3$ to form five-membered ring.

TABLE III-36

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-36-1 | p-Me—Ph | H | H | H | $^n$Bu | H | $CH_3$ | F | OH | H | H | $NH_2$ |
| III-36-2 | p-Me—Ph | H | H | $CH_3$ | $^n$Bu | H | $CH_3$ | F | OH | H | H | $NH_2$ |
| III-36-3 | p-Me—Ph | H | H | $CH(CH_3)_2$ | $^n$Bu | H | $CH_3$ | F | OH | H | H | $NH_2$ |
| III-36-4 | p-Me—Ph | H | H | $CH_2CH(CH_3)_2$ | $^n$Bu | H | $CH_3$ | F | OH | H | H | $NH_2$ |
| III-36-5 | p-Me—Ph | H | H | $CH_2Ph$ | $^n$Bu | H | $CH_3$ | F | OH | H | H | $NH_2$ |
| III-36-6 | p-Me—Ph | H | H | $CH_2$-indol-3-yl | $^n$Bu | H | $CH_3$ | F | OH | H | H | $NH_2$ |
| III-36-7 | p-Me—Ph | H | H | $CH_2CH_2SCH_3$ | $^n$Bu | H | $CH_3$ | F | OH | H | H | $NH_2$ |
| III-36-8 | p-Me—Ph | * | H | * | $^n$Bu | H | $CH_3$ | F | OH | H | H | $NH_2$ |

*$R^2$ and $R^{3b}$ joined together by $(CH_2)_3$ to form five-membered ring.

TABLE III-37

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-37-1 | p-F—Ph | H | H | H | $^n$Bu | H | $CH_3$ | F | OH | H | H | $NH_2$ |
| III-37-2 | p-F—Ph | H | H | $CH_3$ | $^n$Bu | H | $CH_3$ | F | OH | H | H | $NH_2$ |
| III-37-3 | p-F—Ph | H | H | $CH(CH_3)_2$ | $^n$Bu | H | $CH_3$ | F | OH | H | H | $NH_2$ |
| III-37-4 | p-F—Ph | H | H | $CH_2CH(CH_3)_2$ | $^n$Bu | H | $CH_3$ | F | OH | H | H | $NH_2$ |
| III-37-5 | p-F—Ph | H | H | $CH_2Ph$ | $^n$Bu | H | $CH_3$ | F | OH | H | H | $NH_2$ |
| III-37-6 | p-F—Ph | H | H | $CH_2$-indol-3-yl | $^n$Bu | H | $CH_3$ | F | OH | H | H | $NH_2$ |
| III-37-7 | p-F—Ph | H | H | $CH_2CH_2SCH_3$ | $^n$Bu | H | $CH_3$ | F | OH | H | H | $NH_2$ |
| III-37-8 | p-F—Ph | * | H | * | $^n$Bu | H | $CH_3$ | F | OH | H | H | $NH_2$ |

*$R^2$ and $R^{3b}$ joined together by $(CH_2)_3$ to form five-membered ring.

TABLE III-38

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-38-1 | p-Cl—Ph | H | H | H | ⁿBu | H | CH₃ | F | OH | H | H | NH₂ |
| III-38-2 | p-Cl—Ph | H | H | CH₃ | ⁿBu | H | CH₃ | F | OH | H | H | NH₂ |
| III-38-3 | p-Cl—Ph | H | H | CH(CH₃)₂ | ⁿBu | H | CH₃ | F | OH | H | H | NH₂ |
| III-38-4 | p-Cl—Ph | H | H | CH₂CH(CH₃)₂ | ⁿBu | H | CH₃ | F | OH | H | H | NH₂ |
| III-38-5 | p-Cl—Ph | H | H | CH₂Ph | ⁿBu | H | CH₃ | F | OH | H | H | NH₂ |
| III-38-6 | p-Cl—Ph | H | H | CH₂-indol-3-yl | ⁿBu | H | CH₃ | F | OH | H | H | NH₂ |
| III-38-7 | p-Cl—Ph | H | H | CH₂CH₂SCH₃ | ⁿBu | H | CH₃ | F | OH | H | H | NH₂ |
| III-38-8 | p-Cl—Ph | * | H | * | ⁿBu | H | CH₃ | F | OH | H | H | NH₂ |

*R² and R³ᵇ joined together by (CH₂)₃ to form five-membered ring.

TABLE III-39

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-39-1 | p-Br—Ph | H | H | H | ⁿBu | H | CH₃ | F | OH | H | H | NH₂ |
| III-39-2 | p-Br—Ph | H | H | CH₃ | ⁿBu | H | CH₃ | F | OH | H | H | NH₂ |
| III-39-3 | p-Br—Ph | H | H | CH(CH₃)₂ | ⁿBu | H | CH₃ | F | OH | H | H | NH₂ |
| III-39-4 | p-Br—Ph | H | H | CH₂CH(CH₃)₂ | ⁿBu | H | CH₃ | F | OH | H | H | NH₂ |
| III-39-5 | p-Br—Ph | H | H | CH₂Ph | ⁿBu | H | CH₃ | F | OH | H | H | NH₂ |
| III-39-6 | p-Br—Ph | H | H | CH₂-indol-3-yl | ⁿBu | H | CH₃ | F | OH | H | H | NH₂ |
| III-39-7 | p-Br—Ph | H | H | CH₂CH₂SCH₃ | ⁿBu | H | CH₃ | F | OH | H | H | NH₂ |
| III-39-8 | p-Br—Ph | * | H | * | ⁿBu | H | CH₃ | F | OH | H | H | NH₂ |

*R² and R³ᵇ joined together by (CH₂)₃ to form five-membered ring.

TABLE III-40

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-40-1 | p-I—Ph | H | H | H | ⁿBu | H | CH₃ | F | OH | H | H | NH₂ |
| III-40-2 | p-I—Ph | H | H | CH₃ | ⁿBu | H | CH₃ | F | OH | H | H | NH₂ |
| III-40-3 | p-I—Ph | H | H | CH(CH₃)₂ | ⁿBu | H | CH₃ | F | OH | H | H | NH₂ |
| III-40-4 | p-I—Ph | H | H | CH₂CH(CH₃)₂ | ⁿBu | H | CH₃ | F | OH | H | H | NH₂ |
| III-40-5 | p-I—Ph | H | H | CH₂Ph | ⁿBu | H | CH₃ | F | OH | H | H | NH₂ |
| III-40-6 | p-I—Ph | H | H | CH₂-indol-3-yl | ⁿBu | H | CH₃ | F | OH | H | H | NH₂ |
| III-40-7 | p-I—Ph | H | H | CH₂CH₂SCH₃ | ⁿBu | H | CH₃ | F | OH | H | H | NH₂ |
| III-40-8 | p-I—Ph | * | H | * | ⁿBu | H | CH₃ | F | OH | H | H | NH₂ |

*R² and R³ᵇ joined together by (CH₂)₃ to form five-membered ring.

TABLE III-41

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-41-1 | CH₃ | H | H | H | Bz | H | CH₃ | F | OH | H | H | NH₂ |
| III-41-2 | CH₃ | H | H | CH₃ | Bz | H | CH₃ | F | OH | H | H | NH₂ |
| III-41-3 | CH₃ | H | H | CH(CH₃)₂ | Bz | H | CH₃ | F | OH | H | H | NH₂ |
| III-41-4 | CH₃ | H | H | CH₂CH(CH₃)₂ | Bz | H | CH₃ | F | OH | H | H | NH₂ |
| III-41-5 | CH₃ | H | H | CH₂Ph | Bz | H | CH₃ | F | OH | H | H | NH₂ |
| III-41-6 | CH₃ | H | H | CH₂-indol-3-yl | Bz | H | CH₃ | F | OH | H | H | NH₂ |
| III-41-7 | CH₃ | H | H | CH₂CH₂SCH₃ | Bz | H | CH₃ | F | OH | H | H | NH₂ |
| III-41-8 | CH₃ | * | H | * | Bz | H | CH₃ | F | OH | H | H | NH₂ |

*R² and R³ᵇ joined together by (CH₂)₃ to form five-membered ring.

TABLE III-42

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-42-1 | Et | H | H | H | Bz | H | CH₃ | F | OH | H | H | NH₂ |
| III-42-2 | Et | H | H | CH₃ | Bz | H | CH₃ | F | OH | H | H | NH₂ |
| III-42-3 | Et | H | H | CH(CH₃)₂ | Bz | H | CH₃ | F | OH | H | H | NH₂ |
| III-42-4 | Et | H | H | CH₂CH(CH₃)₂ | Bz | H | CH₃ | F | OH | H | H | NH₂ |
| III-42-5 | Et | H | H | CH₂Ph | Bz | H | CH₃ | F | OH | H | H | NH₂ |

TABLE III-42-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-42-6 | Et | H | H | CH₂-indol-3-yl | Bz | H | CH₃ | F | OH | H | H | NH₂ |
| III-42-7 | Et | H | H | CH₂CH₂SCH₃ | Bz | H | CH₃ | F | OH | H | H | NH₂ |
| III-42-8 | Et | * | H | * | Bz | H | CH₃ | F | OH | H | H | NH₂ |

*R² and R³ᵇ joined together by (CH₂)₃ to form five-membered ring.

TABLE III-43

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-43-1 | ⁱPr | H | H | H | Bz | H | CH₃ | F | OH | H | H | NH₂ |
| III-43-2 | ⁱPr | H | H | CH₃ | Bz | H | CH₃ | F | OH | H | H | NH₂ |
| III-43-3 | ⁱPr | H | H | CH(CH₃)₂ | Bz | H | CH₃ | F | OH | H | H | NH₂ |
| III-43-4 | ⁱPr | H | H | CH₂CH(CH₃)₂ | Bz | H | CH₃ | F | OH | H | H | NH₂ |
| III-43-5 | ⁱPr | H | H | CH₂Ph | Bz | H | CH₃ | F | OH | H | H | NH₂ |
| III-43-6 | ⁱPr | H | H | CH₂-indol-3-yl | Bz | H | CH₃ | F | OH | H | H | NH₂ |
| III-43-7 | ⁱPr | H | H | CH₂CH₂SCH₃ | Bz | H | CH₃ | F | OH | H | H | NH₂ |
| III-43-8 | ⁱPr | * | H | * | Bz | H | CH₃ | F | OH | H | H | NH₂ |

*R² and R³ᵇ joined together by (CH₂)₃ to form five-membered ring.

TABLE III-44

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-44-1 | ᵗBu | H | H | H | Bz | H | CH₃ | F | OH | H | H | NH₂ |
| III-44-2 | ᵗBu | H | H | CH₃ | Bz | H | CH₃ | F | OH | H | H | NH₂ |
| III-44-3 | ᵗBu | H | H | CH(CH₃)₂ | Bz | H | CH₃ | F | OH | H | H | NH₂ |
| III-44-4 | ᵗBu | H | H | CH₂CH(CH₃)₂ | Bz | H | CH₃ | F | OH | H | H | NH₂ |
| III-44-5 | ᵗBu | H | H | CH₂Ph | Bz | H | CH₃ | F | OH | H | H | NH₂ |
| III-44-6 | ᵗBu | H | H | CH₂-indol-3-yl | Bz | H | CH₃ | F | OH | H | H | NH₂ |
| III-44-7 | ᵗBu | H | H | CH₂CH₂SCH₃ | Bz | H | CH₃ | F | OH | H | H | NH₂ |
| III-44-8 | ᵗBu | * | H | * | Bz | H | CH₃ | F | OH | H | H | NH₂ |

*R² and R³ᵇ joined together by (CH₂)₃ to form five-membered ring.

TABLE III-45

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-45-1 | Ph | H | H | H | Bz | H | CH₃ | F | OH | H | H | NH₂ |
| III-45-2 | Ph | H | H | CH₃ | Bz | H | CH₃ | F | OH | H | H | NH₂ |
| III-45-3 | Ph | H | H | CH(CH₃)₂ | Bz | H | CH₃ | F | OH | H | H | NH₂ |
| III-45-4 | Ph | H | H | CH₂CH(CH₃)₂ | Bz | H | CH₃ | F | OH | H | H | NH₂ |
| III-45-5 | Ph | H | H | CH₂Ph | Bz | H | CH₃ | F | OH | H | H | NH₂ |
| III-45-6 | Ph | H | H | CH₂-indol-3-yl | Bz | H | CH₃ | F | OH | H | H | NH₂ |
| III-45-7 | Ph | H | H | CH₂CH₂SCH₃ | Bz | H | CH₃ | F | OH | H | H | NH₂ |
| III-45-8 | Ph | * | H | * | Bz | H | CH₃ | F | OH | H | H | NH₂ |

*R² and R³ᵇ joined together by (CH₂)₃ to form five-membered ring.

TABLE III-46

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| III-46-1 | p-Me—Ph | H | H | H | Bz | H | CH₃ | F | OH | H | H | NH₂ |
| III-46-2 | p-Me—Ph | H | H | CH₃ | Bz | H | CH₃ | F | OH | H | H | NH₂ |
| III-46-3 | p-Me—Ph | H | H | CH(CH₃)₂ | Bz | H | CH₃ | F | OH | H | H | NH₂ |
| III-46-4 | p-Me—Ph | H | H | CH₂CH(CH₃)₂ | Bz | H | CH₃ | F | OH | H | H | NH₂ |
| III-46-5 | p-Me—Ph | H | H | CH₂Ph | Bz | H | CH₃ | F | OH | H | H | NH₂ |
| III-46-6 | p-Me—Ph | H | H | CH₂-indol-3-yl | Bz | H | CH₃ | F | OH | H | H | NH₂ |
| III-46-7 | p-Me—Ph | H | H | CH₂CH₂SCH₃ | Bz | H | CH₃ | F | OH | H | H | NH₂ |
| III-46-8 | p-Me—Ph | * | H | * | Bz | H | CH₃ | F | OH | H | H | NH₂ |

*R² and R³ᵇ joined together by (CH₂)₃ to form five-membered ring.

TABLE III-47

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-47-1 | p-F—Ph | H | H | H | Bz | H | $CH_3$ | F | OH | H | H | $NH_2$ |
| III-47-2 | p-F—Ph | H | H | $CH_3$ | Bz | H | $CH_3$ | F | OH | H | H | $NH_2$ |
| III-47-3 | p-F—Ph | H | H | $CH(CH_3)_2$ | Bz | H | $CH_3$ | F | OH | H | H | $NH_2$ |
| III-47-4 | p-F—Ph | H | H | $CH_2CH(CH_3)_2$ | Bz | H | $CH_3$ | F | OH | H | H | $NH_2$ |
| III-47-5 | p-F—Ph | H | H | $CH_2Ph$ | Bz | H | $CH_3$ | F | OH | H | H | $NH_2$ |
| III-47-6 | p-F—Ph | H | H | $CH_2$-indol-3-yl | Bz | H | $CH_3$ | F | OH | H | H | $NH_2$ |
| III-47-7 | p-F—Ph | H | H | $CH_2CH_2SCH_3$ | Bz | H | $CH_3$ | F | OH | H | H | $NH_2$ |
| III-47-8 | p-F—Ph | * | H | * | Bz | H | $CH_3$ | F | OH | H | H | $NH_2$ |

*$R^2$ and $R^{3b}$ joined together by $(CH_2)_3$ to form five-membered ring.

TABLE III-48

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-48-1 | p-Cl—Ph | H | H | H | Bz | H | $CH_3$ | F | OH | H | H | $NH_2$ |
| III-48-2 | p-Cl—Ph | H | H | $CH_3$ | Bz | H | $CH_3$ | F | OH | H | H | $NH_2$ |
| III-48-3 | p-Cl—Ph | H | H | $CH(CH_3)_2$ | Bz | H | $CH_3$ | F | OH | H | H | $NH_2$ |
| III-48-4 | p-Cl—Ph | H | H | $CH_2CH(CH_3)_2$ | Bz | H | $CH_3$ | F | OH | H | H | $NH_2$ |
| III-48-5 | p-Cl—Ph | H | H | $CH_2Ph$ | Bz | H | $CH_3$ | F | OH | H | H | $NH_2$ |
| III-48-6 | p-Cl—Ph | H | H | $CH_2$-indol-3-yl | Bz | H | $CH_3$ | F | OH | H | H | $NH_2$ |
| III-48-7 | p-Cl—Ph | H | H | $CH_2CH_2SCH_3$ | Bz | H | $CH_3$ | F | OH | H | H | $NH_2$ |
| III-48-8 | p-Cl—Ph | * | H | * | Bz | H | $CH_3$ | F | OH | H | H | $NH_2$ |

*$R^2$ and $R^{3b}$ joined together by $(CH_2)_3$ to form five-membered ring.

TABLE III-49

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-49-1 | p-Br—Ph | H | H | H | Bz | H | $CH_3$ | F | OH | H | H | $NH_2$ |
| III-49-2 | p-Br—Ph | H | H | $CH_3$ | Bz | H | $CH_3$ | F | OH | H | H | $NH_2$ |
| III-49-3 | p-Br—Ph | H | H | $CH(CH_3)_2$ | Bz | H | $CH_3$ | F | OH | H | H | $NH_2$ |
| III-49-4 | p-Br—Ph | H | H | $CH_2CH(CH_3)_2$ | Bz | H | $CH_3$ | F | OH | H | H | $NH_2$ |
| III-49-5 | p-Br—Ph | H | H | $CH_2Ph$ | Bz | H | $CH_3$ | F | OH | H | H | $NH_2$ |
| III-49-6 | p-Br—Ph | H | H | $CH_2$-indol-3-yl | Bz | H | $CH_3$ | F | OH | H | H | $NH_2$ |
| III-49-7 | p-Br—Ph | H | H | $CH_2CH_2SCH_3$ | Bz | H | $CH_3$ | F | OH | H | H | $NH_2$ |
| III-49-8 | p-Br—Ph | * | H | * | Bz | H | $CH_3$ | F | OH | H | H | $NH_2$ |

*$R^2$ and $R^{3b}$ joined together by $(CH_2)_3$ to form five-membered ring.

TABLE III-50

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| III-50-1 | p-I—Ph | H | H | H | Bz | H | $CH_3$ | F | OH | H | H | $NH_2$ |
| III-50-2 | p-I—Ph | H | H | $CH_3$ | Bz | H | $CH_3$ | F | OH | H | H | $NH_2$ |
| III-50-3 | p-I—Ph | H | H | $CH(CH_3)_2$ | Bz | H | $CH_3$ | F | OH | H | H | $NH_2$ |
| III-50-4 | p-I—Ph | H | H | $CH_2CH(CH_3)_2$ | Bz | H | $CH_3$ | F | OH | H | H | $NH_2$ |
| III-50-5 | p-I—Ph | H | H | $CH_2Ph$ | Bz | H | $CH_3$ | F | OH | H | H | $NH_2$ |
| III-50-6 | p-I—Ph | H | H | $CH_2$-indol-3-yl | Bz | H | $CH_3$ | F | OH | H | H | $NH_2$ |
| III-50-7 | p-I—Ph | H | H | $CH_2CH_2SCH_3$ | Bz | H | $CH_3$ | F | OH | H | H | $NH_2$ |
| III-50-8 | p-I—Ph | * | H | * | Bz | H | $CH_3$ | F | OH | H | H | $NH_2$ |

*$R^2$ and $R^{3b}$ joined together by $(CH_2)_3$ to form five-membered ring.

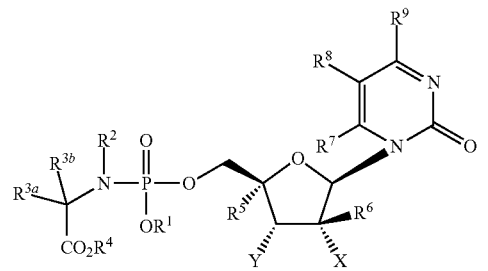

IV

TABLE IV-1

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-1-1 | $CH_3$ | H | H | H | $CH_3$ | H | F | F | OH | H | H | $NH_2$ |
| IV-1-2 | $CH_3$ | H | H | $CH_3$ | $CH_3$ | H | F | F | OH | H | H | $NH_2$ |
| IV-1-3 | $CH_3$ | H | H | $CH(CH_3)_3$ | $CH_3$ | H | F | F | OH | H | H | $NH_2$ |
| IV-1-4 | $CH_3$ | H | H | $CH_2CH(CH_3)_2$ | $CH_3$ | H | F | F | OH | H | H | $NH_2$ |
| IV-1-5 | $CH_3$ | H | H | $CH_2Ph$ | $CH_3$ | H | F | F | OH | H | H | $NH_2$ |
| IV-1-6 | $CH_3$ | H | H | $CH_2$-indol-3-yl | $CH_3$ | H | F | F | OH | H | H | $NH_2$ |
| IV-1-7 | $CH_3$ | H | H | $CH_2CH_2SCH_3$ | $CH_3$ | H | F | F | OH | H | H | $NH_2$ |
| IV-1-8 | $CH_3$ | * | H | * | $CH_3$ | H | F | F | OH | H | H | $NH_2$ |

*$R^2$ and $R^{3b}$ joined together by $(CH_2)_3$ to form five-membered ring.

TABLE IV-2

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-2-1 | Et | H | H | H | $CH_3$ | H | F | F | OH | H | H | $NH_2$ |
| IV-2-2 | Et | H | H | $CH_3$ | $CH_3$ | H | F | F | OH | H | H | $NH_2$ |
| IV-2-3 | Et | H | H | $CH(CH_3)_2$ | $CH_3$ | H | F | F | OH | H | H | $NH_2$ |
| IV-2-4 | Et | H | H | $CH_2CH(CH_3)_2$ | $CH_3$ | H | F | F | OH | H | H | $NH_2$ |
| IV-2-5 | Et | H | H | $CH_2Ph$ | $CH_3$ | H | F | F | OH | H | H | $NH_2$ |
| IV-2-6 | Et | H | H | $CH_2$-indol-3-yl | $CH_3$ | H | F | F | OH | H | H | $NH_2$ |
| IV-2-7 | Et | H | H | $CH_2CH_2SCH_3$ | $CH_3$ | H | F | F | OH | H | H | $NH_2$ |
| IV-2-8 | Et | * | H | * | $CH_3$ | H | F | F | OH | H | H | $NH_2$ |

*$R^2$ and $R^{3b}$ joined together by $(CH_2)_3$ to form five-membered ring.

TABLE IV-3

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-3-1 | $^iPr$ | H | H | H | $CH_3$ | H | F | F | OH | H | H | $NH_2$ |
| IV-3-2 | $^iPr$ | H | H | $CH_3$ | $CH_3$ | H | F | F | OH | H | H | $NH_2$ |
| IV-3-3 | $^iPr$ | H | H | $CH(CH_3)_2$ | $CH_3$ | H | F | F | OH | H | H | $NH_2$ |
| IV-3-4 | $^iPr$ | H | H | $CH_2CH(CH_3)_2$ | $CH_3$ | H | F | F | OH | H | H | $NH_2$ |
| IV-3-5 | $^iPr$ | H | H | $CH_2Ph$ | $CH_3$ | H | F | F | OH | H | H | $NH_2$ |
| IV-3-6 | $^iPr$ | H | H | $CH_2$-indol-3-yl | $CH_3$ | H | F | F | OH | H | H | $NH_2$ |
| IV-3-7 | $^iPr$ | H | H | $CH_2CH_2SCH_3$ | $CH_3$ | H | F | F | OH | H | H | $NH_2$ |
| IV-3-8 | $^iPr$ | * | H | * | $CH_3$ | H | F | F | OH | H | H | $NH_2$ |

*$R^2$ and $R^{3b}$ joined together by $(CH_2)_3$ to form five-membered ring.

TABLE IV-4

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-4-1 | $^tBu$ | H | H | H | $CH_3$ | H | $CH_3$ | F | OH | H | H | $NH_2$ |
| IV-4-2 | $^tBu$ | H | H | $CH_3$ | $CH_3$ | H | $CH_3$ | F | OH | H | H | $NH_2$ |
| IV-4-3 | $^tBu$ | H | H | $CH(CH_3)_2$ | $CH_3$ | H | $CH_3$ | F | OH | H | H | $NH_2$ |
| IV-4-4 | $^tBu$ | H | H | $CH_2CH(CH_3)_2$ | $CH_3$ | H | $CH_3$ | F | OH | H | H | $NH_2$ |
| IV-4-5 | $^tBu$ | H | H | $CH_2Ph$ | $CH_3$ | H | $CH_3$ | F | OH | H | H | $NH_2$ |
| IV-4-6 | $^tBu$ | H | H | $CH_2$-indol-3-yl | $CH_3$ | H | $CH_3$ | F | OH | H | H | $NH_2$ |
| IV-4-7 | $^tBu$ | H | H | $CH_2CH_2SCH_3$ | $CH_3$ | H | $CH_3$ | F | OH | H | H | $NH_2$ |
| IV-4-8 | $^tBu$ | * | H | * | $CH_3$ | H | $CH_3$ | F | OH | H | H | $NH_2$ |

*$R^2$ and $R^{3b}$ joined together by $(CH_2)_3$ to form five-membered ring.

TABLE IV-5

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-5-1 | Ph | H | H | H | $CH_3$ | H | F | F | OH | H | H | $NH_2$ |
| IV-5-2 | Ph | H | H | $CH_3$ | $CH_3$ | H | F | F | OH | H | H | $NH_2$ |
| IV-5-3 | Ph | H | H | $CH(CH_3)_2$ | $CH_3$ | H | F | F | OH | H | H | $NH_2$ |
| IV-5-4 | Ph | H | H | $CH_2CH(CH_3)_2$ | $CH_3$ | H | F | F | OH | H | H | $NH_2$ |
| IV-5-5 | Ph | H | H | $CH_2Ph$ | $CH_3$ | H | F | F | OH | H | H | $NH_2$ |

TABLE IV-5-continued

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-5-6 | Ph | H | H | $CH_2$-indol-3-yl | $CH_3$ | H | F | F | OH | H | H | $NH_2$ |
| IV-5-7 | Ph | H | H | $CH_2CH_2SCH_3$ | $CH_3$ | H | F | F | OH | H | H | $NH_2$ |
| IV-5-8 | Ph | * | H | * | $CH_3$ | H | F | F | OH | H | H | $NH_2$ |

*$R^2$ and $R^{3b}$ joined together by $(CH_2)_3$ to form five-membered ring.

TABLE IV-6

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-6-1 | p-Me—Ph | H | H | H | $CH_3$ | H | F | F | OH | H | H | $NH_2$ |
| IV-6-2 | p-Me—Ph | H | H | $CH_3$ | $CH_3$ | H | F | F | OH | H | H | $NH_2$ |
| IV-6-3 | p-Me—Ph | H | H | $CH(CH_3)_2$ | $CH_3$ | H | F | F | OH | H | H | $NH_2$ |
| IV-6-4 | p-Me—Ph | H | H | $CH_2CH(CH_3)_2$ | $CH_3$ | H | F | F | OH | H | H | $NH_2$ |
| IV-6-5 | p-Me—Ph | H | H | $CH_2Ph$ | $CH_3$ | H | F | F | OH | H | H | $NH_2$ |
| IV-6-6 | p-Me—Ph | H | H | $CH_2$-indol-3-yl | $CH_3$ | H | F | F | OH | H | H | $NH_2$ |
| IV-6-7 | p-Me—Ph | H | H | $CH_2CH_2SCH_3$ | $CH_3$ | H | F | F | OH | H | H | $NH_2$ |
| IV-6-8 | p-Me—Ph | * | H | * | $CH_3$ | H | F | F | OH | H | H | $NH_2$ |

*$R^2$ and $R^{3b}$ joined together by $(CH_2)_3$ to form five-membered ring.

TABLE IV-7

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-7-1 | p-F—Ph | H | H | H | $CH_3$ | H | F | F | OH | H | H | $NH_2$ |
| IV-7-2 | p-F—Ph | H | H | $CH_3$ | $CH_3$ | H | F | F | OH | H | H | $NH_2$ |
| IV-7-3 | p-F—Ph | H | H | $CH(CH_3)_2$ | $CH_3$ | H | F | F | OH | H | H | $NH_2$ |
| IV-7-4 | p-F—Ph | H | H | $CH_2CH(CH_3)_2$ | $CH_3$ | H | F | F | OH | H | H | $NH_2$ |
| IV-7-6 | p-F—Ph | H | H | $CH_2Ph$ | $CH_3$ | H | F | F | OH | H | H | $NH_2$ |
| IV-7-7 | p-F—Ph | H | H | $CH_2$-indol-3-yl | $CH_3$ | H | F | F | OH | H | H | $NH_2$ |
| IV-7-8 | p-F—Ph | H | H | $CH_2CH_2SCH_3$ | $CH_3$ | H | F | F | OH | H | H | $NH_2$ |
| IV-7-20 | p-F—Ph | * | H | * | $CH_3$ | H | F | F | OH | H | H | $NH_2$ |

*$R^2$ and $R^{3b}$ joined together by $(CH_2)_3$ to form five-membered ring.

TABLE IV-8

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-8-1 | p-Cl—Ph | H | H | H | $CH_3$ | H | F | F | OH | H | H | $NH_2$ |
| IV-8-2 | p-Cl—Ph | H | H | $CH_3$ | $CH_3$ | H | F | F | OH | H | H | $NH_2$ |
| IV-8-3 | p-Cl—Ph | H | H | $CH(CH_3)_2$ | $CH_3$ | H | F | F | OH | H | H | $NH_2$ |
| IV-8-4 | p-Cl—Ph | H | H | $CH_2CH(CH_3)_2$ | $CH_3$ | H | F | F | OH | H | H | $NH_2$ |
| IV-8-5 | p-Cl—Ph | H | H | $CH_2Ph$ | $CH_3$ | H | F | F | OH | H | H | $NH_2$ |
| IV-8-6 | p-Cl—Ph | H | H | $CH_2$-indol-3-yl | $CH_3$ | H | F | F | OH | H | H | $NH_2$ |
| IV-8-7 | p-Cl—Ph | H | H | $CH_2CH_2SCH_3$ | $CH_3$ | H | F | F | OH | H | H | $NH_2$ |
| IV-8-8 | p-Cl—Ph | * | H | * | $CH_3$ | H | F | F | OH | H | H | $NH_2$ |

*$R^2$ and $R^{3b}$ joined together by $(CH_2)_3$ to form five-membered ring.

TABLE IV-9

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-9-1 | p-Br—Ph | H | H | H | $CH_3$ | H | F | F | OH | H | H | $NH_2$ |
| IV-9-2 | p-Br—Ph | H | H | $CH_3$ | $CH_3$ | H | F | F | OH | H | H | $NH_2$ |
| IV-9-3 | p-Br—Ph | H | H | $CH(CH_3)_2$ | $CH_3$ | H | F | F | OH | H | H | $NH_2$ |
| IV-9-4 | p-Br—Ph | H | H | $CH_2CH(CH_3)_2$ | $CH_3$ | H | F | F | OH | H | H | $NH_2$ |
| IV-9-6 | p-Br—Ph | H | H | $CH_2Ph$ | $CH_3$ | H | F | F | OH | H | H | $NH_2$ |
| IV-9-7 | p-Br—Ph | H | H | $CH_2$-indol-3-yl | $CH_3$ | H | F | F | OH | H | H | $NH_2$ |
| IV-9-8 | p-Br—Ph | H | H | $CH_2CH_2SCH_3$ | $CH_3$ | H | F | F | OH | H | H | $NH_2$ |
| IV-9-20 | p-Br—Ph | * | H | * | $CH_3$ | H | F | F | OH | H | H | $NH_2$ |

*$R^2$ and $R^{3b}$ joined together by $(CH_2)_3$ to form five-membered ring.

TABLE IV-10

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-10-1 | p-I—Ph | H | H | H | CH$_3$ | H | F | F | OH | H | H | NH$_2$ |
| IV-10-2 | p-I—Ph | H | H | CH$_3$ | CH$_3$ | H | F | F | OH | H | H | NH$_2$ |
| IV-10-3 | p-I—Ph | H | H | CH(CH$_3$)$_2$ | CH$_3$ | H | F | F | OH | H | H | NH$_2$ |
| IV-10-4 | p-I—Ph | H | H | CH$_2$CH(CH$_3$)$_2$ | CH$_3$ | H | F | F | OH | H | H | NH$_2$ |
| IV-10-5 | p-I—Ph | H | H | CH$_2$Ph | CH$_3$ | H | F | F | OH | H | H | NH$_2$ |
| IV-10-6 | p-I—Ph | H | H | CH$_2$-indol-3-yl | CH$_3$ | H | F | F | OH | H | H | NH$_2$ |
| IV-10-7 | p-I—Ph | H | H | CH$_2$CH$_2$SCH$_3$ | CH$_3$ | H | F | F | OH | H | H | NH$_2$ |
| IV-10-8 | p-I—Ph | * | H | * | CH$_3$ | H | F | F | OH | H | H | NH$_2$ |

*R$^2$ and R$^{3b}$ joined together by (CH$_2$)$_3$ to form five-membered ring.

TABLE IV-11

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-11-1 | CH$_3$ | H | H | H | Et | H | F | F | OH | H | H | NH$_2$ |
| IV-11-2 | CH$_3$ | H | H | CH$_3$ | Et | H | F | F | OH | H | H | NH$_2$ |
| IV-11-3 | CH$_3$ | H | H | CH(CH$_3$)$_2$ | Et | H | F | F | OH | H | H | NH$_2$ |
| IV-11-4 | CH$_3$ | H | H | CH$_2$CH(CH$_3$)$_2$ | Et | H | F | F | OH | H | H | NH$_2$ |
| IV-11-5 | CH$_3$ | H | H | CH$_2$Ph | Et | H | F | F | OH | H | H | NH$_2$ |
| IV-11-6 | CH$_3$ | H | H | CH$_2$-indol-3-yl | Et | H | F | F | OH | H | H | NH$_2$ |
| IV-11-7 | CH$_3$ | H | H | CH$_2$CH$_2$SCH$_3$ | Et | H | F | F | OH | H | H | NH$_2$ |
| IV-11-8 | CH$_3$ | * | H | * | Et | H | F | F | OH | H | H | NH$_2$ |

*R$^2$ and R$^{3b}$ joined together by (CH$_2$)$_3$ to form five-membered ring.

TABLE IV-12

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-12-1 | Et | H | H | H | Et | H | F | F | OH | H | H | NH$_2$ |
| IV-12-2 | Et | H | H | CH$_3$ | Et | H | F | F | OH | H | H | NH$_2$ |
| IV-12-3 | Et | H | H | CH(CH$_3$)$_2$ | Et | H | F | F | OH | H | H | NH$_2$ |
| IV-12-4 | Et | H | H | CH$_2$CH(CH$_3$)$_2$ | Et | H | F | F | OH | H | H | NH$_2$ |
| IV-12-5 | Et | H | H | CH$_2$Ph | Et | H | F | F | OH | H | H | NH$_2$ |
| IV-12-6 | Et | H | H | CH$_2$-indol-3-yl | Et | H | F | F | OH | H | H | NH$_2$ |
| IV-12-7 | Et | H | H | CH$_2$CH$_2$SCH$_3$ | Et | H | F | F | OH | H | H | NH$_2$ |
| IV-12-8 | Et | * | H | * | Et | H | F | F | OH | H | H | NH$_2$ |

*R$^2$ and R$^{3b}$ joined together by (CH$_2$)$_3$ to form five-membered ring.

TABLE IV-13

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-13-1 | $^i$Pr | H | H | H | Et | H | F | F | OH | H | H | NH$_2$ |
| IV-13-2 | $^i$Pr | H | H | CH$_3$ | Et | H | F | F | OH | H | H | NH$_2$ |
| IV-13-3 | $^i$Pr | H | H | CH(CH$_3$)$_2$ | Et | H | F | F | OH | H | H | NH$_2$ |
| IV-13-4 | $^i$Pr | H | H | CH$_2$CH(CH$_3$)$_2$ | Et | H | F | F | OH | H | H | NH$_2$ |
| IV-13-5 | $^i$Pr | H | H | CH$_2$Ph | Et | H | F | F | OH | H | H | NH$_2$ |
| IV-13-6 | $^i$Pr | H | H | CH$_2$-indol-3-yl | Et | H | F | F | OH | H | H | NH$_2$ |
| IV-13-7 | $^i$Pr | H | H | CH$_2$CH$_2$SCH$_3$ | Et | H | F | F | OH | H | H | NH$_2$ |
| IV-13-8 | $^i$Pr | * | H | * | Et | H | F | F | OH | H | H | NH$_2$ |

*R$^2$ and R$^{3b}$ joined together by (CH$_2$)$_3$ to form five-membered ring.

TABLE IV-14

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-14-1 | $^t$Bu | H | H | H | Et | H | F | F | OH | H | H | NH$_2$ |
| IV-14-2 | $^t$Bu | H | H | CH$_3$ | Et | H | F | F | OH | H | H | NH$_2$ |
| IV-14-3 | $^t$Bu | H | H | CH(CH$_3$)$_2$ | Et | H | F | F | OH | H | H | NH$_2$ |
| IV-14-4 | $^t$Bu | H | H | CH$_2$CH(CH$_3$)$_2$ | Et | H | F | F | OH | H | H | NH$_2$ |
| IV-14-5 | $^t$Bu | H | H | CH$_2$Ph | Et | H | F | F | OH | H | H | NH$_2$ |

TABLE IV-14-continued

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-14-6 | $^t$Bu | H | H | CH$_2$-indol-3-yl | Et | H | F | F | OH | H | H | NH$_2$ |
| IV-14-7 | $^t$Bu | H | H | CH$_2$CH$_2$SCH$_3$ | Et | H | F | F | OH | H | H | NH$_2$ |
| IV-14-8 | $^t$Bu | * | H | * | Et | H | F | F | OH | H | H | NH$_2$ |

*$R^2$ and $R^{3b}$ joined together by (CH$_2$)$_3$ to form five-membered ring.

TABLE IV-15

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-15-1 | Ph | H | H | H | Et | H | F | F | OH | H | H | NH$_2$ |
| IV-15-2 | Ph | H | H | CH$_3$ | Et | H | F | F | OH | H | H | NH$_2$ |
| IV-15-3 | Ph | H | H | CH(CH$_3$)$_2$ | Et | H | F | F | OH | H | H | NH$_2$ |
| IV-15-4 | Ph | H | H | CH$_2$CH(CH$_3$)$_2$ | Et | H | F | F | OH | H | H | NH$_2$ |
| IV-15-5 | Ph | H | H | CH$_2$Ph | Et | H | F | F | OH | H | H | NH$_2$ |
| IV-15-6 | Ph | H | H | CH$_2$-indol-3-yl | Et | H | F | F | OH | H | H | NH$_2$ |
| IV-15-7 | Ph | H | H | CH$_2$CH$_2$SCH$_3$ | Et | H | F | F | OH | H | H | NH$_2$ |
| IV-15-8 | Ph | * | H | * | Et | H | F | F | OH | H | H | NH$_2$ |

*$R^2$ and $R^{3b}$ joined together by (CH$_2$)$_3$ to form five-membered ring.

TABLE IV-16

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-16-1 | p-Me—Ph | H | H | H | Et | H | F | F | OH | H | H | NH$_2$ |
| IV-16-2 | p-Me—Ph | H | H | CH$_3$ | Et | H | F | F | OH | H | H | NH$_2$ |
| IV-16-3 | p-Me—Ph | H | H | CH(CH$_3$)$_2$ | Et | H | F | F | OH | H | H | NH$_2$ |
| IV-16-4 | p-Me—Ph | H | H | CH$_2$CH(CH$_3$)$_2$ | Et | H | F | F | OH | H | H | NH$_2$ |
| IV-16-5 | p-Me—Ph | H | H | CH$_2$Ph | Et | H | F | F | OH | H | H | NH$_2$ |
| IV-16-6 | p-Me—Ph | H | H | CH$_2$-indol-3-yl | Et | H | F | F | OH | H | H | NH$_2$ |
| IV-16-7 | p-Me—Ph | H | H | CH$_2$CH$_2$SCH$_3$ | Et | H | F | F | OH | H | H | NH$_2$ |
| IV-16-8 | p-Me—Ph | * | H | * | Et | H | F | F | OH | H | H | NH$_2$ |

*$R^2$ and $R^{3b}$ joined together by (CH$_2$)$_3$ to form five-membered ring.

TABLE IV-17

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-17-1 | p-F—Ph | H | H | H | Et | H | F | F | OH | H | H | NH$_2$ |
| IV-17-2 | p-F—Ph | H | H | CH$_3$ | Et | H | F | F | OH | H | H | NH$_2$ |
| IV-17-3 | p-F—Ph | H | H | CH(CH$_3$)$_2$ | Et | H | F | F | OH | H | H | NH$_2$ |
| IV-17-4 | p-F—Ph | H | H | CH$_2$CH(CH$_3$)$_2$ | Et | H | F | F | OH | H | H | NH$_2$ |
| IV-17-5 | p-F—Ph | H | H | CH$_2$Ph | Et | H | F | F | OH | H | H | NH$_2$ |
| IV-17-6 | p-F—Ph | H | H | CH$_2$-indol-3-yl | Et | H | F | F | OH | H | H | NH$_2$ |
| IV-17-7 | p-F—Ph | H | H | CH$_2$CH$_2$SCH$_3$ | Et | H | F | F | OH | H | H | NH$_2$ |
| IV-17-8 | p-F—Ph | * | H | * | Et | H | F | F | OH | H | H | NH$_2$ |

*$R^2$ and $R^{3b}$ joined together by (CH$_2$)$_3$ to form five-membered ring.

TABLE IV-18

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-18-1 | p-Cl—Ph | H | H | H | Et | H | F | F | OH | H | H | NH$_2$ |
| IV-18-2 | p-Cl—Ph | H | H | CH$_3$ | Et | H | F | F | OH | H | H | NH$_2$ |
| IV-18-3 | p-Cl—Ph | H | H | CH(CH$_3$)$_2$ | Et | H | F | F | OH | H | H | NH$_2$ |
| IV-18-4 | p-Cl—Ph | H | H | CH$_2$CH(CH$_3$)$_2$ | Et | H | F | F | OH | H | H | NH$_2$ |
| IV-18-5 | p-Cl—Ph | H | H | CH$_2$Ph | Et | H | F | F | OH | H | H | NH$_2$ |
| IV-18-6 | p-Cl—Ph | H | H | CH$_2$-indol-3-yl | Et | H | F | F | OH | H | H | NH$_2$ |
| IV-18-7 | p-Cl—Ph | H | H | CH$_2$CH$_2$SCH$_3$ | Et | H | F | F | OH | H | H | NH$_2$ |
| IV-18-8 | p-Cl—Ph | * | H | * | Et | H | F | F | OH | H | H | NH$_2$ |

*$R^2$ and $R^{3b}$ joined together by (CH$_2$)$_3$ to form five-membered ring.

TABLE IV-19

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-19-1 | p-Br—Ph | H | H | H | Et | H | F | F | OH | H | H | NH₂ |
| IV-19-2 | p-Br—Ph | H | H | CH₃ | Et | H | F | F | OH | H | H | NH₂ |
| IV-19-3 | p-Br—Ph | H | H | CH(CH₃)₂ | Et | H | F | F | OH | H | H | NH₂ |
| IV-19-4 | p-Br—Ph | H | H | CH₂CH(CH₃)₂ | Et | H | F | F | OH | H | H | NH₂ |
| IV-19-5 | p-Br—Ph | H | H | CH₂Ph | Et | H | F | F | OH | H | H | NH₂ |
| IV-19-6 | p-Br—Ph | H | H | CH₂-indol-3-yl | Et | H | F | F | OH | H | H | NH₂ |
| IV-19-7 | p-Br—Ph | H | H | CH₂CH₂SCH₃ | Et | H | F | F | OH | H | H | NH₂ |
| IV-19-8 | p-Br—Ph | * | H | * | Et | H | F | F | OH | H | H | NH₂ |

*R² and R³ᵇ joined together by (CH₂)₃ to form five-membered ring.

TABLE IV-20

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-20-1 | p-I—Ph | H | H | H | Et | H | F | F | OH | H | H | NH₂ |
| IV-20-2 | p-I—Ph | H | H | CH₃ | Et | H | F | F | OH | H | H | NH₂ |
| IV-20-3 | p-I—Ph | H | H | CH(CH₃)₂ | Et | H | F | F | OH | H | H | NH₂ |
| IV-20-4 | p-I—Ph | H | H | CH₂CH(CH₃)₂ | Et | H | F | F | OH | H | H | NH₂ |
| IV-20-5 | p-I—Ph | H | H | CH₂Ph | Et | H | F | F | OH | H | H | NH₂ |
| IV-20-6 | p-I—Ph | H | H | CH₂-indol-3-yl | Et | H | F | F | OH | H | H | NH₂ |
| IV-20-7 | p-I—Ph | H | H | CH₂CH₂SCH₃ | Et | H | F | F | OH | H | H | NH₂ |
| IV-20-8 | p-I—Ph | * | H | * | Et | H | F | F | OH | H | H | NH₂ |

*R² and R³ᵇ joined together by (CH₂)₃ to form five-membered ring.

TABLE IV-21

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-21-1 | CH₃ | H | H | H | ⁱPr | H | F | F | OH | H | H | NH₂ |
| IV-21-2 | CH₃ | H | H | CH₃ | ⁱPr | H | F | F | OH | H | H | NH₂ |
| IV-21-3 | CH₃ | H | H | CH(CH₃)₂ | ⁱPr | H | F | F | OH | H | H | NH₂ |
| IV-21-4 | CH₃ | H | H | CH₂CH(CH₃)₂ | ⁱPr | H | F | F | OH | H | H | NH₂ |
| IV-21-5 | CH₃ | H | H | CH₂Ph | ⁱPr | H | F | F | OH | H | H | NH₂ |
| IV-21-6 | CH₃ | H | H | CH₂-indol-3-yl | ⁱPr | H | F | F | OH | H | H | NH₂ |
| IV-21-7 | CH₃ | H | H | CH₂CH₂SCH₃ | ⁱPr | H | F | F | OH | H | H | NH₂ |
| IV-21-8 | CH₃ | * | H | * | ⁱPr | H | F | F | OH | H | H | NH₂ |

*R² and R³ᵇ joined together by (CH₂)₃ to form five-membered ring.

TABLE IV-22

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-22-1 | Et | H | H | H | ⁱPr | H | F | F | OH | H | H | NH₂ |
| IV-22-2 | Et | H | H | CH₃ | ⁱPr | H | F | F | OH | H | H | NH₂ |
| IV-22-3 | Et | H | H | CH(CH₃)₂ | ⁱPr | H | F | F | OH | H | H | NH₂ |
| IV-22-4 | Et | H | H | CH₂CH(CH₃)₂ | ⁱPr | H | F | F | OH | H | H | NH₂ |
| IV-22-5 | Et | H | H | CH₂Ph | ⁱPr | H | F | F | OH | H | H | NH₂ |
| IV-22-6 | Et | H | H | CH₂-indol-3-yl | ⁱPr | H | F | F | OH | H | H | NH₂ |
| IV-22-7 | Et | H | H | CH₂CH₂SCH₃ | ⁱPr | H | F | F | OH | H | H | NH₂ |
| IV-22-8 | Et | * | H | * | ⁱPr | H | F | F | OH | H | H | NH₂ |

*R² and R³ᵇ joined together by (CH₂)₃ to form five-membered ring.

TABLE IV-23

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-23-1 | ⁱPr | H | H | H | ⁱPr | H | F | F | OH | H | H | NH₂ |
| IV-23-2 | ⁱPr | H | H | CH₃ | ⁱPr | H | F | F | OH | H | H | NH₂ |
| IV-23-3 | ⁱPr | H | H | CH(CH₃)₂ | ⁱPr | H | F | F | OH | H | H | NH₂ |
| IV-23-4 | ⁱPr | H | H | CH₂CH(CH₃)₂ | ⁱPr | H | F | F | OH | H | H | NH₂ |
| IV-23-5 | ⁱPr | H | H | CH₂Ph | ⁱPr | H | F | F | OH | H | H | NH₂ |

TABLE IV-23-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-23-6 | $^i$Pr | H | H | CH₂-indol-3-yl | $^i$Pr | H | F | F | OH | H | H | NH₂ |
| IV-23-7 | $^i$Pr | H | H | CH₂CH₂SCH₃ | $^i$Pr | H | F | F | OH | H | H | NH₂ |
| IV-23-8 | $^i$Pr | * | H | * | $^i$Pr | H | F | F | OH | H | H | NH₂ |

*R² and R³ᵇ joined together by (CH₂)₃ to form five-membered ring.

TABLE IV-24

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-24-1 | $^t$Bu | H | H | H | $^i$Pr | H | F | F | OH | H | H | NH₂ |
| IV-24-2 | $^t$Bu | H | H | CH₃ | $^i$Pr | H | F | F | OH | H | H | NH₂ |
| IV-24-3 | $^t$Bu | H | H | CH(CH₃)₂ | $^i$Pr | H | F | F | OH | H | H | NH₂ |
| IV-24-4 | $^t$Bu | H | H | CH₂CH(CH₃)₂ | $^i$Pr | H | F | F | OH | H | H | NH₂ |
| IV-24-5 | $^t$Bu | H | H | CH₂Ph | $^i$Pr | H | F | F | OH | H | H | NH₂ |
| IV-24-6 | $^t$Bu | H | H | CH₂-indol-3-yl | $^i$Pr | H | F | F | OH | H | H | NH₂ |
| IV-24-7 | $^t$Bu | H | H | CH₂CH₂SCH₃ | $^i$Pr | H | F | F | OH | H | H | NH₂ |
| IV-24-8 | $^t$Bu | * | H | * | $^i$Pr | H | F | F | OH | H | H | NH₂ |

*R² and R³ᵇ joined together by (CH₂)₃ to form five-membered ring.

TABLE IV-25

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-25-1 | Ph | H | H | H | $^i$Pr | H | F | F | OH | H | H | NH₂ |
| IV-25-2 | Ph | H | H | CH₃ | $^i$Pr | H | F | F | OH | H | H | NH₂ |
| IV-25-3 | Ph | H | H | CH(CH₃)₂ | $^i$Pr | H | F | F | OH | H | H | NH₂ |
| IV-25-4 | Ph | H | H | CH₂CH(CH₃)₂ | $^i$Pr | H | F | F | OH | H | H | NH₂ |
| IV-25-5 | Ph | H | H | CH₂Ph | $^i$Pr | H | F | F | OH | H | H | NH₂ |
| IV-25-6 | Ph | H | H | CH₂-indol-3-yl | $^i$Pr | H | F | F | OH | H | H | NH₂ |
| IV-25-7 | Ph | H | H | CH₂CH₂SCH₃ | $^i$Pr | H | F | F | OH | H | H | NH₂ |
| IV-25-8 | Ph | * | H | * | $^i$Pr | H | F | F | OH | H | H | NH₂ |

*R² and R³ᵇ joined together by (CH₂)₃ to form five-membered ring.

TABLE IV-26

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-26-1 | p-Me—Ph | H | H | H | $^i$Pr | H | F | F | OH | H | H | NH₂ |
| IV-26-2 | p-Me—Ph | H | H | CH₃ | $^i$Pr | H | F | F | OH | H | H | NH₂ |
| IV-26-3 | p-Me—Ph | H | H | CH(CH₃)₂ | $^i$Pr | H | F | F | OH | H | H | NH₂ |
| IV-26-4 | p-Me—Ph | H | H | CH₂CH(CH₃)₂ | $^i$Pr | H | F | F | OH | H | H | NH₂ |
| IV-26-5 | p-Me—Ph | H | H | CH₂Ph | $^i$Pr | H | F | F | OH | H | H | NH₂ |
| IV-26-6 | p-Me—Ph | H | H | CH₂-indol-3-yl | $^i$Pr | H | F | F | OH | H | H | NH₂ |
| IV-26-7 | p-Me—Ph | H | H | CH₂CH₂SCH₃ | $^i$Pr | H | F | F | OH | H | H | NH₂ |
| IV-26-8 | p-Me—Ph | * | H | * | $^i$Pr | H | F | F | OH | H | H | NH₂ |

*R² and R³ᵇ joined together by (CH₂)₃ to form five-membered ring.

TABLE IV-27

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-27-1 | p-F—Ph | H | H | H | $^i$Pr | H | F | F | OH | H | H | NH₂ |
| IV-27-2 | p-F—Ph | H | H | CH₃ | $^i$Pr | H | F | F | OH | H | H | NH₂ |
| IV-27-3 | p-F—Ph | H | H | CH(CH₃)₂ | $^i$Pr | H | F | F | OH | H | H | NH₂ |
| IV-27-4 | p-F—Ph | H | H | CH₂CH(CH₃)₂ | $^i$Pr | H | F | F | OH | H | H | NH₂ |
| IV-27-5 | p-F—Ph | H | H | CH₂Ph | $^i$Pr | H | F | F | OH | H | H | NH₂ |
| IV-27-6 | p-F—Ph | H | H | CH₂-indol-3-yl | $^i$Pr | H | F | F | OH | H | H | NH₂ |
| IV-27-7 | p-F—Ph | H | H | CH₂CH₂SCH₃ | $^i$Pr | H | F | F | OH | H | H | NH₂ |
| IV-27-8 | p-F—Ph | * | H | * | $^i$Pr | H | F | F | OH | H | H | NH₂ |

*R² and R³ᵇ joined together by (CH₂)₃ to form five-membered ring.

TABLE IV-28

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-28-1 | p-Cl—Ph | H | H | H | $^i$Pr | H | F | F | OH | H | H | NH$_2$ |
| IV-28-2 | p-Cl—Ph | H | H | CH$_3$ | $^i$Pr | H | F | F | OH | H | H | NH$_2$ |
| IV-28-3 | p-Cl—Ph | H | H | CH(CH$_3$)$_2$ | $^i$Pr | H | F | F | OH | H | H | NH$_2$ |
| IV-28-4 | p-Cl—Ph | H | H | CH$_2$CH(CH$_3$)$_2$ | $^i$Pr | H | F | F | OH | H | H | NH$_2$ |
| IV-28-5 | p-Cl—Ph | H | H | CH$_2$Ph | $^i$Pr | H | F | F | OH | H | H | NH$_2$ |
| IV-28-6 | p-Cl—Ph | H | H | CH$_2$-indol-3-yl | $^i$Pr | H | F | F | OH | H | H | NH$_2$ |
| IV-28-7 | p-Cl—Ph | H | H | CH$_2$CH$_2$SCH$_3$ | $^i$Pr | H | F | F | OH | H | H | NH$_2$ |
| IV-28-8 | p-Cl—Ph | * | H | * | $^i$Pr | H | F | F | OH | H | H | NH$_2$ |

*R² and R³ᵇ joined together by (CH$_2$)$_3$ to form five-membered ring.

TABLE IV-29

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-29-1 | p-Br—Ph | H | H | H | $^i$Pr | H | F | F | OH | H | H | NH$_2$ |
| IV-29-2 | p-Br—Ph | H | H | CH$_3$ | $^i$Pr | H | F | F | OH | H | H | NH$_2$ |
| IV-29-3 | p-Br—Ph | H | H | CH(CH$_3$)$_2$ | $^i$Pr | H | F | F | OH | H | H | NH$_2$ |
| IV-29-4 | p-Br—Ph | H | H | CH$_2$CH(CH$_3$)$_2$ | $^i$Pr | H | F | F | OH | H | H | NH$_2$ |
| IV-29-5 | p-Br—Ph | H | H | CH$_2$Ph | $^i$Pr | H | F | F | OH | H | H | NH$_2$ |
| IV-29-6 | p-Br—Ph | H | H | CH$_2$-indol-3-yl | $^i$Pr | H | F | F | OH | H | H | NH$_2$ |
| IV-29-7 | p-Br—Ph | H | H | CH$_2$CH$_2$SCH$_3$ | $^i$Pr | H | F | F | OH | H | H | NH$_2$ |
| IV-29-8 | p-Br—Ph | * | H | * | $^i$Pr | H | F | F | OH | H | H | NH$_2$ |

*R² and R³ᵇ joined together by (CH$_2$)$_3$ to form five-membered ring.

TABLE IV-30

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-30-1 | p-I—Ph | H | H | H | $^i$Pr | H | F | F | OH | H | H | NH$_2$ |
| IV-30-2 | p-I—Ph | H | H | CH$_3$ | $^i$Pr | H | F | F | OH | H | H | NH$_2$ |
| IV-30-3 | p-I—Ph | H | H | CH(CH$_3$)$_2$ | $^i$Pr | H | F | F | OH | H | H | NH$_2$ |
| IV-30-4 | p-I—Ph | H | H | CH$_2$CH(CH$_3$)$_2$ | $^i$Pr | H | F | F | OH | H | H | NH$_2$ |
| IV-30-5 | p-I—Ph | H | H | CH$_2$Ph | $^i$Pr | H | F | F | OH | H | H | NH$_2$ |
| IV-30-6 | p-I—Ph | H | H | CH$_2$-indol-3-yl | $^i$Pr | H | F | F | OH | H | H | NH$_2$ |
| IV-30-7 | p-I—Ph | H | H | CH$_2$CH$_2$SCH$_3$ | $^i$Pr | H | F | F | OH | H | H | NH$_2$ |
| IV-30-8 | p-I—Ph | * | H | * | $^i$Pr | H | F | F | OH | H | H | NH$_2$ |

*R² and R³ᵇ joined together by (CH$_2$)$_3$ to form five-membered ring.

TABLE IV-31

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-31-1 | CH$_3$ | H | H | H | $^n$Bu | H | F | F | OH | H | H | NH$_2$ |
| IV-31-2 | CH$_3$ | H | H | CH$_3$ | $^n$Bu | H | F | F | OH | H | H | NH$_2$ |
| IV-31-3 | CH$_3$ | H | H | CH(CH$_3$)$_2$ | $^n$Bu | H | F | F | OH | H | H | NH$_2$ |
| IV-31-4 | CH$_3$ | H | H | CH$_2$CH(CH$_3$)$_2$ | $^n$Bu | H | F | F | OH | H | H | NH$_2$ |
| IV-31-5 | CH$_3$ | H | H | CH$_2$Ph | $^n$Bu | H | F | F | OH | H | H | NH$_2$ |
| IV-31-6 | CH$_3$ | H | H | CH$_2$-indol-3-yl | $^n$Bu | H | F | F | OH | H | H | NH$_2$ |
| IV-31-7 | CH$_3$ | H | H | CH$_2$CH$_2$SCH$_3$ | $^n$Bu | H | F | F | OH | H | H | NH$_2$ |
| IV-31-8 | CH$_3$ | * | H | * | $^n$Bu | H | F | F | OH | H | H | NH$_2$ |

*R² and R³ᵇ joined together by (CH$_2$)$_3$ to form five-membered ring.

TABLE IV-32

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-32-1 | Et | H | H | H | $^n$Bu | H | F | F | OH | H | H | NH$_2$ |
| IV-32-2 | Et | H | H | CH$_3$ | $^n$Bu | H | F | F | OH | H | H | NH$_2$ |
| IV-32-3 | Et | H | H | CH(CH$_3$)$_2$ | $^n$Bu | H | F | F | OH | H | H | NH$_2$ |
| IV-32-4 | Et | H | H | CH$_2$CH(CH$_3$)$_2$ | $^n$Bu | H | F | F | OH | H | H | NH$_2$ |
| IV-32-5 | Et | H | H | CH$_2$Ph | $^n$Bu | H | F | F | OH | H | H | NH$_2$ |

TABLE IV-32-continued

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-32-6 | Et | H | H | CH$_2$-indol-3-yl | $^n$Bu | H | F | F | OH | H | H | NH$_2$ |
| IV-32-7 | Et | H | H | CH$_2$CH$_2$SCH$_3$ | $^n$Bu | H | F | F | OH | H | H | NH$_2$ |
| IV-32-8 | Et | * | H | * | $^n$Bu | H | F | F | OH | H | H | NH$_2$ |

*R$^2$ and R$^{3b}$ joined together by (CH$_2$)$_3$ to form five-membered ring.

TABLE IV-33

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-33-1 | $^i$Pr | H | H | H | $^n$Bu | H | F | F | OH | H | H | NH$_2$ |
| IV-33-2 | $^i$Pr | H | H | CH$_3$ | $^n$Bu | H | F | F | OH | H | H | NH$_2$ |
| IV-33-3 | $^i$Pr | H | H | CH(CH$_3$)$_2$ | $^n$Bu | H | F | F | OH | H | H | NH$_2$ |
| IV-33-4 | $^i$Pr | H | H | CH$_2$CH(CH$_3$)$_2$ | $^n$Bu | H | E | F | OH | H | H | NH$_2$ |
| IV-33-5 | $^i$Pr | H | H | CH$_2$Ph | $^n$Bu | H | F | F | OH | H | H | NH$_2$ |
| IV-33-6 | $^i$Pr | H | H | CH$_2$-indol-3-yl | $^n$Bu | H | F | F | OH | H | H | NH$_2$ |
| IV-33-7 | $^i$Pr | H | H | CH$_2$CH$_2$SCH$_3$ | $^n$Bu | H | F | F | OH | H | H | NH$_2$ |
| IV-33-8 | $^i$Pr | * | H | * | $^n$Bu | H | F | F | OH | H | H | NH$_2$ |

*R$^2$ and R$^{3b}$ joined together by (CH$_2$)$_3$ to form five-membered ring.

TABLE IV-34

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-34-1 | $^t$Bu | H | H | H | $^n$Bu | H | F | F | OH | H | H | NH$_2$ |
| IV-34-2 | $^t$Bu | H | H | CH$_3$ | $^n$Bu | H | F | F | OH | H | H | NH$_2$ |
| IV-34-3 | $^t$Bu | H | H | CH(CH$_3$)$_2$ | $^n$Bu | H | F | F | OH | H | H | NH$_2$ |
| IV-34-4 | $^t$Bu | H | H | CH$_2$CH(CH$_3$)$_2$ | $^n$Bu | H | F | F | OH | H | H | NH$_2$ |
| IV-34-5 | $^t$Bu | H | H | CH$_2$Ph | $^n$Bu | H | F | F | OH | H | H | NH$_2$ |
| IV-34-6 | $^t$Bu | H | H | CH$_2$-indol-3-yl | $^n$Bu | H | F | F | OH | H | H | NH$_2$ |
| IV-34-7 | $^t$Bu | H | H | CH$_2$CH$_2$SCH$_3$ | $^n$Bu | H | F | F | OH | H | H | NH$_2$ |
| IV-34-8 | $^t$Bu | * | H | * | $^n$Bu | H | F | F | OH | H | H | NH$_2$ |

*R$^2$ and R$^{3b}$ joined together by (CH$_2$)$_3$ to form five-membered ring.

TABLE IV-35

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-35-1 | Ph | H | H | H | $^n$Bu | H | F | F | OH | H | H | NH$_2$ |
| IV-35-2 | Ph | H | H | CH$_3$ | $^n$Bu | H | F | F | OH | H | H | NH$_2$ |
| IV-35-3 | Ph | H | H | CH(CH$_3$)$_2$ | $^n$Bu | H | F | F | OH | H | H | NH$_2$ |
| IV-35-4 | Ph | H | H | CH$_2$CH(CH$_3$)$_2$ | $^n$Bu | H | F | F | OH | H | H | NH$_2$ |
| IV-35-5 | Ph | H | H | CH$_2$Ph | $^n$Bu | H | F | F | OH | H | H | NH$_2$ |
| IV-35-6 | Ph | H | H | CH$_2$-indol-3-yl | $^n$Bu | H | F | F | OH | H | H | NH$_2$ |
| IV-35-7 | Ph | H | H | CH$_2$CH$_2$SCH$_3$ | $^n$Bu | H | F | F | OH | H | H | NH$_2$ |
| IV-35-8 | Ph | * | H | * | $^n$Bu | H | F | F | OH | H | H | NH$_2$ |

*R$^2$ and R$^{3b}$ joined together by (CH$_2$)$_3$ to form five-membered ring.

TABLE IV-36

| No | R$^1$ | R$^2$ | R$^{3a}$ | R$^{3b}$ | R$^4$ | R$^5$ | R$^6$ | X | Y | R$^7$ | R8 | R$^9$ |
|---|---|---|---|---|---|---|---|---|---|---|---|---|
| IV-36-1 | p-Me—Ph | H | H | H | $^n$Bu | H | F | F | OH | H | H | NH$_2$ |
| IV-36-2 | p-Me—Ph | H | H | CH$_3$ | $^n$Bu | H | F | F | OH | H | H | NH$_2$ |
| IV-36-3 | p-Me—Ph | H | H | CH(CH$_3$)$_2$ | $^n$Bu | H | F | F | OH | H | H | NH$_2$ |
| IV-36-4 | p-Me—Ph | H | H | CH$_2$CH(CH$_3$)$_2$ | $^n$Bu | H | F | F | OH | H | H | NH$_2$ |
| IV-36-5 | p-Me—Ph | H | H | CH$_2$Ph | $^n$Bu | H | F | F | OH | H | H | NH$_2$ |
| IV-36-6 | p-Me—Ph | H | H | CH$_2$-indol-3-yl | $^n$Bu | H | F | F | OH | H | H | NH$_2$ |
| IV-36-7 | p-Me—Ph | H | H | CH$_2$CH$_2$SCH$_3$ | $^n$Bu | H | F | F | OH | H | H | NH$_2$ |
| IV-36-8 | p-Me—Ph | * | H | * | $^n$Bu | H | F | F | OH | H | H | NH$_2$ |

*R$^2$ and R$^{3b}$ joined together by (CH$_2$)$_3$ to form five-membered ring.

TABLE IV-37

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-37-1 | p-F—Ph | H | H | H | ⁿBu | H | F | F | OH | H | H | NH₂ |
| IV-37-2 | p-F—Ph | H | H | CH₃ | ⁿBu | H | F | F | OH | H | H | NH₂ |
| IV-37-3 | p-F—Ph | H | H | CH(CH₃)₂ | ⁿBu | H | F | F | OH | H | H | NH₂ |
| IV-37-4 | p-P—Ph | H | H | CH₂CH(CH₃)₂ | ⁿBu | H | F | F | OH | H | H | NH₂ |
| IV-37-5 | p-F—Ph | H | H | CH₂Ph | ⁿBu | H | F | F | OH | H | H | NH₂ |
| IV-37-6 | p-F—Ph | H | H | CH₂-indol-3-yl | ⁿBu | H | F | F | OH | H | H | NH₂ |
| IV-37-7 | p-F—Ph | H | H | CH₂CH₂SCH₃ | ⁿBu | H | F | F | OH | H | H | NH₂ |
| IV-37-8 | p-F—Ph | * | H | * | ⁿBu | H | F | F | OH | H | H | NH₂ |

*R² and R³ᵇ joined together by (CH₂)₃ to form five-membered ring.

TABLE IV-38

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-38-1 | p-Cl—Ph | H | H | H | ⁿBu | H | F | F | OH | H | H | NH₂ |
| IV-38-2 | p-Cl—Ph | H | H | CH₃ | ⁿBu | H | F | F | OH | H | H | NH₂ |
| IV-38-3 | p-Cl—Ph | H | H | CH(CH₃)₂ | ⁿBu | H | F | F | OH | H | H | NH₂ |
| IV-38-4 | p-Cl—Ph | H | H | CH₂CH(CH₃)₂ | ⁿBu | H | F | F | OH | H | H | NH₂ |
| IV-38-5 | p-Cl—Ph | H | H | CH₂Ph | ⁿBu | H | F | F | OH | H | H | NH₂ |
| IV-38-6 | p-Cl—Ph | H | H | CH₂-indol-3-yl | ⁿBu | H | F | F | OH | H | H | NH₂ |
| IV-38-7 | p-Cl—Ph | H | H | CH₂CH₂SCH₃ | ⁿBu | H | F | F | OH | H | H | NH₂ |
| IV-38-8 | p-Cl—Ph | * | H | * | ⁿBu | H | F | F | OH | H | H | NH₂ |

*R² and R³ᵇ joined together by (CH₂)₃ to form five-membered ring.

TABLE IV-39

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-39-1 | p-Br—Ph | H | H | H | ⁿBu | H | F | F | OH | H | H | NH₂ |
| IV-39-2 | p-Br—Ph | H | H | CH₃ | ⁿBu | H | F | F | OH | H | H | NH₂ |
| IV-39-3 | p-Br—Ph | H | H | CH(CH₃)₂ | ⁿBu | H | F | F | OH | H | H | NH₂ |
| IV-39-4 | p-Br—Ph | H | H | CH₂CH(CH₃)₂ | ⁿBu | H | F | F | OH | H | H | NH₂ |
| IV-39-5 | p-Br—Ph | H | H | CH₂Ph | ⁿBu | H | F | F | OH | H | H | NH₂ |
| IV-39-6 | p-Br—Ph | H | H | CH₂-indol-3-yl | ⁿBu | H | F | F | OH | H | H | NH₂ |
| IV-39-7 | p-Br—Ph | H | H | CH₂CH₂SCH₃ | ⁿBu | H | F | F | OH | H | H | NH₂ |
| IV-39-8 | p-Br—Ph | * | H | * | ⁿBu | H | F | F | OH | H | H | NH₂ |

*R² and R³ᵇ joined together by (CH₂)₃ to form five-membered ring.

TABLE IV-40

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-40-1 | p-I—Ph | H | H | H | ⁿBu | H | F | F | OH | H | H | NH₂ |
| IV-40-2 | p-I—Ph | H | H | CH₃ | ⁿBu | H | F | F | OH | H | H | NH₂ |
| IV-40-3 | p-I—ph | H | H | CH(CH₃)₂ | ⁿBu | H | F | F | OH | H | H | NH₂ |
| IV-40-4 | p-I—Ph | H | H | CH₂CH(CH₃)₂ | ⁿBu | H | F | F | OH | H | H | NH₂ |
| IV-40-5 | p-I—Ph | H | H | CH₂Ph | ⁿBu | H | F | F | OH | H | H | NH₂ |
| IV-40-6 | p-I—Ph | H | H | CH₂-indol-3-yl | ⁿBu | H | F | F | OH | H | H | NH₂ |
| IV-40-7 | p-I—Ph | H | H | CH₂CH₂SCH₃ | ⁿBu | H | F | F | OH | H | H | NH₂ |
| IV-40-8 | p-I—Ph | * | H | * | ⁿBu | H | F | F | OH | H | H | NH₂ |

*R² and R³ᵇ joined together by (CH₂)₃ to form five-membered ring.

TABLE IV-41

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-41-1 | CH₃ | H | H | H | Bz | H | F | F | OH | H | H | NH₂ |
| IV-41-2 | CH₃ | H | H | CH₃ | Bz | H | F | F | OH | H | H | NH₂ |
| IV-41-3 | CH₃ | H | H | CH(CH₃)₂ | Bz | H | F | F | OH | H | H | NH₂ |
| IV-41-4 | CH₃ | H | H | CH₂CH(CH₃)₂ | Bz | H | F | F | OH | H | H | NH₂ |
| IV-41-5 | CH₃ | H | H | CH₂Ph | Bz | H | F | F | OH | H | H | NH₂ |

TABLE IV-41-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-41-6 | CH₃ | H | H | CH₂-indol-3-yl | Bz | H | F | F | OH | H | H | NH₂ |
| IV-41-7 | CH₃ | H | H | CH₂CH₂SCH₃ | Bz | H | F | F | OH | H | H | NH₂ |
| IV-41-8 | CH₃ | * | H | * | Bz | H | F | F | OH | H | H | NH₂ |

*R² and R³ᵇ joined together by (CH₂)₃ to form five-membered ring.

TABLE IV-42

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-42-1 | Et | H | H | H | Bz | H | F | F | OH | H | H | NH₂ |
| IV-42-2 | Et | H | H | CH₃ | Bz | H | F | F | OH | H | H | NH₂ |
| IV-42-3 | Et | H | H | CH(CH₃)₂ | Bz | H | F | F | OH | H | H | NH₂ |
| IV-42-4 | Et | H | H | CH₂CH(CH₃)₂ | Bz | H | F | F | OH | H | H | NH₂ |
| IV-42-5 | Et | H | H | CH₂Ph | Bz | H | F | F | OH | H | H | NH₂ |
| IV-42-6 | Et | H | H | CH₂-indol-3-yl | Bz | H | F | F | OH | H | H | NH₂ |
| IV-42-7 | Et | H | H | CH₂CH₂SCH₃ | Bz | H | F | F | OH | H | H | NH₂ |
| IV-42-8 | Et | * | H | * | Bz | H | F | F | OH | H | H | NH₂ |

*R² and R³ᵇ joined together by (CH₂)₃ to form five-membered ring.

TABLE IV-43

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-43-1 | ⁱPr | H | H | H | Bz | H | F | F | OH | H | H | NH₂ |
| IV-43-2 | ⁱPr | H | H | CH₃ | Bz | H | F | F | OH | H | H | NH₂ |
| IV-43-3 | ⁱPr | H | H | CH(CH₃)₂ | Bz | H | F | F | OH | H | H | NH₂ |
| IV-43-4 | ⁱPr | H | H | CH₂CH(CH₃)₂ | Bz | H | F | F | OH | H | H | NH₂ |
| IV-43-5 | ⁱPr | H | H | CH₂Ph | Bz | H | F | F | OH | H | H | NH₂ |
| IV-43-6 | ⁱPr | H | H | CH₂-indol-3-yl | Bz | H | F | F | OH | H | H | NH₂ |
| IV-43-7 | ⁱPr | H | H | CH₂CH₂SCH₃ | Bz | H | F | F | OH | H | H | NH₂ |
| IV-43-8 | ⁱPr | * | H | * | Bz | H | F | F | OH | H | H | NH₂ |

*R² and R³ᵇ joined together by (CH₂)₃ to form five-membered ring.

TABLE IV-44

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-44-1 | ᵗBu | H | H | H | Bz | H | F | F | OH | H | H | NH₂ |
| IV-44-2 | ᵗBu | H | H | CH₃ | Bz | H | F | F | OH | H | H | NH₂ |
| IV-44-3 | ᵗBu | H | H | CH(CH₃)₂ | Bz | H | F | F | OH | H | H | NH₂ |
| IV-44-4 | ᵗBu | H | H | CH₂CH(CH₃)₂ | Bz | H | F | F | OH | H | H | NH₂ |
| IV-44-5 | ᵗBu | H | H | CH₂Ph | Bz | H | F | F | OH | H | H | NH₂ |
| IV-44-6 | ᵗBu | H | H | CH₂-indol-3-yl | Bz | H | F | F | OH | H | H | NH₂ |
| IV-44-7 | ᵗBu | H | H | CH₂CH₂SCH₃ | Bz | H | F | F | OH | H | H | NH₂ |
| IV-44-8 | ᵗBu | * | H | * | Bz | H | F | F | OH | H | H | NH₂ |

*R² and R³ᵇ joined together by (CH₂)₃ to form five-membered ring.

TABLE IV-45

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| IV-45-1 | Ph | H | H | H | Bz | H | F | F | OH | H | H | NH₂ |
| IV-45-2 | Ph | H | H | CH₃ | Bz | H | F | F | OH | H | H | NH₂ |
| IV-45-3 | Ph | H | H | CH(CH₃)₂ | Bz | H | F | F | OH | H | H | NH₂ |
| IV-45-4 | Ph | H | H | CH₂CH(CH₃)₂ | Bz | H | F | F | OH | H | H | NH₂ |
| IV-45-5 | Ph | H | H | CH₂Ph | Bz | H | F | F | OH | H | H | NH₂ |
| IV-45-6 | Ph | H | H | CH₂-indol-3-yl | Bz | H | F | F | OH | H | H | NH₂ |
| IV-45-7 | Ph | H | H | CH₂CH₂SCH₃ | Bz | H | F | F | OH | H | H | NH₂ |
| IV-45-8 | Ph | * | H | * | Bz | H | F | F | OH | H | H | NH₂ |

*R² and R³ᵇ joined together by (CH₂)₃ to form five-membered ring.

TABLE IV-46

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-46-1 | p-Me—Ph | H | H | H | Bz | H | F | F | OH | H | H | NH$_2$ |
| IV-46-2 | p-Me—Ph | H | H | CH$_3$ | Bz | H | F | F | OH | H | H | NH$_2$ |
| IV-46-3 | p-Me—Ph | H | H | CH(CH$_3$)$_2$ | Bz | H | F | F | OH | H | H | NH$_2$ |
| IV-46-4 | p-Me—Ph | H | H | CH$_2$CH(CH$_3$)$_2$ | Bz | H | F | F | OH | H | H | NH$_2$ |
| IV-46-5 | p-Me—Ph | H | H | CH$_2$Ph | Bz | H | F | F | OH | H | H | NH$_2$ |
| IV-46-6 | p-Me—Ph | H | H | CH$_2$-indol-3-yl | Bz | H | F | F | OH | H | H | NH$_2$ |
| IV-46-7 | p-Me—Ph | H | H | CH$_2$CH$_2$SCH$_3$ | Bz | H | F | F | OH | H | H | NH$_2$ |
| IV-46-8 | p-Me—Ph | * | H | * | Bz | H | F | F | OH | H | H | NH$_2$ |

*R$^2$ and R$^{3b}$ joined together by (CH$_2$)$_3$ to form five-membered ring.

TABLE IV-47

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-47-1 | p-F—Ph | H | H | H | Bz | H | F | F | OH | H | H | NH$_2$ |
| IV-47-2 | p-F—Ph | H | H | CH$_3$ | Bz | H | F | F | OH | H | H | NH$_2$ |
| IV-47-3 | p-F—Ph | H | H | CH(CH$_3$)$_2$ | Bz | H | F | F | OH | H | H | NH$_2$ |
| IV-47-4 | p-F—Ph | H | H | CH$_2$CH(CH$_3$)$_2$ | Bz | H | F | F | OH | H | H | NH$_2$ |
| IV-47-5 | p-F—Ph | H | H | CH$_2$Ph | Bz | H | F | F | OH | H | H | NH$_2$ |
| IV-47-6 | p-F—Ph | H | H | CH$_2$-indol-3-yl | Bz | H | F | F | OH | H | H | NH$_2$ |
| IV-47-7 | p-F—Ph | H | H | CH$_2$CH$_2$SCH$_3$ | Bz | H | F | F | OH | H | H | NH$_2$ |
| IV-47-8 | p-F—Ph | * | H | * | Bz | H | F | F | OH | H | H | NH$_2$ |

*R$^2$ and R$^{3b}$ joined together by (CH$_2$)$_3$ to form five-membered ring.

TABLE IV-48

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-48-1 | p-Cl—Ph | H | H | H | Bz | H | F | F | OH | H | H | NH$_2$ |
| IV-48-2 | p-Cl—Ph | H | H | CH$_3$ | Bz | H | F | F | OH | H | H | NH$_2$ |
| IV-48-3 | p-Cl—Ph | H | H | CH(CH$_3$)$_2$ | Bz | H | F | F | OH | H | H | NH$_2$ |
| IV-48-4 | p-Cl—Ph | H | H | CH$_2$CH(CH$_3$)$_2$ | Bz | H | F | F | OH | H | H | NH$_2$ |
| IV-48-5 | p-Cl—Ph | H | H | CH$_2$Ph | Bz | H | F | F | OH | H | H | NH$_2$ |
| IV-48-6 | p-Cl—Ph | H | H | CH$_2$-indol-3-yl | Bz | H | F | F | OH | H | H | NH$_2$ |
| IV-48-7 | p-Cl—Ph | H | H | CH$_2$CH$_2$SCH$_3$ | Bz | H | F | F | OH | H | H | NH$_2$ |
| IV-48-8 | p-Cl—Ph | * | H | * | Bz | H | F | F | OH | H | H | NH$_2$ |

*R$^2$ and R$^{3b}$ joined together by (CH$_2$)$_3$ to form five-membered ring.

TABLE IV-49

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-49-1 | p-Br—Ph | H | H | H | Bz | H | F | F | OH | H | H | NH$_2$ |
| IV-49-2 | p-Br—Ph | H | H | CH$_3$ | Bz | H | F | F | OH | H | H | NH$_2$ |
| IV-49-3 | p-Br—Ph | H | H | CH(CH$_3$)$_2$ | Bz | H | F | F | OH | H | H | NH$_2$ |
| IV-49-4 | p-Br—Ph | H | H | CH$_2$CH(CH$_3$)$_2$ | Bz | H | F | F | OH | H | H | NH$_2$ |
| IV-49-5 | p-Br—Ph | H | H | CH$_2$Ph | Bz | H | F | F | OH | H | H | NH$_2$ |
| IV-49-6 | p-Br—Ph | H | H | CH$_2$-indol-3-yl | Bz | H | F | F | OH | H | H | NH$_2$ |
| IV-49-7 | p-Br—Ph | H | H | CH$_2$CH$_2$SCH$_3$ | Bz | H | F | F | OH | H | H | NH$_2$ |
| IV-49-8 | p-Br—Ph | * | H | * | Bz | H | F | F | OH | H | H | NH$_2$ |

*R$^2$ and R$^{3b}$ joined together by (CH$_2$)$_3$ to form five-membered ring.

TABLE IV-50

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| IV-50-1 | p-I—Ph | H | H | H | Bz | H | F | F | OH | H | H | NH$_2$ |
| IV-50-2 | p-I—Ph | H | H | CH$_3$ | Bz | H | F | F | OH | H | H | NH$_2$ |
| IV-50-3 | p-I—Ph | H | H | CH(CH$_3$)$_2$ | Bz | H | F | F | OH | H | H | NH$_2$ |
| IV-50-4 | p-I—Ph | H | H | CH$_2$CH(CH$_3$)$_2$ | Bz | H | F | F | OH | H | H | NH$_2$ |
| IV-50-5 | p-I—Ph | H | H | CH$_2$Ph | Bz | H | F | F | OH | H | H | NH$_2$ |

TABLE IV-50-continued

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| IV-50-6 | p-I—Ph | H | H | $CH_2$-indol-3-yl | Bz | H | F | F | OH | H | H | $NH_2$ |
| IV-50-7 | p-I—Ph | H | H | $CH_2CH_2SCH_3$ | Bz | H | F | F | OH | H | H | $NH_2$ |
| IV-50-8 | p-I—Ph | * | H | * | Bz | H | F | F | OH | H | H | $NH_2$ |

*$R^2$ and $R^{3b}$ joined together by $(CH_2)_3$ to form five-membered ring.

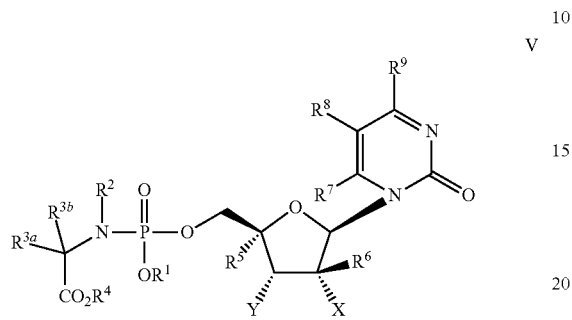

V

TABLE V-1

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-1-1 | $CH_3$ | H | H | H | $CH_3$ | H | H | F | OH | H | H | $NH_2$ |
| V-1-2 | $CH_3$ | H | H | $CH_3$ | $CH_3$ | H | H | F | OH | H | H | $NH_2$ |
| V-1-3 | $CH_3$ | H | H | $CH(CH_3)_2$ | $CH_3$ | H | H | F | OH | H | H | $NH_2$ |
| V-1-4 | $CH_3$ | H | H | $CH_2CH(CH_3)_2$ | $CH_3$ | H | H | F | OH | H | H | $NH_2$ |
| V-1-5 | $CH_3$ | H | H | $CH_2Ph$ | $CH_3$ | H | H | F | OH | H | H | $NH_2$ |
| V-1-6 | $CH_3$ | H | H | $CH_2$-indol-3-yl | $CH_3$ | H | H | F | OH | H | H | $NH_2$ |
| V-1-7 | $CH_3$ | H | H | $CH_2CH_2SCH_3$ | $CH_3$ | H | H | F | OH | H | H | $NH_2$ |
| V-1-8 | $CH_3$ | * | H | * | $CH_3$ | H | H | F | OH | H | H | $NH_2$ |

*$R^2$ and $R^{3b}$ joined together by $(CH_2)_3$ to form five-membered ring.

TABLE V-2

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-2-1 | Et | H | H | H | $CH_3$ | H | H | F | OH | H | H | $NH_2$ |
| V-2-2 | Et | H | H | $CH_3$ | $CH_3$ | H | H | F | OH | H | H | $NH_2$ |
| V-2-3 | Et | H | H | $CH(CH_3)_2$ | $CH_3$ | H | H | F | OH | H | H | $NH_2$ |
| V-2-4 | Et | H | H | $CH_2CH(CH_3)_2$ | $CH_3$ | H | H | F | OH | H | H | $NH_2$ |
| V-2-5 | Et | H | H | $CH_2Ph$ | $CH_3$ | H | H | F | OH | H | H | $NH_2$ |
| V-2-6 | Et | H | H | $CH_2$-indol-3-yl | $CH_3$ | H | H | F | OH | H | H | $NH_2$ |
| V-2-7 | Et | H | H | $CH_2CH_2SCH_3$ | $CH_3$ | H | H | F | OH | H | H | $NH_2$ |
| V-2-8 | Et | * | H | * | $CH_3$ | H | H | F | OH | H | H | $NH_2$ |

*$R^2$ and $R^{3b}$ joined together by $(CH_2)_3$ to form five-membered ring.

TABLE V-3

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-3-1 | $^iPr$ | H | H | H | $CH_3$ | H | H | F | OH | H | H | $NH_2$ |
| V-3-2 | $^iPr$ | H | H | $CH_3$ | $CH_3$ | H | H | F | OH | H | H | $NH_2$ |
| V-3-3 | $^iPr$ | H | H | $CH(CH_3)_2$ | $CH_3$ | H | H | F | OH | H | H | $NH_2$ |
| V-3-4 | $^iPr$ | H | H | $CH_2CH(CH_3)_2$ | $CH_3$ | H | H | F | OH | H | H | $NH_2$ |
| V-3-5 | $^iPr$ | H | H | $CH_2Ph$ | $CH_3$ | H | H | F | OH | H | H | $NH_2$ |
| V-3-6 | $^iPr$ | H | H | $CH_2$-indol-3-yl | $CH_3$ | H | H | F | OH | H | H | $NH_2$ |
| V-3-7 | $^iPr$ | H | H | $CH_2CH_2SCH_3$ | $CH_3$ | H | H | F | OH | H | H | $NH_2$ |
| V-3-8 | $^iPr$ | * | H | * | $CH_3$ | H | H | F | OH | H | H | $NH_2$ |

*$R^2$ and $R^{3b}$ joined together by $(CH_2)_3$ to form five-membered ring.

TABLE V-4

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-4-1 | $^t$Bu | H | H | H | $CH_3$ | H | H | F | OH | H | H | $NH_2$ |
| V-4-2 | $^t$Bu | H | H | $CH_3$ | $CH_3$ | H | H | F | OH | H | H | $NH_2$ |
| V-4-3 | $^t$Bu | H | H | $CH(CH_3)_2$ | $CH_3$ | H | H | F | OH | H | H | $NH_2$ |
| V-4-4 | $^t$Bu | H | H | $CH_2CH(CH_3)_2$ | $CH_3$ | H | H | F | OH | H | H | $NH_2$ |
| V-4-5 | $^t$Bu | H | H | $CH_2Ph$ | $CH_3$ | H | H | F | OH | H | H | $NH_2$ |
| V-4-6 | $^t$Bu | H | H | $CH_2$-indol-3-yl | $CH_3$ | H | H | F | OH | H | H | $NH_2$ |
| V-4-7 | $^t$Bu | H | H | $CH_2CH_2SCH_3$ | $CH_3$ | H | H | F | OH | H | H | $NH_2$ |
| V-4-8 | $^t$Bu | * | H | * | $CH_3$ | H | H | F | OH | H | H | $NH_2$ |

*$R^2$ and $R^{3b}$ joined together by $(CH_2)_3$ to form five-membered ring.

TABLE V-5

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-5-1 | Ph | H | H | H | $CH_3$ | H | H | F | OH | H | H | $NH_2$ |
| V-5-2 | Ph | H | H | $CH_3$ | $CH_3$ | H | H | F | OH | H | H | $NH_2$ |
| V-5-3 | Ph | H | H | $CH(CH_3)_2$ | $CH_3$ | H | H | F | OH | H | H | $NH_2$ |
| V-5-4 | Ph | H | H | $CH_2CH(CH_3)_2$ | $CH_3$ | H | H | F | OH | H | H | $NH_2$ |
| V-5-5 | Ph | H | H | $CH_2Ph$ | $CH_3$ | H | H | F | OH | H | H | $NH_2$ |
| V-5-6 | Ph | H | H | $CH_2$-indol-3-yl | $CH_3$ | H | H | F | OH | H | H | $NH_2$ |
| V-5-7 | Ph | H | H | $CH_2CH_2SCH_3$ | $CH_3$ | H | H | F | OH | H | H | $NH_2$ |
| V-5-8 | Ph | * | H | * | $CH_3$ | H | H | F | OH | H | H | $NH_2$ |

*$R^2$ and $R^{3b}$ joined together by $(CH_2)_3$ to form five-membered ring.

TABLE V-6

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-6-1 | p-Me—Ph | H | H | H | $CH_3$ | H | H | F | OH | H | H | $NH_2$ |
| V-6-2 | p-Me—Ph | H | H | $CH_3$ | $CH_3$ | H | H | F | OH | H | H | $NH_2$ |
| V-6-3 | p-Me—Ph | H | H | $CH(CH_3)_2$ | $CH_3$ | H | H | F | OH | H | H | $NH_2$ |
| V-6-4 | p-Me—Ph | H | H | $CH_2CH(CH_3)_2$ | $CH_3$ | H | H | F | OH | H | H | $NH_2$ |
| V-6-5 | p-Me—Ph | H | H | $CH_2Ph$ | $CH_3$ | H | H | F | OH | H | H | $NH_2$ |
| V-6-6 | p-Me—Ph | H | H | $CH_2$-indol-3-yl | $CH_3$ | H | H | F | OH | H | H | $NH_2$ |
| V-6-7 | p-Me—Ph | H | H | $CH_2CH_2SCH_3$ | $CH_3$ | H | H | F | OH | H | H | $NH_2$ |
| V-6-8 | p-Me—Ph | * | H | * | $CH_3$ | H | H | F | OH | H | H | $NH_2$ |

*$R^2$ and $R^{3b}$ joined together by $(CH_2)_3$ to form five-membered ring.

TABLE V-7

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-7-1 | p-F—Ph | H | H | H | $CH_3$ | H | H | F | OH | H | H | $NH_2$ |
| V-7-2 | p-F—Ph | H | H | $CH_3$ | $CH_3$ | H | H | F | OH | H | H | $NH_2$ |
| V-7-3 | p-F—Ph | H | H | $CH(CH_3)_2$ | $CH_3$ | H | H | F | OH | H | H | $NH_2$ |
| V-7-4 | p-F—Ph | H | H | $CH_2CH(CH_3)_2$ | $CH_3$ | H | H | F | OH | H | H | $NH_2$ |
| V-7-6 | p-F—Ph | H | H | $CH_2Ph$ | $CH_3$ | H | H | F | OH | H | H | $NH_2$ |
| V-7-7 | p-F—Ph | H | H | $CH_2$-indol-3-yl | $CH_3$ | H | H | F | OH | H | H | $NH_2$ |
| V-7-8 | p-F—Ph | H | H | $CH_2CH_2SCH_3$ | $CH_3$ | H | H | F | OH | H | H | $NH_2$ |
| V-7-20 | p-F—Ph | * | H | * | $CH_3$ | H | H | F | OH | H | H | $NH_2$ |

*$R^2$ and $R^{3b}$ joined together by $(CH_2)_3$ to form five-membered ring.

TABLE V-8

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-8-1 | p-Cl—Ph | H | H | H | $CH_3$ | H | H | F | OH | H | H | $NH_2$ |
| V-8-2 | p-Cl—Ph | H | H | $CH_3$ | $CH_3$ | H | H | F | OH | H | H | $NH_2$ |
| V-8-3 | p-Cl—Ph | H | H | $CH(CH_3)_2$ | $CH_3$ | H | H | F | OH | H | H | $NH_2$ |
| V-8-4 | p-Cl—Ph | H | H | $CH_2CH(CH_3)_2$ | $CH_3$ | H | H | F | OH | H | H | $NH_2$ |
| V-8-5 | p-Cl—Ph | H | H | $CH_2Ph$ | $CH_3$ | H | H | F | OH | H | H | $NH_2$ |

TABLE V-8-continued

| No | R[1] | R[2] | R[3a] | R[3b] | R[4] | R[5] | R[6] | X | Y | R[7] | R[8] | R[9] |
|---|---|---|---|---|---|---|---|---|---|---|---|---|
| V-8-6 | p-Cl—Ph | H | H | CH$_2$-indol-3-yl | CH$_3$ | H | H | F | OH | H | H | NH$_2$ |
| V-8-7 | p-Cl—Ph | H | H | CH$_2$CH$_2$SCH$_3$ | CH$_3$ | H | H | F | OH | H | H | NH$_2$ |
| V-8-8 | p-Cl—Ph | * | H | * | CH$_3$ | H | H | F | OH | H | H | NH$_2$ |

*R[2] and R[3b] joined together by (CH$_2$)$_3$ to form five-membered ring.

TABLE V-9

| No | R[1] | R[2] | R[3a] | R[3b] | R[4] | R[5] | R[6] | X | Y | R[7] | R[8] | R[9] |
|---|---|---|---|---|---|---|---|---|---|---|---|---|
| V-9-1 | p-Br—Ph | H | H | H | CH$_3$ | H | H | F | OH | H | H | NH$_2$ |
| V-9-2 | p-Br—Ph | H | H | CH$_3$ | CH$_3$ | H | H | F | OH | H | H | NH$_2$ |
| V-9-3 | p-Br—Ph | H | H | CH(CH$_3$)$_2$ | CH$_3$ | H | H | F | OH | H | H | NH$_2$ |
| V-9-4 | p-Br—Ph | H | H | CH$_2$CH(CH$_3$)$_2$ | CH$_3$ | H | H | F | OH | H | H | NH$_2$ |
| V-9-6 | p-Br—Ph | H | H | CH$_2$Ph | CH$_3$ | H | H | F | OH | H | H | NH$_2$ |
| V-9-7 | p-Br—Ph | H | H | CH$_2$-indol-3-yl | CH$_3$ | H | H | F | OH | H | H | NH$_2$ |
| V-9-8 | p-Br—Ph | H | H | CH$_2$CH$_2$SCH$_3$ | CH$_3$ | H | H | F | OH | H | H | NH$_2$ |
| V-9-20 | p-Br—Ph | * | H | * | CH$_3$ | H | H | F | OH | H | H | NH$_2$ |

*R[2] and R[3b] joined together by (CH$_2$)$_3$ to form five-membered ring.

TABLE V-10

| No | R[1] | R[2] | R[3a] | R[3b] | R[4] | R[5] | R[6] | X | Y | R[7] | R[8] | R[9] |
|---|---|---|---|---|---|---|---|---|---|---|---|---|
| V-10-1 | p-I—Ph | H | H | H | CH$_3$ | H | H | F | OH | H | H | NH$_2$ |
| V-10-2 | p-I—Ph | H | H | CH$_3$ | CH$_3$ | H | H | F | OH | H | H | NH$_2$ |
| V-10-3 | p-I—Ph | H | H | CH(CH$_3$)$_2$ | CH$_3$ | H | H | F | OH | H | H | NH$_2$ |
| V-10-4 | p-I—Ph | H | H | CH$_2$CH(CH$_3$)$_2$ | CH$_3$ | H | H | F | OH | H | H | NH$_2$ |
| V-10-5 | p-I—Ph | H | H | CH$_2$Ph | CH$_3$ | H | H | F | OH | H | H | NH$_2$ |
| V-10-6 | p-I—Ph | H | H | CH$_2$-indol-3-yl | CH$_3$ | H | H | F | OH | H | H | NH$_2$ |
| V-10-7 | p-I—Ph | H | H | CH$_2$CH$_2$SCH$_3$ | CH$_3$ | H | H | F | OH | H | H | NH$_2$ |
| V-10-8 | p-I—Ph | * | H | * | CH$_3$ | H | H | F | OH | H | H | NH$_2$ |

*R[2] and R[3b] joined together by (CH$_2$)$_3$ to form five-membered ring.

TABLE V-11

| No | R[1] | R[2] | R[3a] | R[3b] | R[4] | R[5] | R[6] | X | Y | R[7] | R[8] | R[9] |
|---|---|---|---|---|---|---|---|---|---|---|---|---|
| V-11-1 | CH$_3$ | H | H | H | Et | H | H | F | OH | H | H | NH$_2$ |
| V-11-2 | CH$_3$ | H | H | CH$_3$ | Et | H | H | F | OH | H | H | NH$_2$ |
| V-11-3 | CH$_3$ | H | H | CH(CH$_3$)$_2$ | Et | H | H | F | OH | H | H | NH$_2$ |
| V-11-4 | CH$_3$ | H | H | CH$_2$CH(CH$_3$)$_2$ | Et | H | H | F | OH | H | H | NH$_2$ |
| V-11-5 | CH$_3$ | H | H | CH$_2$Ph | Et | H | H | F | OH | H | H | NH$_2$ |
| V-11-6 | CH$_3$ | H | H | CH$_2$-indol-3-yl | Et | H | H | F | OH | H | H | NH$_2$ |
| V-11-7 | CH$_3$ | H | H | CH$_2$CH$_2$SCH$_3$ | Et | H | H | F | OH | H | H | NH$_2$ |
| V-11-8 | CH$_3$ | * | H | * | Et | H | H | F | OH | H | H | NH$_2$ |

*R[2] and R[3b] joined together by (CH$_2$)$_3$ to form five-membered ring.

TABLE V-12

| No | R[1] | R[2] | R[3a] | R[3b] | R[4] | R[5] | R[6] | X | Y | R[7] | R[8] | R[9] |
|---|---|---|---|---|---|---|---|---|---|---|---|---|
| V-12-1 | Et | H | H | H | Et | H | H | F | OH | H | H | NH$_2$ |
| V-12-2 | Et | H | H | CH$_3$ | Et | H | H | F | OH | H | H | NH$_2$ |
| V-12-3 | Et | H | H | CH(CH$_3$)$_2$ | Et | H | H | F | OH | H | H | NH$_2$ |
| V-12-4 | Et | H | H | CH$_2$CH(CH$_3$)$_2$ | Et | H | H | F | OH | H | H | NH$_2$ |
| V-12-5 | Et | H | H | CH$_2$Ph | Et | H | H | F | OH | H | H | NH$_2$ |
| V-12-6 | Et | H | H | CH$_2$-indol-3-yl | Et | H | H | F | OH | H | H | NH$_2$ |
| V-12-7 | Et | H | H | CH$_2$CH$_2$SCH$_3$ | Et | H | H | F | OH | H | H | NH$_2$ |
| V-12-8 | Et | * | H | * | Et | H | H | F | OH | H | H | NH$_2$ |

*R[2] and R[3b] joined together by (CH$_2$)$_3$ to form five-membered ring.

TABLE V-13

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-13-1 | ⁱPr | H | H | H | Et | H | H | F | OH | H | H | NH₂ |
| V-13-2 | ⁱPr | H | H | CH₃ | Et | H | H | F | OH | H | H | NH₂ |
| V-13-3 | ⁱPr | H | H | CH(CH₃)₂ | Et | H | H | F | OH | H | H | NH₂ |
| V-13-4 | ⁱPr | H | H | CH₂CH(CH₃)₂ | Et | H | H | F | OH | H | H | NH₂ |
| V-13-5 | ⁱPr | H | H | CH₂Ph | Et | H | H | F | OH | H | H | NH₂ |
| V-13-6 | ⁱPr | H | H | CH₂-indol-3-yl | Et | H | H | F | OH | H | H | NH₂ |
| V-13-7 | ⁱPr | H | H | CH₂CH₂SCH₃ | Et | H | H | F | OH | H | H | NH₂ |
| V-13-8 | ⁱPr | * | H | * | Et | H | H | F | OH | H | H | NH₂ |

*R² and R³ᵇ joined together by (CH₂)₃ to form five-membered ring.

TABLE V-14

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-14-1 | ᵗBu | H | H | H | Et | H | H | F | OH | H | H | NH₂ |
| V-14-2 | ᵗBu | H | H | CH₃ | Et | H | H | F | OH | H | H | NH₂ |
| V-14-3 | ᵗBu | H | H | CH(CH₃)₂ | Et | H | H | F | OH | H | H | NH₂ |
| V-14-4 | ᵗBu | H | H | CH₂CH(CH₃)₂ | Et | H | H | F | OH | H | H | NH₂ |
| V-14-5 | ᵗBu | H | H | CH₂Ph | Et | H | H | F | OH | H | H | NH₂ |
| V-14-6 | ᵗBu | H | H | CH₂-indol-3-yl | Et | H | H | F | OH | H | H | NH₂ |
| V-14-7 | ᵗBu | H | H | CH₂CH₂SCH₃ | Et | H | H | F | OH | H | H | NH₂ |
| V-14-8 | ᵗBu | * | H | * | Et | H | H | F | OH | H | H | NH₂ |

*R² and R³ᵇ joined together by (CH₂)₃ to form five-membered ring.

TABLE V-15

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-15-1 | Ph | H | H | H | Et | H | H | F | OH | H | H | NH₂ |
| V-15-2 | Ph | H | H | CH₃ | Et | H | H | F | OH | H | H | NH₂ |
| V-15-3 | Ph | H | H | CH(CH₃)₂ | Et | H | H | F | OH | H | H | NH₂ |
| V-15-4 | Ph | H | H | CH₂CH(CH₃)₂ | Et | H | H | F | OH | H | H | NH₂ |
| V-15-5 | Ph | H | H | CH₂Ph | Et | H | H | F | OH | H | H | NH₂ |
| V-15-6 | Ph | H | H | CH₂-indol-3-yl | Et | H | H | F | OH | H | H | NH₂ |
| V-15-7 | Ph | H | H | CH₂CH₂SCH₃ | Et | H | H | F | OH | H | H | NH₂ |
| V-15-8 | Ph | * | H | * | Et | H | H | F | OH | H | H | NH₂ |

*R² and R³ᵇ joined together by (CH₂)₃ to form five-membered ring.

TABLE V-16

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-16-1 | p-Me—Ph | H | H | H | Et | H | H | F | OH | H | H | NH₂ |
| V-16-2 | p-Me—Ph | H | H | CH₃ | Et | H | H | F | OH | H | H | NH₂ |
| V-16-3 | p-Me—Ph | H | H | CH(CH₃)₂ | Et | H | H | F | OH | H | H | NH₂ |
| V-16-4 | p-Me—Ph | H | H | CH₂CH(CH₃)₂ | Et | H | H | F | OH | H | H | NH₂ |
| V-16-5 | p-Me—Ph | H | H | CH₂Ph | Et | H | H | F | OH | H | H | NH₂ |
| V-16-6 | p-Me—Ph | H | H | CH₂-indol-3-yl | Et | H | H | F | OH | H | H | NH₂ |
| V-16-7 | p-Me—Ph | H | H | CH₂CH₂SCH₃ | Et | H | H | F | OH | H | H | NH₂ |
| V-16-8 | p-Me—Ph | * | H | * | Et | H | H | F | OH | H | H | NH₂ |

*R² and R³ᵇ joined together by (CH₂)₃ to form five-membered ring.

TABLE V-17

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-17-1 | p-F—Ph | H | H | H | Et | H | H | F | OH | H | H | NH₂ |
| V-17-2 | p-F—Ph | H | H | CH₃ | Et | H | H | F | OH | H | H | NH₂ |
| V-17-3 | p-F—Ph | H | H | CH(CH₃)₂ | Et | H | H | F | OH | H | H | NH₂ |
| V-17-4 | p-F—Ph | H | H | CH₂CH(CH₃)₂ | Et | H | H | F | OH | H | H | NH₂ |
| V-17-5 | p-F—Ph | H | H | CH₂Ph | Et | H | H | F | OH | H | H | NH₂ |

TABLE V-17-continued

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-17-6 | p-F—Ph | H | H | CH$_2$-indol-3-yl | Et | H | H | F | OH | H | H | NH$_2$ |
| V-17-7 | p-F—Ph | H | H | CH$_2$CH$_2$SCH$_3$ | Et | H | H | F | OH | H | H | NH$_2$ |
| V-17-8 | p-F—Ph | * | H | * | Et | H | H | F | OH | H | H | NH$_2$ |

*R$^2$ and R$^{3b}$ joined together by (CH$_2$)$_3$ to form five-membered ring.

TABLE V-18

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-18-1 | p-Cl—Ph | H | H | H | Et | H | H | F | OH | H | H | NH$_2$ |
| V-18-2 | p-Cl—Ph | H | H | CH$_3$ | Et | H | H | F | OH | H | H | NH$_2$ |
| V-18-3 | p-Cl—Ph | H | H | CH(CH$_3$)$_2$ | Et | H | H | F | OH | H | H | NH$_2$ |
| V-18-4 | p-Cl—Ph | H | H | CH$_2$CH(CH$_3$)$_2$ | Et | H | H | F | OH | H | H | NH$_2$ |
| V-18-5 | p-Cl—Ph | H | H | CH$_2$Ph | Et | H | H | F | OH | H | H | NH$_2$ |
| V-18-6 | p-Cl—Ph | H | H | CH$_2$-indol-3-yl | Et | H | H | F | OH | H | H | NH$_2$ |
| V-18-7 | p-Cl—Ph | H | H | CH$_2$CH$_2$SCH$_3$ | Et | H | H | F | OH | H | H | NH$_2$ |
| V-18-8 | p-Cl—Ph | * | H | * | Et | H | H | F | OH | H | H | NH$_2$ |

*R$^2$ and R$^{3b}$ joined together by (CH$_2$)$_3$ to form five-membered ring.

TABLE V-19

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-19-1 | p-Br—Ph | H | H | H | Et | H | H | F | OH | H | H | NH$_2$ |
| V-19-2 | p-Br—Ph | H | H | CH$_3$ | Et | H | H | F | OH | H | H | NH$_2$ |
| V-19-3 | p-Br—Ph | H | H | CH(CH$_3$)$_2$ | Et | H | H | F | OH | H | H | NH$_2$ |
| V-19-4 | p-Br—Ph | H | H | CH$_2$CH(CH$_3$)$_2$ | Et | H | H | F | OH | H | H | NH$_2$ |
| V-19-5 | p-Br—Ph | H | H | CH$_2$Ph | Et | H | H | F | OH | H | H | NH$_2$ |
| V-19-6 | p-Br—Ph | H | H | CH$_2$-indol-3-yl | Et | H | H | F | OH | H | H | NH$_2$ |
| V-19-7 | p-Br—Ph | H | H | CH$_2$CH$_2$SCH$_3$ | Et | H | H | F | OH | H | H | NH$_2$ |
| V-19-8 | p-Br—Ph | * | H | * | Et | H | H | F | OH | H | H | NH$_2$ |

*R$^2$ and R$^{3b}$ joined together by (CH$_2$)$_3$ to form five-membered ring.

TABLE V-20

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-20-1 | p-I—Ph | H | H | H | Et | H | H | F | OH | H | H | NH$_2$ |
| V-20-2 | p-I—Ph | H | H | CH$_3$ | Et | H | H | F | OH | H | H | NH$_2$ |
| V-20-3 | p-I—Ph | H | H | CH(CH$_3$)$_2$ | Et | H | H | F | OH | H | H | NH$_2$ |
| V-20-4 | p-I—Ph | H | H | CH$_2$CH(CH$_3$)$_2$ | Et | H | H | F | OH | H | H | NH$_2$ |
| V-20-5 | p-I—Ph | H | H | CH$_2$Ph | Et | H | H | F | OH | H | H | NH$_2$ |
| V-20-6 | p-I—Ph | H | H | CH$_2$-indol-3-yl | Et | H | H | F | OH | H | H | NH$_2$ |
| V-20-7 | p-I—Ph | H | H | CH$_2$CH$_2$SCH$_3$ | Et | H | H | F | OH | H | H | NH$_2$ |
| V-20-8 | p-I—Ph | * | H | * | Et | H | H | F | OH | H | H | NH$_2$ |

*R$^2$ and R$^{3b}$ joined together by (CH$_2$)$_3$ to form five-membered ring.

TABLE V-21

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-21-1 | CH$_3$ | H | H | H | $^i$Pr | H | H | F | OH | H | H | NH$_2$ |
| V-21-2 | CH$_3$ | H | H | CH$_3$ | $^i$Pr | H | H | F | OH | H | H | NH$_2$ |
| V-21-3 | CH$_3$ | H | H | CH(CH$_3$)$_2$ | $^i$Pr | H | H | F | OH | H | H | NH$_2$ |
| V-21-4 | CH$_3$ | H | H | CH$_2$CH(CH$_3$)$_2$ | $^i$Pr | H | H | F | OH | H | H | NH$_2$ |
| V-21-5 | CH$_3$ | H | H | CH$_2$Ph | $^i$Pr | H | H | F | OH | H | H | NH$_2$ |
| V-21-6 | CH$_3$ | H | H | CH$_2$-indol-3-yl | $^i$Pr | H | H | F | OH | H | H | NH$_2$ |
| V-21-7 | CH$_3$ | H | H | CH$_2$CH$_2$SCH$_3$ | $^i$Pr | H | H | F | OH | H | H | NH$_2$ |
| V-21-8 | CH$_3$ | * | H | * | $^i$Pr | H | H | F | OH | H | H | NH$_2$ |

*R$^2$ and R$^{3b}$ joined together by (CH$_2$)$_3$ to form five-membered ring.

TABLE V-22

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-22-1 | Et | H | H | H | $^i$Pr | H | H | F | OH | H | H | NH$_2$ |
| V-22-2 | Et | H | H | CH$_3$ | $^i$Pr | H | H | F | OH | H | H | NH$_2$ |
| V-22-3 | Et | H | H | CH(CH$_3$)$_2$ | $^i$Pr | H | H | F | OH | H | H | NH$_2$ |
| V-22-4 | Et | H | H | CH$_2$CH(CH$_3$)$_2$ | $^i$Pr | H | H | F | OH | H | H | NH$_2$ |
| V-22-5 | Et | H | H | CH$_2$Ph | $^i$Pr | H | H | F | OH | H | H | NH$_2$ |
| V-22-6 | Et | H | H | CH$_2$-indol-3-yl | $^i$Pr | H | H | F | OH | H | H | NH$_2$ |
| V-22-7 | Et | H | H | CH$_2$CH$_2$SCH$_3$ | $^i$Pr | H | H | F | OH | H | H | NH$_2$ |
| V-22-8 | Et | * | H | * | $^i$Pr | H | H | F | OH | H | H | NH$_2$ |

*R² and R³ᵇ joined together by (CH$_2$)$_3$ to form five-membered ring.

TABLE V-23

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-23-1 | $^i$Pr | H | H | H | $^i$Pr | H | H | F | OH | H | H | NH$_2$ |
| V-23-2 | $^i$Pr | H | H | CH$_3$ | $^i$Pr | H | H | F | OH | H | H | NH$_2$ |
| V-23-3 | $^i$Pr | H | H | CH(CH$_3$)$_2$ | $^i$Pr | H | H | F | OH | H | H | NH$_2$ |
| V-23-4 | $^i$Pr | H | H | CH$_2$CH(CH$_3$)$_2$ | $^i$Pr | H | H | F | OH | H | H | NH$_2$ |
| V-23-5 | $^i$Pr | H | H | CH$_2$Ph | $^i$Pr | H | H | F | OH | H | H | NH$_2$ |
| V-23-6 | $^i$Pr | H | H | CH$_2$-indol-3-yl | $^i$Pr | H | H | F | OH | H | H | NH$_2$ |
| V-23-7 | $^i$Pr | H | H | CH$_2$CH$_2$SCH$_3$ | $^i$Pr | H | H | F | OH | H | H | NH$_2$ |
| V-23-8 | $^i$Pr | * | H | * | $^i$Pr | H | H | F | OH | H | H | NH$_2$ |

*R² and R³ᵇ joined together by (CH$_2$)$_3$ to form five-membered ring.

TABLE V-24

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-24-1 | $^t$Bu | H | H | H | $^i$Pr | H | H | F | OH | H | H | NH$_2$ |
| V-24-2 | $^t$Bu | H | H | CH$_3$ | $^i$Pr | H | H | F | OH | H | H | NH$_2$ |
| V-24-3 | $^t$Bu | H | H | CH(CH$_3$)$_2$ | $^i$Pr | H | H | F | OH | H | H | NH$_2$ |
| V-24-4 | $^t$Bu | H | H | CH$_2$CH(CH$_3$)$_2$ | $^i$Pr | H | H | F | OH | H | H | NH$_2$ |
| V-24-5 | $^t$Bu | H | H | CH$_2$Ph | $^i$Pr | H | H | F | OH | H | H | NH$_2$ |
| V-24-6 | $^t$Bu | H | H | CH$_2$-indol-3-yl | $^i$Pr | H | H | F | OH | H | H | NH$_2$ |
| V-24-7 | $^t$Bu | H | H | CH$_2$CH$_2$SCH$_3$ | $^i$Pr | H | H | F | OH | H | H | NH$_2$ |
| V-24-8 | $^t$Bu | * | H | * | $^i$Pr | H | H | F | OH | H | H | NH$_2$ |

*R² and R³ᵇ joined together by (CH$_2$)$_3$ to form five-membered ring.

TABLE V-25

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-25-1 | Ph | H | H | H | $^i$Pr | H | H | F | OH | H | H | NH$_2$ |
| V-25-2 | Ph | H | H | CH$_3$ | $^i$Pr | H | H | F | OH | H | H | NH$_2$ |
| V-25-3 | Ph | H | H | CH(CH$_3$)$_2$ | $^i$Pr | H | H | F | OH | H | H | NH$_2$ |
| V-25-4 | Ph | H | H | CH$_2$CH(CH$_3$)$_2$ | $^i$Pr | H | H | F | OH | H | H | NH$_2$ |
| V-25-5 | Ph | H | H | CH$_2$Ph | $^i$Pr | H | H | F | OH | H | H | NH$_2$ |
| V-25-6 | Ph | H | H | CH$_2$-indol-3-yl | $^i$Pr | H | H | F | OH | H | H | NH$_2$ |
| V-25-7 | Ph | H | H | CH$_2$CH$_2$SCH$_3$ | $^i$Pr | H | H | F | OH | H | H | NH$_2$ |
| V-25-8 | Ph | * | H | * | $^i$Pr | H | H | F | OH | H | H | NH$_2$ |

*R² and R³ᵇ joined together by (CH$_2$)$_3$ to form five-membered ring.

TABLE V-26

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-26-1 | p-Me—Ph | H | H | H | $^i$Pr | H | H | F | OH | H | H | NH$_2$ |
| V-26-2 | p-Me—Ph | H | H | CH$_3$ | $^i$Pr | H | H | F | OH | H | H | NH$_2$ |
| V-26-3 | p-Me—Ph | H | H | CH(CH$_3$)$_2$ | $^i$Pr | H | H | F | OH | H | H | NH$_2$ |
| V-26-4 | p-Me—Ph | H | H | CH$_2$CH(CH$_3$)$_2$ | $^i$Pr | H | H | F | OH | H | H | NH$_2$ |
| V-26-5 | p-Me—Ph | H | H | CH$_2$Ph | $^i$Pr | H | H | F | OH | H | H | NH$_2$ |

TABLE V-26-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-26-6 | p-Me—Ph | H | H | CH₂-indol-3-yl | $^i$Pr | H | H | F | OH | H | H | NH₂ |
| V-26-7 | p-Me—Ph | H | H | CH₂CH₂SCH₃ | $^i$Pr | H | H | F | OH | H | H | NH₂ |
| V-26-8 | p-Me—Ph | * | H | * | $^i$Pr | H | H | F | OH | H | H | NH₂ |

*R² and R³ᵇ joined together by (CH₂)₃ to form five-membered ring.

TABLE V-27

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-27-1 | p-F—Ph | H | H | H | $^i$Pr | H | H | F | OH | H | H | NH₂ |
| V-27-2 | p-F—Ph | H | H | CH₃ | $^i$Pr | H | H | F | OH | H | H | NH₂ |
| V-27-3 | p-F—Ph | H | H | CH(CH₃)₂ | $^i$Pr | H | H | F | OH | H | H | NH₂ |
| V-27-4 | p-F—Ph | H | H | CH₂CH(CH₃)₂ | $^i$Pr | H | H | F | OH | H | H | NH₂ |
| V-27-5 | p-F—Ph | H | H | CH₂Ph | $^i$Pr | H | H | F | OH | H | H | NH₂ |
| V-27-6 | p-F—Ph | H | H | CH₂-indol-3-yl | $^i$Pr | H | H | F | OH | H | H | NH₂ |
| V-27-7 | p-F—Ph | H | H | CH₂CH₂SCH₃ | $^i$Pr | H | H | F | OH | H | H | NH₂ |
| V-27-8 | p-F—Ph | * | H | * | $^i$Pr | H | H | F | OH | H | H | NH₂ |

*R² and R³ᵇ joined together by (CH₂)₃ to form five-membered ring.

TABLE V-28

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-28-1 | p-Cl—Ph | H | H | H | $^i$Pr | H | H | F | OH | H | H | NH₂ |
| V-28-2 | p-Cl—Ph | H | H | CH₃ | $^i$Pr | H | H | F | OH | H | H | NH₂ |
| V-28-3 | p-Cl—Ph | H | H | CH(CH₃)₂ | $^i$Pr | H | H | F | OH | H | H | NH₂ |
| V-28-4 | p-Cl—Ph | H | H | CH₂CH(CH₃)₂ | $^i$Pr | H | H | F | OH | H | H | NH₂ |
| V-28-5 | p-Cl—Ph | H | H | CH₂Ph | $^i$Pr | H | H | F | OH | H | H | NH₂ |
| V-28-6 | p-Cl—Ph | H | H | CH₂-indol-3-yl | $^i$Pr | H | H | F | OH | H | H | NH₂ |
| V-28-7 | p-Cl—Ph | H | H | CH₂CH₂SCH₃ | $^i$Pr | H | H | F | OH | H | H | NH₂ |
| V-28-8 | p-Cl—Ph | * | H | * | $^i$Pr | H | H | F | OH | H | H | NH₂ |

*R² and R³ᵇ joined together by (CH₂)₃ to form five-membered ring.

TABLE V-29

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-29-1 | p-Br—Ph | H | H | H | $^i$Pr | H | H | F | OH | H | H | NH₂ |
| V-29-2 | p-Br—Ph | H | H | CH₃ | $^i$Pr | H | H | F | OH | H | H | NH₂ |
| V-29-3 | p-Br—Ph | H | H | CH(CH₃)₂ | $^i$Pr | H | H | F | OH | H | H | NH₂ |
| V-29-4 | p-Br—Ph | H | H | CH₂CH(CH₃)₂ | $^i$Pr | H | H | F | OH | H | H | NH₂ |
| V-29-5 | p-Br—Ph | H | H | CH₂Ph | $^i$Pr | H | H | F | OH | H | H | NH₂ |
| V-29-6 | p-Br—Ph | H | H | CH₂-indol-3-yl | $^i$Pr | H | H | F | OH | H | H | NH₂ |
| V-29-7 | p-Br—Ph | H | H | CH₂CH₂SCH₃ | $^i$Pr | H | H | F | OH | H | H | NH₂ |
| V-29-8 | p-Br—Ph | * | H | * | $^i$Pr | H | H | F | OH | H | H | NH₂ |

*R² and R³ᵇ joined together by (CH₂)₃ to form five-membered ring.

TABLE V-30

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-30-1 | p-I—Ph | H | H | H | $^i$Pr | H | H | F | OH | H | H | NH₂ |
| V-30-2 | p-I—Ph | H | H | CH₃ | $^i$Pr | H | H | F | OH | H | H | NH₂ |
| V-30-3 | p-I—Ph | H | H | CH(CH₃)₂ | $^i$Pr | H | H | F | OH | H | H | NH₂ |
| V-30-4 | p-I—Ph | H | H | CH₂CH(CH₃)₂ | $^i$Pr | H | H | F | OH | H | H | NH₂ |
| V-30-5 | p-I—Ph | H | H | CH₂Ph | $^i$Pr | H | H | F | OH | H | H | NH₂ |
| V-30-6 | p-I—Ph | H | H | CH₂-indol-3-yl | $^i$Pr | H | H | F | OH | H | H | NH₂ |
| V-30-7 | p-I—Ph | H | H | CH₂CH₂SCH₃ | $^i$Pr | H | H | F | OH | H | H | NH₂ |
| V-30-8 | p-I—Ph | * | H | * | $^i$Pr | H | H | F | OH | H | H | NH₂ |

*R² and R³ᵇ joined together by (CH₂)₃ to form five-membered ring.

TABLE V-31

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-31-1 | $CH_3$ | H | H | H | $^nBu$ | H | H | F | OH | H | H | $NH_2$ |
| V-31-2 | $CH_3$ | H | H | $CH_3$ | $^nBu$ | H | H | F | OH | H | H | $NH_2$ |
| V-31-3 | $CH_3$ | H | H | $CH(CH_3)_2$ | $^nBu$ | H | H | F | OH | H | H | $NH_2$ |
| V-31-4 | $CH_3$ | H | H | $CH_2CH(CH_3)_2$ | $^nBu$ | H | H | F | OH | H | H | $NH_2$ |
| V-31-5 | $CH_3$ | H | H | $CH_2Ph$ | $^nBu$ | H | H | F | OH | H | H | $NH_2$ |
| V-31-6 | $CH_3$ | H | H | $CH_2$-indol-3-yl | $^nBu$ | H | H | F | OH | H | H | $NH_2$ |
| V-31-7 | $CH_3$ | H | H | $CH_2CH_2SCH_3$ | $^nBu$ | H | H | F | OH | H | H | $NH_2$ |
| V-31-8 | $CH_3$ | * | H | * | $^nBu$ | H | H | F | OH | H | H | $NH_2$ |

*$R^2$ and $R^{3b}$ joined together by $(CH_2)_3$ to form five-membered ring.

TABLE V-32

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-32-1 | Et | H | H | H | $^nBu$ | H | H | F | OH | H | H | $NH_2$ |
| V-32-2 | Et | H | H | $CH_3$ | $^nBu$ | H | H | F | OH | H | H | $NH_2$ |
| V-32-3 | Et | H | H | $CH(CH_3)_2$ | $^nBu$ | H | H | F | OH | H | H | $NH_2$ |
| V-32-4 | Et | H | H | $CH_2CH(CH_3)_2$ | $^nBu$ | H | H | F | OH | H | H | $NH_2$ |
| V-32-5 | Et | H | H | $CH_2Ph$ | $^nBu$ | H | H | F | OH | H | H | $NH_2$ |
| V-32-6 | Et | H | H | $CH_2$-indol-3-yl | $^nBu$ | H | H | F | OH | H | H | $NH_2$ |
| V-32-7 | Et | H | H | $CH_2CH_2SCH_3$ | $^nBu$ | H | H | F | OH | H | H | $NH_2$ |
| V-32-8 | Et | * | H | * | $^nBu$ | H | H | F | OH | H | H | $NH_2$ |

*$R^2$ and $R^{3b}$ joined together by $(CH_2)_3$ to form five-membered ring.

TABLE V-33

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-33-1 | $^iPr$ | H | H | H | $^nBu$ | H | H | F | OH | H | H | $NH_2$ |
| V-33-2 | $^iPr$ | H | H | $CH_3$ | $^nBu$ | H | H | F | OH | H | H | $NH_2$ |
| V-33-3 | $^iPr$ | H | H | $CH(CH_3)_2$ | $^nBu$ | H | H | F | OH | H | H | $NH_2$ |
| V-33-4 | $^iPr$ | H | H | $CH_2CH(CH_3)_2$ | $^nBu$ | H | H | F | OH | H | H | $NH_2$ |
| V-33-5 | $^iPr$ | H | H | $CH_2Ph$ | $^nBu$ | H | H | F | OH | H | H | $NH_2$ |
| V-33-6 | $^iPr$ | H | H | $CH_2$-indol-3-yl | $^nBu$ | H | H | F | OH | H | H | $NH_2$ |
| V-33-7 | $^iPr$ | H | H | $CH_2CH_2SCH_3$ | $^nBu$ | H | H | F | OH | H | H | $NH_2$ |
| V-33-8 | $^iPr$ | * | H | * | $^nBu$ | H | H | F | OH | H | H | $NH_2$ |

*$R^2$ and $R^{3b}$ joined together by $(CH_2)_3$ to form five-membered ring.

TABLE V-34

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-34-1 | $^tBu$ | H | H | H | $^nBu$ | H | H | F | OH | H | H | $NH_2$ |
| V-34-2 | $^tBu$ | H | H | $CH_3$ | $^nBu$ | H | H | F | OH | H | H | $NH_2$ |
| V-34-3 | $^tBu$ | H | H | $CH(CH_3)_2$ | $^nBu$ | H | H | F | OH | H | H | $NH_2$ |
| V-34-4 | $^tBu$ | H | H | $CH_2CH(CH_3)_2$ | $^nBu$ | H | H | F | OH | H | H | $NH_2$ |
| V-34-5 | $^tBu$ | H | H | $CH_2Ph$ | $^nBu$ | H | H | F | OH | H | H | $NH_2$ |
| V-34-6 | $^tBu$ | H | H | $CH_2$-indol-3-yl | $^nBu$ | H | H | F | OH | H | H | $NH_2$ |
| V-34-7 | $^tBu$ | H | H | $CH_2CH_2SCH_3$ | $^nBu$ | H | H | F | OH | H | H | $NH_2$ |
| V-34-8 | $^tBu$ | * | H | * | $^nBu$ | H | H | F | OH | H | H | $NH_2$ |

*$R^2$ and $R^{3b}$ joined together by $(CH_2)_3$ to form five-membered ring.

TABLE V-35

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-35-1 | Ph | H | H | H | $^nBu$ | H | H | F | OH | H | H | $NH_2$ |
| V-35-2 | Ph | H | H | $CH_3$ | $^nBu$ | H | H | F | OH | H | H | $NH_2$ |
| V-35-3 | Ph | H | H | $CH(CH_3)_2$ | $^nBu$ | H | H | F | OH | H | H | $NH_2$ |
| V-35-4 | Ph | H | H | $CH_2CH(CH_3)_2$ | $^nBu$ | H | H | F | OH | H | H | $NH_2$ |
| V-35-5 | Ph | H | H | $CH_2Ph$ | $^nBu$ | H | H | F | OH | H | H | $NH_2$ |

TABLE V-35-continued

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-35-6 | Ph | H | H | $CH_2$-indol-3-yl | $^nBu$ | H | H | F | OH | H | H | $NH_2$ |
| V-35-7 | Ph | H | H | $CH_2CH_2SCH_3$ | $^nBu$ | H | H | F | OH | H | H | $NH_2$ |
| V-35-8 | Ph | * | H | * | $^nBu$ | H | H | F | OH | H | H | $NH_2$ |

*$R^2$ and $R^{3b}$ joined together by $(CH_2)_3$ to form five-membered ring.

TABLE V-36

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-36-1 | p-Me—Ph | H | H | H | $^nBu$ | H | H | F | OH | H | H | $NH_2$ |
| V-36-2 | p-Me—Ph | H | H | $CH_3$ | $^nBu$ | H | H | F | OH | H | H | $NH_2$ |
| V-36-3 | p-Me—Ph | H | H | $CH(CH_3)_2$ | $^nBu$ | H | H | F | OH | H | H | $NH_2$ |
| V-36-4 | p-Me—Ph | H | H | $CH_2CH(CH_3)_2$ | $^nBu$ | H | H | F | OH | H | H | $NH_2$ |
| V-36-5 | p-Me—Ph | H | H | $CH_2Ph$ | $^nBu$ | H | H | F | OH | H | H | $NH_2$ |
| V-36-6 | p-Me—Ph | H | H | $CH_2$-indol-3-yl | $^nBu$ | H | H | F | OH | H | H | $NH_2$ |
| V-36-7 | p-Me—Ph | H | H | $CH_2CH_2SCH_3$ | $^nBu$ | H | H | F | OH | H | H | $NH_2$ |
| V-36-8 | p-Me—Ph | * | H | * | $^nBu$ | H | H | F | OH | H | H | $NH_2$ |

*$R^2$ and $R^{3b}$ joined together by $(CH_2)_3$ to form five-membered ring.

TABLE V-37

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-37-1 | p-F—Ph | H | H | H | $^nBu$ | H | H | F | OH | H | H | $NH_2$ |
| V-37-2 | p-F—Ph | H | H | $CH_3$ | $^nBu$ | H | H | F | OH | H | H | $NH_2$ |
| V-37-3 | p-F—Ph | H | H | $CH(CH_3)_2$ | $^nBu$ | H | H | F | OH | H | H | $NH_2$ |
| V-37-4 | p-F—Ph | H | H | $CH_2CH(CH_3)_2$ | $^nBu$ | H | H | F | OH | H | H | $NH_2$ |
| V-37-5 | p-F—Ph | H | H | $CH_2Ph$ | $^nBu$ | H | H | F | OH | H | H | $NH_2$ |
| V-37-6 | p-F—Ph | H | H | $CH_2$-indol-3-yl | $^nBu$ | H | H | F | OH | H | H | $NH_2$ |
| V-37-7 | p-F—Ph | H | H | $CH_2CH_2SCH_3$ | $^nBu$ | H | H | F | OH | H | H | $NH_2$ |
| V-37-8 | p-F—Ph | * | H | * | $^nBu$ | H | H | F | OH | H | H | $NH_2$ |

*$R^2$ and $R^{3b}$ joined together by $(CH_2)_3$ to form five-membered ring.

TABLE V-38

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-38-1 | p-Cl—Ph | H | H | H | $^nBu$ | H | H | F | OH | H | H | $NH_2$ |
| V-38-2 | p-Cl—Ph | H | H | $CH_3$ | $^nBu$ | H | H | F | OH | H | H | $NH_2$ |
| V-38-3 | p-Cl—Ph | H | H | $CH(CH_3)_2$ | $^nBu$ | H | H | F | OH | H | H | $NH_2$ |
| V-38-4 | p-Cl—Ph | H | H | $CH_2CH(CH_3)_2$ | $^nBu$ | H | H | F | OH | H | H | $NH_2$ |
| V-38-5 | p-Cl—Ph | H | H | $CH_2Ph$ | $^nBu$ | H | H | F | OH | H | H | $NH_2$ |
| V-38-6 | p-Cl—Ph | H | H | $CH_2$-indol-3-yl | $^nBu$ | H | H | F | OH | H | H | $NH_2$ |
| V-38-7 | p-Cl—Ph | H | H | $CH_2CH_2SCH_3$ | $^nBu$ | H | H | F | OH | H | H | $NH_2$ |
| V-38-8 | p-Cl—Ph | * | H | * | $^nBu$ | H | H | F | OH | H | H | $NH_2$ |

*$R^2$ and $R^{3b}$ joined together by $(CH_2)_3$ to form five-membered ring.

TABLE V-39

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-39-1 | p-Br—Ph | H | H | H | $^nBu$ | H | H | F | OH | H | H | $NH_2$ |
| V-39-2 | p-Br—Ph | H | H | $CH_3$ | $^nBu$ | H | H | F | OH | H | H | $NH_2$ |
| V-39-3 | p-Br—Ph | H | H | $CH(CH_3)_2$ | $^nBu$ | H | H | F | OH | H | H | $NH_2$ |
| V-39-4 | p-Br—Ph | H | H | $CH_2CH(CH_3)_2$ | $^nBu$ | H | H | F | OH | H | H | $NH_2$ |
| V-39-5 | p-Br—Ph | H | H | $CH_2Ph$ | $^nBu$ | H | H | F | OH | H | H | $NH_2$ |
| V-39-6 | p-Br—Ph | H | H | $CH_2$-indol-3-yl | $^nBu$ | H | H | F | OH | H | H | $NH_2$ |
| V-39-7 | p-Br—Ph | H | H | $CH_2CH_2SCH_3$ | $^nBu$ | H | H | F | OH | H | H | $NH_2$ |
| V-39-8 | p-Br—Ph | * | H | * | $^nBu$ | H | H | F | OH | H | H | $NH_2$ |

*$R^2$ and $R^{3b}$ joined together by $(CH_2)_3$ to form five-membered ring.

TABLE V-40

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-40-1 | p-I—Ph | H | H | H | ⁿBu | H | H | F | OH | H | H | NH₂ |
| V-40-2 | p-I—Ph | H | H | CH₃ | ⁿBu | H | H | F | OH | H | H | NH₂ |
| V-40-3 | p-I—Ph | H | H | CH(CH₃)₂ | ⁿBu | H | H | F | OH | H | H | NH₂ |
| V-40-4 | p-I—Ph | H | H | CH₂CH(CH₃)₂ | ⁿBu | H | H | F | OH | H | H | NH₂ |
| V-40-5 | p-I—Ph | H | H | CH₂Ph | ⁿBu | H | H | F | OH | H | H | NH₂ |
| V-40-6 | p-I—Ph | H | H | CH₂-indol-3-yl | ⁿBu | H | H | F | OH | H | H | NH₂ |
| V-40-7 | p-I—Ph | H | H | CH₂CH₂SCH₃ | ⁿBu | H | H | F | OH | H | H | NH₂ |
| V-40-8 | p-I—Ph | * | H | * | ⁿBu | H | H | F | OH | H | H | NH₂ |

*R² and R³ᵇ joined together by (CH₂)₃ to form five-membered ring.

TABLE V-41

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-41-1 | CH₃ | H | H | H | Bz | H | H | F | OH | H | H | NH₂ |
| V-41-2 | CH₃ | H | H | CH₃ | Bz | H | H | F | OH | H | H | NH₂ |
| V-41-3 | CH₃ | H | H | CH(CH₃)₂ | Bz | H | H | F | OH | H | H | NH₂ |
| V-41-4 | CH₃ | H | H | CH₂CH(CH₃)₂ | Bz | H | H | F | OH | H | H | NH₂ |
| V-41-5 | CH₃ | H | H | CH₂Ph | Bz | H | H | F | OH | H | H | NH₂ |
| V-41-6 | CH₃ | H | H | CH₂-indol-3-yl | Bz | H | H | F | OH | H | H | NH₂ |
| V-41-7 | CH₃ | H | H | CH₂CH₂SCH₃ | Bz | H | H | F | OH | H | H | NH₂ |
| V-41-8 | CH₃ | * | H | * | Bz | H | H | F | OH | H | H | NH₂ |

*R² and R³ᵇ joined together by (CH₂)₃ to form five-membered ring.

TABLE V-42

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-42-1 | Et | H | H | H | Bz | H | H | F | OH | H | H | NH₂ |
| V-42-2 | Et | H | H | CH₃ | Bz | H | H | F | OH | H | H | NH₂ |
| V-42-3 | Et | H | H | CH(CH₃)₂ | Bz | H | H | F | OH | H | H | NH₂ |
| V-42-4 | Et | H | H | CH₂CH(CH₃)₂ | Bz | H | H | F | OH | H | H | NH₂ |
| V-42-5 | Et | H | H | CH₂Ph | Bz | H | H | F | OH | H | H | NH₂ |
| V-42-6 | Et | H | H | CH₂-indol-3-yl | Bz | H | H | F | OH | H | H | NH₂ |
| V-42-7 | Et | H | H | CH₂CH₂SCH₃ | Bz | H | H | F | OH | H | H | NH₂ |
| V-42-8 | Et | * | H | * | Bz | H | H | F | OH | H | H | NH₂ |

*R² and R³ᵇ joined together by (CH₂)₃ to form five-membered ring.

TABLE V-43

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-43-1 | ⁱPr | H | H | H | Bz | H | H | F | OH | H | H | NH₂ |
| V-43-2 | ⁱPr | H | H | CH₃ | Bz | H | H | F | OH | H | H | NH₂ |
| V-43-3 | ⁱPr | H | H | CH(CH₃)₂ | Bz | H | H | F | OH | H | H | NH₂ |
| V-43-4 | ⁱPr | H | H | CH₂CH(CH₃)₂ | Bz | H | H | F | OH | H | H | NH₂ |
| V-43-5 | ⁱPr | H | H | CH₂Ph | Bz | H | H | F | OH | H | H | NH₂ |
| V-43-6 | ⁱPr | H | H | CH₂-indol-3-yl | Bz | H | H | F | OH | H | H | NH₂ |
| V-43-7 | ⁱPr | H | H | CH₂CH₂SCH₃ | Bz | H | H | F | OH | H | H | NH₂ |
| V-43-8 | ⁱPr | * | H | * | Bz | H | H | F | OH | H | H | NH₂ |

*R² and R³ᵇ joined together by (CH₂)₃ to form five-membered ring.

TABLE V-44

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| V-44-1 | ᵗBu | H | H | H | Bz | H | H | F | OH | H | H | NH₂ |
| V-44-2 | ᵗBu | H | H | CH₃ | Bz | H | H | F | OH | H | H | NH₂ |
| V-44-3 | ᵗBu | H | H | CH(CH₃)₂ | Bz | H | H | F | OH | H | H | NH₂ |
| V-44-4 | ᵗBu | H | H | CH₂CH(CH₃)₂ | Bz | H | H | F | OH | H | H | NH₂ |
| V-44-5 | ᵗBu | H | H | CH₂Ph | Bz | H | H | F | OH | H | H | NH₂ |

TABLE V-44-continued

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-44-6 | $^t$Bu | H | H | CH$_2$-indol-3-yl | Bz | H | H | F | OH | H | H | NH$_2$ |
| V-44-7 | $^t$Bu | H | H | CH$_2$CH$_2$SCH$_3$ | Bz | H | H | F | OH | H | H | NH$_2$ |
| V-44-8 | $^t$Bu | * | H | * | Bz | H | H | F | OH | H | H | NH$_2$ |

*R$^2$ and R$^{3b}$ joined together by (CH$_2$)$_3$ to form five-membered ring.

TABLE V-45

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-45-1 | Ph | H | H | H | Bz | H | H | F | OH | H | H | NH$_2$ |
| V-45-2 | Ph | H | H | CH$_3$ | Bz | H | H | F | OH | H | H | NH$_2$ |
| V-45-3 | Ph | H | H | CH(CH$_3$)$_2$ | Bz | H | H | F | OH | H | H | NH$_2$ |
| V-45-4 | Ph | H | H | CH$_2$CH(CH$_3$)$_2$ | Bz | H | H | F | OH | H | H | NH$_2$ |
| V-45-5 | Ph | H | H | CH$_2$Ph | Bz | H | H | F | OH | H | H | NH$_2$ |
| V-45-6 | Ph | H | H | CH$_2$-indol-3-yl | Bz | H | H | F | OH | H | H | NH$_2$ |
| V-45-7 | Ph | H | H | CH$_2$CH$_2$SCH$_3$ | Bz | H | H | F | OH | H | H | NH$_2$ |
| V-45-8 | Ph | * | H | * | Bz | H | H | F | OH | H | H | NH$_2$ |

*R$^2$ and R$^{3b}$ joined together by (CH$_2$)$_3$ to form five-membered ring.

TABLE V-46

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-46-1 | p-Me—Ph | H | H | H | Bz | H | H | F | OH | H | H | NH$_2$ |
| V-46-2 | p-Me—Ph | H | H | CH$_3$ | Bz | H | H | F | OH | H | H | NH$_2$ |
| V-46-3 | p-Me—Ph | H | H | CH(CH$_3$)$_2$ | Bz | H | H | F | OH | H | H | NH$_2$ |
| V-46-4 | p-Me—Ph | H | H | CH$_2$CH(CH$_3$)$_2$ | Bz | H | H | F | OH | H | H | NH$_2$ |
| V-46-5 | p-Me—Ph | H | H | CH$_2$Ph | Bz | H | H | F | OH | H | H | NH$_2$ |
| V-46-6 | p-Me—Ph | H | H | CH$_2$-indol-3-yl | Bz | H | H | F | OH | H | H | NH$_2$ |
| V-46-7 | p-Me—Ph | H | H | CH$_2$CH$_2$SCH$_3$ | Bz | H | H | F | OH | H | H | NH$_2$ |
| V-46-8 | p-Me—Ph | * | H | * | Bz | H | H | F | OH | H | H | NH$_2$ |

*R$^2$ and R$^{3b}$ joined together by (CH$_2$)$_3$ to form five-membered ring.

TABLE V-47

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-47-1 | p-F—Ph | H | H | H | Bz | H | H | F | OH | H | H | NH$_2$ |
| V-47-2 | p-F—Ph | H | H | CH$_3$ | Bz | H | H | F | OH | H | H | NH$_2$ |
| V-47-3 | p-F—Ph | H | H | CH(CH$_3$)$_2$ | Bz | H | H | F | OH | H | H | NH$_2$ |
| V-47-4 | p-F—Ph | H | H | CH$_2$CH(CH$_3$)$_2$ | Bz | H | H | F | OH | H | H | NH$_2$ |
| V-47-5 | p-F—Ph | H | H | CH$_2$Ph | Bz | H | H | F | OH | H | H | NH$_2$ |
| V-47-6 | p-F—Ph | H | H | CH$_2$-indol-3-yl | Bz | H | H | F | OH | H | H | NH$_2$ |
| V-47-7 | p-F—Ph | H | H | CH$_2$CH$_2$SCH$_3$ | Bz | H | H | F | OH | H | H | NH$_2$ |
| V-47-8 | p-F—Ph | * | H | * | Bz | H | H | F | OH | H | H | NH$_2$ |

*R$^2$ and R$^{3b}$ joined together by (CH$_2$)$_3$ to form five-membered ring.

TABLE V-48

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| V-48-1 | p-Cl—Ph | H | H | H | Bz | H | H | F | OH | H | H | NH$_2$ |
| V-48-2 | p-Cl—Ph | H | H | CH$_3$ | Bz | H | H | F | OH | H | H | NH$_2$ |
| V-48-3 | p-Cl—Ph | H | H | CH(CH$_3$)$_2$ | Bz | H | H | F | OH | H | H | NH$_2$ |
| V-48-4 | p-Cl—Ph | H | H | CH$_2$CH(CH$_3$)$_2$ | Bz | H | H | F | OH | H | H | NH$_2$ |
| V-48-5 | p-Cl—Ph | H | H | CH$_2$Ph | Bz | H | H | F | OH | H | H | NH$_2$ |
| V-48-6 | p-Cl—Ph | H | H | CH$_2$-indol-3-yl | Bz | H | H | F | OH | H | H | NH$_2$ |
| V-48-7 | p-Cl—Ph | H | H | CH$_2$CH$_2$SCH$_3$ | Bz | H | H | F | OH | H | H | NH$_2$ |
| V-48-8 | p-Cl—Ph | * | H | * | Bz | H | H | F | OH | H | H | NH$_2$ |

*R$^2$ and R$^{3b}$ joined together by (CH$_2$)$_3$ to form five-membered ring.

TABLE V-49

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-49-1 | p-Br—Ph | H | H | H | Bz | H | H | F | OH | H | H | $NH_2$ |
| V-49-2 | p-Br—Ph | H | H | $CH_3$ | Bz | H | H | F | OH | H | H | $NH_2$ |
| V-49-3 | p-Br—Ph | H | H | $CH(CH_3)_2$ | Bz | H | H | F | OH | H | H | $NH_2$ |
| V-49-4 | p-Br—Ph | H | H | $CH_2CH(CH_3)_2$ | Bz | H | H | F | OH | H | H | $NH_2$ |
| V-49-5 | p-Br—Ph | H | H | $CH_2Ph$ | Bz | H | H | F | OH | H | H | $NH_2$ |
| V-49-6 | p-Br—Ph | H | H | $CH_2$-indol-3-yl | Bz | H | H | F | OH | H | H | $NH_2$ |
| V-49-7 | p-Br—Ph | H | H | $CH_2CH_2SCH_3$ | Bz | H | H | F | OH | H | H | $NH_2$ |
| V-49-8 | p-Br—Ph | * | H | * | Bz | H | H | F | OH | H | H | $NH_2$ |

*$R^2$ and $R^{3b}$ joined together by $(CH_2)_3$ to form five-membered ring.

TABLE V-50

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| V-50-1 | p-I—Ph | H | H | H | Bz | H | H | F | OH | H | H | $NH_2$ |
| V-50-2 | p-I—Ph | H | H | $CH_3$ | Bz | H | H | F | OH | H | H | $NH_2$ |
| V-50-3 | p-I—Ph | H | H | $CH(CH_3)_2$ | Bz | H | H | F | OH | H | H | $NH_2$ |
| V-50-4 | p-I—Ph | H | H | $CH_2CH(CH_3)_2$ | Bz | H | H | F | OH | H | H | $NH_2$ |
| V-50-5 | p-I—Ph | H | H | $CH_2Ph$ | Bz | H | H | F | OH | H | H | $NH_2$ |
| V-50-6 | p-I—Ph | H | H | $CH_2$-indol-3-yl | Bz | H | H | F | OH | H | H | $NH_2$ |
| V-50-7 | p-I—Ph | H | H | $CH_2CH_2SCH_3$ | Bz | H | H | F | OH | H | H | $NH_2$ |
| V-50-8 | p-I—Ph | * | H | * | Bz | H | H | F | OH | H | H | $NH_2$ |

*$R^2$ and $R^{3b}$ joined together by $(CH_2)_3$ to form five-membered ring.

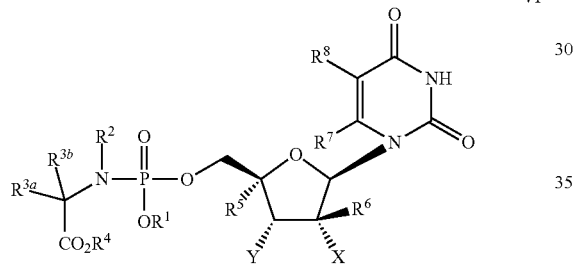

VI

TABLE VI-1

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-1-1 | $CH_3$ | H | H | H | $CH_3$ | H | F | H | OH | H | H |
| VI-1-2 | $CH_3$ | H | H | $CH_3$ | $CH_3$ | H | F | H | OH | H | H |
| VI-1-3 | $CH_3$ | H | H | $CH(CH_3)_2$ | $CH_3$ | H | F | H | OH | H | H |
| VI-1-4 | $CH_3$ | H | H | $CH_2CH(CH_3)_2$ | $CH_3$ | H | F | H | OH | H | H |
| VI-1-5 | $CH_3$ | H | H | $CH_2Ph$ | $CH_3$ | H | F | H | OH | H | H |
| VI-1-6 | $CH_3$ | H | H | $CH_2$-indol-3-yl | $CH_3$ | H | F | H | OH | H | H |
| VI-1-7 | $CH_3$ | H | H | $CH_2CH_2SCH_3$ | $CH_3$ | H | F | H | OH | H | H |
| VI-1-8 | $CH_3$ | * | H | * | $CH_3$ | H | F | H | OH | H | H |

*$R^2$ and $R^{3b}$ joined together by $(CH_2)_3$ to form five-membered ring.

TABLE VI-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-2-1 | Et | H | H | H | $CH_3$ | H | F | H | OH | H | H |
| VI-2-2 | Et | H | H | $CH_3$ | $CH_3$ | H | F | H | OH | H | H |
| VI-2-3 | Et | H | H | $CH(CH_3)_2$ | $CH_3$ | H | F | H | OH | H | H |
| VI-2-4 | Et | H | H | $CH_2CH(CH_3)_2$ | $CH_3$ | H | F | H | OH | H | H |
| VI-2-5 | Et | H | H | $CH_2Ph$ | $CH_3$ | H | F | H | OH | H | H |
| VI-2-6 | Et | H | H | $CH_2$-indol-3-yl | $CH_3$ | H | F | H | OH | H | H |
| VI-2-7 | Et | H | H | $CH_2CH_2SCH_3$ | $CH_3$ | H | F | H | OH | H | H |
| VI-2-8 | Et | * | H | * | $CH_3$ | H | F | H | OH | H | H |

*$R^2$ and $R^{3b}$ joined together by $(CH_2)_3$ to form five-membered ring.

TABLE VI-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-3-1 | $^i$Pr | H | H | H | $CH_3$ | H | F | H | OH | H | H |
| VI-3-2 | $^i$Pr | H | H | $CH_3$ | $CH_3$ | H | F | H | OH | H | H |
| VI-3-3 | $^i$Pr | H | H | $CH(CH_3)_2$ | $CH_3$ | H | F | H | OH | H | H |
| VI-3-4 | $^i$Pr | H | H | $CH_2CH(CH_3)_2$ | $CH_3$ | H | F | H | OH | H | H |
| VI-3-5 | $^i$Pr | H | H | $CH_2Ph$ | $CH_3$ | H | F | H | OH | H | H |
| VI-3-6 | $^i$Pr | H | H | $CH_2$-indol-3-yl | $CH_3$ | H | F | H | OH | H | H |
| VI-3-7 | $^i$Pr | H | H | $CH_2CH_2SCH_3$ | $CH_3$ | H | F | H | OH | H | H |
| VI-3-8 | $^i$Pr | * | H | * | $CH_3$ | H | F | H | OH | H | H |

*$R^2$ and $R^{3b}$ joined together by $(CH_2)_3$ to form five-membered ring.

TABLE VI-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-4-1 | $^t$Bu | H | H | H | $CH_3$ | H | F | H | OH | H | H |
| VI-4-2 | $^t$Bu | H | H | $CH_3$ | $CH_3$ | H | F | H | OH | H | H |
| VI-4-3 | $^t$Bu | H | H | $CH(CH_3)_2$ | $CH_3$ | H | F | H | OH | H | H |
| VI-4-4 | $^t$Bu | H | H | $CH_2CH(CH_3)_2$ | $CH_3$ | H | F | H | OH | H | H |
| VI-4-5 | $^t$Bu | H | H | $CH_2Ph$ | $CH_3$ | H | F | H | OH | H | H |
| VI-4-6 | $^t$Bu | H | H | $CH_2$-indol-3-yl | $CH_3$ | H | F | H | OH | H | H |
| VI-4-7 | $^t$Bu | H | H | $CH_2CH_2SCH_3$ | $CH_3$ | H | F | H | OH | H | H |
| VI-4-8 | $^t$Bu | * | H | * | $CH_3$ | H | F | H | OH | H | H |

*$R^2$ and $R^{3b}$ joined together by $(CH_2)_3$ to form five-membered ring.

TABLE VI-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-5-1 | Ph | H | H | H | $CH_3$ | H | F | H | OH | H | H |
| VI-5-2 | Ph | H | H | $CH_3$ | $CH_3$ | H | F | H | OH | H | H |
| VI-5-3 | Ph | H | H | $CH(CH_3)_2$ | $CH_3$ | H | F | H | OH | H | H |
| VI-5-4 | Ph | H | H | $CH_2CH(CH_3)_2$ | $CH_3$ | H | F | H | OH | H | H |
| VI-5-5 | Ph | H | H | $CH_2Ph$ | $CH_3$ | H | F | H | OH | H | H |
| VI-5-6 | Ph | H | H | $CH_2$-indol-3-yl | $CH_3$ | H | F | H | OH | H | H |
| VI-5-7 | Ph | H | H | $CH_2CH_2SCH_3$ | $CH_3$ | H | F | H | OH | H | H |
| VI-5-8 | Ph | * | H | * | $CH_3$ | H | F | H | OH | H | H |

*$R^2$ and $R^{3b}$ joined together by $(CH_2)_3$ to form five-membered ring.

TABLE VI-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-6-1 | p-Me—Ph | H | H | H | $CH_3$ | H | F | H | OH | H | H |
| VI-6-2 | p-Me—Ph | H | H | $CH_3$ | $CH_3$ | H | F | H | OH | H | H |
| VI-6-3 | p-Me—Ph | H | H | $CH(CH_3)_2$ | $CH_3$ | H | F | H | OH | H | H |
| VI-6-4 | p-Me—Ph | H | H | $CH_2CH(CH_3)_2$ | $CH_3$ | H | F | H | OH | H | H |
| VI-6-5 | p-Me—Ph | H | H | $CH_2Ph$ | $CH_3$ | H | F | H | OH | H | H |
| VI-6-6 | p-Me—Ph | H | H | $CH_2$-indol-3-yl | $CH_3$ | H | F | H | OH | H | H |
| VI-6-7 | p-Me—Ph | H | H | $CH_2CH_2SCH_3$ | $CH_3$ | H | F | H | OH | H | H |
| VI-6-8 | p-Me—Ph | * | H | * | $CH_3$ | H | F | H | OH | H | H |

*$R^2$ and $R^{3b}$ joined together by $(CH_2)_3$ to form five-membered ring.

TABLE VI-7

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-7-1 | p-F—Ph | H | H | H | $CH_3$ | H | F | H | OH | H | H |
| VI-7-2 | p-F—Ph | H | H | $CH_3$ | $CH_3$ | H | F | H | OH | H | H |
| VI-7-3 | p-F—Ph | H | H | $CH(CH_3)_2$ | $CH_3$ | H | F | H | OH | H | H |
| VI-7-4 | p-F—Ph | H | H | $CH_2CH(CH_3)_2$ | $CH_3$ | H | F | H | OH | H | H |
| VI-7-6 | p-F—Ph | H | H | $CH_2Ph$ | $CH_3$ | H | F | H | OH | H | H |

TABLE VI-7-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-7-7 | p-F—Ph | H | H | $CH_2$-indol-3-yl | $CH_3$ | H | F | H | OH | H | H |
| VI-7-8 | p-F—Ph | H | H | $CH_2CH_2SCH_3$ | $CH_3$ | H | F | H | OH | H | H |
| VI-7-20 | p-F—Ph | * | H | * | $CH_3$ | H | F | H | OH | H | H |

*$R^2$ and $R^{3b}$ joined together by $(CH_2)_3$ to form five-membered ring.

TABLE VI-8

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-8-1 | p-Cl—Ph | H | H | H | $CH_3$ | H | F | H | OH | H | H |
| VI-8-2 | p-Cl—Ph | H | H | $CH_3$ | $CH_3$ | H | F | H | OH | H | H |
| VI-8-3 | p-Cl—Ph | H | H | $CH(CH_3)_2$ | $CH_3$ | H | F | H | OH | H | H |
| VI-8-4 | p-Cl—Ph | H | H | $CH_2CH(CH_3)_2$ | $CH_3$ | H | F | H | OH | H | H |
| VI-8-5 | p-Cl—Ph | H | H | $CH_2Ph$ | $CH_3$ | H | F | H | OH | H | H |
| VI-8-6 | p-Cl—Ph | H | H | $CH_2$-indol-3-yl | $CH_3$ | H | F | H | OH | H | H |
| VI-8-7 | p-Cl—Ph | H | H | $CH_2CH_2SCH_3$ | $CH_3$ | H | F | H | OH | H | H |
| VI-8-8 | p-Cl—Ph | * | H | * | $CH_3$ | H | F | H | OH | H | H |

*$R^2$ and $R^{3b}$ joined together by $(CH_2)_3$ to form five-membered ring.

TABLE VI-9

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-9-1 | p-Br—Ph | H | H | H | $CH_3$ | H | F | H | OH | H | H |
| VI-9-2 | p-Br—Ph | H | H | $CH_3$ | $CH_3$ | H | F | H | OH | H | H |
| VI-9-3 | p-Br—Ph | H | H | $CH(CH_3)_2$ | $CH_3$ | H | F | H | OH | H | H |
| VI-9-4 | p-Br—Ph | H | H | $CH_2CH(CH_3)_2$ | $CH_3$ | H | F | H | OH | H | H |
| VI-9-6 | p-Br—Ph | H | H | $CH_2Ph$ | $CH_3$ | H | F | H | OH | H | H |
| VI-9-7 | p-Br—Ph | H | H | $CH_2$-indol-3-yl | $CH_3$ | H | F | H | OH | H | H |
| VI-9-8 | p-Br—Ph | H | H | $CH_2CH_2SCH_3$ | $CH_3$ | H | F | H | OH | H | H |
| VI-9-20 | p-Br—Ph | * | H | * | $CH_3$ | H | F | H | OH | H | H |

*$R^2$ and $R^{3b}$ joined together by $(CH_2)_3$ to form five-membered ring.

TABLE VI-10

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-10-1 | p-I—Ph | H | H | H | $CH_3$ | H | F | H | OH | H | H |
| VI-10-2 | p-I—Ph | H | H | $CH_3$ | $CH_3$ | H | F | H | OH | H | H |
| VI-10-3 | p-I—Ph | H | H | $CH(CH_3)_2$ | $CH_3$ | H | F | H | OH | H | H |
| VI-10-4 | p-I—Ph | H | H | $CH_2CH(CH_3)_2$ | $CH_3$ | H | F | H | OH | H | H |
| VI-10-5 | p-I—Ph | H | H | $CH_2Ph$ | $CH_3$ | H | F | H | OH | H | H |
| VI-10-6 | p-I—Ph | H | H | $CH_2$-indol-3-yl | $CH_3$ | H | F | H | OH | H | H |
| VI-10-7 | p-I—Ph | H | H | $CH_2CH_2SCH_3$ | $CH_3$ | H | F | H | OH | H | H |
| VI-10-8 | p-I—Ph | * | H | * | $CH_3$ | H | F | H | OH | H | H |

*$R^2$ and $R^{3b}$ joined together by $(CH_2)_3$ to form five-membered ring.

TABLE VI-11

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-11-1 | $CH_3$ | H | H | H | Et | H | F | H | OH | H | H |
| VI-11-2 | $CH_3$ | H | H | $CH_3$ | Et | H | F | H | OH | H | H |
| VI-11-3 | $CH_3$ | H | H | $CH(CH_3)_2$ | Et | H | F | H | OH | H | H |
| VI-11-4 | $CH_3$ | H | H | $CH_2CH(CH_3)_2$ | Et | H | F | H | OH | H | H |
| VI-11-5 | $CH_3$ | H | H | $CH_2Ph$ | Et | H | F | H | OH | H | H |
| VI-11-6 | $CH_3$ | H | H | $CH_2$-indol-3-yl | Et | H | F | H | OH | H | H |
| VI-11-7 | $CH_3$ | H | H | $CH_2CH_2SCH_3$ | Et | H | F | H | OH | H | H |
| VI-11-8 | $CH_3$ | * | H | * | Et | H | F | H | OH | H | H |

*$R^2$ and $R^{3b}$ joined together by $(CH_2)_3$ to form five-membered ring.

TABLE VI-12

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-12-1 | Et | H | H | H | Et | H | F | H | OH | H | H |
| VI-12-2 | Et | H | H | CH$_3$ | Et | H | F | H | OH | H | H |
| VI-12-3 | Et | H | H | CH(CH$_3$)$_2$ | Et | H | F | H | OH | H | H |
| VI-12-4 | Et | H | H | CH$_2$CH(CH$_3$)$_2$ | Et | H | F | H | OH | H | H |
| VI-12-5 | Et | H | H | CH$_2$Ph | Et | H | F | H | OH | H | H |
| VI-12-6 | Et | H | H | CH$_2$-indol-3-yl | Et | H | F | H | OH | H | H |
| VI-12-7 | Et | H | H | CH$_2$CH$_2$SCH$_3$ | Et | H | F | H | OH | H | H |
| VI-12-8 | Et | * | H | * | Et | H | F | H | OH | H | H |

*$R^2$ and $R^{3b}$ joined together by (CH$_2$)$_3$ to form five-membered ring.

TABLE VI-13

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-13-1 | $^i$Pr | H | H | H | Et | H | F | H | OH | H | H |
| VI-13-2 | $^i$Pr | H | H | CH$_3$ | Et | H | F | H | OH | H | H |
| VI-13-3 | $^i$Pr | H | H | CH(CH$_3$)$_2$ | Et | H | F | H | OH | H | H |
| VI-13-4 | $^i$Pr | H | H | CH$_2$CH(CH$_3$)$_2$ | Et | H | F | H | OH | H | H |
| VI-13-5 | $^i$Pr | H | H | CH$_2$Ph | Et | H | F | H | OH | H | H |
| VI-13-6 | $^i$Pr | H | H | CH$_2$-indol-3-yl | Et | H | F | H | OH | H | H |
| VI-13-7 | $^i$Pr | H | H | CH$_2$CH$_2$SCH$_3$ | Et | H | F | H | OH | H | H |
| VI-13-8 | $^i$Pr | * | H | * | Et | H | F | H | OH | H | H |

*$R^2$ and $R^{3b}$ joined together by (CH$_2$)$_3$ to form five-membered ring.

TABLE VI-14

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-14-1 | $^t$Bu | H | H | H | Et | H | F | H | OH | H | H |
| VI-14-2 | $^t$Bu | H | H | CH$_3$ | Et | H | F | H | OH | H | H |
| VI-14-3 | $^t$Bu | H | H | CH(CH$_3$)$_2$ | Et | H | F | H | OH | H | H |
| VI-14-4 | $^t$Bu | H | H | CH$_2$CH(CH$_3$)$_2$ | Et | H | F | H | OH | H | H |
| VI-14-5 | $^t$Bu | H | H | CH$_2$Ph | Et | H | F | H | OH | H | H |
| VI-14-6 | $^t$Bu | H | H | CH$_2$-indol-3-yl | Et | H | F | H | OH | H | H |
| VI-14-7 | $^t$Bu | H | H | CH$_2$CH$_2$SCH$_3$ | Et | H | F | H | OH | H | H |
| VI-14-8 | $^t$Bu | * | H | * | Et | H | F | H | OH | H | H |

*$R^2$ and $R^{3b}$ joined together by (CH$_2$)$_3$ to form five-membered ring.

TABLE VI-15

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-15-1 | Ph | H | H | H | Et | H | F | H | OH | H | H |
| VI-15-2 | Ph | H | H | CH$_3$ | Et | H | F | H | OH | H | H |
| VI-15-3 | Ph | H | H | CH(CH$_3$)$_2$ | Et | H | F | H | OH | H | H |
| VI-15-4 | Ph | H | H | CH$_2$CH(CH$_3$)$_2$ | Et | H | F | H | OH | H | H |
| VI-15-5 | Ph | H | H | CH$_2$Ph | Et | H | F | H | OH | H | H |
| VI-15-6 | Ph | H | H | CH$_2$-indol-3-yl | Et | H | F | H | OH | H | H |
| VI-15-7 | Ph | H | H | CH$_2$CH$_2$SCH$_3$ | Et | H | F | H | OH | H | H |
| VI-15-8 | Ph | * | H | * | Et | H | F | H | OH | H | H |

*$R^2$ and $R^{3b}$ joined together by (CH$_2$)$_3$ to form five-membered ring.

TABLE VI-16

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VI-16-1 | p-Me—Ph | H | H | H | Et | H | F | H | OH | H | H |
| VI-16-2 | p-Me—Ph | H | H | CH$_3$ | Et | H | F | H | OH | H | H |
| VI-16-3 | p-Me—Ph | H | H | CH(CH$_3$)$_2$ | Et | H | F | H | OH | H | H |
| VI-16-4 | p-Me—Ph | H | H | CH$_2$CH(CH$_3$)$_2$ | Et | H | F | H | OH | H | H |
| VI-16-5 | p-Me—Ph | H | H | CH$_2$Ph | Et | H | F | H | OH | H | H |

TABLE VI-16-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-16-6 | p-Me—Ph | H | H | CH₂-indol-3-yl | Et | H | F | H | OH | H | H |
| VI-16-7 | p-Me—Ph | H | H | CH₂CH₂SCH₃ | Et | H | F | H | OH | H | H |
| VI-16-8 | p-Me—Ph | * | H | * | Et | H | F | H | OH | H | H |

*R² and R³ joined together by (CH₂)₃ to form five-membered ring.

TABLE VI-17

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-17-1 | p-F—Ph | H | H | H | Et | H | F | H | OH | H | H |
| VI-17-2 | p-F—Ph | H | H | CH₃ | Et | H | F | H | OH | H | H |
| VI-17-3 | p-F—Ph | H | H | CH(CH₃)₂ | Et | H | F | H | OH | H | H |
| VI-17-4 | p-F—Ph | H | H | CH₂CH(CH₃)₂ | Et | H | F | H | OH | H | H |
| VI-17-5 | p-F—Ph | H | H | CH₂Ph | Et | H | F | H | OH | H | H |
| VI-17-6 | p-F—Ph | H | H | CH₂-indol-3-yl | Et | H | F | H | OH | H | H |
| VI-17-7 | p-F—Ph | H | H | CH₂CH₂SCH₃ | Et | H | F | H | OH | H | H |
| VI-17-8 | p-F—Ph | * | H | * | Et | H | F | H | OH | H | H |

*R² and R³ joined together by (CH₂)₃ to form five-membered ring.

TABLE VI-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-18-1 | p-Cl—Ph | H | H | H | Et | H | F | H | OH | H | H |
| VI-18-2 | p-Cl—Ph | H | H | CH₃ | Et | H | F | H | OH | H | H |
| VI-18-3 | p-Cl—Ph | H | H | CH(CH₃)₂ | Et | H | F | H | OH | H | H |
| VI-18-4 | p-Cl—Ph | H | H | CH₂CH(CH₃)₂ | Et | H | F | H | OH | H | H |
| VI-18-5 | p-Cl—Ph | H | H | CH₂Ph | Et | H | F | H | OH | H | H |
| VI-18-6 | p-Cl—Ph | H | H | CH₂-indol-3-yl | Et | H | F | H | OH | H | H |
| VI-18-7 | p-Cl—Ph | H | H | CH₂CH₂SCH₃ | Et | H | F | H | OH | H | H |
| VI-18-8 | p-Cl—Ph | * | H | * | Et | H | F | H | OH | H | H |

*R² and R³ joined together by (CH₂)₃ to form five-membered ring.

TABLE VI-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-19-1 | p-Br—Ph | H | H | H | Et | H | F | H | OH | H | H |
| VI-19-2 | p-Br—Ph | H | H | CH₃ | Et | H | F | H | OH | H | H |
| VI-19-3 | p-Br—Ph | H | H | CH(CH₃)₂ | Et | H | F | H | OH | H | H |
| VI-19-4 | p-Br—Ph | H | H | CH₂CH(CH₃)₂ | Et | H | F | H | OH | H | H |
| VI-19-5 | p-Br—Ph | H | H | CH₂Ph | Et | H | F | H | OH | H | H |
| VI-19-6 | p-Br—Ph | H | H | CH₂-indol-3-yl | Et | H | F | H | OH | H | H |
| VI-19-7 | p-Br—Ph | H | H | CH₂CH₂SCH₃ | Et | H | F | H | OH | H | H |
| VI-19-8 | p-Br—Ph | * | H | * | Et | H | F | H | OH | H | H |

*R² and R³ joined together by (CH₂)₃ to form five-membered ring.

TABLE VI-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-20-1 | p-I—Ph | H | H | H | Et | H | F | H | OH | H | H |
| VI-20-2 | p-I—Ph | H | H | CH₃ | Et | H | F | H | OH | H | H |
| VI-20-3 | p-I—Ph | H | H | CH(CH₃)₂ | Et | H | F | H | OH | H | H |
| VI-20-4 | p-I—Ph | H | H | CH₂CH(CH₃)₂ | Et | H | F | H | OH | H | H |
| VI-20-5 | p-I—Ph | H | H | CH₂Ph | Et | H | F | H | OH | H | H |
| VI-20-6 | p-I—Ph | H | H | CH₂-indol-3-yl | Et | H | F | H | OH | H | H |
| VI-20-7 | p-I—Ph | H | H | CH₂CH₂SCH₃ | Et | H | F | H | OH | H | H |
| VI-20-8 | p-I—Ph | * | H | * | Et | H | F | H | OH | H | H |

*R² and R³ joined together by (CH₂)₃ to form five-membered ring.

TABLE VI-21

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-21-1 | CH$_3$ | H | H | H | $^i$Pr | H | F | H | OH | H | H |
| VI-21-2 | CH$_3$ | H | H | CH$_3$ | $^i$Pr | H | F | H | OH | H | H |
| VI-21-3 | CH$_3$ | H | H | CH(CH$_3$)$_2$ | $^i$Pr | H | F | H | OH | H | H |
| VI-21-4 | CH$_3$ | H | H | CH$_2$CH(CH$_3$)$_2$ | $^i$Pr | H | F | H | OH | H | H |
| VI-21-5 | CH$_3$ | H | H | CH$_2$Ph | $^i$Pr | H | F | H | OH | H | H |
| VI-21-6 | CH$_3$ | H | H | CH$_2$-indol-3-yl | $^i$Pr | H | F | H | OH | H | H |
| VI-21-7 | CH$_3$ | H | H | CH$_2$CH$_2$SCH$_3$ | $^i$Pr | H | F | H | OH | H | H |
| VI-21-8 | CH$_3$ | * | H | * | $^i$Pr | H | F | H | OH | H | H |

*R$^2$ and R$^3$ joined together by (CH$_2$)$_3$ to form five-membered ring.

TABLE VI-22

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-22-1 | Et | H | H | H | $^i$Pr | H | F | H | OH | H | H |
| VI-22-2 | Et | H | H | CH$_3$ | $^i$Pr | H | F | H | OH | H | H |
| VI-22-3 | Et | H | H | CH(CH$_3$)$_2$ | $^i$Pr | H | F | H | OH | H | H |
| VI-22-4 | Et | H | H | CH$_2$CH(CH$_3$)$_2$ | $^i$Pr | H | F | H | OH | H | H |
| VI-22-5 | Et | H | H | CH$_2$Ph | $^i$Pr | H | F | H | OH | H | H |
| VI-22-6 | Et | H | H | CH$_2$-indol-3-yl | $^i$Pr | H | F | H | OH | H | H |
| VI-22-7 | Et | H | H | CH$_2$CH$_2$SCH$_3$ | $^i$Pr | H | F | H | OH | H | H |
| VI-22-8 | Et | * | H | * | $^i$Pr | H | F | H | OH | H | H |

*R$^2$ and R$^3$ joined together by (CH$_2$)$_3$ to form five-membered ring.

TABLE VI-23

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-23-1 | $^i$Pr | H | H | H | $^i$Pr | H | F | H | OH | H | H |
| VI-23-2 | $^i$Pr | H | H | CH$_3$ | $^i$Pr | H | F | H | OH | H | H |
| VI-23-3 | $^i$Pr | H | H | CH(CH$_3$)$_2$ | $^i$Pr | H | F | H | OH | H | H |
| VI-23-4 | $^i$Pr | H | H | CH$_2$CH(CH$_3$)$_2$ | $^i$Pr | H | F | H | OH | H | H |
| VI-23-5 | $^i$Pr | H | H | CH$_2$Ph | $^i$Pr | H | F | H | OH | H | H |
| VI-23-6 | $^i$Pr | H | H | CH$_2$-indol-3-yl | $^i$Pr | H | F | H | OH | H | H |
| VI-23-7 | $^i$Pr | H | H | CH$_2$CH$_2$SCH$_3$ | $^i$Pr | H | F | H | OH | H | H |
| VI-23-8 | $^i$Pr | * | H | * | $^i$Pr | H | F | H | OH | H | H |

*R$^2$ and R$^3$ joined together by (CH$_2$)$_3$ to form five-membered ring.

TABLE VI-24

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-24-1 | $^t$Bu | H | H | H | $^i$Pr | H | F | H | OH | H | H |
| VI-24-2 | $^t$Bu | H | H | CH$_3$ | $^i$Pr | H | F | H | OH | H | H |
| VI-24-3 | $^t$Bu | H | H | CH(CH$_3$)$_2$ | $^i$Pr | H | F | H | OH | H | H |
| VI-24-4 | $^t$Bu | H | H | CH$_2$CH(CH$_3$)$_2$ | $^i$Pr | H | F | H | OH | H | H |
| VI-24-5 | $^t$Bu | H | H | CH$_2$Ph | $^i$Pr | H | F | H | OH | H | H |
| VI-24-6 | $^t$Bu | H | H | CH$_2$-indol-3-yl | $^i$Pr | H | F | H | OH | H | H |
| VI-24-7 | $^t$Bu | H | H | CH$_2$CH$_2$SCH$_3$ | $^i$Pr | H | F | H | OH | H | H |
| VI-24-8 | $^t$Bu | * | H | * | $^i$Pr | H | F | H | OH | H | H |

*R$^2$ and R$^3$ joined together by (CH$_2$)$_3$ to form five-membered ring.

TABLE VI-25

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-25-1 | Ph | H | H | H | $^i$Pr | H | F | H | OH | H | H |
| VI-25-2 | Ph | H | H | CH$_3$ | $^i$Pr | H | F | H | OH | H | H |
| VI-25-3 | Ph | H | H | CH(CH$_3$)$_2$ | $^i$Pr | H | F | H | OH | H | H |
| VI-25-4 | Ph | H | H | CH$_2$CH(CH$_3$)$_2$ | $^i$Pr | H | F | H | OH | H | H |
| VI-25-5 | Ph | H | H | CH$_2$Ph | $^i$Pr | H | F | H | OH | H | H |
| VI-25-6 | Ph | H | H | CH$_2$-indol-3-yl | $^i$Pr | H | F | H | OH | H | H |
| VI-25-7 | Ph | H | H | CH$_2$CH$_2$SCH$_3$ | $^i$Pr | H | F | H | OH | H | H |
| VI-25-8 | Ph | * | H | * | $^i$Pr | H | F | H | OH | H | H |

*R$^2$ and R$^3$ joined together by (CH$_2$)$_3$ to form five-membered ring.

TABLE VI-26

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-26-1 | p-Me—Ph | H | H | H | $^i$Pr | H | F | H | OH | H | H |
| VI-26-2 | p-Me—Ph | H | H | CH$_3$ | $^i$Pr | H | F | H | OH | H | H |
| VI-26-3 | p-Me—Ph | H | H | CH(CH$_3$)$_2$ | $^i$Pr | H | F | H | OH | H | H |
| VI-26-4 | p-Me—Ph | H | H | CH$_2$CH(CH$_3$)$_2$ | $^i$Pr | H | F | H | OH | H | H |
| VI-26-5 | p-Me—Ph | H | H | CH$_2$Ph | $^i$Pr | H | F | H | OH | H | H |
| VI-26-6 | p-Me—Ph | H | H | CH$_2$-indol-3-yl | $^i$Pr | H | F | H | OH | H | H |
| VI-26-7 | p-Me—Ph | H | H | CH$_2$CH$_2$SCH$_3$ | $^i$Pr | H | F | H | OH | H | H |
| VI-26-8 | p-Me—Ph | * | H | * | $^i$Pr | H | F | H | OH | H | H |

*R$^2$ and R$^3$ joined together by (CH$_2$)$_3$ to form five-membered ring.

TABLE VI-27

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-27-1 | p-F—Ph | H | H | H | $^i$Pr | H | F | H | OH | H | H |
| VI-27-2 | p-F—Ph | H | H | CH$_3$ | $^i$Pr | H | F | H | OH | H | H |
| VI-27-3 | p-F—Ph | H | H | CH(CH$_3$)$_2$ | $^i$Pr | H | F | H | OH | H | H |
| VI-27-4 | p-F—Ph | H | H | CH$_2$CH(CH$_3$)$_2$ | $^i$Pr | H | F | H | OH | H | H |
| VI-27-5 | p-F—Ph | H | H | CH$_2$Ph | $^i$Pr | H | F | H | OH | H | H |
| VI-27-6 | p-F—Ph | H | H | CH$_2$-indol-3-yl | $^i$Pr | H | F | H | OH | H | H |
| VI-27-7 | p-F—Ph | H | H | CH$_2$CH$_2$SCH$_3$ | $^i$Pr | H | F | H | OH | H | H |
| VI-27-8 | p-F—Ph | * | H | * | $^i$Pr | H | F | H | OH | H | H |

*R$^2$ and R$^3$ joined together by (CH$_2$)$_3$ to form five-membered ring.

TABLE VI-28

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-28-1 | p-Cl—Ph | H | H | H | $^i$Pr | H | F | H | OH | H | H |
| VI-28-2 | p-Cl—Ph | H | H | CH₃ | $^i$Pr | H | F | H | OH | H | H |
| VI-28-3 | p-Cl—Ph | H | H | CH(CH₃)₂ | $^i$Pr | H | F | H | OH | H | H |
| VI-28-4 | p-Cl—Ph | H | H | CH₂CH(CH₃)₂ | $^i$Pr | H | F | H | OH | H | H |
| VI-28-5 | p-Cl—Ph | H | H | CH₂Ph | $^i$Pr | H | F | H | OH | H | H |
| VI-28-6 | p-Cl—Ph | H | H | CH₂-indol-3-yl | $^i$Pr | H | F | H | OH | H | H |
| VI-28-7 | p-Cl—Ph | H | H | CH₂CH₂SCH₃ | $^i$Pr | H | F | H | OH | H | H |
| VI-28-8 | p-Cl—Ph | * | H | * | $^i$Pr | H | F | H | OH | H | H |

*R² and R³ joined together by (CH₂)₃ to form five-membered ring.

TABLE VI-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-29-1 | p-Br—Ph | H | H | H | $^i$Pr | H | F | H | OH | H | H |
| VI-29-2 | p-Br—Ph | H | H | CH₃ | $^i$Pr | H | F | H | OH | H | H |
| VI-29-3 | p-Br—Ph | H | H | CH(CH₃)₂ | $^i$Pr | H | F | H | OH | H | H |
| VI-29-4 | p-Br—Ph | H | H | CH₂CH(CH₃)₂ | $^i$Pr | H | F | H | OH | H | H |
| VI-29-5 | p-Br—Ph | H | H | CH₂Ph | $^i$Pr | H | F | H | OH | H | H |
| VI-29-6 | p-Br—Ph | H | H | CH₂-indol-3-yl | $^i$Pr | H | F | H | OH | H | H |
| VI-29-7 | p-Br—Ph | H | H | CH₂CH₂SCH₃ | $^i$Pr | H | F | H | OH | H | H |
| VI-29-8 | p-Br—Ph | * | H | * | $^i$Pr | H | F | H | OH | H | H |

*R² and R³ joined together by (CH₂)₃ to form five-membered ring.

TABLE VI-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-30-1 | p-I—Ph | H | H | H | $^i$Pr | H | F | H | OH | H | H |
| VI-30-2 | p-I—Ph | H | H | CH₃ | $^i$Pr | H | F | H | OH | H | H |
| VI-30-3 | p-I—Ph | H | H | CH(CH₃)₂ | $^i$Pr | H | F | H | OH | H | H |
| VI-30-4 | p-I—Ph | H | H | CH₂CH(CH₃)₂ | $^i$Pr | H | F | H | OH | H | H |
| VI-30-5 | p-I—Ph | H | H | CH₂Ph | $^i$Pr | H | F | H | OH | H | H |
| VI-30-6 | p-I—Ph | H | H | CH₂-indol-3-yl | $^i$Pr | H | F | H | OH | H | H |
| VI-30-7 | p-I—Ph | H | H | CH₂CH₂SCH₃ | $^i$Pr | H | F | H | OH | H | H |
| VI-30-8 | p-I—Ph | * | H | * | $^i$Pr | H | F | H | OH | H | H |

*R² and R³ joined together by (CH₂)₃ to form five-membered ring.

TABLE VI-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-31-1 | CH₃ | H | H | H | $^i$Pr | H | F | H | OH | H | H |
| VI-31-2 | CH₃ | H | H | CH₃ | $^i$Pr | H | F | H | OH | H | H |
| VI-31-3 | CH₃ | H | H | CH(CH₃)₂ | $^i$Pr | H | F | H | OH | H | H |
| VI-31-4 | CH₃ | H | H | CH₂CH(CH₃)₂ | $^i$Pr | H | F | H | OH | H | H |
| VI-31-5 | CH₃ | H | H | CH₂Ph | $^i$Pr | H | F | H | OH | H | H |
| VI-31-6 | CH₃ | H | H | CH₂-indol-3-yl | $^i$Pr | H | F | H | OH | H | H |
| VI-31-7 | CH₃ | H | H | CH₂CH₂SCH₃ | $^i$Pr | H | F | H | OH | H | H |
| VI-31-8 | CH₃ | * | H | * | $^i$Pr | H | F | H | OH | H | H |

*R² and R³ᵇ joined together by (CH₂)₃ to form five-membered ring.

TABLE VI-32

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-32-1 | Et | H | H | H | $^n$Bu | H | F | H | OH | H | H |
| VI-32-2 | Et | H | H | CH₃ | $^n$Bu | H | F | H | OH | H | H |
| VI-32-3 | Et | H | H | CH(CH₃)₂ | $^n$Bu | H | F | H | OH | H | H |
| VI-32-4 | Et | H | H | CH₂CH(CH₃)₂ | $^n$Bu | H | F | H | OH | H | H |
| VI-32-5 | Et | H | H | CH₂Ph | $^n$Bu | H | F | H | OH | H | H |
| VI-32-6 | Et | H | H | CH₂-indol-3-yl | $^n$Bu | H | F | H | OH | H | H |
| VI-32-7 | Et | H | H | CH₂CH₂SCH₃ | $^n$Bu | H | F | H | OH | H | H |
| VI-32-8 | Et | * | H | * | $^n$Bu | H | F | H | OH | H | H |

*R² and R³ᵇ joined together by (CH₂)₃ to form five-membered ring.

TABLE VI-33

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-33-1 | $^i$Pr | H | H | H | $^n$Bu | H | F | H | OH | H | H |
| VI-33-2 | $^i$Pr | H | H | CH₃ | $^n$Bu | H | F | H | OH | H | H |
| VI-33-3 | $^i$Pr | H | H | CH(CH₃)₂ | $^n$Bu | H | F | H | OH | H | H |
| VI-33-4 | $^i$Pr | H | H | CH₂CH(CH₃)₂ | $^n$Bu | H | F | H | OH | H | H |
| VI-33-5 | $^i$Pr | H | H | CH₂Ph | $^n$Bu | H | F | H | OH | H | H |
| VI-33-6 | $^i$Pr | H | H | CH₂-indol-3-yl | $^n$Bu | H | F | H | OH | H | H |
| VI-33-7 | $^i$Pr | H | H | CH₂CH₂SCH₃ | $^n$Bu | H | F | H | OH | H | H |
| VI-33-8 | $^i$Pr | * | H | * | $^n$Bu | H | F | H | OH | H | H |

*R² and R³ᵇ joined together by (CH₂)₃ to form five-membered ring.

TABLE VI-34

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-34-1 | $^t$Bu | H | H | H | $^n$Bu | H | F | H | OH | H | H |
| VI-34-2 | $^t$Bu | H | H | CH$_3$ | $^n$Bu | H | F | H | OH | H | H |
| VI-34-3 | $^t$Bu | H | H | CH(CH$_3$)$_2$ | $^n$Bu | H | F | H | OH | H | H |
| VI-34-4 | $^t$Bu | H | H | CH$_2$CH(CH$_3$)$_2$ | $^n$Bu | H | F | H | OH | H | H |
| VI-34-5 | $^t$Bu | H | H | CH$_2$Ph | $^n$Bu | H | F | H | OH | H | H |
| VI-34-6 | $^t$Bu | H | H | CH$_2$-indol-3-yl | $^n$Bu | H | F | H | OH | H | H |
| VI-34-7 | $^t$Bu | H | H | CH$_2$CH$_2$SCH$_3$ | $^n$Bu | H | F | H | OH | H | H |
| VI-34-8 | $^t$Bu | * | H | * | $^n$Bu | H | F | H | OH | H | H |

*R$^2$ and R$^{3b}$ joined together by (CH$_2$)$_3$ to form five-membered ring.

TABLE VI-35

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-35-1 | Ph | H | H | H | $^n$Bu | H | F | H | OH | H | H |
| VI-35-2 | Ph | H | H | CH$_3$ | $^n$Bu | H | F | H | OH | H | H |
| VI-35-3 | Ph | H | H | CH(CH$_3$)$_2$ | $^n$Bu | H | F | H | OH | H | H |
| VI-35-4 | Ph | H | H | CH$_2$CH(CH$_3$)$_2$ | $^n$Bu | H | F | H | OH | H | H |
| VI-35-5 | Ph | H | H | CH$_2$Ph | $^n$Bu | H | F | H | OH | H | H |
| VI-35-6 | Ph | H | H | CH$_2$-indol-3-yl | $^n$Bu | H | F | H | OH | H | H |
| VI-35-7 | Ph | H | H | CH$_2$CH$_2$SCH$_3$ | $^n$Bu | H | F | H | OH | H | H |
| VI-35-8 | Ph | * | H | * | $^n$Bu | H | F | H | OH | H | H |

*R$^2$ and R$^{3b}$ joined together by (CH$_2$)$_3$ to form five-membered ring.

TABLE VI-36

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-36-1 | p-Me—Ph | H | H | H | $^n$Bu | H | F | H | OH | H | H |
| VI-36-2 | p-Me—Ph | H | H | CH$_3$ | $^n$Bu | H | F | H | OH | H | H |
| VI-36-3 | p-Me—Ph | H | H | CH(CH$_3$)$_2$ | $^n$Bu | H | F | H | OH | H | H |
| VI-36-4 | p-Me—Ph | H | H | CH$_2$CH(CH$_3$)$_2$ | $^n$Bu | H | F | H | OH | H | H |
| VI-36-5 | p-Me—Ph | H | H | CH$_2$Ph | $^n$Bu | H | F | H | OH | H | H |
| VI-36-6 | p-Me—Ph | H | H | CH$_2$-indol-3-yl | $^n$Bu | H | F | H | OH | H | H |
| VI-36-7 | p-Me—Ph | H | H | CH$_2$CH$_2$SCH$_3$ | $^n$Bu | H | F | H | OH | H | H |
| VI-36-8 | p-Me—Ph | * | H | * | $^n$Bu | H | F | H | OH | H | H |

*R$^2$ and R$^{3b}$ joined together by (CH$_2$)$_3$ to form five-membered ring.

TABLE VI-37

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-37-1 | p-F—Ph | H | H | H | $^n$Bu | H | F | H | OH | H | H |
| VI-37-2 | p-F—Ph | H | H | CH$_3$ | $^n$Bu | H | F | H | OH | H | H |
| VI-37-3 | p-F—Ph | H | H | CH(CH$_3$)$_2$ | $^n$Bu | H | F | H | OH | H | H |
| VI-37-4 | p-F—Ph | H | H | CH$_2$CH(CH$_3$)$_2$ | $^n$Bu | H | F | H | OH | H | H |
| VI-37-5 | p-F—Ph | H | H | CH$_2$Ph | $^n$Bu | H | F | H | OH | H | H |
| VI-37-6 | p-F—Ph | H | H | CH$_2$-indol-3-yl | $^n$Bu | H | F | H | OH | H | H |
| VI-37-7 | p-F—Ph | H | H | CH$_2$CH$_2$SCH$_3$ | $^n$Bu | H | F | H | OH | H | H |
| VI-37-8 | p-F—Ph | * | H | * | $^n$Bu | H | F | H | OH | H | H |

*R$^2$ and R$^{3b}$ joined together by (CH$_2$)$_3$ to form five-membered ring.

TABLE VI-38

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-38-1 | p-Cl—Ph | H | H | H | $^n$Bu | H | F | H | OH | H | H |
| VI-38-2 | p-Cl—Ph | H | H | CH$_3$ | $^n$Bu | H | F | H | OH | H | H |
| VI-38-3 | p-Cl—Ph | H | H | CH(CH$_3$)$_2$ | $^n$Bu | H | F | H | OH | H | H |
| VI-38-4 | p-Cl—Ph | H | H | CH$_2$CH(CH$_3$)$_2$ | $^n$Bu | H | F | H | OH | H | H |
| VI-38-5 | p-Cl—Ph | H | H | CH$_2$Ph | $^n$Bu | H | F | H | OH | H | H |
| VI-38-6 | p-Cl—Ph | H | H | CH$_2$-indol-3-yl | $^n$Bu | H | F | H | OH | H | H |
| VI-38-7 | p-Cl—Ph | H | H | CH$_2$CH$_2$SCH$_3$ | $^n$Bu | H | F | H | OH | H | H |
| VI-38-8 | p-Cl—Ph | * | H | * | $^n$Bu | H | F | H | OH | H | H |

*R$^2$ and R$^{3b}$ joined together by (CH$_2$)$_3$ to form five-membered ring.

TABLE VI-39

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VI-39-1 | p-Br—Ph | H | H | H | $^n$Bu | H | F | H | OH | H | H |
| VI-39-2 | p-Br—Ph | H | H | CH$_3$ | $^n$Bu | H | F | H | OH | H | H |
| VI-39-3 | p-Br—Ph | H | H | CH(CH$_3$)$_2$ | $^n$Bu | H | F | H | OH | H | H |
| VI-39-4 | p-Br—Ph | H | H | CH$_2$CH(CH$_3$)$_2$ | $^n$Bu | H | F | H | OH | H | H |
| VI-39-5 | p-Br—Ph | H | H | CH$_2$Ph | $^n$Bu | H | F | H | OH | H | H |
| VI-39-6 | p-Br—Ph | H | H | CH$_2$-indol-3-yl | $^n$Bu | H | F | H | OH | H | H |
| VI-39-7 | p-Br—Ph | H | II | CH$_2$CH$_2$SCH$_3$ | $^n$Bu | H | F | H | OH | H | H |
| VI-39-8 | p-Br—Ph | * | H | * | $^n$Bu | H | F | H | OH | H | H |

*R$^2$ and R$^{3b}$ joined together by (CH$_2$)$_3$ to form five-membered ring.

TABLE VI-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-40-1 | p-I—Ph | H | H | H | ⁿBu | H | F | H | OH | H | H |
| VI-40-2 | p-I—Ph | H | H | CH₃ | ⁿBu | H | F | H | OH | H | H |
| VI-40-3 | p-I—Ph | H | H | CH(CH₃)₂ | ⁿBu | H | F | H | OH | H | H |
| VI-40-4 | p-I—Ph | H | H | CH₂CH(CH₃)₂ | ⁿBu | H | F | H | OH | H | H |
| VI-40-5 | p-I—Ph | H | H | CH₂Ph | ⁿBu | H | F | H | OH | H | H |
| VI-40-6 | p-I—Ph | H | H | CH₂-indol-3-yl | ⁿBu | H | F | H | OH | H | H |
| VI-40-7 | p-I—Ph | H | H | CH₂CH₂SCH₃ | ⁿBu | H | F | H | OH | H | H |
| VI-40-8 | p-I—Ph | * | H | * | ⁿBu | H | F | H | OH | H | H |

*R² and R³ᵇ joined together by (CH₂)₃ to form five-membered ring.

TABLE VI-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-41-1 | CH₃ | H | H | H | Bz | H | F | H | OH | H | H |
| VI-41-2 | CH₃ | H | H | CH₃ | Bz | H | F | H | OH | H | H |
| VI-41-3 | CH₃ | H | H | CH(CH₃)₂ | Bz | H | F | H | OH | H | H |
| VI-41-4 | CH₃ | H | H | CH₂CH(CH₃)₂ | Bz | H | F | H | OH | H | H |
| VI-41-5 | CH₃ | H | H | CH₂Ph | Bz | H | F | H | OH | H | H |
| VI-41-6 | CH₃ | H | H | CH₂-indol-3-yl | Bz | H | F | H | OH | H | H |
| VI-41-7 | CH₃ | H | H | CH₂CH₂SCH₃ | Bz | H | F | H | OH | H | H |
| VI-41-8 | CH₃ | * | H | * | Bz | H | F | H | OH | H | H |

*R² and R³ᵇ joined together by (CH₂)₃ to form five-membered ring.

TABLE VI-42

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-42-1 | Et | H | H | H | Bz | H | F | H | OH | H | H |
| VI-42-2 | Et | H | H | CH₃ | Bz | H | F | H | OH | H | H |
| VI-42-3 | Et | H | H | CH(CH₃)₂ | Bz | H | F | H | OH | H | H |
| VI-42-4 | Et | H | H | CH₂CH(CH₃)₂ | Bz | H | F | H | OH | H | H |
| VI-42-5 | Et | H | H | CH₂Ph | Bz | H | F | H | OH | H | H |
| VI-42-6 | Et | H | H | CH₂-indol-3-yl | Bz | H | F | H | OH | H | H |
| VI-42-7 | Et | H | H | CH₂CH₂SCH₃ | Bz | H | F | H | OH | H | H |
| VI-42-8 | Et | * | H | * | Bz | H | F | H | OH | H | H |

*R² and R³ᵇ joined together by (CH₂)₃ to form five-membered ring.

TABLE VI-43

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-43-1 | ⁱPr | H | H | H | Bz | H | F | H | OH | H | H |
| VI-43-2 | ⁱPr | H | H | CH₃ | Bz | H | F | H | OH | H | H |
| VI-43-3 | ⁱPr | H | H | CH(CH₃)₂ | Bz | H | F | H | OH | H | H |
| VI-43-4 | ⁱPr | H | H | CH₂CH(CH₃)₂ | Bz | H | F | H | OH | H | H |
| VI-43-5 | ⁱPr | H | H | CH₂Ph | Bz | H | F | H | OH | H | H |
| VI-43-6 | ⁱPr | H | H | CH₂-indol-3-yl | Bz | H | F | H | OH | H | H |
| VI-43-7 | ⁱPr | H | H | CH₂CH₂SCH₃ | Bz | H | F | H | OH | H | H |
| VI-43-8 | ⁱPr | * | H | * | Bz | H | F | H | OH | H | H |

*R² and R³ᵇ joined together by (CH₂)₃ to form five-membered ring.

TABLE VI-44

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-44-1 | ᵗBu | H | H | H | Bz | H | F | H | OH | H | H |
| VI-44-2 | ᵗBu | H | H | CH₃ | Bz | H | F | H | OH | H | H |
| VI-44-3 | ᵗBu | H | H | CH(CH₃)₂ | Bz | H | F | H | OH | H | H |
| VI-44-4 | ᵗBu | H | H | CH₂CH(CH₃)₂ | Bz | H | F | H | OH | H | H |
| VI-44-5 | ᵗBu | H | H | CH₂Ph | Bz | H | F | H | OH | H | H |
| VI-44-6 | ᵗBu | H | H | CH₂-indol-3-yl | Bz | H | F | H | OH | H | H |
| VI-44-7 | ᵗBu | H | H | CH₂CH₂SCH₃ | Bz | H | F | H | OH | H | H |
| VI-44-8 | ᵗBu | * | H | * | Bz | H | F | H | OH | H | H |

*R² and R³ᵇ joined together by (CH₂)₃ to form five-membered ring.

TABLE VI-45

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-45-1 | Ph | H | H | H | Bz | H | F | H | OH | H | H |
| VI-45-2 | Ph | H | H | CH₃ | Bz | H | F | H | OH | H | H |
| VI-45-3 | Ph | H | H | CH(CH₃)₂ | Bz | H | F | H | OH | H | H |
| VI-45-4 | Ph | H | H | CH₂CH(CH₃)₂ | Bz | H | F | H | OH | H | H |
| VI-45-5 | Ph | H | H | CH₂Ph | Bz | H | F | H | OH | H | H |
| VI-45-6 | Ph | H | H | CH₂-indol-3-yl | Bz | H | F | H | OH | H | H |
| VI-45-7 | Ph | H | H | CH₂CH₂SCH₃ | Bz | H | F | H | OH | H | H |
| VI-45-8 | Ph | * | H | * | Bz | H | F | H | OH | H | H |

*R² and R³ᵇ joined together by (CH₂)₃ to form five-membered ring.

TABLE VI-46

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-46-1 | p-Me—Ph | H | H | H | Bz | H | F | H | OH | H | H |
| VI-46-2 | p-Me—Ph | H | H | CH₃ | Bz | H | F | H | OH | H | H |
| VI-46-3 | p-Me—Ph | H | H | CH(CH₃)₂ | Bz | H | F | H | OH | H | H |
| VI-46-4 | p-Me—Ph | H | H | CH₂CH(CH₃)₂ | Bz | H | F | H | OH | H | H |
| VI-46-5 | p-Me—Ph | H | H | CH₂Ph | Bz | H | F | H | OH | H | H |
| VI-46-6 | p-Me—Ph | H | H | CH₂-indol-3-yl | Bz | H | F | H | OH | H | H |
| VI-46-7 | p-Me—Ph | H | H | CH₂CH₂SCH₃ | Bz | H | F | H | OH | H | H |
| VI-46-8 | p-Me—Ph | * | H | * | Bz | H | F | H | OH | H | H |

*R² and R³ᵇ joined together by (CH₂)₃ to form five-membered ring.

TABLE VI-47

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-47-1 | p-F—Ph | H | H | H | Bz | H | F | H | OH | H | H |
| VI-47-2 | p-F—Ph | H | H | CH₃ | Bz | H | F | H | OH | H | H |
| VI-47-3 | p-F—Ph | H | H | CH(CH₃)₂ | Bz | H | F | H | OH | H | H |
| VI-47-4 | p-F—Ph | H | H | CH₂CH(CH₃)₂ | Bz | H | F | H | OH | H | H |
| VI-47-5 | p-F—Ph | H | H | CH₂Ph | Bz | H | F | H | OH | H | H |
| VI-47-6 | p-F—Ph | H | H | CH₂-indol-3-yl | Bz | H | F | H | OH | H | H |
| VI-47-7 | p-F—Ph | H | H | CH₂CH₂SCH₃ | Bz | H | F | H | OH | H | H |
| VI-47-8 | p-F—Ph | * | H | * | Bz | H | F | H | OH | H | H |

*R² and R³ᵇ joined together by (CH₂)₃ to form five-membered ring.

TABLE VI-48

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-48-1 | p-Cl—Ph | H | H | H | Bz | H | F | H | OH | H | H |
| VI-48-2 | p-Cl—Ph | H | H | CH₃ | Bz | H | F | H | OH | H | H |
| VI-48-3 | p-Cl—Ph | H | H | CH(CH₃)₂ | Bz | H | F | H | OH | H | H |
| VI-48-4 | p-Cl—Ph | H | H | CH₂CH(CH₃)₂ | Bz | H | F | H | OH | H | H |
| VI-48-5 | p-Cl—Ph | H | H | CH₂Ph | Bz | H | F | H | OH | H | H |
| VI-48-6 | p-Cl—Ph | H | H | CH₂-indol-3-yl | Bz | H | F | H | OH | H | H |
| VI-48-7 | p-Cl—Ph | H | H | CH₂CH₂SCH₃ | Bz | H | F | H | OH | H | H |
| VI-48-8 | p-Cl—Ph | * | H | * | Bz | H | F | H | OH | H | H |

*R² and R³ᵇ joined together by (CH₂)₃ to form five-membered ring.

TABLE VI-49

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-49-1 | p-Br—Ph | H | H | H | Bz | H | F | H | OH | H | H |
| VI-49-2 | p-Br—Ph | H | H | CH₃ | Bz | H | F | H | OH | H | H |
| VI-49-3 | p-Br—Ph | H | H | CH(CH₃)₂ | Bz | H | F | H | OH | H | H |
| VI-49-4 | p-Br—Ph | H | H | CH₂CH(CH₃)₂ | Bz | H | F | H | OH | H | H |
| VI-49-5 | p-Br—Ph | H | H | CH₂Ph | Bz | H | F | H | OH | H | H |
| VI-49-6 | p-Br—Ph | H | H | CH₂-indol-3-yl | Bz | H | F | H | OH | H | H |
| VI-49-7 | p-Br—Ph | H | H | CH₂CH₂SCH₃ | Bz | H | F | H | OH | H | H |
| VI-49-8 | p-Br—Ph | * | H | * | Bz | H | F | H | OH | H | H |

*R² and R³ᵇ joined together by (CH₂)₃ to form five-membered ring.

TABLE VI-50

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VI-50-1 | p-I—Ph | H | H | H | Bz | H | F | H | OH | H | H |
| VI-50-2 | p-I—Ph | H | H | CH₃ | Bz | H | F | H | OH | H | H |
| VI-50-3 | p-I—Ph | H | H | CH(CH₃)₂ | Bz | H | F | H | OH | H | H |
| VI-50-4 | p-I—Ph | H | H | CH₂CH(CH₃)₂ | Bz | H | F | H | OH | H | H |
| VI-50-5 | p-I—Ph | H | H | CH₂Ph | Bz | H | F | H | OH | H | H |
| VI-50-6 | p-I—Ph | H | H | CH₂-indol-3-yl | Bz | H | F | H | OH | H | H |
| VI-50-7 | p-I—Ph | H | H | CH₂CH₂SCH₃ | Bz | H | F | H | OH | H | H |
| VI-50-8 | p-I—Ph | * | H | * | Bz | H | F | H | OH | H | H |

*R² and R³ᵇ joined together by (CH₂)₃ to form five-membered ring.

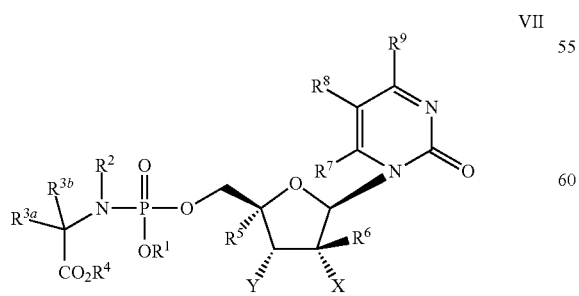

VII

TABLE VII-1

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-1-1 | $CH_3$ | H | H | H | $CH_3$ | H | F | H | OH | H | H | $NH_2$ |
| VII-1-2 | $CH_3$ | H | H | $CH_3$ | $CH_3$ | H | F | H | OH | H | H | $NH_2$ |
| VII-1-3 | $CH_3$ | H | H | $CH(CH_3)_2$ | $CH_3$ | H | F | H | OH | H | H | $NH_2$ |
| VII-1-4 | $CH_3$ | H | H | $CH_2CH(CH_3)_2$ | $CH_3$ | H | F | H | OH | H | H | $NH_2$ |
| VII-1-5 | $CH_3$ | H | H | $CH_2Ph$ | $CH_3$ | H | F | H | OH | H | H | $NH_2$ |
| VII-1-6 | $CH_3$ | H | H | $CH_2$-indol-3-yl | $CH_3$ | H | F | H | OH | H | H | $NH_2$ |
| VII-1-7 | $CH_3$ | H | H | $CH_2CH_2SCH_3$ | $CH_3$ | H | F | H | OH | H | H | $NH_2$ |
| VII-1-8 | $CH_3$ | * | H | * | $CH_3$ | H | F | H | OH | H | H | $NH_2$ |

*$R^2$ and $R^{3b}$ joined together by $(CH_2)_3$ to form five-membered ring.

TABLE VII-2

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-2-1 | Et | H | H | H | $CH_3$ | H | F | H | OH | H | H | $NH_2$ |
| VII-2-2 | Et | H | H | $CH_3$ | $CH_3$ | H | F | H | OH | H | H | $NH_2$ |
| VII-2-3 | Et | H | H | $CH(CH_3)_2$ | $CH_3$ | H | F | H | OH | H | H | $NH_2$ |
| VII-2-4 | Et | H | H | $CH_2CH(CH_3)_2$ | $CH_3$ | H | F | H | OH | H | H | $NH_2$ |
| VII-2-5 | Et | H | H | $CH_2Ph$ | $CH_3$ | H | F | H | OH | H | H | $NH_2$ |
| VII-2-6 | Et | H | H | $CH_2$-indol-3-yl | $CH_3$ | H | F | H | OH | H | H | $NH_2$ |
| VII-2-7 | Et | H | H | $CH_2CH_2SCH_3$ | $CH_3$ | H | F | H | OH | H | H | $NH_2$ |
| VII-2-8 | Et | * | H | * | $CH_3$ | H | F | H | OH | H | H | $NH_2$ |

*$R^2$ and $R^{3b}$ joined together by $(CH_2)_3$ to form five-membered ring.

TABLE VII-3

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-3-1 | $^i$Pr | H | H | H | $CH_3$ | H | F | H | OH | H | H | $NH_2$ |
| VII-3-2 | $^i$Pr | H | H | $CH_3$ | $CH_3$ | H | F | H | OH | H | H | $NH_2$ |
| VII-3-3 | $^i$Pr | H | H | $CH(CH_3)_2$ | $CH_3$ | H | F | H | OH | H | H | $NH_2$ |
| VII-3-4 | $^i$Pr | H | H | $CH_2CH(CH_3)_2$ | $CH_3$ | H | F | H | OH | H | H | $NH_2$ |
| VII-3-5 | $^i$Pr | H | H | $CH_2Ph$ | $CH_3$ | H | F | H | OH | H | H | $NH_2$ |
| VII-3-6 | $^i$Pr | H | H | $CH_2$-indol-3-yl | $CH_3$ | H | F | H | OH | H | H | $NH_2$ |
| VII-3-7 | $^i$Pr | H | H | $CH_2CH_2SCH_3$ | $CH_3$ | H | F | H | OH | H | H | $NH_2$ |
| VII-3-8 | $^i$Pr | * | H | * | $CH_3$ | H | F | H | OH | H | H | $NH_2$ |

*$R^2$ and $R^{3b}$ joined together by $(CH_2)_3$ to form five-membered ring.

TABLE VII-4

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-4-1 | $^t$Bu | H | H | H | $CH_3$ | H | F | H | OH | H | H | $NH_2$ |
| VII-4-2 | $^t$Bu | H | H | $CH_3$ | $CH_3$ | H | F | H | OH | H | H | $NH_2$ |
| VII-4-3 | $^t$Bu | H | H | $CH(CH_3)_2$ | $CH_3$ | H | F | H | OH | H | H | $NH_2$ |
| VII-4-4 | $^t$Bu | H | H | $CH_2CH(CH_3)_2$ | $CH_3$ | H | F | H | OH | H | H | $NH_2$ |
| VII-4-5 | $^t$Bu | H | H | $CH_2Ph$ | $CH_3$ | H | F | H | OH | H | H | $NH_2$ |
| VII-4-6 | $^t$Bu | H | H | $CH_2$-indol-3-yl | $CH_3$ | H | F | H | OH | H | H | $NH_2$ |
| VII-4-7 | $^t$Bu | H | H | $CH_2CH_2SCH_3$ | $CH_3$ | H | F | H | OH | H | H | $NH_2$ |
| VII-4-8 | $^t$Bu | * | H | * | $CH_3$ | H | F | H | OH | H | H | $NH_2$ |

*$R^2$ and $R^{3b}$ joined together by $(CH_2)_3$ to form five-membered ring.

TABLE VII-5

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-5-1 | Ph | H | H | H | $CH_3$ | H | F | H | OH | H | H | $NH_2$ |
| VII-5-2 | Ph | H | H | $CH_3$ | $CH_3$ | H | F | H | OH | H | H | $NH_2$ |
| VII-5-3 | Ph | H | H | $CH(CH_3)_2$ | $CH_3$ | H | F | H | OH | H | H | $NH_2$ |
| VII-5-4 | Ph | H | H | $CH_2CH(CH_3)_2$ | $CH_3$ | H | F | H | OH | H | H | $NH_2$ |
| VII-5-5 | Ph | H | H | $CH_2Ph$ | $CH_3$ | H | F | H | OH | H | H | $NH_2$ |

TABLE VII-5-continued

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-5-6 | Ph | H | H | CH$_2$-indol-3-yl | CH$_3$ | H | F | H | OH | H | H | NH$_2$ |
| VII-5-7 | Ph | H | H | CH$_2$CH$_2$SCH$_3$ | CH$_3$ | H | F | H | OH | H | H | NH$_2$ |
| VII-5-8 | Ph | * | H | * | CH$_3$ | H | F | H | OH | H | H | NH$_2$ |

*R$^2$ and R$^{3b}$ joined together by (CH$_2$)$_3$ to form five-membered ring.

TABLE VII-6

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-6-1 | p-Me—Ph | H | H | H | CH$_3$ | H | F | H | OH | H | H | NH$_2$ |
| VII-6-2 | p-Me—Ph | H | H | CH$_3$ | CH$_3$ | H | F | H | OH | H | H | NH$_2$ |
| VII-6-3 | p-Me—Ph | H | H | CH(CH$_3$)$_2$ | CH$_3$ | H | F | H | OH | H | H | NH$_2$ |
| VII-6-4 | p-Me—Ph | H | H | CH$_2$CH(CH$_3$)$_2$ | CH$_3$ | H | F | H | OH | H | H | NH$_2$ |
| VII-6-5 | p-Me—Ph | H | H | CH$_2$Ph | CH$_3$ | H | F | H | OH | H | H | NH$_2$ |
| VII-6-6 | p-Me—Ph | H | H | CH$_2$-indol-3-yl | CH$_3$ | H | F | H | OH | H | H | NH$_2$ |
| VII-6-7 | p-Me—Ph | H | H | CH$_2$CH$_2$SCH$_3$ | CH$_3$ | H | F | H | OH | H | H | NH$_2$ |
| VII-6-8 | p-Me—Ph | * | H | * | CH$_3$ | H | F | H | OH | H | H | NH$_2$ |

*R$^2$ and R$^{3b}$ joined together by (CH$_2$)$_3$ to form five-membered ring.

TABLE VII-7

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-7-1 | p-F—Ph | H | H | H | CH$_3$ | H | F | H | OH | H | H | NH$_2$ |
| VII-7-2 | p-F—Ph | H | H | CH$_3$ | CH$_3$ | H | F | H | OH | H | H | NH$_2$ |
| VII-7-3 | p-F—Ph | H | H | CH(CH$_3$)$_2$ | CH$_3$ | H | F | H | OH | H | H | NH$_2$ |
| VII-7-4 | p-F—Ph | H | H | CH$_2$CH(CH$_3$)$_2$ | CH$_3$ | H | F | H | OH | H | H | NH$_2$ |
| VII-7-6 | p-F—Ph | H | H | CH$_2$Ph | CH$_3$ | H | F | H | OH | H | H | NH$_2$ |
| VII-7-7 | p-F—Ph | H | H | CH$_2$-indol-3-yl | CH$_3$ | H | F | H | OH | H | H | NH$_2$ |
| VII-7-8 | p-F—Ph | H | H | CH$_2$CH$_2$SCH$_3$ | CH$_3$ | H | F | H | OH | H | H | NH$_2$ |
| VII-7-20 | p-F—Ph | * | H | * | CH$_3$ | H | F | H | OH | H | H | NH$_2$ |

*R$^2$ and R$^{3b}$ joined together by (CH$_2$)$_3$ to form five-membered ring.

TABLE VII-8

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-8-1 | p-Cl—Ph | H | H | H | CH$_3$ | H | F | H | OH | H | H | NH$_2$ |
| VII-8-2 | p-Cl—Ph | H | H | CH$_3$ | CH$_3$ | H | F | H | OH | H | H | NH$_2$ |
| VII-8-3 | p-Cl—Ph | H | H | CH(CH$_3$)$_2$ | CH$_3$ | H | F | H | OH | H | H | NH$_2$ |
| VII-8-4 | p-Cl—Ph | H | H | CH$_2$CH(CH$_3$)$_2$ | CH$_3$ | H | F | H | OH | H | H | NH$_2$ |
| VII-8-5 | p-Cl—Ph | H | H | CH$_2$Ph | CH$_3$ | H | F | H | OH | H | H | NH$_2$ |
| VII-8-6 | p-Cl—Ph | H | H | CH$_2$-indol-3-yl | CH$_3$ | H | F | H | OH | H | H | NH$_2$ |
| VII-8-7 | p-Cl—Ph | H | H | CH$_2$CH$_2$SCH$_3$ | CH$_3$ | H | F | H | OH | H | H | NH$_2$ |
| VII-8-8 | p-Cl—Ph | * | H | * | CH$_3$ | H | F | H | OH | H | H | NH$_2$ |

*R$^2$ and R$^{3b}$ joined together by (CH$_2$)$_3$ to form five-membered ring.

TABLE VII-9

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-9-1 | p-Br—Ph | H | H | H | CH$_3$ | H | F | H | OH | H | H | NH$_2$ |
| VII-9-2 | p-Br—Ph | H | H | CH$_3$ | CH$_3$ | H | F | H | OH | H | H | NH$_2$ |
| VII-9-3 | p-Br—Ph | H | H | CH(CH$_3$)$_2$ | CH$_3$ | H | F | H | OH | H | H | NH$_2$ |
| VII-9-4 | p-Br—Ph | H | H | CH$_2$CH(CH$_3$)$_2$ | CH$_3$ | H | F | H | OH | H | H | NH$_2$ |
| VII-9-6 | p-Br—Ph | H | H | CH$_2$Ph | CH$_3$ | H | F | H | OH | H | H | NH$_2$ |
| VII-9-7 | p-Br—Ph | H | H | CH$_2$-indol-3-yl | CH$_3$ | H | F | H | OH | H | H | NH$_2$ |
| VII-9-8 | p-Br—Ph | H | H | CH$_2$CH$_2$SCH$_3$ | CH$_3$ | H | F | H | OH | H | H | NH$_2$ |
| VII-9-20 | p-Br—Ph | * | H | * | CH$_3$ | H | F | H | OH | H | H | NH$_2$ |

*R$^2$ and R$^{3b}$ joined together by (CH$_2$)$_3$ to form five-membered ring.

TABLE VII-10

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-10-1 | p-I—Ph | H | H | H | $CH_3$ | H | F | H | OH | H | H | $NH_2$ |
| VII-10-2 | p-I—Ph | H | H | $CH_3$ | $CH_3$ | H | F | H | OH | H | H | $NH_2$ |
| VII-10-3 | p-I—Ph | H | H | $CH(CH_3)_2$ | $CH_3$ | H | F | H | OH | H | H | $NH_2$ |
| VII-10-4 | p-I—Ph | H | H | $CH_2CH(CH_3)_2$ | $CH_3$ | H | F | H | OH | H | H | $NH_2$ |
| VII-10-5 | p-I—Ph | H | H | $CH_2Ph$ | $CH_3$ | H | F | H | OH | H | H | $NH_2$ |
| VII-10-6 | p-I—Ph | H | H | $CH_2$-indol-3-yl | $CH_3$ | H | F | H | OH | H | H | $NH_2$ |
| VII-10-7 | p-I—Ph | H | H | $CH_2CH_2SCH_3$ | $CH_3$ | H | F | H | OH | H | H | $NH_2$ |
| VII-10-8 | p-I—Ph | * | H | * | $CH_3$ | H | F | H | OH | H | H | $NH_2$ |

*$R^2$ and $R^{3b}$ joined together by $(CH_2)_3$ to form five-membered ring.

TABLE VII-11

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-11-1 | $CH_3$ | H | H | H | Et | H | F | H | OH | H | H | $NH_2$ |
| VII-11-2 | $CH_3$ | H | H | $CH_3$ | Et | H | F | H | OH | H | H | $NH_2$ |
| VII-11-3 | $CH_3$ | H | H | $CH(CH_3)_2$ | Et | H | F | H | OH | H | H | $NH_2$ |
| VII-11-4 | $CH_3$ | H | H | $CH_2CH(CH_3)_2$ | Et | H | F | H | OH | H | H | $NH_2$ |
| VII-11-5 | $CH_3$ | H | H | $CH_2Ph$ | Et | H | F | H | OH | H | H | $NH_2$ |
| VII-11-6 | $CH_3$ | H | H | $CH_2$-indol-3-yl | Et | H | F | H | OH | H | H | $NH_2$ |
| VII-11-7 | $CH_3$ | H | H | $CH_2CH_2SCH_3$ | Et | H | F | H | OH | H | H | $NH_2$ |
| VII-11-8 | $CH_3$ | * | H | * | Et | H | F | H | OH | H | H | $NH_2$ |

*$R^2$ and $R^{3b}$ joined together by $(CH_2)_3$ to form five-membered ring.

TABLE VII-12

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-12-1 | Et | H | H | H | Et | H | F | H | OH | H | H | $NH_2$ |
| VII-12-2 | Et | H | H | $CH_3$ | Et | H | F | H | OH | H | H | $NH_2$ |
| VII-12-3 | Et | H | H | $CH(CH_3)_2$ | Et | H | F | H | OH | H | H | $NH_2$ |
| VII-12-4 | Et | H | H | $CH_2CH(CH_3)_2$ | Et | H | F | H | OH | H | H | $NH_2$ |
| VII-12-5 | Et | H | H | $CH_2Ph$ | Et | H | F | H | OH | H | H | $NH_2$ |
| VII-12-6 | Et | H | H | $CH_2$-indol-3-yl | Et | H | F | H | OH | H | H | $NH_2$ |
| VII-12-7 | Et | H | H | $CH_2CH_2SCH_3$ | Et | H | F | H | OH | H | H | $NH_2$ |
| VII-12-8 | Et | * | H | * | Et | H | F | H | OH | H | H | $NH_2$ |

*$R^2$ and $R^{3b}$ joined together by $(CH_2)_3$ to form five-membered ring.

TABLE VII-13

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-13-1 | $^iPr$ | H | H | H | Et | H | F | H | OH | H | H | $NH_2$ |
| VII-13-2 | $^iPr$ | H | H | $CH_3$ | Et | H | F | H | OH | H | H | $NH_2$ |
| VII-13-3 | $^iPr$ | H | H | $CH(CH_3)_2$ | Et | H | F | H | OH | H | H | $NH_2$ |
| VII-13-4 | $^iPr$ | H | H | $CH_2CH(CH_3)_2$ | Et | H | F | H | OH | H | H | $NH_2$ |
| VII-13-5 | $^iPr$ | H | H | $CH_2Ph$ | Et | H | F | H | OH | H | H | $NH_2$ |
| VII-13-6 | $^iPr$ | H | H | $CH_2$-indol-3-yl | Et | H | F | H | OH | H | H | $NH_2$ |
| VII-13-7 | $^iPr$ | H | H | $CH_2CH_2SCH_3$ | Et | H | F | H | OH | H | H | $NH_2$ |
| VII-13-8 | $^iPr$ | * | H | * | Et | H | F | H | OH | H | H | $NH_2$ |

*$R^2$ and $R^{3b}$ joined together by $(CH_2)_3$ to form five-membered ring.

TABLE VII-14

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-14-1 | $^tBu$ | H | H | H | Et | H | F | H | OH | H | H | $NH_2$ |
| VII-14-2 | $^tBu$ | H | H | $CH_3$ | Et | H | F | H | OH | H | H | $NH_2$ |
| VII-14-3 | $^tBu$ | H | H | $CH(CH_3)_2$ | Et | H | F | H | OH | H | H | $NH_2$ |
| VII-14-4 | $^tBu$ | H | H | $CH_2CH(CH_3)_2$ | Et | H | F | H | OH | H | H | $NH_2$ |
| VII-14-5 | $^tBu$ | H | H | $CH_2Ph$ | Et | H | F | H | OH | H | H | $NH_2$ |

TABLE VII-14-continued

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-14-6 | $^t$Bu | H | H | CH$_2$-indol-3-yl | Et | H | F | H | OH | H | H | NH$_2$ |
| VII-14-7 | $^t$Bu | H | H | CH$_2$CH$_2$SCH$_3$ | Et | H | F | H | OH | H | H | NH$_2$ |
| VII-14-8 | $^t$Bu | * | H | * | Et | H | F | H | OH | H | H | NH$_2$ |

*R$^2$ and R$^{3b}$ joined together by (CH$_2$)$_3$ to form five-membered ring.

TABLE VII-15

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-15-1 | Ph | H | H | H | Et | H | F | H | OH | H | H | NH$_2$ |
| VII-15-2 | Ph | H | H | CH$_3$ | Et | H | F | H | OH | H | H | NH$_2$ |
| VII-15-3 | Ph | H | H | CH(CH$_3$)$_2$ | Et | H | F | H | OH | H | H | NH$_2$ |
| VII-15-4 | Ph | H | H | CH$_2$CH(CH$_3$)$_2$ | Et | H | F | H | OH | H | H | NH$_2$ |
| VII-15-5 | Ph | H | 11 | CH$_2$Ph | Et | H | F | H | OH | H | H | NH$_2$ |
| VII-15-6 | Ph | H | H | CH$_2$-indol-3-yl | Et | H | F | H | OH | H | H | NH$_2$ |
| VII-15-7 | Ph | H | H | CH$_2$CH$_2$SCH$_3$ | Et | H | F | H | OH | H | H | NH$_2$ |
| VII-15-8 | Ph | * | H | * | Et | H | F | H | OH | H | H | NH$_2$ |

*R$^2$ and R$^{3b}$ joined together by (CH$_2$)$_3$ to form five-membered ring.

TABLE VII-16

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-16-1 | p-Me—Ph | H | H | H | Et | H | F | H | OH | H | H | NH$_2$ |
| VII-16-2 | p-Me—Ph | H | H | CH$_3$ | Et | H | F | H | OH | H | H | NH$_2$ |
| VII-16-3 | p-Me—Ph | H | H | CH(CH$_3$)$_2$ | Et | H | F | H | OH | H | H | NH$_2$ |
| VII-16-4 | p-Me—Ph | H | H | CH$_1$CH(CH$_3$)$_2$ | Et | H | F | H | OH | H | H | NH$_2$ |
| VII-16-5 | p-Me—Ph | H | H | CH$_2$Ph | Et | H | F | H | OH | H | H | NH$_2$ |
| VII-16-6 | p-Me—Ph | H | H | CH$_2$-indol-3-yl | Et | H | F | H | OH | H | H | NH$_2$ |
| VII-16-7 | p-Me—Ph | H | H | CH$_2$CH$_2$SCH$_3$ | Et | H | F | H | OH | H | H | NH$_2$ |
| VII-16-8 | p-Me—Ph | * | H | * | Et | H | F | H | OH | H | H | NH$_2$ |

*R$^2$ and R$^{3b}$ joined together by (CH$_2$)$_3$ to form five-membered ring.

TABLE VII-17

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-17-1 | p-F—Ph | H | H | H | Et | H | F | H | OH | H | H | NH$_2$ |
| VII-17-2 | p-F—Ph | H | H | CH$_3$ | Et | H | F | H | OH | H | H | NH$_2$ |
| VII-17-3 | p-F—Ph | H | H | CH(CH$_3$)$_2$ | Et | H | F | H | OH | H | H | NH$_2$ |
| VII-17-4 | p-F—Ph | H | H | CH$_2$CH(CH$_3$)$_2$ | Et | H | F | H | OH | H | H | NH$_2$ |
| VII-17-5 | p-F—Ph | H | H | CH$_2$Ph | Et | H | F | H | OH | H | H | NH$_2$ |
| VII-17-6 | p-F—Ph | H | H | CH$_2$-indol-3-yl | Et | H | F | H | OH | H | H | NH$_2$ |
| VII-17-7 | p-F—Ph | H | H | CH$_2$CH$_2$SCH$_3$ | Et | H | F | H | OH | H | H | NH$_2$ |
| VII-17-8 | p-F—Ph | * | H | * | Et | H | F | H | OH | H | H | NH$_2$ |

*R$^2$ and R$^{3b}$ joined together by (CH$_2$)$_3$ to form five-membered ring.

TABLE VII-18

| No | R$^1$ | R$^2$ | R$^{3a}$ | R$^{3b}$ | R$^4$ | R$^5$ | R$^6$ | X | Y | R$^7$ | R$^8$ | R$^9$ |
|---|---|---|---|---|---|---|---|---|---|---|---|---|
| VII-18-1 | p-Cl—Ph | H | H | H | Et | H | F | H | OH | H | H | NH$_2$ |
| VII-18-2 | p-Cl—Ph | H | H | CH$_3$ | Et | H | F | H | OH | H | H | NH$_2$ |
| VII-18-3 | p-Cl—Ph | H | H | CH(CH$_3$)$_2$ | Et | H | F | H | OH | H | H | NH$_2$ |
| VII-18-4 | p-Cl—Ph | H | H | CH$_2$CH(CH$_3$)$_2$ | Et | H | F | H | OH | H | H | NH$_2$ |
| VII-18-5 | p-Cl—Ph | H | H | CH$_2$Ph | Et | H | F | H | OH | H | H | NH$_2$ |
| VII-18-6 | p-Cl—Ph | H | H | CH$_2$-indol-3-yl | Et | H | F | H | OH | H | H | NH$_2$ |
| VII-18-7 | p-Cl—Ph | H | H | CH$_2$CH$_2$SCH$_3$ | Et | H | F | H | OH | H | H | NH$_2$ |
| VII-18-8 | p-Cl—Ph | * | H | * | Et | H | F | H | OH | H | H | NH$_2$ |

*R$^2$ and R$^{3b}$ joined together by (CH$_2$)$_3$ to form five-membered ring.

TABLE VII-19

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-19-1 | p-Br—Ph | H | H | H | Et | H | F | H | OH | H | H | $NH_2$ |
| VII-19-2 | p-Br—Ph | H | H | $CH_3$ | Et | H | F | H | OH | H | H | $NH_2$ |
| VII-19-3 | p-Br—Ph | H | H | $CH(CH_3)_2$ | Et | H | F | H | OH | H | H | $NH_2$ |
| VII-19-4 | p-Br—Ph | H | H | $CH_2CH(CH_3)_2$ | Et | H | F | H | OH | H | H | $NH_2$ |
| VII-19-5 | p-Br—Ph | H | H | $CH_2Ph$ | Et | H | F | H | OH | H | H | $NH_2$ |
| VII-19-6 | p-Br—Ph | H | H | $CH_2$-indol-3-yl | Et | H | F | H | OH | H | H | $NH_2$ |
| VII-19-7 | p-Br—Ph | H | H | $CH_2CH_2SCH_3$ | Et | H | F | H | OH | H | H | $NH_2$ |
| VII-19-8 | p-Br—Ph | * | H | * | Et | H | F | H | OH | H | H | $NH_2$ |

*$R^2$ and $R^{3b}$ joined together by $(CH_2)_3$ to form five-membered ring.

TABLE VII-20

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-20-1 | p-I—Ph | H | H | H | Et | H | F | H | OH | H | H | $NH_2$ |
| VII-20-2 | p-I—Ph | H | H | $CH_3$ | Et | H | F | H | OH | H | H | $NH_2$ |
| VII-20-3 | p-I—Ph | H | H | $CH(CH_3)_2$ | Et | H | F | H | OH | H | H | $NH_2$ |
| VII-20-4 | p-I—Ph | H | H | $CH_2CH(CH_3)_2$ | Et | H | F | H | OH | H | H | $NH_2$ |
| VII-20-5 | p-I—Ph | H | H | $CH_2Ph$ | Et | H | F | H | OH | H | H | $NH_2$ |
| VII-20-6 | p-I—Ph | H | H | $CH_2$-indol-3-yl | Et | H | F | H | OH | H | H | $NH_2$ |
| VII-20-7 | p-I—Ph | H | H | $CH_2CH_2SCH_3$ | Et | H | F | H | OH | H | H | $NH_2$ |
| VII-20-8 | p-I—Ph | * | H | * | Et | H | F | H | OH | H | H | $NH_2$ |

*$R^2$ and $R^{3b}$ joined together by $(CH_2)_3$ to form five-membered ring.

TABLE VII-21

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-21-1 | $CH_3$ | H | H | H | $^iPr$ | H | F | H | OH | H | H | $NH_2$ |
| VII-21-2 | $CH_3$ | H | H | $CH_3$ | $^iPr$ | H | F | H | OH | H | H | $NH_2$ |
| VII-21-3 | $CH_3$ | H | H | $CH(CH_3)_2$ | $^iPr$ | H | F | H | OH | H | H | $NH_2$ |
| VII-21-4 | $CH_3$ | H | H | $CH_2CH(CH_3)_2$ | $^iPr$ | H | F | H | OH | H | H | $NH_2$ |
| VII-21-5 | $CH_3$ | H | H | $CH_2Ph$ | $^iPr$ | H | F | H | OH | H | H | $NH_2$ |
| VII-21-6 | $CH_3$ | H | H | $CH_2$-indol-3-yl | $^iPr$ | H | F | H | OH | H | H | $NH_2$ |
| VII-21-7 | $CH_3$ | H | H | $CH_2CH_2SCH_3$ | $^iPr$ | H | F | H | OH | H | H | $NH_2$ |
| VII-21-8 | $CH_3$ | * | H | * | $^iPr$ | H | F | H | OH | H | H | $NH_2$ |

*$R^2$ and $R^{3b}$ joined together by $(CH_2)_3$ to form five-membered ring.

TABLE VII-22

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-22-1 | Et | H | H | H | $^iPr$ | H | F | H | OH | H | H | $NH_2$ |
| VII-22-2 | Et | H | H | $CH_3$ | $^iPr$ | H | F | H | OH | H | H | $NH_2$ |
| VII-22-3 | Et | H | H | $CH(CH_3)_2$ | $^iPr$ | H | F | H | OH | H | H | $NH_2$ |
| VII-22-4 | Et | H | H | $CH_2CH(CH_3)_2$ | $^iPr$ | H | F | H | OH | H | H | $NH_2$ |
| VII-22-5 | Et | H | H | $CH_2Ph$ | $^iPr$ | H | F | H | OH | H | H | $NH_2$ |
| VII-22-6 | Et | H | H | $CH_2$-indol-3-yl | $^iPr$ | H | F | H | OH | H | H | $NH_2$ |
| VII-22-7 | Et | H | H | $CH_2CH_2SCH_3$ | $^iPr$ | H | F | H | OH | H | H | $NH_2$ |
| VII-22-8 | Et | * | H | * | $^iPr$ | H | F | H | OH | H | H | $NH_2$ |

*$R^2$ and $R^{3b}$ joined together by $(CH_2)_3$ to form five-membered ring.

TABLE VII-23

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-23-1 | $^iPr$ | H | H | H | $^iPr$ | H | F | H | OH | H | H | $NH_2$ |
| VII-23-2 | $^iPr$ | H | H | $CH_3$ | $^iPr$ | H | F | H | OH | H | H | $NH_2$ |
| VII-23-3 | $^iPr$ | H | H | $CH(CH_3)_2$ | $^iPr$ | H | F | H | OH | H | H | $NH_2$ |
| VII-23-4 | $^iPr$ | H | H | $CH_2CH(CH_3)_2$ | $^iPr$ | H | F | H | OH | H | H | $NH_2$ |
| VII-23-5 | $^iPr$ | H | H | $CH_2Ph$ | $^iPr$ | H | F | H | OH | H | H | $NH_2$ |

TABLE VII-23-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-23-6 | ⁱPr | H | H | CH₂-indol-3-yl | ⁱPr | H | F | H | OH | H | H | NH₂ |
| VII-23-7 | ⁱPr | H | H | CH₂CH₂SCH₃ | ⁱPr | H | F | H | OH | H | H | NH₂ |
| VII-23-8 | ⁱPr | * | H | * | ⁱPr | H | F | H | OH | H | H | NH₂ |

*R² and R³ᵇ joined together by (CH₂)₃ to form five-membered ring.

TABLE VII-24

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-24-1 | ᵗBu | H | H | H | ⁱPr | H | F | H | OH | H | H | NH₂ |
| VII-24-2 | ᵗBu | H | H | CH₃ | ⁱPr | H | F | H | OH | H | H | NH₂ |
| VII-24-3 | ᵗBu | H | H | CH(CH₃)₂ | ⁱPr | H | F | H | OH | H | H | NH₂ |
| VII-24-4 | ᵗBu | H | H | CH₂CH(CH₃)₂ | ⁱPr | H | F | H | OH | H | H | NH₂ |
| VII-24-5 | ᵗBu | H | H | CH₂Ph | ⁱPr | H | F | H | OH | H | H | NH₂ |
| VII-24-6 | ᵗBu | H | H | CH₂-indol-3-yl | ⁱPr | H | F | H | OH | H | H | NH₂ |
| VII-24-7 | ᵗBu | H | H | CH₂CH₂SCH₃ | ⁱPr | H | F | H | OH | H | H | NH₂ |
| VII-24-8 | ᵗBu | * | H | * | ⁱPr | H | F | H | OH | H | H | NH₂ |

*R² and R³ᵇ joined together by (CH₂)₃ to form five-membered ring.

TABLE VII-25

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-25-1 | Ph | H | H | H | ⁱPr | H | F | H | OH | H | H | NH₂ |
| VII-25-2 | Ph | H | H | CH₃ | ⁱPr | H | F | H | OH | H | H | NH₂ |
| VII-25-3 | Ph | H | H | CH(CH₃)₂ | ⁱPr | H | F | H | OH | H | H | NH₂ |
| VII-25-4 | Ph | H | H | CH₂CH(CH₃)₂ | ⁱPr | H | F | H | OH | H | H | NH₂ |
| VII-25-5 | Ph | H | H | CH₂Ph | ⁱPr | H | F | H | OH | H | H | NH₂ |
| VII-25-6 | Ph | H | H | CH₂-indol-3-yl | ⁱPr | H | F | H | OH | H | H | NH₂ |
| VII-25-7 | Ph | H | H | CH₂CH₂SCH₃ | ⁱPr | H | F | H | OH | H | H | NH₂ |
| VII-25-8 | Ph | * | H | * | ⁱPr | H | F | H | OH | H | H | NH₂ |

*R² and R³ᵇ joined together by (CH₂)₃ to form five-membered ring.

TABLE VII-26

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-26-1 | p-Me—Ph | H | H | H | ⁱPr | H | F | H | OH | H | H | NH₂ |
| VII-26-2 | p-Me—Ph | H | H | CH₃ | ⁱPr | H | F | H | OH | H | H | NH₂ |
| VII-26-3 | p-Me—Ph | H | H | CH(CH₃)₂ | ⁱPr | H | F | H | OH | H | H | NH₂ |
| VII-26-4 | p-Me—Ph | H | H | CH₂CH(CH₃)₂ | ⁱPr | H | F | H | OH | H | H | NH₂ |
| VII-26-5 | p-Me—Ph | H | H | CH₂Ph | ⁱPr | H | F | H | OH | H | H | NH₂ |
| VII-26-6 | p-Me—Ph | H | H | CH₂-indol-3-yl | ⁱPr | H | F | H | OH | H | H | NH₂ |
| VII-26-7 | p-Me—Ph | H | H | CH₂CH₂SCH₃ | ⁱPr | H | F | H | OH | H | H | NH₂ |
| VII-26-8 | p-Me—Ph | * | H | * | ⁱPr | H | F | H | OH | H | H | NH₂ |

*R² and R³ᵇ joined together by (CH₂)₃ to form five-membered ring.

TABLE VII-27

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-27-1 | p-F—Ph | H | H | H | ⁱPr | H | F | H | OH | H | H | NH₂ |
| VII-27-2 | p-F—Ph | H | H | CH₃ | ⁱPr | H | F | H | OH | H | H | NH₂ |
| VII-27-3 | p-F—Ph | H | H | CH(CH₃)₂ | ⁱPr | H | F | H | OH | H | H | NH₂ |
| VII-27-4 | p-F—Ph | H | H | CH₂CH(CH₃)₂ | ⁱPr | H | F | H | OH | H | H | NH₂ |
| VII-27-5 | p-F—Ph | H | H | CH₂Ph | ⁱPr | H | F | H | OH | H | H | NH₂ |
| VII-27-6 | p-F—Ph | H | H | CH₂-indol-3-yl | ⁱPr | H | F | H | OH | H | H | NH₂ |
| VII-27-7 | p-F—Ph | H | H | CH₂CH₂SCH₃ | ⁱPr | H | F | H | OH | H | H | NH₂ |
| VII-27-8 | p-F—Ph | * | H | * | ⁱPr | H | F | H | OH | H | H | NH₂ |

*R² and R³ᵇ joined together by (CH₂)₃ to form five-membered ring.

TABLE VII-28

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-28-1 | p-Cl—Ph | H | H | H | $^i$Pr | H | F | H | OH | H | H | NH$_2$ |
| VII-28-2 | p-Cl—Ph | H | H | CH$_3$ | $^i$Pr | H | F | H | OH | H | H | NH$_2$ |
| VII-28-3 | p-Cl—Ph | H | H | CH(CH$_3$)$_2$ | $^i$Pr | H | F | H | OH | H | H | NH$_2$ |
| VII-28-4 | p-Cl—Ph | H | H | CH$_2$CH(CH$_3$)$_2$ | $^i$Pr | H | F | H | OH | H | H | NH$_2$ |
| VII-28-5 | p-Cl—Ph | H | H | CH$_2$Ph | $^i$Pr | H | F | H | OH | H | H | NH$_2$ |
| VII-28-6 | p-Cl—Ph | H | H | CH$_2$-indol-3-yl | $^i$Pr | H | F | H | OH | H | H | NH$_2$ |
| VII-28-7 | p-Cl—Ph | H | H | CH$_2$CH$_2$SCH$_3$ | $^i$Pr | H | F | H | OH | H | H | NH$_2$ |
| VII-28-8 | p-Cl—Ph | * | H | * | $^i$Pr | H | F | H | OH | H | H | NH$_2$ |

*R² and R³ᵇ joined together by (CH$_2$)$_3$ to form five-membered ring.

TABLE VII-29

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-29-1 | p-Br—Ph | H | H | H | $^i$Pr | H | F | H | OH | H | H | NH$_2$ |
| VII-29-2 | p-Br—Ph | H | H | CH$_3$ | $^i$Pr | H | F | H | OH | H | H | NH$_2$ |
| VII-29-3 | p-Br—Ph | H | H | CH(CH$_3$)$_2$ | $^i$Pr | H | F | H | OH | H | H | NH$_2$ |
| VII-29-4 | p-Br—Ph | H | H | CH$_2$CH(CH$_3$)$_2$ | $^i$Pr | H | F | H | OH | H | H | NH$_2$ |
| VII-29-5 | p-Br—Ph | H | H | CH$_2$Ph | $^i$Pr | H | F | H | OH | H | H | NH$_2$ |
| VII-29-6 | p-Br—Ph | H | H | CH$_2$-indol-3-yl | $^i$Pr | H | F | H | OH | H | H | NH$_2$ |
| VII-29-7 | p-Br—Ph | H | H | CH$_2$CH$_2$SCH$_3$ | $^i$Pr | H | F | H | OH | H | H | NH$_2$ |
| VII-29-8 | p-Br—Ph | * | H | * | $^i$Pr | H | F | H | OH | H | H | NH$_2$ |

*R² and R³ᵇ joined together by (CH$_2$)$_3$ to form five-membered ring.

TABLE VII-30

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-30-1 | p-I—Ph | H | H | H | $^i$Pr | H | F | H | OH | H | H | NH$_2$ |
| VII-30-2 | p-I—Ph | H | H | CH$_3$ | $^i$Pr | H | F | H | OH | H | H | NH$_2$ |
| VII-30-3 | p-I—Ph | H | H | CH(CH$_3$)$_2$ | $^i$Pr | H | F | H | OH | H | H | NH$_2$ |
| VII-30-4 | p-I—Ph | H | H | CH$_2$CH(CH$_3$)$_2$ | $^i$Pr | H | F | H | OH | H | H | NH$_2$ |
| VII-30-5 | p-I—Ph | H | H | CH$_2$Ph | $^i$Pr | H | F | H | OH | H | H | NH$_2$ |
| VII-30-6 | p-I—Ph | H | H | CH$_2$-indol-3-yl | $^i$Pr | H | F | H | OH | H | H | NH$_2$ |
| VII-30-7 | p-I—Ph | H | H | CH$_2$CH$_2$SCH$_3$ | $^i$Pr | H | F | H | OH | H | H | NH$_2$ |
| VII-30-8 | p-I—Ph | * | H | * | $^i$Pr | H | F | H | OH | H | H | NH$_2$ |

*R² and R³ᵇ joined together by (CH$_2$)$_3$ to form five-membered ring.

TABLE VII-31

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-31-1 | CH$_3$ | H | H | H | $^n$Bu | H | F | H | OH | H | H | NH$_2$ |
| VII-31-2 | CH$_3$ | H | H | CH$_3$ | $^n$Bu | H | F | H | OH | H | H | NH$_2$ |
| VII-31-3 | CH$_3$ | H | H | CH(CH$_3$)$_2$ | $^n$Bu | H | F | H | OH | H | H | NH$_2$ |
| VII-31-4 | CH$_3$ | H | H | CH$_2$CH(CH$_3$)$_2$ | $^n$Bu | H | F | H | OH | H | H | NH$_2$ |
| VII-31-5 | CH$_3$ | H | H | CH$_2$Ph | $^n$Bu | H | F | H | OH | H | H | NH$_2$ |
| VII-31-6 | CH$_3$ | H | H | CH$_2$-indol-3-yl | $^n$Bu | H | F | H | OH | H | H | NH$_2$ |
| VII-31-7 | CH$_3$ | H | H | CH$_2$CH$_2$SCH$_3$ | $^n$Bu | H | F | H | OH | H | H | NH$_2$ |
| VII-31-8 | CH$_3$ | * | H | * | $^n$Bu | H | F | H | OH | H | H | NH$_2$ |

*R² and R³ᵇ joined together by (CH$_2$)$_3$ to form five-membered ring.

TABLE VII-32

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-32-1 | Et | H | H | H | $^n$Bu | H | F | H | OH | H | H | NH$_2$ |
| VII-32-2 | Et | H | H | CH$_3$ | $^n$Bu | H | F | H | OH | H | H | NH$_2$ |
| VII-32-3 | Et | H | H | CH(CH$_3$)$_2$ | $^n$Bu | H | F | H | OH | H | H | NH$_2$ |
| VII-32-4 | Et | H | H | CH$_2$CH(CH$_3$)$_2$ | $^n$Bu | H | F | H | OH | H | H | NH$_2$ |
| VII-32-5 | Et | H | H | CH$_2$Ph | $^n$Bu | H | F | H | OH | H | H | NH$_2$ |

TABLE VII-32-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-32-6 | Et | H | H | CH₂-indol-3-yl | ⁿBu | H | F | H | OH | H | H | NH₂ |
| VII-32-7 | Et | H | H | CH₂CH₂SCH₃ | ⁿBu | H | F | H | OH | H | H | NH₂ |
| VII-32-8 | Et | * | H | * | ⁿBu | H | F | H | OH | H | H | NH₂ |

*R² and R³ᵇ joined together by (CH₂)₃ to form five-membered ring.

TABLE VII-33

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-33-1 | ⁱPr | H | H | H | ⁿBu | H | F | H | OH | H | H | NH₂ |
| VII-33-2 | ⁱPr | H | H | CH₃ | ⁿBu | H | F | H | OH | H | H | NH₂ |
| VII-33-3 | ⁱPr | H | H | CH(CH₃)₂ | ⁿBu | H | F | H | OH | H | H | NH₂ |
| VII-33-4 | ⁱPr | H | H | CH₂CH(CH₃)₂ | ⁿBu | H | F | H | OH | H | H | NH₂ |
| VII-33-5 | ⁱPr | H | H | CH₂Ph | ⁿBu | H | F | H | OH | H | H | NH₂ |
| VII-33-6 | ⁱPr | H | H | CH₂-indol-3-yl | ⁿBu | H | F | H | OH | H | H | NH₂ |
| VII-33-7 | ⁱPr | H | H | CH₂CH₂SCH₃ | ⁿBu | H | F | H | OH | H | H | NH₂ |
| VII-33-8 | ⁱPr | * | H | * | ⁿBu | H | F | H | OH | H | H | NH₂ |

*R² and R³ᵇ joined together by (CH₂)₃ to form five-membered ring.

TABLE VII-34

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-34-1 | ᵗBu | H | H | H | ⁿBu | H | F | H | OH | H | H | NH₂ |
| VII-34-2 | ᵗBu | H | H | CH₃ | ⁿBu | H | F | H | OH | H | H | NH₂ |
| VII-34-3 | ᵗBu | H | H | CH(CH₃)₂ | ⁿBu | H | F | H | OH | H | H | NH₂ |
| VII-34-4 | ᵗBu | H | H | CH₂CH(CH₃)₂ | ⁿBu | H | F | H | OH | H | H | NH₂ |
| VII-34-5 | ᵗBu | H | H | CH₂Ph | ⁿBu | H | F | H | OH | H | H | NH₂ |
| VII-34-6 | ᵗBu | H | H | CH₂-indol-3-yl | ⁿBu | H | F | H | OH | H | H | NH₂ |
| VII-34-7 | ᵗBu | H | H | CH₂CH₂SCH₃ | ⁿBu | H | F | H | OH | H | H | NH₂ |
| VII-34-8 | ᵗBu | * | H | * | ⁿBu | H | F | H | OH | H | H | NH₂ |

*R² and R³ᵇ joined together by (CH₂)₃ to form five-membered ring.

TABLE VII-35

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-35-1 | Ph | H | H | H | ⁿBu | H | F | H | OH | H | H | NH₂ |
| VII-35-2 | Ph | H | H | CH₃ | ⁿBu | H | F | H | OH | H | H | NH₂ |
| VII-35-3 | Ph | H | H | CH(CH₃)₂ | ⁿBu | H | F | H | OH | H | H | NH₂ |
| VII-35-4 | Ph | H | H | CH₂CH(CH₃)₂ | ⁿBu | H | F | H | OH | H | H | NH₂ |
| VII-35-5 | Ph | H | H | CH₂Ph | ⁿBu | H | F | H | OH | H | H | NH₂ |
| VII-35-6 | Ph | H | H | CH₂-indol-3-yl | ⁿBu | H | F | H | OH | H | H | NH₂ |
| VII-35-7 | Ph | H | H | CH₂CH₂SCH₃ | ⁿBu | H | F | H | OH | H | H | NH₂ |
| VII-35-8 | Ph | * | H | * | ⁿBu | H | F | H | OH | H | H | NH₂ |

*R² and R³ᵇ joined together by (CH₂)₃ to form five-membered ring.

TABLE VII-36

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-36-1 | p-Me—Ph | H | H | H | ⁿBu | H | F | H | OH | H | H | NH₂ |
| VII-36-2 | p-Me—Ph | H | H | CH₃ | ⁿBu | H | F | H | OH | H | H | NH₂ |
| VII-36-3 | p-Me—Ph | H | H | CH(CH₃)₂ | ⁿBu | H | F | H | OH | H | H | NH₂ |
| VII-36-4 | p-Me—Ph | H | H | CH₂CH(CH₃)₂ | ⁿBu | H | F | H | OH | H | H | NH₂ |
| VII-36-5 | p-Me—Ph | H | H | CH₂Ph | ⁿBu | H | F | H | OH | H | H | NH₂ |
| VII-36-6 | p-Me—Ph | H | H | CH₂-indol-3-yl | ⁿBu | H | F | H | OH | H | H | NH₂ |
| VII-36-7 | p-Me—Ph | H | H | CH₂CH₂SCH₃ | ⁿBu | H | F | H | OH | H | H | NH₂ |
| VII-36-8 | p-Me—Ph | * | H | * | ⁿBu | H | F | H | OH | H | H | NH₂ |

*R² and R³ᵇ joined together by (CH₂)₃ to form five-membered ring.

TABLE VII-37

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-37-1 | p-F—Ph | H | H | H | ⁿBu | H | F | H | OH | H | H | NH₂ |
| VII-37-2 | p-F—Ph | H | H | CH₃ | ⁿBu | H | F | H | OH | H | H | NH₂ |
| VII-37-3 | p-F—Ph | H | H | CH(CH₃)₂ | ⁿBu | H | F | H | OH | H | H | NH₂ |
| VII-37-4 | p-F—Ph | H | H | CH₂CH(CH₃)₂ | ⁿBu | H | F | H | OH | H | H | NH₂ |
| VII-37-5 | p-F—Ph | H | H | CH₂Ph | ⁿBu | H | F | H | OH | H | H | NH₂ |
| VII-37-6 | p-F—Ph | H | H | CH₂-indol-3-yl | ⁿBu | H | F | H | OH | H | H | NH₂ |
| VII-37-7 | p-F—Ph | H | H | CH₂CH₂SCH₃ | ⁿBu | H | F | H | OH | H | H | NH₂ |
| VII-37-8 | p-F—Ph | * | H | * | ⁿBu | H | F | H | OH | H | H | NH₂ |

*R² and R³ᵇ joined together by (CH₂)₃ to form five-membered ring.

TABLE VII-38

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-38-1 | p-Cl—Ph | H | H | H | ⁿBu | H | F | H | OH | H | H | NH₂ |
| VII-38-2 | p-Cl—Ph | H | H | CH₃ | ⁿBu | H | F | H | OH | H | H | NH₂ |
| VII-38-3 | p-Cl—Ph | H | H | CH(CH₃)₂ | ⁿBu | H | F | H | OH | H | H | NH₂ |
| VII-38-4 | p-Cl—Ph | H | H | CH₂CH(CH₃)₂ | ⁿBu | H | F | H | OH | H | H | NH₂ |
| VII-38-5 | p-Cl—Ph | H | H | CH₂Ph | ⁿBu | H | F | H | OH | H | H | NH₂ |
| VII-38-6 | p-Cl—Ph | H | H | CH₂-indol-3-yl | ⁿBu | H | F | H | OH | H | H | NH₂ |
| VII-38-7 | p-Cl—Ph | H | H | CH₂CH₂SCH₃ | ⁿBu | H | F | H | OH | H | H | NH₂ |
| VII-38-8 | p-Cl—Ph | * | H | * | ⁿBu | H | F | H | OH | H | H | NH₂ |

*R² and R³ᵇ joined together by (CH₂)₃ to form five-membered ring.

TABLE VII-39

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-39-1 | p-Br—Ph | H | H | H | ⁿBu | H | F | H | OH | H | H | NH₂ |
| VII-39-2 | p-Br—Ph | H | H | CH₃ | ⁿBu | H | F | H | OH | H | H | NH₂ |
| VII-39-3 | p-Br—Ph | H | H | CH(CH₃)₂ | ⁿBu | H | F | H | OH | H | H | NH₂ |
| VII-39-4 | p-Br—Ph | H | H | CH₂CH(CH₃)₂ | ⁿBu | H | F | H | OH | H | H | NH₂ |
| VII-39-5 | p-Br—Ph | H | H | CH₂Ph | ⁿBu | H | F | H | OH | H | H | NH₂ |
| VII-39-6 | p-Br—Ph | H | H | CH₂-indol-3-yl | ⁿBu | H | F | H | OH | H | H | NH₂ |
| VII-39-7 | p-Br—Ph | H | H | CH₂CH₂SCH₃ | ⁿBu | H | F | H | OH | H | H | NH₂ |
| VII-39-8 | p-Br—Ph | * | H | * | ⁿBu | H | F | H | OH | H | H | NH₂ |

*R² and R³ᵇ joined together by (CH₂)₃ to form five-membered ring.

TABLE VII-40

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-40-1 | p-I—ph | H | H | H | ⁿBu | H | F | H | OH | H | H | NH₂ |
| VII-40-2 | p-I—Ph | H | H | CH₃ | ⁿBu | H | F | H | OH | H | H | NH₂ |
| VII-40-3 | p-I—Ph | H | H | CH(CH₃)₂ | ⁿBu | H | F | H | OH | H | H | NH₂ |
| VII-40-4 | p-I—Ph | H | H | CH₂CH(CH₃)₂ | ⁿBu | H | F | H | OH | H | H | NH₂ |
| VII-40-5 | p-I—Ph | H | H | CH₂Ph | ⁿBu | H | F | H | OH | H | H | NH₂ |
| VII-40-6 | p-I—Ph | H | H | CH₂-indol-3-yl | ⁿBu | H | F | H | OH | H | H | NH₂ |
| VII-40-7 | p-I—Ph | H | H | CH₂CH₂SCH₃ | ⁿBu | H | F | H | OH | H | H | NH₂ |
| VII-40-8 | p-I—Ph | * | H | * | ⁿBu | H | F | H | OH | H | H | NH₂ |

*R² and R³ᵇ joined together by (CH₂)₃ to form five-membered ring.

TABLE VII-41

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-41-1 | CH₃ | H | H | H | Bz | H | F | H | OH | H | H | NH₂ |
| VII-41-2 | CH₃ | H | H | CH₃ | Bz | H | F | H | OH | H | H | NH₂ |
| VII-41-3 | CH₃ | H | H | CH(CH₃)₂ | Bz | H | F | H | OH | H | H | NH₂ |
| VII-41-4 | CH₃ | H | H | CH₂CH(CH₃)₂ | Bz | H | F | H | OH | H | H | NH₂ |
| VII-41-5 | CH₃ | H | H | CH₂Ph | Bz | H | F | H | OH | H | H | NH₂ |

TABLE VII-41-continued

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-41-6 | $CH_3$ | H | H | $CH_2$-indol-3-yl | Bz | H | F | H | OH | H | H | $NH_2$ |
| VII-41-7 | $CH_3$ | H | H | $CH_2CH_2CH_3$ | Bz | H | F | H | OH | H | H | $NH_2$ |
| VII-41-8 | $CH_3$ | * | H | * | Bz | H | F | H | OH | H | H | $NH_2$ |

*$R^2$ and $R^{3b}$ joined together by $(CH_2)_3$ to form five-membered ring.

TABLE VII-42

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-42-1 | Et | H | H | H | Bz | H | F | H | OH | H | H | $NH_2$ |
| VII-42-2 | Et | H | H | $CH_3$ | Bz | H | F | H | OH | H | H | $NH_2$ |
| VII-42-3 | Et | H | H | $CH(CH_3)_2$ | Bz | H | F | H | OH | H | H | $NH_2$ |
| VII-42-4 | Et | H | H | $CH_2CH(CH_3)_2$ | Bz | H | F | H | OH | H | H | $NH_2$ |
| VII-42-5 | Et | H | H | $CH_2Ph$ | Bz | H | F | H | OH | H | H | $NH_2$ |
| VII-42-6 | Et | H | H | $CH_2$-indol-3-yl | Bz | H | F | H | OH | H | H | $NH_2$ |
| VII-42-7 | Et | H | H | $CH_2CH_2CH_3$ | Bz | H | F | H | OH | H | H | $NH_2$ |
| VII-42-8 | Et | * | H | * | Bz | H | F | H | OH | H | H | $NH_2$ |

*$R^2$ and $R^{3b}$ joined together by $(CH_2)_3$ to form five-membered ring.

TABLE VII-43

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-43-1 | $^i$Pr | H | H | H | Bz | H | F | H | OH | H | H | $NH_2$ |
| VII-43-2 | $^i$Pr | H | H | $CH_3$ | Bz | H | F | H | OH | H | H | $NH_2$ |
| VII-43-3 | $^i$Pr | H | H | $CH(CH_3)_2$ | Bz | H | F | H | OH | H | H | $NH_2$ |
| VII-43-4 | $^i$Pr | H | H | $CH_2CH(CH_3)_2$ | Bz | H | F | H | OH | H | H | $NH_2$ |
| VII-43-5 | $^i$Pr | H | H | $CH_2Ph$ | Bz | H | F | H | OH | H | H | $NH_2$ |
| VII-43-6 | $^i$Pr | H | H | $CH_2$-indol-3-yl | Bz | H | F | H | OH | H | H | $NH_2$ |
| VII-43-7 | $^i$Pr | H | H | $CH_2CH_2CH_3$ | Bz | H | F | H | OH | H | H | $NH_2$ |
| VII-43-8 | $^i$Pr | * | H | * | Bz | H | F | H | OH | H | H | $NH_2$ |

*$R^2$ and $R^{3b}$ joined together by $(CH_2)_3$ to form five-membered ring.

TABLE VII-44

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-44-1 | $^t$Bu | H | H | H | Bz | H | F | H | OH | H | H | $NH_2$ |
| VII-44-2 | $^t$Bu | H | H | $CH_3$ | Bz | H | F | H | OH | H | H | $NH_2$ |
| VII-44-3 | $^t$Bu | H | H | $CH(CH_3)_2$ | Bz | H | F | H | OH | H | H | $NH_2$ |
| VII-44-4 | $^t$Bu | H | H | $CH_2CH(CH_3)_2$ | Bz | H | F | H | OH | H | H | $NH_2$ |
| VII-44-5 | $^t$Bu | H | H | $CH_2Ph$ | Bz | H | F | H | OH | H | H | $NH_2$ |
| VII-44-6 | $^t$Bu | H | H | $CH_2$-indol-3-yl | Bz | H | F | H | OH | H | H | $NH_2$ |
| VII-44-7 | $^t$Bu | H | H | $CH_2CH_2CH_3$ | Bz | H | F | H | OH | H | H | $NH_2$ |
| VII-44-8 | $^t$Bu | * | H | * | Bz | H | F | H | OH | H | H | $NH_2$ |

*$R^2$ and $R^{3b}$ joined together by $(CH_2)_3$ to form five-membered ring.

TABLE VII-45

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-45-1 | Ph | H | H | H | Bz | H | F | H | OH | H | H | $NH_2$ |
| VII-45-2 | Ph | H | H | $CH_3$ | Bz | H | F | H | OH | H | H | $NH_2$ |
| VII-45-3 | Ph | H | H | $CH(CH_3)_2$ | Bz | H | F | H | OH | H | H | $NH_2$ |
| VII-45-4 | Ph | H | H | $CH_2CH(CH_3)_2$ | Bz | H | F | H | OH | H | H | $NH_2$ |
| VII-45-5 | Ph | H | H | $CH_2Ph$ | Bz | H | F | H | OH | H | H | $NH_2$ |
| VII-45-6 | Ph | H | H | $CH_2$-indol-3-yl | Bz | H | F | H | OH | H | H | $NH_2$ |
| VII-45-7 | Ph | H | H | $CH_2CH_2CH_3$ | Bz | H | F | H | OH | H | H | $NH_2$ |
| VII-45-8 | Ph | * | H | * | Bz | H | F | H | OH | H | H | $NH_2$ |

*$R^2$ and $R^{3b}$ joined together by $(CH_2)_3$ to form five-membered ring.

TABLE VII-46

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-46-1 | p-Me—Ph | H | H | H | Bz | H | F | H | OH | H | H | $NH_2$ |
| VII-46-2 | p-Me—Ph | H | H | $CH_3$ | Bz | H | F | H | OH | H | H | $NH_2$ |
| VII-46-3 | p-Me—Ph | H | H | $CH(CH_3)_2$ | Bz | H | F | H | OH | H | H | $NH_2$ |
| VII-46-4 | p-Me—Ph | H | H | $CH_2CH(CH_3)_2$ | Bz | H | F | H | OH | H | H | $NH_2$ |
| VII-46-5 | p-Me—Ph | H | H | $CH_2Ph$ | Bz | H | F | H | OH | H | H | $NH_2$ |
| VII-46-6 | p-Me—Ph | H | H | $CH_2$-indol-3-yl | Bz | H | F | H | OH | H | H | $NH_2$ |
| VII-46-7 | p-Me—Ph | H | H | $CH_2CH_2CH_3$ | Bz | H | F | H | OH | H | H | $NH_2$ |
| VII-46-8 | p-Me—Ph | * | H | * | Bz | H | F | H | OH | H | H | $NH_2$ |

*$R^2$ and $R^{3b}$ joined together by $(CH_2)_3$ to form five-membered ring.

TABLE VII-47

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-47-1 | p-F—Ph | H | H | H | Bz | H | F | H | OH | H | H | $NH_2$ |
| VII-47-2 | p-F—Ph | H | H | $CH_3$ | Bz | H | F | H | OH | H | H | $NH_2$ |
| VII-47-3 | p-F—Ph | H | H | $CH(CH_3)_2$ | Bz | H | F | H | OH | H | H | $NH_2$ |
| VII-47-4 | p-F—Ph | H | H | $CH_2CH(CH_3)_2$ | Bz | H | F | H | OH | H | H | $NH_2$ |
| VII-47-5 | p-F—Ph | H | H | $CH_2Ph$ | Bz | H | F | H | OH | H | H | $NH_2$ |
| VII-47-6 | p-F—Ph | H | H | $CH_2$-indol-3-yl | Bz | H | F | H | OH | H | H | $NH_2$ |
| VII-47-7 | p-F—Ph | H | H | $CH_2CH_2CH_3$ | Bz | H | F | H | OH | H | H | $NH_2$ |
| VII-47-8 | p-F—Ph | * | H | * | Bz | H | F | H | OH | H | H | $NH_2$ |

*$R^2$ and $R^{3b}$ joined together by $(CH_2)_3$ to form five-membered ring.

TABLE VII-48

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-48-1 | p-Cl—Ph | H | H | H | Bz | H | F | H | OH | H | H | $NH_2$ |
| VII-48-2 | p-Cl—Ph | H | H | $CH_3$ | Bz | H | F | H | OH | H | H | $NH_2$ |
| VII-48-3 | p-Cl—Ph | H | H | $CH(CH_3)_2$ | Bz | H | F | H | OH | H | H | $NH_2$ |
| VII-48-4 | p-Cl—Ph | H | H | $CH_2CH(CH_3)_2$ | Bz | H | F | H | OH | H | H | $NH_2$ |
| VII-48-5 | p-Cl—Ph | H | H | $CH_2Ph$ | Bz | H | F | H | OH | H | H | $NH_2$ |
| VII-48-6 | p-Cl—Ph | H | H | $CH_2$-indol-3-yl | Bz | H | F | H | OH | H | H | $NH_2$ |
| VII-48-7 | p-Cl—Ph | H | H | $CH_2CH_2CH_3$ | Bz | H | F | H | OH | H | H | $NH_2$ |
| VII-48-8 | p-Cl—Ph | * | H | * | Bz | H | F | H | OH | H | H | $NH_2$ |

*$R^2$ and $R^{3b}$ joined together by $(CH_2)_3$ to form five-membered ring.

TABLE VII-49

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-49-1 | p-Br—Ph | H | H | H | Bz | H | F | H | OH | H | H | $NH_2$ |
| VII-49-2 | p-Br—Ph | H | H | $CH_3$ | Bz | H | F | H | OH | H | H | $NH_2$ |
| VII-49-3 | p-Br—Ph | H | H | $CH(CH_3)_2$ | Bz | H | F | H | OH | H | H | $NH_2$ |
| VII-49-4 | p-Br—Ph | H | H | $CH_2CH(CH_3)_2$ | Bz | H | F | H | OH | H | H | $NH_2$ |
| VII-49-5 | p-Br—Ph | H | H | $CH_2Ph$ | Bz | H | F | H | OH | H | H | $NH_2$ |
| VII-49-6 | p-Br—Ph | H | H | $CH_2$-indol-3-yl | Bz | H | F | H | OH | H | H | $NH_2$ |
| VII-49-7 | p-Br—Ph | H | H | $CH_2CH_2CH_3$ | Bz | H | F | H | OH | H | H | $NH_2$ |
| VII-49-8 | p-Br—Ph | * | H | * | Bz | H | F | H | OH | H | H | $NH_2$ |

*$R^2$ and $R^{3b}$ joined together by $(CH_2)_3$ to form five-membered ring.

TABLE VII-50

| No | $R^1$ | $R^2$ | $R^{3a}$ | $R^{3b}$ | $R^4$ | $R^5$ | $R^6$ | X | Y | $R^7$ | $R^8$ | $R^9$ |
|---|---|---|---|---|---|---|---|---|---|---|---|---|
| VII-50-1 | p-I—Ph | H | H | H | Bz | H | F | H | OH | H | H | $NH_2$ |
| VII-50-2 | p-I—Ph | H | H | $CH_3$ | Bz | H | F | H | OH | H | H | $NH_2$ |
| VII-50-3 | p-I—Ph | H | H | $CH(CH_3)_2$ | Bz | H | F | H | OH | H | H | $NH_2$ |
| VII-50-4 | p-I—Ph | H | H | $CH_2CH(CH_3)_2$ | Bz | H | F | H | OH | H | H | $NH_2$ |
| VII-50-5 | p-I—Ph | H | H | $CH_2Ph$ | Bz | H | F | H | OH | H | H | $NH_2$ |

TABLE VII-50-continued

| No | R¹ | R² | R³ᵃ | R³ᵇ | R⁴ | R⁵ | R⁶ | X | Y | R⁷ | R⁸ | R⁹ |
|---|---|---|---|---|---|---|---|---|---|---|---|---|
| VII-50-6 | p-I—Ph | H | H | CH$_2$-indol-3-yl | Bz | H | F | H | OH | H | H | NH$_2$ |
| VII-50-7 | p-I—Ph | H | H | CH$_2$CH$_2$CH$_3$ | Bz | H | F | H | OH | H | H | NH$_2$ |
| VII-50-8 | p-I—Ph | * | H | * | Bz | H | F | H | OH | H | H | NH$_2$ |

*R² and R³ᵇ joined together by (CH$_2$)$_3$ to form five-membered ring.

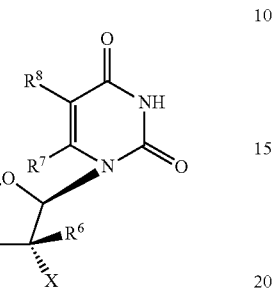

TABLE VIII-1

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-1-1 | CH$_3$ | H | H | H | CH$_3$ | H | CH$_3$ | OH | OH | H | H |
| VIII-1-2 | CH$_3$ | H | H | CH$_3$ | CH$_3$ | H | CH$_3$ | OH | OH | H | H |
| VIII-1-3 | CH$_3$ | H | H | CH(CH$_3$)$_2$ | CH$_3$ | H | CH$_3$ | OH | OH | H | H |
| VIII-1-4 | CH$_3$ | H | H | CH$_2$CH(CH$_3$)$_2$ | CH$_3$ | H | CH$_3$ | OH | OH | H | H |
| VIII-1-5 | CH$_3$ | H | H | CH$_2$Ph | CH$_3$ | H | CH$_3$ | OH | OH | H | H |
| VIII-1-6 | CH$_3$ | H | H | CH$_2$-indol-3-yl | CH$_3$ | H | CH$_3$ | OH | OH | H | H |
| VIII-1-7 | CH$_3$ | H | H | CH$_2$CH$_2$CH$_3$ | CH$_3$ | H | CH$_3$ | OH | OH | H | H |
| VIII-1-8 | CH$_3$ | * | H | * | CH$_3$ | H | CH$_3$ | OH | OH | H | H |

*R² and R³ᵇ joined together by (CH$_2$)$_3$ to form five-membered ring.

TABLE VIII-2

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-2-1 | Et | H | H | H | CH$_3$ | H | CH$_3$ | OH | OH | H | H |
| VIII-2-2 | Et | H | H | CH$_3$ | CH$_3$ | H | CH$_3$ | OH | OH | H | H |
| VIII-2-3 | Et | H | H | CH(CH$_3$)$_2$ | CH$_3$ | H | CH$_3$ | OH | OH | H | H |
| VIII-2-4 | Et | H | H | CH$_2$CH(CH$_3$)$_2$ | CH$_3$ | H | CH$_3$ | OH | OH | H | H |
| VIII-2-5 | Et | H | H | CH$_2$Ph | CH$_3$ | H | CH$_3$ | OH | OH | H | H |
| VIII-2-6 | Et | H | H | CH$_2$-indol-3-yl | CH$_3$ | H | CH$_3$ | OH | OH | H | H |
| VIII-2-7 | Et | H | H | CH$_2$CH$_2$CH$_3$ | CH$_3$ | H | CH$_3$ | OH | OH | H | H |
| VIII-2-8 | Et | * | H | * | CH$_3$ | H | CH$_3$ | OH | OH | H | H |

*R² and R³ᵇ joined together by (CH$_2$)$_3$ to form five-membered ring.

TABLE VIII-3

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-3-1 | $^i$Pr | H | H | H | CH$_3$ | H | CH$_3$ | OH | OH | H | H |
| VIII-3-2 | $^i$Pr | H | H | CH$_3$ | CH$_3$ | H | CH$_3$ | OH | OH | H | H |
| VIII-3-3 | $^i$Pr | H | H | CH(CH$_3$)$_2$ | CH$_3$ | H | CH$_3$ | OH | OH | H | H |
| VIII-3-4 | $^i$Pr | H | H | CH$_2$CH(CH$_3$)$_2$ | CH$_3$ | H | CH$_3$ | OH | OH | H | H |
| VIII-3-5 | $^i$Pr | H | H | CH$_2$Ph | CH$_3$ | H | CH$_3$ | OH | OH | H | H |
| VIII-3-6 | $^i$Pr | H | H | CH$_2$-indol-3-yl | CH$_3$ | H | CH$_3$ | OH | OH | H | H |
| VIII-3-7 | $^i$Pr | H | H | CH$_2$CH$_2$CH$_3$ | CH$_3$ | H | CH$_3$ | OH | OH | H | H |
| VIII-3-8 | $^i$Pr | * | H | * | CH$_3$ | H | CH$_3$ | OH | OH | H | H |

*R² and R³ᵇ joined together by (CH$_2$)$_3$ to form five-membered ring.

TABLE VIII-4

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-4-1 | $^t$Bu | H | H | H | CH$_3$ | H | CH$_3$ | OH | OH | H | H |
| VIII-4-2 | $^t$Bu | H | H | CH$_3$ | CH$_3$ | H | CH$_3$ | OH | OH | H | H |
| VIII-4-3 | $^t$Bu | H | H | CH(CH$_3$)$_2$ | CH$_3$ | H | CH$_3$ | OH | OH | H | H |
| VIII-4-4 | $^t$Bu | H | H | CH$_2$CH(CH$_3$)$_2$ | CH$_3$ | H | CH$_3$ | OH | OH | H | H |
| VIII-4-5 | $^t$Bu | H | H | CH$_2$Ph | CH$_3$ | H | CH$_3$ | OH | OH | H | H |
| VIII-4-6 | $^t$Bu | H | H | CH$_2$-indol-3-yl | CH$_3$ | H | CH$_3$ | OH | OH | H | H |
| VIII-4-7 | $^t$Bu | H | H | CH$_2$CH$_2$CH$_3$ | CH$_3$ | H | CH$_3$ | OH | OH | H | H |
| VIII-4-8 | $^t$Bu | * | H | * | CH$_3$ | H | CH$_3$ | OH | OH | H | H |

*R² and R³ᵇ joined together by (CH$_2$)$_3$ to form five-membered ring.

TABLE VIII-5

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-5-1 | Ph | H | H | H | CH₃ | H | CH₃ | OH | OH | H | H |
| VIII-5-2 | Ph | H | H | CH₃ | CH₃ | H | CH₃ | OH | OH | H | H |
| VIII-5-3 | Ph | H | H | CH(CH₃)₂ | CH₃ | H | CH₃ | OH | OH | H | H |
| VIII-5-4 | Ph | H | H | CH₂CH(CH₃)₂ | CH₃ | H | CH₃ | OH | OH | H | H |
| VIII-5-5 | Ph | H | H | CH₂Ph | CH₃ | H | CH₃ | OH | OH | H | H |
| VIII-5-6 | Ph | H | H | CH₂-indol-3-yl | CH₃ | H | CH₃ | OH | OH | H | H |
| VIII-5-7 | Ph | H | H | CH₂CH₂CH₃ | CH₃ | H | CH₃ | OH | OH | H | H |
| VIII-5-8 | Ph | * | H | * | CH₃ | H | CH₃ | OH | OH | H | H |

*R² and R³ᵇ joined together by (CH₂)₃ to form five-membered ring.

TABLE VIII-6

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-6-1 | p-Me—Ph | H | H | H | CH₃ | H | CH₃ | OH | OH | H | H |
| VIII-6-2 | p-Me—Ph | H | H | CH₃ | CH₃ | H | CH₃ | OH | OH | H | H |
| VIII-6-3 | p-Me—Ph | H | H | CH(CH₃)₂ | CH₃ | H | CH₃ | OH | OH | H | H |
| VIII-6-4 | p-Me—Ph | H | H | CH₂CH(CH₃)₂ | CH₃ | H | CH₃ | OH | OH | H | H |
| VIII-6-5 | p-Me—Ph | H | H | CH₂Ph | CH₃ | H | CH₃ | OH | OH | H | H |
| VIII-6-6 | p-Me—Ph | H | H | CH₂-indol-3-yl | CH₃ | H | CH₃ | OH | OH | H | H |
| VIII-6-7 | p-Me—Ph | H | H | CH₂CH₂SCH₃ | CH₃ | H | CH₃ | OH | OH | H | H |
| VIII-6-8 | p-Me—Ph | * | H | * | CH₃ | H | CH₃ | OH | OH | H | H |

*R² and R³ᵇ joined together by (CH₂)₃ to form five-membered ring.

TABLE VIII-7

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-7-1 | p-F—Ph | H | H | H | CH₃ | H | CH₃ | OH | OH | H | H |
| VIII-7-2 | p-F—Ph | H | H | CH₃ | CH₃ | H | CH₃ | OH | OH | H | H |
| VIII-7-3 | p-F—Ph | H | H | CH(CH₃)₂ | CH₃ | H | CH₃ | OH | OH | H | H |
| VIII-7-4 | p-F—Ph | H | H | CH₂CH(CH₃)₂ | CH₃ | H | CH₃ | OH | OH | H | H |
| VIII-7-6 | p-F—Ph | H | H | CH₂Ph | CH₃ | H | CH₃ | OH | OH | H | H |
| VIII-7-7 | p-F—Ph | H | H | CH₂-indol-3-yl | CH₃ | H | CH₃ | OH | OH | H | H |
| VIII-7-8 | p-F—Ph | H | H | CH₂CH₂SCH₃ | CH₃ | H | CH₃ | OH | OH | H | H |
| VIII-7-20 | p-F—Ph | * | H | * | CH₃ | H | CH₃ | OH | OH | H | H |

*R² and R³ᵇ joined together by (CH₂)₃ to form five-membered ring.

TABLE VIII-8

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-8-1 | p-Cl—Ph | H | H | H | CH₃ | H | CH₃ | OH | OH | H | H |
| VIII-8-2 | p-Cl—Ph | H | H | CH₃ | CH₃ | H | CH₃ | OH | OH | H | H |
| VIII-8-3 | p-Cl—Ph | H | H | CH(CH₃)₂ | CH₃ | H | CH₃ | OH | OH | H | H |
| VIII-8-4 | p-Cl—Ph | H | H | CH₂CH(CH₃)₂ | CH₃ | H | CH₃ | OH | OH | H | H |
| VIII-8-5 | p-Cl—Ph | H | H | CH₂Ph | CH₃ | H | CH₃ | OH | OH | H | H |
| VIII-8-6 | p-Cl—Ph | H | H | CH₂-indol-3-yl | CH₃ | H | CH₃ | OH | OH | H | H |
| VIII-8-7 | p-Cl—Ph | H | H | CH₂CH₂SCH₃ | CH₃ | H | CH₃ | OH | OH | H | H |
| VIII-8-8 | p-Cl—Ph | * | H | * | CH₃ | H | CH₃ | OH | OH | H | H |

*R² and R³ᵇ joined together by (CH₂)₃ to form five-membered ring.

TABLE VIII-9

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-9-1 | p-Br—Ph | H | H | H | CH₃ | H | CH₃ | OH | OH | H | H |
| VIII-9-2 | p-Br—Ph | H | H | CH₃ | CH₃ | H | CH₃ | OH | OH | H | H |
| VIII-9-3 | p-Br—Ph | H | H | CH(CH₃)₂ | CH₃ | H | CH₃ | OH | OH | H | H |
| VIII-9-4 | p-Br—Ph | H | H | CH₂CH(CH₃)₂ | CH₃ | H | CH₃ | OH | OH | H | H |
| VIII-9-6 | p-Br—Ph | H | H | CH₂Ph | CH₃ | H | CH₃ | OH | OH | H | H |
| VIII-9-7 | p-Br—Ph | H | H | CH₂-indol-3-yl | CH₃ | H | CH₃ | OH | OH | H | H |
| VIII-9-8 | p-Br—Ph | H | H | CH₂CH₂SCH₃ | CH₃ | H | CH₃ | OH | OH | H | H |
| VIII-9-20 | p-Br—Ph | * | H | * | CH₃ | H | CH₃ | OH | OH | H | H |

*R² and R³ᵇ joined together by (CH₂)₃ to form five-membered ring.

TABLE VIII-10

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-10-1 | p-I—Ph | H | H | H | CH₃ | H | CH₃ | OH | OH | H | H |
| VIII-10-2 | p-I—Ph | H | H | CH₃ | CH₃ | H | CH₃ | OH | OH | H | H |
| VIII-10-3 | p-I—Ph | H | H | CH(CH₃)₂ | CH₃ | H | CH₃ | OH | OH | H | H |
| VIII-10-4 | p-I—Ph | H | H | CH₂CH(CH₃)₂ | CH₃ | H | CH₃ | OH | OH | H | H |
| VIII-10-5 | p-I—Ph | H | H | CH₂Ph | CH₃ | H | CH₃ | OH | OH | H | H |
| VIII-10-6 | p-I—Ph | H | H | CH₂-indol-3-yl | CH₃ | H | CH₃ | OH | OH | H | H |
| VIII-10-7 | p-I—Ph | H | H | CH₂CH₂SCH₃ | CH₃ | H | CH₃ | OH | OH | H | H |
| VIII-10-8 | p-I—Ph | * | H | * | CH₃ | H | CH₃ | OH | OH | H | H |

*R² and R³ᵇ joined together by (CH₂)₃ to form five-membered ring.

TABLE VIII-11

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-11-1 | CH₃ | H | H | H | Et | H | CH₃ | OH | OH | H | H |
| VIII-11-2 | CH₃ | H | H | CH₃ | Et | H | CH₃ | OH | OH | H | H |
| VIII-11-3 | CH₃ | H | H | CH(CH₃)₂ | Et | H | CH₃ | OH | OH | H | H |
| VIII-11-4 | CH₃ | H | H | CH₂CH(CH₃)₂ | Et | H | CH₃ | OH | OH | H | H |
| VIII-11-5 | CH₃ | H | H | CH₂Ph | Et | H | CH₃ | OH | OH | H | H |
| VIII-11-6 | CH₃ | H | H | CH₂-indol-3-yl | Et | H | CH₃ | OH | OH | H | H |
| VIII-11-7 | CH₃ | H | H | CH₂CH₂SCH₃ | Et | H | CH₃ | OH | OH | H | H |
| VIII-11-8 | CH₃ | * | H | * | Et | H | CH₃ | OH | OH | H | H |

*R² and R³ᵇ joined together by (CH₂)₃ to form five-membered ring.

TABLE VIII-12

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-12-1 | Et | H | H | H | Et | H | CH₃ | OH | OH | H | H |
| VIII-12-2 | Et | H | H | CH₃ | Et | H | CH₃ | OH | OH | H | H |
| VIII-12-3 | Et | H | H | CH(CH₃)₂ | Et | H | CH₃ | OH | OH | H | H |
| VIII-12-4 | Et | H | H | CH₂CH(CH₃)₂ | Et | H | CH₃ | OH | OH | H | H |
| VIII-12-5 | Et | H | H | CH₂Ph | Et | H | CH₃ | OH | OH | H | H |
| VIII-12-6 | Et | H | H | CH₂-indol-3-yl | Et | H | CH₃ | OH | OH | H | H |
| VIII-12-7 | Et | H | H | CH₂CH₂SCH₃ | Et | H | CH₃ | OH | OH | H | H |
| VIII-12-8 | Et | * | H | * | Et | H | CH₃ | OH | OH | H | H |

*R² and R³ᵇ joined together by (CH₂)₃ to form five-membered ring.

TABLE VIII-13

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-13-1 | ⁱPr | H | H | H | Et | H | CH₃ | OH | OH | H | H |
| VIII-13-2 | ⁱPr | H | H | CH₃ | Et | H | CH₃ | OH | OH | H | H |
| VIII-13-3 | ⁱPr | H | H | CH(CH₃)₂ | Et | H | CH₃ | OH | OH | H | H |
| VIII-13-4 | ⁱPr | H | H | CH₂CH(CH₃)₂ | Et | H | CH₃ | OH | OH | H | H |
| VIII-13-5 | ⁱPr | H | H | CH₂Ph | Et | H | CH₃ | OH | OH | H | H |
| VIII-13-6 | ⁱPr | H | H | CH₂-indol-3-yl | Et | H | CH₃ | OH | OH | H | H |
| VIII-13-7 | ⁱPr | H | H | CH₂CH₂SCH₃ | Et | H | CH₃ | OH | OH | H | H |
| VIII-13-8 | ⁱPr | * | H | * | Et | H | CH₃ | OH | OH | H | H |

*R² and R³ᵇ joined together by (CH₂)₃ to form five-membered ring.

TABLE VIII-14

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-14-1 | ᵗBu | H | H | H | Et | H | CH₃ | OH | OH | H | H |
| VIII-14-2 | ᵗBu | H | H | CH₃ | Et | H | CH₃ | OH | OH | H | H |
| VIII-14-3 | ᵗBu | H | H | CH(CH₃)₂ | Et | H | CH₃ | OH | OH | H | H |
| VIII-14-4 | ᵗBu | H | H | CH₂CH(CH₃)₂ | Et | H | CH₃ | OH | OH | H | H |
| VIII-14-5 | ᵗBu | H | H | CH₂Ph | Et | H | CH₃ | OH | OH | H | H |

TABLE VIII-14-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-14-6 | $^t$Bu | H | H | CH$_2$-indol-3-yl | Et | H | CH$_3$ | OH | OH | H | H |
| VIII-14-7 | $^t$Bu | H | H | CH$_2$CH$_2$SCH$_3$ | Et | H | CH$_3$ | OH | OH | H | H |
| VIII-14-8 | $^t$Bu | * | H | * | Et | H | CH$_3$ | OH | OH | H | H |

*$R^2$ and $R^{3b}$ joined together by (CH$_2$)$_3$ to form five-membered ring.

TABLE VIII-15

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-15-1 | Ph | H | H | H | Et | H | CH$_3$ | OH | OH | H | H |
| VIII-15-2 | Ph | H | H | CH$_3$ | Et | H | CH$_3$ | OH | OH | H | H |
| VIII-15-3 | Ph | H | H | CH(CH$_3$)$_2$ | Et | H | CH$_3$ | OH | OH | H | H |
| VIII-15-4 | Ph | H | H | CH$_2$CH(CH$_3$)$_2$ | Et | H | CH$_3$ | OH | OH | H | H |
| VIII-15-5 | Ph | H | H | CH$_2$Ph | Et | H | CH$_3$ | OH | OH | H | H |
| VIII-15-6 | Ph | H | H | CH$_2$-indol-3-yl | Et | H | CH$_3$ | OH | OH | H | H |
| VIII-15-7 | Ph | H | H | CH$_2$CH$_2$SCH$_3$ | Et | H | CH$_3$ | OH | OH | H | H |
| VIII-15-8 | Ph | * | H | * | Et | H | CH$_3$ | OH | OH | H | H |

*$R^2$ and $R^{3b}$ joined together by (CH$_2$)$_3$ to form five-membered ring.

TABLE VIII-16

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-16-1 | p-Me—Ph | H | H | H | Et | H | CH$_3$ | OH | OH | H | H |
| VIII-16-2 | p-Me—Ph | H | H | CH$_3$ | Et | H | CH$_3$ | OH | OH | H | H |
| VIII-16-3 | p-Me—Ph | H | H | CH(CH$_3$)$_2$ | Et | H | CH$_3$ | OH | OH | H | H |
| VIII-16-4 | p-Me—Ph | H | H | CH$_2$CH(CH$_3$)$_2$ | Et | H | CH$_3$ | OH | OH | H | H |
| VIII-16-5 | p-Me—Ph | H | H | CH$_2$Ph | Et | H | CH$_3$ | OH | OH | H | H |
| VIII-16-6 | p-Me—Ph | H | H | CH$_2$-indol-3-yl | Et | H | CH$_3$ | OH | OH | H | H |
| VIII-16-7 | p-Me—Ph | H | H | CH$_2$CH$_2$SCH$_3$ | Et | H | CH$_3$ | OH | OH | H | H |
| VIII-16-8 | p-Me—Ph | * | H | * | Et | H | CH$_3$ | OH | OH | H | H |

*$R^2$ and $R^{3b}$ joined together by (CH$_2$)$_3$ to form five-membered ring.

TABLE VIII-17

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-17-1 | p-F—Ph | H | H | H | Et | H | CH$_3$ | OH | OH | H | H |
| VIII-17-2 | p-F—Ph | H | H | CH$_3$ | Et | H | CH$_3$ | OH | OH | H | H |
| VIII-17-3 | p-F—Ph | H | H | CH(CH$_3$)$_2$ | Et | H | CH$_3$ | OH | OH | H | H |
| VIII-17-4 | p-F—Ph | H | H | CH$_2$CH(CH$_3$)$_2$ | Et | H | CH$_3$ | OH | OH | H | H |
| VIII-17-5 | p-F—Ph | H | H | CH$_2$Ph | Et | H | CH$_3$ | OH | OH | H | H |
| VIII-17-6 | p-F—Ph | H | H | CH$_2$-indol-3-yl | Et | H | CH$_3$ | OH | OH | H | H |
| VIII-17-7 | p-F—Ph | H | H | CH$_2$CH$_2$SCH$_3$ | Et | H | CH$_3$ | OH | OH | H | H |
| VIII-17-8 | p-F—Ph | * | H | * | Et | H | CH$_3$ | OH | OH | H | H |

*$R^2$ and $R^{3b}$ joined together by (CH$_2$)$_3$ to form five-membered ring.

TABLE VIII-18

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-18-1 | p-Cl—Ph | H | H | H | Et | H | CH$_3$ | OH | OH | H | H |
| VIII-18-2 | p-Cl—Ph | H | H | CH$_3$ | Et | H | CH$_3$ | OH | OH | H | H |
| VIII-18-3 | p-Cl—Ph | H | H | CH(CH$_3$)$_2$ | Et | H | CH$_3$ | OH | OH | H | H |
| VIII-18-4 | p-Cl—Ph | H | H | CH$_2$CH(CH$_3$)$_2$ | Et | H | CH$_3$ | OH | OH | H | H |
| VIII-18-5 | p-Cl—Ph | H | H | CH$_2$Ph | Et | H | CH$_3$ | OH | OH | H | H |
| VIII-18-6 | p-Cl—Ph | H | H | CH$_2$-indol-3-yl | Et | H | CH$_3$ | OH | OH | H | H |
| VIII-18-7 | p-Cl—Ph | H | H | CH$_2$CH$_2$SCH$_3$ | Et | H | CH$_3$ | OH | OH | H | H |
| VIII-18-8 | p-Cl—Ph | * | H | * | Et | H | CH$_3$ | OH | OH | H | H |

*$R^2$ and $R^{3b}$ joined together by (CH$_2$)$_3$ to form five-membered ring.

TABLE VIII-19

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-19-1 | p-Br—Ph | H | H | H | Et | H | CH$_3$ | OH | OH | H | H |
| VIII-19-2 | p-Br—Ph | H | H | CH$_3$ | Et | H | CH$_3$ | OH | OH | H | H |
| VIII-19-3 | p-Br—Ph | H | H | CH(CH$_3$)$_2$ | Et | H | CH$_3$ | OH | OH | H | H |
| VIII-19-4 | p-Br—Ph | H | H | CH$_2$CH(CH$_3$)$_2$ | Et | H | CH$_3$ | OH | OH | H | H |
| VIII-19-5 | p-Br—Ph | H | H | CH$_2$Ph | Et | H | CH$_3$ | OH | OH | H | H |
| VIII-19-6 | p-Br—Ph | H | H | CH$_2$-indol-3-yl | Et | H | CH$_3$ | OH | OH | H | H |
| VIII-19-7 | p-Br—Ph | H | H | CH$_2$CH$_2$SCH$_3$ | Et | H | CH$_3$ | OH | OH | H | H |
| VIII-19-8 | p-Br—Ph | * | H | * | Et | H | CH$_3$ | OH | OH | H | H |

*R$^2$ and R$^{3b}$ joined together by (CH$_2$)$_3$ to form five-membered ring.

TABLE VIII-20

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-20-1 | p-I—Ph | H | H | H | Et | H | CH$_3$ | OH | OH | H | H |
| VIII-20-2 | p-I—Ph | H | H | CH$_3$ | Et | H | CH$_3$ | OH | OH | H | H |
| VIII-20-3 | p-I—Ph | H | H | CH(CH$_3$)$_2$ | Et | H | CH$_3$ | OH | OH | H | H |
| VIII-20-4 | p-I—Ph | H | H | CH$_2$CH(CH$_3$)$_2$ | Et | H | CH$_3$ | OH | OH | H | H |
| VIII-20-5 | p-I—Ph | H | H | CH$_2$Ph | Et | H | CH$_3$ | OH | OH | H | H |
| VIII-20-6 | p-I—Ph | H | H | CH$_2$-indol-3-yl | Et | H | CH$_3$ | OH | OH | H | H |
| VIII-20-7 | p-I—Ph | H | H | CH$_2$CH$_2$SCH$_3$ | Et | H | CH$_3$ | OH | OH | H | H |
| VIII-20-8 | p-I—Ph | * | H | * | Et | H | CH$_3$ | OH | OH | H | H |

*R$^2$ and R$^{3b}$ joined together by (CH$_2$)$_3$ to form five-membered ring.

TABLE VIII-21

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-21-1 | CH$_3$ | H | H | H | $^i$Pr | H | CH$_3$ | OH | OH | H | H |
| VIII-21-2 | CH$_3$ | H | H | CH$_3$ | $^i$Pr | H | CH$_3$ | OH | OH | H | H |
| VIII-21-3 | CH$_3$ | H | H | CH(CH$_3$)$_2$ | $^i$Pr | H | CH$_3$ | OH | OH | H | H |
| VIII-21-4 | CH$_3$ | H | H | CH$_2$CH(CH$_3$)$_2$ | $^i$Pr | H | CH$_3$ | OH | OH | H | H |
| VIII-21-5 | CH$_3$ | H | H | CH$_2$Ph | $^i$Pr | H | CH$_3$ | OH | OH | H | H |
| VIII-21-6 | CH$_3$ | H | H | CH$_2$-indol-3-yl | $^i$Pr | H | CH$_3$ | OH | OH | H | H |
| VIII-21-7 | CH$_3$ | H | H | CH$_2$CH$_2$SCH$_3$ | $^i$Pr | H | CH$_3$ | OH | OH | H | H |
| VIII-21-8 | CH$_3$ | * | H | * | $^i$Pr | H | CH$_3$ | OH | OH | H | H |

*R$^2$ and R$^{3b}$ joined together by (CH$_2$)$_3$ to form five-membered ring.

TABLE VIII-22

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-22-1 | Et | H | H | H | $^i$Pr | H | CH$_3$ | OH | OH | H | H |
| VIII-22-2 | Et | H | H | CH$_3$ | $^i$Pr | H | CH$_3$ | OH | OH | H | H |
| VIII-22-3 | Et | H | H | CH(CH$_3$)$_2$ | $^i$Pr | H | CH$_3$ | OH | OH | H | H |
| VIII-22-4 | Et | H | H | CH$_2$CH(CH$_3$)$_2$ | $^i$Pr | H | CH$_3$ | OH | OH | H | H |
| VIII-22-5 | Et | H | H | CH$_2$Ph | $^i$Pr | H | CH$_3$ | OH | OH | H | H |
| VIII-22-6 | Et | H | H | CH$_2$-indol-3-yl | $^i$Pr | H | CH$_3$ | OH | OH | H | H |
| VIII-22-7 | Et | H | H | CH$_2$CH$_2$SCH$_3$ | $^i$Pr | H | CH$_3$ | OH | OH | H | H |
| VIII-22-8 | Et | * | H | * | $^i$Pr | H | CH$_3$ | OH | OH | H | H |

*R$^2$ and R$^{3b}$ joined together by (CH$_2$)$_3$ to form five-membered ring.

TABLE VIII-23

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-23-1 | $^i$Pr | H | H | H | $^i$Pr | H | CH$_3$ | OH | OH | H | H |
| VIII-23-2 | $^i$Pr | H | H | CH$_3$ | $^i$Pr | H | CH$_3$ | OH | OH | H | H |
| VIII-23-3 | $^i$Pr | H | H | CH(CH$_3$)$_2$ | $^i$Pr | H | CH$_3$ | OH | OH | H | H |
| VIII-23-4 | $^i$Pr | H | H | CH$_2$CH(CH$_3$)$_2$ | $^i$Pr | H | CH$_3$ | OH | OH | H | H |
| VIII-23-5 | $^i$Pr | H | H | CH$_2$Ph | $^i$Pr | H | CH$_3$ | OH | OH | H | H |

TABLE VIII-23-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-23-6 | $^i$Pr | H | H | CH$_2$-indol-3-yl | $^i$Pr | H | CH$_3$ | OH | OH | H | H |
| VIII-23-7 | $^i$Pr | H | H | CH$_2$CH$_2$SCH$_3$ | $^i$Pr | H | CH$_3$ | OH | OH | H | H |
| VIII-23-8 | $^i$Pr | * | H | * | $^i$Pr | H | CH$_3$ | OH | OH | H | H |

*R$^2$ and R$^{3b}$ joined together by (CH$_2$)$_3$ to form five-membered ring.

TABLE VIII-24

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-24-1 | $^t$Bu | H | H | H | $^i$Pr | H | CH$_3$ | OH | OH | H | H |
| VIII-24-2 | $^t$Bu | H | H | CH$_3$ | $^i$Pr | H | CH$_3$ | OH | OH | H | H |
| VIII-24-3 | $^t$Bu | H | H | CH(CH$_3$)$_2$ | $^i$Pr | H | CH$_3$ | OH | OH | H | H |
| VIII-24-4 | $^t$Bu | H | H | CH$_2$CH(CH$_3$)$_2$ | $^i$Pr | H | CH$_3$ | OH | OH | H | H |
| VIII-24-5 | $^t$Bu | H | H | CH$_2$Ph | $^i$Pr | H | CH$_3$ | OH | OH | H | H |
| VIII-24-6 | $^t$Bu | H | H | CH$_2$-indol-3-yl | $^i$Pr | H | CH$_3$ | OH | OH | H | H |
| VIII-24-7 | $^t$Bu | H | H | CH$_2$CH$_2$SCH$_3$ | $^i$Pr | H | CH$_3$ | OH | OH | H | H |
| VIII-24-8 | $^t$Bu | * | H | * | $^i$Pr | H | CH$_3$ | OH | OH | H | H |

*R$^2$ and R$^{3b}$ joined together by (CH$_2$)$_3$ to form five-membered ring.

TABLE VIII-25

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-25-1 | Ph | H | H | H | $^i$Pr | H | CH$_3$ | OH | OH | H | H |
| VIII-25-2 | Ph | H | H | CH$_3$ | $^i$Pr | H | CH$_3$ | OH | OH | H | H |
| VIII-25-3 | Ph | H | H | CH(CH$_3$)$_2$ | $^i$Pr | H | CH$_3$ | OH | OH | H | H |
| VIII-25-4 | Ph | H | H | CH$_2$CH(CH$_3$)$_2$ | $^i$Pr | H | CH$_3$ | OH | OH | H | H |
| VIII-25-5 | Ph | H | H | CH$_2$Ph | $^i$Pr | H | CH$_3$ | OH | OH | H | H |
| VIII-25-6 | Ph | H | H | CH$_2$-indol-3-yl | $^i$Pr | H | CH$_3$ | OH | OH | H | H |
| VIII-25-7 | Ph | H | H | CH$_2$CH$_2$SCH$_3$ | $^i$Pr | H | CH$_3$ | OH | OH | H | H |
| VIII-25-8 | Ph | * | H | * | $^i$Pr | H | CH$_3$ | OH | OH | H | H |

*R$^2$ and R$^{3b}$ joined together by (CH$_2$)$_3$ to form five-membered ring.

TABLE VIII-26

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-26-1 | p-Me—Ph | H | H | H | $^i$Pr | H | CH$_3$ | OH | OH | H | H |
| VIII-26-2 | p-Me—Ph | H | H | CH$_3$ | $^i$Pr | H | CH$_3$ | OH | OH | H | H |
| VIII-26-3 | p-Me—Ph | H | H | CH(CH$_3$)$_2$ | $^i$Pr | H | CH$_3$ | OH | OH | H | H |
| VIII-26-4 | p-Me—Ph | H | H | CH$_2$CH(CH$_3$)$_2$ | $^i$Pr | H | CH$_3$ | OH | OH | H | H |
| VIII-26-5 | p-Me—Ph | H | H | CH$_2$Ph | $^i$Pr | H | CH$_3$ | OH | OH | H | H |
| VIII-26-6 | p-Me—Ph | H | H | CH$_2$-indol-3-yl | $^i$Pr | H | CH$_3$ | OH | OH | H | H |
| VIII-26-7 | p-Me—Ph | H | H | CH$_2$CH$_2$SCH$_3$ | $^i$Pr | H | CH$_3$ | OH | OH | H | H |
| VIII-26-8 | p-Me—Ph | * | H | * | $^i$Pr | H | CH$_3$ | OH | OH | H | H |

*R$^2$ and R$^{3b}$ joined together by (CH$_2$)$_3$ to form five-membered ring.

TABLE VIII-27

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-27-1 | p-F—Ph | H | H | H | $^i$Pr | H | CH$_3$ | OH | OH | H | H |
| VIII-27-2 | p-F—Ph | H | H | CH$_3$ | $^i$Pr | H | CH$_3$ | OH | OH | H | H |
| VIII-27-3 | p-F—Ph | H | H | CH(CH$_3$)$_2$ | $^i$Pr | H | CH$_3$ | OH | OH | H | H |
| VIII-27-4 | p-F—Ph | H | H | CH$_2$CH(CH$_3$)$_2$ | $^i$Pr | H | CH$_3$ | OH | OH | H | H |
| VIII-27-5 | p-F—Ph | H | H | CH$_2$Ph | $^i$Pr | H | CH$_3$ | OH | OH | H | H |
| VIII-27-6 | p-F—Ph | H | H | CH$_2$-indol-3-yl | $^i$Pr | H | CH$_3$ | OH | OH | H | H |
| VIII-27-7 | p-F—Ph | H | H | CH$_2$CH$_2$SCH$_3$ | $^i$Pr | H | CH$_3$ | OH | OH | H | H |
| VIII-27-8 | p-F—Ph | * | H | * | $^i$Pr | H | CH$_3$ | OH | OH | H | H |

*R$^2$ and R$^{3b}$ joined together by (CH$_2$)$_3$ to form five-membered ring.

TABLE VIII-28

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-28-1 | p-Cl—Ph | H | H | H | $^i$Pr | H | CH$_3$ | OH | OH | H | H |
| VIII-28-2 | p-Cl—Ph | H | H | CH$_3$ | $^i$Pr | H | CH$_3$ | OH | OH | H | H |
| VIII-28-3 | p-Cl—Ph | H | H | CH(CH$_3$)$_2$ | $^i$Pr | H | CH$_3$ | OH | OH | H | H |
| VIII-28-4 | p-Cl—Ph | H | H | CH$_2$CH(CH$_3$)$_2$ | $^i$Pr | H | CH$_3$ | OH | OH | H | H |
| VIII-28-5 | p-Cl—Ph | H | H | CH$_2$Ph | $^i$Pr | H | CH$_3$ | OH | OH | H | H |
| VIII-28-6 | p-Cl—Ph | H | H | CH$_2$-indol-3-yl | $^i$Pr | H | CH$_3$ | OH | OH | H | H |
| VIII-28-7 | p-Cl—Ph | H | H | CH$_2$CH$_2$SCH$_3$ | $^i$Pr | H | CH$_3$ | OH | OH | H | H |
| VIII-28-8 | p-Cl—Ph | * | H | * | $^i$Pr | H | CH$_3$ | OH | OH | H | H |

*R$^2$ and R$^{3b}$ joined together by (CH$_2$)$_3$ to form five-membered ring.

TABLE VIII-29

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-29-1 | p-Br—Ph | H | H | H | $^i$Pr | H | CH$_3$ | OH | OH | H | H |
| VIII-29-2 | p-Br—Ph | H | H | CH$_3$ | $^i$Pr | H | CH$_3$ | OH | OH | H | H |
| VIII-29-3 | p-Br—Ph | H | H | CH(CH$_3$)$_2$ | $^i$Pr | H | CH$_3$ | OH | OH | H | H |
| VIII-29-4 | p-Br—Ph | H | H | CH$_2$CH(CH$_3$)$_2$ | $^i$Pr | H | CH$_3$ | OH | OH | H | H |
| VIII-29-5 | p-Br—Ph | H | H | CH$_2$Ph | $^i$Pr | H | CH$_3$ | OH | OH | H | H |
| VIII-29-6 | p-Br—Ph | H | H | CH$_2$-indol-3-yl | $^i$Pr | H | CH$_3$ | OH | OH | H | H |
| VIII-29-7 | p-Br—Ph | H | H | CH$_2$CH$_2$SCH$_3$ | $^i$Pr | H | CH$_3$ | OH | OH | H | H |
| VIII-29-8 | p-Br—Ph | * | H | * | $^i$Pr | H | CH$_3$ | OH | OH | H | H |

*R$^2$ and R$^{3b}$ joined together by (CH$_2$)$_3$ to form five-membered ring.

TABLE VIII-30

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-30-1 | p-I—Ph | H | H | H | $^i$Pr | H | CH$_3$ | OH | OH | H | H |
| VIII-30-2 | p-I—Ph | H | H | CH$_3$ | $^i$Pr | H | CH$_3$ | OH | OH | H | H |
| VIII-30-3 | p-I—Ph | H | H | CH(CH$_3$)$_2$ | $^i$Pr | H | CH$_3$ | OH | OH | H | H |
| VIII-30-4 | p-I—Ph | H | H | CH$_2$CH(CH$_3$)$_2$ | $^i$Pr | H | CH$_3$ | OH | OH | H | H |
| VIII-30-5 | p-I—Ph | H | H | CH$_2$Ph | $^i$Pr | H | CH$_3$ | OH | OH | H | H |
| VIII-30-6 | p-I—Ph | H | H | CH$_2$-indol-3-yl | $^i$Pr | H | CH$_3$ | OH | OH | H | H |
| VIII-30-7 | p-I—Ph | H | H | CH$_2$CH$_2$SCH$_3$ | $^i$Pr | H | CH$_3$ | OH | OH | H | H |
| VIII-30-8 | p-I—Ph | * | H | * | $^i$Pr | H | CH$_3$ | OH | OH | H | H |

*R$^2$ and R$^{3b}$ joined together by (CH$_2$)$_3$ to form five-membered ring.

TABLE VIII-31

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-31-1 | CH$_3$ | H | H | H | $^n$Bu | H | CH$_3$ | OH | OH | H | H |
| VIII-31-2 | CH$_3$ | H | H | CH$_3$ | $^n$Bu | H | CH$_3$ | OH | OH | H | H |
| VIII-31-3 | CH$_3$ | H | H | CH(CH$_3$)$_2$ | $^n$Bu | H | CH$_3$ | OH | OH | H | H |
| VIII-31-4 | CH$_3$ | H | H | CH$_2$CH(CH$_3$)$_2$ | $^n$Bu | H | CH$_3$ | OH | OH | H | H |
| VIII-31-5 | CH$_3$ | H | H | CH$_2$Ph | $^n$Bu | H | CH$_3$ | OH | OH | H | H |
| VIII-31-6 | CH$_3$ | H | H | CH$_2$-indol-3-yl | $^n$Bu | H | CH$_3$ | OH | OH | H | H |
| VIII-31-7 | CH$_3$ | H | H | CH$_2$CH$_2$SCH$_3$ | $^n$Bu | H | CH$_3$ | OH | OH | H | H |
| VIII-31-8 | CH$_3$ | * | H | * | $^n$Bu | H | CH$_3$ | OH | OH | H | H |

*R$^2$ and R$^{3b}$ joined together by (CH$_2$)$_3$ to form five-membered ring.

TABLE VIII-32

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-32-1 | Et | H | H | H | $^n$Bu | H | CH$_3$ | OH | OH | H | H |
| VIII-32-2 | Et | H | H | CH$_3$ | $^n$Bu | H | CH$_3$ | OH | OH | H | H |
| VIII-32-3 | Et | H | H | CH(CH$_3$)$_2$ | $^n$Bu | H | CH$_3$ | OH | OH | H | H |
| VIII-32-4 | Et | H | H | CH$_2$CH(CH$_3$)$_2$ | $^n$Bu | H | CH$_3$ | OH | OH | H | H |
| VIII-32-5 | Et | H | H | CH$_2$Ph | $^n$Bu | H | CH$_3$ | OH | OH | H | H |

TABLE VIII-32-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-32-6 | Et | H | H | CH₂-indol-3-yl | ⁿBu | H | CH₃ | OH | OH | H | H |
| VIII-32-7 | Et | H | H | CH₂CH₂SCH₃ | ⁿBu | H | CH₃ | OH | OH | H | H |
| VIII-32-8 | Et | * | H | * | ⁿBu | H | CH₃ | OH | OH | H | H |

*R² and R³ᵇ joined together by (CH₂)₃ to form five-membered ring.

TABLE VIII-33

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-33-1 | ⁱPr | H | H | H | ⁿBu | H | CH₃ | OH | OH | H | H |
| VIII-33-2 | ⁱPr | H | H | CH₃ | ⁿBu | H | CH₃ | OH | OH | H | H |
| VIII-33-3 | ⁱPr | H | H | CH(CH₃)₂ | ⁿBu | H | CH₃ | OH | OH | H | H |
| VIII-33-4 | ⁱPr | H | H | CH₂CH(CH₃)₂ | ⁿBu | H | CH₃ | OH | OH | H | H |
| VIII-33-5 | ⁱPr | H | H | CH₂Ph | ⁿBu | H | CH₃ | OH | OH | H | H |
| VIII-33-6 | ⁱPr | H | H | CH₂-indol-3-yl | ⁿBu | H | CH₃ | OH | OH | H | H |
| VIII-33-7 | ⁱPr | H | H | CH₂CH₂SCH₃ | ⁿBu | H | CH₃ | OH | OH | H | H |
| VIII-33-8 | ⁱPr | * | H | * | ⁿBu | H | CH₃ | OH | OH | H | H |

*R² and R³ᵇ joined together by (CH₂)₃ to form five-membered ring.

TABLE VIII-34

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-34-1 | ᵗBu | H | H | H | ⁿBu | H | CH₃ | OH | OH | H | H |
| VIII-34-2 | ᵗBu | H | H | CH₃ | ⁿBu | H | CH₃ | OH | OH | H | H |
| VIII-34-3 | ᵗBu | H | H | CH(CH₃)₂ | ⁿBu | H | CH₃ | OH | OH | H | H |
| VIII-34-4 | ᵗBu | H | H | CH₂CH(CH₃)₂ | ⁿBu | H | CH₃ | OH | OH | H | H |
| VIII-34-5 | ᵗBu | H | H | CH₂Ph | ⁿBu | H | CH₃ | OH | OH | H | H |
| VIII-34-6 | ᵗBu | H | H | CH₂-indol-3-yl | ⁿBu | H | CH₃ | OH | OH | H | H |
| VIII-34-7 | ᵗBu | H | H | CH₂CH₂SCH₃ | ⁿBu | H | CH₃ | OH | OH | H | H |
| VIII-34-8 | ᵗBu | * | H | * | ⁿBu | H | CH₃ | OH | OH | H | H |

*R² and R³ᵇ joined together by (CH₂)₃ to form five-membered ring.

TABLE VIII-35

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-35-1 | Ph | H | H | H | ⁿBu | H | CH₃ | OH | OH | H | H |
| VIII-35-2 | Ph | H | H | CH₃ | ⁿBu | H | CH₃ | OH | OH | H | H |
| VIII-35-3 | Ph | H | H | CH(CH₃)₂ | ⁿBu | H | CH₃ | OH | OH | H | H |
| VIII-35-4 | Ph | H | H | CH₂CH(CH₃)₂ | ⁿBu | H | CH₃ | OH | OH | H | H |
| VIII-35-5 | Ph | H | H | CH₂Ph | ⁿBu | H | CH₃ | OH | OH | H | H |
| VIII-35-6 | Ph | H | H | CH₂-indol-3-yl | ⁿBu | H | CH₃ | OH | OH | H | H |
| VIII-35-7 | Ph | H | H | CH₂CH₂SCH₃ | ⁿBu | H | CH₃ | OH | OH | H | H |
| VIII-35-8 | Ph | * | H | * | ⁿBu | H | CH₃ | OH | OH | H | H |

*R² and R³ᵇ joined together by (CH₂)₃ to form five-membered ring.

TABLE VIII-36

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-36-1 | p-Me—Ph | H | H | H | ⁿBu | H | CH₃ | OH | OH | H | H |
| VIII-36-2 | p-Me—Ph | H | H | CH₃ | ⁿBu | H | CH₃ | OH | OH | H | H |
| VIII-36-3 | p-Me—Ph | H | H | CH(CH₃)₂ | ⁿBu | H | CH₃ | OH | OH | H | H |
| VIII-36-4 | p-Me—Ph | H | H | CH₂CH(CH₃)₂ | ⁿBu | H | CH₃ | OH | OH | H | H |
| VIII-36-5 | p-Me—Ph | H | H | CH₂Ph | ⁿBu | H | CH₃ | OH | OH | H | H |
| VIII-36-6 | p-Me—Ph | H | H | CH₂-indol-3-yl | ⁿBu | H | CH₃ | OH | OH | H | H |
| VIII-36-7 | p-Me—Ph | H | H | CH₂CH₂SCH₃ | ⁿBu | H | CH₃ | OH | OH | H | H |
| VIII-36-8 | p-Me—Ph | * | H | * | ⁿBu | H | CH₃ | OH | OH | H | H |

*R² and R³ᵇ joined together by (CH₂)₃ to form five-membered ring.

TABLE VIII-37

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-37-1 | p-F—Ph | H | H | H | ⁿBu | H | CH₃ | OH | OH | H | H |
| VIII-37-2 | p-F—Ph | H | H | CH₃ | ⁿBu | H | CH₃ | OH | OH | H | H |
| VIII-37-3 | p-F—Ph | H | H | CH(CH₃)₂ | ⁿBu | H | CH₃ | OH | OH | H | H |
| VIII-37-4 | p-F—Ph | H | H | CH₂CH(CH₃)₂ | ⁿBu | H | CH₃ | OH | OH | H | H |
| VIII-37-5 | p-F—Ph | H | H | CH₂Ph | ⁿBu | H | CH₃ | OH | OH | H | H |
| VIII-37-6 | p-F—Ph | H | H | CH₂-indol-3-yl | ⁿBu | H | CH₃ | OH | OH | H | H |
| VIII-37-7 | p-F—Ph | H | H | CH₂CH₂SCH₃ | ⁿBu | H | CH₃ | OH | OH | H | H |
| VIII-37-8 | p-F—Ph | * | H | * | ⁿBu | H | CH₃ | OH | OH | H | H |

*R² and R³ᵇ joined together by (CH₂)₃ to form five-membered ring.

TABLE VIII-38

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-38-1 | p-Cl—Ph | H | H | H | ⁿBu | H | CH₃ | OH | OH | H | H |
| VIII-38-2 | p-Cl—Ph | H | H | CH₃ | ⁿBu | H | CH₃ | OH | OH | H | H |
| VIII-38-3 | p-Cl—Ph | H | H | CH(CH₃)₂ | ⁿBu | H | CH₃ | OH | OH | H | H |
| VIII-38-4 | p-Cl—Ph | H | H | CH₂CH(CH₃)₂ | ⁿBu | H | CH₃ | OH | OH | H | H |
| VIII-38-5 | p-Cl—Ph | H | H | CH₂Ph | ⁿBu | H | CH₃ | OH | OH | H | H |
| VIII-38-6 | p-Cl—Ph | H | H | CH₂-indol-3-yl | ⁿBu | H | CH₃ | OH | OH | H | H |
| VIII-38-7 | p-Cl—Ph | H | H | CH₂CH₂SCH₃ | ⁿBu | H | CH₃ | OH | OH | H | H |
| VIII-38-8 | p-Cl—Ph | * | H | * | ⁿBu | H | CH₃ | OH | OH | H | H |

*R² and R³ᵇ joined together by (CH₂)₃ to form five-membered ring.

TABLE VIII-39

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-39-1 | p-Br—Ph | H | H | H | ⁿBu | H | CH₃ | OH | OH | H | H |
| VIII-39-2 | p-Br—Ph | H | H | CH₃ | ⁿBu | H | CH₃ | OH | OH | H | H |
| VIII-39-3 | p-Br—Ph | H | H | CH(CH₃)₂ | ⁿBu | H | CH₃ | OH | OH | H | H |
| VIII-39-4 | p-Br—Ph | H | H | CH₂CH(CH₃)₂ | ⁿBu | H | CH₃ | OH | OH | H | H |
| VIII-39-5 | p-Br—Ph | H | H | CH₂Ph | ⁿBu | H | CH₃ | OH | OH | H | H |
| VIII-39-6 | p-Br—Ph | H | H | CH₂-indol-3-yl | ⁿBu | H | CH₃ | OH | OH | H | H |
| VIII-39-7 | p-Br—Ph | H | H | CH₂CH₂SCH₃ | ⁿBu | H | CH₃ | OH | OH | H | H |
| VIII-39-8 | p-Br—Ph | * | H | * | ⁿBu | H | CH₃ | OH | OH | H | H |

*R² and R³ᵇ joined together by (CH₂)₃ to form five-membered ring.

TABLE VIII-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-40-1 | p-I—Ph | H | H | H | ⁿBu | H | CH₃ | OH | OH | H | H |
| VIII-40-2 | p-I—Ph | H | H | CH₃ | ⁿBu | H | CH₃ | OH | OH | H | H |
| VIII-40-3 | p-I—Ph | H | H | CH(CH₃)₂ | ⁿBu | H | CH₃ | OH | OH | H | H |
| VIII-40-4 | p-I—Ph | H | H | CH₂CH(CH₃)₂ | ⁿBu | H | CH₃ | OH | OH | H | H |
| VIII-40-5 | p-I—Ph | H | H | CH₂Ph | ⁿBu | H | CH₃ | OH | OH | H | H |
| VIII-40-6 | p-I—Ph | H | H | CH₂-indol-3-yl | ⁿBu | H | CH₃ | OH | OH | H | H |
| VIII-40-7 | p-I—Ph | H | H | CH₂CH₂SCH₃ | ⁿBu | H | CH₃ | OH | OH | H | H |
| VIII-40-8 | p-I—Ph | * | H | * | ⁿBu | H | CH₃ | OH | OH | H | H |

*R² and R³ᵇ joined together by (CH₂)₃ to form five-membered ring.

TABLE VIII-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-41-1 | CH₃ | H | H | H | Bz | H | CH₃ | OH | OH | H | H |
| VIII-41-2 | CH₃ | H | H | CH₃ | Bz | H | CH₃ | OH | OH | H | H |
| VIII-41-3 | CH₃ | H | H | CH(CH₃)₂ | Bz | H | CH₃ | OH | OH | H | H |
| VIII-41-4 | CH₃ | H | H | CH₂CH(CH₃)₂ | Bz | H | CH₃ | OH | OH | H | H |
| VIII-41-5 | CH₃ | H | H | CH₂Ph | Bz | H | CH₃ | OH | OH | H | H |

TABLE VIII-41-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-41-6 | $CH_3$ | H | H | $CH_2$-indol-3-yl | Bz | H | $CH_3$ | OH | OH | H | H |
| VIII-41-7 | $CH_3$ | H | H | $CH_2CH_2SCH_3$ | Bz | H | $CH_3$ | OH | OH | H | H |
| VIII-41-8 | $CH_3$ | * | H | * | Bz | H | $CH_3$ | OH | OH | H | H |

*$R^2$ and $R^{3b}$ joined together by $(CH_2)_3$ to form five-membered ring.

TABLE VIII-42

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-42-1 | Et | H | H | H | Bz | H | $CH_3$ | OH | OH | H | H |
| VIII-42-2 | Et | H | H | $CH_3$ | Bz | H | $CH_3$ | OH | OH | H | H |
| VIII-42-3 | Et | H | H | $CH(CH_3)_2$ | Bz | H | $CH_3$ | OH | OH | H | H |
| VIII-42-4 | Et | H | H | $CH_2CH(CH_3)_2$ | Bz | H | $CH_3$ | OH | OH | H | H |
| VIII-42-5 | Et | H | H | $CH_2Ph$ | Bz | H | $CH_3$ | OH | OH | H | H |
| VIII-42-6 | Et | H | H | $CH_2$-indol-3-yl | Bz | H | $CH_3$ | OH | OH | H | H |
| VIII-42-7 | Et | H | H | $CH_2CH_2SCH_3$ | Bz | H | $CH_3$ | OH | OH | H | H |
| VIII-42-8 | Et | * | H | * | Bz | H | $CH_3$ | OH | OH | H | H |

*$R^2$ and $R^{3b}$ joined together by $(CH_2)_3$ to form five-membered ring.

TABLE VIII-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-43-1 | $^i$Pr | H | H | H | Bz | H | $CH_3$ | OH | OH | H | H |
| VIII-43-2 | $^i$Pr | H | H | $CH_3$ | Bz | H | $CH_3$ | OH | OH | H | H |
| VIII-43-3 | $^i$Pr | H | H | $CH(CH_3)_2$ | Bz | H | $CH_3$ | OH | OH | H | H |
| VIII-43-4 | $^i$Pr | H | H | $CH_2CH(CH_3)_2$ | Bz | H | $CH_3$ | OH | OH | H | H |
| VIII-43-5 | $^i$Pr | H | H | $CH_2Ph$ | Bz | H | $CH_3$ | OH | OH | H | H |
| VIII-43-6 | $^i$Pr | H | H | $CH_2$-indol-3-yl | Bz | H | $CH_3$ | OH | OH | H | H |
| VIII-43-7 | $^i$Pr | H | H | $CH_2CH_2SCH_3$ | Bz | H | $CH_3$ | OH | OH | H | H |
| VIII-43-8 | $^i$Pr | * | H | * | Bz | H | $CH_3$ | OH | OH | H | H |

*$R^2$ and $R^{3b}$ joined together by $(CH_2)_3$ to form five-membered ring.

TABLE VIII-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-44-1 | $^t$Bu | H | H | H | Bz | H | $CH_3$ | OH | OH | H | H |
| VIII-44-2 | $^t$Bu | H | H | $CH_3$ | Bz | H | $CH_3$ | OH | OH | H | H |
| VIII-44-3 | $^t$Bu | H | H | $CH(CH_3)_2$ | Bz | H | $CH_3$ | OH | OH | H | H |
| VIII-44-4 | $^t$Bu | H | H | $CH_2CH(CH_3)_2$ | Bz | H | $CH_3$ | OH | OH | H | H |
| VIII-44-5 | $^t$Bu | H | H | $CH_2Ph$ | Bz | H | $CH_3$ | OH | OH | H | H |
| VIII-44-6 | $^t$Bu | H | H | $CH_2$-indol-3-yl | Bz | H | $CH_3$ | OH | OH | H | H |
| VIII-44-7 | $^t$Bu | H | H | $CH_2CH_2SCH_3$ | Bz | H | $CH_3$ | OH | OH | H | H |
| VIII-44-8 | $^t$Bu | * | H | * | Bz | H | $CH_3$ | OH | OH | H | H |

*$R^2$ and $R^{3b}$ joined together by $(CH_2)_3$ to form five-membered ring.

TABLE VIII-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| VIII-45-1 | Ph | H | H | H | Bz | H | $CH_3$ | OH | OH | H | H |
| VIII-45-2 | Ph | H | H | $CH_3$ | Bz | H | $CH_3$ | OH | OH | H | H |
| VIII-45-3 | Ph | H | H | $CH(CH_3)_2$ | Bz | H | $CH_3$ | OH | OH | H | H |
| VIII-45-4 | Ph | H | H | $CH_2CH(CH_3)_2$ | Bz | H | $CH_3$ | OH | OH | H | H |
| VIII-45-5 | Ph | H | H | $CH_2Ph$ | Bz | H | $CH_3$ | OH | OH | H | H |
| VIII-45-6 | Ph | H | H | $CH_2$-indol-3-yl | Bz | H | $CH_3$ | OH | OH | H | H |
| VIII-45-7 | Ph | H | H | $CH_2CH_2SCH_3$ | Bz | H | $CH_3$ | OH | OH | H | H |
| VIII-45-8 | Ph | * | H | * | Bz | H | $CH_3$ | OH | OH | H | H |

*$R^2$ and $R^{3b}$ joined together by $(CH_2)_3$ to form five-membered ring.

TABLE VIII-46

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-46-1 | p-Me—Ph | H | H | H | Bz | H | CH$_3$ | OH | OH | H | H |
| VIII-46-2 | p-Me—Ph | H | H | CH$_3$ | Bz | H | CH$_3$ | OH | OH | H | H |
| VIII-46-3 | p-Me—Ph | H | H | CH(CH$_3$)$_2$ | Bz | H | CH$_3$ | OH | OH | H | H |
| VIII-46-4 | p-Me—Ph | H | H | CH$_2$CH(CH$_3$)$_2$ | Bz | H | CH$_3$ | OH | OH | H | H |
| VIII-46-5 | p-Me—Ph | H | H | CH$_2$Ph | Bz | H | CH$_3$ | OH | OH | H | H |
| VIII-46-6 | p-Me—Ph | H | H | CH$_2$-indol-3-yl | Bz | H | CH$_3$ | OH | OH | H | H |
| VIII-46-7 | p-Me—Ph | H | H | CH$_2$CH$_2$SCH$_3$ | Bz | H | CH$_3$ | OH | OH | H | H |
| VIII-46-8 | p-Me—Ph | * | H | * | Bz | H | CH$_3$ | OH | OH | H | H |

*R$^2$ and R$^{3b}$ joined together by (CH$_2$)$_3$ to form five-membered ring.

TABLE VIII-47

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-47-1 | p-F—Ph | H | H | H | Bz | H | CH$_3$ | OH | OH | H | H |
| VIII-47-2 | p-F—Ph | H | H | CH$_3$ | Bz | H | CH$_3$ | OH | OH | H | H |
| VIII-47-3 | p-F—Ph | H | H | CH(CH$_3$)$_2$ | Bz | H | CH$_3$ | OH | OH | H | H |
| VIII-47-4 | p-F—Ph | H | H | CH$_2$CH(CH$_3$)$_2$ | Bz | H | CH$_3$ | OH | OH | H | H |
| VIII-47-5 | p-F—Ph | H | H | CH$_2$Ph | Bz | H | CH$_3$ | OH | OH | H | H |
| VIII-47-6 | p-F—Ph | H | H | CH$_2$-indol-3-yl | Bz | H | CH$_3$ | OH | OH | H | H |
| VIII-47-7 | p-F—Ph | H | H | CH$_2$CH$_2$SCH$_3$ | Bz | H | CH$_3$ | OH | OH | H | H |
| VIII-47-8 | p-F—Ph | * | H | * | Bz | H | CH$_3$ | OH | OH | H | H |

*R$^2$ and R$^{3b}$ joined together by (CH$_2$)$_3$ to form five-membered ring.

TABLE VIII-48

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-48-1 | p-Cl—Ph | H | H | H | Bz | H | CH$_3$ | OH | OH | H | H |
| VIII-48-2 | p-Cl—Ph | H | H | CH$_3$ | Bz | H | CH$_3$ | OH | OH | H | H |
| VIII-48-3 | p-Cl—Ph | H | H | CH(CH$_3$)$_2$ | Bz | H | CH$_3$ | OH | OH | H | H |
| VIII-48-4 | p-Cl—Ph | H | H | CH$_2$CH(CH$_3$)$_2$ | Bz | H | CH$_3$ | OH | OH | H | H |
| VIII-48-5 | p-Cl—Ph | H | H | CH$_2$Ph | Bz | H | CH$_3$ | OH | OH | H | H |
| VIII-48-6 | p-Cl—Ph | H | H | CH$_2$-indol-3-yl | Bz | H | CH$_3$ | OH | OH | H | H |
| VIII-48-7 | p-Cl—Ph | H | H | CH$_2$CH$_2$SCH$_3$ | Bz | H | CH$_3$ | OH | OH | H | H |
| VIII-48-8 | p-Cl—Ph | * | H | * | Bz | H | CH$_3$ | OH | OH | H | H |

*R$^2$ and R$^{3b}$ joined together by (CH$_2$)$_3$ to form five-membered ring.

TABLE VIII-49

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-49-1 | p-Br—Ph | H | H | H | Bz | H | CH$_3$ | OH | OH | H | H |
| VIII-49-2 | p-Br—Ph | H | H | CH$_3$ | Bz | H | CH$_3$ | OH | OH | H | H |
| VIII-49-3 | p-Br—Ph | H | H | CH(CH$_3$)$_2$ | Bz | H | CH$_3$ | OH | OH | H | H |
| VIII-49-4 | p-Br—Ph | H | H | CH$_2$CH(CH$_3$)$_2$ | Bz | H | CH$_3$ | OH | OH | H | H |
| VIII-49-5 | p-Br—Ph | H | H | CH$_2$Ph | Bz | H | CH$_3$ | OH | OH | H | H |
| VIII-49-6 | p-Br—Ph | H | H | CH$_2$-indol-3-yl | Bz | H | CH$_3$ | OH | OH | H | H |
| VIII-49-7 | p-Br—Ph | H | H | CH$_2$CH$_2$SCH$_3$ | Bz | H | CH$_3$ | OH | OH | H | H |
| VIII-49-8 | p-Br—Ph | * | H | * | Bz | H | CH$_3$ | OH | OH | H | H |

*R$^2$ and R$^{3b}$ joined together by (CH$_2$)$_3$ to form five-membered ring.

TABLE VIII-50

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| VIII-50-1 | p-I—Ph | H | H | H | Bz | H | CH$_3$ | OH | OH | H | H |
| VIII-50-2 | p-I—Ph | H | H | CH$_3$ | Bz | H | CH$_3$ | OH | OH | H | H |
| VIII-50-3 | p-I—Ph | H | H | CH(CH$_3$)$_2$ | Bz | H | CH$_3$ | OH | OH | H | H |
| VIII-50-4 | p-I—Ph | H | H | CH$_2$CH(CH$_3$)$_2$ | Bz | H | CH$_3$ | OH | OH | H | H |
| VIII-50-5 | p-I—Ph | H | H | CH$_2$Ph | Bz | H | CH$_3$ | OH | OH | H | H |

TABLE VIII-50-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| VIII-50-6 | p-I—Ph | H | H | CH₂-indol-3-yl | Bz | H | CH₃ | OH | OH | H | H |
| VIII-50-7 | p-I—Ph | H | H | CH₂CH₂SCH₃ | Bz | H | CH₃ | OH | OH | H | H |
| VIII-50-8 | p-I—Ph | * | H | * | Bz | H | CH₃ | OH | OH | H | H |

*R² and R³ᵇ joined together by (CH₂)₃ to form five-membered ring.

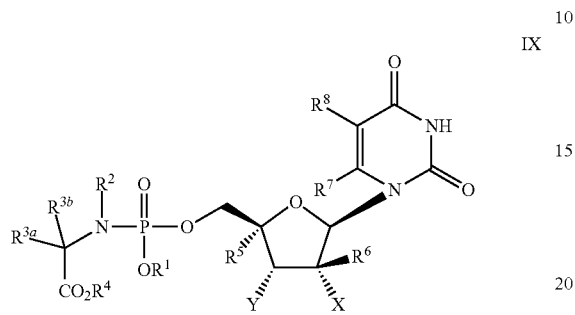

IX

TABLE IX-1

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-1-1 | CH₃ | H | H | H | CH₃ | H | CH₃ | F | OH | H | H |
| IX-1-2 | CH₃ | H | H | CH₃ | CH₃ | H | CH₃ | F | OH | H | H |
| IX-1-3 | CH₃ | H | H | CH(CH₃)₂ | CH₃ | H | CH₃ | F | OH | H | H |
| IX-1-4 | CH₃ | H | H | CH₂CH(CH₃)₂ | CH₃ | H | CH₃ | F | OH | H | H |
| IX-1-5 | CH₃ | H | H | CH₂Ph | CH₃ | H | CH₃ | F | OH | H | H |
| IX-1-6 | CH₃ | H | H | CH₂-indol-3-yl | CH₃ | H | CH₃ | F | OH | H | H |
| IX-1-7 | CH₃ | H | H | CH₂CH₂SCH₃ | CH₃ | H | CH₃ | F | OH | H | H |
| IX-1-8 | CH₃ | * | H | * | CH₃ | H | CH₃ | F | OH | H | H |

*R² and R³ᵇ joined together by (CH₂)₃ to form five-membered ring.

TABLE IX-2

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-2-1 | Et | H | H | H | CH₃ | H | CH₃ | F | OH | H | H |
| IX-2-2 | Et | H | H | CH₃ | CH₃ | H | CH₃ | F | OH | H | H |
| IX-2-3 | Et | H | H | CH(CH₃)₂ | CH₃ | H | CH₃ | F | OH | H | H |
| IX-2-4 | Et | H | H | CH₂CH(CH₃)₂ | CH₃ | H | CH₃ | F | OH | H | H |
| IX-2-5 | Et | H | H | CH₂Ph | CH₃ | H | CH₃ | F | OH | H | H |
| IX-2-6 | Et | H | H | CH₂-indol-3-yl | CH₃ | H | CH₃ | F | OH | H | H |
| IX-2-7 | Et | H | H | CH₂CH₂SCH₃ | CH₃ | H | CH₃ | F | OH | H | H |
| IX-2-8 | Et | * | H | * | CH₃ | H | CH₃ | F | OH | H | H |

*R² and R³ᵇ joined together by (CH₂)₃ to form five-membered ring.

TABLE IX-3

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-3-1 | ⁱPr | H | H | H | CH₃ | H | CH₃ | F | OH | H | H |
| IX-3-2 | ⁱPr | H | H | CH₃ | CH₃ | H | CH₃ | F | OH | H | H |
| IX-3-3 | ⁱPr | H | H | CH(CH₃)₂ | CH₃ | H | CH₃ | F | OH | H | H |
| IX-3-4 | ⁱPr | H | H | CH₂CH(CH₃)₂ | CH₃ | H | CH₃ | F | OH | H | H |
| IX-3-5 | ⁱPr | H | H | CH₂Ph | CH₃ | H | CH₃ | F | OH | H | H |
| IX-3-6 | ⁱPr | H | H | CH₂-indol-3-yl | CH₃ | H | CH₃ | F | OH | H | H |
| IX-3-7 | ⁱPr | H | H | CH₂CH₂SCH₃ | CH₃ | H | CH₃ | F | OH | H | H |
| IX-3-8 | ⁱPr | * | H | * | CH₃ | H | CH₃ | F | OH | H | H |

*R² and R³ᵇ joined together by (CH₂)₃ to form five-membered ring.

TABLE IX-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-4-1 | tBu | H | H | H | CH₃ | H | CH₃ | F | OH | H | H |
| IX-4-2 | tBu | H | H | CH₃ | CH₃ | H | CH₃ | F | OH | H | H |
| IX-4-3 | tBu | H | H | CH(CH₃)₂ | CH₃ | H | CH₃ | F | OH | H | H |
| IX-4-4 | tBu | H | H | CH₂CH(CH₃)₂ | CH₃ | H | CH₃ | F | OH | H | H |
| IX-4-5 | tBu | H | H | CH₂Ph | CH₃ | H | CH₃ | F | OH | H | H |
| IX-4-6 | tBu | H | H | CH₂-indol-3-yl | CH₃ | H | CH₃ | F | OH | H | H |
| IX-4-7 | tBu | H | H | CH₂CH₂SCH₃ | CH₃ | H | CH₃ | F | OH | H | H |
| IX-4-8 | tBu | * | H | * | CH₃ | H | CH₃ | F | OH | H | H |

*$R^2$ and $R^{3b}$ joined together by (CH₂)₃ to form five-membered ring.

TABLE IX-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-5-1 | Ph | H | H | H | CH₃ | H | CH₃ | F | OH | H | H |
| IX-5-2 | Ph | H | H | CH₃ | CH₃ | H | CH₃ | F | OH | H | H |
| IX-5-3 | Ph | H | H | CH(CH₃)₂ | CH₃ | H | CH₃ | F | OH | H | H |
| IX-5-4 | Ph | H | H | CH₂CH(CH₃)₂ | CH₃ | H | CH₃ | F | OH | H | H |
| IX-5-5 | Ph | H | H | CH₂Ph | CH₃ | H | CH₃ | F | OH | H | H |
| IX-5-6 | Ph | H | H | CH₂-indol-3-yl | CH₃ | H | CH₃ | F | OH | H | H |
| IX-5-7 | Ph | H | H | CH₂CH₂SCH₃ | CH₃ | H | CH₃ | F | OH | H | H |
| IX-5-8 | Ph | * | H | * | CH₃ | H | CH₃ | F | OH | H | H |

*$R^2$ and $R^{3b}$ joined together by (CH₂)₃ to form five-membered ring.

TABLE IX-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-6-1 | p-Me—Ph | H | H | H | CH₃ | H | CH₃ | F | OH | H | H |
| IX-6-2 | p-Me—Ph | H | H | CH₃ | CH₃ | H | CH₃ | F | OH | H | H |
| IX-6-3 | p-Me—Ph | H | H | CH(CH₃)₂ | CH₃ | H | CH₃ | F | OH | H | H |
| IX-6-4 | p-Me—Ph | H | H | CH₂CH(CH₃)₂ | CH₃ | H | CH₃ | F | OH | H | H |
| IX-6-5 | p-Me—Ph | H | H | CH₂Ph | CH₃ | H | CH₃ | F | OH | H | H |
| IX-6-6 | p-Me—Ph | H | H | CH₂-indol-3-yl | CH₃ | H | CH₃ | F | OH | H | H |
| IX-6-7 | p-Me—Ph | H | H | CH₂CH₂SCH₃ | CH₃ | H | CH₃ | F | OH | H | H |
| IX-6-8 | p-Me—Ph | * | H | * | CH₃ | H | CH₃ | F | OH | H | H |

*$R^2$ and $R^{3b}$ joined together by (CH₂)₃ to form five-membered ring.

TABLE IX-7

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-7-1 | p-F—Ph | H | H | H | CH₃ | H | CH₃ | F | OH | H | H |
| IX-7-2 | p-F—Ph | H | H | CH₃ | CH₃ | H | CH₃ | F | OH | H | H |
| IX-7-3 | p-F—Ph | H | H | CH(CH₃)₂ | CH₃ | H | CH₃ | F | OH | H | H |
| IX-7-4 | p-F—Ph | H | H | CH₂CH(CH₃)₂ | CH₃ | H | CH₃ | F | OH | H | H |
| IX-7-6 | p-F—Ph | H | H | CH₂Ph | CH₃ | H | CH₃ | F | OH | H | H |
| IX-7-7 | p-F—Ph | H | H | CH₂-indol-3-yl | CH₃ | H | CH₃ | F | OH | H | H |
| IX-7-8 | p-F—Ph | H | H | CH₂CH₂SCH₃ | CH₃ | H | CH₃ | F | OH | H | H |
| IX-7-20 | p-F—Ph | * | H | * | CH₃ | H | CH₃ | F | OH | H | H |

*$R^2$ and $R^{3b}$ joined together by (CH₂)₃ to form five-membered ring.

TABLE IX-8

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-8-1 | p-Cl—Ph | H | H | H | CH₃ | H | CH₃ | F | OH | H | H |
| IX-8-2 | p-Cl—Ph | H | H | CH₃ | CH₃ | H | CH₃ | F | OH | H | H |
| IX-8-3 | p-Cl—Ph | H | H | CH(CH₃)₂ | CH₃ | H | CH₃ | F | OH | H | H |
| IX-8-4 | p-Cl—Ph | H | H | CH₂CH(CH₃)₂ | CH₃ | H | CH₃ | F | OH | H | H |
| IX-8-5 | p-Cl—Ph | H | H | CH₂Ph | CH₃ | H | CH₃ | F | OH | H | H |

TABLE IX-8-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-8-6 | p-Cl—Ph | H | H | CH$_2$-indol-3-yl | CH$_3$ | H | CH$_3$ | F | OH | H | H |
| IX-8-7 | p-Cl—Ph | H | H | CH$_2$CH$_2$SCH$_3$ | CH$_3$ | H | CH$_3$ | F | OH | H | H |
| IX-8-8 | p-Cl—Ph | * | H | * | CH$_3$ | H | CH$_3$ | F | OH | H | H |

*$R^2$ and $R^{3b}$ joined together by (CH$_2$)$_3$ to form five-membered ring.

TABLE IX-9

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-9-1 | p-Br—Ph | H | H | H | CH$_3$ | H | CH$_3$ | F | OH | H | H |
| IX-9-2 | p-Br—Ph | H | H | CH$_3$ | CH$_3$ | H | CH$_3$ | F | OH | H | H |
| IX-9-3 | p-Br—Ph | H | H | CH(CH$_3$)$_2$ | CH$_3$ | H | CH$_3$ | F | OH | H | H |
| IX-9-4 | p-Br—Ph | H | H | CH$_2$CH(CH$_3$)$_2$ | CH$_3$ | H | CH$_3$ | F | OH | H | H |
| IX-9-6 | p-Br—Ph | H | H | CH$_2$Ph | CH$_3$ | H | CH$_3$ | F | OH | H | H |
| IX-9-7 | p-Br—Ph | H | H | CH$_2$-indol-3-yl | CH$_3$ | H | CH$_3$ | F | OH | H | H |
| IX-9-8 | p-Br—Ph | H | H | CH$_2$CH$_2$SCH$_3$ | CH$_3$ | H | CH$_3$ | F | OH | H | H |
| IX-9-20 | p-Br—Ph | * | H | * | CH$_3$ | H | CH$_3$ | F | OH | H | H |

*$R^2$ and $R^{3b}$ joined together by (CH$_2$)$_3$ to form five-membered ring.

TABLE IX-10

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-10-1 | p-I—Ph | H | H | H | CH$_3$ | H | CH$_3$ | F | OH | H | H |
| IX-10-2 | p-I—Ph | H | H | CH$_3$ | CH$_3$ | H | CH$_3$ | F | OH | H | H |
| IX-10-3 | p-I—Ph | H | H | CH(CH$_3$)$_2$ | CH$_3$ | H | CH$_3$ | F | OH | H | H |
| IX-10-4 | p-I—Ph | H | H | CH$_2$CH(CH$_3$)$_2$ | CH$_3$ | H | CH$_3$ | F | OH | H | H |
| IX-10-5 | p-I—Ph | H | H | CH$_2$Ph | CH$_3$ | H | CH$_3$ | F | OH | H | H |
| IX-10-6 | p-I—Ph | H | H | CH$_2$-indol-3-yl | CH$_3$ | H | CH$_3$ | F | OH | H | H |
| IX-10-7 | p-I—Ph | H | H | CH$_2$CH$_2$SCH$_3$ | CH$_3$ | H | CH$_3$ | F | OH | H | H |
| IX-10-8 | p-I—Ph | * | H | * | CH$_3$ | H | CH$_3$ | F | OH | H | H |

*$R^2$ and $R^{3b}$ joined together by (CH$_2$)$_3$ to form five-membered ring.

TABLE IX-11

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-11-1 | CH$_3$ | H | H | H | Et | H | CH$_3$ | F | OH | H | H |
| IX-11-2 | CH$_3$ | H | H | CH$_3$ | Et | H | CH$_3$ | F | OH | H | H |
| IX-11-3 | CH$_3$ | H | H | CH(CH$_3$)$_2$ | Et | H | CH$_3$ | F | OH | H | H |
| IX-11-4 | CH$_3$ | H | H | CH$_2$CH(CH$_3$)$_2$ | Et | H | CH$_3$ | F | OH | H | H |
| IX-11-5 | CH$_3$ | H | H | CH$_2$Ph | Et | H | CH$_3$ | F | OH | H | H |
| IX-11-6 | CH$_3$ | H | H | CH$_2$-indol-3-yl | Et | H | CH$_3$ | F | OH | H | H |
| IX-11-7 | CH$_3$ | H | H | CH$_2$CH$_2$SCH$_3$ | Et | H | CH$_3$ | F | OH | H | H |
| IX-11-8 | CH$_3$ | * | H | * | Et | H | CH$_3$ | F | OH | H | H |

*$R^2$ and $R^{3b}$ joined together by (CH$_2$)$_3$ to form five-membered ring.

TABLE IX-12

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-12-1 | Et | H | H | H | Et | H | CH$_3$ | F | OH | H | H |
| IX-12-2 | Et | H | H | CH$_3$ | Et | H | CH$_3$ | F | OH | H | H |
| IX-12-3 | Et | H | H | CH(CH$_3$)$_2$ | Et | H | CH$_3$ | F | OH | H | H |
| IX-12-4 | Et | H | H | CH$_2$CH(CH$_3$)$_2$ | Et | H | CH$_3$ | F | OH | H | H |
| IX-12-5 | Et | H | H | CH$_2$Ph | Et | H | CH$_3$ | F | OH | H | H |
| IX-12-6 | Et | H | H | CH$_2$-indol-3-yl | Et | H | CH$_3$ | F | OH | H | H |
| IX-12-7 | Et | H | H | CH$_2$CH$_2$SCH$_3$ | Et | H | CH$_3$ | F | OH | H | H |
| IX-12-8 | Et | * | H | * | Et | H | CH$_3$ | F | OH | H | H |

*$R^2$ and $R^{3b}$ joined together by (CH$_2$)$_3$ to form five-membered ring.

TABLE IX-13

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-13-1 | $^i$Pr | H | H | H | Et | H | CH$_3$ | F | OH | H | H |
| IX-13-2 | $^i$Pr | H | H | CH$_3$ | Et | H | CH$_3$ | F | OH | H | H |
| IX-13-3 | $^i$Pr | H | H | CH(CH$_3$)$_2$ | Et | H | CH$_3$ | F | OH | H | H |
| IX-13-4 | $^i$Pr | H | H | CH$_2$CH(CH$_3$)$_2$ | Et | H | CH$_3$ | F | OH | H | H |
| IX-13-5 | $^i$Pr | H | H | CH$_2$Ph | Et | H | CH$_3$ | F | OH | H | H |
| IX-13-6 | $^i$Pr | H | H | CH$_2$-indol-3-yl | Et | H | CH$_3$ | F | OH | H | H |
| IX-13-7 | $^i$Pr | H | H | CH$_2$CH$_2$SCH$_3$ | Et | H | CH$_3$ | F | OH | H | H |
| IX-13-8 | $^i$Pr | * | H | * | Et | H | CH$_3$ | F | OH | H | H |

*$R^2$ and $R^{3b}$ joined together by (CH$_2$)$_3$ to form five-membered ring.

TABLE IX-14

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-14-1 | $^t$Bu | H | H | H | Et | H | CH$_3$ | F | OH | H | H |
| IX-14-2 | $^t$Bu | H | H | CH$_3$ | Et | H | CH$_3$ | F | OH | H | H |
| IX-14-3 | $^t$Bu | H | H | CH(CH$_3$)$_2$ | Et | H | CH$_3$ | F | OH | H | H |
| IX-14-4 | $^t$Bu | H | H | CH$_2$CH(CH$_3$)$_2$ | Et | H | CH$_3$ | F | OH | H | H |
| IX-14-5 | $^t$Bu | H | H | CH$_2$Ph | Et | H | CH$_3$ | F | OH | H | H |
| IX-14-6 | $^t$Bu | H | H | CH$_2$-indol-3-yl | Et | H | CH$_3$ | F | OH | H | H |
| IX-14-7 | $^t$Bu | H | H | CH$_2$CH$_2$SCH$_3$ | Et | H | CH$_3$ | F | OH | H | H |
| IX-14-8 | $^t$Bu | * | H | * | Et | H | CH$_3$ | F | OH | H | H |

*$R^2$ and $R^{3b}$ joined together by (CH$_2$)$_3$ to form five-membered ring.

TABLE IX-15

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-15-1 | Ph | H | H | H | Et | H | CH$_3$ | F | OH | H | H |
| IX-15-2 | Ph | H | H | CH$_3$ | Et | H | CH$_3$ | F | OH | H | H |
| IX-15-3 | Ph | H | H | CH(CH$_3$)$_2$ | Et | H | CH$_3$ | F | OH | H | H |
| IX-15-4 | Ph | H | H | CH$_2$CH(CH$_3$)$_2$ | Et | H | CH$_3$ | F | OH | H | H |
| IX-15-5 | Ph | H | H | CH$_2$Ph | Et | H | CH$_3$ | F | OH | H | H |
| IX-15-6 | Ph | H | H | CH$_2$-indol-3-yl | Et | H | CH$_3$ | F | OH | H | H |
| IX-15-7 | Ph | H | H | CH$_2$CH$_2$SCH$_3$ | Et | H | CH$_3$ | F | OH | H | H |
| IX-15-8 | Ph | * | H | * | Et | H | CH$_3$ | F | OH | H | H |

*$R^2$ and $R^{3b}$ joined together by (CH$_2$)$_3$ to form five-membered ring.

TABLE IX-16

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-16-1 | p-Me—Ph | H | H | H | Et | H | CH$_3$ | F | OH | H | H |
| IX-16-2 | p-Me—Ph | H | H | CH$_3$ | Et | H | CH$_3$ | F | OH | H | H |
| IX-16-3 | p-Me—Ph | H | H | CH(CH$_3$)$_2$ | Et | H | CH$_3$ | F | OH | H | H |
| IX-16-4 | p-Me—Ph | H | H | CH$_2$CH(CH$_3$)$_2$ | Et | H | CH$_3$ | F | OH | H | H |
| IX-16-5 | p-Me—Ph | H | H | CH$_2$Ph | Et | H | CH$_3$ | F | OH | H | H |
| IX-16-6 | p-Me—Ph | H | H | CH$_2$-indol-3-yl | Et | H | CH$_3$ | F | OH | H | H |
| IX-16-7 | p-Me—Ph | H | H | CH$_2$CH$_2$SCH$_3$ | Et | H | CH$_3$ | F | OH | H | H |
| IX-16-8 | p-Me—Ph | * | H | * | Et | H | CH$_3$ | F | OH | H | H |

*$R^2$ and $R^{3b}$ joined together by (CH$_2$)$_3$ to form five-membered ring.

TABLE IX-17

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-17-1 | p-F—Ph | H | H | H | Et | H | CH$_3$ | F | OH | H | H |
| IX-17-2 | p-F—Ph | H | H | CH$_3$ | Et | H | CH$_3$ | F | OH | H | H |
| IX-17-3 | p-F—Ph | H | H | CH(CH$_3$)$_2$ | Et | H | CH$_3$ | F | OH | H | H |
| IX-17-4 | p-F—Ph | H | H | CH$_2$CH(CH$_3$)$_2$ | Et | H | CH$_3$ | F | OH | H | H |
| IX-17-5 | p-F—Ph | H | H | CH$_2$Ph | Et | H | CH$_3$ | F | OH | H | H |

TABLE IX-17-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-17-6 | p-F—Ph | H | H | CH₂-indol-3-yl | Et | H | CH₃ | F | OH | H | H |
| IX-17-7 | p-F—Ph | H | H | CH₂CH₂SCH₃ | Et | H | CH₃ | F | OH | H | H |
| IX-17-8 | p-F—Ph | * | H | * | Et | H | CH₃ | F | OH | H | H |

*R² and R³ᵇ joined together by (CH₂)₃ to form five-membered ring.

TABLE IX-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-18-1 | p-Cl—Ph | H | H | H | Et | H | CH₃ | F | OH | H | H |
| IX-18-2 | p-Cl—Ph | H | H | CH₃ | Et | H | CH₃ | F | OH | H | H |
| IX-18-3 | p-Cl—Ph | H | H | CH(CH₃)₂ | Et | H | CH₃ | F | OH | H | H |
| IX-18-4 | p-Cl—Ph | H | H | CH₂CH(CH₃)₂ | Et | H | CH₃ | F | OH | H | H |
| IX-18-5 | p-Cl—Ph | H | H | CH₂Ph | Et | H | CH₃ | F | OH | H | H |
| IX-18-6 | p-Cl—Ph | H | H | CH₂-indol-3-yl | Et | H | CH₃ | F | OH | H | H |
| IX-18-7 | p-Cl—Ph | H | H | CH₂CH₂SCH₃ | Et | H | CH₃ | F | OH | H | H |
| IX-18-8 | p-Cl—Ph | * | H | * | Et | H | CH₃ | F | OH | H | H |

*R² and R³ᵇ joined together by (CH₂)₃ to form five-membered ring.

TABLE IX-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-19-1 | p-Br—Ph | H | H | H | Et | H | CH₃ | F | OH | H | H |
| IX-19-2 | p-Br—Ph | H | H | CH₃ | Et | H | CH₃ | F | OH | H | H |
| IX-19-3 | p-Br—Ph | H | H | CH(CH₃)₂ | Et | H | CH₃ | F | OH | H | H |
| IX-19-4 | p-Br—Ph | H | H | CH₂CH(CH₃)₂ | Et | H | CH₃ | F | OH | H | H |
| IX-19-5 | p-Br—Ph | H | H | CH₂Ph | Et | H | CH₃ | F | OH | H | H |
| IX-19-6 | p-Br—Ph | H | H | CH₂-indol-3-yl | Et | H | CH₃ | F | OH | H | H |
| IX-19-7 | p-Br—Ph | H | H | CH₂CH₂SCH₃ | Et | H | CH₃ | F | OH | H | H |
| IX-19-8 | p-Br—Ph | * | H | * | Et | H | CH₃ | F | OH | H | H |

*R² and R³ᵇ joined together by (CH₂)₃ to form five-membered ring.

TABLE IX-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-20-1 | p-I—Ph | H | H | H | Et | H | CH₃ | F | OH | H | H |
| IX-20-2 | p-I—Ph | H | H | CH₃ | Et | H | CH₃ | F | OH | H | H |
| IX-20-3 | p-I—Ph | H | H | CH(CH₃)₂ | Et | H | CH₃ | F | OH | H | H |
| IX-20-4 | p-I—Ph | H | H | CH₂CH(CH₃)₂ | Et | H | CH₃ | F | OH | H | H |
| IX-20-5 | p-I—Ph | H | H | CH₂Ph | Et | H | CH₃ | F | OH | H | H |
| IX-20-6 | p-I—Ph | H | H | CH₂-indol-3-yl | Et | H | CH₃ | F | OH | H | H |
| IX-20-7 | p-I—Ph | H | H | CH₂CH₂SCH₃ | Et | H | CH₃ | F | OH | H | H |
| IX-20-8 | p-I—Ph | * | H | * | Et | H | CH₃ | F | OH | H | H |

*R² and R³ᵇ joined together by (CH₂)₃ to form five-membered ring.

TABLE IX-21

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-21-1 | CH₃ | H | H | H | $^i$Pr | H | CH₃ | F | OH | H | H |
| IX-21-2 | CH₃ | H | H | CH₃ | $^i$Pr | H | CH₃ | F | OH | H | H |
| IX-21-3 | CH₃ | H | H | CH(CH₃)₂ | $^i$Pr | H | CH₃ | F | OH | H | H |
| IX-21-4 | CH₃ | H | H | CH₂CH(CH₃)₂ | $^i$Pr | H | CH₃ | F | OH | H | H |
| IX-21-5 | CH₃ | H | H | CH₂Ph | $^i$Pr | H | CH₃ | F | OH | H | H |
| IX-21-6 | CH₃ | H | H | CH₂-indol-3-yl | $^i$Pr | H | CH₃ | F | OH | H | H |
| IX-21-7 | CH₃ | H | H | CH₂CH₂SCH₃ | $^i$Pr | H | CH₃ | F | OH | H | H |
| IX-21-8 | CH₃ | * | H | * | $^i$Pr | H | CH₃ | F | OH | H | H |

*R² and R³ᵇ joined together by (CH₂)₃ to form five-membered ring.

TABLE IX-22

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-22-1 | Et | H | H | H | $^i$Pr | H | $CH_3$ | F | OH | H | H |
| IX-22-2 | Et | H | H | $CH_3$ | $^i$Pr | H | $CH_3$ | F | OH | H | H |
| IX-22-3 | Et | H | H | $CH(CH_3)_2$ | $^i$Pr | H | $CH_3$ | F | OH | H | H |
| IX-22-4 | Et | H | H | $CH_2CH(CH_3)_2$ | $^i$Pr | H | $CH_3$ | F | OH | H | H |
| IX-22-5 | Et | H | H | $CH_2Ph$ | $^i$Pr | H | $CH_3$ | F | OH | H | H |
| IX-22-6 | Et | H | H | $CH_2$-indol-3-yl | $^i$Pr | H | $CH_3$ | F | OH | H | H |
| IX-22-7 | Et | H | H | $CH_2CH_2SCH_3$ | $^i$Pr | H | $CH_3$ | F | OH | H | H |
| IX-22-8 | Et | * | H | * | $^i$Pr | H | $CH_3$ | F | OH | H | H |

*$R^2$ and $R^{3b}$ joined together by $(CH_2)_3$ to form five-membered ring.

TABLE IX-23

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-23-1 | $^i$Pr | H | H | H | $^i$Pr | H | $CH_3$ | F | OH | H | H |
| IX-23-2 | $^i$Pr | H | H | $CH_3$ | $^i$Pr | H | $CH_3$ | F | OH | H | H |
| IX-23-3 | $^i$Pr | H | H | $CH(CH_3)_2$ | $^i$Pr | H | $CH_3$ | F | OH | H | H |
| IX-23-4 | $^i$Pr | H | H | $CH_2CH(CH_3)_2$ | $^i$Pr | H | $CH_3$ | F | OH | H | H |
| IX-23-5 | $^i$Pr | H | H | $CH_2Ph$ | $^i$Pr | H | $CH_3$ | F | OH | H | H |
| IX-23-6 | $^i$Pr | H | H | $CH_2$-indol-3-yl | $^i$Pr | H | $CH_3$ | F | OH | H | H |
| IX-23-7 | $^i$Pr | H | H | $CH_2CH_2SCH_3$ | $^i$Pr | H | $CH_3$ | F | OH | H | H |
| IX-23-8 | $^i$Pr | * | H | * | $^i$Pr | H | $CH_3$ | F | OH | H | H |

*$R^2$ and $R^{3b}$ joined together by $(CH_2)_3$ to form five-membered ring.

TABLE IX-24

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-24-1 | $^t$Bu | H | H | H | $^i$Pr | H | $CH_3$ | F | OH | H | H |
| IX-24-2 | $^t$Bu | H | H | $CH_3$ | $^i$Pr | H | $CH_3$ | F | OH | H | H |
| IX-24-3 | $^t$Bu | H | H | $CH(CH_3)_2$ | $^i$Pr | H | $CH_3$ | F | OH | H | H |
| IX-24-4 | $^t$Bu | H | H | $CH_2CH(CH_3)_2$ | $^i$Pr | H | $CH_3$ | F | OH | H | H |
| IX-24-5 | $^t$Bu | H | H | $CH_2Ph$ | $^i$Pr | H | $CH_3$ | F | OH | H | H |
| IX-24-6 | $^t$Bu | H | H | $CH_2$-indol-3-yl | $^i$Pr | H | $CH_3$ | F | OH | H | H |
| IX-24-7 | $^t$Bu | H | H | $CH_2CH_2SCH_3$ | $^i$Pr | H | $CH_3$ | F | OH | H | H |
| IX-24-8 | $^t$Bu | * | H | * | $^i$Pr | H | $CH_3$ | F | OH | H | H |

*$R^2$ and $R^{3b}$ joined together by $(CH_2)_3$ to form five-membered ring.

TABLE IX-25

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-25-1 | Ph | H | H | H | $^i$Pr | H | $CH_3$ | F | OH | H | H |
| IX-25-2 | Ph | H | H | $CH_3$ | $^i$Pr | H | $CH_3$ | F | OH | H | H |
| IX-25-3 | Ph | H | H | $CH(CH_3)_2$ | $^i$Pr | H | $CH_3$ | F | OH | H | H |
| IX-25-4 | Ph | H | H | $CH_2CH(CH_3)_2$ | $^i$Pr | H | $CH_3$ | F | OH | H | H |
| IX-25-5 | Ph | H | H | $CH_2Ph$ | $^i$Pr | H | $CH_3$ | F | OH | H | H |
| IX-25-6 | Ph | H | H | $CH_2$-indol-3-yl | $^i$Pr | H | $CH_3$ | F | OH | H | H |
| IX-25-7 | Ph | H | H | $CH_2CH_2SCH_3$ | $^i$Pr | H | $CH_3$ | F | OH | H | H |
| IX-25-8 | Ph | * | H | * | $^i$Pr | H | $CH_3$ | F | OH | H | H |

*$R^2$ and $R^{3b}$ joined together by $(CH_2)_3$ to form five-membered ring.

TABLE IX-26

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-26-1 | p-Me—Ph | H | H | H | $^i$Pr | H | $CH_3$ | F | OH | H | H |
| IX-26-2 | p-Me—Ph | H | H | $CH_3$ | $^i$Pr | H | $CH_3$ | F | OH | H | H |
| IX-26-3 | p-Me—Ph | H | H | $CH(CH_3)_2$ | $^i$Pr | H | $CH_3$ | F | OH | H | H |
| IX-26-4 | p-Me—Ph | H | H | $CH_2CH(CH_3)_2$ | $^i$Pr | H | $CH_3$ | F | OH | H | H |
| IX-26-5 | p-Me—Ph | H | H | $CH_2Ph$ | $^i$Pr | H | $CH_3$ | F | OH | H | H |
| IX-26-6 | p-Me—Ph | H | H | $CH_2$-indol-3-yl | $^i$Pr | H | $CH_3$ | F | OH | H | H |
| IX-26-7 | p-Me—Ph | H | H | $CH_2CH_2SCH_3$ | $^i$Pr | H | $CH_3$ | F | OH | H | H |
| IX-26-8 | p-Me—Ph | * | H | * | $^i$Pr | H | $CH_3$ | F | OH | H | H |

*$R^2$ and $R^{3b}$ joined together by $(CH_2)_3$ to form five-membered ring.

TABLE IX-27

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-27-1 | p-F—Ph | H | H | H | $^i$Pr | H | $CH_3$ | F | OH | H | H |
| IX-27-2 | p-F—Ph | H | H | $CH_3$ | $^i$Pr | H | $CH_3$ | F | OH | H | H |
| IX-27-3 | p-F—Ph | H | H | $CH(CH_3)_2$ | $^i$Pr | H | $CH_3$ | F | OH | H | H |
| IX-27-4 | p-F—Ph | H | H | $CH_2CH(CH_3)_2$ | $^i$Pr | H | $CH_3$ | F | OH | H | H |
| IX-27-5 | p-F—Ph | H | H | $CH_2Ph$ | $^i$Pr | H | $CH_3$ | F | OH | H | H |
| IX-27-6 | p-F—Ph | H | H | $CH_2$-indol-3-yl | $^i$Pr | H | $CH_3$ | F | OH | H | H |
| IX-27-7 | p-F—Ph | H | H | $CH_2CH_2SCH_3$ | $^i$Pr | H | $CH_3$ | F | OH | H | H |
| IX-27-8 | p-F—Ph | * | H | * | $^i$Pr | H | $CH_3$ | F | OH | H | H |

*$R^2$ and $R^{3b}$ joined together by $(CH_2)_3$ to form five-membered ring.

TABLE IX-28

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-28-1 | p-Cl—Ph | H | H | H | ⁱPr | H | CH₃ | F | OH | H | H |
| IX-28-2 | p-Cl—Ph | H | H | CH₃ | ⁱPr | H | CH₃ | F | OH | H | H |
| IX-28-3 | p-Cl—Ph | H | H | CH(CH₃)₂ | ⁱPr | H | CH₃ | F | OH | H | H |
| IX-28-4 | p-Cl—Ph | H | H | CH₂CH(CH₃)₂ | ⁱPr | H | CH₃ | F | OH | H | H |
| IX-28-5 | p-Cl—Ph | H | H | CH₂Ph | ⁱPr | H | CH₃ | F | OH | H | H |
| IX-28-6 | p-Cl—Ph | H | H | CH₂-indol-3-yl | ⁱPr | H | CH₃ | F | OH | H | H |
| IX-28-7 | p-Cl—Ph | H | H | CH₂CH₂SCH₃ | ⁱPr | H | CH₃ | F | OH | H | H |
| IX-28-8 | p-Cl—Ph | * | H | * | ⁱPr | H | CH₃ | F | OH | H | H |

*R² and R³ᵇ joined together by (CH₂)₃ to form five-membered ring.

TABLE IX-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-29-1 | p-Br—Ph | H | H | H | ⁱPr | H | CH₃ | F | OH | H | H |
| IX-29-2 | p-Br—Ph | H | H | CH₃ | ⁱPr | H | CH₃ | F | OH | H | H |
| IX-29-3 | p-Br—Ph | H | H | CH(CH₃)₂ | ⁱPr | H | CH₃ | F | OH | H | H |
| IX-29-4 | p-Br—Ph | H | H | CH₂CH(CH₃)₂ | ⁱPr | H | CH₃ | F | OH | H | H |
| IX-29-5 | p-Br—Ph | H | H | CH₂Ph | ⁱPr | H | CH₃ | F | OH | H | H |
| IX-29-6 | p-Br—Ph | H | H | CH₂-indol-3-yl | ⁱPr | H | CH₃ | F | OH | H | H |
| IX-29-7 | p-Br—Ph | H | H | CH₂CH₂SCH₃ | ⁱPr | H | CH₃ | F | OH | H | H |
| IX-29-8 | p-Br—Ph | * | H | * | ⁱPr | H | CH₃ | F | OH | H | H |

*R² and R³ᵇ joined together by (CH₂)₃ to form five-membered ring.

TABLE IX-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-30-1 | p-I—Ph | H | H | H | ⁱPr | H | CH₃ | F | OH | H | H |
| IX-30-2 | p-I—Ph | H | H | CH₃ | ⁱPr | H | CH₃ | F | OH | H | H |
| IX-30-3 | p-I—Ph | H | H | CH(CH₃)₂ | ⁱPr | H | CH₃ | F | OH | H | H |
| IX-30-4 | p-I—Ph | H | H | CH₂CH(CH₃)₂ | ⁱPr | H | CH₃ | F | OH | H | H |
| IX-30-5 | p-I—Ph | H | H | CH₂Ph | ⁱPr | H | CH₃ | F | OH | H | H |
| IX-30-6 | p-I—Ph | H | H | CH₂-indol-3-yl | ⁱPr | H | CH₃ | F | OH | H | H |
| IX-30-7 | p-I—Ph | H | H | CH₂CH₂SCH₃ | ⁱPr | H | CH₃ | F | OH | H | H |
| IX-30-8 | p-I—Ph | * | H | * | ⁱPr | H | CH₃ | F | OH | H | H |

*R² and R³ᵇ joined together by (CH₂)₃ to form five-membered ring.

TABLE IX-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-31-1 | CH₃ | H | H | H | ⁿBu | H | CH₃ | F | OH | H | H |
| IX-31-2 | CH₃ | H | H | CH₃ | ⁿBu | H | CH₃ | F | OH | H | H |
| IX-31-3 | CH₃ | H | H | CH(CH₃)₂ | ⁿBu | H | CH₃ | F | OH | H | H |
| IX-31-4 | CH₃ | H | H | CH₂CH(CH₃)₂ | ⁿBu | H | CH₃ | F | OH | H | H |
| IX-31-5 | CH₃ | H | H | CH₂Ph | ⁿBu | H | CH₃ | F | OH | H | H |
| IX-31-6 | CH₃ | H | H | CH₂-indol-3-yl | ⁿBu | H | CH₃ | F | OH | H | H |
| IX-31-7 | CH₃ | H | H | CH₂CH₂SCH₃ | ⁿBu | H | CH₃ | F | OH | H | H |
| IX-31-8 | CH₃ | * | H | * | ⁿBu | H | CH₃ | F | OH | H | H |

*R² and R³ᵇ joined together by (CH₂)₃ to form five-membered ring.

TABLE IX-32

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-32-1 | Et | H | H | H | ⁿBu | H | CH₃ | F | OH | H | H |
| IX-32-2 | Et | H | H | CH₃ | ⁿBu | H | CH₃ | F | OH | H | H |
| IX-32-3 | Et | H | H | CH(CH₃)₂ | ⁿBu | H | CH₃ | F | OH | H | H |
| IX-32-4 | Et | H | H | CH₂CH(CH₃)₂ | ⁿBu | H | CH₃ | F | OH | H | H |
| IX-32-5 | Et | H | H | CH₂Ph | ⁿBu | H | CH₃ | F | OH | H | H |
| IX-32-6 | Et | H | H | CH₂-indol-3-yl | ⁿBu | H | CH₃ | F | OH | H | H |

TABLE IX-32-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| IX-32-7 | Et | H | H | CH$_2$CH$_2$SCH$_3$ | $^n$Bu | H | CH$_3$ | F | OH | H | H |
| IX-32-8 | Et | * | H | * | $^n$Bu | H | CH$_3$ | F | OH | H | H |

*R$^2$ and R$^{3b}$ joined together by (CH$_2$)$_3$ to form five-membered ring.

TABLE IX-33

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| IX-33-1 | $^i$Pr | H | H | H | $^n$Bu | H | CH$_3$ | F | OH | H | H |
| IX-33-2 | $^i$Pr | H | H | CH$_3$ | $^n$Bu | H | CH$_3$ | F | OH | H | H |
| IX-33-3 | $^i$Pr | H | H | CH(CH$_3$)$_2$ | $^n$Bu | H | CH$_3$ | F | OH | H | H |
| IX-33-4 | $^i$Pr | H | H | CH$_2$CH(CH$_3$)$_2$ | $^n$Bu | H | CH$_3$ | F | OH | H | H |
| IX-33-5 | $^i$Pr | H | H | CH$_2$Ph | $^n$Bu | H | CH$_3$ | F | OH | H | H |
| IX-33-6 | $^i$Pr | H | H | CH$_2$-indol-3-yl | $^n$Bu | H | CH$_3$ | F | OH | H | H |
| IX-33-7 | $^i$Pr | H | H | CH$_2$CH$_2$SCH$_3$ | $^n$Bu | H | CH$_3$ | F | OH | H | H |
| IX-33-8 | $^i$Pr | * | H | * | $^n$Bu | H | CH$_3$ | F | OH | H | H |

*R$^2$ and R$^{3b}$ joined together by (CH$_2$)$_3$ to form five-membered ring.

TABLE IX-34

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| IX-34-1 | $^t$Bu | H | H | H | $^n$Bu | H | CH$_3$ | F | OH | H | H |
| IX-34-2 | $^t$Bu | H | H | CH$_3$ | $^n$Bu | H | CH$_3$ | F | OH | H | H |
| IX-34-3 | $^t$Bu | H | H | CH(CH$_3$)$_2$ | $^n$Bu | H | CH$_3$ | F | OH | H | H |
| IX-34-4 | $^t$Bu | H | H | CH$_2$CH(CH$_3$)$_2$ | $^n$Bu | H | CH$_3$ | F | OH | H | H |
| IX-34-5 | $^t$Bu | H | H | CH$_2$Ph | $^n$Bu | H | CH$_3$ | F | OH | H | H |
| IX-34-6 | $^t$Bu | H | H | CH$_2$-indol-3-yl | $^n$Bu | H | CH$_3$ | F | OH | H | H |
| IX-34-7 | $^t$Bu | H | H | CH$_2$CH$_2$SCH$_3$ | $^n$Bu | H | CH$_3$ | F | OH | H | H |
| IX-34-8 | $^t$Bu | * | H | * | $^n$Bu | H | CH$_3$ | F | OH | H | H |

*R$^2$ and R$^{3b}$ joined together by (CH$_2$)$_3$ to form five-membered ring.

TABLE IX-35

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| IX-35-1 | Ph | H | H | H | $^n$Bu | H | CH$_3$ | F | OH | H | H |
| IX-35-2 | Ph | H | H | CH$_3$ | $^n$Bu | H | CH$_3$ | F | OH | H | H |
| IX-35-3 | Ph | H | H | CH(CH$_3$)$_2$ | $^n$Bu | H | CH$_3$ | F | OH | H | H |
| IX-35-4 | Ph | H | H | CH$_2$CH(CH$_3$)$_2$ | $^n$Bu | H | CH$_3$ | F | OH | H | H |
| IX-35-5 | Ph | H | H | CH$_2$Ph | $^n$Bu | H | CH$_3$ | F | OH | H | H |
| IX-35-6 | Ph | H | H | CH$_2$-indol-3-yl | $^n$Bu | H | CH$_3$ | F | OH | H | H |
| IX-35-7 | Ph | H | H | CH$_2$CH$_2$SCH$_3$ | $^n$Bu | H | CH$_3$ | F | OH | H | H |
| IX-35-8 | Ph | * | H | * | $^n$Bu | H | CH$_3$ | F | OH | H | H |

*R$^2$ and R$^{3b}$ joined together by (CH$_2$)$_3$ to form five-membered ring.

TABLE IX-36

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| IX-36-1 | p-Me—Ph | H | H | H | $^n$Bu | H | CH$_3$ | F | OH | H | H |
| IX-36-2 | p-Me—Ph | H | H | CH$_3$ | $^n$Bu | H | CH$_3$ | F | OH | H | H |
| IX-36-3 | p-Me—Ph | H | H | CH(CH$_3$)$_2$ | $^n$Bu | H | CH$_3$ | F | OH | H | H |
| IX-36-4 | p-Me—Ph | H | H | CH$_2$CH(CH$_3$)$_2$ | $^n$Bu | H | CH$_3$ | F | OH | H | H |
| IX-36-5 | p-Me—Ph | H | H | CH$_2$Ph | $^n$Bu | H | CH$_3$ | F | OH | H | H |
| IX-36-6 | p-Me—Ph | H | H | CH$_2$-indol-3-yl | $^n$Bu | H | CH$_3$ | F | OH | H | H |
| IX-36-7 | p-Me—Ph | H | H | CH$_2$CH$_2$SCH$_3$ | $^n$Bu | H | CH$_3$ | F | OH | H | H |
| IX-36-8 | p-Me—Ph | * | H | * | $^n$Bu | H | CH$_3$ | F | OH | H | H |

*R$^2$ and R$^{3b}$ joined together by (CH$_2$)$_3$ to form five-membered ring.

TABLE IX-37

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| IX-37-1 | p-F—Ph | H | H | H | $^n$Bu | H | CH$_3$ | F | OH | H | H |
| IX-37-2 | p-F—Ph | H | H | CH$_3$ | $^n$Bu | H | CH$_3$ | F | OH | H | H |
| IX-37-3 | p-F—Ph | H | H | CH(CH$_3$)$_2$ | $^n$Bu | H | CH$_3$ | F | OH | H | H |
| IX-37-4 | p-F—Ph | H | H | CH$_2$CH(CH$_3$)$_2$ | $^n$Bu | H | CH$_3$ | F | OH | H | H |
| IX-37-5 | p-F—Ph | H | H | CH$_2$Ph | $^n$Bu | H | CH$_3$ | F | OH | H | H |
| IX-37-6 | p-F—Ph | H | H | CH$_2$-indol-3-yl | $^n$Bu | H | CH$_3$ | F | OH | H | H |
| IX-37-7 | p-F—Ph | H | H | CH$_2$CH$_2$SCH$_3$ | $^n$Bu | H | CH$_3$ | F | OH | H | H |
| IX-37-8 | p-F—Ph | * | H | * | $^n$Bu | H | CH$_3$ | F | OH | H | H |

*R$^2$ and R$^{3b}$ joined together by (CH$_2$)$_3$ to form five-membered ring.

TABLE IX-38

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-38-1 | p-Cl—Ph | H | H | H | ⁿBu | H | CH₃ | F | OH | H | H |
| IX-38-2 | p-Cl—Ph | H | H | CH₃ | ⁿBu | H | CH₃ | F | OH | H | H |
| IX-38-3 | p-Cl—Ph | H | H | CH(CH₃)₂ | ⁿBu | H | CH₃ | F | OH | H | H |
| IX-38-4 | p-Cl—Ph | H | H | CH₂CH(CH₃)₂ | ⁿBu | H | CH₃ | F | OH | H | H |
| IX-38-5 | p-Cl—Ph | H | H | CH₂Ph | ⁿBu | H | CH₃ | F | OH | H | H |
| IX-38-6 | p-Cl—Ph | H | H | CH₂-indol-3-yl | ⁿBu | H | CH₃ | F | OH | H | H |
| IX-38-7 | p-Cl—Ph | H | H | CH₂CH₂SCH₃ | ⁿBu | H | CH₃ | F | OH | H | H |
| IX-38-8 | p-Cl—Ph | * | H | * | ⁿBu | H | CH₃ | F | OH | H | H |

*R² and R³ᵇ joined together by (CH₂)₃ to form five-membered ring.

TABLE IX-39

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-39-1 | p-Br—Ph | H | H | H | ⁿBu | H | CH₃ | F | OH | H | H |
| IX-39-2 | p-Br—Ph | H | H | CH₃ | ⁿBu | H | CH₃ | F | OH | H | H |
| IX-39-3 | p-Br—Ph | H | H | CH(CH₃)₂ | ⁿBu | H | CH₃ | F | OH | H | H |
| IX-39-4 | p-Br—Ph | H | H | CH₂CH(CH₃)₂ | ⁿBu | H | CH₃ | F | OH | H | H |
| IX-39-5 | p-Br—Ph | H | H | CH₂Ph | ⁿBu | H | CH₃ | F | OH | H | H |
| IX-39-6 | p-Br—Ph | H | H | CH₂-indol-3-yl | ⁿBu | H | CH₃ | F | OH | H | H |
| IX-39-7 | p-Br—Ph | H | H | CH₂CH₂SCH₃ | ⁿBu | H | CH₃ | F | OH | H | H |
| IX-39-8 | p-Br—Ph | * | H | * | ⁿBu | H | CH₃ | F | OH | H | H |

*R² and R³ᵇ joined together by (CH₂)₃ to form five-membered ring.

TABLE IX-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-40-1 | p-I—Ph | H | H | H | ⁿBu | H | CH₃ | F | OH | H | H |
| IX-40-2 | p-I—Ph | H | H | CH₃ | ⁿBu | H | CH₃ | F | OH | H | H |
| IX-40-3 | p-I—Ph | H | H | CH(CH₃)₂ | ⁿBu | H | CH₃ | F | OH | H | H |
| IX-40-4 | p-I—Ph | H | H | CH₂CH(CH₃)₂ | ⁿBu | H | CH₃ | F | OH | H | H |
| IX-40-5 | p-I—Ph | H | H | CH₂Ph | ⁿBu | H | CH₃ | F | OH | H | H |
| IX-40-6 | p-I—Ph | H | H | CH₂-indol-3-yl | ⁿBu | H | CH₃ | F | OH | H | H |
| IX-40-7 | p-I—Ph | H | H | CH₂CH₂SCH₃ | ⁿBu | H | CH₃ | F | OH | H | H |
| IX-40-8 | p-I—Ph | * | H | * | ⁿBu | H | CH₃ | F | OH | H | H |

*R² and R³ᵇ joined together by (CH₂)₃ to form five-membered ring.

TABLE IX-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-41-1 | CH₃ | H | H | H | Bz | H | CH₃ | F | OH | H | H |
| IX-41-2 | CH₃ | H | H | CH₃ | Bz | H | CH₃ | F | OH | H | H |
| IX-41-3 | CH₃ | H | H | CH(CH₃)₂ | Bz | H | CH₃ | F | OH | H | H |
| IX-41-4 | CH₃ | H | H | CH₂CH(CH₃)₂ | Bz | H | CH₃ | F | OH | H | H |
| IX-41-5 | CH₃ | H | H | CH₂Ph | Bz | H | CH₃ | F | OH | H | H |
| IX-41-6 | CH₃ | H | H | CH₂-indol-3-yl | Bz | H | CH₃ | F | OH | H | H |
| IX-41-7 | CH₃ | H | H | CH₂CH₂SCH₃ | Bz | H | CH₃ | F | OH | H | H |
| IX-41-8 | CH₃ | * | H | * | Bz | H | CH₃ | F | OH | H | H |

*R² and R³ᵇ joined together by (CH₂)₃ to form five-membered ring.

TABLE IX-42

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| IX-42-1 | Et | H | H | H | Bz | H | CH₃ | F | OH | H | H |
| IX-42-2 | Et | H | H | CH₃ | Bz | H | CH₃ | F | OH | H | H |
| IX-42-3 | Et | H | H | CH(CH₃)₂ | Bz | H | CH₃ | F | OH | H | H |
| IX-42-4 | Et | H | H | CH₂CH(CH₃)₂ | Bz | H | CH₃ | F | OH | H | H |
| IX-42-5 | Et | H | H | CH₂Ph | Bz | H | CH₃ | F | OH | H | H |
| IX-42-6 | Et | H | H | CH₂-indol-3-yl | Bz | H | CH₃ | F | OH | H | H |

TABLE IX-42-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-42-7 | Et | H | H | $CH_2CH_2SCH_3$ | Bz | H | $CH_3$ | F | OH | H | H |
| IX-42-8 | Et | * | H | * | Bz | H | $CH_3$ | F | OH | H | H |

*$R^2$ and $R^{3b}$ joined together by $(CH_2)_3$ to form five-membered ring.

TABLE IX-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-43-1 | $^iPr$ | H | H | H | Bz | H | $CH_3$ | F | OH | H | H |
| IX-43-2 | $^iPr$ | H | H | $CH_3$ | Bz | H | $CH_3$ | F | OH | H | H |
| IX-43-3 | $^iPr$ | H | H | $CH(CH_3)_2$ | Bz | H | $CH_3$ | F | OH | H | H |
| IX-43-4 | $^iPr$ | H | H | $CH_2CH(CH_3)_2$ | Bz | H | $CH_3$ | F | OH | H | H |
| IX-43-5 | $^iPr$ | H | H | $CH_2Ph$ | Bz | H | $CH_3$ | F | OH | H | H |
| IX-43-6 | $^iPr$ | H | H | $CH_2$-indol-3-yl | Bz | H | $CH_3$ | F | OH | H | H |
| IX-43-7 | $^iPr$ | H | H | $CH_2CH_2SCH_3$ | Bz | H | $CH_3$ | F | OH | H | H |
| IX-43-8 | $^iPr$ | * | H | * | Bz | H | $CH_3$ | F | OH | H | H |

*$R^2$ and $R^{3b}$ joined together by $(CH_2)_3$ to form five-membered ring.

TABLE IX-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-44-1 | $^tBu$ | H | H | H | Bz | H | $CH_3$ | F | OH | H | H |
| IX-44-2 | $^tBu$ | H | H | $CH_3$ | Bz | H | $CH_3$ | F | OH | H | H |
| IX-44-3 | $^tBu$ | H | H | $CH(CH_3)_2$ | Bz | H | $CH_3$ | F | OH | H | H |
| IX-44-4 | $^tBu$ | H | H | $CH_2CH(CH_3)_2$ | Bz | H | $CH_3$ | F | OH | H | H |
| IX-44-5 | $^tBu$ | H | H | $CH_2Ph$ | Bz | H | $CH_3$ | F | OH | H | H |
| IX-44-6 | $^tBu$ | H | H | $CH_2$-indol-3-yl | Bz | H | $CH_3$ | F | OH | H | H |
| IX-44-7 | $^tBu$ | H | H | $CH_2CH_2SCH_3$ | Bz | H | $CH_3$ | F | OH | H | H |
| IX-44-8 | $^tBu$ | * | H | * | Bz | H | $CH_3$ | F | OH | H | H |

*$R^2$ and $R^{3b}$ joined together by $(CH_2)_3$ to form five-membered ring.

TABLE IX-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-45-1 | Ph | H | H | H | Bz | H | $CH_3$ | F | OH | H | H |
| IX-45-2 | Ph | H | H | $CH_3$ | Bz | H | $CH_3$ | F | OH | H | H |
| IX-45-3 | Ph | H | H | $CH(CH_3)_2$ | Bz | H | $CH_3$ | F | OH | H | H |
| IX-45-4 | Ph | H | H | $CH_2CH(CH_3)_2$ | Bz | H | $CH_3$ | F | OH | H | H |
| IX-45-5 | Ph | H | H | $CH_2Ph$ | Bz | H | $CH_3$ | F | OH | H | H |
| IX-45-6 | Ph | H | H | $CH_2$-indol-3-yl | Bz | H | $CH_3$ | F | OH | H | H |
| IX-45-7 | Ph | H | H | $CH_2CH_2SCH_3$ | Bz | H | $CH_3$ | F | OH | H | H |
| IX-45-8 | Ph | * | H | * | Bz | H | $CH_3$ | F | OH | H | H |

*$R^2$ and $R^{3b}$ joined together by $(CH_2)_3$ to form five-membered ring.

TABLE IX-46

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-46-1 | p-Me—Ph | H | H | H | Bz | H | $CH_3$ | F | OH | H | H |
| IX-46-2 | p-Me—Ph | H | H | $CH_3$ | Bz | H | $CH_3$ | F | OH | H | H |
| IX-46-3 | p-Me—Ph | H | H | $CH(CH_3)_2$ | Bz | H | $CH_3$ | F | OH | H | H |
| IX-46-4 | p-Me—Ph | H | H | $CH_2CH(CH_3)_2$ | Bz | H | $CH_3$ | F | OH | H | H |
| IX-46-5 | p-Me—Ph | H | H | $CH_2Ph$ | Bz | H | $CH_3$ | F | OH | H | H |
| IX-46-6 | p-Me—Ph | H | H | $CH_2$-indol-3-yl | Bz | H | $CH_3$ | F | OH | H | H |
| IX-46-7 | p-Me—Ph | H | H | $CH_2CH_2SCH_3$ | Bz | H | $CH_3$ | F | OH | H | H |
| IX-46-8 | p-Me—Ph | * | H | * | Bz | H | $CH_3$ | F | OH | H | H |

*$R^2$ and $R^{3b}$ joined together by $(CH_2)_3$ to form five-membered ring.

TABLE IX-47

| No | $R^1$ | $R^2$ | R | $R^{3b}$ | $R^4$ | $R^5$ | $R^6$ | X | Y | $R^7$ | $R^8$ |
|---|---|---|---|---|---|---|---|---|---|---|---|
| IX-47-1 | p-F—Ph | H | H | H | Bz | H | $CH_3$ | F | OH | H | H |
| IX-47-2 | p-F—Ph | H | H | $CH_3$ | Bz | H | $CH_3$ | F | OH | H | H |
| IX-47-3 | p-F—Ph | H | H | $CH(CH_3)_2$ | Bz | H | $CH_3$ | F | OH | H | H |
| IX-47-4 | p-F—Ph | H | H | $CH_2CH(CH_3)_2$ | Bz | H | $CH_3$ | F | OH | H | H |
| IX-47-5 | p-F—Ph | H | H | $CH_2Ph$ | Bz | H | $CH_3$ | F | OH | H | H |
| IX-47-6 | p-F—Ph | H | H | $CH_2$-indol-3-yl | Bz | H | $CH_3$ | F | OH | H | H |
| IX-47-7 | p-F—Ph | H | H | $CH_2CH_2SCH_3$ | Bz | H | $CH_3$ | F | OH | H | H |
| IX-47-8 | p-F—Ph | * | H | * | Bz | H | $CH_3$ | F | OH | H | H |

*$R^2$ and $R^{3b}$ joined together by $(CH_2)_3$ to form five-membered ring.

TABLE IX-48

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-48-1 | p-Cl—Ph | H | H | H | Bz | H | $CH_3$ | F | OH | H | H |
| IX-48-2 | p-Cl—Ph | H | H | $CH_3$ | Bz | H | $CH_3$ | F | OH | H | H |
| IX-48-3 | p-Cl—Ph | H | H | $CH(CH_3)_2$ | Bz | H | $CH_3$ | F | OH | H | H |
| IX-48-4 | p-Cl—Ph | H | H | $CH_2CH(CH_3)_2$ | Bz | H | $CH_3$ | F | OH | H | H |
| IX-48-5 | p-Cl—Ph | H | H | $CH_2Ph$ | Bz | H | $CH_3$ | F | OH | H | H |
| IX-48-6 | p-Cl—Ph | H | H | $CH_2$-indol-3-yl | Bz | H | $CH_3$ | F | OH | H | H |
| IX-48-7 | p-Cl—Ph | H | H | $CH_2CH_2SCH_3$ | Bz | H | $CH_3$ | F | OH | H | H |
| IX-48-8 | p-Cl—Ph | * | H | * | Bz | H | $CH_3$ | F | OH | H | H |

*$R^2$ and $R^{3b}$ joined together by $(CH_2)_3$ to form five-membered ring.

TABLE IX-49

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-49-1 | p-Br—Ph | H | H | H | Bz | H | $CH_3$ | F | OH | H | H |
| IX-49-2 | p-Br—Ph | H | H | $CH_3$ | Bz | H | $CH_3$ | F | OH | H | H |
| IX-49-3 | p-Br—Ph | H | H | $CH(CH_3)_2$ | Bz | H | $CH_3$ | F | OH | H | H |
| IX-49-4 | p-Br—Ph | H | H | $CH_2CH(CH_3)_2$ | Bz | H | $CH_3$ | F | OH | H | H |
| IX-49-5 | p-Br—Ph | H | H | $CH_2Ph$ | Bz | H | $CH_3$ | F | OH | H | H |
| IX-49-6 | p-Br—Ph | H | H | $CH_2$-indol-3-yl | Bz | H | $CH_3$ | F | OH | H | H |
| IX-49-7 | p-Br—Ph | H | H | $CH_2CH_2SCH_3$ | Bz | H | $CH_3$ | F | OH | H | H |
| IX-49-8 | p-Br—Ph | * | H | * | Bz | H | $CH_3$ | F | OH | H | H |

*$R^2$ and $R^{3b}$ joined together by $(CH_2)_3$ to form five-membered ring.

TABLE IX-50

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| IX-50-1 | p-I—Ph | H | H | H | Bz | H | $CH_3$ | F | OH | H | H |
| IX-50-2 | p-I—Ph | H | H | $CH_3$ | Bz | H | $CH_3$ | F | OH | H | H |
| IX-50-3 | p-I—Ph | H | H | $CH(CH_3)_2$ | Bz | H | $CH_3$ | F | OH | H | H |
| IX-50-4 | p-I—Ph | H | H | $CH_2CH(CH_3)_2$ | Bz | H | $CH_3$ | F | OH | H | H |
| IX-50-5 | p-I—Ph | H | H | $CH_2Ph$ | Bz | H | $CH_3$ | F | OH | H | H |
| IX-50-6 | p-I—Ph | H | H | $CH_2$-indol-3-yl | Bz | H | $CH_3$ | F | OH | H | H |
| IX-50-7 | p-I—Ph | H | H | $CH_2CH_2SCH_3$ | Bz | H | $CH_3$ | F | OH | H | H |
| IX-50-8 | p-I—Ph | * | H | * | Bz | H | $CH_3$ | F | OH | H | H |

*$R^2$ and $R^{3b}$ joined together by $(CH_2)_3$ to form five-membered ring.

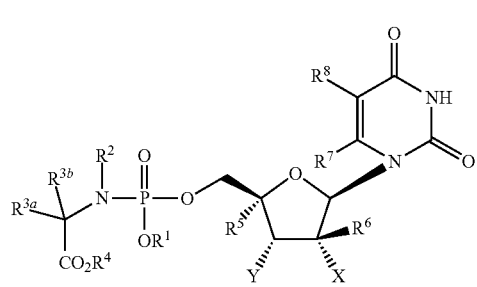

TABLE X-1

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-1-1 | $CH_3$ | H | H | H | $CH_3$ | H | F | F | OH | H | H |
| X-1-2 | $CH_3$ | H | H | $CH_3$ | $CH_3$ | H | F | F | OH | H | H |
| X-1-3 | $CH_3$ | H | H | $CH(CH_3)_2$ | $CH_3$ | H | F | F | OH | H | H |
| X-1-4 | $CH_3$ | H | H | $CH_2CH(CH_3)_2$ | $CH_3$ | H | F | F | OH | H | H |
| X-1-5 | $CH_3$ | H | H | $CH_2Ph$ | $CH_3$ | H | F | F | OH | H | H |
| X-1-6 | $CH_3$ | H | H | $CH_2$-indol-3-yl | $CH_3$ | H | F | F | OH | H | H |
| X-1-7 | $CH_3$ | H | H | $CH_2CH_2SCH_3$ | $CH_3$ | H | F | F | OH | H | H |
| X-1-8 | $CH_3$ | * | H | * | $CH_3$ | H | F | F | OH | H | H |

*$R^2$ and $R^{3b}$ joined together by $(CH_2)_3$ to form five-membered ring.

TABLE X-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-2-1 | Et | H | H | H | $CH_3$ | H | F | F | OH | H | H |
| X-2-2 | Et | H | H | $CH_3$ | $CH_3$ | H | F | F | OH | H | H |
| X-2-3 | Et | H | H | $CH(CH_3)_2$ | $CH_3$ | H | F | F | OH | H | H |
| X-2-4 | Et | H | H | $CH_2CH(CH_3)_2$ | $CH_3$ | H | F | F | OH | H | H |
| X-2-5 | Et | H | H | $CH_2Ph$ | $CH_3$ | H | F | F | OH | H | H |
| X-2-6 | Et | H | H | $CH_2$-indol-3-yl | $CH_3$ | H | F | F | OH | H | H |
| X-2-7 | Et | H | H | $CH_2CH_2SCH_3$ | $CH_3$ | H | F | F | OH | H | H |
| X-2-8 | Et | * | H | * | $CH_3$ | H | F | F | OH | H | H |

*$R^2$ and $R^{3b}$ joined together by $(CH_2)_3$ to form five-membered ring.

TABLE X-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-3-1 | $^iPr$ | H | H | H | $CH_3$ | H | F | F | OH | H | H |
| X-3-2 | $^iPr$ | H | H | $CH_3$ | $CH_3$ | H | F | F | OH | H | H |
| X-3-3 | $^iPr$ | H | H | $CH(CH_3)_2$ | $CH_3$ | H | F | F | OH | H | H |
| X-3-4 | $^iPr$ | H | H | $CH_2CH(CH_3)_2$ | $CH_3$ | H | F | F | OH | H | H |
| X-3-5 | $^iPr$ | H | H | $CH_2Ph$ | $CH_3$ | H | F | F | OH | H | H |
| X-3-6 | $^iPr$ | H | H | $CH_2$-indol-3-yl | $CH_3$ | H | F | F | OH | H | H |
| X-3-7 | $^iPr$ | H | H | $CH_2CH_2SCH_3$ | $CH_3$ | H | F | F | OH | H | H |
| X-3-8 | $^iPr$ | * | H | * | $CH_3$ | H | F | F | OH | H | H |

*$R^2$ and $R^{3b}$ joined together by $(CH_2)_3$ to form five-membered ring.

TABLE X-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-4-1 | $^tBu$ | H | H | H | $CH_3$ | H | F | F | OH | H | H |
| X-4-2 | $^tBu$ | H | H | $CH_3$ | $CH_3$ | H | F | F | OH | H | H |
| X-4-3 | $^tBu$ | H | H | $CH(CH_3)_2$ | $CH_3$ | H | F | F | OH | H | H |
| X-4-4 | $^tBu$ | H | H | $CH_2CH(CH_3)_2$ | $CH_3$ | H | F | F | OH | H | H |
| X-4-5 | $^tBu$ | H | H | $CH_2Ph$ | $CH_3$ | H | F | F | OH | H | H |
| X-4-6 | $^tBu$ | H | H | $CH_2$-indol-3-yl | $CH_3$ | H | F | F | OH | H | H |
| X-4-7 | $^tBu$ | H | H | $CH_2CH_2SCH_3$ | $CH_3$ | H | F | F | OH | H | H |
| X-4-8 | $^tBu$ | * | H | * | $CH_3$ | H | F | F | OH | H | H |

*$R^2$ and $R^{3b}$ joined together by $(CH_2)_3$ to form five-membered ring.

TABLE X-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-5-1 | Ph | H | H | H | $CH_3$ | H | F | F | OH | H | H |
| X-5-2 | Ph | H | H | $CH_3$ | $CH_3$ | H | F | F | OH | H | H |
| X-5-3 | Ph | H | H | $CH(CH_3)_2$ | $CH_3$ | H | F | F | OH | H | H |
| X-5-4 | Ph | H | H | $CH_2CH(CH_3)_2$ | $CH_3$ | H | F | F | OH | H | H |
| X-5-5 | Ph | H | H | $CH_2Ph$ | $CH_3$ | H | F | F | OH | H | H |
| X-5-6 | Ph | H | H | $CH_2$-indol-3-yl | $CH_3$ | H | F | F | OH | H | H |
| X-5-7 | Ph | H | H | $CH_2CH_2SCH_3$ | $CH_3$ | H | F | F | OH | H | H |
| X-5-8 | Ph | * | H | * | $CH_3$ | H | F | F | OH | H | H |

*$R^2$ and $R^{3b}$ joined together by $(CH_2)_3$ to form five-membered ring.

TABLE X-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-6-1 | p-Me—Ph | H | H | H | $CH_3$ | H | F | F | OH | H | H |
| X-6-2 | p-Me—Ph | H | H | $CH_3$ | $CH_3$ | H | F | F | OH | H | H |
| X-6-3 | p-Me—Ph | H | H | $CH(CH_3)_2$ | $CH_3$ | H | F | F | OH | H | H |
| X-6-4 | p-Me—Ph | H | H | $CH_2CH(CH_3)_2$ | $CH_3$ | H | F | F | OH | H | H |
| X-6-5 | p-Me—Ph | H | H | $CH_2Ph$ | $CH_3$ | H | F | F | OH | H | H |
| X-6-6 | p-Me—Ph | H | H | $CH_2$-indol-3-yl | $CH_3$ | H | F | F | OH | H | H |
| X-6-7 | p-Me—Ph | H | H | $CH_2CH_2SCH_3$ | $CH_3$ | H | F | F | OH | H | H |
| X-6-8 | p-Me—Ph | * | H | * | $CH_3$ | H | F | F | OH | H | H |

*$R^2$ and $R^{3b}$ joined together by $(CH_2)_3$ to form five-membered ring.

TABLE X-7

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-7-1 | p-F—Ph | H | H | H | $CH_3$ | H | F | F | OH | H | H |
| X-7-2 | p-F—Ph | H | H | $CH_3$ | $CH_3$ | H | F | F | OH | H | H |
| X-7-3 | p-F—Ph | H | H | $CH(CH_3)_2$ | $CH_3$ | H | F | F | OH | H | H |
| X-7-4 | p-F—Ph | H | H | $CH_2CH(CH_3)_2$ | $CH_3$ | H | F | F | OH | H | H |
| X-7-6 | p-F—Ph | H | H | $CH_2Ph$ | $CH_3$ | H | F | F | OH | H | H |
| X-7-7 | p-F—Ph | H | H | $CH_2$-indol-3-yl | $CH_3$ | H | F | F | OH | H | H |
| X-7-8 | p-F—Ph | H | H | $CH_2CH_2SCH_3$ | $CH_3$ | H | F | F | OH | H | H |
| X-7-20 | p-F—Ph | * | H | * | $CH_3$ | H | F | F | OH | H | H |

*$R^2$ and $R^{3b}$ joined together by $(CH_2)_3$ to form five-membered ring.

TABLE X-8

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-8-1 | p-Cl—Ph | H | H | H | CH₃ | H | F | F | OH | H | H |
| X-8-2 | p-Cl—Ph | H | H | CH₃ | CH₃ | H | F | F | OH | H | H |
| X-8-3 | p-Cl—Ph | H | H | CH(CH₃)₂ | CH₃ | H | F | F | OH | H | H |
| X-8-4 | p-Cl—Ph | H | H | CH₂CH(CH₃)₂ | CH₃ | H | F | F | OH | H | H |
| X-8-5 | p-Cl—Ph | H | H | CH₂Ph | CH₃ | H | F | F | OH | H | H |
| X-8-6 | p-Cl—Ph | H | H | CH₂-indol-3-yl | CH₃ | H | F | F | OH | H | H |
| X-8-7 | p-Cl—Ph | H | H | CH₂CH₂SCH₃ | CH₃ | H | F | F | OH | H | H |
| X-8-8 | p-Cl—Ph | * | H | * | CH₃ | H | F | F | OH | H | H |

*R² and R³ᵇ joined together by (CH₂)₃ to form five-membered ring.

TABLE X-9

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-9-1 | p-Br—Ph | H | H | H | CH₃ | H | F | F | OH | H | H |
| X-9-2 | p-Br—Ph | H | H | CH₃ | CH₃ | H | F | F | OH | H | H |
| X-9-3 | p-Br—Ph | H | H | CH(CH₃)₂ | CH₃ | H | F | F | OH | H | H |
| X-9-4 | p-Br—Ph | H | H | CH₂CH(CH₃)₂ | CH₃ | H | F | F | OH | H | H |
| X-9-5 | p-Br—Ph | H | H | CH₂Ph | CH₃ | H | F | F | OH | H | H |
| X-9-7 | p-Br—Ph | H | H | CH₂-indol-3-yl | CH₃ | H | F | F | OH | H | H |
| X-9-8 | p-Br—Ph | H | H | CH₂CH₂SCH₃ | CH₃ | H | F | F | OH | H | H |
| X-9-20 | p-Br—Ph | * | H | * | CH₃ | H | F | F | OH | H | H |

*R² and R³ᵇ joined together by (CH₂)₃ to form five-membered ring.

TABLE X-10

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-10-1 | p-I—Ph | H | H | H | CH₃ | H | F | F | OH | H | H |
| X-10-2 | p-I—Ph | H | H | CH₃ | CH₃ | H | F | F | OH | H | H |
| X-10-3 | p-I—Ph | H | H | CH(CH₃)₂ | CH₃ | H | F | F | OH | H | H |
| X-10-4 | p-I—Ph | H | H | CH₂CH(CH₃)₂ | CH₃ | H | F | F | OH | H | H |
| X-10-5 | p-I—Ph | H | H | CH₂Ph | CH₃ | H | F | F | OH | H | H |
| X-10-6 | p-I—Ph | H | H | CH₂-indol-3-yl | CH₃ | H | F | F | OH | H | H |
| X-10-7 | p-I—Ph | H | H | CH₂CH₂SCH₃ | CH₃ | H | F | F | OH | H | H |
| X-10-8 | p-I—Ph | * | H | * | CH₃ | H | F | F | OH | H | H |

*R² and R³ᵇ joined together by (CH₂)₃ to form five-membered ring.

TABLE X-11

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-11-1 | CH3 | H | H | H | Et | H | F | F | OH | H | H |
| X-11-2 | CH3 | H | H | CH₃ | Et | H | F | F | OH | H | H |
| X-11-3 | CH3 | H | H | CH(CH₃)₂ | Et | H | F | F | OH | H | H |
| X-11-4 | CH3 | H | H | CH₂CH(CH₃)₂ | Et | H | F | F | OH | H | H |
| X-11-5 | CH3 | H | H | CH₂Ph | Et | H | F | F | OH | H | H |
| X-11-6 | CH3 | H | H | CH₂-indol-3-yl | Et | H | F | F | OH | H | H |
| X-11-7 | CH3 | H | H | CH₂CH₂SCH₃ | Et | H | F | F | OH | H | H |
| X-11-8 | CH3 | * | H | * | Et | H | F | F | OH | H | H |

*R² and R³ᵇ joined together by (CH₂)₃ to form five-membered ring.

TABLE X-12

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-12-1 | Et | H | H | H | Et | H | F | F | OH | H | H |
| X-12-2 | Et | H | H | CH₃ | Et | H | F | F | OH | H | H |
| X-12-3 | Et | H | H | CH(CH₃)₂ | Et | H | F | F | OH | H | H |
| X-12-4 | Et | H | H | CH₂CH(CH₃)₂ | Et | H | F | F | OH | H | H |
| X-12-5 | Et | H | H | CH₂Ph | Et | H | F | F | OH | H | H |
| X-12-6 | Et | H | H | CH₂-indol-3-yl | Et | H | F | F | OH | H | H |
| X-12-7 | Et | H | H | CH₂CH₂SCH₃ | Et | H | F | F | OH | H | H |
| X-12-8 | Et | * | H | * | Et | H | F | F | OH | H | H |

*R² and R³ᵇ joined together by (CH₂)₃ to form five-membered ring.

TABLE X-13

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-13-1 | ⁱPr | H | H | H | Et | H | F | F | OH | H | H |
| X-13-2 | ⁱPr | H | H | CH₃ | Et | H | F | F | OH | H | H |
| X-13-3 | ⁱPr | H | H | CH(CH₃)₂ | Et | H | F | F | OH | H | H |
| X-13-4 | ⁱPr | H | H | CH₂CH(CH₃)₂ | Et | H | F | F | OH | H | H |
| X-13-5 | ⁱPr | H | H | CH₂Ph | Et | H | F | F | OH | H | H |
| X-13-6 | ⁱPr | H | H | CH₂-indol-3-yl | Et | H | F | F | OH | H | H |
| X-13-7 | ⁱPr | H | H | CH₂CH₂SCH₃ | Et | H | F | F | OH | H | H |
| X-13-8 | ⁱPr | * | H | * | Et | H | F | F | OH | H | H |

*R² and R³ᵇ joined together by (CH₂)₃ to form five-membered ring.

TABLE X-14

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-14-1 | $^t$Bu | H | H | H | Et | H | F | F | OH | H | H |
| X-14-2 | $^t$Bu | H | H | $CH_3$ | Et | H | F | F | OH | H | H |
| X-14-3 | $^t$Bu | H | H | $CH(CH_3)_2$ | Et | H | F | F | OH | H | H |
| X-14-4 | $^t$Bu | H | H | $CH_2CH(CH_3)_2$ | Et | H | F | F | OH | H | H |
| X-14-5 | $^t$Bu | H | H | $CH_2Ph$ | Et | H | F | F | OH | H | H |
| X-14-6 | $^t$Bu | H | H | $CH_2$-indol-3-yl | Et | H | F | F | OH | H | H |
| X-14-7 | $^t$Bu | H | H | $CH_2CH_2SCH_3$ | Et | H | F | F | OH | H | H |
| X-14-8 | $^t$Bu | * | H | * | Et | H | F | F | OH | H | H |

*$R^2$ and $R^{3b}$ joined together by $(CH_2)_3$ to form five-membered ring.

TABLE X-15

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-15-1 | Ph | H | H | H | Et | H | F | F | OH | H | H |
| X-15-2 | Ph | H | H | $CH_3$ | Et | H | F | F | OH | H | H |
| X-15-3 | Ph | H | H | $CH(CH_3)_2$ | Et | H | F | F | OH | H | H |
| X-15-4 | Ph | H | H | $CH_2CH(CH_3)_2$ | Et | H | F | F | OH | H | H |
| X-15-5 | Ph | H | H | $CH_2Ph$ | Et | H | F | F | OH | H | H |
| X-15-6 | Ph | H | H | $CH_2$-indol-3-yl | Et | H | F | F | OH | H | H |
| X-15-7 | Ph | H | H | $CH_2CH_2SCH_3$ | Et | H | F | F | OH | H | H |
| X-15-8 | Ph | * | H | * | Et | H | F | F | OH | H | H |

*$R^2$ and $R^{3b}$ joined together by $(CH_2)_3$ to form five-membered ring.

TABLE X-16

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-16-1 | p-Me—Ph | H | H | H | Et | H | F | F | OH | H | H |
| X-16-2 | p-Me—Ph | H | H | $CH_3$ | Et | H | F | F | OH | H | H |
| X-16-3 | p-Me—Ph | H | H | $CH(CH_3)_2$ | Et | H | F | F | OH | H | H |
| X-16-4 | p-Me—Ph | H | H | $CH_2CH(CH_3)_2$ | Et | H | F | F | OH | H | H |
| X-16-5 | p-Me—Ph | H | H | $CH_2Ph$ | Et | H | F | F | OH | H | H |
| X-16-6 | p-Me—Ph | H | H | $CH_2$-indol-3-yl | Et | H | F | F | OH | H | H |
| X-16-7 | p-Me—Ph | H | H | $CH_2CH_2SCH_3$ | Et | H | F | F | OH | H | H |
| X-6-8 | p-Me—Ph | * | H | * | Et | H | F | F | OH | H | H |

*$R^2$ and $R^{3b}$ joined together by $(CH_2)_3$ to form five-membered ring.

TABLE X-17

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-17-1 | p-F—Ph | H | H | H | Et | H | F | F | OH | H | H |
| X-17-2 | p-F—Ph | H | H | $CH_3$ | Et | H | F | F | OH | H | H |
| X-17-3 | p-F—Ph | H | H | $CH(CH_3)_2$ | Et | H | F | F | OH | H | H |
| X-17-4 | p-F—Ph | H | H | $CH_2CH(CH_3)_2$ | Et | H | F | F | OH | H | H |
| X-17-5 | p-F—Ph | H | H | $CH_2Ph$ | Et | H | F | F | OH | H | H |
| X-17-6 | p-F—Ph | H | H | $CH_2$-indol-3-yl | Et | H | F | F | OH | H | H |
| X-17-7 | p-F—Ph | H | H | $CH_2CH_2SCH_3$ | Et | H | F | F | OH | H | H |
| X-17-8 | p-F—Ph | * | H | * | Et | H | F | F | OH | H | H |

*$R^2$ and $R^{3b}$ joined together by $(CH_2)_3$ to form five-membered ring.

TABLE X-18

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-18-1 | p-Cl—Ph | H | H | H | Et | H | F | F | OH | H | H |
| X-18-2 | p-Cl—Ph | H | H | $CH_3$ | Et | H | F | F | OH | H | H |
| X-18-3 | p-Cl—Ph | H | H | $CH(CH_3)_2$ | Et | H | F | F | OH | H | H |
| X-18-4 | p-Cl—Ph | H | H | $CH_2CH(CH_3)_2$ | Et | H | F | F | OH | H | H |
| X-18-5 | p-Cl—Ph | H | H | $CH_2Ph$ | Et | H | F | F | OH | H | H |
| X-18-6 | p-Cl—Ph | H | H | $CH_2$-indol-3-yl | Et | H | F | F | OH | H | H |
| X-18-7 | p-Cl—Ph | H | H | $CH_2CH_2SCH_3$ | Et | H | F | F | OH | H | H |
| X-18-8 | p-Cl—Ph | * | H | * | Et | H | F | F | OH | H | H |

*$R^2$ and $R^{3b}$ joined together by $(CH_2)_3$ to form five-membered ring.

TABLE X-19

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-19-1 | p-Br—Ph | H | H | H | Et | H | F | F | OH | H | H |
| X-19-2 | p-Br—Ph | H | H | $CH_3$ | Et | H | F | F | OH | H | H |
| X-19-3 | p-Br—Ph | H | H | $CH(CH_3)_2$ | Et | H | F | F | OH | H | H |
| X-19-4 | p-Br—Ph | H | H | $CH_2CH(CH_3)_2$ | Et | H | F | F | OH | H | H |
| X-19-5 | p-Br—Ph | H | H | $CH_2Ph$ | Et | H | F | F | OH | H | H |
| X-19-6 | p-Br—Ph | H | H | $CH_2$-indol-3-yl | Et | H | F | F | OH | H | H |
| X-19-7 | p-Br—Ph | H | H | $CH_2CH_2SCH_3$ | Et | H | F | F | OH | H | H |
| X-19-8 | p-Br—Ph | * | H | * | Et | H | F | F | OH | H | H |

*$R^2$ and $R^{3b}$ joined together by $(CH_2)_3$ to form five-membered ring.

TABLE X-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-20-1 | p-I—Ph | H | H | H | Et | H | F | F | OH | H | |
| X-20-2 | p-I—Ph | H | H | CH₃ | Et | H | F | F | OH | H | |
| X-20-3 | p-I—Ph | H | H | CH(CH₃)₂ | Et | H | F | F | OH | H | |
| X-20-4 | p-I—ph | H | H | CH₂CH(CH₃)₂ | Et | H | F | F | OH | H | |
| X-20-5 | p-I—Ph | H | H | CH₂Ph | Et | H | F | F | OH | H | |
| X-20-6 | p-I—Ph | H | H | CH₂-indol-3-yl | Et | H | F | F | OH | H | |
| X-20-7 | p-I—Ph | H | H | CH₂CH₂SCH₃ | Et | H | F | F | OH | H | |
| X-20-8 | p-I—Ph | * | H | * | Et | H | F | F | OH | H | |

*R² and R³ᵇ joined together by (CH₂)₃ to form five-membered ring.

TABLE X-21

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-21-1 | CH₃ | H | H | H | ⁱPr | H | F | F | OH | H | H |
| X-21-2 | CH₃ | H | H | CH₃ | ⁱPr | H | F | F | OH | H | H |
| X-21-3 | CH₃ | H | H | CH(CH₃)₂ | ⁱPr | H | F | F | OH | H | H |
| X-21-4 | CH₃ | H | H | CH₂CH(CH₃)₂ | ⁱPr | H | F | F | OH | H | H |
| X-21-5 | CH₃ | H | H | CH₂Ph | ⁱPr | H | F | F | OH | H | H |
| X-21-6 | CH₃ | H | H | CH₂-indol-3-yl | ⁱPr | H | F | F | OH | H | H |
| X-21-7 | CH₃ | H | H | CH₂CH₂SCH₃ | ⁱPr | H | F | F | OH | H | H |
| X-21-8 | CH₃ | * | H | * | ⁱPr | H | F | F | OH | H | H |

*R² and R³ᵇ joined together by (CH₂)₃ to form five-membered ring.

TABLE X-22

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-22-1 | Et | H | H | H | ⁱPr | H | F | F | OH | H | H |
| X-22-2 | Et | H | H | CH₃ | ⁱPr | H | F | F | OH | H | H |
| X-22-3 | Et | H | H | CH(CH₃)₂ | ⁱPr | H | F | F | OH | H | H |
| X-22-4 | Et | H | H | CH₂CH(CH₃)₂ | ⁱPr | H | F | F | OH | H | H |
| X-22-5 | Et | H | H | CH₂Ph | ⁱPr | H | F | F | OH | H | H |
| X-22-6 | Et | H | H | CH₂-indol-3-yl | ⁱPr | H | F | F | OH | H | H |
| X-22-7 | Et | H | H | CH₂CH₂SCH₃ | ⁱPr | H | F | F | OH | H | H |
| X-22-8 | Et | * | H | * | ⁱPr | H | F | F | OH | H | H |

*R² and R³ᵇ joined together by (CH₂)₃ to form five-membered ring.

TABLE X-23

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-23-1 | ⁱPr | H | H | H | ⁱPr | H | F | F | OH | H | H |
| X-23-2 | ⁱPr | H | H | CH₃ | ⁱPr | H | F | F | OH | H | H |
| X-23-3 | ⁱPr | H | H | CH(CH₃)₂ | ⁱPr | H | F | F | OH | H | H |
| X-23-4 | ⁱPr | H | H | CH₂CH(CH₃)₂ | ⁱPr | H | F | F | OH | H | H |
| X-23-5 | ⁱPr | H | H | CH₂Ph | ⁱPr | H | F | F | OH | H | H |
| X-23-6 | ⁱPr | H | H | CH₂-indol-3-yl | ⁱPr | H | F | F | OH | H | H |
| X-23-7 | ⁱPr | H | H | CH₂CH₂SCH₃ | ⁱPr | H | F | F | OH | H | H |
| X-23-8 | ⁱPr | * | H | * | ⁱPr | H | F | F | OH | H | H |

*R² and R³ᵇ joined together by (CH₂)₃ to form five-membered ring.

TABLE X-24

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-24-1 | ᵗBu | H | H | H | ⁱPr | H | F | F | OH | H | H |
| X-24-2 | ᵗBu | H | H | CH₃ | ⁱPr | H | F | F | OH | H | H |
| X-24-3 | ᵗBu | H | H | CH(CH₃)₂ | ⁱPr | H | F | F | OH | H | H |
| X-24-4 | ᵗBu | H | H | CH₂CH(CH₃)₂ | ⁱPr | H | F | F | OH | H | H |
| X-24-5 | ᵗBu | H | H | CH₂Ph | ⁱPr | H | F | F | OH | H | H |
| X-24-6 | ᵗBu | H | H | CH₂-indol-3-yl | ⁱPr | H | F | F | OH | H | H |
| X-24-7 | ᵗBu | H | H | CH₂CH₂SCH₃ | ⁱPr | H | F | F | OH | H | H |
| X-24-8 | ᵗBu | * | H | * | ⁱPr | H | F | F | OH | H | H |

*R² and R³ᵇ joined together by (CH₂)₃ to form five-membered ring.

TABLE X-25

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-25-1 | Ph | H | H | H | ⁱPr | H | F | F | OH | H | H |
| X-25-2 | Ph | H | H | CH₃ | ⁱPr | H | F | F | OH | H | H |
| X-25-3 | Ph | H | H | CH(CH₃)₂ | ⁱPr | H | F | F | OH | H | H |
| X-25-4 | Ph | H | H | CH₂CH(CH₃)₂ | ⁱPr | H | F | F | OH | H | H |
| X-25-5 | Ph | H | H | CH₂Ph | ⁱPr | H | F | F | OH | H | H |
| X-25-6 | Ph | H | H | CH₂-indol-3-yl | ⁱPr | H | F | F | OH | H | H |
| X-25-7 | Ph | H | H | CH₂CH₂SCH₃ | ⁱPr | H | F | F | OH | H | H |
| X-25-8 | Ph | * | H | * | ⁱPr | H | F | F | OH | H | H |

*R² and R³ᵇ joined together by (CH₂)₃ to form five-membered ring.

TABLE X-26

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-26-1 | p-Me—Ph | H | H | H | ⁱPr | H | F | F | OH | H | H |
| X-26-2 | p-Me—Ph | H | H | CH₃ | ⁱPr | H | F | F | OH | H | H |
| X-26-3 | p-Me—Ph | H | H | CH(CH₃)₂ | ⁱPr | H | F | F | OH | H | H |
| X-26-4 | p-Me—Ph | H | H | CH₂CH(CH₃)₂ | ⁱPr | H | F | F | OH | H | H |
| X-26-5 | p-Me—Ph | H | H | CH₂Ph | ⁱPr | H | F | F | OH | H | H |
| X-26-6 | p-Me—Ph | H | H | CH₂-indol-3-yl | ⁱPr | H | F | F | OH | H | H |
| X-26-7 | p-Me—Ph | H | H | CH₂CH₂SCH₃ | ⁱPr | H | F | F | OH | H | H |
| X-26-8 | p-Me—Ph | * | H | * | ⁱPr | H | F | F | OH | H | H |

*R² and R³ᵇ joined together by (CH₂)₃ to form five-membered ring.

TABLE X-27

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-27-1 | p-F—Ph | H | H | H | ⁱPr | H | F | F | OH | H | H |
| X-27-2 | p-F—Ph | H | H | CH₃ | ⁱPr | H | F | F | OH | H | H |
| X-27-3 | p-F—Ph | H | H | CH(CH₃)₂ | ⁱPr | H | F | F | OH | H | H |
| X-27-4 | p-F—Ph | H | H | CH₂CH(CH₃)₂ | ⁱPr | H | F | F | OH | H | H |
| X-27-5 | p-F—Ph | H | H | CH₂Ph | ⁱPr | H | F | F | OH | H | H |
| X-27-6 | p-F—Ph | H | H | CH₂-indol-3-yl | ⁱPr | H | F | F | OH | H | H |
| X-27-7 | p-F—Ph | H | H | CH₂CH₂SCH₃ | ⁱPr | H | F | F | OH | H | H |
| X-27-8 | p-F—Ph | * | H | * | ⁱPr | H | F | F | OH | H | H |

*R² and R³ᵇ joined together by (CH₂)₃ to form five-membered ring.

TABLE X-28

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-28-1 | p-Cl—Ph | H | H | H | $^i$Pr | H | F | F | OH | H | H |
| X-28-2 | p-Cl—Ph | H | H | $CH_3$ | $^i$Pr | H | F | F | OH | H | H |
| X-28-3 | p-Cl—Ph | H | H | $CH(CH_3)_2$ | $^i$Pr | H | F | F | OH | H | H |
| X-28-4 | p-Cl—Ph | H | H | $CH_2CH(CH_3)_2$ | $^i$Pr | H | F | F | OH | H | H |
| X-28-5 | p-Cl—Ph | H | H | $CH_2Ph$ | $^i$Pr | H | F | F | OH | H | H |
| X-28-6 | p-Cl—Ph | H | H | $CH_2$-indol-3-yl | $^i$Pr | H | F | F | OH | H | H |
| X-28-7 | p-Cl—Ph | H | H | $CH_2CH_2SCH_3$ | $^i$Pr | H | F | F | OH | H | H |
| X-28-8 | p-Cl—Ph | * | H | * | $^i$Pr | H | F | F | OH | H | H |

*$R^2$ and $R^{3b}$ joined together by $(CH_2)_3$ to form five-membered ring.

TABLE X-29

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-29-1 | p-Br—Ph | H | H | H | $^i$Pr | H | F | F | OH | H | H |
| X-29-2 | p-Br—Ph | H | H | $CH_3$ | $^i$Pr | H | F | F | OH | H | H |
| X-29-3 | p-Br—Ph | H | H | $CH(CH_3)_2$ | $^i$Pr | H | F | F | OH | H | H |
| X-29-4 | p-Br—Ph | H | H | $CH_2CH(CH_3)_2$ | $^i$Pr | H | F | F | OH | H | H |
| X-29-5 | p-Br—Ph | H | H | $CH_2Ph$ | $^i$Pr | H | F | F | OH | H | H |
| X-29-6 | p-Br—Ph | H | H | $CH_2$-indol-3-yl | $^i$Pr | H | F | F | OH | H | H |
| X-29-7 | p-Br—Ph | H | H | $CH_2CH_2SCH_3$ | $^i$Pr | H | F | F | OH | H | H |
| X-29-8 | p-Br—Ph | * | H | * | $^i$Pr | H | F | F | OH | H | H |

*$R^2$ and $R^{3b}$ joined together by $(CH_2)_3$ to form five-membered ring.

TABLE X-30

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-30-1 | p-I—Ph | H | H | H | $^i$Pr | H | F | F | OH | H | H |
| X-30-2 | p-I—Ph | H | H | $CH_3$ | $^i$Pr | H | F | F | OH | H | H |
| X-30-3 | p-I—Ph | H | H | $CH(CH_3)_2$ | $^i$Pr | H | F | F | OH | H | H |
| X-30-4 | p-I—Ph | H | H | $CH_2CH(CH_3)_2$ | $^i$Pr | H | F | F | OH | H | H |
| X-30-5 | p-I—Ph | H | H | $CH_2Ph$ | $^i$Pr | H | F | F | OH | H | H |
| X-30-6 | p-I—Ph | H | H | $CH_2$-indol-3-yl | $^i$Pr | H | F | F | OH | H | H |
| X-30-7 | p-I—Ph | H | H | $CH_2CH_2SCH_3$ | $^i$Pr | H | F | F | OH | H | H |
| X-30-8 | p-I—Ph | * | H | * | $^i$Pr | H | F | F | OH | H | H |

*$R^2$ and $R^{3b}$ joined together by $(CH_2)_3$ to form five-membered ring.

TABLE X-31

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-31-1 | $CH_3$ | H | H | H | $^n$Bu | H | F | F | OH | H | H |
| X-31-2 | $CH_3$ | H | H | $CH_3$ | $^n$Bu | H | F | F | OH | H | H |
| X-31-3 | $CH_3$ | H | H | $CH(CH_3)_2$ | $^n$Bu | H | F | F | OH | H | H |
| X-31-4 | $CH_3$ | H | H | $CH_2CH(CH_3)_2$ | $^n$Bu | H | F | F | OH | H | H |
| X-31-5 | $CH_3$ | H | H | $CH_2Ph$ | $^n$Bu | H | F | F | OH | H | H |
| X-31-6 | $CH_3$ | H | H | $CH_2$-indol-3-yl | $^n$Bu | H | F | F | OH | H | H |
| X-31-7 | $CH_3$ | H | H | $CH_2CH_2SCH_3$ | $^n$Bu | H | F | F | OH | H | H |
| X-31-8 | $CH_3$ | * | H | * | $^n$Bu | H | F | F | OH | H | H |

*$R^2$ and $R^{3b}$ joined together by $(CH_2)_3$ to form five-membered ring.

TABLE X-32

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-32-1 | Et | H | H | H | $^n$Bu | H | F | F | OH | H | H |
| X-32-2 | Et | H | H | $CH_3$ | $^n$Bu | H | F | F | OH | H | H |
| X-32-3 | Et | H | H | $CH(CH_3)_2$ | $^n$Bu | H | F | F | OH | H | H |
| X-32-4 | Et | H | H | $CH_2CH(CH_3)_2$ | $^n$Bu | H | F | F | OH | H | H |
| X-32-5 | Et | H | H | $CH_2Ph$ | $^n$Bu | H | F | F | OH | H | H |
| X-32-6 | Et | H | H | $CH_2$-indol-3-yl | $^n$Bu | H | F | F | OH | H | H |

TABLE X-32-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-32-7 | Et | H | H | $CH_2CH_2SCH_3$ | $^nBu$ | H | F | F | OH | H | H |
| X-32-8 | Et | * | H | * | $^nBu$ | H | F | F | OH | H | H |

*$R^2$ and $R^{3b}$ joined together by $(CH_2)_3$ to form five-membered ring.

TABLE X-33

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-33-1 | $^iPr$ | H | H | H | $^nBu$ | H | F | F | OH | H | H |
| X-33-2 | $^iPr$ | H | H | $CH_3$ | $^nBu$ | H | F | F | OH | H | H |
| X-33-3 | $^iPr$ | H | H | $CH(CH_3)_2$ | $^nBu$ | H | F | F | OH | H | H |
| X-33-4 | $^iPr$ | H | H | $CH_2CH(CH_3)_2$ | $^nBu$ | H | F | F | OH | H | H |
| X-33-5 | $^iPr$ | H | H | $CH_2Ph$ | $^nBu$ | H | F | F | OH | H | H |
| X-33-6 | $^iPr$ | H | H | $CH_2$-indol-3-yl | $^nBu$ | H | F | F | OH | H | H |
| X-33-7 | $^iPr$ | H | H | $CH_2CH_2SCH_3$ | $^nBu$ | H | F | F | OH | H | H |
| X-33-8 | $^iPr$ | * | H | * | $^nBu$ | H | F | F | OH | H | H |

*$R^2$ and $R^{3b}$ joined together by $(CH_2)_3$ to form five-membered ring.

TABLE X-34

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-34-1 | $^tBu$ | H | H | H | $^nBu$ | H | F | F | OH | H | H |
| X-34-2 | $^tBu$ | H | H | $CH_3$ | $^nBu$ | H | F | F | OH | H | H |
| X-34-3 | $^tBu$ | H | H | $CH(CH_3)_2$ | $^nBu$ | H | F | F | OH | H | H |
| X-34-4 | $^tBu$ | H | H | $CH_2CH(CH_3)_2$ | $^nBu$ | H | F | F | OH | H | H |
| X-34-5 | $^tBu$ | H | H | $CH_2Ph$ | $^nBu$ | H | F | F | OH | H | H |
| X-34-6 | $^tBu$ | H | H | $CH_2$-indol-3-yl | $^nBu$ | H | F | F | OH | H | H |
| X-34-7 | $^tBu$ | H | H | $CH_2CH_2SCH_3$ | $^nBu$ | H | F | F | OH | H | H |
| X-34-8 | $^tBu$ | * | H | * | $^nBu$ | H | F | F | OH | H | H |

*$R^2$ and $R^{3b}$ joined together by $(CH_2)_3$ to form five-membered ring.

TABLE X-35

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-35-1 | Ph | H | H | H | $^nBu$ | H | F | F | OH | H | H |
| X-35-2 | Ph | H | H | $CH_3$ | $^nBu$ | H | F | F | OH | H | H |
| X-35-3 | Ph | H | H | $CH(CH_3)_2$ | $^nBu$ | H | F | F | OH | H | H |
| X-35-4 | Ph | H | H | $CH_2CH(CH_3)_2$ | $^nBu$ | H | F | F | OH | H | H |
| X-35-5 | Ph | H | H | $CH_2Ph$ | $^nBu$ | H | F | F | OH | H | H |
| X-35-6 | Ph | H | H | $CH_2$-indol-3-yl | $^nBu$ | H | F | F | OH | H | H |
| X-35-7 | Ph | H | H | $CH_2CH_2SCH_3$ | $^nBu$ | H | F | F | OH | H | H |
| X-35-8 | Ph | * | H | * | $^nBu$ | H | F | F | OH | H | H |

*$R^2$ and $R^{3b}$ joined together by $(CH_2)_3$ to form five-membered ring.

TABLE X-36

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-36-1 | p-Me—Ph | H | H | H | $^nBu$ | H | F | F | OH | H | H |
| X-36-2 | p-Me—Ph | H | H | $CH_3$ | $^nBu$ | H | F | F | OH | H | H |
| X-36-3 | p-Me—Ph | H | H | $CH(CH_3)_2$ | $^nBu$ | H | F | F | OH | H | H |
| X-36-4 | p-Me—Ph | H | H | $CH_2CH(CH_3)_2$ | $^nBu$ | H | F | F | OH | H | H |
| X-36-5 | p-Me—Ph | H | H | $CH_2Ph$ | $^nBu$ | H | F | F | OH | H | H |
| X-36-6 | p-Me—Ph | H | H | $CH_2$-indol-3-yl | $^nBu$ | H | F | F | OH | H | H |
| X-36-7 | p-Me—Ph | H | H | $CH_2CH_2SCH_3$ | $^nBu$ | H | F | F | OH | H | H |
| X-36-8 | p-Me—Ph | * | H | * | $^nBu$ | H | F | F | OH | H | H |

*$R^2$ and $R^{3b}$ joined together by $(CH_2)_3$ to form five-membered ring.

TABLE X-37

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-37-1 | p-F—Ph | H | H | H | $^nBu$ | H | F | F | OH | H | H |
| X-37-2 | p-F—Ph | H | H | $CH_3$ | $^nBu$ | H | F | F | OH | H | H |
| X-37-3 | p-F—Ph | H | H | $CH(CH_3)_2$ | $^nBu$ | H | F | F | OH | H | H |
| X-37-4 | p-F—Ph | H | H | $CH_2CH(CH_3)_2$ | $^nBu$ | H | F | F | OH | H | H |
| X-37-5 | p-F—Ph | H | H | $CH_2Ph$ | $^nBu$ | H | F | F | OH | H | H |
| X-37-6 | p-F—Ph | H | H | $CH_2$-indol-3-yl | $^nBu$ | H | F | F | OH | H | H |
| X-37-7 | p-F—Ph | H | H | $CH_2CH_2SCH_3$ | $^nBu$ | H | F | F | OH | H | H |
| X-37-8 | p-F—Ph | * | H | * | $^nBu$ | H | F | F | OH | H | H |

*$R^2$ and $R^{3b}$ joined together by $(CH_2)_3$ to form five-membered ring.

TABLE X-38

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-38-1 | p-Cl—Ph | H | H | H | ⁿBu | H | F | F | OH | H | H |
| X-38-2 | p-Cl—Ph | H | H | CH₃ | ⁿBu | H | F | F | OH | H | H |
| X-38-3 | p-Cl—Ph | H | H | CH(CH₃)₂ | ⁿBu | H | F | F | OH | H | H |
| X-38-4 | p-Cl—Ph | H | H | CH₂CH(CH₃)₂ | ⁿBu | H | F | F | OH | H | H |
| X-38-5 | p-Cl—Ph | H | H | CH₂Ph | ⁿBu | H | F | F | OH | H | H |
| X-38-6 | p-Cl—Ph | H | H | CH₂-indol-3-yl | ⁿBu | H | F | F | OH | H | H |
| X-38-7 | p-Cl—Ph | H | H | CH₂CH₂SCH₃ | ⁿBu | H | F | F | OH | H | H |
| X-38-8 | p-Cl—Ph | * | H | * | ⁿBu | H | F | F | OH | H | H |

*R² and R³ᵇ joined together by (CH₂)₃ to form five-membered ring.

TABLE X-39

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-39-1 | p-Br—Ph | H | H | H | ⁿBu | H | F | F | OH | H | H |
| X-39-2 | p-Br—Ph | H | H | CH₃ | ⁿBu | H | F | F | OH | H | H |
| X-39-3 | p-Br—Ph | H | H | CH(CH₃)₂ | ⁿBu | H | F | F | OH | H | H |
| X-39-4 | p-Br—Ph | H | H | CH₂CH(CH₃)₂ | ⁿBu | H | F | F | OH | H | H |
| X-39-5 | p-Br—Ph | H | H | CH₂Ph | ⁿBu | H | F | F | OH | H | H |
| X-39-6 | p-Br—Ph | H | H | CH₂-indol-3-yl | ⁿBu | H | F | F | OH | H | H |
| X-39-7 | p-Br—Ph | H | H | CH₂CH₂SCH₃ | ⁿBu | H | F | F | OH | H | H |
| X-39-8 | p-Br—Ph | * | H | * | ⁿBu | H | F | F | OH | H | H |

*R² and R³ᵇ joined together by (CH₂)₃ to form five-membered ring.

TABLE X-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-40-1 | p-I—Ph | H | H | H | ⁿBu | H | F | F | OH | H | H |
| X-40-2 | p-I—Ph | H | H | CH₃ | ⁿBu | H | F | F | OH | H | H |
| X-40-3 | p-I—Ph | H | H | CH(CH₃)₂ | ⁿBu | H | F | F | OH | H | H |
| X-40-4 | p-I—Ph | H | H | CH₂CH(CH₃)₂ | ⁿBu | H | F | F | OH | H | H |
| X-40-5 | p-I—Ph | H | H | CH₂Ph | ⁿBu | H | F | F | OH | H | H |
| X-40-6 | p-I—Ph | H | H | CH₂-indol-3-yl | ⁿBu | H | F | F | OH | H | H |
| X-40-7 | p-I—Ph | H | H | CH₂CH₂SCH₃ | ⁿBu | H | F | F | OH | H | H |
| X-40-8 | p-I—Ph | * | H | * | ⁿBu | H | F | F | OH | H | H |

*R² and R³ᵇ joined together by (CH₂)₃ to form five-membered ring.

TABLE X-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-41-1 | CH₃ | H | H | H | Bz | H | F | F | OH | H | H |
| X-41-2 | CH₃ | H | H | CH₃ | Bz | H | F | F | OH | H | H |
| X-41-3 | CH₃ | H | H | CH(CH₃)₂ | Bz | H | F | F | OH | H | H |
| X-41-4 | CH₃ | H | H | CH₂CH(CH₃)₂ | Bz | H | F | F | OH | H | H |
| X-41-5 | CH₃ | H | H | CH₂Ph | Bz | H | F | F | OH | H | H |
| X-41-6 | CH₃ | H | H | CH₂-indol-3-yl | Bz | H | F | F | OH | H | H |
| X-41-7 | CH₃ | H | H | CH₂CH₂SCH₃ | Bz | H | F | F | OH | H | H |
| X-41-8 | CH₃ | * | H | * | Bz | H | F | F | OH | H | H |

*R² and R³ᵇ joined together by (CH₂)₃ to form five-membered ring.

TABLE X-42

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| X-42-1 | Et | H | H | H | Bz | H | F | F | OH | H | H |
| X-42-2 | Et | H | H | CH₃ | Bz | H | F | F | OH | H | H |
| X-42-3 | Et | H | H | CH(CH₃)₂ | Bz | H | F | F | OH | H | H |
| X-42-4 | Et | H | H | CH₂CH(CH₃)₂ | Bz | H | F | F | OH | H | H |
| X-42-5 | Et | H | H | CH₂Ph | Bz | H | F | F | OH | H | H |
| X-42-6 | Et | H | H | CH₂-indol-3-yl | Bz | H | F | F | OH | H | H |

TABLE X-42-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-42-7 | Et | H | H | CH$_2$CH$_2$SCH$_3$ | Bz | H | F | F | OH | H | H |
| X-42-8 | Et | * | H | * | Bz | H | F | F | OH | H | H |

*$R^2$ and $R^{3b}$ joined together by (CH$_2$)$_3$ to form five-membered ring.

TABLE X-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-43-1 | $^i$Pr | H | H | H | Bz | H | F | F | OH | H | H |
| X-43-2 | $^i$Pr | H | H | CH$_3$ | Bz | H | F | F | OH | H | H |
| X-43-3 | $^i$Pr | H | H | CH(CH$_3$)$_2$ | Bz | H | F | F | OH | H | H |
| X-43-4 | $^i$Pr | H | H | CH$_2$CH(CH$_3$)$_2$ | Bz | H | F | F | OH | H | H |
| X-43-5 | $^i$Pr | H | H | CH$_2$Ph | Bz | H | F | F | OH | H | H |
| X-43-6 | $^i$Pr | H | H | CH$_2$-indol-3-yl | Bz | H | F | F | OH | H | H |
| X-43-7 | $^i$Pr | H | H | CH$_2$CH$_2$SCH$_3$ | Bz | H | F | F | OH | H | H |
| X-43-8 | $^i$Pr | * | H | * | Bz | H | F | F | OH | H | H |

*$R^2$ and $R^{3b}$ joined together by (CH$_2$)$_3$ to form five-membered ring.

TABLE X-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-44-1 | $^t$Bu | H | H | H | Bz | H | F | F | OH | H | H |
| X-44-2 | $^t$Bu | H | H | CH$_3$ | Bz | H | F | F | OH | H | H |
| X-44-3 | $^t$Bu | H | H | CH(CH$_3$)$_2$ | Bz | H | F | F | OH | H | H |
| X-44-4 | $^t$Bu | H | H | CH$_2$CH(CH$_3$)$_2$ | Bz | H | F | F | OH | H | H |
| X-44-5 | $^t$Bu | H | H | CH$_2$Ph | Bz | H | F | F | OH | H | H |
| X-44-6 | $^t$Bu | H | H | CH$_2$-indol-3-yl | Bz | H | F | F | OH | H | H |
| X-44-7 | $^t$Bu | H | H | CH$_2$CH$_2$SCH$_3$ | Bz | H | F | F | OH | H | H |
| X-44-8 | $^t$Bu | * | H | * | Bz | H | F | F | OH | H | H |

*$R^2$ and $R^{3b}$ joined together by (CH$_2$)$_3$ to form five-membered ring.

TABLE X-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-45-1 | Ph | H | H | H | Bz | H | F | F | OH | H | H |
| X-45-2 | Ph | H | H | CH$_3$ | Bz | H | F | F | OH | H | H |
| X-45-3 | Ph | H | H | CH(CH$_3$)$_2$ | Bz | H | F | F | OH | H | H |
| X-45-4 | Ph | H | H | CH$_2$CH(CH$_3$)$_2$ | Bz | H | F | F | OH | H | H |
| X-45-5 | Ph | H | H | CH$_2$Ph | Bz | H | F | F | OH | H | H |
| X-45-6 | Ph | H | H | CH$_2$-indol-3-yl | Bz | H | F | F | OH | H | H |
| X-45-7 | Ph | H | H | CH$_2$CH$_2$SCH$_3$ | Bz | H | F | F | OH | H | H |
| X-45-8 | Ph | * | H | * | Bz | H | F | F | OH | H | H |

*$R^2$ and $R^{3b}$ joined together by (CH$_2$)$_3$ to form five-membered ring.

TABLE X-46

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-46-1 | p-Me—Ph | H | H | H | Bz | H | F | F | OH | H | H |
| X-46-2 | p-Me—Ph | H | H | CH$_3$ | Bz | H | F | F | OH | H | H |
| X-46-3 | p-Me—Ph | H | H | CH(CH$_3$)$_2$ | Bz | H | F | F | OH | H | H |
| X-46-4 | p-Me—Ph | H | H | CH$_2$CH(CH$_3$)$_2$ | Bz | H | F | F | OH | H | H |
| X-46-5 | p-Me—Ph | H | H | CH$_2$Ph | Bz | H | F | F | OH | H | H |
| X-46-6 | p-Me—Ph | H | H | CH$_2$-indol-3-yl | Bz | H | F | F | OH | H | H |
| X-46-7 | p-Me—Ph | H | H | CH$_2$CH$_2$SCH$_3$ | Bz | H | F | F | OH | H | H |
| X-46-8 | p-Me—Ph | * | H | * | Bz | H | F | F | OH | H | H |

*$R^2$ and $R^{3b}$ joined together by (CH$_2$)$_3$ to form five-membered ring.

TABLE X-47

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-47-1 | p-F—Ph | H | H | H | Bz | H | F | F | OH | H | H |
| X-47-2 | p-F—Ph | H | H | CH$_3$ | Bz | H | F | F | OH | H | H |
| X-47-3 | p-F—Ph | H | H | CH(CH$_3$)$_2$ | Bz | H | F | F | OH | H | H |
| X-47-4 | p-F—Ph | H | H | CH$_2$CH(CH$_3$)$_2$ | Bz | H | F | F | OH | H | H |
| X-47-5 | p-F—Ph | H | H | CH$_2$Ph | Bz | H | F | F | OH | H | H |
| X-47-6 | p-F—Ph | H | H | CH$_2$-indol-3-yl | Bz | H | F | F | OH | H | H |
| X-47-7 | p-F—Ph | H | H | CH$_2$CH$_2$SCH$_3$ | Bz | H | F | F | OH | H | H |
| X-47-8 | p-F—Ph | * | H | * | Bz | H | F | F | OH | H | H |

*$R^2$ and $R^{3b}$ joined together by (CH$_2$)$_3$ to form five-membered ring.

TABLE X-48

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-48-1 | p-Cl—Ph | H | H | H | Bz | H | F | F | OH | H | H |
| X-48-2 | p-Cl—Ph | H | H | $CH_3$ | Bz | H | F | F | OH | H | H |
| X-48-3 | p-Cl—Ph | H | H | $CH(CH_3)_2$ | Bz | H | F | F | OH | H | H |
| X-48-4 | p-Cl—Ph | H | H | $CH_2CH(CH_3)_2$ | Bz | H | F | F | OH | H | H |
| X-48-5 | p-Cl—Ph | H | H | $CH_2Ph$ | Bz | H | F | F | OH | H | H |
| X-48-6 | p-Cl—Ph | H | H | $CH_2$-indol-3-yl | Bz | H | F | F | OH | H | H |
| X-48-7 | p-Cl—Ph | H | H | $CH_2CH_2SCH_3$ | Bz | H | F | F | OH | H | H |
| X-48-8 | p-Cl—Ph | * | H | * | Bz | H | F | F | OH | H | H |

*$R^2$ and $R^{3b}$ joined together by $(CH_2)_3$ to form five-membered ring.

TABLE X-49

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-49-1 | p-Br—Ph | H | H | H | Bz | H | F | F | OH | H | H |
| X-49-2 | p-Br—Ph | H | H | $CH_3$ | Bz | H | F | F | OH | H | H |
| X-49-3 | p-Br—Ph | H | H | $CH(CH_3)_2$ | Bz | H | F | F | OH | H | H |
| X-49-4 | p-Br—Ph | H | H | $CH_2CH(CH_3)_2$ | Bz | H | F | F | OH | H | H |
| X-49-5 | p-Br—Ph | H | H | $CH_2Ph$ | Bz | H | F | F | OH | H | H |
| X-49-6 | p-Br—Ph | H | H | $CH_2$-indol-3-yl | Bz | H | F | F | OH | H | H |
| X-49-7 | p-Br—Ph | H | H | $CH_2CH_2SCH_3$ | Bz | H | F | F | OH | H | H |
| X-49-8 | p-Br—Ph | * | H | * | Bz | H | F | F | OH | H | H |

*$R^2$ and $R^{3b}$ joined together by $(CH_2)_3$ to form five-membered ring.

TABLE X-50

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| X-50-1 | p-I—Ph | H | H | H | Bz | H | F | F | OH | H | H |
| X-50-2 | p-I—Ph | H | H | $CH_3$ | Bz | H | F | F | OH | H | H |
| X-50-3 | p-I—Ph | H | H | $CH(CH_3)_2$ | Bz | H | F | F | OH | H | H |
| X-50-4 | p-I—Ph | H | H | $CH_2CH(CH_3)_2$ | Bz | H | F | F | OH | H | H |
| X-50-5 | p-I—Ph | H | H | $CH_2Ph$ | Bz | H | F | F | OH | H | H |
| X-50-6 | p-I—Ph | H | H | $CH_2$-indol-3-yl | Bz | H | F | F | OH | H | H |
| X-50-7 | p-I—Ph | H | H | $CH_2CH_2SCH_3$ | Bz | H | F | F | OH | H | H |
| X-50-8 | p-I—Ph | * | H | * | Bz | H | F | F | OH | H | H |

*$R^2$ and $R^{3b}$ joined together by $(CH_2)_3$ to form five-membered ring.

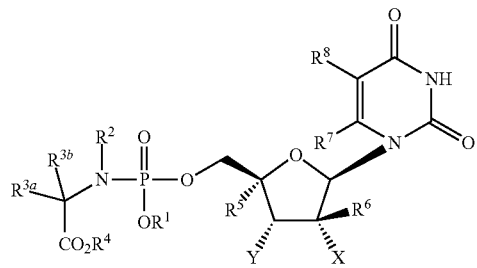

XI

TABLE XI-1

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-1-1 | $CH_3$ | H | H | H | $CH_3$ | H | H | F | OH | H | H |
| XI-1-2 | $CH_3$ | H | H | $CH_3$ | $CH_3$ | H | H | F | OH | H | H |
| XI-1-3 | $CH_3$ | H | H | $CH(CH_3)_2$ | $CH_3$ | H | H | F | OH | H | H |
| XI-1-4 | $CH_3$ | H | H | $CH_2CH(CH_3)_2$ | $CH_3$ | H | H | F | OH | H | H |
| XI-1-5 | $CH_3$ | H | H | $CH_2Ph$ | $CH_3$ | H | H | F | OH | H | H |
| XI-1-6 | $CH_3$ | H | H | $CH_2$-indol-3-yl | $CH_3$ | H | H | F | OH | H | H |
| XI-1-7 | $CH_3$ | H | H | $CH_2CH_2SCH_3$ | $CH_3$ | H | H | F | OH | H | H |
| XI-1-8 | $CH_3$ | * | H | * | $CH_3$ | H | H | F | OH | H | H |

*$R^2$ and $R^{3b}$ joined together by $(CH_2)_3$ to form five-membered ring.

TABLE XI-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-2-1 | Et | H | H | H | $CH_3$ | H | H | F | OH | H | H |
| XI-2-2 | Et | H | H | $CH_3$ | $CH_3$ | H | H | F | OH | H | H |
| XI-2-3 | Et | H | H | $CH(CH_3)_2$ | $CH_3$ | H | H | F | OH | H | H |
| XI-2-4 | Et | H | H | $CH_2CH(CH_3)_2$ | $CH_3$ | H | H | F | OH | H | H |

TABLE XI-2-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-2-5 | Et | H | H | $CH_2Ph$ | $CH_3$ | H | H | F | OH | H | H |
| XI-2-6 | Et | H | H | $CH_2$-indol-3-yl | $CH_3$ | H | H | F | OH | H | H |
| XI-2-7 | Et | H | H | $CH_2CH_2SCH_3$ | $CH_3$ | H | H | F | OH | H | H |
| XI-2-8 | Et | * | H | * | $CH_3$ | H | H | F | OH | H | H |

*$R^2$ and $R^{3b}$ joined together by $(CH_2)_3$ to form five-membered ring.

TABLE XI-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-3-1 | $^iPr$ | H | H | H | $CH_3$ | H | H | F | OH | H | H |
| XI-3-2 | $^iPr$ | H | H | $CH_3$ | $CH_3$ | H | H | F | OH | H | H |
| XI-3-3 | $^iPr$ | H | H | $CH(CH_3)_2$ | $CH_3$ | H | H | F | OH | H | H |
| XI-3-4 | $^iPr$ | H | H | $CH_2CH(CH_3)_2$ | $CH_3$ | H | H | F | OH | H | H |
| XI-3-5 | $^iPr$ | H | H | $CH_2Ph$ | $CH_3$ | H | H | F | OH | H | H |
| XI-3-6 | $^iPr$ | H | H | $CH_2$-indol-3-yl | $CH_3$ | H | H | F | OH | H | H |
| XI-3-7 | $^iPr$ | H | H | $CH_2CH_2SCH_3$ | $CH_3$ | H | H | F | OH | H | H |
| XI-3-8 | $^iPr$ | * | H | * | $CH_3$ | H | H | F | OH | H | H |

*$R^2$ and $R^{3b}$ joined together by $(CH_2)_3$ to form five-membered ring.

TABLE XI-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-4-1 | $^tBu$ | H | H | H | $CH_3$ | H | H | F | OH | H | H |
| XI-4-2 | $^tBu$ | H | H | $CH_3$ | $CH_3$ | H | H | F | OH | H | H |
| XI-4-3 | $^tBu$ | H | H | $CH(CH_3)_2$ | $CH_3$ | H | H | F | OH | H | H |
| XI-4-4 | $^tBu$ | H | H | $CH_2CH(CH_3)_2$ | $CH_3$ | H | H | F | OH | H | H |
| XI-4-5 | $^tBu$ | H | H | $CH_2Ph$ | $CH_3$ | H | H | F | OH | H | H |
| XI-4-6 | $^tBu$ | H | H | $CH_2$-indol-3-yl | $CH_3$ | H | H | F | OH | H | H |
| XI-4-7 | $^tBu$ | H | H | $CH_2CH_2SCH_3$ | $CH_3$ | H | H | F | OH | H | H |
| XI-4-8 | $^tBu$ | * | H | * | $CH_3$ | H | H | F | OH | H | H |

*$R^2$ and $R^{3b}$ joined together by $(CH_2)_3$ to form five-membered ring.

TABLE XI-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-5-1 | Ph | H | H | H | $CH_3$ | H | H | F | OH | H | H |
| XI-5-2 | Ph | H | H | $CH_3$ | $CH_3$ | H | H | F | OH | H | H |
| XI-5-3 | Ph | H | H | $CH(CH_3)_2$ | $CH_3$ | H | H | F | OH | H | H |
| XI-5-4 | Ph | H | H | $CH_2CH(CH_3)_2$ | $CH_3$ | H | H | F | OH | H | H |
| XI-5-5 | Ph | H | H | $CH_2Ph$ | $CH_3$ | H | H | F | OH | H | H |
| XI-5-6 | Ph | H | H | $CH_2$-indol-3-yl | $CH_3$ | H | H | F | OH | H | H |
| XI-5-7 | Ph | H | H | $CH_2CH_2SCH_3$ | $CH_3$ | H | H | F | OH | H | H |
| XI-5-8 | Ph | * | H | * | $CH_3$ | H | H | F | OH | H | H |

*$R^2$ and $R^{3b}$ joined together by $(CH_2)_3$ to form five-membered ring.

TABLE X-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-6-1 | p-Me—Ph | H | H | H | $CH_3$ | H | H | F | OH | H | H |
| XI-6-2 | p-Me—Ph | H | H | $CH_3$ | $CH_3$ | H | H | F | OH | H | H |
| XI-6-3 | p-Me—Ph | H | H | $CH(CH_3)_2$ | $CH_3$ | H | H | F | OH | H | H |
| XI-6-4 | p-Me—Ph | H | H | $CH_2CH(CH_3)_2$ | $CH_3$ | H | H | F | OH | H | H |
| XI-6-5 | p-Me—Ph | H | H | $CH_2Ph$ | $CH_3$ | H | H | F | OH | H | H |
| XI-6-6 | p-Me—Ph | H | H | $CH_2$-indol-3-yl | $CH_3$ | H | H | F | OH | H | H |
| XI-6-7 | p-Me—Ph | H | H | $CH_2CH_2SCH_3$ | $CH_3$ | H | H | F | OH | H | H |
| XI-6-8 | p-Me—Ph | * | H | * | $CH_3$ | H | H | F | OH | H | H |

*$R^2$ and $R^{3b}$ joined together by $(CH_2)_3$ to form five-membered ring.

TABLE XI-7

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-7-1 | p-F—Ph | H | H | H | $CH_3$ | H | H | F | OH | H | H |
| XI-7-2 | p-F—Ph | H | H | $CH_3$ | $CH_3$ | H | H | F | OH | H | H |
| XI-7-3 | p-F—Ph | H | H | $CH(CH_3)_2$ | $CH_3$ | H | H | F | OH | H | H |
| XI-7-4 | p-F—Ph | H | H | $CH_2CH(CH_3)_2$ | $CH_3$ | H | H | F | OH | H | H |
| XI-7-6 | p-F—Ph | H | H | $CH_2Ph$ | $CH_3$ | H | H | F | OH | H | H |
| XI-7-7 | p-F—Ph | H | H | $CH_2$-indol-3-yl | $CH_3$ | H | H | F | OH | H | H |
| XI-7-8 | p-F—Ph | H | H | $CH_2CH_2SCH_3$ | $CH_3$ | H | H | F | OH | H | H |
| XI-7-20 | p-F—Ph | * | H | * | $CH_3$ | H | H | F | OH | H | H |

*$R^2$ and $R^{3b}$ joined together by $(CH_2)_3$ to form five-membered ring.

TABLE XI-8

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-8-1 | p-Cl—Ph | H | H | H | CH$_3$ | H | H | F | OH | H | H |
| XI-8-2 | p-Cl—Ph | H | H | CH$_3$ | CH$_3$ | H | H | F | OH | H | H |
| XI-8-3 | p-Cl—Ph | H | H | CH(CH$_3$)$_2$ | CH$_3$ | H | H | F | OH | H | H |
| XI-8-4 | p-Cl—Ph | H | H | CH$_2$CH(CH$_3$)$_2$ | CH$_3$ | H | H | F | OH | H | H |
| XI-8-5 | p-Cl—Ph | H | H | CH$_2$Ph | CH$_3$ | H | H | F | OH | H | H |
| XI-8-6 | p-Cl—Ph | H | H | CH$_2$-indol-3-yl | CH$_3$ | H | H | F | OH | H | H |
| XI-8-7 | p-Cl—Ph | H | H | CH$_2$CH$_2$SCH$_3$ | CH$_3$ | H | H | F | OH | H | H |
| XI-8-8 | p-Cl—Ph | * | H | * | CH$_3$ | H | H | F | OH | H | H |

*R$^2$ and R$^{3b}$ joined together by (CH$_2$)$_3$ to form five-membered ring.

TABLE XI-9

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-9-1 | p-Br—Ph | H | H | H | CH$_3$ | H | H | F | OH | H | H |
| XI-9-2 | p-Br—Ph | H | H | CH$_3$ | CH$_3$ | H | H | F | OH | H | H |
| XI-9-3 | p-Br—Ph | H | H | CH(CH$_3$)$_2$ | CH$_3$ | H | H | F | OH | H | H |
| XI-9-4 | p-Br—Ph | H | H | CH$_2$CH(CH$_3$)$_2$ | CH$_3$ | H | H | F | OH | H | H |
| XI-9-6 | p-Br—Ph | H | H | CH$_2$Ph | CH$_3$ | H | H | F | OH | H | H |
| XI-9-7 | p-Br—Ph | H | H | CH$_2$-indol-3-yl | CH$_3$ | H | H | F | OH | H | H |
| XI-9-8 | p-Br—Ph | H | H | CH$_2$CH$_2$SCH$_3$ | CH$_3$ | H | H | F | OH | H | H |
| XI-9-20 | p-Br—Ph | * | H | * | CH$_3$ | H | H | F | OH | H | H |

*R$^2$ and R$^{3b}$ joined together by (CH$_2$)$_3$ to form five-membered ring.

TABLE XI-10

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-10-1 | p-I—Ph | H | H | H | CH$_3$ | H | H | F | OH | H | H |
| XI-10-2 | p-I—Ph | H | H | CH$_3$ | CH$_3$ | H | H | F | OH | H | H |
| XI-10-3 | p-I—Ph | H | H | CH(CH$_3$)$_2$ | CH$_3$ | H | H | F | OH | H | H |
| XI-10-4 | p-I—Ph | H | H | CH$_2$CH(CH$_3$)$_2$ | CH$_3$ | H | H | F | OH | H | H |
| XI-10-5 | p-I—Ph | H | H | CH$_2$Ph | CH$_3$ | H | H | F | OH | H | H |
| XI-10-6 | p-I—Ph | H | H | CH$_2$-indol-3-yl | CH$_3$ | H | H | F | OH | H | H |
| XI-10-7 | p-I—Ph | H | H | CH$_2$CH$_2$SCH$_3$ | CH$_3$ | H | H | F | OH | H | H |
| XI-10-8 | p-I—Ph | * | H | * | CH$_3$ | H | H | F | OH | H | H |

*R$^2$ and R$^{3b}$ joined together by (CH$_2$)$_3$ to form five-membered ring.

TABLE XI-11

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-11-1 | CH$_3$ | H | H | H | Et | H | H | F | OH | H | H |
| XI-11-2 | CH$_3$ | H | H | CH$_3$ | Et | H | H | F | OH | H | H |
| XI-11-3 | CH$_3$ | H | H | CH(CH$_3$)$_2$ | Et | H | H | F | OH | H | H |
| XI-11-4 | CH$_3$ | H | H | CH$_2$CH(CH$_3$)$_2$ | Et | H | H | F | OH | H | H |
| XI-11-5 | CH$_3$ | H | H | CH$_2$Ph | Et | H | H | F | OH | H | H |
| XI-11-6 | CH$_3$ | H | H | CH$_2$-indol-3-yl | Et | H | H | F | OH | H | H |
| XI-11-7 | CH$_3$ | H | H | CH$_2$CH$_2$SCH$_3$ | Et | H | H | F | OH | H | H |
| XI-11-8 | CH$_3$ | * | H | * | Et | H | H | F | OH | H | H |

TABLE XI-12

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-12-1 | Et | H | H | H | Et | H | H | F | OH | H | H |

TABLE XI-12-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-12-2 | Et | H | H | CH$_3$ | Et | H | H | F | OH | H | H |
| XI-12-3 | Et | H | H | CH(CH$_3$)$_2$ | Et | H | H | F | OH | H | H |
| XI-12-4 | Et | H | H | CH$_2$CH(CH$_3$)$_2$ | Et | H | H | F | OH | H | H |
| XI-12-5 | Et | H | H | CH$_2$Ph | Et | H | H | F | OH | H | H |
| XI-12-6 | Et | H | H | CH$_2$-indol-3-yl | Et | H | H | F | OH | H | H |
| XI-12-7 | Et | H | H | CH$_2$CH$_2$SCH$_3$ | Et | H | H | F | OH | H | H |
| XI-12-8 | Et | * | H | * | Et | H | H | F | OH | H | H |

TABLE XI-13

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-13-1 | $^i$Pr | H | H | H | Et | H | H | F | OH | H | H |
| XI-13-2 | $^i$Pr | H | H | CH$_3$ | Et | H | H | F | OH | H | H |

TABLE XI-13-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-13-3 | $^i$Pr | H | H | CH(CH₃)₂ | Et | H | H | F | OH | H | H |
| XI-13-4 | $^i$Pr | H | H | CH₂CH(CH₃)₂ | Et | H | H | F | OH | H | H |
| XI-13-5 | $^i$Pr | H | H | CH₂Ph | Et | H | H | F | OH | H | H |
| XI-13-6 | $^i$Pr | H | H | CH₂-indol-3-yl | Et | H | H | F | OH | H | H |
| XI-13-7 | $^i$Pr | H | H | CH₂CH₂SCH₃ | Et | H | H | F | OH | H | H |
| XI-13-8 | $^i$Pr | * | H | * | Et | H | H | F | OH | H | H |

TABLE XI-14

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-14-1 | $^t$Bu | H | H | H | Et | H | H | F | OH | H | H |
| XI-14-2 | $^t$Bu | H | H | CH₃ | Et | H | H | F | OH | H | H |
| XI-14-3 | $^t$Bu | H | H | CH(CH₃)₂ | Et | H | H | F | OH | H | H |
| XI-14-4 | $^t$Bu | H | H | CH₂CH(CH₃)₂ | Et | H | H | F | OH | H | H |
| XI-14-5 | $^t$Bu | H | H | CH₂Ph | Et | H | H | F | OH | H | H |
| XI-14-6 | $^t$Bu | H | H | CH₂-indol-3-yl | Et | H | H | F | OH | H | H |
| XI-14-7 | $^t$Bu | H | H | CH₂CH₂SCH₃ | Et | H | H | F | OH | H | H |
| XI-14-8 | $^t$Bu | * | H | * | Et | H | H | F | OH | H | H |

TABLE XI-15

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-15-1 | Ph | H | H | H | Et | H | H | F | OH | H | H |
| XI-15-2 | Ph | H | H | CH₃ | Et | H | H | F | OH | H | H |
| XI-15-3 | Ph | H | H | CH(CH₃)₂ | Et | H | H | F | OH | H | H |
| XI-15-4 | Ph | H | H | CH₂CH(CH₃)₂ | Et | H | H | F | OH | H | H |
| XI-15-5 | Ph | H | H | CH₂Ph | Et | H | H | F | OH | H | H |
| XI-15-6 | Ph | H | H | CH₂-indol-3-yl | Et | H | H | F | OH | H | H |
| XI-15-7 | Ph | H | H | CH₂CH₂SCH₃ | Et | H | H | F | OH | H | H |
| XI-15-8 | Ph | * | H | * | Et | H | H | F | OH | H | H |

TABLE XI-16

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-16-1 | p-Me—Ph | H | H | H | Et | H | H | F | OH | H | H |
| XI-16-2 | p-Me—Ph | H | H | CH₃ | Et | H | H | F | OH | H | H |
| XI-16-3 | p-Me—Ph | H | H | CH(CH₃)₂ | Et | H | H | F | OH | H | H |
| XI-16-4 | p-Me—Ph | H | H | CH₂CH(CH₃)₂ | Et | H | H | F | OH | H | H |
| XI-16-5 | p-Me—Ph | H | H | CH₂Ph | Et | H | H | F | OH | H | H |
| XI-16-6 | p-Me—Ph | H | H | CH₂-indol-3-yl | Et | H | H | F | OH | H | H |
| XI-16-7 | p-Me—Ph | H | H | CH₂CH₂SCH₃ | Et | H | H | F | OH | H | H |
| XI-16-8 | p-Me—Ph | * | H | * | Et | H | H | F | OH | H | H |

*R² and R³ᵇ joined together by (CH₂)₃ to form five-membered ring.

TABLE XI-17

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-17-1 | p-F—Ph | H | H | H | Et | H | H | F | OH | H | H |
| XI-17-2 | p-F—Ph | H | H | CH₃ | Et | H | H | F | OH | H | H |
| XI-17-3 | p-F—Ph | H | H | CH(CH₃)₂ | Et | H | H | F | OH | H | H |
| XI-17-4 | p-F—Ph | H | H | CH₂CH(CH₃)₂ | Et | H | H | F | OH | H | H |
| XI-17-5 | p-F—Ph | H | H | CH₂Ph | Et | H | H | F | OH | H | H |
| XI-17-6 | p-F—Ph | H | H | CH₂-indol-3-yl | Et | H | H | F | OH | H | H |
| XI-17-7 | p-F—Ph | H | H | CH₂CH₂SCH₃ | Et | H | H | F | OH | H | H |
| XI-17-8 | p-F—Ph | * | H | * | Et | H | H | F | OH | H | H |

*R² and R³ᵇ joined together by (CH₂)₃ to form five-membered ring.

TABLE XI-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-18-1 | p-Cl—Ph | H | H | H | Et | H | H | F | OH | H | H |
| XI-18-2 | p-Cl—Ph | H | H | CH₃ | Et | H | H | F | OH | H | H |
| XI-18-3 | p-Cl—Ph | H | H | CH(CH₃)₂ | Et | H | H | F | OH | H | H |
| XI-18-4 | p-Cl—Ph | H | H | CH₂CH(CH₃)₂ | Et | H | H | F | OH | H | H |
| XI-18-5 | p-Cl—Ph | H | H | CH₂Ph | Et | H | H | F | OH | H | H |

TABLE XI-18-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-18-6 | p-Cl—Ph | H | H | CH₂-indol-3-yl | Et | H | H | F | OH | H | H |
| XI-18-7 | p-Cl—Ph | H | H | CH₂CH₂SCH₃ | Et | H | H | F | OH | H | H |
| XI-18-8 | p-Cl—Ph | * | H | * | Et | H | H | F | OH | H | H |

*R² and R³ᵇ joined together by (CH₂)₃ to form five-membered ring.

TABLE XI-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-19-1 | p-Br—Ph | H | H | H | Et | H | H | F | OH | H | H |
| XI-19-2 | p-Br—Ph | H | H | CH₃ | Et | H | H | F | OH | H | H |
| XI-19-3 | p-Br—Ph | H | H | CH(CH₃)₂ | Et | H | H | F | OH | H | H |
| XI-19-4 | p-Br—Ph | H | H | CH₂CH(CH₃)₂ | Et | H | H | F | OH | H | H |
| XI-19-5 | p-Br—Ph | H | H | CH₂Ph | Et | H | H | F | OH | H | H |
| XI-19-6 | p-Br—Ph | H | H | CH₂-indol-3-yl | Et | H | H | F | OH | H | H |
| XI-19-7 | p-Br—Ph | H | H | CH₂CH₂SCH₃ | Et | H | H | F | OH | H | H |
| XI-19-8 | p-Br—Ph | * | H | * | Et | H | H | F | OH | H | H |

*R² and R³ᵇ joined together by (CH₂)₃ to form five-membered ring.

TABLE XI-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-20-1 | p-I—Ph | H | H | H | Et | H | H | F | OH | H | H |
| XI-20-2 | p-I—Ph | H | H | CH₃ | Et | H | H | F | OH | H | H |
| XI-20-3 | p-I—Ph | H | H | CH(CH₃)₂ | Et | H | H | F | OH | H | H |
| XI-20-4 | p-I—Ph | H | H | CH₂CH(CH₃)₂ | Et | H | H | F | OH | H | H |
| XI-20-5 | p-I—Ph | H | H | CH₂Ph | Et | H | H | F | OH | H | H |
| XI-20-6 | p-I—Ph | H | H | CH₂-indol-3-yl | Et | H | H | F | OH | H | H |
| XI-20-7 | p-I—Ph | H | H | CH₂CH₂SCH₃ | Et | H | H | F | OH | H | H |
| XI-20-8 | p-I—Ph | * | H | * | Et | H | H | F | OH | H | H |

*R² and R³ᵇ joined together by (CH₂)₃ to form five-membered ring.

TABLE XI-21

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-21-1 | CH₃ | H | H | H | ⁱPr | H | H | F | OH | H | H |
| XI-21-2 | CH₃ | H | H | CH₃ | ⁱPr | H | H | F | OH | H | H |
| XI-21-3 | CH₃ | H | H | CH(CH₃)₂ | ⁱPr | H | H | F | OH | H | H |
| XI-21-4 | CH₃ | H | H | CH₂CH(CH₃)₂ | ⁱPr | H | H | F | OH | H | H |
| XI-21-5 | CH₃ | H | H | CH₂Ph | ⁱPr | H | H | F | OH | H | H |
| XI-21-6 | CH₃ | H | H | CH₂-indol-3-yl | ⁱPr | H | H | F | OH | H | H |
| XI-21-7 | CH₃ | H | H | CH₂CH₂SCH₃ | ⁱPr | H | H | F | OH | H | H |
| XI-21-8 | CH₃ | * | H | * | ⁱPr | H | H | F | OH | H | H |

TABLE XI-22

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-22-1 | Et | H | H | H | ⁱPr | H | H | F | OH | H | H |
| XI-22-2 | Et | H | H | CH₃ | ⁱPr | H | H | F | OH | H | H |
| XI-22-3 | Et | H | H | CH(CH₃)₂ | ⁱPr | H | H | F | OH | H | H |
| XI-22-4 | Et | H | H | CH₂CH(CH₃)₂ | ⁱPr | H | H | F | OH | H | H |
| XI-22-5 | Et | H | H | CH₂Ph | ⁱPr | H | H | F | OH | H | H |
| XI-22-6 | Et | H | H | CH₂-indol-3-yl | ⁱPr | H | H | F | OH | H | H |
| XI-22-7 | Et | H | H | CH₂CH₂SCH₃ | ⁱPr | H | H | F | OH | H | H |
| XI-22-8 | Et | * | H | * | ⁱPr | H | H | F | OH | H | H |

*R² and R³ᵇ joined together by (CH₂)₃ to form five-membered ring.

TABLE XI-23

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-23-1 | ⁱPr | H | H | H | ⁱPr | H | H | F | OH | H | H |
| XI-23-2 | ⁱPr | H | H | CH₃ | ⁱPr | H | H | F | OH | H | H |
| XI-23-3 | ⁱPr | H | H | CH(CH₃)₂ | ⁱPr | H | H | F | OH | H | H |
| XI-23-4 | ⁱPr | H | H | CH₂CH(CH₃)₂ | ⁱPr | H | H | F | OH | H | H |
| XI-23-5 | ⁱPr | H | H | CH₂Ph | ⁱPr | H | H | F | OH | H | H |
| XI-23-6 | ⁱPr | H | H | CH₂-indol-3-yl | ⁱPr | H | H | F | OH | H | H |
| XI-23-7 | ⁱPr | H | H | CH₂CH₂SCH₃ | ⁱPr | H | H | F | OH | H | H |
| XI-23-8 | ⁱPr | * | H | * | ⁱPr | H | H | F | OH | H | H |

*R² and R³ᵇ joined together by (CH₂)₃ to form five-membered ring.

TABLE XI-24

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-24-1 | ᵗBu | H | H | H | ⁱPr | H | H | F | OH | H | H |
| XI-24-2 | ᵗBu | H | H | CH₃ | ⁱPr | H | H | F | OH | H | H |
| XI-24-3 | ᵗBu | H | H | CH(CH₃)₂ | ⁱPr | H | H | F | OH | H | H |
| XI-24-4 | ᵗBu | H | H | CH₂CH(CH₃)₂ | ⁱPr | H | H | F | OH | H | H |

TABLE XI-24-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-24-5 | $^t$Bu | H | H | CH$_2$Ph | $^i$Pr | H | H | F | OH | H | H |
| XI-24-6 | $^t$Bu | H | H | CH$_2$-indol-3-yl | $^i$Pr | H | H | F | OH | H | H |
| XI-24-7 | $^t$Bu | H | H | CH$_2$CH$_2$SCH$_3$ | $^i$Pr | H | H | F | OH | H | H |
| XI-24-8 | $^t$Bu | * | H | * | $^i$Pr | H | H | F | OH | H | H |

*$R^2$ and $R^{3b}$ joined together by (CH$_2$)$_3$ to form five-membered ring.

TABLE XI-25

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-25-1 | Ph | H | H | H | $^i$Pr | H | H | F | OH | H | H |
| XI-25-2 | Ph | H | H | CH$_3$ | $^i$Pr | H | H | F | OH | H | H |
| XI-25-3 | Ph | H | H | CH(CH$_3$)$_2$ | $^i$Pr | H | H | F | OH | H | H |
| XI-25-4 | Ph | H | H | CH$_2$CH(CH$_3$)$_2$ | $^i$Pr | H | H | F | OH | H | H |
| XI-25-5 | Ph | H | H | CH$_2$Ph | $^i$Pr | H | H | F | OH | H | H |
| XI-25-6 | Ph | H | H | CH$_2$-indol-3-yl | $^i$Pr | H | H | F | OH | H | H |
| XI-25-7 | Ph | H | H | CH$_2$CH$_2$SCH$_3$ | $^i$Pr | H | H | F | OH | H | H |
| XI-25-8 | Ph | * | H | * | $^i$Pr | H | H | F | OH | H | H |

*$R^2$ and $R^{3b}$ joined together by (CH$_2$)$_3$ to form five-membered ring.

TABLE XI-26

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-26-1 | p-Me—Ph | H | H | H | $^i$Pr | H | H | F | OH | H | H |
| XI-26-2 | p-Me—Ph | H | H | CH$_3$ | $^i$Pr | H | H | F | OH | H | H |
| XI-26-3 | p-Me—Ph | H | H | CH(CH$_3$)$_2$ | $^i$Pr | H | H | F | OH | H | H |
| XI-26-4 | p-Me—Ph | H | H | CH$_2$CH(CH$_3$)$_2$ | $^i$Pr | H | H | F | OH | H | H |
| XI-26-5 | p-Me—Ph | H | H | CH$_2$Ph | $^i$Pr | H | H | F | OH | H | H |
| XI-26-6 | p-Me—Ph | H | H | CH$_2$-indol-3-yl | $^i$Pr | H | H | F | OH | H | H |
| XI-26-7 | p-Me—Ph | H | H | CH$_2$CH$_2$SCH$_3$ | $^i$Pr | H | H | F | OH | H | H |
| XI-26-8 | p-Me—Ph | * | H | * | $^i$Pr | H | H | F | OH | H | H |

*$R^2$ and $R^{3b}$ joined together by (CH$_2$)$_3$ to form five-membered ring.

TABLE XI-27

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-27-1 | p-F—Ph | H | H | H | $^i$Pr | H | H | F | OH | H | H |
| XI-27-2 | p-F—Ph | H | H | CH$_3$ | $^i$Pr | H | H | F | OH | H | H |
| XI-27-3 | p-F—Ph | H | H | CH(CH$_3$)$_2$ | $^i$Pr | H | H | F | OH | H | H |
| XI-27-4 | p-F—Ph | H | H | CH$_2$CH(CH$_3$)$_2$ | $^i$Pr | H | H | F | OH | H | H |
| XI-27-5 | p-F—Ph | H | H | CH$_2$Ph | $^i$Pr | H | H | F | OH | H | H |
| XI-27-6 | p-F—Ph | H | H | CH$_2$-indol-3-yl | $^i$Pr | H | H | F | OH | H | H |
| XI-27-7 | p-F—Ph | H | H | CH$_2$CH$_2$SCH$_3$ | $^i$Pr | H | H | F | OH | H | H |
| XI-27-8 | p-F—Ph | * | H | * | $^i$Pr | H | H | F | OH | H | H |

*$R^2$ and $R^{3b}$ joined together by (CH$_2$)$_3$ to form five-membered ring.

TABLE XI-28

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-28-1 | p-Cl—Ph | H | H | H | $^i$Pr | H | H | F | OH | H | H |
| XI-28-2 | p-Cl—Ph | H | H | CH$_3$ | $^i$Pr | H | H | F | OH | H | H |
| XI-28-3 | p-Cl—Ph | H | H | CH(CH$_3$)$_2$ | $^i$Pr | H | H | F | OH | H | H |
| XI-28-4 | p-Cl—Ph | H | H | CH$_2$CH(CH$_3$)$_2$ | $^i$Pr | H | H | F | OH | H | H |
| XI-28-5 | p-Cl—Ph | H | H | CH$_2$Ph | $^i$Pr | H | H | F | OH | H | H |
| XI-28-6 | p-Cl—Ph | H | H | CH$_2$-indol-3-yl | $^i$Pr | H | H | F | OH | H | H |
| XI-28-7 | p-Cl—Ph | H | H | CH$_2$CH$_2$SCH$_3$ | $^i$Pr | H | H | F | OH | H | H |
| XI-28-8 | p-Cl—Ph | * | H | * | $^i$Pr | H | H | F | OH | H | H |

*$R^2$ and $R^{3b}$ joined together by (CH$_2$)$_3$ to form five-membered ring.

TABLE XI-29

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-29-1 | p-Br—Ph | H | H | H | $^i$Pr | H | H | F | OH | H | H |
| XI-29-2 | p-Br—Ph | H | H | CH$_3$ | $^i$Pr | H | H | F | OH | H | H |
| XI-29-3 | p-Br—Ph | H | H | CH(CH$_3$)$_2$ | $^i$Pr | H | H | F | OH | H | H |
| XI-29-4 | p-Br—Ph | H | H | CH$_2$CH(CH$_3$)$_2$ | $^i$Pr | H | H | F | OH | H | H |
| XI-29-5 | p-Br—Ph | H | H | CH$_2$Ph | $^i$Pr | H | H | F | OH | H | H |
| XI-29-6 | p-Br—Ph | H | H | CH$_2$-indol-3-yl | $^i$Pr | H | H | F | OH | H | H |
| XI-29-7 | p-Br—Ph | H | H | CH$_2$CH$_2$SCH$_3$ | $^i$Pr | H | H | F | OH | H | H |
| XI-29-8 | p-Br—Ph | * | H | * | $^i$Pr | H | H | F | OH | H | H |

*$R^2$ and $R^{3b}$ joined together by (CH$_2$)$_3$ to form five-membered ring.

TABLE XI-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-30-1 | p-I—Ph | H | H | H | ⁱPr | H | H | F | OH | H | H |
| XI-30-2 | p-I—Ph | H | H | CH₃ | ⁱPr | H | H | F | OH | H | H |
| XI-30-3 | p-I—Ph | H | H | CH(CH₃)₂ | ⁱPr | H | H | F | OH | H | H |
| XI-30-4 | p-I—Ph | H | H | CH₂CH(CH₃)₂ | ⁱPr | H | H | F | OH | H | H |
| XI-30-5 | p-I—Ph | H | H | CH₂Ph | ⁱPr | H | H | F | OH | H | H |
| XI-30-6 | p-I—Ph | H | H | CH₂-indol-3-yl | ⁱPr | H | H | F | OH | H | H |
| XI-30-7 | p-I—Ph | H | H | CH₂CH₂SCH₃ | ⁱPr | H | H | F | OH | H | H |
| XI-30-8 | p-I—Ph | * | H | * | ⁱPr | H | H | F | OH | H | H |

*R² and R³ᵇ joined together by (CH₂)₃ to form five-membered ring.

TABLE XI-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-31-1 | CH₃ | H | H | H | ⁿBu | H | H | F | OH | H | H |
| XI-31-2 | CH₃ | H | H | CH₃ | ⁿBu | H | H | F | OH | H | H |
| XI-31-3 | CH₃ | H | H | CH(CH₃)₂ | ⁿBu | H | H | F | OH | H | H |
| XI-31-4 | CH₃ | H | H | CH₂CH(CH₃)₂ | ⁿBu | H | H | F | OH | H | H |
| XI-31-5 | CH₃ | H | H | CH₂Ph | ⁿBu | H | H | F | OH | H | H |
| XI-31-6 | CH₃ | H | H | CH₂-indol-3-yl | ⁿBu | H | H | F | OH | H | H |
| XI-31-7 | CH₃ | H | H | CH₂CH₂SCH₃ | ⁿBu | H | H | F | OH | H | H |
| XI-31-8 | CH₃ | * | H | * | ⁿBu | H | H | F | OH | H | H |

*R² and R³ᵇ joined together by (CH₂)₃ to form five-membered ring.

TABLE XI-32

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-32-1 | Et | H | H | H | ⁿBu | H | H | F | OH | H | H |
| XI-32-2 | Et | H | H | CH₃ | ⁿBu | H | H | F | OH | H | H |
| XI-32-3 | Et | H | H | CH(CH₃)₂ | ⁿBu | H | H | F | OH | H | H |
| XI-32-4 | Et | H | H | CH₂CH(CH₃)₂ | ⁿBu | H | H | F | OH | H | H |
| XI-32-5 | Et | H | H | CH₂Ph | ⁿBu | H | H | F | OH | H | H |
| XI-32-6 | Et | H | H | CH₂-indol-3-yl | ⁿBu | H | H | F | OH | H | H |
| XI-32-7 | Et | H | H | CH₂CH₂SCH₃ | ⁿBu | H | H | F | OH | H | H |
| XI-32-8 | Et | * | H | * | ⁿBu | H | H | F | OH | H | H |

*R² and R³ᵇ joined together by (CH₂)₃ to form five-membered ring.

TABLE XI-33

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-33-1 | ⁱPr | H | H | H | ⁿBu | H | H | F | OH | H | H |
| XI-33-2 | ⁱPr | H | H | CH₃ | ⁿBu | H | H | F | OH | H | H |
| XI-33-3 | ⁱPr | H | H | CH(CH₃)₂ | ⁿBu | H | H | F | OH | H | H |
| XI-33-4 | ⁱPr | H | H | CH₂CH(CH₃)₂ | ⁿBu | H | H | F | OH | H | H |
| XI-33-5 | ⁱPr | H | H | CH₂Ph | ⁿBu | H | H | F | OH | H | H |
| XI-33-6 | ⁱPr | H | H | CH₂-indol-3-yl | ⁿBu | H | H | F | OH | H | H |
| XI-33-7 | ⁱPr | H | H | CH₂CH₂SCH₃ | ⁿBu | H | H | F | OH | H | H |
| XI-33-8 | ⁱPr | * | H | * | ⁿBu | H | H | F | OH | H | H |

*R² and R³ᵇ joined together by (CH₂)₃ to form five-membered ring.

TABLE XI-34

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-34-1 | ᵗBu | H | H | H | ⁿBu | H | H | F | OH | H | H |
| XI-34-2 | ᵗBu | H | H | CH₃ | ⁿBu | H | H | F | OH | H | H |
| XI-34-3 | ᵗBu | H | H | CH(CH₃)₂ | ⁿBu | H | H | F | OH | H | H |
| XI-34-4 | ᵗBu | H | H | CH₂CH(CH₃)₂ | ⁿBu | H | H | F | OH | H | H |
| XI-34-5 | ᵗBu | H | H | CH₂Ph | ⁿBu | H | H | F | OH | H | H |
| XI-34-6 | ᵗBu | H | H | CH₂-indol-3-yl | ⁿBu | H | H | F | OH | H | H |
| XI-34-7 | ᵗBu | H | H | CH₂CH₂SCH₃ | ⁿBu | H | H | F | OH | H | H |
| XI-34-8 | ᵗBu | * | H | * | ⁿBu | H | H | F | OH | H | H |

*R² and R³ᵇ joined together by (CH₂)₃ to form five-membered ring.

TABLE XI-35

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-35-1 | Ph | H | H | H | ⁿBu | H | H | F | OH | H | H |
| XI-35-2 | Ph | H | H | CH₃ | ⁿBu | H | H | F | OH | H | H |
| XI-35-3 | Ph | H | H | CH(CH₃)₂ | ⁿBu | H | H | F | OH | H | H |
| XI-35-4 | Ph | H | H | CH₂CH(CH₃)₂ | ⁿBu | H | H | F | OH | H | H |
| XI-35-5 | Ph | H | H | CH₂Ph | ⁿBu | H | H | F | OH | H | H |
| XI-35-6 | Ph | H | H | CH₂-indol-3-yl | ⁿBu | H | H | F | OH | H | H |
| XI-35-7 | Ph | H | H | CH₂CH₂SCH₃ | ⁿBu | H | H | F | OH | H | H |
| XI-35-8 | Ph | * | H | * | ⁿBu | H | H | F | OH | H | H |

*R² and R³ᵇ joined together by (CH₂)₃ to form five-membered ring.

TABLE XI-36

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XI-36-1 | p-Me—Ph | H | H | H | ⁿBu | H | H | F | OH | H | H |
| XI-36-2 | p-Me—Ph | H | H | CH₃ | ⁿBu | H | H | F | OH | H | H |
| XI-36-3 | p-Me—Ph | H | H | CH(CH₃)₂ | ⁿBu | H | H | F | OH | H | H |
| XI-36-4 | p-Me—Ph | H | H | CH₂CH(CH₃)₂ | ⁿBu | H | H | F | OH | H | H |
| XI-36-5 | p-Me—Ph | H | H | CH₂Ph | ⁿBu | H | H | F | OH | H | H |
| XI-36-6 | p-Me—Ph | H | H | CH₂-indol-3-yl | ⁿBu | H | H | F | OH | H | H |
| XI-36-7 | p-Me—Ph | H | H | CH₂CH₂SCH₃ | ⁿBu | H | H | F | OH | H | H |
| XI-36-8 | p-Me—Ph | * | H | * | ⁿBu | H | H | F | OH | H | H |

*R² and R³ᵇ joined together by (CH₂)₃ to form five-membered ring.

TABLE XI-37

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-37-1 | p-F—Ph | H | H | H | $^n$Bu | H | H | F | OH | H | H |
| XI-37-2 | p-F—Ph | H | H | CH$_3$ | $^n$Bu | H | H | F | OH | H | H |
| XI-37-3 | p-F—Ph | H | H | CH(CH$_3$)$_2$ | $^n$Bu | H | H | F | OH | H | H |
| XI-37-4 | p-F—Ph | H | H | CH$_2$CH(CH$_3$)$_2$ | $^n$Bu | H | H | F | OH | H | H |
| XI-37-5 | p-F—Ph | H | H | CH$_2$Ph | $^n$Bu | H | H | F | OH | H | H |
| XI-37-6 | p-F—Ph | H | H | CH$_2$-indol-3-yl | $^n$Bu | H | H | F | OH | H | H |
| XI-37-7 | p-F—Ph | H | H | CH$_2$CH$_2$SCH$_3$ | $^n$Bu | H | H | F | OH | H | H |
| XI-37-8 | p-F—Ph | * | H | * | $^n$Bu | H | H | F | OH | H | H |

*R$^2$ and R$^{3b}$ joined together by (CH$_2$)$_3$ to form five-membered ring.

TABLE XI-38

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-38-1 | p-Cl—Ph | H | H | H | $^n$Bu | H | H | F | OH | H | H |
| XI-38-2 | p-Cl—Ph | H | H | CH$_3$ | $^n$Bu | H | H | F | OH | H | H |
| XI-38-3 | p-Cl—Ph | H | H | CH(CH$_3$)$_2$ | $^n$Bu | H | H | F | OH | H | H |
| XI-38-4 | p-Cl—Ph | H | H | CH$_2$CH(CH$_3$)$_2$ | $^n$Bu | H | H | F | OH | H | H |
| XI-38-5 | p-Cl—Ph | H | H | CH$_2$Ph | $^n$Bu | H | H | F | OH | H | H |
| XI-38-6 | p-Cl—Ph | H | H | CH$_2$-indol-3-yl | $^n$Bu | H | H | F | OH | H | H |
| XI-38-7 | p-Cl—Ph | H | H | CH$_2$CH$_2$SCH$_3$ | $^n$Bu | H | H | F | OH | H | H |
| XI-38-8 | p-Cl—Ph | * | H | * | $^n$Bu | H | H | F | OH | H | H |

*R$^2$ and R$^{3b}$ joined together by (CH$_2$)$_3$ to form five-membered ring.

TABLE XI-39

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-39-1 | p-Br—Ph | H | H | H | $^n$Bu | H | H | F | OH | H | H |
| XI-39-2 | p-Br—Ph | H | H | CH$_3$ | $^n$Bu | H | H | F | OH | H | H |
| XI-39-3 | p-Br—Ph | H | H | CH(CH$_3$)$_2$ | $^n$Bu | H | H | F | OH | H | H |
| XI-39-4 | p-Br—Ph | H | H | CH$_2$CH(CH$_3$)$_2$ | $^n$Bu | H | H | F | OH | H | H |
| XI-39-5 | p-Br—Ph | H | H | CH$_2$Ph | $^n$Bu | H | H | F | OH | H | H |
| XI-39-6 | p-Br—Ph | H | H | CH$_2$-indol-3-yl | $^n$Bu | H | H | F | OH | H | H |
| XI-39-7 | p-Br—Ph | H | H | CH$_2$CH$_2$SCH$_3$ | $^n$Bu | H | H | F | OH | H | H |
| XI-39-8 | p-Br—Ph | * | H | * | $^n$Bu | H | H | F | OH | H | H |

*R$^2$ and R$^{3b}$ joined together by (CH$_2$)$_3$ to form five-membered ring.

TABLE XI-40

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-40-1 | p-I—Ph | H | H | H | $^n$Bu | H | H | F | OH | H | H |
| XI-40-2 | p-I—Ph | H | H | CH$_3$ | $^n$Bu | H | H | F | OH | H | H |
| XI-40-3 | p-I—Ph | H | H | CH(CH$_3$)$_2$ | $^n$Bu | H | H | F | OH | H | H |
| XI-40-4 | p-I—Ph | H | H | CH$_2$CH(CH$_3$)$_2$ | $^n$Bu | H | H | F | OH | H | H |
| XI-40-5 | p-I—Ph | H | H | CH$_2$Ph | $^n$Bu | H | H | F | OH | H | H |
| XI-40-6 | p-I—Ph | H | H | CH$_2$-indol-3-yl | $^n$Bu | H | H | F | OH | H | H |
| XI-40-7 | p-I—Ph | H | H | CH$_2$CH$_2$SCH$_3$ | $^n$Bu | H | H | F | OH | H | H |
| XI-40-8 | p-I—Ph | * | H | * | $^n$Bu | H | H | F | OH | H | H |

*R$^2$ and R$^{3b}$ joined together by (CH$_2$)$_3$ to form five-membered ring.

TABLE XI-41

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XI-41-1 | CH$_3$ | H | H | H | Bz | H | H | F | OH | H | H |
| XI-41-2 | CH$_3$ | H | H | CH$_3$ | Bz | H | H | F | OH | H | H |
| XI-41-3 | CH$_3$ | H | H | CH(CH$_3$)$_2$ | Bz | H | H | F | OH | H | H |
| XI-41-4 | CH$_3$ | H | H | CH$_2$CH(CH$_3$)$_2$ | Bz | H | H | F | OH | H | H |
| XI-41-5 | CH$_3$ | H | H | CH$_2$Ph | Bz | H | H | F | OH | H | H |
| XI-41-6 | CH$_3$ | H | H | CH$_2$-indol-3-yl | Bz | H | H | F | OH | H | H |

TABLE XI-41-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-41-7 | $CH_3$ | H | H | $CH_2CH_2SCH_3$ | Bz | H | H | F | OH | H | H |
| XI-41-8 | $CH_3$ | * | H | * | Bz | H | H | F | OH | H | H |

*$R^2$ and $R^{3b}$ joined together by $(CH_2)_3$ to form five-membered ring.

TABLE XI-42

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-42-1 | Et | H | H | H | Bz | H | H | F | OH | H | H |
| XI-42-2 | Et | H | H | $CH_3$ | Bz | H | H | F | OH | H | H |
| XI-42-3 | Et | H | H | $CH(CH_3)_2$ | Bz | H | H | F | OH | H | H |
| XI-42-4 | Et | H | H | $CH_2CH(CH_3)_2$ | Bz | H | H | F | OH | H | H |
| XI-42-5 | Et | H | H | $CH_2Ph$ | Bz | H | H | F | OH | H | H |
| XI-42-6 | Et | H | H | $CH_2$-indol-3-yl | Bz | H | H | F | OH | H | H |
| XI-42-7 | Et | H | H | $CH_2CH_2SCH_3$ | Bz | H | H | F | OH | H | H |
| XI-42-8 | Et | * | H | * | Bz | H | H | F | OH | H | H |

*$R^2$ and $R^{3b}$ joined together by $(CH_2)_3$ to form five-membered ring.

TABLE XI-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-43-1 | $^iPr$ | H | H | H | Bz | H | H | F | OH | H | H |
| XI-43-2 | $^iPr$ | H | H | $CH_3$ | Bz | H | H | F | OH | H | H |
| XI-43-3 | $^iPr$ | H | H | $CH(CH_3)_2$ | Bz | H | H | F | OH | H | H |
| XI-43-4 | $^iPr$ | H | H | $CH_2CH(CH_3)_2$ | Bz | H | H | F | OH | H | H |
| XI-43-5 | $^iPr$ | H | H | $CH_2Ph$ | Bz | H | H | F | OH | H | H |
| XI-43-6 | $^iPr$ | H | H | $CH_2$-indol-3-yl | Bz | H | H | F | OH | H | H |
| XI-43-7 | $^iPr$ | H | H | $CH_2CH_2SCH_3$ | Bz | H | H | F | OH | H | H |
| XI-43-8 | $^iPr$ | * | H | * | Bz | H | H | F | OH | H | H |

*$R^2$ and $R^{3b}$ joined together by $(CH_2)_3$ to form five-membered ring.

TABLE XI-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-44-1 | $^tBu$ | H | H | H | Bz | H | H | F | OH | H | H |
| XI-44-2 | $^tBu$ | H | H | $CH_3$ | Bz | H | H | F | OH | H | H |
| XI-44-3 | $^tBu$ | H | H | $CH(CH_3)_2$ | Bz | H | H | F | OH | H | H |
| XI-44-4 | $^tBu$ | H | H | $CH_2CH(CH_3)_2$ | Bz | H | H | F | OH | H | H |
| XI-44-5 | $^tBu$ | H | H | $CH_2Ph$ | Bz | H | H | F | OH | H | H |
| XI-44-6 | $^tBu$ | H | H | $CH_2$-indol-3-yl | Bz | H | H | F | OH | H | H |
| XI-44-7 | $^tBu$ | H | H | $CH_2CH_2SCH_3$ | Bz | H | H | F | OH | H | H |
| XI-44-8 | $^tBu$ | * | H | * | Bz | H | H | F | OH | H | H |

*$R^2$ and $R^{3b}$ joined together by $(CH_2)_3$ to form five-membered ring.

TABLE XI-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-45-1 | Ph | H | H | H | Bz | H | H | F | OH | H | H |
| XI-45-2 | Ph | H | H | $CH_3$ | Bz | H | H | F | OH | H | H |
| XI-45-3 | Ph | H | H | $CH(CH_3)_2$ | Bz | H | H | F | OH | H | H |
| XI-45-4 | Ph | H | H | $CH_2CH(CH_3)_2$ | Bz | H | H | F | OH | H | H |
| XI-45-5 | Ph | H | H | $CH_2Ph$ | Bz | H | H | F | OH | H | H |
| XI-45-6 | Ph | H | H | $CH_2$-indol-3-yl | Bz | H | H | F | OH | H | H |
| XI-45-7 | Ph | H | H | $CH_2CH_2SCH_3$ | Bz | H | H | F | OH | H | H |
| XI-45-8 | Ph | * | H | * | Bz | H | H | F | OH | H | H |

*$R^2$ and $R^{3b}$ joined together by $(CH_2)_3$ to form five-membered ring.

TABLE XI-46

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-46-1 | p-Me—Ph | H | H | H | Bz | H | H | F | OH | H | H |
| XI-46-2 | p-Me—Ph | H | H | $CH_3$ | Bz | H | H | F | OH | H | H |
| XI-46-3 | p-Me—Ph | H | H | $CH(CH_3)_2$ | Bz | H | H | F | OH | H | H |
| XI-46-4 | p-Me—Ph | H | H | $CH_2CH(CH_3)_2$ | Bz | H | H | F | OH | H | H |
| XI-46-5 | p-Me—Ph | H | H | $CH_2Ph$ | Bz | H | H | F | OH | H | H |
| XI-46-6 | p-Me—Ph | H | H | $CH_2$-indol-3-yl | Bz | H | H | F | OH | H | H |
| XI-46-7 | p-Me—Ph | H | H | $CH_2CH_2SCH_3$ | Bz | H | H | F | OH | H | H |
| XI-46-8 | p-Me—Ph | * | H | * | Bz | H | H | F | OH | H | H |

*$R^2$ and $R^{3b}$ joined together by $(CH_2)_3$ to form five-membered ring.

TABLE XI-47

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-47-1 | p-F—Ph | H | H | H | Bz | H | H | F | OH | H | H |
| XI-47-2 | p-F—Ph | H | H | $CH_3$ | Bz | H | H | F | OH | H | H |

TABLE XI-47-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-47-3 | p-F—Ph | H | H | CH(CH$_3$)$_2$ | Bz | H | H | F | OH | H | H |
| XI-47-4 | p-F—Ph | H | H | CH$_2$CH(CH$_3$)$_2$ | Bz | H | H | F | OH | H | H |
| XI-47-5 | p-F—Ph | H | H | CH$_2$Ph | Bz | H | H | F | OH | H | H |
| XI-47-6 | p-F—Ph | H | H | CH$_2$-indol-3-yl | Bz | H | H | F | OH | H | H |
| XI-47-7 | p-F—Ph | H | H | CH$_2$CH$_2$SCH$_3$ | Bz | H | H | F | OH | H | H |
| XI-47-8 | p-F—Ph | * | H | * | Bz | H | H | F | OH | H | H |

*$R^2$ and $R^{3b}$ joined together by (CH$_2$)$_3$ to form five-membered ring.

TABLE XI-48

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-48-1 | p-Cl—Ph | H | H | H | Bz | H | H | F | OH | H | H |
| XI-48-2 | p-Cl—Ph | H | H | CH$_3$ | Bz | H | H | F | OH | H | H |
| XI-48-3 | p-Cl—Ph | H | H | CH(CH$_3$)$_2$ | Bz | H | H | F | OH | H | H |
| XI-48-4 | p-Cl—Ph | H | H | CH$_2$CH(CH$_3$)$_2$ | Bz | H | H | F | OH | H | H |
| XI-48-5 | p-Cl—Ph | H | H | CH$_2$Ph | Bz | H | H | F | OH | H | H |
| XI-48-6 | p-Cl—Ph | H | H | CH$_2$-indol-3-yl | Bz | H | H | F | OH | H | H |
| XI-48-7 | p-Cl—Ph | H | H | CH$_2$CH$_2$SCH$_3$ | Bz | H | H | F | OH | H | H |
| XI-48-8 | p-Cl—Ph | * | H | * | Bz | H | H | F | OH | H | H |

*$R^2$ and $R^{3b}$ joined together by (CH$_2$)$_3$ to form five-membered ring.

TABLE XI-49

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-49-1 | p-Br—Ph | H | H | H | Bz | H | H | F | OH | H | H |
| XI-49-2 | p-Br—Ph | H | H | CH$_3$ | Bz | H | H | F | OH | H | H |
| XI-49-3 | p-Br—Ph | H | H | CH(CH$_3$)$_2$ | Bz | H | H | F | OH | H | H |
| XI-49-4 | p-Br—Ph | H | H | CH$_2$CH(CH$_3$)$_2$ | Bz | H | H | F | OH | H | H |
| XI-49-5 | p-Br—Ph | H | H | CH$_2$Ph | Bz | H | H | F | OH | H | H |
| XI-49-6 | p-Br—Ph | H | H | CH$_2$-indol-3-yl | Bz | H | H | F | OH | H | H |
| XI-49-7 | p-Br—Ph | H | H | CH$_2$CH$_2$SCH$_3$ | Bz | H | H | F | OH | H | H |
| XI-49-8 | p-Br—Ph | * | H | * | Bz | H | H | F | OH | H | H |

*$R^2$ and $R^{3b}$ joined together by (CH$_2$)$_3$ to form five-membered ring.

TABLE XI-50

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XI-50-1 | p-I—Ph | H | H | H | Bz | H | H | F | OH | H | H |
| XI-50-2 | p-I—Ph | H | H | CH$_3$ | Bz | H | H | F | OH | H | H |
| XI-50-3 | p-I—Ph | H | H | CH(CH$_3$)$_2$ | Bz | H | H | F | OH | H | H |
| XI-50-4 | p-I—Ph | H | H | CH$_2$CH(CH$_3$)$_2$ | Bz | H | H | F | OH | H | H |
| XI-50-5 | p-I—Ph | H | H | CH$_2$Ph | Bz | H | H | F | OH | H | H |
| XI-50-6 | p-I—Ph | H | H | CH$_2$-indol-3-yl | Bz | H | H | F | OH | H | H |
| XI-50-7 | p-I—Ph | H | H | CH$_2$CH$_2$SCH$_3$ | Bz | H | H | F | OH | H | H |
| XI-50-8 | p-I—Ph | * | H | * | Bz | H | H | F | OH | H | H |

*$R^2$ and $R^{3b}$ joined together by (CH$_2$)$_3$ to form five-membered ring.

XII

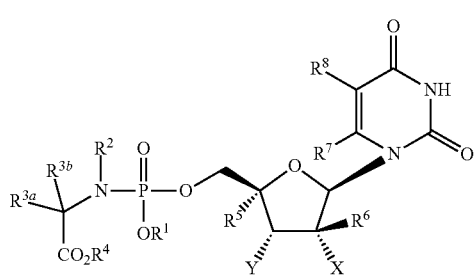

TABLE XII-1

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-1-1 | CH$_3$ | H | H | H | CH$_3$ | N$_3$ | F | F | OH | H | H |
| XII-1-2 | CH$_3$ | H | H | CH$_3$ | CH$_3$ | N$_3$ | F | F | OH | H | H |
| XII-1-3 | CH$_3$ | H | H | CH(CH$_3$)$_2$ | CH$_3$ | N$_3$ | F | F | OH | H | H |
| XII-1-4 | CH$_3$ | H | H | CH$_2$CH(CH$_3$)$_2$ | CH$_3$ | N$_3$ | F | F | OH | H | H |
| XII-1-5 | CH$_3$ | H | H | CH$_2$Ph | CH$_3$ | N$_3$ | F | F | OH | H | H |
| XII-1-6 | CH$_3$ | H | H | CH$_2$-indol-3-yl | CH$_3$ | N$_3$ | F | F | OH | H | H |
| XII-1-7 | CH$_3$ | H | H | CH$_2$CH$_2$SCH$_3$ | CH$_3$ | N$_3$ | F | F | OH | H | H |

TABLE XII-1-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-1-8 | $CH_3$ | * | H | * | $CH_3$ | $N_3$ | F | F | OH | H | H |

TABLE XII-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-2-1 | Et | H | H | H | $CH_3$ | $N_3$ | F | F | OH | H | H |
| XII-2-2 | Et | H | H | $CH_3$ | $CH_3$ | $N_3$ | F | F | OH | H | H |
| XII-2-3 | Et | H | H | $CH(CH_3)_2$ | $CH_3$ | $N_3$ | F | F | OH | H | H |
| XII-2-4 | Et | H | H | $CH_2CH(CH_3)_2$ | $CH_3$ | $N_3$ | F | F | OH | H | H |
| XII-2-5 | Et | H | H | $CH_2Ph$ | $CH_3$ | $N_3$ | F | F | OH | H | H |
| XII-2-6 | Et | H | H | $CH_2$-indol-3-yl | $CH_3$ | $N_3$ | F | F | OH | H | H |
| XII-2-7 | Et | H | H | $CH_2CH_2SCH_3$ | $CH_3$ | $N_3$ | F | F | OH | H | H |
| XII-2-8 | Et | * | H | * | $CH_3$ | $N_3$ | F | F | OH | H | H |

*$R^2$ and $R^{3b}$ joined together by $(CH_2)_3$ to form five-membered ring.

TABLE XII-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-3-1 | $^iPr$ | H | H | H | $CH_3$ | $N_3$ | F | F | OH | H | H |
| XII-3-2 | $^iPr$ | H | H | $CH_3$ | $CH_3$ | $N_3$ | F | F | OH | H | H |
| XII-3-3 | $^iPr$ | H | H | $CH(CH_3)_2$ | $CH_3$ | $N_3$ | F | F | OH | H | H |
| XII-3-4 | $^iPr$ | H | H | $CH_2CH(CH_3)_2$ | $CH_3$ | $N_3$ | F | F | OH | H | H |
| XII-3-5 | $^iPr$ | H | H | $CH_2Ph$ | $CH_3$ | $N_3$ | F | F | OH | H | H |
| XII-3-6 | $^iPr$ | H | H | $CH_2$-indol-3-yl | $CH_3$ | $N_3$ | F | F | OH | H | H |
| XII-3-7 | $^iPr$ | H | H | $CH_2CH_2SCH_3$ | $CH_3$ | $N_3$ | F | F | OH | H | H |
| XII-3-8 | $^iPr$ | * | H | * | $CH_3$ | $N_3$ | F | F | OH | H | H |

*$R^2$ and $R^{3b}$ joined together by $(CH_2)_3$ to form five-membered ring.

TABLE XII-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-4-1 | $^tBu$ | H | H | H | $CH_3$ | $N_3$ | F | F | OH | H | H |
| XII-4-2 | $^tBu$ | H | H | $CH_3$ | $CH_3$ | $N_3$ | F | F | OH | H | H |
| XII-4-3 | $^tBu$ | H | H | $CH(CH_3)_2$ | $CH_3$ | $N_3$ | F | F | OH | H | H |
| XII-4-4 | $^tBu$ | H | H | $CH_2CH(CH_3)_2$ | $CH_3$ | $N_3$ | F | F | OH | H | H |
| XII-4-5 | $^tBu$ | H | H | $CH_2Ph$ | $CH_3$ | $N_3$ | F | F | OH | H | H |
| XII-4-6 | $^tBu$ | H | H | $CH_2$-indol-3-yl | $CH_3$ | $N_3$ | F | F | OH | H | H |
| XII-4-7 | $^tBu$ | H | H | $CH_2CH_2SCH_3$ | $CH_3$ | $N_3$ | F | F | OH | H | H |
| XII-4-8 | $^tBu$ | * | H | * | $CH_3$ | $N_3$ | F | F | OH | H | H |

*$R^2$ and $R^{3b}$ joined together by $(CH_2)_3$ to form five-membered ring.

TABLE XII-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-5-1 | Ph | H | H | H | $CH_3$ | $N_3$ | F | F | OH | H | H |
| XII-5-2 | Ph | H | H | $CH_3$ | $CH_3$ | $N_3$ | F | F | OH | H | H |
| XII-5-3 | Ph | H | H | $CH(CH_3)_2$ | $CH_3$ | $N_3$ | F | F | OH | H | H |
| XII-5-4 | Ph | H | H | $CH_2CH(CH_3)_2$ | $CH_3$ | $N_3$ | F | F | OH | H | H |
| XII-5-5 | Ph | H | H | $CH_2Ph$ | $CH_3$ | $N_3$ | F | F | OH | H | H |
| XII-5-6 | Ph | H | H | $CH_2$-indol-3-yl | $CH_3$ | $N_3$ | F | F | OH | H | H |
| XII-5-7 | Ph | H | H | $CH_2CH_2SCH_3$ | $CH_3$ | $N_3$ | F | F | OH | H | H |
| XII-5-8 | Ph | * | H | * | $CH_3$ | $N_3$ | F | F | OH | H | H |

*$R^2$ and $R^{3b}$ joined together by $(CH_2)_3$ to form five-membered ring.

TABLE XII-6

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-6-1 | p-Me—Ph | H | H | H | CH$_3$ | N$_3$ | F | F | OH | H | H |
| XII-6-2 | p-Me—Ph | H | H | CH$_3$ | CH$_3$ | N$_3$ | F | F | OH | H | H |
| XII-6-3 | p-Me—Ph | H | H | CH(CH$_3$)$_2$ | CH$_3$ | N$_3$ | F | F | OH | H | H |
| XII-6-4 | p-Me—Ph | H | H | CH$_2$CH(CH$_3$)$_2$ | CH$_3$ | N$_3$ | F | F | OH | H | H |
| XII-6-5 | p-Me—Ph | H | H | CH$_2$Ph | CH$_3$ | N$_3$ | F | F | OH | H | H |
| XII-6-6 | p-Me—Ph | H | H | CH$_2$-indol-3-yl | CH$_3$ | N$_3$ | F | F | OH | H | H |
| XII-6-7 | p-Me—Ph | H | H | CH$_2$CH$_2$SCH$_3$ | CH$_3$ | N$_3$ | F | F | OH | H | H |
| XII-6-8 | p-Me—Ph | * | H | * | CH$_3$ | N$_3$ | F | F | OH | H | H |

*R$^2$ and R$^{3b}$ joined together by (CH$_2$)$_3$ to form five-membered ring.

TABLE XII-7

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-7-1 | p-F—Ph | H | H | H | CH$_3$ | N$_3$ | F | F | OH | H | H |
| XII-7-2 | p-F—Ph | H | H | CH$_3$ | CH$_3$ | N$_3$ | F | F | OH | H | H |
| XII-7-3 | p-F—Ph | H | H | CH(CH$_3$)$_2$ | CH$_3$ | N$_3$ | F | F | OH | H | H |
| XII-7-4 | p-F—Ph | H | H | CH$_2$CH(CH$_3$)$_2$ | CH$_3$ | N$_3$ | F | F | OH | H | H |
| XII-7-6 | p-F—Ph | H | H | CH$_2$Ph | CH$_3$ | N$_3$ | F | F | OH | H | H |
| XII-7-7 | p-F—Ph | H | H | CH$_2$-indol-3-yl | CH$_3$ | N$_3$ | F | F | OH | H | H |
| XII-7-8 | p-F—Ph | H | H | CH$_2$CH$_2$SCH$_3$ | CH$_3$ | N$_3$ | F | F | OH | H | H |
| XII-7-20 | p-F—Ph | * | H | * | CH$_3$ | N$_3$ | F | F | OH | H | H |

*R$^2$ and R$^{3b}$ joined together by (CH$_2$)$_3$ to form five-membered ring.

TABLE XII-8

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-8-1 | p-Cl—Ph | H | H | H | CH$_3$ | N$_3$ | F | F | OH | H | H |
| XII-8-2 | p-Cl—Ph | H | H | CH$_3$ | CH$_3$ | N$_3$ | F | F | OH | H | H |
| XII-8-3 | p-Cl—Ph | H | H | CH(CH$_3$)$_2$ | CH$_3$ | N$_3$ | F | F | OH | H | H |
| XII-8-4 | p-Cl—Ph | H | H | CH$_2$CH(CH$_3$)$_2$ | CH$_3$ | N$_3$ | F | F | OH | H | H |
| XII-8-5 | p-Cl—Ph | H | H | CH$_2$Ph | CH$_3$ | N$_3$ | F | F | OH | H | H |
| XII-8-6 | p-Cl—Ph | H | H | CH$_2$-indol-3-yl | CH$_3$ | N$_3$ | F | F | OH | H | H |
| XII-8-7 | p-Cl—Ph | H | H | CH$_2$CH$_2$SCH$_3$ | CH$_3$ | N$_3$ | F | F | OH | H | H |
| XII-8-8 | p-Cl—Ph | * | H | * | CH$_3$ | N$_3$ | F | F | OH | H | H |

*R$^2$ and R$^{3b}$ joined together by (CH$_2$)$_3$ to form five-membered ring.

TABLE XII-9

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-9-1 | p-Br—Ph | H | H | H | CH$_3$ | N$_3$ | F | F | OH | H | H |
| XII-9-2 | p-Br—Ph | H | H | CH$_3$ | CH$_3$ | N$_3$ | F | F | OH | H | H |
| XII-9-3 | p-Br—Ph | H | H | CH(CH$_3$)$_2$ | CH$_3$ | N$_3$ | F | F | OH | H | H |
| XII-9-4 | p-Br—Ph | H | H | CH$_2$CH(CH$_3$)$_2$ | CH$_3$ | N$_3$ | F | F | OH | H | H |
| XII-9-6 | p-Br—Ph | H | H | CH$_2$Ph | CH$_3$ | N$_3$ | F | F | OH | H | H |
| XII-9-7 | p-Br—Ph | H | H | CH$_2$-indol-3-yl | CH$_3$ | N$_3$ | F | F | OH | H | H |
| XII-9-8 | p-Br—Ph | H | H | CH$_2$CH$_2$SCH$_3$ | CH$_3$ | N$_3$ | F | F | OH | H | H |
| XII-9-20 | p-Br—Ph | * | H | * | CH$_3$ | N$_3$ | F | F | OH | H | H |

*R$^2$ and R$^{3b}$ joined together by (CH$_2$)$_3$ to form five-membered ring.

TABLE XII-10

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-10-1 | p-I—Ph | H | H | H | CH$_3$ | N$_3$ | F | F | OH | H | H |
| XII-10-2 | p-I—Ph | H | H | CH$_3$ | CH$_3$ | N$_3$ | F | F | OH | H | H |
| XII-10-3 | p-I—Ph | H | H | CH(CH$_3$)$_2$ | CH$_3$ | N$_3$ | F | F | OH | H | H |
| XII-10-4 | p-I—Ph | H | H | CH$_2$CH(CH$_3$)$_2$ | CH$_3$ | N$_3$ | F | F | OH | H | H |
| XII-10-5 | p-I—Ph | H | H | CH$_2$Ph | CH$_3$ | N$_3$ | F | F | OH | H | H |

TABLE XII-10-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-10-6 | p-I—Ph | H | H | $CH_2$-indol-3-yl | $CH_3$ | $N_3$ | F | F | OH | H | H |
| XII-10-7 | p-I—Ph | H | H | $CH_2CH_2SCH_3$ | $CH_3$ | $N_3$ | F | F | OH | H | H |
| XII-10-8 | p-I—Ph | * | H | * | $CH_3$ | $N_3$ | F | F | OH | H | H |

*$R^2$ and $R^{3b}$ joined together by $(CH_2)_3$ to form five-membered ring.

TABLE XII-11

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-11-1 | $CH_3$ | H | H | H | Et | $N_3$ | F | F | OH | H | H |
| XII-11-2 | $CH_3$ | H | H | $CH_3$ | Et | $N_3$ | F | F | OH | H | H |
| XII-11-3 | $CH_3$ | H | H | $CH(CH_3)_2$ | Et | $N_3$ | F | F | OH | H | H |
| XII-11-4 | $CH_3$ | H | H | $CH_2CH(CH_3)_2$ | Et | $N_3$ | F | F | OH | H | H |
| XII-11-5 | $CH_3$ | H | H | $CH_2Ph$ | Et | $N_3$ | F | F | OH | H | H |
| XII-11-6 | $CH_3$ | H | H | $CH_2$-indol-3-yl | Et | $N_3$ | F | F | OH | H | H |
| XII-11-7 | $CH_3$ | H | H | $CH_2CH_2SCH_3$ | Et | $N_3$ | F | F | OH | H | H |
| XII-11-8 | $CH_3$ | * | H | * | Et | $N_3$ | F | F | OH | H | H |

*$R^2$ and $R^{3b}$ joined together by $(CH_2)_3$ to form five-membered ring.

TABLE XII-12

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-12-1 | Et | H | H | H | Et | $N_3$ | F | F | OH | H | H |
| XII-12-2 | Et | H | H | $CH_3$ | Et | $N_3$ | F | F | OH | H | H |
| XII-12-3 | Et | H | H | $CH(CH_3)_2$ | Et | $N_3$ | F | F | OH | H | H |
| XII-12-4 | Et | H | H | $CH_2CH(CH_3)_2$ | Et | $N_3$ | F | F | OH | H | H |
| XII-12-5 | Et | H | H | $CH_2Ph$ | Et | $N_3$ | F | F | OH | H | H |
| XII-12-6 | Et | H | H | $CH_2$-indol-3-yl | Et | $N_3$ | F | F | OH | H | H |
| XII-12-7 | Et | H | H | $CH_2CH_2SCH_3$ | Et | $N_3$ | F | F | OH | H | H |
| XII-12-8 | Et | * | H | * | Et | $N_3$ | F | F | OH | H | H |

*$R^2$ and $R^{3b}$ joined together by $(CH_2)_3$ to form five-membered ring.

TABLE XII-13

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-13-1 | $^iPr$ | H | H | H | Et | $N_3$ | F | F | OH | H | H |
| XII-13-2 | $^iPr$ | H | H | $CH_3$ | Et | $N_3$ | F | F | OH | H | H |
| XII-13-3 | $^iPr$ | H | H | $CH(CH_3)_2$ | Et | $N_3$ | F | F | OH | H | H |
| XII-13-4 | $^iPr$ | H | H | $CH_2CH(CH_3)_2$ | Et | $N_3$ | F | F | OH | H | H |
| XII-13-5 | $^iPr$ | H | H | $CH_2Ph$ | Et | $N_3$ | F | F | OH | H | H |
| XII-13-6 | $^iPr$ | H | H | $CH_2$-indol-3-yl | Et | $N_3$ | F | F | OH | H | H |
| XII-13-7 | $^iPr$ | H | H | $CH_2CH_2SCH_3$ | Et | $N_3$ | F | F | OH | H | H |
| XII-13-8 | $^iPr$ | * | H | * | Et | $N_3$ | F | F | OH | H | H |

*$R^2$ and $R^{3b}$ joined together by $(CH_2)_3$ to form five-membered ring.

TABLE XII-14

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-14-1 | $^tBu$ | H | H | H | Et | $N_3$ | F | F | OH | H | H |
| XII-14-2 | $^tBu$ | H | H | $CH_3$ | Et | $N_3$ | F | F | OH | H | H |
| XII-14-3 | $^tBu$ | H | H | $CH(CH_3)_2$ | Et | $N_3$ | F | F | OH | H | H |
| XII-14-4 | $^tBu$ | H | H | $CH_2CH(CH_3)_2$ | Et | $N_3$ | F | F | OH | H | H |
| XII-14-5 | $^tBu$ | H | H | $CH_2Ph$ | Et | $N_3$ | F | F | OH | H | H |
| XII-14-6 | $^tBu$ | H | H | $CH_2$-indol-3-yl | Et | $N_3$ | F | F | OH | H | H |
| XII-14-7 | $^tBu$ | H | H | $CH_2CH_2SCH_3$ | Et | $N_3$ | F | F | OH | H | H |
| XII-14-8 | $^tBu$ | * | H | * | Et | $N_3$ | F | F | OH | H | H |

*$R^2$ and $R^{3b}$ joined together by $(CH_2)_3$ to form five-membered ring.

TABLE XII-15

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-15-1 | Ph | H | H | H | Et | $N_3$ | F | F | OH | H | H |
| XII-15-2 | Ph | H | H | $CH_3$ | Et | $N_3$ | F | F | OH | H | H |
| XII-15-3 | Ph | H | H | $CH(CH_3)_2$ | Et | $N_3$ | F | F | OH | H | H |
| XII-15-4 | Ph | H | H | $CH_2CH(CH_3)_2$ | Et | $N_3$ | F | F | OH | H | H |
| XII-15-5 | Ph | H | H | $CH_2Ph$ | Et | $N_3$ | F | F | OH | H | H |
| XII-15-6 | Ph | H | H | $CH_2$-indol-3-yl | Et | $N_3$ | F | F | OH | H | H |
| XII-15-7 | Ph | H | H | $CH_2CH_2SCH_3$ | Et | $N_3$ | F | F | OH | H | H |
| XII-15-8 | Ph | * | H | * | Et | $N_3$ | F | F | OH | H | H |

*$R^2$ and $R^{3b}$ joined together by $(CH_2)_3$ to form five-membered ring.

TABLE XII-16

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-16-1 | p-Me—Ph | H | H | H | Et | $N_3$ | F | F | OH | H | H |
| XII-16-2 | p-Me—Ph | H | H | $CH_3$ | Et | $N_3$ | F | F | OH | H | H |
| XII-16-3 | p-Me—Ph | H | H | $CH(CH_3)_2$ | Et | $N_3$ | F | F | OH | H | H |
| XII-16-4 | p-Me—Ph | H | H | $CH_2CH(CH_3)_2$ | Et | $N_3$ | F | F | OH | H | H |
| XII-16-5 | p-Me—Ph | H | H | $CH_2Ph$ | Et | $N_3$ | F | F | OH | H | H |
| XII-16-4 | p-Me—Ph | H | H | $CH_2$-indol-3-yl | Et | $N_3$ | F | F | OH | H | H |
| XII-16-7 | p-Me—Ph | H | H | $CH_2CH_2SCH_3$ | Et | $N_3$ | F | F | OH | H | H |
| XII-16-8 | p-Me—Ph | * | H | * | Et | $N_3$ | F | F | OH | H | H |

*$R^2$ and $R^{3b}$ joined together by $(CH_2)_3$ to form five-membered ring.

TABLE XII-17

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-17-1 | p-F—Ph | H | H | H | Et | N$_3$ | F | F | OH | H | H |
| XII-17-2 | p-F—Ph | H | H | CH$_3$ | Et | N$_3$ | F | F | OH | H | H |
| XII-17-3 | p-F—Ph | H | H | CH(CH$_3$)$_2$ | Et | N$_3$ | F | F | OH | H | H |
| XII-17-4 | p-F—Ph | H | H | CH$_2$CH(CH$_3$)$_2$ | Et | N$_3$ | F | F | OH | H | H |
| XII-17-5 | p-F—Ph | H | H | CH$_2$Ph | Et | N$_3$ | F | F | OH | H | H |
| XII-17-6 | p-F—Ph | H | H | CH$_2$-indol-3-yl | Et | N$_3$ | F | F | OH | H | H |
| XII-17-7 | p-F—Ph | H | H | CH$_2$CH$_2$SCH$_3$ | Et | N$_3$ | F | F | OH | H | H |
| XII-17-8 | p-F—Ph | * | H | * | Et | N$_3$ | F | F | OH | H | H |

*R$^2$ and R$^{3b}$ joined together by (CH$_2$)$_3$ to form five-membered ring.

TABLE XII-18

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-18-1 | p-Cl—Ph | H | H | H | Et | N$_3$ | F | F | OH | H | H |
| XII-18-2 | p-Cl—Ph | H | H | CH$_3$ | Et | N$_3$ | F | F | OH | H | H |
| XII-18-3 | p-Cl—Ph | H | H | CH(CH$_3$)$_2$ | Et | N$_3$ | F | F | OH | H | H |
| XII-18-4 | p-Cl—Ph | H | H | CH$_2$CH(CH$_3$)$_2$ | Et | N$_3$ | F | F | OH | H | H |
| XII-18-5 | p-Cl—Ph | H | H | CH$_2$Ph | Et | N$_3$ | F | F | OH | H | H |
| XII-18-6 | p-Cl—Ph | H | H | CH$_2$-indol-3-yl | Et | N$_3$ | F | F | OH | H | H |
| XII-18-7 | p-Cl—Ph | H | H | CH$_2$CH$_2$SCH$_3$ | Et | N$_3$ | F | F | OH | H | H |
| XII-18-8 | p-Cl—Ph | * | H | * | Et | N$_3$ | F | F | OH | H | H |

*R$^2$ and R$^{3b}$ joined together by (CH$_2$)$_3$ to form five-membered ring.

TABLE XII-19

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-19-1 | p-Br—Ph | H | H | H | Et | N$_3$ | F | F | OH | H | H |
| XII-19-2 | p-Br—Ph | H | H | CH$_3$ | Et | N$_3$ | F | F | OH | H | H |
| XII-19-3 | p-Br—Ph | H | H | CH(CH$_3$)$_2$ | Et | N$_3$ | F | F | OH | H | H |
| XII-19-4 | p-Br—Ph | H | H | CH$_2$CH(CH$_3$)$_2$ | Et | N$_3$ | F | F | OH | H | H |
| XII-19-5 | p-Br—Ph | H | H | CH$_2$Ph | Et | N$_3$ | F | F | OH | H | H |
| XII-19-6 | p-Br—Ph | H | H | CH$_2$-indol-3-yl | Et | N$_3$ | F | F | OH | H | H |
| XII-19-7 | p-Br—Ph | H | H | CH$_2$CH$_2$SCH$_3$ | Et | N$_3$ | F | F | OH | H | H |
| XII-19-8 | p-Br—Ph | * | H | * | Et | N$_3$ | F | F | OH | H | H |

*R$^2$ and R$^{3b}$ joined together by (CH$_2$)$_3$ to form five-membered ring.

TABLE XII-20

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-20-1 | p-I—Ph | H | H | H | Et | N$_3$ | F | F | OH | H | H |
| XII-20-2 | p-I—Ph | H | H | CH$_3$ | Et | N$_3$ | F | F | OH | H | H |
| XII-20-3 | p-I—Ph | H | H | CH(CH$_3$)$_2$ | Et | N$_3$ | F | F | OH | H | H |
| XII-20-4 | p-I—Ph | H | H | CH$_2$CH(CH$_3$)$_2$ | Et | N$_3$ | F | F | OH | H | H |
| XII-20-5 | p-I—Ph | H | H | CH$_2$Ph | Et | N$_3$ | F | F | OH | H | H |
| XII-20-6 | p-I—Ph | H | H | CH$_2$-indol-3-yl | Et | N$_3$ | F | F | OH | H | H |
| XII-20-7 | p-I—Ph | H | H | CH$_2$CH$_2$SCH$_3$ | Et | N$_3$ | F | F | OH | H | H |
| XII-20-8 | p-I—Ph | * | H | * | Et | N$_3$ | F | F | OH | H | H |

*R$^2$ and R$^{3b}$ joined together by (CH$_2$)$_3$ to form five-membered ring.

TABLE XII-21

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XII-21-1 | CH$_3$ | H | H | H | $^i$Pr | N$_3$ | F | F | OH | H | H |
| XII-21-2 | CH$_3$ | H | H | CH$_3$ | $^i$Pr | N$_3$ | F | F | OH | H | H |
| XII-21-3 | CH$_3$ | H | H | CH(CH$_3$)$_2$ | $^i$Pr | N$_3$ | F | F | OH | H | H |
| XII-21-4 | CH$_3$ | H | H | CH$_2$CH(CH$_3$)$_2$ | $^i$Pr | N$_3$ | F | F | OH | H | H |
| XII-21-5 | CH$_3$ | H | H | CH$_2$Ph | $^i$Pr | N$_3$ | F | F | OH | H | H |
| XII-21-6 | CH$_3$ | H | H | CH$_2$-indol-3-yl | $^i$Pr | N$_3$ | F | F | OH | H | H |

TABLE XII-21-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-21-7 | $CH_3$ | H | H | $CH_2CH_2SCH_3$ | $^iPr$ | $N_3$ | F | F | OH | H | H |
| XII-21-8 | $CH_3$ | * | H | * | $^iPr$ | $N_3$ | F | F | OH | H | H |

*$R^2$ and $R^{3b}$ joined together by $(CH_2)_3$ to form five-membered ring.

TABLE XII-22

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-22-1 | Et | H | H | H | $^iPr$ | $N_3$ | F | F | OH | H | H |
| XII-22-2 | Et | H | H | $CH_3$ | $^iPr$ | $N_3$ | F | F | OH | H | H |
| XII-22-3 | Et | H | H | $CH(CH_3)_2$ | $^iPr$ | $N_3$ | F | F | OH | H | H |
| XII-22-4 | Et | H | H | $CH_2CH(CH_3)_2$ | $^iPr$ | $N_3$ | F | F | OH | H | H |
| XII-22-5 | Et | H | H | $CH_2Ph$ | $^iPr$ | $N_3$ | F | F | OH | H | H |
| XII-22-6 | Et | H | H | $CH_2$-indol-3-yl | $^iPr$ | $N_3$ | F | F | OH | H | H |
| XII-22-7 | Et | H | H | $CH_2CH_2SCH_3$ | $^iPr$ | $N_3$ | F | F | OH | H | H |
| XII-22-8 | Et | * | H | * | $^iPr$ | $N_3$ | F | F | OH | H | H |

*$R^2$ and $R^{3b}$ joined together by $(CH_2)_3$ to form five-membered ring.

TABLE XII-23

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-23-1 | $^iPr$ | H | H | H | $^iPr$ | $N_3$ | F | F | OH | H | H |
| XII-23-2 | $^iPr$ | H | H | $CH_3$ | $^iPr$ | $N_3$ | F | F | OH | H | H |
| XII-23-3 | $^iPr$ | H | H | $CH(CH_3)_2$ | $^iPr$ | $N_3$ | F | F | OH | H | H |
| XII-23-4 | $^iPr$ | H | H | $CH_2CH(CH_3)_2$ | $^iPr$ | $N_3$ | F | F | OH | H | H |
| XII-23-5 | $^iPr$ | H | H | $CH_2Ph$ | $^iPr$ | $N_3$ | F | F | OH | H | H |
| XII-23-6 | $^iPr$ | H | H | $CH_2$-indol-3-yl | $^iPr$ | $N_3$ | F | F | OH | H | H |
| XII-23-7 | $^iPr$ | H | H | $CH_2CH_2SCH_3$ | $^iPr$ | $N_3$ | F | F | OH | H | H |
| XII-23-8 | $^iPr$ | * | H | * | $^iPr$ | $N_3$ | F | F | OH | H | H |

*$R^2$ and $R^{3b}$ joined together by $(CH_2)_3$ to form five-membered ring.

TABLE XII-24

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-24-1 | $^tBu$ | H | H | H | $^iPr$ | $N_3$ | F | F | OH | H | H |
| XII-24-2 | $^tBu$ | H | H | $CH_3$ | $^iPr$ | $N_3$ | F | F | OH | H | H |
| XII-24-3 | $^tBu$ | H | H | $CH(CH_3)_2$ | $^iPr$ | $N_3$ | F | F | OH | H | H |
| XII-24-4 | $^tBu$ | H | H | $CH_2CH(CH_3)_2$ | $^iPr$ | $N_3$ | F | F | OH | H | H |
| XII-24-5 | $^tBu$ | H | H | $CH_2Ph$ | $^iPr$ | $N_3$ | F | F | OH | H | H |
| XII-24-6 | $^tBu$ | H | H | $CH_2$-indol-3-yl | $^iPr$ | $N_3$ | F | F | OH | H | H |
| XII-24-7 | $^tBu$ | H | H | $CH_2CH_2SCH_3$ | $^iPr$ | $N_3$ | F | F | OH | H | H |
| XII-24-8 | $^tBu$ | * | H | * | $^iPr$ | $N_3$ | F | F | OH | H | H |

*$R^2$ and $R^{3b}$ joined together by $(CH_2)_3$ to form five-membered ring.

TABLE XII-25

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-25-1 | Ph | H | H | H | $^iPr$ | $N_3$ | F | F | OH | H | H |
| XII-25-2 | Ph | H | H | $CH_3$ | $^iPr$ | $N_3$ | F | F | OH | H | H |
| XII-25-3 | Ph | H | H | $CH(CH_3)_2$ | $^iPr$ | $N_3$ | F | F | OH | H | H |
| XII-25-4 | Ph | H | H | $CH_2CH(CH_3)_2$ | $^iPr$ | $N_3$ | F | F | OH | H | H |
| XII-25-5 | Ph | H | H | $CH_2Ph$ | $^iPr$ | $N_3$ | F | F | OH | H | H |
| XII-25-6 | Ph | H | H | $CH_2$-indol-3-yl | $^iPr$ | $N_3$ | F | F | OH | H | H |
| XII-25-7 | Ph | H | H | $CH_2CH_2SCH_3$ | $^iPr$ | $N_3$ | F | F | OH | H | H |
| XII-25-8 | Ph | * | H | * | $^iPr$ | $N_3$ | F | F | OH | H | H |

*$R^2$ and $R^{3b}$ joined together by $(CH_2)_3$ to form five-membered ring.

TABLE XII-26

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-26-1 | p-Me—Ph | H | H | H | $^iPr$ | $N_3$ | F | F | OH | H | H |
| XII-26-2 | p-Me—Ph | H | H | $CH_3$ | $^iPr$ | $N_3$ | F | F | OH | H | H |
| XII-26-3 | p-Me—Ph | H | H | $CH(CH_3)_2$ | $^iPr$ | $N_3$ | F | F | OH | H | H |
| XII-26-4 | p-Me—Ph | H | H | $CH_2CH(CH_3)_2$ | $^iPr$ | $N_3$ | F | F | OH | H | H |
| XII-26-5 | p-Me—Ph | H | H | $CH_2Ph$ | $^iPr$ | $N_3$ | F | F | OH | H | H |
| XII-26-6 | p-Me—Ph | H | H | $CH_2$-indol-3-yl | $^iPr$ | $N_3$ | F | F | OH | H | H |
| XII-26-7 | p-Me—Ph | H | H | $CH_2CH_2SCH_3$ | $^iPr$ | $N_3$ | F | F | OH | H | H |
| XII-26-8 | p-Me—Ph | * | H | * | $^iPr$ | $N_3$ | F | F | OH | H | H |

*$R^2$ and $R^{3b}$ joined together by $(CH_2)_3$ to form five-membered ring.

TABLE XII-27

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-27-1 | p-F—Ph | H | H | H | $^iPr$ | $N_3$ | F | F | OH | H | H |
| XII-27-2 | p-F—Ph | H | H | $CH_3$ | $^iPr$ | $N_3$ | F | F | OH | H | H |
| XII-27-3 | p-F—Ph | H | H | $CH(CH_3)_2$ | $^iPr$ | $N_3$ | F | F | OH | H | H |

TABLE XII-27-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XII-27-4 | p-F—Ph | H | H | CH₂CH(CH₃)₂ | $^i$Pr | N₃ | F | F | OH | H | H |
| XII-27-5 | p-F—Ph | H | H | CH₂Ph | $^i$Pr | N₃ | F | F | OH | H | H |
| XII-27-6 | p-F—Ph | H | H | CH₂-indol-3-yl | $^i$Pr | N₃ | F | F | OH | H | H |
| XII-27-7 | p-F—Ph | H | H | CH₂CH₂SCH₃ | $^i$Pr | N₃ | F | F | OH | H | H |
| XII-27-8 | p-F—Ph | * | H | * | $^i$Pr | N₃ | F | F | OH | H | H |

*R² and R³ᵇ joined together by (CH₂)₃ to form five-membered ring.

TABLE XII-28

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XII-28-1 | p-Cl—Ph | H | H | H | $^i$Pr | N₃ | F | F | OH | H | H |
| XII-28-2 | p-Cl—Ph | H | H | CH₃ | $^i$Pr | N₃ | F | F | OH | H | H |
| XII-28-3 | p-Cl—Ph | H | H | CH(CH₃)₂ | $^i$Pr | N₃ | F | F | OH | H | H |
| XII-28-4 | p-Cl—Ph | H | H | CH₂CH(CH₃)₂ | $^i$Pr | N₃ | F | F | OH | H | H |
| XII-28-5 | p-Cl—Ph | H | H | CH₂Ph | $^i$Pr | N₃ | F | F | OH | H | H |
| XII-28-6 | p-Cl—Ph | H | H | CH₂-indol-3-yl | $^i$Pr | N₃ | F | F | OH | H | H |
| XII-28-7 | p-Cl—Ph | H | H | CH₂CH₂SCH₃ | $^i$Pr | N₃ | F | F | OH | H | H |
| XII-28-8 | p-Cl—Ph | * | H | * | $^i$Pr | N₃ | F | F | OH | H | H |

*R² and R³ᵇ joined together by (CH₂)₃ to form five-membered ring.

TABLE XII-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XII-29-1 | p-Br—Ph | H | H | H | $^i$Pr | N₃ | F | F | OH | H | H |
| XII-29-2 | p-Br—Ph | H | H | CH₃ | $^i$Pr | N₃ | F | F | OH | H | H |
| XII-29-3 | p-Br—Ph | H | H | CH(CH₃)₂ | $^i$Pr | N₃ | F | F | OH | H | H |
| XII-29-4 | p-Br—Ph | H | H | CH₂CH(CH₃)₂ | $^i$Pr | N₃ | F | F | OH | H | H |
| XII-29-5 | p-Br—Ph | H | H | CH₂Ph | $^i$Pr | N₃ | F | F | OH | H | H |
| XII-29-6 | p-Br—Ph | H | H | CH₂-indol-3-yl | $^i$Pr | N₃ | F | F | OH | H | H |
| XII-29-7 | p-Br—Ph | H | H | CH₂CH₂SCH₃ | $^i$Pr | N₃ | F | F | OH | H | H |
| XII-29-8 | p-Br—Ph | * | H | * | $^i$Pr | N₃ | F | F | OH | H | H |

*R² and R³ᵇ joined together by (CH₂)₃ to form five-membered ring.

TABLE XII-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XII-30-1 | p-I—Ph | H | H | H | $^i$Pr | N₃ | F | F | OH | H | H |
| XII-30-2 | p-I—Ph | H | H | CH₃ | $^i$Pr | N₃ | F | F | OH | H | H |
| XII-30-3 | p-I—Ph | H | H | CH(CH₃)₂ | $^i$Pr | N₃ | F | F | OH | H | H |
| XII-30-4 | p-I—Ph | H | H | CH₂CH(CH₃)₂ | $^i$Pr | N₃ | F | F | OH | H | H |
| XII-30-5 | p-I—Ph | H | H | CH₂Ph | $^i$Pr | N₃ | F | F | OH | H | H |
| XII-30-6 | p-I—Ph | H | H | CH₂-indol-3-yl | $^i$Pr | N₃ | F | F | OH | H | H |
| XII-30-7 | p-I—Ph | H | H | CH₂CH₂SCH₃ | $^i$Pr | N₃ | F | F | OH | H | H |
| XII-30-8 | p-I—Ph | * | H | * | $^i$Pr | N₃ | F | F | OH | H | H |

*R² and R³ᵇ joined together by (CH₂)₃ to form five-membered ring.

TABLE XII-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XII-31-1 | CH₃ | H | H | H | $^n$Bu | N₃ | F | F | OH | H | H |
| XII-31-2 | CH₃ | H | H | CH₃ | $^n$Bu | N₃ | F | F | OH | H | H |
| XII-31-3 | CH₃ | H | H | CH(CH₃)₂ | $^n$Bu | N₃ | F | F | OH | H | H |
| XII-31-4 | CH₃ | H | H | CH₂CH(CH₃)₂ | $^n$Bu | N₃ | F | F | OH | H | H |
| XII-31-5 | CH₃ | H | H | CH₂Ph | $^n$Bu | N₃ | F | F | OH | H | H |
| XII-31-6 | CH₃ | H | H | CH₂-indol-3-yl | $^n$Bu | N₃ | F | F | OH | H | H |
| XII-31-7 | CH₃ | H | H | CH₂CH₂SCH₃ | $^n$Bu | N₃ | F | F | OH | H | H |
| XII-31-8 | CH₃ | * | H | * | $^n$Bu | N₃ | F | F | OH | H | H |

*R² and R³ᵇ joined together by (CH₂)₃ to form five-membered ring.

TABLE XII-32

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-32-1 | Et | H | H | H | $^n$Bu | $N_3$ | F | F | OH | H | H |
| XII-32-2 | Et | H | H | $CH_3$ | $^n$Bu | $N_3$ | F | F | OH | H | H |
| XII-32-3 | Et | H | H | $CH(CH_3)_2$ | $^n$Bu | $N_3$ | F | F | OH | H | H |
| XII-32-4 | Et | H | H | $CH_2CH(CH_3)_2$ | $^n$Bu | $N_3$ | F | F | OH | H | H |
| XII-32-5 | Et | H | H | $CH_2Ph$ | $^n$Bu | $N_3$ | F | F | OH | H | H |
| XII-32-6 | Et | H | H | $CH_2$-indol-3-yl | $^n$Bu | $N_3$ | F | F | OH | H | H |
| XII-32-7 | Et | H | H | $CH_2CH_2SCH_3$ | $^n$Bu | $N_3$ | F | F | OH | H | H |
| XII-32-8 | Et | * | H | * | | $N_3$ | F | F | OH | H | H |

*$R^2$ and $R^{3b}$ joined together by $(CH_2)_3$ to form five-membered ring.

TABLE XII-33

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-33-1 | $^i$Pr | H | H | H | $^n$Bu | $N_3$ | F | F | OH | H | H |
| XII-33-2 | $^i$Pr | H | H | $CH_3$ | $^n$Bu | $N_3$ | F | F | OH | H | H |
| XII-33-3 | $^i$Pr | H | H | $CH(CH_3)_2$ | $^n$Bu | $N_3$ | F | F | OH | H | H |
| XII-33-4 | $^i$Pr | H | H | $CH_2CH(CH_3)_2$ | $^n$Bu | $N_3$ | F | F | OH | H | H |
| XII-33-5 | $^i$Pr | H | H | $CH_2Ph$ | $^n$Bu | $N_3$ | F | F | OH | H | H |
| XII-33-6 | $^i$Pr | H | H | $CH_2$-indol-3-yl | $^n$Bu | $N_3$ | F | F | OH | H | H |
| XII-33-7 | $^i$Pr | H | H | $CH_2CH_2SCH_3$ | $^n$Bu | $N_3$ | F | F | OH | H | H |
| XII-33-8 | $^i$Pr | * | H | * | | $N_3$ | F | F | OH | H | H |

*$R^2$ and $R^{3b}$ joined together by $(CH_2)_3$ to form five-membered ring.

TABLE XII-34

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-34-1 | $^t$Bu | H | H | H | $^n$Bu | $N_3$ | F | F | OH | H | H |
| XII-34-2 | $^t$Bu | H | H | $CH_3$ | $^n$Bu | $N_3$ | F | F | OH | H | H |
| XII-34-3 | $^t$Bu | H | H | $CH(CH_3)_2$ | $^n$Bu | $N_3$ | F | F | OH | H | H |
| XII-34-4 | $^t$Bu | H | H | $CH_2CH(CH_3)_2$ | $^n$Bu | $N_3$ | F | F | OH | H | H |
| XII-34-5 | $^t$Bu | H | H | $CH_2Ph$ | $^n$Bu | $N_3$ | F | F | OH | H | H |
| XII-34-6 | $^t$Bu | H | H | $CH_2$-indol-3-yl | $^n$Bu | $N_3$ | F | F | OH | H | H |
| XII-34-7 | $^t$Bu | H | H | $CH_2CH_2SCH_3$ | $^n$Bu | $N_3$ | F | F | OH | H | H |
| XII-34-8 | $^t$Bu | * | H | * | | $N_3$ | F | F | OH | H | H |

*$R^2$ and $R^{3b}$ joined together by $(CH_2)_3$ to form five-membered ring.

TABLE XII-35

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-35-1 | Ph | H | H | H | $^n$Bu | $N_3$ | F | F | OH | H | H |
| XII-35-2 | Ph | H | H | $CH_3$ | $^n$Bu | $N_3$ | F | F | OH | H | H |
| XII-35-3 | Ph | H | H | $CH(CH_3)_2$ | $^n$Bu | $N_3$ | F | F | OH | H | H |
| XII-35-4 | Ph | H | H | $CH_2CH(CH_3)_2$ | $^n$Bu | $N_3$ | F | F | OH | H | H |
| XII-35-5 | Ph | H | H | $CH_2Ph$ | $^n$Bu | $N_3$ | F | F | OH | H | H |
| XII-35-6 | Ph | H | H | $CH_2$-indol-3-yl | $^n$Bu | $N_3$ | F | F | OH | H | H |
| XII-35-7 | Ph | H | H | $CH_2CH_2SCH_3$ | $^n$Bu | $N_3$ | F | F | OH | H | H |
| XII-35-8 | Ph | * | H | * | | $N_3$ | F | F | OH | H | H |

*$R^2$ and $R^{3b}$ joined together by $(CH_2)_3$ to form five-membered ring.

TABLE XII-36

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-36-1 | p-Me—Ph | H | H | H | $^n$Bu | $N_3$ | F | F | OH | H | H |
| XII-36-2 | p-Me—Ph | H | H | $CH_3$ | $^n$Bu | $N_3$ | F | F | OH | H | H |
| XII-36-3 | p-Me—Ph | H | H | $CH(CH_3)_2$ | $^n$Bu | $N_3$ | F | F | OH | H | H |
| XII-36-4 | p-Me—Ph | H | H | $CH_2CH(CH_3)_2$ | $^n$Bu | $N_3$ | F | F | OH | H | H |
| XII-36-5 | p-Me—Ph | H | H | $CH_2Ph$ | $^n$Bu | $N_3$ | F | F | OH | H | H |
| XII-36-6 | p-Me—Ph | H | H | $CH_2$-indol-3-yl | $^n$Bu | $N_3$ | F | F | OH | H | H |
| XII-36-7 | p-Me—Ph | H | H | $CH_2CH_2SCH_3$ | $^n$Bu | $N_3$ | F | F | OH | H | H |
| XII-36-8 | p-Me—Ph | * | H | * | $^n$Bu | $N_3$ | F | F | OH | H | H |

*$R^2$ and $R^{3b}$ joined together by $(CH_2)_3$ to form five-membered ring.

TABLE XII-37

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-37-1 | p-F—Ph | H | H | H | $^n$Bu | $N_3$ | F | F | OH | H | H |
| XII-37-2 | p-F—Ph | H | H | $CH_3$ | $^n$Bu | $N_3$ | F | F | OH | H | H |
| XII-37-3 | p-F—Ph | H | H | $CH(CH_3)_2$ | $^n$Bu | $N_3$ | F | F | OH | H | H |
| XII-37-4 | p-F—Ph | H | H | $CH_2CH(CH_3)_2$ | $^n$Bu | $N_3$ | F | F | OH | H | H |
| XII-37-5 | p-F—Ph | H | H | $CH_2Ph$ | $^n$Bu | $N_3$ | F | F | OH | H | H |
| XII-37-6 | p-F—Ph | H | H | $CH_2$-indol-3-yl | $^n$Bu | $N_3$ | F | F | OH | H | H |
| XII-37-7 | p-F—Ph | H | H | $CH_2CH_2SCH_3$ | $^n$Bu | $N_3$ | F | F | OH | H | H |
| XII-37-8 | p-F—Ph | * | H | * | $^n$Bu | $N_3$ | F | F | OH | H | H |

*$R^2$ and $R^{3b}$ joined together by $(CH_2)_3$ to form five-membered ring.

TABLE XII-38

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-38-1 | p-Cl—Ph | H | H | H | $^n$Bu | $N_3$ | F | F | OH | H | H |
| XII-38-2 | p-Cl—Ph | H | H | $CH_3$ | $^n$Bu | $N_3$ | F | F | OH | H | H |
| XII-38-3 | p-Cl—Ph | H | H | $CH(CH_3)_2$ | $^n$Bu | $N_3$ | F | F | OH | H | H |
| XII-38-4 | p-Cl—Ph | H | H | $CH_2CH(CH_3)_2$ | $^n$Bu | $N_3$ | F | F | OH | H | H |
| XII-38-5 | p-Cl—Ph | H | H | $CH_2Ph$ | $^n$Bu | $N_3$ | F | F | OH | H | H |
| XII-38-6 | p-Cl—Ph | H | H | $CH_2$-indol-3-yl | $^n$Bu | $N_3$ | F | F | OH | H | H |
| XII-38-7 | p-Cl—Ph | H | H | $CH_2CH_2SCH_3$ | $^n$Bu | $N_3$ | F | F | OH | H | H |
| XII-38-8 | p-Cl—Ph | * | H | * | $^n$Bu | $N_3$ | F | F | OH | H | H |

*$R^2$ and $R^{3b}$ joined together by $(CH_2)_3$ to form five-membered ring.

TABLE XII-39

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-39-1 | p-Br—Ph | H | H | H | $^n$Bu | $N_3$ | F | F | OH | H | H |
| XII-39-2 | p-Br—Ph | H | H | $CH_3$ | $^n$Bu | $N_3$ | F | F | OH | H | H |
| XII-39-3 | p-Br—Ph | H | H | $CH(CH_3)_2$ | $^n$Bu | $N_3$ | F | F | OH | H | H |
| XII-39-4 | p-Br—Ph | H | H | $CH_2CH(CH_3)_2$ | $^n$Bu | $N_3$ | F | F | OH | H | H |
| XII-39-5 | p-Br—Ph | H | H | $CH_2Ph$ | $^n$Bu | $N_3$ | F | F | OH | H | H |
| XII-39-6 | p-Br—Ph | H | H | $CH_2$-indol-3-yl | $^n$Bu | $N_3$ | F | F | OH | H | H |
| XII-39-7 | p-Br—Ph | H | H | $CH_2CH_2SCH_3$ | $^n$Bu | $N_3$ | F | F | OH | H | H |
| XII-39-8 | p-Br—Ph | * | H | * | $^n$Bu | $N_3$ | F | F | OH | H | H |

*$R^2$ and $R^{3b}$ joined together by $(CH_2)_3$ to form five-membered ring.

TABLE XII-40

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-40-1 | p-I—Ph | H | H | H | $^n$Bu | $N_3$ | F | F | OH | H | H |
| XII-40-2 | p-I—Ph | H | H | $CH_3$ | $^n$Bu | $N_3$ | F | F | OH | H | H |
| XII-40-3 | p-I—Ph | H | H | $CH(CH_3)_2$ | $^n$Bu | $N_3$ | F | F | OH | H | H |
| XII-40-4 | p-I—Ph | H | H | $CH_2CH(CH_3)_2$ | $^n$Bu | $N_3$ | F | F | OH | H | H |
| XII-40-5 | p-I—Ph | H | H | $CH_2Ph$ | $^n$Bu | $N_3$ | F | F | OH | H | H |
| XII-40-6 | p-I—Ph | H | H | $CH_2$-indol-3-yl | $^n$Bu | $N_3$ | F | F | OH | H | H |
| XII-40-7 | p-I—Ph | H | H | $CH_2CH_2SCH_3$ | $^n$Bu | $N_3$ | F | F | OH | H | H |
| XII-40-8 | p-I—Ph | * | H | * | $^n$Bu | $N_3$ | F | F | OH | H | H |

*$R^2$ and $R^{3b}$ joined together by $(CH_2)_3$ to form five-membered ring.

TABLE XII-41

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-41-1 | $CH_3$ | H | H | H | Bz | $N_3$ | F | F | OH | H | H |
| XII-41-2 | $CH_3$ | H | H | $CH_3$ | Bz | $N_3$ | F | F | OH | H | H |
| XII-41-3 | $CH_3$ | H | H | $CH(CH_3)_2$ | Bz | $N_3$ | F | F | OH | H | H |
| XII-41-4 | $CH_3$ | H | H | $CH_2CH(CH_3)_2$ | Bz | $N_3$ | F | F | OH | H | H |
| XII-41-5 | $CH_3$ | H | H | $CH_2Ph$ | Bz | $N_3$ | F | F | OH | H | H |
| XII-41-6 | $CH_3$ | H | H | $CH_2$-indol-3-yl | Bz | $N_3$ | F | F | OH | H | H |
| XII-41-7 | $CH_3$ | H | H | $CH_2CH_2SCH_3$ | Bz | $N_3$ | F | F | OH | H | H |
| XII-41-8 | $CH_3$ | * | H | * | Bz | $N_3$ | F | F | OH | H | H |

*$R^2$ and $R^{3b}$ joined together by $(CH_2)_3$ to form five-membered ring.

TABLE XII-42

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-42-1 | Et | H | H | H | Bz | $N_3$ | F | F | OH | H | H |
| XII-42-2 | Et | H | H | $CH_3$ | Bz | $N_3$ | F | F | OH | H | H |
| XII-42-3 | Et | H | H | $CH(CH_3)_2$ | Bz | $N_3$ | F | F | OH | H | H |
| XII-42-4 | Et | H | H | $CH_2CH(CH_3)_2$ | Bz | $N_3$ | F | F | OH | H | H |
| XII-42-5 | Et | H | H | $CH_2Ph$ | Bz | $N_3$ | F | F | OH | H | H |
| XII-42-6 | Et | H | H | $CH_2$-indol-3-yl | Bz | $N_3$ | F | F | OH | H | H |
| XII-42-7 | Et | H | H | $CH_2CH_2SCH_3$ | Bz | $N_3$ | F | F | OH | H | H |
| XII-42-8 | Et | * | H | * | Bz | $N_3$ | F | F | OH | H | H |

*$R^2$ and $R^{3b}$ joined together by $(CH_2)_3$ to form five-membered ring.

TABLE XII-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-43-1 | $^iPr$ | H | H | H | Bz | $N_3$ | F | F | OH | H | H |
| XII-43-2 | $^iPr$ | H | H | $CH_3$ | Bz | $N_3$ | F | F | OH | H | H |
| XII-43-3 | $^iPr$ | H | H | $CH(CH_3)_2$ | Bz | $N_3$ | F | F | OH | H | H |
| XII-43-4 | $^iPr$ | H | H | $CH_2CH(CH_3)_2$ | Bz | $N_3$ | F | F | OH | H | H |
| XII-43-5 | $^iPr$ | H | H | $CH_2Ph$ | Bz | $N_3$ | F | F | OH | H | H |
| XII-43-6 | $^iPr$ | H | H | $CH_2$-indol-3-yl | Bz | $N_3$ | F | F | OH | H | H |
| XII-43-7 | $^iPr$ | H | H | $CH_2CH_2SCH_3$ | Bz | $N_3$ | F | F | OH | H | H |
| XII-43-8 | $^iPr$ | * | H | * | Bz | $N_3$ | F | F | OH | H | H |

*$R^2$ and $R^{3b}$ joined together by $(CH_2)_3$ to form five-membered ring.

TABLE XII-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-44-1 | $^tBu$ | H | H | H | Bz | $N_3$ | F | F | OH | H | H |
| XII-44-2 | $^tBu$ | H | H | $CH_3$ | Bz | $N_3$ | F | F | OH | H | H |
| XII-44-3 | $^tBu$ | H | H | $CH(CH_3)_2$ | Bz | $N_3$ | F | F | OH | H | H |
| XII-44-4 | $^tBu$ | H | H | $CH_2CH(CH_3)_2$ | Bz | $N_3$ | F | F | OH | H | H |
| XII-44-5 | $^tBu$ | H | H | $CH_2Ph$ | Bz | $N_3$ | F | F | OH | H | H |
| XII-44-6 | $^tBu$ | H | H | $CH_2$-indol-3-yl | Bz | $N_3$ | F | F | OH | H | H |
| XII-44-7 | $^tBu$ | H | H | $CH_2CH_2SCH_3$ | Bz | $N_3$ | F | F | OH | H | H |
| XII-44-8 | $^tBu$ | * | H | * | Bz | $N_3$ | F | F | OH | H | H |

*$R^2$ and $R^{3b}$ joined together by $(CH_2)_3$ to form five-membered ring.

TABLE XII-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-45-1 | Ph | H | H | H | Bz | $N_3$ | F | F | OH | H | H |
| XII-45-2 | Ph | H | H | $CH_3$ | Bz | $N_3$ | F | F | OH | H | H |
| XII-45-3 | Ph | H | H | $CH(CH_3)_2$ | Bz | $N_3$ | F | F | OH | H | H |
| XII-45-4 | Ph | H | H | $CH_2CH(CH_3)_2$ | Bz | $N_3$ | F | F | OH | H | H |
| XII-45-5 | Ph | H | H | $CH_2Ph$ | Bz | $N_3$ | F | F | OH | H | H |
| XII-45-6 | Ph | H | H | $CH_2$-indol-3-yl | Bz | $N_3$ | F | F | OH | H | H |
| XII-45-7 | Ph | H | H | $CH_2CH_2SCH_3$ | Bz | $N_3$ | F | F | OH | H | H |
| XII-45-8 | Ph | * | H | * | Bz | $N_3$ | F | F | OH | H | H |

*$R^2$ and $R^{3b}$ joined together by $(CH_2)_3$ to form five-membered ring.

TABLE XII-46

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-46-1 | p-Me—Ph | H | H | H | Bz | $N_3$ | F | F | OH | H | H |
| XII-46-2 | p-Me—Ph | H | H | $CH_3$ | Bz | $N_3$ | F | F | OH | H | H |
| XII-46-3 | p-Me—Ph | H | H | $CH(CH_3)_2$ | Bz | $N_3$ | F | F | OH | H | H |
| XII-46-4 | p-Me—Ph | H | H | $CH_2CH(CH_3)_2$ | Bz | $N_3$ | F | F | OH | H | H |
| XII-46-5 | p-Me—Ph | H | H | $CH_2Ph$ | Bz | $N_3$ | F | F | OH | H | H |
| XII-46-6 | p-Me—Ph | H | H | $CH_2$-indol-3-yl | Bz | $N_3$ | F | F | OH | H | H |
| XII-46-7 | p-Me—Ph | H | H | $CH_2CH_2SCH_3$ | Bz | $N_3$ | F | F | OH | H | H |
| XII-46-8 | p-Me—Ph | * | H | * | Bz | $N_3$ | F | F | OH | H | H |

*$R^2$ and $R^{3b}$ joined together by $(CH_2)_3$ to form five-membered ring.

TABLE XII-47

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-47-1 | p-F—Ph | H | H | H | Bz | $N_3$ | F | F | OH | H | H |
| XII-47-2 | p-F—Ph | H | H | $CH_3$ | Bz | $N_3$ | F | F | OH | H | H |
| XII-47-3 | p-F—Ph | H | H | $CH(CH_3)_2$ | Bz | $N_3$ | F | F | OH | H | H |
| XII-47-4 | p-F—Ph | H | H | $CH_2CH(CH_3)_2$ | Bz | $N_3$ | F | F | OH | H | H |
| XII-47-5 | p-F—Ph | H | H | $CH_2Ph$ | Bz | $N_3$ | F | F | OH | H | H |
| XII-47-6 | p-F—Ph | H | H | $CH_2$-indol-3-yl | Bz | $N_3$ | F | F | OH | H | H |
| XII-47-7 | p-F—Ph | H | H | $CH_2CH_2SCH_3$ | Bz | $N_3$ | F | F | OH | H | H |
| XII-47-8 | p-F—Ph | * | H | * | Bz | $N_3$ | F | F | OH | H | H |

*$R^2$ and $R^{3b}$ joined together by $(CH_2)_3$ to form five-membered ring.

TABLE XII-48

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XII-48-1 | p-Cl—Ph | H | H | H | Bz | $N_3$ | F | F | OH | H | H |
| XII-48-2 | p-Cl—Ph | H | H | $CH_3$ | Bz | $N_3$ | F | F | OH | H | H |

TABLE XII-48-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XII-48-3 | p-Cl—Ph | H | H | CH(CH₃)₂ | Bz | N₃ | F | F | OH | H | H |
| XII-48-4 | p-Cl—Ph | H | H | CH₂CH(CH₃)₂ | Bz | N₃ | F | F | OH | H | H |
| XII-48-5 | p-Cl—Ph | H | H | CH₂Ph | Bz | N₃ | F | F | OH | H | H |
| XII-48-6 | p-Cl—Ph | H | H | CH₂-indol-3-yl | Bz | N₃ | F | F | OH | H | H |
| XII-48-7 | p-Cl—Ph | H | H | CH₂CH₂SCH₃ | Bz | N₃ | F | F | OH | H | H |
| XII-48-8 | p-Cl—Ph | * | H | * | Bz | N₃ | F | F | OH | H | H |

*R² and R³ᵇ joined together by (CH₂)₃ to form five-membered ring.

TABLE XII-49

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XII-49-1 | p-Br—Ph | H | H | H | Bz | N₃ | F | F | OH | H | H |
| XII-49-2 | p-Br—Ph | H | H | CH₃ | Bz | N₃ | F | F | OH | H | H |
| XII-49-3 | p-Br—Ph | H | H | CH(CH₃)₂ | Bz | N₃ | F | F | OH | H | H |
| XII-49-4 | p-Br—Ph | H | H | CH₂CH(CH₃)₂ | Bz | N₃ | F | F | OH | H | H |
| XII-49-5 | p-Br—Ph | H | H | CH₂Ph | Bz | N₃ | F | F | OH | H | H |
| XII-49-6 | p-Br—Ph | H | H | CH₂-indol-3-yl | Bz | N₃ | F | F | OH | H | H |
| XII-49-7 | p-Br—Ph | H | H | CH₂CH₂SCH₃ | Bz | N₃ | F | F | OH | H | H |
| XII-49-8 | p-Br—Ph | * | H | * | Bz | N₃ | F | F | OH | H | H |

*R² and R³ᵇ joined together by (CH₂)₃ to form five-membered ring.

TABLE XII-50

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XII-50-1 | p-I—Ph | H | H | H | Bz | N₃ | F | F | OH | H | H |
| XII-50-2 | p-I—Ph | H | H | CH₃ | Bz | N₃ | F | F | OH | H | H |
| XII-50-3 | p-I—Ph | H | H | CH(CH₃)₂ | Bz | N₃ | F | F | OH | H | H |
| XII-50-4 | p-I—Ph | H | H | CH₂CH(CH₃)₂ | Bz | N₃ | F | F | OH | H | H |
| XII-50-5 | p-I—Ph | H | H | CH₂Ph | Bz | N₃ | F | F | OH | H | H |
| XII-50-6 | p-I—Ph | H | H | CH₂-indol-3-yl | Bz | N₃ | F | F | OH | H | H |
| XII-50-7 | p-I—Ph | H | H | CH₂CH₂SCH₃ | Bz | N₃ | F | F | OH | H | H |
| XII-50-8 | p-I—Ph | * | H | * | Bz | N₃ | F | F | OH | H | H |

*R² and R³ᵇ joined together by (CH₂)₃ to form five-membered ring.

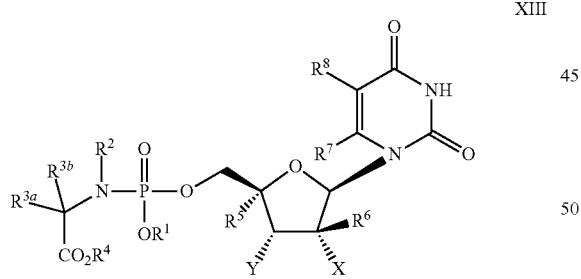

XIII

TABLE XIII-1

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-1-1 | CH₃ | H | H | H | CH₃ | N₃ | H | F | OH | H | H |
| XIII-1-2 | CH₃ | H | H | CH₃ | CH₃ | N₃ | H | F | OH | H | H |
| XIII-1-3 | CH₃ | H | H | CH(CH₃)₂ | CH₃ | N₃ | H | F | OH | H | H |
| XIII-1-4 | CH₃ | H | H | CH₂CH(CH₃)₂ | CH₃ | N₃ | H | F | OH | H | H |
| XIII-1-5 | CH₃ | H | H | CH₂Ph | CH₃ | N₃ | H | F | OH | H | H |
| XIII-1-6 | CH₃ | H | H | CH₂-indol-3-yl | CH₃ | N₃ | H | F | OH | H | H |
| XIII-1-7 | CH₃ | H | H | CH₂CH₂SCH₃ | CH₃ | N₃ | H | F | OH | H | H |
| XIII-1-8 | CH₃ | * | H | * | CH₃ | N₃ | H | F | OH | H | H |

*R² and R³ᵇ joined together by (CH₂)₃ to form five-membered ring.

TABLE XIII-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-2-1 | Et | H | H | H | $CH_3$ | $N_3$ | H | F | OH | H | H |
| XIII-2-2 | Et | H | H | $CH_3$ | $CH_3$ | $N_3$ | H | F | OH | H | H |
| XIII-2-3 | Et | H | H | $CH(CH_3)_2$ | $CH_3$ | $N_3$ | H | F | OH | H | H |
| XIII-2-4 | Et | H | H | $CH_2CH(CH_3)_2$ | $CH_3$ | $N_3$ | H | F | OH | H | H |
| XIII-2-5 | Et | H | H | $CH_2Ph$ | $CH_3$ | $N_3$ | H | F | OH | H | H |
| XIII-2-6 | Et | H | H | $CH_2$-indol-3-yl | $CH_3$ | $N_3$ | H | F | OH | H | H |
| XIII-2-7 | Et | H | H | $CH_2CH_2SCH_3$ | $CH_3$ | $N_3$ | H | F | OH | H | H |
| XIII-2-8 | Et | * | H | * | $CH_3$ | $N_3$ | H | F | OH | H | H |

*$R^2$ and $R^{3b}$ joined together by $(CH_2)_3$ to form five-membered ring.

TABLE XIII-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-3-1 | $^i$Pr | H | H | H | $CH_3$ | $N_3$ | H | F | OH | H | H |
| XIII-3-2 | $^i$Pr | H | H | $CH_3$ | $CH_3$ | $N_3$ | H | F | OH | H | H |
| XIII-3-3 | $^i$Pr | H | H | $CH(CH_3)_2$ | $CH_3$ | $N_3$ | H | F | OH | H | H |
| XIII-3-4 | $^i$Pr | H | H | $CH_2CH(CH_3)_2$ | $CH_3$ | $N_3$ | H | F | OH | H | H |
| XIII-3-5 | $^i$Pr | H | H | $CH_2Ph$ | $CH_3$ | $N_3$ | H | F | OH | H | H |
| XIII-3-6 | $^i$Pr | H | H | $CH_2$-indol-3-yl | $CH_3$ | $N_3$ | H | F | OH | H | H |
| XIII-3-7 | $^i$Pr | H | H | $CH_2CH_2SCH_3$ | $CH_3$ | $N_3$ | H | F | OH | H | H |
| XIII-3-8 | $^i$Pr | * | H | * | $CH_3$ | $N_3$ | H | F | OH | H | H |

*$R^2$ and $R^{3b}$ joined together by $(CH_2)_3$ to form five-membered ring.

TABLE XIII-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-4-1 | $^t$Bu | H | H | H | $CH_3$ | $N_3$ | H | F | OH | H | H |
| XIII-4-2 | $^t$Bu | H | H | $CH_3$ | $CH_3$ | $N_3$ | H | F | OH | H | H |
| XIII-4-3 | $^t$Bu | H | H | $CH(CH_3)_2$ | $CH_3$ | $N_3$ | H | F | OH | H | H |
| XIII-4-4 | $^t$Bu | H | H | $CH_2CH(CH_3)_2$ | $CH_3$ | $N_3$ | H | F | OH | H | H |
| XIII-4-5 | $^t$Bu | H | H | $CH_2Ph$ | $CH_3$ | $N_3$ | H | F | OH | H | H |
| XIII-4-6 | $^t$Bu | H | H | $CH_2$-indol-3-yl | $CH_3$ | $N_3$ | H | F | OH | H | H |
| XIII-4-7 | $^t$Bu | H | H | $CH_2CH_2SCH_3$ | $CH_3$ | $N_3$ | H | F | OH | H | H |
| XIII-4-8 | $^t$Bu | * | H | * | $CH_3$ | $N_3$ | H | F | OH | H | H |

*$R^2$ and $R^{3b}$ joined together by $(CH_2)_3$ to form five-membered ring.

TABLE XIII-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-5-1 | Ph | H | H | H | $CH_3$ | $N_3$ | H | F | OH | H | H |
| XIII-5-2 | Ph | H | H | $CH_3$ | $CH_3$ | $N_3$ | H | F | OH | H | H |
| XIII-5-3 | Ph | H | H | $CH(CH_3)_2$ | $CH_3$ | $N_3$ | H | F | OH | H | H |
| XIII-5-4 | Ph | H | H | $CH_2CH(CH_3)_2$ | $CH_3$ | $N_3$ | H | F | OH | H | H |
| XIII-5-5 | Ph | H | H | $CH_2Ph$ | $CH_3$ | $N_3$ | H | F | OH | H | H |
| XIII-5-6 | Ph | H | H | $CH_2$-indol-3-yl | $CH_3$ | $N_3$ | H | F | OH | H | H |
| XIII-5-7 | Ph | H | H | $CH_2CH_2SCH_3$ | $CH_3$ | $N_3$ | H | F | OH | H | H |
| XIII-5-8 | Ph | * | H | * | $CH_3$ | $N_3$ | H | F | OH | H | H |

*$R^2$ and $R^{3b}$ joined together by $(CH_2)_3$ to form five-membered ring.

TABLE XIII-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-6-1 | p-Me—Ph | H | H | H | $CH_3$ | $N_3$ | H | F | OH | H | H |
| XIII-6-2 | p-Me—Ph | H | H | $CH_3$ | $CH_3$ | $N_3$ | H | F | OH | H | H |
| XIII-6-3 | p-Me—Ph | H | H | $CH(CH_3)_2$ | $CH_3$ | $N_3$ | H | F | OH | H | H |
| XIII-6-4 | p-Me—Ph | H | H | $CH_2CH(CH_3)_2$ | $CH_3$ | $N_3$ | H | F | OH | H | H |
| XIII-6-5 | p-Me—Ph | H | H | $CH_2Ph$ | $CH_3$ | $N_3$ | H | F | OH | H | H |
| XIII-6-6 | p-Me—Ph | H | H | $CH_2$-indol-3-yl | $CH_3$ | $N_3$ | H | F | OH | H | H |
| XIII-6-7 | p-Me—Ph | H | H | $CH_2CH_2SCH_3$ | $CH_3$ | $N_3$ | H | F | OH | H | H |
| XIII-6-8 | p-Me—Ph | * | H | * | $CH_3$ | $N_3$ | H | F | OH | H | H |

*$R^2$ and $R^{3b}$ joined together by $(CH_2)_3$ to form five-membered ring.

TABLE XIII-7

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-7-1 | p-F—Ph | H | H | H | $CH_3$ | $N_3$ | H | F | OH | H | H |
| XIII-7-2 | p-F—Ph | H | H | $CH_3$ | $CH_3$ | $N_3$ | H | F | OH | H | H |
| XIII-7-3 | p-F—Ph | H | H | $CH(CH_3)_2$ | $CH_3$ | $N_3$ | H | F | OH | H | H |
| XIII-7-4 | p-F—Ph | H | H | $CH_2CH(CH_3)_2$ | $CH_3$ | $N_3$ | H | F | OH | H | H |
| XIII-7-6 | p-F—Ph | H | H | $CH_2Ph$ | $CH_3$ | $N_3$ | H | F | OH | H | H |
| XIII-7-7 | p-F—Ph | H | H | $CH_2$-indol-3-yl | $CH_3$ | $N_3$ | H | F | OH | H | H |
| XIII-7-8 | p-F—Ph | H | H | $CH_2CH_2SCH_3$ | $CH_3$ | $N_3$ | H | F | OH | H | H |
| XIII-7-20 | p-F—Ph | * | H | * | $CH_3$ | $N_3$ | H | F | OH | H | H |

*$R^2$ and $R^{3b}$ joined together by $(CH_2)_3$ to form five-membered ring.

TABLE XIII-8

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-8-1 | p-Cl—Ph | H | H | H | $CH_3$ | $N_3$ | H | F | OH | H | H |
| XIII-8-2 | p-Cl—Ph | H | H | $CH_3$ | $CH_3$ | $N_3$ | H | F | OH | H | H |
| XIII-8-3 | p-Cl—Ph | H | H | $CH(CH_3)_2$ | $CH_3$ | $N_3$ | H | F | OH | H | H |
| XIII-8-4 | p-Cl—Ph | H | H | $CH_2CH(CH_3)_2$ | $CH_3$ | $N_3$ | H | F | OH | H | H |
| XIII-8-5 | p-Cl—Ph | H | H | $CH_2Ph$ | $CH_3$ | $N_3$ | H | F | OH | H | H |
| XIII-8-6 | p-Cl—Ph | H | H | $CH_2$-indol-3-yl | $CH_3$ | $N_3$ | H | F | OH | H | H |
| XIII-8-7 | p-Cl—Ph | H | H | $CH_2CH_2SCH_3$ | $CH_3$ | $N_3$ | H | F | OH | H | H |
| XIII-8-8 | p-Cl—Ph | * | H | * | $CH_3$ | $N_3$ | H | F | OH | H | H |

*R² and R³ᵇ joined together by $(CH_2)_3$ to form five-membered ring.

TABLE XIII-9

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-9-1 | p-Br—Ph | H | H | H | $CH_3$ | $N_3$ | H | F | OH | H | H |
| XIII-9-2 | p-Br—Ph | H | H | $CH_3$ | $CH_3$ | $N_3$ | H | F | OH | H | H |
| XIII-9-3 | p-Br—Ph | H | H | $CH(CH_3)_2$ | $CH_3$ | $N_3$ | H | F | OH | H | H |
| XIII-9-4 | p-Br—Ph | H | H | $CH_2CH(CH_3)_2$ | $CH_3$ | $N_3$ | H | F | OH | H | H |
| XIII-9-6 | p-Br—Ph | H | H | $CH_2Ph$ | $CH_3$ | $N_3$ | H | F | OH | H | H |
| XIII-9-7 | p-Br—Ph | H | H | $CH_2$-indol-3-yl | $CH_3$ | $N_3$ | H | F | OH | H | H |
| XIII-9-8 | p-Br—Ph | H | H | $CH_2CH_2SCH_3$ | $CH_3$ | $N_3$ | H | F | OH | H | H |
| XIII-9-20 | p-Br—Ph | * | H | * | $CH_3$ | $N_3$ | H | F | OH | H | H |

*R² and R³ᵇ joined together by $(CH_2)_3$ to form five-membered ring.

TABLE XIII-10

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-10-1 | p-I—Ph | H | H | H | $CH_3$ | $N_3$ | H | F | OH | H | H |
| XIII-10-2 | p-I—Ph | H | H | $CH_3$ | $CH_3$ | $N_3$ | H | F | OH | H | H |
| XIII-10-3 | p-I—Ph | H | H | $CH(CH_3)_2$ | $CH_3$ | $N_3$ | H | F | OH | H | H |
| XIII-10-4 | p-I—Ph | H | H | $CH_2CH(CH_3)_2$ | $CH_3$ | $N_3$ | H | F | OH | H | H |
| XIII-10-5 | p-I—Ph | H | H | $CH_2Ph$ | $CH_3$ | $N_3$ | H | F | OH | H | H |
| XIII-10-6 | p-I—Ph | H | H | $CH_2$-indol-3-yl | $CH_3$ | $N_3$ | H | F | OH | H | H |
| XIII-10-7 | p-I—Ph | H | H | $CH_2CH_2SCH_3$ | $CH_3$ | $N_3$ | H | F | OH | H | H |
| XIII-10-8 | p-I—Ph | * | H | * | $CH_3$ | $N_3$ | H | F | OH | H | H |

*R² and R³ᵇ joined together by $(CH_2)_3$ to form five-membered ring.

TABLE XIII-11

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-11-1 | $CH_3$ | H | H | H | Et | $N_3$ | H | F | OH | H | H |
| XIII-11-2 | $CH_3$ | H | H | $CH_3$ | Et | $N_3$ | H | F | OH | H | H |
| XIII-11-3 | $CH_3$ | H | H | $CH(CH_3)_2$ | Et | $N_3$ | H | F | OH | H | H |
| XIII-11-4 | $CH_3$ | H | H | $CH_2CH(CH_3)_2$ | Et | $N_3$ | H | F | OH | H | H |
| XIII-11-5 | $CH_3$ | H | H | $CH_2Ph$ | Et | $N_3$ | H | F | OH | H | H |
| XIII-11-6 | $CH_3$ | H | H | $CH_2$-indol-3-yl | Et | $N_3$ | H | F | OH | H | H |
| XIII-11-7 | $CH_3$ | H | H | $CH_2CH_2SCH_3$ | Et | $N_3$ | H | F | OH | H | H |
| XIII-11-8 | $CH_3$ | * | H | * | Et | $N_3$ | H | F | OH | H | H |

*R² and R³ᵇ joined together by $(CH_2)_3$ to form five-membered ring.

TABLE XIII-12

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-12-1 | Et | H | H | H | Et | $N_3$ | H | F | OH | H | H |
| XIII-12-2 | E | H | H | $CH_3$ | Et | $N_3$ | H | F | OH | H | H |
| XIII-12-3 | Et | H | H | $CH(CH_3)_2$ | Et | $N_3$ | H | F | OH | H | H |
| XIII-12-4 | Et | H | H | $CH_2CH(CH_3)_2$ | Et | $N_3$ | H | F | OH | H | H |
| XIII-12-5 | Et | H | H | $CH_2Ph$ | Et | $N_3$ | H | F | OH | H | H |
| XIII-12-6 | Et | H | H | $CH_2$-indol-3-yl | Et | $N_3$ | H | F | OH | H | H |
| XIII-12-7 | Et | H | H | $CH_2CH_2SCH_3$ | Et | $N_3$ | H | F | OH | H | H |
| XIII-12-8 | Et | * | H | * | Et | $N_3$ | H | F | OH | H | H |

*R² and R³ᵇ joined together by $(CH_2)_3$ to form five-membered ring.

TABLE XIII-13

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-13-1 | ⁱPr | H | H | H | Et | $N_3$ | H | F | OH | H | H |
| XIII-13-2 | ⁱPr | H | H | $CH_3$ | Et | $N_3$ | H | F | OH | H | H |
| XIII-13-3 | ⁱPr | H | H | $CH(CH_3)_2$ | Et | $N_3$ | H | F | OH | H | H |
| XIII-13-4 | ⁱPr | H | H | $CH_2CH(CH_3)_2$ | Et | $N_3$ | H | F | OH | H | H |
| XIII-13-5 | ⁱPr | H | H | $CH_2Ph$ | Et | $N_3$ | H | F | OH | H | H |
| XIII-13-6 | ⁱPr | H | H | $CH_2$-indol-3-yl | Et | $N_3$ | H | F | OH | H | H |
| XIII-13-7 | ⁱPr | H | H | $CH_2CH_2SCH_3$ | Et | $N_3$ | H | F | OH | H | H |
| XIII-13-8 | ⁱPr | * | H | * | Et | $N_3$ | H | F | OH | H | H |

*R² and R³ᵇ joined together by $(CH_2)_3$ to form five-membered ring.

TABLE XIII-14

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-14-1 | ᵗBu | H | H | H | Et | N₃ | H | F | OH | H | H |
| XIII-14-2 | ᵗBu | H | H | CH₃ | Et | N₃ | H | F | OH | H | H |
| XIII-14-3 | ᵗBu | H | H | CH(CH₃)₂ | Et | N₃ | H | F | OH | H | H |
| XIII-14-4 | ᵗBu | H | H | CH₂CH(CH₃)₂ | Et | N₃ | H | F | OH | H | H |
| XIII-14-5 | ᵗBu | H | H | CH₂Ph | Et | N₃ | H | F | OH | H | H |
| XIII-14-6 | ᵗBu | H | H | CH₂-indol-3-yl | Et | N₃ | H | F | OH | H | H |
| XIII-14-7 | ᵗBu | H | H | CH₂CH₂SCH₃ | Et | N₃ | H | F | OH | H | H |
| XIII-14-8 | ᵗBu | * | H | * | Et | N₃ | H | F | OH | H | H |

*$R^2$ and $R^{3b}$ joined together by $(CH_2)_3$ to form five-membered ring.

TABLE XIII-15

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-15-1 | Ph | H | H | H | Et | N₃ | H | F | OH | H | H |
| XIII-15-2 | Ph | H | H | CH₃ | Et | N₃ | H | F | OH | H | H |
| XIII-15-3 | Ph | H | H | CH(CH₃)₂ | Et | N₃ | H | F | OH | H | H |
| XIII-15-4 | Ph | H | H | CH₂CH(CH₃)₂ | Et | N₃ | H | F | OH | H | H |
| XIII-15-5 | Ph | H | H | CH₂Ph | Et | N₃ | H | F | OH | H | H |
| XIII-15-6 | Ph | H | H | CH₂-indol-3-yl | Et | N₃ | H | F | OH | H | H |
| XIII-15-7 | Ph | H | H | CH₂CH₂SCH₃ | Et | N₃ | H | F | OH | H | H |
| XIII-15-8 | Ph | * | H | * | Et | N₃ | H | F | OH | H | H |

*$R^2$ and $R^{3b}$ joined together by $(CH_2)_3$ to form five-membered ring.

TABLE XIII-16

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-16-1 | p-Me—Ph | H | H | H | Et | N₃ | H | F | OH | H | H |
| XIII-16-2 | p-Me—Ph | H | H | CH₃ | Et | N₃ | H | F | OH | H | H |
| XIII-16-3 | p-Me—Ph | H | H | CH(CH₃)₂ | Et | N₃ | H | F | OH | H | H |
| XIII-16-4 | p-Me—Ph | H | H | CH₂CH(CH₃)₂ | Et | N₃ | H | F | OH | H | H |
| XIII-16-5 | p-Me—Ph | H | H | CH₂Ph | Et | N₃ | H | F | OH | H | H |
| XIII-16-6 | p-Me—Ph | H | H | CH₂-indol-3-yl | Et | N₃ | H | F | OH | H | H |
| XIII-16-7 | p-Me—Ph | H | H | CH₂CH₂SCH₃ | Et | N₃ | H | F | OH | H | H |
| XIII-16-8 | p-Me—Ph | * | H | * | Et | N₃ | H | F | OH | H | H |

*$R^2$ and $R^{3b}$ joined together by $(CH_2)_3$ to form five-membered ring.

TABLE XIII-17

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-17-1 | p-F—Ph | H | H | H | Et | N₃ | H | F | OH | H | H |
| XIII-17-2 | p-F—Ph | H | H | CH₃ | Et | N₃ | H | F | OH | H | H |
| XIII-17-3 | p-F—Ph | H | H | CH(CH₃)₂ | Et | N₃ | H | F | OH | H | H |
| XIII-17-4 | p-F—Ph | H | H | CH₂CH(CH₃)₂ | Et | N₃ | H | F | OH | H | H |
| XIII-17-5 | p-F—Ph | H | H | CH₂Ph | Et | N₃ | H | F | OH | H | H |
| XIII-17-6 | p-F—Ph | H | H | CH₂-indol-3-yl | Et | N₃ | H | F | OH | H | H |
| XIII-17-7 | p-F—Ph | H | H | CH₂CH₂SCH₃ | Et | N₃ | H | F | OH | H | H |
| XIII-17-8 | p-F—Ph | * | H | * | Et | N₃ | H | F | OH | H | H |

*$R^2$ and $R^{3b}$ joined together by $(CH_2)_3$ to form five-membered ring.

TABLE XIII-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-18-1 | p-Cl—Ph | H | H | H | Et | N₃ | H | F | OH | H | H |
| XIII-18-2 | p-Cl—Ph | H | H | CH₃ | Et | N₃ | H | F | OH | H | H |
| XIII-18-3 | p-Cl—Ph | H | H | CH(CH₃)₂ | Et | N₃ | H | F | OH | H | H |
| XIII-18-4 | p-Cl—Ph | H | H | CH₂CH(CH₃)₂ | Et | N₃ | H | F | OH | H | H |
| XIII-18-5 | p-Cl—Ph | H | H | CH₂Ph | Et | N₃ | H | F | OH | H | H |
| XIII-18-6 | p-Cl—Ph | H | H | CH₂-indol-3-yl | Et | N₃ | H | F | OH | H | H |
| XIII-18-7 | p-Cl—Ph | H | H | CH₂CH₂SCH₃ | Et | N₃ | H | F | OH | H | H |
| XIII-18-8 | p-Cl—Ph | * | H | * | Et | N₃ | H | F | OH | H | H |

*$R^2$ and $R^{3b}$ joined together by $(CH_2)_3$ to form five-membered ring.

TABLE XIII-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-19-1 | p-Br—Ph | H | H | H | Et | N₃ | H | F | OH | H | H |
| XIII-19-2 | p-Br—Ph | H | H | CH₃ | Et | N₃ | H | F | OH | H | H |
| XIII-19-3 | p-Br—Ph | H | H | CH(CH₃)₂ | Et | N₃ | H | F | OH | H | H |
| XIII-19-4 | p-Br—Ph | H | H | CH₂CH(CH₃)₂ | Et | N₃ | H | F | OH | H | H |
| XIII-19-5 | p-Br—Ph | H | H | CH₂Ph | Et | N₃ | H | F | OH | H | H |
| XIII-19-6 | p-Br—Ph | H | H | CH₂-indol-3-yl | Et | N₃ | H | F | OH | H | H |
| XIII-19-7 | p-Br—Ph | H | H | CH₂CH₂SCH₃ | Et | N₃ | H | F | OH | H | H |
| XIII-19-8 | p-Br—Ph | * | H | * | Et | N₃ | H | F | OH | H | H |

*$R^2$ and $R^{3b}$ joined together by $(CH_2)_3$ to form five-membered ring.

TABLE XIII-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-20-1 | p-I—Ph | H | H | H | Et | $N_3$ | H | F | OH | H | H |
| XIII-20-2 | p-I—Ph | H | H | $CH_3$ | Et | $N_3$ | H | F | OH | H | H |
| XIII-20-3 | p-I—Ph | H | H | $CH(CH_3)_2$ | Et | $N_3$ | H | F | OH | H | H |
| XIII-20-4 | p-I—Ph | H | H | $CH_2CH(CH_3)_2$ | Et | $N_3$ | H | F | OH | H | H |
| XIII-20-5 | p-I—Ph | H | H | $CH_2Ph$ | Et | $N_3$ | H | F | OH | H | H |
| XIII-20-6 | p-I—Ph | H | H | $CH_2$-indol-3-yl | Et | $N_3$ | H | F | OH | H | H |
| XIII-20-7 | p-I—Ph | H | H | $CH_2CH_2SCH_3$ | Et | $N_3$ | H | F | OH | H | H |
| XIII-20-8 | p-I—Ph | * | H | * | Et | $N_3$ | H | F | OH | H | H |

*R² and R³ᵇ joined together by $(CH_2)_3$ to form five-membered ring.

TABLE XIII-21

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-21-1 | $CH_3$ | H | H | H | $^iPr$ | $N_3$ | H | F | OH | H | H |
| XIII-21-2 | $CH_3$ | H | H | $CH_3$ | $^iPr$ | $N_3$ | H | F | OH | H | H |
| XIII-21-3 | $CH_3$ | H | H | $CH(CH_3)_2$ | $^iPr$ | $N_3$ | H | F | OH | H | H |
| XIII-21-4 | $CH_3$ | H | H | $CH_2CH(CH_3)_2$ | $^iPr$ | $N_3$ | H | F | OH | H | H |
| XIII-21-5 | $CH_3$ | H | H | $CH_2Ph$ | $^iPr$ | $N_3$ | H | F | OH | H | H |
| XIII-21-6 | $CH_3$ | H | H | $CH_2$-indol-3-yl | $^iPr$ | $N_3$ | H | F | OH | H | H |
| XIII-21-7 | $CH_3$ | H | H | $CH_2CH_2SCH_3$ | $^iPr$ | $N_3$ | H | F | OH | H | H |
| XIII-21-8 | $CH_3$ | * | H | * | $^iPr$ | $N_3$ | H | F | OH | H | H |

*R² and R³ᵇ joined together by $(CH_2)_3$ to form five-membered ring.

TABLE XIII-22

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-22-1 | Et | H | H | H | $^iPr$ | $N_3$ | H | F | OH | H | H |
| XIII-22-2 | Et | H | H | $CH_3$ | $^iPr$ | $N_3$ | H | F | OH | H | H |
| XIII-22-3 | Et | H | H | $CH(CH_3)_2$ | $^iPr$ | $N_3$ | H | F | OH | H | H |
| XIII-22-4 | Et | H | H | $CH_2CH(CH_3)_2$ | $^iPr$ | $N_3$ | H | F | OH | H | H |
| XIII-22-5 | Et | H | H | $CH_2Ph$ | $^iPr$ | $N_3$ | H | F | OH | H | H |
| XIII-22-6 | Et | H | H | $CH_2$-indol-3-yl | $^iPr$ | $N_3$ | H | F | OH | H | H |
| XIII-22-7 | Et | H | H | $CH_2CH_2SCH_3$ | $^iPr$ | $N_3$ | H | F | OH | H | H |
| XIII-22-8 | Et | * | H | * | $^iPr$ | $N_3$ | H | F | OH | H | H |

*R² and R³ᵇ joined together by $(CH_2)_3$ to form five-membered ring.

TABLE XIII-23

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-23-1 | $^iPr$ | H | H | H | $^iPr$ | $N_3$ | H | F | OH | H | H |
| XIII-23-2 | $^iPr$ | H | H | $CH_3$ | $^iPr$ | $N_3$ | H | F | OH | H | H |
| XIII-23-3 | $^iPr$ | H | H | $CH(CH_3)_2$ | $^iPr$ | $N_3$ | H | F | OH | H | H |
| XIII-23-4 | $^iPr$ | H | H | $CH_2CH(CH_3)_2$ | $^iPr$ | $N_3$ | H | F | OH | H | H |
| XIII-23-5 | $^iPr$ | H | H | $CH_2Ph$ | $^iPr$ | $N_3$ | H | F | OH | H | H |
| XIII-23-6 | $^iPr$ | H | H | $CH_2$-indol-3-yl | $^iPr$ | $N_3$ | H | F | OH | H | H |
| XIII-23-7 | $^iPr$ | H | H | $CH_2CH_2SCH_3$ | $^iPr$ | $N_3$ | H | F | OH | H | H |
| XIII-23-8 | $^iPr$ | * | H | * | $^iPr$ | $N_3$ | H | F | OH | H | H |

*R² and R³ᵇ joined together by $(CH_2)_3$ to form five-membered ring.

TABLE XIII-24

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-24-1 | $^tBu$ | H | H | H | $^iPr$ | $N_3$ | H | F | OH | H | H |
| XIII-24-2 | $^tBu$ | H | H | $CH_3$ | $^iPr$ | $N_3$ | H | F | OH | H | H |
| XIII-24-3 | $^tBu$ | H | H | $CH(CH_3)_2$ | $^iPr$ | $N_3$ | H | F | OH | H | H |
| XIII-24-4 | $^tBu$ | H | H | $CH_2CH(CH_3)_2$ | $^iPr$ | $N_3$ | H | F | OH | H | H |
| XIII-24-5 | $^tBu$ | H | H | $CH_2Ph$ | $^iPr$ | $N_3$ | H | F | OH | H | H |
| XIII-24-6 | $^tBu$ | H | H | $CH_2$-indol-3-yl | $^iPr$ | $N_3$ | H | F | OH | H | H |
| XIII-24-7 | $^tBu$ | H | H | $CH_2CH_2SCH_3$ | $^iPr$ | $N_3$ | H | F | OH | H | H |
| XIII-24-8 | $^tBu$ | * | H | * | iPr | $N_3$ | H | F | OH | H | H |

*R² and R³ᵇ joined together by $(CH_2)_3$ to form five-membered ring.

TABLE XIII-25

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-25-1 | Ph | H | H | H | $^iPr$ | $N_3$ | H | F | OH | H | H |
| XIII-25-2 | Ph | H | H | $CH_3$ | $^iPr$ | $N_3$ | H | F | OH | H | H |
| XIII-25-3 | Ph | H | H | $CH(CH_3)_2$ | $^iPr$ | $N_3$ | H | F | OH | H | H |
| XIII-25-4 | Ph | H | H | $CH_2CH(CH_3)_2$ | $^iPr$ | $N_3$ | H | F | OH | H | H |
| XIII-25-5 | Ph | H | H | $CH_2Ph$ | $^iPr$ | $N_3$ | H | F | OH | H | H |
| XIII-25-6 | Ph | H | H | $CH_2$-indol-3-yl | $^iPr$ | $N_3$ | H | F | OH | H | H |
| XIII-25-7 | Ph | H | H | $CH_2CH_2SCH_3$ | $^iPr$ | $N_3$ | H | F | OH | H | H |
| XIII-25-8 | Ph | * | H | * | $^iPr$ | $N_3$ | H | F | OH | H | H |

*R² and R³ᵇ joined together by $(CH_2)_3$ to form five-membered ring.

TABLE XIII-26

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIII-26-1 | p-Me—Ph | H | H | H | $^iPr$ | $N_3$ | H | F | OH | H | H |
| XIII-26-2 | p-Me—Ph | H | H | $CH_3$ | $^iPr$ | $N_3$ | H | F | OH | H | H |
| XIII-26-3 | p-Me—Ph | H | H | $CH(CH_3)_2$ | $^iPr$ | $N_3$ | H | F | OH | H | H |
| XIII-26-4 | p-Me—Ph | H | H | $CH_2CH(CH_3)_2$ | $^iPr$ | $N_3$ | H | F | OH | H | H |
| XIII-26-5 | p-Me—Ph | H | H | $CH_2Ph$ | $^iPr$ | $N_3$ | H | F | OH | H | H |
| XIII-26-6 | p-Me—Ph | H | H | $CH_2$-indol-3-yl | $^iPr$ | $N_3$ | H | F | OH | H | H |
| XIII-26-7 | p-Me—Ph | H | H | $CH_2CH_2SCH_3$ | $^iPr$ | $N_3$ | H | F | OH | H | H |
| XIII-26-8 | p-Me—Ph | * | H | * | $^iPr$ | $N_3$ | H | F | OH | H | H |

*R² and R³ᵇ joined together by $(CH_2)_3$ to form five-membered ring.

TABLE XIII-27

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-27-1 | p-F—Ph | H | H | H | $^i$Pr | $N_3$ | H | F | OH | H | H |
| XIII-27-2 | p-F—Ph | H | H | $CH_3$ | $^i$Pr | $N_3$ | H | F | OH | H | H |
| XIII-27-3 | p-F—Ph | H | H | $CH(CH_3)_2$ | $^i$Pr | $N_3$ | H | F | OH | H | H |
| XIII-27-4 | p-F—Ph | H | H | $CH_2CH(CH_3)_2$ | $^i$Pr | $N_3$ | H | F | OH | H | H |
| XIII-27-5 | p-F—Ph | H | H | $CH_2Ph$ | $^i$Pr | $N_3$ | H | F | OH | H | H |
| XIII-27-6 | p-F—Ph | H | H | $CH_2$-indol-3-yl | $^i$Pr | $N_3$ | H | F | OH | H | H |
| XIII-27-7 | p-F—Ph | H | H | $CH_2CH_2SCH_3$ | $^i$Pr | $N_3$ | H | F | OH | H | H |
| XIII-27-8 | p-F—Ph | * | H | * | $^i$Pr | $N_3$ | H | F | OH | H | H |

*$R^2$ and $R^{3b}$ joined together by $(CH_2)_3$ to form five-membered ring.

TABLE XIII-28

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-28-1 | p-Cl—Ph | H | H | H | $^i$Pr | $N_3$ | H | F | OH | H | H |
| XIII-28-2 | p-Cl—Ph | H | H | $CH_3$ | $^i$Pr | $N_3$ | H | F | OH | H | H |
| XIII-28-3 | p-Cl—Ph | H | H | $CH(CH_3)_2$ | $^i$Pr | $N_3$ | H | F | OH | H | H |
| XIII-28-4 | p-Cl—Ph | H | H | $CH_2CH(CH_3)_2$ | $^i$Pr | $N_3$ | H | F | OH | H | H |
| XIII-28-5 | p-Cl—Ph | H | H | $CH_2Ph$ | $^i$Pr | $N_3$ | H | F | OH | H | H |
| XIII-28-6 | p-Cl—Ph | H | H | $CH_2$-indol-3-yl | $^i$Pr | $N_3$ | H | F | OH | H | H |
| XIII-28-7 | p-Cl—Ph | H | H | $CH_2CH_2SCH_3$ | $^i$Pr | $N_3$ | H | F | OH | H | H |
| XIII-28-8 | p-Cl—Ph | * | H | * | $^i$Pr | $N_3$ | H | F | OH | H | H |

*$R^2$ and $R^{3b}$ joined together by $(CH_2)_3$ to form five-membered ring.

TABLE XIII-29

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-29-1 | p-Br—Ph | H | H | H | $^i$Pr | $N_3$ | H | F | OH | H | H |
| XIII-29-2 | p-Br—Ph | H | H | $CH_3$ | $^i$Pr | $N_3$ | H | F | OH | H | H |
| XIII-29-3 | p-Br—Ph | H | H | $CH(CH_3)_2$ | $^i$Pr | $N_3$ | H | F | OH | H | H |
| XIII-29-4 | p-Br—Ph | H | H | $CH_2CH(CH_3)_2$ | $^i$Pr | $N_3$ | H | F | OH | H | H |
| XIII-29-5 | p-Br—Ph | H | H | $CH_2Ph$ | $^i$Pr | $N_3$ | H | F | OH | H | H |
| XIII-29-6 | p-Br—Ph | H | H | $CH_2$-indol-3-yl | $^i$Pr | $N_3$ | H | F | OH | H | H |
| XIII-29-7 | p-Br—Ph | H | H | $CH_2CH_2SCH_3$ | $^i$Pr | $N_3$ | H | F | OH | H | H |
| XIII-29-8 | p-Br—Ph | * | H | * | $^i$Pr | $N_3$ | H | F | OH | H | H |

*$R^2$ and $R^{3b}$ joined together by $(CH_2)_3$ to form five-membered ring.

TABLE XIII-30

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-30-1 | p-I—Ph | H | H | H | $^i$Pr | $N_3$ | H | F | OH | H | H |
| XIII-30-2 | p-I—Ph | H | H | $CH_3$ | $^i$Pr | $N_3$ | H | F | OH | H | H |
| XIII-30-3 | p-I—Ph | H | H | $CH(CH_3)_2$ | $^i$Pr | $N_3$ | H | F | OH | H | H |
| XIII-30-4 | p-I—Ph | H | H | $CH_2CH(CH_3)_2$ | $^i$Pr | $N_3$ | H | F | OH | H | H |
| XIII-30-5 | p-I—Ph | H | H | $CH_2Ph$ | $^i$Pr | $N_3$ | H | F | OH | H | H |
| XIII-30-6 | p-I—Ph | H | H | $CH_2$-indol-3-yl | $^i$Pr | $N_3$ | H | F | OH | H | H |
| XIII-30-7 | p-I—Ph | H | H | $CH_2CH_2SCH_3$ | $^i$Pr | $N_3$ | H | F | OH | H | H |
| XIII-30-8 | p-I—Ph | * | H | * | $^i$Pr | $N_3$ | H | F | OH | H | H |

*$R^2$ and $R^{3b}$ joined together by $(CH_2)_3$ to form five-membered ring.

TABLE XIII-31

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-31-1 | $CH_3$ | H | H | H | $^n$Bu | $N_3$ | H | F | OH | H | H |
| XIII-31-2 | $CH_3$ | H | H | $CH_3$ | $^n$Bu | $N_3$ | H | F | OH | H | H |
| XIII-31-3 | $CH_3$ | H | H | $CH(CH_3)_2$ | $^n$Bu | $N_3$ | H | F | OH | H | H |
| XIII-31-4 | $CH_3$ | H | H | $CH_2CH(CH_3)_2$ | $^n$Bu | $N_3$ | H | F | OH | H | H |
| XIII-31-5 | $CH_3$ | H | H | $CH_2Ph$ | $^n$Bu | $N_3$ | H | F | OH | H | H |
| XIII-31-6 | $CH_3$ | H | H | $CH_2$-indol-3-yl | $^n$Bu | $N_3$ | H | F | OH | H | H |

TABLE XIII-31-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-31-7 | $CH_3$ | H | H | $CH_2CH_2SCH_3$ | $^nBu$ | $N_3$ | H | F | OH | H | H |
| XIII-31-8 | $CH_3$ | * | H | * | $^nBu$ | $N_3$ | H | F | OH | H | H |

*$R^2$ and $R^{3b}$ joined together by $(CH_2)_3$ to form five-membered ring.

TABLE XIII-32

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-32-1 | Et | H | H | H | $^nBu$ | $N_3$ | H | F | OH | H | H |
| XIII-32-2 | Et | H | H | $CH_3$ | $^nBu$ | $N_3$ | H | F | OH | H | H |
| XIII-32-3 | Et | H | H | $CH(CH_3)_2$ | $^nBu$ | $N_3$ | H | F | OH | H | H |
| XIII-32-4 | Et | H | H | $CH_2CH(CH_3)_2$ | $^nBu$ | $N_3$ | H | F | OH | H | H |
| XIII-32-5 | Et | H | H | $CH_2Ph$ | $^nBu$ | $N_3$ | H | F | OH | H | H |
| XIII-32-6 | Et | H | H | $CH_2$-indol-3-yl | $^nBu$ | $N_3$ | H | F | OH | H | H |
| XIII-32-7 | Et | H | H | $CH_2CH_2SCH_3$ | $^nBu$ | $N_3$ | H | F | OH | H | H |
| XIII-32-8 | Et | * | H | * | $^nBu$ | $N_3$ | H | F | OH | H | H |

*$R^2$ and $R^{3b}$ joined together by $(CH_2)_3$ to form five-membered ring.

TABLE XIII-33

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-33-1 | $^iPr$ | H | H | H | $^nBu$ | $N_3$ | H | F | OH | H | H |
| XIII-33-2 | $^iPr$ | H | H | $CH_3$ | $^nBu$ | $N_3$ | H | F | OH | H | H |
| XIII-33-3 | $^iPr$ | H | H | $CH(CH_3)_2$ | $^nBu$ | $N_3$ | H | F | OH | H | H |
| XIII-33-4 | $^iPr$ | H | H | $CH_2CH(CH_3)_2$ | $^nBu$ | $N_3$ | H | F | OH | H | H |
| XIII-33-5 | $^iPr$ | H | H | $CH_2Ph$ | $^nBu$ | $N_3$ | H | F | OH | H | H |
| XIII-33-6 | $^iPr$ | H | H | $CH_2$-indol-3-yl | $^nBu$ | $N_3$ | H | F | OH | H | H |
| XIII-33-7 | $^iPr$ | H | H | $CH_2CH_2SCH_3$ | $^nBu$ | $N_3$ | H | F | OH | H | H |
| XIII-33-8 | $^iPr$ | * | H | * | $^nBu$ | $N_3$ | H | F | OH | H | H |

*$R^2$ and $R^{3b}$ joined together by $(CH_2)_3$ to form five-membered ring.

TABLE XIII-34

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-34-1 | $^tBu$ | H | H | H | $^nBu$ | $N_3$ | H | F | OH | H | H |
| XIII-34-2 | $^tBu$ | H | H | $CH_3$ | $^nBu$ | $N_3$ | H | F | OH | H | H |
| XIII-34-3 | $^tBu$ | H | H | $CH(CH_3)_2$ | $^nBu$ | $N_3$ | H | F | OH | H | H |
| XIII-34-4 | $^tBu$ | H | H | $CH_2CH(CH_3)_2$ | $^nBu$ | $N_3$ | H | F | OH | H | H |
| XIII-34-5 | $^tBu$ | H | H | $CH_2Ph$ | $^nBu$ | $N_3$ | H | F | OH | H | H |
| XIII-34-6 | $^tBu$ | H | H | $CH_2$-indol-3-yl | $^nBu$ | $N_3$ | H | F | OH | H | H |
| XIII-34-7 | $^tBu$ | H | H | $CH_2CH_2SCH_3$ | $^nBu$ | $N_3$ | H | F | OH | H | H |
| XIII-34-8 | $^tBu$ | * | H | * | $^nBu$ | $N_3$ | H | F | OH | H | H |

*$R^2$ and $R^{3b}$ joined together by $(CH_2)_3$ to form five-membered ring.

TABLE XIII-35

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-35-1 | Ph | H | H | H | $^nBu$ | $N_3$ | H | F | OH | H | H |
| XIII-35-2 | Ph | H | H | $CH_3$ | $^nBu$ | $N_3$ | H | F | OH | H | H |
| XIII-35-3 | Ph | H | H | $CH(CH_3)_2$ | $^nBu$ | $N_3$ | H | F | OH | H | H |
| XIII-35-4 | Ph | H | H | $CH_2CH(CH_3)_2$ | $^nBu$ | $N_3$ | H | F | OH | H | H |
| XIII-35-5 | Ph | H | H | $CH_2Ph$ | $^nBu$ | $N_3$ | H | F | OH | H | H |
| XIII-35-6 | Ph | H | H | $CH_2$-indol-3-yl | $^nBu$ | $N_3$ | H | F | OH | H | H |
| XIII-35-7 | Ph | H | H | $CH_2CH_2SCH_3$ | $^nBu$ | $N_3$ | H | F | OH | H | H |
| XIII-35-8 | Ph | * | H | * | $^nBu$ | $N_3$ | H | F | OH | H | H |

*$R^2$ and $R^{3b}$ joined together by $(CH_2)_3$ to form five-membered ring.

TABLE XIII-36

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-36-1 | p-Me—Ph | H | H | H | $^nBu$ | $N_3$ | H | F | OH | H | H |
| XIII-36-2 | p-Me—Ph | H | H | $CH_3$ | $^nBu$ | $N_3$ | H | F | OH | H | H |
| XIII-36-3 | p-Me—Ph | H | H | $CH(CH_3)_2$ | $^nBu$ | $N_3$ | H | F | OH | H | H |
| XIII-36-4 | p-Me—Ph | H | H | $CH_2CH(CH_3)_2$ | $^nBu$ | $N_3$ | H | F | OH | H | H |
| XIII-36-5 | p-Me—Ph | H | H | $CH_2Ph$ | $^nBu$ | $N_3$ | H | F | OH | H | H |
| XIII-36-6 | p-Me—Ph | H | H | $CH_2$-indol-3-yl | $^nBu$ | $N_3$ | H | F | OH | H | H |
| XIII-36-7 | p-Me—Ph | H | H | $CH_2CH_2SCH_3$ | $^nBu$ | $N_3$ | H | F | OH | H | H |
| XIII-36-8 | p-Me—Ph | * | H | * | $^nBu$ | $N_3$ | H | F | OH | H | H |

*$R^2$ and $R^{3b}$ joined together by $(CH_2)_3$ to form five-membered ring.

TABLE XIII-37

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-37-1 | p-F—Ph | H | H | H | $^nBu$ | $N_3$ | H | F | OH | H | H |
| XIII-37-2 | p-F—Ph | H | H | $CH_3$ | $^nBu$ | $N_3$ | H | F | OH | H | H |
| XIII-37-3 | p-F—Ph | H | H | $CH(CH_3)_2$ | $^nBu$ | $N_3$ | H | F | OH | H | H |

TABLE XIII-37-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-37-4 | p-F—Ph | H | H | $CH_2CH(CH_3)_2$ | $^nBu$ | $N_3$ | H | F | OH | H | H |
| XIII-37-5 | p-F—Ph | H | H | $CH_2Ph$ | $^nBu$ | $N_3$ | H | F | OH | H | H |
| XIII-37-6 | p-F—Ph | H | H | $CH_2$-indol-3-yl | $^nBu$ | $N_3$ | H | F | OH | H | H |
| XIII-37-7 | p-F—Ph | H | H | $CH_2CH_2SCH_3$ | $^nBu$ | $N_3$ | H | F | OH | H | H |
| XIII-37-8 | p-F—Ph | * | H | * | $^nBu$ | $N_3$ | H | F | OH | H | H |

*$R^2$ and $R^{3b}$ joined together by $(CH_2)_3$ to form five-membered ring.

TABLE XIII-38

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-38-1 | p-Cl—Ph | H | H | H | $^nBu$ | $N_3$ | H | F | OH | H | H |
| XIII-38-2 | p-Cl—Ph | H | H | $CH_3$ | $^nBu$ | $N_3$ | H | F | OH | H | H |
| XIII-38-3 | p-Cl—Ph | H | H | $CH(CH_3)_2$ | $^nBu$ | $N_3$ | H | F | OH | H | H |
| XIII-38-4 | p-Cl—Ph | H | H | $CH_2CH(CH_3)_2$ | $^nBu$ | $N_3$ | H | F | OH | H | H |
| XIII-38-5 | p-Cl—Ph | H | H | $CH_2Ph$ | $^nBu$ | $N_3$ | H | F | OH | H | H |
| XIII-38-6 | p-Cl—Ph | H | H | $CH_2$-indol-3-yl | $^nBu$ | $N_3$ | H | F | OH | H | H |
| XIII-38-7 | p-Cl—Ph | H | H | $CH_2CH_2SCH_3$ | $^nBu$ | $N_3$ | H | F | OH | H | H |
| XIII-38-8 | p-Cl—Ph | * | H | * | $^nBu$ | $N_3$ | H | F | OH | H | H |

*$R^2$ and $R^{3b}$ joined together by $(CH_2)_3$ to form five-membered ring.

TABLE XIII-39

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-39-1 | p-Br—Ph | H | H | H | $^nBu$ | $N_3$ | H | F | OH | H | H |
| XIII-39-2 | p-Br—Ph | H | H | $CH_3$ | $^nBu$ | $N_3$ | H | F | OH | H | H |
| XIII-39-3 | p-Br—Ph | H | H | $CH(CH_3)_2$ | $^nBu$ | $N_3$ | H | F | OH | H | H |
| XIII-39-4 | p-Br—Ph | H | H | $CH_2CH(CH_3)_2$ | $^nBu$ | $N_3$ | H | F | OH | H | H |
| XIII-39-5 | p-Br—Ph | H | H | $CH_2Ph$ | $^nBu$ | $N_3$ | H | F | OH | H | H |
| XIII-39-6 | p-Br—Ph | H | H | $CH_2$-indol-3-yl | $^nBu$ | $N_3$ | H | F | OH | H | H |
| XIII-39-7 | p-Br—Ph | H | H | $CH_2CH_2SCH_3$ | $^nBu$ | $N_3$ | H | F | OH | H | H |
| XIII-39-8 | p-Br—Ph | * | H | * | $^nBu$ | $N_3$ | H | F | OH | H | H |

*$R^2$ and $R^{3b}$ joined together by $(CH_2)_3$ to form five-membered ring.

TABLE XIII-40

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-40-1 | p-I—Ph | H | H | H | $^nBu$ | $N_3$ | H | F | OH | H | H |
| XIII-40-2 | p-I—Ph | H | H | $CH_3$ | $^nBu$ | $N_3$ | H | F | OH | H | H |
| XIII-40-3 | p-I—Ph | H | H | $CH(CH_3)_2$ | $^nBu$ | $N_3$ | H | F | OH | H | H |
| XIII-40-4 | p-I—Ph | H | H | $CH_2CH(CH_3)_2$ | $^nBu$ | $N_3$ | H | F | OH | H | H |
| XIII-40-5 | p-I—Ph | H | H | $CH_2Ph$ | $^nBu$ | $N_3$ | H | F | OH | H | H |
| XIII-40-6 | p-I—Ph | H | H | $CH_2$-indol-3-yl | $^nBu$ | $N_3$ | H | F | OH | H | H |
| XIII-40-7 | p-I—Ph | H | H | $CH_2CH_2SCH_3$ | $^nBu$ | $N_3$ | H | F | OH | H | H |
| XIII-40-8 | p-I—Ph | * | H | * | $^nBu$ | $N_3$ | H | F | OH | H | H |

*$R^2$ and $R^{3b}$ joined together by $(CH_2)_3$ to form five-membered ring.

TABLE XIII-41

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-41-1 | $CH_3$ | H | H | H | Bz | $N_3$ | H | F | OH | H | H |
| XIII-41-2 | $CH_3$ | H | H | $CH_3$ | Bz | $N_3$ | H | F | OH | H | H |
| XIII-41-3 | $CH_3$ | H | H | $CH(CH_3)_2$ | Bz | $N_3$ | H | F | OH | H | H |
| XIII-41-4 | $CH_3$ | H | H | $CH_2CH(CH_3)_2$ | Bz | $N_3$ | H | F | OH | H | H |
| XIII-41-5 | $CH_3$ | H | H | $CH_2Ph$ | Bz | $N_3$ | H | F | OH | H | H |
| XIII-41-6 | $CH_3$ | H | H | $CH_2$-indol-3-yl | Bz | $N_3$ | H | F | OH | H | H |
| XIII-41-7 | $CH_3$ | H | H | $CH_2CH_2SCH_3$ | Bz | $N_3$ | H | F | OH | H | H |
| XIII-41-8 | $CH_3$ | * | H | * | Bz | $N_3$ | H | F | OH | H | H |

*$R^2$ and $R^{3b}$ joined together by $(CH_2)_3$ to form five-membered ring.

TABLE XIII-42

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-42-1 | Et | H | H | H | Bz | $N_3$ | H | F | OH | H | H |
| XIII-42-2 | Et | H | H | $CH_3$ | Bz | $N_3$ | H | F | OH | H | H |
| XIII-42-3 | Et | H | H | $CH(CH_3)_2$ | Bz | $N_3$ | H | F | OH | H | H |
| XIII-42-4 | Et | H | H | $CH_2CH(CH_3)_2$ | Bz | $N_3$ | H | F | OH | H | H |
| XIII-42-5 | Et | H | H | $CH_2Ph$ | Bz | $N_3$ | H | F | OH | H | H |
| XIII-42-6 | Et | H | H | $CH_2$-indol-3-yl | Bz | $N_3$ | H | F | OH | H | H |
| XIII-42-7 | Et | H | H | $CH_2CH_2SCH_3$ | Bz | $N_3$ | H | F | OH | H | H |
| XIII-42-8 | Et | * | H | * | Bz | $N_3$ | H | F | OH | H | H |

*$R^2$ and $R^{3b}$ joined together by $(CH_2)_3$ to form five-membered ring.

TABLE XIII-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-43-1 | $^iPr$ | H | H | H | Bz | $N_3$ | H | F | OH | H | H |
| XIII-43-2 | $^iPr$ | H | H | $CH_3$ | Bz | $N_3$ | H | F | OH | H | H |
| XIII-43-3 | $^iPr$ | H | H | $CH(CH_3)_2$ | Bz | $N_3$ | H | F | OH | H | H |
| XIII-43-4 | $^iPr$ | H | H | $CH_2CH(CH_3)_2$ | Bz | $N_3$ | H | F | OH | H | H |
| XIII-43-5 | $^iPr$ | H | H | $CH_2Ph$ | Bz | $N_3$ | H | F | OH | H | H |
| XIII-43-6 | $^iPr$ | H | H | $CH_2$-indol-3-yl | Bz | $N_3$ | H | F | OH | H | H |
| XIII-43-7 | $^iPr$ | H | H | $CH_2CH_2SCH_3$ | Bz | $N_3$ | H | F | OH | H | H |
| XIII-43-8 | $^iPr$ | * | H | * | Bz | $N_3$ | H | F | OH | H | H |

*$R^2$ and $R^{3b}$ joined together by $(CH_2)_3$ to form five-membered ring.

TABLE XIII-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-44-1 | $^tBu$ | H | H | H | Bz | $N_3$ | H | F | OH | H | H |
| XIII-44-2 | $^tBu$ | H | H | $CH_3$ | Bz | $N_3$ | H | F | OH | H | H |
| XIII-44-3 | $^tBu$ | H | H | $CH(CH_3)_2$ | Bz | $N_3$ | H | F | OH | H | H |
| XIII-44-4 | $^tBu$ | H | H | $CH_2CH(CH_3)_2$ | Bz | $N_3$ | H | F | OH | H | H |
| XIII-44-5 | $^tBu$ | H | H | $CH_2Ph$ | Bz | $N_3$ | H | F | OH | H | H |
| XIII-44-6 | $^tBu$ | H | H | $CH_2$-indol-3-yl | Bz | $N_3$ | H | F | OH | H | H |
| XIII-44-7 | $^tBu$ | H | H | $CH_2CH_2SCH_3$ | Bz | $N_3$ | H | F | OH | H | H |
| XIII-44-8 | $^tBu$ | * | H | * | Bz | $N_3$ | H | F | OH | H | H |

*$R^2$ and $R^{3b}$ joined together by $(CH_2)_3$ to form five-membered ring.

TABLE XIII-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-45-1 | Ph | H | H | H | Bz | $N_3$ | H | F | OH | H | H |
| XIII-45-2 | Ph | H | H | $CH_3$ | Bz | $N_3$ | H | F | OH | H | H |
| XIII-45-3 | Ph | H | H | $CH(CH_3)_2$ | Bz | $N_3$ | H | F | OH | H | H |
| XIII-45-4 | Ph | H | H | $CH_2CH(CH_3)_2$ | Bz | $N_3$ | H | F | OH | H | H |
| XIII-45-5 | Ph | H | H | $CH_2Ph$ | Bz | $N_3$ | H | F | OH | H | H |
| XIII-45-6 | Ph | H | H | $CH_2$-indol-3-yl | Bz | $N_3$ | H | F | OH | H | H |
| XIII-45-7 | Ph | H | H | $CH_2CH_2SCH_3$ | Bz | $N_3$ | H | F | OH | H | H |
| XIII-45-8 | Ph | * | H | * | Bz | $N_3$ | H | F | OH | H | H |

*$R^2$ and $R^{3b}$ joined together by $(CH_2)_3$ to form five-membered ring.

TABLE XIII-46

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-46-1 | p-Me—Ph | H | H | H | Bz | $N_3$ | H | F | OH | H | H |
| XIII-46-2 | p-Me—Ph | H | H | $CH_3$ | Bz | $N_3$ | H | F | OH | H | H |
| XIII-46-3 | p-Me—Ph | H | H | $CH(CH_3)_2$ | Bz | $N_3$ | H | F | OH | H | H |
| XIII-46-4 | p-Me—Ph | H | H | $CH_2CH(CH_3)_2$ | Bz | $N_3$ | H | F | OH | H | H |
| XIII-46-5 | p-Me—Ph | H | H | $CH_2Ph$ | Bz | $N_3$ | H | F | OH | H | H |
| XIII-46-6 | p-Me—Ph | H | H | $CH_2$-indol-3-yl | Bz | $N_3$ | H | F | OH | H | H |
| XIII-46-7 | p-Me—Ph | H | H | $CH_2CH_2SCH_3$ | Bz | $N_3$ | H | F | OH | H | H |
| XIII-46-8 | p-Me—Ph | * | H | * | Bz | $N_3$ | H | F | OH | H | H |

*$R^2$ and $R^{3b}$ joined together by $(CH_2)_3$ to form five-membered ring.

TABLE XIII-47

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-47-1 | p-F—Ph | H | H | H | Bz | $N_3$ | H | F | OH | H | H |
| XIII-47-2 | p-F—Ph | H | H | $CH_3$ | Bz | $N_3$ | H | F | OH | H | H |
| XIII-47-3 | p-F—Ph | H | H | $CH(CH_3)_2$ | Bz | $N_3$ | H | F | OH | H | H |
| XIII-47-4 | p-F—Ph | H | H | $CH_2CH(CH_3)_2$ | Bz | $N_3$ | H | F | OH | H | H |
| XIII-47-5 | p-F—Ph | H | H | $CH_2Ph$ | Bz | $N_3$ | H | F | OH | H | H |
| XIII-47-6 | p-F—Ph | H | H | $CH_2$-indol-3-yl | Bz | $N_3$ | H | F | OH | H | H |
| XIII-47-7 | p-F—Ph | H | H | $CH_2CH_2SCH_3$ | Bz | $N_3$ | H | F | OH | H | H |
| XIII-47-8 | p-F—Ph | * | H | * | Bz | $N_3$ | H | F | OH | H | H |

*$R^2$ and $R^{3b}$ joined together by $(CH_2)_3$ to form five-membered ring.

TABLE XIII-48

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-48-1 | p-Cl—Ph | H | H | H | Bz | $N_3$ | H | F | OH | H | H |
| XIII-48-2 | p-Cl—Ph | H | H | $CH_3$ | Bz | $N_3$ | H | F | OH | H | H |
| XIII-48-3 | p-Cl—Ph | H | H | $CH(CH_3)_2$ | Bz | $N_3$ | H | F | OH | H | H |
| XIII-48-4 | p-Cl—Ph | H | H | $CH_2CH(CH_3)_2$ | Bz | $N_3$ | H | F | OH | H | H |
| XIII-48-5 | p-Cl—Ph | H | H | $CH_2Ph$ | Bz | $N_3$ | H | F | OH | H | H |
| XIII-48-6 | p-Cl—Ph | H | H | $CH_2$-indol-3-yl | Bz | $N_3$ | H | F | OH | H | H |
| XIII-48-7 | p-Cl—Ph | H | H | $CH_2CH_2SCH_3$ | Bz | $N_3$ | H | F | OH | H | H |
| XIII-48-8 | p-Cl—Ph | * | H | * | Bz | $N_3$ | H | F | OH | H | H |

*$R^2$ and $R^{3b}$ joined together by $(CH_2)_3$ to form five-membered ring.

TABLE XIII-49

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-49-1 | p-Br—Ph | H | H | H | Bz | $N_3$ | H | F | OH | H | H |
| XIII-49-2 | p-Br—Ph | H | H | $CH_3$ | Bz | $N_3$ | H | F | OH | H | H |
| XIII-49-3 | p-Br—Ph | H | H | $CH(CH_3)_2$ | Bz | $N_3$ | H | F | OH | H | H |
| XIII-49-4 | p-Br—Ph | H | H | $CH_2CH(CH_3)_2$ | Bz | $N_3$ | H | F | OH | H | H |
| XIII-49-5 | p-Br—Ph | H | H | $CH_2Ph$ | Bz | $N_3$ | H | F | OH | H | H |
| XIII-49-6 | p-Br—Ph | H | H | $CH_2$-indol-3-yl | Bz | $N_3$ | H | F | OH | H | H |
| XIII-49-7 | p-Br—Ph | H | H | $CH_2CH_2SCH_3$ | Bz | $N_3$ | H | F | OH | H | H |
| XIII-49-8 | p-Br—Ph | * | H | * | Bz | $N_3$ | H | F | OH | H | H |

*$R^2$ and $R^{3b}$ joined together by $(CH_2)_3$ to form five-membered ring.

TABLE XIII-50

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIII-50-1 | p-I—Ph | H | H | H | Bz | $N_3$ | H | F | OH | H | H |
| XIII-50-2 | p-I—Ph | H | H | $CH_3$ | Bz | $N_3$ | H | F | OH | H | H |
| XIII-50-3 | p-I—Ph | H | H | $CH(CH_3)_2$ | Bz | $N_3$ | H | F | OH | H | H |
| XIII-50-4 | p-I—Ph | H | H | $CH_2CH(CH_3)_2$ | Bz | $N_3$ | H | F | OH | H | H |
| XIII-50-5 | p-I—Ph | H | H | $CH_2Ph$ | Bz | $N_3$ | H | F | OH | H | H |
| XIII-50-6 | p-I—Ph | H | H | $CH_2$-indol-3-yl | Bz | $N_3$ | H | F | OH | H | H |
| XIII-50-7 | p-I—Ph | H | H | $CH_2CH_2SCH_3$ | Bz | $N_3$ | H | F | OH | H | H |
| XIII-50-8 | p-I—Ph | * | H | * | Bz | $N_3$ | H | F | OH | H | H |

*$R^2$ and $R^{3b}$ joined together by $(CH_2)_3$ to form five-membered ring.

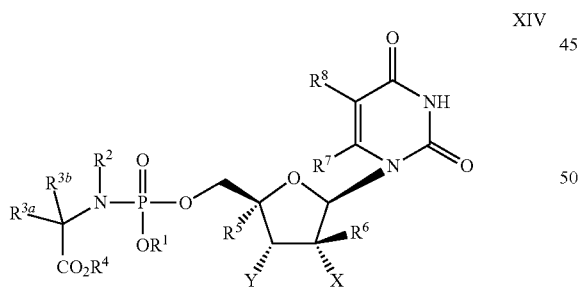

XIV

TABLE XIV-1

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-1-1 | $CH_3$ | H | H | H | $CH_3$ | $N_3$ | F | H | OH | H | H |
| XIV-1-2 | $CH_3$ | H | H | $CH_3$ | $CH_3$ | $N_3$ | F | H | OH | H | H |
| XIV-1-3 | $CH_3$ | H | H | $CH(CH_3)_2$ | $CH_3$ | $N_3$ | F | H | OH | H | H |
| XIV-1-4 | $CH_3$ | H | H | $CH_2CH(CH_3)_2$ | $CH_3$ | $N_3$ | F | H | OH | H | H |
| XIV-1-5 | $CH_3$ | H | H | $CH_2Ph$ | $CH_3$ | $N_3$ | F | H | OH | H | H |
| XIV-1-6 | $CH_3$ | H | H | $CH_2$-indol-3-yl | $CH_3$ | $N_3$ | F | H | OH | H | H |

TABLE XIV-1-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-1-7 | $CH_3$ | H | H | $CH_2CH_2SCH_3$ | $CH_3$ | $N_3$ | F | H | OH | H | H |
| XIV-1-8 | $CH_3$ | * | H | * | $CH_3$ | $N_3$ | F | H | OH | H | H |

*$R^2$ and $R^{3b}$ joined together by $(CH_2)_3$ to form five-membered ring.

TABLE XIV-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-2-1 | Et | H | H | H | $CH_3$ | $N_3$ | F | H | OH | H | H |
| XIV-2-2 | Et | H | H | $CH_3$ | $CH_3$ | $N_3$ | F | H | OH | H | H |
| XIV-2-3 | Et | H | H | $CH(CH_3)_2$ | $CH_3$ | $N_3$ | F | H | OH | H | H |
| XIV-2-4 | Et | H | H | $CH_2CH(CH_3)_2$ | $CH_3$ | $N_3$ | F | H | OH | H | H |
| XIV-2-5 | Et | H | H | $CH_2Ph$ | $CH_3$ | $N_3$ | F | H | OH | H | H |
| XIV-2-6 | Et | H | H | $CH_2$-indol-3-yl | $CH_3$ | $N_3$ | F | H | OH | H | H |
| XIV-2-7 | Et | H | H | $CH_2CH_2SCH_3$ | $CH_3$ | $N_3$ | F | H | OH | H | H |
| XIV-2-8 | Et | * | H | * | $CH_3$ | $N_3$ | F | H | OH | H | H |

*$R^2$ and $R^{3b}$ joined together by $(CH_2)_3$ to form five-membered ring.

TABLE XIV-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-3-1 | $^i$Pr | H | H | H | $CH_3$ | $N_3$ | F | H | OH | H | H |
| XIV-3-2 | $^i$Pr | H | H | $CH_3$ | $CH_3$ | $N_3$ | F | H | OH | H | H |
| XIV-3-3 | $^i$Pr | H | H | $CH(CH_3)_2$ | $CH_3$ | $N_3$ | F | H | OH | H | H |
| XIV-3-4 | $^i$Pr | H | H | $CH_2CH(CH_3)_2$ | $CH_3$ | $N_3$ | F | H | OH | H | H |
| XIV-3-5 | $^i$Pr | H | H | $CH_2Ph$ | $CH_3$ | $N_3$ | F | H | OH | H | H |
| XIV-3-6 | $^i$Pr | H | H | $CH_2$-indol-3-yl | $CH_3$ | $N_3$ | F | H | OH | H | H |
| XIV-3-7 | $^i$Pr | H | H | $CH_2CH_2SCH_3$ | $CH_3$ | $N_3$ | F | H | OH | H | H |
| XIV-3-8 | $^i$Pr | * | H | * | $CH_3$ | $N_3$ | F | H | OH | H | H |

*$R^2$ and $R^{3b}$ joined together by $(CH_2)_3$ to form five-membered ring.

TABLE XIV-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-4-1 | $^t$Bu | H | H | H | $CH_3$ | $N_3$ | F | H | OH | H | H |
| XIV-4-2 | $^t$Bu | H | H | $CH_3$ | $CH_3$ | $N_3$ | F | H | OH | H | H |
| XIV-4-3 | $^t$Bu | H | H | $CH(CH_3)_2$ | $CH_3$ | $N_3$ | F | H | OH | H | H |
| XIV-4-4 | $^t$Bu | H | H | $CH_2CH(CH_3)_2$ | $CH_3$ | $N_3$ | F | H | OH | H | H |
| XIV-4-5 | $^t$Bu | H | H | $CH_2Ph$ | $CH_3$ | $N_3$ | F | H | OH | H | H |
| XIV-4-6 | $^t$Bu | H | H | $CH_2$-indol-3-yl | $CH_3$ | $N_3$ | F | H | OH | H | H |
| XIV-4-7 | $^t$Bu | H | H | $CH_2CH_2SCH_3$ | $CH_3$ | $N_3$ | F | H | OH | H | H |
| XIV-4-8 | $^t$Bu | * | H | * | $CH_3$ | $N_3$ | F | H | OH | H | H |

*$R^2$ and $R^{3b}$ joined together by $(CH_2)_3$ to form five-membered ring.

TABLE XIV-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-5-1 | Ph | H | H | H | $CH_3$ | $N_3$ | F | H | OH | H | H |
| XIV-5-2 | Ph | H | H | $CH_3$ | $CH_3$ | $N_3$ | F | H | OH | H | H |
| XIV-5-3 | Ph | H | H | $CH(CH_3)_2$ | $CH_3$ | $N_3$ | F | H | OH | H | H |
| XIV-5-4 | Ph | H | H | $CH_2CH(CH_3)_2$ | $CH_3$ | $N_3$ | F | H | OH | H | H |
| XIV-5-5 | Ph | H | H | $CH_2Ph$ | $CH_3$ | $N_3$ | F | H | OH | H | H |
| XIV-5-6 | Ph | H | H | $CH_2$-indol-3-yl | $CH_3$ | $N_3$ | F | H | OH | H | H |
| XIV-5-7 | Ph | H | H | $CH_2CH_2SCH_3$ | $CH_3$ | $N_3$ | F | H | OH | H | H |
| XIV-5-8 | Ph | * | H | * | $CH_3$ | $N_3$ | F | H | OH | H | H |

*$R^2$ and $R^{3b}$ joined together by $(CH_2)_3$ to form five-membered ring.

TABLE XIV-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-6-1 | p-Me—Ph | H | H | H | $CH_3$ | $N_3$ | F | H | OH | H | H |
| XIV-6-2 | p-Me—Ph | H | H | $CH_3$ | $CH_3$ | $N_3$ | F | H | OH | H | H |
| XIV-6-3 | p-Me—Ph | H | H | $CH(CH_3)_2$ | $CH_3$ | $N_3$ | F | H | OH | H | H |
| XIV-6-4 | p-Me—Ph | H | H | $CH_2CH(CH_3)_2$ | $CH_3$ | $N_3$ | F | H | OH | H | H |
| XIV-6-5 | p-Me—Ph | H | H | $CH_2Ph$ | $CH_3$ | $N_3$ | F | H | OH | H | H |
| XIV-6-6 | p-Me—Ph | H | H | $CH_2$-indol-3-yl | $CH_3$ | $N_3$ | F | H | OH | H | H |
| XIV-6-7 | p-Me—Ph | H | H | $CH_2CH_2SCH_3$ | $CH_3$ | $N_3$ | F | H | OH | H | H |
| XIV-6-8 | p-Me—Ph | * | H | * | $CH_3$ | $N_3$ | F | H | OH | H | H |

*$R^2$ and $R^{3b}$ joined together by $(CH_2)_3$ to form five-membered ring.

TABLE XIV-7

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-7-1 | p-F—Ph | H | H | H | $CH_3$ | $N_3$ | F | H | OH | H | H |
| XIV-7-2 | p-F—Ph | H | H | $CH_3$ | $CH_3$ | $N_3$ | F | H | OH | H | H |
| XIV-7-3 | p-F—Ph | H | H | $CH(CH_3)_2$ | $CH_3$ | $N_3$ | F | H | OH | H | H |

TABLE XIV-7-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-7-4 | p-F—Ph | H | H | $CH_2CH(CH_3)_2$ | $CH_3$ | $N_3$ | F | H | OH | H | H |
| XIV-7-6 | p-F—Ph | H | H | $CH_2Ph$ | $CH_3$ | $N_3$ | F | H | OH | H | H |
| XIV-7-7 | p-F—Ph | H | H | $CH_2$-indol-3-yl | $CH_3$ | $N_3$ | F | H | OH | H | H |
| XIV-7-8 | p-F—Ph | H | H | $CH_2CH_2SCH_3$ | $CH_3$ | $N_3$ | F | H | OH | H | H |
| XIV-7-20 | p-F—Ph | * | H | * | $CH_3$ | $N_3$ | F | H | OH | H | H |

*$R^2$ and $R^{3b}$ joined together by $(CH_2)_3$ to form five-membered ring.

TABLE XIV-8

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-8-1 | p-Cl—Ph | H | H | H | $CH_3$ | $N_3$ | F | H | OH | H | H |
| XIV-8-2 | p-Cl—Ph | H | H | $CH_3$ | $CH_3$ | $N_3$ | F | H | OH | H | H |
| XIV-8-3 | p-Cl—Ph | H | H | $CH(CH_3)_2$ | $CH_3$ | $N_3$ | F | H | OH | H | H |
| XIV-8-4 | p-Cl—Ph | H | H | $CH_2CH(CH_3)_2$ | $CH_3$ | $N_3$ | F | H | OH | H | H |
| XIV-8-5 | p-Cl—Ph | H | H | $CH_2Ph$ | $CH_3$ | $N_3$ | F | H | OH | H | H |
| XIV-8-6 | p-Cl—Ph | H | H | $CH_2$-indol-3-yl | $CH_3$ | $N_3$ | F | H | OH | H | H |
| XIV-8-7 | p-Cl—Ph | H | H | $CH_2CH_2SCH_3$ | $CH_3$ | $N_3$ | F | H | OH | H | H |
| XIV-8-8 | p-Cl—Ph | * | H | * | $CH_3$ | $N_3$ | F | H | OH | H | H |

*$R^2$ and $R^{3b}$ joined together by $(CH_2)_3$ to form five-membered ring.

TABLE XIV-9

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-9-1 | p-Br—Ph | H | H | H | $CH_3$ | $N_3$ | F | H | OH | H | H |
| XIV-9-2 | p-Br—Ph | H | H | $CH_3$ | $CH_3$ | $N_3$ | F | H | OH | H | H |
| XIV-9-3 | p-Br—Ph | H | H | $CH(CH_3)_2$ | $CH_3$ | $N_3$ | F | H | OH | H | H |
| XIV-9-4 | p-Br—Ph | H | H | $CH_2CH(CH_3)_2$ | $CH_3$ | $N_3$ | F | H | OH | H | H |
| XIV-9-6 | p-Br—Ph | H | H | $CH_2Ph$ | $CH_3$ | $N_3$ | F | H | OH | H | H |
| XIV-9-7 | p-Br—Ph | H | H | $CH_2$-indol-3-yl | $CH_3$ | $N_3$ | F | H | OH | H | H |
| XIV-9-8 | p-Br—Ph | H | H | $CH_2CH_2SCH_3$ | $CH_3$ | $N_3$ | F | H | OH | H | H |
| XIV-9-20 | p-Br—Ph | * | H | * | $CH_3$ | $N_3$ | F | H | OH | H | H |

*$R^2$ and $R^{3b}$ joined together by $(CH_2)_3$ to form five-membered ring.

TABLE XIV-10

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-10-1 | p-I—Ph | H | H | H | $CH_3$ | $N_3$ | F | H | OH | H | H |
| XIV-10-2 | p-I—Ph | H | H | $CH_3$ | $CH_3$ | $N_3$ | F | H | OH | H | H |
| XIV-10-3 | p-I—Ph | H | H | $CH(CH_3)_2$ | $CH_3$ | $N_3$ | F | H | OH | H | H |
| XIV-10-4 | p-I—Ph | H | H | $CH_2CH(CH_3)_2$ | $CH_3$ | $N_3$ | F | H | OH | H | H |
| XIV-10-5 | p-I—Ph | H | H | $CH_2Ph$ | $CH_3$ | $N_3$ | F | H | OH | H | H |
| XIV-10-6 | p-I—Ph | H | H | $CH_2$-indol-3-yl | $CH_3$ | $N_3$ | F | H | OH | H | H |
| XIV-10-7 | p-I—Ph | H | H | $CH_2CH_2SCH_3$ | $CH_3$ | $N_3$ | F | H | OH | H | H |
| XIV-10-8 | p-I—Ph | * | H | * | $CH_3$ | $N_3$ | F | H | OH | H | H |

*$R^2$ and $R^{3b}$ joined together by $(CH_2)_3$ to form five-membered ring.

TABLE XIV-11

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-11-1 | $CH_3$ | H | H | H | Et | $N_3$ | F | H | OH | H | H |
| XIV-11-2 | $CH_3$ | H | H | $CH_3$ | Et | $N_3$ | F | H | OH | H | H |
| XIV-11-3 | $CH_3$ | H | H | $CH(CH_3)_2$ | Et | $N_3$ | F | H | OH | H | H |
| XIV-11-4 | $CH_3$ | H | H | $CH_2CH(CH_3)_2$ | Et | $N_3$ | F | H | OH | H | H |
| XIV-11-5 | $CH_3$ | H | H | $CH_2Ph$ | Et | $N_3$ | F | H | OH | H | H |
| XIV-11-6 | $CH_3$ | H | H | $CH_2$-indol-3-yl | Et | $N_3$ | F | H | OH | H | H |
| XIV-11-7 | $CH_3$ | H | H | $CH_2CH_2SCH_3$ | Et | $N_3$ | F | H | OH | H | H |
| XIV-11-8 | $CH_3$ | * | H | * | Et | $N_3$ | F | H | OH | H | H |

*$R^2$ and $R^{3b}$ joined together by $(CH_2)_3$ to form five-membered ring.

TABLE XIV-12

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIV-12-1 | Et | H | H | H | Et | N$_3$ | F | H | OH | H | H |
| XIV-12-2 | Et | H | H | CH$_3$ | Et | N$_3$ | F | H | OH | H | H |
| XIV-12-3 | Et | H | H | CH(CH$_3$)$_2$ | Et | N$_3$ | F | H | OH | H | H |
| XIV-12-4 | Et | H | H | CH$_2$CH(CH$_3$)$_2$ | Et | N$_3$ | F | H | OH | H | H |
| XIV-12-5 | Et | H | H | CH$_2$Ph | Et | N$_3$ | F | H | OH | H | H |
| XIV-12-6 | Et | H | H | CH$_2$-indol-3-yl | Et | N$_3$ | F | H | OH | H | H |
| XIV-12-7 | Et | H | H | CH$_2$CH$_2$SCH$_3$ | Et | N$_3$ | F | H | OH | H | H |
| XIV-12-8 | Et | * | H | * | Et | N$_3$ | F | H | OH | H | H |

*R$^2$ and R$^{3b}$ joined together by (CH$_2$)$_3$ to form five-membered ring.

TABLE XIV-13

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIV-13-1 | $^i$Pr | H | H | H | Et | N$_3$ | F | H | OH | H | H |
| XIV-13-2 | $^i$Pr | H | H | CH$_3$ | Et | N$_3$ | F | H | OH | H | H |
| XIV-13-3 | $^i$Pr | H | H | CH(CH$_3$)$_2$ | Et | N$_3$ | F | H | OH | H | H |
| XIV-13-4 | $^i$Pr | H | H | CH$_2$CH(CH$_3$)$_2$ | Et | N$_3$ | F | H | OH | H | H |
| XIV-13-5 | $^i$Pr | H | H | CH$_2$Ph | Et | N$_3$ | F | H | OH | H | H |
| XIV-13-6 | $^i$Pr | H | H | CH$_2$-indol-3-yl | Et | N$_3$ | F | H | OH | H | H |
| XIV-13-7 | $^i$Pr | H | H | CH$_2$CH$_2$SCH$_3$ | Et | N$_3$ | F | H | OH | H | H |
| XIV-13-8 | $^i$Pr | * | H | * | Et | N$_3$ | F | H | OH | H | H |

*R$^2$ and R$^{3b}$ joined together by (CH$_2$)$_3$ to form five-membered ring.

TABLE XIV-14

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIV-14-1 | $^t$Bu | H | H | H | Et | N$_3$ | F | H | OH | H | H |
| XIV-14-2 | $^t$Bu | H | H | CH$_3$ | Et | N$_3$ | F | H | OH | H | H |
| XIV-14-3 | $^t$Bu | H | H | CH(CH$_3$)$_2$ | Et | N$_3$ | F | H | OH | H | H |
| XIV-14-4 | $^t$Bu | H | H | CH$_2$CH(CH$_3$)$_2$ | Et | N$_3$ | F | H | OH | H | H |
| XIV-14-5 | $^t$Bu | H | H | CH$_2$Ph | Et | N$_3$ | F | H | OH | H | H |
| XIV-14-6 | $^t$Bu | H | H | CH$_2$-indol-3-yl | Et | N$_3$ | F | H | OH | H | H |
| XIV-14-7 | $^t$Bu | H | H | CH$_2$CH$_2$SCH$_3$ | Et | N$_3$ | F | H | OH | H | H |
| XIV-14-8 | $^t$Bu | * | H | * | Et | N$_3$ | F | H | OH | H | H |

*R$^2$ and R$^{3b}$ joined together by (CH$_2$)$_3$ to form five-membered ring.

TABLE XIV-15

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIV-15-1 | Ph | H | H | H | Et | N$_3$ | F | H | OH | H | H |
| XIV-15-2 | Ph | H | H | CH$_3$ | Et | N$_3$ | F | H | OH | H | H |
| XIV-15-3 | Ph | H | H | CH(CH$_3$)$_2$ | Et | N$_3$ | F | H | OH | H | H |
| XIV-15-4 | Ph | H | H | CH$_2$CH(CH$_3$)$_2$ | Et | N$_3$ | F | H | OH | H | H |
| XIV-15-5 | Ph | H | H | CH$_2$Ph | Et | N$_3$ | F | H | OH | H | H |
| XIV-15-6 | Ph | H | H | CH$_2$-indol-3-yl | Et | N$_3$ | F | H | OH | H | H |
| XIV-15-7 | Ph | H | H | CH$_2$CH$_2$SCH$_3$ | Et | N$_3$ | F | H | OH | H | H |
| XIV-15-8 | Ph | * | H | * | Et | N$_3$ | F | H | OH | H | H |

*R$^2$ and R$^{3b}$ joined together by (CH$_2$)$_3$ to form five-membered ring.

TABLE XIV-16

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIV-16-1 | p-Me—Ph | H | H | H | Et | N$_3$ | F | H | OH | H | H |
| XIV-16-2 | p-Me—Ph | H | H | CH$_3$ | Et | N$_3$ | F | H | OH | H | H |
| XIV-16-3 | p-Me—Ph | H | H | CH(CH$_3$)$_2$ | Et | N$_3$ | F | H | OH | H | H |
| XIV-16-4 | p-Me—Ph | H | H | CH$_2$CH(CH$_3$)$_2$ | Et | N$_3$ | F | H | OH | H | H |
| XIV-16-5 | p-Me—Ph | H | H | CH$_2$Ph | Et | N$_3$ | F | H | OH | H | H |
| XIV-16-6 | p-Me—Ph | H | H | CH$_2$-indol-3-yl | Et | N$_3$ | F | H | OH | H | H |
| XIV-16-7 | p-Me—Ph | H | H | CH$_2$CH$_2$SCH$_3$ | Et | N$_3$ | F | H | OH | H | H |
| XIV-16-8 | p-Me—Ph | * | H | * | Et | N$_3$ | F | H | OH | H | H |

*R$^2$ and R$^{3b}$ joined together by (CH$_2$)$_3$ to form five-membered ring.

TABLE XIV-17

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIV-17-1 | p-F—Ph | H | H | H | Et | N$_3$ | F | H | OH | H | H |
| XIV-17-2 | p-F—Ph | H | H | CH$_3$ | Et | N$_3$ | F | H | OH | H | H |
| XIV-17-3 | p-F—Ph | H | H | CH(CH$_3$)$_2$ | Et | N$_3$ | F | H | OH | H | H |
| XIV-17-4 | p-F—Ph | H | H | CH$_2$CH(CH$_3$)$_2$ | Et | N$_3$ | F | H | OH | H | H |
| XIV-17-5 | p-F—Ph | H | H | CH$_2$Ph | Et | N$_3$ | F | H | OH | H | H |
| XIV-17-6 | p-F—Ph | H | H | CH$_2$-indol-3-yl | Et | N$_3$ | F | H | OH | H | H |
| XIV-17-7 | p-F—Ph | H | H | CH$_2$CH$_2$SCH$_3$ | Et | N$_3$ | F | H | OH | H | H |
| XIV-17-8 | p-F—Ph | * | H | * | Et | N$_3$ | F | H | OH | H | H |

*R$^2$ and R$^{3b}$ joined together by (CH$_2$)$_3$ to form five-membered ring.

TABLE XIV-18

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-18-1 | p-Cl—Ph | H | H | H | Et | $N_3$ | F | H | OH | H | H |
| XIV-18-2 | p-Cl—Ph | H | H | $CH_3$ | Et | $N_3$ | F | H | OH | H | H |
| XIV-18-3 | p-Cl—Ph | H | H | $CH(CH_3)_2$ | Et | $N_3$ | F | H | OH | H | H |
| XIV-18-4 | p-Cl—Ph | H | H | $CH_2CH(CH_3)_2$ | Et | $N_3$ | F | H | OH | H | H |
| XIV-18-5 | p-Cl—Ph | H | H | $CH_2Ph$ | Et | $N_3$ | F | H | OH | H | H |
| XIV-18-6 | p-Cl—Ph | H | H | $CH_2$-indol-3-yl | Et | $N_3$ | F | H | OH | H | H |
| XIV-18-7 | p-Cl—Ph | H | H | $CH_2CH_2SCH_3$ | Et | $N_3$ | F | H | OH | H | H |
| XIV-18-8 | p-Cl—Ph | * | H | * | Et | $N_3$ | F | H | OH | H | H |

*$R^2$ and $R^{3b}$ joined together by $(CH_2)_3$ to form five-membered ring.

TABLE XIV-19

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-19-1 | p-Br—Ph | H | H | H | Et | $N_3$ | F | H | OH | H | H |
| XIV-19-2 | p-Br—Ph | H | H | $CH_3$ | Et | $N_3$ | F | H | OH | H | H |
| XIV-19-3 | p-Br—Ph | H | H | $CH(CH_3)_2$ | Et | $N_3$ | F | H | OH | H | H |
| XIV-19-4 | p-Br—Ph | H | H | $CH_2CH(CH_3)_2$ | Et | $N_3$ | F | H | OH | H | H |
| XIV-19-5 | p-Br—Ph | H | H | $CH_2Ph$ | Et | $N_3$ | F | H | OH | H | H |
| XIV-19-6 | p-Br—Ph | H | H | $CH_2$-indol-3-yl | Et | $N_3$ | F | H | OH | H | H |
| XIV-19-7 | p-Br—Ph | H | H | $CH_2CH_2SCH_3$ | Et | $N_3$ | F | H | OH | H | H |
| XIV-19-8 | p-Br—Ph | * | H | * | Et | $N_3$ | F | H | OH | H | H |

*$R^2$ and $R^{3b}$ joined together by $(CH_2)_3$ to form five-membered ring.

TABLE XIV-20

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-20-1 | p-I—Ph | H | H | H | Et | $N_3$ | F | H | OH | H | H |
| XIV-20-2 | p-I—Ph | H | H | $CH_3$ | Et | $N_3$ | F | H | OH | H | H |
| XIV-20-3 | p-I—Ph | H | H | $CH(CH_3)_2$ | Et | $N_3$ | F | H | OH | H | H |
| XIV-20-4 | p-I—Ph | H | H | $CH_2CH(CH_3)_2$ | Et | $N_3$ | F | H | OH | H | H |
| XIV-20-5 | p-I—Ph | H | H | $CH_2Ph$ | Et | $N_3$ | F | H | OH | H | H |
| XIV-20-6 | p-I—Ph | H | H | $CH_2$-indol-3-yl | Et | $N_3$ | F | H | OH | H | H |
| XIV-20-7 | p-I—Ph | H | H | $CH_2CH_2SCH_3$ | Et | $N_3$ | F | H | OH | H | H |
| XIV-20-8 | p-I—Ph | * | H | * | Et | $N_3$ | F | H | OH | H | H |

*$R^2$ and $R^{3b}$ joined together by $(CH_2)_3$ to form five-membered ring.

TABLE XIV-21

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-21-1 | $CH_3$ | H | H | H | $^iPr$ | $N_3$ | F | H | OH | H | H |
| XIV-21-2 | $CH_3$ | H | H | $CH_3$ | $^iPr$ | $N_3$ | F | H | OH | H | H |
| XIV-21-3 | $CH_3$ | H | H | $CH(CH_3)_2$ | $^iPr$ | $N_3$ | F | H | OH | H | H |
| XIV-21-4 | $CH_3$ | H | H | $CH_2CH(CH_3)_2$ | $^iPr$ | $N_3$ | F | H | OH | H | H |
| XIV-21-5 | $CH_3$ | H | H | $CH_2Ph$ | $^iPr$ | $N_3$ | F | H | OH | H | H |
| XIV-21-6 | $CH_3$ | H | H | $CH_2$-indol-3-yl | $^iPr$ | $N_3$ | F | H | OH | H | H |
| XIV-21-7 | $CH_3$ | H | H | $CH_2CH_2SCH_3$ | $^iPr$ | $N_3$ | F | H | OH | H | H |
| XIV-21-8 | $CH_3$ | * | H | * | $^iPr$ | $N_3$ | F | H | OH | H | H |

*$R^2$ and $R^{3b}$ joined together by $(CH_2)_3$ to form five-membered ring.

TABLE XIV-22

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-22-1 | Et | H | H | H | $^iPr$ | $N_3$ | F | H | OH | H | H |
| XIV-22-2 | Et | H | H | $CH_3$ | $^iPr$ | $N_3$ | F | H | OH | H | H |
| XIV-22-3 | Et | H | H | $CH(CH_3)_2$ | $^iPr$ | $N_3$ | F | H | OH | H | H |
| XIV-22-4 | Et | H | H | $CH_2CH(CH_3)_2$ | $^iPr$ | $N_3$ | F | H | OH | H | H |
| XIV-22-5 | Et | H | H | $CH_2Ph$ | $^iPr$ | $N_3$ | F | H | OH | H | H |
| XIV-22-6 | Et | H | H | $CH_2$-indol-3-yl | $^iPr$ | $N_3$ | F | H | OH | H | H |
| XIV-22-7 | Et | H | H | $CH_2CH_2SCH_3$ | $^iPr$ | $N_3$ | F | H | OH | H | H |
| XIV-22-8 | Et | * | H | * | $^iPr$ | $N_3$ | F | H | OH | H | H |

*$R^2$ and $R^{3b}$ joined together by $(CH_2)_3$ to form five-membered ring.

TABLE XIV-23

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-23-1 | $^i$Pr | H | H | H | $^i$Pr | $N_3$ | F | H | OH | H | H |
| XIV-23-2 | $^i$Pr | H | H | $CH_3$ | $^i$Pr | $N_3$ | F | H | OH | H | H |
| XIV-23-3 | $^i$Pr | H | H | $CH(CH_3)_2$ | $^i$Pr | $N_3$ | F | H | OH | H | H |
| XIV-23-4 | $^i$Pr | H | H | $CH_2CH(CH_3)_2$ | $^i$Pr | $N_3$ | F | H | OH | H | H |
| XIV-23-5 | $^i$Pr | H | H | $CH_2Ph$ | $^i$Pr | $N_3$ | F | H | OH | H | H |
| XIV-23-6 | $^i$Pr | H | H | $CH_2$-indol-3-yl | $^i$Pr | $N_3$ | F | H | OH | H | H |
| XIV-23-7 | $^i$Pr | H | H | $CH_2CH_2SCH_3$ | $^i$Pr | $N_3$ | F | H | OH | H | H |
| XIV-23-8 | $^i$Pr | * | H | * | $^i$Pr | $N_3$ | F | H | OH | H | H |

*$R^2$ and $R^{3b}$ joined together by $(CH_2)_3$ to form five-membered ring.

TABLE XIV-24

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-24-1 | $^t$Bu | H | H | H | $^i$Pr | $N_3$ | F | H | OH | H | H |
| XIV-24-2 | $^t$Bu | H | H | $CH_3$ | $^i$Pr | $N_3$ | F | H | OH | H | H |
| XIV-24-3 | $^t$Bu | H | H | $CH(CH_3)_2$ | $^i$Pr | $N_3$ | F | H | OH | H | H |
| XIV-24-4 | $^t$Bu | H | H | $CH_2CH(CH_3)_2$ | $^i$Pr | $N_3$ | F | H | OH | H | H |
| XIV-24-5 | $^t$Bu | H | H | $CH_2Ph$ | $^i$Pr | $N_3$ | F | H | OH | H | H |
| XIV-24-6 | $^t$Bu | H | H | $CH_2$-indol-3-yl | $^i$Pr | $N_3$ | F | H | OH | H | H |
| XIV-24-7 | $^t$Bu | H | H | $CH_2CH_2SCH_3$ | $^i$Pr | $N_3$ | F | H | OH | H | H |
| XIV-24-8 | $^t$Bu | * | H | * | $^i$Pr | $N_3$ | F | H | OH | H | H |

*$R^2$ and $R^{3b}$ joined together by $(CH_2)_3$ to form five-membered ring.

TABLE XIV-25

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-25-1 | Ph | H | H | H | $^i$Pr | $N_3$ | F | H | OH | H | H |
| XIV-25-2 | Ph | H | H | $CH_3$ | $^i$Pr | $N_3$ | F | H | OH | H | H |
| XIV-25-3 | Ph | H | H | $CH(CH_3)_2$ | $^i$Pr | $N_3$ | F | H | OH | H | H |
| XIV-25-4 | Ph | H | H | $CH_2CH(CH_3)_2$ | $^i$Pr | $N_3$ | F | H | OH | H | H |
| XIV-25-5 | Ph | H | H | $CH_2Ph$ | $^i$Pr | $N_3$ | F | H | OH | H | H |
| XIV-25-6 | Ph | H | H | $CH_2$-indol-3-yl | $^i$Pr | $N_3$ | F | H | OH | H | H |
| XIV-25-7 | Ph | H | H | $CH_2CH_2SCH_3$ | $^i$Pr | $N_3$ | F | H | OH | H | H |
| XIV-25-8 | Ph | * | H | * | $^i$Pr | $N_3$ | F | H | OH | H | H |

*$R^2$ and $R^{3b}$ joined together by $(CH_2)_3$ to form five-membered ring.

TABLE XIV-26

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-26-1 | p-Me—Ph | H | H | H | $^i$Pr | $N_3$ | F | H | OH | H | H |
| XIV-26-2 | p-Me—Ph | H | H | $CH_3$ | $^i$Pr | $N_3$ | F | H | OH | H | H |
| XIV-26-3 | p-Me—Ph | H | H | $CH(CH_3)_2$ | $^i$Pr | $N_3$ | F | H | OH | H | H |
| XIV-26-4 | p-Me—Ph | H | H | $CH_2CH(CH_3)_2$ | $^i$Pr | $N_3$ | F | H | OH | H | H |
| XIV-26-5 | p-Me—Ph | H | H | $CH_2Ph$ | $^i$Pr | $N_3$ | F | H | OH | H | H |
| XIV-26-6 | p-Me—Ph | H | H | $CH_2$-indol-3-yl | $^i$Pr | $N_3$ | F | H | OH | H | H |
| XIV-26-7 | p-Me—Ph | H | H | $CH_2CH_2SCH_3$ | $^i$Pr | $N_3$ | F | H | OH | H | H |
| XIV-26-8 | p-Me—Ph | * | H | * | $^i$Pr | $N_3$ | F | H | OH | H | H |

*$R^2$ and $R^{3b}$ joined together by $(CH_2)_3$ to form five-membered ring.

TABLE XIV-27

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-27-1 | p-F—Ph | H | H | H | $^i$Pr | $N_3$ | F | H | OH | H | H |
| XIV-27-2 | p-F—Ph | H | H | $CH_3$ | $^i$Pr | $N_3$ | F | H | OH | H | H |
| XIV-27-3 | p-F—Ph | H | H | $CH(CH_3)_2$ | $^i$Pr | $N_3$ | F | H | OH | H | H |
| XIV-27-4 | p-F—Ph | H | H | $CH_2CH(CH_3)_2$ | $^i$Pr | $N_3$ | F | H | OH | H | H |
| XIV-27-5 | p-F—Ph | H | H | $CH_2Ph$ | $^i$Pr | $N_3$ | F | H | OH | H | H |
| XIV-27-6 | p-F—Ph | H | H | $CH_2$-indol-3-yl | $^i$Pr | $N_3$ | F | H | OH | H | H |
| XIV-27-7 | p-F—Ph | H | H | $CH_2CH_2SCH_3$ | $^i$Pr | $N_3$ | F | H | OH | H | H |
| XIV-27-8 | p-F—Ph | * | H | * | $^i$Pr | $N_3$ | F | H | OH | H | H |

*$R^2$ and $R^{3b}$ joined together by $(CH_2)_3$ to form five-membered ring.

TABLE XIV-28

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-28-1 | p-Cl—Ph | H | H | H | $^i$Pr | $N_3$ | F | H | OH | H | H |
| XIV-28-2 | p-Cl—Ph | H | H | $CH_3$ | $^i$Pr | $N_3$ | F | H | OH | H | H |

TABLE XIV-28-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-28-3 | p-Cl—Ph | H | H | CH(CH₃)₂ | $^i$Pr | N₃ | F | H | OH | H | H |
| XIV-28-4 | p-Cl—Ph | H | H | CH₂CH(CH₃)₂ | $^i$Pr | N₃ | F | H | OH | H | H |
| XIV-28-5 | p-Cl—Ph | H | H | CH₂Ph | $^i$Pr | N₃ | F | H | OH | H | H |
| XIV-28-6 | p-Cl—Ph | H | H | CH₂-indol-3-yl | $^i$Pr | N₃ | F | H | OH | H | H |
| XIV-28-7 | p-Cl—Ph | H | H | CH₂CH₂SCH₃ | $^i$Pr | N₃ | F | H | OH | H | H |
| XIV-28-8 | p-Cl—Ph | * | H | * | $^i$Pr | N₃ | F | H | OH | H | H |

*R² and R³ᵇ joined together by (CH₂)₃ to form five-membered ring.

TABLE XIV-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-29-1 | p-Br—Ph | H | H | H | $^i$Pr | N₃ | F | H | OH | H | H |
| XIV-29-2 | p-Br—Ph | H | H | CH₃ | $^i$Pr | N₃ | F | H | OH | H | H |
| XIV-29-3 | p-Br—Ph | H | H | CH(CH₃)₂ | $^i$Pr | N₃ | F | H | OH | H | H |
| XIV-29-4 | p-Br—Ph | H | H | CH₂CH(CH₃)₂ | $^i$Pr | N₃ | F | H | OH | H | H |
| XIV-29-5 | p-Br—Ph | H | H | CH₂Ph | $^i$Pr | N₃ | F | H | OH | H | H |
| XIV-29-6 | p-Br—Ph | H | H | CH₂-indol-3-yl | $^i$Pr | N₃ | F | H | OH | H | H |
| XIV-29-7 | p-Br—Ph | H | H | CH₂CH₂SCH₃ | $^i$Pr | N₃ | F | H | OH | H | H |
| XIV-29-8 | p-Br—Ph | * | H | * | $^i$Pr | N₃ | F | H | OH | H | H |

*R² and R³ᵇ joined together by (CH₂)₃ to form five-membered ring.

TABLE XIV-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-30-1 | p-I—Ph | H | H | H | $^i$Pr | N₃ | F | H | OH | H | H |
| XIV-30-2 | p-I—Ph | H | H | CH₃ | $^i$Pr | N₃ | F | H | OH | H | H |
| XIV-30-3 | p-I—Ph | H | H | CH(CH₃)₂ | $^i$Pr | N₃ | F | H | OH | H | H |
| XIV-30-4 | p-I—Ph | H | H | CH₂CH(CH₃)₂ | $^i$Pr | N₃ | F | H | OH | H | H |
| XIV-30-5 | p-I—Ph | H | H | CH₂Ph | $^i$Pr | N₃ | F | H | OH | H | H |
| XIV-30-6 | p-I—Ph | H | H | CH₂-indol-3-yl | $^i$Pr | N₃ | F | H | OH | H | H |
| XIV-30-7 | p-I—Ph | H | H | CH₂CH₂SCH₃ | $^i$Pr | N₃ | F | H | OH | H | H |
| XIV-30-8 | p-I—Ph | * | H | * | $^i$Pr | N₃ | F | H | OH | H | H |

*R² and R³ᵇ joined together by (CH₂)₃ to form five-membered ring.

TABLE XIV-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-31-1 | CH₃ | H | H | H | $^n$Bu | N₃ | F | H | OH | H | H |
| XIV-31-2 | CH₃ | H | H | CH₃ | $^n$Bu | N₃ | F | H | OH | H | H |
| XIV-31-3 | CH₃ | H | H | CH(CH₃)₂ | $^n$Bu | N₃ | F | H | OH | H | H |
| XIV-31-4 | CH₃ | H | H | CH₂CH(CH₃)₂ | $^n$Bu | N₃ | F | H | OH | H | H |
| XIV-31-5 | CH₃ | H | H | CH₂Ph | $^n$Bu | N₃ | F | H | OH | H | H |
| XIV-31-6 | CH₃ | H | H | CH₂-indol-3-yl | $^n$Bu | N₃ | F | H | OH | H | H |
| XIV-31-7 | CH₃ | H | H | CH₂CH₂SCH₃ | $^n$Bu | N₃ | F | H | OH | H | H |
| XIV-31-8 | CH₃ | * | H | * | $^n$Bu | N₃ | F | H | OH | H | H |

*R² and R³ᵇ joined together by (CH₂)₃ to form five-membered ring.

TABLE XIV-32

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-32-1 | Et | H | H | H | $^n$Bu | N₃ | F | H | OH | H | H |
| XIV-32-2 | Et | H | H | CH₃ | $^n$Bu | N₃ | F | H | OH | H | H |
| XIV-32-3 | Et | H | H | CH(CH₃)₂ | $^n$Bu | N₃ | F | H | OH | H | H |
| XIV-32-4 | Et | H | H | CH₂CH(CH₃)₂ | $^n$Bu | N₃ | F | H | OH | H | H |
| XIV-32-5 | Et | H | H | CH₂Ph | $^n$Bu | N₃ | F | H | OH | H | H |
| XIV-32-6 | Et | H | H | CH₂-indol-3-yl | $^n$Bu | N₃ | F | H | OH | H | H |
| XIV-32-7 | Et | H | H | CH₂CH₂SCH₃ | $^n$Bu | N₃ | F | H | OH | H | H |
| XIV-32-8 | Et | * | H | * | $^n$Bu | N₃ | F | H | OH | H | H |

*R² and R³ᵇ joined together by (CH₂)₃ to form five-membered ring.

TABLE XIV-33

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-33-1 | $^i$Pr | H | H | H | $^n$Bu | N₃ | F | H | OH | H | H |
| XIV-33-2 | $^i$Pr | H | H | CH₃ | $^n$Bu | N₃ | F | H | OH | H | H |
| XIV-33-3 | $^i$Pr | H | H | CH(CH₃)₂ | $^n$Bu | N₃ | F | H | OH | H | H |

TABLE XIV-33-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-33-4 | $^i$Pr | H | H | CH$_2$CH(CH$_3$)$_2$ | $^n$Bu | N$_3$ | F | H | OH | H | H |
| XIV-33-5 | $^i$Pr | H | H | CH$_2$Ph | $^n$Bu | N$_3$ | F | H | OH | H | H |
| XIV-33-6 | $^i$Pr | H | H | CH$_2$-indol-3-yl | $^n$Bu | N$_3$ | F | H | OH | H | H |
| XIV-33-7 | $^i$Pr | H | H | CH$_2$CH$_2$SCH$_3$ | $^n$Bu | N$_3$ | F | H | OH | H | H |
| XIV-33-8 | $^i$Pr | * | H | * | $^n$Bu | N$_3$ | F | H | OH | H | H |

*$R^2$ and $R^{3b}$ joined together by (CH$_2$)$_3$ to form five-membered ring.

TABLE XIV-34

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-34-1 | $^t$Bu | H | H | H | $^n$Bu | N$_3$ | F | H | OH | H | H |
| XIV-34-2 | $^t$Bu | H | H | CH$_3$ | $^n$Bu | N$_3$ | F | H | OH | H | H |
| XIV-34-3 | $^t$Bu | H | H | CH(CH$_3$)$_2$ | $^n$Bu | N$_3$ | F | H | OH | H | H |
| XIV-34-4 | $^t$Bu | H | H | CH$_2$CH(CH$_3$)$_2$ | $^n$Bu | N$_3$ | F | H | OH | H | H |
| XIV-34-5 | $^t$Bu | H | H | CH$_2$Ph | $^n$Bu | N$_3$ | F | H | OH | H | H |
| XIV-34-6 | $^t$Bu | H | H | CH$_2$-indol-3-yl | $^n$Bu | N$_3$ | F | H | OH | H | H |
| XIV-34-7 | $^t$Bu | H | H | CH$_2$CH$_2$SCH$_3$ | $^n$Bu | N$_3$ | F | H | OH | H | H |
| XIV-34-8 | $^t$Bu | * | H | * | $^n$Bu | N$_3$ | F | H | OH | H | H |

*$R^2$ and $R^{3b}$ joined together by (CH$_2$)$_3$ to form five-membered ring.

TABLE XIV-35

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-35-1 | Ph | H | H | H | $^n$Bu | N$_3$ | F | H | OH | H | H |
| XIV-35-2 | Ph | H | H | CH$_3$ | $^n$Bu | N$_3$ | F | H | OH | H | H |
| XIV-35-3 | Ph | H | H | CH(CH$_3$)$_2$ | $^n$Bu | N$_3$ | F | H | OH | H | H |
| XIV-35-4 | Ph | H | H | CH$_2$CH(CH$_3$)$_2$ | $^n$Bu | N$_3$ | F | H | OH | H | H |
| XIV-35-5 | Ph | H | H | CH$_2$Ph | $^n$Bu | N$_3$ | F | H | OH | H | H |
| XIV-35-6 | Ph | H | H | CH$_2$-indol-3-yl | $^n$Bu | N$_3$ | F | H | OH | H | H |
| XIV-35-7 | Ph | H | H | CH$_2$CH$_2$SCH$_3$ | $^n$Bu | N$_3$ | F | H | OH | H | H |
| XIV-35-8 | Ph | * | H | * | $^n$Bu | N$_3$ | F | H | OH | H | H |

*$R^2$ and $R^{3b}$ joined together by (CH$_2$)$_3$ to form five-membered ring.

TABLE XIV-36

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-36-1 | p-Me—Ph | H | H | H | $^n$Bu | N$_3$ | F | H | OH | H | H |
| XIV-36-2 | p-Me—Ph | H | H | CH$_3$ | $^n$Bu | N$_3$ | F | H | OH | H | H |
| XIV-36-3 | p-Me—Ph | H | H | CH(CH$_3$)$_2$ | $^n$Bu | N$_3$ | F | H | OH | H | H |
| XIV-36-4 | p-Me—Ph | H | H | CH$_2$CH(CH$_3$)$_2$ | $^n$Bu | N$_3$ | F | H | OH | H | H |
| XIV-36-5 | p-Me—Ph | H | H | CH$_2$Ph | $^n$Bu | N$_3$ | F | H | OH | H | H |
| XIV-36-6 | p-Me—Ph | H | H | CH$_2$-indol-3-yl | $^n$Bu | N$_3$ | F | H | OH | H | H |
| XIV-36-7 | p-Me—Ph | H | H | CH$_2$CH$_2$SCH$_3$ | $^n$Bu | N$_3$ | F | H | OH | H | H |
| XIV-36-8 | p-Me—Ph | * | H | * | $^n$Bu | N$_3$ | F | H | OH | H | H |

*$R^2$ and $R^{3b}$ joined together by (CH$_2$)$_3$ to form five-membered ring.

TABLE XIV-37

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-37-1 | p-F—Ph | H | H | H | $^n$Bu | N$_3$ | F | H | OH | H | H |
| XIV-37-2 | p-F—Ph | H | H | CH$_3$ | $^n$Bu | N$_3$ | F | H | OH | H | H |
| XIV-37-3 | p-F—Ph | H | H | CH(CH$_3$)$_2$ | $^n$Bu | N$_3$ | F | H | OH | H | H |
| XIV-37-4 | p-F—Ph | H | H | CH$_2$CH(CH$_3$)$_2$ | $^n$Bu | N$_3$ | F | H | OH | H | H |
| XIV-37-5 | p-F—Ph | H | H | CH$_2$Ph | $^n$Bu | N$_3$ | F | H | OH | H | H |
| XIV-37-6 | p-F—Ph | H | H | CH$_2$-indol-3-yl | $^n$Bu | N$_3$ | F | H | OH | H | H |
| XIV-37-7 | p-F—Ph | H | H | CH$_2$CH$_2$SCH$_3$ | $^n$Bu | N$_3$ | F | H | OH | H | H |
| XIV-37-8 | p-F—Ph | * | H | * | $^n$Bu | N$_3$ | F | H | OH | H | H |

*$R^2$ and $R^{3b}$ joined together by (CH$_2$)$_3$ to form five-membered ring.

TABLE XIV-38

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIV-38-1 | p-Cl—Ph | H | H | H | $^n$Bu | N$_3$ | F | H | OH | H | H |
| XIV-38-2 | p-Cl—Ph | H | H | CH$_3$ | $^n$Bu | N$_3$ | F | H | OH | H | H |
| XIV-38-3 | p-Cl—Ph | H | H | CH(CH$_3$)$_2$ | $^n$Bu | N$_3$ | F | H | OH | H | H |
| XIV-38-4 | p-Cl—Ph | H | H | CH$_2$CH(CH$_3$)$_2$ | $^n$Bu | N$_3$ | F | H | OH | H | H |
| XIV-38-5 | p-Cl—Ph | H | H | CH$_2$Ph | $^n$Bu | N$_3$ | F | H | OH | H | H |

TABLE XIV-38-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-38-6 | p-Cl—Ph | H | H | CH₂-indol-3-yl | ⁿBu | N₃ | F | H | OH | H | H |
| XIV-38-7 | p-Cl—Ph | H | H | CH₂CH₂SCH₃ | ⁿBu | N₃ | F | H | OH | H | H |
| XIV-38-8 | p-Cl—Ph | * | H | * | ⁿBu | N₃ | F | H | OH | H | H |

*R² and R³ᵇ joined together by (CH₂)₃ to form five-membered ring.

TABLE XIV-39

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-39-1 | p-Br—Ph | H | H | H | ⁿBu | N₃ | F | H | OH | H | H |
| XIV-39-2 | p-Br—Ph | H | H | CH₃ | ⁿBu | N₃ | F | H | OH | H | H |
| XIV-39-3 | p-Br—Ph | H | H | CH(CH₃)₂ | ⁿBu | N₃ | F | H | OH | H | H |
| XIV-39-4 | p-Br—Ph | H | H | CH₂CH(CH₃)₂ | ⁿBu | N₃ | F | H | OH | H | H |
| XIV-39-5 | p-Br—Ph | H | H | CH₂Ph | ⁿBu | N₃ | F | H | OH | H | H |
| XIV-39-6 | p-Br—Ph | H | H | CH₂-indol-3-yl | ⁿBu | N₃ | F | H | OH | H | H |
| XIV-39-7 | p-Br—Ph | H | H | CH₂CH₂SCH₃ | ⁿBu | N₃ | F | H | OH | H | H |
| XIV-39-8 | p-Br—Ph | * | H | * | ⁿBu | N₃ | F | H | OH | H | H |

*R² and R³ᵇ joined together by (CH₂)₃ to form five-membered ring.

TABLE XIV-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-40-1 | p-I—Ph | H | H | H | ⁿBu | N₃ | F | H | OH | H | H |
| XIV-40-2 | p-I—Ph | H | H | CH₃ | ⁿBu | N₃ | F | H | OH | H | H |
| XIV-40-3 | p-I—Ph | H | H | CH(CH₃)₂ | ⁿBu | N₃ | F | H | OH | H | H |
| XIV-40-4 | p-I—Ph | H | H | CH₂CH(CH₃)₂ | ⁿBu | N₃ | F | H | OH | H | H |
| XIV-40-5 | p-I—Ph | H | H | CH₂Ph | ⁿBu | N₃ | F | H | OH | H | H |
| XIV-40-6 | p-I—Ph | H | H | CH₂-indol-3-yl | ⁿBu | N₃ | F | H | OH | H | H |
| XIV-40-7 | p-I—Ph | H | H | CH₂CH₂SCH₃ | ⁿBu | N₃ | F | H | OH | H | H |
| XIV-40-8 | p-I—Ph | * | H | * | ⁿBu | N₃ | F | H | OH | H | H |

*R² and R³ᵇ joined together by (CH₂)₃ to form five-membered ring.

TABLE XIV-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-41-1 | CH₃ | H | H | H | Bz | N₃ | F | H | OH | H | H |
| XIV-41-2 | CH₃ | H | H | CH₃ | Bz | N₃ | F | H | OH | H | H |
| XIV-41-3 | CH₃ | H | H | CH(CH₃)₂ | Bz | N₃ | F | H | OH | H | H |
| XIV-41-4 | CH₃ | H | H | CH₂CH(CH₃)₂ | Bz | N₃ | F | H | OH | H | H |
| XIV-41-5 | CH₃ | H | H | CH₂Ph | Bz | N₃ | F | H | OH | H | H |
| XIV-41-6 | CH₃ | H | H | CH₂-indol-3-yl | Bz | N₃ | F | H | OH | H | H |
| XIV-41-7 | CH₃ | H | H | CH₂CH₂SCH₃ | Bz | N₃ | F | H | OH | H | H |
| XIV-41-8 | CH₃ | * | H | * | Bz | N₃ | F | H | OH | H | H |

*R² and R³ᵇ joined together by (CH₂)₃ to form five-membered ring.

TABLE XIV-42

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-42-1 | Et | H | H | H | Bz | N₃ | F | H | OH | H | H |
| XIV-42-2 | Et | H | H | CH₃ | Bz | N₃ | F | H | OH | H | H |
| XIV-42-3 | Et | H | H | CH(CH₃)₂ | Bz | N₃ | F | H | OH | H | H |
| XIV-42-4 | Et | H | H | CH₂CH(CH₃)₂ | Bz | N₃ | F | H | OH | H | H |
| XIV-42-5 | Et | H | H | CH₂Ph | Bz | N₃ | F | H | OH | H | H |
| XIV-42-6 | Et | H | H | CH₂-indol-3-yl | Bz | N₃ | F | H | OH | H | H |
| XIV-42-7 | Et | H | H | CH₂CH₂SCH₃ | Bz | N₃ | F | H | OH | H | H |
| XIV-42-8 | Et | * | H | * | Bz | N₃ | F | H | OH | H | H |

*R² and R³ᵇ joined together by (CH₂)₃ to form five-membered ring.

TABLE XIV-43

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-43-1 | ⁱPr | H | H | H | Bz | N₃ | F | H | OH | H | H |
| XIV-43-2 | ⁱPr | H | H | CH₃ | Bz | N₃ | F | H | OH | H | H |
| XIV-43-3 | ⁱPr | H | H | CH(CH₃)₂ | Bz | N₃ | F | H | OH | H | H |
| XIV-43-4 | ⁱPr | H | H | CH₂CH(CH₃)₂ | Bz | N₃ | F | H | OH | H | H |
| XIV-43-5 | ⁱPr | H | H | CH₂Ph | Bz | N₃ | F | H | OH | H | H |
| XIV-43-6 | ⁱPr | H | H | CH₂-indol-3-yl | Bz | N₃ | F | H | OH | H | H |
| XIV-43-7 | ⁱPr | H | H | CH₂CH₂SCH₃ | Bz | N₃ | F | H | OH | H | H |
| XIV-43-8 | ⁱPr | * | H | * | Bz | N₃ | F | H | OH | H | H |

*R² and R³ᵇ joined together by (CH₂)₃ to form five-membered ring.

TABLE XIV-44

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-44-1 | ᵗBu | H | H | H | Bz | N₃ | F | H | OH | H | H |
| XIV-44-2 | ᵗBu | H | H | CH₃ | Bz | N₃ | F | H | OH | H | H |
| XIV-44-3 | ᵗBu | H | H | CH(CH₃)₂ | Bz | N₃ | F | H | OH | H | H |
| XIV-44-4 | ᵗBu | H | H | CH₂CH(CH₃)₂ | Bz | N₃ | F | H | OH | H | H |

TABLE XIV-44-continued

| No | R$^1$ | R$^2$ | R$^{3a}$ | R$^{3b}$ | R$^4$ | R$^5$ | R$^6$ | X | Y | R$^7$ | R$^8$ |
| --- | --- | --- | --- | --- | --- | --- | --- | --- | --- | --- | --- |
| XIV-44-5 | $^t$Bu | H | H | CH$_2$Ph | Bz | N$_3$ | F | H | OH | H | H |
| XIV-44-6 | $^t$Bu | H | H | CH$_2$-indol-3-yl | Bz | N$_3$ | F | H | OH | H | H |
| XIV-44-7 | $^t$Bu | H | H | CH$_2$CH$_2$SCH$_3$ | Bz | N$_3$ | F | H | OH | H | H |
| XIV-44-8 | $^t$Bu | * | H | * | Bz | N$_3$ | F | H | OH | H | H |

*R$^2$ and R$^{3b}$ joined together by (CH$_2$)$_3$ to form five-membered ring.

TABLE XIV-45

| No | R$^1$ | R$^2$ | R$^{3a}$ | R$^{3b}$ | R$^4$ | R$^5$ | R$^6$ | X | Y | R$^7$ | R$^8$ |
| --- | --- | --- | --- | --- | --- | --- | --- | --- | --- | --- | --- |
| XIV-45-1 | Ph | H | H | H | Bz | N$_3$ | F | H | OH | H | H |
| XIV-45-2 | Ph | H | H | CH$_3$ | Bz | N$_3$ | F | H | OH | H | H |
| XIV-45-3 | Ph | H | H | CH(CH$_3$)$_2$ | Bz | N$_3$ | F | H | OH | H | H |
| XIV-45-4 | Ph | H | H | CH$_2$CH(CH$_3$)$_2$ | Bz | N$_3$ | F | H | OH | H | H |
| XIV-45-5 | Ph | H | H | CH$_2$Ph | Bz | N$_3$ | F | H | OH | H | H |
| XIV-45-6 | Ph | H | H | CH$_2$-indol-3-yl | Bz | N$_3$ | F | H | OH | H | H |
| XIV-45-7 | Ph | H | H | CH$_2$CH$_2$SCH$_3$ | Bz | N$_3$ | F | H | OH | H | H |
| XIV-45-8 | Ph | * | H | * | Bz | N$_3$ | F | H | OH | H | H |

*R$^2$ and R$^{3b}$ joined together by (CH$_2$)$_3$ to form five-membered ring.

TABLE XIV-46

| No | R$^1$ | R$^2$ | R$^{3a}$ | R$^{3b}$ | R$^4$ | R$^5$ | R$^6$ | X | Y | R$^7$ | R$^8$ |
| --- | --- | --- | --- | --- | --- | --- | --- | --- | --- | --- | --- |
| XIV-46-1 | p-Me—Ph | H | H | H | Bz | N$_3$ | F | H | OH | H | H |
| XIV-46-2 | p-Me—Ph | H | H | CH$_3$ | Bz | N$_3$ | F | H | OH | H | H |
| XIV-46-3 | p-Me—Ph | H | H | CH(CH$_3$)$_2$ | Bz | N$_3$ | F | H | OH | H | H |
| XIV-46-4 | p-Me—Ph | H | H | CH$_2$CH(CH$_3$)$_2$ | Bz | N$_3$ | F | H | OH | H | H |
| XIV-46-5 | p-Me—Ph | H | H | CH$_2$Ph | Bz | N$_3$ | F | H | OH | H | H |
| XIV-46-6 | p-Me—Ph | H | H | CH$_2$-indol-3-yl | Bz | N$_3$ | F | H | OH | H | H |
| XIV-46-7 | p-Me—Ph | H | H | CH$_2$CH$_2$SCH$_3$ | Bz | N$_3$ | F | H | OH | H | H |
| XIV-46-8 | p-Me—Ph | * | H | * | Bz | N$_3$ | F | H | OH | H | H |

*R$^2$ and R$^{3b}$ joined together by (CH$_2$)$_3$ to form five-membered ring.

TABLE XIV-47

| No | R$^1$ | R$^2$ | R$^{3a}$ | R$^{3b}$ | R$^4$ | R$^5$ | R$^6$ | X | Y | R$^7$ | R$^8$ |
| --- | --- | --- | --- | --- | --- | --- | --- | --- | --- | --- | --- |
| XIV-47-1 | p-F—Ph | H | H | H | Bz | N$_3$ | F | H | OH | H | H |
| XIV-47-2 | p-F—Ph | H | H | CH$_3$ | Bz | N$_3$ | F | H | OH | H | H |
| XIV-47-3 | p-F—Ph | H | H | CH(CH$_3$)$_2$ | Bz | N$_3$ | F | H | OH | H | H |
| XIV-47-4 | p-F—Ph | H | H | CH$_2$CH(CH$_3$)$_2$ | Bz | N$_3$ | F | H | OH | H | H |
| XIV-47-5 | p-F—Ph | H | H | CH$_2$Ph | Bz | N$_3$ | F | H | OH | H | H |
| XIV-47-6 | p-F—Ph | H | H | CH$_2$-indol-3-yl | Bz | N$_3$ | F | H | OH | H | H |
| XIV-47-7 | p-F—Ph | H | H | CH$_2$CH$_2$SCH$_3$ | Bz | N$_3$ | F | H | OH | H | H |
| XIV-47-8 | p-F—Ph | * | H | * | Bz | N$_3$ | F | H | OH | H | H |

*R$^2$ and R$^{3b}$ joined together by (CH$_2$)$_3$ to form five-membered ring.

TABLE XIV-48

| No | R$^1$ | R$^2$ | R$^{3a}$ | R$^{3b}$ | R$^4$ | R$^5$ | R$^6$ | X | Y | R$^7$ | R$^8$ |
| --- | --- | --- | --- | --- | --- | --- | --- | --- | --- | --- | --- |
| XIV-48-1 | p-Cl—Ph | H | H | H | Bz | N$_3$ | F | H | OH | H | H |
| XIV-48-2 | p-Cl—Ph | H | H | CH$_3$ | Bz | N$_3$ | F | H | OH | H | H |
| XIV-48-3 | p-Cl—Ph | H | H | CH(CH$_3$)$_2$ | Bz | N$_3$ | F | H | OH | H | H |
| XIV-48-4 | p-Cl—Ph | H | H | CH$_2$CH(CH$_3$)$_2$ | Bz | N$_3$ | F | H | OH | H | H |
| XIV-48-5 | p-Cl—Ph | H | H | CH$_2$Ph | Bz | N$_3$ | F | H | OH | H | H |
| XIV-48-6 | p-Cl—Ph | H | H | CH$_2$-indol-3-yl | Bz | N$_3$ | F | H | OH | H | H |
| XIV-48-7 | p-Cl—Ph | H | H | CH$_2$CH$_2$SCH$_3$ | Bz | N$_3$ | F | H | OH | H | H |
| XIV-48-8 | p-Cl—Ph | * | H | * | Bz | N$_3$ | F | H | OH | H | H |

*R$^2$ and R$^{3b}$ joined together by (CH$_2$)$_3$ to form five-membered ring.

TABLE XIV-49

| No | R$^1$ | R$^2$ | R$^{3a}$ | R$^{3b}$ | R$^4$ | R$^5$ | R$^6$ | X | Y | R$^7$ | R$^8$ |
| --- | --- | --- | --- | --- | --- | --- | --- | --- | --- | --- | --- |
| XIV-49-1 | p-Br—Ph | H | H | H | Bz | N$_3$ | F | H | OH | H | H |
| XIV-49-2 | p-Br—Ph | H | H | CH$_3$ | Bz | N$_3$ | F | H | OH | H | H |
| XIV-49-3 | p-Br—Ph | H | H | CH(CH$_3$)$_2$ | Bz | N$_3$ | F | H | OH | H | H |
| XIV-49-4 | p-Br—Ph | H | H | CH$_2$CH(CH$_3$)$_2$ | Bz | N$_3$ | F | H | OH | H | H |
| XIV-49-5 | p-Br—Ph | H | H | CH$_2$Ph | Bz | N$_3$ | F | H | OH | H | H |
| XIV-49-6 | p-Br—Ph | H | H | CH$_2$-indol-3-yl | Bz | N$_3$ | F | H | OH | H | H |
| XIV-49-7 | p-Br—Ph | H | H | CH$_2$CH$_2$SCH$_3$ | Bz | N$_3$ | F | H | OH | H | H |
| XIV-49-8 | p-Br—Ph | * | H | * | Bz | N$_3$ | F | H | OH | H | H |

*R$^2$ and R$^{3b}$ joined together by (CH$_2$)$_3$ to form five-membered ring.

TABLE XIV-50

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIV-50-1 | p-I—Ph | H | H | H | Bz | N₃ | F | H | OH | H | H |
| XIV-50-2 | p-I—Ph | H | H | CH₃ | Bz | N₃ | F | H | OH | H | H |
| XIV-50-3 | p-I—Ph | H | H | CH(CH₃)₂ | Bz | N₃ | F | H | OH | H | H |
| XIV-50-4 | p-I—Ph | H | H | CH₂CH(CH₃)₂ | Bz | N₃ | F | H | OH | H | H |
| XIV-50-5 | p-I—Ph | H | H | CH₂Ph | Bz | N₃ | F | H | OH | H | H |
| XIV-50-6 | p-I—Ph | H | H | CH₂-indol-3-yl | Bz | N₃ | F | H | OH | H | H |
| XIV-50-7 | p-I—Ph | H | H | CH₂CH₂SCH₃ | Bz | N₃ | F | H | OH | H | H |
| XIV-50-8 | p-I—Ph | * | H | * | Bz | N₃ | F | H | OH | H | H |

*R² and R³ᵇ joined together by (CH₂)₃ to form five-membered ring.

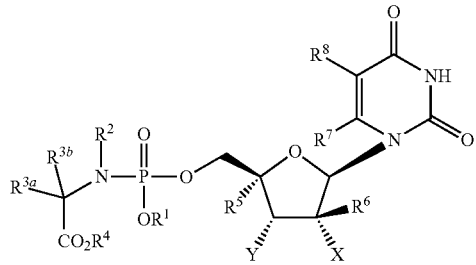

XV

TABLE XV-1

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-1-1 | CH₃ | H | H | H | CH₃ | F | F | H | OH | H | H |
| XV-1-2 | CH₃ | H | H | CH₃ | CH₃ | F | F | H | OH | H | H |
| XV-1-3 | CH₃ | H | H | CH(CH₃)₂ | CH₃ | F | F | H | OH | H | H |
| XV-1-4 | CH₃ | H | H | CH₂CH(CH₃)₂ | CH₃ | F | F | H | OH | H | H |
| XV-1-5 | CH₃ | H | H | CH₂Ph | CH₃ | F | F | H | OH | H | H |
| XV-1-6 | CH₃ | H | H | CH₂-indol-3-yl | CH₃ | F | F | H | OH | H | H |
| XV-1-7 | CH₃ | H | H | CH₂CH₂SCH₃ | CH₃ | F | F | H | OH | H | H |
| XV-1-8 | CH₃ | * | H | * | CH₃ | F | F | H | OH | H | H |

*R² and R³ᵇ joined together by (CH₂)₃ to form five-membered ring.

TABLE XV-2

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-2-1 | Et | H | H | H | CH₃ | F | F | H | OH | H | H |
| XV-2-2 | Et | H | H | CH₃ | CH₃ | F | F | H | OH | H | H |
| XV-2-3 | Et | H | H | CH(CH₃)₂ | CH₃ | F | F | H | OH | H | H |
| XV-2-4 | Et | H | H | CH₂CH(CH₃)₂ | CH₃ | F | F | H | OH | H | H |
| XV-2-5 | Et | H | H | CH₂Ph | CH₃ | F | F | H | OH | H | H |
| XV-2-6 | Et | H | H | CH₂-indol-3-yl | CH₃ | F | F | H | OH | H | H |
| XV-2-7 | Et | H | H | CH₂CH₂SCH₃ | CH₃ | F | F | H | OH | H | H |
| XV-2-8 | Et | * | H | * | CH₃ | F | F | H | OH | H | H |

*R² and R³ᵇ joined together by (CH₂)₃ to form five-membered ring.

TABLE XV-3

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-3-1 | ⁱPr | H | H | H | CH₃ | F | F | H | OH | H | H |
| XV-3-2 | ⁱPr | H | H | CH₃ | CH₃ | F | F | H | OH | H | H |
| XV-3-3 | ⁱPr | H | H | CH(CH₃)₂ | CH₃ | F | F | H | OH | H | H |
| XV-3-4 | ⁱPr | H | H | CH₂CH(CH₃)₂ | CH₃ | F | F | H | OH | H | H |
| XV-3-5 | ⁱPr | H | H | CH₂Ph | CH₃ | F | F | H | OH | H | H |
| XV-3-6 | ⁱPr | H | H | CH₂-indol-3-yl | CH₃ | F | F | H | OH | H | H |
| XV-3-7 | ⁱPr | H | H | CH₂CH₂SCH₃ | CH₃ | F | F | H | OH | H | H |
| XV-3-8 | ⁱPr | * | H | * | CH₃ | F | F | H | OH | H | H |

*R² and R³ᵇ joined together by (CH₂)₃ to form five-membered ring.

TABLE XV-4

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-4-1 | ᵗBu | H | H | H | CH₃ | F | F | H | OH | H | H |
| XV-4-2 | ᵗBu | H | H | CH₃ | CH₃ | F | F | H | OH | H | H |
| XV-4-3 | ᵗBu | H | H | CH(CH₃)₂ | CH₃ | F | F | H | OH | H | H |
| XV-4-4 | ᵗBu | H | H | CH₂CH(CH₃)₂ | CH₃ | F | F | H | OH | H | H |
| XV-4-5 | ᵗBu | H | H | CH₂Ph | CH₃ | F | F | H | OH | H | H |
| XV-4-6 | ᵗBu | H | H | CH₂-indol-3-yl | CH₃ | F | F | H | OH | H | H |
| XV-4-7 | ᵗBu | H | H | CH₂CH₂SCH₃ | CH₃ | F | F | H | OH | H | H |
| XV-4-8 | ᵗBu | * | H | * | CH₃ | F | F | H | OH | H | H |

*R² and R³ᵇ joined together by (CH₂)₃ to form five-membered ring.

TABLE XV-5

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-5-1 | Ph | H | H | H | CH₃ | F | F | H | OH | H | H |
| XV-5-2 | Ph | H | H | CH₃ | CH₃ | F | F | H | OH | H | H |
| XV-5-3 | Ph | H | H | CH(CH₃)₂ | CH₃ | F | F | H | OH | H | H |
| XV-5-4 | Ph | H | H | CH₂CH(CH₃)₂ | CH₃ | F | F | H | OH | H | H |
| XV-5-5 | Ph | H | H | CH₂Ph | CH₃ | F | F | H | OH | H | H |

TABLE XV-5-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-5-6 | Ph | H | H | CH₂-indol-3-yl | CH₃ | F | F | H | OH | H | H |
| XV-5-7 | Ph | H | H | CH₂CH₂SCH₃ | CH₃ | F | F | H | OH | H | H |
| XV-5-8 | Ph | * | H | * | CH₃ | F | F | H | OH | H | H |

*R² and R³ᵇ joined together by (CH₂)₃ to form five-membered ring.

TABLE XV-6

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-6-1 | p-Me—Ph | H | H | H | CH₃ | F | F | H | OH | H | H |
| XV-6-2 | p-Me—Ph | H | H | CH₃ | CH₃ | F | F | H | OH | H | H |
| XV-6-3 | p-Me—Ph | H | H | CH(CH₃)₂ | CH₃ | F | F | H | OH | H | H |
| XV-6-4 | p-Me—Ph | H | H | CH₂CH(CH₃)₂ | CH₃ | F | F | H | OH | H | H |
| XV-6-5 | p-Me—Ph | H | H | CH₂Ph | CH₃ | F | F | H | OH | H | H |
| XV-6-6 | p-Me—Ph | H | H | CH₂-indol-3-yl | CH₃ | F | F | H | OH | H | H |
| XV-6-7 | p-Me—Ph | H | H | CH₂CH₂SCH₃ | CH₃ | F | F | H | OH | H | H |
| XV-6-8 | p-Me—Ph | * | H | * | CH₃ | F | F | H | OH | H | H |

*R² and R³ᵇ joined together by (CH₂)₃ to form five-membered ring.

TABLE XV-7

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-7-1 | p-F—Ph | H | H | H | CH₃ | F | F | H | OH | H | H |
| XV-7-2 | p-F—Ph | H | H | CH₃ | CH₃ | F | F | H | OH | H | H |
| XV-7-3 | p-F—Ph | H | H | CH(CH₃)₂ | CH₃ | F | F | H | OH | H | H |
| XV-7-4 | p-F—Ph | H | H | CH₂CH(CH₃)₂ | CH₃ | F | F | H | OH | H | H |
| XV-7-6 | p-F—Ph | H | H | CH₂Ph | CH₃ | F | F | H | OH | H | H |
| XV-7-7 | p-F—Ph | H | H | CH₂-indol-3-yl | CH₃ | F | F | H | OH | H | H |
| XV-7-8 | p-F—Ph | H | H | CH₂CH₂SCH₃ | CH₃ | F | F | H | OH | H | H |
| XV-7-20 | p-F—Ph | * | H | * | CH₃ | F | F | H | OH | H | H |

*R² and R³ᵇ joined together by (CH₂)₃ to form five-membered ring.

TABLE XV-8

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-8-1 | p-Cl—Ph | H | H | H | CH₃ | F | F | H | OH | H | H |
| XV-8-2 | p-Cl—Ph | H | H | CH₃ | CH₃ | F | F | H | OH | H | H |
| XV-8-3 | p-Cl—Ph | H | H | CH(CH₃)₂ | CH₃ | F | F | H | OH | H | H |
| XV-8-4 | p-Cl—Ph | H | H | CH₂CH(CH₃)₂ | CH₃ | F | F | H | OH | H | H |
| XV-8-5 | p-Cl—Ph | H | H | CH₂Ph | CH₃ | F | F | H | OH | H | H |
| XV-8-6 | p-Cl—Ph | H | H | CH₂-indol-3-yl | CH₃ | F | F | H | OH | H | H |
| XV-8-7 | p-Cl—Ph | H | H | CH₂CH₂SCH₃ | CH₃ | F | F | H | OH | H | H |
| XV-8-8 | p-Cl—Ph | * | H | * | CH₃ | F | F | H | OH | H | H |

*R² and R³ᵇ joined together by (CH₂)₃ to form five-membered ring.

TABLE XV-9

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-9-1 | p-Br—Ph | H | H | H | CH₃ | F | F | H | OH | H | H |
| XV-9-2 | p-Br—Ph | H | H | CH₃ | CH₃ | F | F | H | OH | H | H |
| XV-9-3 | p-Br—Ph | H | H | CH(CH₃)₂ | CH₃ | F | F | H | OH | H | H |
| XV-9-4 | p-Br—Ph | H | H | CH₂CH(CH₃)₂ | CH₃ | F | F | H | OH | H | H |
| XV-9-6 | p-Br—Ph | H | H | CH₂Ph | CH₃ | F | F | H | OH | H | H |
| XV-9-7 | p-Br—Ph | H | H | CH₂-indol-3-yl | CH₃ | F | F | H | OH | H | H |
| XV-9-8 | p-Br—Ph | H | H | CH₂CH₂SCH₃ | CH₃ | F | F | H | OH | H | H |
| XV-9-20 | p-Br—Ph | * | H | * | CH₃ | F | F | H | OH | H | H |

*R² and R³ᵇ joined together by (CH₂)₃ to form five-membered ring.

TABLE XV-10

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-10-1 | p-I—Ph | H | H | H | CH₃ | F | F | H | OH | H | H |
| XV-10-2 | p-I—Ph | H | H | CH₃ | CH₃ | F | F | H | OH | H | H |
| XV-10-3 | p-I—Ph | H | H | CH(CH₃)₂ | CH₃ | F | F | H | OH | H | H |
| XV-10-4 | p-I—Ph | H | H | CH₂CH(CH₃)₂ | CH₃ | F | F | H | OH | H | H |
| XV-10-5 | p-I—Ph | H | H | CH₂Ph | CH₃ | F | F | H | OH | H | H |
| XV-10-6 | p-I—Ph | H | H | CH₂-indol-3-yl | CH₃ | F | F | H | OH | H | H |
| XV-10-7 | p-I—Ph | H | H | CH₂CH₂SCH₃ | CH₃ | F | F | H | OH | H | H |
| XV-10-8 | p-I—Ph | * | H | * | CH₃ | F | F | H | OH | H | H |

*R² and R³ᵇ joined together by (CH₂)₃ to form five-membered ring.

TABLE XV-11

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-11-1 | CH₃ | H | H | H | Et | F | F | H | OH | H | H |
| XV-11-2 | CH₃ | H | H | CH₃ | Et | F | F | H | OH | H | H |
| XV-11-3 | CH₃ | H | H | CH(CH₃)₂ | Et | F | F | H | OH | H | H |
| XV-11-4 | CH₃ | H | H | CH₂CH(CH₃)₂ | Et | F | F | H | OH | H | H |
| XV-11-5 | CH₃ | H | H | CH₂Ph | Et | F | F | H | OH | H | H |
| XV-11-6 | CH₃ | H | H | CH₂-indol-3-yl | Et | F | F | H | OH | H | H |
| XV-11-7 | CH₃ | H | H | CH₂CH₂SCH₃ | Et | F | F | H | OH | H | H |
| XV-11-8 | CH₃ | * | H | * | Et | F | F | H | OH | H | H |

*R² and R³ᵇ joined together by (CH₂)₃ to form five-membered ring.

TABLE XV-12

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-12-1 | Et | H | H | H | Et | F | F | H | OH | H | H |
| XV-12-2 | Et | H | H | CH₃ | Et | F | F | H | OH | H | H |
| XV-12-3 | Et | H | H | CH(CH₃)₂ | Et | F | F | H | OH | H | H |
| XV-12-4 | Et | H | H | CH₂CH(CH₃)₂ | Et | F | F | H | OH | H | H |
| XV-12-5 | Et | H | H | CH₂Ph | Et | F | F | H | OH | H | H |
| XV-12-6 | Et | H | H | CH₂-indol-3-yl | Et | F | F | H | OH | H | H |
| XV-12-7 | Et | H | H | CH₂CH₂SCH₃ | Et | F | F | H | OH | H | H |
| XV-12-8 | Et | * | H | * | Et | F | F | H | OH | H | H |

*R² and R³ᵇ joined together by (CH₂)₃ to form five-membered ring.

TABLE XV-13

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-13-1 | ⁱPr | H | H | H | Et | F | F | H | OH | H | H |
| XV-13-2 | ⁱPr | H | H | CH₃ | Et | F | F | H | OH | H | H |
| XV-13-3 | ⁱPr | H | H | CH(CH₃)₂ | Et | F | F | H | OH | H | H |
| XV-13-4 | ⁱPr | H | H | CH₂CH(CH₃)₂ | Et | F | F | H | OH | H | H |
| XV-13-5 | ⁱPr | H | H | CH₂Ph | Et | F | F | H | OH | H | H |
| XV-13-6 | ⁱPr | H | H | CH₂-indol-3-yl | Et | F | F | H | OH | H | H |
| XV-13-7 | ⁱPr | H | H | CH₂CH₂SCH₃ | Et | F | F | H | OH | H | H |
| XV-13-8 | ⁱPr | * | H | * | Et | F | F | H | OH | H | H |

*R² and R³ᵇ joined together by (CH₂)₃ to form five-membered ring.

TABLE XV-14

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-14-1 | ᵗBu | H | H | H | Et | F | F | H | OH | H | H |
| XV-14-2 | ᵗBu | H | H | CH₃ | Et | F | F | H | OH | H | H |
| XV-14-3 | ᵗBu | H | H | CH(CH₃)₂ | Et | F | F | H | OH | H | H |
| XV-14-4 | ᵗBu | H | H | CH₂CH(CH₃)₂ | Et | F | F | H | OH | H | H |
| XV-14-5 | ᵗBu | H | H | CH₂Ph | Et | F | F | H | OH | H | H |
| XV-14-6 | ᵗBu | H | H | CH₂-indol-3-yl | Et | F | F | H | OH | H | H |
| XV-14-7 | ᵗBu | H | H | CH₂CH₂SCH₃ | Et | F | F | H | OH | H | H |
| XV-14-8 | ᵗBu | * | H | * | Et | F | F | H | OH | H | H |

*R² and R³ᵇ joined together by (CH₂)₃ to form five-membered ring.

TABLE XV-15

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-15-1 | Ph | H | H | H | Et | F | F | H | OH | H | H |
| XV-15-2 | Ph | H | H | CH₃ | Et | F | F | H | OH | H | H |
| XV-15-3 | Ph | H | H | CH(CH₃)₂ | Et | F | F | H | OH | H | H |
| XV-15-4 | Ph | H | H | CH₂CH(CH₃)₂ | Et | F | F | H | OH | H | H |
| XV-15-5 | Ph | H | H | CH₂Ph | Et | F | F | H | OH | H | H |
| XV-15-6 | Ph | H | H | CH₂-indol-3-yl | Et | F | F | H | OH | H | H |
| XV-15-7 | Ph | H | H | CH₂CH₂SCH₃ | Et | F | F | H | OH | H | H |
| XV-15-8 | Ph | * | H | * | Et | F | F | H | OH | H | H |

*R² and R³ᵇ joined together by (CH₂)₃ to form five-membered ring.

TABLE XV-16

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-16-1 | p-Me—Ph | H | H | H | Et | F | F | H | OH | H | H |
| XV-16-2 | p-Me—Ph | H | H | CH₃ | Et | F | F | H | OH | H | H |
| XV-16-3 | p-Me—Ph | H | H | CH(CH₃)₂ | Et | F | F | H | OH | H | H |
| XV-16-4 | p-Me—Ph | H | H | CH₂CH(CH₃)₂ | Et | F | F | H | OH | H | H |
| XV-16-5 | p-Me—Ph | H | H | CH₂Ph | Et | F | F | H | OH | H | H |
| XV-16-6 | p-Me—Ph | H | H | CH₂-indol-3-yl | Et | F | F | H | OH | H | H |
| XV-16-7 | p-Me—Ph | H | H | CH₂CH₂SCH₃ | Et | F | F | H | OH | H | H |
| XV-16-8 | p-Me—Ph | * | H | * | Et | F | F | H | OH | H | H |

*R² and R³ᵇ joined together by (CH₂)₃ to form five-membered ring.

TABLE XV-17

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-17-1 | p-F—Ph | H | H | H | Et | F | F | H | OH | H | H |
| XV-17-2 | p-F—Ph | H | H | CH₃ | Et | F | F | H | OH | H | H |
| XV-17-3 | p-F—Ph | H | H | CH(CH₃)₂ | Et | F | F | H | OH | H | H |
| XV-17-4 | p-F—Ph | H | H | CH₂CH(CH₃)₂ | Et | F | F | H | OH | H | H |
| XV-17-5 | p-F—Ph | H | H | CH₂Ph | Et | F | F | H | OH | H | H |
| XV-17-6 | p-F—Ph | H | H | CH₂-indol-3-yl | Et | F | F | H | OH | H | H |
| XV-17-7 | p-F—Ph | H | H | CH₂CH₂SCH₃ | Et | F | F | H | OH | H | H |
| XV-17-8 | p-F—Ph | * | H | * | Et | F | F | H | OH | H | H |

*R² and R³ᵇ joined together by (CH₂)₃ to form five-membered ring.

TABLE XV-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-18-1 | p-Cl—Ph | H | H | H | Et | F | F | H | OH | H | H |
| XV-18-2 | p-Cl—Ph | H | H | CH₃ | Et | F | F | H | OH | H | H |
| XV-18-3 | p-Cl—Ph | H | H | CH(CH₃)₂ | Et | F | F | H | OH | H | H |
| XV-18-4 | p-Cl—Ph | H | H | CH₂CH(CH₃)₂ | Et | F | F | H | OH | H | H |
| XV-18-5 | p-Cl—Ph | H | H | CH₂Ph | Et | F | F | H | OH | H | H |
| XV-18-6 | p-Cl—Ph | H | H | CH₂-indol-3-yl | Et | F | F | H | OH | H | H |
| XV-18-7 | p-Cl—Ph | H | H | CH₂CH₂SCH₃ | Et | F | F | H | OH | H | H |
| XV-18-8 | p-Cl—Ph | * | H | * | Et | F | F | H | OH | H | H |

*R² and R³ᵇ joined together by (CH₂)₃ to form five-membered ring.

TABLE XV-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-19-1 | p-Br—Ph | H | H | H | Et | F | F | H | OH | H | H |
| XV-19-2 | p-Br—Ph | H | H | CH₃ | Et | F | F | H | OH | H | H |
| XV-19-3 | p-Br—Ph | H | H | CH(CH₃)₂ | Et | F | F | H | OH | H | H |
| XV-19-4 | p-Br—Ph | H | H | CH₂CH(CH₃)₂ | Et | F | F | H | OH | H | H |
| XV-19-5 | p-Br—Ph | H | H | CH₂Ph | Et | F | F | H | OH | H | H |
| XV-19-6 | p-Br—Ph | H | H | CH₂-indol-3-yl | Et | F | F | H | OH | H | H |
| XV-19-7 | p-Br—Ph | H | H | CH₂CH₂SCH₃ | Et | F | F | H | OH | H | H |
| XV-19-8 | p-Br—Ph | * | H | * | Et | F | F | H | OH | H | H |

*R² and R³ᵇ joined together by (CH₂)₃ to form five-membered ring.

TABLE XV-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-20-1 | p-I—Ph | H | H | H | Et | F | F | H | OH | H | H |
| XV-20-2 | p-I—Ph | H | H | CH₃ | Et | F | F | H | OH | H | H |
| XV-20-3 | p-I—Ph | H | H | CH(CH₃)₂ | Et | F | F | H | OH | H | H |
| XV-20-4 | p-I—Ph | H | H | CH₂CH(CH₃)₂ | Et | F | F | H | OH | H | H |
| XV-20-5 | p-I—Ph | H | H | CH₂Ph | Et | F | F | H | OH | H | H |

TABLE XV-20-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-20-6 | p-I—Ph | H | H | CH$_2$-indol-3-yl | Et | F | F | H | OH | H | H |
| XV-20-7 | p-I—Ph | H | H | CH$_2$CH$_2$SCH$_3$ | Et | F | F | H | OH | H | H |
| XV-20-8 | p-I—Ph | * | H | * | Et | F | F | H | OH | H | H |

*R$^2$ and R$^{3b}$ joined together by (CH$_2$)$_3$ to form five-membered ring.

TABLE XV-21

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-21-1 | CH$_3$ | H | H | H | $^i$Pr | F | F | H | OH | H | H |
| XV-21-2 | CH$_3$ | H | H | CH$_3$ | $^i$Pr | F | F | H | OH | H | H |
| XV-21-3 | CH$_3$ | H | H | CH(CH$_3$)$_2$ | $^i$Pr | F | F | H | OH | H | H |
| XV-21-4 | CH$_3$ | H | H | CH$_2$CH(CH$_3$)$_2$ | $^i$Pr | F | F | H | OH | H | H |
| XV-21-5 | CH$_3$ | H | H | CH$_2$Ph | $^i$Pr | F | F | H | OH | H | H |
| XV-21-6 | CH$_3$ | H | H | CH$_2$-indol-3-yl | $^i$Pr | F | F | H | OH | H | H |
| XV-21-7 | CH$_3$ | H | H | CH$_2$CH$_2$SCH$_3$ | $^i$Pr | F | F | H | OH | H | H |
| XV-21-8 | CH$_3$ | * | H | * | $^i$Pr | F | F | H | OH | H | H |

*R$^2$ and R$^{3b}$ joined together by (CH$_2$)$_3$ to form five-membered ring.

TABLE XV-22

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-22-1 | Et | H | H | H | $^i$Pr | F | F | H | OH | H | H |
| XV-22-2 | Et | H | H | CH$_3$ | $^i$Pr | F | F | H | OH | H | H |
| XV-22-3 | Et | H | H | CH(CH$_3$)$_2$ | $^i$Pr | F | F | H | OH | H | H |
| XV-22-4 | Et | H | H | CH$_2$CH(CH$_3$)$_2$ | $^i$Pr | F | F | H | OH | H | H |
| XV-22-5 | Et | H | H | CH$_2$Ph | $^i$Pr | F | F | H | OH | H | H |
| XV-22-6 | Et | H | H | CH$_2$-indol-3-yl | $^i$Pr | F | F | H | OH | H | H |
| XV-22-7 | Et | H | H | CH$_2$CH$_2$SCH$_3$ | $^i$Pr | F | F | H | OH | H | H |
| XV-22-8 | Et | * | H | * | $^i$Pr | F | F | H | OH | H | H |

*R$^2$ and R$^{3b}$ joined together by (CH$_2$)$_3$ to form five-membered ring.

TABLE XV-23

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-23-1 | $^i$Pr | H | H | H | $^i$Pr | F | F | H | OH | H | H |
| XV-23-2 | $^i$Pr | H | H | CH$_3$ | $^i$Pr | F | F | H | OH | H | H |
| XV-23-3 | $^i$Pr | H | H | CH(CH$_3$)$_2$ | $^i$Pr | F | F | H | OH | H | H |
| XV-23-4 | $^i$Pr | H | H | CH$_2$CH(CH$_3$)$_2$ | $^i$Pr | F | F | H | OH | H | H |
| XV-23-5 | $^i$Pr | H | H | CH$_2$Ph | $^i$Pr | F | F | H | OH | H | H |
| XV-23-6 | $^i$Pr | H | H | CH$_2$-indol-3-yl | $^i$Pr | F | F | H | OH | H | H |
| XV-23-7 | $^i$Pr | H | H | CH$_2$CH$_2$SCH$_3$ | $^i$Pr | F | F | H | OH | H | H |
| XV-23-8 | $^i$Pr | * | H | * | $^i$Pr | F | F | H | OH | H | H |

*R$^2$ and R$^{3b}$ joined together by (CH$_2$)$_3$ to form five-membered ring.

TABLE XV-24

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-24-1 | $^t$Bu | H | H | H | $^i$Pr | F | F | H | OH | H | H |
| XV-24-2 | $^t$Bu | H | H | CH$_3$ | $^i$Pr | F | F | H | OH | H | H |
| XV-24-3 | $^t$Bu | H | H | CH(CH$_3$)$_2$ | $^i$Pr | F | F | H | OH | H | H |
| XV-24-4 | $^t$Bu | H | H | CH$_2$CH(CH$_3$)$_2$ | $^i$Pr | F | F | H | OH | H | H |
| XV-24-5 | $^t$Bu | H | H | CH$_2$Ph | $^i$Pr | F | F | H | OH | H | H |
| XV-24-6 | $^t$Bu | H | H | CH$_2$-indol-3-yl | $^i$Pr | F | F | H | OH | H | H |
| XV-24-7 | $^t$Bu | H | H | CH$_2$CH$_2$SCH$_3$ | $^i$Pr | F | F | H | OH | H | H |
| XV-24-8 | $^t$Bu | * | H | * | $^i$Pr | F | F | H | OH | H | H |

*R$^2$ and R$^{3b}$ joined together by (CH$_2$)$_3$ to form five-membered ring.

TABLE XV-25

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-25-1 | Ph | H | H | H | $^i$Pr | F | F | H | OH | H | H |
| XV-25-2 | Ph | H | H | CH$_3$ | $^i$Pr | F | F | H | OH | H | H |
| XV-25-3 | Ph | H | H | CH(CH$_3$)$_2$ | $^i$Pr | F | F | H | OH | H | H |
| XV-25-4 | Ph | H | H | CH$_2$CH(CH$_3$)$_2$ | $^i$Pr | F | F | H | OH | H | H |
| XV-25-5 | Ph | H | H | CH$_2$Ph | $^i$Pr | F | F | H | OH | H | H |
| XV-25-6 | Ph | H | H | CH$_2$-indol-3-yl | $^i$Pr | F | F | H | OH | H | H |
| XV-25-7 | Ph | H | H | CH$_2$CH$_2$SCH$_3$ | $^i$Pr | F | F | H | OH | H | H |
| XV-25-8 | Ph | * | H | * | $^i$Pr | F | F | H | OH | H | H |

*R$^2$ and R$^{3b}$ joined together by (CH$_2$)$_3$ to form five-membered ring.

TABLE XV-26

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-26-1 | p-Me—Ph | H | H | H | $^i$Pr | F | F | H | OH | H | H |
| XV-26-2 | p-Me—Ph | H | H | CH$_3$ | $^i$Pr | F | F | H | OH | H | H |
| XV-26-3 | p-Me—Ph | H | H | CH(CH$_3$)$_2$ | $^i$Pr | F | F | H | OH | H | H |

TABLE XV-26-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-26-4 | p-Me—Ph | H | H | CH₂CH(CH₃)₂ | ⁱPr | F | F | H | OH | H | H |
| XV-26-5 | p-Me—Ph | H | H | CH₂Ph | ⁱPr | F | F | H | OH | H | H |
| XV-26-6 | p-Me—Ph | H | H | CH₂-indol-3-yl | ⁱPr | F | F | H | OH | H | H |
| XV-26-7 | p-Me—Ph | H | H | CH₂CH₂SCH₃ | ⁱPr | F | F | H | OH | H | H |
| XV-26-8 | p-Me—Ph | * | H | * | ⁱPr | F | F | H | OH | H | H |

*R² and R³ᵇ joined together by (CH₂)₃ to form five-membered ring.

TABLE XV-27

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-27-1 | p-F—Ph | H | H | H | ⁱPr | F | F | H | OH | H | H |
| XV-27-2 | p-F—Ph | H | H | CH₃ | ⁱPr | F | F | H | OH | H | H |
| XV-27-3 | p-F—Ph | H | H | CH(CH₃)₂ | ⁱPr | F | F | H | OH | H | H |
| XV-27-4 | p-F—Ph | H | H | CH₂CH(CH₃)₂ | ⁱPr | F | F | H | OH | H | H |
| XV-27-5 | p-F—Ph | H | H | CH₂Ph | ⁱPr | F | F | H | OH | H | H |
| XV-27-6 | p-F—Ph | H | H | CH₂-indol-3-yl | ⁱPr | F | F | H | OH | H | H |
| XV-27-7 | p-F—Ph | H | H | CH₂CH₂SCH₃ | ⁱPr | F | F | H | OH | H | H |
| XV-27-8 | p-F—Ph | * | H | * | ⁱPr | F | F | H | OH | H | H |

*R² and R³ᵇ joined together by (CH₂)₃ to form five-membered ring.

TABLE XV-28

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-28-1 | p-Cl—Ph | H | H | H | ⁱPr | F | F | H | OH | H | H |
| XV-28-2 | p-Cl—Ph | H | H | CH₃ | ⁱPr | F | F | H | OH | H | H |
| XV-28-3 | p-Cl—Ph | H | H | CH(CH₃)₂ | ⁱPr | F | F | H | OH | H | H |
| XV-28-4 | p-Cl—Ph | H | H | CH₂CH(CH₃)₂ | ⁱPr | F | F | H | OH | H | H |
| XV-28-5 | p-Cl—Ph | H | H | CH₂Ph | ⁱPr | F | F | H | OH | H | H |
| XV-28-6 | p-Cl—Ph | H | H | CH₂-indol-3-yl | ⁱPr | F | F | H | OH | H | H |
| XV-28-7 | p-Cl—Ph | H | H | CH₂CH₂SCH₃ | ⁱPr | F | F | H | OH | H | H |
| XV-28-8 | p-Cl—Ph | * | H | * | ⁱPr | F | F | H | OH | H | H |

*R² and R³ᵇ joined together by (CH₂)₃ to form five-membered ring.

TABLE XV-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-29-1 | p-Br—Ph | H | H | H | ⁱPr | F | F | H | OH | H | H |
| XV-29-2 | p-Br—Ph | H | H | CH₃ | ⁱPr | F | F | H | OH | H | H |
| XV-29-3 | p-Br—Ph | H | H | CH(CH₃)₂ | ⁱPr | F | F | H | OH | H | H |
| XV-29-4 | p-Br—Ph | H | H | CH₂CH(CH₃)₂ | ⁱPr | F | F | H | OH | H | H |
| XV-29-5 | p-Br—Ph | H | H | CH₂Ph | ⁱPr | F | F | H | OH | H | H |
| XV-29-6 | p-Br—Ph | H | H | CH₂-indol-3-yl | ⁱPr | F | F | H | OH | H | H |
| XV-29-7 | p-Br—Ph | H | H | CH₂CH₂SCH₃ | ⁱPr | F | F | H | OH | H | H |
| XV-29-8 | p-Br—Ph | * | H | * | ⁱPr | F | F | H | OH | H | H |

*R² and R³ᵇ joined together by (CH₂)₃ to form five-membered ring.

TABLE XV-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-30-1 | p-I—Ph | H | H | H | ⁱPr | F | F | H | OH | H | H |
| XV-30-2 | p-I—Ph | H | H | CH₃ | ⁱPr | F | F | H | OH | H | H |
| XV-30-3 | p-I—Ph | H | H | CH(CH₃)₂ | ⁱPr | F | F | H | OH | H | H |
| XV-30-4 | p-I—Ph | H | H | CH₂CH(CH₃)₂ | ⁱPr | F | F | H | OH | H | H |
| XV-30-5 | p-I—Ph | H | H | CH₂Ph | ⁱPr | F | F | H | OH | H | H |
| XV-30-6 | p-I—Ph | H | H | CH₂-indol-3-yl | ⁱPr | F | F | H | OH | H | H |
| XV-30-7 | p-I—Ph | H | H | CH₂CH₂SCH₃ | ⁱPr | F | F | H | OH | H | H |
| XV-30-8 | p-I—Ph | * | H | * | ⁱPr | F | F | H | OH | H | H |

*R² and R³ᵇ joined together by (CH₂)₃ to form five-membered ring.

TABLE XV-31

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-31-1 | $CH_3$ | H | H | H | $^nBu$ | F | F | H | OH | H | H |
| XV-31-2 | $CH_3$ | H | H | $CH_3$ | $^nBu$ | F | F | H | OH | H | H |
| XV-31-3 | $CH_3$ | H | H | $CH(CH_3)_2$ | $^nBu$ | F | F | H | OH | H | H |
| XV-31-4 | $CH_3$ | H | H | $CH_2CH(CH_3)_2$ | $^nBu$ | F | F | H | OH | H | H |
| XV-31-5 | $CH_3$ | H | H | $CH_2Ph$ | $^nBu$ | F | F | H | OH | H | H |
| XV-31-6 | $CH_3$ | H | H | $CH_2$-indol-3-yl | $^nBu$ | F | F | H | OH | H | H |
| XV-31-7 | $CH_3$ | H | H | $CH_2CH_2SCH_3$ | $^nBu$ | F | F | H | OH | H | H |
| XV-31-8 | $CH_3$ | * | H | * | $^nBu$ | F | F | H | OH | H | H |

*$R^2$ and $R^{3b}$ joined together by $(CH_2)_3$ to form five-membered ring.

TABLE XV-32

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-32-1 | Et | H | H | H | $^nBu$ | F | F | H | OH | H | H |
| XV-32-2 | Et | H | H | $CH_3$ | $^nBu$ | F | F | H | OH | H | H |
| XV-32-3 | Et | H | H | $CH(CH_3)_2$ | $^nBu$ | F | F | H | OH | H | H |
| XV-32-4 | Et | H | H | $CH_2CH(CH_3)_2$ | $^nBu$ | F | F | H | OH | H | H |
| XV-32-5 | Et | H | H | $CH_2Ph$ | $^nBu$ | F | F | H | OH | H | H |
| XV-32-6 | Et | H | H | $CH_2$-indol-3-yl | $^nBu$ | F | F | H | OH | H | H |
| XV-32-7 | Et | H | H | $CH_2CH_2SCH_3$ | $^nBu$ | F | F | H | OH | H | H |
| XV-32-8 | Et | * | H | * | $^nBu$ | F | F | H | OH | H | H |

*$R^2$ and $R^{3b}$ joined together by $(CH_2)_3$ to form five-membered ring.

TABLE XV-33

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-33-1 | $^iPr$ | H | H | H | $^nBu$ | F | F | H | OH | H | H |
| XV-33-2 | $^iPr$ | H | H | $CH_3$ | $^nBu$ | F | F | H | OH | H | H |
| XV-33-3 | $^iPr$ | H | H | $CH(CH_3)_2$ | $^nBu$ | F | F | H | OH | H | H |
| XV-33-4 | $^iPr$ | H | H | $CH_2CH(CH_3)_2$ | $^nBu$ | F | F | H | OH | H | H |
| XV-33-5 | $^iPr$ | H | H | $CH_2Ph$ | $^nBu$ | F | F | H | OH | H | H |
| XV-33-6 | $^iPr$ | H | H | $CH_2$-indol-3-yl | $^nBu$ | F | F | H | OH | H | H |
| XV-33-7 | $^iPr$ | H | H | $CH_2CH_2SCH_3$ | $^nBu$ | F | F | H | OH | H | H |
| XV-33-8 | $^iPr$ | * | H | * | $^nBu$ | F | F | H | OH | H | H |

*$R^2$ and $R^{3b}$ joined together by $(CH_2)_3$ to form five-membered ring.

TABLE XV-34

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-34-1 | $^tBu$ | H | H | H | $^nBu$ | F | F | H | OH | H | H |
| XV-34-2 | $^tBu$ | H | H | $CH_3$ | $^nBu$ | F | F | H | OH | H | H |
| XV-34-3 | $^tBu$ | H | H | $CH(CH_3)_2$ | $^nBu$ | F | F | H | OH | H | H |
| XV-34-4 | $^tBu$ | H | H | $CH_2CH(CH_3)_2$ | $^nBu$ | F | F | H | OH | H | H |
| XV-34-5 | $^tBu$ | H | H | $CH_2Ph$ | $^nBu$ | F | F | H | OH | H | H |
| XV-34-6 | $^tBu$ | H | H | $CH_2$-indol-3-yl | $^nBu$ | F | F | H | OH | H | H |
| XV-34-7 | $^tBu$ | H | H | $CH_2CH_2SCH_3$ | $^nBu$ | F | F | H | OH | H | H |
| XV-34-8 | $^tBu$ | * | H | * | $^nBu$ | F | F | H | OH | H | H |

*$R^2$ and $R^{3b}$ joined together by $(CH_2)_3$ to form five-membered ring.

TABLE XV-35

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-35-1 | Ph | H | H | H | $^nBu$ | F | F | H | OH | H | H |
| XV-35-2 | Ph | H | H | $CH_3$ | $^nBu$ | F | F | H | OH | H | H |
| XV-35-3 | Ph | H | H | $CH(CH_3)_2$ | $^nBu$ | F | F | H | OH | H | H |
| XV-35-4 | Ph | H | H | $CH_2CH(CH_3)_2$ | $^nBu$ | F | F | H | OH | H | H |
| XV-35-5 | Ph | H | H | $CH_2Ph$ | $^nBu$ | F | F | H | OH | H | H |
| XV-35-6 | Ph | H | H | $CH_2$-indol-3-yl | $^nBu$ | F | F | H | OH | H | H |
| XV-35-7 | Ph | H | H | $CH_2CH_2SCH_3$ | $^nBu$ | F | F | H | OH | H | H |
| XV-35-8 | Ph | * | H | * | $^nBu$ | F | F | H | OH | H | H |

*$R^2$ and $R^{3b}$ joined together by $(CH_2)_3$ to form five-membered ring.

TABLE XV-36

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-36-1 | p-Me—Ph | H | H | H | $^nBu$ | F | F | H | OH | H | H |
| XV-36-2 | p-Me—Ph | H | H | $CH_3$ | $^nBu$ | F | F | H | OH | H | H |
| XV-36-3 | p-Me—Ph | H | H | $CH(CH_3)_2$ | $^nBu$ | F | F | H | OH | H | H |
| XV-36-4 | p-Me—Ph | H | H | $CH_2CH(CH_3)_2$ | $^nBu$ | F | F | H | OH | H | H |
| XV-36-5 | p-Me—Ph | H | H | $CH_2Ph$ | $^nBu$ | F | F | H | OH | H | H |
| XV-36-6 | p-Me—Ph | H | H | $CH_2$-indol-3-yl | $^nBu$ | F | F | H | OH | H | H |
| XV-36-7 | p-Me—Ph | H | H | $CH_2CH_2SCH_3$ | $^nBu$ | F | F | H | OH | H | H |
| XV-36-8 | p-Me—Ph | * | H | * | $^nBu$ | F | F | H | OH | H | H |

*$R^2$ and $R^{3b}$ joined together by $(CH_2)_3$ to form five-membered ring.

TABLE XV-37

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-37-1 | p-F—Ph | H | H | H | $^n$Bu | F | F | H | OH | H | H |
| XV-37-2 | p-F—Ph | H | H | CH$_3$ | $^n$Bu | F | F | H | OH | H | H |
| XV-37-3 | p-F—Ph | H | H | CH(CH$_3$)$_2$ | $^n$Bu | F | F | H | OH | H | H |
| XV-37-4 | p-F—Ph | H | H | CH$_2$CH(CH$_3$)$_2$ | $^n$Bu | F | F | H | OH | H | H |
| XV-37-5 | p-F—Ph | H | H | CH$_2$Ph | $^n$Bu | F | F | H | OH | H | H |
| XV-37-6 | p-F—Ph | H | H | CH$_2$-indol-3-yl | $^n$Bu | F | F | H | OH | H | H |
| XV-37-7 | p-F—Ph | H | H | CH$_2$CH$_2$SCH$_3$ | $^n$Bu | F | F | H | OH | H | H |
| XV-37-8 | p-F—Ph | * | H | * | $^n$Bu | F | F | H | OH | H | H |

*R$^2$ and R$^{3b}$ joined together by (CH$_2$)$_3$ to form five-membered ring.

TABLE XV-38

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-38-1 | p-Cl—Ph | H | H | H | $^n$Bu | F | F | H | OH | H | H |
| XV-38-2 | p-Cl—Ph | H | H | CH$_3$ | $^n$Bu | F | F | H | OH | H | H |
| XV-38-3 | p-Cl—Ph | H | H | CH(CH$_3$)$_2$ | $^n$Bu | F | F | H | OH | H | H |
| XV-38-4 | p-Cl—Ph | H | H | CH$_2$CH(CH$_3$)$_2$ | $^n$Bu | F | F | H | OH | H | H |
| XV-38-5 | p-Cl—Ph | H | H | CH$_2$Ph | $^n$Bu | F | F | H | OH | H | H |
| XV-38-6 | p-Cl—Ph | H | H | CH$_2$-indol-3-yl | $^n$Bu | F | F | H | OH | H | H |
| XV-38-7 | p-Cl—Ph | H | H | CH$_2$CH$_2$SCH$_3$ | $^n$Bu | F | F | H | OH | H | H |
| XV-38-8 | p-Cl—Ph | * | H | * | $^n$Bu | F | F | H | OH | H | H |

*R$^2$ and R$^{3b}$ joined together by (CH$_2$)$_3$ to form five-membered ring.

TABLE XV-39

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-39-1 | p-Br—Ph | H | H | H | $^n$Bu | F | F | H | OH | H | H |
| XV-39-2 | p-Br—Ph | H | H | CH$_3$ | $^n$Bu | F | F | H | OH | H | H |
| XV-39-3 | p-Br—Ph | H | H | CH(CH$_3$)$_2$ | $^n$Bu | F | F | H | OH | H | H |
| XV-39-4 | p-Br—Ph | H | H | CH$_2$CH(CH$_3$)$_2$ | $^n$Bu | F | F | H | OH | H | H |
| XV-39-5 | p-Br—Ph | H | H | CH$_2$Ph | $^n$Bu | F | F | H | OH | H | H |
| XV-39-6 | p-Br—Ph | H | H | CH$_2$-indol-3-yl | $^n$Bu | F | F | H | OH | H | H |
| XV-39-7 | p-Br—Ph | H | H | CH$_2$CH$_2$SCH$_3$ | $^n$Bu | F | F | H | OH | H | H |
| XV-39-8 | p-Br—Ph | * | H | * | $^n$Bu | F | F | H | OH | H | H |

*R$^2$ and R$^{3b}$ joined together by (CH$_2$)$_3$ to form five-membered ring.

TABLE XV-40

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-40-1 | p-I—Ph | H | H | H | $^n$Bu | F | F | H | OH | H | H |
| XV-40-2 | p-I—Ph | H | H | CH$_3$ | $^n$Bu | F | F | H | OH | H | H |
| XV-40-3 | p-I—Ph | H | H | CH(CH$_3$)$_2$ | $^n$Bu | F | F | H | OH | H | H |
| XV-40-4 | p-I—Ph | H | H | CH$_2$CH(CH$_3$)$_2$ | $^n$Bu | F | F | H | OH | H | H |
| XV-40-5 | p-I—Ph | H | H | CH$_2$Ph | $^n$Bu | F | F | H | OH | H | H |
| XV-40-6 | p-I—Ph | H | H | CH$_2$-indol-3-yl | $^n$Bu | F | F | H | OH | H | H |
| XV-40-7 | p-I—Ph | H | H | CH$_2$CH$_2$SCH$_3$ | $^n$Bu | F | F | H | OH | H | H |
| XV-40-8 | p-I—Ph | * | H | * | $^n$Bu | F | F | H | OH | H | H |

*R$^2$ and R$^{3b}$ joined together by (CH$_2$)$_3$ to form five-membered ring.

TABLE XV-41

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XV-41-1 | CH$_3$ | H | H | H | Bz | F | F | H | OH | H | H |
| XV-41-2 | CH$_3$ | H | H | CH$_3$ | Bz | F | F | H | OH | H | H |
| XV-41-3 | CH$_3$ | H | H | CH(CH$_3$)$_2$ | Bz | F | F | H | OH | H | H |
| XV-41-4 | CH$_3$ | H | H | CH$_2$CH(CH$_3$)$_2$ | Bz | F | F | H | OH | H | H |
| XV-41-5 | CH$_3$ | H | H | CH$_2$Ph | Bz | F | F | H | OH | H | H |
| XV-41-6 | CH$_3$ | H | H | CH$_2$-indol-3-yl | Bz | F | F | H | OH | H | H |

TABLE XV-41-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-41-7 | $CH_3$ | H | H | $CH_2CH_2SCH_3$ | Bz | F | F | H | OH | H | H |
| XV-41-8 | $CH_3$ | * | H | * | Bz | F | F | H | OH | H | H |

*$R^2$ and $R^{3b}$ joined together by $(CH_2)_3$ to form five-membered ring.

TABLE XV-42

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-42-1 | Et | H | H | H | Bz | F | F | H | OH | H | H |
| XV-42-2 | Et | H | H | $CH_3$ | Bz | F | F | H | OH | H | H |
| XV-42-3 | Et | H | H | $CH(CH_3)_2$ | Bz | F | F | H | OH | H | H |
| XV-42-4 | Et | H | H | $CH_2CH(CH_3)_2$ | Bz | F | F | H | OH | H | H |
| XV-42-5 | Et | H | H | $CH_2Ph$ | Bz | F | F | H | OH | H | H |
| XV-42-6 | Et | H | H | $CH_2$-indol-3-yl | Bz | F | F | H | OH | H | H |
| XV-42-7 | Et | H | H | $CH_2CH_2SCH_3$ | Bz | F | F | H | OH | H | H |
| XV-42-8 | Et | * | H | * | Bz | F | F | H | OH | H | H |

*$R^2$ and $R^{3b}$ joined together by $(CH_2)_3$ to form five-membered ring.

TABLE XV-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-43-1 | $^iPr$ | H | H | H | Bz | F | F | H | OH | H | H |
| XV-43-2 | $^iPr$ | H | H | $CH_3$ | Bz | F | F | H | OH | H | H |
| XV-43-3 | $^iPr$ | H | H | $CH(CH_3)_2$ | Bz | F | F | H | OH | H | H |
| XV-43-4 | $^iPr$ | H | H | $CH_2CH(CH_3)_2$ | Bz | F | F | H | OH | H | H |
| XV-43-5 | $^iPr$ | H | H | $CH_2Ph$ | Bz | F | F | H | OH | H | H |
| XV-43-6 | $^iPr$ | H | H | $CH_2$-indol-3-yl | Bz | F | F | H | OH | H | H |
| XV-43-7 | $^iPr$ | H | H | $CH_2CH_2SCH_3$ | Bz | F | F | H | OH | H | H |
| XV-43-8 | $^iPr$ | * | H | * | Bz | F | F | H | OH | H | H |

*$R^2$ and $R^{3b}$ joined together by $(CH_2)_3$ to form five-membered ring.

TABLE XV-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-44-1 | $^tBu$ | H | H | H | Bz | F | F | H | OH | H | H |
| XV-44-2 | $^tBu$ | H | H | $CH_3$ | Bz | F | F | H | OH | H | H |
| XV-44-3 | $^tBu$ | H | H | $CH(CH_3)_2$ | Bz | F | F | H | OH | H | H |
| XV-44-4 | $^tBu$ | H | H | $CH_2CH(CH_3)_2$ | Bz | F | F | H | OH | H | H |
| XV-44-5 | $^tBu$ | H | H | $CH_2Ph$ | Bz | F | F | H | OH | H | H |
| XV-44-6 | $^tBu$ | H | H | $CH_2$-indol-3-yl | Bz | F | F | H | OH | H | H |
| XV-44-7 | $^tBu$ | H | H | $CH_2CH_2SCH_3$ | Bz | F | F | H | OH | H | H |
| XV-44-8 | $^tBu$ | * | H | * | Bz | F | F | H | OH | H | H |

*$R^2$ and $R^{3b}$ joined together by $(CH_2)_3$ to form five-membered ring.

TABLE XV-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-45-1 | Ph | H | H | H | Bz | F | F | H | OH | H | H |
| XV-45-2 | Ph | H | H | $CH_3$ | Bz | F | F | H | OH | H | H |
| XV-45-3 | Ph | H | H | $CH(CH_3)_2$ | Bz | F | F | H | OH | H | H |
| XV-45-4 | Ph | H | H | $CH_2CH(CH_3)_2$ | Bz | F | F | H | OH | H | H |
| XV-45-5 | Ph | H | H | $CH_2Ph$ | Bz | F | F | H | OH | H | H |
| XV-45-6 | Ph | H | H | $CH_2$-indol-3-yl | Bz | F | F | H | OH | H | H |
| XV-45-7 | Ph | H | H | $CH_2CH_2SCH_3$ | Bz | F | F | H | OH | H | H |
| XV-45-8 | Ph | * | H | * | Bz | F | F | H | OH | H | H |

*$R^2$ and $R^{3b}$ joined together by $(CH_2)_3$ to form five-membered ring.

TABLE XV-46

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-46-1 | p-Me—Ph | H | H | H | Bz | F | F | H | OH | H | H |
| XV-46-2 | p-Me—Ph | H | H | $CH_3$ | Bz | F | F | H | OH | H | H |
| XV-46-3 | p-Me—Ph | H | H | $CH(CH_3)_2$ | Bz | F | F | H | OH | H | H |
| XV-46-4 | p-Me—Ph | H | H | $CH_2CH(CH_3)_2$ | Bz | F | F | H | OH | H | H |
| XV-46-5 | p-Me—Ph | H | H | $CH_2Ph$ | Bz | F | F | H | OH | H | H |
| XV-46-6 | p-Me—Ph | H | H | $CH_2$-indol-3-yl | Bz | F | F | H | OH | H | H |
| XV-46-7 | p-Me—Ph | H | H | $CH_2CH_2SCH_3$ | Bz | F | F | H | OH | H | H |
| XV-46-8 | p-Me—Ph | * | H | * | Bz | F | F | H | OH | H | H |

*$R^2$ and $R^{3b}$ joined together by $(CH_2)_3$ to form five-membered ring.

TABLE XV-47

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XV-47-1 | p-F—Ph | H | H | H | Bz | F | F | H | OH | H | H |
| XV-47-2 | p-F—Ph | H | H | $CH_3$ | Bz | F | F | H | OH | H | H |

TABLE XV-47-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-47-3 | p-F—Ph | H | H | CH(CH₃)₂ | Bz | F | F | H | OH | H | H |
| XV-47-4 | p-F—Ph | H | H | CH₂CH(CH₃)₂ | Bz | F | F | H | OH | H | H |
| XV-47-5 | p-F—Ph | H | H | CH₂Ph | Bz | F | F | H | OH | H | H |
| XV-47-6 | p-F—Ph | H | H | CH₂-indol-3-yl | Bz | F | F | H | OH | H | H |
| XV-47-7 | p-F—Ph | H | H | CH₂CH₂SCH₃ | Bz | F | F | H | OH | H | H |
| XV-47-8 | p-F—Ph | * | H | * | Bz | F | F | H | OH | H | H |

*R² and R³ᵇ joined together by (CH₂)₃ to form five-membered ring.

TABLE XV-48

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-48-1 | p-Cl—Ph | H | H | H | Bz | F | F | H | OH | H | H |
| XV-48-2 | p-Cl—Ph | H | H | CH₃ | Bz | F | F | H | OH | H | H |
| XV-48-3 | p-Cl—Ph | H | H | CH(CH₃)₂ | Bz | F | F | H | OH | H | H |
| XV-48-4 | p-Cl—Ph | H | H | CH₂CH(CH₃)₂ | Bz | F | F | H | OH | H | H |
| XV-48-5 | p-Cl—Ph | H | H | CH₂Ph | Bz | F | F | H | OH | H | H |
| XV-48-6 | p-Cl—Ph | H | H | CH₂-indol-3-yl | Bz | F | F | H | OH | H | H |
| XV-48-7 | p-Cl—Ph | H | H | CH₂CH₂SCH₃ | Bz | F | F | H | OH | H | H |
| XV-48-8 | p-Cl—Ph | * | H | * | Bz | F | F | H | OH | H | H |

*R² and R³ᵇ joined together by (CH₂)₃ to form five-membered ring.

TABLE XV-49

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-49-1 | p-Br—Ph | H | H | H | Bz | F | F | H | OH | H | H |
| XV-49-2 | p-Br—Ph | H | H | CH₃ | Bz | F | F | H | OH | H | H |
| XV-49-3 | p-Br—Ph | H | H | CH(CH₃)₂ | Bz | F | F | H | OH | H | H |
| XV-49-4 | p-Br—Ph | H | H | CH₂CH(CH₃)₂ | Bz | F | F | H | OH | H | H |
| XV-49-5 | p-Br—Ph | H | H | CH₂Ph | Bz | F | F | H | OH | H | H |
| XV-49-6 | p-Br—Ph | H | H | CH₂-indol-3-yl | Bz | F | F | H | OH | H | H |
| XV-49-7 | p-Br—Ph | H | H | CH₂CH₂SCH₃ | Bz | F | F | H | OH | H | H |
| XV-49-8 | p-Br—Ph | * | H | * | Bz | F | F | H | OH | H | H |

*R² and R³ᵇ joined together by (CH₂)₃ to form five-membered ring.

TABLE XV-50

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XV-50-1 | p-I—Ph | H | H | H | Bz | F | F | H | OH | H | H |
| XV-50-2 | p-I—Ph | H | H | CH₃ | Bz | F | F | H | OH | H | H |
| XV-50-3 | p-I—Ph | H | H | CH(CH₃)₂ | Bz | F | F | H | OH | H | H |
| XV-50-4 | p-I—Ph | H | H | CH₂CH(CH₃)₂ | Bz | F | F | H | OH | H | H |
| XV-50-5 | p-I—Ph | H | H | CH₂Ph | Bz | F | F | H | OH | H | H |
| XV-50-6 | p-I—Ph | H | H | CH₂-indol-3-yl | Bz | F | F | H | OH | H | H |
| XV-50-7 | p-I—Ph | H | H | CH₂CH₂SCH₃ | Bz | F | F | H | OH | H | H |
| XV-50-8 | p-I—Ph | * | H | * | Bz | F | F | H | OH | H | H |

*R² and R³ᵇ joined together by (CH₂)₃ to form five-membered ring.

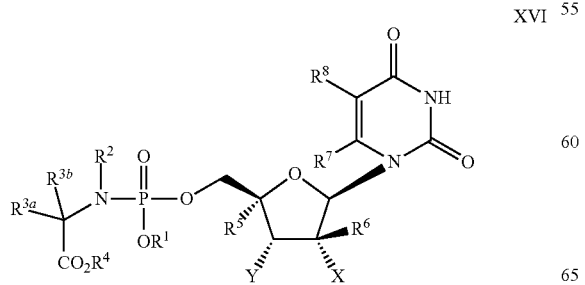

XVI

TABLE XVI-1

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-1-1 | $CH_3$ | H | H | H | $CH_3$ | F | F | F | OH | H | H |
| XVI-1-2 | $CH_3$ | H | H | $CH_3$ | $CH_3$ | F | F | F | OH | H | H |
| XVI-1-3 | $CH_3$ | H | H | $CH(CH_3)_2$ | $CH_3$ | F | F | F | OH | H | H |
| XVI-1-4 | $CH_3$ | H | H | $CH_2CH(CH_3)_2$ | $CH_3$ | F | F | F | OH | H | H |
| XVI-1-5 | $CH_3$ | H | H | $CH_2Ph$ | $CH_3$ | F | F | F | OH | H | H |
| XVI-1-6 | $CH_3$ | H | H | $CH_2$-indol-3-yl | $CH_3$ | F | F | F | OH | H | H |
| XVI-1-7 | $CH_3$ | H | H | $CH_2CH_2SCH_3$ | $CH_3$ | F | F | F | OH | H | H |
| XVI-1-8 | $CH_3$ | * | H | * | $CH_3$ | F | F | F | OH | H | H |

*$R^2$ and $R^{3b}$ joined together by $(CH_2)_3$ to form five-membered ring.

TABLE XVI-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-2-1 | Et | H | H | H | $CH_3$ | F | F | F | OH | H | H |
| XVI-2-2 | Et | H | H | $CH_3$ | $CH_3$ | F | F | F | OH | H | H |
| XVI-2-3 | Et | H | H | $CH(CH_3)_2$ | $CH_3$ | F | F | F | OH | H | H |
| XVI-2-4 | Et | H | H | $CH_2CH(CH_3)_2$ | $CH_3$ | F | F | F | OH | H | H |
| XVI-2-5 | Et | H | H | $CH_2Ph$ | $CH_3$ | F | F | F | OH | H | H |
| XVI-2-6 | Et | H | H | $CH_2$-indol-3-yl | $CH_3$ | F | F | F | OH | H | H |
| XVI-2-7 | Et | H | H | $CH_2CH_2SCH_3$ | $CH_3$ | F | F | F | OH | H | H |
| XVI-2-8 | Et | * | H | * | $CH_3$ | F | F | F | OH | H | H |

*$R^2$ and $R^{3b}$ joined together by $(CH_2)_3$ to form five-membered ring.

TABLE XVI-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-3-1 | $^iPr$ | H | H | H | $CH_3$ | F | F | F | OH | H | H |
| XVI-3-2 | $^iPr$ | H | H | $CH_3$ | $CH_3$ | F | F | F | OH | H | H |
| XVI-3-3 | $^iPr$ | H | H | $CH(CH_3)_2$ | $CH_3$ | F | F | F | OH | H | H |
| XVI-3-4 | $^iPr$ | H | H | $CH_2CH(CH_3)_2$ | $CH_3$ | F | F | F | OH | H | H |
| XVI-3-5 | $^iPr$ | H | H | $CH_2Ph$ | $CH_3$ | F | F | F | OH | H | H |
| XVI-3-6 | $^iPr$ | H | H | $CH_2$-indol-3-yl | $CH_3$ | F | F | F | OH | H | H |
| XVI-3-7 | $^iPr$ | H | H | $CH_2CH_2SCH_3$ | $CH_3$ | F | F | F | OH | H | H |
| XVI-3-8 | $^iPr$ | * | H | * | $CH_3$ | F | F | F | OH | H | H |

*$R^2$ and $R^{3b}$ joined together by $(CH_2)_3$ to form five-membered ring.

TABLE XVI-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-4-1 | $^tBu$ | H | H | H | $CH_3$ | F | F | F | OH | H | H |
| XVI-4-2 | $^tBu$ | H | H | $CH_3$ | $CH_3$ | F | F | F | OH | H | H |
| XVI-4-3 | $^tBu$ | H | H | $CH(CH_3)_2$ | $CH_3$ | F | F | F | OH | H | H |
| XVI-4-4 | $^tBu$ | H | H | $CH_2CH(CH_3)_2$ | $CH_3$ | F | F | F | OH | H | H |
| XVI-4-5 | $^tBu$ | H | H | $CH_2Ph$ | $CH_3$ | F | F | F | OH | H | H |
| XVI-4-6 | $^tBu$ | H | H | $CH_2$-indol-3-yl | $CH_3$ | F | F | F | OH | H | H |
| XVI-4-7 | $^tBu$ | H | H | $CH_2CH_2SCH_3$ | $CH_3$ | F | F | F | OH | H | H |
| XVI-4-8 | $^tBu$ | * | H | * | $CH_3$ | F | F | F | OH | H | H |

*$R^2$ and $R^{3b}$ joined together by $(CH_2)_3$ to form five-membered ring.

TABLE XVI-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-5-1 | Ph | H | H | H | $CH_3$ | F | F | F | OH | H | H |
| XVI-5-2 | Ph | H | H | $CH_3$ | $CH_3$ | F | F | F | OH | H | H |
| XVI-5-3 | Ph | H | H | $CH(CH_3)_2$ | $CH_3$ | F | F | F | OH | H | H |
| XVI-5-4 | Ph | H | H | $CH_2CH(CH_3)_2$ | $CH_3$ | F | F | F | OH | H | H |
| XVI-5-5 | Ph | H | H | $CH_2Ph$ | $CH_3$ | F | F | F | OH | H | H |
| XVI-5-6 | Ph | H | H | $CH_2$-indol-3-yl | $CH_3$ | F | F | F | OH | H | H |
| XVI-5-7 | Ph | H | H | $CH_2CH_2SCH_3$ | $CH_3$ | F | F | F | OH | H | H |
| XVI-5-8 | Ph | * | H | * | $CH_3$ | F | F | F | OH | H | H |

*$R^2$ and $R^{3b}$ joined together by $(CH_2)_3$ to form five-membered ring.

TABLE XVI-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-6-1 | p-Me—Ph | H | H | H | $CH_3$ | F | F | F | OH | H | H |
| XVI-6-2 | p-Me—Ph | H | H | $CH_3$ | $CH_3$ | F | F | F | OH | H | H |
| XVI-6-3 | p-Me—Ph | H | H | $CH(CH_3)_2$ | $CH_3$ | F | F | F | OH | H | H |
| XVI-6-4 | p-Me—Ph | H | H | $CH_2CH(CH_3)_2$ | $CH_3$ | F | F | F | OH | H | H |
| XVI-6-5 | p-Me—Ph | H | H | $CH_2Ph$ | $CH_3$ | F | F | F | OH | H | H |
| XVI-6-6 | p-Me—Ph | H | H | $CH_2$-indol-3-yl | $CH_3$ | F | F | F | OH | H | H |
| XVI-6-7 | p-Me—Ph | H | H | $CH_2CH_2SCH_3$ | $CH_3$ | F | F | F | OH | H | H |
| XVI-6-8 | p-Me—Ph | * | H | * | $CH_3$ | F | F | F | OH | H | H |

*$R^2$ and $R^{3b}$ joined together by $(CH_2)_3$ to form five-membered ring.

TABLE XVI-7

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-7-1 | p-F—Ph | H | H | H | CH$_3$ | F | F | F | OH | H | H |
| XVI-7-2 | p-F—Ph | H | H | CH$_3$ | CH$_3$ | F | F | F | OH | H | H |
| XVI-7-3 | p-F—Ph | H | H | CH(CH$_3$)$_2$ | CH$_3$ | F | F | F | OH | H | H |
| XVI-7-4 | p-F—Ph | H | H | CH$_2$CH(CH$_3$)$_2$ | CH$_3$ | F | F | F | OH | H | H |
| XVI-7-6 | p-F—Ph | H | H | CH$_2$Ph | CH$_3$ | F | F | F | OH | H | H |
| XVI-7-7 | p-F—Ph | H | H | CH$_2$-indol-3-yl | CH$_3$ | F | F | F | OH | H | H |
| XVI-7-8 | p-F—Ph | H | H | CH$_2$CH$_2$SCH$_3$ | CH$_3$ | F | F | F | OH | H | H |
| XVI-7-20 | p-F—Ph | * | H | * | CH$_3$ | F | F | F | OH | H | H |

*R² and R³ᵇ joined together by (CH$_2$)$_3$ to form five-membered ring.

TABLE XVI-8

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-8-1 | p-Cl—Ph | H | H | H | CH$_3$ | F | F | F | OH | H | H |
| XVI-8-2 | p-Cl—Ph | H | H | CH$_3$ | CH$_3$ | F | F | F | OH | H | H |
| XVI-8-3 | p-Cl—Ph | H | H | CH(CH$_3$)$_2$ | CH$_3$ | F | F | F | OH | H | H |
| XVI-8-4 | p-Cl—Ph | H | H | CH$_2$CH(CH$_3$)$_2$ | CH$_3$ | F | F | F | OH | H | H |
| XVI-8-5 | p-Cl—Ph | H | H | CH$_2$Ph | CH$_3$ | F | F | F | OH | H | H |
| XVI-8-6 | p-Cl—Ph | H | H | CH$_2$-indol-3-yl | CH$_3$ | F | F | F | OH | H | H |
| XVI-8-7 | p-Cl—Ph | H | H | CH$_2$CH$_2$SCH$_3$ | CH$_3$ | F | F | F | OH | H | H |
| XVI-8-8 | p-Cl—Ph | * | H | * | CH$_3$ | F | F | F | OH | H | H |

*R² and R³ᵇ joined together by (CH$_2$)$_3$ to form five-membered ring.

TABLE XVI-9

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-9-1 | p-Br—Ph | H | H | H | CH$_3$ | F | F | F | OH | H | H |
| XVI-9-2 | p-Br—Ph | H | H | CH$_3$ | CH$_3$ | F | F | F | OH | H | H |
| XVI-9-3 | p-Br—Ph | H | H | CH(CH$_3$)$_2$ | CH$_3$ | F | F | F | OH | H | H |
| XVI-9-4 | p-Br—Ph | H | H | CH$_2$CH(CH$_3$)$_2$ | CH$_3$ | F | F | F | OH | H | H |
| XVI-9-6 | p-Br—Ph | H | H | CH$_2$Ph | CH$_3$ | F | F | F | OH | H | H |
| XVI-9-7 | p-Br—Ph | H | H | CH$_2$-indol-3-yl | CH$_3$ | F | F | F | OH | H | H |
| XVI-9-8 | p-Br—Ph | H | H | CH$_2$CH$_2$SCH$_3$ | CH$_3$ | F | F | F | OH | H | H |
| XVI-9-20 | p-Br—Ph | * | H | * | CH$_3$ | F | F | F | OH | H | H |

*R² and R³ᵇ joined together by (CH$_2$)$_3$ to form five-membered ring.

TABLE XVI-10

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-10-1 | p-I—Ph | H | H | H | CH$_3$ | F | F | F | OH | H | H |
| XVI-10-2 | p-I—Ph | H | H | CH$_3$ | CH$_3$ | F | F | F | OH | H | H |
| XVI-10-3 | p-I—Ph | H | H | CH(CH$_3$)$_2$ | CH$_3$ | F | F | F | OH | H | H |
| XVI-10-4 | p-I—Ph | H | H | CH$_2$CH(CH$_3$)$_2$ | CH$_3$ | F | F | F | OH | H | H |
| XVI-10-5 | p-I—Ph | H | H | CH$_2$Ph | CH$_3$ | F | F | F | OH | H | H |
| XVI-10-6 | p-I—Ph | H | H | CH$_2$-indol-3-yl | CH$_3$ | F | F | F | OH | H | H |
| XVI-10-7 | p-I—Ph | H | H | CH$_2$CH$_2$SCH$_3$ | CH$_3$ | F | F | F | OH | H | H |
| XVI-10-8 | p-I—Ph | * | H | * | CH$_3$ | F | F | F | OH | H | H |

*R² and R³ᵇ joined together by (CH$_2$)$_3$ to form five-membered ring.

TABLE XVI-11

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-11-1 | CH$_3$ | H | H | H | Et | F | F | F | OH | H | H |
| XVI-11-2 | CH$_3$ | H | H | CH$_3$ | Et | F | F | F | OH | H | H |
| XVI-11-3 | CH$_3$ | H | H | CH(CH$_3$)$_2$ | Et | F | F | F | OH | H | H |
| XVI-11-4 | CH$_3$ | H | H | CH$_2$CH(CH$_3$)$_2$ | Et | F | F | F | OH | H | H |
| XVI-11-5 | CH$_3$ | H | H | CH$_2$Ph | Et | F | F | F | OH | H | H |
| XVI-11-6 | CH$_3$ | H | H | CH$_2$-indol-3-yl | Et | F | F | F | OH | H | H |
| XVI-11-7 | CH$_3$ | H | H | CH$_2$CH$_2$SCH$_3$ | Et | F | F | F | OH | H | H |

TABLE XVI-11-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-11-8 | $CH_3$ | * | H | * | Et | F | F | F | OH | H | H |

*$R^2$ and $R^{3b}$ joined together by $(CH_2)_3$ to form five-membered ring.

TABLE XVI-12

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-12-1 | Et | H | H | H | Et | F | F | F | OH | H | H |
| XVI-12-2 | Et | H | H | $CH_3$ | Et | F | F | F | OH | H | H |
| XVI-12-3 | Et | H | H | $CH(CH_3)_2$ | Et | F | F | F | OH | H | H |
| XVI-12-4 | Et | H | H | $CH_2CH(CH_3)_2$ | Et | F | F | F | OH | H | H |
| XVI-12-5 | Et | H | H | $CH_2Ph$ | Et | F | F | F | OH | H | H |
| XVI-12-6 | Et | H | H | $CH_2$-indol-3-yl | Et | F | F | F | OH | H | H |
| XVI-12-7 | Et | H | H | $CH_2CH_2SCH_3$ | Et | F | F | F | OH | H | H |
| XVI-12-8 | Et | * | H | * | Et | F | F | F | OH | H | H |

*$R^2$ and $R^{3b}$ joined together by $(CH_2)_3$ to form five-membered ring.

TABLE XVI-13

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-13-1 | $^iPr$ | H | H | H | Et | F | F | F | OH | H | H |
| XVI-13-2 | $^iPr$ | H | H | $CH_3$ | Et | F | F | F | OH | H | H |
| XVI-13-3 | $^iPr$ | H | H | $CH(CH_3)_2$ | Et | F | F | F | OH | H | H |
| XVI-13-4 | $^iPr$ | H | H | $CH_2CH(CH_3)_2$ | Et | F | F | F | OH | H | H |
| XVI-13-5 | $^iPr$ | H | H | $CH_2Ph$ | Et | F | F | F | OH | H | H |
| XVI-13-6 | $^iPr$ | H | H | $CH_2$-indol-3-yl | Et | F | F | F | OH | H | H |
| XVI-13-7 | $^iPr$ | H | H | $CH_2CH_2SCH_3$ | Et | F | F | F | OH | H | H |
| XVI-13-8 | $^iPr$ | * | H | * | Et | F | F | F | OH | H | H |

*$R^2$ and $R^{3b}$ joined together by $(CH_2)_3$ to form five-membered ring.

TABLE XVI-14

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-14-1 | $^tBu$ | H | H | H | Et | F | F | F | OH | H | H |
| XVI-14-2 | $^tBu$ | H | H | $CH_3$ | Et | F | F | F | OH | H | H |
| XVI-14-3 | $^tBu$ | H | H | $CH(CH_3)_2$ | Et | F | F | F | OH | H | H |
| XVI-14-4 | $^tBu$ | H | H | $CH_2CH(CH_3)_2$ | Et | F | F | F | OH | H | H |
| XVI-14-5 | $^tBu$ | H | H | $CH_2Ph$ | Et | F | F | F | OH | H | H |
| XVI-14-6 | $^tBu$ | H | H | $CH_2$-indol-3-yl | Et | F | F | F | OH | H | H |
| XVI-14-7 | $^tBu$ | H | H | $CH_2CH_2SCH_3$ | Et | F | F | F | OH | H | H |
| XVI-14-8 | $^tBu$ | * | H | * | Et | F | F | F | OH | H | H |

*$R^2$ and $R^{3b}$ joined together by $(CH_2)_3$ to form five-membered ring.

TABLE XVI-15

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-15-1 | Ph | H | H | H | Et | F | F | F | OH | H | H |
| XVI-15-2 | Ph | H | H | $CH_3$ | Et | F | F | F | OH | H | H |
| XVI-15-3 | Ph | H | H | $CH(CH_3)_2$ | Et | F | F | F | OH | H | H |
| XVI-15-4 | Ph | H | H | $CH_2CH(CH_3)_2$ | Et | F | F | F | OH | H | H |
| XVI-15-5 | Ph | H | H | $CH_2Ph$ | Et | F | F | F | OH | H | H |
| XVI-15-6 | Ph | H | H | $CH_2$-indol-3-yl | Et | F | F | F | OH | H | H |
| XVI-15-7 | Ph | H | H | $CH_2CH_2SCH_3$ | Et | F | F | F | OH | H | H |
| XVI-15-8 | Ph | * | H | * | Et | F | F | F | OH | H | H |

*$R^2$ and $R^{3b}$ joined together by $(CH_2)_3$ to form five-membered ring.

TABLE XVI-16

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-16-1 | p-Me—Ph | H | H | H | Et | F | F | F | OH | H | H |
| XVI-16-2 | p-Me—Ph | H | H | $CH_3$ | Et | F | F | F | OH | H | H |
| XVI-16-3 | p-Me—Ph | H | H | $CH(CH_3)_2$ | Et | F | F | F | OH | H | H |
| XVI-16-4 | p-Me—Ph | H | H | $CH_2CH(CH_3)_2$ | Et | F | F | F | OH | H | H |
| XVI-16-5 | p-Me—Ph | H | H | $CH_2Ph$ | Et | F | F | F | OH | H | H |
| XVI-16-6 | p-Me—Ph | H | H | $CH_2$-indol-3-yl | Et | F | F | F | OH | H | H |
| XVI-16-7 | p-Me—Ph | H | H | $CH_2CH_2SCH_3$ | Et | F | F | F | OH | H | H |
| XVI-16-8 | p-Me—Ph | * | H | * | Et | F | F | F | OH | H | H |

*$R^2$ and $R^{3b}$ joined together by $(CH_2)_3$ to form five-membered ring.

TABLE XVI-17

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-17-1 | p-F—Ph | H | H | H | Et | F | F | F | OH | H | H |
| XVI-17-2 | p-F—Ph | H | H | $CH_3$ | Et | F | F | F | OH | H | H |
| XVI-17-3 | p-F—Ph | H | H | $CH(CH_3)_2$ | Et | F | F | F | OH | H | H |

TABLE XVI-17-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-17-4 | p-F—Ph | H | H | CH$_2$CH(CH$_3$)$_2$ | Et | F | F | F | OH | H | H |
| XVI-17-5 | p-F—Ph | H | H | CH$_2$Ph | Et | F | F | F | OH | H | H |
| XVI-17-6 | p-F—Ph | H | H | CH$_2$-indol-3-yl | Et | F | F | F | OH | H | H |
| XVI-17-7 | p-F—Ph | H | H | CH$_2$CH$_2$SCH$_3$ | Et | F | F | F | OH | H | H |
| XVI-17-8 | p-F—Ph | * | H | * | Et | F | F | F | OH | H | H |

*R² and R³ᵇ joined together by (CH$_2$)$_3$ to form five-membered ring.

TABLE XVI-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-18-1 | p-Cl—Ph | H | H | H | Et | F | F | F | OH | H | H |
| XVI-18-2 | p-Cl—Ph | H | H | CH$_3$ | Et | F | F | F | OH | H | H |
| XVI-18-3 | p-Cl—Ph | H | H | CH(CH$_3$)$_2$ | Et | F | F | F | OH | H | H |
| XVI-18-4 | p-Cl—Ph | H | H | CH$_2$CH(CH$_3$)$_2$ | Et | F | F | F | OH | H | H |
| XVI-18-5 | p-Cl—Ph | H | H | CH$_2$Ph | Et | F | F | F | OH | H | H |
| XVI-18-6 | p-Cl—Ph | H | H | CH$_2$-indol-3-yl | Et | F | F | F | OH | H | H |
| XVI-18-7 | p-Cl—Ph | H | H | CH$_2$CH$_2$SCH$_3$ | Et | F | F | F | OH | H | H |
| XVI-18-8 | p-Cl—Ph | * | H | * | Et | F | F | F | OH | H | H |

*R² and R³ᵇ joined together by (CH$_2$)$_3$ to form five-membered ring.

TABLE XVI-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-19-1 | p-Br—Ph | H | H | H | Et | F | F | F | OH | H | H |
| XVI-19-2 | p-Br—Ph | H | H | CH$_3$ | Et | F | F | F | OH | H | H |
| XVI-19-3 | p-Br—Ph | H | H | CH(CH$_3$)$_2$ | Et | F | F | F | OH | H | H |
| XVI-19-4 | p-Br—Ph | H | H | CH$_2$CH(CH$_3$)$_2$ | Et | F | F | F | OH | H | H |
| XVI-19-5 | p-Br—Ph | H | H | CH$_2$Ph | Et | F | F | F | OH | H | H |
| XVI-19-6 | p-Br—Ph | H | H | CH$_2$-indol-3-yl | Et | F | F | F | OH | H | H |
| XVI-19-7 | p-Br—Ph | H | H | CH$_2$CH$_2$SCH$_3$ | Et | F | F | F | OH | H | H |
| XVI-19-8 | p-Br—Ph | * | H | * | Et | F | F | F | OH | H | H |

*R² and R³ᵇ joined together by (CH$_2$)$_3$ to form five-membered ring.

TABLE XVI-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-20-1 | p-I—Ph | H | H | H | Et | F | F | F | OH | H | H |
| XVI-20-2 | p-I—Ph | H | H | CH$_3$ | Et | F | F | F | OH | H | H |
| XVI-20-3 | p-I—Ph | H | H | CH(CH$_3$)$_2$ | Et | F | F | F | OH | H | H |
| XVI-20-4 | p-I—Ph | H | H | CH$_2$CH(CH$_3$)$_2$ | Et | F | F | F | OH | H | H |
| XVI-20-5 | p-I—Ph | H | H | CH$_2$Ph | Et | F | F | F | OH | H | H |
| XVI-20-6 | p-I—Ph | H | H | CH$_2$-indol-3-yl | Et | F | F | F | OH | H | H |
| XVI-20-7 | p-I—Ph | H | H | CH$_2$CH$_2$SCH$_3$ | Et | F | F | F | OH | H | H |
| XVI-20-8 | p-I—Ph | * | H | * | Et | F | F | F | OH | H | H |

*R² and R³ᵇ joined together by (CH$_2$)$_3$ to form five-membered ring.

TABLE XVI-21

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-21-1 | CH$_3$ | H | H | H | $^i$Pr | F | F | F | OH | H | H |
| XVI-21-2 | CH$_3$ | H | H | CH$_3$ | $^i$Pr | F | F | F | OH | H | H |
| XVI-21-3 | CH$_3$ | H | H | CH(CH$_3$)$_2$ | $^i$Pr | F | F | F | OH | H | H |
| XVI-21-4 | CH$_3$ | H | H | CH$_2$CH(CH$_3$)$_2$ | $^i$Pr | F | F | F | OH | H | H |
| XVI-21-5 | CH$_3$ | H | H | CH$_2$Ph | $^i$Pr | F | F | F | OH | H | H |
| XVI-21-6 | CH$_3$ | H | H | CH$_2$-indol-3-yl | $^i$Pr | F | F | F | OH | H | H |
| XVI-21-7 | CH$_3$ | H | H | CH$_2$CH$_2$SCH$_3$ | $^i$Pr | F | F | F | OH | H | H |
| XVI-21-8 | CH$_3$ | * | H | * | $^i$Pr | F | F | F | OH | H | H |

*R² and R³ᵇ joined together by (CH$_2$)$_3$ to form five-membered ring.

TABLE XVI-22

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-22-1 | Et | H | H | H | $^i$Pr | F | F | F | OH | H | H |
| XVI-22-2 | Et | H | H | CH$_3$ | $^i$Pr | F | F | F | OH | H | H |
| XVI-22-3 | Et | H | H | CH(CH$_3$)$_2$ | $^i$Pr | F | F | F | OH | H | H |
| XVI-22-4 | Et | H | H | CH$_2$CH(CH$_3$)$_2$ | $^i$Pr | F | F | F | OH | H | H |
| XVI-22-5 | Et | H | H | CH$_2$Ph | $^i$Pr | F | F | F | OH | H | H |
| XVI-22-6 | Et | H | H | CH$_2$-indol-3-yl | $^i$Pr | F | F | F | OH | H | H |
| XVI-22-7 | Et | H | H | CH$_2$CH$_2$SCH$_3$ | $^i$Pr | F | F | F | OH | H | H |
| XVI-22-8 | Et | * | H | * | $^i$Pr | F | F | F | OH | H | H |

*$R^2$ and $R^{3b}$ joined together by (CH$_2$)$_3$ to form five-membered ring.

TABLE XVI-23

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-23-1 | $^i$Pr | H | H | H | $^i$Pr | F | F | F | OH | H | H |
| XVI-23-2 | $^i$Pr | H | H | CH$_3$ | $^i$Pr | F | F | F | OH | H | H |
| XVI-23-3 | $^i$Pr | H | H | CH(CH$_3$)$_2$ | $^i$Pr | F | F | F | OH | H | H |
| XVI-23-4 | $^i$Pr | H | H | CH$_2$CH(CH$_3$)$_2$ | $^i$Pr | F | F | F | OH | H | H |
| XVI-23-5 | $^i$Pr | H | H | CH$_2$Ph | $^i$Pr | F | F | F | OH | H | H |
| XVI-23-6 | $^i$Pr | H | H | CH$_2$-indol-3-yl | $^i$Pr | F | F | F | OH | H | H |
| XVI-23-7 | $^i$Pr | H | H | CH$_2$CH$_2$SCH$_3$ | $^i$Pr | F | F | F | OH | H | H |
| XVI-23-8 | $^i$Pr | * | H | * | $^i$Pr | F | F | F | OH | H | H |

*$R^2$ and $R^{3b}$ joined together by (CH$_2$)$_3$ to form five-membered ring.

TABLE XVI-24

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-24-1 | $^t$Bu | H | H | H | $^i$Pr | F | F | F | OH | H | H |
| XVI-24-2 | $^t$Bu | H | H | CH$_3$ | $^i$Pr | F | F | F | OH | H | H |
| XVI-24-3 | $^t$Bu | H | H | CH(CH$_3$)$_2$ | $^i$Pr | F | F | F | OH | H | H |
| XVI-24-4 | $^t$Bu | H | H | CH$_2$CH(CH$_3$)$_2$ | $^i$Pr | F | F | F | OH | H | H |
| XVI-24-5 | $^t$Bu | H | H | CH$_2$Ph | $^i$Pr | F | F | F | OH | H | H |
| XVI-24-6 | $^t$Bu | H | H | CH$_2$-indol-3-yl | $^i$Pr | F | F | F | OH | H | H |
| XVI-24-7 | $^t$Bu | H | H | CH$_2$CH$_2$SCH$_3$ | $^i$Pr | F | F | F | OH | H | H |
| XVI-24-8 | $^t$Bu | * | H | * | $^i$Pr | F | F | F | OH | H | H |

*$R^2$ and $R^{3b}$ joined together by (CH$_2$)$_3$ to form five-membered ring.

TABLE XVI-25

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-25-1 | Ph | H | H | H | $^i$Pr | F | F | F | OH | H | H |
| XVI-25-2 | Ph | H | H | CH$_3$ | $^i$Pr | F | F | F | OH | H | H |
| XVI-25-3 | Ph | H | H | CH(CH$_3$)$_2$ | $^i$Pr | F | F | F | OH | H | H |
| XVI-25-4 | Ph | H | H | CH$_2$CH(CH$_3$)$_2$ | $^i$Pr | F | F | F | OH | H | H |
| XVI-25-5 | Ph | H | H | CH$_2$Ph | $^i$Pr | F | F | F | OH | H | H |
| XVI-25-6 | Ph | H | H | CH$_2$-indol-3-yl | $^i$Pr | F | F | F | OH | H | H |
| XVI-25-7 | Ph | H | H | CH$_2$CH$_2$SCH$_3$ | $^i$Pr | F | F | F | OH | H | H |
| XVI-25-8 | Ph | * | H | * | $^i$Pr | F | F | F | OH | H | H |

*$R^2$ and $R^{3b}$ joined together by (CH$_2$)$_3$ to form five-membered ring.

TABLE XVI-26

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-26-1 | p-Me—Ph | H | H | H | $^i$Pr | F | F | F | OH | H | H |
| XVI-26-2 | p-Me—Ph | H | H | CH$_3$ | $^i$Pr | F | F | F | OH | H | H |
| XVI-26-3 | p-Me—Ph | H | H | CH(CH$_3$)$_2$ | $^i$Pr | F | F | F | OH | H | H |
| XVI-26-4 | p-Me—Ph | H | H | CH$_2$CH(CH$_3$)$_2$ | $^i$Pr | F | F | F | OH | H | H |
| XVI-26-5 | p-Me—Ph | H | H | CH$_2$Ph | $^i$Pr | F | F | F | OH | H | H |
| XVI-26-6 | p-Me—Ph | H | H | CH$_2$-indol-3-yl | $^i$Pr | F | F | F | OH | H | H |
| XVI-26-7 | p-Me—Ph | H | H | CH$_2$CH$_2$SCH$_3$ | $^i$Pr | F | F | F | OH | H | H |
| XVI-26-8 | p-Me—Ph | * | H | * | $^i$Pr | F | F | F | OH | H | H |

*$R^2$ and $R^{3b}$ joined together by (CH$_2$)$_3$ to form five-membered ring.

TABLE XVI-27

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVI-27-1 | p-F—Ph | H | H | H | $^i$Pr | F | F | F | OH | H | H |
| XVI-27-2 | p-F—Ph | H | H | CH$_3$ | $^i$Pr | F | F | F | OH | H | H |
| XVI-27-3 | p-F—Ph | H | H | CH(CH$_3$)$_2$ | $^i$Pr | F | F | F | OH | H | H |
| XVI-27-4 | p-F—Ph | H | H | CH$_2$CH(CH$_3$)$_2$ | $^i$Pr | F | F | F | OH | H | H |
| XVI-27-5 | p-F—Ph | H | H | CH$_2$Ph | $^i$Pr | F | F | F | OH | H | H |
| XVI-27-6 | p-F—Ph | H | H | CH$_2$-indol-3-yl | $^i$Pr | F | F | F | OH | H | H |
| XVI-27-7 | p-F—Ph | H | H | CH$_2$CH$_2$SCH$_3$ | $^i$Pr | F | F | F | OH | H | H |
| XVI-27-8 | p-F—Ph | * | H | * | $^i$Pr | F | F | F | OH | H | H |

*$R^2$ and $R^{3b}$ joined together by (CH$_2$)$_3$ to form five-membered ring.

TABLE XVI-28

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-28-1 | p-Cl—Ph | H | H | H | $^i$Pr | F | F | F | OH | H | H |
| XVI-28-2 | p-Cl—Ph | H | H | CH₃ | $^i$Pr | F | F | F | OH | H | H |
| XVI-28-3 | p-Cl—Ph | H | H | CH(CH₃)₂ | $^i$Pr | F | F | F | OH | H | H |
| XVI-28-4 | p-Cl—Ph | H | H | CH₂CH(CH₃)₂ | $^i$Pr | F | F | F | OH | H | H |
| XVI-28-5 | p-Cl—Ph | H | H | CH₂Ph | $^i$Pr | F | F | F | OH | H | H |
| XVI-28-6 | p-Cl—Ph | H | H | CH₂-indol-3-yl | $^i$Pr | F | F | F | OH | H | H |
| XVI-28-7 | p-Cl—Ph | H | H | CH₂CH₂SCH₃ | $^i$Pr | F | F | F | OH | H | H |
| XVI-28-8 | p-Cl—Ph | * | H | * | $^i$Pr | F | F | F | OH | H | H |

*R² and R³ᵇ joined together by (CH₂)₃ to form five-membered ring.

TABLE XVI-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-29-1 | p-Br—Ph | H | H | H | $^i$Pr | F | F | F | OH | H | H |
| XVI-29-2 | p-Br—Ph | H | H | CH₃ | $^i$Pr | F | F | F | OH | H | H |
| XVI-29-3 | p-Br—Ph | H | H | CH(CH₃)₂ | $^i$Pr | F | F | F | OH | H | H |
| XVI-29-4 | p-Br—Ph | H | H | CH₂CH(CH₃)₂ | $^i$Pr | F | F | F | OH | H | H |
| XVI-29-5 | p-Br—Ph | H | H | CH₂Ph | $^i$Pr | F | F | F | OH | H | H |
| XVI-29-6 | p-Br—Ph | H | H | CH₂-indol-3-yl | $^i$Pr | F | F | F | OH | H | H |
| XVI-29-7 | p-Br—Ph | H | H | CH₂CH₂SCH₃ | $^i$Pr | F | F | F | OH | H | H |
| XVI-29-8 | p-Br—Ph | * | H | * | $^i$Pr | F | F | F | OH | H | H |

*R² and R³ᵇ joined together by (CH₂)₃ to form five-membered ring.

TABLE XVI-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-30-1 | p-I—Ph | H | H | H | $^i$Pr | F | F | F | OH | H | H |
| XVI-30-2 | p-I—Ph | H | H | CH₃ | $^i$Pr | F | F | F | OH | H | H |
| XVI-30-3 | p-I—Ph | H | H | CH(CH₃)₂ | $^i$Pr | F | F | F | OH | H | H |
| XVI-30-4 | p-I—Ph | H | H | CH₂CH(CH₃)₂ | $^i$Pr | F | F | F | OH | H | H |
| XVI-30-5 | p-I—Ph | H | H | CH₂Ph | $^i$Pr | F | F | F | OH | H | H |
| XVI-30-6 | p-I—Ph | H | H | CH₂-indol-3-yl | $^i$Pr | F | F | F | OH | H | H |
| XVI-30-7 | p-I—Ph | H | H | CH₂CH₂SCH₃ | $^i$Pr | F | F | F | OH | H | H |
| XVI-30-8 | p-I—Ph | * | H | * | $^i$Pr | F | F | F | OH | H | H |

*R² and R³ᵇ joined together by (CH₂)₃ to form five-membered ring.

TABLE XVI-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-31-1 | CH₃ | H | H | H | $^n$Bu | F | F | F | OH | H | H |
| XVI-31-2 | CH₃ | H | H | CH₃ | $^n$Bu | F | F | F | OH | H | H |
| XVI-31-3 | CH₃ | H | H | CH(CH₃)₂ | $^n$Bu | F | F | F | OH | H | H |
| XVI-31-4 | CH₃ | H | H | CH₂CH(CH₃)₂ | $^n$Bu | F | F | F | OH | H | H |
| XVI-31-5 | CH₃ | H | H | CH₂Ph | $^n$Bu | F | F | F | OH | H | H |
| XVI-31-6 | CH₃ | H | H | CH₂-indol-3-yl | $^n$Bu | F | F | F | OH | H | H |
| XVI-31-7 | CH₃ | H | H | CH₂CH₂SCH₃ | $^n$Bu | F | F | F | OH | H | H |
| XVI-31-8 | CH₃ | * | H | * | $^n$Bu | F | F | F | OH | H | H |

*R² and R³ᵇ joined together by (CH₂)₃ to form five-membered ring.

TABLE XVI-32

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-32-1 | Et | H | H | H | $^n$Bu | F | F | F | OH | H | H |
| XVI-32-2 | Et | H | H | CH₃ | $^n$Bu | F | F | F | OH | H | H |
| XVI-32-3 | Et | H | H | CH(CH₃)₂ | $^n$Bu | F | F | F | OH | H | H |
| XVI-32-4 | Et | H | H | CH₂CH(CH₃)₂ | $^n$Bu | F | F | F | OH | H | H |
| XVI-32-5 | Et | H | H | CH₂Ph | $^n$Bu | F | F | F | OH | H | H |
| XVI-32-6 | Et | H | H | CH₂-indol-3-yl | $^n$Bu | F | F | F | OH | H | H |
| XVI-32-7 | Et | H | H | CH₂CH₂SCH₃ | $^n$Bu | F | F | F | OH | H | H |
| XVI-32-8 | Et | * | H | * | $^n$Bu | F | F | F | OH | H | H |

*R² and R³ᵇ joined together by (CH₂)₃ to form five-membered ring.

TABLE XVI-33

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVI-33-1 | $^i$Pr | H | H | H | $^n$Bu | F | F | F | OH | H | H |
| XVI-33-2 | $^i$Pr | H | H | CH$_3$ | $^n$Bu | F | F | F | OH | H | H |
| XVI-33-3 | $^i$Pr | H | H | CH(CH$_3$)$_2$ | $^n$Bu | F | F | F | OH | H | H |
| XVI-33-4 | $^i$Pr | H | H | CH$_2$CH(CH$_3$)$_2$ | $^n$Bu | F | F | F | OH | H | H |
| XVI-33-5 | $^i$Pr | H | H | CH$_2$Ph | $^n$Bu | F | F | F | OH | H | H |
| XVI-33-6 | $^i$Pr | H | H | CH$_2$-indol-3-yl | $^n$Bu | F | F | F | OH | H | H |
| XVI-33-7 | $^i$Pr | H | H | CH$_2$CH$_2$SCH$_3$ | $^n$Bu | F | F | F | OH | H | H |
| XVI-33-8 | $^i$Pr | * | H | * | $^n$Bu | F | F | F | OH | H | H |

*R$^2$ and R$^{3b}$ joined together by (CH$_2$)$_3$ to form five-membered ring.

TABLE XVI-34

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVI-34-1 | $^t$Bu | H | H | H | $^n$Bu | F | F | F | OH | H | H |
| XVI-34-2 | $^t$Bu | H | H | CH$_3$ | $^n$Bu | F | F | F | OH | H | H |
| XVI-34-3 | $^t$Bu | H | H | CH(CH$_3$)$_2$ | $^n$Bu | F | F | F | OH | H | H |
| XVI-34-4 | $^t$Bu | H | H | CH$_2$CH(CH$_3$)$_2$ | $^n$Bu | F | F | F | OH | H | H |
| XVI-34-5 | $^t$Bu | H | H | CH$_2$Ph | $^n$Bu | F | F | F | OH | H | H |
| XVI-34-6 | $^t$Bu | H | H | CH$_2$-indol-3-yl | $^n$Bu | F | F | F | OH | H | H |
| XVI-34-7 | $^t$Bu | H | H | CH$_2$CH$_2$SCH$_3$ | $^n$Bu | F | F | F | OH | H | H |
| XVI-34-8 | $^t$Bu | * | H | * | $^n$Bu | F | F | F | OH | H | H |

*R$^2$ and R$^{3b}$ joined together by (CH$_2$)$_3$ to form five-membered ring.

TABLE XVI-35

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVI-35-1 | Ph | H | H | H | $^n$Bu | F | F | F | OH | H | H |
| XVI-35-2 | Ph | H | H | CH$_3$ | $^n$Bu | F | F | F | OH | H | H |
| XVI-35-3 | Ph | H | H | CH(CH$_3$)$_2$ | $^n$Bu | F | F | F | OH | H | H |
| XVI-35-4 | Ph | H | H | CH$_2$CH(CH$_3$)$_2$ | $^n$Bu | F | F | F | OH | H | H |
| XVI-35-5 | Ph | H | H | CH$_2$Ph | $^n$Bu | F | F | F | OH | H | H |
| XVI-35-6 | Ph | H | H | CH$_2$-indol-3-yl | $^n$Bu | F | F | F | OH | H | H |
| XVI-35-7 | Ph | H | H | CH$_2$CH$_2$SCH$_3$ | $^n$Bu | F | F | F | OH | H | H |
| XVI-35-8 | Ph | * | H | * | $^n$Bu | F | F | F | OH | H | H |

*R$^2$ and R$^{3b}$ joined together by (CH$_2$)$_3$ to form five-membered ring.

TABLE XVI-36

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVI-36-1 | p-Me—Ph | H | H | H | $^n$Bu | F | F | F | OH | H | H |
| XVI-36-2 | p-Me—Ph | H | H | CH$_3$ | $^n$Bu | F | F | F | OH | H | H |
| XVI-36-3 | p-Me—Ph | H | H | CH(CH$_3$)$_2$ | $^n$Bu | F | F | F | OH | H | H |
| XVI-36-4 | p-Me—Ph | H | H | CH$_2$CH(CH$_3$)$_2$ | $^n$Bu | F | F | F | OH | H | H |
| XVI-36-5 | p-Me—Ph | H | H | CH$_2$Ph | $^n$Bu | F | F | F | OH | H | H |
| XVI-36-6 | p-Me—Ph | H | H | CH$_2$-indol-3-yl | $^n$Bu | F | F | F | OH | H | H |
| XVI-36-7 | p-Me—Ph | H | H | CH$_2$CH$_2$SCH$_3$ | $^n$Bu | F | F | F | OH | H | H |
| XVI-36-8 | p-Me—Ph | * | H | * | $^n$Bu | F | F | F | OH | H | H |

*R$^2$ and R$^{3b}$ joined together by (CH$_2$)$_3$ to form five-membered ring.

TABLE XVI-37

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVI-37-1 | p-I—Ph | H | H | H | $^n$Bu | F | F | F | OH | H | H |
| XVI-37-2 | p-I—Ph | H | H | CH$_3$ | $^n$Bu | F | F | F | OH | H | H |
| XVI-37-3 | p-I—Ph | H | H | CH(CH$_3$)$_2$ | $^n$Bu | F | F | F | OH | H | H |
| XVI-37-4 | p-I—Ph | H | H | CH$_2$CH(CH$_3$)$_2$ | $^n$Bu | F | F | F | OH | H | H |
| XVI-37-5 | p-I—Ph | H | H | CH$_2$Ph | $^n$Bu | F | F | F | OH | H | H |
| XVI-37-6 | p-I—Ph | H | H | CH$_2$-indol-3-yl | $^n$Bu | F | F | F | OH | H | H |
| XVI-37-7 | p-I—Ph | H | H | CH$_2$CH$_2$SCH$_3$ | $^n$Bu | F | F | F | OH | H | H |
| XVI-37-8 | p-I—Ph | * | H | * | $^n$Bu | F | F | F | OH | H | H |

*R$^2$ and R$^{3b}$ joined together by (CH$_2$)$_3$ to form five-membered ring.

TABLE XVI-38

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVI-38-1 | p-Cl—Ph | H | H | H | $^n$Bu | F | F | F | OH | H | H |
| XVI-38-2 | p-Cl—Ph | H | H | CH$_3$ | $^n$Bu | F | F | F | OH | H | H |

TABLE XVI-38-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-38-3 | p-Cl—Ph | H | H | CH(CH₃)₂ | ⁿBu | F | F | F | OH | H | H |
| XVI-38-4 | p-Cl—Ph | H | H | CH₂CH(CH₃)₂ | ⁿBu | F | F | F | OH | H | H |
| XVI-38-5 | p-Cl—Ph | H | H | CH₂Ph | ⁿBu | F | F | F | OH | H | H |
| XVI-38-6 | p-Cl—Ph | H | H | CH₂-indol-3-yl | ⁿBu | F | F | F | OH | H | H |
| XVI-38-7 | p-Cl—Ph | H | H | CH₂CH₂SCH₃ | ⁿBu | F | F | F | OH | H | H |
| XVI-38-8 | p-Cl—Ph | * | H | * | ⁿBu | F | F | F | OH | H | H |

*R² and R³ᵇ joined together by (CH₂)₃ to form five-membered ring.

TABLE XVI-39

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-39-1 | p-Br—Ph | H | H | H | ⁿBu | F | F | F | OH | H | H |
| XVI-39-2 | p-Br—Ph | H | H | CH₃ | ⁿBu | F | F | F | OH | H | H |
| XVI-39-3 | p-Br—Ph | H | H | CH(CH₃)₂ | ⁿBu | F | F | F | OH | H | H |
| XVI-39-4 | p-Br—Ph | H | H | CH₂CH(CH₃)₂ | ⁿBu | F | F | F | OH | H | H |
| XVI-39-5 | p-Br—Ph | H | H | CH₂Ph | ⁿBu | F | F | F | OH | H | H |
| XVI-39-6 | p-Br—Ph | H | H | CH₂-indol-3-yl | ⁿBu | F | F | F | OH | H | H |
| XVI-39-7 | p-Br—Ph | H | H | CH₂CH₂SCH₃ | ⁿBu | F | F | F | OH | H | H |
| XVI-39-8 | p-Br—Ph | * | H | * | ⁿBu | F | F | F | OH | H | H |

*R² and R³ᵇ joined together by (CH₂)₃ to form five-membered ring.

TABLE XVI-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-40-1 | p-I—Ph | H | H | H | ⁿBu | F | F | F | OH | H | H |
| XVI-40-2 | p-I—Ph | H | H | CH₃ | ⁿBu | F | F | F | OH | H | H |
| XVI-40-3 | p-I—Ph | H | H | CH(CH₃)₂ | ⁿBu | F | F | F | OH | H | H |
| XVI-40-4 | p-I—Ph | H | H | CH₂CH(CH₃)₂ | ⁿBu | F | F | F | OH | H | H |
| XVI-40-5 | p-I—Ph | H | H | CH₂Ph | ⁿBu | F | F | F | OH | H | H |
| XVI-40-6 | p-I—Ph | H | H | CH₂-indol-3-yl | ⁿBu | F | F | F | OH | H | H |
| XVI-40-7 | p-I—Ph | H | H | CH₂CH₂SCH₃ | ⁿBu | F | F | F | OH | H | H |
| XVI-40-8 | p-I—Ph | * | H | * | ⁿBu | F | F | F | OH | H | H |

*R² and R³ᵇ joined together by (CH₂)₃ to form five-membered ring.

TABLE XVI-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-41-1 | CH₃ | H | H | H | Bz | F | F | F | OH | H | H |
| XVI-41-2 | CH₃ | H | H | CH₃ | Bz | F | F | F | OH | H | H |
| XVI-41-3 | CH₃ | H | H | CH(CH₃)₂ | Bz | F | F | F | OH | H | H |
| XVI-41-4 | CH₃ | H | H | CH₂CH(CH₃)₂ | Bz | F | F | F | OH | H | H |
| XVI-41-5 | CH₃ | H | H | CH₂Ph | Bz | F | F | F | OH | H | H |
| XVI-41-6 | CH₃ | H | H | CH₂-indol-3-yl | Bz | F | F | F | OH | H | H |
| XVI-41-7 | CH₃ | H | H | CH₂CH₂SCH₃ | Bz | F | F | F | OH | H | H |
| XVI-41-8 | CH₃ | * | H | * | Bz | F | F | F | OH | H | H |

*R² and R³ᵇ joined together by (CH₂)₃ to form five-membered ring.

TABLE XVI-42

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-42-1 | Et | H | H | H | Bz | F | F | F | OH | H | H |
| XVI-42-2 | Et | H | H | CH₃ | Bz | F | F | F | OH | H | H |
| XVI-42-3 | Et | H | H | CH(CH₃)₂ | Bz | F | F | F | OH | H | H |
| XVI-42-4 | Et | H | H | CH₂CH(CH₃)₂ | Bz | F | F | F | OH | H | H |
| XVI-42-5 | Et | H | H | CH₂Ph | Bz | F | F | F | OH | H | H |
| XVI-42-6 | Et | H | H | CH₂-indol-3-yl | Bz | F | F | F | OH | H | H |
| XVI-42-7 | Et | H | H | CH₂CH₂SCH₃ | Bz | F | F | F | OH | H | H |
| XVI-42-8 | Et | * | H | * | Bz | F | F | F | OH | H | H |

*R² and R³ᵇ joined together by (CH₂)₃ to form five-membered ring.

TABLE XVI-43

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-43-1 | ⁱPr | H | H | H | Bz | F | F | F | OH | H | H |
| XVI-43-2 | ⁱPr | H | H | CH₃ | Bz | F | F | F | OH | H | H |
| XVI-43-3 | ⁱPr | H | H | CH(CH₃)₂ | Bz | F | F | F | OH | H | H |

TABLE XVI-43-continued

| No | $R^1$ | $R^2$ | $R^{3a}$ | $R^{3b}$ | $R^4$ | $R^5$ | $R^6$ | $X$ | $Y$ | $R^7$ | $R^8$ |
|---|---|---|---|---|---|---|---|---|---|---|---|
| XVI-43-4 | $^i$Pr | H | H | $CH_2CH(CH_3)_2$ | Bz | F | F | F | OH | H | H |
| XVI-43-5 | $^i$Pr | H | H | $CH_2Ph$ | Bz | F | F | F | OH | H | H |
| XVI-43-6 | $^i$Pr | H | H | $CH_2$-indol-3-yl | Bz | F | F | F | OH | H | H |
| XVI-43-7 | $^i$Pr | H | H | $CH_2CH_2SCH_3$ | Bz | F | F | F | OH | H | H |
| XVI-43-8 | $^i$Pr | * | H | * | Bz | F | F | F | OH | H | H |

*$R^2$ and $R^{3b}$ joined together by $(CH_2)_3$ to form five-membered ring.

TABLE XVI-44

| No | $R^1$ | $R^2$ | $R^{3a}$ | $R^{3b}$ | $R^4$ | $R^5$ | $R^6$ | $X$ | $Y$ | $R^7$ | $R^8$ |
|---|---|---|---|---|---|---|---|---|---|---|---|
| XVI-44-1 | $^t$Bu | H | H | H | Bz | F | F | F | OH | H | H |
| XVI-44-2 | $^t$Bu | H | H | $CH_3$ | Bz | F | F | F | OH | H | H |
| XVI-44-3 | $^t$Bu | H | H | $CH(CH_3)_2$ | Bz | F | F | F | OH | H | H |
| XVI-44-4 | $^t$Bu | H | H | $CH_2CH(CH_3)_2$ | Bz | F | F | F | OH | H | H |
| XVI-44-5 | $^t$Bu | H | H | $CH_2Ph$ | Bz | F | F | F | OH | H | H |
| XVI-44-6 | $^t$Bu | H | H | $CH_2$-indol-3-yl | Bz | F | F | F | OH | H | H |
| XVI-44-7 | $^t$Bu | H | H | $CH_2CH_2SCH_3$ | Bz | F | F | F | OH | H | H |
| XVI-44-8 | $^t$Bu | * | H | * | Bz | F | F | F | OH | H | H |

*$R^2$ and $R^{3b}$ joined together by $(CH_2)_3$ to form five-membered ring.

TABLE XVI-45

| No | $R^1$ | $R^2$ | $R^{3a}$ | $R^{3b}$ | $R^4$ | $R^5$ | $R^6$ | $X$ | $Y$ | $R^7$ | $R^8$ |
|---|---|---|---|---|---|---|---|---|---|---|---|
| XVI-45-1 | Ph | H | H | H | Bz | F | F | F | OH | H | H |
| XVI-45-2 | Ph | H | H | $CH_3$ | Bz | F | F | F | OH | H | H |
| XVI-45-3 | Ph | H | H | $CH(CH_3)_2$ | Bz | F | F | F | OH | H | H |
| XVI-45-4 | Ph | H | H | $CH_2CH(CH_3)_2$ | Bz | F | F | F | OH | H | H |
| XVI-45-5 | Ph | H | H | $CH_2Ph$ | Bz | F | F | F | OH | H | H |
| XVI-45-6 | Ph | H | H | $CH_2$-indol-3-yl | Bz | F | F | F | OH | H | H |
| XVI-45-7 | Ph | H | H | $CH_2CH_2SCH_3$ | Bz | F | F | F | OH | H | H |
| XVI-45-8 | Ph | * | H | * | Bz | F | F | F | OH | H | H |

*$R^2$ and $R^{3b}$ joined together by $(CH_2)_3$ to form five-membered ring.

TABLE XVI-46

| No | $R^1$ | $R^2$ | $R^{3a}$ | $R^{3b}$ | $R^4$ | $R^5$ | $R^6$ | $X$ | $Y$ | $R^7$ | $R^8$ |
|---|---|---|---|---|---|---|---|---|---|---|---|
| XVI-46-1 | p-Me—Ph | H | H | H | Bz | F | F | F | OH | H | H |
| XVI-46-2 | p-Me—Ph | H | H | $CH_3$ | Bz | F | F | F | OH | H | H |
| XVI-46-3 | p-Me—Ph | H | H | $CH(CH_3)_2$ | Bz | F | F | F | OH | H | H |
| XVI-46-4 | p-Me—Ph | H | H | $CH_2CH(CH_3)_2$ | Bz | F | F | F | OH | H | H |
| XVI-46-5 | p-Me—Ph | H | H | $CH_2Ph$ | Bz | F | F | F | OH | H | H |
| XVI-46-6 | p-Me—Ph | H | H | $CH_2$-indol-3-yl | Bz | F | F | F | OH | H | H |
| XVI-46-7 | p-Me—Ph | H | H | $CH_2CH_2SCH_3$ | Bz | F | F | F | OH | H | H |
| XVI-46-8 | p-Me—Ph | * | H | * | Bz | F | F | F | OH | H | H |

*$R^2$ and $R^{3b}$ joined together by $(CH_2)_3$ to form five-membered ring.

TABLE XVI-47

| No | $R^1$ | $R^2$ | $R^{3a}$ | $R^{3b}$ | $R^4$ | $R^5$ | $R^6$ | $X$ | $Y$ | $R^7$ | $R^8$ |
|---|---|---|---|---|---|---|---|---|---|---|---|
| XVI-47-1 | p-F—Ph | H | H | H | Bz | F | F | F | OH | H | H |
| XVI-47-2 | p-F—Ph | H | H | $CH_3$ | Bz | F | F | F | OH | H | H |
| XVI-47-3 | p-F—Ph | H | H | $CH(CH_3)_2$ | Bz | F | F | F | OH | H | H |
| XVI-47-4 | p-F—Ph | H | H | $CH_2CH(CH_3)_2$ | Bz | F | F | F | OH | H | H |
| XVI-47-5 | p-F—Ph | H | H | $CH_2Ph$ | Bz | F | F | F | OH | H | H |
| XVI-47-6 | p-F—Ph | H | H | $CH_2$-indol-3-yl | Bz | F | F | F | OH | H | H |
| XVI-47-7 | p-F—Ph | H | H | $CH_2CH_2SCH_3$ | Bz | F | F | F | OH | H | H |
| XVI-47-8 | p-F—Ph | * | H | * | Bz | F | F | F | OH | H | H |

*$R^2$ and $R^{3b}$ joined together by $(CH_2)_3$ to form five-membered ring.

TABLE XVI-48

| No | $R^1$ | $R^2$ | $R^{3a}$ | $R^{3b}$ | $R^4$ | $R^5$ | $R^6$ | $X$ | $Y$ | $R^7$ | $R^8$ |
|---|---|---|---|---|---|---|---|---|---|---|---|
| XVI-48-1 | p-Cl—Ph | H | H | H | Bz | F | F | F | OH | H | H |
| XVI-48-2 | p-Cl—Ph | H | H | $CH_3$ | Bz | F | F | F | OH | H | H |
| XVI-48-3 | p-Cl—Ph | H | H | $CH(CH_3)_2$ | Bz | F | F | F | OH | H | H |
| XVI-48-4 | p-Cl—Ph | H | H | $CH_2CH(CH_3)_2$ | Bz | F | F | F | OH | H | H |
| XVI-48-5 | p-Cl—Ph | H | H | $CH_2Ph$ | Bz | F | F | F | OH | H | H |

TABLE XVI-48-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-48-6 | p-Cl—Ph | H | H | CH₂-indol-3-yl | Bz | F | F | F | OH | H | H |
| XVI-48-7 | p-Cl—Ph | H | H | CH₂CH₂SCH₃ | Bz | F | F | F | OH | H | H |
| XVI-48-8 | p-Cl—Ph | * | H | * | Bz | F | F | F | OH | H | H |

*R² and R³ᵇ joined together by (CH₂)₃ to form five-membered ring.

TABLE XVI-49

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-49-1 | p-Br—Ph | H | H | H | Bz | F | F | F | OH | H | H |
| XVI-49-2 | p-Br—Ph | H | H | CH₃ | Bz | F | F | F | OH | H | H |
| XVI-49-3 | p-Br—Ph | H | H | CH(CH₃)₂ | Bz | F | F | F | OH | H | H |
| XVI-49-4 | p-Br—Ph | H | H | CH₂CH(CH₃)₂ | Bz | F | F | F | OH | H | H |
| XVI-49-5 | p-Br—Ph | H | H | CH₂Ph | Bz | F | F | F | OH | H | H |
| XVI-49-6 | p-Br—Ph | H | H | CH₂-indol-3-yl | Bz | F | F | F | OH | H | H |
| XVI-49-7 | p-Br—Ph | H | H | CH₂CH₂SCH₃ | Bz | F | F | F | OH | H | H |
| XVI-49-8 | p-Br—Ph | * | H | * | Bz | F | F | F | OH | H | H |

*R² and R³ᵇ joined together by (CH₂)₃ to form five-membered ring.

TABLE XVI-50

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVI-50-1 | p-I—Ph | H | H | H | Bz | F | F | F | OH | H | H |
| XVI-50-2 | p-I—Ph | H | H | CH₃ | Bz | F | F | F | OH | H | H |
| XVI-50-3 | p-I—Ph | H | H | CH(CH₃)₂ | Bz | F | F | F | OH | H | H |
| XVI-50-4 | p-I—Ph | H | H | CH₂CH(CH₃)₂ | Bz | F | F | F | OH | H | H |
| XVI-50-5 | p-I—Ph | H | H | CH₂Ph | Bz | F | F | F | OH | H | H |
| XVI-50-6 | p-I—Ph | H | H | CH₂-indol-3-yl | Bz | F | F | F | OH | H | H |
| XVI-50-7 | p-I—Ph | H | H | CH₂CH₂SCH₃ | Bz | F | F | F | OH | H | H |
| XVI-50-8 | p-I—Ph | * | H | * | Bz | F | F | F | OH | H | H |

*R² and R³ᵇ joined together by (CH₂)₃ to form five-membered ring.

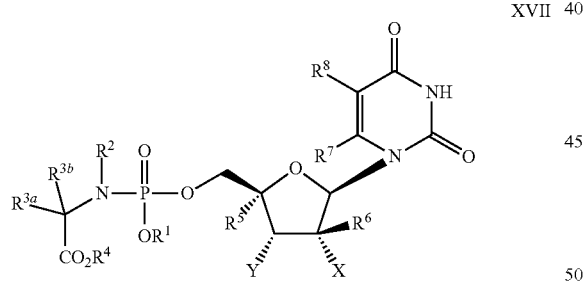

XVII

TABLE XVII-1

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-1-1 | CH₃ | H | H | H | CH₃ | F | H | F | OH | H | H |
| XVII-1-2 | CH₃ | H | H | CH₃ | CH₃ | F | H | F | OH | H | H |
| XVII-1-3 | CH₃ | H | H | CH(CH₃)₂ | CH₃ | F | H | F | OH | H | H |
| XVII-1-4 | CH₃ | H | H | CH₂CH(CH₃)₂ | CH₃ | F | H | F | OH | H | H |
| XVII-1-5 | CH₃ | H | H | CH₂Ph | CH₃ | F | H | F | OH | H | H |
| XVII-1-6 | CH₃ | H | H | CH₂-indol-3-yl | CH₃ | F | H | F | OH | H | H |
| XVII-1-7 | CH₃ | H | H | CH₂CH₂SCH₃ | CH₃ | F | H | F | OH | H | H |
| XVII-1-8 | CH₃ | * | H | * | CH₃ | F | H | F | OH | H | H |

*R² and R³ᵇ joined together by (CH₂)₃ to form five-membered ring.

TABLE XVII-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-2-1 | Et | H | H | H | $CH_3$ | F | H | F | OH | H | H |
| XVII-2-2 | Et | H | H | $CH_3$ | $CH_3$ | F | H | F | OH | H | H |
| XVII-2-3 | Et | H | H | $CH(CH_3)_2$ | $CH_3$ | F | H | F | OH | H | H |
| XVII-2-4 | Et | H | H | $CH_2CH(CH_3)_2$ | $CH_3$ | F | H | F | OH | H | H |
| XVII-2-5 | Et | H | H | $CH_2Ph$ | $CH_3$ | F | H | F | OH | H | H |
| XVII-2-6 | Et | H | H | $CH_2$-indol-3-yl | $CH_3$ | F | H | F | OH | H | H |
| XVII-2-7 | Et | H | H | $CH_2CH_2SCH_3$ | $CH_3$ | F | H | F | OH | H | H |
| XVII-2-8 | Et | * | H | * | $CH_3$ | F | H | F | OH | H | H |

*$R^2$ and $R^{3b}$ joined together by $(CH_2)_3$ to form five-membered ring.

TABLE XVII-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-3-1 | $^iPr$ | H | H | H | $CH_3$ | F | H | F | OH | H | H |
| XVII-3-2 | $^iPr$ | H | H | $CH_3$ | $CH_3$ | F | H | F | OH | H | H |
| XVII-3-3 | $^iPr$ | H | H | $CH(CH_3)_2$ | $CH_3$ | F | H | F | OH | H | H |
| XVII-3-4 | $^iPr$ | H | H | $CH_2CH(CH_3)_2$ | $CH_3$ | F | H | F | OH | H | H |
| XVII-3-5 | $^iPr$ | H | H | $CH_2Ph$ | $CH_3$ | F | H | F | OH | H | H |
| XVII-3-6 | $^iPr$ | H | H | $CH_2$-indol-3-yl | $CH_3$ | F | H | F | OH | H | H |
| XVII-3-7 | $^iPr$ | H | H | $CH_2CH_2SCH_3$ | $CH_3$ | F | H | F | OH | H | H |
| XVII-3-8 | $^iPr$ | * | H | * | $CH_3$ | F | H | F | OH | H | H |

*$R^2$ and $R^{3b}$ joined together by $(CH_2)_3$ to form five-membered ring.

TABLE XVII-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-4-1 | $^tBu$ | H | H | H | $CH_3$ | F | H | F | OH | H | H |
| XVII-4-2 | $^tBu$ | H | H | $CH_3$ | $CH_3$ | F | H | F | OH | H | H |
| XVII-4-3 | $^tBu$ | H | H | $CH(CH_3)_2$ | $CH_3$ | F | H | F | OH | H | H |
| XVII-4-4 | $^tBu$ | H | H | $CH_2CH(CH_3)_2$ | $CH_3$ | F | H | F | OH | H | H |
| XVII-4-5 | $^tBu$ | H | H | $CH_2Ph$ | $CH_3$ | F | H | F | OH | H | H |
| XVII-4-6 | $^tBu$ | H | H | $CH_2$-indol-3-yl | $CH_3$ | F | H | F | OH | H | H |
| XVII-4-7 | $^tBu$ | H | H | $CH_2CH_2SCH_3$ | $CH_3$ | F | H | F | OH | H | H |
| XVII-4-8 | $^tBu$ | * | H | * | $CH_3$ | F | H | F | OH | H | H |

*$R^2$ and $R^{3b}$ joined together by $(CH_2)_3$ to form five-membered ring.

TABLE XVII-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-5-1 | Ph | H | H | H | $CH_3$ | F | H | F | OH | H | H |
| XVII-5-2 | Ph | H | H | $CH_3$ | $CH_3$ | F | H | F | OH | H | H |
| XVII-5-3 | Ph | H | H | $CH(CH_3)_2$ | $CH_3$ | F | H | F | OH | H | H |
| XVII-5-4 | Ph | H | H | $CH_2CH(CH_3)_2$ | $CH_3$ | F | H | F | OH | H | H |
| XVII-5-5 | Ph | H | H | $CH_2Ph$ | $CH_3$ | F | H | F | OH | H | H |
| XVII-5-6 | Ph | H | H | $CH_2$-indol-3-yl | $CH_3$ | F | H | F | OH | H | H |
| XVII-5-7 | Ph | H | H | $CH_2CH_2SCH_3$ | $CH_3$ | F | H | F | OH | H | H |
| XVII-5-8 | Ph | * | H | * | $CH_3$ | F | H | F | OH | H | H |

*$R^2$ and $R^{3b}$ joined together by $(CH_2)_3$ to form five-membered ring.

TABLE XVII-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-6-1 | p-Me—Ph | H | H | H | $CH_3$ | F | H | F | OH | H | H |
| XVII-6-2 | p-Me—Ph | H | H | $CH_3$ | $CH_3$ | F | H | F | OH | H | H |
| XVII-6-3 | p-Me—Ph | H | H | $CH(CH_3)_2$ | $CH_3$ | F | H | F | OH | H | H |
| XVII-6-4 | p-Me—Ph | H | H | $CH_2CH(CH_3)_2$ | $CH_3$ | F | H | F | OH | H | H |
| XVII-6-5 | p-Me—Ph | H | H | $CH_2Ph$ | $CH_3$ | F | H | F | OH | H | H |
| XVII-6-6 | p-Me—Ph | H | H | $CH_2$-indol-3-yl | $CH_3$ | F | H | F | OH | H | H |
| XVII-6-7 | p-Me—Ph | H | H | $CH_2CH_2SCH_3$ | $CH_3$ | F | H | F | OH | H | H |
| XVII-6-8 | p-Me—Ph | * | H | * | $CH_3$ | F | H | F | OH | H | H |

*$R^2$ and $R^{3b}$ joined together by $(CH_2)_3$ to form five-membered ring.

TABLE XVII-7

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-7-1 | p-F—Ph | H | H | H | $CH_3$ | F | H | F | OH | H | H |
| XVII-7-2 | p-F—Ph | H | H | $CH_3$ | $CH_3$ | F | H | F | OH | H | H |
| XVII-7-3 | p-F—Ph | H | H | $CH(CH_3)_2$ | $CH_3$ | F | H | F | OH | H | H |
| XVII-7-4 | p-F—Ph | H | H | $CH_2CH(CH_3)_2$ | $CH_3$ | F | H | F | OH | H | H |
| XVII-7-6 | p-F—Ph | H | H | $CH_2Ph$ | $CH_3$ | F | H | F | OH | H | H |
| XVII-7-7 | p-F—Ph | H | H | $CH_2$-indol-3-yl | $CH_3$ | F | H | F | OH | H | H |
| XVII-7-8 | p-F—Ph | H | H | $CH_2CH_2SCH_3$ | $CH_3$ | F | H | F | OH | H | H |
| XVII-7-20 | p-F—Ph | * | H | * | $CH_3$ | F | H | F | OH | H | H |

*$R^2$ and $R^{3b}$ joined together by $(CH_2)_3$ to form five-membered ring.

TABLE XVII-8

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-8-1 | p-Cl—Ph | H | H | H | CH₃ | F | H | F | OH | H | H |
| XVII-8-2 | p-Cl—Ph | H | H | CH₃ | CH₃ | F | H | F | OH | H | H |
| XVII-8-3 | p-Cl—Ph | H | H | CH(CH₃)₂ | CH₃ | F | H | F | OH | H | H |
| XVII-8-4 | p-Cl—Ph | H | H | CH₂CH(CH₃)₂ | CH₃ | F | H | F | OH | H | H |
| XVII-8-5 | p-Cl—Ph | H | H | CH₂Ph | CH₃ | F | H | F | OH | H | H |
| XVII-8-6 | p-Cl—Ph | H | H | CH₂-indol-3-yl | CH₃ | F | H | F | OH | H | H |
| XVII-8-7 | p-Cl—Ph | H | H | CH₂CH₂SCH₃ | CH₃ | F | H | F | OH | H | H |
| XVII-8-8 | p-Cl—Ph | * | H | * | CH₃ | F | H | F | OH | H | H |

*R² and R³ᵇ joined together by (CH₂)₃ to form five-membered ring.

TABLE XVII-9

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-9-1 | p-Br—Ph | H | H | H | CH₃ | F | H | F | OH | H | H |
| XVII-9-2 | p-Br—Ph | H | H | CH₃ | CH₃ | F | H | F | OH | H | H |
| XVII-9-3 | p-Br—Ph | H | H | CH(CH₃)₂ | CH₃ | F | H | F | OH | H | H |
| XVII-9-4 | p-Br—Ph | H | H | CH₂CH(CH₃)₂ | CH₃ | F | H | F | OH | H | H |
| XVII-9-6 | p-Br—Ph | H | H | CH₂Ph | CH₃ | F | H | F | OH | H | H |
| XVII-9-7 | p-Br—Ph | H | H | CH₂-indol-3-yl | CH₃ | F | H | F | OH | H | H |
| XVII-9-8 | p-Br—Ph | H | H | CH₂CH₂SCH₃ | CH₃ | F | H | F | OH | H | H |
| XVII-9-20 | p-Br—Ph | * | H | * | CH₃ | F | H | F | OH | H | H |

*R² and R³ᵇ joined together by (CH₂)₃ to form five-membered ring.

TABLE XVII-10

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-10-1 | p-I—Ph | H | H | H | CH₃ | F | H | F | OH | H | H |
| XVII-10-2 | p-I—Ph | H | H | CH₃ | CH₃ | F | H | F | OH | H | H |
| XVII-10-3 | p-I—Ph | H | H | CH(CH₃)₂ | CH₃ | F | H | F | OH | H | H |
| XVII-10-4 | p-I—Ph | H | H | CH₂CH(CH₃)₂ | CH₃ | F | H | F | OH | H | H |
| XVII-10-5 | p-I—Ph | H | H | CH₂Ph | CH₃ | F | H | F | OH | H | H |
| XVII-10-6 | p-I—Ph | H | H | CH₂-indol-3-yl | CH₃ | F | H | F | OH | H | H |
| XVII-10-7 | p-I—Ph | H | H | CH₂CH₂SCH₃ | CH₃ | F | H | F | OH | H | H |
| XVII-10-8 | p-I—Ph | * | H | * | CH₃ | F | H | F | OH | H | H |

*R² and R³ᵇ joined together by (CH₂)₃ to form five-membered ring.

TABLE XVII-11

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-11-1 | CH₃ | H | H | H | Et | F | H | F | OH | H | H |
| XVII-11-2 | CH₃ | H | H | CH₃ | Et | F | H | F | OH | H | H |
| XVII-11-3 | CH₃ | H | H | CH(CH₃)₂ | Et | F | H | F | OH | H | H |
| XVII-11-4 | CH₃ | H | H | CH₂CH(CH₃)₂ | Et | F | H | F | OH | H | H |
| XVII-11-5 | CH₃ | H | H | CH₂Ph | Et | F | H | F | OH | H | H |
| XVII-11-6 | CH₃ | H | H | CH₂-indol-3-yl | Et | F | H | F | OH | H | H |
| XVII-11-7 | CH₃ | H | H | CH₂CH₂SCH₃ | Et | F | H | F | OH | H | H |
| XVII-11-8 | CH₃ | * | H | * | Et | F | H | F | OH | H | H |

*R² and R³ᵇ joined together by (CH₂)₃ to form five-membered ring.

TABLE XVII-12

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-12-1 | Et | H | H | H | Et | F | H | F | OH | H | H |
| XVII-12-2 | Et | H | H | CH₃ | Et | F | H | F | OH | H | H |
| XVII-12-3 | Et | H | H | CH(CH₃)₂ | Et | F | H | F | OH | H | H |
| XVII-12-4 | Et | H | H | CH₂CH(CH₃)₂ | Et | F | H | F | OH | H | H |
| XVII-12-5 | Et | H | H | CH₂Ph | Et | F | H | F | OH | H | H |
| XVII-12-6 | Et | H | H | CH₂-indol-3-yl | Et | F | H | F | OH | H | H |
| XVII-12-7 | Et | H | H | CH₂CH₂SCH₃ | Et | F | H | F | OH | H | H |
| XVII-12-8 | Et | * | H | * | Et | F | H | F | OH | H | H |

*R² and R³ᵇ joined together by (CH₂)₃ to form five-membered ring.

TABLE XVII-13

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-13-1 | $^i$Pr | H | H | H | Et | F | H | F | OH | H | H |
| XVII-13-2 | $^i$Pr | H | H | CH$_3$ | Et | F | H | F | OH | H | H |
| XVII-13-3 | $^i$Pr | H | H | CH(CH$_3$)$_2$ | Et | F | H | F | OH | H | H |
| XVII-13-4 | $^i$Pr | H | H | CH$_2$CH(CH$_3$)$_2$ | Et | F | H | F | OH | H | H |
| XVII-13-5 | $^i$Pr | H | H | CH$_2$Ph | Et | F | H | F | OH | H | H |
| XVII-13-6 | $^i$Pr | H | H | CH$_2$-indol-3-yl | Et | F | H | F | OH | H | H |
| XVII-13-7 | $^i$Pr | H | H | CH$_2$CH$_2$SCH$_3$ | Et | F | H | F | OH | H | H |
| XVII-13-8 | $^i$Pr | * | H | * | Et | F | H | F | OH | H | H |

*R² and R³ᵇ joined together by (CH$_2$)$_3$ to form five-membered ring.

TABLE XVII-14

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-14-1 | $^t$Bu | H | H | H | Et | F | H | F | OH | H | H |
| XVII-14-2 | $^t$Bu | H | H | CH$_3$ | Et | F | H | F | OH | H | H |
| XVII-14-3 | $^t$Bu | H | H | CH(CH$_3$)$_2$ | Et | F | H | F | OH | H | H |
| XVII-14-4 | $^t$Bu | H | H | CH$_2$CH(CH$_3$)$_2$ | Et | F | H | F | OH | H | H |
| XVII-14-5 | $^t$Bu | H | H | CH$_2$Ph | Et | F | H | F | OH | H | H |
| XVII-14-6 | $^t$Bu | H | H | CH$_2$-indol-3-yl | Et | F | H | F | OH | H | H |
| XVII-14-7 | $^t$Bu | H | H | CH$_2$CH$_2$SCH$_3$ | Et | F | H | F | OH | H | H |
| XVII-14-8 | $^t$Bu | * | H | * | Et | F | H | F | OH | H | H |

*R² and R³ᵇ joined together by (CH$_2$)$_3$ to form five-membered ring.

TABLE XVII-15

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-15-1 | Ph | H | H | H | Et | F | H | F | OH | H | H |
| XVII-15-2 | Ph | H | H | CH$_3$ | Et | F | H | F | OH | H | H |
| XVII-15-3 | Ph | H | H | CH(CH$_3$)$_2$ | Et | F | H | F | OH | H | H |
| XVII-15-4 | Ph | H | H | CH$_2$CH(CH$_3$)$_2$ | Et | F | H | F | OH | H | H |
| XVII-15-5 | Ph | H | H | CH$_2$Ph | Et | F | H | F | OH | H | H |
| XVII-15-6 | Ph | H | H | CH$_2$-indol-3-yl | Et | F | H | F | OH | H | H |
| XVII-15-7 | Ph | H | H | CH$_2$CH$_2$SCH$_3$ | Et | F | H | F | OH | H | H |
| XVII-15-8 | Ph | * | H | * | Et | F | H | F | OH | H | H |

*R² and R³ᵇ joined together by (CH$_2$)$_3$ to form five-membered ring.

TABLE XVII-16

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-16-1 | p-Me—Ph | H | H | H | Et | F | H | F | OH | H | H |
| XVII-16-2 | p-Me—Ph | H | H | CH$_3$ | Et | F | H | F | OH | H | H |
| XVII-16-3 | p-Me—Ph | H | H | CH(CH$_3$)$_2$ | Et | F | H | F | OH | H | H |
| XVII-16-4 | p-Me—Ph | H | H | CH$_2$CH(CH$_3$)$_2$ | Et | F | H | F | OH | H | H |
| XVII-16-5 | p-Me—Ph | H | H | CH$_2$Ph | Et | F | H | F | OH | H | H |
| XVII-16-6 | p-Me—Ph | H | H | CH$_2$-indol-3-yl | Et | F | H | F | OH | H | H |
| XVII-16-7 | p-Me—Ph | H | H | CH$_2$CH$_2$SCH$_3$ | Et | F | H | F | OH | H | H |
| XVII-16-8 | p-Me—Ph | * | H | * | Et | F | H | F | OH | H | H |

*R² and R³ᵇ joined together by (CH$_2$)$_3$ to form five-membered ring.

TABLE XVII-17

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-17-1 | p-F—Ph | H | H | H | Et | F | H | F | OH | H | H |
| XVII-17-2 | p-F—Ph | H | H | CH$_3$ | Et | F | H | F | OH | H | H |
| XVII-17-3 | p-F—Ph | H | H | CH(CH$_3$)$_2$ | Et | F | H | F | OH | H | H |
| XVII-17-4 | p-F—Ph | H | H | CH$_2$CH(CH$_3$)$_2$ | Et | F | H | F | OH | H | H |
| XVII-17-5 | p-F—Ph | H | H | CH$_2$Ph | Et | F | H | F | OH | H | H |
| XVII-17-6 | p-F—Ph | H | H | CH$_2$-indol-3-yl | Et | F | H | F | OH | H | H |
| XVII-17-7 | p-F—Ph | H | H | CH$_2$CH$_2$SCH$_3$ | Et | F | H | F | OH | H | H |
| XVII-17-8 | p-F—Ph | * | H | * | Et | F | H | F | OH | H | H |

*R² and R³ᵇ joined together by (CH$_2$)$_3$ to form five-membered ring.

TABLE XVII-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-18-1 | p-Cl—Ph | H | H | H | Et | F | H | F | OH | H | H |
| XVII-18-2 | p-Cl—Ph | H | H | CH$_3$ | Et | F | H | F | OH | H | H |

TABLE XVII-18-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-18-3 | p-Cl—Ph | H | H | CH(CH$_3$)$_2$ | Et | F | H | F | OH | H | H |
| XVII-18-4 | p-Cl—Ph | H | H | CH$_2$CH(CH$_3$)$_2$ | Et | F | H | F | OH | H | H |
| XVII-18-5 | p-Cl—Ph | H | H | CH$_2$Ph | Et | F | H | F | OH | H | H |
| XVII-18-6 | p-Cl—Ph | H | H | CH$_2$-indol-3-yl | Et | F | H | F | OH | H | H |
| XVII-18-7 | p-Cl—Ph | H | H | CH$_2$CH$_2$SCH$_3$ | Et | F | H | F | OH | H | H |
| XVII-18-8 | p-Cl—Ph | * | H | * | Et | F | H | F | OH | H | H |

*R$^2$ and R$^{3b}$ joined together by (CH$_2$)$_3$ to form five-membered ring.

TABLE XVII-19

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-19-1 | p-Br—Ph | H | H | H | Et | F | H | F | OH | H | H |
| XVII-19-2 | p-Br—Ph | H | H | CH$_3$ | Et | F | H | F | OH | H | H |
| XVII-19-3 | p-Br—Ph | H | H | CH(CH$_3$)$_2$ | Et | F | H | F | OH | H | H |
| XVII-19-4 | p-Br—Ph | H | H | CH$_2$CH(CH$_3$)$_2$ | Et | F | H | F | OH | H | H |
| XVII-19-5 | p-Br—Ph | H | H | CH$_2$Ph | Et | F | H | F | OH | H | H |
| XVII-19-6 | p-Br—Ph | H | H | CH$_2$-indol-3-yl | Et | F | H | F | OH | H | H |
| XVII-19-7 | p-Br—Ph | H | H | CH$_2$CH$_2$SCH$_3$ | Et | F | H | F | OH | H | H |
| XVII-19-8 | p-Br—Ph | * | H | * | Et | F | H | F | OH | H | H |

*R$^2$ and R$^{3b}$ joined together by (CH$_2$)$_3$ to form five-membered ring.

TABLE XVII-20

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-20-1 | p-I—Ph | H | H | H | Et | F | H | F | OH | H | H |
| XVII-20-2 | p-I—Ph | H | H | CH$_3$ | Et | F | H | F | OH | H | H |
| XVII-20-3 | p-I—Ph | H | H | CH(CH$_3$)$_2$ | Et | F | H | F | OH | H | H |
| XVII-20-4 | p-I—Ph | H | H | CH$_2$CH(CH$_3$)$_2$ | Et | F | H | F | OH | H | H |
| XVII-20-5 | p-I—Ph | H | H | CH$_2$Ph | Et | F | H | F | OH | H | H |
| XVII-20-6 | p-I—Ph | H | H | CH$_2$-indol-3-yl | Et | F | H | F | OH | H | H |
| XVII-20-7 | p-I—Ph | H | H | CH$_2$CH$_2$SCH$_3$ | Et | F | H | F | OH | H | H |
| XVII-20-8 | p-I—Ph | * | H | * | Et | F | H | F | OH | H | H |

*R$^2$ and R$^{3b}$ joined together by (CH$_2$)$_3$ to form five-membered ring.

TABLE XVII-21

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-21-1 | CH$_3$ | H | H | H | $^i$Pr | F | H | F | OH | H | H |
| XVII-21-2 | CH$_3$ | H | H | CH$_3$ | $^i$Pr | F | H | F | OH | H | H |
| XVII-21-3 | CH$_3$ | H | H | CH(CH$_3$)$_2$ | $^i$Pr | F | H | F | OH | H | H |
| XVII-21-4 | CH$_3$ | H | H | CH$_2$CH(CH$_3$)$_2$ | $^i$Pr | F | H | F | OH | H | H |
| XVII-21-5 | CH$_3$ | H | H | CH$_2$Ph | $^i$Pr | F | H | F | OH | H | H |
| XVII-21-6 | CH$_3$ | H | H | CH$_2$-indol-3-yl | $^i$Pr | F | H | F | OH | H | H |
| XVII-21-7 | CH$_3$ | H | H | CH$_2$CH$_2$SCH$_3$ | $^i$Pr | F | H | F | OH | H | H |
| XVII-21-8 | CH$_3$ | * | H | * | $^i$Pr | F | H | F | OH | H | H |

*R$^2$ and R$^{3b}$ joined together by (CH$_2$)$_3$ to form five-membered ring.

TABLE XVII-22

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-22-1 | Et | H | H | H | $^i$Pr | F | H | F | OH | H | H |
| XVII-22-2 | Et | H | H | CH$_3$ | $^i$Pr | F | H | F | OH | H | H |
| XVII-22-3 | Et | H | H | CH(CH$_3$)$_2$ | $^i$Pr | F | H | F | OH | H | H |
| XVII-22-4 | Et | H | H | CH$_2$CH(CH$_3$)$_2$ | $^i$Pr | F | H | F | OH | H | H |
| XVII-22-5 | Et | H | H | CH$_2$Ph | $^i$Pr | F | H | F | OH | H | H |
| XVII-22-6 | Et | H | H | CH$_2$-indol-3-yl | $^i$Pr | F | H | F | OH | H | H |
| XVII-22-7 | Et | H | H | CH$_2$CH$_2$SCH$_3$ | $^i$Pr | F | H | F | OH | H | H |
| XVII-22-8 | Et | * | H | * | $^i$Pr | F | H | F | OH | H | H |

*R$^2$ and R$^{3b}$ joined together by (CH$_2$)$_3$ to form five-membered ring.

TABLE XVII-23

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-23-1 | $^i$Pr | H | H | H | $^i$Pr | F | H | F | OH | H | H |
| XVII-23-2 | $^i$Pr | H | H | CH$_3$ | $^i$Pr | F | H | F | OH | H | H |
| XVII-23-3 | $^i$Pr | H | H | CH(CH$_3$)$_2$ | $^i$Pr | F | H | F | OH | H | H. |

TABLE XVII-23-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-23-4 | $^i$Pr | H | H | CH$_2$CH(CH$_3$)$_2$ | $^i$Pr | F | H | F | OH | H | H |
| XVII-23-5 | $^i$Pr | H | H | CH$_2$Ph | $^i$Pr | F | H | F | OH | H | H |
| XVII-23-6 | $^i$Pr | H | H. | CH$_2$-indol-3-yl | $^i$Pr | F | H | F | OH | H | H |
| XVII-23-7 | $^i$Pr | H | H | CH$_2$CH$_2$SCH$_3$ | $^i$Pr | F | H | F | OH | H | H |
| XVII-23-8 | $^i$Pr | * | H | * | $^i$Pr | F | H | F | OH | H | H |

*R$^2$ and R$^{3b}$ joined together by (CH$_2$)$_3$ to form five-membered ring.

TABLE XVII-24

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-24-1 | $^t$Bu | H | H | H | $^i$Pr | F | H | F | OH | H | H |
| XVII-24-2 | $^t$Bu | H | H | CH$_3$ | $^i$Pr | F | H | F | OH | H | H |
| XVII-24-3 | $^t$Bu | H | H | CH(CH$_3$)$_2$ | $^i$Pr | F | H | F | OH | H | H |
| XVII-24-4 | $^t$Bu | H | H | CH$_2$CH(CH$_3$)$_2$ | $^i$Pr | F | H | F | OH | H | H |
| XVII-24-5 | $^t$Bu | H | H | CH$_2$Ph | $^i$Pr | F | H | F | OH | H | H |
| XVII-24-6 | $^t$Bu | H | H | CH$_2$-indol-3-yl | $^i$Pr | F | H | F | OH | H | H |
| XVII-24-7 | $^t$Bu | H | H | CH$_2$CH$_2$SCH$_3$ | $^i$Pr | F | H | F | OH | H | H |
| XVII-24-8 | $^t$Bu | * | H | * | $^i$Pr | F | H | F | OH | H | H |

*R$^2$ and R$^{3b}$ joined together by (CH$_2$)$_3$ to form five-membered ring.

TABLE XVII-25

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-25-1 | Ph | H | H | H | $^i$Pr | F | H | F | OH | H | H |
| XVII-25-2 | Ph | H | H | CH$_3$ | $^i$Pr | F | H | F | OH | H | H |
| XVII-25-3 | Ph | H | H | CH(CH$_3$)$_2$ | $^i$Pr | F | H | F | OH | H | H |
| XVII-25-4 | Ph | H | H | CH$_2$CH(CH$_3$)$_2$ | $^i$Pr | F | H | F | OH | H | H |
| XVII-25-5 | Ph | H | H | CH$_2$Ph | $^i$Pr | F | H | F | OH | H | H |
| XVII-25-6 | Ph | H | H | CH$_2$-indol-3-yl | $^i$Pr | F | H | F | OH | H | H |
| XVII-25-7 | Ph | H | H | CH$_2$CH$_2$SCH$_3$ | $^i$Pr | F | H | F | OH | H | H |
| XVII-25-8 | Ph | * | H | * | $^i$Pr | F | H | F | OH | H | H |

*R$^2$ and R$^{3b}$ joined together by (CH$_2$)$_3$ to form five-membered ring.

TABLE XVII-26

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-26-1 | p-Me—Ph | H | H | H | $^i$Pr | F | H | F | OH | H | H |
| XVII-26-2 | p-Me—Ph | H | H | CH$_3$ | $^i$Pr | F | H | F | OH | H | H |
| XVII-26-3 | p-Me—Ph | H | H | CH(CH$_3$)$_2$ | $^i$Pr | F | H | F | OH | H | H |
| XVII-26-4 | p-Me—Ph | H | H | CH$_2$CH(CH$_3$)$_2$ | $^i$Pr | F | H | F | OH | H | H |
| XVII-26-5 | p-Me—Ph | H | H | CH$_2$Ph | $^i$Pr | F | H | F | OH | H | H |
| XVII-26-6 | p-Me—Ph | H | H | CH$_2$-indol-3-yl | $^i$Pr | F | H | F | OH | H | H |
| XVII-26-7 | p-Me—Ph | H | H | CH$_2$CH$_2$SCH$_3$ | $^i$Pr | F | H | F | OH | H | H |
| XVII-26-8 | p-Me—Ph | * | H | * | $^i$Pr | F | H | F | OH | H | H |

*R$^2$ and R$^{3b}$ joined together by (CH$_2$)$_3$ to form five-membered ring.

TABLE XVII-27

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-27-1 | p-F—Ph | H | H | H | $^i$Pr | F | H | F | OH | H | H |
| XVII-27-2 | p-F—Ph | H | H | CH$_3$ | $^i$Pr | F | H | F | OH | H | H |
| XVII-27-3 | p-F—Ph | H | H | CH(CH$_3$)$_2$ | $^i$Pr | F | H | F | OH | H | H |
| XVII-27-4 | p-F—Ph | H | H | CH$_2$CH(CH$_3$)$_2$ | $^i$Pr | F | H | F | OH | H | H |
| XVII-27-5 | p-F—Ph | H | H | CH$_2$Ph | $^i$Pr | F | H | F | OH | H | H |
| XVII-27-6 | p-F—Ph | H | H | CH$_2$-indol-3-yl | $^i$Pr | F | H | F | OH | H | H |
| XVII-27-7 | p-F—Ph | H | H | CH$_2$CH$_2$SCH$_3$ | $^i$Pr | F | H | F | OH | H | H |
| XVII-27-8 | p-F—Ph | * | H | * | $^i$Pr | F | H | F | OH | H | H |

*R$^2$ and R$^{3b}$ joined together by (CH$_2$)$_3$ to form five-membered ring.

TABLE XVII-28

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVII-28-1 | p-Cl—Ph | H | H | H | $^i$Pr | F | H | F | OH | H | H |
| XVII-28-2 | p-Cl—Ph | H | H | CH$_3$ | $^i$Pr | F | H | F | OH | H | H |
| XVII-28-3 | p-Cl—Ph | H | H | CH(CH$_3$)$_2$ | $^i$Pr | F | H | F | OH | H | H |
| XVII-28-4 | p-Cl—Ph | H | H | CH$_2$CH(CH$_3$)$_2$ | $^i$Pr | F | H | F | OH | H | H |
| XVII-28-5 | p-Cl—Ph | H | H | CH$_2$Ph | $^i$Pr | F | H | F | OH | H | H |

TABLE XVII-28-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-28-6 | p-Cl—Ph | H | H | CH₂-indol-3-yl | ⁱPr | F | H | F | OH | H | H |
| XVII-28-7 | p-Cl—Ph | H | H | CH₂CH₂SCH₃ | ⁱPr | F | H | F | OH | H | H |
| XVII-28-8 | p-Cl—Ph | * | H | * | ⁱPr | F | H | F | OH | H | H |

*R² and R³ᵇ joined together by (CH₂)₃ to form five-membered ring.

TABLE XVII-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-29-1 | p-Br—Ph | H | H | H | ⁱPr | F | H | F | OH | H | H |
| XVII-29-2 | p-Br—Ph | H | H | CH₃ | ⁱPr | F | H | F | OH | H | H |
| XVII-29-3 | p-Br—Ph | H | H | CH(CH₃)₂ | ⁱPr | F | H | F | OH | H | H |
| XVII-29-4 | p-Br—Ph | H | H | CH₂CH(CH₃)₂ | ⁱPr | F | H | F | OH | H | H |
| XVII-29-5 | p-Br—Ph | H | H | CH₂Ph | ⁱPr | F | H | F | OH | H | H |
| XVII-29-6 | p-Br—Ph | H | H | CH₂-indol-3-yl | ⁱPr | F | H | F | OH | H | H |
| XVII-29-7 | p-Br—Ph | H | H | CH₂CH₂SCH₃ | ⁱPr | F | H | F | OH | H | H |
| XVII-29-8 | p-Br—Ph | * | H | * | ⁱPr | F | H | F | OH | H | H |

*R² and R³ᵇ joined together by (CH₂)₃ to form five-membered ring.

TABLE XVII-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-30-1 | p-I—Ph | H | H | H | ⁱPr | F | H | F | OH | H | H |
| XVII-30-2 | p-I—Ph | H | H | CH₃ | ⁱPr | F | H | F | OH | H | H |
| XVII-30-3 | p-I—Ph | H | H | CH(CH₃)₂ | ⁱPr | F | H | F | OH | H | H |
| XVII-30-4 | p-I—Ph | H | H | CH₂CH(CH₃)₂ | ⁱPr | F | H | F | OH | H | H |
| XVII-30-5 | p-I—Ph | H | H | CH₂Ph | ⁱPr | F | H | F | OH | H | H |
| XVII-30-6 | p-I—Ph | H | H | CH₂-indol-3-yl | ⁱPr | F | H | F | OH | H | H |
| XVII-30-7 | p-I—Ph | H | H | CH₂CH₂SCH₃ | ⁱPr | F | H | F | OH | H | H |
| XVII-30-8 | p-I—Ph | * | H | * | ⁱPr | F | H | F | OH | H | H |

*R² and R³ᵇ joined together by (CH₂)₃ to form five-membered ring.

TABLE XVII-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-31-1 | CH₃ | H | H | H | ⁿBu | F | H | F | OH | H | H |
| XVII-31-2 | CH₃ | H | H | CH₃ | ⁿBu | F | H | F | OH | H | H |
| XVII-31-3 | CH₃ | H | H | CH(CH₃)₂ | ⁿBu | F | H | F | OH | H | H |
| XVII-31-4 | CH₃ | H | H | CH₂CH(CH₃)₂ | ⁿBu | F | H | F | OH | H | H |
| XVII-31-5 | CH₃ | H | H | CH₂Ph | ⁿBu | F | H | F | OH | H | H |
| XVII-31-6 | CH₃ | H | H | CH₂-indol-3-yl | ⁿBu | F | H | F | OH | H | H |
| XVII-31-7 | CH₃ | H | H | CH₂CH₂SCH₃ | ⁿBu | F | H | F | OH | H | H |
| XVII-31-8 | CH₃ | * | H | * | ⁿBu | F | H | F | OH | H | H |

*R² and R³ᵇ joined together by (CH₂)₃ to form five-membered ring.

TABLE XVII-32

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-32-1 | Et | H | H | H | ⁿBu | F | H | F | OH | H | H |
| XVII-32-2 | Et | H | H | CH₃ | ⁿBu | F | H | F | OH | H | H |
| XVII-32-3 | Et | H | H | CH(CH₃)₂ | ⁿBu | F | H | F | OH | H | H |
| XVII-32-4 | Et | H | H | CH₂CH(CH₃)₂ | ⁿBu | F | H | F | OH | H | H |
| XVII-32-5 | Et | H | H | CH₂Ph | ⁿBu | F | H | F | OH | H | H |
| XVII-32-6 | Et | H | H | CH₂-indol-3-yl | ⁿBu | F | H | F | OH | H | H |
| XVII-32-7 | Et | H | H | CH₂CH₂SCH₃ | ⁿBu | F | H | F | OH | H | H |
| XVII-32-8 | Et | * | H | * | ⁿBu | F | H | F | OH | H | H |

*R² and R³ᵇ joined together by (CH₂)₃ to form five-membered ring.

TABLE XVII-33

| No | R[1] | R[2] | R[3a] | R[3b] | R[4] | R[5] | R[6] | X | Y | R[7] | R[8] |
|---|---|---|---|---|---|---|---|---|---|---|---|
| XVII-33-1 | iPr | H | H | H | nBu | F | H | F | OH | H | H |
| XVII-33-2 | iPr | H | H | CH$_3$ | nBu | F | H | F | OH | H | H |
| XVII-33-3 | iPr | H | H | CH(CH$_3$)$_2$ | nBu | F | H | F | OH | H | H |
| XVII-33-4 | iPr | H | H | CH$_2$CH(CH$_3$)$_2$ | nBu | F | H | F | OH | H | H |
| XVII-33-5 | iPr | H | H | CH$_2$Ph | nBu | F | H | F | OH | H | H |
| XVII-33-6 | iPr | H | H | CH$_2$-indol-3-yl | nBu | F | H | F | OH | H | H |
| XVII-33-7 | iPr | H | H | CH$_2$CH$_2$SCH$_3$ | nBu | F | H | F | OH | H | H |
| XVII-33-8 | iPr | * | H | * | nBu | F | H | F | OH | H | H |

*R[2] and R[3b] joined together by (CH$_2$)$_3$ to form five-membered ring.

TABLE XVII-34

| No | R[1] | R[2] | R[3a] | R[3b] | R[4] | R[5] | R[6] | X | Y | R[7] | R[8] |
|---|---|---|---|---|---|---|---|---|---|---|---|
| XVII-34-1 | tBu | H | H | H | nBu | F | H | F | OH | H | H |
| XVII-34-2 | tBu | H | H | CH$_3$ | nBu | F | H | F | OH | H | H |
| XVII-34-3 | tBu | H | H | CH(CH$_3$)$_2$ | nBu | F | H | F | OH | H | H |
| XVII-34-4 | tBu | H | H | CH$_2$CH(CH$_3$)$_2$ | nBu | F | H | F | OH | H | H |
| XVII-34-5 | tBu | H | H | CH$_2$Ph | nBu | F | H | F | OH | H | H |
| XVII-34-6 | tBu | H | H | CH$_2$-indol-3-yl | nBu | F | H | F | OH | H | H |
| XVII-34-7 | tBu | H | H | CH$_2$CH$_2$SCH$_3$ | nBu | F | H | F | OH | H | H |
| XVII-34-8 | tBu | * | H | * | nBu | F | H | F | OH | H | H |

*R[2] and R[3b] joined together by (CH$_2$)$_3$ to form five-membered ring.

TABLE XVII-35

| No | R[1] | R[2] | R[3a] | R[3b] | R[4] | R[5] | R[6] | X | Y | R[7] | R[8] |
|---|---|---|---|---|---|---|---|---|---|---|---|
| XVII-35-1 | Ph | H | H | H | nBu | F | H | F | OH | H | H |
| XVII-35-2 | Ph | H | H | CH$_3$ | nBu | F | H | F | OH | H | H |
| XVII-35-3 | Ph | H | H | CH(CH$_3$)$_2$ | nBu | F | H | F | OH | H | H |
| XVII-35-4 | Ph | H | H | CH$_2$CH(CH$_3$)$_2$ | nBu | F | H | F | OH | H | H |
| XVII-35-5 | Ph | H | H | CH$_2$Ph | nBu | F | H | F | OH | H | H |
| XVII-35-6 | Ph | H | H | CH$_2$-indol-3-yl | nBu | F | H | F | OH | H | H |
| XVII-35-7 | Ph | H | H | CH$_2$CH$_2$SCH$_3$ | nBu | F | H | F | OH | H | H |
| XVII-35-8 | Ph | * | H | * | nBu | F | H | F | OH | H | H |

*R[2] and R[3b] joined together by (CH$_2$)$_3$ to form five-membered ring.

TABLE XVII-36

| No | R[1] | R[2] | R[3a] | R[3b] | R[4] | R[5] | R[6] | X | Y | R[7] | R[8] |
|---|---|---|---|---|---|---|---|---|---|---|---|
| XVII-36-1 | p-Me—Ph | H | H | H | nBu | F | H | F | OH | H | H |
| XVII-36-2 | p-Me—Ph | H | H | CH$_3$ | nBu | F | H | F | OH | H | H |
| XVII-36-3 | p-Me—Ph | H | H | CH(CH$_3$)$_2$ | nBu | F | H | F | OH | H | H |
| XVII-36-4 | p-Me—Ph | H | H | CH$_2$CH(CH$_3$)$_2$ | nBu | F | H | F | OH | H | H |
| XVII-36-5 | p-Me—Ph | H | H | CH$_2$Ph | nBu | F | H | F | OH | H | H |
| XVII-36-6 | p-Me—Ph | H | H | CH$_2$-indol-3-yl | nBu | F | H | F | OH | H | H |
| XVII-36-7 | p-Me—Ph | H | H | CH$_2$CH$_2$SCH$_3$ | nBu | F | H | F | OH | H | H |
| XVII-36-8 | p-Me—Ph | * | H | * | nBu | F | H | F | OH | H | H |

*R[2] and R[3b] joined together by (CH$_2$)$_3$ to form five-membered ring.

TABLE XVII-37

| No | R[1] | R[2] | R[3a] | R[3b] | R[4] | R[5] | R[6] | X | Y | R[7] | R[8] |
|---|---|---|---|---|---|---|---|---|---|---|---|
| XVII-37-1 | p-F—Ph | H | H | H | nBu | F | H | F | OH | H | H |
| XVII-37-2 | p-F—Ph | H | H | CH$_3$ | nBu | F | H | F | OH | H | H |
| XVII-37-3 | p-F—Ph | H | H | CH(CH$_3$)$_2$ | nBu | F | H | F | OH | H | H |

TABLE XVII-37-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-37-4 | p-F—Ph | H | H | CH₂CH(CH₃)₂ | ⁿBu | F | H | F | OH | H | H |
| XVII-37-5 | p-F—Ph | H | H | CH₂Ph | ⁿBu | F | H | F | OH | H | H |
| XVII-37-6 | p-F—Ph | H | H | CH₂-indol-3-yl | ⁿBu | F | H | F | OH | H | H |
| XVII-37-7 | p-F—Ph | H | H | CH₂CH₂SCH₃ | ⁿBu | F | H | F | OH | H | H |
| XVII-37-8 | p-F—Ph | * | H | * | ⁿBu | F | H | F | OH | H | H |

*R² and R³ᵇ joined together by (CH₂)₃ to form five-membered ring.

TABLE XVII-38

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-38-1 | p-Cl—Ph | H | H | H | ⁿBu | F | H | F | OH | H | H |
| XVII-38-2 | p-Cl—Ph | H | H | CH₃ | ⁿBu | F | H | F | OH | H | H |
| XVII-38-3 | p-Cl—Ph | H | H | CH(CH₃)₂ | ⁿBu | F | H | F | OH | H | H |
| XVII-38-4 | p-Cl—Ph | H | H | CH₂CH(CH₃)₂ | ⁿBu | F | H | F | OH | H | H |
| XVII-38-5 | p-Cl—Ph | H | H | CH₂Ph | ⁿBu | F | H | F | OH | H | H |
| XVII-38-6 | p-Cl—Ph | H | H | CH₂-indol-3-yl | ⁿBu | F | H | F | OH | H | H |
| XVII-38-7 | p-Cl—Ph | H | H | CH₂CH₂SCH₃ | ⁿBu | F | H | F | OH | H | H |
| XVII-38-8 | p-Cl—Ph | * | H | * | ⁿBu | F | H | F | OH | H | H |

*R² and R³ᵇ joined together by (CH₂)₃ to form five-membered ring.

TABLE XVII-39

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-39-1 | p-Br—Ph | H | H | H | ⁿBu | F | H | F | OH | H | H |
| XVII-39-2 | p-Br—Ph | H | H | CH₃ | ⁿBu | F | H | F | OH | H | H |
| XVII-39-3 | p-Br—Ph | H | H | CH(CH₃)₂ | ⁿBu | F | H | F | OH | H | H |
| XVII-39-4 | p-Br—Ph | H | H | CH₂CH(CH₃)₂ | ⁿBu | F | H | F | OH | H | H |
| XVII-39-5 | p-Br—Ph | H | H | CH₂Ph | ⁿBu | F | H | F | OH | H | H |
| XVII-39-6 | p-Br—Ph | H | H | CH₂-indol-3-yl | ⁿBu | F | H | F | OH | H | H |
| XVII-39-7 | p-Br—Ph | H | H | CH₂CH₂SCH₃ | ⁿBu | F | H | F | OH | H | H |
| XVII-39-8 | p-Br—Ph | * | H | * | ⁿBu | F | H | F | OH | H | H |

*R² and R³ᵇ joined together by (CH₂)₃ to form five-membered ring.

TABLE XVII-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-40-1 | p-I—Ph | H | H | H | ⁿBu | F | H | F | OH | H | H |
| XVII-40-2 | p-I—Ph | H | H | CH₃ | ⁿBu | F | H | F | OH | H | H |
| XVII-40-3 | p-I—Ph | H | H | CH(CH₃)₂ | ⁿBu | F | H | F | OH | H | H |
| XVII-40-4 | p-I—Ph | H | H | CH₂CH(CH₃)₂ | ⁿBu | F | H | F | OH | H | H |
| XVII-40-5 | p-I—Ph | H | H | CH₂Ph | ⁿBu | F | H | F | OH | H | H |
| XVII-40-6 | p-I—Ph | H | H | CH₂-indol-3-yl | ⁿBu | F | H | F | OH | H | H |
| XVII-40-7 | p-I—Ph | H | H | CH₂CH₂SCH₃ | ⁿBu | F | H | F | OH | H | H |
| XVII-40-8 | p-I—Ph | * | H | * | ⁿBu | F | H | F | OH | H | H |

*R² and R³ᵇ joined together by (CH₂)₃ to form five-membered ring.

TABLE XVII-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-41-1 | CH₃ | H | H | H | Bz | F | H | F | OH | H | H |
| XVII-41-2 | CH₃ | H | H | CH₃ | Bz | F | H | F | OH | H | H |
| XVII-41-3 | CH₃ | H | H | CH(CH₃)₂ | Bz | F | H | F | OH | H | H |
| XVII-41-4 | CH₃ | H | H | CH₂CH(CH₃)₂ | Bz | F | H | F | OH | H | H |
| XVII-41-5 | CH₃ | H | H | CH₂Ph | Bz | F | H | F | OH | H | H |
| XVII-41-6 | CH₃ | H | H | CH₂-indol-3-yl | Bz | F | H | F | OH | H | H |
| XVII-41-7 | CH₃ | H | H | CH₂CH₂SCH₃ | Bz | F | H | F | OH | H | H |
| XVII-41-8 | CH₃ | * | H | * | Bz | F | H | F | OH | H | H |

*R² and R³ᵇ joined together by (CH₂)₃ to form five-membered ring.

TABLE XVII-42

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-42-1 | Et | H | H | H | Bz | F | H | F | OH | H | H |
| XVII-42-2 | Et | H | H | CH$_3$ | Bz | F | H | F | OH | H | H |
| XVII-42-3 | Et | H | H | CH(CH$_3$)$_2$ | Bz | F | H | F | OH | H | H |
| XVII-42-4 | Et | H | H | CH$_2$CH(CH$_3$)$_2$ | Bz | F | H | F | OH | H | H |
| XVII-42-5 | Et | H | H | CH$_2$Ph | Bz | F | H | F | OH | H | H |
| XVII-42-6 | Et | H | H | CH$_2$-indol-3-yl | Bz | F | H | F | OH | H | H |
| XVII-42-7 | Et | H | H | CH$_2$CH$_2$SCH$_3$ | Bz | F | H | F | OH | H | H |
| XVII-42-8 | Et | * | H | * | Bz | F | H | F | OH | H | H |

*$R^2$ and $R^{3b}$ joined together by (CH$_2$)$_3$ to form five-membered ring.

TABLE XVII-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-43-1 | $^i$Pr | H | H | H | Bz | F | H | F | OH | H | H |
| XVII-43-2 | $^i$Pr | H | H | CH$_3$ | Bz | F | H | F | OH | H | H |
| XVII-43-3 | $^i$Pr | H | H | CH(CH$_3$)$_2$ | Bz | F | H | F | OH | H | H |
| XVII-43-4 | $^i$Pr | H | H | CH$_2$CH(CH$_3$)$_2$ | Bz | F | H | F | OH | H | H |
| XVII-43-5 | $^i$Pr | H | H | CH$_2$Ph | Bz | F | H | F | OH | H | H |
| XVII-43-6 | $^i$Pr | H | H | CH$_2$-indol-3-yl | Bz | F | H | F | OH | H | H |
| XVII-43-7 | $^i$Pr | H | H | CH$_2$CH$_2$SCH$_3$ | Bz | F | H | F | OH | H | H |
| XVII-43-8 | $^i$Pr | * | H | * | Bz | F | H | F | OH | H | H |

*$R^2$ and $R^{3b}$ joined together by (CH$_2$)$_3$ to form five-membered ring.

TABLE XVII-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-44-1 | $^t$Bu | H | H | H | Bz | F | H | F | OH | H | H |
| XVII-44-2 | $^t$Bu | H | H | CH$_3$ | Bz | F | H | F | OH | H | H |
| XVII-44-3 | $^t$Bu | H | H | CH(CH$_3$)$_2$ | Bz | F | H | F | OH | H | H |
| XVII-44-4 | $^t$Bu | H | H | CH$_2$CH(CH$_3$)$_2$ | Bz | F | H | F | OH | H | H |
| XVII-44-5 | $^t$Bu | H | H | CH$_2$Ph | Bz | F | H | F | OH | H | H |
| XVII-44-6 | $^t$Bu | H | H | CH$_2$-indol-3-yl | Bz | F | H | F | OH | H | H |
| XVII-44-7 | $^t$Bu | H | H | CH$_2$CH$_2$SCH$_3$ | Bz | F | H | F | OH | H | H |
| XVII-44-8 | $^t$Bu | * | H | * | Bz | F | H | F | OH | H | H |

*$R^2$ and $R^{3b}$ joined together by (CH$_2$)$_3$ to form five-membered ring.

TABLE XVII-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-45-1 | Ph | H | H | H | Bz | F | H | F | OH | H | H |
| XVII-45-2 | Ph | H | H | CH$_3$ | Bz | F | H | F | OH | H | H |
| XVII-45-3 | Ph | H | H | CH(CH$_3$)$_2$ | Bz | F | H | F | OH | H | H |
| XVII-45-4 | Ph | H | H | CH$_2$CH(CH$_3$)$_2$ | Bz | F | H | F | OH | H | H |
| XVII-45-5 | Ph | H | H | CH$_2$Ph | Bz | F | H | F | OH | H | H |
| XVII-45-6 | Ph | H | H | CH$_2$-indol-3-yl | Bz | F | H | F | OH | H | H |
| XVII-45-7 | Ph | H | H | CH$_2$CH$_2$SCH$_3$ | Bz | F | H | F | OH | H | H |
| XVII-45-8 | Ph | * | H | * | Bz | F | H | F | OH | H | H |

*$R^2$ and $R^{3b}$ joined together by (CH$_2$)$_3$ to form five-membered ring.

TABLE XVII-46

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-46-1 | p-Me—Ph | H | H | H | Bz | F | H | F | OH | H | H |
| XVII-46-2 | p-Me—Ph | H | H | CH$_3$ | Bz | F | H | F | OH | H | H |
| XVII-46-3 | p-Me—Ph | H | H | CH(CH$_3$)$_2$ | Bz | F | H | F | OH | H | H |
| XVII-46-4 | p-Me—Ph | H | H | CH$_2$CH(CH$_3$)$_2$ | Bz | F | H | F | OH | H | H |
| XVII-46-5 | p-Me—Ph | H | H | CH$_2$Ph | Bz | F | H | F | OH | H | H |
| XVII-46-6 | p-Me—Ph | H | H | CH$_2$-indol-3-yl | Bz | F | H | F | OH | H | H |
| XVII-46-7 | p-Me—Ph | H | H | CH$_2$CH$_2$SCH$_3$ | Bz | F | H | F | OH | H | H |
| XVII-46-8 | p-Me—Ph | * | H | * | Bz | F | H | F | OH | H | H |

*$R^2$ and $R^{3b}$ joined together by (CH$_2$)$_3$ to form five-membered ring.

TABLE XVII-47

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVII-47-1 | p-F—Ph | H | H | H | Bz | F | H | F | OH | H | H |
| XVII-47-2 | p-F—Ph | H | H | CH$_3$ | Bz | F | H | F | OH | H | H |
| XVII-47-3 | p-F—Ph | H | H | CH(CH$_3$)$_2$ | Bz | F | H | F | OH | H | H |
| XVII-47-4 | p-F—Ph | H | H | CH$_2$CH(CH$_3$)$_2$ | Bz | F | H | F | OH | H | H |
| XVII-47-5 | p-F—Ph | H | H | CH$_2$Ph | Bz | F | H | F | OH | H | H |
| XVII-47-6 | p-F—Ph | H | H | CH$_2$-indol-3-yl | Bz | F | H | F | OH | H | H |
| XVII-47-7 | p-F—Ph | H | H | CH$_2$CH$_2$SCH$_3$ | Bz | F | H | F | OH | H | H |
| XVII-47-8 | p-F—Ph | * | H | * | Bz | F | H | F | OH | H | H |

*$R^2$ and $R^{3b}$ joined together by (CH$_2$)$_3$ to form five-membered ring.

TABLE XVII-48

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-48-1 | p-Cl—Ph | H | H | H | Bz | F | H | F | OH | H | H |
| XVII-48-2 | p-Cl—Ph | H | H | CH₃ | Bz | F | H | F | OH | H | H |
| XVII-48-3 | p-Cl—Ph | H | H | CH(CH₃)₂ | Bz | F | H | F | OH | H | H |
| XVII-48-4 | p-Cl—Ph | H | H | CH₂CH(CH₃)₂ | Bz | F | H | F | OH | H | H |
| XVII-48-5 | p-Cl—Ph | H | H | CH₂Ph | Bz | F | H | F | OH | H | H |
| XVII-48-6 | p-Cl—Ph | H | H | CH₂-indol-3-yl | Bz | F | H | F | OH | H | H |
| XVII-48-7 | p-Cl—Ph | H | H | CH₂CH₂SCH₃ | Bz | F | H | F | OH | H | H |
| XVII-48-8 | p-Cl—Ph | * | H | * | Bz | F | H | F | OH | H | H |

*R² and R³ᵇ joined together by (CH₂)₃ to form five-membered ring.

TABLE XVII-49

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-49-1 | p-Br—Ph | H | H | H | Bz | F | H | F | OH | H | H |
| XVII-49-2 | p-Br—Ph | H | H | CH₃ | Bz | F | H | F | OH | H | H |
| XVII-49-3 | p-Br—Ph | H | H | CH(CH₃)₂ | Bz | F | H | F | OH | H | H |
| XVII-49-4 | p-Br—Ph | H | H | CH₂CH(CH₃)₂ | Bz | F | H | F | OH | H | H |
| XVII-49-5 | p-Br—Ph | H | H | CH₂Ph | Bz | F | H | F | OH | H | H |
| XVII-49-6 | p-Br—Ph | H | H | CH₂-indol-3-yl | Bz | F | H | F | OH | H | H |
| XVII-49-7 | p-Br—Ph | H | H | CH₂CH₂SCH₃ | Bz | F | H | F | OH | H | H |
| XVII-49-8 | p-Br—Ph | * | H | * | Bz | F | H | F | OH | H | H |

*R² and R³ᵇ joined together by (CH₂)₃ to form five-membered ring.

TABLE XVII-50

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVII-50-1 | p-I—Ph | H | H | H | Bz | F | H | F | OH | H | H |
| XVII-50-2 | p-I—Ph | H | H | CH₃ | Bz | F | H | F | OH | H | H |
| XVII-50-3 | p-I—Ph | H | H | CH(CH₃)₂ | Bz | F | H | F | OH | H | H |
| XVII-50-4 | p-I—Ph | H | H | CH₂CH(CH₃)₂ | Bz | F | H | F | OH | H | H |
| XVII-50-5 | p-I—Ph | H | H | CH₂Ph | Bz | F | H | F | OH | H | H |
| XVII-50-6 | p-I—Ph | H | H | CH₂-indol-3-yl | Bz | F | H | F | OH | H | H |
| XVII-50-7 | p-I—Ph | H | H | CH₂CH₂SCH₃ | Bz | F | H | F | OH | H | H |
| XVII-50-8 | p-I—Ph | * | H | * | Bz | F | H | F | OH | H | H |

*R² and R³ᵇ joined together by (CH₂)₃ to form five-membered ring.

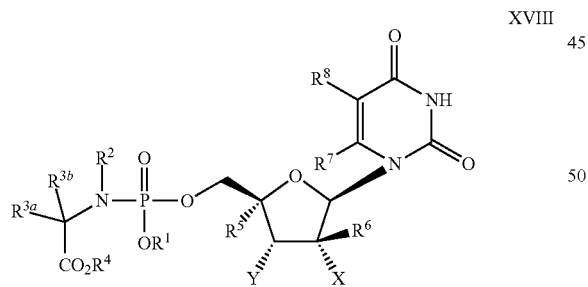

XVIII

TABLE XVIII-1

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-1-1 | CH₃ | H | H | H | CH₃ | OCH₃ | F | H | OH | H | H |
| XVIII-1-2 | CH₃ | H | H | CH₃ | CH₃ | OCH₃ | F | H | OH | H | H |
| XVIII-1-3 | CH₃ | H | H | CH(CH₃)₂ | CH₃ | OCH₃ | F | H | OH | H | H |
| XVIII-1-4 | CH₃ | H | H | CH₂CH(CH₃)₂ | CH₃ | OCH₃ | F | H | OH | H | H |
| XVIII-1-5 | CH₃ | H | H | CH₂Ph | CH₃ | OCH₃ | F | H | OH | H | H |
| XVIII-1-6 | CH₃ | H | H | CH₂-indol-3-yl | CH₃ | OCH₃ | F | H | OH | H | H |

TABLE XVIII-1-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-1-7 | $CH_3$ | H | H | $CH_2CH_2SCH_3$ | $CH_3$ | $OCH_3$ | F | H | OH | H | H |
| XVIII-1-8 | $CH_3$ | * | H | * | $CH_3$ | $OCH_3$ | F | H | OH | H | H |

*$R^2$ and $R^{3b}$ joined together by $(CH_2)_3$ to form five-membered ring.

TABLE XVIII-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-2-1 | Et | H | H | H | $CH_3$ | $OCH_3$ | F | H | OH | H | H |
| XVIII-2-2 | Et | H | H | $CH_3$ | $CH_3$ | $OCH_3$ | F | H | OH | H | H |
| XVIII-2-3 | Et | H | H | $CH(CH_3)_2$ | $CH_3$ | $OCH_3$ | F | H | OH | H | H |
| XVIII-2-4 | Et | H | H | $CH_2CH(CH_3)_2$ | $CH_3$ | $OCH_3$ | F | H | OH | H | H |
| XVIII-2-5 | Et | H | H | $CH_2Ph$ | $CH_3$ | $OCH_3$ | F | H | OH | H | H |
| XVIII-2-6 | Et | H | H | $CH_2$-indol-3-yl | $CH_3$ | $OCH_3$ | F | H | OH | H | H |
| XVIII-2-7 | Et | H | H | $CH_2CH_2SCH_3$ | $CH_3$ | $OCH_3$ | F | H | OH | H | H |
| XVIII-2-8 | Et | * | H | * | $CH_3$ | $OCH_3$ | F | H | OH | H | H |

*$R^2$ and $R^{3b}$ joined together by $(CH_2)_3$ to form five-membered ring.

TABLE XVIII-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-3-1 | $^iPr$ | H | H | H | $CH_3$ | $OCH_3$ | F | H | OH | H | H |
| XVIII-3-2 | $^iPr$ | H | H | $CH_3$ | $CH_3$ | $OCH_3$ | F | H | OH | H | H |
| XVIII-3-3 | $^iPr$ | H | H | $CH(CH_3)_2$ | $CH_3$ | $OCH_3$ | F | H | OH | H | H |
| XVIII-3-4 | $^iPr$ | H | H | $CH_2CH(CH_3)_2$ | $CH_3$ | $OCH_3$ | F | H | OH | H | H |
| XVIII-3-5 | $^iPr$ | H | H | $CH_2Ph$ | $CH_3$ | $OCH_3$ | F | H | OH | H | H |
| XVIII-3-6 | $^iPr$ | H | H | $CH_2$-indol-3-yl | $CH_3$ | $OCH_3$ | F | H | OH | H | H |
| XVIII-3-7 | $^iPr$ | H | H | $CH_2CH_2SCH_3$ | $CH_3$ | $OCH_3$ | F | H | OH | H | H |
| XVIII-3-8 | $^iPr$ | * | H | * | $CH_3$ | $OCH_3$ | F | H | OH | H | H |

*$R^2$ and $R^{3b}$ joined together by $(CH_2)_3$ to form five-membered ring.

TABLE XVIII-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-4-1 | $^tBu$ | H | H | H | $CH_3$ | $OCH_3$ | F | H | OH | H | H |
| XVIII-4-2 | $^tBu$ | H | H | $CH_3$ | $CH_3$ | $OCH_3$ | F | H | OH | H | H |
| XVIII-4-3 | $^tBu$ | H | H | $CH(CH_3)_2$ | $CH_3$ | $OCH_3$ | F | H | OH | H | H |
| XVIII-4-4 | $^tBu$ | H | H | $CH_2CH(CH_3)_2$ | $CH_3$ | $OCH_3$ | F | H | OH | H | H |
| XVIII-4-5 | $^tBu$ | H | H | $CH_2Ph$ | $CH_3$ | $OCH_3$ | F | H | OH | H | H |
| XVIII-4-6 | $^tBu$ | H | H | $CH_2$-indol-3-yl | $CH_3$ | $OCH_3$ | F | H | OH | H | H |
| XVIII-4-7 | $^tBu$ | H | H | $CH_2CH_2SCH_3$ | $CH_3$ | $OCH_3$ | F | H | OH | H | H |
| XVIII-4-8 | $^tBu$ | * | H | * | $CH_3$ | $OCH_3$ | F | H | OH | H | H |

*$R^2$ and $R^{3b}$ joined together by $(CH_2)_3$ to form five-membered ring.

TABLE XVIII-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-5-1 | Ph | H | H | H | $CH_3$ | $OCH_3$ | F | H | OH | H | H |
| XVIII-5-2 | Ph | H | H | $CH_3$ | $CH_3$ | $OCH_3$ | F | H | OH | H | H |
| XVIII-5-3 | Ph | H | H | $CH(CH_3)_2$ | $CH_3$ | $OCH_3$ | F | H | OH | H | H |
| XVIII-5-4 | Ph | H | H | $CH_2CH(CH_3)_2$ | $CH_3$ | $OCH_3$ | F | H | OH | H | H |
| XVIII-5-5 | Ph | H | H | $CH_2Ph$ | $CH_3$ | $OCH_3$ | F | H | OH | H | H |
| XVIII-5-6 | Ph | H | H | $CH_2$-indol-3-yl | $CH_3$ | $OCH_3$ | F | H | OH | H | H |
| XVIII-5-7 | Ph | H | H | $CH_2CH_2SCH_3$ | $CH_3$ | $OCH_3$ | F | H | OH | H | H |
| XVIII-5-8 | Ph | * | H | * | $CH_3$ | $OCH_3$ | F | H | OH | H | H |

*$R^2$ and $R^{3b}$ joined together by $(CH_2)_3$ to form five-membered ring.

TABLE XVIII-6

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-6-1 | p-Me—Ph | H | H | H | CH₃ | OCH₃ | F | H | OH | H | H |
| XVIII-6-2 | p-Me—Ph | H | H | CH₃ | CH₃ | OCH₃ | F | H | OH | H | H |
| XVIII-6-3 | p-Me—Ph | H | H | CH(CH₃)₂ | CH₃ | OCH₃ | F | H | OH | H | H |
| XVIII-6-4 | p-Me—Ph | H | H | CH₂CH(CH₃)₂ | CH₃ | OCH₃ | F | H | OH | H | H |
| XVIII-6-5 | p-Me—Ph | H | H | CH₂Ph | CH₃ | OCH₃ | F | H | OH | H | H |
| XVIII-6-6 | p-Me—Ph | H | H | CH₂-indol-3-yl | CH₃ | OCH₃ | F | H | OH | H | H |
| XVIII-6-7 | p-Me—Ph | H | H | CH₂CH₂SCH₃ | CH₃ | OCH₃ | F | H | OH | H | H |
| XVIII-6-8 | p-Me—Ph | * | H | * | CH₃ | OCH₃ | F | H | OH | H | H |

*R² and R³ᵇ joined together by (CH₂)₃ to form five-membered ring.

TABLE XVIII-7

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-7-1 | p-F—Ph | H | H | H | CH₃ | OCH₃ | F | H | OH | H | H |
| XVIII-7-2 | p-F—Ph | H | H | CH₃ | CH₃ | OCH₃ | F | H | OH | H | H |
| XVIII-7-3 | p-F—Ph | H | H | CH(CH₃)₂ | CH₃ | OCH₃ | F | H | OH | H | H |
| XVIII-7-4 | p-F—Ph | H | H | CH₂CH(CH₃)₂ | CH₃ | OCH₃ | F | H | OH | H | H |
| XVIII-7-6 | p-F—Ph | H | H | CH₂Ph | CH₃ | OCH₃ | F | H | OH | H | H |
| XVIII-7-7 | p-F—Ph | H | H | CH₂-indol-3-yl | CH₃ | OCH₃ | F | H | OH | H | H |
| XVIII-7-8 | p-F—Ph | H | H | CH₂CH₂SCH₃ | CH₃ | OCH₃ | F | H | OH | H | H |
| XVIII-7-20 | p-F—Ph | * | H | * | CH₃ | OCH₃ | F | H | OH | H | H |

*R² and R³ᵇ joined together by (CH₂)₃ to form five-membered ring.

TABLE XVIII-8

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-8-1 | p-Cl—Ph | H | H | H | CH₃ | OCH₃ | F | H | OH | H | H |
| XVIII-8-2 | p-Cl—Ph | H | H | CH₃ | CH₃ | OCH₃ | F | H | OH | H | H |
| XVIII-8-3 | p-Cl—Ph | H | H | CH(CH₃)₂ | CH₃ | OCH₃ | F | H | OH | H | H |
| XVIII-8-4 | p-Cl—Ph | H | H | CH₂CH(CH₃)₂ | CH₃ | OCH₃ | F | H | OH | H | H |
| XVIII-8-5 | p-Cl—Ph | H | H | CH₂Ph | CH₃ | OCH₃ | F | H | OH | H | H |
| XVIII-8-6 | p-Cl—Ph | H | H | CH₂-indol-3-yl | CH₃ | OCH₃ | F | H | OH | H | H |
| XVIII-8-7 | p-Cl—Ph | H | H | CH₂CH₂SCH₃ | CH₃ | OCH₃ | F | H | OH | H | H |
| XVIII-8-8 | p-Cl—Ph | * | H | * | CH₃ | OCH₃ | F | H | OH | H | H |

*R² and R³ᵇ joined together by (CH₂)₃ to form five-membered ring.

TABLE XVIII-9

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-9-1 | p-Br—Ph | H | H | H | CH₃ | OCH₃ | F | H | OH | H | H |
| XVIII-9-2 | p-Br—Ph | H | H | CH₃ | CH₃ | OCH₃ | F | H | OH | H | H |
| XVIII-9-3 | p-Br—Ph | H | H | CH(CH₃)₂ | CH₃ | OCH₃ | F | H | OH | H | H |
| XVIII-9-4 | p-Br—Ph | H | H | CH₂CH(CH₃)₂ | CH₃ | OCH₃ | F | H | OH | H | H |
| XVIII-9-6 | p-Br—Ph | H | H | CH₂Ph | CH₃ | OCH₃ | F | H | OH | H | H |
| XVIII-9-7 | p-Br—Ph | H | H | CH₂-indol-3-yl | CH₃ | OCH₃ | F | H | OH | H | H |
| XVIII-9-8 | p-Br—Ph | H | H | CH₂CH₂SCH₃ | CH₃ | OCH₃ | F | H | OH | H | H |
| XVIII-9-20 | p-Br—Ph | * | H | * | CH₃ | OCH₃ | F | H | OH | H | H |

*R² and R³ᵇ joined together by (CH₂)₃ to form five-membered ring.

TABLE XVIII-10

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-10-1 | p-I—Ph | H | H | H | CH₃ | OCH₃ | F | H | OH | H | H |
| XVIII-10-2 | p-I—Ph | H | H | CH₃ | CH₃ | OCH₃ | F | H | OH | H | H |
| XVIII-10-3 | p-I—Ph | H | H | CH(CH₃)₂ | CH₃ | OCH₃ | F | H | OH | H | H |

TABLE XVIII-10-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-10-4 | p-I—Ph | H | H | CH₂CH(CH₃)₂ | CH₃ | OCH₃ | F | H | OH | H | H |
| XVIII-10-5 | p-I—Ph | H | H | CH₂Ph | CH₃ | OCH₃ | F | H | OH | H | H |
| XVIII-10-6 | p-I—Ph | H | H | CH₂-indol-3-yl | CH₃ | OCH₃ | F | H | OH | H | H |
| XVIII-10-7 | p-I—Ph | H | H | CH₂CH₂SCH₃ | CH₃ | OCH₃ | F | H | OH | H | H |
| XVIII-10-8 | p-I—Ph | * | H | * | CH₃ | OCH₃ | F | H | OH | H | H |

*R² and R³ᵇ joined together by (CH₂)₃ to form five-membered ring.

TABLE XVIII-11

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-11-1 | CH₃ | H | H | H | Et | OCH₃ | F | H | OH | H | H |
| XVIII-11-2 | CH₃ | H | H | CH₃ | Et | OCH₃ | F | H | OH | H | H |
| XVIII-11-3 | CH₃ | H | H | CH(CH₃)₂ | Et | OCH₃ | F | H | OH | H | H |
| XVIII-11-4 | CH₃ | H | H | CH₂CH(CH₃)₂ | Et | OCH₃ | F | H | OH | H | H |
| XVIII-11-5 | CH₃ | H | H | CH₂Ph | Et | OCH₃ | F | H | OH | H | H |
| XVIII-11-6 | CH₃ | H | H | CH₂-indol-3-yl | Et | OCH₃ | F | H | OH | H | H |
| XVIII-11-7 | CH₃ | H | H | CH₂CH₂SCH₃ | Et | OCH₃ | F | H | OH | H | H |
| XVIII-11-8 | CH₃ | * | H | * | Et | OCH₃ | F | H | OH | H | H |

*R² and R³ᵇ joined together by (CH₂)₃ to form five-membered ring.

TABLE XVIII-12

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-12-1 | Et | H | H | H | Et | OCH₃ | F | H | OH | H | H |
| XVIII-12-2 | Et | H | H | CH₃ | Et | OCH₃ | F | H | OH | H | H |
| XVIII-12-3 | Et | H | H | CH(CH₃)₂ | Et | OCH₃ | F | H | OH | H | H |
| XVIII-12-4 | Et | H | H | CH₂CH(CH₃)₂ | Et | OCH₃ | F | H | OH | H | H |
| XVIII-12-5 | Et | H | H | CH₂Ph | Et | OCH₃ | F | H | OH | H | H |
| XVIII-12-6 | Et | H | H | CH₂-indol-3-yl | Et | OCH₃ | F | H | OH | H | H |
| XVIII-12-7 | Et | H | H | CH₂CH₂SCH₃ | Et | OCH₃ | F | H | OH | H | H |
| XVIII-12-8 | Et | * | H | * | Et | OCH₃ | F | H | OH | H | H |

*R² and R³ᵇ joined together by (CH₂)₃ to form five-membered ring.

TABLE XVIII-13

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-13-1 | ⁱPr | H | H | H | Et | OCH₃ | F | H | OH | H | H |
| XVIII-13-2 | ⁱPr | H | H | CH₃ | Et | OCH₃ | F | H | OH | H | H |
| XVIII-13-3 | ⁱPr | H | H | CH(CH₃)₂ | Et | OCH₃ | F | H | OH | H | H |
| XVIII-13-4 | ⁱPr | H | H | CH₂CH(CH₃)₂ | Et | OCH₃ | F | H | OH | H | H |
| XVIII-13-5 | ⁱPr | H | H | CH₂Ph | Et | OCH₃ | F | H | OH | H | H |
| XVIII-13-6 | ⁱPr | H | H | CH₂-indol-3-yl | Et | OCH₃ | F | H | OH | H | H |
| XVIII-13-7 | ⁱPr | H | H | CH₂CH₂SCH₃ | Et | OCH₃ | F | H | OH | H | H |
| XVIII-13-8 | ⁱPr | * | H | * | Et | OCH₃ | F | H | OH | H | H |

*R² and R³ᵇ joined together by (CH₂)₃ to form five-membered ring.

TABLE XVIII-14

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-14-1 | ᵗBu | H | H | H | Et | OCH₃ | F | H | OH | H | H |
| XVIII-14-2 | ᵗBu | H | H | CH₃ | Et | OCH₃ | F | H | OH | H | H |
| XVIII-14-3 | ᵗBu | H | H | CH(CH₃)₂ | Et | OCH₃ | F | H | OH | H | H |
| XVIII-14-4 | ᵗBu | H | H | CH₂CH(CH₃)₂ | Et | OCH₃ | F | H | OH | H | H |
| XVIII-14-5 | ᵗBu | H | H | CH₂Ph | Et | OCH₃ | F | H | OH | H | H |
| XVIII-14-6 | ᵗBu | H | H | CH₂-indol-3-yl | Et | OCH₃ | F | H | OH | H | H |
| XVIII-14-7 | ᵗBu | H | H | CH₂CH₂SCH₃ | Et | OCH₃ | F | H | OH | H | H |
| XVIII-14-8 | ᵗBu | * | H | * | Et | OCH₃ | F | H | OH | H | H |

*R² and R³ᵇ joined together by (CH₂)₃ to form five-membered ring.

TABLE XVIII-15

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-15-1 | Ph | H | H | H | Et | OCH₃ | F | H | OH | H | H |
| XVIII-15-2 | Ph | H | H | CH₃ | Et | OCH₃ | F | H | OH | H | H |
| XVIII-15-3 | Ph | H | H | CH(CH₃)₂ | Et | OCH₃ | F | H | OH | H | H |
| XVIII-15-4 | Ph | H | H | CH₂CH(CH₃)₂ | Et | OCH₃ | F | H | OH | H | H |
| XVIII-15-5 | Ph | H | H | CH₂Ph | Et | OCH₃ | F | H | OH | H | H |
| XVIII-15-6 | Ph | H | H | CH₂-indol-3-yl | Et | OCH₃ | F | H | OH | H | H |
| XVIII-15-7 | Ph | H | H | CH₂CH₂SCH₃ | Et | OCH₃ | F | H | OH | H | H |
| XVIII-15-8 | Ph | * | H | * | Et | OCH₃ | F | H | OH | H | H |

*R² and R³ᵇ joined together by (CH₂)₃ to form five-membered ring.

TABLE XVIII-16

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-16-1 | p-Me—Ph | H | H | H | Et | OCH₃ | F | H | OH | H | H |
| XVIII-16-2 | p-Me—Ph | H | H | CH₃ | Et | OCH₃ | F | H | OH | H | H |
| XVIII-16-3 | p-Me—Ph | H | H | CH(CH₃)₂ | Et | OCH₃ | F | H | OH | H | H |
| XVIII-16-4 | p-Me—Ph | H | H | CH₂CH(CH₃)₂ | Et | OCH₃ | F | H | OH | H | H |
| XVIII-16-5 | p-Me—Ph | H | H | CH₂Ph | Et | OCH₃ | F | H | OH | H | H |
| XVIII-16-6 | p-Me—Ph | H | H | CH₂-indol-3-yl | Et | OCH₃ | F | H | OH | H | H |
| XVIII-16-7 | p-Me—Ph | H | H | CH₂CH₂SCH₃ | Et | OCH₃ | F | H | OH | H | H |
| XVIII-16-8 | p-Me—Ph | * | H | * | Et | OCH₃ | F | H | OH | H | H |

*R² and R³ᵇ joined together by (CH₂)₃ to form five-membered ring.

TABLE XVIII-17

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-17-1 | p-F—Ph | H | H | H | Et | OCH₃ | F | H | OH | H | H |
| XVIII-17-2 | p-F—Ph | H | H | CH₃ | Et | OCH₃ | F | H | OH | H | H |
| XVIII-17-3 | p-F—Ph | H | H | CH(CH₃)₂ | Et | OCH₃ | F | H | OH | H | H |
| XVIII-17-4 | p-F—Ph | H | H | CH₂CH(CH₃)₂ | Et | OCH₃ | F | H | OH | H | H |
| XVIII-17-5 | p-F—Ph | H | H | CH₂Ph | Et | OCH₃ | F | H | OH | H | H |
| XVIII-17-6 | p-F—Ph | H | H | CH₂-indol-3-yl | Et | OCH₃ | F | H | OH | H | H |
| XVIII-17-7 | p-F—Ph | H | H | CH₂CH₂SCH₃ | Et | OCH₃ | F | H | OH | H | H |
| XVIII-17-8 | p-F—Ph | * | H | * | Et | OCH₃ | F | H | OH | H | H |

*R² and R³ᵇ joined together by (CH₂)₃ to form five-membered ring.

TABLE XVIII-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-18-1 | p-Cl—Ph | H | H | H | Et | OCH₃ | F | H | OH | H | H |
| XVIII-18-2 | p-Cl—Ph | H | H | CH₃ | Et | OCH₃ | F | H | OH | H | H |
| XVIII-18-3 | p-Cl—Ph | H | H | CH(CH₃)₂ | Et | OCH₃ | F | H | OH | H | H |
| XVIII-18-4 | p-Cl—Ph | H | H | CH₂CH(CH₃)₂ | Et | OCH₃ | F | H | OH | H | H |
| XVIII-18-5 | p-Cl—Ph | H | H | CH₂Ph | Et | OCH₃ | F | H | OH | H | H |
| XVIII-18-6 | p-Cl—Ph | H | H | CH₂-indol-3-yl | Et | OCH₃ | F | H | OH | H | H |
| XVIII-18-7 | p-Cl—Ph | H | H | CH₂CH₂SCH₃ | Et | OCH₃ | F | H | OH | H | H |
| XVIII-18-8 | p-Cl—Ph | * | H | * | Et | OCH₃ | F | H | OH | H | H |

*R² and R³ᵇ joined together by (CH₂)₃ to form five-membered ring.

TABLE XVIII-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-19-1 | p-Br—Ph | H | H | H | Et | OCH₃ | F | H | OH | H | H |
| XVIII-19-2 | p-Br—Ph | H | H | CH₃ | Et | OCH₃ | F | H | OH | H | H |
| XVIII-19-3 | p-Br—Ph | H | H | CH(CH₃)₂ | Et | OCH₃ | F | H | OH | H | H |
| XVIII-19-4 | p-Br—Ph | H | H | CH₂CH(CH₃)₂ | Et | OCH₃ | F | H | OH | H | H |
| XVIII-19-5 | p-Br—Ph | H | H | CH₂Ph | Et | OCH₃ | F | H | OH | H | H |

TABLE XVIII-19-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-19-6 | p-Br—Ph | H | H | CH₂-indol-3-yl | Et | OCH₃ | F | H | OH | H | H |
| XVIII-19-7 | p-Br—Ph | H | H | CH₂CH₂SCH₃ | Et | OCH₃ | F | H | OH | H | H |
| XVIII-19-8 | p-Br—Ph | * | H | * | Et | OCH₃ | F | H | OH | H | H |

*R² and R³ᵇ joined together by (CH₂)₃ to form five-membered ring.

TABLE XVIII-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-20-1 | p-I—Ph | H | H | H | Et | OCH₃ | F | H | OH | H | H |
| XVIII-20-2 | p-I—Ph | H | H | CH₃ | Et | OCH₃ | F | H | OH | H | H |
| XVIII-20-3 | p-I—Ph | H | H | CH(CH₃)₂ | Et | OCH₃ | F | H | OH | H | H |
| XVIII-20-4 | p-I—Ph | H | H | CH₂CH(CH₃)₂ | Et | OCH₃ | F | H | OH | H | H |
| XVIII-20-5 | p-I—Ph | H | H | CH₂Ph | Et | OCH₃ | F | H | OH | H | H |
| XVIII-20-6 | p-I—Ph | H | H | CH₂-indol-3-yl | Et | OCH₃ | F | H | OH | H | H |
| XVIII-20-7 | p-I—Ph | H | H | CH₂CH₂SCH₃ | Et | OCH₃ | F | H | OH | H | H |
| XVIII-20-8 | p-I—Ph | * | H | * | Et | OCH₃ | F | H | OH | H | H |

*R² and R³ᵇ joined together by (CH₂)₃ to form five-membered ring.

TABLE XVIII-21

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-21-1 | CH₃ | H | H | H | ⁱPr | OCH₃ | F | H | OH | H | H |
| XVIII-21-2 | CH₃ | H | H | CH₃ | ⁱPr | OCH₃ | F | H | OH | H | H |
| XVIII-21-3 | CH₃ | H | H | CH(CH₃)₂ | ⁱPr | OCH₃ | F | H | OH | H | H |
| XVIII-21-4 | CH₃ | H | H | CH₂CH(CH₃)₂ | ⁱPr | OCH₃ | F | H | OH | H | H |
| XVIII-21-5 | CH₃ | H | H | CH₂Ph | ⁱPr | OCH₃ | F | H | OH | H | H |
| XVIII-21-6 | CH₃ | H | H | CH₂-indol-3-yl | ⁱPr | OCH₃ | F | H | OH | H | H |
| XVIII-21-7 | CH₃ | H | H | CH₂CH₂SCH₃ | ⁱPr | OCH₃ | F | H | OH | H | H |
| XVIII-21-8 | CH₃ | * | H | * | ⁱPr | OCH₃ | F | H | OH | H | H |

*R² and R³ᵇ joined together by (CH₂)₃ to form five-membered ring.

TABLE XVIII-22

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-22-1 | Et | H | H | H | ⁱPr | OCH₃ | F | H | OH | H | H |
| XVIII-22-2 | Et | H | H | CH₃ | ⁱPr | OCH₃ | F | H | OH | H | H |
| XVIII-22-3 | Et | H | H | CH(CH₃)₂ | ⁱPr | OCH₃ | F | H | OH | H | H |
| XVIII-22-4 | Et | H | H | CH₂CH(CH₃)₂ | ⁱPr | OCH₃ | F | H | OH | H | H |
| XVIII-22-5 | Et | H | H | CH₂Ph | ⁱPr | OCH₃ | F | H | OH | H | H |
| XVIII-22-6 | Et | H | H | CH₂-indol-3-yl | ⁱPr | OCH₃ | F | H | OH | H | H |
| XVIII-22-7 | Et | H | H | CH₂CH₂SCH₃ | ⁱPr | OCH₃ | F | H | OH | H | H |
| XVIII-22-8 | Et | * | H | * | ⁱPr | OCH₃ | F | H | OH | H | H |

*R² and R³ᵇ joined together by (CH₂)₃ to form five-membered ring.

TABLE XVIII-23

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-23-1 | ⁱPr | H | H | H | ⁱPr | OCH₃ | F | H | OH | H | H |
| XVIII-23-2 | ⁱPr | H | H | CH₃ | ⁱPr | OCH₃ | F | H | OH | H | H |
| XVIII-23-3 | ⁱPr | H | H | CH(CH₃)₂ | ⁱPr | OCH₃ | F | H | OH | H | H |
| XVIII-23-4 | ⁱPr | H | H | CH₂CH(CH₃)₂ | ⁱPr | OCH₃ | F | H | OH | H | H |
| XVIII-23-5 | ⁱPr | H | H | CH₂Ph | ⁱPr | OCH₃ | F | H | OH | H | H |
| XVIII-23-6 | ⁱPr | H | H | CH₂-indol-3-yl | ⁱPr | OCH₃ | F | H | OH | H | H |
| XVIII-23-7 | ⁱPr | H | H | CH₂CH₂SCH₃ | ⁱPr | OCH₃ | F | H | OH | H | H |
| XVIII-23-8 | ⁱPr | * | H | * | ⁱPr | OCH₃ | F | H | OH | H | H |

*R² and R³ᵇ joined together by (CH₂)₃ to form five-membered ring.

TABLE XVIII-24

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-24-1 | ᵗBu | H | H | H | ⁱPr | OCH₃ | F | H | OH | H | H |
| XVIII-24-2 | ᵗBu | H | H | CH₃ | ⁱPr | OCH₃ | F | H | OH | H | H |
| XVIII-24-3 | ᵗBu | H | H | CH(CH₃)₂ | ⁱPr | OCH₃ | F | H | OH | H | H |
| XVIII-24-4 | ᵗBu | H | H | CH₂CH(CH₃)₂ | ⁱPr | OCH₃ | F | H | OH | H | H |
| XVIII-24-5 | ᵗBu | H | H | CH₂Ph | ⁱPr | OCH₃ | F | H | OH | H | H |
| XVIII-24-6 | ᵗBu | H | H | CH₂-indol-3-yl | ⁱPr | OCH₃ | F | H | OH | H | H |
| XVIII-24-7 | ᵗBu | H | H | CH₂CH₂SCH₃ | ⁱPr | OCH₃ | F | H | OH | H | H |
| XVIII-24-8 | ᵗBu | * | H | * | ⁱPr | OCH₃ | F | H | OH | H | H |

*R² and R³ᵇ joined together by (CH₂)₃ to form five-membered ring.

TABLE XVIII-25

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-25-1 | Ph | H | H | H | ⁱPr | OCH₃ | F | H | OH | H | H |
| XVIII-25-2 | Ph | H | H | CH₃ | ⁱPr | OCH₃ | F | H | OH | H | H |
| XVIII-25-3 | Ph | H | H | CH(CH₃)₂ | ⁱPr | OCH₃ | F | H | OH | H | H |
| XVIII-25-4 | Ph | H | H | CH₂CH(CH₃)₂ | ⁱPr | OCH₃ | F | H | OH | H | H |
| XVIII-25-5 | Ph | H | H | CH₂Ph | ⁱPr | OCH₃ | F | H | OH | H | H |
| XVIII-25-6 | Ph | H | H | CH₂-indol-3-yl | ⁱPr | OCH₃ | F | H | OH | H | H |
| XVIII-25-7 | Ph | H | H | CH₂CH₂SCH₃ | ⁱPr | OCH₃ | F | H | OH | H | H |
| XVIII-25-8 | Ph | * | H | * | ⁱPr | OCH₃ | F | H | OH | H | H |

*R² and R³ᵇ joined together by (CH₂)₃ to form five-membered ring.

TABLE XVIII-26

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-26-1 | p-Me—Ph | H | H | H | ⁱPr | OCH₃ | F | H | OH | H | H |
| XVIII-26-2 | p-Me—Ph | H | H | CH₃ | ⁱPr | OCH₃ | F | H | OH | H | H |
| XVIII-26-3 | p-Me—Ph | H | H | CH(CH₃)₂ | ⁱPr | OCH₃ | F | H | OH | H | H |
| XVIII-26-4 | p-Me—Ph | H | H | CH₂CH(CH₃)₂ | ⁱPr | OCH₃ | F | H | OH | H | H |
| XVIII-26-5 | p-Me—Ph | H | H | CH₂Ph | ⁱPr | OCH₃ | F | H | OH | H | H |
| XVIII-26-6 | p-Me—Ph | H | H | CH₂-indol-3-yl | ⁱPr | OCH₃ | F | H | OH | H | H |
| XVIII-26-7 | p-Me—Ph | H | H | CH₂CH₂SCH₃ | ⁱPr | OCH₃ | F | H | OH | H | H |
| XVIII-26-8 | p-Me—Ph | * | H | * | ⁱPr | OCH₃ | F | H | OH | H | H |

*R² and R³ᵇ joined together by (CH₂)₃ to form five-membered ring.

TABLE XVIII-27

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-27-1 | p-F—Ph | H | H | H | ⁱPr | OCH₃ | F | H | OH | H | H |
| XVIII-27-2 | p-F—Ph | H | H | CH₃ | ⁱPr | OCH₃ | F | H | OH | H | H |
| XVIII-27-3 | p-F—Ph | H | H | CH(CH₃)₂ | ⁱPr | OCH₃ | F | H | OH | H | H |
| XVIII-27-4 | p-F—Ph | H | H | CH₂CH(CH₃)₂ | ⁱPr | OCH₃ | F | H | OH | H | H |
| XVIII-27-5 | p-F—Ph | H | H | CH₂Ph | ⁱPr | OCH₃ | F | H | OH | H | H |
| XVIII-27-6 | p-F—Ph | H | H | CH₂-indol-3-yl | ⁱPr | OCH₃ | F | H | OH | H | H |
| XVIII-27-7 | p-F—Ph | H | H | CH₂CH₂SCH₃ | ⁱPr | OCH₃ | F | H | OH | H | H |
| XVIII-27-8 | p-F—Ph | * | H | * | ⁱPr | OCH₃ | F | H | OH | H | H |

*R² and R³ᵇ joined together by (CH₂)₃ to form five-membered ring.

TABLE XVIII-28

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-28-1 | p-Cl—Ph | H | H | H | ⁱPr | OCH₃ | F | H | OH | H | H |
| XVIII-28-2 | p-Cl—Ph | H | H | CH₃ | ⁱPr | OCH₃ | F | H | OH | H | H |
| XVIII-28-3 | p-Cl—Ph | H | H | CH(CH₃)₂ | ⁱPr | OCH₃ | F | H | OH | H | H |

TABLE XVIII-28-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-28-4 | p-Cl—Ph | H | H | CH₂CH(CH₃)₂ | ⁱPr | OCH₃ | F | H | OH | H | H |
| XVIII-28-5 | p-Cl—Ph | H | H | CH₂Ph | ⁱPr | OCH₃ | F | H | OH | H | H |
| XVIII-28-6 | p-Cl—Ph | H | H | CH₂-indol-3-yl | ⁱPr | OCH₃ | F | H | OH | H | H |
| XVIII-28-7 | p-Cl—Ph | H | H | CH₂CH₂SCH₃ | ⁱPr | OCH₃ | F | H | OH | H | H |
| XVIII-28-8 | p-Cl—Ph | * | H | * | ⁱPr | OCH₃ | F | H | OH | H | H |

*R² and R³ᵇ joined together by (CH₂)₃ to form five-membered ring.

TABLE XVIII-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-29-1 | p-Br—Ph | H | H | H | ⁱPr | OCH₃ | F | H | OH | H | H |
| XVIII-29-2 | p-Br—Ph | H | H | CH₃ | ⁱPr | OCH₃ | F | H | OH | H | H |
| XVIII-29-3 | p-Br—Ph | H | H | CH(CH₃)₂ | ⁱPr | OCH₃ | F | H | OH | H | H |
| XVIII-29-4 | p-Br—Ph | H | H | CH₂CH(CH₃)₂ | ⁱPr | OCH₃ | F | H | OH | H | H |
| XVIII-29-5 | p-Br—Ph | H | H | CH₂Ph | ⁱPr | OCH₃ | F | H | OH | H | H |
| XVIII-29-6 | p-Br—Ph | H | H | CH₂-indol-3-yl | ⁱPr | OCH₃ | F | H | OH | H | H |
| XVIII-29-7 | p-Br—Ph | H | H | CH₂CH₂SCH₃ | ⁱPr | OCH₃ | F | H | OH | H | H |
| XVIII-29-8 | p-Br—Ph | * | H | * | ⁱPr | OCH₃ | F | H | OH | H | H |

*R² and R³ᵇ joined together by (CH₂)₃ to form five-membered ring.

TABLE XVIII-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-30-1 | p-I—Ph | H | H | H | ⁱPr | OCH₃ | F | H | OH | H | H |
| XVIII-30-2 | p-I—Ph | H | H | CH₃ | ⁱPr | OCH₃ | F | H | OH | H | H |
| XVIII-30-3 | p-I—Ph | H | H | CH(CH₃)₂ | ⁱPr | OCH₃ | F | H | OH | H | H |
| XVIII-30-4 | p-I—Ph | H | H | CH₂CH(CH₃)₂ | ⁱPr | OCH₃ | F | H | OH | H | H |
| XVIII-30-5 | p-I—Ph | H | H | CH₂Ph | ⁱPr | OCH₃ | F | H | OH | H | H |
| XVIII-30-6 | p-I—Ph | H | H | CH₂-indol-3-yl | ⁱPr | OCH₃ | F | H | OH | H | H |
| XVIII-30-7 | p-I—Ph | H | H | CH₂CH₂SCH₃ | ⁱPr | OCH₃ | F | H | OH | H | H |
| XVIII-30-8 | p-I—Ph | * | H | * | ⁱPr | OCH₃ | F | H | OH | H | H |

*R² and R³ᵇ joined together by (CH₂)₃ to form five-membered ring.

TABLE XVIII-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-31-1 | CH₃ | H | H | H | ⁿBu | OCH₃ | F | H | OH | H | H |
| XVIII-31-2 | CH₃ | H | H | CH₃ | ⁿBu | OCH₃ | F | H | OH | H | H |
| XVIII-31-3 | CH₃ | H | H | CH(CH₃)₂ | ⁿBu | OCH₃ | F | H | OH | H | H |
| XVIII-31-4 | CH₃ | H | H | CH₂CH(CH₃)₂ | ⁿBu | OCH₃ | F | H | OH | H | H |
| XVIII-31-5 | CH₃ | H | H | CH₂Ph | ⁿBu | OCH₃ | F | H | OH | H | H |
| XVIII-31-6 | CH₃ | H | H | CH₂-indol-3-yl | ⁿBu | OCH₃ | F | H | OH | H | H |
| XVIII-31-7 | CH₃ | H | H | CH₂CH₂SCH₃ | ⁿBu | OCH₃ | F | H | OH | H | H |
| XVIII-31-8 | CH₃ | * | H | * | ⁿBu | OCH₃ | F | H | OH | H | H |

*R² and R³ᵇ joined together by (CH₂)₃ to form five-membered ring.

TABLE XVIII-32

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XVIII-32-1 | Et | H | H | H | ⁿBu | OCH₃ | F | H | OH | H | H |
| XVIII-32-2 | Et | H | H | CH₃ | ⁿBu | OCH₃ | F | H | OH | H | H |
| XVIII-32-3 | Et | H | H | CH(CH₃)₂ | ⁿBu | OCH₃ | F | H | OH | H | H |
| XVIII-32-4 | Et | H | H | CH₂CH(CH₃)₂ | ⁿBu | OCH₃ | F | H | OH | H | H |
| XVIII-32-5 | Et | H | H | CH₂Ph | ⁿBu | OCH₃ | F | H | OH | H | H |
| XVIII-32-6 | Et | H | H | CH₂-indol-3-yl | ⁿBu | OCH₃ | F | H | OH | H | H |
| XVIII-32-7 | Et | H | H | CH₂CH₂SCH₃ | ⁿBu | OCH₃ | F | H | OH | H | H |
| XVIII-32-8 | Et | * | H | * | ⁿBu | OCH₃ | F | H | OH | H | H |

*R² and R³ᵇ joined together by (CH₂)₃ to form five-membered ring.

TABLE XVIII-33

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-33-1 | $^i$Pr | H | H | H | $^n$Bu | OCH$_3$ | F | H | OH | H | H |
| XVIII-33-2 | $^i$Pr | H | H | CH$_3$ | $^n$Bu | OCH$_3$ | F | H | OH | H | H |
| XVIII-33-3 | $^i$Pr | H | H | CH(CH$_3$)$_2$ | $^n$Bu | OCH$_3$ | F | H | OH | H | H |
| XVIII-33-4 | $^i$Pr | H | H | CH$_2$CH(CH$_3$)$_2$ | $^n$Bu | OCH$_3$ | F | H | OH | H | H |
| XVIII-33-5 | $^i$Pr | H | H | CH$_2$Ph | $^n$Bu | OCH$_3$ | F | H | OH | H | H |
| XVIII-33-6 | $^i$Pr | H | H | CH$_2$-indol-3-yl | $^n$Bu | OCH$_3$ | F | H | OH | H | H |
| XVIII-33-7 | $^i$Pr | H | H | CH$_2$CH$_2$SCH$_3$ | $^n$Bu | OCH$_3$ | F | H | OH | H | H |
| XVIII-33-8 | $^i$Pr | * | H | * | $^n$Bu | OCH$_3$ | F | H | OH | H | H |

*R$^2$ and R$^{3b}$ joined together by (CH$_2$)$_3$ to form five-membered ring.

TABLE XVIII-34

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-34-1 | $^t$Bu | H | H | H | $^n$Bu | OCH$_3$ | F | H | OH | H | H |
| XVIII-34-2 | $^t$Bu | H | H | CH$_3$ | $^n$Bu | OCH$_3$ | F | H | OH | H | H |
| XVIII-34-3 | $^t$Bu | H | H | CH(CH$_3$)$_2$ | $^n$Bu | OCH$_3$ | F | H | OH | H | H |
| XVIII-34-4 | $^t$Bu | H | H | CH$_2$CH(CH$_3$)$_2$ | $^n$Bu | OCH$_3$ | F | H | OH | H | H |
| XVIII-34-5 | $^t$Bu | H | H | CH$_2$Ph | $^n$Bu | OCH$_3$ | F | H | OH | H | H |
| XVIII-34-6 | $^t$Bu | H | H | CH$_2$-indol-3-yl | $^n$Bu | OCH$_3$ | F | H | OH | H | H |
| XVIII-34-7 | $^t$Bu | H | H | CH$_2$CH$_2$SCH$_3$ | $^n$Bu | OCH$_3$ | F | H | OH | H | H |
| XVIII-34-8 | $^t$Bu | * | H | * | $^n$Bu | OCH$_3$ | F | H | OH | H | H |

*R$^2$ and R$^{3b}$ joined together by (CH$_2$)$_3$ to form five-membered ring.

TABLE XVIII-35

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-35-1 | Ph | H | H | H | $^n$Bu | OCH$_3$ | F | H | OH | H | H |
| XVIII-35-2 | Ph | H | H | CH$_3$ | $^n$Bu | OCH$_3$ | F | H | OH | H | H |
| XVIII-35-3 | Ph | H | H | CH(CH$_3$)$_2$ | $^n$Bu | OCH$_3$ | F | H | OH | H | H |
| XVIII-35-4 | Ph | H | H | CH$_2$CH(CH$_3$)$_2$ | $^n$Bu | OCH$_3$ | F | H | OH | H | H |
| XVIII-35-5 | Ph | H | H | CH$_2$Ph | $^n$Bu | OCH$_3$ | F | H | OH | H | H |
| XVIII-35-6 | Ph | H | H | CH$_2$-indol-3-yl | $^n$Bu | OCH$_3$ | F | H | OH | H | H |
| XVIII-35-7 | Ph | H | H | CH$_2$CH$_2$SCH$_3$ | $^n$Bu | OCH$_3$ | F | H | OH | H | H |
| XVIII-35-8 | Ph | * | H | * | $^n$Bu | OCH$_3$ | F | H | OH | H | H |

*R$^2$ and R$^{3b}$ joined together by (CH$_2$)$_3$ to form five-membered ring.

TABLE XVIII-36

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-36-1 | p-Me—Ph | H | H | H | $^n$Bu | OCH$_3$ | F | H | OH | H | H |
| XVIII-36-2 | p-Me—Ph | H | H | CH$_3$ | $^n$Bu | OCH$_3$ | F | H | OH | H | H |
| XVIII-36-3 | p-Me—Ph | H | H | CH(CH$_3$)$_2$ | $^n$Bu | OCH$_3$ | F | H | OH | H | H |
| XVIII-36-4 | p-Me—Ph | H | H | CH$_2$CH(CH$_3$)$_2$ | $^n$Bu | OCH$_3$ | F | H | OH | H | H |
| XVIII-36-5 | p-Me—Ph | H | H | CH$_2$Ph | $^n$Bu | OCH$_3$ | F | H | OH | H | H |
| XVIII-36-6 | p-Me—Ph | H | H | CH$_2$-indol-3-yl | $^n$Bu | OCH$_3$ | F | H | OH | H | H |
| XVIII-36-7 | p-Me—Ph | H | H | CH$_2$CH$_2$SCH$_3$ | $^n$Bu | OCH$_3$ | F | H | OH | H | H |
| XVIII-36-8 | p-Me—Ph | * | H | * | $^n$Bu | OCH$_3$ | F | H | OH | H | H |

*R$^2$ and R$^{3b}$ joined together by (CH$_2$)$_3$ to form five-membered ring.

TABLE XVIII-37

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-37-1 | p-F—Ph | H | H | H | $^n$Bu | OCH$_3$ | F | H | OH | H | H |
| XVIII-37-2 | p-F—Ph | H | H | CH$_3$ | $^n$Bu | OCH$_3$ | F | H | OH | H | H |
| XVIII-37-3 | p-F—Ph | H | H | CH(CH$_3$)$_2$ | $^n$Bu | OCH$_3$ | F | H | OH | H | H |
| XVIII-37-4 | p-F—Ph | H | H | CH$_2$CH(CH$_3$)$_2$ | $^n$Bu | OCH$_3$ | F | H | OH | H | H |
| XVIII-37-5 | p-F—Ph | H | H | CH$_2$Ph | $^n$Bu | OCH$_3$ | F | H | OH | H | H |

TABLE XVIII-37-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-37-6 | p-F—Ph | H | H | $CH_2$-indol-3-yl | $^nBu$ | $OCH_3$ | F | H | OH | H | H |
| XVIII-37-7 | p-F—Ph | H | H | $CH_2CH_2SCH_3$ | $^nBu$ | $OCH_3$ | F | H | OH | H | H |
| XVIII-37-8 | p-F—Ph | * | H | * | $^nBu$ | $OCH_3$ | F | H | OH | H | H |

*$R^2$ and $R^{3b}$ joined together by $(CH_2)_3$ to form five-membered ring.

TABLE XVIII-38

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-38-1 | p-Cl—Ph | H | H | H | $^nBu$ | $OCH_3$ | F | H | OH | H | H |
| XVIII-38-2 | p-Cl—Ph | H | H | $CH_3$ | $^nBu$ | $OCH_3$ | F | H | OH | H | H |
| XVIII-38-3 | p-Cl—Ph | H | H | $CH(CH_3)_2$ | $^nBu$ | $OCH_3$ | F | H | OH | H | H |
| XVIII-38-4 | p-Cl—Ph | H | H | $CH_2CH(CH_3)_2$ | $^nBu$ | $OCH_3$ | F | H | OH | H | H |
| XVIII-38-5 | p-Cl—Ph | H | H | $CH_2Ph$ | $^nBu$ | $OCH_3$ | F | H | OH | H | H |
| XVIII-38-6 | p-Cl—Ph | H | H | $CH_2$-indol-3-yl | $^nBu$ | $OCH_3$ | F | H | OH | H | H |
| XVIII-38-7 | p-Cl—Ph | H | H | $CH_2CH_2SCH_3$ | $^nBu$ | $OCH_3$ | F | H | OH | H | H |
| XVIII-38-8 | p-Cl—Ph | * | H | * | $^nBu$ | $OCH_3$ | F | H | OH | H | H |

*$R^2$ and $R^{3b}$ joined together by $(CH_2)_3$ to form five-membered ring.

TABLE XVIII-39

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-39-1 | p-Br—Ph | H | H | H | $^nBu$ | $OCH_3$ | F | H | OH | H | H |
| XVIII-39-2 | p-Br—Ph | H | H | $CH_3$ | $^nBu$ | $OCH_3$ | F | H | OH | H | H |
| XVIII-39-3 | p-Br—Ph | H | H | $CH(CH_3)_2$ | $^nBu$ | $OCH_3$ | F | H | OH | H | H |
| XVIII-39-4 | p-Br—Ph | H | H | $CH_2CH(CH_3)_2$ | $^nBu$ | $OCH_3$ | F | H | OH | H | H |
| XVIII-39-5 | p-Br—Ph | H | H | $CH_2Ph$ | $^nBu$ | $OCH_3$ | F | H | OH | H | H |
| XVIII-39-6 | p-Br—Ph | H | H | $CH_2$-indol-3-yl | $^nBu$ | $OCH_3$ | F | H | OH | H | H |
| XVIII-39-7 | p-Br—Ph | H | H | $CH_2CH_2SCH_3$ | $^nBu$ | $OCH_3$ | F | H | OH | H | H |
| XVIII-39-8 | p-Br—Ph | * | H | * | $^nBu$ | $OCH_3$ | F | H | OH | H | H |

*$R^2$ and $R^{3b}$ joined together by $(CH_2)_3$ to form five-membered ring.

TABLE XVIII-40

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-40-1 | p-I—Ph | H | H | H | $^nBu$ | $OCH_3$ | F | H | OH | H | H |
| XVIII-40-2 | p-I—Ph | H | H | $CH_3$ | $^nBu$ | $OCH_3$ | F | H | OH | H | H |
| XVIII-40-3 | p-I—Ph | H | H | $CH(CH_3)_2$ | $^nBu$ | $OCH_3$ | F | H | OH | H | H |
| XVIII-40-4 | p-I—Ph | H | H | $CH_2CH(CH_3)_2$ | $^nBu$ | $OCH_3$ | F | H | OH | H | H |
| XVIII-40-5 | p-I—Ph | H | H | $CH_2Ph$ | $^nBu$ | $OCH_3$ | F | H | OH | H | H |
| XVIII-40-6 | p-I—Ph | H | H | $CH_2$-indol-3-yl | $^nBu$ | $OCH_3$ | F | H | OH | H | H |
| XVIII-40-7 | p-I—Ph | H | H | $CH_2CH_2SCH_3$ | $^nBu$ | $OCH_3$ | F | H | OH | H | H |
| XVIII-40-8 | p-I—Ph | * | H | * | $^nBu$ | $OCH_3$ | F | H | OH | H | H |

*$R^2$ and $R^{3b}$ joined together by $(CH_2)_3$ to form five-membered ring.

TABLE XVIII-41

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-41-1 | $CH_3$ | H | H | H | Bz | $OCH_3$ | F | H | OH | H | H |
| XVIII-41-2 | $CH_3$ | H | H | $CH_3$ | Bz | $OCH_3$ | F | H | OH | H | H |
| XVIII-41-3 | $CH_3$ | H | H | $CH(CH_3)_2$ | Bz | $OCH_3$ | F | H | OH | H | H |
| XVIII-41-4 | $CH_3$ | H | H | $CH_2CH(CH_3)_2$ | Bz | $OCH_3$ | F | H | OH | H | H |
| XVIII-41-5 | $CH_3$ | H | H | $CH_2Ph$ | Bz | $OCH_3$ | F | H | OH | H | H |
| XVIII-41-6 | $CH_3$ | H | H | $CH_2$-indol-3-yl | Bz | $OCH_3$ | F | H | OH | H | H |
| XVIII-41-7 | $CH_3$ | H | H | $CH_2CH_2SCH_3$ | Bz | $OCH_3$ | F | H | OH | H | H |
| XVIII-41-8 | $CH_3$ | * | H | * | Bz | $OCH_3$ | F | H | OH | H | H |

*$R^2$ and $R^{3b}$ joined together by $(CH_2)_3$ to form five-membered ring.

TABLE XVIII-42

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-42-1 | Et | H | H | H | Bz | OCH$_3$ | F | H | OH | H | H |
| XVIII-42-2 | Et | H | H | CH$_3$ | Bz | OCH$_3$ | F | H | OH | H | H |
| XVIII-42-3 | Et | H | H | CH(CH$_3$)$_2$ | Bz | OCH$_3$ | F | H | OH | H | H |
| XVIII-42-4 | Et | H | H | CH$_2$CH(CH$_3$)$_2$ | Bz | OCH$_3$ | F | H | OH | H | H |
| XVIII-42-5 | Et | H | H | CH$_2$Ph | Bz | OCH$_3$ | F | H | OH | H | H |
| XVIII-42-6 | Et | H | H | CH$_2$-indol-3-yl | Bz | OCH$_3$ | F | H | OH | H | H |
| XVIII-42-7 | Et | H | H | CH$_2$CH$_2$SCH$_3$ | Bz | OCH$_3$ | F | H | OH | H | H |
| XVIII-42-8 | Et | * | H | * | Bz | OCH$_3$ | F | H | OH | H | H |

*$R^2$ and $R^{3b}$ joined together by (CH$_2$)$_3$ to form five-membered ring.

TABLE XVIII-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-43-1 | $^i$Pr | H | H | H | Bz | OCH$_3$ | F | H | OH | H | H |
| XVIII-43-2 | $^i$Pr | H | H | CH$_3$ | Bz | OCH$_3$ | F | H | OH | H | H |
| XVIII-43-3 | $^i$Pr | H | H | CH(CH$_3$)$_2$ | Bz | OCH$_3$ | F | H | OH | H | H |
| XVIII-43-4 | $^i$Pr | H | H | CH$_2$CH(CH$_3$)$_2$ | Bz | OCH$_3$ | F | H | OH | H | H |
| XVIII-43-5 | $^i$Pr | H | H | CH$_2$Ph | Bz | OCH$_3$ | F | H | OH | H | H |
| XVIII-43-6 | $^i$Pr | H | H | CH$_2$-indol-3-yl | Bz | OCH$_3$ | F | H | OH | H | H |
| XVIII-43-7 | $^i$Pr | H | H | CH$_2$CH$_2$SCH$_3$ | Bz | OCH$_3$ | F | H | OH | H | H |
| XVIII-43-8 | $^i$Pr | * | H | * | Bz | OCH$_3$ | F | H | OH | H | H |

*$R^2$ and $R^{3b}$ joined together by (CH$_2$)$_3$ to form five-membered ring.

TABLE XVIII-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-44-1 | $^t$Bu | H | H | H | Bz | OCH$_3$ | F | H | OH | H | H |
| XVIII-44-2 | $^t$Bu | H | H | CH$_3$ | Bz | OCH$_3$ | F | H | OH | H | H |
| XVIII-44-3 | $^t$Bu | H | H | CH(CH$_3$)$_2$ | Bz | OCH$_3$ | F | H | OH | H | H |
| XVIII-44-4 | $^t$Bu | H | H | CH$_2$CH(CH$_3$)$_2$ | Bz | OCH$_3$ | F | H | OH | H | H |
| XVIII-44-5 | $^t$Bu | H | H | CH$_2$Ph | Bz | OCH$_3$ | F | H | OH | H | H |
| XVIII-44-6 | $^t$Bu | H | H | CH$_2$-indol-3-yl | Bz | OCH$_3$ | F | H | OH | H | H |
| XVIII-44-7 | $^t$Bu | H | H | CH$_2$CH$_2$SCH$_3$ | Bz | OCH$_3$ | F | H | OH | H | H |
| XVIII-44-8 | $^t$Bu | * | H | * | Bz | OCH$_3$ | F | H | OH | H | H |

*$R^2$ and $R^{3b}$ joined together by (CH$_2$)$_3$ to form five-membered ring.

TABLE XVIII-45

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-45-1 | Ph | H | H | H | Bz | OCH$_3$ | F | H | OH | H | H |
| XVIII-45-2 | Ph | H | H | CH$_3$ | Bz | OCH$_3$ | F | H | OH | H | H |
| XVIII-45-3 | Ph | H | H | CH(CH$_3$)$_2$ | Bz | OCH$_3$ | F | H | OH | H | H |
| XVIII-45-4 | Ph | H | H | CH$_2$CH(CH$_3$)$_2$ | Bz | OCH$_3$ | F | H | OH | H | H |
| XVIII-45-5 | Ph | H | H | CH$_2$Ph | Bz | OCH$_3$ | F | H | OH | H | H |
| XVIII-45-6 | Ph | H | H | CH$_2$-indol-3-yl | Bz | OCH$_3$ | F | H | OH | H | H |
| XVIII-45-7 | Ph | H | H | CH$_2$CH$_2$SCH$_3$ | Bz | OCH$_3$ | F | H | OH | H | H |
| XVIII-45-8 | Ph | * | H | * | Bz | OCH$_3$ | F | H | OH | H | H |

*$R^2$ and $R^{3b}$ joined together by (CH$_2$)$_3$ to form five-membered ring.

TABLE XVIII-46

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XVIII-46-1 | p-Me—Ph | H | H | H | Bz | OCH$_3$ | F | H | OH | H | H |
| XVIII-46-2 | p-Me—Ph | H | H | CH$_3$ | Bz | OCH$_3$ | F | H | OH | H | H |
| XVIII-46-3 | p-Me—Ph | H | H | CH(CH$_3$)$_2$ | Bz | OCH$_3$ | F | H | OH | H | H |

TABLE XVIII-46-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-46-4 | p-Me—Ph | H | H | CH$_2$CH(CH$_3$)$_2$ | Bz | OCH$_3$ | F | H | OH | H | H |
| XVIII-46-5 | p-Me—Ph | H | H | CH$_2$Ph | Bz | OCH$_3$ | F | H | OH | H | H |
| XVIII-46-6 | p-Me—Ph | H | H | CH$_2$-indol-3-yl | Bz | OCH$_3$ | F | H | OH | H | H |
| XVIII-46-7 | p-Me—Ph | H | H | CH$_2$CH$_2$SCH$_3$ | Bz | OCH$_3$ | F | H | OH | H | H |
| XVIII-46-8 | p-Me—Ph | * | H | * | Bz | OCH$_3$ | F | H | OH | H | H |

*R$^2$ and R$^{3b}$ joined together by (CH$_2$)$_3$ to form five-membered ring.

TABLE XVIII-47

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-47-1 | p-F—Ph | H | H | H | Bz | OCH$_3$ | F | H | OH | H | H |
| XVIII-47-2 | p-F—Ph | H | H | CH$_3$ | Bz | OCH$_3$ | F | H | OH | H | H |
| XVIII-47-3 | p-F—Ph | H | H | CH(CH$_3$)$_2$ | Bz | OCH$_3$ | F | H | OH | H | H |
| XVIII-47-4 | p-F—Ph | H | H | CH$_2$CH(CH$_3$)$_2$ | Bz | OCH$_3$ | F | H | OH | H | H |
| XVIII-47-5 | p-F—Ph | H | H | CH$_2$Ph | Bz | OCH$_3$ | F | H | OH | H | H |
| XVIII-47-6 | p-F—Ph | H | H | CH$_2$-indol-3-yl | Bz | OCH$_3$ | F | H | OH | H | H |
| XVIII-47-7 | p-F—Ph | H | H | CH$_2$CH$_2$SCH$_3$ | Bz | OCH$_3$ | F | H | OH | H | H |
| XVIII-47-8 | p-F—Ph | * | H | * | Bz | OCH$_3$ | F | H | OH | H | H |

*R$^2$ and R$^{3b}$ joined together by (CH$_2$)$_3$ to form five-membered ring.

TABLE XVIII-48

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-48-1 | p-Cl—Ph | H | H | H | Bz | OCH$_3$ | F | H | OH | H | H |
| XVIII-48-2 | p-Cl—Ph | H | H | CH$_3$ | Bz | OCH$_3$ | F | H | OH | H | H |
| XVIII-48-3 | p-Cl—Ph | H | H | CH(CH$_3$)$_2$ | Bz | OCH$_3$ | F | H | OH | H | H |
| XVIII-48-4 | p-Cl—Ph | H | H | CH$_2$CH(CH$_3$)$_2$ | Bz | OCH$_3$ | F | H | OH | H | H |
| XVIII-48-5 | p-Cl—Ph | H | H | CH$_2$Ph | Bz | OCH$_3$ | F | H | OH | H | H |
| XVIII-48-6 | p-Cl—Ph | H | H | CH$_2$-indol-3-yl | Bz | OCH$_3$ | F | H | OH | H | H |
| XVIII-48-7 | p-Cl—Ph | H | H | CH$_2$CH$_2$SCH$_3$ | Bz | OCH$_3$ | F | H | OH | H | H |
| XVIII-48-8 | p-Cl—Ph | * | H | * | Bz | OCH$_3$ | F | H | OH | H | H |

*R$^2$ and R$^{3b}$ joined together by (CH$_2$)$_3$ to form five-membered ring.

TABLE XVIII-49

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-49-1 | p-Br—Ph | H | H | H | Bz | OCH$_3$ | F | H | OH | H | H |
| XVIII-49-2 | p-Br—Ph | H | H | CH$_3$ | Bz | OCH$_3$ | F | H | OH | H | H |
| XVIII-49-3 | p-Br—Ph | H | H | CH(CH$_3$)$_2$ | Bz | OCH$_3$ | F | H | OH | H | H |
| XVIII-49-4 | p-Br—Ph | H | H | CH$_2$CH(CH$_3$)$_2$ | Bz | OCH$_3$ | F | H | OH | H | H |
| XVIII-49-5 | p-Br—Ph | H | H | CH$_2$Ph | Bz | OCH$_3$ | F | H | OH | H | H |
| XVIII-49-6 | p-Br—Ph | H | H | CH$_2$-indol-3-yl | Bz | OCH$_3$ | F | H | OH | H | H |
| XVIII-49-7 | p-Br—Ph | H | H | CH$_2$CH$_2$SCH$_3$ | Bz | OCH$_3$ | F | H | OH | H | H |
| XVIII-49-8 | p-Br—Ph | * | H | * | Bz | OCH$_3$ | F | H | OH | H | H |

*R$^2$ and R$^{3b}$ joined together by (CH$_2$)$_3$ to form five-membered ring.

TABLE XVIII-50

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XVIII-50-1 | p-I—Ph | H | H | H | Bz | OCH$_3$ | F | H | OH | H | H |
| XVIII-50-2 | p-I—Ph | H | H | CH$_3$ | Bz | OCH$_3$ | F | H | OH | H | H |
| XVIII-50-3 | p-I—Ph | H | H | CH(CH$_3$)$_2$ | Bz | OCH$_3$ | F | H | OH | H | H |
| XVIII-50-4 | p-I—Ph | H | H | CH$_2$CH(CH$_3$)$_2$ | Bz | OCH$_3$ | F | H | OH | H | H |
| XVIII-50-5 | p-I—Ph | H | H | CH$_2$Ph | Bz | OCH$_3$ | F | H | OH | H | H |
| XVIII-50-6 | p-I—Ph | H | H | CH$_2$-indol-3-yl | Bz | OCH$_3$ | F | H | OH | H | H |
| XVIII-50-7 | p-I—Ph | H | H | CH$_2$CH$_2$SCH$_3$ | Bz | OCH$_3$ | F | H | OH | H | H |
| XVIII-50-8 | p-I—Ph | * | H | * | Bz | OCH$_3$ | F | H | OH | H | H |

*R$^2$ and R$^{3b}$ joined together by (CH$_2$)$_3$ to form five-membered ring.

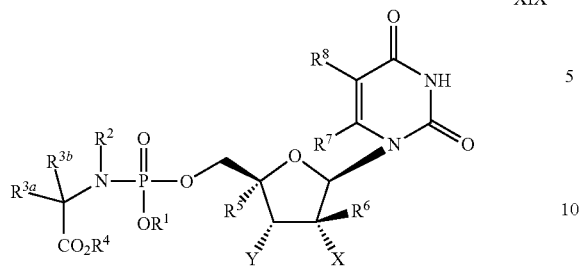

XIX

TABLE XIX-1

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-1-1 | $CH_3$ | H | H | H | $CH_3$ | $OCH_3$ | F | F | OH | H | H |
| XIX-1-2 | $CH_3$ | H | H | $CH_3$ | $CH_3$ | $OCH_3$ | F | F | OH | H | H |
| XIX-1-3 | $CH_3$ | H | H | $CH(CH_3)_2$ | $CH_3$ | $OCH_3$ | F | F | OH | H | H |
| XIX-1-4 | $CH_3$ | H | H | $CH_2CH(CH_3)_2$ | $CH_3$ | $OCH_3$ | F | F | OH | H | H |
| XIX-1-5 | $CH_3$ | H | H | $CH_2Ph$ | $CH_3$ | $OCH_3$ | F | F | OH | H | H |
| XIX-1-6 | $CH_3$ | H | H | $CH_2$-indol-3-yl | $CH_3$ | $OCH_3$ | F | F | OH | H | H |
| XIX-1-7 | $CH_3$ | H | H | $CH_2CH_2SCH_3$ | $CH_3$ | $OCH_3$ | F | F | OH | H | H |
| XIX-1-8 | $CH_3$ | * | H | * | $CH_3$ | $OCH_3$ | F | F | OH | H | H |

*$R^2$ and $R^{3b}$ joined together by $(CH_2)_3$ to form five-membered ring.

TABLE XIX-2

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-2-1 | Et | H | H | H | $CH_3$ | $OCH_3$ | F | F | OH | H | H |
| XIX-2-2 | Et | H | H | $CH_3$ | $CH_3$ | $OCH_3$ | F | F | OH | H | H |
| XIX-2-3 | Et | H | H | $CH(CH_3)_2$ | $CH_3$ | $OCH_3$ | F | F | OH | H | H |
| XIX-2-4 | Et | H | H | $CH_2CH(CH_3)_2$ | $CH_3$ | $OCH_3$ | F | F | OH | H | H |
| XIX-2-5 | Et | H | H | $CH_2Ph$ | $CH_3$ | $OCH_3$ | F | F | OH | H | H |
| XIX-2-6 | Et | H | H | $CH_2$-indol-3-yl | $CH_3$ | $OCH_3$ | F | F | OH | H | H |
| XIX-2-7 | Et | H | H | $CH_2CH_2SCH_3$ | $CH_3$ | $OCH_3$ | F | F | OH | H | H |
| XIX-2-8 | Et | * | H | * | $CH_3$ | $OCH_3$ | F | F | OH | H | H |

*$R^2$ and $R^{3b}$ joined together by $(CH_2)_3$ to form five-membered ring.

TABLE XIX-3

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-3-1 | $^i$Pr | H | H | H | $CH_3$ | $OCH_3$ | F | F | OH | H | H |
| XIX-3-2 | $^i$Pr | H | H | $CH_3$ | $CH_3$ | $OCH_3$ | F | F | OH | H | H |
| XIX-3-3 | $^i$Pr | H | H | $CH(CH_3)_2$ | $CH_3$ | $OCH_3$ | F | F | OH | H | H |
| XIX-3-4 | $^i$Pr | H | H | $CH_2CH(CH_3)_2$ | $CH_3$ | $OCH_3$ | F | F | OH | H | H |
| XIX-3-5 | $^i$Pr | H | H | $CH_2Ph$ | $CH_3$ | $OCH_3$ | F | F | OH | H | H |
| XIX-3-6 | $^i$Pr | H | H | $CH_2$-indol-3-yl | $CH_3$ | $OCH_3$ | F | F | OH | H | H |
| XIX-3-7 | $^i$Pr | H | H | $CH_2CH_2SCH_3$ | $CH_3$ | $OCH_3$ | F | F | OH | H | H |
| XIX-3-8 | $^i$Pr | * | H | * | $CH_3$ | $OCH_3$ | F | F | OH | H | H |

*$R^2$ and $R^{3b}$ joined together by $(CH_2)_3$ to form five-membered ring.

TABLE XIX-4

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-4-1 | $^t$Bu | H | H | H | $CH_3$ | $OCH_3$ | F | F | OH | H | H |
| XIX-4-2 | $^t$Bu | H | H | $CH_3$ | $CH_3$ | $OCH_3$ | F | F | OH | H | H |
| XIX-4-3 | $^t$Bu | H | H | $CH(CH_3)_2$ | $CH_3$ | $OCH_3$ | F | F | OH | H | H |
| XIX-4-4 | $^t$Bu | H | H | $CH_2CH(CH_3)_2$ | $CH_3$ | $OCH_3$ | F | F | OH | H | H |
| XIX-4-5 | $^t$Bu | H | H | $CH_2Ph$ | $CH_3$ | $OCH_3$ | F | F | OH | H | H |
| XIX-4-6 | $^t$Bu | H | H | $CH_2$-indol-3-yl | $CH_3$ | $OCH_3$ | F | F | OH | H | H |

TABLE XIX-4-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-4-7 | $^tBu$ | H | H | $CH_2CH_2SCH_3$ | $CH_3$ | $OCH_3$ | F | F | OH | H | H |
| XIX-4-8 | $^tBu$ | * | H | * | $CH_3$ | $OCH_3$ | F | F | OH | H | H |

*$R^2$ and $R^{3b}$ joined together by $(CH_2)_3$ to form five-membered ring.

TABLE XIX-5

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-5-1 | Ph | H | H | H | $CH_3$ | $OCH_3$ | F | F | OH | H | H |
| XIX-5-2 | Ph | H | H | $CH_3$ | $CH_3$ | $OCH_3$ | F | F | OH | H | H |
| XIX-5-3 | Ph | H | H | $CH(CH_3)_2$ | $CH_3$ | $OCH_3$ | F | F | OH | H | H |
| XIX-5-4 | Ph | H | H | $CH_2CH(CH_3)_2$ | $CH_3$ | $OCH_3$ | F | F | OH | H | H |
| XIX-5-5 | Ph | H | H | $CH_2Ph$ | $CH_3$ | $OCH_3$ | F | F | OH | H | H |
| XIX-5-6 | Ph | H | H | $CH_2$-indol-3-yl | $CH_3$ | $OCH_3$ | F | F | OH | H | H |
| XIX-5-7 | Ph | H | H | $CH_2CH_2SCH_3$ | $CH_3$ | $OCH_3$ | F | F | OH | H | H |
| XIX-5-8 | Ph | * | H | * | $CH_3$ | $OCH_3$ | F | F | OH | H | H |

*$R^2$ and $R^{3b}$ joined together by $(CH_2)_3$ to form five-membered ring.

TABLE XIX-6

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-6-1 | p-Me—Ph | H | H | H | $CH_3$ | $OCH_3$ | F | H | OH | H | H |
| XIX-6-2 | p-Me—Ph | H | H | $CH_3$ | $CH_3$ | $OCH_3$ | F | H | OH | H | H |
| XIX-6-3 | p-Me—Ph | H | H | $CH(CH_3)_2$ | $CH_3$ | $OCH_3$ | F | H | OH | H | H |
| XIX-6-4 | p-Me—Ph | H | H | $CH_2CH(CH_3)_2$ | $CH_3$ | $OCH_3$ | F | H | OH | H | H |
| XIX-6-5 | p-Me—Ph | H | H | $CH_2Ph$ | $CH_3$ | $OCH_3$ | F | H | OH | H | H |
| XIX-6-6 | p-Me—Ph | H | H | $CH_2$-indol-3-yl | $CH_3$ | $OCH_3$ | F | H | OH | H | H |
| XIX-6-7 | p-Me—Ph | H | H | $CH_2CH_2SCH_3$ | $CH_3$ | $OCH_3$ | F | H | OH | H | H |
| XIX-6-8 | p-Me—Ph | * | H | * | $CH_3$ | $OCH_3$ | F | H | OH | H | H |

*$R^2$ and $R^{3b}$ joined together by $(CH_2)_3$ to form five-membered ring.

TABLE XIX-7

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-7-1 | p-F—Ph | H | H | H | $CH_3$ | $OCH_3$ | F | H | OH | H | H |
| XIX-7-2 | p-F—Ph | H | H | $CH_3$ | $CH_3$ | $OCH_3$ | F | H | OH | H | H |
| XIX-7-3 | p-F—Ph | H | H | $CH(CH_3)_2$ | $CH_3$ | $OCH_3$ | F | H | OH | H | H |
| XIX-7-4 | p-F—Ph | H | H | $CH_2CH(CH_3)_2$ | $CH_3$ | $OCH_3$ | F | H | OH | H | H |
| XIX-7-6 | p-F—Ph | H | H | $CH_2Ph$ | $CH_3$ | $OCH_3$ | F | H | OH | H | H |
| XIX-7-7 | p-F—Ph | H | H | $CH_2$-indol-3-yl | $CH_3$ | $OCH_3$ | F | H | OH | H | H |
| XIX-7-8 | p-F—Ph | H | H | $CH_2CH_2SCH_3$ | $CH_3$ | $OCH_3$ | F | H | OH | H | H |
| XIX-7-20 | p-F—Ph | * | H | * | $CH_3$ | $OCH_3$ | F | H | OH | H | H |

*$R^2$ and $R^{3b}$ joined together by $(CH_2)_3$ to form five-membered ring.

TABLE XIX-8

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XIX-8-1 | p-Cl—Ph | H | H | H | $CH_3$ | $OCH_3$ | F | H | OH | H | H |
| XIX-8-2 | p-Cl—Ph | H | H | $CH_3$ | $CH_3$ | $OCH_3$ | F | H | OH | H | H |
| XIX-8-3 | p-Cl—Ph | H | H | $CH(CH_3)_2$ | $CH_3$ | $OCH_3$ | F | H | OH | H | H |
| XIX-8-4 | p-Cl—Ph | H | H | $CH_2CH(CH_3)_2$ | $CH_3$ | $OCH_3$ | F | H | OH | H | H |
| XIX-8-5 | p-Cl—Ph | H | H | $CH_2Ph$ | $CH_3$ | $OCH_3$ | F | H | OH | H | H |
| XIX-8-6 | p-Cl—Ph | H | H | $CH_2$-indol-3-yl | $CH_3$ | $OCH_3$ | F | H | OH | H | H |
| XIX-8-7 | p-Cl—Ph | H | H | $CH_2CH_2SCH_3$ | $CH_3$ | $OCH_3$ | F | H | OH | H | H |
| XIX-8-8 | p-Cl—Ph | * | H | * | $CH_3$ | $OCH_3$ | F | H | OH | H | H |

*$R^2$ and $R^{3b}$ joined together by $(CH_2)_3$ to form five-membered ring.

TABLE XIX-9

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIX-9-1 | p-Br—Ph | H | H | H | CH$_3$ | OCH$_3$ | F | H | OH | H | H |
| XIX-9-2 | p-Br—Ph | H | H | CH$_3$ | CH$_3$ | OCH$_3$ | F | H | OH | H | H |
| XIX-9-3 | p-Br—Ph | H | H | CH(CH$_3$)$_2$ | CH$_3$ | OCH$_3$ | F | H | OH | H | H |
| XIX-9-4 | p-Br—Ph | H | H | CH$_2$CH(CH$_3$)$_2$ | CH$_3$ | OCH$_3$ | F | H | OH | H | H |
| XIX-9-6 | p-Br—Ph | H | H | CH$_2$Ph | CH$_3$ | OCH$_3$ | F | H | OH | H | H |
| XIX-9-7 | p-Br—Ph | H | H | CH$_2$-indol-3-yl | CH$_3$ | OCH$_3$ | F | H | OH | H | H |
| XIX-9-8 | p-Br—Ph | H | H | CH$_2$CH$_2$SCH$_3$ | CH$_3$ | OCH$_3$ | F | H | OH | H | H |
| XIX-9-20 | p-Br—Ph | * | H | * | CH$_3$ | OCH$_3$ | F | H | OH | H | H |

*R$^2$ and R$^{3b}$ joined together by (CH$_2$)$_3$ to form five-membered ring.

TABLE XIX-10

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIX-10-1 | p-I—Ph | H | H | H | CH$_3$ | OCH$_3$ | F | H | OH | H | H |
| XIX-10-2 | p-I—Ph | H | H | CH$_3$ | CH$_3$ | OCH$_3$ | F | H | OH | H | H |
| XIX-10-3 | p-I—Ph | H | H | CH(CH$_3$)$_2$ | CH$_3$ | OCH$_3$ | F | H | OH | H | H |
| XIX-10-4 | p-I—Ph | H | H | CH$_2$CH(CH$_3$)$_2$ | CH$_3$ | OCH$_3$ | F | H | OH | H | H |
| XIX-10-5 | p-I—Ph | H | H | CH$_2$Ph | CH$_3$ | OCH$_3$ | F | H | OH | H | H |
| XIX-10-6 | p-I—Ph | H | H | CH$_2$-indol-3-yl | CH$_3$ | OCH$_3$ | F | H | OH | H | H |
| XIX-10-7 | p-I—Ph | H | H | CH$_2$CH$_2$SCH$_3$ | CH$_3$ | OCH$_3$ | F | H | OH | H | H |
| XIX-10-8 | p-I—Ph | * | H | * | CH$_3$ | OCH$_3$ | F | H | OH | H | H |

*R$^2$ and R$^{3b}$ joined together by (CH$_2$)$_3$ to form five-membered ring.

TABLE XIX-11

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIX-11-1 | CH$_3$ | H | H | H | Et | OCH$_3$ | F | F | OH | H | H |
| XIX-11-2 | CH$_3$ | H | H | CH$_3$ | Et | OCH$_3$ | F | F | OH | H | H |
| XIX-11-3 | CH$_3$ | H | H | CH(CH$_3$)$_2$ | Et | OCH$_3$ | F | F | OH | H | H |
| XIX-11-4 | CH$_3$ | H | H | CH$_2$CH(CH$_3$)$_2$ | Et | OCH$_3$ | F | F | OH | H | H |
| XIX-11-5 | CH$_3$ | H | H | CH$_2$Ph | Et | OCH$_3$ | F | F | OH | H | H |
| XIX-11-6 | CH$_3$ | H | H | CH$_2$-indol-3-yl | Et | OCH$_3$ | F | F | OH | H | H |
| XIX-11-7 | CH$_3$ | H | H | CH$_2$CH$_2$SCH$_3$ | Et | OCH$_3$ | F | F | OH | H | H |
| XIX-11-8 | CH$_3$ | * | H | * | Et | OCH$_3$ | F | F | OH | H | H |

*R$^2$ and R$^{3b}$ joined together by (CH$_2$)$_3$ to form five-membered ring.

TABLE XIX-12

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIX-12-1 | Et | H | H | H | Et | OCH$_3$ | F | F | OH | H | H |
| XIX-12-2 | Et | H | H | CH$_3$ | Et | OCH$_3$ | F | F | OH | H | H |
| XIX-12-3 | Et | H | H | CH(CH$_3$)$_2$ | Et | OCH$_3$ | F | F | OH | H | H |
| XIX-12-4 | Et | H | H | CH$_2$CH(CH$_3$)$_2$ | Et | OCH$_3$ | F | F | OH | H | H |
| XIX-12-5 | Et | H | H | CH$_2$Ph | Et | OCH$_3$ | F | F | OH | H | H |
| XIX-12-6 | Et | H | H | CH$_2$-indol-3-yl | Et | OCH$_3$ | F | F | OH | H | H |
| XIX-12-7 | Et | H | H | CH$_2$CH$_2$SCH$_3$ | Et | OCH$_3$ | F | F | OH | H | H |
| XIX-12-8 | Et | * | H | * | Et | OCH$_3$ | F | F | OH | H | H |

*R$^2$ and R$^{3b}$ joined together by (CH$_2$)$_3$ to form five-membered ring.

TABLE XIX-13

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XIX-13-1 | $^i$Pr | H | H | H | Et | OCH$_3$ | F | F | OH | H | H |
| XIX-13-2 | $^i$Pr | H | H | CH$_3$ | Et | OCH$_3$ | F | F | OH | H | H |
| XIX-13-3 | $^i$Pr | H | H | CH(CH$_3$)$_2$ | Et | OCH$_3$ | F | F | OH | H | H |

TABLE XIX-13-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-13-4 | $^i$Pr | H | H | CH₂CH(CH₃)₂ | Et | OCH₃ | F | F | OH | H | H |
| XIX-13-5 | $^i$Pr | H | H | CH₂Ph | Et | OCH₃ | F | F | OH | H | H |
| XIX-13-6 | $^i$Pr | H | H | CH₂-indol-3-yl | Et | OCH₃ | F | F | OH | H | H |
| XIX-13-7 | $^i$Pr | H | H | CH₂CH₂SCH₃ | Et | OCH₃ | F | F | OH | H | H |
| XIX-13-8 | $^i$Pr | * | H | * | Et | OCH₃ | F | F | OH | H | H |

*R² and R³ᵇ joined together by (CH₂)₃ to form five-membered ring.

TABLE XIX-14

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-14-1 | $^t$Bu | H | H | H | Et | OCH₃ | F | F | OH | H | H |
| XIX-14-2 | $^t$Bu | H | H | CH₃ | Et | OCH₃ | F | F | OH | H | H |
| XIX-14-3 | $^t$Bu | H | H | CH(CH₃)₂ | Et | OCH₃ | F | F | OH | H | H |
| XIX-14-4 | $^t$Bu | H | H | CH₂CH(CH₃)₂ | Et | OCH₃ | F | F | OH | H | H |
| XIX-14-5 | $^t$Bu | H | H | CH₂Ph | Et | OCH₃ | F | F | OH | H | H |
| XIX-14-6 | $^t$Bu | H | H | CH₂-indol-3-yl | Et | OCH₃ | F | F | OH | H | H |
| XIX-14-7 | $^t$Bu | H | H | CH₂CH₂SCH₃ | Et | OCH₃ | F | F | OH | H | H |
| XIX-14-8 | $^t$Bu | * | H | * | Et | OCH₃ | F | F | OH | H | H |

*R² and R³ᵇ joined together by (CH₂)₃ to form five-membered ring.

TABLE XIX-15

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-15-1 | Ph | H | H | H | Et | OCH₃ | F | F | OH | H | H |
| XIX-15-2 | Ph | H | H | CH₃ | Et | OCH₃ | F | F | OH | H | H |
| XIX-15-3 | Ph | H | H | CH(CH₃)₂ | Et | OCH₃ | F | F | OH | H | H |
| XIX-15-4 | Ph | H | H | CH₂CH(CH₃)₂ | Et | OCH₃ | F | F | OH | H | H |
| XIX-15-5 | Ph | H | H | CH₂Ph | Et | OCH₃ | F | F | OH | H | H |
| XIX-15-6 | Ph | H | H | CH₂-indol-3-yl | Et | OCH₃ | F | F | OH | H | H |
| XIX-15-7 | Ph | H | H | CH₂CH₂SCH₃ | Et | OCH₃ | F | F | OH | H | H |
| XIX-15-8 | Ph | * | H | * | Et | OCH₃ | F | F | OH | H | H |

*R² and R³ᵇ joined together by (CH₂)₃ to form five-membered ring.

TABLE XIX-16

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-16-1 | p-Me—Ph | H | H | H | Et | OCH₃ | F | F | OH | H | H |
| XIX-16-2 | p-Me—Ph | H | H | CH₃ | Et | OCH₃ | F | F | OH | H | H |
| XIX-16-3 | p-Me—Ph | H | H | CH(CH₃)₂ | Et | OCH₃ | F | F | OH | H | H |
| XIX-16-4 | p-Me—Ph | H | H | CH₂CH(CH₃)₂ | Et | OCH₃ | F | F | OH | H | H |
| XIX-16-5 | p-Me—Ph | H | H | CH₂Ph | Et | OCH₃ | F | F | OH | H | H |
| XIX-16-6 | p-Me—Ph | H | H | CH₂-indol-3-yl | Et | OCH₃ | F | F | OH | H | H |
| XIX-16-7 | p-Me—Ph | H | H | CH₂CH₂SCH₃ | Et | OCH₃ | F | F | OH | H | H |
| XIX-16-8 | p-Me—Ph | * | H | * | Et | OCH₃ | F | F | OH | H | H |

*R² and R³ᵇ joined together by (CH₂)₃ to form five-membered ring.

TABLE XIX-17

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-17-1 | p-F—Ph | H | H | H | Et | OCH₃ | F | F | OH | H | H |
| XIX-17-2 | p-F—Ph | H | H | CH₃ | Et | OCH₃ | F | F | OH | H | H |
| XIX-17-3 | p-F—Ph | H | H | CH(CH₃)₂ | Et | OCH₃ | F | F | OH | H | H |
| XIX-17-4 | p-F—Ph | H | H | CH₂CH(CH₃)₂ | Et | OCH₃ | F | F | OH | H | H |
| XIX-17-5 | p-F—Ph | H | H | CH₂Ph | Et | OCH₃ | F | F | OH | H | H |
| XIX-17-6 | p-F—Ph | H | H | CH₂-indol-3-yl | Et | OCH₃ | F | F | OH | H | H |
| XIX-17-7 | p-F—Ph | H | H | CH₂CH₂SCH₃ | Et | OCH₃ | F | F | OH | H | H |
| XIX-17-8 | p-F—Ph | * | H | * | Et | OCH₃ | F | F | OH | H | H |

*R² and R³ᵇ joined together by (CH₂)₃ to form five-membered ring.

TABLE XIX-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-18-1 | p-Cl—Ph | H | H | H | Et | OCH₃ | F | F | OH | H | H |
| XIX-18-2 | p-Cl—Ph | H | H | CH₃ | Et | OCH₃ | F | F | OH | H | H |
| XIX-18-3 | p-Cl—Ph | H | H | CH(CH₃)₂ | Et | OCH₃ | F | F | OH | H | H |
| XIX-18-4 | p-Cl—Ph | H | H | CH₂CH(CH₃)₂ | Et | OCH₃ | F | F | OH | H | H |
| XIX-18-5 | p-Cl—Ph | H | H | CH₂Ph | Et | OCH₃ | F | F | OH | H | H |
| XIX-18-6 | p-Cl—Ph | H | H | CH₂-indol-3-yl | Et | OCH₃ | F | F | OH | H | H |
| XIX-18-7 | p-Cl—Ph | H | H | CH₂CH₂SCH₃ | Et | OCH₃ | F | F | OH | H | H |
| XIX-18-8 | p-Cl—Ph | * | H | * | Et | OCH₃ | F | F | OH | H | H |

*R² and R³ᵇ joined together by (CH₂)₃ to form five-membered ring.

TABLE XIX-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-19-1 | p-Br—Ph | H | H | H | Et | OCH₃ | F | F | OH | H | H |
| XIX-19-2 | p-Br—Ph | H | H | CH₃ | Et | OCH₃ | F | F | OH | H | H |
| XIX-19-3 | p-Br—Ph | H | H | CH(CH₃)₂ | Et | OCH₃ | F | F | OH | H | H |
| XIX-19-4 | p-Br—Ph | H | H | CH₂CH(CH₃)₂ | Et | OCH₃ | F | F | OH | H | H |
| XIX-19-5 | p-Br—Ph | H | H | CH₂Ph | Et | OCH₃ | F | F | OH | H | H |
| XIX-19-6 | p-Br—Ph | H | H | CH₂-indol-3-yl | Et | OCH₃ | F | F | OH | H | H |
| XIX-19-7 | p-Br—Ph | H | H | CH₂CH₂SCH₃ | Et | OCH₃ | F | F | OH | H | H |
| XIX-19-8 | p-Br—Ph | * | H | * | Et | OCH₃ | F | F | OH | H | H |

*R² and R³ᵇ joined together by (CH₂)₃ to form five-membered ring.

TABLE XIX-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-20-1 | p-I—Ph | H | H | H | Et | OCH₃ | F | F | OH | H | H |
| XIX-20-2 | p-I—Ph | H | H | CH₃ | Et | OCH₃ | F | F | OH | H | H |
| XIX-20-3 | p-I—Ph | H | H | CH(CH₃)₂ | Et | OCH₃ | F | F | OH | H | H |
| XIX-20-4 | p-I—Ph | H | H | CH₂CH(CH₃)₂ | Et | OCH₃ | F | F | OH | H | H |
| XIX-20-5 | p-I—Ph | H | H | CH₂Ph | Et | OCH₃ | F | F | OH | H | H |
| XIX-20-6 | p-I—Ph | H | H | CH₂-indol-3-yl | Et | OCH₃ | F | F | OH | H | H |
| XIX-20-7 | p-I—Ph | H | H | CH₂CH₂SCH₃ | Et | OCH₃ | F | F | OH | H | H |
| XIX-20-8 | p-I—Ph | * | H | * | Et | OCH₃ | F | F | OH | H | H |

*R² and R³ᵇ joined together by (CH₂)₃ to form five-membered ring.

TABLE XIX-21

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-21-1 | CH₃ | H | H | H | $^i$Pr | OCH₃ | F | F | OH | H | H |
| XIX-21-2 | CH₃ | H | H | CH₃ | $^i$Pr | OCH₃ | F | F | OH | H | H |
| XIX-21-3 | CH₃ | H | H | CH(CH₃)₂ | $^i$Pr | OCH₃ | F | F | OH | H | H |
| XIX-21-4 | CH₃ | H | H | CH₂CH(CH₃)₂ | $^i$Pr | OCH₃ | F | F | OH | H | H |
| XIX-21-5 | CH₃ | H | H | CH₂Ph | $^i$Pr | OCH₃ | F | F | OH | H | H |
| XIX-21-6 | CH₃ | H | H | CH₂-indol-3-yl | $^i$Pr | OCH₃ | F | F | OH | H | H |
| XIX-21-7 | CH₃ | H | H | CH₂CH₂SCH₃ | $^i$Pr | OCH₃ | F | F | OH | H | H |
| XIX-21-8 | CH₃ | * | H | * | $^i$Pr | OCH₃ | F | F | OH | H | H |

*R² and R³ᵇ joined together by (CH₂)₃ to form five-membered ring.

TABLE XIX-22

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-22-1 | Et | H | H | H | $^i$Pr | OCH₃ | F | F | OH | H | H |
| XIX-22-2 | Et | H | H | CH₃ | $^i$Pr | OCH₃ | F | F | OH | H | H |
| XIX-22-3 | Et | H | H | CH(CH₃)₂ | $^i$Pr | OCH₃ | F | F | OH | H | H |
| XIX-22-4 | Et | H | H | CH₂CH(CH₃)₂ | $^i$Pr | OCH₃ | F | F | OH | H | H |
| XIX-22-5 | Et | H | H | CH₂Ph | $^i$Pr | OCH₃ | F | F | OH | H | H |

TABLE XIX-22-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-22-6 | Et | H | H | CH₂-indol-3-yl | $^i$Pr | OCH₃ | F | F | OH | H | H |
| XIX-22-7 | Et | H | H | CH₂CH₂SCH₃ | $^i$Pr | OCH₃ | F | F | OH | H | H |
| XIX-22-8 | Et | * | H | * | $^i$Pr | OCH₃ | F | F | OH | H | H |

*R² and R³ᵇ joined together by (CH₂)₃ to form five-membered ring.

TABLE XIX-23

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-23-1 | $^i$Pr | H | H | H | $^i$Pr | OCH₃ | F | F | OH | H | H |
| XIX-23-2 | $^i$Pr | H | H | CH₃ | $^i$Pr | OCH₃ | F | F | OH | H | H |
| XIX-23-3 | $^i$Pr | H | H | CH(CH₃)₂ | $^i$Pr | OCH₃ | F | F | OH | H | H |
| XIX-23-4 | $^i$Pr | H | H | CH₂CH(CH₃)₂ | $^i$Pr | OCH₃ | F | F | OH | H | H |
| XIX-23-5 | $^i$Pr | H | H | CH₂Ph | $^i$Pr | OCH₃ | F | F | OH | H | H |
| XIX-23-6 | $^i$Pr | H | H | CH₂-indol-3-yl | $^i$Pr | OCH₃ | F | F | OH | H | H |
| XIX-23-7 | $^i$Pr | H | H | CH₂CH₂SCH₃ | $^i$Pr | OCH₃ | F | F | OH | H | H |
| XIX-23-8 | $^i$Pr | * | H | * | $^i$Pr | OCH₃ | F | F | OH | H | H |

*R² and R³ᵇ joined together by (CH₂)₃ to form five-membered ring.

TABLE XIX-24

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-24-1 | $^t$Bu | H | H | H | $^i$Pr | OCH₃ | F | F | OH | H | H |
| XIX-24-2 | $^t$Bu | H | H | CH₃ | $^i$Pr | OCH₃ | F | F | OH | H | H |
| XIX-24-3 | $^t$Bu | H | H | CH(CH₃)₂ | $^i$Pr | OCH₃ | F | F | OH | H | H |
| XIX-24-4 | $^t$Bu | H | H | CH₂CH(CH₃)₂ | $^i$Pr | OCH₃ | F | F | OH | H | H |
| XIX-24-5 | $^t$Bu | H | H | CH₂Ph | $^i$Pr | OCH₃ | F | F | OH | H | H |
| XIX-24-6 | $^t$Bu | H | H | CH₂-indol-3-yl | $^i$Pr | OCH₃ | F | F | OH | H | H |
| XIX-24-7 | $^t$Bu | H | H | CH₂CH₂SCH₃ | $^i$Pr | OCH₃ | F | F | OH | H | H |
| XIX-24-8 | $^t$Bu | * | H | * | $^i$Pr | OCH₃ | F | F | OH | H | H |

*R² and R³ᵇ joined together by (CH₂)₃ to form five-membered ring.

TABLE XIX-25

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-25-1 | Ph | H | H | H | $^i$Pr | OCH₃ | F | F | OH | H | H |
| XIX-25-2 | Ph | H | H | CH₃ | $^i$Pr | OCH₃ | F | F | OH | H | H |
| XIX-25-3 | Ph | H | H | CH(CH₃)₂ | $^i$Pr | OCH₃ | F | F | OH | H | H |
| XIX-25-4 | Ph | H | H | CH₂CH(CH₃)₂ | $^i$Pr | OCH₃ | F | F | OH | H | H |
| XIX-25-5 | Ph | H | H | CH₂Ph | $^i$Pr | OCH₃ | F | F | OH | H | H |
| XIX-25-6 | Ph | H | H | CH₂-indol-3-yl | $^i$Pr | OCH₃ | F | F | OH | H | H |
| XIX-25-7 | Ph | H | H | CH₂CH₂SCH₃ | $^i$Pr | OCH₃ | F | F | OH | H | H |
| XIX-25-8 | Ph | * | H | * | $^i$Pr | OCH₃ | F | F | OH | H | H |

*R² and R³ᵇ joined together by (CH₂)₃ to form five-membered ring.

TABLE XIX-26

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-26-1 | p-Me—Ph | H | H | H | $^i$Pr | OCH₃ | F | F | OH | H | H |
| XIX-26-2 | p-Me—Ph | H | H | CH₃ | $^i$Pr | OCH₃ | F | F | OH | H | H |
| XIX-26-3 | p-Me—Ph | H | H | CH(CH₃)₂ | $^i$Pr | OCH₃ | F | F | OH | H | H |
| XIX-26-4 | p-Me—Ph | H | H | CH₂CH(CH₃)₂ | $^i$Pr | OCH₃ | F | F | OH | H | H |
| XIX-26-5 | p-Me—Ph | H | H | CH₂Ph | $^i$Pr | OCH₃ | F | F | OH | H | H |
| XIX-26-6 | p-Me—Ph | H | H | CH₂-indol-3-yl | $^i$Pr | OCH₃ | F | F | OH | H | H |
| XIX-26-7 | p-Me—Ph | H | H | CH₂CH₂SCH₃ | $^i$Pr | OCH₃ | F | F | OH | H | H |
| XIX-26-8 | p-Me—Ph | * | H | * | $^i$Pr | OCH₃ | F | F | OH | H | H |

*R² and R³ᵇ joined together by (CH₂)₃ to form five-membered ring.

TABLE XIX-27

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-27-1 | p-F—Ph | H | H | H | $^i$Pr | OCH₃ | F | F | OH | H | H |
| XIX-27-2 | p-F—Ph | H | H | CH₃ | $^i$Pr | OCH₃ | F | F | OH | H | H |
| XIX-27-3 | p-F—Ph | H | H | CH(CH₃)₂ | $^i$Pr | OCH₃ | F | F | OH | H | H |
| XIX-27-4 | p-F—Ph | H | H | CH₂CH(CH₃)₂ | $^i$Pr | OCH₃ | F | F | OH | H | H |
| XIX-27-5 | p-F—Ph | H | H | CH₂Ph | $^i$Pr | OCH₃ | F | F | OH | H | H |
| XIX-27-6 | p-F—Ph | H | H | CH₂-indol-3-yl | $^i$Pr | OCH₃ | F | F | OH | H | H |
| XIX-27-7 | p-F—Ph | H | H | CH₂CH₂SCH₃ | $^i$Pr | OCH₃ | F | F | OH | H | H |
| XIX-27-8 | p-F—Ph | * | H | * | $^i$Pr | OCH₃ | F | F | OH | H | H |

*R² and R³ᵇ joined together by (CH₂)₃ to form five-membered ring.

TABLE XIX-28

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-28-1 | p-Cl—Ph | H | H | H | $^i$Pr | OCH₃ | F | F | OH | H | H |
| XIX-28-2 | p-Cl—Ph | H | H | CH₃ | $^i$Pr | OCH₃ | F | F | OH | H | H |
| XIX-28-3 | p-Cl—Ph | H | H | CH(CH₃)₂ | $^i$Pr | OCH₃ | F | F | OH | H | H |
| XIX-28-4 | p-Cl—Ph | H | H | CH₂CH(CH₃)₂ | $^i$Pr | OCH₃ | F | F | OH | H | H |
| XIX-28-5 | p-Cl—Ph | H | H | CH₂Ph | $^i$Pr | OCH₃ | F | F | OH | H | H |
| XIX-28-6 | p-Cl—Ph | H | H | CH₂-indol-3-yl | $^i$Pr | OCH₃ | F | F | OH | H | H |
| XIX-28-7 | p-Cl—Ph | H | H | CH₂CH₂SCH₃ | $^i$Pr | OCH₃ | F | F | OH | H | H |
| XIX-28-8 | p-Cl—Ph | * | H | * | $^i$Pr | OCH₃ | F | F | OH | H | H |

*R² and R³ᵇ joined together by (CH₂)₃ to form five-membered ring.

TABLE XIX-29

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-29-1 | p-Br—Ph | H | H | H | $^i$Pr | OCH₃ | F | F | OH | H | H |
| XIX-29-2 | p-Br—Ph | H | H | CH₃ | $^i$Pr | OCH₃ | F | F | OH | H | H |
| XIX-29-3 | p-Br—Ph | H | H | CH(CH₃)₂ | $^i$Pr | OCH₃ | F | F | OH | H | H |
| XIX-29-4 | p-Br—Ph | H | H | CH₂CH(CH₃)₂ | $^i$Pr | OCH₃ | F | F | OH | H | H |
| XIX-29-5 | p-Br—Ph | H | H | CH₂Ph | $^i$Pr | OCH₃ | F | F | OH | H | H |
| XIX-29-6 | p-Br—Ph | H | H | CH₂-indol-3-yl | $^i$Pr | OCH₃ | F | F | OH | H | H |
| XIX-29-7 | p-Br—Ph | H | H | CH₂CH₂SCH₃ | $^i$Pr | OCH₃ | F | F | OH | H | H |
| XIX-29-8 | p-Br—Ph | * | H | * | $^i$Pr | OCH₃ | F | F | OH | H | H |

*R² and R³ᵇ joined together by (CH₂)₃ to form five-membered ring.

TABLE XIX-30

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-30-1 | p-I—Ph | H | H | H | $^i$Pr | OCH₃ | F | F | OH | H | H |
| XIX-30-2 | p-I—Ph | H | H | CH₃ | $^i$Pr | OCH₃ | F | F | OH | H | H |
| XIX-30-3 | p-I—Ph | H | H | CH(CH₃)₂ | $^i$Pr | OCH₃ | F | F | OH | H | H |
| XIX-30-4 | p-I—Ph | H | H | CH₂CH(CH₃)₂ | $^i$Pr | OCH₃ | F | F | OH | H | H |
| XIX-30-5 | p-I—Ph | H | H | CH₂Ph | $^i$Pr | OCH₃ | F | F | OH | H | H |
| XIX-30-6 | p-I—Ph | H | H | CH₂-indol-3-yl | $^i$Pr | OCH₃ | F | F | OH | H | H |
| XIX-30-7 | p-I—Ph | H | H | CH₂CH₂SCH₃ | $^i$Pr | OCH₃ | F | F | OH | H | H |
| XIX-30-8 | p-I—Ph | * | H | * | $^i$Pr | OCH₃ | F | F | OH | H | H |

*R² and R³ᵇ joined together by (CH₂)₃ to form five-membered ring.

TABLE XIX-31

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-31-1 | CH₃ | H | H | H | $^n$Bu | OCH₃ | F | F | OH | H | H |
| XIX-31-2 | CH₃ | H | H | CH₃ | $^n$Bu | OCH₃ | F | F | OH | H | H |
| XIX-31-3 | CH₃ | H | H | CH(CH₃)₂ | $^n$Bu | OCH₃ | F | F | OH | H | H |

TABLE XIX-31-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-31-4 | CH₃ | H | H | CH₂CH(CH₃)₂ | ⁿBu | OCH₃ | F | F | OH | H | H |
| XIX-31-5 | CH₃ | H | H | CH₂Ph | ⁿBu | OCH₃ | F | F | OH | H | H |
| XIX-31-6 | CH₃ | H | H | CH₂-indol-3-yl | ⁿBu | OCH₃ | F | F | OH | H | H |
| XIX-31-7 | CH₃ | H | H | CH₂CH₂SCH₃ | ⁿBu | OCH₃ | F | F | OH | H | H |
| XIX-31-8 | CH₃ | * | H | * | ⁿBu | OCH₃ | F | F | OH | H | H |

*R² and R³ᵇ joined together by (CH₂)₃ to form five-membered ring.

TABLE XIX-32

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-32-1 | Et | H | H | H | ⁿBu | OCH₃ | F | F | OH | H | H |
| XIX-32-2 | Et | H | H | CH₃ | ⁿBu | OCH₃ | F | F | OH | H | H |
| XIX-32-3 | Et | H | H | CH(CH₃)₂ | ⁿBu | OCH₃ | F | F | OH | H | H |
| XIX-32-4 | Et | H | H | CH₂CH(CH₃)₂ | ⁿBu | OCH₃ | F | F | OH | H | H |
| XIX-32-5 | Et | H | H | CH₂Ph | ⁿBu | OCH₃ | F | F | OH | H | H |
| XIX-32-6 | Et | H | H | CH₂-indol-3-yl | ⁿBu | OCH₃ | F | F | OH | H | H |
| XIX-32-7 | Et | H | H | CH₂CH₂SCH₃ | ⁿBu | OCH₃ | F | F | OH | H | H |
| XIX-32-8 | Et | * | H | * | ⁿBu | OCH₃ | F | F | OH | H | H |

*R² and R³ᵇ joined together by (CH₂)₃ to form five-membered ring.

TABLE XIX-33

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-33-1 | ⁱPr | H | H | H | ⁿBu | OCH₃ | F | F | OH | H | H |
| XIX-33-2 | ⁱPr | H | H | CH₃ | ⁿBu | OCH₃ | F | F | OH | H | H |
| XIX-33-3 | ⁱPr | H | H | CH(CH₃)₂ | ⁿBu | OCH₃ | F | F | OH | H | H |
| XIX-33-4 | ⁱPr | H | H | CH₂CH(CH₃)₂ | ⁿBu | OCH₃ | F | F | OH | H | H |
| XIX-33-5 | ⁱPr | H | H | CH₂Ph | ⁿBu | OCH₃ | F | F | OH | H | H |
| XIX-33-6 | ⁱPr | H | H | CH₂-indol-3-yl | ⁿBu | OCH₃ | F | F | OH | H | H |
| XIX-33-7 | ⁱPr | H | H | CH₂CH₂SCH₃ | ⁿBu | OCH₃ | F | F | OH | H | H |
| XIX-33-8 | ⁱPr | * | H | * | ⁿBu | OCH₃ | F | F | OH | H | H |

*R² and R³ᵇ joined together by (CH₂)₃ to form five-membered ring.

TABLE XIX-34

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-34-1 | ᵗBu | H | H | H | ⁿBu | OCH₃ | F | F | OH | H | H |
| XIX-34-2 | ᵗBu | H | H | CH₃ | ⁿBu | OCH₃ | F | F | OH | H | H |
| XIX-34-3 | ᵗBu | H | H | CH(CH₃)₂ | ⁿBu | OCH₃ | F | F | OH | H | H |
| XIX-34-4 | ᵗBu | H | H | CH₂CH(CH₃)₂ | ⁿBu | OCH₃ | F | F | OH | H | H |
| XIX-34-5 | ᵗBu | H | H | CH₂Ph | ⁿBu | OCH₃ | F | F | OH | H | H |
| XIX-34-6 | ᵗBu | H | H | CH₂-indol-3-yl | ⁿBu | OCH₃ | F | F | OH | H | H |
| XIX-34-7 | ᵗBu | H | H | CH₂CH₂SCH₃ | ⁿBu | OCH₃ | F | F | OH | H | H |
| XIX-34-8 | ᵗBu | * | H | * | ⁿBu | OCH₃ | F | F | OH | H | H |

*R² and R³ᵇ joined together by (CH₂)₃ to form five-membered ring.

TABLE XIX-35

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-35-1 | Ph | H | H | H | ⁿBu | OCH₃ | F | F | OH | H | H |
| XIX-35-2 | Ph | H | H | CH₃ | ⁿBu | OCH₃ | F | F | OH | H | H |
| XIX-35-3 | Ph | H | H | CH(CH₃)₂ | ⁿBu | OCH₃ | F | F | OH | H | H |
| XIX-35-4 | Ph | H | H | CH₂CH(CH₃)₂ | ⁿBu | OCH₃ | F | F | OH | H | H |
| XIX-35-5 | Ph | H | H | CH₂Ph | ⁿBu | OCH₃ | F | F | OH | H | H |
| XIX-35-6 | Ph | H | H | CH₂-indol-3-yl | ⁿBu | OCH₃ | F | F | OH | H | H |
| XIX-35-7 | Ph | H | H | CH₂CH₂SCH₃ | ⁿBu | OCH₃ | F | F | OH | H | H |
| XIX-35-8 | Ph | * | H | * | ⁿBu | OCH₃ | F | F | OH | H | H |

*R² and R³ᵇ joined together by (CH₂)₃ to form five-membered ring.

TABLE XIX-36

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-36-1 | p-Me—Ph | H | H | H | ⁿBu | OCH₃ | F | F | OH | H | H |
| XIX-36-2 | p-Me—Ph | H | H | CH₃ | ⁿBu | OCH₃ | F | F | OH | H | H |
| XIX-36-3 | p-Me—Ph | H | H | CH(CH₃)₂ | ⁿBu | OCH₃ | F | F | OH | H | H |
| XIX-36-4 | p-Me—Ph | H | H | CH₂CH(CH₃)₂ | ⁿBu | OCH₃ | F | F | OH | H | H |
| XIX-36-5 | p-Me—Ph | H | H | CH₂Ph | ⁿBu | OCH₃ | F | F | OH | H | H |
| XIX-36-6 | p-Me—Ph | H | H | CH₂-indol-3-yl | ⁿBu | OCH₃ | F | F | OH | H | H |
| XIX-36-7 | p-Me—Ph | H | H | CH₂CH₂SCH₃ | ⁿBu | OCH₃ | F | F | OH | H | H |
| XIX-36-8 | p-Me—Ph | * | H | * | ⁿBu | OCH₃ | F | F | OH | H | H |

*R² and R³ᵇ joined together by (CH₂)₃ to form five-membered ring.

TABLE XIX-37

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-37-1 | p-F—Ph | H | H | H | ⁿBu | OCH₃ | F | F | OH | H | H |
| XIX-37-2 | p-F—Ph | H | H | CH₃ | ⁿBu | OCH₃ | F | F | OH | H | H |
| XIX-37-3 | p-F—Ph | H | H | CH(CH₃)₂ | ⁿBu | OCH₃ | F | F | OH | H | H |
| XIX-37-4 | p-F—Ph | H | H | CH₂CH(CH₃)₂ | ⁿBu | OCH₃ | F | F | OH | H | H |
| XIX-37-5 | p-F—Ph | H | H | CH₂Ph | ⁿBu | OCH₃ | F | F | OH | H | H |
| XIX-37-6 | p-F—Ph | H | H | CH₂-indol-3-yl | ⁿBu | OCH₃ | F | F | OH | H | H |
| XIX-37-7 | p-F—Ph | H | H | CH₂CH₂SCH₃ | ⁿBu | OCH₃ | F | F | OH | H | H |
| XIX-37-8 | p-F—Ph | * | H | * | ⁿBu | OCH₃ | F | F | OH | H | H |

*R² and R³ᵇ joined together by (CH₂)₃ to form five-membered ring.

TABLE XIX-38

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-38-1 | p-Cl—Ph | H | H | H | ⁿBu | OCH₃ | F | F | OH | H | H |
| XIX-38-2 | p-Cl—Ph | H | H | CH₃ | ⁿBu | OCH₃ | F | F | OH | H | H |
| XIX-38-3 | p-Cl—Ph | H | H | CH(CH₃)₂ | ⁿBu | OCH₃ | F | F | OH | H | H |
| XIX-38-4 | p-Cl—Ph | H | H | CH₂CH(CH₃)₂ | ⁿBu | OCH₃ | F | F | OH | H | H |
| XIX-38-5 | p-Cl—Ph | H | H | CH₂Ph | ⁿBu | OCH₃ | F | F | OH | H | H |
| XIX-38-6 | p-Cl—Ph | H | H | CH₂-indol-3-yl | ⁿBu | OCH₃ | F | F | OH | H | H |
| XIX-38-7 | p-Cl—Ph | H | H | CH₂CH₂SCH₃ | ⁿBu | OCH₃ | F | F | OH | H | H |
| XIX-38-8 | p-Cl—Ph | * | H | * | ⁿBu | OCH₃ | F | F | OH | H | H |

*R² and R³ᵇ joined together by (CH₂)₃ to form five-membered ring.

TABLE XIX-39

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-39-1 | p-Br—Ph | H | H | H | ⁿBu | OCH₃ | F | F | OH | H | H |
| XIX-39-2 | p-Br—Ph | H | H | CH₃ | ⁿBu | OCH₃ | F | F | OH | H | H |
| XIX-39-3 | p-Br—Ph | H | H | CH(CH₃)₂ | ⁿBu | OCH₃ | F | F | OH | H | H |
| XIX-39-4 | p-Br—Ph | H | H | CH₂CH(CH₃)₂ | ⁿBu | OCH₃ | F | F | OH | H | H |
| XIX-39-5 | p-Br—Ph | H | H | CH₂Ph | ⁿBu | OCH₃ | F | F | OH | H | H |
| XIX-39-6 | p-Br—Ph | H | H | CH₂-indol-3-yl | ⁿBu | OCH₃ | F | F | OH | H | H |
| XIX-39-7 | p-Br—Ph | H | H | CH₂CH₂SCH₃ | ⁿBu | OCH₃ | F | F | OH | H | H |
| XIX-39-8 | p-Br—Ph | * | H | * | ⁿBu | OCH₃ | F | F | OH | H | H |

*R² and R³ᵇ joined together by (CH₂)₃ to form five-membered ring.

TABLE XIX-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-40-1 | p-I—Ph | H | H | H | ⁿBu | OCH₃ | F | F | OH | H | H |
| XIX-40-2 | p-I—Ph | H | H | CH₃ | ⁿBu | OCH₃ | F | F | OH | H | H |
| XIX-40-3 | p-I—Ph | H | H | CH(CH₃)₂ | ⁿBu | OCH₃ | F | F | OH | H | H |
| XIX-40-4 | p-I—Ph | H | H | CH₂CH(CH₃)₂ | ⁿBu | OCH₃ | F | F | OH | H | H |
| XIX-40-5 | p-I—Ph | H | H | CH₂Ph | ⁿBu | OCH₃ | F | F | OH | H | H |

TABLE XIX-40-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-40-6 | p-I—Ph | H | H | CH₂-indol-3-yl | ⁿBu | OCH₃ | F | F | OH | H | H |
| XIX-40-7 | p-I—Ph | H | H | CH₂CH₂SCH₃ | ⁿBu | OCH₃ | F | F | OH | H | H |
| XIX-40-8 | p-I—Ph | * | H | * | ⁿBu | OCH₃ | F | F | OH | H | H |

*R² and R³ᵇ joined together by (CH₂)₃ to form five-membered ring.

TABLE XIX-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-41-1 | CH₃ | H | H | H | Bz | OCH₃ | F | F | OH | H | H |
| XIX-41-2 | CH₃ | H | H | CH₃ | Bz | OCH₃ | F | F | OH | H | H |
| XIX-41-3 | CH₃ | H | H | CH(CH₃)₂ | Bz | OCH₃ | F | F | OH | H | H |
| XIX-41-4 | CH₃ | H | H | CH₂CH(CH₃)₂ | Bz | OCH₃ | F | F | OH | H | H |
| XIX-41-5 | CH₃ | H | H | CH₂Ph | Bz | OCH₃ | F | F | OH | H | H |
| XIX-41-6 | CH₃ | H | H | CH₂-indol-3-yl | Bz | OCH₃ | F | F | OH | H | H |
| XIX-41-7 | CH₃ | H | H | CH₂CH₂SCH₃ | Bz | OCH₃ | F | F | OH | H | H |
| XIX-41-8 | CH₃ | * | H | * | Bz | OCH₃ | F | F | OH | H | H |

*R² and R³ᵇ joined together by (CH₂)₃ to form five-membered ring.

TABLE XIX-42

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-42-1 | Et | H | H | H | Bz | OCH₃ | F | F | OH | H | H |
| XIX-42-2 | Et | H | H | CH₃ | Bz | OCH₃ | F | F | OH | H | H |
| XIX-42-3 | Et | H | H | CH(CH₃)₂ | Bz | OCH₃ | F | F | OH | H | H |
| XIX-42-4 | Et | H | H | CH₂CH(CH₃)₂ | Bz | OCH₃ | F | F | OH | H | H |
| XIX-42-5 | Et | H | H | CH₂Ph | Bz | OCH₃ | F | F | OH | H | H |
| XIX-42-6 | Et | H | H | CH₂-indol-3-yl | Bz | OCH₃ | F | F | OH | H | H |
| XIX-42-7 | Et | H | H | CH₂CH₂SCH₃ | Bz | OCH₃ | F | F | OH | H | H |
| XIX-42-8 | Et | * | H | * | Bz | OCH₃ | F | F | OH | H | H |

*R² and R³ᵇ joined together by (CH₂)₃ to form five-membered ring.

TABLE XIX-43

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-43-1 | ⁱPr | H | H | H | Bz | OCH₃ | F | F | OH | H | H |
| XIX-43-2 | ⁱPr | H | H | CH₃ | Bz | OCH₃ | F | F | OH | H | H |
| XIX-43-3 | ⁱPr | H | H | CH(CH₃)₂ | Bz | OCH₃ | F | F | OH | H | H |
| XIX-43-4 | ⁱPr | H | H | CH₂CH(CH₃)₂ | Bz | OCH₃ | F | F | OH | H | H |
| XIX-43-5 | ⁱPr | H | H | CH₂Ph | Bz | OCH₃ | F | F | OH | H | H |
| XIX-43-6 | ⁱPr | H | H | CH₂-indol-3-yl | Bz | OCH₃ | F | F | OH | H | H |
| XIX-43-7 | ⁱPr | H | H | CH₂CH₂SCH₃ | Bz | OCH₃ | F | F | OH | H | H |
| XIX-43-8 | ⁱPr | * | H | * | Bz | OCH₃ | F | F | OH | H | H |

*R² and R³ᵇ joined together by (CH₂)₃ to form five-membered ring.

TABLE XIX-44

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-44-1 | ᵗBu | H | H | H | Bz | OCH₃ | F | F | OH | H | H |
| XIX-44-2 | ᵗBu | H | H | CH₃ | Bz | OCH₃ | F | F | OH | H | H |
| XIX-44-3 | ᵗBu | H | H | CH(CH₃)₂ | Bz | OCH₃ | F | F | OH | H | H |
| XIX-44-4 | ᵗBu | H | H | CH₂CH(CH₃)₂ | Bz | OCH₃ | F | F | OH | H | H |
| XIX-44-5 | ᵗBu | H | H | CH₂Ph | Bz | OCH₃ | F | F | OH | H | H |
| XIX-44-6 | ᵗBu | H | H | CH₂-indol-3-yl | Bz | OCH₃ | F | F | OH | H | H |
| XIX-44-7 | ᵗBu | H | H | CH₂CH₂SCH₃ | Bz | OCH₃ | F | F | OH | H | H |
| XIX-44-8 | ᵗBu | * | H | * | Bz | OCH₃ | F | F | OH | H | H |

*R² and R³ᵇ joined together by (CH₂)₃ to form five-membered ring.

TABLE XIX-45

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-45-1 | Ph | H | H | H | Bz | OCH₃ | F | F | OH | H | H |
| XIX-45-2 | Ph | H | H | CH₃ | Bz | OCH₃ | F | F | OH | H | H |
| XIX-45-3 | Ph | H | H | CH(CH₃)₂ | Bz | OCH₃ | F | F | OH | H | H |
| XIX-45-4 | Ph | H | H | CH₂CH(CH₃)₂ | Bz | OCH₃ | F | F | OH | H | H |
| XIX-45-5 | Ph | H | H | CH₂Ph | Bz | OCH₃ | F | F | OH | H | H |
| XIX-45-6 | Ph | H | H | CH₂-indol-3-yl | Bz | OCH₃ | F | F | OH | H | H |
| XIX-45-7 | Ph | H | H | CH₂CH₂SCH₃ | Bz | OCH₃ | F | F | OH | H | H |
| XIX-45-8 | Ph | * | H | * | Bz | OCH₃ | F | F | OH | H | H |

*R² and R³ᵇ joined together by (CH₂)₃ to form five-membered ring.

TABLE XIX-46

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-46-1 | p-Me—Ph | H | H | H | Bz | OCH₃ | F | F | OH | H | H |
| XIX-46-2 | p-Me—Ph | H | H | CH₃ | Bz | OCH₃ | F | F | OH | H | H |
| XIX-46-3 | p-Me—Ph | H | H | CH(CH₃)₂ | Bz | OCH₃ | F | F | OH | H | H |
| XIX-46-4 | p-Me—Ph | H | H | CH₂CH(CH₃)₂ | Bz | OCH₃ | F | F | OH | H | H |
| XIX-46-5 | p-Me—Ph | H | H | CH₂Ph | Bz | OCH₃ | F | F | OH | H | H |
| XIX-46-6 | p-Me—Ph | H | H | CH₂-indol-3-yl | Bz | OCH₃ | F | F | OH | H | H |
| XIX-46-7 | p-Me—Ph | H | H | CH₂CH₂SCH₃ | Bz | OCH₃ | F | F | OH | H | H |
| XIX-46-8 | p-Me—Ph | * | H | * | Bz | OCH₃ | F | F | OH | H | H |

*R² and R³ᵇ joined together by (CH₂)₃ to form five-membered ring.

TABLE XIX-47

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-47-1 | p-F—Ph | H | H | H | Bz | OCH₃ | F | F | OH | H | H |
| XIX-47-2 | p-F—Ph | H | H | CH₃ | Bz | OCH₃ | F | F | OH | H | H |
| XIX-47-3 | p-F—Ph | H | H | CH(CH₃)₂ | Bz | OCH₃ | F | F | OH | H | H |
| XIX-47-4 | p-F—Ph | H | H | CH₂CH(CH₃)₂ | Bz | OCH₃ | F | F | OH | H | H |
| XIX-47-5 | p-F—Ph | H | H | CH₂Ph | Bz | OCH₃ | F | F | OH | H | H |
| XIX-47-6 | p-F—Ph | H | H | CH₂-indol-3-yl | Bz | OCH₃ | F | F | OH | H | H |
| XIX-47-7 | p-F—Ph | H | H | CH₂CH₂SCH₃ | Bz | OCH₃ | F | F | OH | H | H |
| XIX-47-8 | p-F—Ph | * | H | * | Bz | OCH₃ | F | F | OH | H | H |

*R² and R³ᵇ joined together by (CH₂)₃ to form five-membered ring.

TABLE XIX-48

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-48-1 | p-Cl—Ph | H | H | H | Bz | OCH₃ | F | F | OH | H | H |
| XIX-48-2 | p-Cl—Ph | H | H | CH₃ | Bz | OCH₃ | F | F | OH | H | H |
| XIX-48-3 | p-Cl—Ph | H | H | CH(CH₃)₂ | Bz | OCH₃ | F | F | OH | H | H |
| XIX-48-4 | p-Cl—Ph | H | H | CH₂CH(CH₃)₂ | Bz | OCH₃ | F | F | OH | H | H |
| XIX-48-5 | p-Cl—Ph | H | H | CH₂Ph | Bz | OCH₃ | F | F | OH | H | H |
| XIX-48-6 | p-Cl—Ph | H | H | CH₂-indol-3-yl | Bz | OCH₃ | F | F | OH | H | H |
| XIX-48-7 | p-Cl—Ph | H | H | CH₂CH₂SCH₃ | Bz | OCH₃ | F | F | OH | H | H |
| XIX-48-8 | p-Cl—Ph | * | H | * | Bz | OCH₃ | F | F | OH | H | H |

*R² and R³ᵇ joined together by (CH₂)₃ to form five-membered ring.

TABLE XIX-49

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-49-1 | p-Br—Ph | H | H | H | Bz | OCH₃ | F | F | OH | H | H |
| XIX-49-2 | p-Br—Ph | H | H | CH₃ | Bz | OCH₃ | F | F | OH | H | H |
| XIX-49-3 | p-Br—Ph | H | H | CH(CH₃)₂ | Bz | OCH₃ | F | F | OH | H | H |
| XIX-49-4 | p-Br—Ph | H | H | CH₂CH(CH₃)₂ | Bz | OCH₃ | F | F | OH | H | H |
| XIX-49-5 | p-Br—Ph | H | H | CH₂Ph | Bz | OCH₃ | F | F | OH | H | H |
| XIX-49-6 | p-Br—Ph | H | H | CH₂-indol-3-yl | Bz | OCH₃ | F | F | OH | H | H |
| XIX-49-7 | p-Br—Ph | H | H | CH₂CH₂SCH₃ | Bz | OCH₃ | F | F | OH | H | H |
| XIX-49-8 | p-Br—Ph | * | H | * | Bz | OCH₃ | F | F | OH | H | H |

*R² and R³ᵇ joined together by (CH₂)₃ to form five-membered ring.

TABLE XIX-50

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-50-1 | p-I—Ph | H | H | H | Bz | OCH₃ | F | F | OH | H | H |
| XIX-50-2 | p-I—Ph | H | H | CH₃ | Bz | OCH₃ | F | F | OH | H | H |
| XIX-50-3 | p-I—Ph | H | H | CH(CH₃)₂ | Bz | OCH₃ | F | F | OH | H | H |
| XIX-50-4 | p-I—Ph | H | H | CH₂CH(CH₃)₂ | Bz | OCH₃ | F | F | OH | H | H |
| XIX-50-5 | p-I—Ph | H | H | CH₂Ph | Bz | OCH₃ | F | F | OH | H | H |

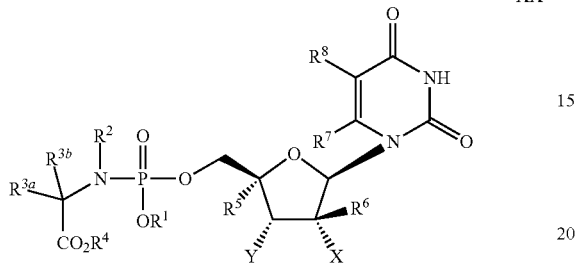

XX

TABLE XX-1

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-1-1 | CH₃ | H | H | H | CH₃ | OCH₃ | H | F | OH | H | H |
| XX-1-2 | CH₃ | H | H | CH₃ | CH₃ | OCH₃ | H | F | OH | H | H |
| XX-1-3 | CH₃ | H | H | CH(CH₃)₂ | CH₃ | OCH₃ | H | F | OH | H | H |
| XX-1-4 | CH₃ | H | H | CH₂CH(CH₃)₂ | CH₃ | OCH₃ | H | F | OH | H | H |
| XX-1-5 | CH₃ | H | H | CH₂Ph | CH₃ | OCH₃ | H | F | OH | H | H |
| XX-1-6 | CH₃ | H | H | CH₂-indol-3-yl | CH₃ | OCH₃ | H | F | OH | H | H |
| XX-1-7 | CH₃ | H | H | CH₂CH₂SCH₃ | CH₃ | OCH₃ | H | F | OH | H | H |
| XX-1-8 | CH₃ | * | H | * | CH₃ | OCH₃ | H | F | OH | H | H |

*R² and R³ᵇ joined together by (CH₂)₃ to form five-membered ring.

TABLE XX-2

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-2-1 | Et | H | H | H | CH₃ | OCH₃ | H | F | OH | H | H |
| XX-2-2 | Et | H | H | CH₃ | CH₃ | OCH₃ | H | F | OH | H | H |
| XX-2-3 | Et | H | H | CH(CH₃)₂ | CH₃ | OCH₃ | H | F | OH | H | H |
| XX-2-4 | Et | H | H | CH₂CH(CH₃)₂ | CH₃ | OCH₃ | H | F | OH | H | H |
| XX-2-5 | Et | H | H | CH₂Ph | CH₃ | OCH₃ | H | F | OH | H | H |
| XX-2-6 | Et | H | H | CH₂-indol-3-yl | CH₃ | OCH₃ | H | F | OH | H | H |
| XX-2-7 | Et | H | H | CH₂CH₂SCH₃ | CH₃ | OCH₃ | H | F | OH | H | H |
| XX-2-8 | Et | * | H | * | CH₃ | OCH₃ | H | F | OH | H | H |

*R² and R³ᵇ joined together by (CH₂)₃ to form five-membered ring.

TABLE XX-3

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-3-1 | ⁱPr | H | H | H | CH₃ | OCH₃ | H | F | OH | H | H |
| XX-3-2 | ⁱPr | H | H | CH₃ | CH₃ | OCH₃ | H | F | OH | H | H |
| XX-3-3 | ⁱPr | H | H | CH(CH₃)₂ | CH₃ | OCH₃ | H | F | OH | H | H |
| XX-3-4 | ⁱPr | H | H | CH₂CH(CH₃)₂ | CH₃ | OCH₃ | H | F | OH | H | H |
| XX-3-5 | ⁱPr | H | H | CH₂Ph | CH₃ | OCH₃ | H | F | OH | H | H |
| XX-3-6 | ⁱPr | H | H | CH₂-indol-3-yl | CH₃ | OCH₃ | H | F | OH | H | H |
| XX-3-7 | ⁱPr | H | H | CH₂CH₂SCH₃ | CH₃ | OCH₃ | H | F | OH | H | H |
| XX-3-8 | ⁱPr | * | H | * | CH₃ | OCH₃ | H | F | OH | H | H |

*R² and R³ᵇ joined together by (CH₂)₃ to form five-membered ring.

TABLE XIX-50-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XIX-50-6 | p-I—Ph | H | H | CH₂-indol-3-yl | Bz | OCH₃ | F | F | OH | H | H |
| XIX-50-7 | p-I—Ph | H | H | CH₂CH₂SCH₃ | Bz | OCH₃ | F | F | OH | H | H |
| XIX-50-8 | p-I—Ph | * | H | * | Bz | OCH₃ | F | F | OH | H | H |

*R² and R³ᵇ joined together by (CH₂)₃ to form five-membered ring.

TABLE XX-4

| No | R¹ | R² | R³ᵃ | R³ᵇ | R⁴ | R⁵ | R⁶ | X | Y | R⁷ | R⁸ |
| --- | --- | --- | --- | --- | --- | --- | --- | --- | --- | --- | --- |
| XX-4-1 | tBu | H | H | H | CH₃ | OCH₃ | H | F | OH | H | H |
| XX-4-2 | tBu | H | H | CH₃ | CH₃ | OCH₃ | H | F | OH | H | H |
| XX-4-3 | tBu | H | H | CH(CH₃)₂ | CH₃ | OCH₃ | H | F | OH | H | H |
| XX-4-4 | tBu | H | H | CH₂CH(CH₃)₂ | CH₃ | OCH₃ | H | F | OH | H | H |
| XX-4-5 | tBu | H | H | CH₂Ph | CH₃ | OCH₃ | H | F | OH | H | H |
| XX-4-6 | tBu | H | H | CH₂-indol-3-yl | CH₃ | OCH₃ | H | F | OH | H | H |
| XX-4-7 | tBu | H | H | CH₂CH₂SCH₃ | CH₃ | OCH₃ | H | F | OH | H | H |
| XX-4-8 | tBu | * | H | * | CH₃ | OCH₃ | H | F | OH | H | H |

*R² and R³ᵇ joined together by (CH₂)₃ to form five-membered ring.

TABLE XX-5

| No | R¹ | R² | R³ᵃ | R³ᵇ | R⁴ | R⁵ | R⁶ | X | Y | R⁷ | R⁸ |
| --- | --- | --- | --- | --- | --- | --- | --- | --- | --- | --- | --- |
| XX-5-1 | Ph | H | H | H | CH₃ | OCH₃ | H | F | OH | H | H |
| XX-5-2 | Ph | H | H | CH₃ | CH₃ | OCH₃ | H | F | OH | H | H |
| XX-5-3 | Ph | H | H | CH(CH₃)₂ | CH₃ | OCH₃ | H | F | OH | H | H |
| XX-5-4 | Ph | H | H | CH₂CH(CH₃)₂ | CH₃ | OCH₃ | H | F | OH | H | H |
| XX-5-5 | Ph | H | H | CH₂Ph | CH₃ | OCH₃ | H | F | OH | H | H |
| XX-5-6 | Ph | H | H | CH₂-indol-3-yl | CH₃ | OCH₃ | H | F | OH | H | H |
| XX-5-7 | Ph | H | H | CH₂CH₂SCH₃ | CH₃ | OCH₃ | H | F | OH | H | H |
| XX-5-8 | Ph | * | H | * | CH₃ | OCH₃ | H | F | OH | H | H |

*R² and R³ᵇ joined together by (CH₂)₃ to form five-membered ring.

TABLE XX-6

| No | R¹ | R² | R³ᵃ | R³ᵇ | R⁴ | R⁵ | R⁶ | X | Y | R⁷ | R⁸ |
| --- | --- | --- | --- | --- | --- | --- | --- | --- | --- | --- | --- |
| XX-6-1 | p-Me—Ph | H | H | H | CH₃ | OCH₃ | H | F | OH | H | H |
| XX-6-2 | p-Me—Ph | H | H | CH₃ | CH₃ | OCH₃ | H | F | OH | H | H |
| XX-6-3 | p-Me—Ph | H | H | CH(CH₃)₂ | CH₃ | OCH₃ | H | F | OH | H | H |
| XX-6-4 | p-Me—Ph | H | H | CH₂CH(CH₃)₂ | CH₃ | OCH₃ | H | F | OH | H | H |
| XX-6-5 | p-Me—Ph | H | H | CH₂Ph | CH₃ | OCH₃ | H | F | OH | H | H |
| XX-6-6 | p-Me—Ph | H | H | CH₂-indol-3-yl | CH₃ | OCH₃ | H | F | OH | H | H |
| XX-6-7 | p-Me—Ph | H | H | CH₂CH₂SCH₃ | CH₃ | OCH₃ | H | F | OH | H | H |
| XX-6-8 | p-Me—Ph | * | H | * | CH₃ | OCH₃ | H | F | OH | H | H |

*R² and R³ᵇ joined together by (CH₂)₃ to form five-membered ring.

TABLE XX-7

| No | R¹ | R² | R³ᵃ | R³ᵇ | R⁴ | R⁵ | R⁶ | X | Y | R⁷ | R⁸ |
| --- | --- | --- | --- | --- | --- | --- | --- | --- | --- | --- | --- |
| XX-7-1 | p-F—Ph | H | H | H | CH₃ | OCH₃ | H | F | OH | H | H |
| XX-7-2 | p-F—Ph | H | H | CH₃ | CH₃ | OCH₃ | H | F | OH | H | H |
| XX-7-3 | p-F—Ph | H | H | CH(CH₃)₂ | CH₃ | OCH₃ | H | F | OH | H | H |
| XX-7-4 | p-F—Ph | H | H | CH₂CH(CH₃)₂ | CH₃ | OCH₃ | H | F | OH | H | H |
| XX-7-6 | p-F—Ph | H | H | CH₂Ph | CH₃ | OCH₃ | H | F | OH | H | H |
| XX-7-7 | p-F—Ph | H | H | CH₂-indol-3-yl | CH₃ | OCH₃ | H | F | OH | H | H |
| XX-7-8 | p-F—Ph | H | H | CH₂CH₂SCH₃ | CH₃ | OCH₃ | H | F | OH | H | H |
| XX-7-20 | p-F—Ph | * | H | * | CH₃ | OCH₃ | H | F | OH | H | H |

*R² and R³ᵇ joined together by (CH₂)₃ to form five-membered ring.

TABLE XX-8

| No | R¹ | R² | R³ᵃ | R³ᵇ | R⁴ | R⁵ | R⁶ | X | Y | R⁷ | R⁸ |
| --- | --- | --- | --- | --- | --- | --- | --- | --- | --- | --- | --- |
| XX-8-1 | p-Cl—Ph | H | H | H | CH₃ | OCH₃ | H | F | OH | H | H |
| XX-8-2 | p-Cl—Ph | H | H | CH₃ | CH₃ | OCH₃ | H | F | OH | H | H |
| XX-8-3 | p-Cl—Ph | H | H | CH(CH₃)₂ | CH₃ | OCH₃ | H | F | OH | H | H |
| XX-8-4 | p-Cl—Ph | H | H | CH₂CH(CH₃)₂ | CH₃ | OCH₃ | H | F | OH | H | H |
| XX-8-5 | p-Cl—Ph | H | H | CH₂Ph | CH₃ | OCH₃ | H | F | OH | H | H |

TABLE XX-8-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-8-6 | p-Cl—Ph | H | H | $CH_2$-indol-3-yl | $CH_3$ | $OCH_3$ | H | F | OH | H | H |
| XX-8-7 | p-Cl—Ph | H | H | $CH_2CH_2SCH_3$ | $CH_3$ | $OCH_3$ | H | F | OH | H | H |
| XX-8-8 | p-Cl—Ph | * | H | * | $CH_3$ | $OCH_3$ | H | F | OH | H | H |

*$R^2$ and $R^{3b}$ joined together by $(CH_2)_3$ to form five-membered ring.

TABLE XX-9

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-9-1 | p-Br—Ph | H | H | H | $CH_3$ | $OCH_3$ | H | F | OH | H | H |
| XX-9-2 | p-Br—Ph | H | H | $CH_3$ | $CH_3$ | $OCH_3$ | H | F | OH | H | H |
| XX-9-3 | p-Br—Ph | H | H | $CH(CH_3)_2$ | $CH_3$ | $OCH_3$ | H | F | OH | H | H |
| XX-9-4 | p-Br—Ph | H | H | $CH_2CH(CH_3)_2$ | $CH_3$ | $OCH_3$ | H | F | OH | H | H |
| XX-9-6 | p-Br—Ph | H | H | $CH_2Ph$ | $CH_3$ | $OCH_3$ | H | F | OH | H | H |
| XX-9-7 | p-Br—Ph | H | H | $CH_2$-indol-3-yl | $CH_3$ | $OCH_3$ | H | F | OH | H | H |
| XX-9-8 | p-Br—Ph | H | H | $CH_2CH_2SCH_3$ | $CH_3$ | $OCH_3$ | H | F | OH | H | H |
| XX-9-20 | p-Br—Ph | * | H | * | $CH_3$ | $OCH_3$ | H | F | OH | H | H |

*$R^2$ and $R^{3b}$ joined together by $(CH_2)_3$ to form five-membered ring.

TABLE XX-10

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-10-1 | p-I—Ph | H | H | H | $CH_3$ | $OCH_3$ | H | F | OH | H | H |
| XX-10-2 | p-I—Ph | H | H | $CH_3$ | $CH_3$ | $OCH_3$ | H | F | OH | H | H |
| XX-10-3 | p-I—Ph | H | H | $CH(CH_3)_2$ | $CH_3$ | $OCH_3$ | H | F | OH | H | H |
| XX-10-4 | p-I—Ph | H | H | $CH_2CH(CH_3)_2$ | $CH_3$ | $OCH_3$ | H | F | OH | H | H |
| XX-10-5 | p-I—Ph | H | H | $CH_2Ph$ | $CH_3$ | $OCH_3$ | H | F | OH | H | H |
| XX-10-6 | p-I—Ph | H | H | $CH_2$-indol-3-yl | $CH_3$ | $OCH_3$ | H | F | OH | H | H |
| XX-10-7 | p-I—Ph | H | H | $CH_2CH_2SCH_3$ | $CH_3$ | $OCH_3$ | H | F | OH | H | H |
| XX-10-8 | p-I—Ph | * | H | * | $CH_3$ | $OCH_3$ | H | F | OH | H | H |

*$R^2$ and $R^{3b}$ joined together by $(CH_2)_3$ to form five-membered ring.

TABLE XX-11

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-11-1 | $CH_3$ | H | H | H | Et | $OCH_3$ | H | F | OH | H | H |
| XX-11-2 | $CH_3$ | H | H | $CH_3$ | Et | $OCH_3$ | H | F | OH | H | H |
| XX-11-3 | $CH_3$ | H | H | $CH(CH_3)_2$ | Et | $OCH_3$ | H | F | OH | H | H |
| XX-11-4 | $CH_3$ | H | H | $CH_2CH(CH_3)_2$ | Et | $OCH_3$ | H | F | OH | H | H |
| XX-11-5 | $CH_3$ | H | H | $CH_2Ph$ | Et | $OCH_3$ | H | F | OH | H | H |
| XX-11-6 | $CH_3$ | H | H | $CH_2$-indol-3-yl | Et | $OCH_3$ | H | F | OH | H | H |
| XX-11-7 | $CH_3$ | H | H | $CH_2CH_2SCH_3$ | Et | $OCH_3$ | H | F | OH | H | H |
| XX-11-8 | $CH_3$ | * | H | * | Et | $OCH_3$ | H | F | OH | H | H |

*$R^2$ and $R^{3b}$ joined together by $(CH_2)_3$ to form five-membered ring.

TABLE XX-12

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-12-1 | Et | H | H | H | Et | $OCH_3$ | H | F | OH | H | H |
| XX-12-2 | Et | H | H | $CH_3$ | Et | $OCH_3$ | H | F | OH | H | H |
| XX-12-3 | Et | H | H | $CH(CH_3)_2$ | Et | $OCH_3$ | H | F | OH | H | H |
| XX-12-4 | Et | H | H | $CH_2CH(CH_3)_2$ | Et | $OCH_3$ | H | F | OH | H | H |
| XX-12-5 | Et | H | H | $CH_2Ph$ | Et | $OCH_3$ | H | F | OH | H | H |
| XX-12-6 | Et | H | H | $CH_2$-indol-3-yl | Et | $OCH_3$ | H | F | OH | H | H |
| XX-12-7 | Et | H | H | $CH_2CH_2SCH_3$ | Et | $OCH_3$ | H | F | OH | H | H |
| XX-12-8 | Et | * | H | * | Et | $OCH_3$ | H | F | OH | H | H |

*$R^2$ and $R^{3b}$ joined together by $(CH_2)_3$ to form five-membered ring.

TABLE XX-13

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-13-1 | $^i$Pr | H | H | H | Et | OCH$_3$ | H | F | OH | H | H |
| XX-13-2 | $^i$Pr | H | H | CH$_3$ | Et | OCH$_3$ | H | F | OH | H | H |
| XX-13-3 | $^i$Pr | H | H | CH(CH$_3$)$_2$ | Et | OCH$_3$ | H | F | OH | H | H |
| XX-13-4 | $^i$Pr | H | H | CH$_2$CH(CH$_3$)$_2$ | Et | OCH$_3$ | H | F | OH | H | H |
| XX-13-5 | $^i$Pr | H | H | CH$_2$Ph | Et | OCH$_3$ | H | F | OH | H | H |
| XX-13-6 | $^i$Pr | H | H | CH$_2$-indol-3-yl | Et | OCH$_3$ | H | F | OH | H | H |
| XX-13-7 | $^i$Pr | H | H | CH$_2$CH$_2$SCH$_3$ | Et | OCH$_3$ | H | F | OH | H | H |
| XX-13-8 | $^i$Pr | * | H | * | Et | OCH$_3$ | H | F | OH | H | H |

*R² and R³ᵇ joined together by (CH$_2$)$_3$ to form five-membered ring.

TABLE XX-14

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-14-1 | $^t$Bu | H | H | H | Et | OCH$_3$ | H | F | OH | H | H |
| XX-14-2 | $^t$Bu | H | H | CH$_3$ | Et | OCH$_3$ | H | F | OH | H | H |
| XX-14-3 | $^t$Bu | H | H | CH(CH$_3$)$_2$ | Et | OCH$_3$ | H | F | OH | H | H |
| XX-14-4 | $^t$Bu | H | H | CH$_2$CH(CH$_3$)$_2$ | Et | OCH$_3$ | H | F | OH | H | H |
| XX-14-5 | $^t$Bu | H | H | CH$_2$Ph | Et | OCH$_3$ | H | F | OH | H | H |
| XX-14-6 | $^t$Bu | H | H | CH$_2$-indol-3-yl | Et | OCH$_3$ | H | F | OH | H | H |
| XX-14-7 | $^t$Bu | H | H | CH$_2$CH$_2$SCH$_3$ | Et | OCH$_3$ | H | F | OH | H | H |
| XX-14-8 | $^t$Bu | * | H | * | Et | OCH$_3$ | H | F | OH | H | H |

*R² and R³ᵇ joined together by (CH$_2$)$_3$ to form five-membered ring.

TABLE XX-15

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-15-1 | Ph | H | H | H | Et | OCH$_3$ | H | F | OH | H | H |
| XX-15-2 | Ph | H | H | CH$_3$ | Et | OCH$_3$ | H | F | OH | H | H |
| XX-15-3 | Ph | H | H | CH(CH$_3$)$_2$ | Et | OCH$_3$ | H | F | OH | H | H |
| XX-15-4 | Ph | H | H | CH$_2$CH(CH$_3$)$_2$ | Et | OCH$_3$ | H | F | OH | H | H |
| XX-15-5 | Ph | H | H | CH$_2$Ph | Et | OCH$_3$ | H | F | OH | H | H |
| XX-15-6 | Ph | H | H | CH$_2$-indol-3-yl | Et | OCH$_3$ | H | F | OH | H | H |
| XX-15-7 | Ph | H | H | CH$_2$CH$_2$SCH$_3$ | Et | OCH$_3$ | H | F | OH | H | H |
| XX-15-8 | Ph | * | H | * | Et | OCH$_3$ | H | F | OH | H | H |

*R² and R³ᵇ joined together by (CH$_2$)$_3$ to form five-membered ring.

TABLE XX-16

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-16-1 | p-Me—Ph | H | H | H | Et | OCH$_3$ | H | F | OH | H | H |
| XX-16-2 | p-Me—Ph | H | H | CH$_3$ | Et | OCH$_3$ | H | F | OH | H | H |
| XX-16-3 | p-Me—Ph | H | H | CH(CH$_3$)$_2$ | Et | OCH$_3$ | H | F | OH | H | H |
| XX-16-4 | p-Me—Ph | H | H | CH$_2$CH(CH$_3$)$_2$ | Et | OCH$_3$ | H | F | OH | H | H |
| XX-16-5 | p-Me—Ph | H | H | CH$_2$Ph | Et | OCH$_3$ | H | F | OH | H | H |
| XX-16-6 | p-Me—Ph | H | H | CH$_2$-indol-3-yl | Et | OCH$_3$ | H | F | OH | H | H |
| XX-16-7 | p-Me—Ph | H | H | CH$_2$CH$_2$SCH$_3$ | Et | OCH$_3$ | H | F | OH | H | H |
| XX-16-8 | p-Me—Ph | * | H | * | Et | OCH$_3$ | H | F | OH | H | H |

*R² and R³ᵇ joined together by (CH$_2$)$_3$ to form five-membered ring.

TABLE XX-17

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-17-1 | p-F—Ph | H | H | H | Et | OCH$_3$ | H | F | OH | H | H |
| XX-17-2 | p-F—Ph | H | H | CH$_3$ | Et | OCH$_3$ | H | F | OH | H | H |
| XX-17-3 | p-F—Ph | H | H | CH(CH$_3$)$_2$ | Et | OCH$_3$ | H | F | OH | H | H |
| XX-17-4 | p-F—Ph | H | H | CH$_2$CH(CH$_3$)$_2$ | Et | OCH$_3$ | H | F | OH | H | H |
| XX-17-5 | p-F—Ph | H | H | CH$_2$Ph | Et | OCH$_3$ | H | F | OH | H | H |
| XX-17-6 | p-F—Ph | H | H | CH$_2$-indol-3-yl | Et | OCH$_3$ | H | F | OH | H | H |
| XX-17-7 | p-F—Ph | H | H | CH$_2$CH$_2$SCH$_3$ | Et | OCH$_3$ | H | F | OH | H | H |
| XX-17-8 | p-F—Ph | * | H | * | Et | OCH$_3$ | H | F | OH | H | H |

*R² and R³ᵇ joined together by (CH$_2$)$_3$ to form five-membered ring.

TABLE XX-18

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-18-1 | p-Cl—Ph | H | H | H | Et | OCH$_3$ | H | F | OH | H | H |
| XX-18-2 | p-Cl—Ph | H | H | CH$_3$ | Et | OCH$_3$ | H | F | OH | H | H |

TABLE XX-18-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-18-3 | p-Cl—Ph | H | H | CH(CH₃)₂ | Et | OCH₃ | H | F | OH | H | H |
| XX-18-4 | p-Cl—Ph | H | H | CH₂CH(CH₃)₂ | Et | OCH₃ | H | F | OH | H | H |
| XX-18-5 | p-Cl—Ph | H | H | CH₂Ph | Et | OCH₃ | H | F | OH | H | H |
| XX-18-6 | p-Cl—Ph | H | H | CH₂-indol-3-yl | Et | OCH₃ | H | F | OH | H | H |
| XX-18-7 | p-Cl—Ph | H | H | CH₂CH₂SCH₃ | Et | OCH₃ | H | F | OH | H | H |
| XX-18-8 | p-Cl—Ph | * | H | * | Et | OCH₃ | H | F | OH | H | H |

*R² and R³ᵇ joined together by (CH₂)₃ to form five-membered ring.

TABLE XX-19

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-19-1 | p-Br—Ph | H | H | H | Et | OCH₃ | H | F | OH | H | H |
| XX-19-2 | p-Br—Ph | H | H | CH₃ | Et | OCH₃ | H | F | OH | H | H |
| XX-19-3 | p-Br—Ph | H | H | CH(CH₃)₂ | Et | OCH₃ | H | F | OH | H | H |
| XX-19-4 | p-Br—Ph | H | H | CH₂CH(CH₃)₂ | Et | OCH₃ | H | F | OH | H | H |
| XX-19-5 | p-Br—Ph | H | H | CH₂Ph | Et | OCH₃ | H | F | OH | H | H |
| XX-19-6 | p-Br—Ph | H | H | CH₂-indol-3-yl | Et | OCH₃ | H | F | OH | H | H |
| XX-19-7 | p-Br—Ph | H | H | CH₂CH₂SCH₃ | Et | OCH₃ | H | F | OH | H | H |
| XX-19-8 | p-Br—Ph | * | H | * | Et | OCH₃ | H | F | OH | H | H |

*R² and R³ᵇ joined together by (CH₂)₃ to form five-membered ring.

TABLE XX-20

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-20-1 | p-I—Ph | H | H | H | Et | OCH₃ | H | F | OH | H | H |
| XX-20-2 | p-I—Ph | H | H | CH₃ | Et | OCH₃ | H | F | OH | H | H |
| XX-20-3 | p-I—Ph | H | H | CH(CH₃)₂ | Et | OCH₃ | H | F | OH | H | H |
| XX-20-4 | p-I—Ph | H | H | CH₂CH(CH₃)₂ | Et | OCH₃ | H | F | OH | H | H |
| XX-20-5 | p-I—Ph | H | H | CH₂Ph | Et | OCH₃ | H | F | OH | H | H |
| XX-20-6 | p-I—Ph | H | H | CH₂-indol-3-yl | Et | OCH₃ | H | F | OH | H | H |
| XX-20-7 | p-I—Ph | H | H | CH₂CH₂SCH₃ | Et | OCH₃ | H | F | OH | H | H |
| XX-20-8 | p-I—Ph | * | H | * | Et | OCH₃ | H | F | OH | H | H |

*R² and R³ᵇ joined together by (CH₂)₃ to form five-membered ring.

TABLE XX-21

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-21-1 | CH₃ | H | H | H | ⁱPr | OCH₃ | H | F | OH | H | H |
| XX-21-2 | CH₃ | H | H | CH₃ | ⁱPr | OCH₃ | H | F | OH | H | H |
| XX-21-3 | CH₃ | H | H | CH(CH₃)₂ | ⁱPr | OCH₃ | H | F | OH | H | H |
| XX-21-4 | CH₃ | H | H | CH₂CH(CH₃)₂ | ⁱPr | OCH₃ | H | F | OH | H | H |
| XX-21-5 | CH₃ | H | H | CH₂Ph | ⁱPr | OCH₃ | H | F | OH | H | H |
| XX-21-6 | CH₃ | H | H | CH₂-indol-3-yl | ⁱPr | OCH₃ | H | F | OH | H | H |
| XX-21-7 | CH₃ | H | H | CH₂CH₂SCH₃ | ⁱPr | OCH₃ | H | F | OH | H | H |
| XX-21-8 | CH₃ | * | H | * | ⁱPr | OCH₃ | H | F | OH | H | H |

*R² and R³ᵇ joined together by (CH₂)₃ to form five-membered ring.

TABLE XX-22

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-22-1 | Et | H | H | H | ⁱPr | OCH₃ | H | F | OH | H | H |
| XX-22-2 | Et | H | H | CH₃ | ⁱPr | OCH₃ | H | F | OH | H | H |
| XX-22-3 | Et | H | H | CH(CH₃)₂ | ⁱPr | OCH₃ | H | F | OH | H | H |
| XX-22-4 | Et | H | H | CH₂CH(CH₃)₂ | ⁱPr | OCH₃ | H | F | OH | H | H |
| XX-22-5 | Et | H | H | CH₂Ph | ⁱPr | OCH₃ | H | F | OH | H | H |
| XX-22-6 | Et | H | H | CH₂-indol-3-yl | ⁱPr | OCH₃ | H | F | OH | H | H |
| XX-22-7 | Et | H | H | CH₂CH₂SCH₃ | ⁱPr | OCH₃ | H | F | OH | H | H |
| XX-22-8 | Et | * | H | * | ⁱPr | OCH₃ | H | F | OH | H | H |

*R² and R³ᵇ joined together by (CH₂)₃ to form five-membered ring.

TABLE XX-23

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-23-1 | ⁱPr | H | H | H | ⁱPr | OCH₃ | H | F | OH | H | H |
| XX-23-2 | ⁱPr | H | H | CH₃ | ⁱPr | OCH₃ | H | F | OH | H | H |
| XX-23-3 | ⁱPr | H | H | CH(CH₃)₂ | ⁱPr | OCH₃ | H | F | OH | H | H |
| XX-23-4 | ⁱPr | H | H | CH₂CH(CH₃)₂ | ⁱPr | OCH₃ | H | F | OH | H | H |
| XX-23-5 | ⁱPr | H | H | CH₂Ph | ⁱPr | OCH₃ | H | F | OH | H | H |
| XX-23-6 | ⁱPr | H | H | CH₂-indol-3-yl | ⁱPr | OCH₃ | H | F | OH | H | H |
| XX-23-7 | ⁱPr | H | H | CH₂CH₂SCH₃ | ⁱPr | OCH₃ | H | F | OH | H | H |
| XX-23-8 | ⁱPr | * | H | * | ⁱPr | OCH₃ | H | F | OH | H | H |

*R² and R³ᵇ joined together by (CH₂)₃ to form five-membered ring.

TABLE XX-24

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-24-1 | ᵗBu | H | H | H | ⁱPr | OCH₃ | H | F | OH | H | H |
| XX-24-2 | ᵗBu | H | H | CH₃ | ⁱPr | OCH₃ | H | F | OH | H | H |
| XX-24-3 | ᵗBu | H | H | CH(CH₃)₂ | ⁱPr | OCH₃ | H | F | OH | H | H |
| XX-24-4 | ᵗBu | H | H | CH₂CH(CH₃)₂ | ⁱPr | OCH₃ | H | F | OH | H | H |
| XX-24-5 | ᵗBu | H | H | CH₂Ph | ⁱPr | OCH₃ | H | F | OH | H | H |
| XX-24-6 | ᵗBu | H | H | CH₂-indol-3-yl | ⁱPr | OCH₃ | H | F | OH | H | H |
| XX-24-7 | ᵗBu | H | H | CH₂CH₂SCH₃ | ⁱPr | OCH₃ | H | F | OH | H | H |
| XX-24-8 | ᵗBu | * | H | * | ⁱPr | OCH₃ | H | F | OH | H | H |

*R² and R³ᵇ joined together by (CH₂)₃ to form five-membered ring.

TABLE XX-25

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-25-1 | Ph | H | H | H | ⁱPr | OCH₃ | H | F | OH | H | H |
| XX-25-2 | Ph | H | H | CH₃ | ⁱPr | OCH₃ | H | F | OH | H | H |
| XX-25-3 | Ph | H | H | CH(CH₃)₂ | ⁱPr | OCH₃ | H | F | OH | H | H |
| XX-25-4 | Ph | H | H | CH₂CH(CH₃)₂ | ⁱPr | OCH₃ | H | F | OH | H | H |
| XX-25-5 | Ph | H | H | CH₂Ph | ⁱPr | OCH₃ | H | F | OH | H | H |
| XX-25-6 | Ph | H | H | CH₂-indol-3-yl | ⁱPr | OCH₃ | H | F | OH | H | H |
| XX-25-7 | Ph | H | H | CH₂CH₂SCH₃ | ⁱPr | OCH₃ | H | F | OH | H | H |
| XX-25-8 | Ph | * | H | * | ⁱPr | OCH₃ | H | F | OH | H | H |

*R² and R³ᵇ joined together by (CH₂)₃ to form five-membered ring.

TABLE XX-26

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-26-1 | p-Me—Ph | H | H | H | ⁱPr | OCH₃ | H | F | OH | H | H |
| XX-26-2 | p-Me—Ph | H | H | CH₃ | ⁱPr | OCH₃ | H | F | OH | H | H |
| XX-26-3 | p-Me—Ph | H | H | CH(CH₃)₂ | ⁱPr | OCH₃ | H | F | OH | H | H |
| XX-26-4 | p-Me—Ph | H | H | CH₂CH(CH₃)₂ | ⁱPr | OCH₃ | H | F | OH | H | H |
| XX-26-5 | p-Me—Ph | H | H | CH₂Ph | ⁱPr | OCH₃ | H | F | OH | H | H |
| XX-26-6 | p-Me—Ph | H | H | CH₂-indol-3-yl | ⁱPr | OCH₃ | H | F | OH | H | H |
| XX-26-7 | p-Me—Ph | H | H | CH₂CH₂SCH₃ | ⁱPr | OCH₃ | H | F | OH | H | H |
| XX-26-8 | p-Me—Ph | * | H | * | ⁱPr | OCH₃ | H | F | OH | H | H |

*R² and R³ᵇ joined together by (CH₂)₃ to form five-membered ring.

TABLE XX-27

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-27-1 | p-F—Ph | H | H | H | ⁱPr | OCH₃ | H | F | OH | H | H |
| XX-27-2 | p-F—Ph | H | H | CH₃ | ⁱPr | OCH₃ | H | F | OH | H | H |
| XX-27-3 | p-F—Ph | H | H | CH(CH₃)₂ | ⁱPr | OCH₃ | H | F | OH | H | H |
| XX-27-4 | p-F—Ph | H | H | CH₂CH(CH₃)₂ | ⁱPr | OCH₃ | H | F | OH | H | H |
| XX-27-5 | p-F—Ph | H | H | CH₂Ph | ⁱPr | OCH₃ | H | F | OH | H | H |
| XX-27-6 | p-F—Ph | H | H | CH₂-indol-3-yl | ⁱPr | OCH₃ | H | F | OH | H | H |
| XX-27-7 | p-F—Ph | H | H | CH₂CH₂SCH₃ | ⁱPr | OCH₃ | H | F | OH | H | H |
| XX-27-8 | p-F—Ph | * | H | * | ⁱPr | OCH₃ | H | F | OH | H | H |

*R² and R³ᵇ joined together by (CH₂)₃ to form five-membered ring.

TABLE XX-28

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-28-1 | p-Cl—Ph | H | H | H | ⁱPr | OCH₃ | H | F | OH | H | H |
| XX-28-2 | p-Cl—Ph | H | H | CH₃ | ⁱPr | OCH₃ | H | F | OH | H | H |
| XX-28-3 | p-Cl—Ph | H | H | CH(CH₃)₂ | ⁱPr | OCH₃ | H | F | OH | H | H |
| XX-28-4 | p-Cl—Ph | H | H | CH₂CH(CH₃)₂ | ⁱPr | OCH₃ | H | F | OH | H | H |
| XX-28-5 | p-Cl—Ph | H | H | CH₂Ph | ⁱPr | OCH₃ | H | F | OH | H | H |

TABLE XX-28-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-28-6 | p-Cl—Ph | H | H | CH$_2$-indol-3-yl | $^i$Pr | OCH$_3$ | H | F | OH | H | H |
| XX-28-7 | p-Cl—Ph | H | H | CH$_2$CH$_2$SCH$_3$ | $^i$Pr | OCH$_3$ | H | F | OH | H | H |
| XX-28-8 | p-Cl—Ph | * | H | * | $^i$Pr | OCH$_3$ | H | F | OH | H | H |

*R$^2$ and R$^{3b}$ joined together by (CH$_2$)$_3$ to form five-membered ring.

TABLE XX-29

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-29-1 | p-Br—Ph | H | H | H | $^i$Pr | OCH$_3$ | H | F | OH | H | H |
| XX-29-2 | p-Br—Ph | H | H | CH$_3$ | $^i$Pr | OCH | H | F | OH | H | H |
| XX-29-3 | p-Br—Ph | H | H | CH(CH$_3$)$_2$ | $^i$Pr | OCH$_3$ | H | F | OH | H | H |
| XX-29-4 | p-Br—Ph | H | H | CH$_2$CH(CH$_3$)$_2$ | $^i$Pr | OCH$_3$ | H | F | OH | H | H |
| XX-29-5 | p-Br—Ph | H | H | CH$_2$Ph | $^i$Pr | OCH$_3$ | H | F | OH | H | H |
| XX-29-6 | p-Br—Ph | H | H | CH$_2$-indol-3-yl | $^i$Pr | OCH$_3$ | H | F | OH | H | H |
| XX-29-7 | p-Br—Ph | H | H | CH$_2$CH$_2$SCH$_3$ | $^i$Pr | OCH$_3$ | H | F | OH | H | H |
| XX-29-8 | p-Br—Ph | * | H | * | $^i$Pr | OCH$_3$ | H | F | OH | H | H |

*R$^2$ and R$^{3b}$ joined together by (CH$_2$)$_3$ to form five-membered ring.

TABLE XX-30

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-30-1 | p-I—Ph | H | H | H | $^i$Pr | OCH$_3$ | H | F | OH | H | H |
| XX-30-2 | p-I—Ph | H | H | CH$_3$ | $^i$Pr | OCH$_3$ | H | F | OH | H | H |
| XX-30-3 | p-I—Ph | H | H | CH(CH$_3$)$_2$ | $^i$Pr | OCH$_3$ | H | F | OH | H | H |
| XX-30-4 | p-I—Ph | H | H | CH$_2$CH(CH$_3$)$_2$ | $^i$Pr | OCH$_3$ | H | F | OH | H | H |
| XX-30-5 | p-I—Ph | H | H | CH$_2$Ph | $^i$Pr | OCH$_3$ | H | F | OH | H | H |
| XX-30-6 | p-I—Ph | H | H | CH$_2$-indol-3-yl | $^i$Pr | OCH$_3$ | H | F | OH | H | H |
| XX-30-7 | p-I—Ph | H | H | CH$_2$CH$_2$SCH$_3$ | $^i$Pr | OCH$_3$ | H | F | OH | H | H |
| XX-30-8 | p-I—Ph | * | H | * | $^i$Pr | OCH$_3$ | H | F | OH | H | H |

*R$^2$ and R$^{3b}$ joined together by (CH$_2$)$_3$ to form five-membered ring.

TABLE XX-31

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-31-1 | CH$_3$ | H | H | H | $^n$Bu | OCH$_3$ | H | F | OH | H | H |
| XX-31-2 | CH$_3$ | H | H | CH$_3$ | $^n$Bu | OCH$_3$ | H | F | OH | H | H |
| XX-31-3 | CH$_3$ | H | H | CH(CH$_3$)$_2$ | $^n$Bu | OCH$_3$ | H | F | OH | H | H |
| XX-31-4 | CH$_3$ | H | H | CH$_2$CH(CH$_3$)$_2$ | $^n$Bu | OCH$_3$ | H | F | OH | H | H |
| XX-31-5 | CH$_3$ | H | H | CH$_2$Ph | $^n$Bu | OCH$_3$ | H | F | OH | H | H |
| XX-31-6 | CH$_3$ | H | H | CH$_2$-indol-3-yl | $^n$Bu | OCH$_3$ | H | F | OH | H | H |
| XX-31-7 | CH$_3$ | H | H | CH$_2$CH$_2$SCH$_3$ | $^n$Bu | OCH$_3$ | H | F | OH | H | H |
| XX-31-8 | CH$_3$ | * | H | * | $^n$Bu | OCH$_3$ | H | F | OH | H | H |

*R$^2$ and R$^{3b}$ joined together by (CH$_2$)$_3$ to form five-membered ring.

TABLE XX-32

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-32-1 | Et | H | H | H | $^n$Bu | OCH$_3$ | H | F | OH | H | H |
| XX-32-2 | Et | H | H | CH$_3$ | $^n$Bu | OCH$_3$ | H | F | OH | H | H |
| XX-32-3 | Et | H | H | CH(CH$_3$)$_2$ | $^n$Bu | OCH$_3$ | H | F | OH | H | H |
| XX-32-4 | Et | H | H | CH$_2$CH(CH$_3$)$_2$ | $^n$Bu | OCH$_3$ | H | F | OH | H | H |
| XX-32-5 | Et | H | H | CH$_2$Ph | $^n$Bu | OCH$_3$ | H | F | OH | H | H |
| XX-32-6 | Et | H | H | CH$_2$-indol-yl | $^n$Bu | OCH$_3$ | H | F | OH | H | H |
| XX-32-7 | Et | H | H | CH$_2$CH$_2$SCH$_3$ | $^n$Bu | OCH$_3$ | H | F | OH | H | H |
| XX-32-8 | Et | * | H | * | $^n$Bu | OCH$_3$ | H | F | OH | H | H |

*R$^2$ and R$^{3b}$ joined together by (CH$_2$)$_3$ to form five-membered ring.

TABLE XX-33

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-33-1 | $^i$Pr | H | H | H | $^n$Bu | OCH$_3$ | H | F | OH | H | H |
| XX-33-2 | $^i$Pr | H | H | CH$_3$ | $^n$Bu | OCH$_3$ | H | F | OH | H | H |
| XX-33-3 | $^i$Pr | H | H | CH(CH$_3$)$_2$ | $^n$Bu | OCH$_3$ | H | F | OH | H | H |
| XX-33-4 | $^i$Pr | H | H | CH$_2$CH(CH$_3$)$_2$ | $^n$Bu | OCH$_3$ | H | F | OH | H | H |
| XX-33-5 | $^i$Pr | H | H | CH$_2$Ph | $^n$Bu | OCH$_3$ | H | F | OH | H | H |
| XX-33-6 | $^i$Pr | H | H | CH$_2$-indol-3-yl | $^n$Bu | OCH$_3$ | H | F | OH | H | H |
| XX-33-7 | $^i$Pr | H | H | CH$_2$CH$_2$SCH$_3$ | $^n$Bu | OCH$_3$ | H | F | OH | H | H |
| XX-33-8 | $^i$Pr | * | H | * | $^n$Bu | OCH$_3$ | H | F | OH | H | H |

*R$^2$ and R$^{3b}$ joined together by (CH$_2$)$_3$ to form five-membered ring.

TABLE XX-34

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-34-1 | $^t$Bu | H | H | H | $^n$Bu | OCH$_3$ | H | F | OH | H | H |
| XX-34-2 | $^t$Bu | H | H | CH$_3$ | $^n$Bu | OCH$_3$ | H | F | OH | H | H |
| XX-34-3 | $^t$Bu | H | H | CH(CH$_3$)$_2$ | $^n$Bu | OCH$_3$ | H | F | OH | H | H |
| XX-34-4 | $^t$Bu | H | H | CH$_2$CH(CH$_3$)$_2$ | $^n$Bu | OCH$_3$ | H | F | OH | H | H |
| XX-34-5 | $^t$Bu | H | H | CH$_2$Ph | $^n$Bu | OCH$_3$ | H | F | OH | H | H |
| XX-34-6 | $^t$Bu | H | H | CH$_2$-indol-3-yl | $^n$Bu | OCH$_3$ | H | F | OH | H | H |
| XX-34-7 | $^t$Bu | H | H | CH$_2$CH$_2$SCH$_3$ | $^n$Bu | OCH$_3$ | H | F | OH | H | H |
| XX-34-8 | $^t$Bu | * | H | * | $^n$Bu | OCH$_3$ | H | F | OH | H | H |

*R$^2$ and R$^{3b}$ joined together by (CH$_2$)$_3$ to form five-membered ring.

TABLE XX-35

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-35-1 | Ph | H | H | H | $^n$Bu | OCH$_3$ | H | F | OH | H | H |
| XX-35-2 | Ph | H | H | CH$_3$ | $^n$Bu | OCH$_3$ | H | F | OH | H | H |
| XX-35-3 | Ph | H | H | CH(CH$_3$)$_2$ | $^t$Bu | OCH$_3$ | H | F | OH | H | H |
| XX-35-4 | Ph | H | H | CH$_2$CH(CH$_3$)$_2$ | $^n$Bu | OCH$_3$ | H | F | OH | H | H |
| XX-35-5 | Ph | H | H | CH$_2$Ph | $^n$Bu | OCH$_3$ | H | F | OH | H | H |
| XX-35-6 | Ph | H | H | CH$_2$-indol-3-yl | $^n$Bu | OCH$_3$ | H | F | OH | H | H |
| XX-35-7 | Ph | H | H | CH$_2$CH$_2$SCH$_3$ | $^n$Bu | OCH$_3$ | H | F | OH | H | H |
| XX-35-8 | Ph | * | H | * | $^n$Bu | OCH$_3$ | H | F | OH | H | H |

*R$^2$ and R$^{3b}$ joined together by (CH$_2$)$_3$ to form five-membered ring.

TABLE XX-36

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-36-1 | p-Me—Ph | H | H | H | $^n$Bu | OCH$_3$ | H | F | OH | H | H |
| XX-36-2 | p-Me—Ph | H | H | CH$_3$ | $^n$Bu | OCH$_3$ | H | F | OH | H | H |
| XX-36-3 | p-Me—Ph | H | H | CH(CH$_3$)$_2$ | $^n$Bu | OCH$_3$ | H | F | OH | H | H |
| XX-36-4 | p-Me—Ph | H | H | CH$_2$CH(CH$_3$)$_2$ | $^n$Bu | OCH$_3$ | H | F | OH | H | H |
| XX-36-5 | p-Me—Ph | H | H | CH$_2$Ph | $^n$Bu | OCH$_3$ | H | F | OH | H | H |
| XX-36-6 | p-Me—Ph | H | H | CH$_2$-indol-3-yl | $^n$Bu | OCH$_3$ | H | F | OH | H | H |
| XX-36-7 | p-Me—Ph | H | H | CH$_2$CH$_2$SCH$_3$ | $^n$Bu | OCH$_3$ | H | F | OH | H | H |
| XX-36-8 | p-Me—Ph | * | H | * | $^n$Bu | OCH$_3$ | H | F | OH | H | H |

*R$^2$ and R$^{3b}$ joined together by (CH$_2$)$_3$ to form five-membered ring.

TABLE XX-37

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-37-1 | p-F—Ph | H | H | H | $^n$Bu | OCH$_3$ | H | F | OH | H | H |
| XX-37-2 | p-F—Ph | H | H | CH$_3$ | $^n$Bu | OCH$_3$ | H | F | OH | H | H |
| XX-37-3 | p-F—Ph | H | H | CH(CH$_3$)$_2$ | $^n$Bu | OCH$_3$ | H | F | OH | H | H |
| XX-37-4 | p-F—Ph | H | H | CH$_2$CH(CH$_3$)$_2$ | $^n$Bu | OCH$_3$ | H | F | OH | H | H |
| XX-37-5 | p-F—Ph | H | H | CH$_2$Ph | $^n$Bu | OCH$_3$ | H | F | OH | H | H |
| XX-37-6 | p-F—Ph | H | H | CH$_2$-indol-3-yl | $^n$Bu | OCH$_3$ | H | F | OH | H | H |
| XX-37-7 | p-F—Ph | H | H | CH$_2$CH$_2$SCH$_3$ | $^n$Bu | OCH$_3$ | H | F | OH | H | H |
| XX-37-8 | p-F—Ph | * | H | * | $^n$Bu | OCH$_3$ | H | F | OH | H | H |

*R$^2$ and R$^{3b}$ joined together by (CH$_2$)$_3$ to form five-membered ring.

TABLE XX-38

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-38-1 | p-Cl—Ph | H | H | H | ⁿBu | OCH₃ | H | F | OH | H | H |
| XX-38-2 | p-Cl—Ph | H | H | CH₃ | ⁿBu | OCH₃ | H | F | OH | H | H |
| XX-38-3 | p-Cl—Ph | H | H | CH(CH₃)₂ | ⁿBu | OCH₃ | H | F | OH | H | H |
| XX-38-4 | p-Cl—Ph | H | H | CH₂CH(CH₃)₂ | ⁿBu | OCH₃ | H | F | OH | H | H |
| XX-38-5 | p-Cl—Ph | H | H | CH₂Ph | ⁿBu | OCH₃ | H | F | OH | H | H |
| XX-38-6 | p-Cl—Ph | H | H | CH₂-indol-3-yl | ⁿBu | OCH₃ | H | F | OH | H | H |
| XX-38-7 | p-Cl—Ph | H | H | CH₂CH₂SCH₃ | ⁿBu | OCH₃ | H | F | OH | H | H |
| XX-38-8 | p-Cl—Ph | * | H | * | ⁿBu | OCH₃ | H | F | OH | H | H |

*R² and R³ᵇ joined together by (CH₂)₃ to form five-membered ring.

TABLE XX-39

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-39-1 | p-Br—Ph | H | H | H | ⁿBu | OCH₃ | H | F | OH | H | H |
| XX-39-2 | p-Br—Ph | H | H | CH₃ | ⁿBu | OCH₃ | H | F | OH | H | H |
| XX-39-3 | p-Br—Ph | H | H | CH(CH₃)₂ | ⁿBu | OCH₃ | H | F | OH | H | H |
| XX-39-4 | p-Br—Ph | H | H | CH₂CH(CH₃)₂ | ⁿBu | OCH₃ | H | F | OH | H | H |
| XX-39-5 | p-Br—Ph | H | H | CH₂Ph | ⁿBu | OCH₃ | H | F | OH | H | H |
| XX-39-6 | p-Br—Ph | H | H | CH₂-indol-3-yl | ⁿBu | OCH₃ | H | F | OH | H | H |
| XX-39-7 | p-Br—Ph | H | H | CH₂CH₂SCH₃ | ⁿBu | OCH₃ | H | F | OH | H | H |
| XX-39-8 | p-Br—Ph | * | H | * | ⁿBu | OCH₃ | H | F | OH | H | H |

*R² and R³ᵇ joined together by (CH₂)₃ to form five-membered ring.

TABLE XX-40

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-40-1 | p-I—Ph | H | H | H | ⁿBu | OCH₃ | H | F | OH | H | H |
| XX-40-2 | p-I—Ph | H | H | CH₃ | ⁿBu | OCH₃ | H | F | OH | H | H |
| XX-40-3 | p-I—Ph | H | H | CH(CH₃)₂ | ⁿBu | OCH₃ | H | F | OH | H | H |
| XX-40-4 | p-I—Ph | H | H | CH₂CH(CH₃)₂ | ⁿBu | OCH₃ | H | F | OH | H | H |
| XX-40-5 | p-I—Ph | H | H | CH₂Ph | ⁿBu | OCH₃ | H | F | OH | H | H |
| XX-40-6 | p-I—Ph | H | H | CH₂-indol-3-yl | ⁿBu | OCH₃ | H | F | OH | H | H |
| XX-40-7 | p-I—Ph | H | H | CH₂CH₂SCH₃ | ⁿBu | OCH₃ | H | F | OH | H | H |
| XX-40-8 | p-I—Ph | * | H | * | ⁿBu | OCH₃ | H | F | OH | H | H |

*R² and R³ᵇ joined together by (CH₂)₃ to form five-membered ring.

TABLE XX-41

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-41-1 | CH₃ | H | H | H | Bz | OCH₃ | H | F | OH | H | H |
| XX-41-2 | CH₃ | H | H | CH₃ | Bz | OCH₃ | H | F | OH | H | H |

TABLE XX-41-continued

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-41-3 | $CH_3$ | H | H | $CH(CH_3)_2$ | Bz | $OCH_3$ | H | F | OH | H | H |
| XX-41-4 | $CH_3$ | H | H | $CH_2CH(CH_3)_2$ | Bz | $OCH_3$ | H | F | OH | H | H |
| XX-41-5 | $CH_3$ | H | H | $CH_2Ph$ | Bz | $OCH_3$ | H | F | OH | H | H |
| XX-41-6 | $CH_3$ | H | H | $CH_2$-indol-3-yl | Bz | $OCH_3$ | H | F | OH | H | H |
| XX-41-7 | $CH_3$ | H | H | $CH_2CH_2SCH_3$ | Bz | $OCH_3$ | H | F | OH | H | H |
| XX-41-8 | $CH_3$ | * | H | * | Bz | $OCH_3$ | H | F | OH | H | H |

*$R^2$ and $R^{3b}$ joined together by $(CH_2)_3$ to form five-membered ring.

TABLE XX-42

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-42-1 | Et | H | H | H | Bz | $OCH_3$ | H | F | OH | H | H |
| XX-42-2 | Et | H | H | $CH_3$ | Bz | $OCH_3$ | H | F | OH | H | H |
| XX-42-3 | Et | H | H | $CH(CH_3)_2$ | Bz | $OCH_3$ | H | F | OH | H | H |
| XX-42-4 | Et | H | H | $CH_2CH(CH_3)_2$ | Bz | $OCH_3$ | H | F | OH | H | H |
| XX-42-5 | Et | H | H | $CH_2Ph$ | Bz | $OCH_3$ | H | F | OH | H | H |
| XX-42-6 | Et | H | H | $CH_2$-indol-3-yl | Bz | $OCH_3$ | H | F | OH | H | H |
| XX-42-7 | Et | H | H | $CH_2CH_2SCH_3$ | Bz | $OCH_3$ | H | F | OH | H | H |
| XX-42-8 | Et | * | H | * | Bz | $OCH_3$ | H | F | OH | H | H |

*$R^2$ and $R^{3b}$ joined together by $(CH_2)_3$ to form five-membered ring.

TABLE XX-43

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-43-1 | $^iPr$ | H | H | H | Bz | $OCH_3$ | H | F | OH | H | H |
| XX-43-2 | $^iPr$ | H | H | $CH_3$ | Bz | $OCH_3$ | H | F | OH | H | H |
| XX-43-3 | $^iPr$ | H | H | $CH(CH_3)_2$ | Bz | $OCH_3$ | H | F | OH | H | H |
| XX-43-4 | $^iPr$ | H | H | $CH_2CH(CH_3)_2$ | Bz | $OCH_3$ | H | F | OH | H | H |
| XX-43-5 | $^iPr$ | H | H | $CH_2Ph$ | Bz | $OCH_3$ | H | F | OH | H | H |
| XX-43-6 | $^iPr$ | H | H | $CH_2$-indol-3-yl | Bz | $OCH_3$ | H | F | OH | H | H |
| XX-43-7 | $^iPr$ | H | H | $CH_2CH_2SCH_3$ | Bz | $OCH_3$ | H | F | OH | H | H |
| XX-43-8 | $^iPr$ | * | H | * | Bz | $OCH_3$ | H | F | OH | H | H |

*$R^2$ and $R^{3b}$ joined together by $(CH_2)_3$ to form five-membered ring.

TABLE XX-44

| No | $R^1$ | $R^2$ | $R^{3a}$ | $R^{3b}$ | $R^4$ | $R^5$ | $R^6$ | X | Y | $R^7$ | $R^8$ |
|---|---|---|---|---|---|---|---|---|---|---|---|
| XX-44-1 | $^tBu$ | H | H | H | Bz | $OCH_3$ | H | F | OH | H | H |
| XX-44-2 | $^tBu$ | H | H | $CH_3$ | Bz | $OCH_3$ | H | F | OH | H | H |

TABLE XX-44-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-44-3 | ᵗBu | H | H | CH(CH₃)₂ | Bz | OCH₃ | H | F | OH | H | H |
| XX-44-4 | ᵗBu | H | H | CH₂CH(CH₃)₂ | Bz | OCH₃ | H | F | OH | H | H |
| XX-44-5 | ᵗBu | H | H | CH₂Ph | Bz | OCH₃ | H | F | OH | H | H |
| XX-44-6 | ᵗBu | H | H | CH₂-indol-3-yl | Bz | OCH₃ | H | F | OH | H | H |
| XX-44-7 | ᵗBu | H | H | CH₂CH₂SCH₃ | Bz | OCH₃ | H | F | OH | H | H |
| XX-44-8 | ᵗBu | * | H | * | Bz | OCH₃ | H | F | OH | H | H |

*R² and R³ᵇ joined together by (CH₂)₃ to form five-membered ring.

TABLE XX-45

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-45-1 | Ph | H | H | H | Bz | OCH₃ | H | F | OH | H | H |
| XX-45-2 | Ph | H | H | CH₃ | Bz | OCH₃ | H | F | OH | H | H |
| XX-45-3 | Ph | H | H | CH(CH₃)₂ | Bz | OCH₃ | H | F | OH | H | H |
| XX-45-4 | Ph | H | H | CH₂CH(CH₃)₂ | Bz | OCH₃ | H | F | OH | H | H |
| XX-45-5 | Ph | H | H | CH₂Ph | Bz | OCH₃ | H | F | OH | H | H |
| XX-45-6 | Ph | H | H | CH₂-indol-3-yl | Bz | OCH₃ | H | F | OH | H | H |
| XX-45-7 | Ph | H | H | CH₂CH₂SCH₃ | Bz | OCH₃ | H | F | OH | H | H |
| XX-45-8 | Ph | * | H | * | Bz | OCH₃ | H | F | OH | H | H |

*R² and R³ᵇ joined together by (CH₂)₃ to form five-membered ring.

TABLE XX-46

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-46-1 | p-Me—Ph | H | H | H | Bz | OCH₃ | H | F | OH | H | H |
| XX-46-2 | p-Me—Ph | H | H | CH₃ | Bz | OCH₃ | H | F | OH | H | H |
| XX-46-3 | p-Me—Ph | H | H | CH(CH₃)₂ | Bz | OCH₃ | H | F | OH | H | H |
| XX-46-4 | p-Me—Ph | H | H | CH₂CH(CH₃)₂ | Bz | OCH₃ | H | F | OH | H | H |
| XX-46-5 | p-Me—Ph | H | H | CH₂Ph | Bz | OCH₃ | H | F | OH | H | H |
| XX-46-6 | p-Me—Ph | H | H | CH₂-indol-3-yl | Bz | OCH₃ | H | F | OH | H | H |
| XX-46-7 | p-Me—Ph | H | H | CH₂CH₂SCH₃ | Bz | OCH₃ | H | F | OH | H | H |
| XX-46-8 | p-Me—Ph | * | H | * | Bz | OCH₃ | H | F | OH | H | H |

*R² and R³ᵇ joined together by (CH₂)₃ to form five-membered ring.

TABLE XX-47

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-47-1 | p-F—Ph | H | H | H | Bz | OCH₃ | H | F | OH | H | H |
| XX-47-2 | p-F—Ph | H | H | CH₃ | Bz | OCH₃ | H | F | OH | H | H |

TABLE XX-47-continued

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-47-3 | p-F—Ph | H | H | CH(CH$_3$)$_2$ | Bz | OCH$_3$ | H | F | OH | H | H |
| XX-47-4 | p-F—Ph | H | H | CH$_2$CH(CH$_3$)$_2$ | Bz | OCH$_3$ | H | F | OH | H | H |
| XX-47-5 | p-F—Ph | H | H | CH$_2$Ph | Bz | OCH$_3$ | H | F | OH | H | H |
| XX-47-6 | p-F—Ph | H | H | CH$_2$-indol-3-yl | Bz | OCH$_3$ | H | F | OH | H | H |
| XX-47-7 | p-F—Ph | H | H | CH$_2$CH$_2$SCH$_3$ | Bz | OCH$_3$ | H | F | OH | H | H |
| XX-47-8 | p-F—Ph | * | H | * | Bz | OCH$_3$ | H | F | OH | H | H |

*R$^2$ and R$^{3b}$ joined together by (CH$_2$)$_3$ to form five-membered ring.

TABLE XX-48

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-48-1 | p-Cl—Ph | H | H | H | Bz | OCH$_3$ | H | F | OH | H | H |
| XX-48-2 | p-Cl—Ph | H | H | CH$_3$ | Bz | OCH$_3$ | H | F | OH | H | H |
| XX-48-3 | p-Cl—Ph | H | H | CH(CH$_3$)$_2$ | Bz | OCH$_3$ | H | F | OH | H | H |
| XX-48-4 | p-Cl—Ph | H | H | CH$_2$CH(CH$_3$)$_2$ | Bz | OCH$_3$ | H | F | OH | H | H |
| XX-48-5 | p-Cl—Ph | H | H | CH$_2$Ph | Bz | OCH$_3$ | H | F | OH | H | H |
| XX-48-6 | p-Cl—Ph | H | H | CH$_2$-indol-3-yl | Bz | OCH$_3$ | H | F | OH | H | H |
| XX-48-7 | p-Cl—Ph | H | H | CH$_2$CH$_2$SCH$_3$ | Bz | OCH$_3$ | H | F | OH | H | H |
| XX-48-8 | p-Cl—Ph | * | H | * | Bz | OCH$_3$ | H | F | OH | H | H |

*R$^2$ and R$^{3b}$ joined together by (CH$_2$)$_3$ to form five-membered ring.

TABLE XX-49

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-49-1 | p-Br—Ph | H | H | H | Bz | OCH$_3$ | H | F | OH | H | H |
| XX-49-2 | p-Br—Ph | H | H | CH$_3$ | Bz | OCH$_3$ | H | F | OH | H | H |
| XX-49-3 | p-Br—Ph | H | H | CH(CH$_3$)$_2$ | Bz | OCH$_3$ | H | F | OH | H | H |
| XX-49-4 | p-Br—Ph | H | H | CH$_2$CH(CH$_3$)$_2$ | Bz | OCH$_3$ | H | F | OH | H | H |
| XX-49-5 | p-Br—Ph | H | H | CH$_2$Ph | Bz | OCH$_3$ | H | F | OH | H | H |
| XX-49-6 | p-Br—Ph | H | H | CH$_2$-indol-3-yl | Bz | OCH$_3$ | H | F | OH | H | H |
| XX-49-7 | p-Br—Ph | H | H | CH$_2$CH$_2$SCH$_3$ | Bz | OCH$_3$ | H | F | OH | H | H |
| XX-49-8 | p-Br—Ph | * | H | * | Bz | OCH$_3$ | H | F | OH | H | H |

*R$^2$ and R$^{3b}$ joined together by (CH$_2$)$_3$ to form five-membered ring.

TABLE XX-50

| No | R$^1$ | R$^2$ | R$^{3a}$ | R$^{3b}$ | R$^4$ | R$^5$ | R$^6$ | X | Y | R$^7$ | R$^8$ |
|---|---|---|---|---|---|---|---|---|---|---|---|
| XX-50-1 | p-I—Ph | H | H | H | Bz | OCH$_3$ | H | F | OH | H | H |

TABLE XX-50-continued

| No | R¹ | R² | R³ᵃ | R³ᵇ | R⁴ | R⁵ | R⁶ | X | Y | R⁷ | R⁸ |
|---|---|---|---|---|---|---|---|---|---|---|---|
| XX-50-2 | p-I—Ph | H | H | $CH_3$ | Bz | $OCH_3$ | H | F | OH | H | H |
| XX-50-3 | p-I—Ph | H | H | $CH(CH_3)_2$ | Bz | $OCH_3$ | H | F | OH | H | H |
| XX-50-4 | p-I—Ph | H | H | $CH_2CH(CH_3)_2$ | Bz | $OCH_3$ | H | F | OH | H | H |
| XX-50-5 | p-I—Ph | H | H | $CH_2Ph$ | Bz | $OCH_3$ | H | F | OH | H | H |
| XX-50-6 | p-I—Ph | H | H | $CH_2$-indol-3-yl | Bz | $OCH_3$ | H | F | OH | H | H |
| XX-50-7 | p-I—Ph | H | H | $CH_2CH_2SCH_3$ | Bz | $OCH_3$ | H | F | OH | H | H |
| XX-50-8 | p-I—Ph | * | H | * | Bz | $OCH_3$ | H | F | OH | H | H |

*R² and R³ᵇ joined together by $(CH_2)_3$ to form five-membered ring.

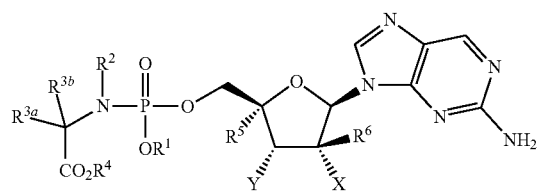

XXI

TABLE XXI-1

| No | R¹ | R² | R³ᵃ | R³ᵇ | R⁴ | R⁵ | R⁶ | X | Y |
|---|---|---|---|---|---|---|---|---|---|
| XXI-1-1 | $CH_3$ | H | H | H | $CH_3$ | H | $CH_3$ | F | OH |
| XXI-1-2 | $CH_3$ | H | H | $CH_3$ | $CH_3$ | H | $CH_3$ | F | OH |
| XXI-1-3 | $CH_3$ | H | H | $CH(CH_3)_2$ | $CH_3$ | H | $CH_3$ | F | OH |
| XXI-1-4 | $CH_3$ | H | H | $CH_2CH(CH_3)_2$ | $CH_3$ | H | $CH_3$ | F | OH |
| XXI-1-5 | $CH_3$ | H | H | $CH_2Ph$ | $CH_3$ | H | $CH_3$ | F | OH |
| XXI-1-6 | $CH_3$ | H | H | $CH_2$-indol-3-yl | $CH_3$ | H | $CH_3$ | F | OH |
| XXI-1-7 | $CH_3$ | H | H | $CH_2CH_2SCH_3$ | $CH_3$ | H | $CH_3$ | F | OH |
| XXI-1-8 | $CH_3$ | * | H | * | $CH_3$ | H | $CH_3$ | F | OH |

*R² and R³ᵇ joined together by $(CH_2)_3$ to form five-membered ring.

TABLE XXI-2

| No | R¹ | R² | R³ᵃ | R³ᵇ | R⁴ | R⁵ | R⁶ | X | Y |
|---|---|---|---|---|---|---|---|---|---|
| XXI-2-1 | Et | H | H | H | $CH_3$ | H | $CH_3$ | F | OH |
| XXI-2-2 | Et | H | H | $CH_3$ | $CH_3$ | H | $CH_3$ | F | OH |
| XXI-2-3 | Et | H | H | $CH(CH_3)_2$ | $CH_3$ | H | $CH_3$ | F | OH |
| XXI-2-4 | Et | H | H | $CH_2CH(CH_3)_2$ | $CH_3$ | H | $CH_3$ | F | OH |
| XXI-2-5 | Et | H | H | $CH_2Ph$ | $CH_3$ | H | $CH_3$ | F | OH |
| XXI-2-6 | Et | H | H | $CH_2$-indol-3-yl | $CH_3$ | H | $CH_3$ | F | OH |
| XXI-2-7 | Et | H | H | $CH_2CH_2SCH_3$ | $CH_3$ | H | $CH_3$ | F | OH |
| XXI-2-8 | Et | * | H | * | $CH_3$ | H | $CH_3$ | F | OH |

*R² and R³ᵇ joined together by $(CH_2)_3$ to form five-membered ring.

TABLE XXI-3

| No | R¹ | R² | R³ᵃ | R³ᵇ | R⁴ | R⁵ | R⁶ | X | Y |
|---|---|---|---|---|---|---|---|---|---|
| XXI-3-1 | ⁱPr | H | H | H | $CH_3$ | H | $CH_3$ | F | OH |
| XXI-3-2 | ⁱPr | H | H | $CH_3$ | $CH_3$ | H | $CH_3$ | F | OH |
| XXI-3-3 | ⁱPr | H | H | $CH(CH_3)_2$ | $CH_3$ | H | $CH_3$ | F | OH |
| XXI-3-4 | ⁱPr | H | H | $CH_2CH(CH_3)_2$ | $CH_3$ | H | $CH_3$ | F | OH |
| XXI-3-5 | ⁱPr | H | H | $CH_2Ph$ | $CH_3$ | H | $CH_3$ | F | OH |
| XXI-3-6 | ⁱPr | H | H | $CH_2$-indol-3-yl | $CH_3$ | H | $CH_3$ | F | OH |
| XXI-3-7 | ⁱPr | H | H | $CH_2CH_2SCH_3$ | $CH_3$ | H | $CH_3$ | F | OH |
| XXI-3-8 | ⁱPr | * | H | * | $CH_3$ | H | $CH_3$ | F | OH |

*R² and R³ᵇ joined together by $(CH_2)_3$ to form five-membered ring.

TABLE XXI-4

| No | R¹ | R² | R³ᵃ | R³ᵇ | R⁴ | R⁵ | R⁶ | X | Y |
|---|---|---|---|---|---|---|---|---|---|
| XXI-4-1 | ᵗBu | H | H | H | $CH_3$ | H | $CH_3$ | F | OH |
| XXI-4-2 | ᵗBu | H | H | $CH_3$ | $CH_3$ | H | $CH_3$ | F | OH |
| XXI-4-3 | ᵗBu | H | H | $CH(CH_3)_2$ | $CH_3$ | H | $CH_3$ | F | OH |
| XXI-4-4 | ᵗBu | H | H | $CH_2CH(CH_3)_2$ | $CH_3$ | H | $CH_3$ | F | OH |
| XXI-4-5 | ᵗBu | H | H | $CH_2Ph$ | $CH_3$ | H | $CH_3$ | F | OH |
| XXI-4-6 | ᵗBu | H | H | $CH_2$-indol-3-yl | $CH_3$ | H | $CH_3$ | F | OH |
| XXI-4-7 | ᵗBu | H | H | $CH_2CH_2SCH_3$ | $CH_3$ | H | $CH_3$ | F | OH |
| XXI-4-8 | ᵗBu | * | H | * | $CH_3$ | H | $CH_3$ | F | OH |

*R² and R³ᵇ joined together by $(CH_2)_3$ to form five-membered ring.

TABLE XXI-5

| No | R¹ | R² | R³ᵃ | R³ᵇ | R⁴ | R⁵ | R⁶ | X | Y |
|---|---|---|---|---|---|---|---|---|---|
| XXI-5-1 | Ph | H | H | H | $CH_3$ | H | $CH_3$ | F | OH |
| XXI-5-2 | Ph | H | H | $CH_3$ | $CH_3$ | H | $CH_3$ | F | OH |
| XXI-5-3 | Ph | H | H | $CH(CH_3)_2$ | $CH_3$ | H | $CH_3$ | F | OH |
| XXI-5-4 | Ph | H | H | $CH_2CH(CH_3)_2$ | $CH_3$ | H | $CH_3$ | F | OH |
| XXI-5-5 | Ph | H | H | $CH_2Ph$ | $CH_3$ | H | $CH_3$ | F | OH |
| XXI-5-6 | Ph | H | H | $CH_2$-indol-3-yl | $CH_3$ | H | $CH_3$ | F | OH |
| XXI-5-7 | Ph | H | H | $CH_2CH_2SCH_3$ | $CH_3$ | H | $CH_3$ | F | OH |
| XXI-5-8 | Ph | * | H | * | $CH_3$ | H | $CH_3$ | F | OH |

*R² and R³ᵇ joined together by $(CH_2)_3$ to form five-membered ring.

TABLE XXI-6

| No | R¹ | R² | R³ᵃ | R³ᵇ | R⁴ | R⁵ | R⁶ | X | Y |
|---|---|---|---|---|---|---|---|---|---|
| XXI-6-1 | p-Me—Ph | H | H | H | $CH_3$ | H | $CH_3$ | F | OH |
| XXI-6-2 | p-Me—Ph | H | H | $CH_3$ | $CH_3$ | H | $CH_3$ | F | OH |
| XXI-6-3 | p-Me—Ph | H | H | $CH(CH_3)_2$ | $CH_3$ | H | $CH_3$ | F | OH |
| XXI-6-4 | p-Me—Ph | H | H | $CH_2CH(CH_3)_2$ | $CH_3$ | H | $CH_3$ | F | OH |
| XXI-6-5 | p-Me—Ph | H | H | $CH_2Ph$ | $CH_3$ | H | $CH_3$ | F | OH |
| XXI-6-6 | p-Me—Ph | H | H | $CH_2$-indol-3-yl | $CH_3$ | H | $CH_3$ | F | OH |

TABLE XXI-6-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-6-7 | p-Me—Ph | H | H | $CH_2CH_2SCH_3$ | $CH_3$ | H | $CH_3$ | F | OH |
| XXI-6-8 | p-Me—Ph | * | H | * | $CH_3$ | H | $CH_3$ | F | OH |

*$R^2$ and $R^{3b}$ joined together by $(CH_2)_3$ to form five-membered ring.

TABLE XXI-7

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-7-1 | p-F—Ph | H | H | H | $CH_3$ | H | $CH_3$ | F | OH |
| XXI-7-2 | p-F—Ph | H | H | $CH_3$ | $CH_3$ | H | $CH_3$ | F | OH |
| XXI-7-3 | p-F—Ph | H | H | $CH(CH_3)_2$ | $CH_3$ | H | $CH_3$ | F | OH |
| XXI-7-4 | p-F—Ph | H | H | $CH_2CH(CH_3)_2$ | $CH_3$ | H | $CH_3$ | F | OH |
| XXI-7-5 | p-F—Ph | H | H | $CH_2Ph$ | $CH_3$ | H | $CH_3$ | F | OH |
| XXI-7-6 | p-F—Ph | H | H | $CH_2$-indol-3-yl | $CH_3$ | H | $CH_3$ | F | OH |
| XXI-7-7 | p-F—Ph | H | H | $CH_2CH_2SCH_3$ | $CH_3$ | H | $CH_3$ | F | OH |
| XXI-7-8 | p-F—Ph | * | H | * | $CH_3$ | H | $CH_3$ | F | OH |

*$R^2$ and $R^{3b}$ joined together by $(CH_2)_3$ to form five-membered ring.

TABLE XXI-8

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-8-1 | p-Cl—Ph | H | H | H | $CH_3$ | H | $CH_3$ | F | OH |
| XXI-8-2 | p-Cl—Ph | H | H | $CH_3$ | $CH_3$ | H | $CH_3$ | F | OH |
| XXI-8-3 | p-Cl—Ph | H | H | $CH(CH_3)_2$ | $CH_3$ | H | $CH_3$ | F | OH |
| XXI-8-4 | p-Cl—Ph | H | H | $CH_2CH(CH_3)_2$ | $CH_3$ | H | $CH_3$ | F | OH |
| XXI-8-5 | p-Cl—Ph | H | H | $CH_2Ph$ | $CH_3$ | H | $CH_3$ | F | OH |
| XXI-8-6 | p-Cl—Ph | H | H | $CH_2$-indol-3-yl | $CH_3$ | H | $CH_3$ | F | OH |
| XXI-8-7 | p-Cl—Ph | H | H | $CH_2CH_2SCH_3$ | $CH_3$ | H | $CH_3$ | F | OH |
| XXI-8-8 | p-Cl—Ph | * | H | * | $CH_3$ | H | $CH_3$ | F | OH |

*$R^2$ and $R^{3b}$ joined together by $(CH_2)_3$ to form five-membered ring.

TABLE XXI-9

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-9-1 | p-Br—Ph | H | H | H | $CH_3$ | H | $CH_3$ | F | OH |
| XXI-9-2 | p-Br—Ph | H | H | $CH_3$ | $CH_3$ | H | $CH_3$ | F | OH |
| XXI-9-3 | p-Br—Ph | H | H | $CH(CH_3)_2$ | $CH_3$ | H | $CH_3$ | F | OH |
| XXI-9-4 | p-Br—Ph | H | H | $CH_2CH(CH_3)_2$ | $CH_3$ | H | $CH_3$ | F | OH |
| XXI-9-5 | p-Br—Ph | H | H | $CH_2Ph$ | $CH_3$ | H | $CH_3$ | F | OH |
| XXI-9-6 | p-Br—Ph | H | H | $CH_2$-indol-3-yl | $CH_3$ | H | $CH_3$ | F | OH |
| XXI-9-7 | p-Br—Ph | H | H | $CH_2CH_2SCH_3$ | $CH_3$ | H | $CH_3$ | F | OH |
| XXI-9-8 | p-Br—Ph | * | H | * | $CH_3$ | H | $CH_3$ | F | OH |

*$R^2$ and $R^{3b}$ joined together by $(CH_2)_3$ to form five-membered ring.

TABLE XXI-10

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-10-1 | p-I—Ph | H | H | H | $CH_3$ | H | $CH_3$ | F | OH |
| XXI-10-2 | p-I—Ph | H | H | $CH_3$ | $CH_3$ | H | $CH_3$ | F | OH |
| XXI-10-3 | p-I—Ph | H | H | $CH(CH_3)_2$ | $CH_3$ | H | $CH_3$ | F | OH |
| XXI-10-4 | p-I—Ph | H | H | $CH_2CH(CH_3)_2$ | $CH_3$ | H | $CH_3$ | F | OH |
| XXI-10-5 | p-I—Ph | H | H | $CH_2Ph$ | $CH_3$ | H | $CH_3$ | F | OH |
| XXI-10-6 | p-I—Ph | H | H | $CH_2$-indol-3-yl | $CH_3$ | H | $CH_3$ | F | OH |
| XXI-10-7 | p-I—Ph | H | H | $CH_2CH_2SCH_3$ | $CH_3$ | H | $CH_3$ | F | OH |
| XXI-10-8 | p-I—Ph | * | H | * | $CH_3$ | H | $CH_3$ | F | OH |

*$R^2$ and $R^{3b}$ joined together by $(CH_2)_3$ to form five-membered ring.

TABLE XXI-11

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-11-1 | $CH_3$ | H | H | H | Et | H | $CH_3$ | F | OH |
| XXI-11-2 | $CH_3$ | H | H | $CH_3$ | Et | H | $CH_3$ | F | OH |
| XXI-11-3 | $CH_3$ | H | H | $CH(CH_3)_2$ | Et | H | $CH_3$ | F | OH |
| XXI-11-4 | $CH_3$ | H | H | $CH_2CH(CH_3)_2$ | Et | H | $CH_3$ | F | OH |
| XXI-11-5 | $CH_3$ | H | H | $CH_2Ph$ | Et | H | $CH_3$ | F | OH |
| XXI-11-6 | $CH_3$ | H | H | $CH_2$-indol-3-yl | Et | H | $CH_3$ | F | OH |
| XXI-11-7 | $CH_3$ | H | H | $CH_2CH_2SCH_3$ | Et | H | $CH_3$ | F | OH |
| XXI-11-8 | $CH_3$ | * | H | * | Et | H | $CH_3$ | F | OH |

*$R^2$ and $R^{3b}$ joined together by $(CH_2)_3$ to form five-membered ring.

TABLE XXI-12

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-12-1 | Et | H | H | H | Et | H | $CH_3$ | F | OH |
| XXI-12-2 | Et | H | H | $CH_3$ | Et | H | $CH_3$ | F | OH |
| XXI-12-3 | Et | H | H | $CH(CH_3)_2$ | Et | H | $CH_3$ | F | OH |
| XXI-12-4 | Et | H | H | $CH_2CH(CH_3)_2$ | Et | H | $CH_3$ | F | OH |
| XXI-12-5 | Et | H | H | $CH_2Ph$ | Et | H | $CH_3$ | F | OH |
| XXI-12-6 | Et | H | H | $CH_2$-indol-3-yl | Et | H | $CH_3$ | F | OH |
| XXI-12-7 | Et | H | H | $CH_2CH_2SCH_3$ | Et | H | $CH_3$ | F | OH |
| XXI-12-8 | Et | * | H | * | Et | H | $CH_3$ | F | OH |

*$R^2$ and $R^{3b}$ joined together by $(CH_2)_3$ to form five-membered ring.

TABLE XXI-13

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-13-1 | $^i$Pr | H | H | H | Et | H | $CH_3$ | F | OH |
| XXI-13-2 | $^i$Pr | H | H | $CH_3$ | Et | H | $CH_3$ | F | OH |
| XXI-13-3 | $^i$Pr | H | H | $CH(CH_3)_2$ | Et | H | $CH_3$ | F | OH |
| XXI-13-4 | $^i$Pr | H | H | $CH_2CH(CH_3)_2$ | Et | H | $CH_3$ | F | OH |
| XXI-13-5 | $^i$Pr | H | H | $CH_2Ph$ | Et | H | $CH_3$ | F | OH |
| XXI-13-6 | $^i$Pr | H | H | $CH_2$-indol-3-yl | Et | H | $CH_3$ | F | OH |
| XXI-13-7 | $^i$Pr | H | H | $CH_2CH_2SCH_3$ | Et | H | $CH_3$ | F | OH |
| XXI-13-8 | $^i$Pr | * | H | * | Et | H | $CH_3$ | F | OH |

*$R^2$ and $R^{3b}$ joined together by $(CH_2)_3$ to form five-membered ring.

TABLE XXI-14

| No | R¹ | R² | R³ᵃ | R³ᵇ | R⁴ | R⁵ | R⁶ | X | Y |
|---|---|---|---|---|---|---|---|---|---|
| XXI-14-1 | $^t$Bu | H | H | H | Et | H | CH₃ | F | OH |
| XXI-14-2 | $^t$Bu | H | H | CH₃ | Et | H | CH₃ | F | OH |
| XXI-14-3 | $^t$Bu | H | H | CH(CH₃)₂ | Et | H | CH₃ | F | OH |
| XXI-14-4 | $^t$Bu | H | H | CH₂CH(CH₃)₂ | Et | H | CH₃ | F | OH |
| XXI-14-5 | $^t$Bu | H | H | CH₂Ph | Et | H | CH₃ | F | OH |
| XXI-14-6 | $^t$Bu | H | H | CH₂-indol-3-yl | Et | H | CH₃ | F | OH |
| XXI-14-7 | $^t$Bu | H | H | CH₂CH₂SCH₃ | Et | H | CH₃ | F | OH |
| XXI-14-8 | $^t$Bu | * | H | * | Et | H | CH₃ | F | OH |

*R² and R³ᵇ joined together by (CH₂)₃ to form five-membered ring.

TABLE XXI-15

| No | R¹ | R² | R³ᵃ | R³ᵇ | R⁴ | R⁵ | R⁶ | X | Y |
|---|---|---|---|---|---|---|---|---|---|
| XXI-15-1 | Ph | H | H | H | Et | H | CH₃ | F | OH |
| XXI-15-2 | Ph | H | H | CH₃ | Et | H | CH₃ | F | OH |
| XXI-15-3 | Ph | H | H | CH(CH₃)₂ | Et | H | CH₃ | F | OH |
| XXI-15-4 | Ph | H | H | CH₂CH(CH₃)₂ | Et | H | CH₃ | F | OH |
| XXI-15-5 | Ph | H | H | CH₂Ph | Et | H | CH₃ | F | OH |
| XXI-15-6 | Ph | H | H | CH₂-indol-3-yl | Et | H | CH₃ | F | OH |
| XXI-15-7 | Ph | H | H | CH₂CH₂SCH₃ | Et | H | CH₃ | F | OH |
| XXI-15-8 | Ph | * | H | * | Et | H | CH₃ | F | OH |

*R² and R³ᵇ joined together by (CH₂)₃ to form five-membered ring.

TABLE XXI-16

| No | R¹ | R² | R³ᵃ | R³ᵇ | R⁴ | R⁵ | R⁶ | X | Y |
|---|---|---|---|---|---|---|---|---|---|
| XXI-16-1 | p-Me—Ph | H | H | H | Et | H | CH₃ | F | OH |
| XXI-16-2 | p-Me—Ph | H | H | CH₃ | Et | H | CH₃ | F | OH |
| XXI-16-3 | p-Me—Ph | H | H | CH(CH₃)₂ | Et | H | CH₃ | F | OH |
| XXI-16-4 | p-Me—Ph | H | H | CH₂CH(CH₃)₂ | Et | H | CH₃ | F | OH |
| XXI-16-5 | p-Me—Ph | H | H | CH₂Ph | Et | H | CH₃ | F | OH |
| XXI-16-6 | p-Me—Ph | H | H | CH₂-indol-3-yl | Et | H | CH₃ | F | OH |
| XXI-16-7 | p-Me—Ph | H | H | CH₂CH₂SCH₃ | Et | H | CH₃ | F | OH |
| XXI-16-8 | p-Me—Ph | * | H | * | Et | H | CH₃ | F | OH |

*R² and R³ᵇ joined together by (CH₂)₃ to form five-membered ring.

TABLE XXI-17

| No | R¹ | R² | R³ᵃ | R³ᵇ | R⁴ | R⁵ | R⁶ | X | Y |
|---|---|---|---|---|---|---|---|---|---|
| XXI-17-1 | p-F—Ph | H | H | H | Et | H | CH₃ | F | OH |
| XXI-17-2 | p-F—Ph | H | H | CH₃ | Et | H | CH₃ | F | OH |
| XXI-17-3 | p-F—Ph | H | H | CH(CH₃)₂ | Et | H | CH₃ | F | OH |
| XXI-17-4 | p-F—Ph | H | H | CH₂CH(CH₃)₂ | Et | H | CH₃ | F | OH |
| XXI-17-5 | p-F—Ph | H | H | CH₂Ph | Et | H | CH₃ | F | OH |
| XXI-17-6 | p-F—Ph | H | H | CH₂-indol-3-yl | Et | H | CH₃ | F | OH |
| XXI-17-7 | p-F—Ph | H | H | CH₂CH₂SCH₃ | Et | H | CH₃ | F | OH |
| XXI-17-8 | p-F—Ph | * | H | * | Et | H | CH₃ | F | OH |

*R² and R³ᵇ joined together by (CH₂)₃ to form five-membered ring.

TABLE XXI-18

| No | R¹ | R² | R³ᵃ | R³ᵇ | R⁴ | R⁵ | R⁶ | X | Y |
|---|---|---|---|---|---|---|---|---|---|
| XXI-18-1 | p-Cl—Ph | H | H | H | Et | H | CH₃ | F | OH |
| XXI-18-2 | p-Cl—Ph | H | H | CH₃ | Et | H | CH₃ | F | OH |
| XXI-18-3 | p-Cl—Ph | H | H | CH(CH₃)₂ | Et | H | CH₃ | F | OH |
| XXI-18-4 | p-Cl—Ph | H | H | CH₂CH(CH₃)₂ | Et | H | CH₃ | F | OH |
| XXI-18-5 | p-Cl—Ph | H | H | CH₂Ph | Et | H | CH₃ | F | OH |
| XXI-18-6 | p-Cl—Ph | H | H | CH₂-indol-3-yl | Et | H | CH₃ | F | OH |
| XXI-18-7 | p-Cl—Ph | H | H | CH₂CH₂SCH₃ | Et | H | CH₃ | F | OH |
| XXI-18-8 | p-Cl—Ph | * | H | * | Et | H | CH₃ | F | OH |

*R² and R³ᵇ joined together by (CH₂)₃ to form five-membered ring.

TABLE XXI-19

| No | R¹ | R² | R³ᵃ | R³ᵇ | R⁴ | R⁵ | R⁶ | X | Y |
|---|---|---|---|---|---|---|---|---|---|
| XXI-19-1 | p-Br—Ph | H | H | H | Et | H | CH₃ | F | OH |
| XXI-19-2 | p-Br—Ph | H | H | CH₃ | Et | H | CH₃ | F | OH |
| XXI-19-3 | p-Br—Ph | H | H | CH(CH₃)₂ | Et | H | CH₃ | F | OH |
| XXI-19-4 | p-Br—Ph | H | H | CH₂CH(CH₃)₂ | Et | H | CH₃ | F | OH |
| XXI-19-5 | p-Br—Ph | H | H | CH₂Ph | Et | H | CH₃ | F | OH |
| XXI-19-6 | p-Br—Ph | H | H | CH₂-indol-3-yl | Et | H | CH₃ | F | OH |
| XXI-19-7 | p-Br—Ph | H | H | CH₂CH₂SCH₃ | Et | H | CH₃ | F | OH |
| XXI-19-8 | p-Br—Ph | * | H | * | Et | H | CH₃ | F | OH |

*R² and R³ᵇ joined together by (CH₂)₃ to form five-membered ring.

TABLE XXI-20

| No | R¹ | R² | R³ᵃ | R³ᵇ | R⁴ | R⁵ | R⁶ | X | Y |
|---|---|---|---|---|---|---|---|---|---|
| XXI-20-1 | p-I—Ph | H | H | H | Et | H | CH₃ | F | OH |
| XXI-20-2 | p-I—Ph | H | H | CH₃ | Et | H | CH₃ | F | OH |
| XXI-20-3 | p-I—Ph | H | H | CH(CH₃)₂ | Et | H | CH₃ | F | OH |
| XXI-20-4 | p-I—Ph | H | H | CH₂CH(CH₃)₂ | Et | H | CH₃ | F | OH |
| XXI-20-5 | p-I—Ph | H | H | CH₂Ph | Et | H | CH₃ | F | OH |
| XXI-20-6 | p-I—Ph | H | H | CH₂-indol-3-yl | Et | H | CH₃ | F | OH |
| XXI-20-7 | p-I—Ph | H | H | CH₂CH₂SCH₃ | Et | H | CH₃ | F | OH |
| XXI-20-8 | p-I—Ph | * | H | * | Et | H | CH₃ | F | OH |

*R² and R³ᵇ joined together by (CH₂)₃ to form five-membered ring.

TABLE XXI-21

| No | R¹ | R² | R³ᵃ | R³ᵇ | R⁴ | R⁵ | R⁶ | X | Y |
|---|---|---|---|---|---|---|---|---|---|
| XXI-21-1 | CH₃ | H | H | H | $^i$Pr | H | CH₃ | F | OH |
| XXI-21-2 | CH₃ | H | H | CH₃ | $^i$Pr | H | CH₃ | F | OH |
| XXI-21-3 | CH₃ | H | H | CH(CH₃)₂ | $^i$Pr | H | CH₃ | F | OH |
| XXI-21-4 | CH₃ | H | H | CH₂CH(CH₃)₂ | $^i$Pr | H | CH₃ | F | OH |
| XXI-21-5 | CH₃ | H | H | CH₂Ph | $^i$Pr | H | CH₃ | F | OH |
| XXI-21-6 | CH₃ | H | H | CH₂-indol-3-yl | $^i$Pr | H | CH₃ | F | OH |
| XXI-21-7 | CH₃ | H | H | CH₂CH₂SCH₃ | $^i$Pr | H | CH₃ | F | OH |
| XXI-21-8 | CH₃ | * | H | * | $^i$Pr | H | CH₃ | F | OH |

*R² and R³ᵇ joined together by (CH₂)₃ to form five-membered ring.

TABLE XXI-22

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-22-1 | Et | H | H | H | $^i$Pr | H | $CH_3$ | F | OH |
| XXI-22-2 | Et | H | H | $CH_3$ | $^i$Pr | H | $CH_3$ | F | OH |
| XXI-22-3 | Et | H | H | $CH(CH_3)_2$ | $^i$Pr | H | $CH_3$ | F | OH |
| XXI-22-4 | Et | H | H | $CH_2CH(CH_3)_2$ | $^i$Pr | H | $CH_3$ | F | OH |
| XXI-22-5 | Et | H | H | $CH_2Ph$ | $^i$Pr | H | $CH_3$ | F | OH |
| XXI-22-6 | Et | H | H | $CH_2$-indol-3-yl | $^i$Pr | H | $CH_3$ | F | OH |
| XXI-22-7 | Et | H | H | $CH_2CH_2SCH_3$ | $^i$Pr | H | $CH_3$ | F | OH |
| XXI-22-8 | Et | * | H | * | $^i$Pr | H | $CH_3$ | F | OH |

*$R^2$ and $R^{3b}$ joined together by $(CH_2)_3$ to form five-membered ring.

TABLE XXI-23

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-23-1 | $^i$Pr | H | H | H | $^i$Pr | H | $CH_3$ | F | OH |
| XXI-23-2 | $^i$Pr | H | H | $CH_3$ | $^i$Pr | H | $CH_3$ | F | OH |
| XXI-23-3 | $^i$Pr | H | H | $CH(CH_3)_2$ | $^i$Pr | H | $CH_3$ | F | OH |
| XXI-23-4 | $^i$Pr | H | H | $CH_2CH(CH_3)_2$ | $^i$Pr | H | $CH_3$ | F | OH |
| XXI-23-5 | $^i$Pr | H | H | $CH_2Ph$ | $^i$Pr | H | $CH_3$ | F | OH |
| XXI-23-6 | $^i$Pr | H | H | $CH_2$-indol-3-yl | $^i$Pr | H | $CH_3$ | F | OH |
| XXI-23-7 | $^i$Pr | H | H | $CH_2CH_2SCH_3$ | $^i$Pr | H | $CH_3$ | F | OH |
| XXI-23-8 | $^i$Pr | * | H | * | $^i$Pr | H | $CH_3$ | F | OH |

*$R^2$ and $R^{3b}$ joined together by $(CH_2)_3$ to form five-membered ring.

TABLE XXI-24

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-24-1 | $^t$Bu | H | H | H | $^i$Pr | H | $CH_3$ | F | OH |
| XXI-24-2 | $^t$Bu | H | H | $CH_3$ | $^i$Pr | H | $CH_3$ | F | OH |
| XXI-24-3 | $^t$Bu | H | H | $CH(CH_3)_2$ | $^i$Pr | H | $CH_3$ | F | OH |
| XXI-24-4 | $^t$Bu | H | H | $CH_2CH(CH_3)_2$ | $^i$Pr | H | $CH_3$ | F | OH |
| XXI-24-5 | $^t$Bu | H | H | $CH_2Ph$ | $^i$Pr | H | $CH_3$ | F | OH |
| XXI-24-6 | $^t$Bu | H | H | $CH_2$-indol-3-yl | $^i$Pr | H | $CH_3$ | F | OH |
| XXI-24-7 | $^t$Bu | H | H | $CH_2CH_2SCH_3$ | $^i$Pr | H | $CH_3$ | F | OH |
| XXI-24-8 | $^t$Bu | * | H | * | $^i$Pr | H | $CH_3$ | F | OH |

*$R^2$ and $R^{3b}$ joined together by $(CH_2)_3$ to form five-membered ring.

TABLE XXI-25

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-25-1 | Ph | H | H | H | $^i$Pr | H | $CH_3$ | F | OH |
| XXI-25-2 | Ph | H | H | $CH_3$ | $^i$Pr | H | $CH_3$ | F | OH |
| XXI-25-3 | Ph | H | H | $CH(CH_3)_2$ | $^i$Pr | H | $CH_3$ | F | OH |
| XXI-25-4 | Ph | H | H | $CH_2CH(CH_3)_2$ | $^i$Pr | H | $CH_3$ | F | OH |
| XXI-25-5 | Ph | H | H | $CH_2Ph$ | $^i$Pr | H | $CH_3$ | F | OH |
| XXI-25-6 | Ph | H | H | $CH_2$-indol-3-yl | $^i$Pr | H | $CH_3$ | F | OH |
| XXI-25-7 | Ph | H | H | $CH_2CH_2SCH_3$ | $^i$Pr | H | $CH_3$ | F | OH |
| XXI-25-8 | Ph | * | H | * | $^i$Pr | H | $CH_3$ | F | OH |

*$R^2$ and $R^{3b}$ joined together by $(CH_2)_3$ to form five-membered ring.

TABLE XXI-26

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-26-1 | p-Me—Ph | H | H | H | $^i$Pr | H | $CH_3$ | F | OH |
| XXI-26-2 | p-Me—Ph | H | H | $CH_3$ | $^i$Pr | H | $CH_3$ | F | OH |
| XXI-26-3 | p-Me—Ph | H | H | $CH(CH_3)_2$ | $^i$Pr | H | $CH_3$ | F | OH |
| XXI-26-4 | p-Me—Ph | H | H | $CH_2CH(CH_3)_2$ | $^i$Pr | H | $CH_3$ | F | OH |
| XXI-26-5 | p-Me—Ph | H | H | $CH_2Ph$ | $^i$Pr | H | $CH_3$ | F | OH |
| XXI-26-6 | p-Me—Ph | H | H | $CH_2$-indol-3-yl | $^i$Pr | H | $CH_3$ | F | OH |
| XXI-26-7 | p-Me—Ph | H | H | $CH_2CH_2SCH_3$ | $^i$Pr | H | $CH_3$ | F | OH |
| XXI-26-8 | p-Me—Ph | * | H | * | $^i$Pr | H | $CH_3$ | F | OH |

*$R^2$ and $R^{3b}$ joined together by $(CH_2)_3$ to form five-membered ring.

TABLE XXI-27

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-27-1 | p-F—Ph | H | H | H | $^i$Pr | H | $CH_3$ | F | OH |
| XXI-27-2 | p-F—Ph | H | H | $CH_3$ | $^i$Pr | H | $CH_3$ | F | OH |
| XXI-27-3 | p-F—Ph | H | H | $CH(CH_3)_2$ | $^i$Pr | H | $CH_3$ | F | OH |
| XXI-27-4 | p-F—Ph | H | H | $CH_2CH(CH_3)_2$ | $^i$Pr | H | $CH_3$ | F | OH |
| XXI-27-5 | p-F—Ph | H | H | $CH_2Ph$ | $^i$Pr | H | $CH_3$ | F | OH |
| XXI-27-6 | p-F—Ph | H | H | $CH_2$-indol-3-yl | $^i$Pr | H | $CH_3$ | F | OH |
| XXI-27-7 | p-F—Ph | H | H | $CH_2CH_2SCH_3$ | $^i$Pr | H | $CH_3$ | F | OH |
| XXI-27-8 | p-F—Ph | * | H | * | $^i$Pr | H | $CH_3$ | F | OH |

*$R^2$ and $R^{3b}$ joined together by $(CH_2)_3$ to form five-membered ring.

TABLE XXI-28

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-28-1 | p-Cl—Ph | H | H | H | $^i$Pr | H | $CH_3$ | F | OH |
| XXI-28-2 | p-Cl—Ph | H | H | $CH_3$ | $^i$Pr | H | $CH_3$ | F | OH |
| XXI-28-3 | p-Cl—Ph | H | H | $CH(CH_3)_2$ | $^i$Pr | H | $CH_3$ | F | OH |
| XXI-28-4 | p-Cl—Ph | H | H | $CH_2CH(CH_3)_2$ | $^i$Pr | H | $CH_3$ | F | OH |
| XXI-28-5 | p-Cl—Ph | H | H | $CH_2Ph$ | $^i$Pr | H | $CH_3$ | F | OH |
| XXI-28-6 | p-Cl—Ph | H | H | $CH_2$-indol-3-yl | $^i$Pr | H | $CH_3$ | F | OH |
| XXI-28-7 | p-Cl—Ph | H | H | $CH_2CH_2SCH_3$ | $^i$Pr | H | $CH_3$ | F | OH |
| XXI-28-8 | p-Cl—Ph | * | H | * | $^i$Pr | H | $CH_3$ | F | OH |

*$R^2$ and $R^{3b}$ joined together by $(CH_2)_3$ to form five-membered ring.

TABLE XXI-29

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-29-1 | p-Br—Ph | H | H | H | $^i$Pr | H | $CH_3$ | F | OH |
| XXI-29-2 | p-Br—Ph | H | H | $CH_3$ | $^i$Pr | H | $CH_3$ | F | OH |
| XXI-29-3 | p-Br—Ph | H | H | $CH(CH_3)_2$ | $^i$Pr | H | $CH_3$ | F | OH |
| XXI-29-4 | p-Br—Ph | H | H | $CH_2CH(CH_3)_2$ | $^i$Pr | H | $CH_3$ | F | OH |
| XXI-29-5 | p-Br—Ph | H | H | $CH_2Ph$ | $^i$Pr | H | $CH_3$ | F | OH |
| XXI-29-6 | p-Br—Ph | H | H | $CH_2$-indol-3-yl | $^i$Pr | H | $CH_3$ | F | OH |
| XXI-29-7 | p-Br—Ph | H | H | $CH_2CH_2SCH_3$ | $^i$Pr | H | $CH_3$ | F | OH |
| XXI-29-8 | p-Br—Ph | * | H | * | $^i$Pr | H | $CH_3$ | F | OH |

*$R^2$ and $R^{3b}$ joined together by $(CH_2)_3$ to form five-membered ring.

TABLE XXI-30

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXI-30-1 | p-I—Ph | H | H | H | $^i$Pr | H | $CH_3$ | F | OH |
| XXI-30-2 | p-I—Ph | H | H | $CH_3$ | $^i$Pr | H | $CH_3$ | F | OH |

TABLE XXI-30-continued

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-30-3 | p-I—Ph | H | H | CH(CH$_3$)$_2$ | $^i$Pr | H | CH$_3$ | F | OH |
| XXI-30-4 | p-I—Ph | H | H | CH$_2$CH(CH$_3$)$_2$ | $^i$Pr | H | CH$_3$ | F | OH |
| XXI-30-5 | p-I—Ph | H | H | CH$_2$Ph | $^i$Pr | H | CH$_3$ | F | OH |
| XXI-30-6 | p-I—Ph | H | H | CH$_2$-indol-3-yl | $^i$Pr | H | CH$_3$ | F | OH |
| XXI-30-7 | p-I—Ph | H | H | CH$_2$CH$_2$SCH$_3$ | $^i$Pr | H | CH$_3$ | F | OH |
| XXI-30-8 | p-I—Ph | * | H | * | $^i$Pr | H | CH$_3$ | F | OH |

*R$^2$ and R$^{3b}$ joined together by (CH$_2$)$_3$ to form five-membered ring.

TABLE XXI-31

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-31-1 | CH$_3$ | H | H | H | $^n$Bu | H | CH$_3$ | F | OH |
| XXI-31-2 | CH$_3$ | H | H | CH$_3$ | $^n$Bu | H | CH$_3$ | F | OH |
| XXI-31-3 | CH$_3$ | H | H | CH(CH$_3$)$_2$ | $^n$Bu | H | CH$_3$ | F | OH |
| XXI-31-4 | CH$_3$ | H | H | CH$_2$CH(CH$_3$)$_2$ | $^n$Bu | H | CH$_3$ | F | OH |
| XXI-31-5 | CH$_3$ | H | H | CH$_2$Ph | $^n$Bu | H | CH$_3$ | F | OH |
| XXI-31-6 | CH$_3$ | H | H | CH$_2$-indol-3-yl | $^n$Bu | H | CH$_3$ | F | OH |
| XXI-31-7 | CH$_3$ | H | H | CH$_2$CH$_2$SCH$_3$ | $^n$Bu | H | CH$_3$ | F | OH |
| XXI-31-8 | CH$_3$ | * | H | * | $^n$Bu | H | CH$_3$ | F | OH |

*R$^2$ and R$^{3b}$ joined together by (CH$_2$)$_3$ to form five-membered ring.

TABLE XXI-32

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-32-1 | Et | H | H | H | $^n$Bu | H | CH$_3$ | F | OH |
| XXI-32-2 | Et | H | H | CH$_3$ | $^n$Bu | H | CH$_3$ | F | OH |
| XXI-32-3 | Et | H | H | CH(CH$_3$)$_2$ | $^n$Bu | H | CH$_3$ | F | OH |
| XXI-32-4 | Et | H | H | CH$_2$CH(CH$_3$)$_2$ | $^n$Bu | H | CH$_3$ | F | OH |
| XXI-32-5 | Et | H | H | CH$_2$Ph | $^n$Bu | H | CH$_3$ | F | OH |
| XXI-32-6 | Et | H | H | CH$_2$-indol-3-yl | $^n$Bu | H | CH$_3$ | F | OH |
| XXI-32-7 | Et | H | H | CH$_2$CH$_2$SCH$_3$ | $^n$Bu | H | CH$_3$ | F | OH |
| XXI-32-8 | Et | * | H | * | $^n$Bu | H | CH$_3$ | F | OH |

*R$^2$ and R$^{3b}$ joined together by (CH$_2$)$_3$ to form five-membered ring.

TABLE XXI-33

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-33-1 | $^i$Pr | H | H | H | $^n$Bu | H | CH$_3$ | F | OH |
| XXI-33-2 | $^i$Pr | H | H | CH$_3$ | $^n$Bu | H | CH$_3$ | F | OH |
| XXI-33-3 | $^i$Pr | H | H | CH(CH$_3$)$_2$ | $^n$Bu | H | CH$_3$ | F | OH |
| XXI-33-4 | $^i$Pr | H | H | CH$_2$CH(CH$_3$)$_2$ | $^n$Bu | H | CH$_3$ | F | OH |
| XXI-33-5 | $^i$Pr | H | H | CH$_2$Ph | $^n$Bu | H | CH$_3$ | F | OH |
| XXI-33-6 | $^i$Pr | H | H | CH$_2$-indol-3-yl | $^n$Bu | H | CH$_3$ | F | OH |
| XXI-33-7 | $^i$Pr | H | H | CH$_2$CH$_2$SCH$_3$ | $^n$Bu | H | CH$_3$ | F | OH |
| XXI-33-8 | $^i$Pr | * | H | * | $^n$Bu | H | CH$_3$ | F | OH |

*R$^2$ and R$^{3b}$ joined together by (CH$_2$)$_3$ to form five-membered ring.

TABLE XXI-34

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-34-1 | $^t$Bu | H | H | H | $^n$Bu | H | CH$_3$ | F | OH |
| XXI-34-2 | $^t$Bu | H | H | CH$_3$ | $^n$Bu | H | CH$_3$ | F | OH |
| XXI-34-3 | $^t$Bu | H | H | CH(CH$_3$)$_2$ | $^n$Bu | H | CH$_3$ | F | OH |
| XXI-34-4 | $^t$Bu | H | H | CH$_2$CH(CH$_3$)$_2$ | $^n$Bu | H | CH$_3$ | F | OH |
| XXI-34-5 | $^t$Bu | H | H | CH$_2$Ph | $^n$Bu | H | CH$_3$ | F | OH |
| XXI-34-6 | $^t$Bu | H | H | CH$_2$-indol-3-yl | $^n$Bu | H | CH$_3$ | F | OH |
| XXI-34-7 | $^t$Bu | H | H | CH$_2$CH$_2$SCH$_3$ | $^n$Bu | H | CH$_3$ | F | OH |
| XXI-34-8 | $^t$Bu | * | H | * | $^n$Bu | H | CH$_3$ | F | OH |

*R$^2$ and R$^{3b}$ joined together by (CH$_2$)$_3$ to form five-membered ring.

TABLE XXI-35

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-35-1 | Ph | H | H | H | $^n$Bu | H | CH$_3$ | F | OH |
| XXI-35-2 | Ph | H | H | CH$_3$ | $^n$Bu | H | CH$_3$ | F | OH |
| XXI-35-3 | Ph | H | H | CH(CH$_3$)$_2$ | $^n$Bu | H | CH$_3$ | F | OH |
| XXI-35-4 | Ph | H | H | CH$_2$CH(CH$_3$)$_2$ | $^n$Bu | H | CH$_3$ | F | OH |
| XXI-35-5 | Ph | H | H | CH$_2$Ph | $^n$Bu | H | CH$_3$ | F | OH |
| XXI-35-6 | Ph | H | H | CH$_2$-indol-3-yl | $^n$Bu | H | CH$_3$ | F | OH |
| XXI-35-7 | Ph | H | H | CH$_2$CH$_2$SCH$_3$ | $^n$Bu | H | CH$_3$ | F | OH |
| XXI-35-8 | Ph | * | H | * | $^n$Bu | H | CH$_3$ | F | OH |

*R$^2$ and R$^{3b}$ joined together by (CH$_2$)$_3$ to form five-membered ring.

TABLE XXI-36

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-36-1 | p-Me—Ph | H | H | H | $^n$Bu | H | CH$_3$ | F | OH |
| XXI-36-2 | p-Me—Ph | H | H | CH$_3$ | $^n$Bu | H | CH$_3$ | F | OH |
| XXI-36-3 | p-Me—Ph | H | H | CH(CH$_3$)$_2$ | $^n$Bu | H | CH$_3$ | F | OH |
| XXI-36-4 | p-Me—Ph | H | H | CH$_2$CH(CH$_3$)$_2$ | $^n$Bu | H | CH$_3$ | F | OH |
| XXI-36-5 | p-Me—Ph | H | H | CH$_2$Ph | $^n$Bu | H | CH$_3$ | F | OH |
| XXI-36-6 | p-Me—Ph | H | H | CH$_2$-indol-3-yl | $^n$Bu | H | CH$_3$ | F | OH |
| XXI-36-7 | p-Me—Ph | H | H | CH$_2$CH$_2$SCH$_3$ | $^n$Bu | H | CH$_3$ | F | OH |
| XXI-36-8 | p-Me—Ph | * | H | * | $^n$Bu | H | CH$_3$ | F | OH |

*R$^2$ and R$^{3b}$ joined together by (CH$_2$)$_3$ to form five-membered ring.

TABLE XXI-37

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-37-1 | p-F—Ph | H | H | H | $^n$Bu | H | CH$_3$ | F | OH |
| XXI-37-2 | p-F—Ph | H | H | CH$_3$ | $^n$Bu | H | CH$_3$ | F | OH |
| XXI-37-3 | p-F—Ph | H | H | CH(CH$_3$)$_2$ | $^n$Bu | H | CH$_3$ | F | OH |
| XXI-37-4 | p-F—Ph | H | H | CH$_2$CH(CH$_3$)$_2$ | $^n$Bu | H | CH$_3$ | F | OH |
| XXI-37-5 | p-F—Ph | H | H | CH$_2$Ph | $^n$Bu | H | CH$_3$ | F | OH |
| XXI-37-6 | p-F—Ph | H | H | CH$_2$-indol-3-yl | $^n$Bu | H | CH$_3$ | F | OH |
| XXI-37-7 | p-F—Ph | H | H | CH$_2$CH$_2$SCH$_3$ | $^n$Bu | H | CH$_3$ | F | OH |
| XXI-37-8 | p-F—Ph | * | H | * | $^n$Bu | H | CH$_3$ | F | OH |

*R$^2$ and R$^{3b}$ joined together by (CH$_2$)$_3$ to form five-membered ring.

TABLE XXI-38

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-38-1 | p-Cl—Ph | H | H | H | $^n$Bu | H | CH$_3$ | F | OH |
| XXI-38-2 | p-Cl—Ph | H | H | CH$_3$ | $^n$Bu | H | CH$_3$ | F | OH |
| XXI-38-3 | p-Cl—Ph | H | H | CH(CH$_3$)$_2$ | $^n$Bu | H | CH$_3$ | F | OH |
| XXI-38-4 | p-Cl—Ph | H | H | CH$_2$CH(CH$_3$)$_2$ | $^n$Bu | H | CH$_3$ | F | OH |
| XXI-38-5 | p-Cl—Ph | H | H | CH$_2$Ph | $^n$Bu | H | CH$_3$ | F | OH |
| XXI-38-6 | p-Cl—Ph | H | H | CH$_2$-indol-3-yl | $^n$Bu | H | CH$_3$ | F | OH |
| XXI-38-7 | p-Cl—Ph | H | H | CH$_2$CH$_2$SCH$_3$ | $^n$Bu | H | CH$_3$ | F | OH |
| XXI-38-8 | p-Cl—Ph | * | H | * | $^n$Bu | H | CH$_3$ | F | OH |

*R$^2$ and R$^{3b}$ joined together by (CH$_2$)$_3$ to form five-membered ring.

TABLE XXI-39

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXI-39-1 | p-Br—Ph | H | H | H | $^n$Bu | H | CH$_3$ | F | OH |
| XXI-39-2 | p-Br—Ph | H | H | CH$_3$ | $^n$Bu | H | CH$_3$ | F | OH |
| XXI-39-3 | p-Br—Ph | H | H | CH(CH$_3$)$_2$ | $^n$Bu | H | CH$_3$ | F | OH |
| XXI-39-4 | p-Br—Ph | H | H | CH$_2$CH(CH$_3$)$_2$ | $^n$Bu | H | CH$_3$ | F | OH |
| XXI-39-5 | p-Br—Ph | H | H | CH$_2$Ph | $^n$Bu | H | CH$_3$ | F | OH |
| XXI-39-6 | p-Br—Ph | H | H | CH$_2$-indol-3-yl | $^n$Bu | H | CH$_3$ | F | OH |
| XXI-39-7 | p-Br—Ph | H | H | CH$_2$CH$_2$SCH$_3$ | $^n$Bu | H | CH$_3$ | F | OH |
| XXI-39-8 | p-Br—Ph | * | H | * | $^n$Bu | H | CH$_3$ | F | OH |

*R$^2$ and R$^{3b}$ joined together by (CH$_2$)$_3$ to form five-membered ring.

TABLE XXI-40

| No | R¹ | R² | R³ᵃ | R³ᵇ | R⁴ | R⁵ | R⁶ | X | Y |
|---|---|---|---|---|---|---|---|---|---|
| XXI-40-1 | p-I—Ph | H | H | H | ⁿBu | H | CH₃ | F | OH |
| XXI-40-2 | p-I—Ph | H | H | CH₃ | ⁿBu | H | CH₃ | F | OH |
| XXI-40-3 | p-I—Ph | H | H | CH(CH₃)₂ | ⁿBu | H | CH₃ | F | OH |
| XXI-40-4 | p-I—Ph | H | H | CH₂CH(CH₃)₂ | ⁿBu | H | CH₃ | F | OH |
| XXI-40-5 | p-I—Ph | H | H | CH₂Ph | ⁿBu | H | CH₃ | F | OH |
| XXI-40-6 | p-I—Ph | H | H | CH₂-indol-3-yl | ⁿBu | H | CH₃ | F | OH |
| XXI-40-7 | p-I—Ph | H | H | CH₂CH₂SCH₃ | ⁿBu | H | CH₃ | F | OH |
| XXI-40-8 | p-I—Ph | * | H | * | ⁿBu | H | CH₃ | F | OH |

*R² and R³ᵇ joined together by (CH₂)₃ to form five-membered ring.

TABLE XXI-41

| No | R¹ | R² | R³ᵃ | R³ᵇ | R⁴ | R⁵ | R⁶ | X | Y |
|---|---|---|---|---|---|---|---|---|---|
| XXI-41-1 | CH₃ | H | H | H | Bz | H | CH₃ | F | OH |
| XXI-41-2 | CH₃ | H | H | CH₃ | Bz | H | CH₃ | F | OH |
| XXI-41-3 | CH₃ | H | H | CH(CH₃)₂ | Bz | H | CH₃ | F | OH |
| XXI-41-4 | CH₃ | H | H | CH₂CH(CH₃)₂ | Bz | H | CH₃ | F | OH |
| XXI-41-5 | CH₃ | H | H | CH₂Ph | Bz | H | CH₃ | F | OH |
| XXI-41-6 | CH₃ | H | H | CH₂-indol-3-yl | Bz | H | CH₃ | F | OH |
| XXI-41-7 | CH₃ | H | H | CH₂CH₂SCH₃ | Bz | H | CH₃ | F | OH |
| XXI-41-8 | CH₃ | * | H | * | Bz | H | CH₃ | F | OH |

*R² and R³ᵇ joined together by (CH₂)₃ to form five-membered ring.

TABLE XXI-42

| No | R¹ | R² | R³ᵃ | R³ᵇ | R⁴ | R⁵ | R⁶ | X | Y |
|---|---|---|---|---|---|---|---|---|---|
| XXI-42-1 | Et | H | H | H | Bz | H | CH₃ | F | OH |
| XXI-42-2 | Et | H | H | CH₃ | Bz | H | CH₃ | F | OH |
| XXI-42-3 | Et | H | H | CH(CH₃)₂ | Bz | H | CH₃ | F | OH |
| XXI-42-4 | Et | H | H | CH₂CH(CH₃)₂ | Bz | H | CH₃ | F | OH |
| XXI-42-5 | Et | H | H | CH₂Ph | Bz | H | CH₃ | F | OH |
| XXI-42-6 | Et | H | H | CH₂-indol-3-yl | Bz | H | CH₃ | F | OH |
| XXI-42-7 | Et | H | H | CH₂CH₂SCH₃ | Bz | H | CH₃ | F | OH |
| XXI-42-8 | Et | * | H | * | Bz | H | CH₃ | F | OH |

*R² and R³ᵇ oined together by (CH₂)₃ to form five-membered ring.

TABLE XXI-43

| No | R¹ | R² | R³ᵃ | R³ᵇ | R⁴ | R⁵ | R⁶ | X | Y |
|---|---|---|---|---|---|---|---|---|---|
| XXI-43-1 | ⁱPr | H | H | H | Bz | H | CH₃ | F | OH |
| XXI-43-2 | ⁱPr | H | H | CH₃ | Bz | H | CH₃ | F | OH |
| XXI-43-3 | ⁱPr | H | H | CH(CH₃)₂ | Bz | H | CH₃ | F | OH |
| XXI-43-4 | ⁱPr | H | H | CH₂CH(CH₃)₂ | Bz | H | CH₃ | F | OH |
| XXI-43-5 | ⁱPr | H | H | CH₂Ph | Bz | H | CH₃ | F | OH |
| XXI-43-6 | ⁱPr | H | H | CH₂-indol-3-yl | Bz | H | CH₃ | F | OH |
| XXI-43-7 | ⁱPr | H | H | CH₂CH₂SCH₃ | Bz | H | CH₃ | F | OH |
| XXI-43-8 | ⁱPr | * | H | * | Bz | H | CH₃ | F | OH |

*R² and R³ᵇ joined together by (CH₂)₃ to form five-membered ring.

TABLE XXI-44

| No | R¹ | R² | R³ᵃ | R³ᵇ | R⁴ | R⁵ | R⁶ | X | Y |
|---|---|---|---|---|---|---|---|---|---|
| XXI-44-1 | ᵗBu | H | H | H | Bz | H | CH₃ | F | OH |
| XXI-44-2 | ᵗBu | H | H | CH₃ | Bz | H | CH₃ | F | OH |
| XXI-44-3 | ᵗBu | H | H | CH(CH₃)₂ | Bz | H | CH₃ | F | OH |
| XXI-44-4 | ᵗBu | H | H | CH₂CH(CH₃)₂ | Bz | H | CH₃ | F | OH |
| XXI-44-5 | ᵗBu | H | H | CH₂Ph | Bz | H | CH₃ | F | OH |
| XXI-44-6 | ᵗBu | H | H | CH₂-indol-3-yl | Bz | H | CH₃ | F | OH |
| XXI-44-7 | ᵗBu | H | H | CH₂CH₂SCH₃ | Bz | H | CH₃ | F | OH |
| XXI-44-8 | ᵗBu | * | H | * | Bz | H | CH₃ | F | OH |

*R² and R³ᵇ joined together by (CH₂)₃ to form five-membered ring.

TABLE XXI-45

| No | R¹ | R² | R³ᵃ | R³ᵇ | R⁴ | R⁵ | R⁶ | X | Y |
|---|---|---|---|---|---|---|---|---|---|
| XXI-45-1 | Ph | H | H | H | Bz | H | CH₃ | F | OH |
| XXI-45-2 | Ph | H | H | CH₃ | Bz | H | CH₃ | F | OH |
| XXI-45-3 | Ph | H | H | CH(CH₃)₂ | Bz | H | CH₃ | F | OH |
| XXI-45-4 | Ph | H | H | CH₂CH(CH₃)₂ | Bz | H | CH₃ | F | OH |
| XXI-45-5 | Ph | H | H | CH₂Ph | Bz | H | CH₃ | F | OH |
| XXI-45-6 | Ph | H | H | CH₂-indol-3-yl | Bz | H | CH₃ | F | OH |
| XXI-45-7 | Ph | H | H | CH₂CH₂SCH₃ | Bz | H | CH₃ | F | OH |
| XXI-45-8 | Ph | * | H | * | Bz | H | CH₃ | F | OH |

*R² and R³ᵇ joined together by (CH₂)₃ to form five-membered ring.

TABLE XXL-46

| No | R¹ | R² | R³ᵃ | R³ᵇ | R⁴ | R⁵ | R⁶ | X | Y |
|---|---|---|---|---|---|---|---|---|---|
| XXI-46-1 | p-Me—Ph | H | H | H | Bz | H | CH₃ | F | OH |
| XXI-46-2 | p-Me—Ph | H | H | CH₃ | Bz | H | CH₃ | F | OH |
| XXI-46-3 | p-Me—Ph | H | H | CH(CH₃)₂ | Bz | H | CH₃ | F | OH |
| XXI-46-4 | p-Me—Ph | H | H | CH₂CH(CH₃)₂ | Bz | H | CH₃ | F | OH |
| XXI-46-5 | p-Me—Ph | H | H | CH₂Ph | Bz | H | CH₃ | F | OH |
| XXI-46-6 | p-Me—Ph | H | H | CH₂-indol-3-yl | Bz | H | CH₃ | F | OH |
| XXI-46-7 | p-Me—Ph | H | H | CH₂CH₂SCH₃ | Bz | H | CH₃ | F | OH |
| XXI-46-8 | p-Me—Ph | * | H | * | Bz | H | CH₃ | F | OH |

*R² and R³ᵇ joined together by (CH₂)₃ to form five-membered ring.

TABLE XXI-47

| No | R¹ | R² | R³ᵃ | R³ᵇ | R⁴ | R⁵ | R⁶ | X | Y |
|---|---|---|---|---|---|---|---|---|---|
| XXI-47-1 | p-F—Ph | H | H | H | Bz | H | CH₃ | F | OH |
| XXI-47-2 | p-F—Ph | H | H | CH₃ | Bz | H | CH₃ | F | OH |
| XXI-47-3 | p-F—Ph | H | H | CH(CH₃)₂ | Bz | H | CH₃ | F | OH |
| XXI-47-4 | p-F—Ph | H | H | CH₂CH(CH₃)₂ | Bz | H | CH₃ | F | OH |
| XXI-47-5 | p-F—Ph | H | H | CH₂Ph | Bz | H | CH₃ | F | OH |
| XXI-47-6 | p-F—Ph | H | H | CH₂-indol-3-yl | Bz | H | CH₃ | F | OH |
| XXI-47-7 | p-F—Ph | H | H | CH₂CH₂SCH₃ | Bz | H | CH₃ | F | OH |
| XXI-47-8 | p-F—Ph | * | H | * | Bz | H | CH₃ | F | OH |

*R² and R³ᵇ joined together by (CH₂)₃ to form five-membered ring.

TABLE XXI-48

| No | R¹ | R² | R³ᵃ | R³ᵇ | R⁴ | R⁵ | R⁶ | X | Y |
|---|---|---|---|---|---|---|---|---|---|
| XXI-48-1 | p-Cl—Ph | H | H | H | Bz | H | CH₃ | F | OH |
| XXI-48-2 | p-Cl—Ph | H | H | CH₃ | Bz | H | CH₃ | F | OH |
| XXI-48-3 | p-Cl—Ph | H | H | CH(CH₃)₂ | Bz | H | CH₃ | F | OH |
| XXI-48-4 | p-Cl—Ph | H | H | CH₂CH(CH₃)₂ | Bz | H | CH₃ | F | OH |
| XXI-48-5 | p-Cl—Ph | H | H | CH₂Ph | Bz | H | CH₃ | F | OH |
| XXI-48-6 | p-Cl—Ph | H | H | CH₂-indol-3-yl | Bz | H | CH₃ | F | OH |
| XXI-48-7 | p-Cl—Ph | H | H | CH₂CH₂SCH₃ | Bz | H | CH₃ | F | OH |
| XXI-48-8 | p-Cl—Ph | * | H | * | Bz | H | CH₃ | F | OH |

*R² and R³ᵇ joined together by (CH₂)₃ to form five-membered ring.

TABLE XXI-49

| No | R¹ | R² | R³ᵃ | R³ᵇ | R⁴ | R⁵ | R⁶ | X | Y |
|---|---|---|---|---|---|---|---|---|---|
| XXI-49-1 | p-Br—Ph | H | H | H | Bz | H | CH₃ | F | OH |
| XXI-49-2 | p-Br—Ph | H | H | CH₃ | Bz | H | CH₃ | F | OH |
| XXI-49-3 | p-Br—Ph | H | H | CH(CH₃)₂ | Bz | H | CH₃ | F | OH |

TABLE XXI-49-continued

| No | R¹ | R² | R³ᵃ | R³ᵇ | R⁴ | R⁵ | R⁶ | X | Y |
|---|---|---|---|---|---|---|---|---|---|
| XXI-49-4 | p-Br—Ph | H | H | CH₂CH(CH₃)₂ | Bz | H | CH₃ | F | OH |
| XXI-49-5 | p-Br—Ph | H | H | CH₂Ph | Bz | H | CH₃ | F | OH |
| XXI-49-6 | p-Br—Ph | H | H | CH₂-indol-3-yl | Bz | H | CH₃ | F | OH |
| XXI-49-7 | p-Br—Ph | H | H | CH₂CH₂SCH₃ | Bz | H | CH₃ | F | OH |
| XXI-49-8 | p-Br—Ph | * | H | * | Bz | H | CH₃ | F | OH |

*R² and R³ᵇ joined together by (CH₂)₃ to form five-membered ring.

TABLE XXI-50

| No | R¹ | R² | R³ᵃ | R³ᵇ | R⁴ | R⁵ | R⁶ | X | Y |
|---|---|---|---|---|---|---|---|---|---|
| XXI-50-1 | p-I—Ph | H | H | H | Bz | H | CH₃ | F | OH |
| XXI-50-2 | p-I—Ph | H | H | CH₃ | Bz | H | CH₃ | F | OH |
| XXI-50-3 | p-I—Ph | H | H | CH(CH₃)₂ | Bz | H | CH₃ | F | OH |
| XXI-50-4 | p-I—Ph | H | H | CH₂CH(CH₃)₂ | Bz | H | CH₃ | F | OH |
| XXI-50-5 | p-I—Ph | H | H | CH₂Ph | Bz | H | CH₃ | F | OH |
| XXI-50-6 | p-I—Ph | H | H | CH₂-indol-3-yl | Bz | H | CH₃ | F | OH |
| XXI-50-7 | p-I—Ph | H | H | CH₂CH₂SCH₃ | Bz | H | CH₃ | F | OH |
| XXI-50-8 | p-I—Ph | * | H | * | Bz | H | CH₃ | F | OH |

*R² and R³ᵇ joined together by (CH₂)₃ to form five-membered ring.

XXII

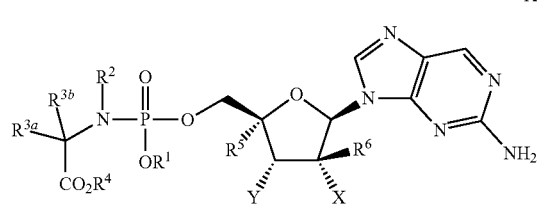

TABLE XXII-1

| No | R¹ | R² | R³ᵃ | R³ᵇ | R⁴ | R⁵ | R⁶ | X | Y |
|---|---|---|---|---|---|---|---|---|---|
| XXII-1-1 | CH₃ | H | H | H | CH₃ | H | F | H | OH |
| XXII-1-2 | CH₃ | H | H | CH₃ | CH₃ | H | F | H | OH |
| XXII-1-3 | CH₃ | H | H | CH(CH₃)₂ | CH₃ | H | F | H | OH |
| XXII-1-4 | CH₃ | H | H | CH₂CH(CH₃)₂ | CH₃ | H | F | H | OH |
| XXII-1-5 | CH₃ | H | H | CH₂Ph | CH₃ | H | F | H | OH |
| XXII-1-6 | CH₃ | H | H | CH₂-indol-3-yl | CH₃ | H | F | H | OH |
| XXII-1-7 | CH₃ | H | H | CH₂CH₂SCH₃ | CH₃ | H | F | H | OH |
| XXII-1-8 | CH₃ | * | H | * | CH₃ | H | F | H | OH |

*R² and R³ᵇ joined together by (CH₂)₃ to form five-membered ring.

TABLE XXII-2

| No | R¹ | R² | R³ᵃ | R³ᵇ | R⁴ | R⁵ | R⁶ | X | Y |
|---|---|---|---|---|---|---|---|---|---|
| XXII-2-1 | Et | H | H | H | CH₃ | H | F | H | OH |
| XXII-2-2 | Et | H | H | CH₃ | CH₃ | H | F | H | OH |
| XXII-2-3 | Et | H | H | CH(CH₃)₂ | CH₃ | H | F | H | OH |
| XXII-2-4 | Et | H | H | CH₂CH(CH₃)₂ | CH₃ | H | F | H | OH |
| XXII-2-5 | Et | H | H | CH₂Ph | CH₃ | H | F | H | OH |
| XXII-2-6 | Et | H | H | CH₂-indol-3-yl | CH₃ | H | F | H | OH |
| XXII-2-7 | Et | H | H | CH₂CH₂SCH₃ | CH₃ | H | F | H | OH |
| XXII-2-8 | Et | * | H | * | CH₃ | H | F | H | OH |

*R² and R³ᵇ joined together by (CH₂)₃ to form five-membered ring.

TABLE XXII-3

| No | R¹ | R² | R³ᵃ | R³ᵇ | R⁴ | R⁵ | R⁶ | X | Y |
|---|---|---|---|---|---|---|---|---|---|
| XXII-3-1 | ⁱPr | H | H | H | CH₃ | H | F | H | OH |
| XXII-3-2 | ⁱPr | H | H | CH₃ | CH₃ | H | F | H | OH |
| XXII-3-3 | ⁱPr | H | H | CH(CH₃)₂ | CH₃ | H | F | H | OH |
| XXII-3-4 | ⁱPr | H | H | CH₂CH(CH₃)₂ | CH₃ | H | F | H | OH |
| XXII-3-5 | ⁱPr | H | H | CH₂Ph | CH₃ | H | F | H | OH |
| XXII-3-6 | ⁱPr | H | H | CH₂-indol-3-yl | CH₃ | H | F | H | OH |
| XXII-3-7 | ⁱPr | H | H | CH₂CH₂SCH₃ | CH₃ | H | F | H | OH |
| XXII-3-8 | ⁱPr | * | H | * | CH₃ | H | F | H | OH |

*R² and R³ᵇ joined together by (CH₂)₃ to form five-membered ring.

TABLE XXII-4

| No | R¹ | R² | R³ᵃ | R³ᵇ | R⁴ | R⁵ | R⁶ | X | Y |
|---|---|---|---|---|---|---|---|---|---|
| XXII-4-1 | ᵗBu | H | H | H | CH₃ | H | F | H | OH |
| XXII-4-2 | ᵗBu | H | H | CH₃ | CH₃ | H | F | H | OH |
| XXII-4-3 | ᵗBu | H | H | CH(CH₃)₂ | CH₃ | H | F | H | OH |
| XXII-4-4 | ᵗBu | H | H | CH₂CH(CH₃)₂ | CH₃ | H | F | H | OH |
| XXII-4-5 | ᵗBu | H | H | CH₂Ph | CH₃ | H | F | H | OH |
| XXII-4-6 | ᵗBu | H | H | CH₂-indol-3-yl | CH₃ | H | F | H | OH |
| XXII-4-7 | ᵗBu | H | H | CH₂CH₂SCH₃ | CH₃ | H | F | H | OH |
| XXII-4-8 | ᵗBu | * | H | * | CH₃ | H | F | H | OH |

*R² and R³ᵇ joined together by (CH₂)₃ to form five-membered ring.

TABLE XXII-5

| No | R¹ | R² | R³ᵃ | R³ᵇ | R⁴ | R⁵ | R⁶ | X | Y |
|---|---|---|---|---|---|---|---|---|---|
| XXII-5-1 | Ph | H | H | H | CH₃ | H | F | H | OH |
| XXII-5-2 | Ph | H | H | CH₃ | CH₃ | H | F | H | OH |
| XXII-5-3 | Ph | H | H | CH(CH₃)₂ | CH₃ | H | F | H | OH |
| XXII-5-4 | Ph | H | H | CH₂CH(CH₃)₂ | CH₃ | H | F | H | OH |
| XXII-5-5 | Ph | H | H | CH₂Ph | CH₃ | H | F | H | OH |
| XXII-5-6 | Ph | H | H | CH₂-indol-3-yl | CH₃ | H | F | H | OH |
| XXII-5-7 | Ph | H | H | CH₂CH₂SCH₃ | CH₃ | H | F | H | OH |
| XXII-5-8 | Ph | * | H | * | CH₃ | H | F | H | OH |

*R² and R³ᵇ joined together by (CH₂)₃ to form five-membered ring.

TABLE XXII-6

| No | R¹ | R² | R³ᵃ | R³ᵇ | R⁴ | R⁵ | R⁶ | X | Y |
|---|---|---|---|---|---|---|---|---|---|
| XXII-6-1 | p-Me—Ph | H | H | H | CH₃ | H | F | H | OH |
| XXII-6-2 | p-Me—Ph | H | H | CH₃ | CH₃ | H | F | H | OH |
| XXII-6-3 | p-Me—Ph | H | H | CH(CH₃)₂ | CH₃ | H | F | H | OH |
| XXII-6-4 | p-Me—Ph | H | H | CH₂CH(CH₃)₂ | CH₃ | H | F | H | OH |
| XXII-6-5 | p-Me—Ph | H | H | CH₂Ph | CH₃ | H | F | H | OH |
| XXII-6-6 | p-Me—Ph | H | H | CH₂-indol-3-yl | CH₃ | H | F | H | OH |
| XXII-6-7 | p-Me—Ph | H | H | CH₂CH₂SCH₃ | CH₃ | H | F | H | OH |
| XXII-6-8 | p-Me—Ph | * | H | * | CH₃ | H | F | H | OH |

*R² and R³ᵇ joined together by (CH₂)₃ to form five-membered ring.

TABLE XXII-7

| No | R¹ | R² | R³ᵃ | R³ᵇ | R⁴ | R⁵ | R⁶ | X | Y |
|---|---|---|---|---|---|---|---|---|---|
| XXII-7-1 | p-F—Ph | H | H | H | CH₃ | H | F | H | OH |
| XXII-7-2 | p-F—Ph | H | H | CH₃ | CH₃ | H | F | H | OH |
| XXII-7-3 | p-F—Ph | H | H | CH(CH₃)₂ | CH₃ | H | F | H | OH |
| XXII-7-4 | p-F—Ph | H | H | CH₂CH(CH₃)₂ | CH₃ | H | F | H | OH |
| XXII-7-5 | p-F—Ph | H | H | CH₂Ph | CH₃ | H | F | H | OH |

TABLE XXII-7-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-7-7 | p-F—Ph | H | H | CH$_2$-indol-3-yl | CH$_3$ | H | F | H | OH |
| XXII-7-8 | p-F—Ph | H | H | CH$_2$CH$_2$SCH$_3$ | CH$_3$ | H | F | H | OH |
| XXII-7-20 | p-F—Ph | * | H | * | CH$_3$ | H | F | H | OH |

*$R^2$ and $R^{3b}$ joined together by (CH$_2$)$_3$ to form five-membered ring.

TABLE XXII-8

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-8-1 | p-Cl—Ph | H | H | H | CH$_3$ | H | F | H | OH |
| XXII-8-2 | p-Cl—Ph | H | H | CH$_3$ | CH$_3$ | H | F | H | OH |
| XXII-8-3 | p-Cl—Ph | H | H | CH(CH$_3$)$_2$ | CH$_3$ | H | F | H | OH |
| XXII-8-4 | p-Cl—Ph | H | H | CH$_2$CH(CH$_3$)$_2$ | CH$_3$ | H | F | H | OH |
| XXII-8-5 | p-Cl—Ph | H | H | CH$_2$Ph | CH$_3$ | H | F | H | OH |
| XXII-8-6 | p-Cl—Ph | H | H | CH$_2$-indol-3-yl | CH$_3$ | H | F | H | OH |
| XXII-8-7 | p-Cl—Ph | H | H | CH$_2$CH$_2$SCH$_3$ | CH$_3$ | H | F | H | OH |
| XXII-8-8 | p-Cl—Ph | * | H | * | CH$_3$ | H | F | H | OH |

*$R^2$ and $R^{3b}$ joined together by (CH$_2$)$_3$ to form five-membered ring.

TABLE XXII-9

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-9-1 | p-Br—Ph | H | H | H | CH$_3$ | H | F | H | OH |
| XXII-9-2 | p-Br—Ph | H | H | CH$_3$ | CH$_3$ | H | F | H | OH |
| XXII-9-3 | p-Br—Ph | H | H | CH(CH$_3$)$_2$ | CH$_3$ | H | F | H | OH |
| XXII-9-4 | p-Br—Ph | H | H | CH$_2$CH(CH$_3$)$_2$ | CH$_3$ | H | F | H | OH |
| XXII-9-6 | p-Br—Ph | H | H | CH$_2$Ph | CH$_3$ | H | F | H | OH |
| XXII-9-7 | p-Br—Ph | H | H | CH$_2$-indol-3-yl | CH$_3$ | H | F | H | OH |
| XXII-9-8 | p-Br—Ph | H | H | CH$_2$CH$_2$SCH$_3$ | CH$_3$ | H | F | H | OH |
| XXII-9-20 | p-Br—Ph | * | H | * | CH$_3$ | H | F | H | OH |

*$R^2$ and $R^{3b}$ joined together by (CH$_2$)$_3$ to form five-membered ring.

TABLE XXII-10

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-10-1 | p-I—Ph | H | H | H | CH$_3$ | H | F | H | OH |
| XXII-10-2 | p-I—Ph | H | H | CH$_3$ | CH$_3$ | H | F | H | OH |
| XXII-10-3 | p-I—Ph | H | H | CH(CH$_3$)$_2$ | CH$_3$ | H | F | H | OH |
| XXII-10-4 | p-I—Ph | H | H | CH$_2$CH(CH$_3$)$_2$ | CH$_3$ | H | F | H | OH |
| XXII-10-5 | p-I—Ph | H | H | CH$_2$Ph | CH$_3$ | H | F | H | OH |
| XXII-10-6 | p-I—Ph | H | H | CH$_2$-indol-3-yl | CH$_3$ | H | F | H | OH |
| XXII-10-7 | p-I—Ph | H | H | CH$_2$CH$_2$SCH$_3$ | CH$_3$ | H | F | H | OH |
| XXII-10-8 | p-I—Ph | * | H | * | CH$_3$ | H | F | H | OH |

*$R^2$ and $R^{3b}$ joined together by (CH$_2$)$_3$ to form five-membered ring.

TABLE XXII-11

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-11-1 | CH$_3$ | H | H | H | Et | H | F | H | OH |
| XXII-11-2 | CH$_3$ | H | H | CH$_3$ | Et | H | F | H | OH |
| XXII-11-3 | CH$_3$ | H | H | CH(CH$_3$)$_2$ | Et | H | F | H | OH |
| XXII-11-4 | CH$_3$ | H | H | CH$_2$CH(CH$_3$)$_2$ | Et | H | F | H | OH |
| XXII-11-5 | CH$_3$ | H | H | CH$_2$Ph | Et | H | F | H | OH |
| XXII-11-6 | CH$_3$ | H | H | CH$_2$-indol-3-yl | Et | H | F | H | OH |
| XXII-11-7 | CH$_3$ | H | H | CH$_2$CH$_2$SCH$_3$ | Et | H | F | H | OH |
| XXII-11-8 | CH$_3$ | * | H | * | Et | H | F | H | OH |

*$R^2$ and $R^{3b}$ joined together by (CH$_2$)$_3$ to form five-membered ring.

TABLE XXII-12

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-12-1 | Et | H | H | H | Et | H | F | H | OH |
| XXII-12-2 | Et | H | H | CH$_3$ | Et | H | F | H | OH |
| XXII-12-3 | Et | H | H | CH(CH$_3$)$_2$ | Et | H | F | H | OH |
| XXII-12-4 | Et | H | H | CH$_2$CH(CH$_3$)$_2$ | Et | H | F | H | OH |
| XXII-12-5 | Et | H | H | CH$_2$Ph | Et | H | F | H | OH |
| XXII-12-6 | Et | H | H | CH$_2$-indol-3-yl | Et | H | F | H | OH |
| XXII-12-7 | Et | H | H | CH$_2$CH$_2$SCH$_3$ | Et | H | F | H | OH |
| XXII-12-8 | Et | * | H | * | Et | H | F | H | OH |

*$R^2$ and $R^{3b}$ joined together by (CH$_2$)$_3$ to form five-membered ring.

TABLE XXII-13

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-13-1 | $^i$Pr | H | H | H | Et | H | F | H | OH |
| XXII-13-2 | $^i$Pr | H | H | CH$_3$ | Et | H | F | H | OH |
| XXII-13-3 | $^i$Pr | H | H | CH(CH$_3$)$_2$ | Et | H | F | H | OH |
| XXII-13-4 | $^i$Pr | H | H | CH$_2$CH(CH$_3$)$_2$ | Et | H | F | H | OH |
| XXII-13-5 | $^i$Pr | H | H | CH$_2$Ph | Et | H | F | H | OH |
| XXII-13-6 | $^i$Pr | H | H | CH$_2$-indol-3-yl | Et | H | F | H | OH |
| XXII-13-7 | $^i$Pr | H | H | CH$_2$CH$_2$SCH$_3$ | Et | H | F | H | OH |
| XXII-13-8 | $^i$Pr | * | H | * | Et | H | F | H | OH |

*$R^2$ and $R^{3b}$ joined together by (CH$_2$)$_3$ to form five-membered ring.

TABLE XXII-14

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-14-1 | $^t$Bu | H | H | H | Et | H | F | H | OH |
| XXII-14-2 | $^t$Bu | H | H | CH$_3$ | Et | H | F | H | OH |
| XXII-14-3 | $^t$Bu | H | H | CH(CH$_3$)$_2$ | Et | H | F | H | OH |
| XXII-14-4 | $^t$Bu | H | H | CH$_2$CH(CH$_3$)$_2$ | Et | H | F | H | OH |
| XXII-14-5 | $^t$Bu | H | H | CH$_2$Ph | Et | H | F | H | OH |
| XXII-14-6 | $^t$Bu | H | H | CH$_2$-indol-3-yl | Et | H | F | H | OH |
| XXII-14-7 | $^t$Bu | H | H | CH$_2$CH$_2$SCH$_3$ | Et | H | F | H | OH |
| XXII-14-8 | $^t$Bu | * | H | * | Et | H | F | H | OH |

*$R^2$ and $R^{3b}$ joined together by (CH$_2$)$_3$ to form five-membered ring.

TABLE XXII-15

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-15-1 | Ph | H | H | H | Et | H | F | H | OH |
| XXII-15-2 | Ph | H | H | CH$_3$ | Et | H | F | H | OH |
| XXII-15-3 | Ph | H | H | CH(CH$_3$)$_2$ | Et | H | F | H | OH |
| XXII-15-4 | Ph | H | H | CH$_2$CH(CH$_3$)$_2$ | Et | H | F | H | OH |
| XXII-15-5 | Ph | H | H | CH$_2$Ph | Et | H | F | H | OH |
| XXII-15-6 | Ph | H | H | CH$_2$-indol-3-yl | Et | H | F | H | OH |
| XXII-15-7 | Ph | H | H | CH$_2$CH$_2$SCH$_3$ | Et | H | F | H | OH |
| XXII-15-8 | Ph | * | H | * | Et | H | F | H | OH |

*$R^2$ and $R^{3b}$ joined together by (CH$_2$)$_3$ to form five-membered ring.

TABLE XXII-16

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-16-1 | p-Me—Ph | H | H | H | Et | H | F | H | OH |
| XXII-16-2 | p-Me—Ph | H | H | CH$_3$ | Et | H | F | H | OH |
| XXII-16-3 | p-Me—Ph | H | H | CH(CH$_3$)$_2$ | Et | H | F | H | OH |
| XXII-16-4 | p-Me—Ph | H | H | CH$_2$CH(CH$_3$)$_2$ | Et | H | F | H | OH |
| XXII-16-5 | p-Me—Ph | H | H | CH$_2$Ph | Et | H | F | H | OH |
| XXII-16-6 | p-Me—Ph | H | H | CH$_2$-indol-3-yl | Et | H | F | H | OH |
| XXII-16-7 | p-Me—Ph | H | H | CH$_2$CH$_2$SCH$_3$ | Et | H | F | H | OH |
| XXII-16-8 | p-Me—Ph | * | H | * | Et | H | F | H | OH |

*$R^2$ and $R^{3b}$ joined together by (CH$_2$)$_3$ to form five-membered ring.

TABLE XXII-17

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-17-1 | p-F—Ph | H | H | H | Et | H | F | H | OH |
| XXII-17-2 | p-F—Ph | H | H | CH$_3$ | Et | H | F | H | OH |
| XXII-17-3 | p-F—Ph | H | H | CH(CH$_3$)$_2$ | Et | H | F | H | OH |
| XXII-17-4 | p-F—Ph | H | H | CH$_2$CH(CH$_3$)$_2$ | Et | H | F | H | OH |
| XXII-17-5 | p-F—Ph | H | H | CH$_2$Ph | Et | H | F | H | OH |
| XXII-17-6 | p-F—Ph | H | H | CH$_2$-indol-3-yl | Et | H | F | H | OH |
| XXII-17-7 | p-F—Ph | H | H | CH$_2$CH$_2$SCH$_3$ | Et | H | F | H | OH |
| XXII-17-8 | p-F—Ph | * | H | * | Et | H | F | H | OH |

*$R^2$ and $R^{3b}$ joined together by (CH$_2$)$_3$ to form five-membered ring.

TABLE XXII-18

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-18-1 | p-Cl—Ph | H | H | H | Et | H | F | H | OH |
| XXII-18-2 | p-Cl—Ph | H | H | CH$_3$ | Et | H | F | H | OH |
| XXII-18-3 | p-Cl—Ph | H | H | CH(CH$_3$)$_2$ | Et | H | F | H | OH |
| XXII-18-4 | p-Cl—Ph | H | H | CH$_2$CH(CH$_3$)$_2$ | Et | H | F | H | OH |
| XXII-18-5 | p-Cl—Ph | H | H | CH$_2$Ph | Et | H | F | H | OH |
| XXII-18-6 | p-Cl—Ph | H | H | CH$_2$-indol-3-yl | Et | H | F | H | OH |
| XXII-18-7 | p-Cl—Ph | H | H | CH$_2$CH$_2$SCH$_3$ | Et | H | F | H | OH |
| XXII-18-8 | p-Cl—Ph | * | H | * | Et | H | F | H | OH |

*$R^2$ and $R^{3b}$ joined together by (CH$_2$)$_3$ to form five-membered ring.

TABLE XXII-19

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-19-1 | p-Br—Ph | H | H | H | Et | H | F | H | OH |
| XXII-19-2 | p-Br—Ph | H | H | CH$_3$ | Et | H | F | H | OH |
| XXII-19-3 | p-Br—Ph | H | H | CH(CH$_3$)$_2$ | Et | H | F | H | OH |
| XXII-19-4 | p-Br—Ph | H | H | CH$_2$CH(CH$_3$)$_2$ | Et | H | F | H | OH |
| XXII-19-5 | p-Br—Ph | H | H | CH$_2$Ph | Et | H | F | H | OH |
| XXII-19-6 | p-Br—Ph | H | H | CH$_2$-indol-3-yl | Et | H | F | H | OH |
| XXII-19-7 | p-Br—Ph | H | H | CH$_2$CH$_2$SCH$_3$ | Et | H | F | H | OH |
| XXII-19-8 | p-Br—Ph | * | H | * | Et | H | F | H | OH |

*$R^2$ and $R^{3b}$ joined together by (CH$_2$)$_3$ to form five-membered ring.

TABLE XXII-20

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-20-1 | p-I—Ph | H | H | H | Et | H | F | H | OH |
| XXII-20-2 | p-I—Ph | H | H | CH$_3$ | Et | H | F | H | OH |
| XXII-20-3 | p-I—Ph | H | H | CH(CH$_3$)$_2$ | Et | H | F | H | OH |
| XXII-20-4 | p-I—Ph | H | H | CH$_2$CH(CH$_3$)$_2$ | Et | H | F | H | OH |
| XXII-20-5 | p-I—Ph | H | H | CH$_2$Ph | Et | H | F | H | OH |
| XXII-20-6 | p-I—Ph | H | H | CH$_2$-indol-3-yl | Et | H | F | H | OH |
| XXII-20-7 | p-I—Ph | H | H | CH$_2$CH$_2$SCH$_3$ | Et | H | F | H | OH |
| XXII-20-8 | p-I—Ph | * | H | * | Et | H | F | H | OH |

*$R^2$ and $R^{3b}$ joined together by (CH$_2$)$_3$ to form five-membered ring.

TABLE XXII-21

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-21-1 | CH$_3$ | H | H | H | $^i$Pr | H | F | H | OH |
| XXII-21-2 | CH$_3$ | H | H | CH$_3$ | $^i$Pr | H | F | H | OH |
| XXII-21-3 | CH$_3$ | H | H | CH(CH$_3$)$_2$ | $^i$Pr | H | F | H | OH |
| XXII-21-4 | CH$_3$ | H | H | CH$_2$CH(CH$_3$)$_2$ | $^i$Pr | H | F | H | OH |
| XXII-21-5 | CH$_3$ | H | H | CH$_2$Ph | $^i$Pr | H | F | H | OH |
| XXII-21-6 | CH$_3$ | H | H | CH$_2$-indol-3-yl | $^i$Pr | H | F | H | OH |
| XXII-21-7 | CH$_3$ | H | H | CH$_2$CH$_2$SCH$_3$ | $^i$Pr | H | F | H | OH |
| XXII-21-8 | CH$_3$ | * | H | * | $^i$Pr | H | F | H | OH |

*$R^2$ and $R^{3b}$ joined together by (CH$_2$)$_3$ to form five-membered ring.

TABLE XXII-22

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-22-1 | Et | H | H | H | $^i$Pr | H | F | H | OH |
| XXII-22-2 | Et | H | H | CH$_3$ | $^i$Pr | H | F | H | OH |
| XXII-22-3 | Et | H | H | CH(CH$_3$)$_2$ | $^i$Pr | H | F | H | OH |
| XXII-22-4 | Et | H | H | CH$_2$CH(CH$_3$)$_2$ | $^i$Pr | H | F | H | OH |
| XXII-22-5 | Et | H | H | CH$_2$Ph | $^i$Pr | H | F | H | OH |
| XXII-22-6 | Et | H | H | CH$_2$-indol-3-yl | $^i$Pr | H | F | H | OH |
| XXII-22-7 | Et | H | H | CH$_2$CH$_2$SCH$_3$ | $^i$Pr | H | F | H | OH |
| XXII-22-8 | Et | * | H | * | $^i$Pr | H | F | H | OH |

*$R^2$ and $R^{3b}$ joined together by (CH$_2$)$_3$ to form five-membered ring.

TABLE XXII-23

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-23-1 | $^i$Pr | H | H | H | $^i$Pr | H | F | H | OH |
| XXII-23-2 | $^i$Pr | H | H | CH$_3$ | $^i$Pr | H | F | H | OH |
| XXII-23-3 | $^i$Pr | H | H | CH(CH$_3$)$_2$ | $^i$Pr | H | F | H | OH |
| XXII-23-4 | $^i$Pr | H | H | CH$_2$CH(CH$_3$)$_2$ | $^i$Pr | H | F | H | OH |
| XXII-23-5 | $^i$Pr | H | H | CH$_2$Ph | $^i$Pr | H | F | H | OH |
| XXII-23-6 | $^i$Pr | H | H | CH$_2$-indol-3-yl | $^i$Pr | H | F | H | OH |
| XXII-23-7 | $^i$Pr | H | H | CH$_2$CH$_2$SCH$_3$ | $^i$Pr | H | F | H | OH |
| XXII-23-8 | $^i$Pr | * | H | * | $^i$Pr | H | F | H | OH |

*$R^2$ and $R^{3b}$ joined together by (CH$_2$)$_3$ to form five-membered ring.

TABLE XXII-24

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-24-1 | $^t$Bu | H | H | H | $^i$Pr | H | F | H | OH |
| XXII-24-2 | $^t$Bu | H | H | CH$_3$ | $^i$Pr | H | F | H | OH |
| XXII-24-3 | $^t$Bu | H | H | CH(CH$_3$)$_2$ | $^i$Pr | H | F | H | OH |
| XXII-24-4 | $^t$Bu | H | H | CH$_2$CH(CH$_3$)$_2$ | $^i$Pr | H | F | H | OH |
| XXII-24-5 | $^t$Bu | H | H | CH$_2$Ph | $^i$Pr | H | F | H | OH |
| XXII-24-6 | $^t$Bu | H | H | CH$_2$-indol-3-yl | $^i$Pr | H | F | H | OH |
| XXII-24-7 | $^t$Bu | H | H | CH$_2$CH$_2$SCH$_3$ | $^i$Pr | H | F | H | OH |
| XXII-24-8 | $^t$Bu | * | H | * | $^i$Pr | H | F | H | OH |

*$R^2$ and $R^{3b}$ joined together by (CH$_2$)$_3$ to form five-membered ring.

TABLE XXII-25

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-25-1 | Ph | H | H | H | $^i$Pr | H | F | H | OH |
| XXII-25-2 | Ph | H | H | CH$_3$ | $^i$Pr | H | F | H | OH |
| XXII-25-3 | Ph | H | H | CH(CH$_3$)$_2$ | $^i$Pr | H | F | H | OH |
| XXII-25-4 | Ph | H | H | CH$_2$CH(CH$_3$)$_2$ | $^i$Pr | H | F | H | OH |
| XXII-25-5 | Ph | H | H | CH$_2$Ph | $^i$Pr | H | F | H | OH |
| XXII-25-6 | Ph | H | H | CH$_2$-indol-3-yl | $^i$Pr | H | F | H | OH |
| XXII-25-7 | Ph | H | H | CH$_2$CH$_2$SCH$_3$ | $^i$Pr | H | F | H | OH |
| XXII-25-8 | Ph | * | H | * | $^i$Pr | H | F | H | OH |

*$R^2$ and $R^{3b}$ joined together by (CH$_2$)$_3$ to form five-membered ring.

TABLE XXII-26

| No | R¹ | R² | R³ᵃ | R³ᵇ | R⁴ | R⁵ | R⁶ | X | Y |
|---|---|---|---|---|---|---|---|---|---|
| XXII-26-1 | p-Me—Ph | H | H | H | $^i$Pr | H | F | H | OH |
| XXII-26-2 | p-Me—Ph | H | H | CH₃ | $^i$Pr | H | F | H | OH |
| XXII-26-3 | p-Me—Ph | H | H | CH(CH₃)₂ | $^i$Pr | H | F | H | OH |
| XXII-26-4 | p-Me—Ph | H | H | CH₂CH(CH₃)₂ | $^i$Pr | H | F | H | OH |
| XXII-26-5 | p-Me—Ph | H | H | CH₂Ph | $^i$Pr | H | F | H | OH |
| XXII-26-6 | p-Me—Ph | H | H | CH₂-indol-3-yl | $^i$Pr | H | F | H | OH |
| XXII-26-7 | p-Me—Ph | H | H | CH₂CH₂SCH₃ | $^i$Pr | H | F | H | OH |
| XXII-26-8 | p-Me—Ph | * | H | * | $^i$Pr | H | F | H | OH |

*R² and R³ᵇ joined together by (CH₂)₃ to form five-membered ring.

TABLE XXII-27

| No | R¹ | R² | R³ᵃ | R³ᵇ | R⁴ | R⁵ | R⁶ | X | Y |
|---|---|---|---|---|---|---|---|---|---|
| XXII-27-1 | p-F—Ph | H | H | H | $^i$Pr | H | F | H | OH |
| XXII-27-2 | p-F—Ph | H | H | CH₃ | $^i$Pr | H | F | H | OH |
| XXII-27-3 | p-F—Ph | H | H | CH(CH₃)₂ | $^i$Pr | H | F | H | OH |
| XXII-27-4 | p-F—Ph | H | H | CH₂CH(CH₃)₂ | $^i$Pr | H | F | H | OH |
| XXII-27-5 | p-F—Ph | H | H | CH₂Ph | $^i$Pr | H | F | H | OH |
| XXII-27-6 | p-F—Ph | H | H | CH₂-indol-3-yl | $^i$Pr | H | F | H | OH |
| XXII-27-7 | p-F—Ph | H | H | CH₂CH₂SCH₃ | $^i$Pr | H | F | H | OH |
| XXII-27-8 | p-F—Ph | * | H | * | $^i$Pr | H | F | H | OH |

*R² and R³ᵇ joined together by (CH₂)₃ to form five-membered ring.

TABLE XXII-28

| No | R¹ | R² | R³ᵃ | R³ᵇ | R⁴ | R⁵ | R⁶ | X | Y |
|---|---|---|---|---|---|---|---|---|---|
| XXII-28-1 | p-Cl—Ph | H | H | H | $^i$Pr | H | F | H | OH |
| XXII-28-2 | p-Cl—Ph | H | H | CH₃ | $^i$Pr | H | F | H | OH |
| XXII-28-3 | p-Cl—Ph | H | H | CH(CH₃)₂ | $^i$Pr | H | F | H | OH |
| XXII-28-4 | p-Cl—Ph | H | H | CH₂CH(CH₃)₂ | $^i$Pr | H | F | H | OH |
| XXII-28-5 | p-Cl—Ph | H | H | CH₂Ph | $^i$Pr | H | F | H | OH |
| XXII-28-6 | p-Cl—Ph | H | H | CH₂-indol-3-yl | $^i$Pr | H | F | H | OH |
| XXII-28-7 | p-Cl—Ph | H | H | CH₂CH₂SCH₃ | $^i$Pr | H | F | H | OH |
| XXII-28-8 | p-Cl—Ph | * | H | * | $^i$Pr | H | F | H | OH |

*R² and R³ᵇ joined together by (CH₂)₃ to form five-membered ring.

TABLE XXII-29

| No | R¹ | R² | R³ᵃ | R³ᵇ | R⁴ | R⁵ | R⁶ | X | Y |
|---|---|---|---|---|---|---|---|---|---|
| XXII-29-1 | p-Br—Ph | H | H | H | $^i$Pr | H | F | H | OH |
| XXII-29-2 | p-Br—Ph | H | H | CH₃ | $^i$Pr | H | F | H | OH |
| XXII-29-3 | p-Br—Ph | H | H | CH(CH₃)₂ | $^i$Pr | H | F | H | OH |
| XXII-29-4 | p-Br—Ph | H | H | CH₂CH(CH₃)₂ | $^i$Pr | H | F | H | OH |
| XXII-29-5 | p-Br—Ph | H | H | CH₂Ph | $^i$Pr | H | F | H | OH |
| XXII-29-6 | p-Br—Ph | H | H | CH₂-indol-3-yl | $^i$Pr | H | F | H | OH |
| XXII-29-7 | p-Br—Ph | H | H | CH₂CH₂SCH₃ | $^i$Pr | H | F | H | OH |
| XXII-29-8 | p-Br—Ph | * | H | * | $^i$Pr | H | F | H | OH |

*R² and R³ᵇ joined together by (CH₂)₃ to form five-membered ring.

TABLE XXII-30

| No | R¹ | R² | R³ᵃ | R³ᵇ | R⁴ | R⁵ | R⁶ | X | Y |
|---|---|---|---|---|---|---|---|---|---|
| XXII-30-1 | p-I—Ph | H | H | H | $^i$Pr | H | F | H | OH |
| XXII-30-2 | p-I—Ph | H | H | CH₃ | $^i$Pr | H | F | H | OH |
| XXII-30-3 | p-I—Ph | H | H | CH(CH₃)₂ | $^i$Pr | H | F | H | OH |
| XXII-30-4 | p-I—Ph | H | H | CH₂CH(CH₃)₂ | $^i$Pr | H | F | H | OH |
| XXII-30-5 | p-I—Ph | H | H | CH₂Ph | $^i$Pr | H | F | H | OH |
| XXII-30-6 | p-I—Ph | H | H | CH₂-indol-3-yl | $^i$Pr | H | F | H | OH |
| XXII-30-7 | p-I—Ph | H | H | CH₂CH₂SCH₃ | $^i$Pr | H | F | H | OH |
| XXII-30-8 | p-I—Ph | * | H | * | $^i$Pr | H | F | H | OH |

*R² and R³ᵇ joined together by (CH₂)₃ to form five-membered ring.

TABLE XXII-31

| No | R¹ | R² | R³ᵃ | R³ᵇ | R⁴ | R⁵ | R⁶ | X | Y |
|---|---|---|---|---|---|---|---|---|---|
| XXII-31-1 | $CH_3$ | H | H | H | $^nBu$ | H | F | H | OH |
| XXII-31-2 | $CH_3$ | H | H | $CH_3$ | $^nBu$ | H | F | H | OH |
| XXII-31-3 | $CH_3$ | H | H | $CH(CH_3)_2$ | $^nBu$ | H | F | H | OH |
| XXII-31-4 | $CH_3$ | H | H | $CH_2CH(CH_3)_2$ | $^nBu$ | H | F | H | OH |
| XXII-31-5 | $CH_3$ | H | H | $CH_2Ph$ | $^nBu$ | H | F | H | OH |
| XXII-31-6 | $CH_3$ | H | H | $CH_2$-indol-3-yl | $^nBu$ | H | F | H | OH |
| XXII-31-7 | $CH_3$ | H | H | $CH_2CH_2SCH_3$ | $^nBu$ | H | F | H | OH |
| XXII-31-8 | $CH_3$ | * | H | * | $^nBu$ | H | F | H | OH |

*R² and R³ᵇ joined together by $(CH_2)_3$ to form five-membered ring.

TABLE XXII-32

| No | R¹ | R² | R³ᵃ | R³ᵇ | R⁴ | R⁵ | R⁶ | X | Y |
|---|---|---|---|---|---|---|---|---|---|
| XXII-32-1 | Et | H | H | H | $^nBu$ | H | F | H | OH |
| XXII-32-2 | Et | H | H | $CH_3$ | $^nBu$ | H | F | H | OH |
| XXII-32-3 | Et | H | H | $CH(CH_3)_2$ | $^nBu$ | H | F | H | OH |
| XXII-32-4 | Et | H | H | $CH_2CH(CH_3)_2$ | $^nBu$ | H | F | H | OH |
| XXII-32-5 | Et | H | H | $CH_2Ph$ | $^nBu$ | H | F | H | OH |
| XXII-32-6 | Et | H | H | $CH_2$-indol-3-yl | $^nBu$ | H | F | H | OH |
| XXII-32-7 | Et | H | H | $CH_2CH_2SCH_3$ | $^nBu$ | H | F | H | OH |
| XXII-32-8 | Et | * | H | * | $^nBu$ | H | F | H | OH |

*R² and R³ᵇ joined together by $(CH_2)_3$ to form five-membered ring.

TABLE XXII-33

| No | R¹ | R² | R³ᵃ | R³ᵇ | R⁴ | R⁵ | R⁶ | X | Y |
|---|---|---|---|---|---|---|---|---|---|
| XXII-33-1 | $^iPr$ | H | H | H | $^nBu$ | H | F | H | OH |
| XXII-33-2 | $^iPr$ | H | H | $CH_3$ | $^nBu$ | H | F | H | OH |
| XXII-33-3 | $^iPr$ | H | H | $CH(CH_3)_2$ | $^nBu$ | H | F | H | OH |
| XXII-33-4 | $^iPr$ | H | H | $CH_2CH(CH_3)_2$ | $^nBu$ | H | F | H | OH |
| XXII-33-5 | $^iPr$ | H | H | $CH_2Ph$ | $^nBu$ | H | F | H | OH |
| XXII-33-6 | $^iPr$ | H | H | $CH_2$-indol-3-yl | $^nBu$ | H | F | H | OH |
| XXII-33-7 | $^iPr$ | H | H | $CH_2CH_2SCH_3$ | $^nBu$ | H | F | H | OH |
| XXII-33-8 | $^iPr$ | * | H | * | $^nBu$ | H | F | H | OH |

*R² and R³ᵇ joined together by $(CH_2)_3$ to form five-membered ring.

TABLE XXII-34

| No | R¹ | R² | R³ᵃ | R³ᵇ | R⁴ | R⁵ | R⁶ | X | Y |
|---|---|---|---|---|---|---|---|---|---|
| XXII-34-1 | $^tBu$ | H | H | H | $^nBu$ | H | F | H | OH |
| XXII-34-2 | $^tBu$ | H | H | $CH_3$ | $^nBu$ | H | F | H | OH |
| XXII-34-3 | $^tBu$ | H | H | $CH(CH_3)_2$ | $^nBu$ | H | F | H | OH |
| XXII-34-4 | $^tBu$ | H | H | $CH_2CH(CH_3)_2$ | $^nBu$ | H | F | H | OH |
| XXII-34-5 | $^tBu$ | H | H | $CH_2Ph$ | $^nBu$ | H | F | H | OH |
| XXII-34-6 | $^tBu$ | H | H | $CH_2$-indol-3-yl | $^nBu$ | H | F | H | OH |
| XXII-34-7 | $^tBu$ | H | H | $CH_2CH_2SCH_3$ | $^nBu$ | H | F | H | OH |
| XXII-34-8 | $^tBu$ | * | H | * | $^nBu$ | H | F | H | OH |

*R² and R³ᵇ joined together by $(CH_2)_3$ to form five-membered ring.

TABLE XXII-35

| No | R¹ | R² | R³ᵃ | R³ᵇ | R⁴ | R⁵ | R⁶ | X | Y |
|---|---|---|---|---|---|---|---|---|---|
| XXII-35-1 | Ph | H | H | H | $^nBu$ | H | F | H | OH |
| XXII-35-2 | Ph | H | H | $CH_3$ | $^nBu$ | H | F | H | OH |
| XXII-35-3 | Ph | H | H | $CH(CH_3)_2$ | $^nBu$ | H | F | H | OH |
| XXII-35-4 | Ph | H | H | $CH_2CH(CH_3)_2$ | $^nBu$ | H | F | H | OH |
| XXII-35-5 | Ph | H | H | $CH_2Ph$ | $^nBu$ | H | F | H | OH |
| XXII-35-6 | Ph | H | H | $CH_2$-indol-3-yl | $^nBu$ | H | F | H | OH |
| XXII-35-7 | Ph | H | H | $CH_2CH_2SCH_3$ | $^nBu$ | H | F | H | OH |
| XXII-35-8 | Ph | * | H | * | $^nBu$ | H | F | H | OH |

*R² and R³ᵇ joined together by $(CH_2)_3$ to form five-membered ring.

TABLE XXII-36

| No | R¹ | R² | R³ᵃ | R³ᵇ | R⁴ | R⁵ | R⁶ | X | Y |
|---|---|---|---|---|---|---|---|---|---|
| XXII-36-1 | p-Me—Ph | H | H | H | $^nBu$ | H | F | H | OH |
| XXII-36-2 | p-Me—Ph | H | H | $CH_3$ | $^nBu$ | H | F | H | OH |
| XXII-36-3 | p-Me—Ph | H | H | $CH(CH_3)_2$ | $^nBu$ | H | F | H | OH |
| XXII-36-4 | p-Me—Ph | H | H | $CH_2CH(CH_3)_2$ | $^nBu$ | H | F | H | OH |
| XXII-36-5 | p-Me—Ph | H | H | $CH_2Ph$ | $^nBu$ | H | F | H | OH |
| XXII-36-6 | p-Me—Ph | H | H | $CH_2$-indol-3-yl | $^nBu$ | H | F | H | OH |
| XXII-36-7 | p-Me—Ph | H | H | $CH_2CH_2SCH_3$ | $^nBu$ | H | F | H | OH |
| XXII-36-8 | p-Me—Ph | * | H | * | $^nBu$ | H | F | H | OH |

*R² and R³ᵇ joined together by $(CH_2)_3$ to form five-membered ring.

TABLE XXII-37

| No | R¹ | R² | R³ᵃ | R³ᵇ | R⁴ | R⁵ | R⁶ | X | Y |
|---|---|---|---|---|---|---|---|---|---|
| XXII-37-1 | p-F—Ph | H | H | H | $^nBu$ | H | F | H | OH |
| XXII-37-2 | p-F—Ph | H | H | $CH_3$ | $^nBu$ | H | F | H | OH |
| XXII-37-3 | p-F—Ph | H | H | $CH(CH_3)_2$ | $^nBu$ | H | F | H | OH |
| XXII-37-4 | p-F—Ph | H | H | $CH_2CH(CH_3)_2$ | $^nBu$ | H | F | H | OH |
| XXII-37-5 | p-F—Ph | H | H | $CH_2Ph$ | $^nBu$ | H | F | H | OH |
| XXII-37-6 | p-F—Ph | H | H | $CH_2$-indol-3-yl | $^nBu$ | H | F | H | OH |
| XXII-37-7 | p-F—Ph | H | H | $CH_2CH_2SCH_3$ | $^nBu$ | H | F | H | OH |
| XXII-37-8 | p-F—Ph | * | H | * | $^nBu$ | H | F | H | OH |

*R² and R³ᵇ joined together by $(CH_2)_3$ to form five-membered ring.

TABLE XXII-38

| No | R¹ | R² | R³ᵃ | R³ᵇ | R⁴ | R⁵ | R⁶ | X | Y |
|---|---|---|---|---|---|---|---|---|---|
| XXII-38-1 | p-Cl—Ph | H | H | H | ⁿBu | H | F | H | OH |
| XXII-38-2 | p-Cl—Ph | H | H | CH₃ | ⁿBu | H | F | H | OH |
| XXII-38-3 | p-Cl—Ph | H | H | CH(CH₃)₂ | ⁿBu | H | F | H | OH |
| XXII-38-4 | p-Cl—Ph | H | H | CH₂CH(CH₃)₂ | ⁿBu | H | F | H | OH |
| XXII-38-5 | p-Cl—Ph | H | H | CH₂Ph | ⁿBu | H | F | H | OH |
| XXII-38-6 | p-Cl—Ph | H | H | CH₂-indol-3-yl | ⁿBu | H | F | H | OH |
| XXII-38-7 | p-Cl—Ph | H | H | CH₂CH₂SCH₃ | ⁿBu | H | F | H | OH |
| XXII-38-8 | p-Cl—Ph | * | H | * | ⁿBu | H | F | H | OH |

*R² and R³ᵇ joined together by (CH₂)₃ to form five-membered ring.

TABLE XXII-39

| No | R¹ | R² | R³ᵃ | R³ᵇ | R⁴ | R⁵ | R⁶ | X | Y |
|---|---|---|---|---|---|---|---|---|---|
| XXII-39-1 | p-Br—Ph | H | H | H | ⁿBu | H | F | H | OH |
| XXII-39-2 | p-Br—Ph | H | H | CH₃ | ⁿBu | H | F | H | OH |
| XXII-39-3 | p-Br—Ph | H | H | CH(CH₃)₂ | ⁿBu | H | F | H | OH |
| XXII-39-4 | p-Br—Ph | H | H | CH₂CH(CH₃)₂ | ⁿBu | H | F | H | OH |
| XXII-39-5 | p-Br—Ph | H | H | CH₂Ph | ⁿBu | H | F | H | OH |
| XXII-39-6 | p-Br—Ph | H | H | CH₂-indol-3-yl | ⁿBu | H | F | H | OH |
| XXII-39-7 | p-Br—Ph | H | H | CH₂CH₂SCH₃ | ⁿBu | H | F | H | OH |
| XXII-39-8 | p-Br—Ph | * | H | * | ⁿBu | H | F | H | OH |

*R² and R³ᵇ joined together by (CH₂)₃ to form five-membered ring.

TABLE XXII-40

| No | R¹ | R² | R³ᵃ | R³ᵇ | R⁴ | R⁵ | R⁶ | X | Y |
|---|---|---|---|---|---|---|---|---|---|
| XXII-40-1 | p-I—Ph | H | H | H | ⁿBu | H | F | H | OH |
| XXII-40-2 | p-I—Ph | H | H | CH₃ | ⁿBu | H | F | H | OH |
| XXII-40-3 | p-I—Ph | H | H | CH(CH₃)₂ | ⁿBu | H | F | H | OH |
| XXII-40-4 | p-I—Ph | H | H | CH₂CH(CH₃)₂ | ⁿBu | H | F | H | OH |
| XXII-40-5 | p-I—Ph | H | H | CH₂Ph | ⁿBu | H | F | H | OH |
| XXII-40-6 | p-I—Ph | H | H | CH₂-indol-3-yl | ⁿBu | H | F | H | OH |
| XXII-40-7 | p-I—Ph | H | H | CH₂CH₂SCH₃ | ⁿBu | H | F | H | OH |
| XXII-40-8 | p-I—Ph | * | H | * | ⁿBu | H | F | H | OH |

*R² and R³ᵇ joined together by (CH₂)₃ to form five-membered ring.

TABLE XXII-41

| No | R¹ | R² | R³ᵃ | R³ᵇ | R⁴ | R⁵ | R⁶ | X | Y |
|---|---|---|---|---|---|---|---|---|---|
| XXII-41-1 | CH₃ | H | H | H | Bz | H | F | H | OH |
| XXII-41-2 | CH₃ | H | H | CH₃ | Bz | H | F | H | OH |
| XXII-41-3 | CH₃ | H | H | CH(CH₃)₂ | Bz | H | F | H | OH |
| XXII-41-4 | CH₃ | H | H | CH₂CH(CH₃)₂ | Bz | H | F | H | OH |
| XXII-41-5 | CH₃ | H | H | CH₂Ph | Bz | H | F | H | OH |
| XXII-41-6 | CH₃ | H | H | CH₂-indol-3-yl | Bz | H | F | H | OH |
| XXII-41-7 | CH₃ | H | H | CH₂CH₂SCH₃ | Bz | H | F | H | OH |
| XXII-41-8 | CH₃ | * | H | * | Bz | H | F | H | OH |

*R² and R³ᵇ joined together by (CH₂)₃ to form five-membered ring.

TABLE XXII-42

| No | R¹ | R² | R³ᵃ | R³ᵇ | R⁴ | R⁵ | R⁶ | X | Y |
|---|---|---|---|---|---|---|---|---|---|
| XXII-42-1 | Et | H | H | H | Bz | H | F | H | OH |
| XXII-42-2 | Et | H | H | CH₃ | Bz | H | F | H | OH |
| XXII-42-3 | Et | H | H | CH(CH₃)₂ | Bz | H | F | H | OH |
| XXII-42-4 | Et | H | H | CH₂CH(CH₃)₂ | Bz | H | F | H | OH |
| XXII-42-5 | Et | H | H | CH₂Ph | Bz | H | F | H | OH |
| XXII-42-6 | Et | H | H | CH₂-indol-3-yl | Bz | H | F | H | OH |
| XXII-42-7 | Et | H | H | CH₂CH₂SCH₃ | Bz | H | F | H | OH |
| XXII-42-8 | Et | * | H | * | Bz | H | F | H | OH |

*R² and R³ᵇ joined together by (CH₂)₃ to form five-membered ring.

TABLE XXII-43

| No | R¹ | R² | R³ᵃ | R³ᵇ | R⁴ | R⁵ | R⁶ | X | Y |
|---|---|---|---|---|---|---|---|---|---|
| XXII-43-1 | ⁱPr | H | H | H | Bz | H | F | H | OH |
| XXII-43-2 | ⁱPr | H | H | CH₃ | Bz | H | F | H | OH |
| XXII-43-3 | ⁱPr | H | H | CH(CH₃)₂ | Bz | H | F | H | OH |
| XXII-43-4 | ⁱPr | H | H | CH₂CH(CH₃)₂ | Bz | H | F | H | OH |
| XXII-43-5 | ⁱPr | H | H | CH₂Ph | Bz | H | F | H | OH |
| XXII-43-6 | ⁱPr | H | H | CH₂-indol-3-yl | Bz | H | F | H | OH |
| XXII-43-7 | ⁱPr | H | H | CH₂CH₂SCH₃ | Bz | H | F | H | OH |
| XXII-43-8 | ⁱPr | * | H | * | Bz | H | F | H | OH |

*R² and R³ᵇ joined together by (CH₂)₃ to form five-membered ring.

TABLE XXII-44

| No | R¹ | R² | R³ᵃ | R³ᵇ | R⁴ | R⁵ | R⁶ | X | Y |
|---|---|---|---|---|---|---|---|---|---|
| XXII-44-1 | ᵗBu | H | H | H | Bz | H | F | H | OH |
| XXII-44-2 | ᵗBu | H | H | CH₃ | Bz | H | F | H | OH |
| XXII-44-3 | ᵗBu | H | H | CH(CH₃)₂ | Bz | H | F | H | OH |
| XXII-44-4 | ᵗBu | H | H | CH₂CH(CH₃)₂ | Bz | H | F | H | OH |
| XXII-44-5 | ᵗBu | H | H | CH₂Ph | Bz | H | F | H | OH |
| XXII-44-6 | ᵗBu | H | H | CH₂-indol-3-yl | Bz | H | F | H | OH |
| XXII-44-7 | ᵗBu | H | H | CH₂CH₂SCH₃ | Bz | H | F | H | OH |
| XXII-44-8 | ᵗBu | * | H | * | Bz | H | F | H | OH |

*R² and R³ᵇ joined together by (CH₂)₃ to form five-membered ring.

TABLE XXII-45

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-45-1 | Ph | H | H | H | Bz | H | F | H | OH |
| XXII-45-2 | Ph | H | H | CH$_3$ | Bz | H | F | H | OH |
| XXII-45-3 | Ph | H | H | CH(CH$_3$)$_2$ | Bz | H | F | H | OH |
| XXII-45-4 | Ph | H | H | CH$_2$CH(CH$_3$)$_2$ | Bz | H | F | H | OH |
| XXII-45-5 | Ph | H | H | CH$_2$Ph | Bz | H | F | H | OH |
| XXII-45-6 | Ph | H | H | CH$_2$-indol-3-yl | Bz | H | F | H | OH |
| XXII-45-7 | Ph | H | H | CH$_2$CH$_2$SCH$_3$ | Bz | H | F | H | OH |
| XXII-45-8 | Ph | * | H | * | Bz | H | F | H | OH |

*$R^2$ and $R^{3b}$ joined together by (CH$_2$)$_3$ to form five-membered ring.

TABLE XXII-46

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-46-1 | p-Me—Ph | H | H | H | Bz | H | F | H | OH |
| XXII-46-2 | p-Me—Ph | H | H | CH$_3$ | Bz | H | F | H | OH |
| XXII-46-3 | p-Me—Ph | H | H | CH(CH$_3$)$_2$ | Bz | H | F | H | OH |
| XXII-46-4 | p-Me—Ph | H | H | CH$_2$CH(CH$_3$)$_2$ | Bz | H | F | H | OH |
| XXII-46-5 | p-Me—Ph | H | H | CH$_2$Ph | Bz | H | F | H | OH |
| XXII-46-6 | p-Me—Ph | H | H | CH$_2$-indol-3-yl | Bz | H | F | H | OH |
| XXII-46-7 | p-Me—Ph | H | H | CH$_2$CH$_2$SCH$_3$ | Bz | H | F | H | OH |
| XXII-46-8 | p-Me—Ph | * | H | * | Bz | H | F | H | OH |

*$R^2$ and $R^{3b}$ joined together by (CH$_2$)$_3$ to form five-membered ring.

TABLE XXII-47

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-47-1 | p-F—Ph | H | H | H | Bz | H | F | H | OH |
| XXII-47-2 | p-F—Ph | H | H | CH$_3$ | Bz | H | F | H | OH |
| XXII-47-3 | p-F—Ph | H | H | CH(CH$_3$)$_2$ | Bz | H | F | H | OH |
| XXII-47-4 | p-F—Ph | H | H | CH$_2$CH(CH$_3$)$_2$ | Bz | H | F | H | OH |
| XXII-47-5 | p-F—Ph | H | H | CH$_2$Ph | Bz | H | F | H | OH |
| XXII-47-6 | p-F—Ph | H | H | CH$_2$-indol-3-yl | Bz | H | F | H | OH |
| XXII-47-7 | p-F—Ph | H | H | CH$_2$CH$_2$SCH$_3$ | Bz | H | F | H | OH |
| XXII-47-8 | p-F—Ph | * | H | * | Bz | H | F | H | OH |

*$R^2$ and $R^{3b}$ joined together by (CH$_2$)$_3$ to form five-membered ring.

TABLE XXII-48

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-48-1 | p-Cl—Ph | H | H | H | Bz | H | F | H | OH |
| XXII-48-2 | p-Cl—Ph | H | H | CH$_3$ | Bz | H | F | H | OH |
| XXII-48-3 | p-Cl—Ph | H | H | CH(CH$_3$)$_2$ | Bz | H | F | H | OH |
| XXII-48-4 | p-Cl—Ph | H | H | CH$_2$CH(CH$_3$)$_2$ | Bz | H | F | H | OH |
| XXII-48-5 | p-Cl—Ph | H | H | CH$_2$Ph | Bz | H | F | H | OH |
| XXII-48-6 | p-Cl—Ph | H | H | CH$_2$-indol-3-yl | Bz | H | F | H | OH |
| XXII-48-7 | p-Cl—Ph | H | H | CH$_2$CH$_2$SCH$_3$ | Bz | H | F | H | OH |
| XXII-48-8 | p-Cl—Ph | * | H | * | Bz | H | F | H | OH |

*$R^2$ and $R^{3b}$ joined together by (CH$_2$)$_3$ to form five-membered ring.

TABLE XXII-49

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXII-49-1 | p-Br—Ph | H | H | H | Bz | H | F | H | OH |
| XXII-49-2 | p-Br—Ph | H | H | CH$_3$ | Bz | H | F | H | OH |
| XXII-49-3 | p-Br—Ph | H | H | CH(CH$_3$)$_2$ | Bz | H | F | H | OH |
| XXII-49-4 | p-Br—Ph | H | H | CH$_2$CH(CH$_3$)$_2$ | Bz | H | F | H | OH |
| XXII-49-5 | p-Br—Ph | H | H | CH$_2$Ph | Bz | H | F | H | OH |
| XXII-49-6 | p-Br—Ph | H | H | CH$_2$-indol-3-yl | Bz | H | F | H | OH |
| XXII-49-7 | p-Br—Ph | H | H | CH$_2$CH$_2$SCH$_3$ | Bz | H | F | H | OH |
| XXII-49-8 | p-Br—Ph | * | H | * | Bz | H | F | H | OH |

*$R^2$ and $R^{3b}$ joined together by (CH$_2$)$_3$ to form five-membered ring.

TABLE XXII-50

| No | R¹ | R² | R³ᵃ | R³ᵇ | R⁴ | R⁵ | R⁶ | X | Y |
|---|---|---|---|---|---|---|---|---|---|
| XXII-50-1 | p-I—Ph | H | H | H | Bz | H | F | H | OH |
| XXII-50-2 | p-I—Ph | H | H | CH₃ | Bz | H | F | H | OH |
| XXII-50-3 | p-I—Ph | H | H | CH(CH₃)₂ | Bz | H | F | H | OH |
| XXII-50-4 | p-I—Ph | H | H | CH₂CH(CH₃)₂ | Bz | H | F | H | OH |
| XXII-50-5 | p-I—Ph | H | H | CH₂Ph | Bz | H | F | H | OH |
| XXII-50-6 | p-I—Ph | H | H | CH₂-indol-3-yl | Bz | H | F | H | OH |
| XXII-50-7 | p-I—Ph | H | H | CH₂CH₂SCH₃ | Bz | H | F | H | OH |
| XXII-50-8 | p-I—Ph | * | H | * | Bz | H | F | H | OH |

*R² and R³ᵇ joined together by (CH₂)₃ to form five-membered ring.

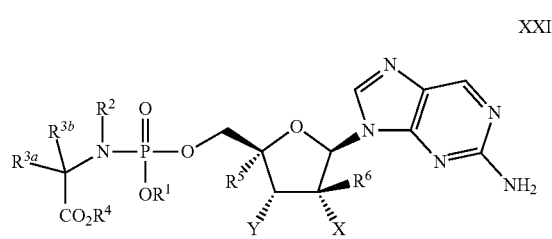

XXIII

TABLE XXIII-1

| No | R¹ | R² | R³ᵃ | R³ᵇ | R⁴ | R⁵ | R⁶ | X | Y |
|---|---|---|---|---|---|---|---|---|---|
| XXIII-1-1 | CH₃ | H | H | H | CH₃ | H | F | F | OH |
| XXIII-1-2 | CH₃ | H | H | CH₃ | CH₃ | H | F | F | OH |
| XXIII-1-3 | CH₃ | H | H | CH(CH₃)₂ | CH₃ | H | F | F | OH |
| XXIII-1-4 | CH₃ | H | H | CH₂CH(CH₃)₂ | CH₃ | H | F | F | OH |
| XXIII-1-5 | CH₃ | H | H | CH₂Ph | CH₃ | H | F | F | OH |
| XXIII-1-6 | CH₃ | H | H | CH₂-indol-3-yl | CH₃ | H | F | F | OH |
| XXIII-1-7 | CH₃ | H | H | CH₂CH₂SCH₃ | CH₃ | H | F | F | OH |
| XXIII-1-8 | CH₃ | * | H | * | CH₃ | H | F | F | OH |

*R² and R³ᵇ joined together by (CH₂)₃ to form five-membered ring.

TABLE XXIII-2

| No | R¹ | R² | R³ᵃ | R³ᵇ | R⁴ | R⁵ | R⁶ | X | Y |
|---|---|---|---|---|---|---|---|---|---|
| XXIII-2-1 | Et | H | H | H | CH₃ | H | F | F | OH |
| XXIII-2-2 | Et | H | H | CH₃ | CH₃ | H | F | F | OH |
| XXIII-2-3 | Et | H | H | CH(CH₃)₂ | CH₃ | H | F | F | OH |
| XXIII-2-4 | Et | H | H | CH₂CH(CH₃)₂ | CH₃ | H | F | F | OH |
| XXIII-2-5 | Et | H | H | CH₂Ph | CH₃ | H | F | F | OH |
| XXIII-2-6 | Et | H | H | CH₂-indol-3-yl | CH₃ | H | F | F | OH |
| XXIII-2-7 | Et | H | H | CH₂CH₂SCH₃ | CH₃ | H | F | F | OH |
| XXIII-2-8 | Et | * | H | * | CH₃ | H | F | F | OH |

*R² and R³ᵇ joined together by (CH₂)₃ to form five-membered ring.

TABLE XXIII-3

| No | R¹ | R² | R³ᵃ | R³ᵇ | R⁴ | R⁵ | R⁶ | X | Y |
|---|---|---|---|---|---|---|---|---|---|
| XXIII-3-1 | ⁱPr | H | H | H | CH₃ | H | F | F | OH |
| XXIII-3-2 | ⁱPr | H | H | CH₃ | CH₃ | H | F | F | OH |
| XXIII-3-3 | ⁱPr | H | H | CH(CH₃)₂ | CH₃ | H | F | F | OH |
| XXIII-3-4 | ⁱPr | H | H | CH₂CH(CH₃)₂ | CH₃ | H | F | F | OH |
| XXIII-3-5 | ⁱPr | H | H | CH₂Ph | CH₃ | H | F | F | OH |
| XXIII-3-6 | ⁱPr | H | H | CH₂-indol-3-yl | CH₃ | H | F | F | OH |
| XXIII-3-7 | ⁱPr | H | H | CH₂CH₂SCH₃ | CH₃ | H | F | F | OH |
| XXIII-3-8 | ⁱPr | * | H | * | CH₃ | H | F | F | OH |

*R² and R³ᵇ joined together by (CH₂)₃ to form five-membered ring.

TABLE XXIII-4

| No | R¹ | R² | R³ᵃ | R³ᵇ | R⁴ | R⁵ | R⁶ | X | Y |
|---|---|---|---|---|---|---|---|---|---|
| XXIII-4-1 | ᵗBu | H | H | H | CH₃ | H | F | F | OH |
| XXIII-4-2 | ᵗBu | H | H | CH₃ | CH₃ | H | F | F | OH |
| XXIII-4-3 | ᵗBu | H | H | CH(CH₃)₂ | CH₃ | H | F | F | OH |
| XXIII-4-4 | ᵗBu | H | H | CH₂CH(CH₃)₂ | CH₃ | H | F | F | OH |
| XXIII-4-5 | ᵗBu | H | H | CH₂Ph | CH₃ | H | F | F | OH |
| XXIII-4-6 | ᵗBu | H | H | CH₂-indol-3-yl | CH₃ | H | F | F | OH |
| XXIII-4-7 | ᵗBu | H | H | CH₂CH₂SCH₃ | CH₃ | H | F | F | OH |
| XXIII-4-8 | ᵗBu | * | H | * | CH₃ | H | F | F | OH |

*R² and R³ᵇ joined together by (CH₂)₃ to form five-membered ring.

TABLE XXIII-5

| No | R¹ | R² | R³ᵃ | R³ᵇ | R⁴ | R⁵ | R⁶ | X | Y |
|---|---|---|---|---|---|---|---|---|---|
| XXIII-5-1 | Ph | H | H | H | CH₃ | H | F | F | OH |
| XXIII-5-2 | Ph | H | H | CH₃ | CH₃ | H | F | F | OH |
| XXIII-5-3 | Ph | H | H | CH(CH₃)₂ | CH₃ | H | F | F | OH |
| XXIII-5-4 | Ph | H | H | CH₂CH(CH₃)₂ | CH₃ | H | F | F | OH |
| XXIII-5-5 | Ph | H | H | CH₂Ph | CH₃ | H | F | F | OH |
| XXIII-5-6 | Ph | H | H | CH₂-indol-3-yl | CH₃ | H | F | F | OH |
| XXIII-5-7 | Ph | H | H | CH₂CH₂SCH₃ | CH₃ | H | F | F | OH |
| XXIII-5-8 | Ph | * | H | * | CH₃ | H | F | F | OH |

*R² and R³ᵇ joined together by (CH₂)₃ to form five-membered ring.

TABLE XXIII-6

| No | R¹ | R² | R³ᵃ | R³ᵇ | R⁴ | R⁵ | R⁶ | X | Y |
|---|---|---|---|---|---|---|---|---|---|
| XXIII-6-1 | p-Me—Ph | H | H | H | CH₃ | H | F | F | OH |
| XXIII-6-2 | p-Me—Ph | H | H | CH₃ | CH₃ | H | F | F | OH |
| XXIII-6-3 | p-Me—Ph | H | H | CH(CH₃)₂ | CH₃ | H | F | F | OH |
| XXIII-6-4 | p-Me—Ph | H | H | CH₂CH(CH₃)₂ | CH₃ | H | F | F | OH |
| XXIII-6-5 | p-Me—Ph | H | H | CH₂Ph | CH₃ | H | F | F | OH |
| XXIII-6-6 | p-Me—Ph | H | H | CH₂-indol-3-yl | CH₃ | H | F | F | OH |
| XXIII-6-7 | p-Me—Ph | H | H | CH₂CH₂SCH₃ | CH₃ | H | F | F | OH |
| XXIII-6-8 | p-Me—Ph | * | H | * | CH₃ | H | F | F | OH |

*R² and R³ᵇ joined together by (CH₂)₃ to form five-membered ring.

TABLE XXIII-7

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-7-1 | p-F—Ph | H | H | H | $CH_3$ | H | F | F | OH |
| XXIII-7-2 | p-F—Ph | H | H | $CH_3$ | $CH_3$ | H | F | F | OH |
| XXIII-7-3 | p-F—Ph | H | H | $CH(CH_3)_2$ | $CH_3$ | H | F | F | OH |
| XXIII-7-4 | p-F—Ph | H | H | $CH_2CH(CH_3)_2$ | $CH_3$ | H | F | F | OH |
| XXIII-7-6 | p-F—Ph | H | H | $CH_2Ph$ | $CH_3$ | H | F | F | OH |
| XXIII-7-7 | p-F—Ph | H | H | $CH_2$-indol-3-yl | $CH_3$ | H | F | F | OH |
| XXIII-7-8 | p-F—Ph | H | H | $CH_2CH_2SCH_3$ | $CH_3$ | H | F | F | OH |
| XXIII-7-20 | p-F—Ph | * | H | * | $CH_3$ | H | F | F | OH |

*$R^2$ and $R^{3b}$ joined together by $(CH_2)_3$ to form five-membered ring.

TABLE XXIII-8

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-8-1 | p-Cl—Ph | H | H | H | $CH_3$ | H | F | F | OH |
| XXIII-8-2 | p-Cl—Ph | H | H | $CH_3$ | $CH_3$ | H | F | F | OH |
| XXIII-8-3 | p-Cl—Ph | H | H | $CH(CH_3)_2$ | $CH_3$ | H | F | F | OH |
| XXIII-8-4 | p-Cl—Ph | H | H | $CH_2CH(CH_3)_2$ | $CH_3$ | H | F | F | OH |
| XXIII-8-5 | p-Cl—Ph | H | H | $CH_2Ph$ | $CH_3$ | H | F | F | OH |
| XXIII-8-6 | p-Cl—Ph | H | H | $CH_2$-indol-3-yl | $CH_3$ | H | F | F | OH |
| XXIII-8-7 | p-Cl—Ph | H | H | $CH_2CH_2SCH_3$ | $CH_3$ | H | F | F | OH |
| XXIII-8-8 | p-Cl—Ph | * | H | * | $CH_3$ | H | F | F | OH |

*$R^2$ and $R^{3b}$ joined together by $(CH_2)_3$ to form five-membered ring.

TABLE XXIII-9

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-9-1 | p-Br—Ph | H | H | H | $CH_3$ | H | F | F | OH |
| XXIII-9-2 | p-Br—Ph | H | H | $CH_3$ | $CH_3$ | H | F | F | OH |
| XXIII-9-3 | p-Br—Ph | H | H | $CH(CH_3)_2$ | $CH_3$ | H | F | F | OH |
| XXIII-9-4 | p-Br—Ph | H | H | $CH_2CH(CH_3)_2$ | $CH_3$ | H | F | F | OH |
| XXIII-9-6 | p-Br—Ph | H | H | $CH_2Ph$ | $CH_3$ | H | F | F | OH |
| XXIII-9-7 | p-Br—Ph | H | H | $CH_2$-indol-3-yl | $CH_3$ | H | F | F | OH |
| XXIII-9-8 | p-Br—Ph | H | H | $CH_2CH_2SCH_3$ | $CH_3$ | H | F | F | OH |
| XXIII-9-20 | p-Br—Ph | * | H | * | $CH_3$ | H | F | F | OH |

*$R^2$ and $R^{3b}$ joined together by $(CH_2)_3$ to form five-membered ring.

TABLE XXIII-10

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-10-1 | p-I—Ph | H | H | H | $CH_3$ | H | F | F | OH |
| XXIII-10-2 | p-I—Ph | H | H | $CH_3$ | $CH_3$ | H | F | F | OH |
| XXIII-10-3 | p-I—Ph | H | H | $CH(CH_3)_2$ | $CH_3$ | H | F | F | OH |
| XXIII-10-4 | p-I—Ph | H | H | $CH_2CH(CH_3)_2$ | $CH_3$ | H | F | F | OH |
| XXIII-10-5 | p-I—Ph | H | H | $CH_2Ph$ | $CH_3$ | H | F | F | OH |
| XXIII-10-6 | p-I—Ph | H | H | $CH_2$-indol-3-yl | $CH_3$ | H | F | F | OH |
| XXIII-10-7 | p-I—Ph | H | H | $CH_2CH_2SCH_3$ | $CH_3$ | H | F | F | OH |
| XXIII-10-8 | p-I—Ph | * | H | * | $CH_3$ | H | F | F | OH |

*$R^2$ and $R^{3b}$ joined together by $(CH_2)_3$ to form five-membered ring.

TABLE XXIII-11

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-11-1 | $CH_3$ | H | H | H | Et | H | F | F | OH |
| XXIII-11-2 | $CH_3$ | H | H | $CH_3$ | Et | H | F | F | OH |
| XXIII-11-3 | $CH_3$ | H | H | $CH(CH_3)_2$ | Et | H | F | F | OH |
| XXIII-11-4 | $CH_3$ | H | H | $CH_2CH(CH_3)_2$ | Et | H | F | F | OH |
| XXIII-11-5 | $CH_3$ | H | H | $CH_2Ph$ | Et | H | F | F | OH |
| XXIII-11-6 | $CH_3$ | H | H | $CH_2$-indol-3-yl | Et | H | F | F | OH |
| XXIII-11-7 | $CH_3$ | H | H | $CH_2CH_2SCH_3$ | Et | H | F | F | OH |
| XXIII-11-8 | $CH_3$ | * | H | * | Et | H | F | F | OH |

*$R^2$ and $R^{3b}$ joined together by $(CH_2)_3$ to form five-membered ring.

TABLE XXIII-12

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-12-1 | Et | H | H | H | Et | H | F | F | OH |
| XXIII-12-2 | Et | H | H | $CH_3$ | Et | H | F | F | OH |
| XXIII-12-3 | Et | H | H | $CH(CH_3)_2$ | Et | H | F | F | OH |
| XXIII-12-4 | Et | H | H | $CH_2CH(CH_3)_2$ | Et | H | F | F | OH |
| XXIII-12-5 | Et | H | H | $CH_2Ph$ | Et | H | F | F | OH |
| XXIII-12-6 | Et | H | H | $CH_2$-indol-3-yl | Et | H | F | F | OH |
| XXIII-12-7 | Et | H | H | $CH_2CH_2SCH_3$ | Et | H | F | F | OH |
| XXIII-12-8 | Et | * | H | * | Et | H | F | F | OH |

*$R^2$ and $R^{3b}$ joined together by $(CH_2)_3$ to form five-membered ring.

TABLE XXIII-13

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-13-1 | $^iPr$ | H | H | H | Et | H | F | F | OH |
| XXIII-13-2 | $^iPr$ | H | H | $CH_3$ | Et | H | F | F | OH |
| XXIII-13-3 | $^iPr$ | H | H | $CH(CH_3)_2$ | Et | H | F | F | OH |
| XXIII-13-4 | $^iPr$ | H | H | $CH_2CH(CH_3)_2$ | Et | H | F | F | OH |
| XXIII-13-5 | $^iPr$ | H | H | $CH_2Ph$ | Et | H | F | F | OH |
| XXIII-13-6 | $^iPr$ | H | H | $CH_2$-indol-3-yl | Et | H | F | F | OH |
| XXIII-13-7 | $^iPr$ | H | H | $CH_2CH_2SCH_3$ | Et | H | F | F | OH |
| XXIII-13-8 | $^iPr$ | * | H | * | Et | H | F | F | OH |

*$R^2$ and $R^{3b}$ joined together by $(CH_2)_3$ to form five-membered ring.

TABLE XXIII-14

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-14-1 | $^tBu$ | H | H | H | Et | H | F | F | OH |
| XXIII-14-2 | $^tBu$ | H | H | $CH_3$ | Et | H | F | F | OH |
| XXIII-14-3 | $^tBu$ | H | H | $CH(CH_3)_2$ | Et | H | F | F | OH |
| XXIII-14-4 | $^tBu$ | H | H | $CH_2CH(CH_3)_2$ | Et | H | F | F | OH |
| XXIII-14-5 | $^tBu$ | H | H | $CH_2Ph$ | Et | H | F | F | OH |
| XXIII-14-6 | $^tBu$ | H | H | $CH_2$-indol-3-yl | Et | H | F | F | OH |
| XXIII-14-7 | $^tBu$ | H | H | $CH_2CH_2SCH_3$ | Et | H | F | F | OH |
| XXIII-14-8 | $^tBu$ | * | H | * | Et | H | F | F | OH |

*$R^2$ and $R^{3b}$ joined together by $(CH_2)_3$ to form five-membered ring.

TABLE XXIII-15

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-15-1 | Ph | H | H | H | Et | H | F | F | OH |
| XXIII-15-2 | Ph | H | H | $CH_3$ | Et | H | F | F | OH |
| XXIII-15-3 | Ph | H | H | $CH(CH_3)_2$ | Et | H | F | F | OH |
| XXIII-15-4 | Ph | H | H | $CH_2CH(CH_3)_2$ | Et | H | F | F | OH |
| XXIII-15-5 | Ph | H | H | $CH_2Ph$ | Et | H | F | F | OH |
| XXIII-15-6 | Ph | H | H | $CH_2$-indol-3-yl | Et | H | F | F | OH |
| XXIII-15-7 | Ph | H | H | $CH_2CH_2SCH_3$ | Et | H | F | F | OH |
| XXIII-15-8 | Ph | * | H | * | Et | H | F | F | OH |

*$R^2$ and $R^{3b}$ joined together by $(CH_2)_3$ to form five-membered ring.

TABLE XXIII-16

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-16-1 | p-Me—Ph | H | H | H | Et | H | F | F | OH |
| XXIII-16-2 | p-Me—Ph | H | H | $CH_3$ | Et | H | F | F | OH |
| XXIII-16-3 | p-Me—Ph | H | H | $CH(CH_3)_2$ | Et | H | F | F | OH |
| XXIII-16-4 | p-Me—Ph | H | H | $CH_2CH(CH_3)_2$ | Et | H | F | F | OH |
| XXIII-16-5 | p-Me—Ph | H | H | $CH_2Ph$ | Et | H | F | F | OH |
| XXIII-16-6 | p-Me—Ph | H | H | $CH_2$-indol-3-yl | Et | H | F | F | OH |
| XXIII-16-7 | p-Me—Ph | H | H | $CH_2CH_2SCH_3$ | Et | H | F | F | OH |
| XXIII-16-8 | p-Me—Ph | * | H | * | Et | H | F | F | OH |

*$R^2$ and $R^{3b}$ joined together by $(CH_2)_3$ to form five-membered ring.

TABLE XXIII-17

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-17-1 | p-F—Ph | H | H | H | Et | H | F | F | OH |
| XXIII-17-2 | p-F—Ph | H | H | $CH_3$ | Et | H | F | F | OH |
| XXIII-17-3 | p-F—Ph | H | H | $CH(CH_3)_2$ | Et | H | F | F | OH |
| XXIII-17-4 | p-F—Ph | H | H | $CH_2CH(CH_3)_2$ | Et | H | F | F | OH |
| XXIII-17-5 | p-F—Ph | H | H | $CH_2Ph$ | Et | H | F | F | OH |
| XXIII-17-6 | p-F—Ph | H | H | $CH_2$-indol-3-yl | Et | H | F | F | OH |
| XXIII-17-7 | p-F—Ph | H | H | $CH_2CH_2SCH_3$ | Et | H | F | F | OH |
| XXIII-17-8 | p-F—Ph | * | H | * | Et | H | F | F | OH |

*$R^2$ and $R^{3b}$ joined together by $(CH_2)_3$ to form five-membered ring.

TABLE XXIII-18

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-18-1 | p-Cl—Ph | H | H | H | Et | H | F | F | OH |
| XXIII-18-2 | p-Cl—Ph | H | H | $CH_3$ | Et | H | F | F | OH |
| XXIII-18-3 | p-Cl—Ph | H | H | $CH(CH_3)_2$ | Et | H | F | F | OH |
| XXIII-18-4 | p-Cl—Ph | H | H | $CH_2CH(CH_3)_2$ | Et | H | F | F | OH |
| XXIII-18-5 | p-Cl—Ph | H | H | $CH_2Ph$ | Et | H | F | F | OH |
| XXIII-18-6 | p-Cl—Ph | H | H | $CH_2$-indol-3-yl | Et | H | F | F | OH |
| XXIII-18-7 | p-Cl—Ph | H | H | $CH_2CH_2SCH_3$ | Et | H | F | F | OH |
| XXIII-18-8 | p-Cl—Ph | * | H | * | Et | H | F | F | OH |

*$R^2$ and $R^{3b}$ joined together by $(CH_2)_3$ to form five-membered ring.

TABLE XXIII-19

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-19-1 | p-Br—Ph | H | H | H | Et | H | F | F | OH |
| XXIII-19-2 | p-Br—Ph | H | H | $CH_3$ | Et | H | F | F | OH |
| XXIII-19-3 | p-Br—Ph | H | H | $CH(CH_3)_2$ | Et | H | F | F | OH |
| XXIII-19-4 | p-Br—Ph | H | H | $CH_2CH(CH_3)_2$ | Et | H | F | F | OH |
| XXIII-19-5 | p-Br—Ph | H | H | $CH_2Ph$ | Et | H | F | F | OH |
| XXIII-19-6 | p-Br—Ph | H | H | $CH_2$-indol-3-yl | Et | H | F | F | OH |
| XXIII-19-7 | p-Br—Ph | H | H | $CH_2CH_2SCH_3$ | Et | H | F | F | OH |
| XXIII-19-8 | p-Br—Ph | * | H | * | Et | H | F | F | OH |

*$R^2$ and $R^{3b}$ joined together by $(CH_2)_3$ to form five-membered ring.

TABLE XXIII-20

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-20-1 | p-I—Ph | H | H | H | Et | H | F | F | OH |
| XXIII-20-2 | p-I—Ph | H | H | $CH_3$ | Et | H | F | F | OH |
| XXIII-20-3 | p-I—Ph | H | H | $CH(CH_3)_2$ | Et | H | F | F | OH |
| XXIII-20-4 | p-I—Ph | H | H | $CH_2CH(CH_3)_2$ | Et | H | F | F | OH |
| XXIII-20-5 | p-I—Ph | H | H | $CH_2Ph$ | Et | H | F | F | OH |
| XXIII-20-6 | p-I—Ph | H | H | $CH_2$-indol-3-yl | Et | H | F | F | OH |
| XXIII-20-7 | p-I—Ph | H | H | $CH_2CH_2SCH_3$ | Et | H | F | F | OH |
| XXIII-20-8 | p-I—Ph | * | H | * | Et | H | F | F | OH |

*$R^2$ and $R^{3b}$ joined together by $(CH_2)_3$ to form five-membered ring.

TABLE XXIII-21

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-21-1 | $CH_3$ | H | H | H | $^iPr$ | H | F | F | OH |
| XXIII-21-2 | $CH_3$ | H | H | $CH_3$ | $^iPr$ | H | F | F | OH |
| XXIII-21-3 | $CH_3$ | H | H | $CH(CH_3)_2$ | $^iPr$ | H | F | F | OH |
| XXIII-21-4 | $CH_3$ | H | H | $CH_2CH(CH_3)_2$ | $^iPr$ | H | F | F | OH |
| XXIII-21-5 | $CH_3$ | H | H | $CH_2Ph$ | $^iPr$ | H | F | F | OH |
| XXIII-21-6 | $CH_3$ | H | H | $CH_2$-indol-3-yl | $^iPr$ | H | F | F | OH |
| XXIII-21-7 | $CH_3$ | H | H | $CH_2CH_2SCH_3$ | $^iPr$ | H | F | F | OH |
| XXIII-21-8 | $CH_3$ | * | H | * | $^iPr$ | H | F | F | OH |

*$R^2$ and $R^{3b}$ joined together by $(CH_2)_3$ to form five-membered ring.

TABLE XXIII-22

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-22-1 | Et | H | H | H | $^iPr$ | H | F | F | OH |
| XXIII-22-2 | Et | H | H | $CH_3$ | $^iPr$ | H | F | F | OH |
| XXIII-22-3 | Et | H | H | $CH(CH_3)_2$ | $^iPr$ | H | F | F | OH |
| XXIII-22-4 | Et | H | H | $CH_2CH(CH_3)_2$ | $^iPr$ | H | F | F | OH |
| XXIII-22-5 | Et | H | H | $CH_2Ph$ | $^iPr$ | H | F | F | OH |
| XXIII-22-6 | Et | H | H | $CH_2$-indol-3-yl | $^iPr$ | H | F | F | OH |
| XXIII-22-7 | Et | H | H | $CH_2CH_2SCH_3$ | $^iPr$ | H | F | F | OH |
| XXIII-22-8 | Et | * | H | * | $^iPr$ | H | F | F | OH |

*$R^2$ and $R^{3b}$ joined together by $(CH_2)_3$ to form five-membered ring.

TABLE XXIII-23

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-23-1 | $^iPr$ | H | H | H | $^iPr$ | H | F | F | OH |
| XXIII-23-2 | $^iPr$ | H | H | $CH_3$ | $^iPr$ | H | F | F | OH |
| XXIII-23-3 | $^iPr$ | H | H | $CH(CH_3)_2$ | $^iPr$ | H | F | F | OH |
| XXIII-23-4 | $^iPr$ | H | H | $CH_2CH(CH_3)_2$ | $^iPr$ | H | F | F | OH |
| XXIII-23-5 | $^iPr$ | H | H | $CH_2Ph$ | $^iPr$ | H | F | F | OH |
| XXIII-23-6 | $^iPr$ | H | H | $CH_2$-indol-3-yl | $^iPr$ | H | F | F | OH |
| XXIII-23-7 | $^iPr$ | H | H | $CH_2CH_2SCH_3$ | $^iPr$ | H | F | F | OH |
| XXIII-23-8 | $^iPr$ | * | H | * | $^iPr$ | H | F | F | OH |

*$R^2$ and $R^{3b}$ joined together by $(CH_2)_3$ to form five-membered ring.

TABLE XXIII-24

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-24-1 | $^tBu$ | H | H | H | $^iPr$ | H | F | F | OH |
| XXIII-24-2 | $^tBu$ | H | H | $CH_3$ | $^iPr$ | H | F | F | OH |
| XXIII-24-3 | $^tBu$ | H | H | $CH(CH_3)_2$ | $^iPr$ | H | F | F | OH |
| XXIII-24-4 | $^tBu$ | H | H | $CH_2CH(CH_3)_2$ | $^iPr$ | H | F | F | OH |
| XXIII-24-5 | $^tBu$ | H | H | $CH_2Ph$ | $^iPr$ | H | F | F | OH |
| XXIII-24-6 | $^tBu$ | H | H | $CH_2$-indol-3-yl | $^iPr$ | H | F | F | OH |
| XXIII-24-7 | $^tBu$ | H | H | $CH_2CH_2SCH_3$ | $^iPr$ | H | F | F | OH |
| XXIII-24-8 | $^tBu$ | * | H | * | $^iPr$ | H | F | F | OH |

*$R^2$ and $R^{3b}$ joined together by $(CH_2)_3$ to form five-membered ring.

TABLE XXIII-25

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-25-1 | Ph | H | H | H | $^iPr$ | H | F | F | OH |
| XXIII-25-2 | Ph | H | H | $CH_3$ | $^iPr$ | H | F | F | OH |
| XXIII-25-3 | Ph | H | H | $CH(CH_3)_2$ | $^iPr$ | H | F | F | OH |
| XXIII-25-4 | Ph | H | H | $CH_2CH(CH_3)_2$ | $^iPr$ | H | F | F | OH |
| XXIII-25-5 | Ph | H | H | $CH_2Ph$ | $^iPr$ | H | F | F | OH |
| XXIII-25-6 | Ph | H | H | $CH_2$-indol-3-yl | $^iPr$ | H | F | F | OH |
| XXIII-25-7 | Ph | H | H | $CH_2CH_2SCH_3$ | $^iPr$ | H | F | F | OH |
| XXIII-25-8 | Ph | * | H | * | $^iPr$ | H | F | F | OH |

*$R^2$ and $R^{3b}$ joined together by $(CH_2)_3$ to form five-membered ring.

TABLE XXIII-26

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-26-1 | p-Me—Ph | H | H | H | $^i$Pr | H | F | F | OH |
| XXIII-26-2 | p-Me—Ph | H | H | $CH_3$ | $^i$Pr | H | F | F | OH |
| XXIII-26-3 | p-Me—Ph | H | H | $CH(CH_3)_2$ | $^i$Pr | H | F | F | OH |
| XXIII-26-4 | p-Me—Ph | H | H | $CH_2CH(CH_3)_2$ | $^i$Pr | H | F | F | OH |
| XXIII-26-5 | p-Me—Ph | H | H | $CH_2Ph$ | $^i$Pr | H | F | F | OH |
| XXIII-26-6 | p-Me—Ph | H | H | $CH_2$-indol-3-yl | $^i$Pr | H | F | F | OH |
| XXIII-26-7 | p-Me—Ph | H | H | $CH_2CH_2SCH_3$ | $^i$Pr | H | F | F | OH |
| XXIII-26-8 | p-Me—Ph | * | H | * | $^i$Pr | H | F | F | OH |

*$R^2$ and $R^{3b}$ joined together by $(CH_2)_3$ to form five-membered ring.

TABLE XXIII-27

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-27-1 | p-F—Ph | H | H | H | $^i$Pr | H | F | F | OH |
| XXIII-27-2 | p-F—Ph | H | H | $CH_3$ | $^i$Pr | H | F | F | OH |
| XXIII-27-3 | p-F—Ph | H | H | $CH(CH_3)_2$ | $^i$Pr | H | F | F | OH |
| XXIII-27-4 | p-F—Ph | H | H | $CH_2CH(CH_3)_2$ | $^i$Pr | H | F | F | OH |
| XXIII-27-5 | p-F—Ph | H | H | $CH_2Ph$ | $^i$Pr | H | F | F | OH |
| XXIII-27-6 | p-F—Ph | H | H | $CH_2$-indol-3-yl | $^i$Pr | H | F | F | OH |
| XXIII-27-7 | p-F—Ph | H | H | $CH_2CH_2SCH_3$ | $^i$Pr | H | F | F | OH |
| XXIII-27-8 | p-F—Ph | * | H | * | $^i$Pr | H | F | F | OH |

*$R^2$ and $R^{3b}$ joined together by $(CH_2)_3$ to form five-membered ring.

TABLE XXIII-28

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-28-1 | p-Cl—Ph | H | H | H | $^i$Pr | H | F | F | OH |
| XXIII-28-2 | p-Cl—Ph | H | H | $CH_3$ | $^i$Pr | H | F | F | OH |
| XXIII-28-3 | p-Cl—Ph | H | H | $CH(CH_3)_2$ | $^i$Pr | H | F | F | OH |
| XXIII-28-4 | p-Cl—Ph | H | H | $CH_2CH(CH_3)_2$ | $^i$Pr | H | F | F | OH |
| XXIII-28-5 | p-Cl—Ph | H | H | $CH_2Ph$ | $^i$Pr | H | F | F | OH |
| XXIII-28-6 | p-Cl—Ph | H | H | $CH_2$-indol-3-yl | $^i$Pr | H | F | F | OH |
| XXIII-28-7 | p-Cl—Ph | H | H | $CH_2CH_2SCH_3$ | $^i$Pr | H | F | F | OH |
| XXIII-28-8 | p-Cl—Ph | * | H | * | $^i$Pr | H | F | F | OH |

*$R^2$ and $R^{3b}$ joined together by $(CH_2)_3$ to form five-membered ring.

TABLE XXIII-29

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-29-1 | p-Br—Ph | H | H | H | $^i$Pr | H | F | F | OH |
| XXIII-29-2 | p-Br—Ph | H | H | $CH_3$ | $^i$Pr | H | F | F | OH |
| XXIII-29-3 | p-Br—Ph | H | H | $CH(CH_3)_2$ | $^i$Pr | H | F | F | OH |
| XXIII-29-4 | p-Br—Ph | H | H | $CH_2CH(CH_3)_2$ | $^i$Pr | H | F | F | OH |
| XXIII-29-5 | p-Br—Ph | H | H | $CH_2Ph$ | $^i$Pr | H | F | F | OH |
| XXIII-29-6 | p-Br—Ph | H | H | $CH_2$-indol-3-yl | $^i$Pr | H | F | F | OH |
| XXIII-29-7 | p-Br—Ph | H | H | $CH_2CH_2SCH_3$ | $^i$Pr | H | F | F | OH |
| XXIII-29-8 | p-Br—Ph | * | H | * | $^i$Pr | H | F | F | OH |

*$R^2$ and $R^{3b}$ joined together by $(CH_2)_3$ to form five-membered ring.

TABLE XXIII-30

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-30-1 | p-I—Ph | H | H | H | $^i$Pr | H | F | F | OH |
| XXIII-30-2 | p-I—Ph | H | H | $CH_3$ | $^i$Pr | H | F | F | OH |
| XXIII-30-3 | p-I—Ph | H | H | $CH(CH_3)_2$ | $^i$Pr | H | F | F | OH |
| XXIII-30-4 | p-I—Ph | H | H | $CH_2CH(CH_3)_2$ | $^i$Pr | H | F | F | OH |
| XXIII-30-5 | p-I—Ph | H | H | $CH_2Ph$ | $^i$Pr | H | F | F | OH |
| XXIII-30-6 | p-I—Ph | H | H | $CH_2$-indol-3-yl | $^i$Pr | H | F | F | OH |
| XXIII-30-7 | p-I—Ph | H | H | $CH_2CH_2SCH_3$ | $^i$Pr | H | F | F | OH |
| XXIII-30-8 | p-I—Ph | * | H | * | $^i$Pr | H | F | F | OH |

*$R^2$ and $R^{3b}$ joined together by $(CH_2)_3$ to form five-membered ring.

TABLE XXIII-31

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-31-1 | $CH_3$ | H | H | H | $^n$Bu | H | F | F | OH |
| XXIII-31-2 | $CH_3$ | H | H | $CH_3$ | $^n$Bu | H | F | F | OH |
| XXIII-31-3 | $CH_3$ | H | H | $CH(CH_3)_2$ | $^n$Bu | H | F | F | OH |
| XXIII-31-4 | $CH_3$ | H | H | $CH_2CH(CH_3)_2$ | $^n$Bu | H | F | F | OH |
| XXIII-31-5 | $CH_3$ | H | H | $CH_2Ph$ | $^n$Bu | H | F | F | OH |
| XXIII-31-6 | $CH_3$ | H | H | $CH_2$-indol-3-yl | $^n$Bu | H | F | F | OH |
| XXIII-31-7 | $CH_3$ | H | H | $CH_2CH_2SCH_3$ | $^n$Bu | H | F | F | OH |
| XXIII-31-8 | $CH_3$ | * | H | * | $^n$Bu | H | F | F | OH |

*$R^2$ and $R^{3b}$ joined together by $(CH_2)_3$ to form five-membered ring.

TABLE XXIII-32

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-32-1 | Et | H | H | H | $^n$Bu | H | F | F | OH |
| XXIII-32-2 | Et | H | H | $CH_3$ | $^n$Bu | H | F | F | OH |
| XXIII-32-3 | Et | H | H | $CH(CH_3)_2$ | $^n$Bu | H | F | F | OH |
| XXIII-32-4 | Et | H | H | $CH_2CH(CH_3)_2$ | $^n$Bu | H | F | F | OH |
| XXIII-32-5 | Et | H | H | $CH_2Ph$ | $^n$Bu | H | F | F | OH |
| XXIII-32-6 | Et | H | H | $CH_2$-indol-3-yl | $^n$Bu | H | F | F | OH |
| XXIII-32-7 | Et | H | H | $CH_2CH_2SCH_3$ | $^n$Bu | H | F | F | OH |
| XXIII-32-8 | Et | * | H | * | $^n$Bu | H | F | F | OH |

*$R^2$ and $R^{3b}$ joined together by $(CH_2)_3$ to form five-membered ring.

TABLE XXIII-33

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIII-33-1 | $^i$Pr | H | H | H | $^n$Bu | H | F | F | OH |
| XXIII-33-2 | $^i$Pr | H | H | $CH_3$ | $^n$Bu | H | F | F | OH |

TABLE XXIII-33-continued

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIII-33-3 | $^i$Pr | H | H | CH(CH$_3$)$_2$ | $^n$Bu | H | F | F | OH |
| XXIII-33-4 | $^i$Pr | H | H | CH$_2$CH(CH$_3$)$_2$ | $^n$Bu | H | F | F | OH |
| XXIII-33-5 | $^i$Pr | H | H | CH$_2$Ph | $^n$Bu | H | F | F | OH |
| XXIII-33-6 | $^i$Pr | H | H | CH$_2$-indol-3-yl | $^n$Bu | H | F | F | OH |
| XXIII-33-7 | $^i$Pr | H | H | CH$_2$CH$_2$SCH$_3$ | $^n$Bu | H | F | F | OH |
| XXIII-33-8 | $^i$Pr | * | H | * | $^n$Bu | H | F | F | OH |

*R$^2$ and R$^{3b}$ joined together by (CH$_2$)$_3$ to form five-membered ring.

TABLE XXIII-34

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIII-34-1 | $^t$Bu | H | H | H | $^n$Bu | H | F | F | OH |
| XXIII-34-2 | $^t$Bu | H | H | CH$_3$ | $^n$Bu | H | F | F | OH |
| XXIII-34-3 | $^t$Bu | H | H | CH(CH$_3$)$_2$ | $^n$Bu | H | F | F | OH |
| XXIII-34-4 | $^t$Bu | H | H | CH$_2$CH(CH$_3$)$_2$ | $^n$Bu | H | F | F | OH |
| XXIII-34-5 | $^t$Bu | H | H | CH$_2$Ph | $^n$Bu | H | F | F | OH |
| XXIII-34-6 | $^t$Bu | H | H | CH$_2$-indol-3-yl | $^n$Bu | H | F | F | OH |
| XXIII-34-7 | $^t$Bu | H | H | CH$_2$CH$_2$SCH$_3$ | $^n$Bu | H | F | F | OH |
| XXIII-34-8 | $^t$Bu | * | H | * | $^n$Bu | H | F | F | OH |

*R$^2$ and R$^{3b}$ joined together by (CH$_2$)$_3$ to form five-membered ring.

TABLE XXIII-35

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIII-35-1 | Ph | H | H | H | $^n$Bu | H | F | F | OH |
| XXIII-35-2 | Ph | H | H | CH$_3$ | $^n$Bu | H | F | F | OH |
| XXIII-35-3 | Ph | H | H | CH(CH$_3$)$_2$ | $^n$Bu | H | F | F | OH |
| XXIII-35-4 | Ph | H | H | CH$_2$CH(CH$_3$)$_2$ | $^n$Bu | H | F | F | OH |
| XXIII-35-5 | Ph | H | H | CH$_2$Ph | $^n$Bu | H | F | F | OH |
| XXIII-35-6 | Ph | H | H | CH$_2$-indol-3-yl | $^n$Bu | H | F | F | OH |
| XXIII-35-7 | Ph | H | H | CH$_2$CH$_2$SCH$_3$ | $^n$Bu | H | F | F | OH |
| XXIII-35-8 | Ph | * | H | * | $^n$Bu | H | F | F | OH |

*R$^2$ and R$^{3b}$ joined together by (CH$_2$)$_3$ to form five-membered ring.

TABLE XXIII-36

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIII-36-1 | p-Me—Ph | H | H | H | $^n$Bu | H | F | F | OH |
| XXIII-36-2 | p-Me—Ph | H | H | CH$_3$ | $^n$Bu | H | F | F | OH |
| XXIII-36-3 | p-Me—Ph | H | H | CH(CH$_3$)$_2$ | $^n$Bu | H | F | F | OH |
| XXIII-36-4 | p-Me—Ph | H | H | CH$_2$CH(CH$_3$)$_2$ | $^n$Bu | H | F | F | OH |
| XXIII-36-5 | p-Me—Ph | H | H | CH$_2$Ph | $^n$Bu | H | F | F | OH |
| XXIII-36-6 | p-Me—Ph | H | H | CH$_2$-indol-3-yl | $^n$Bu | H | F | F | OH |
| XXIII-36-7 | p-Me—Ph | H | H | CH$_2$CH$_2$SCH$_3$ | $^n$Bu | H | F | F | OH |
| XXIII-36-8 | p-Me—Ph | * | H | * | $^n$Bu | H | F | F | OH |

*R$^2$ and R$^{3b}$ joined together by (CH$_2$)$_3$ to form five-membered ring.

TABLE XXIII-37

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIII-37-1 | p-F—Ph | H | H | H | $^n$Bu | H | F | F | OH |
| XXIII-37-2 | p-F—Ph | H | H | CH$_3$ | $^n$Bu | H | F | F | OH |
| XXIII-37-3 | p-F—Ph | H | H | CH(CH$_3$)$_2$ | $^n$Bu | H | F | F | OH |
| XXIII-37-4 | p-F—Ph | H | H | CH$_2$CH(CH$_3$)$_2$ | $^n$Bu | H | F | F | OH |
| XXIII-37-5 | p-F—Ph | H | H | CH$_2$Ph | $^n$Bu | H | F | F | OH |
| XXIII-37-6 | p-F—Ph | H | H | CH$_2$-indol-3-yl | $^n$Bu | H | F | F | OH |
| XXIII-37-7 | p-F—Ph | H | H | CH$_2$CH$_2$SCH$_3$ | $^n$Bu | H | F | F | OH |
| XXIII-37-8 | p-F—Ph | * | H | * | $^n$Bu | H | F | F | OH |

*R$^2$ and R$^{3b}$ joined together by (CH$_2$)$_3$ to form five-membered ring.

TABLE XXIII-38

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIII-38-1 | p-Cl—Ph | H | H | H | $^n$Bu | H | F | F | OH |
| XXIII-38-2 | p-Cl—Ph | H | H | CH$_3$ | $^n$Bu | H | F | F | OH |
| XXIII-38-3 | p-Cl—Ph | H | H | CH(CH$_3$)$_2$ | $^n$Bu | H | F | F | OH |
| XXIII-38-4 | p-Cl—Ph | H | H | CH$_2$CH(CH$_3$)$_2$ | $^n$Bu | H | F | F | OH |
| XXIII-38-5 | p-Cl—Ph | H | H | CH$_2$Ph | $^n$Bu | H | F | F | OH |
| XXIII-38-6 | p-Cl—Ph | H | H | CH$_2$-indol-3-yl | $^n$Bu | H | F | F | OH |
| XXIII-38-7 | p-Cl—Ph | H | H | CH$_2$CH$_2$SCH$_3$ | $^n$Bu | H | F | F | OH |
| XXIII-38-8 | p-Cl—Ph | * | H | * | $^n$Bu | H | F | F | OH |

*R$^2$ and R$^{3b}$ joined together by (CH$_2$)$_3$ to form five-membered ring.

TABLE XXIII-39

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIII-39-1 | p-Br—Ph | H | H | H | $^n$Bu | H | F | F | OH |
| XXIII-39-2 | p-Br—Ph | H | H | CH$_3$ | $^n$Bu | H | F | F | OH |
| XXIII-39-3 | p-Br—Ph | H | H | CH(CH$_3$)$_2$ | $^n$Bu | H | F | F | OH |
| XXIII-39-4 | p-Br—Ph | H | H | CH$_2$CH(CH$_3$)$_2$ | $^n$Bu | H | F | F | OH |
| XXIII-39-5 | p-Br—Ph | H | H | CH$_2$Ph | $^n$Bu | H | F | F | OH |
| XXIII-39-6 | p-Br—Ph | H | H | CH$_2$-indol-3-yl | $^n$Bu | H | F | F | OH |
| XXIII-39-7 | p-Br—Ph | H | H | CH$_2$CH$_2$SCH$_3$ | $^n$Bu | H | F | F | OH |
| XXIII-39-8 | p-Br—Ph | * | H | * | $^n$Bu | H | F | F | OH |

*R$^2$ and R$^{3b}$ joined together by (CH$_2$)$_3$ to form five-membered ring.

Table XXIII-40

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIII-40-1 | p-I—Ph | H | H | H | $^n$Bu | H | F | F | OH |
| XXIII-40-2 | p-I—Ph | H | H | CH$_3$ | $^n$Bu | H | F | F | OH |
| XXIII-40-3 | p-I—Ph | H | H | CH(CH$_3$)$_2$ | $^n$Bu | H | F | F | OH |
| XXIII-40-4 | p-I—Ph | H | H | CH$_2$CH(CH$_3$)$_2$ | $^n$Bu | H | F | F | OH |
| XXIII-40-5 | p-I—Ph | H | H | CH$_2$Ph | $^n$Bu | H | F | F | OH |
| XXIII-40-6 | p-I—Ph | H | H | CH$_2$-indol-3-yl | $^n$Bu | H | F | F | OH |

Table XXIII-40-continued

| No | R¹ | R² | R³ᵃ | R³ᵇ | R⁴ | R⁵ | R⁶ | X | Y |
|---|---|---|---|---|---|---|---|---|---|
| XXIII-40-7 | p-I—Ph | H | H | CH₂CH₂SCH₃ | ⁿBu | H | F | F | OH |
| XXIII-40-8 | p-I—Ph | * | H | * | ⁿBu | H | F | F | OH |

*R² and R³ᵇ joined together by (CH₂)₃ to form five-membered ring.

TABLE XXIII-41

| No | R¹ | R² | R³ᵃ | R³ᵇ | R⁴ | R⁵ | R⁶ | X | Y |
|---|---|---|---|---|---|---|---|---|---|
| XXIII-41-1 | CH₃ | H | H | H | Bz | H | F | F | OH |
| XXIII-41-2 | CH₃ | H | H | CH₃ | Bz | H | F | F | OH |
| XXIII-41-3 | CH₃ | H | H | CH(CH₃)₂ | Bz | H | F | F | OH |
| XXIII-41-4 | CH₃ | H | H | CH₂CH(CH₃)₂ | Bz | H | F | F | OH |
| XXIII-41-5 | CH₃ | H | H | CH₂Ph | Bz | H | F | F | OH |
| XXIII-41-6 | CH₃ | H | H | CH₂-indol-3-yl | Bz | H | F | F | OH |
| XXIII-41-7 | CH₃ | H | H | CH₂CH₂SCH₃ | Bz | H | F | F | OH |
| XXIII-41-8 | CH₃ | * | H | * | Bz | H | F | F | OH |

*R² and R³ᵇ joined together by (CH₂)₃ to form five-membered ring.

TABLE XXIII-42

| No | R¹ | R² | R³ᵃ | R³ᵇ | R⁴ | R⁵ | R⁶ | X | Y |
|---|---|---|---|---|---|---|---|---|---|
| XXIII-42-1 | Et | H | H | H | Bz | H | F | F | OH |
| XXIII-42-2 | Et | H | H | CH₃ | Bz | H | F | F | OH |
| XXIII-42-3 | Et | H | H | CH(CH₃)₂ | Bz | H | F | F | OH |
| XXIII-42-4 | Et | H | H | CH₂CH(CH₃)₂ | Bz | H | F | F | OH |
| XXIII-42-5 | Et | H | H | CH₂Ph | Bz | H | F | F | OH |
| XXIII-42-6 | Et | H | H | CH₂-indol-3-yl | Bz | H | F | F | OH |
| XXIII-42-7 | Et | H | H | CH₂CH₂SCH₃ | Bz | H | F | F | OH |
| XXIII-42-8 | Et | * | H | * | Bz | H | F | F | OH |

*R² and R³ᵇ joined together by (CH₂)₃ to form five-membered ring.

TABLE XXIII-43

| No | R¹ | R² | R³ᵃ | R³ᵇ | R⁴ | R⁵ | R⁶ | X | Y |
|---|---|---|---|---|---|---|---|---|---|
| XXIII-43-1 | ⁱPr | H | H | H | Bz | H | F | F | OH |
| XXIII-43-2 | ⁱPr | H | H | CH₃ | Bz | H | F | F | OH |
| XXIII-43-3 | ⁱPr | H | H | CH(CH₃)₂ | Bz | H | F | F | OH |
| XXIII-43-4 | ⁱPr | H | H | CH₂CH(CH₃)₂ | Bz | H | F | F | OH |
| XXIII-43-5 | ⁱPr | H | H | CH₂Ph | Bz | H | F | F | OH |
| XXIII-43-6 | ⁱPr | H | H | CH₂-indol-3-yl | Bz | H | F | F | OH |
| XXIII-43-7 | ⁱPr | H | H | CH₂CH₂SCH₃ | Bz | H | F | F | OH |
| XXIII-43-8 | ⁱPr | * | H | * | Bz | H | F | F | OH |

*R² and R³ᵇ joined together by (CH₂)₃ to form five-membered ring.

TABLE XXIII-44

| No | R¹ | R² | R³ᵃ | R³ᵇ | R⁴ | R⁵ | R⁶ | X | Y |
|---|---|---|---|---|---|---|---|---|---|
| XXIII-44-1 | ᵗBu | H | H | H | Bz | H | F | F | OH |
| XXIII-44-2 | ᵗBu | H | H | CH₃ | Bz | H | F | F | OH |
| XXIII-44-3 | ᵗBu | H | H | CH(CH₃)₂ | Bz | H | F | F | OH |
| XXIII-44-4 | ᵗBu | H | H | CH₂CH(CH₃)₂ | Bz | H | F | F | OH |
| XXIII-44-5 | ᵗBu | H | H | CH₂Ph | Bz | H | F | F | OH |
| XXIII-44-6 | ᵗBu | H | H | CH₂-indol-3-yl | Bz | H | F | F | OH |
| XXIII-44-7 | ᵗBu | H | H | CH₂CH₂SCH₃ | Bz | H | F | F | OH |
| XXIII-44-8 | ᵗBu | * | H | * | Bz | H | F | F | OH |

*R² and R³ᵇ joined together by (CH₂)₃ to form five-membered ring.

TABLE XXIII-45

| No | R¹ | R² | R³ᵃ | R³ᵇ | R⁴ | R⁵ | R⁶ | X | Y |
|---|---|---|---|---|---|---|---|---|---|
| XXIII-45-1 | Ph | H | H | H | Bz | H | F | F | OH |
| XXIII-45-2 | Ph | H | H | CH₃ | Bz | H | F | F | OH |
| XXIII-45-3 | Ph | H | H | CH(CH₃)₂ | Bz | H | F | F | OH |
| XXIII-45-4 | Ph | H | H | CH₂CH(CH₃)₂ | Bz | H | F | F | OH |
| XXIII-45-5 | Ph | H | H | CH₂Ph | Bz | H | F | F | OH |
| XXIII-45-6 | Ph | H | H | CH₂-indol-3-yl | Bz | H | F | F | OH |
| XXIII-45-7 | Ph | H | H | CH₂CH₂SCH₃ | Bz | H | F | F | OH |
| XXIII-45-8 | Ph | * | H | * | Bz | H | F | F | OH |

*R² and R³ᵇ joined together by (CH₂)₃ to form five-membered ring.

TABLE XXIII-46

| No | R¹ | R² | R³ᵃ | R³ᵇ | R⁴ | R⁵ | R⁶ | X | Y |
|---|---|---|---|---|---|---|---|---|---|
| XXIII-46-1 | p-Me—Ph | H | H | H | Bz | H | F | F | OH |
| XXIII-46-2 | p-Me—Ph | H. | H | CH₃ | Bz | H | F | F | OH |
| XXIII-46-3 | p-Me—Ph | H | H | CH(CH₃)₂ | Bz | H | F | F | OH |
| XXIII-46-4 | p-Me—Ph | H | H | CH₂CH(CH₃)₂ | Bz | H | F | F | OH |
| XXIII-46-5 | p-Me—Ph | H | H | CH₂Ph | Bz | H | F | F | OH |
| XXIII-46-6 | p-Me—Ph | H | H | CH₂-indol-3-yl | Bz | H | F | F | OH |
| XXIII-46-7 | p-Me—Ph | H | H | CH₂CH₂SCH₃ | Bz | H | F | F | OH |
| XXIII-46-8 | p-Me—Ph | * | H | * | Bz | H | F | F | OH |

*R² and R³ᵇ joined together by (CH₂)₃ to form five-membered ring.

TABLE XXIII-47

| No | R¹ | R² | R³ᵃ | R³ᵇ | R⁴ | R⁵ | R⁶ | X | Y |
|---|---|---|---|---|---|---|---|---|---|
| XXIII-47-1 | p-F—Ph | H | H | H | Bz | H | F | F | OH |
| XXIII-47-2 | p-F—Ph | H | H | CH₃ | Bz | H | F | F | OH |
| XXIII-47-3 | p-F—Ph | H | H | CH(CH₃)₂ | Bz | H | F | F | OH |
| XXIII-47-4 | p-F—Ph | H | H | CH₂CH(CH₃)₂ | Bz | H | F | F | OH |
| XXIII-47-5 | p-F—Ph | H | H | CH₂Ph | Bz | H | F | F | OH |
| XXIII-47-6 | p-F—Ph | H | H | CH₂-indol-3-yl | Bz | H | F | F | OH |
| XXIII-47-7 | p-F—Ph | H | H | CH₂CH₂SCH₃ | Bz | H | F | F | OH |
| XXIII-47-8 | p-F—Ph | * | H | * | Bz | H | F | F | OH |

*R² and R³ᵇ joined together by (CH₂)₃ to form five-membered ring.

TABLE XXIII-48

| No | R¹ | R² | R³ᵃ | R³ᵇ | R⁴ | R⁵ | R⁶ | X | Y |
|---|---|---|---|---|---|---|---|---|---|
| XXIII-48-1 | p-Cl—Ph | H | H | H | Bz | H | F | F | OH |
| XXIII-48-2 | p-Cl—Ph | H | H | CH₃ | Bz | H | F | F | OH |
| XXIII-48-3 | p-Cl—Ph | H | H | CH(CH₃)₂ | Bz | H | F | F | OH |
| XXIII-48-4 | p-Cl—Ph | H | H | CH₂CH(CH₃)₂ | Bz | H | F | F | OH |
| XXIII-48-5 | p-Cl—Ph | H | H | CH₂Ph | Bz | H | F | F | OH |
| XXIII-48-6 | p-Cl—Ph | H | H | CH₂-indol-3-yl | Bz | H | F | F | OH |
| XXIII-48-7 | p-Cl—Ph | H | H | CH₂CH₂SCH₃ | Bz | H | F | F | OH |
| XXIII-48-8 | p-Cl—Ph | * | H | * | Bz | H | F | F | OH |

*R² and R³ᵇ joined together by (CH₂)₃ to form five-membered ring.

TABLE XXIII-49

| No | R¹ | R² | R$^{3a}$ | R$^{3b}$ | R⁴ | R⁵ | R⁶ | X | Y |
|---|---|---|---|---|---|---|---|---|---|
| XXIII-49-1 | p-Br—Ph | H | H | H | Bz | H | F | F | OH |
| XXIII-49-2 | p-Br—Ph | H | H | CH₃ | Bz | H | F | F | OH |
| XXIII-49-3 | p-Br—Ph | H | H | CH(CH₃)₂ | Bz | H | F | F | OH |
| XXIII-49-4 | p-Br—Ph | H | H | CH₂CH(CH₃)₂ | Bz | H | F | F | OH |
| XXIII-49-5 | p-Br—Ph | H | H | CH₂Ph | Bz | H | F | F | OH |
| XXIII-49-6 | p-Br—Ph | H | H | CH₂-indol-3-yl | Bz | M | F | F | OH |
| XXIII-49-7 | p-Br—Ph | H | H | CH₂CH₂SCH₃ | Bz | H | F | F | OH |
| XXIII-49-8 | p-Br—Ph | * | H | * | Bz | H | F | F | OH |

*R² and R$^{3b}$ joined together by (CH₂)₃ to form five-membered ring.

TABLE XXIII-50

| No | R¹ | R² | R$^{3a}$ | R$^{3b}$ | R⁴ | R⁵ | R⁶ | X | Y |
|---|---|---|---|---|---|---|---|---|---|
| XXIII-50-1 | p-I—Ph | H | H | H | Bz | H | F | F | OH |
| XXIII-50-2 | p-I—Ph | H | H | CH₃ | Bz | H | F | F | OH |
| XXIII-50-3 | p-I—Ph | H | H | CH(CH₃)₂ | Bz | H | F | F | OH |
| XXIII-50-4 | p-I—Ph | H | H | CH₂CH(CH₃)₂ | Bz | H | F | F | OH |
| XXIII-50-5 | p-I—Ph | H | H | CH₂Ph | Bz | H | F | F | OH |
| XXIII-50-6 | p-I—Ph | H | H | CH₂-indol-3-yl | Bz | H | F | F | OH |
| XXIII-50-7 | p-I—Ph | H | H | CH₂CH₂SCH₃ | Bz | H | F | F | OH |
| XXIII-50-8 | p-I—Ph | * | H | * | Bz | H | F | F | OH |

*R² and R$^{3b}$ joined together by (CH₂)₃ to form five-membered ring.

XXIV

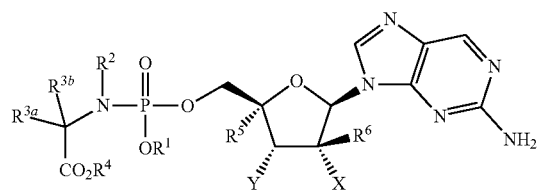

TABLE XXIV-1

| No | R¹ | R² | R$^{3a}$ | R$^{3b}$ | R⁴ | R⁵ | R⁶ | X | Y |
|---|---|---|---|---|---|---|---|---|---|
| XXIV-1-1 | CH3 | H | H | H | CH3 | H | H | F | OH |
| XXIV-1-2 | CH3 | H | H | CH₃ | CH3 | H | H | F | OH |
| XXIV-1-3 | CH3 | H | H | CH(CH₃)₂ | CH3 | H | H | F | OH |
| XXIV-1-4 | CH3 | H | H | CH₂CH(CH₃)₂ | CH3 | H | H | F | OH |
| XXIV-1-5 | CH3 | H | H | CH₂Ph | CH3 | H | H | F | OH |
| XXIV-1-6 | CH3 | H | H | CH₂-indol-3-yl | CH3 | H | H | F | OH |
| XXIV-1-7 | CH3 | H | H | CH₂CH₂SCH₃ | CH3 | H | H | F | OH |
| XXIV-1-8 | CH3 | * | H | * | CH3 | H | H | F | OH |

*R² and R$^{3b}$ joined together by (CH₂)₃ to form five-membered ring.

TABLE XXIV-2

| No | R¹ | R² | R$^{3a}$ | R$^{3b}$ | R⁴ | R⁵ | R⁶ | X | Y |
|---|---|---|---|---|---|---|---|---|---|
| XXIV-2-1 | Et | H | H | H | CH₃ | H | H | F | OH |
| XXIV-2-2 | Et | H | H | CH₃ | CH₃ | H | H | F | OH |
| XXIV-2-3 | Et | H | H | CH(CH₃)₂ | CH₃ | H | H | F | OH |
| XXIV-2-4 | Et | H | H | CH₂CH(CH₃)₂ | CH₃ | H | H | F | OH |
| XXIV-2-5 | Et | H | H | CH₂Ph | CH₃ | H | H | F | OH |
| XXIV-2-6 | Et | H | H | CH₂-indol-3-yl | CH₃ | H | H | F | OH |
| XXIV-2-7 | Et | H | H | CH₂CH₂SCH₃ | CH₃ | H | H | F | OH |
| XXIV-2-8 | Et | * | H | * | CH₃ | H | H | F | OH |

*R² and R$^{3b}$ joined together by (CH₂)₃ to form five-membered ring.

TABLE XXIV-3

| No | R¹ | R² | R$^{3a}$ | R$^{3b}$ | R⁴ | R⁵ | R⁶ | X | Y |
|---|---|---|---|---|---|---|---|---|---|
| XXIV-3-1 | $^i$Pr | H | H | H | CH₃ | H | H | F | OH |
| XXIV-3-2 | $^i$Pr | H | H | CH₃ | CH₃ | H | H | F | OH |
| XXIV-3-3 | $^i$Pr | H | H | CH(CH₃)₂ | CH₃ | H | H | F | OH |
| XXIV-3-4 | $^i$Pr | H | H | CH₂CH(CH₃)₂ | CH₃ | H | H | F | OH |
| XXIV-3-5 | $^i$Pr | H | H | CH₂Ph | CH₃ | H | H | F | OH |
| XXIV-3-6 | $^i$Pr | H | H | CH₂-indol-3-yl | CH₃ | H | H | F | OH |
| XXIV-3-7 | $^i$Pr | H | H | CH₂CH₂SCH₃ | CH₃ | H | H | F | OH |
| XXIV-3-8 | $^i$Pr | * | H | * | CH₃ | H | H | F | OH |

*R² and R$^{3b}$ joined together by (CH₂)₃ to form five-membered ring.

TABLE XXIV-4

| No | R¹ | R² | R$^{3a}$ | R$^{3b}$ | R⁴ | R⁵ | R⁶ | X | Y |
|---|---|---|---|---|---|---|---|---|---|
| XXIV-4-1 | $^t$Bu | H | H | H | CH₃ | H | H | F | OH |
| XXIV-4-2 | $^t$Bu | H | H | CH₃ | CH₃ | H | H | F | OH |
| XXIV-4-3 | $^t$Bu | H | H | CH(CH₃)₂ | CH₃ | H | H | F | OH |
| XXIV-4-4 | $^t$Bu | H | H | CH₂CH(CH₃)₂ | CH₃ | H | H | F | OH |
| XXIV-4-5 | $^t$Bu | H | H | CH₂Ph | CH₃ | H | H | F | OH |
| XXIV-4-6 | $^t$Bu | H | H | CH₂-indol-3-yl | CH₃ | H | H | F | OH |
| XXIV-4-7 | $^t$Bu | H | H | CH₂CH₂SCH₃ | CH₃ | H | H | F | OH |
| XXIV-4-8 | $^t$Bu | * | H | * | CH₃ | H | H | F | OH |

*R² and R$^{3b}$ joined together by (CH₂)₃ to form five-membered ring.

TABLE XXIV-5

| No | R¹ | R² | R$^{3a}$ | R$^{3b}$ | R⁴ | R⁵ | R⁶ | X | Y |
|---|---|---|---|---|---|---|---|---|---|
| XXIV-5-1 | Ph | H | H | H | CH₃ | H | H | F | OH |
| XXIV-5-2 | Ph | H | H | CH₃ | CH₃ | H | H | F | OH |
| XXIV-5-3 | Ph | H | H | CH(CH₃)₂ | CH₃ | H | H | F | OH |
| XXIV-5-4 | Ph | H | H | CH₂CH(CH₃)₂ | CH₃ | H | H | F | OH |
| XXIV-5-5 | Ph | H | H | CH₂Ph | CH₃ | H | H | F | OH |
| XXIV-5-6 | Ph | H | H | CH₂-indol-3-yl | CH₃ | H | H | F | OH |
| XXIV-5-7 | Ph | H | H | CH₂CH₂SCH₃ | CH₃ | H | H | F | OH |
| XXIV-5-8 | Ph | * | H | * | CH₃ | H | H | F | OH |

*R² and R$^{3b}$ joined together by (CH₂)₃ to form five-membered ring.

TABLE XXIV-6

| No | R¹ | R² | R$^{3a}$ | R$^{3b}$ | R⁴ | R⁵ | R⁶ | X | Y |
|---|---|---|---|---|---|---|---|---|---|
| XXIV-6-1 | p-Me—Ph | H | H | H | CH₃ | H | H | F | OH |
| XXIV-6-2 | p-Me—Ph | H | H | CH₃ | CH₃ | H | H | F | OH |
| XXIV-6-3 | p-Me—Ph | H | H | CH(CH₃)₂ | CH₃ | H | H | F | OH |
| XXIV-6-4 | p-Me—Ph | H | H | CH₂CH(CH₃)₂ | CH₃ | H | H | F | OH |
| XXIV-6-5 | p-Me—Ph | H | H | CH₂Ph | CH₃ | H | H | F | OH |
| XXIV-6-6 | p-Me—Ph | H | H | CH₂-indol-3-yl | CH₃ | H | H | F | OH |
| XXIV-6-7 | p-Me—Ph | H | H | CH₂CH₂SCH₃ | CH₃ | H | H | F | OH |
| XXIV-6-8 | p-Me—Ph | * | H | * | CH₃ | H | H | F | OH |

*R² and R$^{3b}$ joined together by (CH₂)₃ to form five-membered ring.

TABLE XXIV-7

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIV-7-1 | p-F—Ph | H | H | H | CH$_3$ | H | H | F | OH |
| XXIV-7-2 | p-F—Ph | H | H | CH$_3$ | CH$_3$ | H | H | F | OH |
| XXIV-7-3 | p-F—Ph | H | H | CH(CH$_3$)$_2$ | CH$_3$ | H | H | F | OH |
| XXIV-7-4 | p-F—Ph | H | H | CH$_2$CH(CH$_3$)$_2$ | CH$_3$ | H | H | F | OH |
| XXIV-7-6 | p-F—Ph | H | H | CH$_2$Ph | CH$_3$ | H | H | F | OH |
| XXIV-7-7 | p-F—Ph | H | H | CH$_2$-indol-3-yl | CH$_3$ | H | H | F | OH |
| XXIV-7-8 | p-F—Ph | H | H | CH$_2$CH$_2$SCH$_3$ | CH$_3$ | H | H | F | OH |
| XXIV-7-20 | p-F—Ph | * | H | * | CH$_3$ | H | H | F | OH |

*R$^2$ and R$^{3b}$ joined together by (CH$_2$)$_3$ to form five-membered ring.

TABLE XXIV-8

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIV-8-1 | p-Cl—Ph | H | H | H | CH$_3$ | H | H | F | OH |
| XXIV-8-2 | p-Cl—Ph | H | H | CH$_3$ | CH$_3$ | H | H | F | OH |
| XXIV-8-3 | p-Cl—Ph | H | H | CH(CH$_3$)$_2$ | CH$_3$ | H | H | F | OH |
| XXIV-8-4 | p-Cl—Ph | H | H | CH$_2$CH(CH$_3$)$_2$ | CH$_3$ | H | H | F | OH |
| XXIV-8-5 | p-Cl—Ph | H | H | CH$_2$Ph | CH$_3$ | H | H | F | OH |
| XXIV-8-6 | p-Cl—Ph | H | H | CH$_2$-indol-3-yl | CH$_3$ | H | H | F | OH |
| XXIV-8-7 | p-Cl—Ph | H | H | CH$_2$CH$_2$SCH$_3$ | CH$_3$ | H | H | F | OH |
| XXIV-8-8 | p-Cl—Ph | * | H | * | CH$_3$ | H | H | F | OH |

*R$^2$ and R$^{3b}$ joined together by (CH$_2$)$_3$ to form five-membered ring.

TABLE XXIV-9

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIV-9-1 | p-Br—Ph | H | H | H | CH$_3$ | H | H | F | OH |
| XXIV-9-2 | p-Br—Ph | H | H | CH$_3$ | CH$_3$ | H | H | F | OH |
| XXIV-9-3 | p-Br—Ph | H | H | CH(CH$_3$)$_2$ | CH$_3$ | H | H | F | OH |
| XXIV-9-4 | p-Br—Ph | H | H | CH$_2$CH(CH$_3$)$_2$ | CH$_3$ | H | H | F | OH |
| XXIV-9-6 | p-Br—Ph | H | H | CH$_2$Ph | CH$_3$ | H | H | F | OH |
| XXIV-9-7 | p-Br—Ph | H | H | CH$_2$-indol-3-yl | CH$_3$ | H | H | F | OH |
| XXIV-9-8 | p-Br—Ph | H | H | CH$_2$CH$_2$SCH$_3$ | CH$_3$ | H | H | F | OH |
| XXIV-9-20 | p-Br—Ph | * | H | * | CH$_3$ | H | H | F | OH |

*R$^2$ and R$^{3b}$ joined together by (CH$_2$)$_3$ to form five-membered ring.

TABLE XXIV-10

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIV-10-1 | p-I—Ph | H | H | H | CH$_3$ | H | H | F | OH |
| XXIV-10-2 | p-I—Ph | H | H | CH$_3$ | CH$_3$ | H | H | F | OH |
| XXIV-10-3 | p-I—Ph | H | H | CH(CH$_3$)$_2$ | CH$_3$ | H | H | F | OH |
| XXIV-10-4 | p-I—Ph | H | H | CH$_2$CH(CH$_3$)$_2$ | CH$_3$ | H | H | F | OH |
| XXIV-10-5 | p-I—Ph | H | H | CH$_2$Ph | CH$_3$ | H | H | F | OH |
| XXIV-10-6 | p-I—Ph | H | H | CH$_2$-indol-3-yl | CH$_3$ | H | H | F | OH |
| XXIV-10-7 | p-I—Ph | H | H | CH$_2$CH$_2$SCH$_3$ | CH$_3$ | H | H | F | OH |
| XXIV-10-8 | p-I—Ph | * | H | * | CH$_3$ | H | H | F | OH |

*R$^2$ and R$^{3b}$ joined together by (CH$_2$)$_3$ to form five-membered ring.

TABLE XXIV-11

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIV-11-1 | CH$_3$ | H | H | H | Et | H | H | F | OH |
| XXIV-11-2 | CH$_3$ | H | H | CH$_3$ | Et | H | H | F | OH |
| XXIV-11-3 | CH$_3$ | H | H | CH(CH$_3$)$_2$ | Et | H | H | F | OH |
| XXIV-11-4 | CH$_3$ | H | H | CH$_2$CH(CH$_3$)$_2$ | Et | H | H | F | OH |
| XXIV-11-5 | CH$_3$ | H | H | CH$_2$Ph | Et | H | H | F | OH |
| XXIV-11-6 | CH$_3$ | H | H | CH$_2$-indol-3-yl | Et | H | H | F | OH |
| XXIV-11-7 | CH$_3$ | H | H | CH$_2$CH$_2$SCH$_3$ | Et | H | H | F | OH |
| XXIV-11-8 | CH$_3$ | * | H | * | Et | H | H | F | OH |

*R$^2$ and R$^{3b}$ joined together by (CH$_2$)$_3$ to form five-membered ring.

TABLE XXIV-12

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIV-12-1 | Et | H | H | H | Et | H | H | F | OH |
| XXIV-12-2 | Et | H | H | CH$_3$ | Et | H | H | F | OH |
| XXIV-12-3 | Et | H | H | CH(CH$_3$)$_2$ | Et | H | H | F | OH |
| XXIV-12-4 | Et | H | H | CH$_2$CH(CH$_3$)$_2$ | Et | H | H | F | OH |
| XXIV-12-5 | Et | H | H | CH$_2$Ph | Et | H | H | F | OH |
| XXIV-12-6 | Et | H | H | CH$_2$-indol-3-yl | Et | H | H | F | OH |
| XXIV-12-7 | Et | H | H | CH$_2$CH$_2$SCH$_3$ | Et | H | H | F | OH |
| XXIV-12-8 | Et | * | H | * | Et | H | H | F | OH |

*R$^2$ and R$^{3b}$ joined together by (CH$_2$)$_3$ to form five-membered ring.

TABLE XXIV-13

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIV-13-1 | $^i$Pr | H | H | H | Et | H | H | F | OH |
| XXIV-13-2 | $^i$Pr | H | H | CH$_3$ | Et | H | H | F | OH |
| XXIV-13-3 | $^i$Pr | H | H | CH(CH$_3$)$_2$ | Et | H | H | F | OH |
| XXIV-13-4 | $^i$Pr | H | H | CH$_2$CH(CH$_3$)$_2$ | Et | H | H | F | OH |
| XXIV-13-5 | $^i$Pr | H | H | CH$_2$Ph | Et | H | H | F | OH |
| XXIV-13-6 | $^i$Pr | H | H | CH$_2$-indol-3-yl | Et | H | H | F | OH |
| XXIV-13-7 | $^i$Pr | H | H | CH$_2$CH$_2$SCH$_3$ | Et | H | H | F | OH |
| XXIV-13-8 | $^i$Pr | * | H | * | Et | H | H | F | OH |

*R$^2$ and R$^{3b}$ joined together by (CH$_2$)$_3$ to form five-membered ring.

TABLE XXIV-14

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIV-14-1 | $^t$Bu | H | H | H | Et | H | H | F | OH |
| XXIV-14-2 | $^t$Bu | H | H | CH$_3$ | Et | H | H | F | OH |
| XXIV-14-3 | $^t$Bu | H | H | CH(CH$_3$)$_2$ | Et | H | H | F | OH |
| XXIV-14-4 | $^t$Bu | H | H | CH$_2$CH(CH$_3$)$_2$ | Et | H | H | F | OH |
| XXIV-14-5 | $^t$Bu | H | H | CH$_2$Ph | Et | H | H | F | OH |
| XXIV-14-6 | $^t$Bu | H | H | CH$_2$-indol-3-yl | Et | H | H | F | OH |
| XXIV-14-7 | $^t$Bu | H | H | CH$_2$CH$_2$SCH$_3$ | Et | H | H | F | OH |
| XXIV-14-8 | $^t$Bu | * | H | * | Et | H | H | F | OH |

*R$^2$ and R$^{3b}$ joined together by (CH$_2$)$_3$ to form five-membered ring.

TABLE XXIV-15

| No | R¹ | R² | R³ᵃ | R³ᵇ | R⁴ | R⁵ | R⁶ | X | Y |
|---|---|---|---|---|---|---|---|---|---|
| XXIV-15-1 | Ph | H | H | H | Et | H | H | F | OH |
| XXIV-15-2 | Ph | H | H | CH₃ | Et | H | H | F | OH |
| XXIV-15-3 | Ph | H | H | CH(CH₃)₂ | Et | H | H | F | OH |
| XXIV-15-4 | Ph | H | H | CH₂CH(CH₃)₂ | Et | H | H | F | OH |
| XXIV-15-5 | Ph | H | H | CH₂Ph | Et | H | H | F | OH |
| XXIV-15-6 | Ph | H | H | CH₂-indol-3-yl | Et | H | H | F | OH |
| XXIV-15-7 | Ph | H | H | CH₂CH₂SCH₃ | Et | H | H | F | OH |
| XXIV-15-8 | Ph | * | H | * | Et | H | H | F | OH |

*R² and R³ᵇ joined together by (CH₂)₃ to form five-membered ring.

TABLE XXIV-16

| No | R¹ | R² | R³ᵃ | R³ᵇ | R⁴ | R⁵ | R⁶ | X | Y |
|---|---|---|---|---|---|---|---|---|---|
| XXIV-16-1 | p-Me—Ph | H | H | H | Et | H | H | F | OH |
| XXIV-16-2 | p-Me—Ph | H | H | CH₃ | Et | H | H | F | OH |
| XXIV-16-3 | p-Me—Ph | H | H | CH(CH₃)₂ | Et | H | H | F | OH |
| XXIV-16-4 | p-Me—Ph | H | H | CH₂CH(CH₃)₂ | Et | H | H | F | OH |
| XXIV-16-5 | p-Me—Ph | H | H | CH₂Ph | Et | H | H | F | OH |
| XXIV-16-6 | p-Me—Ph | H | H | CH₂-indol-3-yl | Et | H | H | F | OH |
| XXIV-16-7 | p-Me—Ph | H | H | CH₂CH₂SCH₃ | Et | H | H | F | OH |
| XXIV-16-8 | p-Me—Ph | * | H | * | Et | H | H | F | OH |

*R² and R³ᵇ joined together by (CH₂)₃ to form five-membered ring.

TABLE XXIV-17

| No | R¹ | R² | R³ᵃ | R³ᵇ | R⁴ | R⁵ | R⁶ | X | Y |
|---|---|---|---|---|---|---|---|---|---|
| XXIV-17-1 | p-F—Ph | H | H | H | Et | H | H | F | OH |
| XXIV-17-2 | p-F—Ph | H | H | CH₃ | Et | H | H | F | OH |
| XXIV-17-3 | p-F—Ph | H | H | CH(CH₃)₂ | Et | H | H | F | OH |
| XXIV-17-4 | p-F—Ph | H | H | CH₂CH(CH₃)₂ | Et | H | H | F | OH |
| XXIV-17-5 | p-F—Ph | H | H | CH₂Ph | Et | H | H | F | OH |
| XXIV-17-6 | p-F—Ph | H | H | CH₂-indol-3-yl | Et | H | H | F | OH |
| XXIV-17-7 | p-F—Ph | H | H | CH₂CH₂SCH₃ | Et | H | H | F | OH |
| XXIV-17-8 | p-F—Ph | * | H | * | Et | H | H | F | OH |

*R² and R³ᵇ joined together by (CH₂)₃ to form five-membered ring.

TABLE XXIV-18

| No | R¹ | R² | R³ᵃ | R³ᵇ | R⁴ | R⁵ | R⁶ | X | Y |
|---|---|---|---|---|---|---|---|---|---|
| XXIV-18-1 | p-Cl—Ph | H | H | H | Et | H | H | F | OH |
| XXIV-18-2 | p-Cl—Ph | H | H | CH₃ | Et | H | H | F | OH |
| XXIV-18-3 | p-Cl—Ph | H | H | CH(CH₃)₂ | Et | H | H | F | OH |
| XXIV-18-4 | p-Cl—Ph | H | H | CH₂CH(CH₃)₂ | Et | H | H | F | OH |
| XXIV-18-5 | p-Cl—Ph | H | H | CH₂Ph | Et | H | H | F | OH |
| XXIV-18-6 | p-Cl—Ph | H | H | CH₂-indol-3-yl | Et | H | H | F | OH |
| XXIV-18-7 | p-Cl—Ph | H | H | CH₂CH₂SCH₃ | Et | H | H | F | OH |
| XXIV-18-8 | p-Cl—Ph | * | H | * | Et | H | H | F | OH |

*R² and R³ᵇ joined together by (CH₂)₃ to form five-membered ring.

TABLE XXIV-19

| No | R¹ | R² | R³ᵃ | R³ᵇ | R⁴ | R⁵ | R⁶ | X | Y |
|---|---|---|---|---|---|---|---|---|---|
| XXIV-19-1 | p-Br—Ph | H | H | H | Et | H | H | F | OH |
| XXIV-19-2 | p-Br—Ph | H | H | CH₃ | Et | H | H | F | OH |
| XXIV-19-3 | p-Br—Ph | H | H | CH(CH₃)₂ | Et | H | H | F | OH |
| XXIV-19-4 | p-Br—Ph | H | H | CH₂CH(CH₃)₂ | Et | H | H | F | OH |
| XXIV-19-5 | p-Br—Ph | H | H | CH₂Ph | Et | H | H | F | OH |
| XXIV-19-6 | p-Br—Ph | H | H | CH₂-indol-3-yl | Et | H | H | F | OH |
| XXIV-19-7 | p-Br—Ph | H | H | CH₂CH₂SCH₃ | Et | H | H | F | OH |
| XXIV-19-8 | p-Br—Ph | * | H | * | Et | H | H | F | OH |

*R² and R³ᵇ joined together by (CH₂)₃ to form five-membered ring.

TABLE XXIV-20

| No | R¹ | R² | R³ᵃ | R³ᵇ | R⁴ | R⁵ | R⁶ | X | Y |
|---|---|---|---|---|---|---|---|---|---|
| XXIV-20-1 | p-I—Ph | H | H | H | Et | H | H | F | OH |
| XXIV-20-2 | p-I—Ph | H | H | CH₃ | Et | H | H | F | OH |
| XXIV-20-3 | p-I—Ph | H | H | CH(CH₃)₂ | Et | H | H | F | OH |
| XXIV-20-4 | p-I—Ph | H | H | CH₂CH(CH₃)₂ | Et | H | H | F | OH |
| XXIV-20-5 | p-I—Ph | H | H | CH₂Ph | Et | H | H | F | OH |
| XXIV-20-6 | p-I—Ph | H | H | CH₂-indol-3-yl | Et | H | H | F | OH |
| XXIV-20-7 | p-I—Ph | H | H | CH₂CH₂SCH₃ | Et | H | H | F | OH |
| XXIV-20-8 | p-I—Ph | * | H | * | Et | H | H | F | OH |

*R² and R³ᵇ joined together by (CH₂)₃ to form five-membered ring.

TABLE XXIV-21

| No | R¹ | R² | R³ᵃ | R³ᵇ | R⁴ | R⁵ | R⁶ | X | Y |
|---|---|---|---|---|---|---|---|---|---|
| XXIV-21-1 | CH₃ | H | H | H | ⁱPr | H | H | F | OH |
| XXIV-21-2 | CH₃ | H | H | CH₃ | ⁱPr | H | H | F | OH |
| XXIV-21-3 | CH₃ | H | H | CH(CH₃)₂ | ⁱPr | H | H | F | OH |
| XXIV-21-4 | CH₃ | H | H | CH₂CH(CH₃)₂ | ⁱPr | H | H | F | OH |
| XXIV-21-5 | CH₃ | H | H | CH₂Ph | ⁱPr | H | H | F | OH |
| XXIV-21-6 | CH₃ | H | H | CH₂-indol-3-yl | ⁱPr | H | H | F | OH |
| XXIV-21-7 | CH₃ | H | H | CH₂CH₂SCH₃ | ⁱPr | H | H | F | OH |
| XXIV-21-8 | CH₃ | * | H | * | ⁱPr | H | H | F | OH |

*R² and R³ᵇ joined together by (CH₂)₃ to form five-membered ring.

TABLE XXIV-22

| No | R¹ | R² | R³ᵃ | R³ᵇ | R⁴ | R⁵ | R⁶ | X | Y |
|---|---|---|---|---|---|---|---|---|---|
| XXIV-22-1 | Et | H | H | H | ⁱPr | H | H | F | OH |
| XXIV-22-2 | Et | H | H | CH₃ | ⁱPr | H | H | F | OH |
| XXIV-22-3 | Et | H | H | CH(CH₃)₂ | ⁱPr | H | H | F | OH |
| XXIV-22-4 | Et | H | H | CH₂CH(CH₃)₂ | ⁱPr | H | H | F | OH |
| XXIV-22-5 | Et | H | H | CH₂Ph | ⁱPr | H | H | F | OH |
| XXIV-22-6 | Et | H | H | CH₂-indol-3-yl | ⁱPr | H | H | F | OH |
| XXIV-22-7 | Et | H | H | CH₂CH₂SCH₃ | ⁱPr | H | H | F | OH |
| XXIV-22-8 | Et | * | H | * | ⁱPr | H | H | F | OH |

*R² and R³ᵇ joined together by (CH₂)₃ to form five-membered ring.

TABLE XXIV-23

| No | R¹ | R² | R³ᵃ | R³ᵇ | R⁴ | R⁵ | R⁶ | X | Y |
|---|---|---|---|---|---|---|---|---|---|
| XXIV-23-1 | ⁱPr | H | H | H | ⁱPr | H | H | F | OH |
| XXIV-23-2 | ⁱPr | H | H | CH₃ | ⁱPr | H | H | F | OH |
| XXIV-23-3 | ⁱPr | H | H | CH(CH₃)₂ | ⁱPr | H | H | F | OH |
| XXIV-23-4 | ⁱPr | H | H | CH₂CH(CH₃)₂ | ⁱPr | H | H | F | OH |
| XXIV-23-5 | ⁱPr | H | H | CH₂Ph | ⁱPr | H | H | F | OH |

TABLE XXIV-23-continued

| No | R¹ | R² | R³ᵃ | R³ᵇ | R⁴ | R⁵ | R⁶ | X | Y |
|---|---|---|---|---|---|---|---|---|---|
| XXIV-23-6 | ⁱPr | H | H | CH₂-indol-3-yl | ⁱPr | H | H | F | OH |
| XXIV-23-7 | ⁱPr | H | H | CH₂CH₂SCH₃ | ⁱPr | H | H | F | OH |
| XXIV-23-8 | ⁱPr | * | H | * | ⁱPr | H | H | F | OH |

*R² and R³ᵇ joined together by (CH₂)₃ to form five-membered ring.

TABLE XXIV-24

| No | R¹ | R² | R³ᵃ | R³ᵇ | R⁴ | R⁵ | R⁶ | X | Y |
|---|---|---|---|---|---|---|---|---|---|
| XXIV-24-1 | ᵗBu | H | H | H | ⁱPr | H | H | F | OH |
| XXIV-24-2 | ᵗBu | H | H | CH₃ | ⁱPr | H | H | F | OH |
| XXIV-24-3 | ᵗBu | H | H | CH(CH₃)₂ | ⁱPr | H | H | F | OH |
| XXIV-24-4 | ᵗBu | H | H | CH₂CH(CH₃)₂ | ⁱPr | H | H | F | OH |
| XXIV-24-5 | ᵗBu | H | H | CH₂Ph | ⁱPr | H | H | F | OH |
| XXIV-24-6 | ᵗBu | H | H | CH₂-indol-3-yl | ⁱPr | H | H | F | OH |
| XXIV-24-7 | ᵗBu | H | H | CH₂CH₂SCH₃ | ⁱPr | H | H | F | OH |
| XXIV-24-8 | ᵗBu | * | H | * | ⁱPr | H | H | F | OH |

*R² and R³ᵇ joined together by (CH₂)₃ to form five-membered ring.

TABLE XXIV-25

| No | R¹ | R² | R³ᵃ | R³ᵇ | R⁴ | R⁵ | R⁶ | X | Y |
|---|---|---|---|---|---|---|---|---|---|
| XXIV-25-1 | Ph | H | H | H | ⁱPr | H | H | F | OH |
| XXIV-25-2 | Ph | H | H | CH₃ | ⁱPr | H | H | F | OH |
| XXIV-25-3 | Ph | H | H | CH(CH₃)₂ | ⁱPr | H | H | F | OH |
| XXIV-25-4 | Ph | H | H | CH₂CH(CH₃)₂ | ⁱPr | H | H | F | OH |
| XXIV-25-5 | Ph | H | H | CH₂Ph | ⁱPr | H | H | F | OH |
| XXIV-25-6 | Ph | H | H | CH₂-indol-3-yl | ⁱPr | H | H | F | OH |
| XXIV-25-7 | Ph | H | H | CH₂CH₂SCH₃ | ⁱPr | H | H | F | OH |
| XXIV-25-8 | Ph | * | H | * | ⁱPr | H | H | F | OH |

*R² and R³ᵇ joined together by (CH₂)₃ to form five-membered ring.

TABLE XXIV-26

| No | R¹ | R² | R³ᵃ | R³ᵇ | R⁴ | R⁵ | R⁶ | X | Y |
|---|---|---|---|---|---|---|---|---|---|
| XXIV-26-1 | p-Me—Ph | H | H | H | ⁱPr | H | H | F | OH |
| XXIV-26-2 | p-Me—Ph | H | H | CH₃ | ⁱPr | H | H | F | OH |
| XXIV-26-3 | p-Me—Ph | H | H | CH(CH₃)₂ | ⁱPr | H | H | F | OH |
| XXIV-26-4 | p-Me—Ph | H | H | CH₂CH(CH₃)₂ | ⁱPr | H | H | F | OH |
| XXIV-26-5 | p-Me—Ph | H | H | CH₂Ph | ⁱPr | H | H | F | OH |
| XXIV-26-6 | p-Me—Ph | H | H | CH₂-indol-3-yl | ⁱPr | H | H | F | OH |
| XXIV-26-7 | p-Me—Ph | H | H | CH₂CH₂SCH₃ | ⁱPr | H | H | F | OH |
| XXIV-26-8 | p-Me—Ph | * | H | * | ⁱPr | H | H | F | OH |

*R² and R³ᵇ joined together by (CH₂)₃ to form five-membered ring.

TABLE XXIV-27

| No | R¹ | R² | R³ᵃ | R³ᵇ | R⁴ | R⁵ | R⁶ | X | Y |
|---|---|---|---|---|---|---|---|---|---|
| XXIV-27-1 | p-F—Ph | H | H | H | ⁱPr | H | H | F | OH |
| XXIV-27-2 | p-F—Ph | H | H | CH₃ | ⁱPr | H | H | F | OH |
| XXIV-27-3 | p-F—Ph | H | H | CH(CH₃)₂ | ⁱPr | H | H | F | OH |
| XXIV-27-4 | p-F—Ph | H | H | CH₂CH(CH₃)₂ | ⁱPr | H | H | F | OH |
| XXIV-27-5 | p-F—Ph | H | H | CH₂Ph | ⁱPr | H | H | F | OH |
| XXIV-27-6 | p-F—Ph | H | H | CH₂-indol-3-yl | ⁱPr | H | H | F | OH |
| XXIV-27-7 | p-F—Ph | H | H | CH₂CH₂SCH₃ | ⁱPr | H | H | F | OH |
| XXIV-27-8 | p-F—Ph | * | H | * | ⁱPr | H | H | F | OH |

*R² and R³ᵇ joined together by (CH₂)₃ to form five-membered ring.

TABLE XXIV-28

| No | R¹ | R² | R³ᵃ | R³ᵇ | R⁴ | R⁵ | R⁶ | X | Y |
|---|---|---|---|---|---|---|---|---|---|
| XXIV-28-1 | p-Cl—Ph | H | H | H | ⁱPr | H | H | F | OH |
| XXIV-28-2 | p-Cl—Ph | H | H | CH₃ | ⁱPr | H | H | F | OH |
| XXIV-28-3 | p-Cl—Ph | H | H | CH(CH₃)₂ | ⁱPr | H | H | F | OH |
| XXIV-28-4 | p-Cl—Ph | H | H | CH₂CH(CH₃)₂ | ⁱPr | H | H | F | OH |
| XXIV-28-5 | p-Cl—Ph | H | H | CH₂Ph | ⁱPr | H | H | F | OH |
| XXIV-28-6 | p-Cl—Ph | H | H | CH₂-indol-3-yl | ⁱPr | H | H | F | OH |
| XXIV-28-7 | p-Cl—Ph | H | H | CH₂CH₂SCH₃ | ⁱPr | H | H | F | OH |
| XXIV-28-8 | p-Cl—Ph | * | H | * | ⁱPr | H | H | F | OH |

*R² and R³ᵇ joined together by (CH₂)₃ to form five-membered ring.

TABLE XXIV-29

| No | R¹ | R² | R³ᵃ | R³ᵇ | R⁴ | R⁵ | R⁶ | X | Y |
|---|---|---|---|---|---|---|---|---|---|
| XXIV-29-1 | p-Br—Ph | H | H | H | ⁱPr | H | H | F | OH |
| XXIV-29-2 | p-Br—Ph | H | H | CH₃ | ⁱPr | H | H | F | OH |
| XXIV-29-3 | p-Br—Ph | H | H | CH(CH₃)₂ | ⁱPr | H | H | F | OH |
| XXIV-29-4 | p-Br—Ph | H | H | CH₂CH(CH₃)₂ | ⁱPr | H | H | F | OH |
| XXIV-29-5 | p-Br—Ph | H | H | CH₂Ph | ⁱPr | H | H | F | OH |
| XXIV-29-6 | p-Br—Ph | H | H | CH₂-indol-3-yl | ⁱPr | H | H | F | OH |
| XXIV-29-7 | p-Br—Ph | H | H | CH₂CH₂SCH₃ | ⁱPr | H | H | F | OH |
| XXIV-29-8 | p-Br—Ph | * | H | * | ⁱPr | H | H | F | OH |

*R² and R³ᵇ joined together by (CH₂)₃ to form five-membered ring.

TABLE XXIV-30

| No | R¹ | R² | R³ᵃ | R³ᵇ | R⁴ | R⁵ | R⁶ | X | Y |
|---|---|---|---|---|---|---|---|---|---|
| XXIV-30-1 | p-I—Ph | H | H | H | ⁱPr | H | H | F | OH |
| XXIV-30-2 | p-I—Ph | H | H | CH₃ | ⁱPr | H | H | F | OH |
| XXIV-30-3 | p-I—Ph | H | H | CH(CH₃)₂ | ⁱPr | H | H | F | OH |
| XXIV-30-4 | p-I—Ph | H | H | CH₂CH(CH₃)₂ | ⁱPr | H | H | F | OH |
| XXIV-30-5 | p-I—Ph | H | H | CH₂Ph | ⁱPr | H | H | F | OH |
| XXIV-30-6 | p-I—Ph | H | H | CH₂-indol-3-yl | ⁱPr | H | H | F | OH |
| XXIV-30-7 | p-I—Ph | H | H | CH₂CH₂SCH₃ | ⁱPr | H | H | F | OH |
| XXIV-30-8 | p-I—Ph | * | H | * | ⁱPr | H | H | F | OH |

*R² and R³ᵇ joined together by (CH₂)₃ to form five-membered ring.

TABLE XXIV-31

| No | R¹ | R² | R³ᵃ | R³ᵇ | R⁴ | R⁵ | R⁶ | X | Y |
|---|---|---|---|---|---|---|---|---|---|
| XXIV-31-1 | CH₃ | H | H | H | ⁿBu | H | H | F | OH |
| XXIV-31-2 | CH₃ | H | H | CH₃ | ⁿBu | H | H | F | OH |
| XXIV-31-3 | CH₃ | H | H | CH(CH₃)₂ | ⁿBu | H | H | F | OH |
| XXIV-31-4 | CH₃ | H | H | CH₂CH(CH₃)₂ | ⁿBu | H | H | F | OH |
| XXIV-31-5 | CH₃ | H | H | CH₂Ph | ⁿBu | H | H | F | OH |
| XXIV-31-6 | CH₃ | H | H | CH₂-indol-3-yl | ⁿBu | H | H | F | OH |
| XXIV-31-7 | CH₃ | H | H | CH₂CH₂SCH₃ | ⁿBu | H | H | F | OH |
| XXIV-31-8 | CH₃ | * | H | * | ⁿBu | H | H | F | OH |

*R² and R³ᵇ joined together by (CH₂)₃ to form five-membered ring.

TABLE XXIV-32

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-32-1 | Et | H | H | H | $^n$Bu | H | H | F | OH |
| XXIV-32-2 | Et | H | H | $CH_3$ | $^n$Bu | H | H | F | OH |
| XXIV-32-3 | Et | H | H | $CH(CH_3)_2$ | $^n$Bu | H | H | F | OH |
| XXIV-32-4 | Et | H | H | $CH_2CH(CH_3)_2$ | $^n$Bu | H | H | F | OH |
| XXIV-32-5 | Et | H | H | $CH_2Ph$ | $^n$Bu | H | H | F | OH |
| XXIV-32-6 | Et | H | H | $CH_2$-indol-3-yl | $^n$Bu | H | H | F | OH |
| XXIV-32-7 | Et | H | H | $CH_2CH_2SCH_3$ | $^n$Bu | H | H | F | OH |
| XXIV-32-8 | Et | * | H | * | $^n$Bu | H | H | F | OH |

*$R^2$ and $R^{3b}$ joined together by $(CH_2)_3$ to form five-membered ring.

TABLE XXIV-33

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-33-1 | $^i$Pr | H | H | H | $^n$Bu | H | H | F | OH |
| XXIV-33-2 | $^i$Pr | H | H | $CH_3$ | $^n$Bu | H | H | F | OH |
| XXIV-33-3 | $^i$Pr | H | H | $CH(CH_3)_2$ | $^n$Bu | H | H | F | OH |
| XXIV-33-4 | $^i$Pr | H | H | $CH_2CH(CH_3)_2$ | $^n$Bu | H | H | F | OH |
| XXIV-33-5 | $^i$Pr | H | H | $CH_2Ph$ | $^n$Bu | H | H | F | OH |
| XXIV-33-6 | $^i$Pr | H | H | $CH_2$-indol-3-yl | $^n$Bu | H | H | F | OH |
| XXIV-33-7 | $^i$Pr | H | H | $CH_2CH_2SCH_3$ | $^n$Bu | H | H | F | OH |
| XXIV-33-8 | $^i$Pr | * | H | * | $^n$Bu | H | H | F | OH |

*$R^2$ and $R^{3b}$ joined together by $(CH_2)_3$ to form five-membered ring.

TABLE XXIV-34

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-34-1 | $^t$Bu | H | H | H | $^n$Bu | H | H | F | OH |
| XXIV-34-2 | $^t$Bu | H | H | $CH_3$ | $^n$Bu | H | H | F | OH |
| XXIV-34-3 | $^t$Bu | H | H | $CH(CH_3)_2$ | $^n$Bu | H | H | F | OH |
| XXIV-34-4 | $^t$Bu | H | H | $CH_2CH(CH_3)_2$ | $^n$Bu | H | H | F | OH |
| XXIV-34-5 | $^t$Bu | H | H | $CH_2Ph$ | $^n$Bu | H | H | F | OH |
| XXIV-34-6 | $^t$Bu | H | H | $CH_2$-indol-3-yl | $^n$Bu | H | H | F | OH |
| XXIV-34-7 | $^t$Bu | H | H | $CH_2CH_2SCH_3$ | $^n$Bu | H | H | F | OH |
| XXIV-34-8 | $^t$Bu | * | H | * | $^n$Bu | H | H | F | OH |

*$R^2$ and $R^{3b}$ joined together by $(CH_2)_3$ to form five-membered ring.

TABLE XXIV-35

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-35-1 | Ph | H | H | H | $^n$Bu | H | H | F | OH |
| XXIV-35-2 | Ph | H | H | $CH_3$ | $^n$Bu | H | H | F | OH |
| XXIV-35-3 | Ph | H | H | $CH(CH_3)_2$ | $^n$Bu | H | H | F | OH |
| XXIV-35-4 | Ph | H | H | $CH_2CH(CH_3)_2$ | $^n$Bu | H | H | F | OH |
| XXIV-35-5 | Ph | H | H | $CH_2Ph$ | $^n$Bu | H | H | F | OH |
| XXIV-35-6 | Ph | H | H | $CH_2$-indol-3-yl | $^n$Bu | H | H | F | OH |
| XXIV-35-7 | Ph | H | H | $CH_2CH_2SCH_3$ | $^n$Bu | H | H | F | OH |
| XXIV-35-8 | Ph | * | H | * | $^n$Bu | H | H | F | OH |

*$R^2$ and $R^{3b}$ joined together by $(CH_2)_3$ to form five-membered ring.

TABLE XXIV-36

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-36-1 | p-Me—Ph | H | H | H | $^n$Bu | H | H | F | OH |
| XXIV-36-2 | p-Me—Ph | H | H | $CH_3$ | $^n$Bu | H | H | F | OH |
| XXIV-36-3 | p-Me—Ph | H | H | $CH(CH_3)_2$ | $^n$Bu | H | H | F | OH |
| XXIV-36-4 | p-Me—Ph | H | H | $CH_2CH(CH_3)_2$ | $^n$Bu | H | H | F | OH |
| XXIV-36-5 | p-Me—Ph | H | H | $CH_2Ph$ | $^n$Bu | H | H | F | OH |
| XXIV-36-6 | p-Me—Ph | H | H | $CH_2$-indol-3-yl | $^n$Bu | H | H | F | OH |
| XXIV-36-7 | p-Me—Ph | H | H | $CH_2CH_2SCH_3$ | $^n$Bu | H | H | F | OH |
| XXIV-36-8 | p-Me—Ph | * | H | * | $^n$Bu | H | H | F | OH |

*$R^2$ and $R^{3b}$ joined together by $(CH_2)_3$ to form five-membered ring.

TABLE XXIV-37

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-37-1 | p-F—Ph | H | H | H | $^n$Bu | H | H | F | OH |
| XXIV-37-2 | p-F—Ph | H | H | $CH_3$ | $^n$Bu | H | H | F | OH |
| XXIV-37-3 | p-F—Ph | H | H | $CH(CH_3)_2$ | $^n$Bu | H | H | F | OH |
| XXIV-37-4 | p-F—Ph | H | H | $CH_2CH(CH_3)_2$ | $^n$Bu | H | H | F | OH |
| XXIV-37-5 | p-F—Ph | H | H | $CH_2Ph$ | $^n$Bu | H | H | F | OH |
| XXIV-37-6 | p-F—Ph | H | H | $CH_2$-indol-3-yl | $^n$Bu | H | H | F | OH |
| XXIV-37-7 | p-F—Ph | H | H | $CH_2CH_2SCH_3$ | $^n$Bu | H | H | F | OH |
| XXIV-37-8 | p-F—Ph | * | H | * | $^n$Bu | H | H | F | OH |

*$R^2$ and $R^{3b}$ joined together by $(CH_2)_3$ to form five-membered ring.

TABLE XXIV-38

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-38-1 | p-Cl—Ph | H | H | H | $^n$Bu | H | H | F | OH |
| XXIV-38-2 | p-Cl—Ph | H | H | $CH_3$ | $^n$Bu | H | H | F | OH |
| XXIV-38-3 | p-Cl—Ph | H | H | $CH(CH_3)_2$ | $^n$Bu | H | H | F | OH |
| XXIV-38-4 | p-Cl—Ph | H | H | $CH_2CH(CH_3)_2$ | $^n$Bu | H | H | F | OH |
| XXIV-38-5 | p-Cl—Ph | H | H | $CH_2Ph$ | $^n$Bu | H | H | F | OH |
| XXIV-38-6 | p-Cl—Ph | H | H | $CH_2$-indol-3-yl | $^n$Bu | H | H | F | OH |
| XXIV-38-7 | p-Cl—Ph | H | H | $CH_2CH_2SCH_3$ | $^n$Bu | H | H | F | OH |
| XXIV-38-8 | p-Cl—Ph | * | H | * | $^n$Bu | H | H | F | OH |

*$R^2$ and $R^{3b}$ joined together by $(CH_2)_3$ to form five-membered ring.

TABLE XXIV-39

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-39-1 | p-Br—Ph | H | H | H | $^n$Bu | H | H | F | OH |
| XXIV-39-2 | p-Br—Ph | H | H | $CH_3$ | $^n$Bu | H | H | F | OH |
| XXIV-39-3 | p-Br—Ph | H | H | $CH(CH_3)_2$ | $^n$Bu | H | H | F | OH |
| XXIV-39-4 | p-Br—Ph | H | H | $CH_2CH(CH_3)_2$ | $^n$Bu | H | H | F | OH |
| XXIV-39-5 | p-Br—Ph | H | H | $CH_2Ph$ | $^n$Bu | H | H | F | OH |
| XXIV-39-6 | p-Br—Ph | H | H | $CH_2$-indol-3-yl | $^n$Bu | H | H | F | OH |
| XXIV-39-7 | p-Br—Ph | H | H | $CH_2CH_2SCH_3$ | $^n$Bu | H | H | F | OH |
| XXIV-39-8 | p-Br—Ph | * | H | * | $^n$Bu | H | H | F | OH |

*$R^2$ and $R^{3b}$ joined together by $(CH_2)_3$ to form five-membered ring.

TABLE XXIV-40

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIV-40-1 | p-I—Ph | H | H | H | $^n$Bu | H | H | F | OH |
| XXIV-40-2 | p-I—Ph | H | H | $CH_3$ | $^n$Bu | H | H | F | OH |

TABLE XXIV-40-continued

| No | R¹ | R² | R³ᵃ | R³ᵇ | R⁴ | R⁵ | R⁶ | X | Y |
|---|---|---|---|---|---|---|---|---|---|
| XXIV-40-3 | p-I—Ph | H | H | CH(CH₃)₂ | ⁿBu | H | H | F | OH |
| XXIV-40-4 | p-I—Ph | H | H | CH₂CH(CH₃)₂ | ⁿBu | H | H | F | OH |
| XXIV-40-5 | p-I—Ph | H | H | CH₂Ph | ⁿBu | H | H | F | OH |
| XXIV-40-6 | p-I—Ph | H | H | CH₂-indol-3-yl | ⁿBu | H | H | F | OH |
| XXIV-40-7 | p-I—Ph | H | H | CH₂CH₂SCH₃ | ⁿBu | H | H | F | OH |
| XXIV-40-8 | p-I—Ph | * | H | * | ⁿBu | H | H | F | OH |

*R² and R³ᵇ joined together by (CH₂)₃ to form five-membered ring.

TABLE XXIV-41

| No | R¹ | R² | R³ᵃ | R³ᵇ | R⁴ | R⁵ | R⁶ | X | Y |
|---|---|---|---|---|---|---|---|---|---|
| XXIV-41-1 | CH₃ | H | H | H | Bz | H | H | F | OH |
| XXIV-41-2 | CH₃ | H | H | CH₃ | Bz | H | H | F | OH |
| XXIV-41-3 | CH₃ | H | H | CH(CH₃)₂ | Bz | H | H | F | OH |
| XXIV-41-4 | CH₃ | H | H | CH₂CH(CH₃)₂ | Bz | H | H | F | OH |
| XXIV-41-5 | CH₃ | H | H | CH₂Ph | Bz | H | H | F | OH |
| XXIV-41-6 | CH₃ | H | H | CH₂-indol-3-yl | Bz | H | H | F | OH |
| XXIV-41-7 | CH₃ | H | H | CH₂CH₂SCH₃ | Bz | H | H | F | OH |
| XXIV-41-8 | CH₃ | * | H | * | Bz | H | H | F | OH |

*R² and R³ᵇ joined together by (CH₂)₃ to form five-membered ring.

TABLE XXIV-42

| No | R¹ | R² | R³ᵃ | R³ᵇ | R⁴ | R⁵ | R⁶ | X | Y |
|---|---|---|---|---|---|---|---|---|---|
| XXIV-42-1 | Et | H | H | H | Bz | H | H | F | OH |
| XXIV-42-2 | Et | H | H | CH₃ | Bz | H | H | F | OH |
| XXIV-42-3 | Et | H | H | CH(CH₃)₂ | Bz | H | H | F | OH |
| XXIV-42-4 | Et | H | H | CH₂CH(CH₃)₂ | Bz | H | H | F | OH |
| XXIV-42-5 | Et | H | H | CH₂Ph | Bz | H | H | F | OH |
| XXIV-42-6 | Et | H | H | CH₂-indol-3-yl | Bz | H | H | F | OH |
| XXIV-42-7 | Et | H | H | CH₂CH₂SCH₃ | Bz | H | H | F | OH |
| XXIV-42-8 | Et | * | H | * | Bz | H | H | F | OH |

*R² and R³ᵇ joined together by (CH₂)₃ to form five-membered ring.

TABLE XXIV-43

| No | R¹ | R² | R³ᵃ | R³ᵇ | R⁴ | R⁵ | R⁶ | X | Y |
|---|---|---|---|---|---|---|---|---|---|
| XXIV-43-1 | ⁱPr | H | H | H | Bz | H | H | F | OH |
| XXIV-43-2 | ⁱPr | H | H | CH₃ | Bz | H | H | F | OH |
| XXIV-43-3 | ⁱPr | H | H | CH(CH₃)₂ | Bz | H | H | F | OH |
| XXIV-43-4 | ⁱPr | H | H | CH₂CH(CH₃)₂ | Bz | H | H | F | OH |
| XXIV-43-5 | ⁱPr | H | H | CH₂Ph | Bz | H | H | F | OH |
| XXIV-43-6 | ⁱPr | H | H | CH₂-indol-3-yl | Bz | H | H | F | OH |
| XXIV-43-7 | ⁱPr | H | H | CH₂CH₂SCH₃ | Bz | H | H | F | OH |
| XXIV-43-8 | ⁱPr | * | H | * | Bz | H | H | F | OH |

*R² and R³ᵇ joined together by (CH₂)₃ to form five-membered ring.

TABLE XXIV-44

| No | R¹ | R² | R³ᵃ | R³ᵇ | R⁴ | R⁵ | R⁶ | X | Y |
|---|---|---|---|---|---|---|---|---|---|
| XXIV-44-1 | ᵗBu | H | H | H | Bz | H | H | F | OH |
| XXIV-44-2 | ᵗBu | H | H | CH₃ | Bz | H | H | F | OH |
| XXIV-44-3 | ᵗBu | H | H | CH(CH₃)₂ | Bz | H | H | F | OH |
| XXIV-44-4 | ᵗBu | H | H | CH₂CH(CH₃)₂ | Bz | H | H | F | OH |
| XXIV-44-5 | ᵗBu | H | H | CH₂Ph | Bz | H | H | F | OH |
| XXIV-44-6 | ᵗBu | H | H | CH₂-indol-3-yl | Bz | H | H | F | OH |
| XXIV-44-7 | ᵗBu | H | H | CH₂CH₂SCH₃ | Bz | H | H | F | OH |
| XXIV-44-8 | ᵗBu | * | H | * | Bz | H | H | F | OH |

*R² and R³ᵇ joined together by (CH₂)₃ to form five-membered ring.

TABLE XXIV-45

| No | R¹ | R² | R³ᵃ | R³ᵇ | R⁴ | R⁵ | R⁶ | X | Y |
|---|---|---|---|---|---|---|---|---|---|
| XXIV-45-1 | Ph | H | H | H | Bz | H | H | F | OH |
| XXIV-45-2 | Ph | H | H | CH₃ | Bz | H | H | F | OH |
| XXIV-45-3 | Ph | H | H | CH(CH₃)₂ | Bz | H | H | F | OH |
| XXIV-45-4 | Ph | H | H | CH₂CH(CH₃)₂ | Bz | H | H | F | OH |
| XXIV-45-5 | Ph | H | H | CH₂Ph | Bz | H | H | F | OH |
| XXIV-45-6 | Ph | H | H | CH₂-indol-3-yl | Bz | H | H | F | OH |
| XXIV-45-7 | Ph | H | H | CH₂CH₂SCH₃ | Bz | H | H | F | OH |
| XXIV-45-8 | Ph | * | H | * | Bz | H | H | F | OH |

*R² and R³ᵇ joined together by (CH₂)₃ to form five-membered ring.

TABLE XXIV-46

| No | R¹ | R² | R³ᵃ | R³ᵇ | R⁴ | R⁵ | R⁶ | X | Y |
|---|---|---|---|---|---|---|---|---|---|
| XXIV-46-1 | p-Me—Ph | H | H | H | Bz | H | H | F | OH |
| XXIV-46-2 | p-Me—Ph | H | H | CH₃ | Bz | H | H | F | OH |
| XXIV-46-3 | p-Me—Ph | H | H | CH(CH₃)₂ | Bz | H | H | F | OH |
| XXIV-46-4 | p-Me—Ph | H | H | CH₂CH(CH₃)₂ | Bz | H | H | F | OH |
| XXIV-46-5 | p-Me—Ph | H | H | CH₂Ph | Bz | H | H | F | OH |
| XXIV-46-6 | p-Me—Ph | H | H | CH₂-indol-3-yl | Bz | H | H | F | OH |
| XXIV-46-7 | p-Me—Ph | H | H | CH₂CH₂SCH₃ | Bz | H | H | F | OH |
| XXIV-46-8 | p-Me—Ph | * | H | * | Bz | H | H | F | OH |

*R² and R³ᵇ joined together by (CH₂)₃ to form five-membered ring.

TABLE XXIV-47

| No | R¹ | R² | R³ᵃ | R³ᵇ | R⁴ | R⁵ | R⁶ | X | Y |
|---|---|---|---|---|---|---|---|---|---|
| XXIV-47-1 | p-F—Ph | H | H | H | Bz | H | H | F | OH |
| XXIV-47-2 | p-F—Ph | H | H | CH₃ | Bz | H | H | F | OH |
| XXIV-47-3 | p-F—Ph | H | H | CH(CH₃)₂ | Bz | H | H | F | OH |
| XXIV-47-4 | p-F—Ph | H | H | CH₂CH(CH₃)₂ | Bz | H | H | F | OH |
| XXIV-47-5 | p-F—Ph | H | H | CH₂Ph | Bz | H | H | F | OH |
| XXIV-47-6 | p-F—Ph | H | H | CH₂-indol-3-yl | Bz | H | H | F | OH |
| XXIV-47-7 | p-F—Ph | H | H | CH₂CH₂SCH₃ | Bz | H | H | F | OH |
| XXIV-47-8 | p-F—Ph | * | H | * | Bz | H | H | F | OH |

*R² and R³ᵇ joined together by (CH₂)₃ to form five-membered ring.

TABLE XXIV-48

| No | R¹ | R² | R³ᵃ | R³ᵇ | R⁴ | R⁵ | R⁶ | X | Y |
|---|---|---|---|---|---|---|---|---|---|
| XXIV-48-1 | p-Cl—Ph | H | H | H | Bz | H | H | F | OH |
| XXIV-48-2 | p-Cl—Ph | H | H | CH₃ | Bz | H | H | F | OH |
| XXIV-48-3 | p-Cl—Ph | H | H | CH(CH₃)₂ | Bz | H | H | F | OH |
| XXIV-48-4 | p-Cl—Ph | H | H | CH₂CH(CH₃)₂ | Bz | H | H | F | OH |
| XXIV-48-5 | p-Cl—Ph | H | H | CH₂Ph | Bz | H | H | F | OH |
| XXIV-48-6 | p-Cl—Ph | H | H | CH₂-indol-3-yl | Bz | H | H | F | OH |
| XXIV-48-7 | p-Cl—Ph | H | H | CH₂CH₂SCH₃ | Bz | H | H | F | OH |
| XXIV-48-8 | p-Cl—Ph | * | H | * | Bz | H | H | F | OH |

*R² and R³ᵇ joined together by (CH₂)₃ to form five-membered ring.

TABLE XXIV-49

| No | R¹ | R² | R³ᵃ | R³ᵇ | R⁴ | R⁵ | R⁶ | X | Y |
|---|---|---|---|---|---|---|---|---|---|
| XXIV-49-1 | p-Br—Ph | H | H | H | Bz | H | H | F | OH |
| XXIV-49-2 | p-Br—Ph | H | H | CH₃ | Bz | H | H | F | OH |
| XXIV-49-3 | p-Br—Ph | H | H | CH(CH₃)₂ | Bz | H | H | F | OH |
| XXIV-49-4 | p-Br—Ph | H | H | CH₂CH(CH₃)₂ | Bz | H | H | F | OH |
| XXIV-49-5 | p-Br—Ph | H | H | CH₂Ph | Bz | H | H | F | OH |
| XXIV-49-6 | p-Br—Ph | H | H | CH₂-indol-3-yl | Bz | H | H | F | OH |
| XXIV-49-7 | p-Br—Ph | H | H | CH₂CH₂SCH₃ | Bz | H | H | F | OH |
| XXIV-49-8 | p-Br—Ph | * | H | * | Bz | H | H | F | OH |

*R² and R³ᵇ joined together by (CH₂)₃ to form five-membered ring.

TABLE XXIV-50

| No | R¹ | R² | R³ᵃ | R³ᵇ | R⁴ | R⁵ | R⁶ | X | Y |
|---|---|---|---|---|---|---|---|---|---|
| XXIV-50-1 | p-I—Ph | H | H | H | Bz | H | H | F | OH |
| XXIV-50-2 | p-I—Ph | H | H | CH₃ | Bz | H | H | F | OH |
| XXIV-50-3 | p-I—Ph | H | H | CH(CH₃)₂ | Bz | H | H | F | OH |
| XXIV-50-4 | p-I—Ph | H | H | CH₂CH(CH₃)₂ | Bz | H | H | F | OH |
| XXIV-50-5 | p-I—Ph | H | H | CH₂Ph | Bz | H | H | F | OH |
| XXIV-50-6 | p-I—Ph | H | H | CH₂-indol-3-yl | Bz | H | H | F | OH |
| XXIV-50-7 | p-I—Ph | H | H | CH₂CH₂SCH₃ | Bz | H | H | F | OH |
| XXIV-50-8 | p-I—Ph | * | H | * | Bz | H | H | F | OH |

*R² and R³ᵇ joined together by (CH₂)₃ to form five-membered ring.

XXV

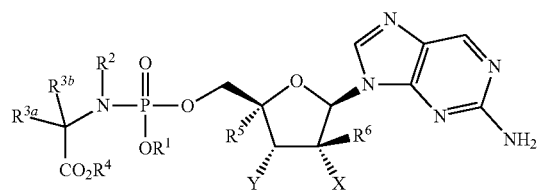

TABLE XXV-1

| No | R¹ | R² | R³ᵃ | R³ᵇ | R⁴ | R⁵ | R⁶ | X | Y |
|---|---|---|---|---|---|---|---|---|---|
| XXV-1-1 | CH₃ | H | H | H | CH₃ | H | CH₃ | F | OH |
| XXV-1-2 | CH₃ | H | H | CH₃ | CH₃ | H | CH₃ | F | OH |
| XXV-1-3 | CH₃ | H | H | CH(CH₃)₂ | CH₃ | H | CH₃ | F | OH |
| XXV-1-4 | CH₃ | H | H | CH₂CH(CH₃)₂ | CH₃ | H | CH₃ | F | OH |
| XXV-1-5 | CH₃ | H | H | CH₂Ph | CH₃ | H | CH₃ | F | OH |
| XXV-1-6 | CH₃ | H | H | CH₂-indol-3-yl | CH₃ | H | CH₃ | F | OH |
| XXV-1-7 | CH₃ | H | H | CH₂CH₂SCH₃ | CH₃ | H | CH₃ | F | OH |
| XXV-1-8 | CH₃ | * | H | * | CH₃ | H | CH₃ | F | OH |

*R² and R³ᵇ joined together by (CH₂)₃ to form five-membered ring.

TABLE XXV-2

| No | R¹ | R² | R³ᵃ | R³ᵇ | R⁴ | R⁵ | R⁶ | X | Y |
|---|---|---|---|---|---|---|---|---|---|
| XXV-2-1 | Et | H | H | H | CH₃ | H | CH₃ | F | OH |
| XXV-2-2 | Et | H | H | CH₃ | CH₃ | H | CH₃ | F | OH |
| XXV-2-3 | Et | H | H | CH(CH₃)₂ | CH₃ | H | CH₃ | F | OH |
| XXV-2-4 | Et | H | H | CH₂CH(CH₃)₂ | CH₃ | H | CH₃ | F | OH |
| XXV-2-5 | Et | H | H | CH₂Ph | CH₃ | H | CH₃ | F | OH |
| XXV-2-6 | Et | H | H | CH₂-indol-3-yl | CH₃ | H | CH₃ | F | OH |
| XXV-2-7 | Et | H | H | CH₂CH₂SCH₃ | CH₃ | H | CH₃ | F | OH |
| XXV-2-8 | Et | * | H | * | CH₃ | H | CH₃ | F | OH |

*R² and R³ᵇ joined together by (CH₂)₃ to form five-membered ring.

TABLE XXV-3

| No | R¹ | R² | R³ᵃ | R³ᵇ | R⁴ | R⁵ | R⁶ | X | Y |
|---|---|---|---|---|---|---|---|---|---|
| XXV-3-1 | ⁱPr | H | H | H | CH₃ | H | CH₃ | F | OH |
| XXV-3-2 | ⁱPr | H | H | CH₃ | CH₃ | H | CH₃ | F | OH |
| XXV-3-3 | ⁱPr | H | H | CH(CH₃)₂ | CH₃ | H | CH₃ | F | OH |
| XXV-3-4 | ⁱPr | H | H | CH₂CH(CH₃)₂ | CH₃ | H | CH₃ | F | OH |
| XXV-3-5 | ⁱPr | H | H | CH₂Ph | CH₃ | H | CH₃ | F | OH |
| XXV-3-6 | ⁱPr | H | H | CH₂-indol-3-yl | CH₃ | H | CH₃ | F | OH |
| XXV-3-7 | ⁱPr | H | H | CH₂CH₂SCH₃ | CH₃ | H | CH₃ | F | OH |
| XXV-3-8 | ⁱPr | * | H | * | CH₃ | H | CH₃ | F | OH |

*R² and R³ᵇ joined together by (CH₂)₃ to form five-membered ring.

TABLE XXV-4

| No | R¹ | R² | R³ᵃ | R³ᵇ | R⁴ | R⁵ | R⁶ | X | Y |
|---|---|---|---|---|---|---|---|---|---|
| XXV-4-1 | ᵗBu | H | H | H | CH₃ | H | CH₃ | F | OH |
| XXV-4-2 | ᵗBu | H | H | CH₃ | CH₃ | H | CH₃ | F | OH |
| XXV-4-3 | ᵗBu | H | H | CH(CH₃)₂ | CH₃ | H | CH₃ | F | OH |
| XXV-4-4 | ᵗBu | H | H | CH₂CH(CH₃)₂ | CH₃ | H | CH₃ | F | OH |
| XXV-4-5 | ᵗBu | H | H | CH₂Ph | CH₃ | H | CH₃ | F | OH |
| XXV-4-6 | ᵗBu | H | H | CH₂-indol-3-yl | CH₃ | H | CH₃ | F | OH |
| XXV-4-7 | ᵗBu | H | H | CH₂CH₂SCH₃ | CH₃ | H | CH₃ | F | OH |
| XXV-4-8 | ᵗBu | * | H | * | CH₃ | H | CH₃ | F | OH |

*R² and R³ᵇ joined together by (CH₂)₃ to form five-membered ring.

TABLE XXV-5

| No | R¹ | R² | R³ᵃ | R³ᵇ | R⁴ | R⁵ | R⁶ | X | Y |
|---|---|---|---|---|---|---|---|---|---|
| XXV-5-1 | Ph | H | H | H | CH₃ | H | CH₃ | F | OH |
| XXV-5-2 | Ph | H | H | CH₃ | CH₃ | H | CH₃ | F | OH |
| XXV-5-3 | Ph | H | H | CH(CH₃)₂ | CH₃ | H | CH₃ | F | OH |
| XXV-5-4 | Ph | H | H | CH₂CH(CH₃)₂ | CH₃ | H | CH₃ | F | OH |
| XXV-5-5 | Ph | H | H | CH₂Ph | CH₃ | H | CH₃ | F | OH |
| XXV-5-6 | Ph | H | H | CH₂-indol-3-yl | CH₃ | H | CH₃ | F | OH |
| XXV-5-7 | Ph | H | H | CH₂CH₂SCH₃ | CH₃ | H | CH₃ | F | OH |
| XXV-5-8 | Ph | * | H | * | CH₃ | H | CH₃ | F | OH |

*R² and R³ᵇ joined together by (CH₂)₃ to form five-membered ring.

TABLE XXV-6

| No | R¹ | R² | R³ᵃ | R³ᵇ | R⁴ | R⁵ | R⁶ | X | Y |
|---|---|---|---|---|---|---|---|---|---|
| XXV-6-1 | p-Me—Ph | H | H | H | CH₃ | H | CH₃ | F | OH |
| XXV-6-2 | p-Me—Ph | H | H | CH₃ | CH₃ | H | CH₃ | F | OH |
| XXV-6-3 | p-Me—Ph | H | H | CH(CH₃)₂ | CH₃ | H | CH₃ | F | OH |
| XXV-6-4 | p-Me—Ph | H | H | CH₂CH(CH₃)₂ | CH₃ | H | CH₃ | F | OH |
| XXV-6-5 | p-Me—Ph | H | H | CH₂Ph | CH₃ | H | CH₃ | F | OH |
| XXV-6-6 | p-Me—Ph | H | H | CH₂-indol-3-yl | CH₃ | H | CH₃ | F | OH |
| XXV-6-7 | p-Me—Ph | H | H | CH₂CH₂SCH₃ | CH₃ | H | CH₃ | F | OH |
| XXV-6-8 | p-Me—Ph | * | H | * | CH₃ | H | CH₃ | F | OH |

*R² and R³ᵇ joined together by (CH₂)₃ to form five-membered ring.

TABLE XXV-7

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-7-1 | p-F—Ph | H | H | H | CH$_3$ | H | CH$_3$ | F | OH |
| XXV-7-2 | p-F—Ph | H | H | CH$_3$ | CH$_3$ | H | CH$_3$ | F | OH |
| XXV-7-3 | p-F—Ph | H | H | CH(CH$_3$)$_2$ | CH$_3$ | H | CH$_3$ | F | OH |
| XXV-7-4 | p-F—Ph | H | H | CH$_2$CH(CH$_3$)$_2$ | CH$_3$ | H | CH$_3$ | F | OH |
| XXV-7-6 | p-F—Ph | H | H | CH$_2$Ph | CH$_3$ | H | CH$_3$ | F | OH |
| XXV-7-7 | p-F—Ph | H | H | CH$_2$-indol-3-yl | CH$_3$ | H | CH$_3$ | F | OH |
| XXV-7-8 | p-F—Ph | H | H | CH$_2$CH$_2$SCH$_3$ | CH$_3$ | H | CH$_3$ | F | OH |
| XXV-7-20 | p-F—Ph | * | H | * | CH$_3$ | H | CH$_3$ | F | OH |

*R$^2$ and R$^{3b}$ joined together by (CH$_2$)$_3$ to form five-membered ring.

TABLE XXV-8

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-8-1 | p-Cl—Ph | H | H | H | CH$_3$ | H | CH$_3$ | F | OH |
| XXV-8-2 | p-Cl—Ph | H | H | CH$_3$ | CH$_3$ | H | CH$_3$ | F | OH |
| XXV-8-3 | p-Cl—Ph | H | H | CH(CH$_3$)$_2$ | CH$_3$ | H | CH$_3$ | F | OH |
| XXV-8-4 | p-Cl—Ph | H | H | CH$_2$CH(CH$_3$)$_2$ | CH$_3$ | H | CH$_3$ | F | OH |
| XXV-8-5 | p-Cl—Ph | H | H | CH$_2$Ph | CH$_3$ | H | CH$_3$ | F | OH |
| XXV-8-6 | p-Cl—Ph | H | H | CH$_2$-indol-3-yl | CH$_3$ | H | CH$_3$ | F | OH |
| XXV-8-7 | p-Cl—Ph | H | H | CH$_2$CH$_2$SCH$_3$ | CH$_3$ | H | CH$_3$ | F | OH |
| XXV-8-8 | p-Cl—Ph | * | H | * | CH$_3$ | H | CH$_3$ | F | OH |

*R$^2$ and R$^{3b}$ joined together by (CH$_2$)$_3$ to form five-membered ring.

TABLE XXV-9

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-9-1 | p-Br—Ph | H | H | H | CH$_3$ | H | CH$_3$ | F | OH |
| XXV-9-2 | p-Br—Ph | H | H | CH$_3$ | CH$_3$ | H | CH$_3$ | F | OH |
| XXV-9-3 | p-Br—Ph | H | H | CH(CH$_3$)$_2$ | CH$_3$ | H | CH$_3$ | F | OH |
| XXV-9-4 | p-Br—Ph | H | H | CH$_2$CH(CH$_3$)$_2$ | CH$_3$ | H | CH$_3$ | F | OH |
| XXV-9-6 | p-Br—Ph | H | H | CH$_2$Ph | CH$_3$ | H | CH$_3$ | F | OH |
| XXV-9-7 | p-Br—Ph | H | H | CH$_2$-indol-3-yl | CH$_3$ | H | CH$_3$ | F | OH |
| XXV-9-8 | p-Br—Ph | H | H | CH$_2$CH$_2$SCH$_3$ | CH$_3$ | H | CH$_3$ | F | OH |
| XXV-9-20 | p-Br—Ph | * | H | * | CH$_3$ | H | CH$_3$ | F | OH |

*R$^2$ and R$^{3b}$ joined together by (CH$_2$)$_3$ to form five-membered ring.

TABLE XXV-10

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-10-1 | p-I—Ph | H | H | H | CH$_3$ | H | CH$_3$ | F | OH |
| XXV-10-2 | p-I—Ph | H | H | CH$_3$ | CH$_3$ | H | CH$_3$ | F | OH |
| XXV-10-3 | p-I—Ph | H | H | CH(CH$_3$)$_2$ | CH$_3$ | H | CH$_3$ | F | OH |
| XXV-10-4 | p-I—Ph | H | H | CH$_2$CH(CH$_3$)$_2$ | CH$_3$ | H | CH$_3$ | F | OH |
| XXV-10-5 | p-I—Ph | H | H | CH$_2$Ph | CH$_3$ | H | CH$_3$ | F | OH |
| XXV-10-6 | p-I—Ph | H | H | CH$_2$-indol-3-yl | CH$_3$ | H | CH$_3$ | F | OH |
| XXV-10-7 | p-I—Ph | H | H | CH$_2$CH$_2$SCH$_3$ | CH$_3$ | H | CH$_3$ | F | OH |
| XXV-10-8 | p-I—Ph | * | H | * | CH$_3$ | H | CH$_3$ | F | OH |

*R$^2$ and R$^{3b}$ joined together by (CH$_2$)$_3$ to form five-membered ring.

TABLE XXV-11

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-11-1 | CH$_3$ | H | H | H | Et | H | CH$_3$ | F | OH |
| XXV-11-2 | CH$_3$ | H | H | CH$_3$ | Et | H | CH$_3$ | F | OH |
| XXV-11-3 | CH$_3$ | H | H | CH(CH$_3$)$_2$ | Et | H | CH$_3$ | F | OH |
| XXV-11-4 | CH$_3$ | H | H | CH$_2$CH(CH$_3$)$_2$ | Et | H | CH$_3$ | F | OH |
| XXV-11-5 | CH$_3$ | H | H | CH$_2$Ph | Et | H | CH$_3$ | F | OH |
| XXV-11-6 | CH$_3$ | H | H | CH$_2$-indol-3-yl | Et | H | CH$_3$ | F | OH |
| XXV-11-7 | CH$_3$ | H | H | CH$_2$CH$_2$SCH$_3$ | Et | H | CH$_3$ | F | OH |
| XXV-11-8 | CH$_3$ | * | H | * | Et | H | CH$_3$ | F | OH |

*R$^2$ and R$^{3b}$ joined together by (CH$_2$)$_3$ to form five-membered ring.

TABLE XXV-12

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-12-1 | Et | H | H | H | Et | H | CH$_3$ | F | OH |
| XXV-12-2 | Et | H | H | CH$_3$ | Et | H | CH$_3$ | F | OH |
| XXV-12-3 | Et | H | H | CH(CH$_3$)$_2$ | Et | H | CH$_3$ | F | OH |
| XXV-12-4 | Et | H | H | CH$_2$CH(CH$_3$)$_2$ | Et | H | CH$_3$ | F | OH |
| XXV-12-5 | Et | H | H | CH$_2$Ph | Et | H | CH$_3$ | F | OH |
| XXV-12-6 | Et | H | H | CH$_2$-indol-3-yl | Et | H | CH$_3$ | F | OH |
| XXV-12-7 | Et | H | H | CH$_2$CH$_2$SCH$_3$ | Et | H | CH$_3$ | F | OH |
| XXV-12-8 | Et | * | H | * | Et | H | CH$_3$ | F | OH |

*R$^2$ and R$^{3b}$ joined together by (CH$_2$)$_3$ to form five-membered ring.

TABLE XXV-13

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-13-1 | $^i$Pr | H | H | H | Et | H | CH$_3$ | F | OH |
| XXV-13-2 | $^i$Pr | H | H | CH$_3$ | Et | H | CH$_3$ | F | OH |
| XXV-13-3 | $^i$Pr | H | H | CH(CH$_3$)$_2$ | Et | H | CH$_3$ | F | OH |
| XXV-13-4 | $^i$Pr | H | H | CH$_2$CH(CH$_3$)$_2$ | Et | H | CH$_3$ | F | OH |
| XXV-13-5 | $^i$Pr | H | H | CH$_2$Ph | Et | H | CH$_3$ | F | OH |
| XXV-13-6 | $^i$Pr | H | H | CH$_2$-indol-3-yl | Et | H | CH$_3$ | F | OH |
| XXV-13-7 | $^i$Pr | H | H | CH$_2$CH$_2$SCH$_3$ | Et | H | CH$_3$ | F | OH |
| XXV-13-8 | $^i$Pr | * | H | * | Et | H | CH$_3$ | F | OH |

*R$^2$ and R$^{3b}$ joined together by (CH$_2$)$_3$ to form five-membered ring.

TABLE XXV-14

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-14-1 | $^t$Bu | H | H | H | Et | H | CH$_3$ | F | OH |
| XXV-14-2 | $^t$Bu | H | H | CH$_3$ | Et | H | CH$_3$ | F | OH |
| XXV-14-3 | $^t$Bu | H | H | CH(CH$_3$)$_2$ | Et | H | CH$_3$ | F | OH |
| XXV-14-4 | $^t$Bu | H | H | CH$_2$CH(CH$_3$)$_2$ | Et | H | CH$_3$ | F | OH |
| XXV-14-5 | $^t$Bu | H | H | CH$_2$Ph | Et | H | CH$_3$ | F | OH |
| XXV-14-6 | $^t$Bu | H | H | CH$_2$-indol-3-yl | Et | H | CH$_3$ | F | OH |
| XXV-14-7 | $^t$Bu | H | H | CH$_2$CH$_2$SCH$_3$ | Et | H | CH$_3$ | F | OH |
| XXV-14-8 | $^t$Bu | * | H | * | Et | H | CH$_3$ | F | OH |

*R$^2$ and R$^{3b}$ joined together by (CH$_2$)$_3$ to form five-membered ring.

TABLE XXV-15

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-15-1 | Ph | H | H | H | Et | H | CH$_3$ | F | OH |
| XXV-15-2 | Ph | H | H | CH$_3$ | Et | H | CH$_3$ | F | OH |
| XXV-15-3 | Ph | H | H | CH(CH$_3$)$_2$ | Et | H | CH$_3$ | F | OH |
| XXV-15-4 | Ph | H | H | CH$_2$CH(CH$_3$)$_2$ | Et | H | CH$_3$ | F | OH |
| XXV-15-5 | Ph | H | H | CH$_2$Ph | Et | H | CH$_3$ | F | OH |
| XXV-15-6 | Ph | H | H | CH$_2$-indol-3-yl | Et | H | CH$_3$ | F | OH |
| XXV-15-7 | Ph | H | H | CH$_2$CH$_2$SCH$_3$ | Et | H | CH$_3$ | F | OH |
| XXV-15-8 | Ph | * | H | * | Et | H | CH$_3$ | F | OH |

*R$^2$ and R$^{3b}$ joined together by (CH$_2$)$_3$ to form five-membered ring.

TABLE XXV-16

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-16-1 | p-Me—Ph | H | H | H | Et | H | CH$_3$ | F | OH |
| XXV-16-2 | p-Me—Ph | H | H | CH$_3$ | Et | H | CH$_3$ | F | OH |
| XXV-16-3 | p-Me—Ph | H | H | CH(CH$_3$)$_2$ | Et | H | CH$_3$ | F | OH |
| XXV-16-4 | p-Me—Ph | H | H | CH$_2$CH(CH$_3$)$_2$ | Et | H | CH$_3$ | F | OH |
| XXV-16-5 | p-Me—Ph | H | H | CH$_2$Ph | Et | H | CH$_3$ | F | OH |
| XXV-16-6 | p-Me—Ph | H | H | CH$_2$-indol-3-yl | Et | H | CH$_3$ | F | OH |
| XXV-16-7 | p-Me—Ph | H | H | CH$_2$CH$_2$SCH$_3$ | Et | H | CH$_3$ | F | OH |
| XXV-16-8 | p-Me—Ph | * | H | * | Et | H | CH$_3$ | F | OH |

*R$^2$ and R$^{3b}$ joined together by (CH$_2$)$_3$ to form five-membered ring.

TABLE XXV-17

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-17-1 | p-F—Ph | H | H | H | Et | H | CH$_3$ | F | OH |
| XXV-17-2 | p-F—Ph | H | H | CH$_3$ | Et | H | CH$_3$ | F | OH |
| XXV-17-3 | p-F—Ph | H | H | CH(CH$_3$)$_2$ | Et | H | CH$_3$ | F | OH |
| XXV-17-4 | p-F—Ph | H | H | CH$_2$CH(CH$_3$)$_2$ | Et | H | CH$_3$ | F | OH |
| XXV-17-5 | p-F—Ph | H | H | CH$_2$Ph | Et | H | CH$_3$ | F | OH |
| XXV-17-6 | p-F—Ph | H | H | CH$_2$-indol-3-yl | Et | H | CH$_3$ | F | OH |
| XXV-17-7 | p-F—Ph | H | H | CH$_2$CH$_2$SCH$_3$ | Et | H | CH$_3$ | F | OH |
| XXV-17-8 | p-F—Ph | * | H | * | Et | H | CH$_3$ | F | OH |

*R$^2$ and R$^{3b}$ joined together by (CH$_2$)$_3$ to form five-membered ring.

TABLE XXV-18

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-18-1 | p-Cl—Ph | H | H | H | Et | H | CH$_3$ | F | OH |
| XXV-18-2 | p-Cl—Ph | H | H | CH$_3$ | Et | H | CH$_3$ | F | OH |
| XXV-18-3 | p-Cl—Ph | H | H | CH(CH$_3$)$_2$ | Et | H | CH$_3$ | F | OH |
| XXV-18-4 | p-Cl—Ph | H | H | CH$_2$CH(CH$_3$)$_2$ | Et | H | CH$_3$ | F | OH |
| XXV-18-5 | p-Cl—Ph | H | H | CH$_2$Ph | Et | H | CH$_3$ | F | OH |
| XXV-18-6 | p-Cl—Ph | H | H | CH$_2$-indol-3-yl | Et | H | CH$_3$ | F | OH |
| XXV-18-7 | p-Cl—Ph | H | H | CH$_2$CH$_2$SCH$_3$ | Et | H | CH$_3$ | F | OH |
| XXV-18-8 | p-Cl—Ph | * | H | * | Et | H | CH$_3$ | F | OH |

*R$^2$ and R$^{3b}$ joined together by (CH$_2$)$_3$ to form five-membered ring.

TABLE XXV-19

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXV-19-1 | p-Br—Ph | H | H | H | Et | H | CH$_3$ | F | OH |
| XXV-19-2 | p-Br—Ph | H | H | CH$_3$ | Et | H | CH$_3$ | F | OH |
| XXV-19-3 | p-Br—Ph | H | H | CH(CH$_3$)$_2$ | Et | H | CH$_3$ | F | OH |
| XXV-19-4 | p-Br—Ph | H | H | CH$_2$CH(CH$_3$)$_2$ | Et | H | CH$_3$ | F | OH |
| XXV-19-5 | p-Br—Ph | H | H | CH$_2$Ph | Et | H | CH$_3$ | F | OH |
| XXV-19-6 | p-Br—Ph | H | H | CH$_2$-indol-3-yl | Et | H | CH$_3$ | F | OH |
| XXV-19-7 | p-Br—Ph | H | H | CH$_2$CH$_2$SCH$_3$ | Et | H | CH$_3$ | F | OH |
| XXV-19-8 | p-Br—Ph | * | H | * | Et | H | CH$_3$ | F | OH |

*R$^2$ and R$^{3b}$ joined together by (CH$_2$)$_3$ to form five-membered ring.

TABLE XXV-20

| No | R¹ | R² | R³ᵃ | R³ᵇ | R⁴ | R⁵ | R⁶ | X | Y |
|---|---|---|---|---|---|---|---|---|---|
| XXV-20-1 | p-I—Ph | H | H | H | Et | H | CH₃ | F | OH |
| XXV-20-2 | p-I—Ph | H | H | CH₃ | Et | H | CH₃ | F | OH |
| XXV-20-3 | p-I—Ph | H | H | CH(CH₃)₂ | Et | H | CH₃ | F | OH |
| XXV-20-4 | p-I—Ph | H | H | CH₂CH(CH₃)₂ | Et | H | CH₃ | F | OH |
| XXV-20-5 | p-I—Ph | H | H | CH₂Ph | Et | H | CH₃ | F | OH |
| XXV-20-6 | p-I—Ph | H | H | CH₂-indol-3-yl | Et | H | CH₃ | F | OH |
| XXV-20-7 | p-I—Ph | H | H | CH₂CH₂SCH₃ | Et | H | CH₃ | F | OH |
| XXV-20-8 | p-I—Ph | * | H | * | Et | H | CH₃ | F | OH |

*R² and R³ᵇ joined together by (CH₂)₃ to form five-membered ring.

TABLE XXV-21

| No | R¹ | R² | R³ᵃ | R³ᵇ | R⁴ | R⁵ | R⁶ | X | Y |
|---|---|---|---|---|---|---|---|---|---|
| XXV-21-1 | CH₃ | H | H | H | ⁱPr | H | CH₃ | F | OH |
| XXV-21-2 | CH₃ | H | H | CH₃ | ⁱPr | H | CH₃ | F | OH |
| XXV-21-3 | CH₃ | H | H | CH(CH₃)₂ | ⁱPr | H | CH₃ | F | OH |
| XXV-21-4 | CH₃ | H | H | CH₂CH(CH₃)₂ | ⁱPr | H | CH₃ | F | OH |
| XXV-21-5 | CH₃ | H | H | CH₂Ph | ⁱPr | H | CH₃ | F | OH |
| XXV-21-6 | CH₃ | H | H | CH₂-indol-3-yl | ⁱPr | H | CH₃ | F | OH |
| XXV-21-7 | CH₃ | H | H | CH₂CH₂SCH₃ | ⁱPr | H | CH₃ | F | OH |
| XXV-21-8 | CH₃ | * | H | * | ⁱPr | H | CH₃ | F | OH |

*R² and R³ᵇ joined together by (CH₂)₃ to form five-membered ring.

TABLE XXV-22

| No | R¹ | R² | R³ᵃ | R³ᵇ | R⁴ | R⁵ | R⁶ | X | Y |
|---|---|---|---|---|---|---|---|---|---|
| XXV-22-1 | Et | H | H | H | ⁱPr | H | CH₃ | F | OH |
| XXV-22-2 | Et | H | H | CH₃ | ⁱPr | H | CH₃ | F | OH |
| XXV-22-3 | Et | H | H | CH(CH₃)₂ | ⁱPr | H | CH₃ | F | OH |
| XXV-22-4 | Et | H | H | CH₂CH(CH₃)₂ | ⁱPr | H | CH₃ | F | OH |
| XXV-22-5 | Et | H | H | CH₂Ph | ⁱPr | H | CH₃ | F | OH |
| XXV-22-6 | Et | H | H | CH₂-indol-3-yl | ⁱPr | H | CH₃ | F | OH |
| XXV-22-7 | Et | H | H | CH₂CH₂SCH₃ | ⁱPr | H | CH₃ | F | OH |
| XXV-22-8 | Et | * | H | * | ⁱPr | H | CH₃ | F | OH |

*R² and R³ᵇ joined together by (CH₂)₃ to form five-membered ring.

TABLE XXV-23

| No | R¹ | R² | R³ᵃ | R³ᵇ | R⁴ | R⁵ | R⁶ | X | Y |
|---|---|---|---|---|---|---|---|---|---|
| XXV-23-1 | ⁱPr | H | H | H | ⁱPr | H | CH₃ | F | OH |
| XXV-23-2 | ⁱPr | H | H | CH₃ | ⁱPr | H | CH₃ | F | OH |
| XXV-23-3 | ⁱPr | H | H | CH(CH₃)₂ | ⁱPr | H | CH₃ | F | OH |
| XXV-23-4 | ⁱPr | H | H | CH₂CH(CH₃)₂ | ⁱPr | H | CH₃ | F | OH |
| XXV-23-5 | ⁱPr | H | H | CH₂Ph | ⁱPr | H | CH₃ | F | OH |
| XXV-23-6 | ⁱPr | H | H | CH₂-indol-3-yl | ⁱPr | H | CH₃ | F | OH |
| XXV-23-7 | ⁱPr | H | H | CH₂CH₂SCH₃ | ⁱPr | H | CH₃ | F | OH |
| XXV-23-8 | ⁱPr | * | H | * | ⁱPr | H | CH₃ | F | OH |

*R² and R³ᵇ joined together by (CH₂)₃ to form five-membered ring.

TABLE XXV-24

| No | R¹ | R² | R³ᵃ | R³ᵇ | R⁴ | R⁵ | R⁶ | X | Y |
|---|---|---|---|---|---|---|---|---|---|
| XXV-24-1 | ᵗBu | H | H | H | ⁱPr | H | CH₃ | F | OH |
| XXV-24-2 | ᵗBu | H | H | CH₃ | ⁱPr | H | CH₃ | F | OH |
| XXV-24-3 | ᵗBu | H | H | CH(CH₃)₂ | ⁱPr | H | CH₃ | F | OH |
| XXV-24-4 | ᵗBu | H | H | CH₂CH(CH₃)₂ | ⁱPr | H | CH₃ | F | OH |
| XXV-24-5 | ᵗBu | H | H | CH₂Ph | ⁱPr | H | CH₃ | F | OH |
| XXV-24-6 | ᵗBu | H | H | CH₂-indol-3-yl | ⁱPr | H | CH₃ | F | OH |
| XXV-24-7 | ᵗBu | H | H | CH₂CH₂SCH₃ | ⁱPr | H | CH₃ | F | OH |
| XXV-24-8 | ᵗBu | * | H | * | ⁱPr | H | CH₃ | F | OH |

*R² and R³ᵇ joined together by (CH₂)₃ to form five-membered ring.

TABLE XXV-25

| No | R¹ | R² | R³ᵃ | R³ᵇ | R⁴ | R⁵ | R⁶ | X | Y |
|---|---|---|---|---|---|---|---|---|---|
| XXV-25-1 | Ph | H | H | H | ⁱPr | H | CH₃ | F | OH |
| XXV-25-2 | Ph | H | H | CH₃ | ⁱPr | H | CH₃ | F | OH |
| XXV-25-3 | Ph | H | H | CH(CH₃)₂ | ⁱPr | H | CH₃ | F | OH |
| XXV-25-4 | Ph | H | H | CH₂CH(CH₃)₂ | ⁱPr | H | CH₃ | F | OH |
| XXV-25-5 | Ph | H | H | CH₂Ph | ⁱPr | H | CH₃ | F | OH |
| XXV-25-6 | Ph | H | H | CH₂-indol-3-yl | ⁱPr | H | CH₃ | F | OH |
| XXV-25-7 | Ph | H | H | CH₂CH₂SCH₃ | ⁱPr | H | CH₃ | F | OH |
| XXV-25-8 | Ph | * | H | * | ⁱPr | H | CH₃ | F | OH |

*R² and R³ᵇ joined together by (CH₂)₃ to form five-membered ring.

TABLE XXV-26

| No | R¹ | R² | R³ᵃ | R³ᵇ | R⁴ | R⁵ | R⁶ | X | Y |
|---|---|---|---|---|---|---|---|---|---|
| XXV-26-1 | p-Me—Ph | H | H | H | ⁱPr | H | CH₃ | F | OH |
| XXV-26-2 | p-Me—Ph | H | H | CH₃ | ⁱPr | H | CH₃ | F | OH |
| XXV-26-3 | p-Me—Ph | H | H | CH(CH₃)₂ | ⁱPr | H | CH₃ | F | OH |
| XXV-26-4 | p-Me—Ph | H | H | CH₂CH(CH₃)₂ | ⁱPr | H | CH₃ | F | OH |
| XXV-26-5 | p-Me—Ph | H | H | CH₂Ph | ⁱPr | H | CH₃ | F | OH |
| XXV-26-6 | p-Me—Ph | H | H | CH₂-indol-3-yl | ⁱPr | H | CH₃ | F | OH |
| XXV-26-7 | p-Me—Ph | H | H | CH₂CH₂SCH₃ | ⁱPr | H | CH₃ | F | OH |
| XXV-26-8 | p-Me—Ph | * | H | * | ⁱPr | H | CH₃ | F | OH |

*R² and R³ᵇ joined together by (CH₂)₃ to form five-membered ring.

TABLE XXV-27

| No | R¹ | R² | R³ᵃ | R³ᵇ | R⁴ | R⁵ | R⁶ | X | Y |
|---|---|---|---|---|---|---|---|---|---|
| XXV-27-1 | p-F—Ph | H | H | H | ⁱPr | H | CH₃ | F | OH |
| XXV-27-2 | p-F—Ph | H | H | CH₃ | ⁱPr | H | CH₃ | F | OH |
| XXV-27-3 | p-F—Ph | H | H | CH(CH₃)₂ | ⁱPr | H | CH₃ | F | OH |
| XXV-27-4 | p-F—Ph | H | H | CH₂CH(CH₃)₂ | ⁱPr | H | CH₃ | F | OH |
| XXV-27-5 | p-F—Ph | H | H | CH₂Ph | ⁱPr | H | CH₃ | F | OH |
| XXV-27-6 | p-F—Ph | H | H | CH₂-indol-3-yl | ⁱPr | H | CH₃ | F | OH |
| XXV-27-7 | p-F—Ph | H | H | CH₂CH₂SCH₃ | ⁱPr | H | CH₃ | F | OH |
| XXV-21-8 | p-F—Ph | * | H | * | ⁱPr | H | CH₃ | F | OH |

*R² and R³ᵇ joined together by (CH₂)₃ to form five-membered ring.

TABLE XXV-28

| No | R¹ | R² | R³ᵃ | R³ᵇ | R⁴ | R⁵ | R⁶ | X | Y |
|---|---|---|---|---|---|---|---|---|---|
| XXV-28-1 | p-Cl—Ph | H | H | H | $^i$Pr | H | CH₃ | F | OH |
| XXV-28-2 | p-Cl—Ph | H | H | CH₃ | $^i$Pr | H | CH₃ | F | OH |
| XXV-28-3 | p-Cl—Ph | H | H | CH(CH₃)₂ | $^i$Pr | H | CH₃ | F | OH |
| XXV-28-4 | p-Cl—Ph | H | H | CH₂CH(CH₃)₂ | $^i$Pr | H | CH₃ | F | OH |
| XXV-28-5 | p-Cl—Ph | H | H | CH₂Ph | $^i$Pr | H | CH₃ | F | OH |
| XXV-28-6 | p-Cl—Ph | H | H | CH₂-indol-3-yl | $^i$Pr | H | CH₃ | F | OH |
| XXV-28-7 | p-Cl—Ph | H | H | CH₂CH₂SCH₃ | $^i$Pr | H | CH₃ | F | OH |
| XXV-28-8 | p-Cl—Ph | * | H | * | $^i$Pr | H | CH₃ | F | OH |

*R² and R³ᵇ joined together by (CH₂)₃ to form five-membered ring.

TABLE XXV-29

| No | R¹ | R² | R³ᵃ | R³ᵇ | R⁴ | R⁵ | R⁶ | X | Y |
|---|---|---|---|---|---|---|---|---|---|
| XXV-29-1 | p-Br—Ph | H | H | H | $^i$Pr | H | CH₃ | F | OH |
| XXV-29-2 | p-Br—Ph | H | H | CH₃ | $^i$Pr | H | CH₃ | F | OH |
| XXV-29-3 | p-Br—Ph | H | H | CH(CH₃)₂ | $^i$Pr | H | CH₃ | F | OH |
| XXV-29-4 | p-Br—Ph | H | H | CH₂CH(CH₃)₂ | $^i$Pr | H | CH₃ | F | OH |
| XXV-29-5 | p-Br—Ph | H | H | CH₂Ph | $^i$Pr | H | CH₃ | F | OH |
| XXV-29-6 | p-Br—Ph | H | H | CH₂-indol-3-yl | $^i$Pr | H | CH₃ | F | OH |
| XXV-29-7 | p-Br—Ph | H | H | CH₂CH₂SCH₃ | $^i$Pr | H | CH₃ | F | OH |
| XXV-29-8 | p-Br—Ph | * | H | * | $^i$Pr | H | CH₃ | F | OH |

*R² and R³ᵇ joined together by (CH₂)₃ to form five-membered ring.

TABLE XXV-30

| No | R¹ | R² | R³ᵃ | R³ᵇ | R⁴ | R⁵ | R⁶ | X | Y |
|---|---|---|---|---|---|---|---|---|---|
| XXV-30-1 | p-I—Ph | H | H | H | $^i$Pr | H | CH₃ | F | OH |
| XXV-30-2 | p-I—Ph | H | H | CH₃ | $^i$Pr | H | CH₃ | F | OH |
| XXV-30-3 | p-I—Ph | H | H | CH(CH₃)₂ | $^i$Pr | H | CH₃ | F | OH |
| XXV-30-4 | p-I—Ph | H | H | CH₂CH(CH₃)₂ | $^i$Pr | H | CH₃ | F | OH |
| XXV-30-5 | p-I—Ph | H | H | CH₂Ph | $^i$Pr | H | CH₃ | F | OH |
| XXV-30-6 | p-I—Ph | H | H | CH₂-indol-3-yl | $^i$Pr | H | CH₃ | F | OH |
| XXV-30-7 | p-I—Ph | H | H | CH₂CH₂SCH₃ | $^i$Pr | H | CH₃ | F | OH |
| XXV-30-8 | p-I—Ph | * | H | * | $^i$Pr | H | CH₃ | F | OH |

*R² and R³ᵇ joined together by (CH₂)₃ to form five-membered ring.

TABLE XXV-31

| No | R¹ | R² | R³ᵃ | R³ᵇ | R⁴ | R⁵ | R⁶ | X | Y |
|---|---|---|---|---|---|---|---|---|---|
| XXV-31-1 | CH₃ | H | H | H | $^n$Bu | H | CH₃ | F | OH |
| XXV-31-2 | CH₃ | H | H | CH₃ | $^n$Bu | H | CH₃ | F | OH |
| XXV-31-3 | CH₃ | H | H | CH(CH₃)₂ | $^n$Bu | H | CH₃ | F | OH |
| XXV-31-4 | CH₃ | H | H | CH₂CH(CH₃)₂ | $^n$Bu | H | CH₃ | F | OH |
| XXV-31-5 | CH₃ | H | H | CH₂Ph | $^n$Bu | H | CH₃ | F | OH |
| XXV-31-6 | CH₃ | H | H | CH₂-indol-3-yl | $^n$Bu | H | CH₃ | F | OH |
| XXV-31-7 | CH₃ | H | H | CH₂CH₂SCH₃ | $^n$Bu | H | CH₃ | F | OH |
| XXV-31-8 | CH₃ | * | H | * | $^n$Bu | H | CH₃ | F | OH |

*R² and R³ᵇ joined together by (CH₂)₃ to form five-membered ring.

TABLE XXV-32

| No | R¹ | R² | R³ᵃ | R³ᵇ | R⁴ | R⁵ | R⁶ | X | Y |
|---|---|---|---|---|---|---|---|---|---|
| XXV-32-1 | Et | H | H | H | $^n$Bu | H | CH₃ | F | OH |
| XXV-32-2 | Et | H | H | CH₃ | $^n$Bu | H | CH₃ | F | OH |
| XXV-32-3 | Et | H | H | CH(CH₃)₂ | $^n$Bu | H | CH₃ | F | OH |
| XXV-32-4 | Et | H | H | CH₂CH(CH₃)₂ | $^n$Bu | H | CH₃ | F | OH |
| XXV-32-5 | Et | H | H | CH₂Ph | $^n$Bu | H | CH₃ | F | OH |
| XXV-32-6 | Et | H | H | CH₂-indol-3-yl | $^n$Bu | H | CH₃ | F | OH |
| XXV-32-7 | Et | H | H | CH₂CH₂SCH₃ | $^n$Bu | H | CH₃ | F | OH |
| XXV-32-8 | Et | * | H | * | $^n$Bu | H | CH₃ | F | OH |

*R² and R³ᵇ joined together by (CH₂)₃ to form five-membered ring.

TABLE XXV-33

| No | R¹ | R² | R³ᵃ | R³ᵇ | R⁴ | R⁵ | R⁶ | X | Y |
|---|---|---|---|---|---|---|---|---|---|
| XXV-33-1 | $^i$Pr | H | H | H | $^n$Bu | H | CH₃ | F | OH |
| XXV-33-2 | $^i$Pr | H | H | CH₃ | $^n$Bu | H | CH₃ | F | OH |
| XXV-33-3 | $^i$Pr | H | H | CH(CH₃)₂ | $^n$Bu | H | CH₃ | F | OH |
| XXV-33-4 | $^i$Pr | H | H | CH₂CH(CH₃)₂ | $^n$Bu | H | CH₃ | F | OH |
| XXV-33-5 | $^i$Pr | H | H | CH₂Ph | $^n$Bu | H | CH₃ | F | OH |
| XXV-33-6 | $^i$Pr | H | H | CH₂-indol-3-yl | $^n$Bu | H | CH₃ | F | OH |
| XXV-33-7 | $^i$Pr | H | H | CH₂CH₂SCH₃ | $^n$Bu | H | CH₃ | F | OH |
| XXV-33-8 | $^i$Pr | * | H | * | $^n$Bu | H | CH₃ | F | OH |

*R² and R³ᵇ joined together by (CH₂)₃ to form five-membered ring.

TABLE XXV-34

| No | R¹ | R² | R³ᵃ | R³ᵇ | R⁴ | R⁵ | R⁶ | X | Y |
|---|---|---|---|---|---|---|---|---|---|
| XXV-34-1 | $^t$Bu | H | H | H | $^n$Bu | H | CH₃ | F | OH |
| XXV-34-2 | $^t$Bu | H | H | CH₃ | $^n$Bu | H | CH₃ | F | OH |
| XXV-34-3 | $^t$Bu | H | H | CH(CH₃)₂ | $^n$Bu | H | CH₃ | F | OH |
| XXV-34-4 | $^t$Bu | H | H | CH₂CH(CH₃)₂ | $^n$Bu | H | CH₃ | F | OH |
| XXV-34-5 | $^t$Bu | H | H | CH₂Ph | $^n$Bu | H | CH₃ | F | OH |
| XXV-34-6 | $^t$Bu | H | H | CH₂-indol-3-yl | $^n$Bu | H | CH₃ | F | OH |
| XXV-34-7 | $^t$Bu | H | H | CH₂CH₂SCH₃ | $^n$Bu | H | CH₃ | F | OH |
| XXV-34-8 | $^t$Bu | * | H | * | $^n$Bu | H | CH₃ | F | OH |

*R² and R³ᵇ joined together by (CH₂)₃ to form five-membered ring.

TABLE XXV-35

| No | R¹ | R² | R³ᵃ | R³ᵇ | R⁴ | R⁵ | R⁶ | X | Y |
|---|---|---|---|---|---|---|---|---|---|
| XXV-35-1 | Ph | H | H | H | $^n$Bu | H | CH₃ | F | OH |
| XXV-35-2 | Ph | H | H | CH₃ | $^n$Bu | H | CH₃ | F | OH |
| XXV-35-3 | Ph | H | H | CH(CH₃)₂ | $^n$Bu | H | CH₃ | F | OH |
| XXV-35-4 | Ph | H | H | CH₂CH(CH₃)₂ | $^n$Bu | H | CH₃ | F | OH |
| XXV-35-5 | Ph | H | H | CH₂Ph | $^n$Bu | H | CH₃ | F | OH |
| XXV-35-6 | Ph | H | H | CH₂-indol-3-yl | $^n$Bu | H | CH₃ | F | OH |
| XXV-35-7 | Ph | H | H | CH₂CH₂SCH₃ | $^n$Bu | H | CH₃ | F | OH |
| XXV-35-8 | Ph | * | H | * | $^n$Bu | H | CH₃ | F | OH |

*R² and R³ᵇ joined together by (CH₂)₃ to form five-membered ring.

TABLE XXV-36

| No | R¹ | R² | R³ᵃ | R³ᵇ | R⁴ | R⁵ | R⁶ | X | Y |
|---|---|---|---|---|---|---|---|---|---|
| XXV-36-1 | p-Me—Ph | H | H | H | $^n$Bu | H | CH₃ | F | OH |
| XXV-36-2 | p-Me—Ph | H | H | CH₃ | $^n$Bu | H | CH₃ | F | OH |
| XXV-36-3 | p-Me—Ph | H | H | CH(CH₃)₂ | $^n$Bu | H | CH₃ | F | OH |
| XXV-36-4 | p-Me—Ph | H | H | CH₂CH(CH₃)₂ | $^n$Bu | H | CH₃ | F | OH |
| XXV-36-5 | p-Me—Ph | H | H | CH₂Ph | $^n$Bu | H | CH₃ | F | OH |
| XXV-36-6 | p-Me—Ph | H | H | CH₂-indol-3-yl | $^n$Bu | H | CH₃ | F | OH |

TABLE XXV-36-continued

| No | R¹ | R² | R³ᵃ | R³ᵇ | R⁴ | R⁵ | R⁶ | X | Y |
|---|---|---|---|---|---|---|---|---|---|
| XXV-36-7 | p-Me—Ph | H | H | CH₂CH₂SCH₃ | ⁿBu | H | CH₃ | F | OH |
| XXV-36-8 | p-Me—Ph | * | H | * | ⁿBu | H | CH₃ | F | OH |

*R² and R³ᵇ joined together by (CH₂)₃ to form five-membered ring.

TABLE XXV-37

| No | R¹ | R² | R³ᵃ | R³ᵇ | R⁴ | R⁵ | R⁶ | X | Y |
|---|---|---|---|---|---|---|---|---|---|
| XXV-37-1 | p-F—Ph | H | H | H | ⁿBu | H | CH₃ | F | OH |
| XXV-37-2 | p-F—Ph | H | H | CH₃ | ⁿBu | H | CH₃ | F | OH |
| XXV-37-3 | p-F—Ph | H | H | CH(CH₃)₂ | ⁿBu | H | CH₃ | F | OH |
| XXV-37-4 | p-F—Ph | H | H | CH₂CH(CH₃)₂ | ⁿBu | H | CH₃ | F | OH |
| XXV-37-5 | p-F—Ph | H | H | CH₂Ph | ⁿBu | H | CH₃ | F | OH |
| XXV-37-6 | p-F—Ph | H | H | CH₂-indol-3-yl | ⁿBu | H | CH₃ | F | OH |
| XXV-37-7 | p-F—Ph | H | H | CH₂CH₂SCH₃ | ⁿBu | H | CH₃ | F | OH |
| XXV-37-8 | p-F—Ph | * | H | * | ⁿBu | H | CH₃ | F | OH |

*R² and R³ᵇ joined together by (CH₂)₃ to form five-membered ring.

TABLE XXV-38

| No | R¹ | R² | R³ᵃ | R³ᵇ | R⁴ | R⁵ | R⁶ | X | Y |
|---|---|---|---|---|---|---|---|---|---|
| XXV-38-1 | p-Cl—Ph | H | H | H | ⁿBu | H | CH₃ | F | OH |
| XXV-38-2 | p-Cl—Ph | H | H | CH₃ | ⁿBu | H | CH₃ | F | OH |
| XXV-38-3 | p-Cl—Ph | H | H | CH(CH₃)₂ | ⁿBu | H | CH₃ | F | OH |
| XXV-38-4 | p-Cl—Ph | H | H | CH₂CH(CH₃)₂ | ⁿBu | H | CH₃ | F | OH |
| XXV-38-5 | p-Cl—Ph | H | H | CH₂Ph | ⁿBu | H | CH₃ | F | OH |
| XXV-38-6 | p-Cl—Ph | H | H | CH₂-indol-3-yl | ⁿBu | H | CH₃ | F | OH |
| XXV-38-7 | p-Cl—Ph | H | H | CH₂CH₂SCH₃ | ⁿBu | H | CH₃ | F | OH |
| XXV-38-8 | p-Cl—Ph | * | H | * | ⁿBu | H | CH₃ | F | OH |

*R² and R³ᵇ joined together by (CH₂)₃ to form five-membered ring.

TABLE XXV-39

| No | R¹ | R² | R³ᵃ | R³ᵇ | R⁴ | R⁵ | R⁶ | X | Y |
|---|---|---|---|---|---|---|---|---|---|
| XXV-39-1 | p-Br—Ph | H | H | H | ⁿBu | H | CH₃ | F | OH |
| XXV-39-2 | p-Br—Ph | H | H | CH₃ | ⁿBu | H | CH₃ | F | OH |
| XXV-39-3 | p-Br—Ph | H | H | CH(CH₃)₂ | ⁿBu | H | CH₃ | F | OH |
| XXV-39-4 | p-Br—Ph | H | H | CH₂CH(CH₃)₂ | ⁿBu | H | CH₃ | F | OH |
| XXV-39-5 | p-Br—Ph | H | H | CH₂Ph | ⁿBu | H | CH₃ | F | OH |
| XXV-39-6 | p-Br—Ph | H | H | CH₂-indol-3-yl | ⁿBu | H | CH₃ | F | OH |
| XXV-39-7 | p-Br—Ph | H | H | CH₂CH₂SCH₃ | ⁿBu | H | CH₃ | F | OH |
| XXV-39-8 | p-Br—Ph | * | H | * | ⁿBu | H | CH₃ | F | OH |

*R² and R³ᵇ joined together by (CH₂)₃ to form five-membered ring.

TABLE XXV-40

| No | R¹ | R² | R³ᵃ | R³ᵇ | R⁴ | R⁵ | R⁶ | X | Y |
|---|---|---|---|---|---|---|---|---|---|
| XXV-40-1 | p-I—Ph | H | H | H | ⁿBu | H | CH₃ | F | OH |
| XXV-40-2 | p-I—Ph | H | H | CH₃ | ⁿBu | H | CH₃ | F | OH |
| XXV-40-3 | p-I—Ph | H | H | CH(CH₃)₂ | ⁿBu | H | CH₃ | F | OH |
| XXV-40-4 | p-I—Ph | H | H | CH₂CH(CH₃)₂ | ⁿBu | H | CH₃ | F | OH |
| XXV-40-5 | p-I—Ph | H | H | CH₂Ph | ⁿBu | H | CH₃ | F | OH |
| XXV-40-6 | p-I—Ph | H | H | CH₂-indol-3-yl | ⁿBu | H | CH₃ | F | OH |
| XXV-40-7 | p-I—Ph | H | H | CH₂CH₂SCH₃ | ⁿBu | H | CH₃ | F | OH |
| XXV-40-8 | p-I—Ph | * | H | * | ⁿBu | H | CH₃ | F | OH |

*R² and R³ᵇ joined together by (CH₂)₃ to form five-membered ring.

TABLE XXV-41

| No | R¹ | R² | R³ᵃ | R³ᵇ | R⁴ | R⁵ | R⁶ | X | Y |
|---|---|---|---|---|---|---|---|---|---|
| XXV-41-1 | CH₃ | H | H | H | Bz | H | CH₃ | F | OH |
| XXV-41-2 | CH₃ | H | H | CH₃ | Bz | H | CH₃ | F | OH |
| XXV-41-3 | CH₃ | H | H | CH(CH₃)₂ | Bz | H | CH₃ | F | OH |
| XXV-41-4 | CH₃ | H | H | CH₂CH(CH₃)₂ | Bz | H | CH₃ | F | OH |
| XXV-41-5 | CH₃ | H | H | CH₂Ph | Bz | H | CH₃ | F | OH |
| XXV-41-6 | CH₃ | H | H | CH₂-indol-3-yl | Bz | H | CH₃ | F | OH |
| XXV-41-7 | CH₃ | H | H | CH₂CH₂SCH₃ | Bz | H | CH₃ | F | OH |
| XXV-41-8 | CH₃ | * | H | * | Bz | H | CH₃ | F | OH |

*R² and R³ᵇ joined together by (CH₂)₃ to form five-membered ring.

TABLE XXV-42

| No | R¹ | R² | R³ᵃ | R³ᵇ | R⁴ | R⁵ | R⁶ | X | Y |
|---|---|---|---|---|---|---|---|---|---|
| XXV-42-1 | Et | H | H | H | Bz | H | CH₃ | F | OH |
| XXV-42-2 | Et | H | H | CH₃ | Bz | H | CH₃ | F | OH |
| XXV-42-3 | Et | H | H | CH(CH₃)₂ | Bz | H | CH₃ | F | OH |
| XXV-42-4 | Et | H | H | CH₂CH(CH₃)₂ | Bz | H | CH₃ | F | OH |
| XXV-42-5 | Et | H | H | CH₂Ph | Bz | H | CH₃ | F | OH |
| XXV-42-6 | Et | H | H | CH₂-indol-3-yl | Bz | H | CH₃ | F | OH |
| XXV-42-7 | Et | H | H | CH₂CH₂SCH₃ | Bz | H | CH₃ | F | OH |
| XXV-42-8 | Et | * | H | * | Bz | H | CH₃ | F | OH |

*R² and R³ᵇ joined together by (CH₂)₃ to form five-membered ring.

TABLE XXV-43

| No | R¹ | R² | R³ᵃ | R³ᵇ | R⁴ | R⁵ | R⁶ | X | Y |
|---|---|---|---|---|---|---|---|---|---|
| XXV-43-1 | ⁱPr | H | H | H | Bz | H | CH₃ | F | OH |
| XXV-43-2 | ⁱPr | H | H | CH₃ | Bz | H | CH₃ | F | OH |
| XXV-43-3 | ⁱPr | H | H | CH(CH₃)₂ | Bz | H | CH₃ | F | OH |
| XXV-43-4 | ⁱPr | H | H | CH₂CH(CH₃)₂ | Bz | H | CH₃ | F | OH |
| XXV-43-5 | ⁱPr | H | H | CH₂Ph | Bz | H | CH₃ | F | OH |
| XXV-43-6 | ⁱPr | H | H | CH₂-indol-3-yl | Bz | H | CH₃ | F | OH |
| XXV-43-7 | ⁱPr | H | H | CH₂CH₂SCH₃ | Bz | H | CH₃ | F | OH |
| XXV-43-8 | ⁱPr | * | H | * | Bz | H | CH₃ | F | OH |

*R² and R³ᵇ joined together by (CH₂)₃ to form five-membered ring.

TABLE XXV-44

| No | R¹ | R² | R³ᵃ | R³ᵇ | R⁴ | R⁵ | R⁶ | X | Y |
|---|---|---|---|---|---|---|---|---|---|
| XXV-44-1 | ᵗBu | H | H | H | Bz | H | CH₃ | F | OH |
| XXV-44-2 | ᵗBu | H | H | CH₃ | Bz | H | CH₃ | F | OH |
| XXV-44-3 | ᵗBu | H | H | CH(CH₃)₂ | Bz | H | CH₃ | F | OH |
| XXV-44-4 | ᵗBu | H | H | CH₂CH(CH₃)₂ | Bz | H | CH₃ | F | OH |
| XXV-44-5 | ᵗBu | H | H | CH₂Ph | Bz | H | CH₃ | F | OH |
| XXV-44-6 | ᵗBu | H | H | CH₂-indol-3-yl | Bz | H | CH₃ | F | OH |
| XXV-44-7 | ᵗBu | H | H | CH₂CH₂SCH₃ | Bz | H | CH₃ | F | OH |
| XXV-44-8 | ᵗBu | * | H | * | Bz | H | CH₃ | F | OH |

*R² and R³ᵇ joined together by (CH₂)₃ to form five-membered ring.

TABLE XXV-45

| No | R¹ | R² | R³ᵃ | R³ᵇ | R⁴ | R⁵ | R⁶ | X | Y |
|---|---|---|---|---|---|---|---|---|---|
| XXV-45-1 | Ph | H | H | H | Bz | H | CH₃ | F | OH |
| XXV-45-2 | Ph | H | H | CH₃ | Bz | H | CH₃ | F | OH |
| XXV-45-3 | Ph | H | H | CH(CH₃)₂ | Bz | H | CH₃ | F | OH |
| XXV-45-4 | Ph | H | H | CH₂CH(CH₃)₂ | Bz | H | CH₃ | F | OH |
| XXV-45-5 | Ph | H | H | CH₂Ph | Bz | H | CH₃ | F | OH |

TABLE XXV-45-continued

| No | R¹ | R² | R³ᵃ | R³ᵇ | R⁴ | R⁵ | R⁶ | X | Y |
|---|---|---|---|---|---|---|---|---|---|
| XXV-45-6 | Ph | H | H | CH₂-indol-3-yl | Bz | H | CH₃ | F | OH |
| XXV-45-7 | Ph | H | H | CH₂CH₂SCH₃ | Bz | H | CH₃ | F | OH |
| XXV-45-8 | Ph | * | H | * | Bz | H | CH₃ | F | OH |

*R² and R³ᵇ joined together by (CH₂)₃ to form five-membered ring.

TABLE XXV-46

| No | R¹ | R² | R³ᵃ | R³ᵇ | R⁴ | R⁵ | R⁶ | X | Y |
|---|---|---|---|---|---|---|---|---|---|
| XXV-46-1 | p-Me—Ph | H | H | H | Bz | H | CH₃ | F | OH |
| XXV-46-2 | p-Me—Ph | H | H | CH₃ | Bz | H | CH₃ | F | OH |
| XXV-46-3 | p-Me—Ph | H | H | CH(CH₃)₂ | Bz | H | CH₃ | F | OH |
| XXV-46-4 | p-Me—Ph | H | H | CH₂CH(CH₃)₂ | Bz | H | CH₃ | F | OH |
| XXV-46-5 | p-Me—Ph | H | H | CH₂Ph | Bz | H | CH₃ | F | OH |
| XXV-46-6 | p-Me—Ph | H | H | CH₂-indol-3-yl | Bz | H | CH₃ | F | OH |
| XXV-46-7 | p-Me—Ph | H | H | CH₂CH₂SCH₃ | Bz | H | CH₃ | F | OH |
| XXV-46-8 | p-Me—Ph | * | H | * | Bz | H | CH₃ | F | OH |

*R² and R³ᵇ joined together by (CH₂)₃ to form five-membered ring.

TABLE XXV-47

| No | R¹ | R² | R³ᵃ | R³ᵇ | R⁴ | R⁵ | R⁶ | X | Y |
|---|---|---|---|---|---|---|---|---|---|
| XXV-47-1 | p-F—Ph | H | H | H | Bz | H | CH₃ | F | OH |
| XXV-47-2 | p-F—Ph | H | H | CH₃ | Bz | H | CH₃ | F | OH |
| XXV-47-3 | p-F—Ph | H | H | CH(CH₃)₂ | Bz | H | CH₃ | F | OH |
| XXV-47-4 | p-F—Ph | H | H | CH₂CH(CH₃)₂ | Bz | H | CH₃ | F | OH |
| XXV-47-5 | p-F—Ph | H | H | CH₂Ph | Bz | H | CH₃ | F | OH |
| XXV-47-6 | p-F—Ph | H | H | CH₂-indol-3-yl | Bz | H | CH₃ | F | OH |
| XXV-47-7 | p-F—Ph | H | H | CH₂CH₂SCH₃ | Bz | H | CH₃ | F | OH |
| XXV-47-8 | p-F—Ph | * | H | * | Bz | H | CH₃ | F | OH |

*R² and R³ᵇ joined together by (CH₂)₃ to form five-membered ring.

TABLE XXV-48

| No | R¹ | R² | R³ᵃ | R³ᵇ | R⁴ | R⁵ | R⁶ | X | Y |
|---|---|---|---|---|---|---|---|---|---|
| XXV-48-1 | p-Cl—Ph | H | H | H | Bz | H | CH₃ | F | OH |
| XXV-48-2 | p-Cl—Ph | H | H | CH₃ | Bz | H | CH₃ | F | OH |
| XXV-48-3 | p-Cl—Ph | H | H | CH(CH₃)₂ | Bz | H | CH₃ | F | OH |
| XXV-48-4 | p-Cl—Ph | H | H | CH₂CH(CH₃)₂ | Bz | H | CH₃ | F | OH |
| XXV-48-5 | p-Cl—Ph | H | H | CH₂Ph | Bz | H | CH₃ | F | OH |
| XXV-48-6 | p-Cl—Ph | H | H | CH₂-indol-3-yl | Bz | H | CH₃ | F | OH |
| XXV-48-7 | p-Cl—Ph | H | H | CH₂CH₂SCH₃ | Bz | H | CH₃ | F | OH |
| XXV-48-8 | p-Cl—Ph | * | H | * | Bz | H | CH₃ | F | OH |

*R² and R³ᵇ joined together by (CH₂)₃ to form five-membered ring.

TABLE XXV-49

| No | R¹ | R² | R³ᵃ | R³ᵇ | R⁴ | R⁵ | R⁶ | X | Y |
|---|---|---|---|---|---|---|---|---|---|
| XXV-49-1 | p-Br—Ph | H | H | H | Bz | H | CH₃ | F | OH |
| XXV-49-2 | p-Br—Ph | H | H | CH₃ | Bz | H | CH₃ | F | OH |
| XXV-49-3 | p-Br—Ph | H | H | CH(CH₃)₂ | Bz | H | CH₃ | F | OH |
| XXV-49-4 | p-Br—Ph | H | H | CH₂CH(CH₃)₂ | Bz | H | CH₃ | F | OH |
| XXV-49-5 | p-Br—Ph | H | H | CH₂Ph | Bz | H | CH₃ | F | OH |
| XXV-49-6 | p-Br—Ph | H | H | CH₂-indol-3-yl | Bz | H | CH₃ | F | OH |
| XXV-49-7 | p-Br—Ph | H | H | CH₂CH₂SCH₃ | Bz | H | CH₃ | F | OH |
| XXV-49-8 | p-Br—Ph | * | H | * | Bz | H | CH₃ | F | OH |

*R² and R³ᵇ joined together by (CH₂)₃ to form five-membered ring.

TABLE XXV-50

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXV-50-1 | p-I—Ph | H | H | H | Bz | H | $CH_3$ | F | OH |
| XXV-50-2 | p-I—Ph | H | H | $CH_3$ | Bz | H | $CH_3$ | F | OH |
| XXV-50-3 | p-I—Ph | H | H | $CH(CH_3)_2$ | Bz | H | $CH_3$ | F | OH |
| XXV-50-4 | p-I—Ph | H | H | $CH_2CH(CH_3)_2$ | Bz | H | $CH_3$ | F | OH |
| XXV-50-5 | p-I—Ph | H | H | $CH_2Ph$ | Bz | H | $CH_3$ | F | OH |
| XXV-50-6 | p-I—Ph | H | H | $CH_2$-indol-3-yl | Bz | H | $CH_3$ | F | OH |
| XXV-50-7 | p-I—Ph | H | H | $CH_2CH_2SCH_3$ | Bz | H | $CH_3$ | F | OH |
| XXV-50-8 | p-I—Ph | * | H | * | Bz | H | $CH_3$ | F | OH |

*$R^2$ and $R^{3b}$ joined together by $(CH_2)_3$ to form five-membered ring.

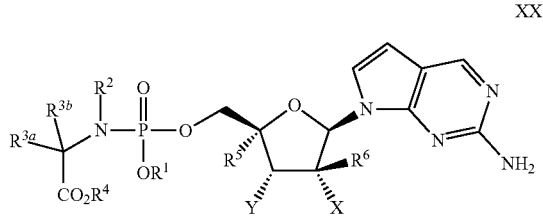

XXVI

TABLE XXVI-1

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-1-1 | $CH_3$ | H | H | H | $CH_3$ | H | F | H | OH |
| XXVI-1-2 | $CH_3$ | H | H | $CH_3$ | $CH_3$ | H | F | H | OH |
| XXVI-1-3 | $CH_3$ | H | H | $CH(CH_3)_2$ | $CH_3$ | H | F | H | OH |
| XXVI-1-4 | $CH_3$ | H | H | $CH_2CH(CH_3)_2$ | $CH_3$ | H | F | H | OH |
| XXVI-1-5 | $CH_3$ | H | H | $CH_2Ph$ | $CH_3$ | H | F | H | OH |
| XXVI-1-6 | $CH_3$ | H | H | $CH_2$-indol-3-yl | $CH_3$ | H | F | H | OH |
| XXVI-1-7 | $CH_3$ | H | H | $CH_2CH_2SCH_3$ | $CH_3$ | H | F | H | OH |
| XXVI-1-8 | $CH_3$ | * | H | * | $CH_3$ | H | F | H | OH |

*$R^2$ and $R^{3b}$ joined together by $(CH_2)_3$ to form five-membered ring.

TABLE XXVI-2

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-2-1 | Et | H | H | H | $CH_3$ | H | F | H | OH |
| XXVI-2-2 | Et | H | H | $CH_3$ | $CH_3$ | H | F | H | OH |
| XXVI-2-3 | Et | H | H | $CH(CH_3)_2$ | $CH_3$ | H | F | H | OH |
| XXVI-2-4 | Et | H | H | $CH_2CH(CH_3)_2$ | $CH_3$ | H | F | H | OH |
| XXVI-2-5 | Et | H | H | $CH_2Ph$ | $CH_3$ | H | F | H | OH |
| XXVI-2-6 | Et | H | H | $CH_2$-indol-3-yl | $CH_3$ | H | F | H | OH |
| XXVI-2-7 | Et | H | H | $CH_2CH_2SCH_3$ | $CH_3$ | H | F | H | OH |
| XXVI-2-8 | Et | * | H | * | $CH_3$ | H | F | H | OH |

*$R^2$ and $R^{3b}$ joined together by $(CH_2)_3$ to form five-membered ring.

TABLE XXVI-3

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-3-1 | $^iPr$ | H | H | H | $CH_3$ | H | F | H | OH |
| XXVI-3-2 | $^iPr$ | H | H | $CH_3$ | $CH_3$ | H | F | H | OH |
| XXVI-3-3 | $^iPr$ | H | H | $CH(CH_3)_2$ | $CH_3$ | H | F | H | OH |
| XXVI-3-4 | $^iPr$ | H | H | $CH_2CH(CH_3)_2$ | $CH_3$ | H | F | H | OH |
| XXVI-3-5 | $^iPr$ | H | H | $CH_2Ph$ | $CH_3$ | H | F | H | OH |
| XXVI-3-6 | $^iPr$ | H | H | $CH_2$-indol-3-yl | $CH_3$ | H | F | H | OH |
| XXVI-3-7 | $^iPr$ | H | H | $CH_2CH_2SCH_3$ | $CH_3$ | H | F | H | OH |
| XXVI-3-8 | $^iPr$ | * | H | * | $CH_3$ | H | F | H | OH |

*$R^2$ and $R^{3b}$ joined together by $(CH_2)_3$ to form five-membered ring.

TABLE XXVI-4

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-4-1 | $^tBu$ | H | H | H | $CH_3$ | H | F | H | OH |
| XXVI-4-2 | $^tBu$ | H | H | $CH_3$ | $CH_3$ | H | F | H | OH |
| XXVI-4-3 | $^tBu$ | H | H | $CH(CH_3)_2$ | $CH_3$ | H | F | H | OH |
| XXVI-4-4 | $^tBu$ | H | H | $CH_2CH(CH_3)_2$ | $CH_3$ | H | F | H | OH |
| XXVI-4-5 | $^tBu$ | H | H | $CH_2Ph$ | $CH_3$ | H | F | H | OH |
| XXVI-4-6 | $^tBu$ | H | H | $CH_2$-indol-3-yl | $CH_3$ | H | F | H | OH |
| XXVI-4-7 | $^tBu$ | H | H | $CH_2CH_2SCH_3$ | $CH_3$ | H | F | H | OH |
| XXVI-4-8 | $^tBu$ | * | H | * | $CH_3$ | H | F | H | OH |

*$R^2$ and $R^{3b}$ joined together by $(CH_2)_3$ to form five-membered ring.

TABLE XXVI-5

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-5-1 | Ph | H | H | H | $CH_3$ | H | F | H | OH |
| XXVI-5-2 | Ph | H | H | $CH_3$ | $CH_3$ | H | F | H | OH |
| XXVI-5-3 | Ph | H | H | $CH(CH_3)_2$ | $CH_3$ | H | F | H | OH |
| XXVI-5-4 | Ph | H | H | $CH_2CH(CH_3)_2$ | $CH_3$ | H | F | H | OH |
| XXVI-5-5 | Ph | H | H | $CH_2Ph$ | $CH_3$ | H | F | H | OH |
| XXVI-5-6 | Ph | H | H | $CH_2$-indol-3-yl | $CH_3$ | H | F | H | OH |
| XXVI-5-7 | Ph | H | H | $CH_2CH_2SCH_3$ | $CH_3$ | H | F | H | OH |
| XXVI-5-8 | Ph | * | H | * | $CH_3$ | H | F | H | OH |

*$R^2$ and $R^{3b}$ joined together by $(CH_2)_3$ to form five-membered ring.

TABLE XXVI-6

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-6-1 | p-Me—Ph | H | H | H | $CH_3$ | H | F | H | OH |
| XXVI-6-2 | p-Me—Ph | H | H | $CH_3$ | $CH_3$ | H | F | H | OH |
| XXVI-6-3 | p-Me—Ph | H | H | $CH(CH_3)_2$ | $CH_3$ | H | F | H | OH |
| XXVI-6-4 | p-Me—Ph | H | H | $CH_2CH(CH_3)_2$ | $CH_3$ | H | F | H | OH |
| XXVI-6-5 | p-Me—Ph | H | H | $CH_2Ph$ | $CH_3$ | H | F | H | OH |
| XXVI-6-6 | p-Me—Ph | H | H | $CH_2$-indol-3-yl | $CH_3$ | H | F | H | OH |
| XXVI-6-7 | p-Me—Ph | H | H | $CH_2CH_2SCH_3$ | $CH_3$ | H | F | H | OH |
| XXVI-6-8 | p-Me—Ph | * | H | * | $CH_3$ | H | F | H | OH |

*$R^2$ and $R^{3b}$ joined together by $(CH_2)_3$ to form five-membered ring.

TABLE XXVI-7

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXVI-7-1 | p-F—Ph | H | H | H | CH$_3$ | H | F | H | OH |
| XXVI-7-2 | p-F—Ph | H | H | CH$_3$ | CH$_3$ | H | F | H | OH |
| XXVI-7-3 | p-F—Ph | H | H | CH(CH$_3$)$_2$ | CH$_3$ | H | F | H | OH |
| XXVI-7-4 | p-F—Ph | H | H | CH$_2$CH(CH$_3$)$_2$ | CH$_3$ | H | F | H | OH |
| XXVI-7-6 | p-F—Ph | H | H | CH$_2$Ph | CH$_3$ | H | F | H | OH |
| XXVI-7-7 | p-F—Ph | H | H | CH$_2$-indol-3-yl | CH$_3$ | H | F | H | OH |
| XXVI-7-8 | p-F—Ph | H | H | CH$_2$CH$_2$SCH$_3$ | CH$_3$ | H | F | H | OH |
| XXVI-7-20 | p-F—Ph | * | H | * | CH$_3$ | H | F | H | OH |

*R$^2$ and R$^{3b}$ joined together by (CH$_2$)$_3$ to form five-membered ring.

TABLE XXVI-8

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXVI-8-1 | p-Cl—Ph | H | H | H | CH$_3$ | H | F | H | OH |
| XXVI-8-2 | p-Cl—Ph | H | H | CH$_3$ | CH$_3$ | H | F | H | OH |
| XXVI-8-3 | p-Cl—Ph | H | H | CH(CH$_3$)$_2$ | CH$_3$ | H | F | H | OH |
| XXVI-8-4 | p-Cl—Ph | H | H | CH$_2$CH(CH$_3$)$_2$ | CH$_3$ | H | F | H | OH |
| XXVI-8-5 | p-Cl—Ph | H | H | CH$_2$Ph | CH$_3$ | H | F | H | OH |
| XXVI-8-6 | p-Cl—Ph | H | H | CH$_2$-indol-3-yl | CH$_3$ | H | F | H | OH |
| XXVI-8-7 | p-Cl—Ph | H | H | CH$_2$CH$_2$SCH$_3$ | CH$_3$ | H | F | H | OH |
| XXVI-8-8 | p-Cl—Ph | * | H | * | CH$_3$ | H | F | H | OH |

*R$^2$ and R$^{3b}$ joined together by (CH$_2$)$_3$ to form five-membered ring.

TABLE XXVI-9

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXVI-9-1 | p-Br—Ph | H | H | H | CH$_3$ | H | F | H | OH |
| XXVI-9-2 | p-Br—Ph | H | H | CH$_3$ | CH$_3$ | H | F | H | OH |
| XXVI-9-3 | p-Br—Ph | H | H | CH(CH$_3$)$_2$ | CH$_3$ | H | F | H | OH |
| XXVI-9-4 | p-Br—Ph | H | H | CH$_2$CH(CH$_3$)$_2$ | CH$_3$ | H | F | H | OH |
| XXVI-9-6 | p-Br—Ph | H | H | CH$_2$Ph | CH$_3$ | H | F | H | OH |
| XXVI-9-7 | p-Br—Ph | H | H | CH$_2$-indol-3-yl | CH$_3$ | H | F | H | OH |
| XXVI-9-8 | p-Br—Ph | H | H | CH$_2$CH$_2$SCH$_3$ | CH$_3$ | H | F | H | OH |
| XXVI-9-20 | p-Br—Ph | * | H | * | CH$_3$ | H | F | H | OH |

*R$^2$ and R$^{3b}$ joined together by (CH$_2$)$_3$ to form five-membered ring.

TABLE XXVI-10

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXVI-10-1 | p-I—Ph | H | H | H | CH$_3$ | H | F | H | OH |
| XXVI-10-2 | p-I—Ph | H | H | CH$_3$ | CH$_3$ | H | F | H | OH |
| XXVI-10-3 | p-I—Ph | H | H | CH(CH$_3$)$_2$ | CH$_3$ | H | F | H | OH |
| XXVI-10-4 | p-I—Ph | H | H | CH$_2$CH(CH$_3$)$_2$ | CH$_3$ | H | F | H | OH |
| XXVI-10-5 | p-I—Ph | H | H | CH$_2$Ph | CH$_3$ | H | F | H | OH |
| XXVI-10-6 | p-I—Ph | H | H | CH$_2$-indol-3-yl | CH$_3$ | H | F | H | OH |
| XXVI-10-7 | p-I—Ph | H | H | CH$_2$CH$_2$SCH$_3$ | CH$_3$ | H | F | H | OH |
| XXVI-10-8 | p-I—Ph | * | H | * | CH$_3$ | H | F | H | OH |

*R$^2$ and R$^{3b}$ joined together by (CH$_2$)$_3$ to form five-membered ring.

TABLE XXVI-11

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXVI-11-1 | CH$_3$ | H | H | H | Et | H | F | H | OH |
| XXVI-11-2 | CH$_3$ | H | H | CH$_3$ | Et | H | F | H | OH |
| XXVI-11-3 | CH$_3$ | H | H | CH(CH$_3$)$_2$ | Et | H | F | H | OH |
| XXVI-11-4 | CH$_3$ | H | H | CH$_2$CH(CH$_3$)$_2$ | Et | H | F | H | OH |
| XXVI-11-5 | CH$_3$ | H | H | CH$_2$Ph | Et | H | F | H | OH |
| XXVI-11-6 | CH$_3$ | H | H | CH$_2$-indol-3-yl | Et | H | F | H | OH |
| XXVI-11-7 | CH$_3$ | H | H | CH$_2$CH$_2$SCH$_3$ | Et | H | F | H | OH |
| XXVI-11-8 | CH$_3$ | * | H | * | Et | H | F | H | OH |

*R$^2$ and R$^{3b}$ joined together by (CH$_2$)$_3$ to form five-membered ring.

TABLE XXVI-12

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXVI-12-1 | Et | H | H | H | Et | H | F | H | OH |
| XXVI-12-2 | Et | H | H | CH$_3$ | Et | H | F | H | OH |
| XXVI-12-3 | Et | H | H | CH(CH$_3$)$_2$ | Et | H | F | H | OH |

TABLE XXVI-12-continued

| No | R¹ | R² | R³ᵃ | R³ᵇ | R⁴ | R⁵ | R⁶ | X | Y |
|---|---|---|---|---|---|---|---|---|---|
| XXVI-12-4 | Et | H | H | CH₂CH(CH₃)₂ | Et | H | F | H | OH |
| XXVI-12-5 | Et | H | H | CH₂Ph | Et | H | F | H | OH |
| XXVI-12-6 | Et | H | H | CH₂-indol-3-yl | Et | H | F | H | OH |
| XXVI-12-7 | Et | H | H | CH₂CH₂SCH₃ | Et | H | F | H | OH |
| XXVI-12-8 | Et | * | H | * | Et | H | F | H | OH |

*R² and R³ᵇ joined together by (CH₂)₃ to form five-membered ring.

TABLE XXVI-13

| No | R¹ | R² | R³ᵃ | R³ᵇ | R⁴ | R⁵ | R⁶ | X | Y |
|---|---|---|---|---|---|---|---|---|---|
| XXVI-13-1 | ⁱPr | H | H | H | Et | H | F | H | OH |
| XXVI-13-2 | ⁱPr | H | H | CH₃ | Et | H | F | H | OH |
| XXVI-13-3 | ⁱPr | H | H | CH(CH₃)₂ | Et | H | F | H | OH |
| XXVI-13-4 | ⁱPr | H | H | CH₂CH(CH₃)₂ | Et | H | F | H | OH |
| XXVI-13-5 | ⁱPr | H | H | CH₂Ph | Et | H | F | H | OH |
| XXVI-13-6 | ⁱPr | H | H | CH₂-indol-3-yl | Et | H | F | H | OH |
| XXVI-13-7 | ⁱPr | H | H | CH₂CH₂SCH₃ | Et | H | F | H | OH |
| XXVI-13-8 | ⁱPr | * | H | * | Et | H | F | H | OH |

*R² and R³ᵇ joined together by (CH₂)₃ to form five-membered ring.

TABLE XXVI-14

| No | R¹ | R² | R³ᵃ | R³ᵇ | R⁴ | R⁵ | R⁶ | X | Y |
|---|---|---|---|---|---|---|---|---|---|
| XXVI-14-1 | ᵗBu | H | H | H | Et | H | F | H | OH |
| XXVI-14-2 | ᵗBu | H | H | CH₃ | Et | H | F | H | OH |
| XXVI-14-3 | ᵗBu | H | H | CH(CH₃)₂ | Et | H | F | H | OH |
| XXVI-14-4 | ᵗBu | H | H | CH₂CH(CH₃)₂ | Et | H | F | H | OH |
| XXVI-14-5 | ᵗBu | H | H | CH₂Ph | Et | H | F | H | OH |
| XXVI-14-6 | ᵗBu | H | H | CH₂-indol-3-yl | Et | H | F | H | OH |
| XXVI-14-7 | ᵗBu | H | H | CH₂CH₂SCH₃ | Et | H | F | H | OH |
| XXVI-14-8 | ᵗBu | * | H | * | Et | H | F | H | OH |

*R² and R³ᵇ joined together by (CH₂)₃ to form five-membered ring.

TABLE XXVI-15

| No | R¹ | R² | R³ᵃ | R³ᵇ | R⁴ | R⁵ | R⁶ | X | Y |
|---|---|---|---|---|---|---|---|---|---|
| XXVI-15-1 | Ph | H | H | H | Et | H | F | H | OH |
| XXVI-15-2 | Ph | H | H | CH₃ | Et | H | F | H | OH |
| XXVI-15-3 | Ph | H | H | CH(CH₃)₂ | Et | H | F | H | OH |
| XXVI-15-4 | Ph | H | H | CH₂CH(CH₃)₂ | Et | H | F | H | OH |
| XXVI-15-5 | Ph | H | H | CH₂Ph | Et | H | F | H | OH |
| XXVI-15-6 | Ph | H | H | CH₂-indol-3-yl | Et | H | F | H | OH |
| XXVI-15-7 | Ph | H | H | CH₂CH₂SCH₃ | Et | H | F | H | OH |
| XXVI-15-8 | Ph | * | H | * | Et | H | F | H | OH |

*R² and R³ᵇ joined together by (CH₂)₃ to form five-membered ring.

TABLE XXVI-16

| No | R¹ | R² | R³ᵃ | R³ᵇ | R⁴ | R⁵ | R⁶ | X | Y |
|---|---|---|---|---|---|---|---|---|---|
| XXVI-16-1 | p-Me—Ph | H | H | H | Et | H | F | H | OH |
| XXVI-16-2 | p-Me—Ph | H | H | CH₃ | Et | H | F | H | OH |
| XXVI-16-3 | p-Me—Ph | H | H | CH(CH₃)₂ | Et | H | F | H | OH |
| XXVI-16-4 | p-Me—Ph | H | H | CH₂CH(CH₃)₂ | Et | H | F | H | OH |
| XXVI-16-5 | p-Me—Ph | H | H | CH₂Ph | Et | H | F | H | OH |
| XXVI-16-6 | p-Me—Ph | H | H | CH₂-indol-3-yl | Et | H | F | H | OH |
| XXVI-16-7 | p-Me—Ph | H | H | CH₂CH₂SCH₃ | Et | H | F | H | OH |
| XXVI-16-8 | p-Me—Ph | * | H | * | Et | H | F | H | OH |

*R² and R³ᵇ joined together by (CH₂)₃ to form five-membered ring.

TABLE XXVI-17

| No | R¹ | R² | R³ᵃ | R³ᵇ | R⁴ | R⁵ | R⁶ | X | Y |
|---|---|---|---|---|---|---|---|---|---|
| XXVI-17-1 | p-F—Ph | H | H | H | Et | H | F | H | OH |
| XXVI-17-2 | p-F—Ph | H | H | CH₃ | Et | H | F | H | OH |
| XXVI-17-3 | p-F—Ph | H | H | CH(CH₃)₂ | Et | H | F | H | OH |
| XXVI-17-4 | p-F—Ph | H | H | CH₂CH(CH₃)₂ | Et | H | F | H | OH |
| XXVI-17-5 | p-F—Ph | H | H | CH₂Ph | Et | H | F | H | OH |
| XXVI-17-6 | p-F—Ph | H | H | CH₂-indol-3-yl | Et | H | F | H | OH |
| XXVI-17-7 | p-F—Ph | H | H | CH₂CH₂SCH₃ | Et | H | F | H | OH |
| XXVI-17-8 | p-F—Ph | * | H | * | Et | H | F | H | OH |

*R² and R³ᵇ joined together by (CH₂)₃ to form five-membered ring.

TABLE XXVI-18

| No | R¹ | R² | R³ᵃ | R³ᵇ | R⁴ | R⁵ | R⁶ | X | Y |
|---|---|---|---|---|---|---|---|---|---|
| XXVI-18-1 | p-Cl—Ph | H | H | H | Et | H | F | H | OH |
| XXVI-18-2 | p-Cl—Ph | H | H | CH₃ | Et | H | F | H | OH |
| XXVI-18-3 | p-Cl—Ph | H | H | CH(CH₃)₂ | Et | H | F | H | OH |
| XXVI-18-4 | p-Cl—Ph | H | H | CH₂CH(CH₃)₂ | Et | H | F | H | OH |
| XXVI-18-5 | p-Cl—Ph | H | H | CH₂Ph | Et | H | F | H | OH |
| XXVI-18-6 | p-Cl—Ph | H | H | CH₂-indol-3-yl | Et | H | F | H | OH |
| XXVI-18-7 | p-Cl—Ph | H | H | CH₂CH₂SCH₃ | Et | H | F | H | OH |
| XXVI-18-8 | p-Cl—Ph | * | H | * | Et | H | F | H | OH |

*R² and R³ᵇ joined together by (CH₂)₃ to form five-membered ring.

TABLE XXVI-19

| No | R¹ | R² | R³ᵃ | R³ᵇ | R⁴ | R⁵ | R⁶ | X | Y |
|---|---|---|---|---|---|---|---|---|---|
| XXVI-19-1 | p-Br—Ph | H | H | H | Et | H | F | H | OH |
| XXVI-19-2 | p-Br—Ph | H | H | CH₃ | Et | H | F | H | OH |
| XXVI-19-3 | p-Br—Ph | H | H | CH(CH₃)₂ | Et | H | F | H | OH |
| XXVI-19-4 | p-Br—Ph | H | H | CH₂CH(CH₃)₂ | Et | H | F | H | OH |
| XXVI-19-5 | p-Br—Ph | H | H | CH₂Ph | Et | H | F | H | OH |
| XXVI-19-6 | p-Br—Ph | H | H | CH₂-indol-3-yl | Et | H | F | H | OH |
| XXVI-19-7 | p-Br—Ph | H | H | CH₂CH₂SCH₃ | Et | H | F | H | OH |
| XXVI-19-8 | p-Br—Ph | * | H | * | Et | H | F | H | OH |

*R² and R³ᵇ joined together by (CH₂)₃ to form five-membered ring.

TABLE XXVI-20

| No | R¹ | R² | R³ᵃ | R³ᵇ | R⁴ | R⁵ | R⁶ | X | Y |
|---|---|---|---|---|---|---|---|---|---|
| XXVI-20-1 | p-I—Ph | H | H | H | Et | H | F | H | OH |
| XXVI-20-2 | p-I—Ph | H | H | CH₃ | Et | H | F | H | OH |
| XXVI-20-3 | p-I—Ph | H | H | CH(CH₃)₂ | Et | H | F | H | OH |
| XXVI-20-4 | p-I—Ph | H | H | CH₂CH(CH₃)₂ | Et | H | F | H | OH |
| XXVI-20-5 | p-I—Ph | H | H | CH₂Ph | Et | H | F | H | OH |

TABLE XXVI-20-continued

| No | R¹ | R² | R³ᵃ | R³ᵇ | R⁴ | R⁵ | R⁶ | X | Y |
|---|---|---|---|---|---|---|---|---|---|
| XXVI-20-6 | p-I—Ph | H | H | CH$_2$-indol-3-yl | Et | H | F | H | OH |
| XXVI-20-7 | p-I—Ph | H | H | CH$_2$CH$_2$SCH$_3$ | Et | H | F | H | OH |
| XXVI-20-8 | p-I—Ph | * | H | * | Et | H | F | H | OH |

*R² and R³ᵇ joined together by (CH$_2$)$_3$ to form five-membered ring.

TABLE XXVI-21

| No | R¹ | R² | R³ᵃ | R³ᵇ | R⁴ | R⁵ | R⁶ | X | Y |
|---|---|---|---|---|---|---|---|---|---|
| XXVI-21-1 | CH$_3$ | H | H | H | $^i$Pr | H | F | H | OH |
| XXVI-21-2 | CH$_3$ | H | H | CH$_3$ | $^i$Pr | H | F | H | OH |
| XXVI-21-3 | CH$_3$ | H | H | CH(CH$_3$)$_2$ | $^i$Pr | H | F | H | OH |
| XXVI-21-4 | CH$_3$ | H | H | CH$_2$CH(CH$_3$)$_2$ | $^i$Pr | H | F | H | OH |
| XXVI-21-5 | CH$_3$ | H | H | CH$_2$Ph | $^i$Pr | H | F | H | OH |
| XXVI-21-6 | CH$_3$ | H | H | CH$_2$-indol-3-yl | $^i$Pr | H | F | H | OH |
| XXVI-21-7 | CH$_3$ | H | H | CH$_2$CH$_2$SCH$_3$ | $^i$Pr | H | F | H | OH |
| XXVI-21-8 | CH$_3$ | * | H | * | $^i$Pr | H | F | H | OH |

*R² and R³ᵇ joined together by (CH$_2$)$_3$ to form five-membered ring.

TABLE XXVI-21

| No | R¹ | R² | R³ᵃ | R³ᵇ | R⁴ | R⁵ | R⁶ | X | Y |
|---|---|---|---|---|---|---|---|---|---|
| XXVI-21-1 | CH$_3$ | H | H | H | $^i$Pr | H | F | H | OH |
| XXVI-21-2 | CH$_3$ | H | H | CH$_3$ | $^i$Pr | H | F | H | OH |
| XXVI-21-3 | CH$_3$ | H | H | CH(CH$_3$)$_2$ | $^i$Pr | H | F | H | OH |
| XXVI-21-4 | CH$_3$ | H | H | CH$_2$CH(CH$_3$)$_2$ | $^i$Pr | H | F | H | OH |
| XXVI-21-5 | CH$_3$ | H | H | CH$_2$Ph | $^i$Pr | H | F | H | OH |
| XXVI-21-6 | CH$_3$ | H | H | CH$_2$-indol-3-yl | $^i$Pr | H | F | H | OH |
| XXVI-21-7 | CH$_3$ | H | H | CH$_2$CH$_2$SCH$_3$ | $^i$Pr | H | F | H | OH |
| XXVI-21-8 | CH$_3$ | * | H | * | $^i$Pr | H | F | H | OH |

*R² and R³ᵇ joined together by (CH$_2$)$_3$ to form five-membered ring.

TABLE XXVI-22

| No | R¹ | R² | R³ᵃ | R³ᵇ | R⁴ | R⁵ | R⁶ | X | Y |
|---|---|---|---|---|---|---|---|---|---|
| XXVI-22-1 | Et | H | H | H | $^i$Pr | H | F | H | OH |
| XXVI-22-2 | Et | H | H | CH$_3$ | $^i$Pr | H | F | H | OH |
| XXVI-22-3 | Et | H | H | CH(CH$_3$)$_2$ | $^i$Pr | H | F | H | OH |
| XXVI-22-4 | Et | H | H | CH$_2$CH(CH$_3$)$_2$ | $^i$Pr | H | F | H | OH |
| XXVI-22-5 | Et | H | H | CH$_2$Ph | $^i$Pr | H | F | H | OH |
| XXVI-22-6 | Et | H | H | CH$_2$-indol-3-yl | $^i$Pr | H | F | H | OH |
| XXVI-22-7 | Et | H | H | CH$_2$CH$_2$SCH$_3$ | $^i$Pr | H | F | H | OH |
| XXVI-22-8 | Et | * | H | * | $^i$Pr | H | F | H | OH |

*R² and R³ᵇ joined together by (CH$_2$)$_3$ to form five-membered ring.

TABLE XXVI-23

| No | R¹ | R² | R³ᵃ | R³ᵇ | R⁴ | R⁵ | R⁶ | X | Y |
|---|---|---|---|---|---|---|---|---|---|
| XXVI-23-1 | $^i$Pr | H | H | H | $^i$Pr | H | F | H | OH |
| XXVI-23-2 | $^i$Pr | H | H | CH$_3$ | $^i$Pr | H | F | H | OH |
| XXVI-23-3 | $^i$Pr | H | H | CH(CH$_3$)$_2$ | $^i$Pr | H | F | H | OH |
| XXVI-23-4 | $^i$Pr | H | H | CH$_2$CH(CH$_3$)$_2$ | $^i$Pr | H | F | H | OH |
| XXVI-23-5 | $^i$Pr | H | H | CH$_2$Ph | $^i$Pr | H | F | H | OH |
| XXVI-23-6 | $^i$Pr | H | H | CH$_2$-indol-3-yl | $^i$Pr | H | F | H | OH |
| XXVI-23-7 | $^i$Pr | H | H | CH$_2$CH$_2$SCH$_3$ | $^i$Pr | H | F | H | OH |
| XXVI-23-8 | $^i$Pr | * | H | * | $^i$Pr | H | F | H | OH |

*R² and R³ᵇ joined together by (CH$_2$)$_3$ to form five-membered ring.

TABLE XXVI-24

| No | R¹ | R² | R³ᵃ | R³ᵇ | R⁴ | R⁵ | R⁶ | X | Y |
|---|---|---|---|---|---|---|---|---|---|
| XXVI-24-1 | $^t$Bu | H | H | H | $^i$Pr | H | F | H | OH |
| XXVI-24-2 | $^t$Bu | H | H | CH$_3$ | $^i$Pr | H | F | H | OH |
| XXVI-24-3 | $^t$Bu | H | H | CH(CH$_3$)$_2$ | $^i$Pr | H | F | H | OH |

TABLE XXVI-24-continued

| No | R¹ | R² | R³ᵃ | R³ᵇ | R⁴ | R⁵ | R⁶ | X | Y |
|---|---|---|---|---|---|---|---|---|---|
| XXVI-24-4 | $^t$Bu | H | H | CH$_2$CH(CH$_3$)$_2$ | $^i$Pr | H | F | H | OH |
| XXVI-24-5 | $^t$Bu | H | H | CH$_2$Ph | $^i$Pr | H | F | H | OH |
| XXVI-24-6 | $^t$Bu | H | H | CH$_2$-indol-3-yl | $^i$Pr | H | F | H | OH |
| XXVI-24-7 | $^t$Bu | H | H | CH$_2$CH$_2$SCH$_3$ | $^i$Pr | H | F | H | OH |
| XXVI-24-8 | $^t$Bu | * | H | * | $^i$Pr | H | F | H | OH |

*R² and R³ᵇ joined together by (CH$_2$)$_3$ to form five-membered ring.

TABLE XXVI-25

| No | R¹ | R² | R³ᵃ | R³ᵇ | R⁴ | R⁵ | R⁶ | X | Y |
|---|---|---|---|---|---|---|---|---|---|
| XXVI-25-1 | Ph | H | H | H | $^i$Pr | H | F | H | OH |
| XXVI-25-2 | Ph | H | H | CH$_3$ | $^i$Pr | H | F | H | OH |
| XXVI-25-3 | Ph | H | H | CH(CH$_3$)$_2$ | $^i$Pr | H | F | H | OH |
| XXVI-25-4 | Ph | H | H | CH$_2$CH(CH$_3$)$_2$ | $^i$Pr | H | F | H | OH |
| XXVI-25-5 | Ph | H | H | CH$_2$Ph | $^i$Pr | H | F | H | OH |
| XXVI-25-6 | Ph | H | H | CH$_2$-indol-3-yl | $^i$Pr | H | F | H | OH |
| XXVI-25-7 | Ph | H | H | CH$_2$CH$_2$SCH$_3$ | $^i$Pr | H | F | H | OH |
| XXVI-25-8 | Ph | * | H | * | $^i$Pr | H | F | H | OH |

*R² and R³ᵇ joined together by (CH$_2$)$_3$ to form five-membered ring.

TABLE XXVI-26

| No | R¹ | R² | R³ᵃ | R³ᵇ | R⁴ | R⁵ | R⁶ | X | Y |
|---|---|---|---|---|---|---|---|---|---|
| XXVI-26-1 | p-Me—Ph | H | H | H | $^i$Pr | H | F | H | OH |
| XXVI-26-2 | p-Me—Ph | H | H | CH$_3$ | $^i$Pr | H | F | H | OH |
| XXVI-26-3 | p-Me—Ph | H | H | CH(CH$_3$)$_2$ | $^i$Pr | H | F | H | OH |
| XXVI-26-4 | p-Me—Ph | H | H | CH$_2$CH(CH$_3$)$_2$ | $^i$Pr | H | F | H | OH |
| XXVI-26-5 | p-Me—Ph | H | H | CH$_2$Ph | $^i$Pr | H | F | H | OH |
| XXVI-26-6 | p-Me—Ph | H | H | CH$_2$-indol-3-yl | $^i$Pr | H | F | H | OH |
| XXVI-26-7 | p-Me—Ph | H | H | CH$_2$CH$_2$SCH$_3$ | $^i$Pr | H | F | H | OH |
| XXVI-26-8 | p-Me—Ph | * | H | * | $^i$Pr | H | F | H | OH |

*R² and R³ᵇ joined together by (CH$_2$)$_3$ to form five-membered ring.

TABLE XXVI-27

| No | R¹ | R² | R³ᵃ | R³ᵇ | R⁴ | R⁵ | R⁶ | X | Y |
|---|---|---|---|---|---|---|---|---|---|
| XXVI-27-1 | p-F—Ph | H | H | H | $^i$Pr | H | F | H | OH |
| XXVI-27-2 | p-F—Ph | H | H | CH$_3$ | $^i$Pr | H | F | H | OH |
| XXVI-27-3 | p-F—Ph | H | H | CH(CH$_3$)$_2$ | $^i$Pr | H | F | H | OH |
| XXVI-27-4 | p-F—Ph | H | H | CH$_2$CH(CH$_3$)$_2$ | $^i$Pr | H | F | H | OH |
| XXVI-27-5 | p-F—Ph | H | H | CH$_2$Ph | $^i$Pr | H | F | H | OH |
| XXVI-27-6 | p-F—Ph | H | H | CH$_2$-indol-3-yl | $^i$Pr | H | F | H | OH |
| XXVI-27-7 | p-F—Ph | H | H | CH$_2$CH$_2$SCH$_3$ | $^i$Pr | H | F | H | OH |
| XXVI-27-8 | p-F—Ph | * | H | * | $^i$Pr | H | F | H | OH |

*R² and R³ᵇ joined together by (CH$_2$)$_3$ to form five-membered ring.

TABLE XXVI-28

| No | R¹ | R² | R³ᵃ | R³ᵇ | R⁴ | R⁵ | R⁶ | X | Y |
|---|---|---|---|---|---|---|---|---|---|
| XXVI-28-1 | p-Cl—Ph | H | H | H | $^i$Pr | H | F | H | OH |
| XXVI-28-2 | p-Cl—Ph | H | H | CH$_3$ | $^i$Pr | H | F | H | OH |
| XXVI-28-3 | p-Cl—Ph | H | H | CH(CH$_3$)$_2$ | $^i$Pr | H | F | H | OH |

TABLE XXVI-28-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-28-4 | p-Cl—Ph | H | H | CH$_2$CH(CH$_3$)$_2$ | $^i$Pr | H | F | H | OH |
| XXVI-28-5 | p-Cl—Ph | H | H | CH$_2$Ph | $^i$Pr | H | F | H | OH |
| XXVI-28-6 | p-Cl—Ph | H | H | CH$_2$-indol-3-yl | $^i$Pr | H | F | H | OH |
| XXVI-28-7 | p-Cl—Ph | H | H | CH$_2$CH$_2$SCH$_3$ | $^i$Pr | H | F | H | OH |
| XXVI-28-8 | p-Cl—Ph | * | H | * | $^i$Pr | H | F | H | OH |

*$R^2$ and $R^{3b}$ joined together by (CH$_2$)$_3$ to form five-membered ring.

TABLE XXVI-29

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-29-1 | p-Br—Ph | H | H | H | $^i$Pr | H | F | H | OH |
| XXVI-29-2 | p-Br—Ph | H | H | CH$_3$ | $^i$Pr | H | F | H | OH |
| XXVI-29-3 | p-Br—Ph | H | H | CH(CH$_3$)$_2$ | $^i$Pr | H | F | H | OH |
| XXVI-29-4 | p-Br—Ph | H | H | CH$_2$CH(CH$_3$)$_2$ | $^i$Pr | H | F | H | OH |
| XXVI-29-5 | p-Br—Ph | H | H | CH$_2$Ph | $^i$Pr | H | F | H | OH |
| XXVI-29-6 | p-Br—Ph | H | H | CH$_2$-indol-3-yl | $^i$Pr | H | F | H | OH |
| XXVI-29-7 | p-Br—Ph | H | H | CH$_2$CH$_2$SCH$_3$ | $^i$Pr | H | F | H | OH |
| XXVI-29-8 | p-Br—Ph | * | H | * | $^i$Pr | H | F | H | OH |

*$R^2$ and $R^{3b}$ joined together by (CH$_2$)$_3$ to form five-membered ring.

TABLE XXVI-30

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-30-1 | p-I—Ph | H | H | H | $^i$Pr | H | F | H | OH |
| XXVI-30-2 | p-I—Ph | H | H | CH$_3$ | $^i$Pr | H | F | H | OH |
| XXVI-30-3 | p-I—Ph | H | H | CH(CH$_3$)$_2$ | $^i$Pr | H | F | H | OH |
| XXVI-30-4 | p-I—Ph | H | H | CH$_2$CH(CH$_3$)$_2$ | $^i$Pr | H | F | H | OH |
| XXVI-30-5 | p-I—Ph | H | H | CH$_2$Ph | $^i$Pr | H | F | H | OH |
| XXVI-30-6 | p-I—Ph | H | H | CH$_2$-indol-3-yl | $^i$Pr | H | F | H | OH |
| XXVI-30-7 | p-I—Ph | H | H | CH$_2$CH$_2$SCH$_3$ | $^i$Pr | H | F | H | OH |
| XXVI-30-8 | p-I—Ph | * | H | * | $^i$Pr | H | F | H | OH |

*$R^2$ and $R^{3b}$ joined together by (CH$_2$)$_3$ to form five-membered ring.

TABLE XXVI-31

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-31-1 | CH$_3$ | H | H | H | $^n$Bu | H | F | H | OH |
| XXVI-31-2 | CH$_3$ | H | H | CH$_3$ | $^n$Bu | H | F | H | OH |
| XXVI-31-3 | CH$_3$ | H | H | CH(CH$_3$)$_2$ | $^n$Bu | H | F | H | OH |
| XXVI-31-4 | CH$_3$ | H | H | CH$_2$CH(CH$_3$)$_2$ | $^n$Bu | H | F | H | OH |
| XXVI-31-5 | CH$_3$ | H | H | CH$_2$Ph | $^n$Bu | H | F | H | OH |
| XXVI-31-6 | CH$_3$ | H | H | CH$_2$-indol-3-yl | $^n$Bu | H | F | H | OH |
| XXVI-31-7 | CH$_3$ | H | H | CH$_2$CH$_2$SCH$_3$ | $^n$Bu | H | F | H | OH |
| XXVI-31-8 | CH$_3$ | * | H | * | $^n$Bu | H | F | H | OH |

*$R^2$ and $R^{3b}$ joined together by (CH$_2$)$_3$ to form five-membered ring.

TABLE XXVI-32

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-32-1 | Et | H | H | H | $^n$Bu | H | F | H | OH |
| XXVI-32-2 | Et | H | H | CH$_3$ | $^n$Bu | H | F | H | OH |
| XXVI-32-3 | Et | H | H | CH(CH$_3$)$_2$ | $^n$Bu | H | F | H | OH |

TABLE XXVI-32-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-32-4 | Et | H | H | CH$_2$CH(CH$_3$)$_2$ | $^n$Bu | H | F | H | OH |
| XXVI-32-5 | Et | H | H | CH$_2$Ph | $^n$Bu | H | F | H | OH |
| XXVI-32-6 | Et | H | H | CH$_2$-indol-3-yl | $^n$Bu | H | F | H | OH |
| XXVI-32-7 | Et | H | H | CH$_2$CH$_2$SCH$_3$ | $^n$Bu | H | F | H | OH |
| XXVI-32-8 | Et | * | H | * | $^n$Bu | H | F | H | OH |

*$R^2$ and $R^{3b}$ joined together by (CH$_2$)$_3$ to form five-membered ring.

TABLE XXVI-33

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-33-1 | $^i$Pr | H | H | H | $^n$Bu | H | F | H | OH |
| XXVI-33-2 | $^i$Pr | H | H | CH$_3$ | $^n$Bu | H | F | H | OH |
| XXVI-33-3 | $^i$Pr | H | H | CH(CH$_3$)$_2$ | $^n$Bu | H | F | H | OH |
| XXVI-33-4 | $^i$Pr | H | H | CH$_2$CH(CH$_3$)$_2$ | $^n$Bu | H | F | H | OH |
| XXVI-33-5 | $^i$Pr | H | H | CH$_2$Ph | $^n$Bu | H | F | H | OH |
| XXVI-33-6 | $^i$Pr | H | H | CH$_2$-indol-3-yl | $^n$Bu | H | F | H | OH |
| XXVI-33-7 | $^i$Pr | H | H | CH$_2$CH$_2$SCH$_3$ | $^n$Bu | H | F | H | OH |
| XXVI-33-8 | $^i$Pr | * | H | * | $^n$Bu | H | F | H | OH |

*$R^2$ and $R^{3b}$ joined together by (CH$_2$)$_3$ to form five-membered ring.

TABLE XXVI-34

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-34-1 | $^t$Bu | H | H | H | $^n$Bu | H | F | H | OH |
| XXVI-34-2 | $^t$Bu | H | H | CH$_3$ | $^n$Bu | H | F | H | OH |
| XXVI-34-3 | $^t$Bu | H | H | CH(CH$_3$)$_2$ | $^n$Bu | H | F | H | OH |
| XXVI-34-4 | $^t$Bu | H | H | CH$_2$CH(CH$_3$)$_2$ | $^n$Bu | H | F | H | OH |
| XXVI-34-5 | $^t$Bu | H | H | CH$_2$Ph | $^n$Bu | H | F | H | OH |
| XXVI-34-6 | $^t$Bu | H | H | CH$_2$-indol-3-yl | $^n$Bu | H | F | H | OH |
| XXVI-34-7 | $^t$Bu | H | H | CH$_2$CH$_2$SCH$_3$ | $^n$Bu | H | F | H | OH |
| XXVI-34-8 | $^t$Bu | * | H | * | $^n$Bu | H | F | H | OH |

*$R^2$ and $R^{3b}$ joined together by (CH$_2$)$_3$ to form five-membered ring.

TABLE XXVI-35

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-35-1 | Ph | H | H | H | $^n$Bu | H | F | H | OH |
| XXVI-35-2 | Ph | H | H | CH$_3$ | $^n$Bu | H | F | H | OH |
| XXVI-35-3 | Ph | H | H | CH(CH$_3$)$_2$ | $^n$Bu | H | F | H | OH |
| XXVI-35-4 | Ph | H | H | CH$_2$CH(CH$_3$)$_2$ | $^n$Bu | H | F | H | OH |
| XXVI-35-5 | Ph | H | H | CH$_2$Ph | $^n$Bu | H | F | H | OH |
| XXVI-35-6 | Ph | H | H | CH$_2$-indol-3-yl | $^n$Bu | H | F | H | OH |
| XXVI-35-7 | Ph | H | H | CH$_2$CH$_2$SCH$_3$ | $^n$Bu | H | F | H | OH |
| XXVI-35-8 | Ph | * | H | * | $^n$Bu | H | F | H | OH |

*$R^2$ and $R^{3b}$ joined together by (CH$_2$)$_3$ to form five-membered ring.

TABLE XXVI-37

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-37-1 | p-F—Ph | H | H | H | $^n$Bu | H | F | H | OH |
| XXVI-37-2 | p-F—Ph | H | H | CH$_3$ | $^n$Bu | H | F | H | OH |
| XXVI-37-3 | p-F—Ph | H | H | CH(CH$_3$)$_2$ | $^n$Bu | H | F | H | OH |
| XXVI-37-4 | p-F—Ph | H | H | CH$_2$CH(CH$_3$)$_2$ | $^n$Bu | H | F | H | OH |
| XXVI-37-5 | p-F—Ph | H | H | CH$_2$Ph | $^n$Bu | H | F | H | OH |
| XXVI-37-6 | p-F—Ph | H | H | CH$_2$-indol-3-yl | $^n$Bu | H | F | H | OH |
| XXVI-37-7 | p-F—Ph | H | H | CH$_2$CH$_2$SCH$_3$ | $^n$Bu | H | F | H | OH |
| XXVI-37-8 | p-F—Ph | * | H | * | $^n$Bu | H | F | H | OH |

*$R^2$ and $R^{3b}$ joined together by (CH$_2$)$_3$ to form five-membered ring.

TABLE XXVI-38

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-38-1 | p-Cl—Ph | H | H | H | $^n$Bu | H | F | H | OH |
| XXVI-38-2 | p-Cl—Ph | H | H | $CH_3$ | $^n$Bu | H | F | H | OH |
| XXVI-38-3 | p-Cl—Ph | H | H | $CH(CH_3)_2$ | $^n$Bu | H | F | H | OH |
| XXVI-38-4 | p-Cl—Ph | H | H | $CH_2CH(CH_3)_2$ | $^n$Bu | H | F | H | OH |
| XXVI-38-5 | p-Cl—Ph | H | H | $CH_2Ph$ | $^n$Bu | H | F | H | OH |
| XXVI-38-6 | p-Cl—Ph | H | H | $CH_2$-indol-3-yl | $^n$Bu | H | F | H | OH |
| XXVI-38-7 | p-Cl—Ph | H | H | $CH_2CH_2SCH_3$ | $^n$Bu | H | F | H | OH |
| XXVI-38-8 | p-Cl—Ph | * | H | * | $^n$Bu | H | F | H | OH |

*$R^2$ and $R^{3b}$ joined together by $(CH_2)_3$ to form five-membered ring.

TABLE XXVI-39

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-39-1 | p-Br—Ph | H | H | H | $^n$Bu | H | F | H | OH |
| XXVI-39-2 | p-Br—Ph | H | H | $CH_3$ | $^n$Bu | H | F | H | OH |
| XXVI-39-3 | p-Br—Ph | H | H | $CH(CH_3)_2$ | $^n$Bu | H | F | H | OH |
| XXVI-39-4 | p-Br—Ph | H | H | $CH_2CH(CH_3)_2$ | $^n$Bu | H | F | H | OH |
| XXVI-39-5 | p-Br—Ph | H | H | $CH_2Ph$ | $^n$Bu | H | F | H | OH |
| XXVI-39-6 | p-Br—Ph | H | H | $CH_2$-indol-3-yl | $^n$Bu | H | F | H | OH |
| XXVI-39-7 | p-Br—Ph | H | H | $CH_2CH_2SCH_3$ | $^n$Bu | H | F | H | OH |
| XXVI-39-8 | p-Br—Ph | * | H | * | $^n$Bu | H | F | H | OH |

*$R^2$ and $R^{3b}$ joined together by $(CH_2)_3$ to form five-membered ring.

TABLE XXVI-40

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-40-1 | p-I—Ph | H | H | H | $^n$Bu | H | F | H | OH |
| XXVI-40-2 | p-I—Ph | H | H | $CH_3$ | $^n$Bu | H | F | H | OH |
| XXVI-40-3 | p-I—Ph | H | H | $CH(CH_3)_2$ | $^n$Bu | H | F | H | OH |
| XXVI-40-4 | p-I—Ph | H | H | $CH_2CH(CH_3)_2$ | $^n$Bu | H | F | H | OH |
| XXVI-40-5 | p-I—Ph | H | H | $CH_2Ph$ | $^n$Bu | H | F | H | OH |
| XXVI-40-6 | p-I—Ph | H | H | $CH_2$-indol-3-yl | $^n$Bu | H | F | H | OH |
| XXVI-40-7 | p-I—Ph | H | H | $CH_2CH_2SCH_3$ | $^n$Bu | H | F | H | OH |
| XXVI-40-8 | p-I—Ph | * | H | * | $^n$Bu | H | F | H | OH |

*$R^2$ and $R^{3b}$ joined together by $(CH_2)_3$ to form five-membered ring.

TABLE XXVI-41

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-41-1 | $CH_3$ | H | H | H | Bz | H | F | H | OH |
| XXVI-41-2 | $CH_3$ | H | H | $CH_3$ | Bz | H | F | H | OH |
| XXVI-41-3 | $CH_3$ | H | H | $CH(CH_3)_2$ | Bz | H | F | H | OH |
| XXVI-41-4 | $CH_3$ | H | H | $CH_2CH(CH_3)_2$ | Bz | H | F | H | OH |
| XXVI-41-5 | $CH_3$ | H | H | $CH_2Ph$ | Bz | H | F | H | OH |
| XXVI-41-6 | $CH_3$ | H | H | $CH_2$-indol-3-yl | Bz | H | F | H | OH |
| XXVI-41-7 | $CH_3$ | H | H | $CH_2CH_2SCH_3$ | Bz | H | F | H | OH |
| XXVI-41-8 | $CH_3$ | * | H | * | Bz | H | F | H | OH |

*$R^2$ and $R^{3b}$ joined together by $(CH_2)_3$ to form five-membered ring.

TABLE XXVI-42

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-42-1 | Et | H | H | H | Bz | H | F | H | OH |
| XXVI-42-2 | Et | H | H | $CH_3$ | Bz | H | F | H | OH |
| XXVI-42-3 | Et | H | H | $CH(CH_3)_2$ | Bz | H | F | H | OH |
| XXVI-42-4 | Et | H | H | $CH_2CH(CH_3)_2$ | Bz | H | F | H | OH |
| XXVI-42-5 | Et | H | H | $CH_2Ph$ | Bz | H | F | H | OH |
| XXVI-42-6 | Et | H | H | $CH_2$-indol-3-yl | Bz | H | F | H | OH |
| XXVI-42-7 | Et | H | H | $CH_2CH_2SCH_3$ | Bz | H | F | H | OH |
| XXVI-42-8 | Et | * | H | * | Bz | H | F | H | OH |

*$R^2$ and $R^{3b}$ joined together by $(CH_2)_3$ to form five-membered ring.

TABLE XXVI-43

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-43-1 | $^i$Pr | H | H | H | Bz | H | F | H | OH |
| XXVI-43-2 | $^i$Pr | H | H | $CH_3$ | Bz | H | F | H | OH |
| XXVI-43-3 | $^i$Pr | H | H | $CH(CH_3)_2$ | Bz | H | F | H | OH |
| XXVI-43-4 | $^i$Pr | H | H | $CH_2CH(CH_3)_2$ | Bz | H | F | H | OH |
| XXVI-43-5 | $^i$Pr | H | H | $CH_2Ph$ | Bz | H | F | H | OH |
| XXVI-43-6 | $^i$Pr | H | H | $CH_2$-indol-3-yl | Bz | H | F | H | OH |
| XXVI-43-7 | $^i$Pr | H | H | $CH_2CH_2SCH_3$ | Bz | H | F | H | OH |
| XXVI-43-8 | $^i$Pr | * | H | * | Bz | H | F | H | OH |

*$R^2$ and $R^{3b}$ joined together by $(CH_2)_3$ to form five-membered ring.

TABLE XXVI-44

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-44-1 | $^t$Bu | H | H | H | Bz | H | F | H | OH |
| XXVI-44-2 | $^t$Bu | H | H | $CH_3$ | Bz | H | F | H | OH |
| XXVI-44-3 | $^t$Bu | H | H | $CH(CH_3)_2$ | Bz | H | F | H | OH |
| XXVI-44-4 | $^t$Bu | H | H | $CH_2CH(CH_3)_2$ | Bz | H | F | H | OH |
| XXVI-44-5 | $^t$Bu | H | H | $CH_2Ph$ | Bz | H | F | H | OH |
| XXVI-44-6 | $^t$Bu | H | H | $CH_2$-indol-3-yl | Bz | H | F | H | OH |
| XXVI-44-7 | $^t$Bu | H | H | $CH_2CH_2SCH_3$ | Bz | H | F | H | OH |
| XXVI-44-8 | $^t$Bu | * | H | * | Bz | H | F | H | OH |

*$R^2$ and $R^{3b}$ joined together by $(CH_2)_3$ to form five-membered ring.

TABLE XXVI-45

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-45-1 | Ph | H | H | H | Bz | H | F | H | OH |
| XXVI-45-2 | Ph | H | H | $CH_3$ | Bz | H | F | H | OH |
| XXVI-45-3 | Ph | H | H | $CH(CH_3)_2$ | Bz | H | F | H | OH |
| XXVI-45-4 | Ph | H | H | $CH_2CH(CH_3)_2$ | Bz | H | F | H | OH |
| XXVI-45-5 | Ph | H | H | $CH_2Ph$ | Bz | H | F | H | OH |
| XXVI-45-6 | Ph | H | H | $CH_2$-indol-3-yl | Bz | H | F | H | OH |
| XXVI-45-7 | Ph | H | H | $CH_2CH_2SCH_3$ | Bz | H | F | H | OH |
| XXVI-45-8 | Ph | * | H | * | Bz | H | F | H | OH |

*$R^2$ and $R^{3b}$ joined together by $(CH_2)_3$ to form five-membered ring.

TABLE XXVI-46

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-46-1 | p-Me—Ph | H | H | H | Bz | H | F | H | OH |
| XXVI-46-2 | p-Me—Ph | H | H | $CH_3$ | Bz | H | F | H | OH |
| XXVI-46-3 | p-Me—Ph | H | H | $CH(CH_3)_2$ | Bz | H | F | H | OH |
| XXVI-46-4 | p-Me—Ph | H | H | $CH_2CH(CH_3)_2$ | Bz | H | F | H | OH |
| XXVI-46-5 | p-Me—Ph | H | H | $CH_2Ph$ | Bz | H | F | H | OH |
| XXVI-46-6 | p-Me—Ph | H | H | $CH_2$-indol-3-yl | Bz | H | F | H | OH |

TABLE XXVI-46-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-46-7 | p-Me—Ph | H | H | $CH_2CH_2SCH_3$ | Bz | H | F | H | OH |
| XXVI-46-8 | p-Me—Ph | * | H | * | Bz | H | F | H | OH |

*$R^2$ and $R^{3b}$ joined together by $(CH_2)_3$ to form five-membered ring.

TABLE XXVI-47

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-47-1 | p-F—Ph | H | H | H | Bz | H | F | H | OH |
| XXVI-47-2 | p-F—Ph | H | H | $CH_3$ | Bz | H | F | H | OH |
| XXVI-47-3 | p-F—Ph | H | H | $CH(CH_3)_2$ | Bz | H | F | H | OH |
| XXVI-47-4 | p-F—Ph | H | H | $CH_2CH(CH_3)_2$ | Bz | H | F | H | OH |
| XXVI-47-5 | p-F—Ph | H | H | $CH_2Ph$ | Bz | H | F | H | OH |
| XXVI-47-6 | p-F—Ph | H | H | $CH_2$-indol-3-yl | Bz | H | F | H | OH |
| XXVI-47-7 | p-F—Ph | H | H | $CH_2CH_2SCH_3$ | Bz | H | F | H | OH |
| XXVI-47-8 | p-F—Ph | * | H | * | Bz | H | F | H | OH |

*$R^2$ and $R^{3b}$ joined together by $(CH_2)_3$ to form five-membered ring.

TABLE XXVI-48

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-48-1 | p-Cl—Ph | H | H | H | Bz | H | F | H | OH |
| XXVI-48-2 | p-Cl—Ph | H | H | $CH_3$ | Bz | H | F | H | OH |
| XXVI-48-3 | p-Cl—Ph | H | H | $CH(CH_3)_2$ | Bz | H | F | H | OH |
| XXVI-48-4 | p-Cl—Ph | H | H | $CH_2CH(CH_3)_2$ | Bz | H | F | H | OH |
| XXVI-48-5 | p-Cl—Ph | H | H | $CH_2Ph$ | Bz | H | F | H | OH |
| XXVI-48-6 | p-Cl—Ph | H | H | $CH_2$-indol-3-yl | Bz | H | F | H | OH |
| XXVI-48-7 | p-Cl—Ph | H | H | $CH_2CH_2SCH_3$ | Bz | H | F | H | OH |
| XXVI-48-8 | p-Cl—Ph | * | H | * | Bz | H | F | H | OH |

*$R^2$ and $R^{3b}$ joined together by $(CH_2)_3$ to form five-membered ring.

TABLE XXVI-49

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-49-1 | p-Br—Ph | H | H | H | Bz | H | F | H | OH |
| XXVI-49-2 | p-Br—Ph | H | H | $CH_3$ | Bz | H | F | H | OH |
| XXVI-49-3 | p-Br—Ph | H | H | $CH(CH_3)_2$ | Bz | H | F | H | OH |
| XXVI-49-4 | p-Br—Ph | H | H | $CH_2CH(CH_3)_2$ | Bz | H | F | H | OH |
| XXVI-49-5 | p-Br—Ph | H | H | $CH_2Ph$ | Bz | H | F | H | OH |
| XXVI-49-6 | p-Br—Ph | H | H | $CH_2$-indol-3-yl | Bz | H | F | H | OH |
| XXVI-49-7 | p-Br—Ph | H | H | $CH_2CH_2SCH_3$ | Bz | H | F | H | OH |
| XXVI-49-8 | p-Br—Ph | * | H | * | Bz | H | F | H | OH |

*$R^2$ and $R^{3b}$ joined together by $(CH_2)_3$ to form five-membered ring.

TABLE XXVI-50

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVI-50-1 | p-I—Ph | H | H | H | Bz | H | F | H | OH |
| XXVI-50-2 | p-I—Ph | H | H | $CH_3$ | Bz | H | F | H | OH |
| XXVI-50-3 | p-I—Ph | H | H | $CH(CH_3)_2$ | Bz | H | F | H | OH |
| XXVI-50-4 | p-I—Ph | H | H | $CH_2CH(CH_3)_2$ | Bz | H | F | H | OH |
| XXVI-50-5 | p-I—Ph | H | H | $CH_2Ph$ | Bz | H | F | H | OH |
| XXVI-50-6 | p-I—Ph | H | H | $CH_2$-indol-3-yl | Bz | H | F | H | OH |
| XXVI-50-7 | p-I—Ph | H | H | $CH_2CH_2SCH_3$ | Bz | H | F | H | OH |
| XXVI-50-8 | p-I—Ph | * | H | * | Bz | H | F | H | OH |

*$R^2$ and $R^{3b}$ joined together by $(CH_2)_3$ to form five-membered ring.

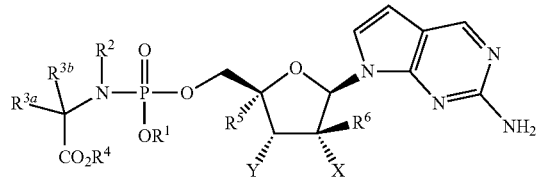

XXVII

TABLE XXVII-1

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-1-1 | $CH_3$ | H | H | H | $CH_3$ | H | F | F | OH |
| XXVII-1-2 | $CH_3$ | H | H | $CH_3$ | $CH_3$ | H | F | F | OH |
| XXVII-1-3 | $CH_3$ | H | H | $CH(CH_3)_2$ | $CH_3$ | H | F | F | OH |
| XXVII-1-4 | $CH_3$ | H | H | $CH_2CH(CH_3)_2$ | $CH_3$ | H | F | F | OH |
| XXVII-1-5 | $CH_3$ | H | H | $CH_2Ph$ | $CH_3$ | H | F | F | OH |
| XXVII-1-6 | $CH_3$ | H | H | $CH_2$-indol-3-yl | $CH_3$ | H | F | F | OH |
| XXVII-1-7 | $CH_3$ | H | H | $CH_2CH_2SCH_3$ | $CH_3$ | H | F | F | OH |
| XXVII-1-8 | $CH_3$ | * | H | * | $CH_3$ | H | F | F | OH |

*$R^2$ and $R^{3b}$ joined together by $(CH_2)_3$ to form five-membered ring.

TABLE XXVII-2

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-2-1 | Et | H | H | H | $CH_3$ | H | F | F | OH |
| XXVII-2-2 | Et | H | H | $CH_3$ | $CH_3$ | H | F | F | OH |
| XXVII-2-3 | Et | H | H | $CH(CH_3)_2$ | $CH_3$ | H | F | F | OH |
| XXVII-2-4 | Et | H | H | $CH_2CH(CH_3)_2$ | $CH_3$ | H | F | F | OH |
| XXVII-2-5 | Et | H | H | $CH_2Ph$ | $CH_3$ | H | F | F | OH |
| XXVII-2-6 | Et | H | H | $CH_2$-indol-3-yl | $CH_3$ | H | F | F | OH |
| XXVII-2-7 | Et | H | H | $CH_2CH_2SCH_3$ | $CH_3$ | H | F | F | OH |
| XXVII-2-8 | Et | * | H | * | $CH_3$ | H | F | F | OH |

*$R^2$ and $R^{3b}$ joined together by $(CH_2)_3$ to form five-membered ring.

TABLE XXVII-3

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-3-1 | $^iPr$ | H | H | H | $CH_3$ | H | F | F | OH |
| XXVII-3-2 | $^iPr$ | H | H | $CH_3$ | $CH_3$ | H | F | F | OH |
| XXVII-3-3 | $^iPr$ | H | H | $CH(CH_3)_2$ | $CH_3$ | H | F | F | OH |
| XXVII-3-4 | $^iPr$ | H | H | $CH_2CH(CH_3)_2$ | $CH_3$ | H | F | F | OH |
| XXVII-3-5 | $^iPr$ | H | H | $CH_2Ph$ | $CH_3$ | H | F | F | OH |
| XXVII-3-6 | $^iPr$ | H | H | $CH_2$-indol-3-yl | $CH_3$ | H | F | F | OH |
| XXVII-3-7 | $^iPr$ | H | H | $CH_2CH_2SCH_3$ | $CH_3$ | H | F | F | OH |
| XXVII-3-8 | $^iPr$ | * | H | * | $CH_3$ | H | F | F | OH |

*$R^2$ and $R^{3b}$ joined together by $(CH_2)_3$ to form five-membered ring.

TABLE XXVII-4

| No | R¹ | R² | R³ᵃ | R³ᵇ | R⁴ | R⁵ | R⁶ | X | Y |
|---|---|---|---|---|---|---|---|---|---|
| XXVII-4-1 | ᵗBu | H | H | H | CH₃ | H | F | F | OH |
| XXVII-4-2 | ᵗBu | H | H | CH₃ | CH₃ | H | F | F | OH |
| XXVII-4-3 | ᵗBu | H | H | CH(CH₃)₂ | CH₃ | H | F | F | OH |
| XXVII-4-4 | ᵗBu | H | H | CH₂CH(CH₃)₂ | CH₃ | H | F | F | OH |
| XXVII-4-5 | ᵗBu | H | H | CH₂Ph | CH₃ | H | F | F | OH |
| XXVII-4-6 | ᵗBu | H | H | CH₂-indol-3-yl | CH₃ | H | F | F | OH |
| XXVII-4-7 | ᵗBu | H | H | CH₂CH₂SCH₃ | CH₃ | H | F | F | OH |
| XXVII-4-8 | ᵗBu | * | H | * | CH₃ | H | F | F | OH |

*R² and R³ᵇ joined together by (CH₂)₃ to form five-membered ring.

TABLE XXVII-5

| No | R¹ | R² | R³ᵃ | R³ᵇ | R⁴ | R⁵ | R⁶ | X | Y |
|---|---|---|---|---|---|---|---|---|---|
| XXVII-5-1 | Ph | H | H | H | CH₃ | H | F | F | OH |
| XXVII-5-2 | Ph | H | H | CH₃ | CH₃ | H | F | F | OH |
| XXVII-5-3 | Ph | H | H | CH(CH₃)₂ | CH₃ | H | F | F | OH |
| XXVII-5-4 | Ph | H | H | CH₂CH(CH₃)₂ | CH₃ | H | F | F | OH |
| XXVII-5-5 | Ph | H | H | CH₂Ph | CH₃ | H | F | F | OH |
| XXVII-5-6 | Ph | H | H | CH₂-indol-3-yl | CH₃ | H | F | F | OH |
| XXVII-5-7 | Ph | H | H | CH₂CH₂SCH₃ | CH₃ | H | F | F | OH |
| XXVII-5-8 | Ph | * | H | * | CH₃ | H | F | F | OH |

*R² and R³ᵇ joined together by (CH₂)₃ to form five-membered ring.

TABLE XXVII-6

| No | R¹ | R² | R³ᵃ | R³ᵇ | R⁴ | R⁵ | R⁶ | X | Y |
|---|---|---|---|---|---|---|---|---|---|
| XXVII-6-1 | p-Me—Ph | H | H | H | CH₃ | H | F | F | OH |
| XXVII-6-2 | p-Me—Ph | H | H | CH₃ | CH₃ | H | F | F | OH |
| XXVII-6-3 | p-Me—Ph | H | H | CH(CH₃)₂ | CH₃ | H | F | F | OH |
| XXVII-6-4 | p-Me—Ph | H | H | CH₂CH(CH₃)₂ | CH₃ | H | F | F | OH |
| XXVII-6-5 | p-Me—Ph | H | H | CH₂Ph | CH₃ | H | F | F | OH |
| XXVII-6-6 | p-Me—Ph | H | H | CH₂-indol-3-yl | CH₃ | H | F | F | OH |
| XXVII-6-7 | p-Me—Ph | H | H | CH₂CH₂SCH₃ | CH₃ | H | F | F | OH |
| XXVII-6-8 | p-Me—Ph | * | H | * | CH₃ | H | F | F | OH |

*R² and R³ᵇ joined together by (CH₂)₃ to form five-membered ring.

TABLE XXVII-7

| No | R¹ | R² | R³ᵃ | R³ᵇ | R⁴ | R⁵ | R⁶ | X | Y |
|---|---|---|---|---|---|---|---|---|---|
| XXVII-7-1 | p-F—Ph | H | H | H | CH₃ | H | F | F | OH |
| XXVII-7-2 | p-F—Ph | H | H | CH₃ | CH₃ | H | F | F | OH |
| XXVII-7-3 | p-F—Ph | H | H | CH(CH₃)₂ | CH₃ | H | F | F | OH |
| XXVII-7-4 | p-F—Ph | H | H | CH₂CH(CH₃)₂ | CH₃ | H | F | F | OH |
| XXVII-7-5 | p-F—Ph | H | H | CH₂Ph | CH₃ | H | F | F | OH |
| XXVII-7-6 | p-F—Ph | H | H | CH₂-indol-3-yl | CH₃ | H | F | F | OH |
| XXVII-7-7 | p-F—Ph | H | H | CH₂CH₂SCH₃ | CH₃ | H | F | F | OH |
| XXVII-7-8 | p-F—Ph | * | H | * | CH₃ | H | F | F | OH |

*R² and R³ᵇ joined together by (CH₂)₃ to form five-membered ring.

TABLE XXVII-8

| No | R¹ | R² | R³ᵃ | R³ᵇ | R⁴ | R⁵ | R⁶ | X | Y |
|---|---|---|---|---|---|---|---|---|---|
| XXVII-8-1 | p-Cl—Ph | H | H | H | CH₃ | H | F | F | OH |
| XXVII-8-2 | p-Cl—Ph | H | H | CH₃ | CH₃ | H | F | F | OH |
| XXVII-8-3 | p-Cl—Ph | H | H | CH(CH₃)₂ | CH₃ | H | F | F | OH |
| XXVII-8-4 | p-Cl—Ph | H | H | CH₂CH(CH₃)₂ | CH₃ | H | F | F | OH |
| XXVII-8-5 | p-Cl—Ph | H | H | CH₂Ph | CH₃ | H | F | F | OH |
| XXVII-8-6 | p-Cl—Ph | H | H | CH₂-indol-3-yl | CH₃ | H | F | F | OH |
| XXVII-8-7 | p-Cl—Ph | H | H | CH₂CH₂SCH₃ | CH₃ | H | F | F | OH |
| XXVII-8-8 | p-Cl—Ph | * | H | * | CH₃ | H | F | F | OH |

*R² and R³ᵇ joined together by (CH₂)₃ to form five-membered ring.

TABLE XXVII-9

| No | R¹ | R² | R³ᵃ | R³ᵇ | R⁴ | R⁵ | R⁶ | X | Y |
|---|---|---|---|---|---|---|---|---|---|
| XXVII-9-1 | p-Br—Ph | H | H | H | CH₃ | H | F | F | OH |
| XXVII-9-2 | p-Br—Ph | H | H | CH₃ | CH₃ | H | F | F | OH |
| XXVII-9-3 | p-Br—Ph | H | H | CH(CH₃)₂ | CH₃ | H | F | F | OH |
| XXVII-9-4 | p-Br—Ph | H | H | CH₂CH(CH₃)₂ | CH₃ | H | F | F | OH |
| XXVII-9-5 | p-Br—Ph | H | H | CH₂Ph | CH₃ | H | F | F | OH |
| XXVII-9-6 | p-Br—Ph | H | H | CH₂-indol-3-yl | CH₃ | H | F | F | OH |
| XXVII-9-7 | p-Br—Ph | H | H | CH₂CH₂SCH₃ | CH₃ | H | F | F | OH |
| XXVII-9-8 | p-Br—Ph | * | H | * | CH₃ | H | F | F | OH |

*R² and R³ᵇ joined together by (CH₂)₃ to form five-membered ring.

TABLE XXVII-10

| No | R¹ | R² | R³ᵃ | R³ᵇ | R⁴ | R⁵ | R⁶ | X | Y |
|---|---|---|---|---|---|---|---|---|---|
| XXVII-10-1 | p-I—Ph | H | H | H | CH₃ | H | F | F | OH |
| XXVII-10-2 | p-I—Ph | H | H | CH₃ | CH₃ | H | F | F | OH |
| XXVII-10-3 | p-I—Ph | H | H | CH(CH₃)₂ | CH₃ | H | F | F | OH |
| XXVII-10-4 | p-I—Ph | H | H | CH₂CH(CH₃)₂ | CH₃ | H | F | F | OH |
| XXVII-10-5 | p-I—Ph | H | H | CH₂Ph | CH₃ | H | F | F | OH |
| XXVII-10-6 | p-I—Ph | H | H | CH₂-indol-3-yl | CH₃ | H | F | F | OH |
| XXVII-10-7 | p-I—Ph | H | H | CH₂CH₂SCH₃ | CH₃ | H | F | F | OH |
| XXVII-10-8 | p-I—Ph | * | H | * | CH₃ | H | F | F | OH |

*R² and R³ᵇ joined together by (CH₂)₃ to form five-membered ring.

TABLE XXVII-11

| No | R¹ | R² | R³ᵃ | R³ᵇ | R⁴ | R⁵ | R⁶ | X | Y |
|---|---|---|---|---|---|---|---|---|---|
| XXVII-11-1 | CH₃ | H | H | H | Et | H | F | F | OH |
| XXVII-11-2 | CH₃ | H | H | CH₃ | Et | H | F | F | OH |
| XXVII-11-3 | CH₃ | H | H | CH(CH₃)₂ | Et | H | F | F | OH |
| XXVII-11-4 | CH₃ | H | H | CH₂CH(CH₃)₂ | Et | H | F | F | OH |
| XXVII-11-5 | CH₃ | H | H | CH₂Ph | Et | H | F | F | OH |

TABLE XXVII-11-continued

| No | R¹ | R² | R³ᵃ | R³ᵇ | R⁴ | R⁵ | R⁶ | X | Y |
|---|---|---|---|---|---|---|---|---|---|
| XXVII-11-6 | CH₃ | H | H | CH₂-indol-3-yl | Et | H | F | F | OH |
| XXVII-11-7 | CH₃ | H | H | CH₂CH₂SCH₃ | Et | H | F | F | OH |
| XXVII-11-8 | CH₃ | * | H | * | Et | H | F | F | OH |

*R² and R³ᵇ joined together by (CH₂)₃ to form five-membered ring.

TABLE XXVII-12

| No | R¹ | R² | R³ᵃ | R³ᵇ | R⁴ | R⁵ | R⁶ | X | Y |
|---|---|---|---|---|---|---|---|---|---|
| XXVII-12-1 | Et | H | H | H | Et | H | F | F | OH |
| XXVII-12-2 | Et | H | H | CH₃ | Et | H | F | F | OH |
| XXVII-12-3 | Et | H | H | CH(CH₃)₂ | Et | H | F | F | OH |
| XXVII-12-4 | Et | H | H | CH₂CH(CH₃)₂ | Et | H | F | F | OH |
| XXVII-12-5 | Et | H | H | CH₂Ph | Et | H | F | F | OH |
| XXVII-12-6 | Et | H | H | CH₂-indol-3-yl | Et | H | F | F | OH |
| XXVII-12-7 | Et | H | H | CH₂CH₂SCH₃ | Et | H | F | F | OH |
| XXVII-12-8 | Et | * | H | * | Et | H | F | F | OH |

*R² and R³ᵇ joined together by (CH₂)₃ to form five-membered ring.

TABLE XXVII-13

| No | R¹ | R² | R³ᵃ | R³ᵇ | R⁴ | R⁵ | R⁶ | X | Y |
|---|---|---|---|---|---|---|---|---|---|
| XXVII-13-1 | ⁱPr | H | H | H | Et | H | F | F | OH |
| XXVII-13-2 | ⁱPr | H | H | CH₃ | Et | H | F | F | OH |
| XXVII-13-3 | ⁱPr | H | H | CH(CH₃)₂ | Et | H | F | F | OH |
| XXVII-13-4 | ⁱPr | H | H | CH₂CH(CH₃)₂ | Et | H | F | F | OH |
| XXVII-13-5 | ⁱPr | H | H | CH₂Ph | Et | H | F | F | OH |
| XXVII-13-6 | ⁱPr | H | H | CH₂-indol-3-yl | Et | H | F | F | OH |
| XXVII-13-7 | ⁱPr | H | H | CH₂CH₂SCH₃ | Et | H | F | F | OH |
| XXVII-13-8 | ⁱPr | * | H | * | Et | H | F | F | OH |

*R² and R³ᵇ joined together by (CH₂)₃ to form five-membered ring.

TABLE XXVII-14

| No | R¹ | R² | R³ᵃ | R³ᵇ | R⁴ | R⁵ | R⁶ | X | Y |
|---|---|---|---|---|---|---|---|---|---|
| XXVII-14-1 | ᵗBu | H | H | H | Et | H | F | F | OH |
| XXVII-14-2 | ᵗBu | H | H | CH₃ | Et | H | F | F | OH |
| XXVII-14-3 | ᵗBu | H | H | CH(CH₃)₂ | Et | H | F | F | OH |
| XXVII-14-4 | ᵗBu | H | H | CH₂CH(CH₃)₂ | Et | H | F | F | OH |
| XXVII-14-5 | ᵗBu | H | H | CH₂Ph | Et | H | F | F | OH |
| XXVII-14-6 | ᵗBu | H | H | CH₂-indol-3-yl | Et | H | F | F | OH |
| XXVII-14-7 | ᵗBu | H | H | CH₂CH₂SCH₃ | Et | H | F | F | OH |
| XXVII-14-8 | ᵗBu | * | H | * | Et | H | F | F | OH |

*R² and R³ᵇ joined together by (CH₂)₃ to form five-membered ring.

TABLE XXVII-15

| No | R¹ | R² | R³ᵃ | R³ᵇ | R⁴ | R⁵ | R⁶ | X | Y |
|---|---|---|---|---|---|---|---|---|---|
| XXVII-15-1 | Ph | H | H | H | Et | H | F | F | OH |
| XXVII-15-2 | Ph | H | H | CH₃ | Et | H | F | F | OH |
| XXVII-15-3 | Ph | H | H | CH(CH₃)₂ | Et | H | F | F | OH |
| XXVII-15-4 | Ph | H | H | CH₂CH(CH₃)₂ | Et | H | F | F | OH |
| XXVII-15-5 | Ph | H | H | CH₂Ph | Et | H | F | F | OH |
| XXVII-15-6 | Ph | H | H | CH₂-indol-3-yl | Et | H | F | F | OH |
| XXVII-15-7 | Ph | H | H | CH₂CH₂SCH₃ | Et | H | F | F | OH |
| XXVII-2-8 | Ph | * | H | * | Et | H | F | F | OH |

*R² and R³ᵇ joined together by (CH₂)₃ to form five-membered ring.

TABLE XXVII-16

| No | R¹ | R² | R³ᵃ | R³ᵇ | R⁴ | R⁵ | R⁶ | X | Y |
|---|---|---|---|---|---|---|---|---|---|
| XXVII-16-1 | p-Me—Ph | H | H | H | Et | H | F | F | OH |
| XXVII-16-2 | p-Me—Ph | H | H | CH₃ | Et | H | F | F | OH |
| XXVII-16-3 | p-Me—Ph | H | H | CH(CH₃)₂ | Et | H | F | F | OH |
| XXVII-16-4 | p-Me—Ph | H | H | CH₂CH(CH₃)₂ | Et | H | F | F | OH |
| XXVII-16-5 | p-Me—Ph | H | H | CH₂Ph | Et | H | F | F | OH |
| XXVII-16-6 | p-Me—Ph | H | H | CH₂-indol-3-yl | Et | H | F | F | OH |
| XXVII-16-7 | p-Me—Ph | H | H | CH₂CH₂SCH₃ | Et | H | F | F | OH |
| XXVII-16-8 | p-Me—Ph | * | H | * | Et | H | F | F | OH |

*R² and R³ᵇ joined together by (CH₂)₃ to form five-membered ring.

TABLE XXVII-17

| No | R¹ | R² | R³ᵃ | R³ᵇ | R⁴ | R⁵ | R⁶ | X | Y |
|---|---|---|---|---|---|---|---|---|---|
| XXVII-17-1 | p-F—Ph | H | H | H | Et | H | F | F | OH |
| XXVII-17-2 | p-F—Ph | H | H | CH₃ | Et | H | F | F | OH |
| XXVII-17-3 | p-F—Ph | H | H | CH(CH₃)₂ | Et | H | F | F | OH |
| XXVII-17-4 | p-F—Ph | H | H | CH₂CH(CH₃)₂ | Et | H | F | F | OH |
| XXVII-17-5 | p-F—Ph | H | H | CH₂Ph | Et | H | F | F | OH |
| XXVII-17-6 | p-F—Ph | H | H | CH₂-indol-3-yl | Et | H | F | F | OH |
| XXVII-17-7 | p-F—Ph | H | H | CH₂CH₂SCH₃ | Et | H | F | F | OH |
| XXVII-17-8 | p-F—Ph | * | H | * | Et | H | F | F | OH |

*R² and R³ᵇ joined together by (CH₂)₃ to form five-membered ring.

TABLE XXVII-18

| No | R¹ | R² | R³ᵃ | R³ᵇ | R⁴ | R⁵ | R⁶ | X | Y |
|---|---|---|---|---|---|---|---|---|---|
| XXVII-18-1 | p-Cl—Ph | H | H | H | Et | H | F | F | OH |
| XXVII-18-2 | p-Cl—Ph | H | H | CH₃ | Et | H | F | F | OH |
| XXVII-18-3 | p-Cl—Ph | H | H | CH(CH₃)₂ | Et | H | F | F | OH |
| XXVII-18-4 | p-Cl—Ph | H | H | CH₂CH(CH₃)₂ | Et | H | F | F | OH |
| XXVII-18-5 | p-Cl—Ph | H | H | CH₂Ph | Et | H | F | F | OH |
| XXVII-18-6 | p-Cl—Ph | H | H | CH₂-indol-3-yl | Et | H | F | F | OH |
| XXVII-18-7 | p-Cl—Ph | H | H | CH₂CH₂SCH₃ | Et | H | F | F | OH |
| XXVII-18-8 | p-Cl—Ph | * | H | * | Et | H | F | F | OH |

*R² and R³ᵇ joined together by (CH₂)₃ to form five-membered ring.

TABLE XXVII-19

| No | R¹ | R² | R³ᵃ | R³ᵇ | R⁴ | R⁵ | R⁶ | X | Y |
|---|---|---|---|---|---|---|---|---|---|
| XXVII-19-1 | p-Br—Ph | H | H | H | Et | H | F | F | OH |
| XXVII-19-2 | p-Br—Ph | H | H | CH₃ | Et | H | F | F | OH |
| XXVII-19-3 | p-Br—Ph | H | H | CH(CH₃)₂ | Et | H | F | F | OH |

TABLE XXVII-19-continued

| No | R¹ | R² | R³ᵃ | R³ᵇ | R⁴ | R⁵ | R⁶ | X | Y |
|---|---|---|---|---|---|---|---|---|---|
| XXVII-19-4 | p-Br—Ph | H | H | CH₂CH(CH₃)₂ | Et | H | F | F | OH |
| XXVII-19-5 | p-Br—Ph | H | H | CH₂Ph | Et | H | F | F | OH |
| XXVII-19-6 | p-Br—Ph | H | H | CH₂-indol-3-yl | Et | H | F | F | OH |
| XXVII-19-7 | p-Br—Ph | H | H | CH₂CH₂SCH₃ | Et | H | F | F | OH |
| XXVII-19-8 | p-Br—Ph | * | H | * | Et | H | F | F | OH |

*R² and R³ᵇ joined together by (CH₂)₃ to form five-membered ring.

TABLE XXVII-20

| No | R¹ | R² | R³ᵃ | R³ᵇ | R⁴ | R⁵ | R⁶ | X | Y |
|---|---|---|---|---|---|---|---|---|---|
| XXVII-20-1 | p-I—Ph | H | H | H | Et | H | F | F | OH |
| XXVII-20-2 | p-I—Ph | H | H | CH₃ | Et | H | F | F | OH |
| XXVII-20-3 | p-I—Ph | H | H | CH(CH₃)₂ | Et | H | F | F | OH |
| XXVII-20-4 | p-I—Ph | H | H | CH₂CH(CH₃)₂ | Et | H | F | F | OH |
| XXVII-20-5 | p-I—Ph | H | H | CH₂Ph | Et | H | F | F | OH |
| XXVII-20-6 | p-I—Ph | H | H | CH₂-indol-3-yl | Et | H | F | F | OH |
| XXVII-20-7 | p-I—Ph | H | H | CH₂CH₂SCH₃ | Et | H | F | F | OH |
| XXVII-20-8 | p-I—Ph | * | H | * | Et | H | F | F | OH |

*R² and R³ᵇ joined together by (CH₂)₃ to form five-membered ring.

TABLE XXVII-21

| No | R¹ | R² | R³ᵃ | R³ᵇ | R⁴ | R⁵ | R⁶ | X | Y |
|---|---|---|---|---|---|---|---|---|---|
| XXVII-21-1 | CH₃ | H | H | H | ⁱPr | H | F | F | OH |
| XXVII-21-2 | CH₃ | H | H | CH₃ | ⁱPr | H | F | F | OH |
| XXVII-21-3 | CH₃ | H | H | CH(CH₃)₂ | ⁱPr | H | F | F | OH |
| XXVII-21-4 | CH₃ | H | H | CH₂CH(CH₃)₂ | ⁱPr | H | F | F | OH |
| XXVII-21-5 | CH₃ | H | H | CH₂Ph | ⁱPr | H | F | F | OH |
| XXVII-21-6 | CH₃ | H | H | CH₂-indol-3-yl | ⁱPr | H | F | F | OH |
| XXVII-21-7 | CH₃ | H | H | CH₂CH₂SCH₃ | ⁱPr | H | F | F | OH |
| XXVII-21-8 | CH₃ | * | H | * | ⁱPr | H | F | F | OH |

*R² and R³ᵇ joined together by (CH₂)₃ to form five-membered ring.

TABLE XXVII-22

| No | R¹ | R² | R³ᵃ | R³ᵇ | R⁴ | R⁵ | R⁶ | X | Y |
|---|---|---|---|---|---|---|---|---|---|
| XXVII-22-1 | Et | H | H | H | ⁱPr | H | F | F | OH |
| XXVII-22-2 | Et | H | H | CH₃ | ⁱPr | H | F | F | OH |
| XXVII-22-3 | Et | H | H | CH(CH₃)₂ | ⁱPr | H | F | F | OH |
| XXVII-22-4 | Et | H | H | CH₂CH(CH₃)₂ | ⁱPr | H | F | F | OH |
| XXVII-22-5 | Et | H | H | CH₂Ph | ⁱPr | H | F | F | OH |
| XXVII-22-6 | Et | H | H | CH₂-indol-3-yl | ⁱPr | H | F | F | OH |
| XXVII-22-7 | Et | H | H | CH₂CH₂SCH₃ | ⁱPr | H | F | F | OH |
| XXVII-22-8 | Et | * | H | * | ⁱPr | H | F | F | OH |

*R² and R³ᵇ joined together by (CH₂)₃ to form five-membered ring.

TABLE XXVII-23

| No | R¹ | R² | R³ᵃ | R³ᵇ | R⁴ | R⁵ | R⁶ | X | Y |
|---|---|---|---|---|---|---|---|---|---|
| XXVII-23-1 | ⁱPr | H | H | H | ⁱPr | H | F | F | OH |
| XXVII-23-2 | ⁱPr | H | H | CH₃ | ⁱPr | H | F | F | OH |
| XXVII-23-3 | ⁱPr | H | H | CH(CH₃)₂ | ⁱPr | H | F | F | OH |
| XXVII-23-4 | ⁱPr | H | H | CH₂CH(CH₃)₂ | ⁱPr | H | F | F | OH |
| XXVII-23-5 | ⁱPr | H | H | CH₂Ph | ⁱPr | H | F | F | OH |
| XXVII-23-6 | ⁱPr | H | H | CH₂-indol-3-yl | ⁱPr | H | F | F | OH |
| XXVII-23-7 | ⁱPr | H | H | CH₂CH₂SCH₃ | ⁱPr | H | F | F | OH |
| XXVII-23-8 | ⁱPr | * | H | * | ⁱPr | H | F | F | OH |

*R² and R³ᵇ joined together by (CH₂)₃ to form five-membered ring.

TABLE XXVII-24

| No | R¹ | R² | R³ᵃ | R³ᵇ | R⁴ | R⁵ | R⁶ | X | Y |
|---|---|---|---|---|---|---|---|---|---|
| XXVII-24-1 | ᵗBu | H | H | H | ⁱPr | H | F | F | OH |
| XXVII-24-2 | ᵗBu | H | H | CH₃ | ⁱPr | H | F | F | OH |
| XXVII-24-3 | ᵗBu | H | H | CH(CH₃)₂ | ⁱPr | H | F | F | OH |
| XXVII-24-4 | ᵗBu | H | H | CH₂CH(CH₃)₂ | ⁱPr | H | F | F | OH |
| XXVII-24-5 | ᵗBu | H | H | CH₂Ph | ⁱPr | H | F | F | OH |
| XXVII-24-6 | ᵗBu | H | H | CH₂-indol-3-yl | ⁱPr | H | F | F | OH |
| XXVII-24-7 | ᵗBu | H | H | CH₂CH₂SCH₃ | ⁱPr | H | F | F | OH |
| XXVII-24-8 | ᵗBu | * | H | * | ⁱPr | H | F | F | OH |

*R² and R³ᵇ joined together by (CH₂)₃ to form five-membered ring.

TABLE XXVII-25

| No | R¹ | R² | R³ᵃ | R³ᵇ | R⁴ | R⁵ | R⁶ | X | Y |
|---|---|---|---|---|---|---|---|---|---|
| XXVII-25-1 | Ph | H | H | H | ⁱPr | H | F | F | OH |
| XXVII-25-2 | Ph | H | H | CH₃ | ⁱPr | H | F | F | OH |
| XXVII-25-3 | Ph | H | H | CH(CH₃)₂ | ⁱPr | H | F | F | OH |
| XXVII-25-4 | Ph | H | H | CH₂CH(CH₃)₂ | ⁱPr | H | F | F | OH |
| XXVII-25-5 | Ph | H | H | CH₂Ph | ⁱPr | H | F | F | OH |
| XXVII-25-6 | Ph | H | H | CH₂-indol-3-yl | ⁱPr | H | F | F | OH |
| XXVII-25-7 | Ph | H | H | CH₂CH₂SCH₃ | ⁱPr | H | F | F | OH |
| XXVII-25-8 | Ph | * | H | * | ⁱPr | H | F | F | OH |

*R² and R³ᵇ joined together by (CH₂)₃ to form five-membered ring.

TABLE XXVII-26

| No | R¹ | R² | R³ᵃ | R³ᵇ | R⁴ | R⁵ | R⁶ | X | Y |
|---|---|---|---|---|---|---|---|---|---|
| XXVII-26-1 | p-Me—Ph | H | H | H | $^i$Pr | H | F | F | OH |
| XXVII-26-2 | p-Me—Ph | H | H | CH₃ | $^i$Pr | H | F | F | OH |
| XXVII-26-3 | p-Me—Ph | H | H | CH(CH₃)₂ | $^i$Pr | H | F | F | OH |
| XXVII-26-4 | p-Me—Ph | H | H | CH₂CH(CH₃)₂ | $^i$Pr | H | F | F | OH |
| XXVII-26-5 | p-Me—Ph | H | H | CH₂Ph | $^i$Pr | H | F | F | OH |
| XXVII-26-6 | p-Me—Ph | H | H | CH₂-indol-3-yl | $^i$Pr | H | F | F | OH |
| XXVII-26-7 | p-Me—Ph | H | H | CH₂CH₂SCH₃ | $^i$Pr | H | F | F | OH |
| XXVII-26-8 | p-Me—Ph | * | H | * | $^i$Pr | H | F | F | OH |

*R² and R³ᵇ joined together by (CH₂)₃ to form five-membered ring.

TABLE XXVII-27

| No | R¹ | R² | R³ᵃ | R³ᵇ | R⁴ | R⁵ | R⁶ | X | Y |
|---|---|---|---|---|---|---|---|---|---|
| XXVII-27-1 | p-F—Ph | H | H | H | $^i$Pr | H | F | F | OH |
| XXVII-27-2 | p-F—Ph | H | H | CH₃ | $^i$Pr | H | F | F | OH |
| XXVII-27-3 | p-F—Ph | H | H | CH(CH₃)₂ | $^i$Pr | H | F | F | OH |
| XXVII-27-4 | p-F—Ph | H | H | CH₂CH(CH₃)₂ | $^i$Pr | H | F | F | OH |
| XXVII-27-5 | p-F—Ph | H | H | CH₂Ph | $^i$Pr | H | F | F | OH |
| XXVII-27-6 | p-F—Ph | H | H | CH₂-indol-3-yl | $^i$Pr | H | F | F | OH |
| XXVII-27-7 | p-F—Ph | H | H | CH₂CH₂SCH₃ | $^i$Pr | H | F | F | OH |
| XXVII-27-8 | p-F—Ph | * | H | * | $^i$Pr | H | F | F | OH |

*R² and R³ᵇ joined together by (CH₂)₃ to form five-membered ring.

TABLE XXVII-28

| No | R¹ | R² | R³ᵃ | R³ᵇ | R⁴ | R⁵ | R⁶ | X | Y |
|---|---|---|---|---|---|---|---|---|---|
| XXVII-28-1 | p-Cl—Ph | H | H | H | $^i$Pr | H | F | F | OH |
| XXVII-28-2 | p-Cl—Ph | H | H | CH₃ | $^i$Pr | H | F | F | OH |
| XXVII-28-3 | p-Cl—Ph | H | H | CH(CH₃)₂ | $^i$Pr | H | F | F | OH |
| XXVII-28-4 | p-Cl—Ph | H | H | CH₂CH(CH₃)₂ | $^i$Pr | H | F | F | OH |
| XXVII-28-5 | p-Cl—Ph | H | H | CH₂Ph | $^i$Pr | H | F | F | OH |
| XXVII-28-6 | p-Cl—Ph | H | H | CH₂-indol-3-yl | $^i$Pr | H | F | F | OH |
| XXVII-28-7 | p-Cl—Ph | H | H | CH₂CH₂SCH₃ | $^i$Pr | H | F | F | OH |
| XXVII-28-8 | p-Cl—Ph | * | H | * | $^i$Pr | H | F | F | OH |

*R² and R³ᵇ joined together by (CH₂)₃ to form five-membered ring.

TABLE XXVII-29

| No | R¹ | R² | R³ᵃ | R³ᵇ | R⁴ | R⁵ | R⁶ | X | Y |
|---|---|---|---|---|---|---|---|---|---|
| XXVII-29-1 | p-Br—Ph | H | H | H | $^i$Pr | H | F | F | OH |
| XXVII-29-2 | p-Br—Ph | H | H | CH₃ | $^i$Pr | H | F | F | OH |
| XXVII-29-3 | p-Br—Ph | H | H | CH(CH₃)₂ | $^i$Pr | H | F | F | OH |
| XXVII-29-4 | p-Br—Ph | H | H | CH₂CH(CH₃)₂ | $^i$Pr | H | F | F | OH |
| XXVII-29-5 | p-Br—Ph | H | H | CH₂Ph | $^i$Pr | H | F | F | OH |
| XXVII-29-6 | p-Br—Ph | H | H | CH₂-indol-3-yl | $^i$Pr | H | F | F | OH |
| XXVII-29-7 | p-Br—Ph | H | H | CH₂CH₂SCH₃ | $^i$Pr | H | F | F | OH |
| XXVII-29-8 | p-Br—Ph | * | H | * | $^i$Pr | H | F | F | OH |

*R² and R³ᵇ joined together by (CH₂)₃ to form five-membered ring.

TABLE XXVII-30

| No | R¹ | R² | R³ᵃ | R³ᵇ | R⁴ | R⁵ | R⁶ | X | Y |
|---|---|---|---|---|---|---|---|---|---|
| XXVII-30-1 | p-I—Ph | H | H | H | $^i$Pr | H | F | F | OH |
| XXVII-30-2 | p-I—Ph | H | H | CH₃ | $^i$Pr | H | F | F | OH |
| XXVII-30-3 | p-I—Ph | H | H | CH(CH₃)₂ | $^i$Pr | H | F | F | OH |
| XXVII-30-4 | p-I—Ph | H | H | CH₂CH(CH₃)₂ | $^i$Pr | H | F | F | OH |
| XXVII-30-5 | p-I—Ph | H | H | CH₂Ph | $^i$Pr | H | F | F | OH |
| XXVII-30-6 | p-I—Ph | H | H | CH₂-indol-3-yl | $^i$Pr | H | F | F | OH |
| XXVII-30-7 | p-I—Ph | H | H | CH₂CH₂SCH₃ | $^i$Pr | H | F | F | OH |
| XXVII-30-8 | p-I—Ph | * | H | * | $^i$Pr | H | F | F | OH |

*R² and R³ᵇ joined together by (CH₂)₃ to form five-membered ring.

TABLE XXVII-31

| No | R¹ | R² | R³ᵃ | R³ᵇ | R⁴ | R⁵ | R⁶ | X | Y |
|---|---|---|---|---|---|---|---|---|---|
| XXVII-31-1 | CH₃ | H | H | H | $^n$Bu | H | F | F | OH |
| XXVII-31-2 | CH₃ | H | H | CH₃ | $^n$Bu | H | F | F | OH |
| XXVII-31-3 | CH₃ | H | H | CH(CH₃)₂ | $^n$Bu | H | F | F | OH |
| XXVII-31-4 | CH₃ | H | H | CH₂CH(CH₃)₂ | $^n$Bu | H | F | F | OH |
| XXVII-31-5 | CH₃ | H | H | CH₂Ph | $^n$Bu | H | F | F | OH |
| XXVII-31-6 | CH₃ | H | H | CH₂-indol-3-yl | $^n$Bu | H | F | F | OH |
| XXVII-31-7 | CH₃ | H | H | CH₂CH₂SCH₃ | $^n$Bu | H | F | F | OH |
| XXVII-31-8 | CH₃ | * | H | * | $^n$Bu | H | F | F | OH |

*R² and R³ᵇ joined together by (CH₂)₃ to form five-membered ring.

TABLE XXVII-32

| No | R¹ | R² | R³ᵃ | R³ᵇ | R⁴ | R⁵ | R⁶ | X | Y |
|---|---|---|---|---|---|---|---|---|---|
| XXVII-32-1 | Et | H | H | H | $^n$Bu | H | F | F | OH |
| XXVII-32-2 | Et | H | H | CH₃ | $^n$Bu | H | F | F | OH |
| XXVII-32-3 | Et | H | H | CH(CH₃)₂ | $^n$Bu | H | F | F | OH |
| XXVII-32-4 | Et | H | H | CH₂CH(CH₃)₂ | $^n$Bu | H | F | F | OH |
| XXVII-32-5 | Et | H | H | CH₂Ph | $^n$Bu | H | F | F | OH |
| XXVII-32-6 | Et | H | H | CH₂-indol-3-yl | $^n$Bu | H | F | F | OH |
| XXVII-32-7 | Et | H | H | CH₂CH₂SCH₃ | $^n$Bu | H | F | F | OH |
| XXVII-32-8 | Et | * | H | * | $^n$Bu | H | F | F | OH |

*R² and R³ᵇ joined together by (CH₂)₃ to form five-membered ring.

TABLE XXVII-33

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-33-1 | $^iPr$ | H | H | H | $^nBu$ | H | F | F | OH |
| XXVII-33-2 | $^iPr$ | H | H | $CH_3$ | $^nBu$ | H | F | F | OH |
| XXVII-33-3 | $^iPr$ | H | H | $CH(CH_3)_2$ | $^nBu$ | H | F | F | OH |
| XXVII-33-4 | $^iPr$ | H | H | $CH_2CH(CH_3)_2$ | $^nBu$ | H | F | F | OH |
| XXVII-33-5 | $^iPr$ | H | H | $CH_2Ph$ | $^nBu$ | H | F | F | OH |
| XXVII-33-6 | $^iPr$ | H | H | $CH_2$-indol-3-yl | $^nBu$ | H | F | F | OH |
| XXVII-33-7 | $^iPr$ | H | H | $CH_2CH_2SCH_3$ | $^nBu$ | H | F | F | OH |
| XXVII-33-8 | $^iPr$ | * | H | * | $^nBu$ | H | F | F | OH |

*$R^2$ and $R^{3b}$ joined together by $(CH_2)_3$ to form five-membered ring.

TABLE XXVII-34

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-34-1 | $^tBu$ | H | H | H | $^nBu$ | H | F | F | OH |
| XXVII-34-2 | $^tBu$ | H | H | $CH_3$ | $^nBu$ | H | F | F | OH |
| XXVII-34-3 | $^tBu$ | H | H | $CH(CH_3)_2$ | $^nBu$ | H | F | F | OH |
| XXVII-34-4 | $^tBu$ | H | H | $CH_2CH(CH_3)_2$ | $^nBu$ | H | F | F | OH |
| XXVII-34-5 | $^tBu$ | H | H | $CH_2Ph$ | $^nBu$ | H | F | F | OH |
| XXVII-34-6 | $^tBu$ | H | H | $CH_2$-indol-3-yl | $^nBu$ | H | F | F | OH |
| XXVII-34-7 | $^tBu$ | H | H | $CH_2CH_2SCH_3$ | $^nBu$ | H | F | F | OH |
| XXVII-34-8 | $^tBu$ | * | H | * | $^nBu$ | H | F | F | OH |

*$R^2$ and $R^{3b}$ joined together by $(CH_2)_3$ to form five-membered ring.

TABLE XXVII-35

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-35-1 | Ph | H | H | H | $^nBu$ | H | F | F | OH |
| XXVII-35-2 | Ph | H | H | $CH_3$ | $^nBu$ | H | F | F | OH |
| XXVII-35-3 | Ph | H | H | $CH(CH_3)_2$ | $^nBu$ | H | F | F | OH |
| XXVII-35-4 | Ph | H | H | $CH_2CH(CH_3)_2$ | $^nBu$ | H | F | F | OH |
| XXVII-35-5 | Ph | H | H | $CH_2Ph$ | $^nBu$ | H | F | F | OH |
| XXVII-35-6 | Ph | H | H | $CH_2$-indol-3-yl | $^nBu$ | H | F | F | OH |
| XXVII-35-7 | Ph | H | H | $CH_2CH_2SCH_3$ | $^nBu$ | H | F | F | OH |
| XXVII-35-8 | Ph | * | H | * | $^nBu$ | H | F | F | OH |

*$R^2$ and $R^{3b}$ joined together by $(CH_2)_3$ to form five-membered ring.

TABLE XXVII-36

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-36-1 | p-Me—Ph | H | H | H | $^nBu$ | H | F | F | OH |
| XXVII-36-2 | p-Me—Ph | H | H | $CH_3$ | $^nBu$ | H | F | F | OH |
| XXVII-36-3 | p-Me—Ph | H | H | $CH(CH_3)_2$ | $^nBu$ | H | F | F | OH |
| XXVII-36-4 | p-Me—Ph | H | H | $CH_2CH(CH_3)_2$ | $^nBu$ | H | F | F | OH |
| XXVII-36-5 | p-Me—Ph | H | H | $CH_2Ph$ | $^nBu$ | H | F | F | OH |
| XXVII-36-6 | p-Me—Ph | H | H | $CH_2$-indol-3-yl | $^nBu$ | H | F | F | OH |
| XXVII-36-7 | p-Me—Ph | H | H | $CH_2CH_2SCH_3$ | $^nBu$ | H | F | F | OH |
| XXVII-36-8 | p-Me—Ph | * | H | * | $^nBu$ | H | F | F | OH |

*$R^2$ and $R^{3b}$ joined together by $(CH_2)_3$ to form five-membered ring.

TABLE XXVII-37

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-37-1 | p-F—Ph | H | H | H | $^nBu$ | H | F | F | OH |
| XXVII-37-2 | p-F—Ph | H | H | $CH_3$ | $^nBu$ | H | F | F | OH |
| XXVII-37-3 | p-F—Ph | H | H | $CH(CH_3)_2$ | $^nBu$ | H | F | F | OH |
| XXVII-37-4 | p-F—Ph | H | H | $CH_2CH(CH_3)_2$ | $^nBu$ | H | F | F | OH |
| XXVII-37-5 | p-F—Ph | H | H | $CH_2Ph$ | $^nBu$ | H | F | F | OH |
| XXVII-37-6 | p-F—Ph | H | H | $CH_2$-indol-3-yl | $^nBu$ | H | F | F | OH |
| XXVII-37-7 | p-F—Ph | H | H | $CH_2CH_2SCH_3$ | $^nBu$ | H | F | F | OH |
| XXVII-37-8 | p-F—Ph | * | H | * | $^nBu$ | H | F | F | OH |

*$R^2$ and $R^{3b}$ joined together by $(CH_2)_3$ to form five-membered ring.

TABLE XXVII-38

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-38-1 | p-Cl—Ph | H | H | H | $^nBu$ | H | F | F | OH |
| XXVII-38-2 | p-Cl—Ph | H | H | $CH_3$ | $^nBu$ | H | F | F | OH |
| XXVII-38-3 | p-Cl—Ph | H | H | $CH(CH_3)_2$ | $^nBu$ | H | F | F | OH |
| XXVII-38-4 | p-Cl—Ph | H | H | $CH_2CH(CH_3)_2$ | $^nBu$ | H | F | F | OH |
| XXVII-38-5 | p-Cl—Ph | H | H | $CH_2Ph$ | $^nBu$ | H | F | F | OH |
| XXVII-38-6 | p-Cl—Ph | H | H | $CH_2$-indol-3-yl | $^nBu$ | H | F | F | OH |
| XXVII-38-7 | p-Cl—Ph | H | H | $CH_2CH_2SCH_3$ | $^nBu$ | H | F | F | OH |
| XXVII-38-8 | p-Cl—Ph | * | H | * | $^nBu$ | H | F | F | OH |

*$R^2$ and $R^{3b}$ joined together by $(CH_2)_3$ to form five-membered ring.

TABLE XXVII-39

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-39-1 | p-Br—Ph | H | H | H | $^nBu$ | H | F | F | OH |
| XXVII-39-2 | p-Br—Ph | H | H | $CH_3$ | $^nBu$ | H | F | F | OH |
| XXVII-39-3 | p-Br—Ph | H | H | $CH(CH_3)_2$ | $^nBu$ | H | F | F | OH |
| XXVII-39-4 | p-Br—Ph | H | H | $CH_2CH(CH_3)_2$ | $^nBu$ | H | F | F | OH |
| XXVII-39-5 | p-Br—Ph | H | H | $CH_2Ph$ | $^nBu$ | H | F | F | OH |
| XXVII-39-6 | p-Br—Ph | H | H | $CH_2$-indol-3-yl | $^nBu$ | H | F | F | OH |
| XXVII-39-7 | p-Br—Ph | H | H | $CH_2CH_2SCH_3$ | $^nBu$ | H | F | F | OH |
| XXVII-39-8 | p-Br—Ph | * | H | * | $^nBu$ | H | F | F | OH |

*$R^2$ and $R^{3b}$ joined together by $(CH_2)_3$ to form five-membered ring.

TABLE XXVII-40

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-40-1 | p-I—Ph | H | H | H | $^nBu$ | H | F | F | OH |
| XXVII-40-2 | p-I—Ph | H | H | $CH_3$ | $^nBu$ | H | F | F | OH |
| XXVII-40-3 | p-I—Ph | H | H | $CH(CH_3)_2$ | $^nBu$ | H | F | F | OH |
| XXVII-40-4 | p-I—Ph | H | H | $CH_2CH(CH_3)_2$ | $^nBu$ | H | F | F | OH |
| XXVII-40-5 | p-I—Ph | H | H | $CH_2Ph$ | $^nBu$ | H | F | F | OH |
| XXVII-40-6 | p-I—Ph | H | H | $CH_2$-indol-3-yl | $^nBu$ | H | F | F | OH |
| XXVII-40-7 | p-I—Ph | H | H | $CH_2CH_2SCH_3$ | $^nBu$ | H | F | F | OH |
| XXVII-40-8 | p-I—Ph | * | H | * | $^nBu$ | H | F | F | OH |

*$R^2$ and $R^{3b}$ joined together by $(CH_2)_3$ to form five-membered ring.

TABLE XXVII-41

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVII-41-1 | $CH_3$ | H | H | H | Bz | H | F | F | OH |
| XXVII-41-2 | $CH_3$ | H | H | $CH_3$ | Bz | H | F | F | OH |

TABLE XXVII-41-continued

| No | R¹ | R² | R³ᵃ | R³ᵇ | R⁴ | R⁵ | R⁶ | X | Y |
|---|---|---|---|---|---|---|---|---|---|
| XXVII-41-3 | CH₃ | H | H | CH(CH₃)₂ | Bz | H | F | F | OH |
| XXVII-41-4 | CH₃ | H | H | CH₂CH(CH₃)₂ | Bz | H | F | F | OH |
| XXVII-41-5 | CH₃ | H | H | CH₂Ph | Bz | H | F | F | OH |
| XXVII-41-6 | CH₃ | H | H | CH₂-indol-3-yl | Bz | H | F | F | OH |
| XXVII-41-7 | CH₃ | H | H | CH₂CH₂SCH₃ | Bz | H | F | F | OH |
| XXVII-41-8 | CH₃ | * | H | * | Bz | H | F | F | OH |

*R² and R³ᵇ joined together by (CH₂)₃ to form five-membered ring.

TABLE XXVII-42

| No | R¹ | R² | R³ᵃ | R³ᵇ | R⁴ | R⁵ | R⁶ | X | Y |
|---|---|---|---|---|---|---|---|---|---|
| XXVII-42-1 | Et | H | H | H | Bz | H | F | F | OH |
| XXVII-42-2 | Et | H | H | CH₃ | Bz | H | F | F | OH |
| XXVII-42-3 | Et | H | H | CH(CH₃)₂ | Bz | H | F | F | OH |
| XXVII-42-4 | Et | H | H | CH₂CH(CH₃)₂ | Bz | H | F | F | OH |
| XXVII-42-5 | Et | H | H | CH₂Ph | Bz | H | F | F | OH |
| XXVII-42-6 | Et | H | H | CH₂-indol-3-yl | Bz | H | F | F | OH |
| XXVII-42-7 | Et | H | H | CH₂CH₂SCH₃ | Bz | H | F | F | OH |
| XXVII-42-8 | Et | * | H | * | Bz | H | F | F | OH |

*R² and R³ᵇ joined together by (CH₂)₃ to form five-membered ring.

TABLE XXVII-43

| No | R¹ | R² | R³ᵃ | R³ᵇ | R⁴ | R⁵ | R⁶ | X | Y |
|---|---|---|---|---|---|---|---|---|---|
| XXVII-43-1 | ⁱPr | H | H | H | Bz | H | F | F | OH |
| XXVII-43-2 | ⁱPr | H | H | CH₃ | Bz | H | F | F | OH |
| XXVII-43-3 | ⁱPr | H | H | CH(CH₃)₂ | Bz | H | F | F | OH |
| XXVII-43-4 | ⁱPr | H | H | CH₂CH(CH₃)₂ | Bz | H | F | F | OH |
| XXVII-43-5 | ⁱPr | H | H | CH₂Ph | Bz | H | F | F | OH |
| XXVII-43-6 | ⁱPr | H | H | CH₂-indol-3-yl | Bz | H | F | F | OH |
| XXVII-43-7 | ⁱPr | H | H | CH₂CH₂SCH₃ | Bz | H | F | F | OH |
| XXVII-43-8 | ⁱPr | * | H | * | Bz | H | F | F | OH |

*R² and R³ᵇ joined together by (CH₂)₃ to form five-membered ring.

TABLE XXVII-44

| No | R¹ | R² | R³ᵃ | R³ᵇ | R⁴ | R⁵ | R⁶ | X | Y |
|---|---|---|---|---|---|---|---|---|---|
| XXVII-44-1 | ᵗBu | H | H | H | Bz | H | F | F | OH |
| XXVII-44-2 | ᵗBu | H | H | CH₃ | Bz | H | F | F | OH |
| XXVII-44-3 | ᵗBu | H | H | CH(CH₃)₂ | Bz | H | F | F | OH |
| XXVII-44-4 | ᵗBu | H | H | CH₂CH(CH₃)₂ | Bz | H | F | F | OH |
| XXVII-44-5 | ᵗBu | H | H | CH₂Ph | Bz | H | F | F | OH |
| XXVII-44-6 | ᵗBu | H | H | CH₂-indol-3-yl | Bz | H | F | F | OH |
| XXVII-44-7 | ᵗBu | H | H | CH₂CH₂SCH₃ | Bz | H | F | F | OH |
| XXVII-44-8 | ᵗBu | * | H | * | Bz | H | F | F | OH |

*R² and R³ᵇ joined together by (CH₂)₃ to form five-membered ring.

TABLE XXVII-45

| No | R¹ | R² | R³ᵃ | R³ᵇ | R⁴ | R⁵ | R⁶ | X | Y |
|---|---|---|---|---|---|---|---|---|---|
| XXVII-45-1 | Ph | H | H | H | Bz | H | F | F | OH |
| XXVII-45-2 | Ph | H | H | CH₃ | Bz | H | F | F | OH |
| XXVII-45-3 | Ph | H | H | CH(CH₃)₂ | Bz | H | F | F | OH |
| XXVII-45-4 | Ph | H | H | CH₂CH(CH₃)₂ | Bz | H | F | F | OH |
| XXVII-45-5 | Ph | H | H | CH₂Ph | Bz | H | F | F | OH |
| XXVII-45-6 | Ph | H | H | CH₂-indol-3-yl | Bz | H | F | F | OH |
| XXVII-45-7 | Ph | H | H | CH₂CH₂SCH₃ | Bz | H | F | F | OH |
| XXVII-45-8 | Ph | * | H | * | Bz | H | F | F | OH |

*R² and R³ᵇ joined together by (CH₂)₃ to form five-membered ring.

TABLE XXVII-46

| No | R¹ | R² | R³ᵃ | R³ᵇ | R⁴ | R⁵ | R⁶ | X | Y |
|---|---|---|---|---|---|---|---|---|---|
| XXVII-46-1 | p-Me—Ph | H | H | H | Bz | H | F | F | OH |
| XXVII-46-2 | p-Me—Ph | H | H | CH₃ | Bz | H | F | F | OH |
| XXVII-46-3 | p-Me—Ph | H | H | CH(CH₃)₂ | Bz | H | F | F | OH |
| XXVII-46-4 | p-Me—Ph | H | H | CH₂CH(CH₃)₂ | Bz | H | F | F | OH |
| XXVII-46-5 | p-Me—Ph | H | H | CH₂Ph | Bz | H | F | F | OH |
| XXVII-46-6 | p-Me—Ph | H | H | CH₂-indol-3-yl | Bz | H | F | F | OH |
| XXVII-46-7 | p-Me—Ph | H | H | CH₂CH₂SCH₃ | Bz | H | F | F | OH |
| XXVII-46-8 | p-Me—Ph | * | H | * | Bz | H | F | F | OH |

*R² and R³ᵇ joined together by (CH₂)₃ to form five-membered ring.

TABLE XXVII-47

| No | R¹ | R² | R³ᵃ | R³ᵇ | R⁴ | R⁵ | R⁶ | X | Y |
|---|---|---|---|---|---|---|---|---|---|
| XXVII-47-1 | p-F—Ph | H | H | H | Bz | H | F | F | OH |
| XXVII-47-2 | p-F—Ph | H | H | CH₃ | Bz | H | F | F | OH |
| XXVII-47-3 | p-F—Ph | H | H | CH(CH₃)₂ | Bz | H | F | F | OH |
| XXVII-47-4 | p-F—Ph | H | H | CH₂CH(CH₃)₂ | Bz | H | F | F | OH |
| XXVII-47-5 | p-F—Ph | H | H | CH₂Ph | Bz | H | F | F | OH |
| XXVII-47-6 | p-F—Ph | H | H | CH₂-indol-3-yl | Bz | H | F | F | OH |
| XXVII-47-7 | p-F—Ph | H | H | CH₂CH₂SCH₃ | Bz | H | F | F | OH |
| XXVII-47-8 | p-F—Ph | * | H | * | Bz | H | F | F | OH |

*R² and R³ᵇ joined together by (CH₂)₃ to form five-membered ring.

TABLE XXVII-48

| No | R¹ | R² | R³ᵃ | R³ᵇ | R⁴ | R⁵ | R⁶ | X | Y |
|---|---|---|---|---|---|---|---|---|---|
| XXVII-48-1 | p-Cl—Ph | H | H | H | Bz | H | F | F | OH |
| XXVII-48-2 | p-Cl—Ph | H | H | CH₃ | Bz | H | F | F | OH |
| XXVII-48-3 | p-Cl—Ph | H | H | CH(CH₃)₂ | Bz | H | F | F | OH |
| XXVII-48-4 | p-Cl—Ph | H | H | CH₂CH(CH₃)₂ | Bz | H | F | F | OH |
| XXVII-48-5 | p-Cl—Ph | H | H | CH₂Ph | Bz | H | F | F | OH |
| XXVII-48-6 | p-Cl—Ph | H | H | CH₂-indol-3-yl | Bz | H | F | F | OH |
| XXVII-48-7 | p-Cl—Ph | H | H | CH₂CH₂SCH₃ | Bz | H | F | F | OH |
| XXVII-48-8 | p-Cl—Ph | * | H | * | Bz | H | F | F | OH |

*R² and R³ᵇ joined together by (CH₂)₃ to form five-membered ring.

TABLE XXVII-49

| No | R¹ | R² | R³ᵃ | R³ᵇ | R⁴ | R⁵ | R⁶ | X | Y |
|---|---|---|---|---|---|---|---|---|---|
| XXVII-49-1 | p-Br—Ph | H | H | H | Bz | H | F | F | OH |
| XXVII-49-2 | p-Br—Ph | H | H | CH₃ | Bz | H | F | F | OH |
| XXVII-49-3 | p-Br—Ph | H | H | CH(CH₃)₂ | Bz | H | F | F | OH |
| XXVII-49-4 | p-Br—Ph | H | H | CH₂CH(CH₃)₂ | Bz | H | F | F | OH |
| XXVII-49-5 | p-Br—Ph | H | H | CH₂Ph | Bz | H | F | F | OH |
| XXVII-49-6 | p-Br—Ph | H | H | CH₂-indol-3-yl | Bz | H | F | F | OH |

TABLE XXVII-49-continued

| No | R¹ | R² | R³ᵃ | R³ᵇ | R⁴ | R⁵ | R⁶ | X | Y |
|---|---|---|---|---|---|---|---|---|---|
| XXVII-49-7 | p-Br—Ph | H | H | $CH_2CH_2SCH_3$ | Bz | H | F | F | OH |
| XXVII-49-8 | p-Br—Ph | * | H | * | Bz | H | F | F | OH |

*$R^2$ and $R^{3b}$ joined together by $(CH_2)_3$ to form five-membered ring.

TABLE XXVII-50

| No | R¹ | R² | R³ᵃ | R³ᵇ | R⁴ | R⁵ | R⁶ | X | Y |
|---|---|---|---|---|---|---|---|---|---|
| XXVII-50-1 | p-I—Ph | H | H | H | Bz | H | F | F | OH |
| XXVII-50-2 | p-I—Ph | H | H | $CH_3$ | Bz | H | F | F | OH |
| XXVII-50-3 | p-I—Ph | H | H | $CH(CH_3)_2$ | Bz | H | F | F | OH |
| XXVII-50-4 | p-I—Ph | H | H | $CH_2CH(CH_3)_2$ | Bz | H | F | F | OH |
| XXVII-50-5 | p-I—Ph | H | H | $CH_2Ph$ | Bz | H | F | F | OH |
| XXVII-50-6 | p-I—Ph | H | H | $CH_2$-indol-3-yl | Bz | H | F | F | OH |
| XXVII-50-7 | p-I—Ph | H | H | $CH_2CH_2SCH_3$ | Bz | H | F | F | OH |
| XXVII-50-8 | p-I—Ph | * | H | * | Bz | H | F | F | OH |

*$R^2$ and $R^{3b}$ joined together by $(CH_2)_3$ to form five-membered ring.

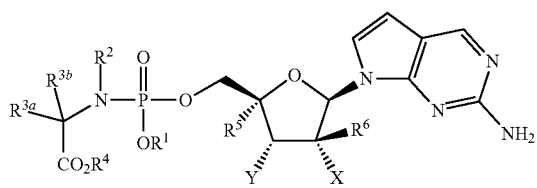

XXVIII

TABLE XXVIII-1

| No | R¹ | R² | R³ᵃ | R³ᵇ | R⁴ | R⁵ | R⁶ | X | Y |
|---|---|---|---|---|---|---|---|---|---|
| XXVIII-1-1 | $CH_3$ | H | H | H | $CH_3$ | H | H | F | OH |
| XXVIII-1-2 | $CH_3$ | H | H | $CH_3$ | $CH_3$ | H | H | F | OH |
| XXVIII-1-3 | $CH_3$ | H | H | $CH(CH_3)_2$ | $CH_3$ | H | H | F | OH |
| XXVIII-1-4 | $CH_3$ | H | H | $CH_2CH(CH_3)_2$ | $CH_3$ | H | H | F | OH |
| XXVIII-1-5 | $CH_3$ | H | H | $CH_2Ph$ | $CH_3$ | H | H | F | OH |
| XXVIII-1-6 | $CH_3$ | H | H | $CH_2$-indol-3-yl | $CH_3$ | H | H | F | OH |
| XXVIII-1-7 | $CH_3$ | H | H | $CH_2CH_2SCH_3$ | $CH_3$ | H | H | F | OH |
| XXVIII-1-8 | $CH_3$ | * | H | * | $CH_3$ | H | H | F | OH |

*$R^2$ and $R^{3b}$ joined together by $(CH_2)_3$ to form five-membered ring.

TABLE XXVIII-2

| No | R¹ | R² | R³ᵃ | R³ᵇ | R⁴ | R⁵ | R⁶ | X | Y |
|---|---|---|---|---|---|---|---|---|---|
| XXVIII-2-1 | Et | H | H | H | $CH_3$ | H | H | F | OH |
| XXVIII-2-2 | Et | H | H | $CH_3$ | $CH_3$ | H | H | F | OH |
| XXVIII-2-3 | Et | H | H | $CH(CH_3)_2$ | $CH_3$ | H | H | F | OH |
| XXVIII-2-4 | Et | H | H | $CH_2CH(CH_3)_2$ | $CH_3$ | H | H | F | OH |
| XXVIII-2-5 | Et | H | H | $CH_2Ph$ | $CH_3$ | H | H | F | OH |
| XXVIII-2-6 | Et | H | H | $CH_2$-indol-3-yl | $CH_3$ | H | H | F | OH |
| XXVIII-2-7 | Et | H | H | $CH_2CH_2SCH_3$ | $CH_3$ | H | H | F | OH |
| XXVIII-2-8 | Et | * | H | * | $CH_3$ | H | H | F | OH |

*$R^2$ and $R^{3b}$ joined together by $(CH_2)_3$ to form five-membered ring.

TABLE XXVIII-3

| No | R¹ | R² | R³ᵃ | R³ᵇ | R⁴ | R⁵ | R⁶ | X | Y |
|---|---|---|---|---|---|---|---|---|---|
| XXVIII-3-1 | $^iPr$ | H | H | H | $CH_3$ | H | H | F | OH |
| XXVIII-3-2 | $^iPr$ | H | H | $CH_3$ | $CH_3$ | H | H | F | OH |
| XXVIII-3-3 | $^iPr$ | H | H | $CH(CH_3)_2$ | $CH_3$ | H | H | F | OH |
| XXVIII-3-4 | $^iPr$ | H | H | $CH_2CH(CH_3)_2$ | $CH_3$ | H | H | F | OH |
| XXVIII-3-5 | $^iPr$ | H | H | $CH_2Ph$ | $CH_3$ | H | H | F | OH |
| XXVIII-3-6 | $^iPr$ | H | H | $CH_2$-indol-3-yl | $CH_3$ | H | H | F | OH |
| XXVIII-3-7 | $^iPr$ | H | H | $CH_2CH_2SCH_3$ | $CH_3$ | H | H | F | OH |
| XXVIII-3-8 | $^iPr$ | * | H | * | $CH_3$ | H | H | F | OH |

*$R^2$ and $R^{3b}$ joined together by $(CH_2)_3$ to form five-membered ring.

TABLE XXVIII-4

| No | R¹ | R² | R³ᵃ | R³ᵇ | R⁴ | R⁵ | R⁶ | X | Y |
|---|---|---|---|---|---|---|---|---|---|
| XXVIII-4-1 | $^tBu$ | H | H | H | $CH_3$ | H | H | F | OH |
| XXVIII-4-2 | $^tBu$ | H | H | $CH_3$ | $CH_3$ | H | H | F | OH |
| XXVIII-4-3 | $^tBu$ | H | H | $CH(CH_3)_2$ | $CH_3$ | H | H | F | OH |
| XXVIII-4-4 | $^tBu$ | H | H | $CH_2CH(CH_3)_2$ | $CH_3$ | H | H | F | OH |
| XXVIII-4-5 | $^tBu$ | H | H | $CH_2Ph$ | $CH_3$ | H | H | F | OH |
| XXVIII-4-6 | $^tBu$ | H | H | $CH_2$-indol-3-yl | $CH_3$ | H | H | F | OH |
| XXVIII-4-7 | $^tBu$ | H | H | $CH_2CH_2SCH_3$ | $CH_3$ | H | H | F | OH |
| XXVIII-4-8 | $^tBu$ | * | H | * | $CH_3$ | H | H | F | OH |

*$R^2$ and $R^{3b}$ joined together by $(CH_2)_3$ to form five-membered ring.

TABLE XXVIII-5

| No | R¹ | R² | R³ᵃ | R³ᵇ | R⁴ | R⁵ | R⁶ | X | Y |
|---|---|---|---|---|---|---|---|---|---|
| XXVIII-5-1 | Ph | H | H | H | $CH_3$ | H | H | F | OH |
| XXVIII-5-2 | Ph | H | H | $CH_3$ | $CH_3$ | H | H | F | OH |
| XXVIII-5-3 | Ph | H | H | $CH(CH_3)_2$ | $CH_3$ | H | H | F | OH |
| XXVIII-5-4 | Ph | H | H | $CH_2CH(CH_3)_2$ | $CH_3$ | H | H | F | OH |
| XXVIII-5-5 | Ph | H | H | $CH_2Ph$ | $CH_3$ | H | H | F | OH |
| XXVIII-5-6 | Ph | H | H | $CH_2$-indol-3-yl | $CH_3$ | H | H | F | OH |
| XXVIII-5-7 | Ph | H | H | $CH_2CH_2SCH_3$ | $CH_3$ | H | H | F | OH |
| XXVIII-5-8 | Ph | * | H | * | $CH_3$ | H | H | F | OH |

*$R^2$ and $R^{3b}$ joined together by $(CH_2)_3$ to form five-membered ring.

TABLE XXVIII-6

| No | R¹ | R² | R³ᵃ | R³ᵇ | R⁴ | R⁵ | R⁶ | X | Y |
|---|---|---|---|---|---|---|---|---|---|
| XXVIII-6-1 | p-Me—Ph | H | H | H | $CH_3$ | H | H | F | OH |
| XXVIII-6-2 | p-Me—Ph | H | H | $CH_3$ | $CH_3$ | H | H | F | OH |
| XXVIII-6-3 | p-Me—Ph | H | H | $CH(CH_3)_2$ | $CH_3$ | H | H | F | OH |
| XXVIII-6-4 | p-Me—Ph | H | H | $CH_2CH(CH_3)_2$ | $CH_3$ | H | H | F | OH |
| XXVIII-6-5 | p-Me—Ph | H | H | $CH_2Ph$ | $CH_3$ | H | H | F | OH |
| XXVIII-6-6 | p-Me—Ph | H | H | $CH_2$-indol-3-yl | $CH_3$ | H | H | F | OH |
| XXVIII-6-7 | p-Me—Ph | H | H | $CH_2CH_2SCH_3$ | $CH_3$ | H | H | F | OH |
| XXVIII-6-8 | p-Me—Ph | * | H | * | $CH_3$ | H | H | F | OH |

*$R^2$ and $R^{3b}$ joined together by $(CH_2)_3$ to form five-membered ring.

TABLE XXVIII-7

| No | R¹ | R² | R³ᵃ | R³ᵇ | R⁴ | R⁵ | R⁶ | X | Y |
|---|---|---|---|---|---|---|---|---|---|
| XXVIII-7-1 | p-F—Ph | H | H | H | $CH_3$ | H | H | F | OH |
| XXVIII-7-2 | p-F—Ph | H | H | $CH_3$ | $CH_3$ | H | H | F | OH |
| XXVIII-7-3 | p-F—Ph | H | H | $CH(CH_3)_2$ | $CH_3$ | H | H | F | OH |

TABLE XXVIII-7-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-7-4 | p-F—Ph | H | H | $CH_2CH(CH_3)_2$ | $CH_3$ | H | H | F | OH |
| XXVIII-7-6 | p-F—Ph | H | H | $CH_2Ph$ | $CH_3$ | H | H | F | OH |
| XXVIII-7-7 | p-F—Ph | H | H | $CH_2$-indol-3-yl | $CH_3$ | H | H | F | OH |
| XXVIII-7-8 | p-F—Ph | H | H | $CH_2CH_2SCH_3$ | $CH_3$ | H | H | F | OH |
| XXVIII-7-20 | p-F—Ph | * | H | * | | $CH_3$ | H | H | F | OH |

*$R^2$ and $R^{3b}$ joined together by $(CH_2)_3$ to form five-membered ring.

TABLE XXVIII-8

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-8-1 | p-Cl—Ph | H | H | H | $CH_3$ | H | H | F | OH |
| XXVIII-8-2 | p-Cl—Ph | H | H | $CH_3$ | $CH_3$ | H | H | F | OH |
| XXVIII-8-3 | p-Cl—Ph | H | H | $CH(CH_3)_2$ | $CH_3$ | H | H | F | OH |
| XXVIII-8-4 | p-Cl—Ph | H | H | $CH_2CH(CH_3)_2$ | $CH_3$ | H | H | F | OH |
| XXVIII-8-5 | p-Cl—Ph | H | H | $CH_2Ph$ | $CH_3$ | H | H | F | OH |
| XXVIII-8-6 | p-Cl—Ph | H | H | $CH_2$-indol-3-yl | $CH_3$ | H | H | F | OH |
| XXVIII-8-7 | p-Cl—Ph | H | H | $CH_2CH_2SCH_3$ | $CH_3$ | H | H | F | OH |
| XXVIII-8-8 | p-Cl—Ph | * | H | * | $CH_3$ | H | H | F | OH |

*$R^2$ and $R^{3b}$ joined together by $(CH_2)_3$ to form five-membered ring.

TABLE XXVIII-9

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-9-1 | p-Br—Ph | H | H | H | $CH_3$ | H | H | F | OH |
| XXVIII-9-2 | p-Br—Ph | H | H | $CH_3$ | $CH_3$ | H | H | F | OH |
| XXVIII-9-3 | p-Br—Ph | H | H | $CH(CH_3)_2$ | $CH_3$ | H | H | F | OH |
| XXVIII-9-4 | p-Br—Ph | H | H | $CH_2CH(CH_3)_2$ | $CH_3$ | H | H | F | OH |
| XXVIII-9-6 | p-Br—Ph | H | H | $CH_2Ph$ | $CH_3$ | H | H | F | OH |
| XXVIII-9-7 | p-Br—Ph | H | H | $CH_2$-indol-3-yl | $CH_3$ | H | H | F | OH |
| XXVIII-9-8 | p-Br—Ph | H | H | $CH_2CH_2SCH_3$ | $CH_3$ | H | H | F | OH |
| XXVIII-9-20 | p-Br—Ph | * | H | * | $CH_3$ | H | H | F | OH |

*$R^2$ and $R^{3b}$ joined together by $(CH_2)_3$ to form five-membered ring.

TABLE XXVIII-10

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-10-1 | p-I—Ph | H | H | H | $CH_3$ | H | H | F | OH |
| XXVIII-10-2 | p-I—Ph | H | H | $CH_3$ | $CH_3$ | H | H | F | OH |
| XXVIII-10-3 | p-I—Ph | H | H | $CH(CH_3)_2$ | $CH_3$ | H | H | F | OH |
| XXVIII-10-4 | p-I—Ph | H | H | $CH_2CH(CH_3)_2$ | $CH_3$ | H | H | F | OH |
| XXVIII-10-5 | p-I—Ph | H | H | $CH_2Ph$ | $CH_3$ | H | H | F | OH |

TABLE XXVIII-10-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-10-6 | p-I—Ph | H | H | $CH_2$-indol-3-yl | $CH_3$ | H | H | F | OH |
| XXVIII-10-7 | p-I—Ph | H | H | $CH_2CH_2SCH_3$ | $CH_3$ | H | H | F | OH |
| XXVIII-10-8 | p-I—Ph | * | H | * | $CH_3$ | H | H | F | OH |

*$R^2$ and $R^{3b}$ joined together by $(CH_2)_3$ to form five-membered ring.

TABLE XXVIII-11

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-11-1 | $CH_3$ | H | H | H | Et | H | H | F | OH |
| XXVIII-11-2 | $CH_3$ | H | H | $CH_3$ | Et | H | H | F | OH |
| XXVIII-11-3 | $CH_3$ | H | H | $CH(CH_3)_2$ | Et | H | H | F | OH |
| XXVIII-11-4 | $CH_3$ | H | H | $CH_2CH(CH_3)_2$ | Et | H | H | F | OH |
| XXVIII-11-5 | $CH_3$ | H | H | $CH_2Ph$ | Et | H | H | F | OH |
| XXVIII-11-6 | $CH_3$ | H | H | $CH_2$-indol-3-yl | Et | H | H | F | OH |
| XXVIII-11-7 | $CH_3$ | H | H | $CH_2CH_2SCH_3$ | Et | H | H | F | OH |
| XXVIII-11-8 | $CH_3$ | * | H | * | Et | H | H | F | OH |

*$R^2$ and $R^{3b}$ joined together by $(CH_2)_3$ to form five-membered ring.

TABLE XXVIII-12

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-12-1 | Et | H | H | H | Et | H | H | F | OH |
| XXVIII-12-2 | Et | H | H | $CH_3$ | Et | H | H | F | OH |
| XXVIII-12-3 | Et | H | H | $CH(CH_3)_2$ | Et | H | H | F | OH |
| XXVIII-12-4 | Et | H | H | $CH_2CH(CH_3)_2$ | Et | H | H | F | OH |
| XXVIII-12-5 | Et | H | H | $CH_2Ph$ | Et | H | H | F | OH |
| XXVIII-12-6 | Et | H | H | $CH_2$-indol-3-yl | Et | H | H | F | OH |
| XXVIII-12-7 | Et | H | H | $CH_2CH_2SCH_3$ | Et | H | H | F | OH |
| XXVIII-12-8 | Et | * | H | * | Et | H | H | F | OH |

*$R^2$ and $R^{3b}$ joined together by $(CH_2)_3$ to form five-membered ring.

TABLE XXVIII-13

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-13-1 | $^i$Pr | H | H | H | Et | H | H | F | OH |
| XXVIII-13-2 | $^i$Pr | H | H | $CH_3$ | Et | H | H | F | OH |
| XXVIII-13-3 | $^i$Pr | H | H | $CH(CH_3)_2$ | Et | H | H | F | OH |
| XXVIII-13-4 | $^i$Pr | H | H | $CH_2CH(CH_3)_2$ | Et | H | H | F | OH |
| XXVIII-13-5 | $^i$Pr | H | H | $CH_2Ph$ | Et | H | H | F | OH |
| XXVIII-13-6 | $^i$Pr | H | H | $CH_2$-indol-3-yl | Et | H | H | F | OH |
| XXVIII-13-7 | $^i$Pr | H | H | $CH_2CH_2SCH_3$ | Et | H | H | F | OH |
| XXVIII-13-8 | $^i$Pr | * | H | * | Et | H | H | F | OH |

*$R^2$ and $R^{3b}$ joined together by $(CH_2)_3$ to form five-membered ring.

TABLE XXVIII-14

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-14-1 | $^t$Bu | H | H | H | Et | H | H | F | OH |
| XXVIII-14-2 | $^t$Bu | H | H | $CH_3$ | Et | H | H | F | OH. |
| XXVIII-14-3 | $^t$Bu | H | H | $CH(CH_3)_2$ | Et | H | H | F | OH |
| XXVIII-14-4 | $^t$Bu | H | H | $CH_2CH(CH_3)_2$ | Et | H | H | F | OH |
| XXVIII-14-5 | $^t$Bu | H | H | $CH_2Ph$ | Et | H | H | F | OH |
| XXVIII-14-6 | $^t$Bu | H | H | $CH_2$-indol-3-yl | Et | H | H | F | OH |
| XXVIII-14-7 | $^t$Bu | H | H | $CH_2CH_2SCH_3$ | Et | H | H | F | OH |
| XXVIII-14-8 | $^t$Bu | * | H | * | Et | H | H | F | OH |

*$R_2$ and $R^{3b}$ joined together by $(CH_2)_3$ to form five-membered ring.

TABLE XXVIII-15

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-15-1 | Ph | H | H | H | Et | H | H | F | OH |
| XXVIII-15-2 | Ph | H | H | $CH_3$ | Et | H | H | F | OH |
| XXVIII-15-3 | Ph | H | H | $CH(CH_3)_2$ | Et | H | H | F | OH |
| XXVIII-15-4 | Ph | H | H | $CH_2CH(CH_3)_2$ | Et | H | H | F | OH |
| XXVIII-15-5 | Ph | H | H | $CH_2Ph$ | Et | H | H | F | OH |
| XXVIII-15-6 | Ph | H | H | $CH_2$-indol-3-yl | Et | H | H | F | OH |
| XXVIII-15-7 | Ph | H | H | $CH_2CH_2SCH_3$ | Et | H | H | F | OH |
| XXVIII-15-8 | Ph | * | H | * | Et | H | H | F | OH |

*$R^2$ and $R^{3b}$ joined together by $(CH_2)_3$ to form five-membered ring.

TABLE XXVIII-16

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-16-1 | p-Me-Ph | H | H | H | Et | H | H | F | OH |
| XXVIII-16-2 | p-Me-Ph | H | H | $CH_3$ | Et | H | H | F | OH |
| XXVIII-16-3 | p-Me-Ph | H | H | $CH(CH_3)_2$ | Et | H | H | F | OH |
| XXVIII-16-4 | p-Me-Ph | H | H | $CH_2CH(CH_3)_2$ | Et | H | H | F | OH |
| XXVIII-16-5 | p-Me-Ph | H | H | $CH_2Ph$ | Et | H | H | F | OH |
| XXVIII-16-6 | p-Me-Ph | H | H | $CH_2$-indol-3-yl | Et | H | H | F | OH |
| XXVIII-16-7 | p-Me-Ph | H | H | $CH_2CH_2SCH_3$ | Et | H | H | F | OH |
| XXVIII-16-8 | p-Me-Ph | * | H | * | Et | H | H | F | OH |

*$R^2$ and $R^{3b}$ joined together by $(CH_2)_3$ to form five-membered ring.

TABLE XXVIII-17

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-17-1 | p-F-Ph | H | H | H | Et | H | H | F | OH |
| XXVIII-17-2 | p-F-Ph | H | H | $CH_3$ | Et | H | H | F | OH |
| XXVIII-17-3 | p-F-Ph | H | H | $CH(CH_3)_2$ | Et | H | H | F | OH |
| XXVIII-17-4 | p-F-Ph | H | H | $CH_2CH(CH_3)_2$ | Et | H | H | F | OH |
| XXVIII-17-5 | p-F-Ph | H | H | $CH_2Ph$ | Et | H | H | F | OH |
| XXVIII-17-6 | p-F-Ph | H | H | $CH_2$-indol-3-yl | Et | H | H | F | OH |
| XXVIII-17-7 | p-F-Ph | H | H | $CH_2CH_2SCH_3$ | Et | H | H | F | OH |
| XXVIII-17-8 | p-F-Ph | * | H | * | Et | H | H | F | OH |

*$R^2$ and $R^{3b}$ joined together by $(CH_2)_3$ to form five-membered ring.

TABLE XXVIII-18

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-18-1 | p-Cl-Ph | H | H | H | Et | H | H | F | OH |
| XXVIII-18-2 | p-Cl-Ph | H | H | $CH_3$ | Et | H | H | F | OH |
| XXVIII-18-3 | p-Cl-Ph | H | H | $CH(CH_3)_2$ | Et | H | H | F | OH |
| XXVIII-18-4 | p-Cl-Ph | H | H | $CH_2CH(CH_3)_2$ | Et | H | H | F | OH |
| XXVIII-18-5 | p-Cl-Ph | H | H | $CH_2Ph$ | Et | H | H | F | OH |
| XXVIII-18-6 | p-Cl-Ph | H | H | $CH_2$-indol-3-yl | Et | H | H | F | OH |
| XXVIII-18-7 | p-Cl-Ph | H | H | $CH_2CH_2SCH_3$ | Et | H | H | F | OH |
| XXVIII-18-8 | p-Cl-Ph | * | H | * | Et | H | H | F | OH |

*$R^2$ and $R^{3b}$ joined together by $(CH_2)_3$ to form five-membered ring.

TABLE XXVIII-19

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-19-1 | p-Br-Ph | H | H | H | Et | H | H | F | OH |
| XXVIII-19-2 | p-Br-Ph | H | H | $CH_3$ | Et | H | H | F | OH |
| XXVIII-19-3 | p-Br-Ph | H | H | $CH(CH_3)_2$ | Et | H | H | F | OH |
| XXVIII-19-4 | p-Br-Ph | H | H | $CH_2CH(CH_3)_2$ | Et | H | H | F | OH |
| XXVIII-19-5 | p-Br-Ph | H | H | $CH_2Ph$ | Et | H | H | F | OH |
| XXVIII-19-6 | p-Br-Ph | H | H | $CH_2$-indol-3-yl | Et | H | H | F | OH |
| XXVIII-19-7 | p-Br-Ph | H | H | $CH_2CH_2SCH_3$ | Et | H | H | F | OH |
| XXVIII-19-8 | p-Br-Ph | * | H | * | Et | H | H | F | OH |

*$R^2$ and $R^{3b}$ joined together by $(CH_2)_3$ to form five-membered ring.

TABLE XXVIII-20

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-20-1 | p-I-Ph | H | H | H | Et | H | H | F | OH |
| XXVIII-20-2 | p-I-Ph | H | H | $CH_3$ | Et | H | H | F | OH |
| XXVIII-20-3 | p-I-Ph | H | H | $CH(CH_3)_2$ | Et | H | H | F | OH |
| XXVIII-20-4 | p-I-Ph | H | H | $CH_2CH(CH_3)_2$ | Et | H | H | F | OH |
| XXVIII-20-5 | p-I-Ph | H | H | $CH_2Ph$ | Et | H | H | F | OH |
| XXVIII-20-6 | p-I-Ph | H | H | $CH_2$-indol-3-yl | Et | H | H | F | OH |
| XXVIII-20-7 | p-I-Ph | H | H | $CH_2CH_2SCH_3$ | Et | H | H | F | OH |
| XXVIII-20-8 | p-I-Ph | * | H | * | Et | H | H | F | OH |

*$R^2$ and $R^{3b}$ joined together by $(CH_2)_3$ to form five-membered ring.

TABLE XXVIII-21

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-21-1 | $CH_3$ | H | H | H | $^iPr$ | H | H | F | OH |
| XXVIII-21-2 | $CH_3$ | H | H | $CH_3$ | $^iPr$ | H | H | F | OH |
| XXVIII-21-3 | $CH_3$ | H | H | $CH(CH_3)_2$ | $^iPr$ | H | H | F | OH |
| XXVIII-21-4 | $CH_3$ | H | H | $CH_2CH(CH_3)_2$ | $^iPr$ | H | H | F | OH |
| XXVIII-21-5 | $CH_3$ | H | H | $CH_2Ph$ | $^iPr$ | H | H | F | OH |
| XXVIII-21-6 | $CH_3$ | H | H | $CH_2$-indol-3-yl | $^iPr$ | H | H | F | OH |
| XXVIII-21-7 | $CH_3$ | H | H | $CH_2CH_2SCH_3$ | $^iPr$ | H | H | F | OH |
| XXVIII-21-8 | $CH_3$ | * | H | * | $^iPr$ | H | H | F | OH |

*$R^2$ and $R^{3b}$ joined together by $(CH_2)_3$ to form five-membered ring.

TABLE XXVIII-22

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-22-1 | Et | H | H | H | $^iPr$ | H | H | F | OH |
| XXVIII-22.2 | Et | H | H | $CH_3$ | $^iPr$ | H | H | F | OH |
| XXVIII-22-3 | Et | H | H | $CH(CH_3)_2$ | $^iPr$ | H | H | F | OH |
| XXVIII-22-4 | Et | H | H | $CH_2CH(CH_3)_2$ | $^iPr$ | H | H | F | OH |
| XXVIII-22-5 | Et | H | H | $CH_2Ph$ | $^iPr$ | H | H | F | OH |
| XXVIII-22-6 | Et | H | H | $CH_2$-indol-3-yl | $^iPr$ | H | H | F | OH |
| XXVIII-22-7 | Et | H | H | $CH_2CH_2SCH_3$ | $^iPr$ | H | H | F | OH |
| XXVIII-22-8 | Et | * | H | * | $^iPr$ | H | H | F | OH |

*$R^2$ and $R^{3b}$ joined together by $(CH_2)_3$ to form five-membered ring.

TABLE XXVIII-23

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-23-1 | $^iPr$ | H | H | H | $^iPr$ | H | H | F | OH |
| XXVIII-23-2 | $^iPr$ | H | H | $CH_3$ | $^iPr$ | H | H | F | OH |
| XXVIII-23-3 | $^iPr$ | H | H | $CH(CH_3)_2$ | $^iPr$ | H | H | F | OH |
| XXVIII-23-4 | $^iPr$ | H | H | $CH_2CH(CH_3)_2$ | $^iPr$ | H | H | F | OH |
| XXVIII-23-5 | $^iPr$ | H | H | $CH_2Ph$ | $^iPr$ | H | H | F | OH |
| XXVIII-23-6 | $^iPr$ | H | H | $CH_2$-indol-3-yl | $^iPr$ | H | H | F | OH |
| XXVIII-23-7 | $^iPr$ | H | H | $CH_2CH_2SCH_3$ | $^iPr$ | H | H | F | OH |
| XXVIII-23-8 | $^iPr$ | H | H | * | $^iPr$ | H | H | H | OH |

*$R^2$ and $R^{3b}$ joined together by $(CH_2)_3$ to form five-membered ring.

TABLE XXVIII-24

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-24-1 | $^tBu$ | H | H | H | $^iPr$ | H | H | F | OH |
| XXVIII-24-2 | $^tBu$ | H | H | $CH_3$ | $^iPr$ | H | H | F | OH |
| XXVIII-24-3 | $^tBu$ | H | H | $CH(CH_3)_2$ | $^iPr$ | H | H | F | OH |
| XXVIII-24-4 | $^tBu$ | H | H | $CH_2CH(CH_3)_2$ | $^iPr$ | H | H | F | OH |
| XXVIII-24-5 | $^tBu$ | H | H | $CH_2Ph$ | $^iPr$ | H | H | F | OH |
| XXVIII-24-6 | $^tBu$ | H | H | $CH_2$-indol-3-yl | $^iPr$ | H | H | F | OH |
| XXVIII-24-7 | $^tBu$ | H | H | $CH_2CH_2SCH_3$ | $^iPr$ | H | H | F | OH |
| XXVIII-24-8 | $^tBu$ | * | H | * | $^iPr$ | H | H | F | OH |

*$R^2$ and $R^{3b}$ joined together by $(CH_2)_3$ to form five-membered ring.

TABLE XXVIII-25

| No | R¹ | R² | R³ᵃ | R³ᵇ | R⁴ | R⁵ | R⁶ | X | Y |
|---|---|---|---|---|---|---|---|---|---|
| XXVIII-25-1 | Ph | H | H | H | $^i$Pr | H | H | F | OH |
| XXVIII-25-2 | Ph | H | H | CH₃ | $^i$Pr | H | H | F | OH |
| XXVIII-25-3 | Ph | H | H | CH(CH₃)₂ | $^i$Pr | H | H | F | OH |
| XXVIII-25-4 | Ph | H | H | CH₂CH(CH₃)₂ | $^i$Pr | H | H | F | OH |
| XXVIII-25-5 | Ph | H | H | CH₂Ph | $^i$Pr | H | H | F | OH |
| XXVIII-25-6 | Ph | H | H | CH₂-indol-3-yl | $^i$Pr | H | H | F | OH |
| XXVIII-25-7 | Ph | H | H | CH₂CH₂SCH₃ | $^i$Pr | H | H | F | OH |
| XXVIII-25-8 | Ph | * | H | * | $^i$Pr | H | H | F | OH |

*R² and R³ᵇ joined together by (CH₂)₃ to form five-membered ring.

TABLE XXVIII-26

| No | R¹ | R² | R³ᵃ | R³ᵇ | R⁴ | R⁵ | R⁶ | X | Y |
|---|---|---|---|---|---|---|---|---|---|
| XXVIII-26-1 | p-Me-Ph | H | H | H | $^i$Pr | H | H | F | OH |
| XXVIII-26-2 | p-Me-Ph | H | H | CH₃ | $^i$Pr | H | H | F | OH |
| XXVIII-26-3 | p-Me-Ph | H | H | CH(CH₃)₂ | $^i$Pr | H | H | F | OH |
| XXVIII-26-4 | p-Me-Ph | H | H | CH₂CH(CH₃)₂ | $^i$Pr | H | H | F | OH |
| XXVIII-26-5 | p-Me-Ph | H | H | CH₂Ph | $^i$Pr | H | H | F | OH |
| XXVIII-26-6 | p-Me-Ph | H | H | CH₂-indol-3-yl | $^i$Pr | H | H | F | OH |
| XXVIII-26-7 | p-Me-Ph | H | H | CH₂CH₂SCH₃ | $^i$Pr | H | H | F | OH |
| XXVIII-26-8 | p-Me-Ph | * | H | * | $^i$Pr | H | H | F | OH |

*R² and R³ᵇ joined together by (CH₂)₃ to form five-membered ring.

TABLE XXVIII-27

| No | R¹ | R² | R³ᵃ | R³ᵇ | R⁴ | R⁵ | R⁶ | X | Y |
|---|---|---|---|---|---|---|---|---|---|
| XXVIII-27-1 | p-F—Ph | H | H | H | $^i$Pr | H | H | F | OH |
| XXVIII-27-2 | p-F—Ph | H | H | CH₃ | $^i$Pr | H | H | F | OH |
| XXVIII-27-3 | p-F—Ph | H | H | CH(CH₃)₂ | $^i$Pr | H | H | F | OH |
| XXVIII-27-4 | p-F—Ph | H | H | CH₂CH(CH₃)₂ | $^i$Pr | H | H | F | OH |
| XXVIII-27-5 | p-F—Ph | H | H | CH₂Ph | $^i$Pr | H | H | F | OH |
| XXVIII-27-6 | p-F—Ph | H | H | CH₂-indol-3-yl | $^i$Pr | H | H | F | OH |
| XXVIII-27-7 | p-F—Ph | H | H | CH₂CH₂SCH₃ | $^i$Pr | H | H | F | OH |
| XXVIII-27-8 | p-F—Ph | * | H | * | $^i$Pr | H | H | F | OH |

*R² and R³ᵇ joined together by (CH₂)₃ to form five-membered ring.

TABLE XXVIII-28

| No | R¹ | R² | R³ᵃ | R³ᵇ | R⁴ | R⁵ | R⁶ | X | Y |
|---|---|---|---|---|---|---|---|---|---|
| XXVIII-28-1 | p-Cl—Ph | H | H | H | $^i$Pr | H | H | F | OH |
| XXVIII-28-2 | p-Cl—Ph | H | H | CH₃ | $^i$Pr | H | H | F | OH |
| XXVIII-28-3 | p-Cl—Ph | H | H | CH(CH₃)₂ | $^i$Pr | H | H | F | OH |
| XXVIII-28-4 | p-Cl—Ph | H | H | CH₂CH(CH₃)₂ | $^i$Pr | H | H | F | OH |
| XXVIII-28-5 | p-Cl—Ph | H | H | CH₂Ph | $^i$Pr | H | H | F | OH |
| XXVIII-28-6 | p-Cl—Ph | H | H | CH₂-indol-3-yl | $^i$Pr | H | H | F | OH |
| XXVIII-28-7 | p-Cl—Ph | H | H | CH₂CH₂SCH₃ | $^i$Pr | H | H | F | OH |
| XXVIII-28-8 | p-Cl—Ph | * | H | * | $^i$Pr | H | H | F | OH |

*R² and R³ᵇ joined together by (CH₂)₃ to form five-membered ring.

TABLE XXVIII-29

| No | R¹ | R² | R³ᵃ | R³ᵇ | R⁴ | R⁵ | R⁶ | X | Y |
|---|---|---|---|---|---|---|---|---|---|
| XXVIII-29-1 | p-Br—Ph | H | H | H | $^i$Pr | H | H | F | OH |
| XXVIII-29-2 | p-Br—Ph | H | H | CH₃ | $^i$Pr | H | H | F | OH |
| XXVIII-29-3 | p-Br—Ph | H | H | CH(CH₃)₂ | $^i$Pr | H | H | F | OH |
| XXVIII-29-4 | p-Br—Ph | H | H | CH₂CH(CH₃)₂ | $^i$Pr | H | H | F | OH |
| XXVIII-29-5 | p-Br—Ph | H | H | CH₂Ph | $^i$Pr | H | H | F | OH |
| XXVIII-29-6 | p-Br—Ph | H | H | CH₂-indol-3-yl | $^i$Pr | H | H | F | OH |
| XXVIII-29-7 | p-Br—Ph | H | H | CH₂CH₂SCH₃ | $^i$Pr | H | H | F | OH |
| XXVIII-29-8 | p-Br—Ph | * | H | * | $^i$Pr | H | H | F | OH |

*R² and R³ᵇ joined together by (CH₂)₃ to form five-membered ring.

TABLE XXVIII-30

| No | R¹ | R² | R³ᵃ | R³ᵇ | R⁴ | R⁵ | R⁶ | X | Y |
|---|---|---|---|---|---|---|---|---|---|
| XXVIII-30-1 | p-I—Ph | H | H | H | $^i$Pr | H | H | F | OH |
| XXVIII-30-2 | p-I—Ph | H | H | CH₃ | $^i$Pr | H | H | F | OH |
| XXVIII-30-3 | p-I—Ph | H | H | CH(CH₃)₂ | $^i$Pr | H | H | F | OH |
| XXVIII-30-4 | p-I—Ph | H | H | CH₂CH(CH₃)₂ | $^i$Pr | H | H | F | OH |
| XXVIII-30-5 | p-I—Ph | H | H | CH₂Ph | $^i$Pr | H | H | F | OH |
| XXVIII-30-6 | p-I—Ph | H | H | CH₂-indol-3-yl | $^i$Pr | H | H | F | OH |
| XXVIII-30-7 | p-I—Ph | H | H | CH₂CH₂SCH₃ | $^i$Pr | H | H | F | OH |
| XXVIII-30-8 | p-I—Ph | * | H | * | $^i$Pr | H | H | F | OH |

*R² and R³ᵇ joined together by (CH₂)₃ to form five-membered ring.

TABLE XXVIII-31

| No | R¹ | R² | R³ᵃ | R³ᵇ | R⁴ | R⁵ | R⁶ | X | Y |
|---|---|---|---|---|---|---|---|---|---|
| XXVIII-31-1 | CH₃ | H | H | H | $^n$Bu | H | H | F | OH |
| XXVIII-31-2 | CH₃ | H | H | CH₃ | $^n$Bu | H | H | F | OH |
| XXVIII-31-3 | CH₃ | H | H | CH(CH₃)₂ | $^n$Bu | H | H | F | OH |
| XXVIII-31-4 | CH₃ | H | H | CH₂CH(CH₃)₂ | $^n$Bu | H | H | F | OH |
| XXVIII-31-5 | CH₃ | H | H | CH₂Ph | $^n$Bu | H | H | F | OH |
| XXVIII-31-6 | CH₃ | H | H | CH₂-indol-3-yl | $^n$Bu | H | H | F | OH |
| XXVIII-31-7 | CH₃ | H | H | CH₂CH₂SCH₃ | $^n$Bu | H | H | F | OH |
| XXVIII-31-8 | CH₃ | * | H | * | $^n$Bu | H | H | F | OH |

*R² and R³ᵇ joined together by (CH₂)₃ to form five-membered ring.

TABLE XXVIII-32

| No | R¹ | R² | R³ᵃ | R³ᵇ | R⁴ | R⁵ | R⁶ | X | Y |
|---|---|---|---|---|---|---|---|---|---|
| XXVIII-32-1 | Et | H | H | H | $^n$Bu | H | H | F | OH |
| XXVIII-32-2 | Et | H | H | CH₃ | $^n$Bu | H | H | F | OH |
| XXVIII-32-3 | Et | H | H | CH(CH₃)₂ | $^n$Bu | H | H | F | OH |
| XXVIII-32-4 | Et | H | H | CH₂CH(CH₃)₂ | $^n$Bu | H | H | F | OH |
| XXVIII-32-5 | Et | H | H | CH₂Ph | $^n$Bu | H | H | F | OH |
| XXVIII-32-6 | Et | H | H | CH₂-indol-3-yl | $^n$Bu | H | H | F | OH |
| XXVIII-32-7 | Et | H | H | CH₂CH₂SCH₃ | $^n$Bu | H | H | F | OH |
| XXVIII-32-8 | Et | * | H | * | $^n$Bu | H | H | F | OH |

*R² and R³ᵇ joined together by (CH₂)₃ to form five-membered ring.

TABLE XXVIII-33

| No | R¹ | R² | R³ᵃ | R³ᵇ | R⁴ | R⁵ | R⁶ | X | Y |
|---|---|---|---|---|---|---|---|---|---|
| XXVIII-33-1 | $^i$Pr | H | H | H | $^n$Bu | H | H | F | OH |
| XXVIII-33-2 | $^i$Pr | H | H | CH₃ | $^n$Bu | H | H | F | OH |
| XXVIII-33-3 | $^i$Pr | H | H | CH(CH₃)₂ | $^n$Bu | H | H | F | OH |
| XXVIII-33-4 | $^i$Pr | H | H | CH₂CH(CH₃)₂ | $^n$Bu | H | H | F | OH |
| XXVIII-33-5 | $^i$Pr | H | H | CH₂Ph | $^n$Bu | H | H | F | OH |
| XXVIII-33-6 | $^i$Pr | H | H | CH₂-indol-3-yl | $^n$Bu | H | H | F | OH |
| XXVIII-33-7 | $^i$Pr | H | H | CH₂CH₂SCH₃ | $^n$Bu | H | H | F | OH |
| XXVIII-33-8 | $^i$Pr | * | H | * | $^n$Bu | H | H | F | OH |

*R² and R³ᵇ joined together by (CH₂)₃ to form five-membered ring.

TABLE XXVIII-34

| No | R¹ | R² | R³ᵃ | R³ᵇ | R⁴ | R⁵ | R⁶ | X | Y |
|---|---|---|---|---|---|---|---|---|---|
| XXVIII-34-1 | ᵗBu | H | H | H | ⁿBu | H | H | F | OH |
| XXVIII-34-2 | ᵗBu | H | H | CH₃ | ⁿBu | H | H | F | OH |
| XXVIII-34-3 | ᵗBu | H | H | CH(CH₃)₂ | ⁿBu | H | H | F | OH |
| XXVIII-34-4 | ᵗBu | H | H | CH₂CH(CH₃)₂ | ⁿBu | H | H | F | OH |
| XXVIII-34-5 | ᵗBu | H | H | CH₂Ph | ⁿBu | H | H | F | OH |
| XXVIII-34-6 | ᵗBu | H | H | CH₂-indol-3-yl | ⁿBu | H | H | F | OH |
| XXVIII-34-7 | ᵗBu | H | H | CH₂CH₂SCH₃ | ⁿBu | H | H | F | OH |
| XXVIII-34-8 | ᵗBu | * | H | * | ⁿBu | H | H | F | OH |

*R² and R³ᵇ joined together by (CH₂)₃ to form five-membered ring.

TABLE XXVIII-35

| No | R¹ | R² | R³ᵃ | R³ᵇ | R⁴ | R⁵ | R⁶ | X | Y |
|---|---|---|---|---|---|---|---|---|---|
| XXVIII-35-1 | Ph | H | H | H | ⁿBu | H | H | F | OH |
| XXVIII-35-2 | Ph | H | H | CH₃ | ⁿBu | H | H | F | OH |
| XXVIII-35-3 | Ph | H | H | CH(CH₃)₂ | ⁿBu | H | H | F | OH |
| XXVIII-35-4 | Ph | H | H | CH₂CH(CH₃)₂ | ⁿBu | H | H | F | OH |
| XXVIII-35-5 | Ph | H | H | CH₂Ph | ⁿBu | H | H | F | OH |
| XXVIII-35-6 | Ph | H | H | CH₂-indol-3-yl | ⁿBu | H | H | F | OH |
| XXVIII-35-7 | Ph | H | H | CH₂CH₂SCH₃ | ⁿBu | H | H | F | OH |
| XXVIII-35-8 | Ph | * | H | * | ⁿBu | H | H | F | OH |

*R² and R³ᵇ joined together by (CH₂)₃ to form five-membered ring.

TABLE XXVIII-36

| No | R¹ | R² | R³ᵃ | R³ᵇ | R⁴ | R⁵ | R⁶ | X | Y |
|---|---|---|---|---|---|---|---|---|---|
| XXVIII-36-1 | p-Me—Ph | H | H | H | ⁿBu | H | H | F | OH |
| XXVIII-36-2 | p-Me—Ph | H | H | CH₃ | ⁿBu | H | H | F | OH |
| XXVIII-36-3 | p-Me—Ph | H | H | CH(CH₃)₂ | ⁿBu | H | H | F | OH |
| XXVIII-36-4 | p-Me—Ph | H | H | CH₂CH(CH₃)₂ | ⁿBu | H | H | F | OH |
| XXVIII-36-5 | p-Me—Ph | H | H | CH₂Ph | ⁿBu | H | H | F | OH |
| XXVIII-36-6 | p-Me—Ph | H | H | CH₂-indol-3-yl | ⁿBu | H | H | F | OH |
| XXVIII-36-7 | p-Me—Ph | H | H | CH₂CH₂SCH₃ | ⁿBu | H | H | F | OH |
| XXVIII-36-8 | p-Me—Ph | * | H | * | ⁿBu | H | H | F | OH |

*R² and R³ᵇ joined together by (CH₂)₃ to form five-membered ring.

TABLE XXVIII-37

| No | R¹ | R² | R³ᵃ | R³ᵇ | R⁴ | R⁵ | R⁶ | X | Y |
|---|---|---|---|---|---|---|---|---|---|
| XXVIII-37-1 | p-F—Ph | H | H | H | ⁿBu | H | H | F | OH |
| XXVIII-37-2 | p-F—Ph | H | H | CH₃ | ⁿBu | H | H | F | OH |
| XXVIII-37-3 | p-F—Ph | H | H | CH(CH₃)₂ | ⁿBu | H | H | F | OH |
| XXVIII-37-4 | p-F—Ph | H | H | CH₂CH(CH₃)₂ | ⁿBu | H | H | F | OH |
| XXVIII-37-5 | p-F—Ph | H | H | CH₂Ph | ⁿBu | H | H | F | OH |
| XXVIII-37-6 | p-F—Ph | H | H | CH₂-indol-3-yl | ⁿBu | H | H | F | OH |
| XXVIII-37-7 | p-F—Ph | H | H | CH₂CH₂SCH₃ | ⁿBu | H | H | F | OH |
| XXVIII-37-8 | p-F—Ph | * | H | * | ⁿBu | H | H | F | OH |

*R² and R³ᵇ joined together by (CH₂)₃ to form five-membered ring.

TABLE XXVIII-38

| No | R¹ | R² | R³ᵃ | R³ᵇ | R⁴ | R⁵ | R⁶ | X | Y |
|---|---|---|---|---|---|---|---|---|---|
| XXVIII-38-1 | p-Cl—Ph | H | H | H | ⁿBu | H | H | F | OH |
| XXVIII-38-2 | p-Cl—Ph | H | H | CH₃ | ⁿBu | H | H | F | OH |
| XXVIII-38-3 | p-Cl—Ph | H | H | CH(CH₃)₂ | ⁿBu | H | H | F | OH |
| XXVIII-38-4 | p-Cl—Ph | H | H | CH₂CH(CH₃)₂ | ⁿBu | H | H | F | OH |
| XXVIII-38-5 | p-Cl—Ph | H | H | CH₂Ph | ⁿBu | H | H | F | OH |
| XXVIII-38-6 | p-Cl—Ph | H | H | CH₂-indol-3-yl | ⁿBu | H | H | F | OH |
| XXVIII-38-7 | p-Cl—Ph | H | H | CH₂CH₂SCH₃ | ⁿBu | H | H | F | OH |
| XXVIII-38-8 | p-Cl—Ph | * | H | * | ⁿBu | H | H | F | OH |

*R² and R³ᵇ joined together by (CH₂)₃ to form five-membered ring.

TABLE XXVIII-39

| No | R¹ | R² | R³ᵃ | R³ᵇ | R⁴ | R⁵ | R⁶ | X | Y |
|---|---|---|---|---|---|---|---|---|---|
| XXVIII-39-1 | p-Br—Ph | H | H | H | ⁿBu | H | H | F | OH |
| XXVIII-39-2 | p-Br—Ph | H | H | CH₃ | ⁿBu | H | H | F | OH |
| XXVIII-39-3 | p-Br—Ph | H | H | CH(CH₃)₂ | ⁿBu | H | H | F | OH |
| XXVIII-39-4 | p-Br—Ph | H | H | CH₂CH(CH₃)₂ | ⁿBu | H | H | F | OH |
| XXVIII-39-5 | p-Br—Ph | H | H | CH₂Ph | ⁿBu | H | H | F | OH |
| XXVIII-39-6 | p-Br—Ph | H | H | CH₂-indol-3-yl | ⁿBu | H | H | F | OH |
| XXVIII-39-7 | p-Br—Ph | H | H | CH₂CH₂SCH₃ | ⁿBu | H | H | F | OH |
| XXVIII-39-8 | p-Br—Ph | * | H | * | ⁿBu | H | H | F | OH |

*R² and R³ᵇ joined together by (CH₂)₃ to form five-membered ring.

TABLE XXVIII-40

| No | R¹ | R² | R³ᵃ | R³ᵇ | R⁴ | R⁵ | R⁶ | X | Y |
|---|---|---|---|---|---|---|---|---|---|
| XXVIII-40-1 | p-I—Ph | H | H | H | ⁿBu | H | H | F | OH |
| XXVIII-40-2 | p-I—Ph | H | H | CH₃ | ⁿBu | H | H | F | OH |
| XXVIII-40-3 | p-I—Ph | H | H | CH(CH₃)₂ | ⁿBu | H | H | F | OH |
| XXVIII-40-4 | p-I—Ph | H | H | CH₂CH(CH₃)₂ | ⁿBu | H | H | F | OH |
| XXVIII-40-5 | p-I—Ph | H | H | CH₂Ph | ⁿBu | H | H | F | OH |
| XXVIII-40-6 | p-I—Ph | H | H | CH₂-indol-3-yl | ⁿBu | H | H | F | OH |
| XXVIII-40-7 | p-I—Ph | H | H | CH₂CH₂SCH₃ | ⁿBu | H | H | F | OH |
| XXVIII-40-8 | p-I—Ph | * | H | * | ⁿBu | H | H | F | OH |

*R² and R³ᵇ joined together by (CH₂)₃ to form five-membered ring.

TABLE XXVIII-41

| No | R¹ | R² | R³ᵃ | R³ᵇ | R⁴ | R⁵ | R⁶ | X | Y |
|---|---|---|---|---|---|---|---|---|---|
| XXVIII-41-1 | CH₃ | H | H | H | Bz | H | H | F | OH |
| XXVIII-41-2 | CH₃ | H | H | CH₃ | Bz | H | H | F | OH |
| XXVIII-41-3 | CH₃ | H | H | CH(CH₃)₂ | Bz | H | H | F | OH |
| XXVIII-41-4 | CH₃ | H | H | CH₂CH(CH₃)₂ | Bz | H | H | F | OH |
| XXVIII-41-5 | CH₃ | H | H | CH₂Ph | Bz | H | H | F | OH |
| XXVIII-41-6 | CH₃ | H | H | CH₂-indol-3-yl | Bz | H | H | F | OH |
| XXVIII-41-7 | CH₃ | H | H | CH₂CH₂SCH₃ | Bz | H | H | F | OH |
| XXVIII-41-8 | CH₃ | * | H | * | Bz | H | H | F | OH |

*R² and R³ᵇ joined together by (CH₂)₃ to form five-membered ring.

TABLE XXVIII-42

| No | R¹ | R² | R³ᵃ | R³ᵇ | R⁴ | R⁵ | R⁶ | X | Y |
|---|---|---|---|---|---|---|---|---|---|
| XXVIII-42-1 | Et | H | H | H | Bz | H | H | F | OH |
| XXVIII-42-2 | Et | H | H | CH₃ | Bz | H | H | F | OH |

TABLE XXVIII-42-continued

| No | R¹ | R² | R³ᵃ | R³ᵇ | R⁴ | R⁵ | R⁶ | X | Y |
|---|---|---|---|---|---|---|---|---|---|
| XXVIII-42-3 | Et | H | H | CH(CH₃)₂ | Bz | H | H | F | OH |
| XXVIII-42-4 | Et | H | H | CH₂CH(CH₃)₂ | Bz | H | H | F | OH |
| XXVIII-42-5 | Et | H | H | CH₂Ph | Bz | H | H | F | OH |
| XXVIII-42-6 | Et | H | H | CH₂-indol-3-yl | Bz | H | H | F | OH |
| XXVIII-42-7 | Et | H | H | CH₂CH₂SCH₃ | Bz | H | H | F | OH |
| XXVIII-42-8 | Et | * | H | * | Bz | H | H | F | OH |

*R² and R³ᵇ joined together by (CH₂)₃ to form five-membered ring.

TABLE XXVIII-43

| No | R¹ | R² | R³ᵃ | R³ᵇ | R⁴ | R⁵ | R⁶ | X | Y |
|---|---|---|---|---|---|---|---|---|---|
| XXVIII-43-1 | ⁱPr | H | H | H | Bz | H | H | F | OH |
| XXVIII-43-2 | ⁱPr | H | H | CH₃ | Bz | H | H | F | OH |
| XXVIII-43-3 | ⁱPr | H | H | CH(CH₃)₂ | Bz | H | H | F | OH |
| XXVIII-43-4 | ⁱPr | H | H | CH₂CH(CH₃)₂ | Bz | H | H | F | OH |
| XXVIII-43-5 | ⁱPr | H | H | CH₂Ph | Bz | H | H | F | OH |
| XXVIII-43-6 | ⁱPr | H | H | CH₂-indol-3-yl | Bz | H | H | F | OH |
| XXVIII-43-7 | ⁱPr | H | H | CH₂CH₂SCH₃ | Bz | H | H | F | OH |
| XXVIII-43-8 | ⁱPr | * | H | * | Bz | H | H | F | OH |

*R² and R³ᵇ joined together by (CH₂)₃ to form five-membered ring.

TABLE XXVIII-44

| No | R¹ | R² | R³ᵃ | R³ᵇ | R⁴ | R⁵ | R⁶ | X | Y |
|---|---|---|---|---|---|---|---|---|---|
| XXVIII-44-1 | ᵗBu | H | H | H | Bz | H | H | F | OH |
| XXVIII-44-2 | ᵗBu | H | H | CH₃ | Bz | H | H | F | OH |
| XXVIII-44-3 | ᵗBu | H | H | CH(CH₃)₂ | Bz | H | H | F | OH |
| XXVIII-44-4 | ᵗBu | H | H | CH₂CH(CH₃)₂ | Bz | H | H | F | OH |
| XXVIII-44-5 | ᵗBu | H | H | CH₂Ph | Bz | H | H | F | OH |
| XXVIII-44-6 | ᵗBu | H | H | CH₂-indol-3-yl | Bz | H | H | F | OH |
| XXVIII-44-7 | ᵗBu | H | H | CH₂CH₂SCH₃ | Bz | H | H | F | OH |
| XXVIII-44-8 | ᵗBu | * | H | * | Bz | H | H | F | OH |

*R² and R³ᵇ joined together by (CH₂)₃ to form five-membered ring.

TABLE XXVIII-45

| No | R¹ | R² | R³ᵃ | R³ᵇ | R⁴ | R⁵ | R⁶ | X | Y |
|---|---|---|---|---|---|---|---|---|---|
| XXVIII-45-1 | Ph | H | H | H | Bz | H | H | F | OH |
| XXVIII-45-2 | Ph | H | H | CH₃ | Bz | H | H | F | OH |
| XXVIII-45-3 | Ph | H | H | CH(CH₃)₂ | Bz | H | H | F | OH |
| XXVIII-45-4 | Ph | H | H | CH₂CH(CH₃)₂ | Bz | H | H | F | OH |
| XXVIII-45-5 | Ph | H | H | CH₂Ph | Bz | H | H | F | OH |
| XXVIII-45-6 | Ph | H | H | CH₂-indol-3-yl | Bz | H | H | F | OH |
| XXVIII-45-7 | Ph | H | H | CH₂CH₂SCH₃ | Bz | H | H | F | OH |
| XXVIII-45-8 | Ph | * | H | * | Bz | H | H | F | OH |

*R² and R³ᵇ joined together by (CH₂)₃ to form five-membered ring.

TABLE XXVIII-46

| No | R¹ | R² | R³ᵃ | R³ᵇ | R⁴ | R⁵ | R⁶ | X | Y |
|---|---|---|---|---|---|---|---|---|---|
| XXVIII-46-1 | p-Me—Ph | H | H | H | Bz | H | H | F | OH |
| XXVIII-46-2 | p-Me—Ph | H | H | CH₃ | Bz | H | H | F | OH |
| XXVIII-46-3 | p-Me—Ph | H | H | CH(CH₃)₂ | Bz | H | H | F | OH |
| XXVIII-46-4 | p-Me—Ph | H | H | CH₂CH(CH₃)₂ | Bz | H | H | F | OH |
| XXVIII-46-5 | p-Me—Ph | H | H | CH₂Ph | Bz | H | H | F | OH |
| XXVIII-46-6 | p-Me—Ph | H | H | CH₂-indol-3-yl | Bz | H | H | F | OH |
| XXVIII-46-7 | p-Me—Ph | H | H | CH₂CH₂SCH₃ | Bz | H | H | F | OH |
| XXVIII-46-8 | p-Me—Ph | * | H | * | Bz | H | H | F | OH |

*R² and R³ᵇ joined together by (CH₂)₃ to form five-membered ring.

TABLE XXVIII-47

| No | R¹ | R² | R³ᵃ | R³ᵇ | R⁴ | R⁵ | R⁶ | X | Y |
|---|---|---|---|---|---|---|---|---|---|
| XXVIII-47-1 | p-F—Ph | H | H | H | Bz | H | H | F | OH |
| XXVIII-47-2 | p-F—Ph | H | H | CH₃ | Bz | H | H | F | OH |
| XXVIII-47-3 | p-F—Ph | H | H | CH(CH₃)₂ | Bz | H | H | F | OH |
| XXVIII-47-4 | p-F—Ph | H | H | CH₂CH(CH₃)₂ | Bz | H | H | F | OH |
| XXVIII-47-5 | p-F—Ph | H | H | CH₂Ph | Bz | H | H | F | OH |
| XXVIII-47-6 | p-F—Ph | H | H | CH₂-indol-3-yl | Bz | H | H | F | OH |
| XXVIII-47-7 | p-F—Ph | H | H | CH₂CH₂SCH₃ | Bz | H | H | F | OH |
| XXVIII-47-8 | p-F—Ph | * | H | * | Bz | H | H | F | OH |

*R² and R³ᵇ joined together by (CH₂)₃ to form five-membered ring.

TABLE XXVIII-48

| No | R¹ | R² | R³ᵃ | R³ᵇ | R⁴ | R⁵ | R⁶ | X | Y |
|---|---|---|---|---|---|---|---|---|---|
| XXVIII-48-1 | p-Cl—Ph | H | H | H | Bz | H | H | F | OH |
| XXVIII-48-2 | p-Cl—Ph | H | H | CH₃ | Bz | H | H | F | OH |
| XXVIII-48-3 | p-Cl—Ph | H | H | CH(CH₃)₂ | Bz | H | H | F | OH |
| XXVIII-48-4 | p-Cl—Ph | H | H | CH₂CH(CH₃)₂ | Bz | H | H | F | OH |
| XXVIII-48-5 | p-Cl—Ph | H | H | CH₂Ph | Bz | H | H | F | OH |
| XXVIII-48-6 | p-Cl—Ph | H | H | CH₂-indol-3-yl | Bz | H | H | F | OH |
| XXVIII-48-7 | p-Cl—Ph | H | H | CH₂CH₂SCH₃ | Bz | H | H | F | OH |
| XXVIII-48-8 | p-Cl—Ph | * | H | * | Bz | H | H | F | OH |

*R² and R³ᵇ joined together by (CH₂)₃ to form five-membered ring.

TABLE XXVIII-49

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-49-1 | p-Br—Ph | H | H | H | Bz | H | H | F | OH |
| XXVIII-49-2 | p-Br—Ph | H | H | $CH_3$ | Bz | H | H | F | OH |
| XXVIII-49-3 | p-Br—ph | H | H | $CH(CH_3)_2$ | Bz | H | H | F | OH |
| XXVIII-49-4 | p-Br—Ph | H | H | $CH_2CH(CH_3)_2$ | Bz | H | H | F | OH |
| XXVIII-49-5 | p-Br—Ph | H | H | $CH_2Ph$ | Bz | H | H | F | OH |
| XXVIII-49-6 | p-Br—Ph | H | H | $CH_2$-indol-3-yl | Bz | H | H | F | OH |
| XXVIII-49-7 | p-Br—Ph | H | H | $CH_2CH_2SCH_3$ | Bz | H | H | F | OH |
| XXVIII-49-8 | p-Br—Ph | * | H | * | Bz | H | H | F | OH |

*$R^2$ and $R^{3b}$ joined together by $(CH_2)_3$ to form five-membered ring.

TABLE XXVIII-50

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXVIII-50-1 | p-I—Ph | H | H | H | Bz | H | H | F | OH |
| XXVIII-50-2 | p-I—Ph | H | H | $CH_3$ | Bz | H | H | F | OH |
| XXVIII-50-3 | p-I—Ph | H | H | $CH(CH_3)_2$ | Bz | H | H | F | OH |
| XXVIII-50-4 | p-I—Ph | H | H | $CH_2CH(CH_3)_2$ | Bz | H | H | F | OH |
| XXVIII-50-5 | p-I—Ph | H | H | $CH_2Ph$ | Bz | H | H | F | OH |
| XXVIII-50-6 | p-I—Ph | H | H | $CH_2$-indol-3-yl | Bz | H | H | F | OH |
| XXVIII-50-7 | p-I—Ph | H | H | $CH_2CH_2SCH_3$ | Bz | H | H | F | OH |
| XXVIII-50-8 | p-I—Ph | * | H | * | Bz | H | H | F | OH |

*$R^2$ and $R^{3b}$ joined together by $(CH_2)_3$ to form five-membered ring.

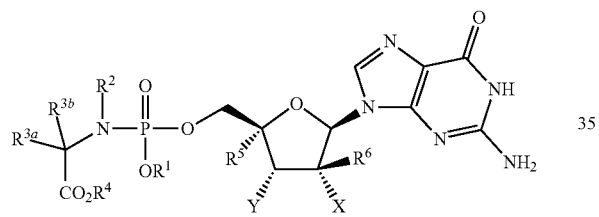

XXIX

TABLE XXIX-1

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIX-1-1 | $CH_3$ | H | H | H | $CH_3$ | H | $CH_3$ | F | OH |
| XXIX-1-2 | $CH_3$ | H | H | $CH_3$ | $CH_3$ | H | $CH_3$ | F | OH |
| XXIX-1-3 | $CH_3$ | H | H | $CH(CH_3)_2$ | $CH_3$ | H | $CH_3$ | F | OH |
| XXIX-1-4 | $CH_3$ | H | H | $CH_2CH(CH_3)_2$ | $CH_3$ | H | $CH_3$ | F | OH |
| XXIX-1-5 | $CH_3$ | H | H | $CH_2Ph$ | $CH_3$ | H | $CH_3$ | F | OH |
| XXIX-1-6 | $CH_3$ | H | H | $CH_2$-indol-3-yl | $CH_3$ | H | $CH_3$ | F | OH |
| XXIX-1-7 | $CH_3$ | H | H | $CH_2CH_2SCH_3$ | $CH_3$ | H | $CH_3$ | F | OH |
| XXIX-1-8 | $CH_3$ | * | H | * | $CH_3$ | H | $CH_3$ | F | OH |

*$R^2$ and $R^{3b}$ joined together by $(CH_2)_3$ to form five-membered ring.

TABLE XXIX-2

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIX-2-1 | Et | H | H | H | $CH_3$ | H | $CH_3$ | F | OH |
| XXIX-2-2 | Et | H | H | $CH_3$ | $CH_3$ | H | $CH_3$ | F | OH |
| XXIX-2-3 | Et | H | H | $CH(CH_3)_2$ | $CH_3$ | H | $CH_3$ | F | OH |
| XXIX-2-4 | Et | H | H | $CH_2CH(CH_3)_2$ | $CH_3$ | H | $CH_3$ | F | OH |
| XXIX-2-5 | Et | H | H | $CH_2Ph$ | $CH_3$ | H | $CH_3$ | F | OH |
| XXIX-2-6 | Et | H | H | $CH_2$-indol-3-yl | $CH_3$ | H | $CH_3$ | F | OH |
| XXIX-2-7 | Et | H | H | $CH_2CH_2SCH_3$ | $CH_3$ | H | $CH_3$ | F | OH |
| XXIX-2-8 | Et | * | H | * | $CH_3$ | H | $CH_3$ | F | OH |

*$R^2$ and $R^{3b}$ joined together by $(CH_2)_3$ to form five-membered ring.

TABLE XXIX-3

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIX-3-1 | $^i$Pr | H | H | H | $CH_3$ | H | $CH_3$ | F | OH |
| XXIX-3-2 | $^i$Pr | H | H | $CH_3$ | $CH_3$ | H | $CH_3$ | F | OH |
| XXIX-3-3 | $^i$Pr | H | H | $CH(CH_3)_2$ | $CH_3$ | H | $CH_3$ | F | OH |
| XXIX-3-4 | $^i$Pr | H | H | $CH_2CH(CH_3)_2$ | $CH_3$ | H | $CH_3$ | F | OH |
| XXIX-3-5 | $^i$Pr | H | H | $CH_2Ph$ | $CH_3$ | H | $CH_3$ | F | OH |
| XXIX-3-6 | $^i$Pr | H | H | $CH_2$-indol-3-yl | $CH_3$ | H | $CH_3$ | F | OH |
| XXIX-3-7 | $^i$Pr | H | H | $CH_2CH_2SCH_3$ | $CH_3$ | H | $CH_3$ | F | OH |
| XXIX-3-8 | $^i$Pr | * | H | * | $CH_3$ | H | $CH_3$ | F | OH |

*$R^2$ and $R^{3b}$ joined together by $(CH_2)_3$ to form five-membered ring.

TABLE XXIX-4

| No | R¹ | R² | R³ᵃ | R³ᵇ | R⁴ | R⁵ | R⁶ | X | Y |
|---|---|---|---|---|---|---|---|---|---|
| XXIX-4-1 | ᵗBu | H | H | H | CH₃ | H | CH₃ | F | OH |
| XXIX-4-2 | ᵗBu | H | H | CH₃ | CH₃ | H | CH₃ | F | OH |
| XXIX-4-3 | ᵗBu | H | H | CH(CH₃)₂ | CH₃ | H | CH₃ | F | OH |
| XXIX-4-4 | ᵗBu | H | H | CH₂CH(CH₃)₂ | CH₃ | H | CH₃ | F | OH |
| XXIX-4-5 | ᵗBu | H | H | CH₂Ph | CH₃ | H | CH₃ | F | OH |
| XXIX-4-6 | ᵗBu | H | H | CH₂-indol-3-yl | CH₃ | H | CH₃ | F | OH |
| XXIX-4-7 | ᵗBu | H | H | CH₂CH₂SCH₃ | CH₃ | H | CH₃ | F | OH |
| XXIX-4-8 | ᵗBu | * | H | * | CH₃ | H | CH₃ | F | OH |

*$R^2$ and $R^{3b}$ joined together by (CH₂)₃ to form five-membered ring.

TABLE XXIX-5

| No | R¹ | R² | R³ᵃ | R³ᵇ | R⁴ | R⁵ | R⁶ | X | Y |
|---|---|---|---|---|---|---|---|---|---|
| XXIX-5-1 | Ph | H | H | H | CH₃ | H | CH₃ | F | OH |
| XXIX-5-2 | Ph | H | H | CH₃ | CH₃ | H | CH₃ | F | OH |
| XXIX-5-3 | Ph | H | H | CH(CH₃)₂ | CH₃ | H | CH₃ | F | OH |
| XXIX-5-4 | Ph | H | H | CH₂CH(CH₃)₂ | CH₃ | H | CH₃ | F | OH |
| XXIX-5-5 | Ph | H | H | CH₂Ph | CH₃ | H | CH₃ | F | OH |
| XXIX-5-6 | Ph | H | H | CH₂-indol-3-yl | CH₃ | H | CH₃ | F | OH |
| XXIX-5-7 | Ph | H | H | CH₂CH₂SCH₃ | CH₃ | H | CH₃ | F | OH |
| XXIX-5-8 | Ph | * | H | * | CH₃ | H | CH₃ | F | OH |

*$R^2$ and $R^{3b}$ joined together by (CH₂)₃ to form five-membered ring.

TABLE XXIX-6

| No | R¹ | R² | R³ᵃ | R³ᵇ | R⁴ | R⁵ | R⁶ | X | Y |
|---|---|---|---|---|---|---|---|---|---|
| XXIX-6-1 | p-Me—Ph | H | H | H | CH₃ | H | CH₃ | F | OH |
| XXIX-6-2 | p-Me—Ph | H | H | CH₃ | CH₃ | H | CH₃ | F | OH |
| XXIX-6-3 | p-Me—Ph | H | H | CH(CH₃)₂ | CH₃ | H | CH₃ | F | OH |
| XXIX-6-4 | p-Me—Ph | H | H | CH₂CH(CH₃)₂ | CH₃ | H | CH₃ | F | OH |
| XXIX-6-5 | p-Me—Ph | H | H | CH₂Ph | CH₃ | H | CH₃ | F | OH |
| XXIX-6-6 | p-Me—Ph | H | H | CH₂-indol-3-yl | CH₃ | H | CH₃ | F | OH |
| XXIX-6-7 | p-Me—Ph | H | H | CH₂CH₂SCH₃ | CH₃ | H | CH₃ | F | OH |
| XXIX-6-8 | p-Me—Ph | * | H | * | CH₃ | H | CH₃ | F | OH |

*$R^2$ and $R^{3b}$ joined together by (CH₂)₃ to form five-membered ring.

TABLE XXIX-7

| No | R¹ | R² | R³ᵃ | R³ᵇ | R⁴ | R⁵ | R⁶ | X | Y |
|---|---|---|---|---|---|---|---|---|---|
| XXIX-7-1 | p-F—Ph | H | H | H | CH₃ | H | CH₃ | F | OH |
| XXIX-7-2 | p-F—Ph | H | H | CH₃ | CH₃ | H | CH₃ | F | OH |
| XXIX-7-3 | p-F—Ph | H | H | CH(CH₃)₂ | CH₃ | H | CH₃ | F | OH |
| XXIX-7-4 | p-F—Ph | H | H | CH₂CH(CH₃)₂ | CH₃ | H | CH₃ | F | OH |
| XXIX-7-6 | p-F—Ph | H | H | CH₂Ph | CH₃ | H | CH₃ | F | OH |
| XXIX-7-7 | p-F—Ph | H | H | CH₂-indol-3-yl | CH₃ | H | CH₃ | F | OH |
| XXIX-7-8 | p-F—Ph | H | H | CH₂CH₂SCH₃ | CH₃ | H | CH₃ | F | OH |
| XXIX-7-20 | p-F—Ph | * | H | * | CH₃ | H | CH₃ | F | OH |

*$R^2$ and $R^{3b}$ joined together by (CH₂)₃ to form five-membered ring.

TABLE XXIX-8

| No | R¹ | R² | R³ᵃ | R³ᵇ | R⁴ | R⁵ | R⁶ | X | Y |
|---|---|---|---|---|---|---|---|---|---|
| XXIX-8-1 | p-Cl—Ph | H | H | H | CH₃ | H | CH₃ | F | OH |
| XXIX-8-2 | p-Cl—Ph | H | H | CH₃ | CH₃ | H | CH₃ | F | OH |
| XXIX-8-3 | p-Cl—Ph | H | H | CH(CH₃)₂ | CH₃ | H | CH₃ | F | OH |
| XXIX-8-4 | p-Cl—Ph | H | H | CH₂CH(CH₃)₂ | CH₃ | H | CH₃ | F | OH |
| XXIX-8-5 | p-Cl—Ph | H | H | CH₂Ph | CH₃ | H | CH₃ | F | OH |
| XXIX-8-6 | p-Cl—Ph | H | H | CH₂-indol-3-yl | CH₃ | H | CH₃ | F | OH |
| XXIX-8-7 | p-Cl—Ph | H | H | CH₂CH₂SCH₃ | CH₃ | H | CH₃ | F | OH |
| XXIX-8-8 | p-Cl—Ph | * | H | * | CH₃ | H | CH₃ | F | OH |

*$R^2$ and $R^{3b}$ joined together by (CH₂)₃ to form five-membered ring.

TABLE XXIX-9

| No | R¹ | R² | R³ᵃ | R³ᵇ | R⁴ | R⁵ | R⁶ | X | Y |
|---|---|---|---|---|---|---|---|---|---|
| XXIX-9-1 | p-Br—Ph | H | H | H | CH₃ | H | CH₃ | F | OH |
| XXIX-9-2 | p-Br—Ph | H | H | CH₃ | CH₃ | H | CH₃ | F | OH |
| XXIX-9-3 | p-Br—Ph | H | H | CH(CH₃)₂ | CH₃ | H | CH₃ | F | OH |

TABLE XXIX-9-continued

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIX-9-4 | p-Br—Ph | H | H | CH$_2$CH(CH$_3$)$_2$ | CH$_3$ | H | CH$_3$ | F | OH |
| XXIX-9-6 | p-Br—Ph | H | H | CH$_2$Ph | CH$_3$ | H | CH$_3$ | F | OH |
| XXIX-9-7 | p-Br—Ph | H | H | CH$_2$-indol-3-yl | CH$_3$ | H | CH$_3$ | F | OH |
| XXIX-9-8 | p-Br—Ph | H | H | CH$_2$CH$_2$SCH$_3$ | CH$_3$ | H | CH$_3$ | F | OH |
| XXIX-9-20 | p-Br—Ph | * | H | * | CH$_3$ | H | CH$_3$ | F | OH |

*R$^2$ and R$^{3b}$ joined together by (CH$_2$)$_3$ to form five-membered ring.

TABLE XXIX-10

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIX-10-1 | p-I—Ph | H | H | H | CH$_3$ | H | CH$_3$ | F | OH |
| XXIX-10-2 | p-I—Ph | H | H | CH$_3$ | CH$_3$ | H | CH$_3$ | F | OH |
| XXIX-10-3 | p-I—Ph | H | H | CH(CH$_3$)$_2$ | CH$_3$ | H | CH$_3$ | F | OH |
| XXIX-10-4 | p-I—Ph | H | H | CH$_2$CH(CH$_3$)$_2$ | CH$_3$ | H | CH$_3$ | F | OH |
| XXIX-10-5 | p-I—Ph | H | H | CH$_2$Ph | CH$_3$ | H | CH$_3$ | F | OH |
| XXIX-10-6 | p-I—Ph | H | H | CH$_2$-indol-3-yl | CH$_3$ | H | CH$_3$ | F | OH |
| XXIX-10-7 | p-I—Ph | H | H | CH$_2$CH$_2$SCH$_3$ | CH$_3$ | H | CH$_3$ | F | OH |
| XXIX-10-8 | p-I—Ph | * | H | * | CH$_3$ | H | CH$_3$ | F | OH |

*R$^2$ and R$^{3b}$ joined together by (CH$_2$)$_3$ to form five-membered ring.

TABLE XXIX-11

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIX-11-1 | CH$_3$ | H | H | H | Et | H | CH$_3$ | F | OH |
| XXIX-11-2 | CH$_3$ | H | H | CH$_3$ | Et | H | CH$_3$ | F | OH |
| XXIX-11-3 | CH$_3$ | H | H | CH(CH$_3$)$_2$ | Et | H | CH$_3$ | F | OH |
| XXIX-11-4 | CH$_3$ | H | H | CH$_2$CH(CH$_3$)$_2$ | Et | H | CH$_3$ | F | OH |
| XXIX-11-5 | CH$_3$ | H | H | CH$_2$Ph | Et | H | CH$_3$ | F | OH |
| XXIX-11-6 | CH$_3$ | H | H | CH$_2$-indol-3-yl | Et | H | CH$_3$ | F | OH |
| XXIX-11-7 | CH$_3$ | H | H | CH$_2$CH$_2$SCH$_3$ | Et | H | CH$_3$ | F | OH |
| XXIX-11-8 | CH$_3$ | * | H | * | Et | H | CH$_3$ | F | OH |

*R$^2$ and R$^{3b}$ joined together by (CH$_2$)$_3$ to form five-membered ring.

TABLE XXIX-12

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIX-12-1 | Et | H | H | H | Et | H | CH$_3$ | F | OH |
| XXIX-12-2 | Et | H | H | CH$_3$ | Et | H | CH$_3$ | F | OH |
| XXIX-12-3 | Et | H | H | CH(CH$_3$)$_2$ | Et | H | CH$_3$ | F | OH |
| XXIX-12-4 | Et | H | H | CH$_2$CH(CH$_3$)$_2$ | Et | H | CH$_3$ | F | OH |
| XXIX-12-5 | Et | H | H | CH$_2$Ph | Et | H | CH$_3$ | F | OH |
| XXIX-12-6 | Et | H | H | CH$_2$-indol-3-yl | Et | H | CH$_3$ | F | OH |
| XXIX-12-7 | Et | H | H | CH$_2$CH$_2$SCH$_3$ | Et | H | CH$_3$ | F | OH |
| XXIX-12-8 | Et | * | H | * | Et | H | CH$_3$ | F | OH |

*R$^2$ and R$^{3b}$ joined together by (CH$_2$)$_3$ to form five-membered ring.

TABLE XXIX-13

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIX-13-1 | $^i$Pr | H | H | H | Et | H | CH$_3$ | F | OH |
| XXIX-13-2 | $^i$Pr | H | H | CH$_3$ | Et | H | CH$_3$ | F | OH |
| XXIX-13-3 | $^i$Pr | H | H | CH(CH$_3$)$_2$ | Et | H | CH$_3$ | F | OH |
| XXIX-13-4 | $^i$Pr | H | H | CH$_2$CH(CH$_3$)$_2$ | Et | H | CH$_3$ | F | OH |
| XXIX-13-5 | $^i$Pr | H | H | CH$_2$Ph | Et | H | CH$_3$ | F | OH |
| XXIX-13-6 | $^i$Pr | H | H | CH$_2$-indol-3-yl | Et | H | CH$_3$ | F | OH |
| XXIX-13-7 | $^i$Pr | H | H | CH$_2$CH$_2$SCH$_3$ | Et | H | CH$_3$ | F | OH |
| XXIX-13-8 | $^i$Pr | * | H | * | Et | H | CH$_3$ | F | OH |

*R$^2$ and R$^{3b}$ joined together by (CH$_2$)$_3$ to form five-membered ring.

TABLE XXIX-14

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIX-14-1 | $^t$Bu | H | H | H | Et | H | CH$_3$ | F | OH |
| XXIX-14-2 | $^t$Bu | H | H | CH$_3$ | Et | H | CH$_3$ | F | OH |
| XXIX-14-3 | $^t$Bu | H | H | CH(CH$_3$)$_2$ | Et | H | CH$_3$ | F | OH |
| XXIX-14-4 | $^t$Bu | H | H | CH$_2$CH(CH$_3$)$_2$ | Et | H | CH$_3$ | F | OH |
| XXIX-14-5 | $^t$Bu | H | H | CH$_2$Ph | Et | H | CH$_3$ | F | OH |
| XXIX-14-6 | $^t$Bu | H | H | CH$_2$-indol-3-yl | Et | H | CH$_3$ | F | OH |
| XXIX-14-7 | $^t$Bu | H | H | CH$_2$CH$_2$SCH$_3$ | Et | H | CH$_3$ | F | OH |
| XXIX-14-8 | $^t$Bu | * | H | * | Et | H | CH$_3$ | F | OH |

*R$^2$ and R$^{3b}$ joined together by (CH$_2$)$_3$ to form five-membered ring.

TABLE XXIX-15

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIX-15-1 | Ph | H | H | H | Et | H | CH$_3$ | F | OH |
| XXIX-15-2 | Ph | H | H | CH$_3$ | Et | H | CH$_3$ | F | OH |
| XXIX-15-3 | Ph | H | H | CH(CH$_3$)$_2$ | Et | H | CH$_3$ | F | OH |
| XXIX-15-4 | Ph | H | H | CH$_2$CH(CH$_3$)$_2$ | Et | H | CH$_3$ | F | OH |
| XXIX-15-5 | Ph | H | H | CH$_2$Ph | Et | H | CH$_3$ | F | OH |
| XXIX-15-6 | Ph | H | H | CH$_2$-indol-3-yl | Et | H | CH$_3$ | F | OH |
| XXIX-15-7 | Ph | H | H | CH$_2$CH$_2$SCH$_3$ | Et | H | CH$_3$ | F | OH |
| XXIX-15-8 | Ph | * | H | * | Et | H | CH$_3$ | F | OH |

*R$^2$ and R$^{3b}$ joined together by (CH$_2$)$_3$ to form five-membered ring.

TABLE XXIX-16

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXIX-16-1 | p-Me—Ph | H | H | H | Et | H | CH$_3$ | F | OH |
| XXIX-16-2 | p-Me—Ph | H | H | CH$_3$ | Et | H | CH$_3$ | F | OH |
| XXIX-16-3 | p-Me—Ph | H | H | CH(CH$_3$)$_2$ | Et | H | CH$_3$ | F | OH |
| XXIX-16-4 | p-Me—Ph | H | H | CH$_2$CH(CH$_3$)$_2$ | Et | H | CH$_3$ | F | OH |
| XXIX-16-5 | p-Me—Ph | H | H | CH$_2$Ph | Et | H | CH$_3$ | F | OH |
| XXIX-16-6 | p-Me—Ph | H | H | CH$_2$-indol-3-yl | Et | H | CH$_3$ | F | OH |
| XXIX-16-7 | p-Me—Ph | H | H | CH$_2$CH$_2$SCH$_3$ | Et | H | CH$_3$ | F | OH |
| XXIX-16-8 | p-Me—Ph | * | H | * | Et | H | CH$_3$ | F | OH |

*R$^2$ and R$^{3b}$ joined together by (CH$_2$)$_3$ to form five-membered ring.

TABLE XXIX-17

| No | R¹ | R² | R³ᵃ | R³ᵇ | R⁴ | R⁵ | R⁶ | X | Y |
|---|---|---|---|---|---|---|---|---|---|
| XXIX-17-1 | p-F—Ph | H | H | H | Et | H | $CH_3$ | F | OH |
| XXIX-17-2 | p-F—Ph | H | H | $CH_3$ | Et | H | $CH_3$ | F | OH |
| XXIX-17-3 | p-F—Ph | H | H | $CH(CH_3)_2$ | Et | H | $CH_3$ | F | OH |
| XXIX-17-4 | p-F—Ph | H | H | $CH_2CH(CH_3)_2$ | Et | H | $CH_3$ | F | OH |
| XXIX-17-5 | p-F—Ph | H | H | $CH_2Ph$ | Et | H | $CH_3$ | F | OH |
| XXIX-17-6 | p-F—Ph | H | H | $CH_2$-indol-3-yl | Et | H | $CH_3$ | F | OH |
| XXIX-17-7 | p-F—Ph | H | H | $CH_2CH_2SCH_3$ | Et | H | $CH_3$ | F | OH |
| XXIX-17-8 | p-F—Ph | * | H | * | Et | H | $CH_3$ | F | OH |

*$R^2$ and $R^{3b}$ joined together by $(CH_2)_3$ to form five-membered ring.

TABLE XXIX-18

| No | R¹ | R² | R³ᵃ | R³ᵇ | R⁴ | R⁵ | R⁶ | X | Y |
|---|---|---|---|---|---|---|---|---|---|
| XXIX-18-1 | p-Cl—Ph | H | H | H | Et | H | $CH_3$ | F | OH |
| XXIX-18-2 | p-Cl—Ph | H | H | $CH_3$ | Et | H | $CH_3$ | F | OH |
| XXIX-18-3 | p-Cl—Ph | H | H | $CH(CH_3)_2$ | Et | H | $CH_3$ | F | OH |
| XXIX-18-4 | p-Cl—Ph | H | H | $CH_2CH(CH_3)_2$ | Et | H | $CH_3$ | F | OH |
| XXIX-18-5 | p-Cl—Ph | H | H | $CH_2Ph$ | Et | H | $CH_3$ | F | OH |
| XXIX-18-6 | p-Cl—Ph | H | H | $CH_2$-indol-3-yl | Et | H | $CH_3$ | F | OH |
| XXIX-18-7 | p-Cl—Ph | H | H | $CH_2CH_2SCH_3$ | Et | H | $CH_3$ | F | OH |
| XXIX-18-8 | p-Cl—Ph | * | H | * | Et | H | $CH_3$ | F | OH |

*$R^2$ and $R^{3b}$ joined together by $(CH_2)_3$ to form five-membered ring.

TABLE XXIX-19

| No | R¹ | R² | R³ᵃ | R³ᵇ | R⁴ | R⁵ | R⁶ | X | Y |
|---|---|---|---|---|---|---|---|---|---|
| XXIX-19-1 | p-Br—Ph | H | H | H | Et | H | $CH_3$ | F | OH |
| XXIX-19-2 | p-Br—Ph | H | H | $CH_3$ | Et | H | $CH_3$ | F | OH |
| XXIX-19-3 | p-Br—Ph | H | H | $CH(CH_3)_2$ | Et | H | $CH_3$ | F | OH |
| XXIX-19-4 | p-Br—Ph | H | H | $CH_2CH(CH_3)_2$ | Et | H | $CH_3$ | F | OH |
| XXIX-19-5 | p-Br—Ph | H | H | $CH_2Ph$ | Et | H | $CH_3$ | F | OH |
| XXIX-19-6 | p-Br—Ph | H | H | $CH_2$-indol-3-yl | Et | H | $CH_3$ | F | OH |
| XXIX-19-7 | p-Br—Ph | H | H | $CH_2CH_2SCH_3$ | Et | H | $CH_3$ | F | OH |
| XXIX-19-8 | p-Br—Ph | * | H | * | Et | H | $CH_3$ | F | OH |

*$R^2$ and $R^{3b}$ joined together by $(CH_2)_3$ to form five-membered ring.

TABLE XXIX-20

| No | R¹ | R² | R³ᵃ | R³ᵇ | R⁴ | R⁵ | R⁶ | X | Y |
|---|---|---|---|---|---|---|---|---|---|
| XXIX-20-1 | p-I—Ph | H | H | H | Et | H | $CH_3$ | F | OH |
| XXIX-20-2 | p-I—Ph | H | H | $CH_3$ | Et | H | $CH_3$ | F | OH |
| XXIX-20-3 | p-I—Ph | H | H | $CH(CH_3)_2$ | Et | H | $CH_3$ | F | OH |
| XXIX-20-4 | p-I—Ph | H | H | $CH_2CH(CH_3)_2$ | Et | H | $CH_3$ | F | OH |
| XXIX-20-5 | p-I—Ph | H | H | $CH_2Ph$ | Et | H | $CH_3$ | F | OH |
| XXIX-20-6 | p-I—Ph | H | H | $CH_2$-indol-3-yl | Et | H | $CH_3$ | F | OH |
| XXIX-20-7 | p-I—Ph | H | H | $CH_2CH_2SCH_3$ | Et | H | $CH_3$ | F | OH |
| XXIX-20-8 | p-I—Ph | * | H | * | Et | H | $CH_3$ | F | OH |

*$R^2$ and $R^{3b}$ joined together by $(CH_2)_3$ to form five-membered ring.

TABLE XXIX-21

| No | R¹ | R² | R³ᵃ | R³ᵇ | R⁴ | R⁵ | R⁶ | X | Y |
|---|---|---|---|---|---|---|---|---|---|
| XXIX-21-1 | $CH_3$ | H | H | H | $^iPr$ | H | $CH_3$ | F | OH |
| XXIX-21-2 | $CH_3$ | H | H | $CH_3$ | $^iPr$ | H | $CH_3$ | F | OH |
| XXIX-21-3 | $CH_3$ | H | H | $CH(CH_3)_2$ | $^iPr$ | H | $CH_3$ | F | OH |
| XXIX-21-4 | $CH_3$ | H | H | $CH_2CH(CH_3)_2$ | $^iPr$ | H | $CH_3$ | F | OH |
| XXIX-21-5 | $CH_3$ | H | H | $CH_2Ph$ | $^iPr$ | H | $CH_3$ | F | OH |
| XXIX-21-6 | $CH_3$ | H | H | $CH_2$-indol-3-yl | $^iPr$ | H | $CH_3$ | F | OH |
| XXIX-21-7 | $CH_3$ | H | H | $CH_2CH_2SCH_3$ | $^iPr$ | H | $CH_3$ | F | OH |
| XXIX-21-8 | $CH_3$ | * | H | * | $^iPr$ | H | $CH_3$ | F | OH |

*$R^2$ and $R^{3b}$ joined together by $(CH_2)_3$ to form five-membered ring.

TABLE XXIX-22

| No | R¹ | R² | R³ᵃ | R³ᵇ | R⁴ | R⁵ | R⁶ | X | Y |
|---|---|---|---|---|---|---|---|---|---|
| XXIX-22-1 | Et | H | H | H | $^iPr$ | H | $CH_3$ | F | OH |
| XXIX-22-2 | Et | H | H | $CH_3$ | $^iPr$ | H | $CH_3$ | F | OH |
| XXIX-22-3 | Et | H | H | $CH(CH_3)_2$ | $^iPr$ | H | $CH_3$ | F | OH |
| XXIX-22-4 | Et | H | H | $CH_2CH(CH_3)_2$ | $^iPr$ | H | $CH_3$ | F | OH |
| XXIX-22-5 | Et | H | H | $CH_2Ph$ | $^iPr$ | H | $CH_3$ | F | OH |
| XXIX-22-6 | Et | H | H | $CH_2$-indol-3-yl | $^iPr$ | H | $CH_3$ | F | OH |
| XXIX-22-7 | Et | H | H | $CH_2CH_2SCH_3$ | $^iPr$ | H | $CH_3$ | F | OH |
| XXIX-22-8 | Et | * | H | * | $^iPr$ | H | $CH_3$ | F | OH |

*$R^2$ and $R^{3b}$ joined together by $(CH_2)_3$ to form five-membered ring.

TABLE XXIX-23

| No | R¹ | R² | R³ᵃ | R³ᵇ | R⁴ | R⁵ | R⁶ | X | Y |
|---|---|---|---|---|---|---|---|---|---|
| XXIX-23-1 | $^iPr$ | H | H | H | $^iPr$ | H | $CH_3$ | F | OH |
| XXIX-23-2 | $^iPr$ | H | H | $CH_3$ | $^iPr$ | H | $CH_3$ | F | OH |
| XXIX-23-3 | $^iPr$ | H | H | $CH(CH_3)_2$ | $^iPr$ | H | $CH_3$ | F | OH |
| XXIX-23-4 | $^iPr$ | H | H | $CH_2CH(CH_3)_2$ | $^iPr$ | H | $CH_3$ | F | OH |
| XXIX-23-5 | $^iPr$ | H | H | $CH_2Ph$ | $^iPr$ | H | $CH_3$ | F | OH |
| XXIX-23-6 | $^iPr$ | H | H | $CH_2$-indol-3-yl | $^iPr$ | H | $CH_3$ | F | OH |
| XXIX-23-7 | $^iPr$ | H | H | $CH_2CH_2SCH_3$ | $^iPr$ | H | $CH_3$ | F | OH |
| XXIX-23-8 | $^iPr$ | * | H | * | $^iPr$ | H | $CH_3$ | F | OH |

*$R^2$ and $R^{3b}$ joined together by $(CH_2)_3$ to form five-membered ring.

TABLE XXIX-24

| No | R¹ | R² | R³ᵃ | R³ᵇ | R⁴ | R⁵ | R⁶ | X | Y |
|---|---|---|---|---|---|---|---|---|---|
| XXIX-24-1 | $^tBu$ | H | H | H | $^iPr$ | H | $CH_3$ | F | OH |
| XXIX-24-2 | $^tBu$ | H | H | $CH_3$ | $^iPr$ | H | $CH_3$ | F | OH |
| XXIX-24-3 | $^tBu$ | H | H | $CH(CH_3)_2$ | $^iPr$ | H | $CH_3$ | F | OH |
| XXIX-24-4 | $^tBu$ | H | H | $CH_2CH(CH_3)_2$ | $^iPr$ | H | $CH_3$ | F | OH |
| XXIX-24-5 | $^tBu$ | H | H | $CH_2Ph$ | $^iPr$ | H | $CH_3$ | F | OH |
| XXIX-24-6 | $^tBu$ | H | H | $CH_2$-indol-3-yl | $^iPr$ | H | $CH_3$ | F | OH |
| XXIX-24-7 | $^tBu$ | H | H | $CH_2CH_2SCH_3$ | $^iPr$ | H | $CH_3$ | F | OH |
| XXIX-24-8 | $^tBu$ | * | H | * | $^iPr$ | H | $CH_3$ | F | OH |

*$R^2$ and $R^{3b}$ joined together by $(CH_2)_3$ to form five-membered ring.

TABLE XXIX-25

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIX-25-1 | Ph | H | H | H | $^i$Pr | H | $CH_3$ | F | OH |
| XXIX-25-2 | Ph | H | H | $CH_3$ | $^i$Pr | H | $CH_3$ | F | OH |
| XXIX-25-3 | Ph | H | H | $CH(CH_3)_2$ | $^i$Pr | H | $CH_3$ | F | OH |
| XXIX-25-4 | Ph | H | H | $CH_2CH(CH_3)_2$ | $^i$Pr | H | $CH_3$ | F | OH |
| XXIX-25-5 | Ph | H | H | $CH_2Ph$ | $^i$Pr | H | $CH_3$ | F | OH |
| XXIX-25-6 | Ph | H | H | $CH_2$-indol-3-yl | $^i$Pr | H | $CH_3$ | F | OH |
| XXIX-25-7 | Ph | H | H | $CH_2CH_2SCH_3$ | $^i$Pr | H | $CH_3$ | F | OH |
| XXIX-25-8 | Ph | * | H | * | $^i$Pr | H | $CH_3$ | F | OH |

*$R^2$ and $R^{3b}$ joined together by $(CH_2)_3$ to form five-membered ring.

TABLE XXIX-26

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIX-26-1 | p-Me—Ph | H | H | H | $^i$Pr | H | $CH_3$ | F | OH |
| XXIX-26-2 | p-Me—Ph | H | H | $CH_3$ | $^i$Pr | H | $CH_3$ | F | OH |
| XXIX-26-3 | p-Me—Ph | H | H | $CH(CH_3)_2$ | $^i$Pr | H | $CH_3$ | F | OH |
| XXIX-26-4 | p-Me—Ph | H | H | $CH_2CH(CH_3)_2$ | $^i$Pr | H | $CH_3$ | F | OH |
| XXIX-26-5 | p-Me—Ph | H | H | $CH_2Ph$ | $^i$Pr | H | $CH_3$ | F | OH |
| XXIX-26-6 | p-Me—Ph | H | H | $CH_2$-indol-3-yl | $^i$Pr | H | $CH_3$ | F | OH |
| XXIX-26-7 | p-Me—Ph | H | H | $CH_2CH_2SCH_3$ | $^i$Pr | H | $CH_3$ | F | OH |
| XXIX-26-8 | p-Me—Ph | * | H | * | $^i$Pr | H | $CH_3$ | F | OH |

*$R^2$ and $R^{3b}$ joined together by $(CH_2)_3$ to form five-membered ring.

TABLE XXIX-27

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIX-27-1 | p-F—Ph | H | H | H | $^i$Pr | H | $CH_3$ | F | OH |
| XXIX-27-2 | p-F—Ph | H | H | $CH_3$ | $^i$Pr | H | $CH_3$ | F | OH |
| XXIX-27-3 | p-F—Ph | H | H | $CH(CH_3)_2$ | $^i$Pr | H | $CH_3$ | F | OH |
| XXIX-27-4 | p-F—Ph | H | H | $CH_2CH(CH_3)_2$ | $^i$Pr | H | $CH_3$ | F | OH |
| XXIX-27-5 | p-F—Ph | H | H | $CH_2Ph$ | $^i$Pr | H | $CH_3$ | F | OH |
| XXIX-27-6 | p-F—Ph | H | H | $CH_2$-indol-3-yl | $^i$Pr | H | $CH_3$ | F | OH |
| XXIX-27-7 | p-F—Ph | H | H | $CH_2CH_2SCH_3$ | $^i$Pr | H | $CH_3$ | F | OH |
| XXIX-27-8 | p-F—Ph | * | H | * | $^i$Pr | H | $CH_3$ | F | OH |

*$R^2$ and $R^{3b}$ joined together by $(CH_2)_3$ to form five-membered ring.

TABLE XXIX-28

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIX-28-1 | p-Cl—Ph | H | H | H | $^i$Pr | H | $CH_3$ | F | OH |
| XXIX-28-2 | p-Cl—Ph | H | H | $CH_3$ | $^i$Pr | H | $CH_3$ | F | OH |
| XXIX-28-3 | p-Cl—Ph | H | H | $CH(CH_3)_2$ | $^i$Pr | H | $CH_3$ | F | OH |
| XXIX-28-4 | p-Cl—Ph | H | H | $CH_2CH(CH_3)_2$ | $^i$Pr | H | $CH_3$ | F | OH |
| XXIX-28-5 | p-Cl—Ph | H | H | $CH_2Ph$ | $^i$Pr | H | $CH_3$ | F | OH |
| XXIX-28-6 | p-Cl—Ph | H | H | $CH_2$-indol-3-yl | $^i$Pr | H | $CH_3$ | F | OH |
| XXIX-28-7 | p-Cl—Ph | H | H | $CH_2CH_2SCH_3$ | $^i$Pr | H | $CH_3$ | F | OH |
| XXIX-28-8 | p-Cl—Ph | * | H | * | $^i$Pr | H | $CH_3$ | F | OH |

*$R^2$ and $R^{3b}$ joined together by $(CH_2)_3$ to form five-membered ring.

TABLE XXIX-29

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXIX-29-1 | p-Br—Ph | H | H | H | $^i$Pr | H | $CH_3$ | F | OH |
| XXIX-29-2 | p-Br—Ph | H | H | $CH_3$ | $^i$Pr | H | $CH_3$ | F | OH |
| XXIX-29-3 | p-Br—Ph | H | H | $CH(CH_3)_2$ | $^i$Pr | H | $CH_3$ | F | OH |
| XXIX-29-4 | p-Br—Ph | H | H | $CH_2CH(CH_3)_2$ | $^i$Pr | H | $CH_3$ | F | OH |
| XXIX-29-5 | p-Br—Ph | H | H | $CH_2Ph$ | $^i$Pr | H | $CH_3$ | F | OH |
| XXIX-29-6 | p-Br—Ph | H | H | $CH_2$-indol-3-yl | $^i$Pr | H | $CH_3$ | F | OH |
| XXIX-29-7 | p-Br—Ph | H | H | $CH_2CH_2SCH_3$ | $^i$Pr | H | $CH_3$ | F | OH |
| XXIX-29-8 | p-Br—Ph | * | H | * | $^i$Pr | H | $CH_3$ | F | OH |

*$R^2$ and $R^{3b}$ joined together by $(CH_2)_3$ to form five-membered ring.

TABLE XXIX-30

| No | R¹ | R² | R³ᵃ | R³ᵇ | R⁴ | R⁵ | R⁶ | X | Y |
|---|---|---|---|---|---|---|---|---|---|
| XXIX-30-1 | p-I—Ph | H | H | H | $^i$Pr | H | $CH_3$ | F | OH |
| XXIX-30-2 | p-I—Ph | H | H | $CH_3$ | $^i$Pr | H | $CH_3$ | F | OH |
| XXIX-30-3 | p-I—Ph | H | H | $CH(CH_3)_2$ | $^i$Pr | H | $CH_3$ | F | OH |
| XXIX-30-4 | p-I—Ph | H | H | $CH_2CH(CH_3)_2$ | $^i$Pr | H | $CH_3$ | F | OH |
| XXIX-30-5 | p-I—Ph | H | H | $CH_2Ph$ | $^i$Pr | H | $CH_3$ | F | OH |
| XXIX-30-6 | p-I—Ph | H | H | $CH_2$-indol-3-yl | $^i$Pr | H | $CH_3$ | F | OH |
| XXIX-30-7 | p-I—Ph | H | H | $CH_2CH_2SCH_3$ | $^i$Pr | H | $CH_3$ | F | OH |
| XXIX-30-8 | p-I—Ph | * | H | * | $^i$Pr | H | $CH_3$ | F | OH |

*R² and R³ᵇ joined together by $(CH_2)_3$ to form five-membered ring.

TABLE XXIX-31

| No | R¹ | R² | R³ᵃ | R³ᵇ | R⁴ | R⁵ | R⁶ | X | Y |
|---|---|---|---|---|---|---|---|---|---|
| XXIX-31-1 | $CH_3$ | H | H | H | $^n$Bu | H | $CH_3$ | F | OH |
| XXIX-31-2 | $CH_3$ | H | H | $CH_3$ | $^n$Bu | H | $CH_3$ | F | OH |
| XXIX-31-3 | $CH_3$ | H | H | $CH(CH_3)_2$ | $^n$Bu | H | $CH_3$ | F | OH |
| XXIX-31-4 | $CH_3$ | H | H | $CH_2CH(CH_3)_2$ | $^n$Bu | H | $CH_3$ | F | OH |
| XXIX-31-5 | $CH_3$ | H | H | $CH_2Ph$ | $^n$Bu | H | $CH_3$ | F | OH |
| XXIX-31-6 | $CH_3$ | H | H | $CH_2$-indol-3-yl | $^n$Bu | H | $CH_3$ | F | OH |
| XXIX-31-7 | $CH_3$ | H | H | $CH_2CH_2SCH_3$ | $^n$Bu | H | $CH_3$ | F | OH |
| XXIX-31-8 | $CH_3$ | * | H | * | $^n$Bu | H | $CH_3$ | F | OH |

*R² and R³ᵇ joined together by $(CH_2)_3$ to form five-membered ring.

TABLE XXIX-32

| No | R¹ | R² | R³ᵃ | R³ᵇ | R⁴ | R⁵ | R⁶ | X | Y |
|---|---|---|---|---|---|---|---|---|---|
| XXIX-32-1 | Et | H | H | H | $^n$Bu | H | $CH_3$ | F | OH |
| XXIX-32-2 | Et | H | H | $CH_3$ | $^n$Bu | H | $CH_3$ | F | OH |
| XXIX-32-3 | Et | H | H | $CH(CH_3)_2$ | $^n$Bu | H | $CH_3$ | F | OH |
| XXIX-32-4 | Et | H | H | $CH_2CH(CH_3)_2$ | $^n$Bu | H | $CH_3$ | F | OH |
| XXIX-32-5 | Et | H | H | $CH_2Ph$ | $^n$Bu | H | $CH_3$ | F | OH |
| XXIX-32-6 | Et | H | H | $CH_2$-indol-3-yl | $^n$Bu | H | $CH_3$ | F | OH |
| XXIX-32-7 | Et | H | H | $CH_2CH_2SCH_3$ | $^n$Bu | H | $CH_3$ | F | OH |
| XXIX-32-8 | Et | * | H | * | $^n$Bu | H | $CH_3$ | F | OH |

*R² and R³ᵇ joined together by $(CH_2)_3$ to form five-membered ring.

TABLE XXIX-33

| No | R¹ | R² | R³ᵃ | R³ᵇ | R⁴ | R⁵ | R⁶ | X | Y |
|---|---|---|---|---|---|---|---|---|---|
| XXIX-33-1 | $^i$Pr | H | H | H | $^n$Bu | H | $CH_3$ | F | OH |
| XXIX-33-2 | $^i$Pr | H | H | $CH_3$ | $^n$Bu | H | $CH_3$ | F | OH |
| XXIX-33-3 | $^i$Pr | H | H | $CH(CH_3)_2$ | $^n$Bu | H | $CH_3$ | F | OH |
| XXIX-33-4 | $^i$Pr | H | H | $CH_2CH(CH_3)_2$ | $^n$Bu | H | $CH_3$ | F | OH |
| XXIX-33-5 | $^i$Pr | H | H | $CH_2Ph$ | $^n$Bu | H | $CH_3$ | F | OH |
| XXIX-33-6 | $^i$Pr | H | H | $CH_2$-indol-3-yl | $^n$Bu | H | $CH_3$ | F | OH |
| XXIX-33-7 | $^i$Pr | H | H | $CH_2CH_2SCH_3$ | $^n$Bu | H | $CH_3$ | F | OH |
| XXIX-33-8 | $^i$Pr | * | H | * | $^n$Bu | H | $CH_3$ | F | OH |

*R² and R³ᵇ joined together by $(CH_2)_3$ to form five-membered ring.

TABLE XXIX-34

| No | R¹ | R² | R³ᵃ | R³ᵇ | R⁴ | R⁵ | R⁶ | X | Y |
|---|---|---|---|---|---|---|---|---|---|
| XXIX-34-1 | $^t$Bu | H | H | H | $^n$Bu | H | $CH_3$ | F | OH |
| XXIX-34-2 | $^t$Bu | H | H | $CH_3$ | $^n$Bu | H | $CH_3$ | F | OH |
| XXIX-34-3 | $^t$Bu | H | H | $CH(CH_3)_2$ | $^n$Bu | H | $CH_3$ | F | OH |
| XXIX-34-4 | $^t$Bu | H | H | $CH_2CH(CH_3)_2$ | $^n$Bu | H | $CH_3$ | F | OH |
| XXIX-34-5 | $^t$Bu | H | H | $CH_2Ph$ | $^n$Bu | H | $CH_3$ | F | OH |
| XXIX-34-6 | $^t$Bu | H | H | $CH_2$-indol-3-yl | $^n$Bu | H | $CH_3$ | F | OH |
| XXIX-34-7 | $^t$Bu | H | H | $CH_2CH_2SCH_3$ | $^n$Bu | H | $CH_3$ | F | OH |
| XXIX-34-8 | $^t$Bu | * | H | * | $^n$Bu | H | $CH_3$ | F | OH |

*R² and R³ᵇ joined together by $(CH_2)_3$ to form five-membered ring.

TABLE XXIX-35

| No | R¹ | R² | R³ᵃ | R³ᵇ | R⁴ | R⁵ | R⁶ | X | Y |
|---|---|---|---|---|---|---|---|---|---|
| XXIX-35-1 | Ph | H | H | H | $^n$Bu | H | $CH_3$ | F | OH |
| XXIX-35-2 | Ph | H | H | $CH_3$ | $^n$Bu | H | $CH_3$ | F | OH |
| XXIX-35-3 | Ph | H | H | $CH(CH_3)_2$ | $^n$Bu | H | $CH_3$ | F | OH |
| XXIX-35-4 | Ph | H | H | $CH_2CH(CH_3)_2$ | $^n$Bu | H | $CH_3$ | F | OH |
| XXIX-35-5 | Ph | H | H | $CH_2Ph$ | $^n$Bu | H | $CH_3$ | F | OH |
| XXIX-35-6 | Ph | H | H | $CH_2$-indol-3-yl | $^n$Bu | H | $CH_3$ | F | OH |
| XXIX-35-7 | Ph | H | H | $CH_2CH_2SCH_3$ | $^n$Bu | H | $CH_3$ | F | OH |
| XXIX-35-8 | Ph | * | H | * | $^n$Bu | H | $CH_3$ | F | OH |

*R² and R³ᵇ joined together by $(CH_2)_3$ to form five-membered ring.

TABLE XXIX-36

| No | R¹ | R² | R³ᵃ | R³ᵇ | R⁴ | R⁵ | R⁶ | X | Y |
|---|---|---|---|---|---|---|---|---|---|
| XXIX-36-1 | p-Me—Ph | H | H | H | $^n$Bu | H | $CH_3$ | F | OH |
| XXIX-36-2 | p-Me—Ph | H | H | $CH_3$ | $^n$Bu | H | $CH_3$ | F | OH |
| XXIX-36-3 | p-Me—Ph | H | H | $CH(CH_3)_2$ | $^n$Bu | H | $CH_3$ | F | OH |
| XXIX-36-4 | p-Me—Ph | H | H | $CH_2CH(CH_3)_2$ | $^n$Bu | H | $CH_3$ | F | OH |
| XXIX-36-5 | p-Me—Ph | H | H | $CH_2Ph$ | $^n$Bu | H | $CH_3$ | F | OH |
| XXIX-36-6 | p-Me—Ph | H | H | $CH_2$-indol-3-yl | $^n$Bu | H | $CH_3$ | F | OH |
| XXIX-36-7 | p-Me—Ph | H | H | $CH_2CH_2SCH_3$ | $^n$Bu | H | $CH_3$ | F | OH |
| XXIX-36-8 | p-Me—Ph | * | H | * | $^n$Bu | H | $CH_3$ | F | OH |

*R² and R³ᵇ joined together by $(CH_2)_3$ to form five-membered ring.

TABLE XXIX-37

| No | R¹ | R² | R³ᵃ | R³ᵇ | R⁴ | R⁵ | R⁶ | X | Y |
|---|---|---|---|---|---|---|---|---|---|
| XXIX-37-1 | p-F—Ph | H | H | H | ⁿBu | H | CH₃ | F | OH |
| XXIX-37-2 | p-F—Ph | H | H | CH₃ | ⁿBu | H | CH₃ | F | OH |
| XXIX-37-3 | p-F—Ph | H | H | CH(CH₃)₂ | ⁿBu | H | CH₃ | F | OH |
| XXIX-37-4 | p-F—Ph | H | H | CH₂CH(CH₃)₂ | ⁿBu | H | CH₃ | F | OH |
| XXIX-37-5 | p-F—Ph | H | H | CH₂Ph | ⁿBu | H | CH₃ | F | OH |
| XXIX-37-6 | p-F—Ph | H | H | CH₂-indol-3-yl | ⁿBu | H | CH₃ | F | OH |
| XXIX-37-7 | p-F—Ph | H | H | CH₂CH₂SCH₃ | ⁿBu | H | CH₃ | F | OH |
| XXIX-37-8 | p-F—Ph | * | H | * | ⁿBu | H | CH₃ | F | OH |

*R² and R³ᵇ joined together by (CH₂)₃ to form five-membered ring.

TABLE XXIX-38

| No | R¹ | R² | R³ᵃ | R³ᵇ | R⁴ | R⁵ | R⁶ | X | Y |
|---|---|---|---|---|---|---|---|---|---|
| XXIX-38-1 | p-Cl—Ph | H | H | H | ⁿBu | H | CH₃ | F | OH |
| XXIX-38-2 | p-Cl—Ph | H | H | CH₃ | ⁿBu | H | CH₃ | F | OH |
| XXIX-38-3 | p-Cl—Ph | H | H | CH(CH₃)₂ | ⁿBu | H | CH₃ | F | OH |
| XXIX-38-4 | p-Cl—Ph | H | H | CH₂CH(CH₃)₂ | ⁿBu | H | CH₃ | F | OH |
| XXIX-38-5 | p-Cl—Ph | H | H | CH₂Ph | ⁿBu | H | CH₃ | F | OH |
| XXIX-38-6 | p-Cl—Ph | H | H | CH₂-indol-3-yl | ⁿBu | H | CH₃ | F | OH |
| XXIX-38-7 | p-Cl—Ph | H | H | CH₂CH₂SCH₃ | ⁿBu | H | CH₃ | F | OH |
| XXIX-38-8 | p-Cl—Ph | * | H | * | ⁿBu | H | CH₃ | F | OH |

*R² and R³ᵇ joined together by (CH₂)₃ to form five-membered ring.

TABLE XXIX-39

| No | R¹ | R² | R³ᵃ | R³ᵇ | R⁴ | R⁵ | R⁶ | X | Y |
|---|---|---|---|---|---|---|---|---|---|
| XXIX-39-1 | p-Br—Ph | H | H | H | ⁿBu | H | CH₃ | F | OH |
| XXIX-39-2 | p-Br—Ph | H | H | CH₃ | ⁿBu | H | CH₃ | F | OH |
| XXIX-39-3 | p-Br—Ph | H | H | CH(CH₃)₂ | ⁿBu | H | CH₃ | F | OH |
| XXIX-39-4 | p-Br—Ph | H | H | CH₂CH(CH₃)₂ | ⁿBu | H | CH₃ | F | OH |
| XXIX-39-5 | p-Br—Ph | H | H | CH₂Ph | ⁿBu | H | CH₃ | F | OH |
| XXIX-39-6 | p-Br—Ph | H | H | CH₂-indol-3-yl | ⁿBu | H | CH₃ | F | OH |
| XXIX-39-7 | p-Br—Ph | H | H | CH₂CH₂SCH₃ | ⁿBu | H | CH₃ | F | OH |
| XXIX-39-8 | p-Br—Ph | * | H | * | ⁿBu | H | CH₃ | F | OH |

*R² and R³ᵇ joined together by (CH₂)₃ to form five-membered ring.

TABLE XXIX-40

| No | R¹ | R² | R³ᵃ | R³ᵇ | R⁴ | R⁵ | R⁶ | X | Y |
|---|---|---|---|---|---|---|---|---|---|
| XXIX-40-1 | p-I—Ph | H | H | H | ⁿBu | H | CH₃ | F | OH |
| XXIX-40-2 | p-I—Ph | H | H | CH₃ | ⁿBu | H | CH₃ | F | OH |
| XXIX-40-3 | p-I—Ph | H | H | CH(CH₃)₂ | ⁿBu | H | CH₃ | F | OH |
| XXIX-40-4 | p-I—Ph | H | H | CH₂CH(CH₃)₂ | ⁿBu | H | CH₃ | F | OH |
| XXIX-40-5 | p-I—Ph | H | H | CH₂Ph | ⁿBu | H | CH₃ | F | OH |
| XXIX-40-6 | p-I—Ph | H | H | CH₂-indol-3-yl | ⁿBu | H | CH₃ | F | OH |
| XXIX-40-7 | p-I—Ph | H | H | CH₂CH₂SCH₃ | ⁿBu | H | CH₃ | F | OH |
| XXIX-40-8 | p-I—Ph | * | H | * | ⁿBu | H | CH₃ | F | OH |

*R² and R³ᵇ joined together by (CH₂)₃ to form five-membered ring.

TABLE XXIX-41

| No | R¹ | R² | R³ᵃ | R³ᵇ | R⁴ | R⁵ | R⁶ | X | Y |
|---|---|---|---|---|---|---|---|---|---|
| XXIX-41-1 | CH₃ | H | H | H | Bz | H | CH₃ | F | OH |
| XXIX-41-2 | CH₃ | H | H | CH₃ | Bz | H | CH₃ | F | OH |
| XXIX-41-3 | CH₃ | H | H | CH(CH₃)₂ | Bz | H | CH₃ | F | OH |
| XXIX-41-4 | CH₃ | H | H | CH₂CH(CH₃)₂ | Bz | H | CH₃ | F | OH |
| XXIX-41-5 | CH₃ | H | H | CH₂Ph | Bz | H | CH₃ | F | OH |
| XXIX-41-6 | CH₃ | H | H | CH₂-indol-3-yl | Bz | H | CH₃ | F | OH |
| XXIX-41-7 | CH₃ | H | H | CH₂CH₂SCH₃ | Bz | H | CH₃ | F | OH |
| XXIX-41-8 | CH₃ | * | H | * | Bz | H | CH₃ | F | OH |

*R² and R³ᵇ joined together by (CH₂)₃ to form five-membered ring.

TABLE XXIX-42

| No | R¹ | R² | R³ᵃ | R³ᵇ | R⁴ | R⁵ | R⁶ | X | Y |
|---|---|---|---|---|---|---|---|---|---|
| XXIX-42-1 | Et | H | H | H | Bz | H | CH₃ | F | OH |
| XXIX-42-2 | Et | H | H | CH₃ | Bz | H | CH₃ | F | OH |
| XXIX-42-3 | Et | H | H | CH(CH₃)₂ | Bz | H | CH₃ | F | OH |
| XXIX-42-4 | Et | H | H | CH₂CH(CH₃)₂ | Bz | H | CH₃ | F | OH |
| XXIX-42-5 | Et | H | H | CH₂Ph | Bz | H | CH₃ | F | OH |
| XXIX-42-6 | Et | H | H | CH₂-indol-3-yl | Bz | H | CH₃ | F | OH |
| XXIX-42-7 | Et | H | H | CH₂CH₂SCH₃ | Bz | H | CH₃ | F | OH |
| XXIX-42-8 | Et | * | H | * | Bz | H | CH₃ | F | OH |

*R² and R³ᵇ joined together by (CH₂)₃ to form five-membered ring.

TABLE XXIX-43

| No | R¹ | R² | R³ᵃ | R³ᵇ | R⁴ | R⁵ | R⁶ | X | Y |
|---|---|---|---|---|---|---|---|---|---|
| XXIX-43-1 | ⁱPr | H | H | H | Bz | H | CH₃ | F | OH |
| XXIX-43-2 | ⁱPr | H | H | CH₃ | Bz | H | CH₃ | F | OH |
| XXIX-43-3 | ⁱPr | H | H | CH(CH₃)₂ | Bz | H | CH₃ | F | OH |
| XXIX-43-4 | ⁱPr | H | H | CH₂CH(CH₃)₂ | Bz | H | CH₃ | F | OH |
| XXIX-43-5 | ⁱPr | H | H | CH₂Ph | Bz | H | CH₃ | F | OH |
| XXIX-43-6 | ⁱPr | H | H | CH₂-indol-3-yl | Bz | H | CH₃ | F | OH |
| XXIX-43-7 | ⁱPr | H | H | CH₂CH₂SCH₃ | Bz | H | CH₃ | F | OH |
| XXIX-43-8 | ⁱPr | * | H | * | Bz | H | CH₃ | F | OH |

*R² and R³ᵇ joined together by (CH₂)₃ to form five-membered ring.

TABLE XXIX-44

| No | R¹ | R² | R³ᵃ | R³ᵇ | R⁴ | R⁵ | R⁶ | X | Y |
|---|---|---|---|---|---|---|---|---|---|
| XXIX-44-1 | ᵗBu | H | H | H | Bz | H | CH₃ | F | OH |
| XXIX-44-2 | ᵗBu | H | H | CH₃ | Bz | H | CH₃ | F | OH |
| XXIX-44-3 | ᵗBu | H | H | CH(CH₃)₂ | Bz | H | CH₃ | F | OH |
| XXIX-44-4 | ᵗBu | H | H | CH₂CH(CH₃)₂ | Bz | H | CH₃ | F | OH |
| XXIX-44-5 | ᵗBu | H | H | CH₂Ph | Bz | H | CH₃ | F | OH |
| XXIX-44-6 | ᵗBu | H | H | CH₂-indol-3-yl | Bz | H | CH₃ | F | OH |
| XXIX-44-7 | ᵗBu | H | H | CH₂CH₂SCH₃ | Bz | H | CH₃ | F | OH |
| XXIX-44-8 | ᵗBu | * | H | * | Bz | H | CH₃ | F | OH |

*R² and R³ᵇ joined together by (CH₂)₃ to form five-membered ring.

TABLE XXIX-45

| No | R¹ | R² | R³ᵃ | R³ᵇ | R⁴ | R⁵ | R⁶ | X | Y |
|---|---|---|---|---|---|---|---|---|---|
| XXIX-45-1 | Ph | H | H | H | Bz | H | CH₃ | F | OH |
| XXIX-45-2 | Ph | H | H | CH₃ | Bz | H | CH₃ | F | OH |
| XXIX-45-3 | Ph | H | H | CH(CH₃)₂ | Bz | H | CH₃ | F | OH |
| XXIX-45-4 | Ph | H | H | CH₂CH(CH₃)₂ | Bz | H | CH₃ | F | OH |
| XXIX-45-5 | Ph | H | H | CH₂Ph | Bz | H | CH₃ | F | OH |
| XXIX-45-6 | Ph | H | H | CH₂-indol-3-yl | Bz | H | CH₃ | F | OH |
| XXIX-45-7 | Ph | H | H | CH₂CH₂SCH₃ | Bz | H | CH₃ | F | OH |
| XXIX-45-8 | Ph | * | H | * | Bz | H | CH₃ | F | OH |

*$R^2$ and $R^{3b}$ joined together by (CH₂)₃ to form five-membered ring.

TABLE XXIX-46

| No | R¹ | R² | R³ᵃ | R³ᵇ | R⁴ | R⁵ | R⁶ | X | Y |
|---|---|---|---|---|---|---|---|---|---|
| XXIX-46-1 | p-Me—Ph | H | H | H | Bz | H | CH₃ | F | OH |
| XXIX-46-2 | p-Me—Ph | H | H | CH₃ | Bz | H | CH₃ | F | OH |
| XXIX-46-3 | p-Me—Ph | H | H | CH(CH₃)₂ | Bz | H | CH₃ | F | OH |
| XXIX-46-4 | p-Me—Ph | H | H | CH₂CH(CH₃)₂ | Bz | H | CH₃ | F | OH |
| XXIX-46-5 | p-Me—Ph | H | H | CH₂Ph | Bz | H | CH₃ | F | OH |
| XXIX-46-6 | p-Me—Ph | H | H | CH₂-indol-3-yl | Bz | H | CH₃ | F | OH |
| XXIX-46-7 | p-Me—Ph | H | H | CH₂CH₂SCH₃ | Bz | H | CH₃ | F | OH |
| XXIX-46-8 | p-Me—Ph | * | H | * | Bz | H | CH₃ | F | OH |

*$R^2$ and $R^{3b}$ joined together by (CH₂)₃ to form five-membered ring.

TABLE XXIX-47

| No | R¹ | R² | R³ᵃ | R³ᵇ | R⁴ | R⁵ | R⁶ | X | Y |
|---|---|---|---|---|---|---|---|---|---|
| XXIX-47-1 | p-F—Ph | H | H | H | Bz | H | CH₃ | F | OH |
| XXIX-47-2 | p-F—Ph | H | H | CH₃ | Bz | H | CH₃ | F | OH |
| XXIX-47-3 | p-F—Ph | H | H | CH(CH₃)₂ | Bz | H | CH₃ | F | OH |
| XXIX-47-4 | p-F—Ph | H | H | CH₂CH(CH₃)₂ | Bz | H | CH₃ | F | OH |
| XXIX-47-5 | p-F—Ph | H | H | CH₂Ph | Bz | H | CH₃ | F | OH |
| XXIX-47-6 | p-F—Ph | H | H | CH₂-indol-3-yl | Bz | H | CH₃ | F | OH |
| XXIX-47-7 | p-F—Ph | H | H | CH₂CH₂SCH₃ | Bz | H | CH₃ | F | OH |
| XXIX-47-8 | p-F—Ph | * | H | * | Bz | H | CH₃ | F | OH |

*$R^2$ and $R^{3b}$ joined together by (CH₂)₃ to form five-membered ring.

TABLE XXIX-48

| No | R¹ | R² | R³ᵃ | R³ᵇ | R⁴ | R⁵ | R⁶ | X | Y |
|---|---|---|---|---|---|---|---|---|---|
| XXIX-48-1 | p-Cl—Ph | H | H | H | Bz | H | CH₃ | F | OH |
| XXIX-48-2 | p-Cl—Ph | H | H | CH₃ | Bz | H | CH₃ | F | OH |
| XXIX-48-3 | p-Cl—Ph | H | H | CH(CH₃)₂ | Bz | H | CH₃ | F | OH |
| XXIX-48-4 | p-Cl—Ph | H | H | CH₂CH(CH₃)₂ | Bz | H | CH₃ | F | OH |
| XXIX-48-5 | p-Cl—Ph | H | H | CH₂Ph | Bz | H | CH₃ | F | OH |
| XXIX-48-6 | p-Cl—Ph | H | H | CH₂-indol-3-yl | Bz | H | CH₃ | F | OH |
| XXIX-48-7 | p-Cl—Ph | H | H | CH₂CH₂SCH₃ | Bz | H | CH₃ | F | OH |

TABLE XXIX-48-continued

| No | R¹ | R² | R³ᵃ | R³ᵇ | R⁴ | R⁵ | R⁶ | X | Y |
|---|---|---|---|---|---|---|---|---|---|
| XXIX-48-8 | p-Cl—Ph | * | H | * | Bz | H | CH₃ | F | OH |

*$R^2$ and $R^{3b}$ joined together by (CH₂)₃ to form five-membered ring.

TABLE XXIX-49

| No | R¹ | R² | R³ᵃ | R³ᵇ | R⁴ | R⁵ | R⁶ | X | Y |
|---|---|---|---|---|---|---|---|---|---|
| XXIX-49-1 | p-Br—Ph | H | H | H | Bz | H | CH₃ | F | OH |
| XXIX-49-2 | p-Br—Ph | H | H | CH₃ | Bz | H | CH₃ | F | OH |
| XXIX-49-3 | p-Br—Ph | H | H | CH(CH₃)₂ | Bz | H | CH₃ | F | OH |
| XXIX-49-4 | p-Br—Ph | H | H | CH₂CH(CH₃)₂ | Bz | H | CH₃ | F | OH |
| XXIX-49-5 | p-Br—Ph | H | H | CH₂Ph | Bz | H | CH₃ | F | OH |
| XXIX-49-6 | p-Br—Ph | H | H | CH₂-indol-3-yl | Bz | H | CH₃ | F | OH |
| XXIX-49-7 | p-Br—Ph | H | H | CH₂CH₂SCH₃ | Bz | H | CH₃ | F | OH |
| XXIX-49-8 | p-Br—Ph | * | H | * | Bz | H | CH₃ | F | OH |

*$R^2$ and $R^{3b}$ joined together by (CH₂)₃ to form five-membered ring.

TABLE XXIX-50

| No | R¹ | R² | R³ᵃ | R³ᵇ | R⁴ | R⁵ | R⁶ | X | Y |
|---|---|---|---|---|---|---|---|---|---|
| XXIX-50-1 | p-I—Ph | H | H | H | Bz | H | CH₃ | F | OH |
| XXIX-50-2 | p-I—Ph | H | H | CH₃ | Bz | H | CH₃ | F | OH |
| XXIX-50-3 | p-I—Ph | H | H | CH(CH₃)₂ | Bz | H | CH₃ | F | OH |
| XXIX-50-4 | p-I—Ph | H | H | CH₂CH(CH₃)₂ | Bz | H | CH₃ | F | OH |
| XXIX-50-5 | p-I—Ph | H | H | CH₂Ph | Bz | H | CH₃ | F | OH |
| XXIX-50-6 | p-I—Ph | H | H | CH₂-indol-3-yl | Bz | H | CH₃ | F | OH |
| XXIX-50-7 | p-I—Ph | H | H | CH₂CH₂SCH₃ | Bz | H | CH₃ | F | OH |
| XXIX-50-8 | p-I—Ph | * | H | * | Bz | H | CH₃ | F | OH |

*$R^2$ and $R^{3b}$ joined together by (CH₂)₃ to form five-membered ring.

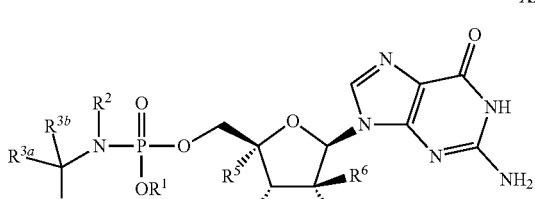

XXX

TABLE XXX-1

| No | R¹ | R² | R³ᵃ | R³ᵇ | R⁴ | R⁵ | R⁶ | X | Y |
|---|---|---|---|---|---|---|---|---|---|
| XXX-1-1 | CH₃ | H | H | H | CH₃ | H | F | H | OH |
| XXX-1-2 | CH₃ | H | H | CH₃ | CH₃ | H | F | H | OH |

TABLE XXX-1-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-1-3 | $CH_3$ | H | H | $CH(CH_3)_2$ | $CH_3$ | H | F | H | OH |
| XXX-1-4 | $CH_3$ | H | H | $CH_2CH(CH_3)_2$ | $CH_3$ | H | F | H | OH |
| XXX-1-5 | $CH_3$ | H | H | $CH_2Ph$ | $CH_3$ | H | F | H | OH |
| XXX-1-6 | $CH_3$ | H | H | $CH_2$-indol-3-yl | $CH_3$ | H | F | H | OH |
| XXX-1-7 | $CH_3$ | H | H | $CH_2CH_2SCH_3$ | $CH_3$ | H | F | H | OH |
| XXX-1-8 | $CH_3$ | * | H | * | $CH_3$ | H | F | H | OH |

*$R^2$ and $R^{3b}$ joined together by $(CH_2)_3$ to form five-membered ring.

TABLE XXX-2

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-2-1 | Et | H | H | H | $CH_3$ | H | F | H | OH |
| XXX-2-2 | Et | H | H | $CH_3$ | $CH_3$ | H | F | H | OH |
| XXX-2-3 | Et | H | H | $CH(CH_3)_2$ | $CH_3$ | H | F | H | OH |
| XXX-2-4 | Et | H | H | $CH_2CH(CH_3)_2$ | $CH_3$ | H | F | H | OH |
| XXX-2-5 | Et | H | H | $CH_2Ph$ | $CH_3$ | H | F | H | OH |
| XXX-2-6 | Et | H | H | $CH_2$-indol-3-yl | $CH_3$ | H | F | H | OH |
| XXX-2-7 | Et | H | H | $CH_2CH_2SCH_3$ | $CH_3$ | H | F | H | OH |
| XXX-2-8 | Et | * | H | * | $CH_3$ | H | F | H | OH |

*$R^2$ and $R^{3b}$ joined together by $(CH_2)_3$ to form five-membered ring.

TABLE XXX-3

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-3-1 | $^iPr$ | H | H | H | $CH_3$ | H | F | H | OH |
| XXX-3-2 | $^iPr$ | H | H | $CH_3$ | $CH_3$ | H | F | H | OH |
| XXX-3-3 | $^iPr$ | H | H | $CH(CH_3)_2$ | $CH_3$ | H | F | H | OH |
| XXX-3-4 | $^iPr$ | H | H | $CH_2CH(CH_3)_2$ | $CH_3$ | H | F | H | OH |
| XXX-3-5 | $^iPr$ | H | H | $CH_2Ph$ | $CH_3$ | H | F | H | OH |
| XXX-3-6 | $^iPr$ | H | H | $CH_2$-indol-3-yl | $CH_3$ | H | F | H | OH |
| XXX-3-7 | $^iPr$ | H | H | $CH_2CH_2SCH_3$ | $CH_3$ | H | F | H | OH |
| XXX-3-8 | $^iPr$ | * | H | * | $CH_3$ | H | F | H | OH |

*$R^2$ and $R^{3b}$ joined together by $(CH_2)_3$ to form five-membered ring.

TABLE XXX-4

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-4-1 | $^tBu$ | H | H | H | $CH_3$ | H | F | H | OH |
| XXX-4-2 | $^tBu$ | H | H | $CH_3$ | $CH_3$ | H | F | H | OH |
| XXX-4-3 | $^tBu$ | H | H | $CH(CH_3)_2$ | $CH_3$ | H | F | H | OH |
| XXX-4-4 | $^tBu$ | H | H | $CH_2CH(CH_3)_2$ | $CH_3$ | H | F | H | OH |
| XXX-4-5 | $^tBu$ | H | H | $CH_2Ph$ | $CH_3$ | H | F | H | OH |
| XXX-4-6 | $^tBu$ | H | H | $CH_2$-indol-3-yl | $CH_3$ | H | F | H | OH |
| XXX-4-7 | $^tBu$ | H | H | $CH_2CH_2SCH_3$ | $CH_3$ | H | F | H | OH |
| XXX-4-8 | $^tBu$ | * | H | * | $CH_3$ | H | F | H | OH |

*$R^2$ and $R^{3b}$ joined together by $(CH_2)_3$ to form five-membered ring.

TABLE XXX-5

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-5-1 | Ph | H | H | H | $CH_3$ | H | F | H | OH |
| XXX-5-2 | Ph | H | H | $CH_3$ | $CH_3$ | H | F | H | OH |
| XXX-5-3 | Ph | H | H | $CH(CH_3)_2$ | $CH_3$ | H | F | H | OH |
| XXX-5-4 | Ph | H | H | $CH_2CH(CH_3)_2$ | $CH_3$ | H | F | H | OH |
| XXX-5-5 | Ph | H | H | $CH_2Ph$ | $CH_3$ | H | F | H | OH |
| XXX-5-6 | Ph | H | H | $CH_2$-indol-3-yl | $CH_3$ | H | F | H | OH |
| XXX-5-7 | Ph | H | H | $CH_2CH_2SCH_3$ | $CH_3$ | H | F | H | OH |
| XXX-5-8 | Ph | * | H | * | $CH_3$ | H | F | H | OH |

*$R^2$ and $R^{3b}$ joined together by $(CH_2)_3$ to form five-membered ring.

TABLE XXX-6

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-6-1 | p-Me—Ph | H | H | H | $CH_3$ | H | F | H | OH |
| XXX-6-2 | p-Me—Ph | H | H | $CH_3$ | $CH_3$ | H | F | H | OH |
| XXX-6-3 | p-Me—Ph | H | H | $CH(CH_3)_2$ | $CH_3$ | H | F | H | OH |
| XXX-6-4 | p-Me—Ph | H | H | $CH_2CH(CH_3)_2$ | $CH_3$ | H | F | H | OH |
| XXX-6-5 | p-Me—Ph | H | H | $CH_2Ph$ | $CH_3$ | H | F | H | OH |
| XXX-6-6 | p-Me—Ph | H | H | $CH_2$-indol-3-yl | $CH_3$ | H | F | H | OH |
| XXX-6-7 | p-Me—Ph | H | H | $CH_2CH_2SCH_3$ | $CH_3$ | H | F | H | OH |
| XXX-6-8 | p-Me—Ph | * | H | * | $CH_3$ | H | F | H | OH |

*$R^2$ and $R^{3b}$ joined together by $(CH_2)_3$ to form five-membered ring.

TABLE XXX-7

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-7-1 | p-F—Ph | H | H | H | $CH_3$ | H | F | H | OH |
| XXX-7-2 | p-F—Ph | H | H | $CH_3$ | $CH_3$ | H | F | H | OH |
| XXX-7-3 | p-F—Ph | H | H | $CH(CH_3)_2$ | $CH_3$ | H | F | H | OH |
| XXX-7-4 | p-F—Ph | H | H | $CH_2CH(CH_3)_2$ | $CH_3$ | H | F | H | OH |
| XXX-7-5 | p-F—Ph | H | H | $CH_2Ph$ | $CH_3$ | H | F | H | OH |
| XXX-7-6 | p-F—Ph | H | H | $CH_2$-indol-3-yl | $CH_3$ | H | F | H | OH |
| XXX-7-7 | p-F—Ph | H | H | $CH_2CH_2SCH_3$ | $CH_3$ | H | F | H | OH |
| XXX-7-8 | p-F—Ph | * | H | * | $CH_3$ | H | F | H | OH |

*$R^2$ and $R^{3b}$ joined together by $(CH_2)_3$ to form five-membered ring.

TABLE XXX-8

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-8-1 | p-Cl—Ph | H | H | H | $CH_3$ | H | F | H | OH |
| XXX-8-2 | p-Cl—Ph | H | H | $CH_3$ | $CH_3$ | H | F | H | OH |

TABLE XXX-8-continued

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXX-8-3 | p-Cl—Ph | H | H | CH(CH$_3$)$_2$ | CH$_3$ | H | F | H | OH |
| XXX-8-4 | p-Cl—Ph | H | H | CH$_2$CH(CH$_3$)$_2$ | CH$_3$ | H | F | H | OH |
| XXX-8-5 | p-Cl—Ph | H | H | CH$_2$Ph | CH$_3$ | H | F | H | OH |
| XXX-8-6 | p-Cl—Ph | H | H | CH$_2$-indol-3-yl | CH$_3$ | H | F | H | OH |
| XXX-8-7 | p-Cl—Ph | H | H | CH$_2$CH$_2$SCH$_3$ | CH$_3$ | H | F | H | OH |
| XXX-8-8 | p-Cl—Ph | * | H | * | CH$_3$ | H | F | H | OH |

*R$^2$ and R$^{3b}$ joined together by (CH$_2$)$_3$ to form five-membered ring.

TABLE XXX-9

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXX-9-1 | p-Br—Ph | H | H | H | CH$_3$ | H | F | H | OH |
| XXX-9-2 | p-Br—Ph | H | H | CH$_3$ | CH$_3$ | H | F | H | OH |
| XXX-9-3 | p-Br—Ph | H | H | CH(CH$_3$)$_2$ | CH$_3$ | H | F | H | OH |
| XXX-9-4 | p-Br—Ph | H | H | CH$_2$CH(CH$_3$)$_2$ | CH$_3$ | H | F | H | OH |
| XXX-9-5 | p-Br—Ph | H | H | CH$_2$Ph | CH$_3$ | H | F | H | OH |
| XXX-9-6 | p-Br—Ph | H | H | CH$_2$-indol-3-yl | CH$_3$ | H | F | H | OH |
| XXX-9-7 | p-Br—Ph | H | H | CH$_2$CH$_2$SCH$_3$ | CH$_3$ | H | F | H | OH |
| XXX-9-8 | p-Br—Ph | * | H | * | CH$_3$ | H | F | H | OH |

*R$^2$ and R$^{3b}$ joined together by (CH$_2$)$_3$ to form five-membered ring.

TABLE XXX-10

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXX-10-1 | p-I—Ph | H | H | H | CH$_3$ | H | F | H | OH |
| XXX-10-2 | p-I—Ph | H | H | CH$_3$ | CH$_3$ | H | F | H | OH |
| XXX-10-3 | p-I—Ph | H | H | CH(CH$_3$)$_2$ | CH$_3$ | H | F | H | OH |
| XXX-10-4 | p-I—Ph | H | H | CH$_2$CH(CH$_3$)$_2$ | CH$_3$ | H | F | H | OH |
| XXX-10-5 | p-I—Ph | H | H | CH$_2$Ph | CH$_3$ | H | F | H | OH |
| XXX-10-6 | p-I—Ph | H | H | CH$_2$-indol-3-yl | CH$_3$ | H | F | H | OH |
| XXX-10-7 | p-I—Ph | H | H | CH$_2$CH$_2$SCH$_3$ | CH$_3$ | H | F | H | OH |
| XXX-10-8 | p-I—Ph | * | H | * | CH$_3$ | H | F | H | OH |

*R$^2$ and R$^{3b}$ joined together by (CH$_2$)$_3$ to form five-membered ring.

TABLE XXX-11

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXX-11-1 | CH$_3$ | H | H | H | Et | H | F | H | OH |
| XXX-11-2 | CH$_3$ | H | H | CH$_3$ | Et | H | F | H | OH |
| XXX-11-3 | CH$_3$ | H | H | CH(CH$_3$)$_2$ | Et | H | F | H | OH |
| XXX-11-4 | CH$_3$ | H | H | CH$_2$CH(CH$_3$)$_2$ | Et | H | F | H | OH |
| XXX-11-5 | CH$_3$ | H | H | CH$_2$Ph | Et | H | F | H | OH |
| XXX-11-6 | CH$_3$ | H | H | CH$_2$-indol-3-yl | Et | H | F | H | OH |
| XXX-11-7 | CH$_3$ | H | H | CH$_2$CH$_2$SCH$_3$ | Et | H | F | H | OH |
| XXX-11-8 | CH$_3$ | * | H | * | Et | H | F | H | OH |

*R$^2$ and R$^{3b}$ joined together by (CH$_2$)$_3$ to form five-membered ring.

TABLE XXX-12

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXX-12-1 | Et | H | H | H | Et | H | F | H | OH |
| XXX-12-2 | Et | H | H | CH$_3$ | Et | H | F | H | OH |
| XXX-12-3 | Et | H | H | CH(CH$_3$)$_2$ | Et | H | F | H | OH |
| XXX-12-4 | Et | H | H | CH$_2$CH(CH$_3$)$_2$ | Et | H | F | H | OH |
| XXX-12-5 | Et | H | H | CH$_2$Ph | Et | H | F | H | OH |
| XXX-12-6 | Et | H | H | CH$_2$-indol-3-yl | Et | H | F | H | OH |
| XXX-12-7 | Et | H | H | CH$_2$CH$_2$SCH$_3$ | Et | H | F | H | OH |
| XXX-12-8 | Et | * | H | * | Et | H | F | H | OH |

*R$^2$ and R$^{3b}$ joined together by (CH$_2$)$_3$ to form five-membered ring.

TABLE XXX-13

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXX-13-1 | $^i$Pr | H | H | H | Et | H | F | H | OH |
| XXX-13-2 | $^i$Pr | H | H | CH$_3$ | Et | H | F | H | OH |
| XXX-13-3 | $^i$Pr | H | H | CH(CH$_3$)$_2$ | Et | H | F | H | OH |
| XXX-13-4 | $^i$Pr | H | H | CH$_2$CH(CH$_3$)$_2$ | Et | H | F | H | OH |
| XXX-13-5 | $^i$Pr | H | H | CH$_2$Ph | Et | H | F | H | OH |
| XXX-13-6 | $^i$Pr | H | H | CH$_2$-indol-3-yl | Et | H | F | H | OH |
| XXX-13-7 | $^i$Pr | H | H | CH$_2$CH$_2$SCH$_3$ | Et | H | F | H | OH |
| XXX-13-8 | $^i$Pr | * | H | * | Et | H | F | H | OH |

*R$^2$ and R$^{3b}$ joined together by (CH$_2$)$_3$ to form five-membered ring.

TABLE XXX-14

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXX-14-1 | $^t$Bu | H | H | H | Et | H | F | H | OH |
| XXX-14-2 | $^t$Bu | H | H | CH$_3$ | Et | H | F | H | OH |
| XXX-14-3 | $^t$Bu | H | H | CH(CH$_3$)$_2$ | Et | H | F | H | OH |
| XXX-14-4 | $^t$Bu | H | H | CH$_2$CH(CH$_3$)$_2$ | Et | H | F | H | OH |
| XXX-14-5 | $^t$Bu | H | H | CH$_2$Ph | Et | H | F | H | OH |
| XXX-14-6 | $^t$Bu | H | H | CH$_2$-indol-3-yl | Et | H | F | H | OH |
| XXX-14-7 | $^t$Bu | H | H | CH$_2$CH$_2$SCH$_3$ | Et | H | F | H | OH |
| XXX-14-8 | $^t$Bu | * | H | * | Et | H | F | H | OH |

*R$^2$ and R$^{3b}$ joined together by (CH$_2$)$_3$ to form five-membered ring.

TABLE XXX-15

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXX-15-1 | Ph | H | H | H | Et | H | F | H | OH |
| XXX-15-2 | Ph | H | H | CH$_3$ | Et | H | F | H | OH |
| XXX-15-3 | Ph | H | H | CH(CH$_3$)$_2$ | Et | H | F | H | OH |
| XXX-15-4 | Ph | H | H | CH$_2$CH(CH$_3$)$_2$ | Et | H | F | H | OH |
| XXX-15-5 | Ph | H | H | CH$_2$Ph | Et | H | F | H | OH |
| XXX-15-6 | Ph | H | H | CH$_2$-indol-3-yl | Et | H | F | H | OH |
| XXX-15-7 | Ph | H | H | CH$_2$CH$_2$SCH$_3$ | Et | H | F | H | OH |
| XXX-15-8 | Ph | * | H | * | Et | H | F | H | OH |

*R$^2$ and R$^{3b}$ joined together by (CH$_2$)$_3$ to form five-membered ring.

TABLE XXX-16

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-16-1 | p-Me—Ph | H | H | H | Et | H | F | H | OH |
| XXX-16-2 | p-Me—Ph | H | H | CH$_3$ | Et | H | F | H | OH |
| XXX-16-3 | p-Me—Ph | H | H | CH(CH$_3$)$_2$ | Et | H | F | H | OH |
| XXX-16-4 | p-Me—Ph | H | H | CH$_2$CH(CH$_3$)$_2$ | Et | H | F | H | OH |
| XXX-16-5 | p-Me—Ph | H | H | CH$_2$Ph | Et | H | F | H | OH |
| XXX-16-6 | p-Me—Ph | H | H | CH$_2$-indol-3-yl | Et | H | F | H | OH |
| XXX-16-7 | p-Me—Ph | H | H | CH$_2$CH$_2$SCH$_3$ | Et | H | F | H | OH |
| XXX-16-8 | p-Me—Ph | * | H | * | Et | H | F | H | OH |

*$R^2$ and $R^{3b}$ joined together by (CH$_2$)$_3$ to form five-membered ring.

TABLE XXX-17

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-17-1 | p-F—Ph | H | H | H | Et | H | F | H | OH |
| XXX-17-2 | p-F—Ph | H | H | CH$_3$ | Et | H | F | H | OH |
| XXX-17-3 | p-F—Ph | H | H | CH(CH$_3$)$_2$ | Et | H | F | H | OH |
| XXX-17-4 | p-F—Ph | H | H | CH$_2$CH(CH$_3$)$_2$ | Et | H | F | H | OH |
| XXX-17-5 | p-F—Ph | H | H | CH$_2$Ph | Et | H | F | H | OH |
| XXX-17-6 | p-F—Ph | H | H | CH$_2$-indol-3-yl | Et | H | F | H | OH |
| XXX-17-7 | p-F—Ph | H | H | CH$_2$CH$_2$SCH$_3$ | Et | H | F | H | OH |
| XXX-17-8 | p-F—Ph | * | H | * | Et | H | F | H | OH |

*$R^2$ and $R^{3b}$ joined together by (CH$_2$)$_3$ to form five-membered ring.

TABLE XXX-18

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-18-1 | p-Cl—Ph | H | H | H | Et | H | F | H | OH |
| XXX-18-2 | p-Cl—Ph | H | H | CH$_3$ | Et | H | F | H | OH |
| XXX-18-3 | p-Cl—Ph | H | H | CH(CH$_3$)$_2$ | Et | H | F | H | OH |
| XXX-18-4 | p-Cl—Ph | H | H | CH$_2$CH(CH$_3$)$_2$ | Et | H | F | H | OH |
| XXX-18-5 | p-Cl—Ph | H | H | CH$_2$Ph | Et | H | F | H | OH |
| XXX-18-6 | p-Cl—Ph | H | H | CH$_2$-indol-3-yl | Et | H | F | H | OH |
| XXX-18-7 | p-Cl—Ph | H | H | CH$_2$CH$_2$SCH$_3$ | Et | H | F | H | OH |
| XXX-18-8 | p-Cl—Ph | * | H | * | Et | H | F | H | OH |

*$R^2$ and $R^{3b}$ joined together by (CH$_2$)$_3$ to form five-membered ring.

TABLE XXX-19

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-19-1 | p-Br—Ph | H | H | H | Et | H | F | H | OH |
| XXX-19-2 | p-Br—Ph | H | H | CH$_3$ | Et | H | F | H | OH |
| XXX-19-3 | p-Br—Ph | H | H | CH(CH$_3$)$_2$ | Et | H | F | H | OH |
| XXX-19-4 | p-Br—Ph | H | H | CH$_2$CH(CH$_3$)$_2$ | Et | H | F | H | OH |
| XXX-19-5 | p-Br—Ph | H | H | CH$_2$Ph | Et | H | F | H | OH |
| XXX-19-6 | p-Br—Ph | H | H | CH$_2$-indol-3-yl | Et | H | F | H | OH |
| XXX-19-7 | p-Br—Ph | H | H | CH$_2$CH$_2$SCH$_3$ | Et | H | F | H | OH |
| XXX-19-8 | p-Br—Ph | * | H | * | Et | H | F | H | OH |

*$R^2$ and $R^{3b}$ joined together by (CH$_2$)$_3$ to form five-membered ring.

TABLE XXX-20

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-20-1 | p-I—Ph | H | H | H | Et | H | F | H | OH |
| XXX-20-2 | p-I—Ph | H | H | CH$_3$ | Et | H | F | H | OH |
| XXX-20-3 | p-I—Ph | H | H | CH(CH$_3$)$_2$ | Et | H | F | H | OH |
| XXX-20-4 | p-I—Ph | H | H | CH$_2$CH(CH$_3$)$_2$ | Et | H | F | H | OH |
| XXX-20-5 | p-I—Ph | H | H | CH$_2$Ph | Et | H | F | H | OH |
| XXX-20-6 | p-I—Ph | H | H | CH$_2$-indol-3-yl | Et | H | F | H | OH |
| XXX-20-7 | p-I—Ph | H | H | CH$_2$CH$_2$SCH$_3$ | Et | H | F | H | OH |
| XXX-20-8 | p-I—Ph | * | H | * | Et | H | F | H | OH |

*$R^2$ and $R^{3b}$ joined together by (CH$_2$)$_3$ to form five-membered ring.

TABLE XXX-21

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-21-1 | CH$_3$ | H | H | H | $^i$Pr | H | F | H | OH |
| XXX-21-2 | CH$_3$ | H | H | CH$_3$ | $^i$Pr | H | F | H | OH |
| XXX-21-3 | CH$_3$ | H | H | CH(CH$_3$)$_2$ | $^i$Pr | H | F | H | OH |
| XXX-21-4 | CH$_3$ | H | H | CH$_2$CH(CH$_3$)$_2$ | $^i$Pr | H | F | H | OH |
| XXX-21-5 | CH$_3$ | H | H | CH$_2$Ph | $^i$Pr | H | F | H | OH |
| XXX-21-6 | CH$_3$ | H | H | CH$_2$-indol-3-yl | $^i$Pr | H | F | H | OH |
| XXX-21-7 | CH$_3$ | H | H | CH$_2$CH$_2$SCH$_3$ | $^i$Pr | H | F | H | OH |
| XXX-21-8 | CH$_3$ | * | H | * | $^i$Pr | H | F | H | OH |

*$R^2$ and $R^{3b}$ joined together by (CH$_2$)$_3$ to form five-membered ring.

TABLE XXX-22

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-22-1 | Et | H | H | H | $^i$Pr | H | F | H | OH |
| XXX-22-2 | Et | H | H | CH$_3$ | $^i$Pr | H | F | H | OH |
| XXX-22-3 | Et | H | H | CH(CH$_3$)$_2$ | $^i$Pr | H | F | H | OH |
| XXX-22-4 | Et | H | H | CH$_2$CH(CH$_3$)$_2$ | $^i$Pr | H | F | H | OH |
| XXX-22-5 | Et | H | H | CH$_2$Ph | $^i$Pr | H | F | H | OH |
| XXX-22-6 | Et | H | H | CH$_2$-indol-3-yl | $^i$Pr | H | F | H | OH |
| XXX-22-7 | Et | H | H | CH$_2$CH$_2$SCH$_3$ | $^i$Pr | H | F | H | OH |
| XXX-22-8 | Et | * | H | * | $^i$Pr | H | F | H | OH |

*$R^2$ and $R^{3b}$ joined together by (CH$_2$)$_3$ to form five-membered ring.

TABLE XXX-23

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-23-1 | $^i$Pr | H | H | H | $^i$Pr | H | F | H | OH |
| XXX-23-2 | $^i$Pr | H | H | CH$_3$ | $^i$Pr | H | F | H | OH |
| XXX-23-3 | $^i$Pr | H | H | CH(CH$_3$)$_2$ | $^i$Pr | H | F | H | OH |
| XXX-23-4 | $^i$Pr | H | H | CH$_2$CH(CH$_3$)$_2$ | $^i$Pr | H | F | H | OH |
| XXX-23-5 | $^i$Pr | H | H | CH$_2$Ph | $^i$Pr | H | F | H | OH |
| XXX-23-6 | $^i$Pr | H | H | CH$_2$-indol-3-yl | $^i$Pr | H | F | H | OH |
| XXX-23-7 | $^i$Pr | H | H | CH$_2$CH$_2$SCH$_3$ | $^i$Pr | H | F | H | OH |
| XXX-23-8 | $^i$Pr | * | H | * | $^i$Pr | H | F | H | OH |

*$R^2$ and $R^{3b}$ joined together by (CH$_2$)$_3$ to form five-membered ring.

TABLE XXX-24

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-24-1 | $^t$Bu | H | H | H | $^i$Pr | H | F | H | OH |
| XXX-24-2 | $^t$Bu | H | H | CH$_3$ | $^i$Pr | H | F | H | OH |
| XXX-24-3 | $^t$Bu | H | H | CH(CH$_3$)$_2$ | $^i$Pr | H | F | H | OH |
| XXX-24-4 | $^t$Bu | H | H | CH$_2$CH(CH$_3$)$_2$ | $^i$Pr | H | F | H | OH |
| XXX-24-5 | $^t$Bu | H | H | CH$_2$Ph | $^i$Pr | H | F | H | OH |
| XXX-24-6 | $^t$Bu | H | H | CH$_2$-indol-3-yl | $^i$Pr | H | F | H | OH |
| XXX-24-7 | $^t$Bu | H | H | CH$_2$CH$_2$SCH$_3$ | $^i$Pr | H | F | H | OH |
| XXX-24-8 | $^t$Bu | * | H | * | $^i$Pr | H | F | H | OH |

*$R^2$ and $R^{3b}$ joined together by (CH$_2$)$_3$ to form five-membered ring.

TABLE XXX-25

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-25-1 | Ph | H | H | H | $^i$Pr | H | F | H | OH |
| XXX-25-2 | Ph | H | H | CH$_3$ | $^i$Pr | H | F | H | OH |
| XXX-25-3 | Ph | H | H | CH(CH$_3$)$_2$ | $^i$Pr | H | F | H | OH |
| XXX-25-4 | Ph | H | H | CH$_2$CH(CH$_3$)$_2$ | $^i$Pr | H | F | H | OH |
| XXX-25-5 | Ph | H | H | CH$_2$Ph | $^i$Pr | H | F | H | OH |
| XXX-25-6 | Ph | H | H | CH$_2$-indol-3-yl | $^i$Pr | H | F | H | OH |
| XXX-25-7 | Ph | H | H | CH$_2$CH$_2$SCH$_3$ | $^i$Pr | H | F | H | OH |
| XXX-25-8 | Ph | * | H | * | $^i$Pr | H | F | H | OH |

*$R^2$ and $R^{3b}$ joined together by (CH$_2$)$_3$ to form five-membered ring.

TABLE XXX-26

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-26-1 | p-Me—Ph | H | H | H | $^i$Pr | H | F | H | OH |
| XXX-26-2 | p-Me—Ph | H | H | CH$_3$ | $^i$Pr | H | F | H | OH |
| XXX-26-3 | p-Me—Ph | H | H | CH(CH$_3$)$_2$ | $^i$Pr | H | F | H | OH |
| XXX-26-4 | p-Me—Ph | H | H | CH$_2$CH(CH$_3$)$_2$ | $^i$Pr | H | F | H | OH |
| XXX-26-5 | p-Me—Ph | H | H | CH$_2$Ph | $^i$Pr | H | F | H | OH |
| XXX-26-6 | p-Me—Ph | H | H | CH$_2$-indol-3-yl | $^i$Pr | H | F | H | OH |
| XXX-26-7 | p-Me—Ph | H | H | CH$_2$CH$_2$SCH$_3$ | $^i$Pr | H | F | H | OH |
| XXX-26-8 | p-Me—Ph | * | H | * | $^i$Pr | H | F | H | OH |

*$R^2$ and $R^{3b}$ joined together by (CH$_2$)$_3$ to form five-membered ring.

TABLE XXX-27

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-27-1 | p-F—Ph | H | H | H | $^i$Pr | H | F | H | OH |
| XXX-27-2 | p-F—Ph | H | H | CH$_3$ | $^i$Pr | H | F | H | OH |
| XXX-27-3 | p-F—Ph | H | H | CH(CH$_3$)$_2$ | $^i$Pr | H | F | H | OH |
| XXX-27-4 | p-F—Ph | H | H | CH$_2$CH(CH$_3$)$_2$ | $^i$Pr | H | F | H | OH |
| XXX-27-5 | p-F—Ph | H | H | CH$_2$Ph | $^i$Pr | H | F | H | OH |
| XXX-27-6 | p-F—Ph | H | H | CH$_2$-indol-3-yl | $^i$Pr | H | F | H | OH |
| XXX-27-7 | p-F—Ph | H | H | CH$_2$CH$_2$SCH$_3$ | $^i$Pr | H | F | H | OH |
| XXX-27-8 | p-F—Ph | * | H | * | $^i$Pr | H | F | H | OH |

*$R^2$ and $R^{3b}$ joined together by (CH$_2$)$_3$ to form five-membered ring.

TABLE XXX-28

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-28-1 | p-Cl—Ph | H | H | H | $^i$Pr | H | F | H | OH |
| XXX-28-2 | p-Cl—Ph | H | H | CH$_3$ | $^i$Pr | H | F | H | OH |
| XXX-28-3 | p-Cl—Ph | H | H | CH(CH$_3$)$_2$ | $^i$Pr | H | F | H | OH |
| XXX-28-4 | p-Cl—Ph | H | H | CH$_2$CH(CH$_3$)$_2$ | $^i$Pr | H | F | H | OH |
| XXX-28-5 | p-Cl—Ph | H | H | CH$_2$Ph | $^i$Pr | H | F | H | OH |
| XXX-28-6 | p-Cl—Ph | H | H | CH$_2$-indol-3-yl | $^i$Pr | H | F | H | OH |
| XXX-28-7 | p-Cl—Ph | H | H | CH$_2$CH$_2$SCH$_3$ | $^i$Pr | H | F | H | OH |
| XXX-28-8 | p-Cl—Ph | * | H | * | $^i$Pr | H | F | H | OH |

*$R^2$ and $R^{3b}$ joined together by (CH$_2$)$_3$ to form five-membered ring.

TABLE XXX-29

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-29-1 | p-Br—Ph | H | H | H | $^i$Pr | H | F | H | OH |
| XXX-29-2 | p-Br—Ph | H | H | CH$_3$ | $^i$Pr | H | F | H | OH |
| XXX-29-3 | p-Br—Ph | H | H | CH(CH$_3$)$_2$ | $^i$Pr | H | F | H | OH |
| XXX-29-4 | p-Br—Ph | H | H | CH$_2$CH(CH$_3$)$_2$ | $^i$Pr | H | F | H | OH |
| XXX-29-5 | p-Br—Ph | H | H | CH$_2$Ph | $^i$Pr | H | F | H | OH |
| XXX-29-6 | p-Br—Ph | H | H | CH$_2$-indol-3-yl | $^i$Pr | H | F | H | OH |
| XXX-29-7 | p-Br—Ph | H | H | CH$_2$CH$_2$SCH$_3$ | $^i$Pr | H | F | H | OH |
| XXX-29-8 | p-Br—Ph | * | H | * | $^i$Pr | H | F | H | OH |

*$R^2$ and $R^{3b}$ joined together by (CH$_2$)$_3$ to form five-membered ring.

TABLE XXX-30

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-30-1 | p-I—Ph | H | H | H | $^i$Pr | H | F | H | OH |
| XXX-30-2 | p-I—Ph | H | H | CH$_3$ | $^i$Pr | H | F | H | OH |
| XXX-30-3 | p-I—Ph | H | H | CH(CH$_3$)$_2$ | $^i$Pr | H | F | H | OH |
| XXX-30-4 | p-I—Ph | H | H | CH$_2$CH(CH$_3$)$_2$ | $^i$Pr | H | F | H | OH |
| XXX-30-5 | p-I—Ph | H | H | CH$_2$Ph | $^i$Pr | H | F | H | OH |
| XXX-30-6 | p-I—Ph | H | H | CH$_2$-indol-3-yl | $^i$Pr | H | F | H | OH |
| XXX-30-7 | p-I—Ph | H | H | CH$_2$CH$_2$SCH$_3$ | $^i$Pr | H | F | H | OH |
| XXX-30-8 | p-I—Ph | * | H | * | $^i$Pr | H | F | H | OH |

*$R^2$ and $R^{3b}$ joined together by (CH$_2$)$_3$ to form five-membered ring.

TABLE XXX-31

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-31-1 | CH$_3$ | H | H | H | $^n$Bu | H | F | H | OH |
| XXX-31-2 | CH$_3$ | H | H | CH$_3$ | $^n$Bu | H | F | H | OH |
| XXX-31-3 | CH$_3$ | H | H | CH(CH$_3$)$_2$ | $^n$Bu | H | F | H | OH |
| XXX-31-4 | CH$_3$ | H | H | CH$_2$CH(CH$_3$)$_2$ | $^n$Bu | H | F | H | OH |
| XXX-31-5 | CH$_3$ | H | H | CH$_2$Ph | $^n$Bu | H | F | H | OH |
| XXX-31-6 | CH$_3$ | H | H | CH$_2$-indol-3-yl | $^n$Bu | H | F | H | OH |
| XXX-31-7 | CH$_3$ | H | H | CH$_2$CH$_2$SCH$_3$ | $^n$Bu | H | F | H | OH |
| XXX-31-8 | CH$_3$ | * | H | * | $^n$Bu | H | F | H | OH |

*$R^2$ and $R^{3b}$ joined together by (CH$_2$)$_3$ to form five-membered ring.

TABLE XXX-32

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-32-1 | Et | H | H | H | $^n$Bu | H | F | H | OH |
| XXX-32-2 | Et | H | H | CH$_3$ | $^n$Bu | H | F | H | OH |
| XXX-32-3 | Et | H | H | CH(CH$_3$)$_2$ | $^n$Bu | H | F | H | OH |
| XXX-32-4 | Et | H | H | CH$_2$CH(CH$_3$)$_2$ | $^n$Bu | H | F | H | OH |
| XXX-32-5 | Et | H | H | CH$_2$Ph | $^n$Bu | H | F | H | OH |
| XXX-32-6 | Et | H | H | CH$_2$-indol-3-yl | $^n$Bu | H | F | H | OH |
| XXX-32-7 | Et | H | H | CH$_2$CH$_2$SCH$_3$ | $^n$Bu | H | F | H | OH |
| XXX-32-8 | Et | * | H | * | $^n$Bu | H | F | H | OH |

*$R^2$ and $R^{3b}$ joined together by (CH$_2$)$_3$ to form five-membered ring.

TABLE XXX-33

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-33-1 | $^i$Pr | H | H | H | $^n$Bu | H | F | H | OH |
| XXX-33-2 | $^i$Pr | H | H | CH$_3$ | $^n$Bu | H | F | H | OH |
| XXX-33-3 | $^i$Pr | H | H | CH(CH$_3$)$_2$ | $^n$Bu | H | F | H | OH |
| XXX-33-4 | $^i$Pr | H | H | CH$_2$CH(CH$_3$)$_2$ | $^n$Bu | H | F | H | OH |
| XXX-33-5 | $^i$Pr | H | H | CH$_2$Ph | $^n$Bu | H | F | H | OH |
| XXX-33-6 | $^i$Pr | H | H | CH$_2$-indol-3-yl | $^n$Bu | H | F | H | OH |
| XXX-33-7 | $^i$Pr | H | H | CH$_2$CH$_2$SCH$_3$ | $^n$Bu | H | F | H | OH |
| XXX-33-8 | $^i$Pr | * | H | * | $^n$Bu | H | F | H | OH |

*$R^2$ and $R^{3b}$ joined together by (CH$_2$)$_3$ to form five-membered ring.

TABLE XXX-34

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-34-1 | $^t$Bu | H | H | H | $^n$Bu | H | F | H | OH |
| XXX-34-2 | $^t$Bu | H | H | CH$_3$ | $^n$Bu | H | F | H | OH |
| XXX-34-3 | $^t$Bu | H | H | CH(CH$_3$)$_2$ | $^n$Bu | H | F | H | OH |
| XXX-34-4 | $^t$Bu | H | H | CH$_2$CH(CH$_3$)$_2$ | $^n$Bu | H | F | H | OH |
| XXX-34-5 | $^t$Bu | H | H | CH$_2$Ph | $^n$Bu | H | F | H | OH |
| XXX-34-6 | $^t$Bu | H | H | CH$_2$-indol-3-yl | $^n$Bu | H | F | H | OH |
| XXX-34-7 | $^t$Bu | H | H | CH$_2$CH$_2$SCH$_3$ | $^n$Bu | H | F | H | OH |
| XXX-34-8 | $^t$Bu | * | H | * | $^n$Bu | H | F | H | OH |

*$R^2$ and $R^{3b}$ joined together by (CH$_2$)$_3$ to form five-membered ring.

TABLE XXX-35

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-35-1 | Ph | H | H | H | $^n$Bu | H | F | H | OH |
| XXX-35-2 | Ph | H | H | CH$_3$ | $^n$Bu | H | F | H | OH |
| XXX-35-3 | Ph | H | H | CH(CH$_3$)$_2$ | $^n$Bu | H | F | H | OH |
| XXX-35-4 | Ph | H | H | CH$_2$CH(CH$_3$)$_2$ | $^n$Bu | H | F | H | OH |
| XXX-35-5 | Ph | H | H | CH$_2$Ph | $^n$Bu | H | F | H | OH |
| XXX-35-6 | Ph | H | H | CH$_2$-indol-3-yl | $^n$Bu | H | F | H | OH |
| XXX-35-7 | Ph | H | H | CH$_2$CH$_2$SCH$_3$ | $^n$Bu | H | F | H | OH |
| XXX-35-8 | Ph | * | H | * | $^n$Bu | H | F | H | OH |

*$R^2$ and $R^{3b}$ joined together by (CH$_2$)$_3$ to form five-membered ring.

TABLE XXX-36

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-36-1 | p-Me—Ph | H | H | H | $^n$Bu | H | F | H | OH |
| XXX-36-2 | p-Me—Ph | H | H | $CH_3$ | $^n$Bu | H | F | H | OH |
| XXX-36-3 | p-Me—Ph | H | H | $CH(CH_3)_2$ | $^n$Bu | H | F | H | OH |
| XXX-36-4 | p-Me—Ph | H | H | $CH_2CH(CH_3)_2$ | $^n$Bu | H | F | H | OH |
| XXX-36-5 | p-Me—Ph | H | H | $CH_2Ph$ | $^n$Bu | H | F | H | OH |
| XXX-36-6 | p-Me—Ph | H | H | $CH_2$-indol-3-yl | $^n$Bu | H | F | H | OH |
| XXX-36-7 | p-Me—Ph | H | H | $CH_2CH_2SCH_3$ | $^n$Bu | H | F | H | OH |
| XXX-36-8 | p-Me—Ph | * | H | * | $^n$Bu | H | F | H | OH |

*$R^2$ and $R^{3b}$ joined together by $(CH_2)_3$ to form five-membered ring.

TABLE XXX-37

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-37-1 | p-F—Ph | H | H | H | $^n$Bu | H | F | H | OH |
| XXX-37-2 | p-F—Ph | H | H | $CH_3$ | $^n$Bu | H | F | H | OH |
| XXX-37-3 | p-F—Ph | H | H | $CH(CH_3)_2$ | $^n$Bu | H | F | H | OH |
| XXX-37-4 | p-F—Ph | H | H | $CH_2CH(CH_3)_2$ | $^n$Bu | H | F | H | OH |
| XXX-37-5 | p-F—Ph | H | H | $CH_2Ph$ | $^n$Bu | H | F | H | OH |
| XXX-37-6 | p-F—Ph | H | H | $CH_2$-indol-3-yl | $^n$Bu | H | F | H | OH |
| XXX-37-7 | p-F—Ph | H | H | $CH_2CH_2SCH_3$ | $^n$Bu | H | F | H | OH |
| XXX-37-8 | p-F—Ph | * | H | * | $^n$Bu | H | F | H | OH |

*$R^2$ and $R^{3b}$ joined together by $(CH_2)_3$ to form five-membered ring.

TABLE XXX-38

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-38-1 | p-Cl—Ph | H | H | H | $^n$Bu | H | F | H | OH |
| XXX-38-2 | p-Cl—Ph | H | H | $CH_3$ | $^n$Bu | H | F | H | OH |
| XXX-38-3 | p-Cl—Ph | H | H | $CH(CH_3)_2$ | $^n$Bu | H | F | H | OH |
| XXX-38-4 | p-Cl—Ph | H | H | $CH_2CH(CH_3)_2$ | $^n$Bu | H | F | H | OH |
| XXX-38-5 | p-Cl—Ph | H | H | $CH_2Ph$ | $^n$Bu | H | F | H | OH |
| XXX-38-6 | p-Cl—Ph | H | H | $CH_2$-indol-3-yl | $^n$Bu | H | F | H | OH |
| XXX-38-7 | p-Cl—Ph | H | H | $CH_2CH_2SCH_3$ | $^n$Bu | H | F | H | OH |
| XXX-38-8 | p-Cl—Ph | * | H | * | $^n$Bu | H | F | H | OH |

*$R^2$ and $R^{3b}$ joined together by $(CH_2)_3$ to form five-membered ring.

TABLE XXX-39

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-39-1 | p-Br—Ph | H | H | H | $^n$Bu | H | F | H | OH |
| XXX-39-2 | p-Br—Ph | H | H | $CH_3$ | $^n$Bu | H | F | H | OH |
| XXX-39-3 | p-Br—Ph | H | H | $CH(CH_3)_2$ | $^n$Bu | H | F | H | OH |
| XXX-39-4 | p-Br—Ph | H | H | $CH_2CH(CH_3)_2$ | $^n$Bu | H | F | H | OH |
| XXX-39-5 | p-Br—Ph | H | H | $CH_2Ph$ | $^n$Bu | H | F | H | OH |
| XXX-39-6 | p-Br—Ph | H | H | $CH_2$-indol-3-yl | $^n$Bu | H | F | H | OH |
| XXX-39-7 | p-Br—Ph | H | H | $CH_2CH_2SCH_3$ | $^n$Bu | H | F | H | OH |
| XXX-39-8 | p-Br—Ph | * | H | * | $^n$Bu | H | F | H | OH |

*$R^2$ and $R^{3b}$ joined together by $(CH_2)_3$ to form five-membered ring.

TABLE XXX-40

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-40-1 | p-I—Ph | H | H | H | $^n$Bu | H | F | H | OH |
| XXX-40-2 | p-I—Ph | H | H | $CH_3$ | $^n$Bu | H | F | H | OH |
| XXX-40-3 | p-I—Ph | H | H | $CH(CH_3)_2$ | $^n$Bu | H | F | H | OH |
| XXX-40-4 | p-I—Ph | H | H | $CH_2CH(CH_3)_2$ | $^n$Bu | H | F | H | OH |
| XXX-40-5 | p-I—Ph | H | H | $CH_2Ph$ | $^n$Bu | H | F | H | OH |
| XXX-40-6 | p-I—Ph | H | H | $CH_2$-indol-3-yl | $^n$Bu | H | F | H | OH |
| XXX-40-7 | p-I—Ph | H | H | $CH_2CH_2SCH_3$ | $^n$Bu | H | F | H | OH |
| XXX-40-8 | p-I—Ph | * | H | * | $^n$Bu | H | F | H | OH |

*$R^2$ and $R^{3b}$ joined together by $(CH_2)_3$ to form five-membered ring.

TABLE XXX-41

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-41-1 | $CH_3$ | H | H | H | Bz | H | F | H | OH |
| XXX-41-2 | $CH_3$ | H | H | $CH_3$ | Bz | H | F | H | OH |
| XXX-41-3 | $CH_3$ | H | H | $CH(CH_3)_2$ | Bz | H | F | H | OH |
| XXX-41-4 | $CH_3$ | H | H | $CH_2CH(CH_3)_2$ | Bz | H | F | H | OH |
| XXX-41-5 | $CH_3$ | H | H | $CH_2Ph$ | Bz | H | F | H | OH |
| XXX-41-6 | $CH_3$ | H | H | $CH_2$-indol-3-yl | Bz | H | F | H | OH |
| XXX-41-7 | $CH_3$ | H | H | $CH_2CH_2SCH_3$ | Bz | H | F | H | OH |
| XXX-41-8 | $CH_3$ | * | H | * | Bz | H | F | H | OH |

*$R^2$ and $R^{3b}$ joined together by $(CH_2)_3$ to form five-membered ring.

TABLE XXX-42

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-42-1 | Et | H | H | H | Bz | H | F | H | OH |
| XXX-42-2 | Et | H | H | $CH_3$ | Bz | H | F | H | OH |
| XXX-42-3 | Et | H | H | $CH(CH_3)_2$ | Bz | H | F | H | OH |
| XXX-42-4 | Et | H | H | $CH_2CH(CH_3)_2$ | Bz | H | F | H | OH |
| XXX-42-5 | Et | H | H | $CH_2Ph$ | Bz | H | F | H | OH |
| XXX-42-6 | Et | H | H | $CH_2$-indol-3-yl | Bz | H | F | H | OH |
| XXX-42-7 | Et | H | H | $CH_2CH_2SCH_3$ | Bz | H | F | H | OH |
| XXX-42-8 | Et | * | H | * | Bz | H | F | H | OH |

*$R^2$ and $R^{3b}$ joined together by $(CH_2)_3$ to form five-membered ring.

TABLE XXX-43

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-43-1 | $^i$Pr | H | H | H | Bz | H | F | H | OH |
| XXX-43-2 | $^i$Pr | H | H | $CH_3$ | Bz | H | F | H | OH |
| XXX-43-3 | $^i$Pr | H | H | $CH(CH_3)_2$ | Bz | H | F | H | OH |
| XXX-43-4 | $^i$Pr | H | H | $CH_2CH(CH_3)_2$ | Bz | H | F | H | OH |
| XXX-43-5 | $^i$Pr | H | H | $CH_2Ph$ | Bz | H | F | H | OH |
| XXX-43-6 | $^i$Pr | H | H | $CH_2$-indol-3-yl | Bz | H | F | H | OH |
| XXX-43-7 | $^i$Pr | H | H | $CH_2CH_2SCH_3$ | Bz | H | F | H | OH |
| XXX-43-8 | $^i$Pr | * | H | * | Bz | H | F | H | OH |

*$R^2$ and $R^{3b}$ joined together by $(CH_2)_3$ to form five-membered ring.

TABLE XXX-44

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-44-1 | $^t$Bu | H | H | H | Bz | H | F | H | OH |
| XXX-44-2 | $^t$Bu | H | H | $CH_3$ | Bz | H | F | H | OH |
| XXX-44-3 | $^t$Bu | H | H | $CH(CH_3)_2$ | Bz | H | F | H | OH |
| XXX-44-4 | $^t$Bu | H | H | $CH_2CH(CH_3)_2$ | Bz | H | F | H | OH |
| XXX-44-5 | $^t$Bu | H | H | $CH_2Ph$ | Bz | H | F | H | OH |
| XXX-44-6 | $^t$Bu | H | H | $CH_2$-indol-3-yl | Bz | H | F | H | OH |
| XXX-44-7 | $^t$Bu | H | H | $CH_2CH_2SCH_3$ | Bz | H | F | H | OH |
| XXX-44-8 | $^t$Bu | * | H | * | Bz | H | F | H | OH |

*$R^2$ and $R^{3b}$ joined together by $(CH_2)_3$ to form five-membered ring.

TABLE XXX-45

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXX-45-1 | Ph | H | H | H | Bz | H | F | H | OH |
| XXX-45-2 | Ph | H | H | $CH_3$ | Bz | H | F | H | OH |
| XXX-45-3 | Ph | H | H | $CH(CH_3)_2$ | Bz | H | F | H | OH |
| XXX-45-4 | Ph | H | H | $CH_2CH(CH_3)_2$ | Bz | H | F | H | OH |
| XXX-45-5 | Ph | H | H | $CH_2Ph$ | Bz | H | F | H | OH |
| XXX-45-6 | Ph | H | H | $CH_2$-indol-3-yl | Bz | H | F | H | OH |
| XXX-45-7 | Ph | H | H | $CH_2CH_2SCH_3$ | Bz | H | F | H | OH |
| XXX-45-8 | Ph | * | H | * | Bz | H | F | H | OH |

*$R^2$ and $R^{3b}$ joined together by $(CH_2)_3$ to form five-membered ring.

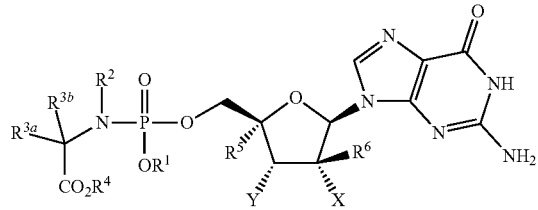

XXXI

TABLE XXX-46

| No | R¹ | R² | R³ᵃ | R³ᵇ | R⁴ | R⁵ | R⁶ | X | Y |
|---|---|---|---|---|---|---|---|---|---|
| XXX-46-1 | p-Me—Ph | H | H | H | Bz | H | F | H | OH |
| XXX-46-2 | p-Me—Ph | H | H | CH₃ | Bz | H | F | H | OH |
| XXX-46-3 | p-Me—Ph | H | H | CH(CH₃)₂ | Bz | H | F | H | OH |
| XXX-46-4 | p-Me—Ph | H | H | CH₂CH(CH₃)₂ | Bz | H | F | H | OH |
| XXX-46-5 | p-Me—Ph | H | H | CH₂Ph | Bz | H | F | H | OH |
| XXX-46-6 | p-Me—Ph | H | H | CH₂-indol-3-yl | Bz | H | F | H | OH |
| XXX-46-7 | p-Me—Ph | H | H | CH₂CH₂SCH₃ | Bz | H | F | H | OH |
| XXX-46-8 | p-Me—Ph | * | H | * | Bz | H | F | H | OH |

*R² and R³ᵇ joined together by (CH₂)₃ to form five-membered ring.

TABLE XXX-47

| No | R¹ | R² | R³ᵃ | R³ᵇ | R⁴ | R⁵ | R⁶ | X | Y |
|---|---|---|---|---|---|---|---|---|---|
| XXX-47-1 | p-F—Ph | H | H | H | Bz | H | F | H | OH |
| XXX-47-2 | p-F—Ph | H | H | CH₃ | Bz | H | F | H | OH |
| XXX-47-3 | p-F—Ph | H | H | CH(CH₃)₂ | Bz | H | F | H | OH |
| XXX-47-4 | p-F—Ph | H | H | CH₂CH(CH₃)₂ | Bz | H | F | H | OH |
| XXX-47-5 | p-F—Ph | H | H | CH₂Ph | Bz | H | F | H | OH |
| XXX-47-6 | p-F—Ph | H | H | CH₂-indol-3-yl | Bz | H | F | H | OH |
| XXX-47-7 | p-F—Ph | H | H | CH₂CH₂SCH₃ | Bz | H | F | H | OH |
| XXX-47-8 | p-F—Ph | * | H | * | Bz | H | F | H | OH |

*R² and R³ᵇ joined together by (CH₂)₃ to form five-membered ring.

TABLE XXX-48

| No | R¹ | R² | R³ᵃ | R³ᵇ | R⁴ | R⁵ | R⁶ | X | Y |
|---|---|---|---|---|---|---|---|---|---|
| XXX-48-1 | p-Cl—Ph | H | H | H | Bz | H | F | H | OH |
| XXX-48-2 | p-Cl—Ph | H | H | CH₃ | Bz | H | F | H | OH |
| XXX-48-3 | p-Cl—Ph | H | H | CH(CH₃)₂ | Bz | H | F | H | OH |
| XXX-48-4 | p-Cl—Ph | H | H | CH₂CH(CH₃)₂ | Bz | H | F | H | OH |
| XXX-48-5 | p-Cl—Ph | H | H | CH₂Ph | Bz | H | F | H | OH |
| XXX-48-6 | p-Cl—Ph | H | H | CH₂-indol-3-yl | Bz | H | F | H | OH |
| XXX-48-7 | p-Cl—Ph | H | H | CH₂CH₂SCH₃ | Bz | H | F | H | OH |
| XXX-48-8 | p-Cl—Ph | * | H | * | Bz | H | F | H | OH |

*R² and R³ᵇ joined together by (CH₂)₃ to form five-membered ring.

TABLE XXX-49

| No | R¹ | R² | R³ᵃ | R³ᵇ | R⁴ | R⁵ | R⁶ | X | Y |
|---|---|---|---|---|---|---|---|---|---|
| XXX-49-1 | p-Br—Ph | H | H | H | Bz | H | F | H | OH |
| XXX-49-2 | p-Br—Ph | H | H | CH₃ | Bz | H | F | H | OH |
| XXX-49-3 | p-Br—Ph | H | H | CH(CH₃)₂ | Bz | H | F | H | OH |
| XXX-49-4 | p-Br—Ph | H | H | CH₂CH(CH₃)₂ | Bz | H | F | H | OH |
| XXX-49-5 | p-Br—Ph | H | H | CH₂Ph | Bz | H | F | H | OH |
| XXX-49-6 | p-Br—Ph | H | H | CH₂-indol-3-yl | Bz | H | F | H | OH |
| XXX-49-7 | p-Br—Ph | H | H | CH₂CH₂SCH₃ | Bz | H | F | H | OH |
| XXX-49-8 | p-Br—Ph | * | H | * | Bz | H | F | H | OH |

*R² and R³ᵇ joined together by (CH₂)₃ to form five-membered ring.

TABLE XXX-50

| No | R¹ | R² | R³ᵃ | R³ᵇ | R⁴ | R⁵ | R⁶ | X | Y |
|---|---|---|---|---|---|---|---|---|---|
| XXX-50-1 | p-I—Ph | H | H | H | Bz | H | F | H | OH |
| XXX-50-2 | p-I—Ph | H | H | CH₃ | Bz | H | F | H | OH |
| XXX-50-3 | p-I—Ph | H | H | CH(CH₃)₂ | Bz | H | F | H | OH |
| XXX-50-4 | p-I—Ph | H | H | CH₂CH(CH₃)₂ | Bz | H | F | H | OH |
| XXX-50-5 | p-I—Ph | H | H | CH₂Ph | Bz | H | F | H | OH |
| XXX-50-6 | p-I—Ph | H | H | CH₂-indol-3-yl | Bz | H | F | H | OH |
| XXX-50-7 | p-I—Ph | H | H | CH₂CH₂SCH₃ | Bz | H | F | H | OH |
| XXX-50-8 | p-I—Ph | * | H | * | Bz | H | F | H | OH |

*R² and R³ᵇ joined together by (CH₂)₃ to form five-membered ring.

TABLE XXXI-1

| No | R¹ | R² | R³ᵃ | R³ᵇ | R⁴ | R⁵ | R⁶ | X | Y |
|---|---|---|---|---|---|---|---|---|---|
| XXXI-1-1 | CH₃ | H | H | H | CH₃ | H | F | F | OH |
| XXXI-1-2 | CH₃ | H | H | CH₃ | CH₃ | H | F | F | OH |
| XXXI-1-3 | CH₃ | H | H | CH(CH₃)₂ | CH₃ | H | F | F | OH |
| XXXI-1-4 | CH₃ | H | H | CH₂CH(CH₃)₂ | CH₃ | H | F | F | OH |
| XXXI-1-5 | CH₃ | H | H | CH₂Ph | CH₃ | H | F | F | OH |
| XXXI-1-6 | CH₃ | H | H | CH₂-indol-3-yl | CH₃ | H | F | F | OH |
| XXXI-1-7 | CH₃ | H | H | CH₂CH₂SCH₃ | CH₃ | H | F | F | OH |
| XXXI-1-8 | CH₃ | * | H | * | CH₃ | H | F | F | OH |

*R² and R³ᵇ joined together by (CH₂)₃ to form five-membered ring.

TABLE XXXI-2

| No | R¹ | R² | R³ᵃ | R³ᵇ | R⁴ | R⁵ | R⁶ | X | Y |
|---|---|---|---|---|---|---|---|---|---|
| XXXI-2-1 | Et | H | H | H | CH₃ | H | F | F | OH |
| XXXI-2-2 | Et | H | H | CH₃ | CH₃ | H | F | F | OH |
| XXXI-2-3 | Et | H | H | CH(CH₃)₂ | CH₃ | H | F | F | OH |
| XXXI-2-4 | Et | H | H | CH₂CH(CH₃)₂ | CH₃ | H | F | F | OH |
| XXXI-2-5 | Et | H | H | CH₂Ph | CH₃ | H | F | F | OH |
| XXXI-2-6 | Et | H | H | CH₂-indol-3-yl | CH₃ | H | F | F | OH |
| XXXI-2-7 | Et | H | H | CH₂CH₂SCH₃ | CH₃ | H | F | F | OH |
| XXXI-2-8 | Et | * | H | * | CH₃ | H | F | F | OH |

*R² and R³ᵇ joined together by (CH₂)₃ to form five-membered ring.

TABLE XXXI-3

| No | R¹ | R² | R³ᵃ | R³ᵇ | R⁴ | R⁵ | R⁶ | X | Y |
|---|---|---|---|---|---|---|---|---|---|
| XXXI-3-1 | ⁱPr | H | H | H | CH₃ | H | F | F | OH |
| XXXI-3-2 | ⁱPr | H | H | CH₃ | CH₃ | H | F | F | OH |
| XXXI-3-3 | ⁱPr | H | H | CH(CH₃)₂ | CH₃ | H | F | F | OH |
| XXXI-3-4 | ⁱPr | H | H | CH₂CH(CH₃)₂ | CH₃ | H | F | F | OH |
| XXXI-3-5 | ⁱPr | H | H | CH₂Ph | CH₃ | H | F | F | OH |
| XXXI-3-6 | ⁱPr | H | H | CH₂-indol-3-yl | CH₃ | H | F | F | OH |
| XXXI-3-7 | ⁱPr | H | H | CH₂CH₂SCH₃ | CH₃ | H | F | F | OH |
| XXXI-3-8 | ⁱPr | * | H | * | CH₃ | H | F | F | OH |

*R² and R³ᵇ joined together by (CH₂)₃ to form five-membered ring.

TABLE XXXI-4

| No | R¹ | R² | R³ᵃ | R³ᵇ | R⁴ | R⁵ | R⁶ | X | Y |
|---|---|---|---|---|---|---|---|---|---|
| XXXI-4-1 | ᵗBu | H | H | H | CH₃ | H | F | F | OH |
| XXXI-4-2 | ᵗBu | H | H | CH₃ | CH₃ | H | F | F | OH |
| XXXI-4-3 | ᵗBu | H | H | CH(CH₃)₂ | CH₃ | H | F | F | OH |
| XXXI-4-4 | ᵗBu | H | H | CH₂CH(CH₃)₂ | CH₃ | H | F | F | OH |
| XXXI-4-5 | ᵗBu | H | H | CH₂Ph | CH₃ | H | F | F | OH |
| XXXI-4-6 | ᵗBu | H | H | CH₂-indol-3-yl | CH₃ | H | F | F | OH |
| XXXI-4-7 | ᵗBu | H | H | CH₂CH₂SCH₃ | CH₃ | H | F | F | OH |
| XXXI-4-8 | ᵗBu | * | H | * | CH₃ | H | F | F | OH |

*R² and R³ᵇ joined together by (CH₂)₃ to form five-membered ring.

TABLE XXXI-5

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXI-5-1 | Ph | H | H | H | CH$_3$ | H | F | F | OH |
| XXXI-5-2 | Ph | H | H | CH$_3$ | CH$_3$ | H | F | F | OH |
| XXXI-5-3 | Ph | H | H | CH(CH$_3$)$_2$ | CH$_3$ | H | F | F | OH |
| XXXI-5-4 | Ph | H | H | CH$_2$CH(CH$_3$)$_2$ | CH$_3$ | H | F | F | OH |
| XXXI-5-5 | Ph | H | H | CH$_2$Ph | CH$_3$ | H | F | F | OH |
| XXXI-5-6 | Ph | H | H | CH$_2$-indol-3-yl | CH$_3$ | H | F | F | OH |
| XXXI-5-7 | Ph | H | H | CH$_2$CH$_2$SCH$_3$ | CH$_3$ | H | F | F | OH |
| XXXI-5-8 | Ph | * | H | * | CH$_3$ | H | F | F | OH |

*R$^2$ and R$^{3b}$ joined together by (CH$_2$)$_3$ to form five-membered ring.

TABLE XXXI-6

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXI-6-1 | p-Me—Ph | H | H | H | CH$_3$ | H | F | F | OH |
| XXXI-6-2 | p-Me—Ph | H | H | CH$_3$ | CH$_3$ | H | F | F | OH |
| XXXI-6-3 | p-Me—Ph | H | H | CH(CH$_3$)$_2$ | CH$_3$ | H | F | F | OH |
| XXXI-6-4 | p-Me—Ph | H | H | CH$_2$CH(CH$_3$)$_2$ | CH$_3$ | H | F | F | OH |
| XXXI-6-5 | p-Me—Ph | H | H | CH$_2$Ph | CH$_3$ | H | F | F | OH |
| XXXI-6-6 | p-Me—Ph | H | H | CH$_2$-indol-3-yl | CH$_3$ | H | F | F | OH |
| XXXI-6-7 | p-Me—Ph | H | H | CH$_2$CH$_2$SCH$_3$ | CH$_3$ | H | F | F | OH |
| XXXI-6-8 | p-Me—Ph | * | H | * | CH$_3$ | H | F | F | OH |

*R$^2$ and R$^{3b}$ joined together by (CH$_2$)$_3$ to form five-membered ring.

TABLE XXXI-7

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXI-7-1 | p-F—Ph | H | H | H | CH$_3$ | H | F | F | OH |
| XXXI-7-2 | p-F—Ph | H | H | CH$_3$ | CH$_3$ | H | F | F | OH |
| XXXI-7-3 | p-F—Ph | H | H | CH(CH$_3$)$_2$ | CH$_3$ | H | F | F | OH |
| XXXI-7-4 | p-F—Ph | H | H | CH$_2$CH(CH$_3$)$_2$ | CH$_3$ | H | F | F | OH |
| XXXI-7-6 | p-F—Ph | H | H | CH$_2$Ph | CH$_3$ | H | F | F | OH |
| XXXI-7-7 | p-F—Ph | H | H | CH$_2$-indol-3-yl | CH$_3$ | H | F | F | OH |
| XXXI-7-8 | p-F—Ph | H | H | CH$_2$CH$_2$SCH$_3$ | CH$_3$ | H | F | F | OH |
| XXXI-7-20 | p-F—Ph | * | H | * | CH$_3$ | H | F | F | OH |

*R$^2$ and R$^{3b}$ joined together by (CH$_2$)$_3$ to form five-membered ring.

TABLE XXXI-8

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXI-8-1 | p-Cl—Ph | H | H | H | CH$_3$ | H | F | F | OH |
| XXXI-8-2 | p-Cl—Ph | H | H | CH$_3$ | CH$_3$ | H | F | F | OH |
| XXXI-8-3 | p-Cl—Ph | H | H | CH(CH$_3$)$_2$ | CH$_3$ | H | F | F | OH |
| XXXI-8-4 | p-Cl—Ph | H | H | CH$_2$CH(CH$_3$)$_2$ | CH$_3$ | H | F | F | OH |
| XXXI-8-5 | p-Cl—Ph | H | H | CH$_2$Ph | CH$_3$ | H | F | F | OH |
| XXXI-8-6 | p-Cl—Ph | H | H | CH$_2$-indol-3-yl | CH$_3$ | H | F | F | OH |
| XXXI-8-7 | p-Cl—Ph | H | H | CH$_2$CH$_2$SCH$_3$ | CH$_3$ | H | F | F | OH |
| XXXI-8-8 | p-Cl—Ph | * | H | * | CH$_3$ | H | F | F | OH |

*R$^2$ and R$^{3b}$ joined together by (CH$_2$)$_3$ to form five-membered ring.

TABLE XXXI-9

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXI-9-1 | p-Br—Ph | H | H | H | CH$_3$ | H | F | F | OH |
| XXXI-9-2 | p-Br—Ph | H | H | CH$_3$ | CH$_3$ | H | F | F | OH |
| XXXI-9-3 | p-Br—Ph | H | H | CH(CH$_3$)$_2$ | CH$_3$ | H | F | F | OH |
| XXXI-9-4 | p-Br—Ph | H | H | CH$_2$CH(CH$_3$)$_2$ | CH | H | F | F | OH |
| XXXI-9-6 | p-Br—Ph | H | H | CH$_2$Ph | CH$_3$ | H | F | F | OH |
| XXXI-9-7 | p-Br—Ph | H | H | CH$_2$-indol-3-yl | CH$_3$ | H | F | F | OH |
| XXXI-9-8 | p-Br—Ph | H | H | CH$_2$CH$_2$SCH$_3$ | CH$_3$ | H | F | F | OH |
| XXXI-9-20 | p-Br—Ph | * | H | * | CH$_3$ | H | F | F | OH |

*R$^2$ and R$^{3b}$ joined together by (CH$_2$)$_3$ to form five-membered ring.

TABLE XXXI-10

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXI-10-1 | p-I—Ph | H | H | H | CH$_3$ | H | F | F | OH |
| XXXI-10-2 | p-I—Ph | H | H | CH$_3$ | CH$_3$ | H | F | F | OH |
| XXXI-10-3 | p-I—Ph | H | H | CH(CH$_3$)$_2$ | CH$_3$ | H | F | F | OH |
| XXXI-10-4 | p-I—Ph | H | H | CH$_2$CH(CH$_3$)$_2$ | CH$_3$ | H | F | F | OH |
| XXXI-10-5 | p-I—Ph | H | H | CH$_2$Ph | CH$_3$ | H | F | F | OH |
| XXXI-10-6 | p-I—Ph | H | H | CH$_2$-indol-3-yl | CH$_3$ | H | F | F | OH |
| XXXI-10-7 | p-I—Ph | H | H | CH$_2$CH$_2$SCH$_3$ | CH$_3$ | H | F | F | OH |
| XXXI-10-8 | p-I—Ph | * | H | * | CH$_3$ | H | F | F | OH |

*R$^2$ and R$^{3b}$ joined together by (CH$_2$)$_3$ to form five-membered ring.

TABLE XXXI-11

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXI-11-1 | CH$_3$ | H | H | H | Et | H | F | F | OH |
| XXXI-11-2 | CH$_3$ | H | H | CH$_3$ | Et | H | F | F | OH |
| XXXI-11-3 | CH$_3$ | H | H | CH(CH$_3$)$_2$ | Et | H | F | F | OH |
| XXXI-11-4 | CH$_3$ | H | H | CH$_2$CH(CH$_3$)$_2$ | Et | H | F | F | OH |
| XXXI-11-5 | CH$_3$ | H | H | CH$_2$Ph | Et | H | F | F | OH |
| XXXI-11-6 | CH$_3$ | H | H | CH$_2$-indol-3-yl | Et | H | F | F | OH |
| XXXI-11-7 | CH$_3$ | H | H | CH$_2$CH$_2$SCH$_3$ | Et | H | F | F | OH |
| XXXI-11-8 | CH$_3$ | * | H | * | Et | H | F | F | OH |

*R$^2$ and R$^{3b}$ joined together by (CH$_2$)$_3$ to form five-membered ring.

TABLE XXXI-12

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXI-12-1 | Et | H | H | H | Et | H | F | F | OH |
| XXXI-12-2 | Et | H | H | CH$_3$ | Et | H | F | F | OH |

TABLE XXXI-12-continued

| No | R¹ | R² | R³ᵃ | R³ᵇ | R⁴ | R⁵ | R⁶ | X | Y |
|---|---|---|---|---|---|---|---|---|---|
| XXXI-12-3 | Et | H | H | CH(CH₃)₂ | Et | H | F | F | OH |
| XXXI-12-4 | Et | H | H | CH₂CH(CH₃)₂ | Et | H | F | F | OH |
| XXXI-12-5 | Et | H | H | CH₂Ph | Et | H | F | F | OH |
| XXXI-12-6 | Et | H | H | CH₂-indol-3-yl | Et | H | F | F | OH |
| XXXI-12-7 | Et | H | H | CH₂CH₂SCH₃ | Et | H | F | F | OH |
| XXXI-12-8 | Et | * | H | * | Et | H | F | F | OH |

*R² and R³ᵇ joined together by (CH₂)₃ to form five-membered ring.

TABLE XXXI-13

| No | R¹ | R² | R³ᵃ | R³ᵇ | R⁴ | R⁵ | R⁶ | X | Y |
|---|---|---|---|---|---|---|---|---|---|
| XXXI-13-1 | ⁱPr | H | H | H | Et | H | F | F | OH |
| XXXI-13-2 | ⁱPr | H | H | CH₃ | Et | H | F | F | OH |
| XXXI-13-3 | ⁱPr | H | H | CH(CH₃)₂ | Et | H | F | F | OH |
| XXXI-13-4 | ⁱPr | H | H | CH₂CH(CH₃)₂ | Et | H | F | F | OH |
| XXXI-13-5 | ⁱPr | H | H | CH₂Ph | Et | H | F | F | OH |
| XXXI-13-6 | ⁱPr | H | H | CH₂-indol-3-yl | Et | H | F | F | OH |
| XXXI-13-7 | ⁱPr | H | H | CH₂CH₂SCH₃ | Et | H | F | F | OH |
| XXXI-13-8 | ⁱPr | * | H | * | Et | H | F | F | OH |

*R² and R³ᵇ joined together by (CH₂)₃ to form five-membered ring.

TABLE XXXI-14

| No | R¹ | R² | R³ᵃ | R³ᵇ | R⁴ | R⁵ | R⁶ | X | Y |
|---|---|---|---|---|---|---|---|---|---|
| XXXI-14-1 | ᵗBu | H | H | H | Et | H | F | F | OH |
| XXXI-14-2 | ᵗBu | H | H | CH₃ | Et | H | F | F | OH |
| XXXI-14-3 | ᵗBu | H | H | CH(CH₃)₂ | Et | H | F | F | OH |
| XXXI-14-4 | ᵗBu | H | H | CH₂CH(CH₃)₂ | Et | H | F | F | OH |
| XXXI-14-5 | ᵗBu | H | H | CH₂Ph | Et | H | F | F | OH |
| XXXI-14-6 | ᵗBu | H | H | CH₂-indol-3-yl | Et | H | F | F | OH |
| XXXI-14-7 | ᵗBu | H | H | CH₂CH₂SCH₃ | Et | H | F | F | OH |
| XXXI-14-8 | ᵗBu | * | H | * | Et | H | F | F | OH |

*R² and R³ᵇ joined together by (CH₂)₃ to form five-membered ring.

TABLE XXXI-15

| No | R¹ | R² | R³ᵃ | R³ᵇ | R⁴ | R⁵ | R⁶ | X | Y |
|---|---|---|---|---|---|---|---|---|---|
| XXXI-15-1 | Ph | H | H | H | Et | H | F | F | OH |
| XXXI-15-2 | Ph | H | H | CH₃ | Et | H | F | F | OH |
| XXXI-15-3 | Ph | H | H | CH(CH₃)₂ | Et | H | F | F | OH |
| XXXI-15-4 | Ph | H | H | CH₂CH(CH₃)₂ | Et | H | F | F | OH |
| XXXI-15-5 | Ph | H | H | CH₂Ph | Et | H | F | F | OH |
| XXXI-15-6 | Ph | H | H | CH₂-indol-3-yl | Et | H | F | F | OH |
| XXXI-15-7 | Ph | H | H | CH₂CH₂SCH₃ | Et | H | F | F | OH |
| XXXI-15-8 | Ph | * | H | * | Et | H | F | F | OH |

*R² and R³ᵇ joined together by (CH₂)₃ to form five-membered ring.

TABLE XXXI-16

| No | R¹ | R² | R³ᵃ | R³ᵇ | R⁴ | R⁵ | R⁶ | X | Y |
|---|---|---|---|---|---|---|---|---|---|
| XXXI-16-1 | p-Me—Ph | H | H | H | Et | H | F | F | OH |
| XXXI-16-2 | p-Me—Ph | H | H | CH₃ | Et | H | F | F | OH |
| XXXI-16-3 | p-Me—Ph | H | H | CH(CH₃)₂ | Et | H | F | F | OH |
| XXXI-16-4 | p-Me—Ph | H | H | CH₂CH(CH₃)₂ | Et | H | F | F | OH |
| XXXI-16-5 | p-Me—Ph | H | H | CH₂Ph | Et | H | F | F | OH |
| XXXI-16-6 | p-Me—Ph | H | H | CH₂-indol-3-yl | Et | H | F | F | OH |
| XXXI-16-7 | p-Me—Ph | H | H | CH₂CH₂SCH₃ | Et | H | F | F | OH |
| XXXI-16-8 | p-Me—Ph | * | H | * | Et | H | F | F | OH |

*R² and R³ᵇ joined together by (CH₂)₃ to form five-membered ring.

TABLE XXXI-17

| No | R¹ | R² | R³ᵃ | R³ᵇ | R⁴ | R⁵ | R⁶ | X | Y |
|---|---|---|---|---|---|---|---|---|---|
| XXXI-17-1 | p-F—Ph | H | H | H | Et | H | F | F | OH |
| XXXI-17-2 | p-F—Ph | H | H | CH₃ | Et | H | F | F | OH |
| XXXI-17-3 | p-F—Ph | H | H | CH(CH₃)₂ | Et | H | F | F | OH |
| XXXI-17-4 | p-F—Ph | H | H | CH₂CH(CH₃)₂ | Et | H | F | F | OH |
| XXXI-17-5 | p-F—Ph | H | H | CH₂Ph | Et | H | F | F | OH |
| XXXI-17-6 | p-F—Ph | H | H | CH₂-indol-3-yl | Et | H | F | F | OH |
| XXXI-17-7 | p-F—Ph | H | H | CH₂CH₂SCH₃ | Et | H | F | F | OH |
| XXXI-17-8 | p-F—Ph | * | H | * | Et | H | F | F | OH |

*R² and R³ᵇ joined together by (CH₂)₃ to form five-membered ring.

TABLE XXXI-18

| No | R¹ | R² | R³ᵃ | R³ᵇ | R⁴ | R⁵ | R⁶ | X | Y |
|---|---|---|---|---|---|---|---|---|---|
| XXXI-18-1 | p-Cl—Ph | H | H | H | Et | H | F | F | OH |
| XXXI-18-2 | p-Cl—Ph | H | H | CH₃ | Et | H | F | F | OH |
| XXXI-18-3 | p-Cl—Ph | H | H | CH(CH₃)₂ | Et | H | F | F | OH |
| XXXI-18-4 | p-Cl—Ph | H | H | CH₂CH(CH₃)₂ | Et | H | F | F | OH |
| XXXI-18-5 | p-Cl—Ph | H | H | CH₂Ph | Et | H | F | F | OH |
| XXXI-18-6 | p-Cl—Ph | H | H | CH₂-indol-3-yl | Et | H | F | F | OH |
| XXXI-18-7 | p-Cl—Ph | H | H | CH₂CH₂SCH₃ | Et | H | F | F | OH |
| XXXI-18-8 | p-Cl—Ph | * | H | * | Et | H | F | F | OH |

*R² and R³ᵇ joined together by (CH₂)₃ to form five-membered ring.

TABLE XXXI-19

| No | R¹ | R² | R³ᵃ | R³ᵇ | R⁴ | R⁵ | R⁶ | X | Y |
|---|---|---|---|---|---|---|---|---|---|
| XXXI-19-1 | p-Br—Ph | H | H | H | Et | H | F | F | OH |
| XXXI-19-2 | p-Br—Ph | H | H | CH₃ | Et | H | F | F | OH |
| XXXI-19-3 | p-Br—Ph | H | H | CH(CH₃)₂ | Et | H | F | F | OH |
| XXXI-19-4 | p-Br—Ph | H | H | CH₂CH(CH₃)₂ | Et | H | F | F | OH |
| XXXI-19-5 | p-Br—Ph | H | H | CH₂Ph | Et | H | F | F | OH |
| XXXI-19-6 | p-Br—Ph | H | H | CH₂-indol-3-yl | Et | H | F | F | OH |
| XXXI-19-7 | p-Br—Ph | H | H | CH₂CH₂SCH₃ | Et | H | F | F | OH |
| XXXI-19-8 | p-Br—Ph | * | H | * | Et | H | F | F | OH |

*R² and R³ᵇ joined together by (CH₂)₃ to form five-membered ring.

TABLE XXXI-20

| No | R¹ | R² | R³ᵃ | R³ᵇ | R⁴ | R⁵ | R⁶ | X | Y |
|---|---|---|---|---|---|---|---|---|---|
| XXXI-20-1 | p-I—Ph | H | H | H | Et | H | F | F | OH |
| XXXI-20-2 | p-I—Ph | H | H | CH₃ | Et | H | F | F | OH |
| XXXI-20-3 | p-I—Ph | H | H | CH(CH₃)₂ | Et | H | F | F | OH |
| XXXI-20-4 | p-I—Ph | H | H | CH₂CH(CH₃)₂ | Et | H | F | F | OH |

TABLE XXXI-20-continued

| No | R¹ | R² | R³ᵃ | R³ᵇ | R⁴ | R⁵ | R⁶ | X | Y |
|---|---|---|---|---|---|---|---|---|---|
| XXXI-20-5 | p-I—Ph | H | H | CH₂Ph | Et | H | F | F | OH |
| XXXI-20-6 | p-I—Ph | H | H | CH₂-indol-3-yl | Et | H | F | F | OH |
| XXXI-20-7 | p-I—Ph | H | H | CH₂CH₂SCH₃ | Et | H | F | F | OH |
| XXXI-20-8 | p-I—Ph | * | H | * | Et | H | F | F | OH |

*R² and R³ᵇ joined together by (CH₂)₃ to form five-membered ring.

TABLE XXXI-21

| No | R¹ | R² | R³ᵃ | R³ᵇ | R⁴ | R⁵ | R⁶ | X | Y |
|---|---|---|---|---|---|---|---|---|---|
| XXXI-21-1 | CH₃ | H | H | H | ⁱPr | H | F | F | OH |
| XXXI-21-2 | CH₃ | H | H | CH₃ | ⁱPr | H | F | F | OH |
| XXXI-21-3 | CH₃ | H | H | CH(CH₃)₂ | ⁱPr | H | F | F | OH |
| XXXI-21-4 | CH₃ | H | H | CH₂CH(CH₃)₂ | ⁱPr | H | F | F | OH |
| XXXI-21-5 | CH₃ | H | H | CH₂Ph | ⁱPr | H | F | F | OH |
| XXXI-21-6 | CH₃ | H | H | CH₂-indol-3-yl | ⁱPr | H | F | F | OH |
| XXXI-21-7 | CH₃ | H | H | CH₂CH₂SCH₃ | ⁱPr | H | F | F | OH |
| XXXI-21-8 | CH₃ | * | H | * | ⁱPr | H | F | F | OH |

*R² and R³ᵇ joined together by (CH₂)₃ to form five-membered ring.

TABLE XXXI-22

| No | R¹ | R² | R³ᵃ | R³ᵇ | R⁴ | R⁵ | R⁶ | X | Y |
|---|---|---|---|---|---|---|---|---|---|
| XXXI-22-1 | Et | H | H | H | ⁱPr | H | F | F | OH |
| XXXI-22-2 | Et | H | H | CH₃ | ⁱPr | H | F | F | OH |
| XXXI-22-3 | Et | H | H | CH(CH₃)₂ | ⁱPr | H | F | F | OH |
| XXXI-22-4 | Et | H | H | CH₂CH(CH₃)₂ | ⁱPr | H | F | F | OH |
| XXXI-22-5 | Et | H | H | CH₂Ph | ⁱPr | H | F | F | OH |
| XXXI-22-6 | Et | H | H | CH₂-indol-3-yl | ⁱPr | H | F | F | OH |
| XXXI-22-7 | Et | H | H | CH₂CH₂SCH₃ | ⁱPr | H | F | F | OH |
| XXXI-22-8 | Et | * | H | * | ⁱPr | H | F | F | OH |

*R² and R³ᵇ joined together by (CH₂)₃ to form five-membered ring.

TABLE XXXI-23

| No | R¹ | R² | R³ᵃ | R³ᵇ | R⁴ | R⁵ | R⁶ | X | Y |
|---|---|---|---|---|---|---|---|---|---|
| XXXI-23-1 | ⁱPr | H | H | H | ⁱPr | H | F | F | OH |
| XXXI-23-2 | ⁱPr | H | H | CH₃ | ⁱPr | H | F | F | OH |
| XXXI-23-3 | ⁱPr | H | H | CH(CH₃)₂ | ⁱPr | H | F | F | OH |
| XXXI-23-4 | ⁱPr | H | H | CH₂CH(CH₃)₂ | ⁱPr | H | F | F | OH |
| XXXI-23-5 | ⁱPr | H | H | CH₂Ph | ⁱPr | H | F | F | OH |
| XXXI-23-6 | ⁱPr | H | H | CH₂-indol-3-yl | ⁱPr | H | F | F | OH |
| XXXI-23-7 | ⁱPr | H | H | CH₂CH₂SCH₃ | ⁱPr | H | F | F | OH |
| XXXI-23-8 | ⁱPr | * | H | * | ⁱPr | H | F | F | OH |

*R² and R³ᵇ joined together by (CH₂)₃ to form five-membered ring.

TABLE XXXI-24

| No | R¹ | R² | R³ᵃ | R³ᵇ | R⁴ | R⁵ | R⁶ | X | Y |
|---|---|---|---|---|---|---|---|---|---|
| XXXI-24-1 | ᵗBu | H | H | H | ⁱPr | H | F | F | OH |
| XXXI-24-2 | ᵗBu | H | H | CH₃ | ⁱPr | H | F | F | OH |
| XXXI-24-3 | ᵗBu | H | H | CH(CH₃)₂ | ⁱPr | H | F | F | OH |
| XXXI-24-4 | ᵗBu | H | H | CH₂CH(CH₃)₂ | ⁱPr | H | F | F | OH |
| XXXI-24-5 | ᵗBu | H | H | CH₂Ph | ⁱPr | H | F | F | OH |
| XXXI-24-6 | ᵗBu | H | H | CH₂-indol-3-yl | ⁱPr | H | F | F | OH |
| XXXI-24-7 | ᵗBu | H | H | CH₂CH₂SCH₃ | ⁱPr | H | F | F | OH |
| XXXI-24-8 | ᵗBu | * | H | * | ⁱPr | H | F | F | OH |

*R² and R³ᵇ joined together by (CH₂)₃ to form five-membered ring.

TABLE XXXI-25

| No | R¹ | R² | R³ᵃ | R³ᵇ | R⁴ | R⁵ | R⁶ | X | Y |
|---|---|---|---|---|---|---|---|---|---|
| XXXI-25-1 | Ph | H | H | H | ⁱPr | H | F | F | OH |
| XXXI-25-2 | Ph | H | H | CH₃ | ⁱPr | H | F | F | OH |
| XXXI-25-3 | Ph | H | H | CH(CH₃)₂ | ⁱPr | H | F | F | OH |
| XXXI-25-4 | Ph | H | H | CH₂CH(CH₃)₂ | ⁱPr | H | F | F | OH |
| XXXI-25-5 | Ph | H | H | CH₂Ph | ⁱPr | H | F | F | OH |
| XXXI-25-6 | Ph | H | H | CH₂-indol-3-yl | ⁱPr | H | F | F | OH |
| XXXI-25-7 | Ph | H | H | CH₂CH₂SCH₃ | ⁱPr | H | F | F | OH |
| XXXI-25-8 | Ph | * | H | * | ⁱPr | H | F | F | OH |

*R² and R³ᵇ joined together by (CH₂)₃ to form five-membered ring.

TABLE XXXI-26

| No | R¹ | R² | R³ᵃ | R³ᵇ | R⁴ | R⁵ | R⁶ | X | Y |
|---|---|---|---|---|---|---|---|---|---|
| XXXI-26-1 | p-Me—Ph | H | H | H | ⁱPr | H | F | F | OH |
| XXXI-26-2 | p-Me—Ph | H | H | CH₃ | ⁱPr | H | F | F | OH |
| XXXI-26-3 | p-Me—Ph | H | H | CH(CH₃)₂ | ⁱPr | H | F | F | OH |
| XXXI-26-4 | p-Me—Ph | H | H | CH₂CH(CH₃)₂ | ⁱPr | H | F | F | OH |
| XXXI-26-5 | p-Me—Ph | H | H | CH₂Ph | ⁱPr | H | F | F | OH |
| XXXI-26-6 | p-Me—Ph | H | H | CH₂-indol-3-yl | ⁱPr | H | F | F | OH |
| XXXI-26-7 | p-Me—Ph | H | H | CH₂CH₂SCH₃ | ⁱPr | H | F | F | OH |
| XXXI-26-8 | p-Me—Ph | * | H | * | ⁱPr | H | F | F | OH |

*R² and R³ᵇ joined together by (CH₂)₃ to form five-membered ring.

TABLE XXXI-27

| No | R¹ | R² | R³ᵃ | R³ᵇ | R⁴ | R⁵ | R⁶ | X | Y |
|---|---|---|---|---|---|---|---|---|---|
| XXXI-27-1 | p-F—Ph | H | H | H | ⁱPr | H | F | F | OH |
| XXXI-27-2 | p-F—Ph | H | H | CH₃ | ⁱPr | H | F | F | OH |
| XXXI-27-3 | p-F—Ph | H | H | CH(CH₃)₂ | ⁱPr | H | F | F | OH |
| XXXI-27-4 | p-F—Ph | H | H | CH₂CH(CH₃)₂ | ⁱPr | H | F | F | OH |
| XXXI-27-5 | p-F—Ph | H | H | CH₂Ph | ⁱPr | H | F | F | OH |
| XXXI-27-6 | p-F—Ph | H | H | CH₂-indol-3-yl | ⁱPr | H | F | F | OH |
| XXXI-27-7 | p-F—Ph | H | H | CH₂CH₂SCH₃ | ⁱPr | H | F | F | OH |
| XXXI-27-8 | p-F—Ph | * | H | * | ⁱPr | H | F | F | OH |

*R² and R³ᵇ joined together by (CH₂)₃ to form five-membered ring.

TABLE XXXI-28

| No | R¹ | R² | R³ᵃ | R³ᵇ | R⁴ | R⁵ | R⁶ | X | Y |
|---|---|---|---|---|---|---|---|---|---|
| XXXI-28-1 | p-Cl—Ph | H | H | H | ⁱPr | H | F | F | OH |
| XXXI-28-2 | p-Cl—Ph | H | H | CH₃ | ⁱPr | H | F | F | OH |
| XXXI-28-3 | p-Cl—Ph | H | H | CH(CH₃)₂ | ⁱPr | H | F | F | OH |
| XXXI-28-4 | p-Cl—Ph | H | H | CH₂CH(CH₃)₂ | ⁱPr | H | F | F | OH |
| XXXI-28-5 | p-Cl—Ph | H | H | CH₂Ph | ⁱPr | H | F | F | OH |
| XXXI-28-6 | p-Cl—Ph | H | H | CH₂-indol-3-yl | ⁱPr | H | F | F | OH |
| XXXI-28-7 | p-Cl—Ph | H | H | CH₂CH₂SCH₃ | ⁱPr | H | F | F | OH |
| XXXI-28-8 | p-Cl—Ph | * | H | * | ⁱPr | H | F | F | OH |

*R² and R³ᵇ joined together by (CH₂)₃ to form five-membered ring.

TABLE XXXI-29

| No | R¹ | R² | R³ᵃ | R³ᵇ | R⁴ | R⁵ | R⁶ | X | Y |
|---|---|---|---|---|---|---|---|---|---|
| XXXI-29-1 | p-Br—Ph | H | H | H | ⁱPr | H | F | F | OH |
| XXXI-29-2 | p-Br—Ph | H | H | CH₃ | ⁱPr | H | F | F | OH |
| XXXI-29-3 | p-Br—Ph | H | H | CH(CH₃)₂ | ⁱPr | H | F | F | OH |
| XXXI-29-4 | p-Br—Ph | H | H | CH₂CH(CH₃)₂ | ⁱPr | H | F | F | OH |
| XXXI-29-5 | p-Br—Ph | H | H | CH₂Ph | ⁱPr | H | F | F | OH |
| XXXI-29-6 | p-Br—Ph | H | H | CH₂-indol-3-yl | ⁱPr | H | F | F | OH |
| XXXI-29-7 | p-Br—Ph | H | H | CH₂CH₂SCH₃ | ⁱPr | H | F | F | OH |
| XXXI-29-8 | p-Br—Ph | * | H | * | ⁱPr | H | F | F | OH |

*R² and R³ᵇ joined together by (CH₂)₃ to form five-membered ring.

TABLE XXXI-30

| No | R¹ | R² | R³ᵃ | R³ᵇ | R⁴ | R⁵ | R⁶ | X | Y |
|---|---|---|---|---|---|---|---|---|---|
| XXXI-30-1 | p-I—Ph | H | H | H | ⁱPr | H | F | F | OH |
| XXXI-30-2 | p-I—Ph | H | H | CH₃ | ⁱPr | H | F | F | OH |
| XXXI-30-3 | p-I—Ph | H | H | CH(CH₃)₂ | ⁱPr | H | F | F | OH |
| XXXI-30-4 | p-I—Ph | H | H | CH₂CH(CH₃)₂ | ⁱPr | H | F | F | OH |
| XXXI-30-5 | p-I—Ph | H | H | CH₂Ph | ⁱPr | H | F | F | OH |
| XXXI-30-6 | p-I—Ph | H | H | CH₂-indol-3-yl | ⁱPr | H | F | F | OH |
| XXXI-30-7 | p-I—Ph | H | H | CH₂CH₂SCH₃ | ⁱPr | H | F | F | OH |
| XXXI-30-8 | p-I—Ph | * | H | * | ⁱPr | H | F | F | OH |

*R² and R³ᵇ joined together by (CH₂)₃ to form five-membered ring.

TABLE XXXI-31

| No | R¹ | R² | R³ᵃ | R³ᵇ | R⁴ | R⁵ | R⁶ | X | Y |
|---|---|---|---|---|---|---|---|---|---|
| XXXI-31-1 | CH₃ | H | H | H | ⁿBu | H | F | F | OH |
| XXXI-31-2 | CH₃ | H | H | CH₃ | ⁿBu | H | F | F | OH |
| XXXI-31-3 | CH₃ | H | H | CH(CH₃)₂ | ⁿBu | H | F | F | OH |
| XXXI-31-4 | CH₃ | H | H | CH₂CH(CH₃)₂ | ⁿBu | H | F | F | OH |
| XXXI-31-5 | CH₃ | H | H | CH₂Ph | ⁿBu | H | F | F | OH |
| XXXI-31-6 | CH₃ | H | H | CH₂-indol-3-yl | ⁿBu | H | F | F | OH |
| XXXI-31-7 | CH₃ | H | H | CH₂CH₂SCH₃ | ⁿBu | H | F | F | OH |
| XXXI-31-8 | CH₃ | * | H | * | ⁿBu | H | F | F | OH |

*R² and R³ᵇ joined together by (CH₂)₃ to form five-membered ring.

TABLE XXXI-32

| No | R¹ | R² | R³ᵃ | R³ᵇ | R⁴ | R⁵ | R⁶ | X | Y |
|---|---|---|---|---|---|---|---|---|---|
| XXXI-32-1 | Et | H | H | H | ⁿBu | H | F | F | OH |
| XXXI-32-2 | Et | H | H | CH₃ | ⁿBu | H | F | F | OH |
| XXXI-32-3 | Et | H | H | CH(CH₃)₂ | ⁿBu | H | F | F | OH |
| XXXI-32-4 | Et | H | H | CH₂CH(CH₃)₂ | ⁿBu | H | F | F | OH |
| XXXI-32-5 | Et | H | H | CH₂Ph | ⁿBu | H | F | F | OH |
| XXXI-32-6 | Et | H | H | CH₂-indol-3-yl | ⁿBu | H | F | F | OH |
| XXXI-32-7 | Et | H | H | CH₂CH₂SCH₃ | ⁿBu | H | F | F | OH |
| XXXI-32-8 | Et | * | H | * | ⁿBu | H | F | F | OH |

*R² and R³ᵇ joined together by (CH₂)₃ to form five-membered ring.

TABLE XXXI-33

| No | R¹ | R² | R³ᵃ | R³ᵇ | R⁴ | R⁵ | R⁶ | X | Y |
|---|---|---|---|---|---|---|---|---|---|
| XXXI-33-1 | ⁱPr | H | H | H | ⁿBu | H | F | F | OH |
| XXXI-33-2 | ⁱPr | H | H | CH₃ | ⁿBu | H | F | F | OH |
| XXXI-33-3 | ⁱPr | H | H | CH(CH₃)₂ | ⁿBu | H | F | F | OH |
| XXXI-33-4 | ⁱPr | H | H | CH₂CH(CH₃)₂ | ⁿBu | H | F | F | OH |
| XXXI-33-5 | ⁱPr | H | H | CH₂Ph | ⁿBu | H | F | F | OH |
| XXXI-33-6 | ⁱPr | H | H | CH₂-indol-3-yl | ⁿBu | H | F | F | OH |
| XXXI-33-7 | ⁱPr | H | H | CH₂CH₂SCH₃ | ⁿBu | H | F | F | OH |
| XXXI-33-8 | ⁱPr | * | H | * | ⁿBu | H | F | F | OH |

*R² and R³ᵇ joined together by (CH₂)₃ to form five-membered ring.

TABLE XXXI-34

| No | R¹ | R² | R³ᵃ | R³ᵇ | R⁴ | R⁵ | R⁶ | X | Y |
|---|---|---|---|---|---|---|---|---|---|
| XXXI-34-1 | ᵗBu | H | H | H | ⁿBu | H | F | F | OH |
| XXXI-34-2 | ᵗBu | H | H | CH₃ | ⁿBu | H | F | F | OH |
| XXXI-34-3 | ᵗBu | H | H | CH(CH₃)₂ | ⁿBu | H | F | F | OH |
| XXXI-34-4 | ᵗBu | H | H | CH₂CH(CH₃)₂ | ⁿBu | H | F | F | OH |
| XXXI-34-5 | ᵗBu | H | H | CH₂Ph | ⁿBu | H | F | F | OH |
| XXXI-34-6 | ᵗBu | H | H | CH₂-indol-3-yl | ⁿBu | H | F | F | OH |
| XXXI-34-7 | ᵗBu | H | H | CH₂CH₂SCH₃ | ⁿBu | H | F | F | OH |
| XXXI-34-8 | ᵗBu | * | H | * | ⁿBu | H | F | F | OH |

*R² and R³ᵇ joined together by (CH₂)₃ to form five-membered ring.

TABLE XXXI-35

| No | R¹ | R² | R³ᵃ | R³ᵇ | R⁴ | R⁵ | R⁶ | X | Y |
|---|---|---|---|---|---|---|---|---|---|
| XXXI-35-1 | Ph | H | H | H | ⁿBu | H | F | F | OH |
| XXXI-35-2 | Ph | H | H | CH₃ | ⁿBu | H | F | F | OH |
| XXXI-35-3 | Ph | H | H | CH(CH₃)₂ | ⁿBu | H | F | F | OH |
| XXXI-35-4 | Ph | H | H | CH₂CH(CH₃)₂ | ⁿBu | H | F | F | OH |
| XXXI-35-5 | Ph | H | H | CH₂Ph | ⁿBu | H | F | F | OH |
| XXXI-35-6 | Ph | H | H | CH₂-indol-3-yl | ⁿBu | H | F | F | OH |
| XXXI-35-7 | Ph | H | H | CH₂CH₂SCH₃ | ⁿBu | H | F | F | OH |
| XXXI-35-8 | Ph | * | H | * | ⁿBu | H | F | F | OH |

*R² and R³ᵇ joined together by (CH₂)₃ to form five-membered ring.

TABLE XXXI-36

| No | R¹ | R² | R³ᵃ | R³ᵇ | R⁴ | R⁵ | R⁶ | X | Y |
|---|---|---|---|---|---|---|---|---|---|
| XXXI-36-1 | p-Me—Ph | H | H | H | ⁿBu | H | F | F | OH |
| XXXI-36-2 | p-Me—Ph | H | H | CH₃ | ⁿBu | H | F | F | OH |
| XXXI-36-3 | p-Me—Ph | H | H | CH(CH₃)₂ | ⁿBu | H | F | F | OH |
| XXXI-36-4 | p-Me—Ph | H | H | CH₂CH(CH₃)₂ | ⁿBu | H | F | F | OH |
| XXXI-36-5 | p-Me—Ph | H | H | CH₂Ph | ⁿBu | H | F | F | OH |
| XXXI-36-6 | p-Me—Ph | H | H | CH₂-indol-3-yl | ⁿBu | H | F | F | OH |
| XXXI-36-7 | p-Me—Ph | H | H | CH₂CH₂SCH₃ | ⁿBu | H | F | F | OH |
| XXXI-36-8 | p-Me—Ph | * | H | * | ⁿBu | H | F | F | OH |

*R² and R³ᵇ joined together by (CH₂)₃ to form five-membered ring.

TABLE XXXI-37

| No | R¹ | R² | R³ᵃ | R³ᵇ | R⁴ | R⁵ | R⁶ | X | Y |
|---|---|---|---|---|---|---|---|---|---|
| XXXI-37-1 | p-F—Ph | H | H | H | ⁿBu | H | F | F | OH |
| XXXI-37-2 | p-F—Ph | H | H | CH₃ | ⁿBu | H | F | F | OH |
| XXXI-37-3 | p-F—Ph | H | H | CH(CH₃)₂ | ⁿBu | H | F | F | OH |
| XXXI-37-4 | p-F—Ph | H | H | CH₂CH(CH₃)₂ | ⁿBu | H | F | F | OH |
| XXXI-37-5 | p-F—Ph | H | H | CH₂Ph | ⁿBu | H | F | F | OH |

TABLE XXXI-37-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-37-6 | p-F—Ph | H | H | CH$_2$-indol-3-yl | $^n$Bu | H | F | F | OH |
| XXXI-37-7 | p-F—Ph | H | H | CH$_2$CH$_2$SCH$_3$ | $^n$Bu | H | F | F | OH |
| XXXI-37-8 | p-F—Ph | * | H | * | $^n$Bu | H | F | F | OH |

*$R^2$ and $R^{3b}$ joined together by (CH$_2$)$_3$ to form five-membered ring.

TABLE XXXI-38

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-38-1 | p-Cl—Ph | H | H | H | $^n$Bu | H | F | F | OH |
| XXXI-38-2 | p-Cl—Ph | H | H | CH$_3$ | $^n$Bu | H | F | F | OH |
| XXXI-38-3 | p-Cl—Ph | H | H | CH(CH$_3$)$_2$ | $^n$Bu | H | F | F | OH |
| XXXI-38-4 | p-Cl—Ph | H | H | CH$_2$CH(CH$_3$)$_2$ | $^n$Bu | H | F | F | OH |
| XXXI-38-5 | p-Cl—Ph | H | H | CH$_2$Ph | $^n$Bu | H | F | F | OH |
| XXXI-38-6 | p-Cl—Ph | H | H | CH$_2$-indol-3-yl | $^n$Bu | H | F | F | OH |
| XXXI-38-7 | p-Cl—Ph | H | H | CH$_2$CH$_2$SCH$_3$ | $^n$Bu | H | F | F | OH |
| XXXI-38-8 | p-Cl—Ph | * | H | * | $^n$Bu | H | F | F | OH |

*$R^2$ and $R^{3b}$ joined together by (CH$_2$)$_3$ to form five-membered ring.

TABLE XXXI-39

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-39-1 | p-Br—Ph | H | H | H | $^n$Bu | H | F | F | OH |
| XXXI-39-2 | p-Br—Ph | H | H | CH$_3$ | $^n$Bu | H | F | F | OH |
| XXXI-39-3 | p-Br—Ph | H | H | CH(CH$_3$)$_2$ | $^n$Bu | H | F | F | OH |
| XXXI-39-4 | p-Br—Ph | H | H | CH$_2$CH(CH$_3$)$_2$ | $^n$Bu | H | F | F | OH |
| XXXI-39-5 | p-Br—Ph | H | H | CH$_2$Ph | $^n$Bu | H | F | F | OH |
| XXXI-39-6 | p-Br—Ph | H | H | CH$_2$-indol-3-yl | $^n$Bu | H | F | F | OH |
| XXXI-39-7 | p-Br—Ph | H | H | CH$_2$CH$_2$SCH$_3$ | $^n$Bu | H | F | F | OH |
| XXXI-39-8 | p-Br—Ph | * | H | * | $^n$Bu | H | F | F | OH |

*$R^2$ and $R^{3b}$ joined together by (CH$_2$)$_3$ to form five-membered ring.

TABLE XXXI-40

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-40-1 | p-I—Ph | H | H | H | $^n$Bu | H | F | F | OH |
| XXXI-40-2 | p-I—Ph | H | H | CH$_3$ | $^n$Bu | H | F | F | OH |
| XXXI-40-3 | p-I—Ph | H | H | CH(CH$_3$)$_2$ | $^n$Bu | H | F | F | OH |
| XXXI-40-4 | p-I—Ph | H | H | CH$_2$CH(CH$_3$)$_2$ | $^n$Bu | H | F | F | OH |
| XXXI-40-5 | p-I—Ph | H | H | CH$_2$Ph | $^n$Bu | H | F | F | OH |
| XXXI-40-6 | p-I—Ph | H | H | CH$_2$-indol-3-yl | $^n$Bu | H | F | F | OH |
| XXXI-40-7 | p-I—Ph | H | H | CH$_2$CH$_2$SCH$_3$ | $^n$Bu | H | F | F | OH |
| XXXI-40-8 | p-I—Ph | * | H | * | $^n$Bu | H | F | F | OH |

*$R^2$ and $R^{3b}$ joined together by (CH$_2$)$_3$ to form five-membered ring.

TABLE XXXI-41

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-41-1 | CH$_3$ | H | H | H | Bz | H | F | F | OH |
| XXXI-41-2 | CH$_3$ | H | H | CH$_3$ | Bz | H | F | F | OH |
| XXXI-41-3 | CH$_3$ | H | H | CH(CH$_3$)$_2$ | Bz | H | F | F | OH |
| XXXI-41-4 | CH$_3$ | H | H | CH$_2$CH(CH$_3$)$_2$ | Bz | H | F | F | OH |
| XXXI-41-5 | CH$_3$ | H | H | CH$_2$Ph | Bz | H | F | F | OH |
| XXXI-41-6 | CH$_3$ | H | H | CH$_2$-indol-3-yl | Bz | H | F | F | OH |
| XXXI-41-7 | CH$_3$ | H | H | CH$_2$CH$_2$SCH$_3$ | Bz | H | F | F | OH |
| XXXI-41-8 | CH$_3$ | * | H | * | Bz | H | F | F | OH |

*$R^2$ and $R^{3b}$ joined together by (CH$_2$)$_3$ to form five-membered ring.

TABLE XXXI-42

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-42-1 | Et | H | H | H | Bz | H | F | F | OH |
| XXXI-42-2 | Et | H | H | CH$_3$ | Bz | H | F | F | OH |
| XXXI-42-3 | Et | H | H | CH(CH$_3$)$_2$ | Bz | H | F | F | OH |
| XXXI-42-4 | Et | H | H | CH$_2$CH(CH$_3$)$_2$ | Bz | H | F | F | OH |
| XXXI-42-5 | Et | H | H | CH$_2$Ph | Bz | H | F | F | OH |
| XXXI-42-6 | Et | H | H | CH$_2$-indol-3-yl | Bz | H | F | F | OH |
| XXXI-42-7 | Et | H | H | CH$_2$CH$_2$SCH$_3$ | Bz | H | F | F | OH |
| XXXI-42-8 | Et | * | H | * | Bz | H | F | F | OH |

*$R^2$ and $R^{3b}$ joined together by (CH$_2$)$_3$ to form five-membered ring.

TABLE XXXI-43

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-43-1 | $^i$Pr | H | H | H | Bz | H | F | F | OH |
| XXXI-43-2 | $^i$Pr | H | H | CH$_3$ | Bz | H | F | F | OH |
| XXXI-43-3 | $^i$Pr | H | H | CH(CH$_3$)$_2$ | Bz | H | F | F | OH |
| XXXI-43-4 | $^i$Pr | H | H | CH$_2$CH(CH$_3$)$_2$ | Bz | H | F | F | OH |
| XXXI-43-5 | $^i$Pr | H | H | CH$_2$Ph | Bz | H | F | F | OH |
| XXXI-43-6 | $^i$Pr | H | H | CH$_2$-indol-3-yl | Bz | H | F | F | OH |
| XXXI-43-7 | $^i$Pr | H | H | CH$_2$CH$_2$SCH$_3$ | Bz | H | F | F | OH |
| XXXI-43-8 | $^i$Pr | * | H | * | Bz | H | F | F | OH |

*$R^2$ and $R^{3b}$ joined together by (CH$_2$)$_3$ to form five-membered ring.

TABLE XXXI-44

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-44-1 | $^t$Bu | H | H | H | Bz | H | F | F | OH |
| XXXI-44-2 | $^t$Bu | H | H | CH$_3$ | Bz | H | F | F | OH |
| XXXI-44-3 | $^t$Bu | H | H | CH(CH$_3$)$_2$ | Bz | H | F | F | OH |
| XXXI-44-4 | $^t$Bu | H | H | CH$_2$CH(CH$_3$)$_2$ | Bz | H | F | F | OH |
| XXXI-44-5 | $^t$Bu | H | H | CH$_2$Ph | Bz | H | F | F | OH |
| XXXI-44-6 | $^t$Bu | H | H | CH$_2$-indol-3-yl | Bz | H | F | F | OH |
| XXXI-44-7 | $^t$Bu | H | H | CH$_2$CH$_2$SCH$_3$ | Bz | H | F | F | OH |
| XXXI-44-8 | $^t$Bu | * | H | * | Bz | H | F | F | OH |

*$R^2$ and $R^{3b}$ joined together by (CH$_2$)$_3$ to form five-membered ring.

TABLE XXXI-45

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXI-45-1 | Ph | H | H | H | Bz | H | F | F | OH |
| XXXI-45-2 | Ph | H | H | CH$_3$ | Bz | H | F | F | OH |
| XXXI-45-3 | Ph | H | H | CH(CH$_3$)$_2$ | Bz | H | F | F | OH |
| XXXI-45-4 | Ph | H | H | CH$_2$CH(CH$_3$)$_2$ | Bz | H | F | F | OH |
| XXXI-45-5 | Ph | H | H | CH$_2$Ph | Bz | H | F | F | OH |
| XXXI-45-6 | Ph | H | H | CH$_2$-indol-3-yl | Bz | H | F | F | OH |
| XXXI-45-7 | Ph | H | H | CH$_2$CH$_2$SCH$_3$ | Bz | H | F | F | OH |
| XXXI-45-8 | Ph | * | H | * | Bz | H | F | F | OH |

*$R^2$ and $R^{3b}$ joined together by (CH$_2$)$_3$ to form five-membered ring.

TABLE XXXI-46

| No | R¹ | R² | R³ᵃ | R³ᵇ | R⁴ | R⁵ | R⁶ | X | Y |
|---|---|---|---|---|---|---|---|---|---|
| XXXI-46-1 | p-Me—Ph | H | H | H | Bz | H | F | F | OH |
| XXXI-46-2 | p-Me—Ph | H | H | $CH_3$ | Bz | H | F | F | OH |
| XXXI-46-3 | p-Me—Ph | H | H | $CH(CH_3)_2$ | Bz | H | F | F | OH |
| XXXI-46-4 | p-Me—Ph | H | H | $CH_2CH(CH_3)_2$ | Bz | H | F | F | OH |
| XXXI-46-5 | p-Me—Ph | H | H | $CH_2Ph$ | Bz | H | F | F | OH |
| XXXI-46-6 | p-Me—Ph | H | H | $CH_2$-indol-3-yl | Bz | H | F | F | OH |
| XXXI-46-7 | p-Me—Ph | H | H | $CH_2CH_2SCH_3$ | Bz | H | F | F | OH |
| XXXI-46-8 | p-Me—Ph | * | H | * | Bz | H | F | F | OH |

*$R^2$ and $R^{3b}$ joined together by $(CH_2)_3$ to form five-membered ring.

TABLE XXXI-47

| No | R¹ | R² | R³ᵃ | R³ᵇ | R⁴ | R⁵ | R⁶ | X | Y |
|---|---|---|---|---|---|---|---|---|---|
| XXXI-47-1 | p-F—Ph | H | H | H | Bz | H | F | F | OH |
| XXXI-47-2 | p-F—Ph | H | H | $CH_3$ | Bz | H | F | F | OH |
| XXXI-47-3 | p-F—Ph | H | H | $CH(CH_3)_2$ | Bz | H | F | F | OH |
| XXXI-47-4 | p-F—Ph | H | H | $CH_2CH(CH_3)_2$ | Bz | H | F | F | OH |
| XXXI-47-5 | p-F—Ph | H | H | $CH_2Ph$ | Bz | H | F | F | OH |
| XXXI-47-6 | p-F—Ph | H | H | $CH_2$-indol-3-yl | Bz | H | F | F | OH |
| XXXI-47-7 | p-F—Ph | H | H | $CH_2CH_2SCH_3$ | Bz | H | F | F | OH |
| XXXI-47-8 | p-F—Ph | * | H | * | Bz | H | F | F | OH |

*$R^2$ and $R^{3b}$ joined together by $(CH_2)_3$ to form five-membered ring.

TABLE XXXI-48

| No | R¹ | R² | R³ᵃ | R³ᵇ | R⁴ | R⁵ | R⁶ | X | Y |
|---|---|---|---|---|---|---|---|---|---|
| XXXI-48-1 | p-Cl—Ph | H | H | H | Bz | H | F | F | OH |
| XXXI-48-2 | p-Cl—Ph | H | H | $CH_3$ | Bz | H | F | F | OH |
| XXXI-48-3 | p-Cl—Ph | H | H | $CH(CH_3)_2$ | Bz | H | F | F | OH |
| XXXI-48-4 | p-Cl—Ph | H | H | $CH_2CH(CH_3)_2$ | Bz | H | F | F | OH |
| XXXI-48-5 | p-Cl—Ph | H | H | $CH_2Ph$ | Bz | H | F | F | OH |
| XXXI-48-6 | p-Cl—Ph | H | H | $CH_2$-indol-3-yl | Bz | H | F | F | OH |
| XXXI-48-7 | p-Cl—Ph | H | H | $CH_2CH_2SCH_3$ | Bz | H | F | F | OH |
| XXXI-48-8 | p-Cl—Ph | * | H | * | Bz | H | F | F | OH |

*$R^2$ and $R^{3b}$ joined together by $(CH_2)_3$ to form five-membered ring.

TABLE XXXI-49

| No | R¹ | R² | R³ᵃ | R³ᵇ | R⁴ | R⁵ | R⁶ | X | Y |
|---|---|---|---|---|---|---|---|---|---|
| XXXI-49-1 | p-Br—Ph | H | H | H | Bz | H | F | F | OH |
| XXXI-49-2 | p-Br—Ph | H | H | $CH_3$ | Bz | H | F | F | OH |
| XXXI-49-3 | p-Br—Ph | H | H | $CH(CH_3)_2$ | Bz | H | F | F | OH |
| XXXI-49-4 | p-Br—Ph | H | H | $CH_2CH(CH_3)_2$ | Bz | H | F | F | OH |
| XXXI-49-5 | p-Br—Ph | H | H | $CH_2Ph$ | Bz | H | F | F | OH |
| XXXI-49-6 | p-Br—Ph | H | H | $CH_2$-indol-3-yl | Bz | H | F | F | OH |
| XXXI-49-7 | p-Br—Ph | H | H | $CH_2CH_2SCH_3$ | Bz | H | F | F | OH |
| XXXI-49-8 | p-Br—Ph | * | H | * | Bz | H | F | F | OH |

*$R^2$ and $R^{3b}$ joined together by $(CH_2)_3$ to form five-membered ring.

TABLE XXXI-50

| No | R¹ | R² | R³ᵃ | R³ᵇ | R⁴ | R⁵ | R⁶ | X | Y |
|---|---|---|---|---|---|---|---|---|---|
| XXXI-50-1 | p-I—Ph | H | H | H | Bz | H | F | F | OH |
| XXXI-50-2 | p-I—Ph | H | H | $CH_3$ | Bz | H | F | F | OH |
| XXXI-50-3 | p-I—Ph | H | H | $CH(CH_3)_2$ | Bz | H | F | F | OH |
| XXXI-50-4 | p-I—Ph | H | H | $CH_2CH(CH_3)_2$ | Bz | H | F | F | OH |
| XXXI-50-5 | p-I—Ph | H | H | $CH_2Ph$ | Bz | H | F | F | OH |
| XXXI-50-6 | p-I—Ph | H | H | $CH_2$-indol-3-yl | Bz | H | F | F | OH |
| XXXI-50-7 | p-I—Ph | H | H | $CH_2CH_2SCH_3$ | Bz | H | F | F | OH |
| XXXI-50-8 | p-I—Ph | * | H | * | Bz | H | F | F | OH |

*$R^2$ and $R^{3b}$ joined together by $(CH_2)_3$ to form five-membered ring.

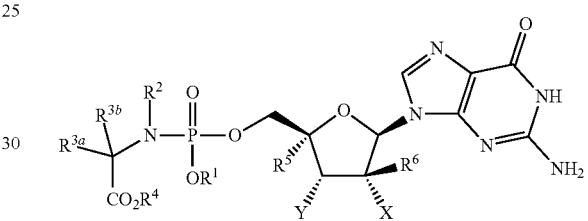

XXXII

TABLE XXXII-1

| No | R¹ | R² | R³ᵃ | R³ᵇ | R⁴ | R⁵ | R⁶ | X | Y |
|---|---|---|---|---|---|---|---|---|---|
| XXXII-1-1 | $CH_3$ | H | H | H | $CH_3$ | H | H | F | OH |
| XXXII-1-2 | $CH_3$ | H | H | $CH_3$ | $CH_3$ | H | H | F | OH |
| XXXII-1-3 | $CH_3$ | H | H | $CH(CH_3)_2$ | $CH_3$ | H | H | F | OH |
| XXXII-1-4 | $CH_3$ | H | H | $CH_2CH(CH_3)_2$ | $CH_3$ | H | H | F | OH |
| XXXII-1-5 | $CH_3$ | H | H | $CH_2Ph$ | $CH_3$ | H | H | F | OH |
| XXXII-1-6 | $CH_3$ | H | H | $CH_2$-indol-3-yl | $CH_3$ | H | H | F | OH |
| XXXII-1-7 | $CH_3$ | H | H | $CH_2CH_2SCH_3$ | $CH_3$ | H | H | F | OH |
| XXXII-1-8 | $CH_3$ | * | H | * | $CH_3$ | H | H | F | OH |

*$R^2$ and $R^{3b}$ joined together by $(CH_2)_3$ to form five-membered ring.

TABLE XXXII-2

| No | R¹ | R² | R³ᵃ | R³ᵇ | R⁴ | R⁵ | R⁶ | X | Y |
|---|---|---|---|---|---|---|---|---|---|
| XXXII-2-1 | Et | H | H | H | $CH_3$ | H | H | F | OH |
| XXXII-2-2 | Et | H | H | $CH_3$ | $CH_3$ | H | H | F | OH |
| XXXII-2-3 | Et | H | H | $CH(CH_3)_2$ | $CH_3$ | H | H | F | OH |
| XXXII-2-4 | Et | H | H | $CH_2CH(CH_3)_2$ | $CH_3$ | H | H | F | OH |
| XXXII-2-5 | Et | H | H | $CH_2Ph$ | $CH_3$ | H | H | F | OH |
| XXXII-2-6 | Et | H | H | $CH_2$-indol-3-yl | $CH_3$ | H | H | F | OH |
| XXXII-2-7 | Et | H | H | $CH_2CH_2SCH_3$ | $CH_3$ | H | H | F | OH |
| XXXII-2-8 | Et | * | H | * | $CH_3$ | H | H | F | OH |

*$R^2$ and $R^{3b}$ joined together by $(CH_2)_3$ to form five-membered ring.

TABLE XXXII-3

| No | R¹ | R² | R³ᵃ | R³ᵇ | R⁴ | R⁵ | R⁶ | X | Y |
|---|---|---|---|---|---|---|---|---|---|
| XXXII-3-1 | $^i$Pr | H | H | H | $CH_3$ | H | H | F | OH |
| XXXII-3-2 | $^i$Pr | H | H | $CH_3$ | $CH_3$ | H | H | F | OH |

TABLE XXXII-3-continued

| No | R¹ | R² | R³ᵃ | R³ᵇ | R⁴ | R⁵ | R⁶ | X | Y |
|---|---|---|---|---|---|---|---|---|---|
| XXXII-3-3 | $^i$Pr | H | H | CH(CH₃)₂ | CH₃ | H | H | F | OH |
| XXXII-3-4 | $^i$Pr | H | H | CH₂CH(CH₃)₂ | CH₃ | H | H | F | OH |
| XXXII-3-5 | $^i$Pr | H | H | CH₂Ph | CH₃ | H | H | F | OH |
| XXXII-3-6 | $^i$Pr | H | H | CH₂-indol-3-yl | CH₃ | H | H | F | OH |
| XXXII-3-7 | $^i$Pr | H | H | CH₂CH₂SCH₃ | CH₃ | H | H | F | OH |
| XXXII-3-8 | $^i$Pr | * | H | * | CH₃ | H | H | F | OH |

*R² and R³ᵇ joined together by (CH₂)₃ to form five-membered ring.

TABLE XXXII-4

| No | R¹ | R² | R³ᵃ | R³ᵇ | R⁴ | R⁵ | R⁶ | X | Y |
|---|---|---|---|---|---|---|---|---|---|
| XXXII-4-1 | $^t$Bu | H | H | H | CH₃ | H | H | F | OH |
| XXXII-4-2 | $^t$Bu | H | H | CH₃ | CH₃ | H | H | F | OH |
| XXXII-4-3 | $^t$Bu | H | H | CH(CH₃)₂ | CH₃ | H | H | F | OH |
| XXXII-4-4 | $^t$Bu | H | H | CH₂CH(CH₃)₂ | CH₃ | H | H | F | OH |
| XXXII-4-5 | $^t$Bu | H | H | CH₂Ph | CH₃ | H | H | F | OH |
| XXXII-4-6 | $^t$Bu | H | H | CH₂-indol-3-yl | CH₃ | H | H | F | OH |
| XXXII-4-7 | $^t$Bu | H | H | CH₂CH₂SCH₃ | CH₃ | H | H | F | OH |
| XXXII-4-8 | $^t$Bu | * | H | * | CH₃ | H | H | F | OH |

*R² and R³ᵇ joined together by (CH₂)₃ to form five-membered ring.

TABLE XXXII-5

| No | R¹ | R² | R³ᵃ | R³ᵇ | R⁴ | R⁵ | R⁶ | X | Y |
|---|---|---|---|---|---|---|---|---|---|
| XXXII-5-1 | Ph | H | H | H | CH₃ | H | H | F | OH |
| XXXII-5-2 | Ph | H | H | CH₃ | CH₃ | H | H | F | OH |

TABLE XXXII-5-continued

| No | R¹ | R² | R³ᵃ | R³ᵇ | R⁴ | R⁵ | R⁶ | X | Y |
|---|---|---|---|---|---|---|---|---|---|
| XXXII-5-3 | Ph | H | H | CH(CH₃)₂ | CH₃ | H | H | F | OH |
| XXXII-5-4 | Ph | H | H | CH₂CH(CH₃)₂ | CH₃ | H | H | F | OH |
| XXXII-5-5 | Ph | H | H | CH₂Ph | CH₃ | H | H | F | OH |
| XXXII-5-6 | Ph | H | H | CH₂-indol-3-yl | CH₃ | H | H | F | OH |
| XXXII-5-7 | Ph | H | H | CH₂CH₂SCH₃ | CH₃ | H | H | F | OH |
| XXXII-5-8 | Ph | * | H | * | CH₃ | H | H | F | OH |

*R² and R³ᵇ joined together by (CH₂)₃ to form five-membered ring.

TABLE XXXII-6

| No | R¹ | R² | R³ᵃ | R³ᵇ | R⁴ | R⁵ | R⁶ | X | Y |
|---|---|---|---|---|---|---|---|---|---|
| XXXII-6-1 | p-Me—Ph | H | H | H | CH₃ | H | H | F | OH |
| XXXII-6-2 | p-Me—Ph | H | H | CH₃ | CH₃ | H | H | F | OH |
| XXXII-6-3 | p-Me—Ph | H | H | CH(CH₃)₂ | CH₃ | H | H | F | OH |
| XXXII-6-4 | p-Me—Ph | H | H | CH₂CH(CH₃)₂ | CH₃ | H | H | F | OH |
| XXXII-6-5 | p-Me—Ph | H | H | CH₂Ph | CH₃ | H | H | F | OH |
| XXXII-6-6 | p-Me—Ph | H | H | CH₂-indol-3-yl | CH₃ | H | H | F | OH |
| XXXII-6-7 | p-Me—Ph | H | H | CH₂CH₂SCH₃ | CH₃ | H | H | F | OH |
| XXXII-6-8 | p-Me—Ph | * | H | * | CH₃ | H | H | F | OH |

*R² and R³ᵇ joined together by (CH₂)₃ to form five-membered ring.

TABLE XXXII-7

| No | R¹ | R² | R³ᵃ | R³ᵇ | R⁴ | R⁵ | R⁶ | X | Y |
|---|---|---|---|---|---|---|---|---|---|
| XXXII-7-1 | p-F—Ph | H | H | H | CH₃ | H | H | F | OH |
| XXXII-7-2 | p-F—Ph | H | H | CH₃ | CH₃ | H | H | F | OH |
| XXXII-7-3 | p-F—Ph | H | H | CH(CH₃)₂ | CH₃ | H | H | F | OH |
| XXXII-7-4 | p-F—Ph | H | H | CH₂CH(CH₃)₂ | CH₃ | H | H | F | OH |
| XXXII-7-6 | p-F—Ph | H | H | CH₂Ph | CH₃ | H | H | F | OH |
| XXXII-7-7 | p-F—Ph | H | H | CH₂-indol-3-yl | CH₃ | H | H | F | OH |
| XXXII-7-8 | p-F—Ph | H | H | CH₂CH₂SCH₃ | CH₃ | H | H | F | OH |
| XXXII-7-20 | p-F—Ph | * | H | * | CH₃ | H | H | F | OH |

*R² and R³ᵇ joined together by (CH₂)₃ to form five-membered ring.

TABLE XXXII-8

| No | R¹ | R² | R³ᵃ | R³ᵇ | R⁴ | R⁵ | R⁶ | X | Y |
|---|---|---|---|---|---|---|---|---|---|
| XXXII-8-1 | p-Cl—Ph | H | H | H | CH₃ | H | H | F | OH |
| XXXII-8-2 | p-Cl—Ph | H | H | CH₃ | CH₃ | H | H | F | OH |
| XXXII-8-3 | p-Cl—Ph | H | H | CH(CH₃)₂ | CH₃ | H | H | F | OH |
| XXXII-8-4 | p-Cl—Ph | H | H | CH₂CH(CH₃)₂ | CH₃ | H | H | F | OH |
| XXXII-8-5 | p-Cl—Ph | H | H | CH₂Ph | CH₃ | H | H | F | OH |
| XXXII-8-6 | p-Cl—Ph | H | H | CH₂-indol-3-yl | CH₃ | H | H | F | OH |
| XXXII-8-7 | p-Cl—Ph | H | H | CH₂CH₂SCH₃ | CH₃ | H | H | F | OH |
| XXXII-8-8 | p-Cl—Ph | * | H | * | CH₃ | H | H | F | OH |

*R² and R³ᵇ joined together by (CH₂)₃ to form five-membered ring.

TABLE XXXII-9

| No | R¹ | R² | R³ᵃ | R³ᵇ | R⁴ | R⁵ | R⁶ | X | Y |
|---|---|---|---|---|---|---|---|---|---|
| XXXII-9-1 | p-Br—Ph | H | H | H | CH₃ | H | H | F | OH |
| XXXII-9-2 | p-Br—Ph | H | H | CH₃ | CH₃ | H | H | F | OH |
| XXXII-9-3 | p-Br—Ph | H | H | CH(CH₃)₂ | CH₃ | H | H | F | OH |

TABLE XXXII-9-continued

| No | R¹ | R² | $R^{3a}$ | $R^{3b}$ | R⁴ | R⁵ | R⁶ | X | Y |
|---|---|---|---|---|---|---|---|---|---|
| XXXII-9-4 | p-Br—Ph | H | H | $CH_2CH(CH_3)_2$ | $CH_3$ | H | H | F | OH |
| XXXII-9-6 | p-Br—Ph | H | H | $CH_2Ph$ | $CH_3$ | H | H | F | OH |
| XXXII-9-7 | p-Br—Ph | H | H | $CH_2$-indol-3-yl | $CH_3$ | H | H | F | OH |
| XXXII-9-8 | p-Br—Ph | H | H | $CH_2CH_2SCH_3$ | $CH_3$ | H | H | F | OH |
| XXXII-9-20 | p-Br—Ph | * | H | * | $CH_3$ | H | H | F | OH |

*R² and $R^{3b}$ joined together by $(CH_2)_3$ to form five-membered ring.

TABLE XXXII-10

| No | R¹ | R² | $R^{3a}$ | $R^{3b}$ | R⁴ | R⁵ | R⁶ | X | Y |
|---|---|---|---|---|---|---|---|---|---|
| XXXII-10-1 | p-I—Ph | H | H | H | $CH_3$ | H | H | F | OH |
| XXXII-10-2 | p-I—Ph | H | H | $CH_3$ | $CH_3$ | H | H | F | OH |
| XXXII-10-3 | p-I—Ph | H | H | $CH(CH_3)_2$ | $CH_3$ | H | H | F | OH |
| XXXII-10-4 | p-I—Ph | H | H | $CH_2CH(CH_3)_2$ | $CH_3$ | H | H | F | OH |
| XXXII-10-5 | p-I—ph | H | H | $CH_2Ph$ | $CH_3$ | H | H | F | OH |
| XXXII-10-6 | p-I—Ph | H | H | $CH_2$-indol-3-yl | $CH_3$ | H | H | F | OH |
| XXXII-10-7 | p-I—Ph | H | H | $CH_2CH_2SCH_3$ | $CH_3$ | H | H | F | OH |
| XXXII-10-8 | p-I—Ph | * | H | * | $CH_3$ | H | H | F | OH |

*R² and $R^{3b}$ joined together by $(CH_2)_3$ to form five-membered ring.

TABLE XXXII-11

| No | R¹ | R² | $R^{3a}$ | $R^{3b}$ | R⁴ | R⁵ | R⁶ | X | Y |
|---|---|---|---|---|---|---|---|---|---|
| XXXII-11-1 | $CH_3$ | H | H | H | Et | H | H | F | OH |
| XXXII-11-2 | $CH_3$ | H | H | $CH_3$ | Et | H | H | F | OH |
| XXXII-11-3 | $CH_3$ | H | H | $CH(CH_3)_2$ | Et | H | H | F | OH |
| XXXII-11-4 | $CH_3$ | H | H | $CH_2CH(CH_3)_2$ | Et | H | H | F | OH |
| XXXII-11-5 | $CH_3$ | H | H | $CH_2Ph$ | Et | H | H | F | OH |
| XXXII-11-6 | $CH_3$ | H | H | $CH_2$-indol-3-yl | Et | H | H | F | OH |
| XXXII-11-7 | $CH_3$ | H | H | $CH_2CH_2SCH_3$ | Et | H | H | F | OH |
| XXXII-11-8 | $CH_3$ | * | H | * | Et | H | H | F | OH |

*R² and $R^{3b}$ joined together by $(CH_2)_3$ to form five-membered ring.

TABLE XXXII-12

| No | R¹ | R² | $R^{3a}$ | $R^{3b}$ | R⁴ | R⁵ | R⁶ | X | Y |
|---|---|---|---|---|---|---|---|---|---|
| XXXII-12-1 | Et | H | H | H | Et | H | H | F | OH |
| XXXII-12-2 | Et | H | H | $CH_3$ | Et | H | H | F | OH |
| XXXII-12-3 | Et | H | H | $CH(CH_3)_2$ | Et | H | H | F | OH |
| XXXII-12-4 | Et | H | H | $CH_2CH(CH_3)_2$ | Et | H | H | F | OH |
| XXXII-12-5 | Et | H | H | $CH_2Ph$ | Et | H | H | F | OH |
| XXXII-12-6 | Et | H | H | $CH_2$-indol-3-yl | Et | H | H | F | OH |
| XXXII-12-7 | Et | H | H | $CH_2CH_2SCH_3$ | Et | H | H | F | OH |
| XXXII-12-8 | Et | * | H | * | Et | H | H | F | OH |

*R² and $R^{3b}$ joined together by $(CH_2)_3$ to form five-membered ring.

TABLE XXXII-13

| No | R¹ | R² | $R^{3a}$ | $R^{3b}$ | R⁴ | R⁵ | R⁶ | X | Y |
|---|---|---|---|---|---|---|---|---|---|
| XXXII-13-1 | $^iPr$ | H | H | H | Et | H | H | F | OH |
| XXXII-13-2 | $^iPr$ | H | H | $CH_3$ | Et | H | H | F | OH |
| XXXII-13-3 | $^iPr$ | H | H | $CH(CH_3)_2$ | Et | H | H | F | OH |
| XXXII-13-4 | $^iPr$ | H | H | $CH_2CH(CH_3)_2$ | Et | H | H | F | OH |
| XXXII-13-5 | $^iPr$ | H | H | $CH_2Ph$ | Et | H | H | F | OH |
| XXXII-13-6 | $^iPr$ | H | H | $CH_2$-indol-3-yl | Et | H | H | F | OH |
| XXXII-13-7 | $^iPr$ | H | H | $CH_2CH_2SCH_3$ | Et | H | H | F | OH |
| XXXII-13-8 | $^iPr$ | * | H | * | Et | H | H | F | OH |

*R² and $R^{3b}$ joined together by $(CH_2)_3$ to form five-membered ring.

TABLE XXXII-14

| No | R¹ | R² | $R^{3a}$ | $R^{3b}$ | R⁴ | R⁵ | R⁶ | X | Y |
|---|---|---|---|---|---|---|---|---|---|
| XXXII-14-1 | $^tBu$ | H | H | H | Et | H | H | F | OH |
| XXXII-14-2 | $^tBu$ | H | H | $CH_3$ | Et | H | H | F | OH |
| XXXII-14-3 | $^tBu$ | H | H | $CH(CH_3)_2$ | Et | H | H | F | OH |
| XXXII-14-4 | $^tBu$ | H | H | $CH_2CH(CH_3)_2$ | Et | H | H | F | OH |
| XXXII-14-5 | $^tBu$ | H | H | $CH_2Ph$ | Et | H | H | F | OH |
| XXXII-14-6 | $^tBu$ | H | H | $CH_2$-indol-3-yl | Et | H | H | F | OH |
| XXXII-14-7 | $^tBu$ | H | H | $CH_2CH_2SCH_3$ | Et | H | H | F | OH |
| XXXII-14-8 | $^tBu$ | * | H | * | Et | H | H | F | OH |

*R² and $R^{3b}$ joined together by $(CH_2)_3$ to form five-membered ring.

TABLE XXXII-15

| No | R¹ | R² | $R^{3a}$ | $R^{3b}$ | R⁴ | R⁵ | R⁶ | X | Y |
|---|---|---|---|---|---|---|---|---|---|
| XXXII-15-1 | Ph | H | H | H | Et | H | H | F | OH |
| XXXII-15-2 | Ph | H | H | $CH_3$ | Et | H | H | F | OH |
| XXXII-15-3 | Ph | H | H | $CH(CH_3)_2$ | Et | H | H | F | OH |
| XXXII-15-4 | Ph | H | H | $CH_2CH(CH_3)_2$ | Et | H | H | F | OH |
| XXXII-15-5 | Ph | H | H | $CH_2Ph$ | Et | H | H | F | OH |
| XXXII-15-6 | Ph | H | H | $CH_2$-indol-3-yl | Et | H | H | F | OH |
| XXXII-15-7 | Ph | H | H | $CH_2CH_2SCH_3$ | Et | H | H | F | OH |
| XXXII-15-8 | Ph | * | H | * | Et | H | H | F | OH |

*R² and $R^{3b}$ joined together by $(CH_2)_3$ to form five-membered ring.

TABLE XXXII-16

| No | R¹ | R² | $R^{3a}$ | $R^{3b}$ | R⁴ | R⁵ | R⁶ | X | Y |
|---|---|---|---|---|---|---|---|---|---|
| XXXII-16-1 | p-Me—Ph | H | H | H | Et | H | H | F | OH |
| XXXII-16-2 | p-Me—Ph | H | H | $CH_3$ | Et | H | H | F | OH |
| XXXII-16-3 | p-Me—Ph | H | H | $CH(CH_3)_2$ | Et | H | H | F | OH |

TABLE XXXII-16-continued

| No | R¹ | R² | R³ᵃ | R³ᵇ | R⁴ | R⁵ | R⁶ | X | Y |
|---|---|---|---|---|---|---|---|---|---|
| XXXII-16-4 | p-Me—Ph | H | H | CH₂CH(CH₃)₂ | Et | H | H | F | OH |
| XXXII-16-5 | p-Me—Ph | H | H | CH₂Ph | Et | H | H | F | OH |
| XXXII-16-6 | p-Me—Ph | H | H | CH₂-indol-3-yl | Et | H | H | F | OH |
| XXXII-16-7 | p-Me—Ph | H | H | CH₂CH₂SCH₃ | Et | H | H | F | OH |
| XXXII-16-8 | p-Me—Ph | * | H | * | Et | H | H | F | OH |

*R² and R³ᵇ joined together by (CH₂)₃ to form five-membered ring.

TABLE XXXII-17

| No | R¹ | R² | R³ᵃ | R³ᵇ | R⁴ | R⁵ | R⁶ | X | Y |
|---|---|---|---|---|---|---|---|---|---|
| XXXII-17-1 | p-F—Ph | H | H | H | Et | H | H | F | OH |
| XXXII-17-2 | p-F—Ph | H | H | CH₃ | Et | H | H | F | OH |
| XXXII-17-3 | p-F—Ph | H | H | CH(CH₃)₂ | Et | H | H | F | OH |
| XXXII-17-4 | p-F—Ph | H | H | CH₂CH(CH₃)₂ | Et | H | H | F | OH |
| XXXII-17-5 | p-F—Ph | H | H | CH₂Ph | Et | H | H | F | OH |
| XXXII-17-6 | p-F—Ph | H | H | CH₂-indol-3-yl | Et | H | H | F | OH |
| XXXII-17-7 | p-F—Ph | H | H | CH₂CH₂SCH₃ | Et | H | H | F | OH |
| XXXII-17-8 | p-F—Ph | * | H | * | Et | H | H | F | OH |

*R² and R³ᵇ joined together by (CH₂)₃ to form five-membered ring.

TABLE XXXII-18

| No | R¹ | R² | R³ᵃ | R³ᵇ | R⁴ | R⁵ | R⁶ | X | Y |
|---|---|---|---|---|---|---|---|---|---|
| XXXII-18-1 | p-Cl—Ph | H | H | H | Et | H | H | F | OH |
| XXXII-18-2 | p-Cl—Ph | H | H | CH₃ | Et | H | H | F | OH |
| XXXII-18-3 | p-Cl—Ph | H | H | CH(CH₃)₂ | Et | H | H | F | OH |
| XXXII-18-4 | p-Cl—Ph | H | H | CH₂CH(CH₃)₂ | Et | H | H | F | OH |
| XXXII-18-5 | p-Cl—Ph | H | H | CH₂Ph | Et | H | H | F | OH |
| XXXII-18-6 | p-Cl—Ph | H | H | CH₂-indol-3-yl | Et | H | H | F | OH |
| XXXII-18-7 | p-Cl—Ph | H | H | CH₂CH₂SCH₃ | Et | H | H | F | OH |
| XXXII-18-8 | p-Cl—Ph | * | H | * | Et | H | H | F | OH |

*R² and R³ᵇ joined together by (CH₂)₃ to form five-membered ring.

TABLE XXXII-19

| No | R¹ | R² | R³ᵃ | R³ᵇ | R⁴ | R⁵ | R⁶ | X | Y |
|---|---|---|---|---|---|---|---|---|---|
| XXXII-19-1 | p-Br—Ph | H | H | H | Et | H | H | F | OH |
| XXXII-19-2 | p-Br—Ph | H | H | CH₃ | Et | H | H | F | OH |
| XXXII-19-3 | p-Br—Ph | H | H | CH(CH₃)₂ | Et | H | H | F | OH |
| XXXII-19-4 | p-Br—Ph | H | H | CH₂CH(CH₃)₂ | Et | H | H | F | OH |
| XXXII-19-5 | p-Br—Ph | H | H | CH₂Ph | Et | H | H | F | OH |
| XXXII-19-6 | p-Br—Ph | H | H | CH₂-indol-3-yl | Et | H | H | F | OH |
| XXXII-19-7 | p-Br—Ph | H | H | CH₂CH₂SCH₃ | Et | H | H | F | OH |
| XXXII-19-8 | p-Br—Ph | * | H | * | Et | H | H | F | OH |

*R² and R³ᵇ joined together by (CH₂)₃ to form five-membered ring.

TABLE XXXII-20

| No | R¹ | R² | R³ᵃ | R³ᵇ | R⁴ | R⁵ | R⁶ | X | Y |
|---|---|---|---|---|---|---|---|---|---|
| XXXII-20-1 | p-I—Ph | H | H | H | Et | H | H | F | OH |
| XXXII-20-2 | p-I—Ph | H | H | CH₃ | Et | H | H | F | OH |
| XXXII-20-3 | p-I—Ph | H | H | CH(CH₃)₂ | Et | H | H | F | OH |
| XXXII-20-4 | p-I—Ph | H | H | CH₂CH(CH₃)₂ | Et | H | H | F | OH |
| XXXII-20-5 | p-I—Ph | H | H | CH₂Ph | Et | H | H | F | OH |
| XXXII-20-6 | p-I—Ph | H | H | CH₂-indol-3-yl | Et | H | H | F | OH |
| XXXII-20-7 | p-I—Ph | H | H | CH₂CH₂SCH₃ | Et | H | H | F | OH |
| XXXII-20-8 | p-I—Ph | * | H | * | Et | H | H | F | OH |

*R² and R³ᵇ joined together by (CH₂)₃ to form five-membered ring.

TABLE XXXII-21

| No | R¹ | R² | R³ᵃ | R³ᵇ | R⁴ | R⁵ | R⁶ | X | Y |
|---|---|---|---|---|---|---|---|---|---|
| XXXII-21-1 | CH₃ | H | H | H | ⁱPr | H | H | F | OH |
| XXXII-21-2 | CH₃ | H | H | CH₃ | ⁱPr | H | H | F | OH |
| XXXII-21-3 | CH₃ | H | H | CH(CH₃)₂ | ⁱPr | H | H | F | OH |
| XXXII-21-4 | CH₃ | H | H | CH₂CH(CH₃)₂ | ⁱPr | H | H | F | OH |
| XXXII-21-5 | CH₃ | H | H | CH₂Ph | ⁱPr | H | H | F | OH |
| XXXII-21-6 | CH₃ | H | H | CH₂-indol-3-yl | ⁱPr | H | H | F | OH |
| XXXII-21-7 | CH₃ | H | H | CH₂CH₂SCH₃ | ⁱPr | H | H | F | OH |
| XXXII-21-8 | CH₃ | * | H | * | ⁱPr | H | H | F | OH |

*R² and R³ᵇ joined together by (CH₂)₃ to form five-membered ring.

TABLE XXXII-22

| No | R¹ | R² | R³ᵃ | R³ᵇ | R⁴ | R⁵ | R⁶ | X | Y |
|---|---|---|---|---|---|---|---|---|---|
| XXXII-22-1 | Et | H | H | H | ⁱPr | H | H | F | OH |
| XXXII-22-2 | Et | H | H | CH₃ | ⁱPr | H | H | F | OH |
| XXXII-22-3 | Et | H | H | CH(CH₃)₂ | ⁱPr | H | H | F | OH |
| XXXII-22-4 | Et | H | H | CH₂CH(CH₃)₂ | ⁱPr | H | H | F | OH |
| XXXII-22-5 | Et | H | H | CH₂Ph | ⁱPr | H | H | F | OH |
| XXXII-22-6 | Et | H | H | CH₂-indol-3-yl | ⁱPr | H | H | F | OH |
| XXXII-22-7 | Et | H | H | CH₂CH₂SCH₃ | ⁱPr | H | H | F | OH |
| XXXII-22-8 | Et | * | H | * | ⁱPr | H | H | F | OH |

*R² and R³ᵇ joined together by (CH₂)₃ to form five-membered ring.

TABLE XXXII-23

| No | R¹ | R² | R³ᵃ | R³ᵇ | R⁴ | R⁵ | R⁶ | X | Y |
|---|---|---|---|---|---|---|---|---|---|
| XXXII-23-1 | ⁱPr | H | H | H | ⁱPr | H | H | F | OH |
| XXXII-23-2 | ⁱPr | H | H | CH₃ | ⁱPr | H | H | F | OH |
| XXXII-23-3 | ⁱPr | H | H | CH(CH₃)₂ | ⁱPr | H | H | F | OH |
| XXXII-23-4 | ⁱPr | H | H | CH₂CH(CH₃)₂ | ⁱPr | H | H | F | OH |
| XXXII-23-5 | ⁱPr | H | H | CH₂Ph | ⁱPr | H | H | F | OH |
| XXXII-23-6 | ⁱPr | H | H | CH₂-indol-3-yl | ⁱPr | H | H | F | OH |
| XXXII-23-7 | ⁱPr | H | H | CH₂CH₂SCH₃ | ⁱPr | H | H | F | OH |
| XXXII-23-8 | ⁱPr | * | H | * | ⁱPr | H | H | F | OH |

*R² and R³ᵇ joined together by (CH₂)₃ to form five-membered ring.

TABLE XXXII-24

| No | R¹ | R² | R³ᵃ | R³ᵇ | R⁴ | R⁵ | R⁶ | X | Y |
|---|---|---|---|---|---|---|---|---|---|
| XXXII-24-1 | ᵗBu | H | H | H | ⁱPr | H | H | F | OH |
| XXXII-24-2 | ᵗBu | H | H | CH₃ | ⁱPr | H | H | F | OH |
| XXXII-24-3 | ᵗBu | H | H | CH(CH₃)₂ | ⁱPr | H | H | F | OH |
| XXXII-24-4 | ᵗBu | H | H | CH₂CH(CH₃)₂ | ⁱPr | H | H | F | OH |
| XXXII-24-5 | ᵗBu | H | H | CH₂Ph | ⁱPr | H | H | F | OH |
| XXXII-24-6 | ᵗBu | H | H | CH₂-indol-3-yl | ⁱPr | H | H | F | OH |
| XXXII-24-7 | ᵗBu | H | H | CH₂CH₂SCH₃ | ⁱPr | H | H | F | OH |
| XXXII-24-8 | ᵗBu | * | H | * | ⁱPr | H | H | F | OH |

*R² and R³ᵇ joined together by (CH₂)₃ to form five-membered ring.

TABLE XXXII-25

| No | R¹ | R² | R³ᵃ | R³ᵇ | R⁴ | R⁵ | R⁶ | X | Y |
|---|---|---|---|---|---|---|---|---|---|
| XXXII-25-1 | Ph | H | H | H | ⁱPr | H | H | F | OH |
| XXXII-25-2 | Ph | H | H | CH₃ | ⁱPr | H | H | F | OH |
| XXXII-25-3 | Ph | H | H | CH(CH₃)₂ | ⁱPr | H | H | F | OH |
| XXXII-25-4 | Ph | H | H | CH₂CH(CH₃)₂ | ⁱPr | H | H | F | OH |
| XXXII-25-5 | Ph | H | H | CH₂Ph | ⁱPr | H | H | F | OH |
| XXXII-25-6 | Ph | H | H | CH₂-indol-3-yl | ⁱPr | H | H | F | OH |
| XXXII-25-7 | Ph | H | H | CH₂CH₂SCH₃ | ⁱPr | H | H | F | OH |
| XXXII-25-8 | Ph | * | H | * | ⁱPr | H | H | F | OH |

*R² and R³ᵇ joined together by (CH₂)₃ to form five-membered ring.

TABLE XXXII-26

| No | R¹ | R² | R³ᵃ | R³ᵇ | R⁴ | R⁵ | R⁶ | X | Y |
|---|---|---|---|---|---|---|---|---|---|
| XXXII-26-1 | p-Me—Ph | H | H | H | ⁱPr | H | H | F | OH |
| XXXII-26-2 | p-Me—Ph | H | H | CH₃ | ⁱPr | H | H | F | OH |
| XXXII-26-3 | p-Me—Ph | H | H | CH(CH₃)₂ | ⁱPr | H | H | F | OH |
| XXXII-26-4 | p-Me—Ph | H | H | CH₂CH(CH₃)₂ | ⁱPr | H | H | F | OH |
| XXXII-26-5 | p-Me—Ph | H | H | CH₂Ph | ⁱPr | H | H | F | OH |
| XXXII-26-6 | p-Me—Ph | H | H | CH₂-indol-3-yl | ⁱPr | H | H | F | OH |
| XXXII-26-7 | p-Me—Ph | H | H | CH₂CH₂SCH₃ | ⁱPr | H | H | F | OH |
| XXXII-26-8 | p-Me—Ph | * | H | * | ⁱPr | H | H | F | OH |

*R² and R³ᵇ joined together by (CH₂)₃ to form five-membered ring.

TABLE XXXII-27

| No | R¹ | R² | R³ᵃ | R³ᵇ | R⁴ | R⁵ | R⁶ | X | Y |
|---|---|---|---|---|---|---|---|---|---|
| XXXII-27-1 | p-F—Ph | H | H | H | ⁱPr | H | H | F | OH |
| XXXII-27-2 | p-F—Ph | H | H | CH₃ | ⁱPr | H | H | F | OH |
| XXXII-27-3 | p-F—Ph | H | H | CH(CH₃)₂ | ⁱPr | H | H | F | OH |
| XXXII-27-4 | p-F—Ph | H | H | CH₂CH(CH₃)₂ | ⁱPr | H | H | F | OH |
| XXXII-27-5 | p-F—Ph | H | H | CH₂Ph | ⁱPr | H | H | F | OH |
| XXXII-27-6 | p-F—Ph | H | H | CH₂-indol-3-yl | ⁱPr | H | H | F | OH |
| XXXII-27-7 | p-F—Ph | H | H | CH₂CH₂SCH₃ | ⁱPr | H | H | F | OH |
| XXXII-27-8 | p-F—Ph | * | H | * | ⁱPr | H | H | F | OH |

*R² and R³ᵇ joined together by (CH₂)₃ to form five-membered ring.

TABLE XXXII-28

| No | R¹ | R² | R³ᵃ | R³ᵇ | R⁴ | R⁵ | R⁶ | X | Y |
|---|---|---|---|---|---|---|---|---|---|
| XXXII-28-1 | p-Cl—Ph | H | H | H | $^i$Pr | H | H | F | OH |
| XXXII-28-2 | p-Cl—Ph | H | H | CH$_3$ | $^i$Pr | H | H | F | OH |
| XXXII-28-3 | p-Cl—Ph | H | H | CH(CH$_3$)$_2$ | $^i$Pr | H | H | F | OH |
| XXXII-28-4 | p-Cl—Ph | H | H | CH$_2$CH(CH$_3$)$_2$ | $^i$Pr | H | H | F | OH |
| XXXII-28-5 | p-Cl—Ph | H | H | CH$_2$Ph | $^i$Pr | H | H | F | OH |
| XXXII-28-6 | p-Cl—Ph | H | H | CH$_2$-indol-3-yl | $^i$Pr | H | H | F | OH |
| XXXII-28-7 | p-Cl—Ph | H | H | CH$_2$CH$_2$SCH$_3$ | $^i$Pr | H | H | F | OH |
| XXXII-28-8 | p-Cl—Ph | * | H | * | $^i$Pr | H | H | F | OH |

*R² and R³ᵇ joined together by (CH$_2$)$_3$ to form five-membered ring.

TABLE XXXII-29

| No | R¹ | R² | R³ᵃ | R³ᵇ | R⁴ | R⁵ | R⁶ | X | Y |
|---|---|---|---|---|---|---|---|---|---|
| XXXII-29-1 | p-Br—Ph | H | H | H | $^i$Pr | H | H | F | OH |
| XXXII-29-2 | p-Br—Ph | H | H | CH$_3$ | $^i$Pr | H | H | F | OH |
| XXXII-29-3 | p-Br—Ph | H | H | CH(CH$_3$)$_2$ | $^i$Pr | H | H | F | OH |
| XXXII-29-4 | p-Br—Ph | H | H | CH$_2$CH(CH$_3$)$_2$ | $^i$Pr | H | H | F | OH |
| XXXII-29-5 | p-Br—Ph | H | H | CH$_2$Ph | $^i$Pr | H | H | F | OH |
| XXXII-29-6 | p-Br—Ph | H | H | CH$_2$-indol-3-yl | $^i$Pr | H | H | F | OH |
| XXXII-29-7 | p-Br—Ph | H | H | CH$_2$CH$_2$SCH$_3$ | $^i$Pr | H | H | F | OH |
| XXXII-29-8 | p-Br—Ph | * | H | * | $^i$Pr | H | H | F | OH |

*R² and R³ᵇ joined together by (CH$_2$)$_3$ to form five-membered ring.

Table XXXII-30

| No | R¹ | R² | R³ᵃ | R³ᵇ | R⁴ | R⁵ | R⁶ | X | Y |
|---|---|---|---|---|---|---|---|---|---|
| XXXII-30-1 | p-I—Ph | H | H | H | $^i$Pr | H | H | F | OH |
| XXXII-30-2 | p-I—Ph | H | H | CH$_3$ | $^i$Pr | H | H | F | OH |
| XXXII-30-3 | p-I—Ph | H | H | CH(CH$_3$)$_2$ | $^i$Pr | H | H | F | OH |
| XXXII-30-4 | p-I—Ph | H | H | CH$_2$CH(CH$_3$)$_2$ | $^i$Pr | H | H | F | OH |
| XXXII-30-5 | p-I—Ph | H | H | CH$_2$Ph | $^i$Pr | H | H | F | OH |
| XXXII-30-6 | p-I—Ph | H | H | CH$_2$-indol-3-yl | $^i$Pr | H | H | F | OH |
| XXXII-30-7 | p-I—Ph | H | H | CH$_2$CH$_2$SCH$_3$ | $^i$Pr | H | H | F | OH |
| XXXII-30-8 | p-I—Ph | * | H | * | $^i$Pr | H | H | F | OH |

*R² and R³ᵇ joined together by (CH$_2$)$_3$ to form five-membered ring.

TABLE XXXII-31

| No | R¹ | R² | R³ᵃ | R³ᵇ | R⁴ | R⁵ | R⁶ | X | Y |
|---|---|---|---|---|---|---|---|---|---|
| XXXII-31-1 | CH$_3$ | H | H | H | $^n$Bu | H | H | F | OH |
| XXXII-31-2 | CH$_3$ | H | H | CH$_3$ | $^n$Bu | H | H | F | OH |
| XXXII-31-3 | CH$_3$ | H | H | CH(CH$_3$)$_2$ | $^n$Bu | H | H | F | OH |
| XXXII-31-4 | CH$_3$ | H | H | CH$_2$CH(CH$_3$)$_2$ | $^n$Bu | H | H | F | OH |
| XXXII-31-5 | CH$_3$ | H | H | CH$_2$Ph | $^n$Bu | H | H | F | OH |
| XXXII-31-6 | CH$_3$ | H | H | CH$_2$-indol-3-yl | $^n$Bu | H | H | F | OH |
| XXXII-31-7 | CH$_3$ | H | H | CH$_2$CH$_2$SCH$_3$ | $^n$Bu | H | H | F | OH |
| XXXII-31-8 | CH$_3$ | * | H | * | $^n$Bu | H | H | F | OH |

*R² and R³ᵇ joined together by (CH$_2$)$_3$ to form five-membered ring.

TABLE XXXII-32

| No | R¹ | R² | R³ᵃ | R³ᵇ | R⁴ | R⁵ | R⁶ | X | Y |
|---|---|---|---|---|---|---|---|---|---|
| XXXII-32-1 | Et | H | H | H | $^n$Bu | H | H | F | OH |
| XXXII-32-2 | Et | H | H | CH$_3$ | $^n$Bu | H | H | F | OH |
| XXXII-32-3 | Et | H | H | CH(CH$_3$)$_2$ | $^n$Bu | H | H | F | OH |
| XXXII-32-4 | Et | H | H | CH$_2$CH(CH$_3$)$_2$ | $^n$Bu | H | H | F | OH |
| XXXII-32-5 | Et | H | H | CH$_2$Ph | $^n$Bu | H | H | F | OH |
| XXXII-32-6 | Et | H | H | CH$_2$-indol-3-yl | $^n$Bu | H | H | F | OH |
| XXXII-32-7 | Et | H | H | CH$_2$CH$_2$SCH$_3$ | $^n$Bu | H | H | F | OH |
| XXXII-32-8 | Et | * | H | * | $^n$Bu | H | H | F | OH |

*R² and R³ᵇ joined together by (CH$_2$)$_3$ to form five-membered ring.

TABLE XXXII-33

| No | R¹ | R² | R³ᵃ | R³ᵇ | R⁴ | R⁵ | R⁶ | X | Y |
|---|---|---|---|---|---|---|---|---|---|
| XXXII-33-1 | $^i$Pr | H | H | H | $^n$Bu | H | H | F | OH |
| XXXII-33-2 | $^i$Pr | H | H | CH$_3$ | $^n$Bu | H | H | F | OH |
| XXXII-33-3 | $^i$Pr | H | H | CH(CH$_3$)$_2$ | $^n$Bu | H | H | F | OH |
| XXXII-33-4 | $^i$Pr | H | H | CH$_2$CH(CH$_3$)$_2$ | $^n$Bu | H | H | F | OH |
| XXXII-33-5 | $^i$Pr | H | H | CH$_2$Ph | $^n$Bu | H | H | F | OH |
| XXXII-33-6 | $^i$Pr | H | H | CH$_2$-indol-3-yl | $^n$Bu | H | H | F | OH |
| XXXII-33-7 | $^i$Pr | H | H | CH$_2$CH$_2$SCH$_3$ | $^n$Bu | H | H | F | OH |
| XXXII-33-8 | $^i$Pr | * | H | * | $^n$Bu | H | H | F | OH |

*R² and R³ᵇ joined together by (CH$_2$)$_3$ to form five-membered ring.

TABLE XXXII-34

| No | R¹ | R² | R³ᵃ | R³ᵇ | R⁴ | R⁵ | R⁶ | X | Y |
|---|---|---|---|---|---|---|---|---|---|
| XXXII-34-1 | $^t$Bu | H | H | H | $^n$Bu | H | H | F | OH |
| XXXII-34-2 | $^t$Bu | H | H | CH$_3$ | $^n$Bu | H | H | F | OH |
| XXXII-34-3 | $^t$Bu | H | H | CH(CH$_3$)$_2$ | $^n$Bu | H | H | F | OH |
| XXXII-34-4 | $^t$Bu | H | H | CH$_2$CH(CH$_3$)$_2$ | $^n$Bu | H | H | F | OH |
| XXXII-34-5 | $^t$Bu | H | H | CH$_2$Ph | $^n$Bu | H | H | F | OH |
| XXXII-34-6 | $^t$Bu | H | H | CH$_2$-indol-3-yl | $^n$Bu | H | H | F | OH |
| XXXII-34-7 | $^t$Bu | H | H | CH$_2$CH$_2$SCH$_3$ | $^n$Bu | H | H | F | OH |
| XXXII-34-8 | $^t$Bu | * | H | * | $^n$Bu | H | H | F | OH |

*R² and R³ᵇ joined together by (CH$_2$)$_3$ to form five-membered ring.

TABLE XXXII-35

| No | R¹ | R² | R³ᵃ | R³ᵇ | R⁴ | R⁵ | R⁶ | X | Y |
|---|---|---|---|---|---|---|---|---|---|
| XXXII-35-1 | Ph | H | H | H | $^n$Bu | H | H | F | OH |
| XXXII-35-2 | Ph | H | H | CH$_3$ | $^n$Bu | H | H | F | OH |
| XXXII-35-3 | Ph | H | H | CH(CH$_3$)$_2$ | $^n$Bu | H | H | F | OH |
| XXXII-35-4 | Ph | H | H | CH$_2$CH(CH$_3$)$_2$ | $^n$Bu | H | H | F | OH |
| XXXII-35-5 | Ph | H | H | CH$_2$Ph | $^n$Bu | H | H | F | OH |
| XXXII-35-6 | Ph | H | H | CH$_2$-indol-3-yl | $^n$Bu | H | H | F | OH |
| XXXII-48-7 | Ph | H | H | CH$_2$CH$_2$SCH$_3$ | $^n$Bu | H | H | F | OH |
| XXXII-35-8 | Ph | * | H | * | $^n$Bu | H | H | F | OH |

*R² and R³ᵇ joined together by (CH$_2$)$_3$ to form five-membered ring.

TABLE XXXII-36

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXII-36-1 | p-Me—Ph | H | H | H | $^n$Bu | H | H | F | OH |
| XXXII-36-2 | p-Me—Ph | H | H | CH$_3$ | $^n$Bu | H | H | F | OH |
| XXXII-36-3 | p-Me—Ph | H | H | CH(CH$_3$)$_2$ | $^n$Bu | H | H | F | OH |
| XXXII-36-4 | p-Me—Ph | H | H | CH$_2$CH(CH$_3$)$_2$ | $^n$Bu | H | H | F | OH |
| XXXII-36-5 | p-Me—Ph | H | H | CH$_2$Ph | $^n$Bu | H | H | F | OH |
| XXXII-36-6 | p-Me—Ph | H | H | CH$_2$-indol-3-yl | $^n$Bu | H | H | F | OH |
| XXXII-36-7 | p-Me—Ph | H | H | CH$_2$CH$_2$SCH$_3$ | $^n$Bu | H | H | F | OH |
| XXXII-36-8 | p-Me—Ph | * | H | * | $^n$Bu | H | H | F | OH |

*R$^2$ and R$^{3b}$ joined together by (CH$_2$)$_3$ to form five-membered ring.

TABLE XXXII-37

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXII-37-1 | p-F—Ph | H | H | H | $^n$Bu | H | H | F | OH |
| XXXII-37-2 | p-F—Ph | H | H | CH$_3$ | $^n$Bu | H | H | F | OH |
| XXXII-37-3 | p-F—Ph | H | H | CH(CH$_3$)$_2$ | $^n$Bu | H | H | F | OH |
| XXXII-37-4 | p-F—Ph | H | H | CH$_2$CH(CH$_3$)$_2$ | $^n$Bu | H | H | F | OH |
| XXXII-37-5 | p-F—Ph | H | H | CH$_2$Ph | $^n$Bu | H | H | F | OH |
| XXXII-37-6 | p-F—Ph | H | H | CH$_2$-indol-3-yl | $^n$Bu | H | H | F | OH |
| XXXII-37-7 | p-F—Ph | H | H | CH$_2$CH$_2$SCH$_3$ | $^n$Bu | H | H | F | OH |
| XXXII-37-8 | p-F—Ph | * | H | * | $^n$Bu | H | H | F | OH |

*R$^2$ and R$^{3b}$ joined together by (CH$_2$)$_3$ to form five-membered ring.

TABLE XXXII-38

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXII-38-1 | p-Cl—Ph | H | H | H | $^n$Bu | H | H | F | OH |
| XXXII-38-2 | p-Cl—Ph | H | H | CH$_3$ | $^n$Bu | H | H | F | OH |
| XXXII-38-3 | p-Cl—Ph | H | H | CH(CH$_3$)$_2$ | $^n$Bu | H | H | F | OH |
| XXXII-38-4 | p-Cl—Ph | H | H | CH$_2$CH(CH$_3$)$_2$ | $^n$Bu | H | H | F | OH |
| XXXII-38-5 | p-Cl—Ph | H | H | CH$_2$Ph | $^n$Bu | H | H | F | OH |
| XXXII-38-6 | p-Cl—Ph | H | H | CH$_2$-indol-3-yl | $^n$Bu | H | H | F | OH |
| XXXII-38-7 | p-Cl—Ph | H | H | CH$_2$CH$_2$SCH$_3$ | $^n$Bu | H | H | F | OH |
| XXXII-38-8 | p-Cl—Ph | * | H | * | $^n$Bu | H | H | F | OH |

*R$^2$ and R$^{3b}$ joined together by (CH$_2$)$_3$ to form five-membered ring.

TABLE XXXII-39

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXII-39-1 | p-Br—Ph | H | H | H | $^n$Bu | H | H | F | OH |
| XXXII-39-2 | p-Br—Ph | H | H | CH$_3$ | $^n$Bu | H | H | F | OH |
| XXXII-39-3 | p-Br—Ph | H | H | CH(CH$_3$)$_2$ | $^n$Bu | H | H | F | OH |
| XXXII-39-4 | p-Br—Ph | H | H | CH$_2$CH(CH$_3$)$_2$ | $^n$Bu | H | H | F | OH |
| XXXII-39-5 | p-Br—Ph | H | H | CH$_2$Ph | $^n$Bu | H | H | F | OH |
| XXXII-39-6 | p-Br—Ph | H | H | CH$_2$-indol-3-yl | $^n$Bu | H | H | F | OH |
| XXXII-39-7 | p-Br—Ph | H | H | CH$_2$CH$_2$SCH$_3$ | $^n$Bu | H | H | F | OH |
| XXXII-39-8 | p-Br—Ph | * | H | * | $^n$Bu | H | H | F | OH |

*R$^2$ and R$^{3b}$ joined together by (CH$_2$)$_3$ to form five-membered ring.

TABLE XXXII-40

| No | R$^1$ | R$^2$ | R$^{3a}$ | R$^{3b}$ | R$^4$ | R$^5$ | R$^6$ | X | Y |
|---|---|---|---|---|---|---|---|---|---|
| XXXII-40-1 | p-I—Ph | H | H | H | $^n$Bu | H | H | F | OH |
| XXXII-40-2 | p-I—Ph | H | H | CH$_3$ | $^n$Bu | H | H | F | OH |
| XXXII-40-3 | p-I—Ph | H | H | CH(CH$_3$)$_2$ | $^n$Bu | H | H | F | OH |
| XXXII-40-4 | p-I—Ph | H | H | CH$_2$CH(CH$_3$)$_2$ | $^n$Bu | H | H | F | OH |
| XXXII-40-5 | p-I—Ph | H | H | CH$_2$Ph | $^n$Bu | H | H | F | OH |
| XXXII-40-6 | p-I—Ph | H | H | CH$_2$-indol-3-yl | $^n$Bu | H | H | F | OH |
| XXXII-40-7 | p-I—Ph | H | H | CH$_2$CH$_2$SCH$_3$ | $^n$Bu | H | H | F | OH |
| XXXII-40-8 | p-I—Ph | * | H | * | $^n$Bu | H | H | F | OH |

*R$^2$ and R$^{3b}$ joined together by (CH$_2$)$_3$ to form five-membered ring.

TABLE XXXII-41

| No | R¹ | R² | R³ᵃ | R³ᵇ | R⁴ | R⁵ | R⁶ | X | Y |
|---|---|---|---|---|---|---|---|---|---|
| XXXII-41-1 | $CH_3$ | H | H | H | Bz | H | H | F | OH |
| XXXII-41-2 | $CH_3$ | H | H | $CH_3$ | Bz | H | H | F | OH |
| XXXII-41-3 | $CH_3$ | H | H | $CH(CH_3)_2$ | Bz | H | H | F | OH |
| XXXII-41-4 | $CH_3$ | H | H | $CH_2CH(CH_3)_2$ | Bz | H | H | F | OH |
| XXXII-41-5 | $CH_3$ | H | H | $CH_2Ph$ | Bz | H | H | F | OH |
| XXXII-41-6 | $CH_3$ | H | H | $CH_2$-indol-3-yl | Bz | H | H | F | OH |
| XXXII-41-7 | $CH_3$ | H | H | $CH_2CH_2SCH_3$ | Bz | H | H | F | OH |
| XXXII-41-8 | $CH_3$ | * | H | * | Bz | H | H | F | OH |

*R² and R³ᵇ joined together by $(CH_2)_3$ to form five-membered ring.

TABLE XXXII-42

| No | R¹ | R² | R³ᵃ | R³ᵇ | R⁴ | R⁵ | R⁶ | X | Y |
|---|---|---|---|---|---|---|---|---|---|
| XXXII-42-1 | Et | H | H | H | Bz | H | H | F | OH |
| XXXII-42-2 | Et | H | H | $CH_3$ | Bz | H | H | F | OH |
| XXXII-42-3 | Et | H | H | $CH(CH_3)_2$ | Bz | H | H | F | OH |
| XXXII-42-4 | Et | H | H | $CH_2CH(CH_3)_2$ | Bz | H | H | F | OH |
| XXXII-42-5 | Et | H | H | $CH_2Ph$ | Bz | H | H | F | OH |
| XXXII-42-6 | Et | H | H | $CH_2$-indol-3-yl | Bz | H | H | F | OH |
| XXXII-42-7 | Et | H | H | $CH_2CH_2SCH_3$ | Bz | H | H | F | OH |
| XXXII-42-8 | Et | * | H | * | Bz | H | H | F | OH |

*R² and R³ᵇ joined together by $(CH_2)_3$ to form five-membered ring.

TABLE XXXII-43

| No | R¹ | R² | R³ᵃ | R³ᵇ | R⁴ | R⁵ | R⁶ | X | Y |
|---|---|---|---|---|---|---|---|---|---|
| XXXII-43-1 | ⁱPr | H | H | H | Bz | H | H | F | OH |
| XXXII-43-2 | ⁱPr | H | H | $CH_3$ | Bz | H | H | F | OH |
| XXXII-43-3 | ⁱPr | H | H | $CH(CH_3)_2$ | Bz | H | H | F | OH |
| XXXII-43-4 | ⁱPr | H | H | $CH_2CH(CH_3)_2$ | Bz | H | H | F | OH |
| XXXII-43-5 | ⁱPr | H | H | $CH_2Ph$ | Bz | H | H | F | OH |
| XXXII-43-6 | ⁱPr | H | H | $CH_2$-indol-3-yl | Bz | H | H | F | OH |
| XXXII-43-7 | ⁱPr | H | H | $CH_2CH_2SCH_3$ | Bz | H | H | F | OH |
| XXXII-43-8 | ⁱPr | * | H | * | Bz | H | H | F | OH |

*R² and R³ᵇ joined together by $(CH_2)_3$ to form five-membered ring.

TABLE XXXII-44

| No | R¹ | R² | R³ᵃ | R³ᵇ | R⁴ | R⁵ | R⁶ | X | Y |
|---|---|---|---|---|---|---|---|---|---|
| XXXII-44-1 | ᵗBu | H | H | H | Bz | H | H | F | OH |
| XXXII-44-2 | ᵗBu | H | H | $CH_3$ | Bz | H | H | F | OH |
| XXXII-44-3 | ᵗBu | H | H | $CH(CH_3)_2$ | Bz | H | H | F | OH |
| XXXII-44-4 | ᵗBu | H | H | $CH_2CH(CH_3)_2$ | Bz | H | H | F | OH |
| XXXII-44-5 | ᵗBu | H | H | $CH_2Ph$ | Bz | H | H | F | OH |
| XXXII-44-6 | ᵗBu | H | H | $CH_2$-indol-3-yl | Bz | H | H | F | OH |
| XXXII-44-7 | ᵗBu | H | H | $CH_2CH_2SCH_3$ | Bz | H | H | F | OH |
| XXXII-44-8 | ᵗBu | * | H | * | Bz | H | H | F | OH |

*R² and R³ᵇ joined together by $(CH_2)_3$ to form five-membered ring.

TABLE XXXII-45

| No | R¹ | R² | R³ᵃ | R³ᵇ | R⁴ | R⁵ | R⁶ | X | Y |
|---|---|---|---|---|---|---|---|---|---|
| XXXII-45-1 | Ph | H | H | H | Bz | H | H | F | OH |
| XXXII-45-2 | Ph | H | H | $CH_3$ | Bz | H | H | F | OH |
| XXXII-45-3 | Ph | H | H | $CH(CH_3)_2$ | Bz | H | H | F | OH |
| XXXII-45-4 | Ph | H | H | $CH_2CH(CH_3)_2$ | Bz | H | H | F | OH |
| XXXII-45-5 | Ph | H | H | $CH_2Ph$ | Bz | H | H | F | OH |
| XXXII-45-6 | Ph | H | H | $CH_2$-indol-3-yl | Bz | H | H | F | OH |
| XXXII-45-7 | Ph | H | H | $CH_2CH_2SCH_3$ | Bz | H | H | F | OH |
| XXXII-45-8 | Ph | * | H | * | Bz | H | H | F | OH |

*R² and R³ᵇ joined together by $(CH_2)_3$ to form five-membered ring.

TABLE XXXII-46

| No | R¹ | R² | R³ᵃ | R³ᵇ | R⁴ | R⁵ | R⁶ | X | Y |
|---|---|---|---|---|---|---|---|---|---|
| XXXII-46-1 | p-Me—Ph | H | H | H | Bz | H | H | F | OH |
| XXXII-46-2 | p-Me—Ph | H | H | $CH_3$ | Bz | H | H | F | OH |
| XXXII-46-3 | p-Me—Ph | H | H | $CH(CH_3)_2$ | Bz | H | H | F | OH |
| XXXII-46-4 | p-Me—Ph | H | H | $CH_2CH(CH_3)_2$ | Bz | H | H | F | OH |
| XXXII-46-5 | p-Me—Ph | H | H | $CH_2Ph$ | Bz | H | H | F | OH |
| XXXII-46-6 | p-Me—Ph | H | H | $CH_2$-indol-3-yl | Bz | H | H | F | OH |
| XXXII-46-7 | p-Me—Ph | H | H | $CH_2CH_2SCH_3$ | Bz | H | H | F | OH |
| XXXII-46-8 | p-Me—Ph | * | H | * | Bz | H | H | F | OH |

*R² and R³ᵇ joined together by $(CH_2)_3$ to form five-membered ring.

TABLE XXXII-47

| No | R¹ | R² | R³ᵃ | R³ᵇ | R⁴ | R⁵ | R⁶ | X | Y |
|---|---|---|---|---|---|---|---|---|---|
| XXXII-47-1 | p-F—Ph | H | H | H | Bz | H | H | F | OH |
| XXXII-47-2 | p-F—Ph | H | H | $CH_3$ | Bz | H | H | F | OH |
| XXXII-47-3 | p-F—Ph | H | H | $CH(CH_3)_2$ | Bz | H | H | F | OH |
| XXXII-47-4 | p-F—Ph | H | H | $CH_2CH(CH_3)_2$ | Bz | H | H | F | OH |
| XXXII-47-5 | p-F—Ph | H | H | $CH_2Ph$ | Bz | H | H | F | OH |
| XXXII-47-6 | p-F—Ph | H | H | $CH_2$-indol-3-yl | Bz | H | H | F | OH |
| XXXII-47-7 | p-F—Ph | H | H | $CH_2CH_2SCH_3$ | Bz | H | H | F | OH |
| XXXII-47-8 | p-F—Ph | * | H | * | Bz | H | H | F | OH |

*R² and R³ᵇ joined together by $(CH_2)_3$ to form five-membered ring.

TABLE XXXII-48

| No | R¹ | R² | R³ᵃ | R³ᵇ | R⁴ | R⁵ | R⁶ | X | Y |
|---|---|---|---|---|---|---|---|---|---|
| XXXII-48-1 | p-Cl—Ph | H | H | H | Bz | H | H | F | OH |
| XXXII-48-2 | p-Cl—Ph | H | H | $CH_3$ | Bz | H | H | F | OH |

TABLE XXXII-48-continued

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXII-48-3 | p-Cl—Ph | H | H | CH(CH$_3$)$_2$ | Bz | H | H | F | OH |
| XXXII-48-4 | p-Cl—Ph | H | H | CH$_2$CH(CH$_3$)$_2$ | Bz | H | H | F | OH |
| XXXII-48-5 | p-Cl—Ph | H | H | CH$_2$Ph | Bz | H | H | F | OH |
| XXXII-48-6 | p-Cl—Ph | H | H | CH$_2$-indol-3-yl | Bz | H | H | F | OH |
| XXXII-48-7 | p-Cl—Ph | H | H | CH$_2$CH$_2$SCH$_3$ | Bz | H | H | F | OH |
| XXXII-48-8 | p-Cl—Ph | * | H | * | Bz | H | H | F | OH |

*$R^2$ and $R^{3b}$ joined together by (CH$_2$)$_3$ to form five-membered ring.

TABLE XXXII-49

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXII-49-1 | p-Br—Ph | H | H | H | Bz | H | H | F | OH |
| XXXII-49-2 | p-Br—Ph | H | H | CH$_3$ | Bz | H | H | F | OH |
| XXXII-49-3 | p-Br—Ph | H | H | CH(CH$_3$)$_2$ | Bz | H | H | F | OH |
| XXXII-49-4 | p-Br—Ph | H | H | CH$_2$CH(CH$_3$)$_2$ | Bz | H | H | F | OH |
| XXXII-49-5 | p-Br—Ph | H | H | CH$_2$Ph | Bz | H | H | F | OH |
| XXXII-49-6 | p-Br—Ph | H | H | CH$_2$-indol-3-yl | Bz | H | H | F | OH |
| XXXII-49-7 | p-Br—Ph | H | H | CH$_2$CH$_2$SCH$_3$ | Bz | H | H | F | OH |
| XXXII-49-8 | p-Br—Ph | * | H | * | Bz | H | H | F | OH |

*$R^2$ and $R^{3b}$ joined together by (CH$_2$)$_3$ to form five-membered ring.

TABLE XXXII-50

| No | $R^1$ | $R^2$ | $R^{3a}$ | $R^{3b}$ | $R^4$ | $R^5$ | $R^6$ | X | Y |
|---|---|---|---|---|---|---|---|---|---|
| XXXII-50-1 | p-I—Ph | H | H | H | Bz | H | H | F | OH |
| XXXII-50-2 | p-I—Ph | H | H | CH$_3$ | Bz | H | H | F | OH |
| XXXII-50-3 | p-I—Ph | H | H | CH(CH$_3$)$_2$ | Bz | H | H | F | OH |
| XXXII-50-4 | p-I—Ph | H | H | CH$_2$CH(CH$_3$)$_2$ | Bz | H | H | F | OH |
| XXXII-50-5 | p-I—Ph | H | H | CH$_2$Ph | Bz | H | H | F | OH |
| XXXII-50-6 | p-I—Ph | H | H | CH$_2$-indol-3-yl | Bz | H | H | F | OH |
| XXXII-50-7 | p-I—Ph | H | H | CH$_2$CH$_2$SCH$_3$ | Bz | H | H | F | OH |
| XXXII-50-8 | p-I—Ph | * | H | * | Bz | H | H | F | OH |

*$R^2$ and $R^{3b}$ joined together by (CH$_2$)$_3$ to form five-membered ring.

DOSAGE, ADMINISTRATION, AND USE

A sixth embodiment of the present invention is directed to a composition for the treatment of any of the viral agents disclosed herein said composition comprising a pharmaceutically acceptable medium selected from among an excipient, carrier, diluent, and equivalent medium and a compound, that is intended to include its salts (acid or basic addition salts), hydrates, solvates, and crystalline forms can be obtained, represented by formula I.

It is contemplated that the formulation of the sixth embodiment can contain any of the compounds contemplated in any of the aspects of the first, second, third, fourth, and fifth embodiments or those specifically recited in the tables above or exemplified herein, either alone or in combination with another compound of the present invention.

The compounds of the present invention may be formulated in a wide variety of oral administration dosage forms and carriers. Oral administration can be in the form of tablets, coated tablets, hard and soft gelatin capsules, solutions, emulsions, syrups, or suspensions. Compounds of the present invention are efficacious when administered by suppository administration, among other routes of administration. The most convenient manner of administration is generally oral using a convenient daily dosing regimen which can be adjusted according to the severity of the disease and the patient's response to the antiviral medication.

A compound or compounds of the present invention, as well as their pharmaceutically acceptable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound as used herein means a salt that is pharmaceutically acceptable and that possesses the desired pharmacological activity of the parent compound.

Such salts include: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, and $NH_gR''_{4-g}{}^+$, in which R'' is a $C_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

Solid form preparations include powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs and aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

Suitable formulations along with pharmaceutical carriers, diluents and excipients are described in Remington: The Science and Awake of Pharmacy 1995, edited by E. W. Martin, Mack Publishing Company, 19th edition, Easton, Pa., which is hereby incorporated by reference. The compounds of the present invention can also be encapsulated in liposomes, such as those disclosed in U.S. Pat. Nos. 6,180,134, 5,192,549, 5,376,380, 6,060,080, 6,132,763, each of which is incorporated by reference. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (e.g., salt formulation), which are well within the ordinary skill in the art. It is also well within the ordinary skill of the art to modify the route of administration and dosage regimen of a particular compound in order to manage the pharmacokinetics of the present compounds for maximum beneficial effect in patients.

A seventh embodiment of the present invention is directed to a use of the compound represented by formula I in the manufacture of a medicament for the treatment of any condition the result of an infection by any one of the following viral agents: hepatitis C virus, West Nile virus, yellow fever virus, dengue virus, rhinovirus, polio virus, hepatitis A virus, bovine viral diarrhea virus and Japanese encephalitis virus.

The term "medicament" means a substance used in a method of treatment and/or prophylaxis of a subject in need thereof, wherein the substance includes, but is not limited to, a composition, a formulation, a dosage form, and the like, comprising the compound of formula I. It is contemplated that the compound of the use of the compound represented by formula I in the manufacture of a medicament for the treatment of any of the antiviral conditions disclosed herein of the seventh embodiment can be any of the compounds contemplated in any of the aspects of the first, second, third, fourth, fifth embodiments or those specifically recited in the tables above or exemplified herein, either alone or in combination with another compound of the present invention. A medicament includes, but is not limited to, any one of the compositions contemplated by the sixth embodiment of the present invention.

A eighth embodiment of the present invention is directed to a method of treatment and/or prophylaxis in a subject in need thereof said method comprises administering a therapeutically effective amount of the compound represented by formula I to the subject.

A first aspect of the eighth embodiment is directed to a method of treatment and/or prophylaxis in a subject in need thereof said method comprises administering a therapeutically effective of at least two or more different compounds falling within the scope of the compound represented by formula I to the subject.

A second aspect of the eighth embodiment is directed to a method of treatment and/or prophylaxis in a subject in need thereof said method comprises alternatively or concurrently administering a therapeutically effective of at least two compounds falling within the scope of the compound represented by formula I to the subject.

It is intended that a subject in need thereof is one that has any condition the result of an infection by any of the viral agents disclosed herein, which includes, but is not limited to, hepatitis C virus, West Nile virus, yellow fever virus, dengue virus, rhinovirus, polio virus, hepatitis A virus, bovine viral diarrhea virus or Japanese encephalitis virus, flaviviridae viruses or pestiviruses or hepaciviruses or a viral agent causing symptoms equivalent or comparable to any of the above-listed viruses.

The term "subject" means a mammal, which includes, but is not limited to, cattle, pigs, sheep, chicken, turkey, buffalo, llama, ostrich, dogs, cats, and humans, preferably the subject is a human. It is contemplated that in the method of treating a subject thereof of the sixth embodiment can be any of the compounds contemplated in any of the aspects of the first, second, and third embodiments or those specifically recited in the tables above, either alone or in combination with another compound of the present invention.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.1 and about 10 g, including all values in between, such as 0.25, 0.5, 0.75, 1, 1, 5, 2, 2, 5, 3, 3, 5, 4, 4, 5, 5, 5, 5, 6, 6, 5, 7, 7, 5, 8, 8, 5, 9, and 9.5, per day should be appropriate in monotherapy and/or in combination therapy. A preferred daily dosage is between about 0.5 and about 7.5 g per day, more preferred 1.5 and about 6.0 g per day. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on personal knowledge, experience and the disclosures of this application, to ascertain a therapeutically effective amount of the compounds of the present invention for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyl-transpeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

A third aspect of the eighth embodiment, is directed to a method of treatment and/or prophylaxis in a subject in need thereof said method comprises administering to the subject a therapeutically effective of a compound represented by formula I and a therapeutically effective amount of another antiviral agent; wherein the administration is concurrent or alternative. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours. Examples of "another antiviral agents" include, but are not limited to: HCV NS3 protease inhibitors (see WO 2008010921, WO 2008010921, EP 1881001, WO 2007015824, WO 2007014925, WO 2007014926, WO 2007014921, WO 2007014920, WO 2007014922, US 2005267018, WO 2005095403, WO 2005037214, WO 2004094452, US 2003187018, WO 200364456, WO 2005028502, and WO 2003006490); HCV NS5B Inhibitors (see US 2007275947, US20072759300, WO2007095269, WO 2007092000, WO 2007076034, WO 200702602, US 2005-98125, WO 2006093801, US 2006166964, WO 2006065590, WO 2006065335, US 2006040927, US 2006040890, WO 2006020082, WO 2006012078, WO 2005123087, US 2005154056, US 2004229840, WO 2004065367, WO 2004003138, WO 2004002977, WO 2004002944, WO 2004002940, WO 2004000858, WO 2003105770, WO 2003010141, WO 2002057425, WO 2002057287, WO 2005021568, WO 2004041201, US 20060293306, US 20060194749, US 20060241064, U.S. Pat. No. 6,784,166, WO 2007088148, WO 2007039142, WO 2005103045, WO 2007039145, WO 2004096210, and WO 2003037895); HCV NS4 Inhibitors (see WO 2007070556 and WO 2005067900); HCV NS5a Inhibitors (see US 2006276511, WO 2006120252, WO 2006120251, WO 2006100310, WO 2006035061); Toll-like receptor agonists (see WO 2007093901); and other inhibitors (see WO 2004035571, WO 2004014852, WO 2004014313, WO 2004009020 WO 2003101993, WO 2000006529).

A fourth aspect of the eighth embodiment, is directed to a method of treatment in a subject in need thereof said method comprises alternatively or concurrently administering a therapeutically effective of a compound represented by for mula I and another antiviral agent to the subject. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours.

A fifth aspect of the eighth embodiment, is directed to a method of treatment and/or prophylaxis in a subject in need thereof said method comprises administering to the subject a therapeutically effective of at least one compound represented by formula and a therapeutically effective amount of another antiviral agent; wherein the administration is concurrent or alternative. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours.

A sixth aspect of the eighth embodiment, is directed to a method of treatment in a subject in need thereof said method comprises alternatively or concurrently administering a therapeutically effective of at least one compound represented by formula I and another antiviral agent to the subject. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours.

It is contemplated that the another antiviral agent includes, but is not limited to interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

PROCESS FOR PREPARATION

An ninth embodiment of the present invention is directed to a process for preparing the compound of formula I, which comprises reacting a suitably substituted phosphochloridate compound 4 with a nucleoside analog 5

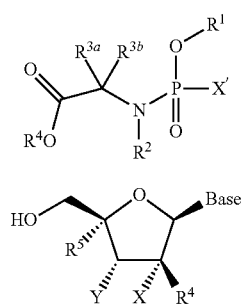

wherein the substituents $R^1, R^2, R^{3a}, R^{3b}, R^4, R^5, X, Y, R^6$, and base have their meanings as disclosed in the Detailed Description of the invention and X' is a leaving group, such as Cl, Br, I, tosylate, mesylate, trifluoroacetate, trifluorosulfonate, pentafluorophenoxide, p-NO$_2$-phenoxide, or other commonly used leaving groups as disclosed in *Advanced Organic Chemistry* by March, Fourth Edition. Leaving groups and methods that can be used to effect the formation of a phosphoramidate nucleoside conjugate are found in US 20060142238 and WO 2007095269. Preferably, the leaving group is Cl.

This reaction is performed in an anhydrous aprotic solvent such tetrahydrofuran, dioxane, or both tetrahydrofuran and dioxane, or any functional equivalent thereof, with tetrahydrofuran being the preferred solvent. The reaction is typically initiated at a temperature range from −78° C. to 40° C. with the preferred reaction temperature being between 0° C. and room temperature. The nucleoside is first stirred with a base (5 to 12 equivalents) such as N-methylimidazole, collidine, pyridine, 2,6-lutidine, 2,6-$^t$Bu-pyridine, etc. a tertiary amine base, such as triethylamine, diisopropylethylamine, etc., or an alkyl Grignard reagent, such as tBuMgCl, tBuMgBr, MeMgCl, MeMgBr, etc. The phosphorochloridate (3-10 equivalents) is dissolved in the reaction solvent and added to the mixture of the nucleoside and base. The reaction is then allowed to stir over a period of time at a temperature between room temperature and 40° C. for a period of 30 min to 24 hr. with the preferred reaction temperature being room temperature and time being 24 hr. The solvent is removed from the reaction mixture and the product is purified by chromatography on silica gel.

A tenth embodiment of the present invention is directed to a product obtained by a process which comprises reacting a suitably substituted phosphochloridate compound 4 with a nucleoside analog 5

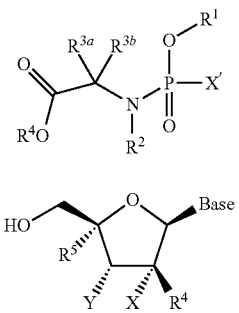

wherein the substituents $R^1, R^2, R^{3a}, R^{3b}, R^4, R^5, X, Y, R^6$, X', and base have their meanings as disclosed in the Detailed Description of the Invention.

This reaction can be performed in an anhydrous aprotic solvent or other suitable solvent, such as tetrahydrofuran, dioxane, or a mixture of tetrahydrofuran and dioxane, with tetrahydrofuran being the preferred solvent. The reaction is typically initiated at a temperature range from −78° C. to 40° C. with the preferred reaction temperature being between 0° C. and room temperature. The nucleoside is first stirred with a base (5 to 12 equivalents) such as N-methylimidazole, a tertiary amine base or tButyl Magnesium Chloride. A phosphorochloridate (3-10 equivalents (or suitable "phosphoro-(leaving group)-date")) is dissolved in the reaction solvent and added to the mixture of the nucleoside and base. The reaction is then allowed to stir over a period of time at a temperature between room temperature and 40° C. for a period of 30 min to 24 hr. with the preferred reaction temperature being room temperature and time being 24 hr. The solvent is removed from the reaction mixture and the product is purified by chromatography on silica gel.

Compounds and Preparation

Phosphoramidate compounds of the present invention can be prepared by condensation of a nucleoside analog 5 with a suitably substituted phosphochloridate compound 4 (Scheme 1). The nucleoside analog is made by conventional procedures disclosed in any one of U.S. Published Application Nos. 2005/0009737, 2006/0199783, 2006/0122146, and 2007/0197463, each of which is incorporated by reference in its entirety.

Disclosed 1H-NMR values were recorded on a Varian AS-400 instrument. Mass spectral data were obtain using either a Micromass-Quattromicro API or a Waters Acquity.

Thus, by way of example only, a suitably substituted phenol can be reacted with phosphorus oxychloride (1) to afford an aryloxy phosphorodichloridate 2 (see Example 1) which is subsequently treated with a acid addition salt of an α-amino acid ester in the presence of TEA to afford an aryloxy phosphorochloridate 4. This arylalkoxy-amino acid phosphoramidate is reacted with the nucleoside analog to provide the product 1 (for procedure see, e.g., C. McGuigan et al. Antiviral Res. 1992 17:311-321; D. Curley et al. Antiviral Res. 1990 14:345-356; McGuigan et al. Antiviral Chem. Chemother 1990 1(2):107-113).

Scheme 1

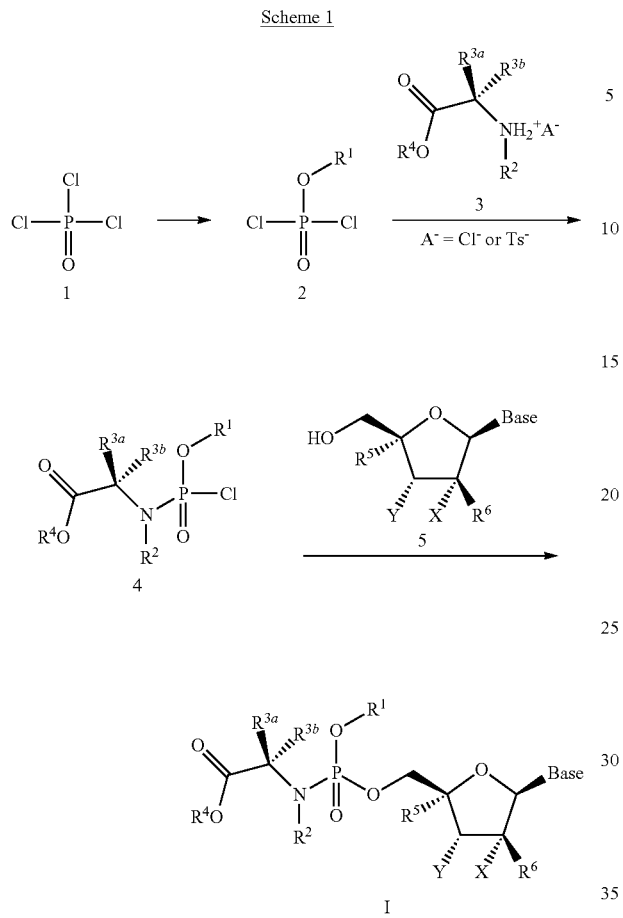

The preparation of nucleoside phosphoramidates requires reacting an appropriately substituted phosphochloridate with a nucleoside containing a free 5'-hydroxyl moiety. In cases where only one hydroxyl group is present, preparation of the phosphoramidate usually proceeds smoothly when the phosphochloridate is reacted with the desired nucleoside. In cases where the nucleoside contains more than one free hydroxyl group, preparation of the appropriately protected nucleoside might be required. Silyl, acetonide or other alcohol protecting groups known in the art might be warranted for protection of the sugar moiety. For protection of the nucleoside base, protecting a free amino group may require amidine protection strategy.

Condensation of the phosphochloridate can be carried out on the unprotected nucleoside. Since the 5'-OH group of a nucleoside is much less hindered than the 3'-OH group, selective phosphoramidation is possible under carefully controlled conditions. After condensation to form a protected phosphoramidate nucleoside, deprotection to obtain the free phosphoramidate nucleoside can be carried out using standard protocols for nucleic acid chemistry. In many cases, the desired product is readily separated from the starting material using column chromatography on silica gel. The synthetic scheme is summarized in Scheme 1.

A further understanding of the disclosed embodiments will be appreciated by consideration of the following examples, which are only meant to be illustrative, and not limit the disclosed invention.

EXAMPLE 1

General Procedure for Preparation of Phosphorodichloridates

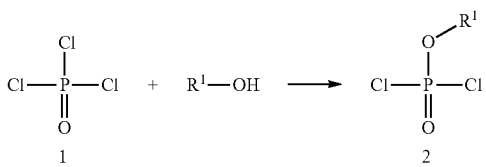

A solution of the appropriate phenol $R^1$—OH (1 eq) and triethylamine (1 eq.) in anhydrous ether was added dropwise to a stirred solution of phosphoryl trichloride 1 (1 eq) at 0° C. over a period of 3 hours under nitrogen. Then the temperature was warmed to room temperature, and the reaction was stirred overnight. The triethylamine salt was quickly removed with suction filtration and the filtrate concentrated in vacuo to dryness to afford 2 as an oil which was used without further purification.

EXAMPLE 2

General Procedure for Preparation of Phosphorochloridates

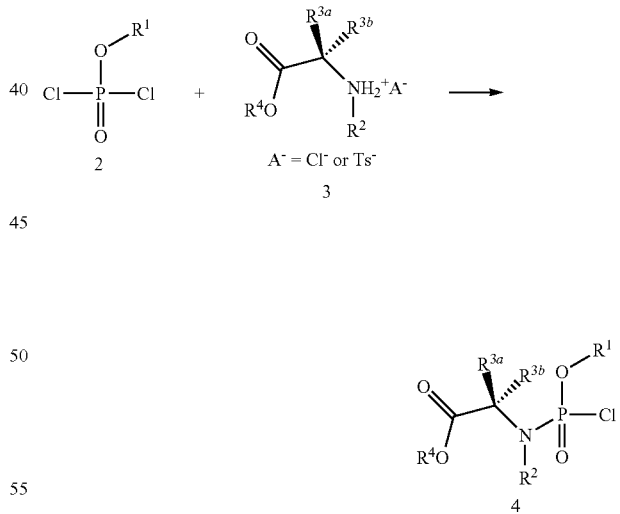

A solution of triethylamine (2 eq) in anhydrous dichloromethane was added dropwise to a solution of aryloxyphosphodichloridate 2 (1 eq) and the appropriate amino ester 3 (1 eq) in anhydrous dichloromethane with vigorous stirring at −78° C. over a period of 30 to 120 minutes. Then the reaction temperature was allowed to warm to room temperature and stirred over night. Solvent was removed. The residue was washed with ethyl ether and filtered, the filtrate was dried over reduced pressure to give 4.

EXAMPLE 3

General Procedures for Nucleoside Phosphoramidate Derivatives

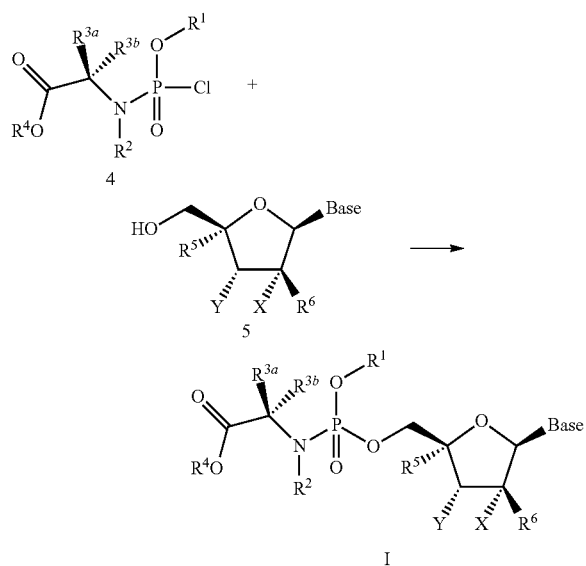

A solution of the appropriate phosphorochloridate 4 (6.5 equivalents) in anhydrous tetrahydrofuran (THF) was added to a mixture of nucleoside 5 (1 equivalent) and N-methylimidazole (8 equivalents) in anhydrous THF with vigorous stirring at room temperature and the reaction mixture was stirred overnight. The solvent was removed in vacuo and the crude was purified by column chromatography and/or preparative thin layer chromatography to give 1.

EXAMPLE 4

Preparation of 2'-deoxy-2'-fluoro-2'-C-methyluridine

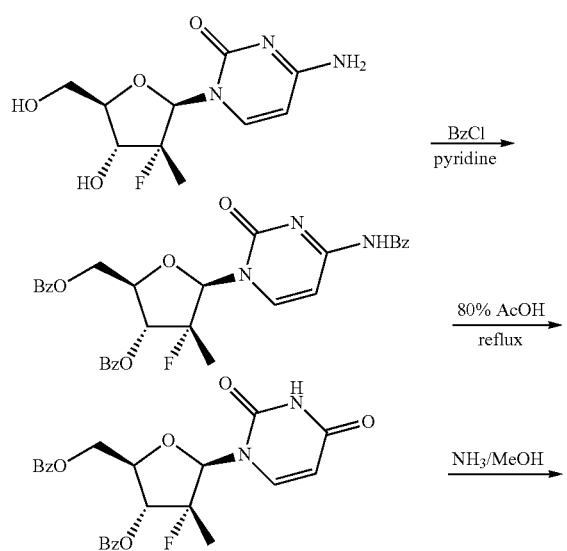

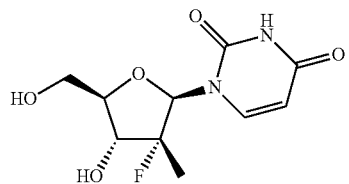

2'-Deoxy-2'-fluoro-2'-C-methylcytidine (1.0 g, 1 eq) (Clark, J., et al., J. Med. Chem., 2005, 48, 5504-5508) was dissolved in 10 ml of anhydrous pyridine and concentrated to dryness in vacuo. The resulting syrup was dissolved in 20 ml of anhydrous pyridine under nitrogen and cooled to 0° C. with stirring. The brown solution was treated with benzoyl chloride (1.63 g, 3 eq) dropwise over 10 min. The ice bath was removed and stirring continued for 1.5 h whereby thin-layer chromatography (TLC) showed no remaining starting material. The mixture was quenched by addition of water (0.5 ml) and concentrated to dryness. The residue was dissolved in 50 mL of dichloromethane (DCM) and washed with saturated NaHCO$_3$ aqueous solution and H$_2$O. The organic phase was dried over NaSO$_4$ and filtered, concentrated to dryness to give N$^4$,3',5'-tribenzoyl-2'-Deoxy-2'-fluoro-2'-C-methylcytidine (2.0 g, Yield: 91%).

N$^4$,3',5'-tribenzoyl-2'-Deoxy-2'-fluoro-2'-C-methylcytidine (2.0 g, 1 eq) was refluxed in 80% aqueous AcOH overnight. After cooling and standing at room temperature (15° C.), most of the product precipitated and then was filtered through a sintered funnel. White precipitate was washed with water and co-evaporated with toluene to give a white solid. The filtrate was concentrated and co-evaporated with toluene to give additional product which was washed with water to give a white solid. Combining the two batches of white solid gave 1.50 g of 3',5'-dibenzoyl-2'-Deoxy-2'-fluoro-2'-C-methyluridine (Yield: 91%).

To a solution of 3',5'-dibenzoyl-2'-Deoxy-2'-fluoro-2'-C-methyluridine (1.5 g, 1 eq) in MeOH (10 mL) was added a solution of saturated ammonia in MeOH (20 mL). The reaction mixture was stirred at 0° C. for 30 min, and then warmed to room temperature slowly. After the reaction mixture was stirred for another 18 hours, the reaction mixture was evaporated under reduced pressure to give the residue, which was purified by column chromatography to afford pure compound 2'-deoxy-2'-fluoro-2'-C-methyluridine (500 mg, Yield: 60%).

EXAMPLE 5

Preparation of 2'-Deoxy-2'-fluoro-2'-C-methyluridine 5'-(phenyl methoxy-alanyl phosphate)

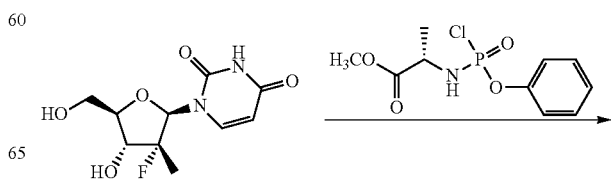

-continued

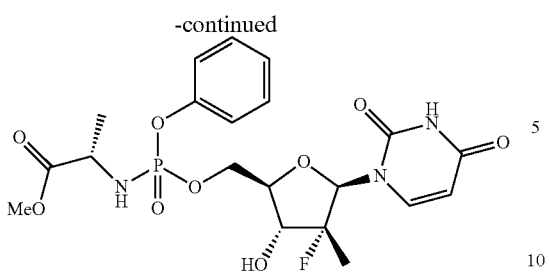

-continued

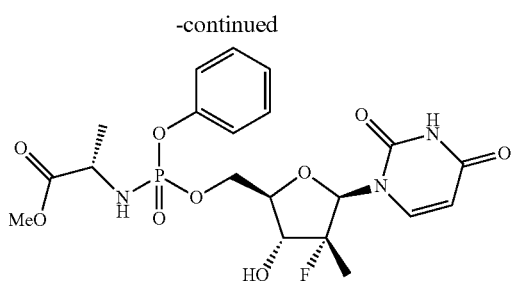

Phenyl methoxyalaninyl phosphorochloridate (1 g, 6.5 eq) dissolved in 3 mL of THF was added to a mixture of 2'-Deoxy-2"-fluoro-2'-C-methyluridine (0.15 g, 1 eq) and N-methylimidazole (0.3 g, 8 eq) in 3 mL THF with vigorous stirring at room temperature, then the reaction was stirred overnight. Solvent was removed by reduced pressure. The resulting crude product was dissolved in methanol purified by prep-HPLC on a YMC 25×30×2 mm column using a water/acetonitrile gradient elution mobile phase. The acetonitrile and water were removed under reduced pressure to give the desired product (50.1 mg, 15.6%). $^1$H NMR (DMSO-$d_6$) δ 1.20-127 (m, 6H), 3.58 (d, J=16.0 Hz, 3H), 3.75-3.92 (m, 2H), 4.015-4.379 (m, 2H), 5.54 (t, J=10.2 Hz, 1H), 5.83-5.91 (m, 1H), 6.00-6.16 (m, 1H), 7.18 (d, J=8.0 Hz, 2H), 7.22 (s, 1H), 7.35 (t, J=4.4 Hz, 2H), 7.55 (s, 1H), 11.52 (s, 1H); MS, m/e 502 (M+1)$^+$.

EXAMPLE 6

Preparation of 2'-Deoxy-2'-fluoro-2'-C-methyluridine 5'-(phenyl methoxy-valyl phosphate)

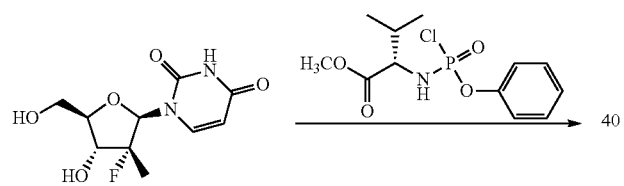

Phenyl methoxy-valyl phosphorochloridate (0.6 g, 3.6 eq) dissolved in 3 mL of THF was added to a mixture of 2'-Deoxy-2'-fluoro-2'-C-methyluridine (0.15 g, 1 eq) and N-methylimidazole (0.44 g, 9 eq) in 3 mL THF with vigorous stirring at room temperature, then the reaction was stirred overnight. Solvent was removed by reduced pressure. The resulting crude product was dissolved in methanol purified by prep-HPLC on a YMC 25×30×2 mm column using a water/acetonitrile gradient elution mobile phase. The acetonitrile and water were removed under reduced pressure to give the desired product (60 mg, 20%). $^1$H NMR (DMSO-$d_6$) δ 0.74-0.847 (m, 6H), 1.20-1.28 (m, 3H), 1.89-1.92 (m, 1H), 3.50-3.54 (m, 1H), 3.58 (d, J=10.4 Hz, 3H), 3.72-3.95 (m, 1H), 4.03-4.05 (m, 1H), 4.23-4.43 (m, 2H), 5.56 (t, J=16.0 Hz, 1H), 5.85-5.92 (m, 1H), 6.01-6.07 (m, 1H), 7.16-7.21 (m, 3H), 7.37 (t, J=8 Hz, 2H), 7.55-7.60 (m, 1H), 11.52 (s, 1H); MS, m/e 530 (M+1)$^+$.

EXAMPLE 7

Preparation of 2'Deoxy-2'-fluoro-2'-C-methyluridine 5'-(4-bromophenyl methoxy-valyl phosphate)

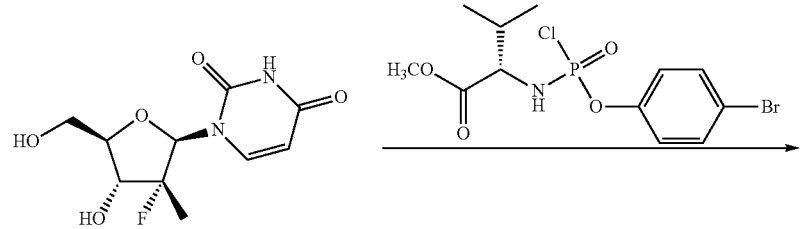

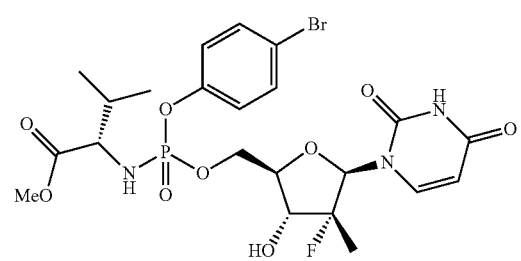

4-Bromophenyl methoxy-valyl phosphorochloridate (1 g, 3.4 eq) dissolved in 3 mL of THF was added to a mixture of 2'-deoxy-2'-fluoro-2'-C-methyluridine (0.2 g, 1 eq) and N-methylimidazole (0.35 g, 6 eq) in 3 mL THF with vigorous stirring at room temperature, then the reaction was stirred overnight. Solvent was removed by reduced pressure. The resulting crude product was dissolved in methanol purified by prep-HPLC on a YMC 25×30×2 mm column using a water/acetonitrile gradient elution mobile phase. The acetonitrile and water were removed reduced pressure to give the desired product (120 mg, 26%). $^1$H NMR (DMSO-$d_6$) δ 0.72-0.82 (m, 6H), 1.19-1.26 (m, 3H), 1.86-1.92 (m, 1H), 3.48-3.50 (m, 1H), 3.56 (d, J=12.0 Hz, 3H), 3.72-3.89 (m, 1H), 3.96-4.03 (m, 1H), 4.22-4.37 (m, 2H), 5.54-5.60 (m, 1H), 5.85-5.91 (m, 1H), 5.98-6.13 (m, 1H), 7.15 (d, J=8.0 Hz, 2H), 7.49-7.56 (m, 3H), 11.53 (s, 1H); MS, m/e 608 (M+1)$^+$.

EXAMPLE 8

Preparation of 2'-Deoxy-2'-fluoro-2'-C-methyluridine 5'-(4-bromophenyl methoxy-alanyl phosphate)

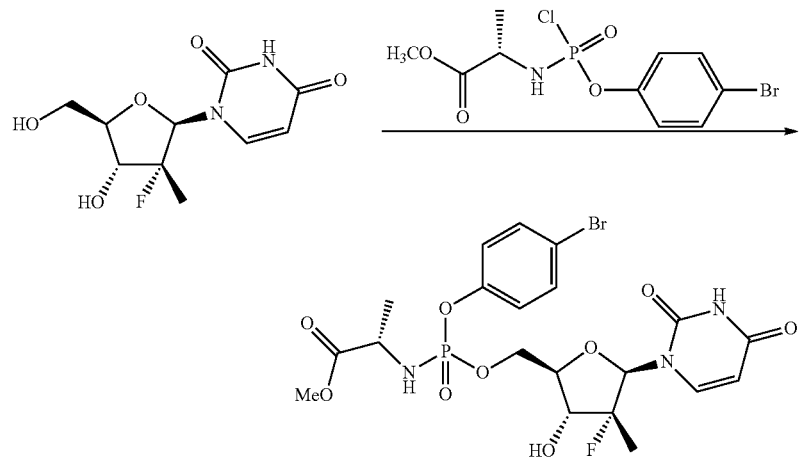

4-Bromophenyl methoxy-alanyl phosphorochloridate (0.6 g, 5 eq) dissolved in 3 mL of THF was added to a mixture of 2'-deoxy-2'-fluoro-2'-C-methyluridine (0.15 g, 1 eq) and N-methylimidazole (0.3 g, 7.8 eq) in 3 mL THF with vigorous stirring at room temperature, then the reaction was stirred overnight. Solvent was removed by reduced pressure. The resulting crude product was dissolved in methanol purified by prep-HPLC on a YMC 25×30×2 mm column using a water/acetonitrile gradient elution mobile phase. The acetonitrile and water were removed under reduced pressure to give the desired product (40 mg, 12%); $^1$H NMR (DMSO-$d_6$) δ 1.20-1.26 (m, 6H), 3.57 (d, J=2.8 Hz, 3H), 3.84 (s, 1H), 3.97-4.03 (m, 1H), 4.21-4.25 (m, 1H), 4.33-4.37 (m, 2H), 5.54-5.60 (m, 1H), 5.83-5.89 (m, 1H), 5.98-6.19 (m, 1H), 7.16 (t, J=10.2 Hz, 2H), 7.52-7.57 (m, 3H), 11.52 (s, 1H); MS, m/e 580(M+1)$^+$.

EXAMPLE 9

Preparation of N$^4$—(N,N-dimethylformamidinyl)-2'-deoxy-2'-fluoro-2'-C-methylcytidine

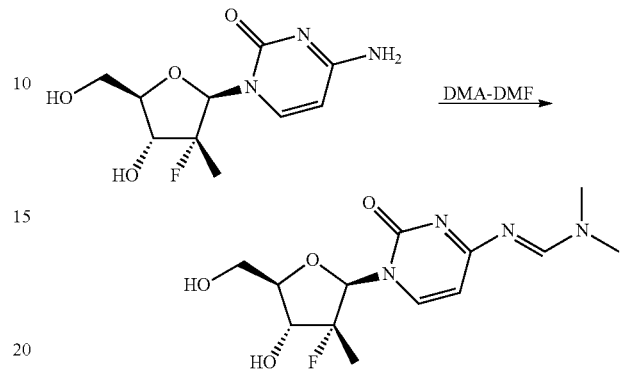

2'-Deoxy-2'-fluoro-2'-C-methylcytidine (500 mg, 1.9 mmol) was stirred with dimethylformamide dimethyl acetal in DMF (10 mL). The resulting mixture was stirred at room temperature overnight. After solvent removal the crude product was used for next step without further purification.

EXAMPLE 10

Preparation of 2'-Deoxy-2'-fluoro-2'-C-methylcytidine 5'-(phenyl methoxy-alanyl phosphate)

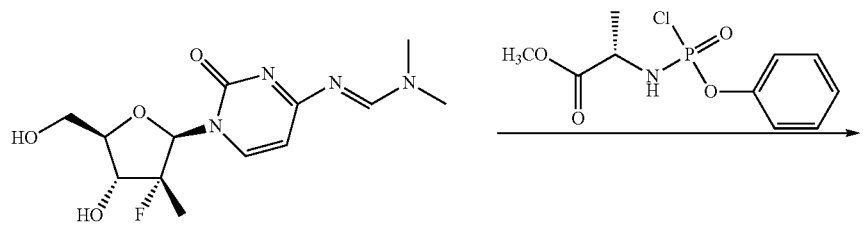

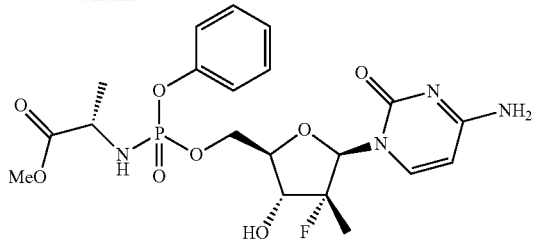

Phenyl methoxyalaninyl phosphorochloridate (0.6 g, 6 eq) dissolved in 3 mL of THF was added to a mixture of N⁴—(N, N-dimethylformamidinyl)-2'-deoxy-2'-fluoro-2'-C-methyl-cytidine (0.15 g, 1 eq) and N-methylimidazole (0.3 g, 7.8 eq) in 3 mL THF with vigorous stirring at room temperature, then the reaction was stirred overnight. Solvent was removed by reduced pressure. The resulting crude product was dissolved in methanol purified by prep-HPLC on a YMC 25×30×2 mm column using a water/acetonitrile gradient elution mobile phase. The acetonitrile and water were removed under reduced pressure to give the desired product (62 mg, 20.6%). $^1$H NMR (DMSO-$d_6$) δ 1.16 (d, J=23.2 Hz, 3H), 122 (d, J=7.2 Hz, 3H), 3.56 (S, 3H), 3.69-3.75 (d, J=25.6 Hz, 1H), 3.82-3.86 (m, 1H), 3.96-3.98 (m, 1H), 4.21-4.34 (m, 2H), 5.68 (d, J=7.2 Hz, 1H), 5.75-5.77 (m, 1H), 6.07-6.16 (m, 1H), 7.15-7.19 (m, 3H), 7.2 (d, J=9.2 Hz, 2H), 7.39 (t, J=7.8 Hz, 2H), 7.48 (d, J=9.2 Hz, 1H); MS, m/e 501(M+1)$^+$.

EXAMPLE 11

Preparation of 2'-Deoxy-2'-fluoro-2'-C-methylcytidine 5'-(4-bromophenyl methoxy-valyl phosphate)

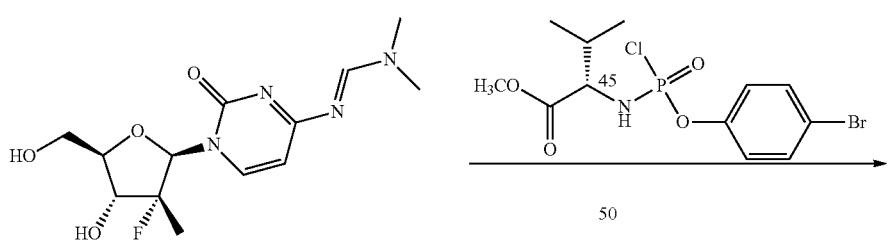

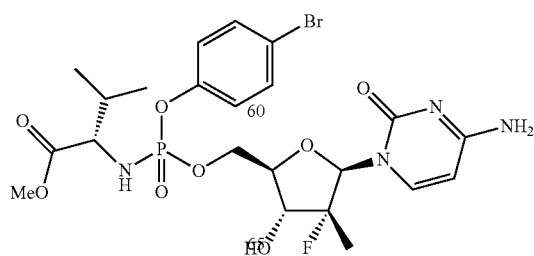

4-Bromophenyl methoxy-valyl phosphorochloridate (1.0 g, 3.4 eq.) dissolved in 3 mL of THF was added to a mixture of $N^4$—(N,N-dimethylformamidinyl)-2'-deoxy-2'-fluoro-2'-C-methylcytidine (0.2 g, 1 eq.) and N-methyl imidazole (0.35 g, 6 eq.) in 3 mL THF with vigorous stirring at room temperature, then the reaction was stirred overnight. Solvent was removed by reduced pressure. The resulting crude product was dissolved in methanol purified by prep-HPLC on a YMC 25×30×2 mm column using a water/acetonitrile gradient elution mobile phase. The acetonitrile and water were removed under reduced pressure to give the desired product as a white solid (59 mg, 13%); $^1$H NMR (DMSO-$d_6$) δ 0.74-0.83 (m, 6H), 1.12-1.20 (m, 3H), 1.89-1.92 (m, 1H), 3.49-3.51 (m, 1H), 3.55 (s, 3H), 3.59-3.68 (m, 1H), 3.72-3.83 (m, 1H), 4.21-4.39 (m, 2H), 5.70-5.72 (m, 1H), 5.76-5.83 (m, 1H), 6.04-6.16 (m, 1H), 7.15 (d, J=13.0 Hz, 2H), 7.26 (s, 1H), 7.33 (s, 1H), 7.46-7.55 (m, 1H), 7.56 (d, J=4.4 Hz, 2H); MS, m/e 607 (M+1)$^+$.

EXAMPLE 12

Preparation of 2'-deoxy-2'-fluoro-2'-C-methylcytidine 5'-(phenyl methoxy-valyl phosphate)

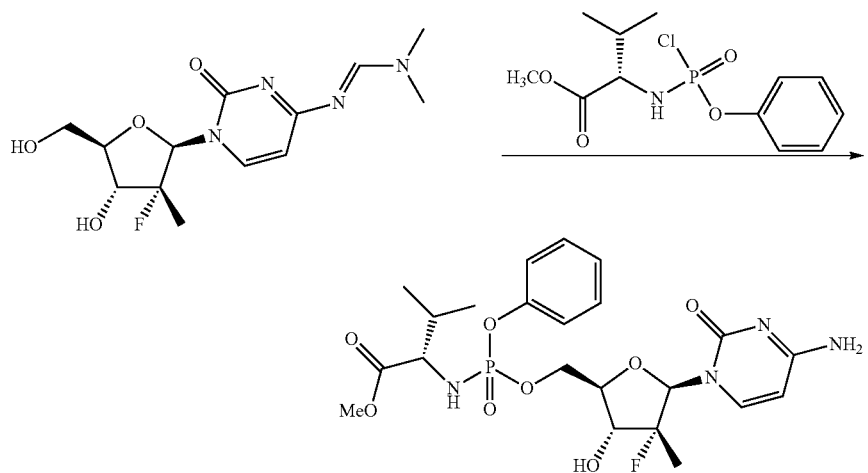

Phenyl methoxy-valyl phosphorochloridate (0.6 g, 6 eq) dissolved in 3 mL of THF was added to a mixture of $N^4$—(N,N-dimethylformamidinyl)-2'-deoxy-2'-fluoro-2'-C-methylcytidine (0.15 g, 1 eq) and N-methylimidazole (0.3 g, 7.8 eq) in 3 mL THF with vigorous stirring at room temperature, then the reaction was stirred overnight. Solvent was removed by reduced pressure. The resulting crude product was dissolved in methanol purified by prep-HPLC on a YMC 25×30×2 mm column using a water/acetonitrile gradient elution mobile phase. The acetonitrile and water were removed under reduced pressure to give the desired product as a white solid (86 mg, 42.9%). $^1$H NMR (DMSO-$d_6$) δ 0.72-0.80 (m, 6H), 1.09-1.18 (m, 3H), 1.87-1.920n, 1H), 3.47-3.51 (m, 1H), 3.58 (s, 3H), 3.71-3.75 (m, 1H), 3.97 (t, J=11.2 Hz, 1H), 4.22-4.37 (m, 2H), 5.70 (d, J=8.0 Hz, 1H), 5.76-5.84 (m, 1H), 6.01-6.15 (m, 1H), 7.13-7.18 (m, 3H), 7.27 (s, 2H), 7.34 (d, J=4.0 Hz, 2H), 7.46-7.50 (m, 1H); MS, m/e 529 (M+1)$^+$.

EXAMPLES

Example numbers 13-54 and 56-66 are prepared using similar procedures described for examples 5-8. The example number, compound identification, and NMR/MS details are

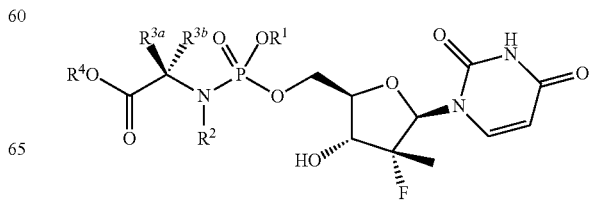

| Ex. | R¹ | R² | R³ᵃ | R³ᵇ | R⁴ | NMR/MS |
|---|---|---|---|---|---|---|
| 13 | Ph | H | H | Me | Et | 1H NMR (DMSO-d₆) δ 1.12-1.16 (m, 3H), 1.20-1.28 (m, 6H), 3.70-390 (m, 2H), 4.00-4.08 (m, 3H), 4.18-1.45 (m, 2H), 5.52-5.58 (m, 1H), 5.85-5.98 (m, 1H), 6.00-6.20 (m, 2H), 7.16-7.23 (m, 3H), 7.37-7.40 (m, 2H), 7.54-7.60 (m, 1H), 11.54 (s, 1H); MS, m/e 516.1 (M + 1)+ |
| 14 | 1-Napth | H | H | Me | Bn | 1H NMR (DMSO-d₆) δ 1.18-1.30 (m, 6H), 3.78-4.10 (m, 3H), 4.38-4.49 (m, 2H), 4.99-5.11 (m, 2H), 5.28-5.40 (m, 1H), 5.85-6.10 (m, 2H), 6.30-6.41 (m, 1H), 7.28-7.32 (m, 5H), 7.41-7.60 (m, 5H), 7.73-7.76 (m, 1H), 7.94-8.11 (m, 1H), 8.13-8.15 (m, 1H), 11.50 (s, 1H); MS, m/e 628.4 (M + 1)+ |
| 15 | Ph | H | H | H | Me | 1H NMR (DMSO-d₆) δ 1.22 (d, J = 22.4 Hz, 3H), 3.59 (s, 3H), 3.63-3.69 (m, 2H), 3.74-3.8 (m, 1H), 4.02 (d, J = 11.2 Hz, 1H), 4.23-4.28 (m, 1H), 4.40-4.43 (m, 1H), 5.57-5.60 (m, 1H), 5.89 (d, J = 6.8 Hz, 1H), 6.00-606 (m, 2H), 7.15-7.23 (m, 3H), 7.35-7.39 (m, 2H), 7.52 (d, J = 8 Hz, 1H), 11.52 (S, 1H); MS, m/e 4887.97 (M + 1)+ |
| 16 | 2,4-Cl—Ph | H | H | Me | Me | 1H NMR (DMSO-d₆) δ 1.22-1.28 (m, 6H), 3.57-3.60 (m, 3H), 3.84-3.92 (m, 2H), 4.00-4.04 (m, 1H), 4.31-4.44 (m, 2H), 5.54-5.61 (m, 1H), 5.85-6.10 (m, 2H), 6.32-6.43 (m, 1H), 7.44-7.54 (m, 3H), 7.72-7.75 (m, 1H), 11.54 (s, 1H); MS m/e 570.2 (M + 1)+ |
| 17 | 1-Napth | H | H | Me | Me | 1H NMR (DMSO-d₆) δ 1.15-1.27 (m, 6H), 3.51-3.55 (d, 3H), 3.85-3.96 (m, 2H), 4.00-4.10 (m, 1H), 4.30-4.46 (m, 2H), 5.31-5.39 (m, 1H), 5.89-6.05 (, 2H), 6.22-6.34 (m, 1H), 7.44-7.60 (m, 5H), 7.73-7.77 (m, 1H), 7.93-7.96 (m, 1H), 8.12-8.14 (m, 1H), 11.50 (s, 1H); MS, m/e 552.1 (M + 1)+ |
| 18 | Ph | * | H | * | Me | 1H NMR (DMSO-d₆) δ 1.19 (d, J = 22.8 Hz, 3H), 1.69-1.84 (m, 3H), 1.99-2.04 (m, 1H), 3.16-3.21 (m, 2H), 3.58 (s, 3H), 3.68-3.8 (m, 1H), 4.00 (m, 1H), 4.01-4.13 (m, 1H), 4.22-4.25 (m, 1H), 4.5 (d, J = 11.2 Hz, 1H), 5.54 (d, J = 8.0 Hz, 1H), 5.86 (s, 1H), 5.6 (d, J = 19.6 Hz, 1H), 7.15-7.2 (m, 3H), 7.34 (t, J = 8.0 Hz, 2H), 7.51 (d, J = 8.0 Hz, 1H), 11.38 (s, 1H); MS, m/e 527.93 (M + 1)+ |
| 19 | Ph | H | H | Me | n-Bu | 1H NMR (DMSO-d₆) δ 0.80-0.90 (m, 3H), 1.20-1.35 (m, 8H), 1.48-1.55 (m, 2H), 3.78-3.88 (m, 2H), 3.95-4.08 (m, 3H), 4.22-4.45 (m, 2H), 5.55-5.57 (t, 1H), 5.85-6.18 (m, 3H), 7.14-7.23 (m, 3H), 7.35-7.40 (m, 2H), 7.51-7.60 (d, 1H), 11.50 (s, 1H); MS m/e 544.2 (M + 1)+ |
| 20 | Ph | H | H | Me | Bn | 1H NMR (DMSO-d₆) δ 1.20-1.30 (m, 6H), 3.72-4.05 (m, 3H), 4.23-4.27 (m, 1H), 4.32-4.45 (m, 1H), 5.07-5.10 (t, 2H), 5.52-5.56 (t, 1H), 5.86-6.10 (m, 2H), 6.13-6.21 (m, 1H), 7.15-7.21 (m, 3H), 7.29-7.40 (m, 7H), 7.51-7.56 (d, 1H), 11.50 (s, 1H); MS, m/e 578.2 (M + 1)+ |
| 21 | 4-F—Ph | H | H | Me | Me | 1H NMR (DMSO-d₆) δ 1.28-1.34 (m, 6H), 3.64 (d, J = 4 Hz, 3H), 3.85-3.96 (m, 2H), 4.06-4.12 (m, 1H), 4.30-4.34 (m, 1H), 4.40-4.47 (m, 1H), 5.62-5.67 (m, 1H), 5.94-6.01 (m, 1H), 6.09 (d, J = 18.8 Hz, 1H), 6.17-6.26 (m, 1H), 7.27-7.33 (m, 4H), 7.62 (d, J = 7.6 Hz, 1H), 11.61 (s, 1H); MS, m/e 519.94 (M + 1)+ |
| 22 | 4-Cl—Ph | H | H | Me | Me | 1H NMR (DMSO-d₆) δ 1.22-1.28 (m, 6H), 3.58 (d, 2H), 3.70-3.95 (m, 2H), 3.95-4.08 (m, 1H), 4.23-4.45 (m, 2H), 5.55-5.61 (t, 1H), 5.85-6.10 (m, 2H), 6.15-6.23 (m, 1H), 7.20-7.26 (m, 2H), 7.43-7.46 (m, 2H), 7.54-7.57 (d, 1H), 11.50 (s, 1H); MS, m/e 536.1 (M + 1)+ |
| 23 | 3,4-Cl—Ph | H | H | Me | Me | 1H NMR (DMSO-d₆) δ 1.13 (m, 6H), 3.49 (s, 3H), 3.61-3.85 (m, 2H), 3.90-3.93 (m, 1H), 4.16-4.22 (m, 1H), 4.27-4.31 (m, 1H), 5.47-5.52 (m, 1H), 5.82 (d, J = 11.6 Hz, 1H), 5.93 (d, J = 19.2 Hz, 1H), 6.15-6.25 (m, 1H), 7.13 (t, J = 9.6 Hz, 1H), 7.43 (d, J = 12 Hz, 2H), 7.57 (d, J = 6.0 Hz, 1H), 11.43 (s, 1H); MS, m/e 569.85 (M + 1)+ |
| 24 | Ph | H | H | Me | 2-Bu | 1H NMR (DMS)-d₆) δ 0.83 (d, J = 6.8 Hz, 6H), 1.20-1.26 (m.,6H), 1.79-1.86 (m, 1H), 3.73-3.90 (m, 4H), 4,01 (t, J = 11.2 Hz, 1H), 4.21-4.28 (m,1H), 4.33-4.42 (m, 1H), 5.54 (t, J = 7.6 Hz, 1H), 5.85-5.92 (m, 1H), 5.99-6.13 (m, 2H), 7.19 (t, J = 8 Hz, 3H), 7.36 (t, J = 7.6 Hz, 2H), 7.53 (d, J = 7.6 Hz, 1H), 11.52 (s, 1H); MS, m/e 544,00 (M + 1)+ |
| 25 | Ph | H | H | Mc | i-Pr | 1H NMR (DMSO-d₆) δ 1.13-1.28 (m, 12H), 3.74-3.81 (m, 2H), 3.95-4.08 (m, 1H), 4.20-4.45 (m, 2H), 4.83-4.87 (m, 1H), 5.52-5.58 (m, 1H), 5.84-6.15 (mm 3H), 7.17-7.23 (m, 3H), 7.35-7.39 (m, 2H), 7.54-7.57 (m, 1H), 11.50 (s, 1H); MS, m/e 530.2 (M + 1)+ |
| 26 | 4-MeO—Ph | H | H | Me | n-Bu | 1HNMR (400 MHz, DMSO-d₆): δ = 0.78-0.82 (m, 3H), 1.29-1.47 (m, 8H), 1.49.1.54 (m, 2H), 3.66-3.87 (m, 5H), 3.96-4.02 (m, 1H), 4.21-4.39 (m, 2H), 5.57 (t, J = 12.0 Hz, 1H), 5.84-6.05 (m, 3H), 6.90 (dd, J1 = 8.0 Hz, J2 = 4.0 Hz, 2H), 7.09-7.14 (dd, J1 = 16.0 Hz, J2 - 4.0 Hz, 2H), 7.55 (d, J = 8.0 Hz, 1H), 11.48-11.62 (s, 1H) |
| 27 | 4-F—Ph | H | H | Me | Et | 1H NMR (DMSO-d₆) δ 1.12.1.28 (m, 9H), 3.72-3.94 (m, 2H), 3.98-4.10 (m,3H), 4.21-4.42 (m, 2H), 5.55-5.61 (m, 1H), 5.85-6.20 (m, 3H), 7.18-7.25 (m, 4H), 7.55-7.58 (d, 1H), 11.50 (s, 1H); MS, m/e 533.90 (M + 1)+ |
| 28 | 4-F—Ph | H | H | Me | i-Pr | 1H NMR (DMSO-d₆) δ 1.13.130 (m, 12H), 3.74-3.85 (m, 2H), 3.98-4.06 (m,1H), 4.23-4.41 (m,2H), 4.83-4.87 (m, 1H), 5.55-5.61 (t, 1H), 5.85-6.12 (m, 3H), 7.18-7.24 (m, 4H), 7.55-7.58 (d, 1H), 11.50 (s, 1H); MS, m/e 547.91(M + 1)+ |
| 29 | 4-F—Ph | H | H | Mc | Bn | 1H NMR (DMSO-d₄) δ 1.10.1.23 (m, 6H), 3.63-3.89 (m, 3H), 4.10-4.30 (m ,2H), 4.96-5.00 (m, 2H), 5.46-5.50 (t, 1H), 5.75-5.96 (m, 2H), 6.04-6.12 (m,1H), 7.05-7.11 (m, 4H), 7.20-7.24 (d, 5H), 7.42-7.45 (d, 1H), 11,50 (s, 1H); MS, m/e 595.94 (M + 1)+ |
| 30 | 4-MeO—Ph | H | H | Me | i-Pr | 1HNMR (400 MHz, DMSO-d₆): δ = 1.15-1.27 (m, 12H), 3.71-3.89 (m, 5H), 3.98-4.02 (m, 1H), 4.22-4.25 (m, 1H), 4.33-4.39 (m, 1H), 4.84- |

-continued

| Ex. | R¹ | R² | R³ᵃ | R³ᵇ | R⁴ | NMR/MS |
|---|---|---|---|---|---|---|
| | | | | | | 4.87 (m, 1H), 5.57 (t, J = 12.0 Hz, 1H), 5.91-6.03 (m, 3H), 6.90 (d, J = 8.0 Hz, 2H), 7.09-7.14 (m, 2H), 7.55 (d, J = 8.0 Hz, 1H), 11.51 (s, 1H) |
| 31 | 2-Cl—Ph | H | H | Me | Bn | 1H NMR (DMSO-d₆) δ 1.23 (m, 6H), 3.93-4.00 (m, 3H), 4.27-4.40 (m, 2H), 5.0 (t, J = 7.2 Hz, 2H), 5.53 (m, 1H), 5.80-6.0 (m, 2H), 6.30 (m,1H), 7.15 (d, J = 2.4 Hz, 1H), 7,27 (m, 6H), 7.51 (m, 3H), 11.5 (s, 1H); MS, m/e 579.87 (M + 1)+/ 596.78 (M + 18)+ |
| 32 | 2,4-Cl—Ph | H | H | Me | n-Bu | 1H NMR (DMSO-d₆) δ = 0.82 (m, 3H), 1.47 (m, 2H), 3.86 (m, 2H), 3.84 (m, 3H), 4.27-4.43 (m, 2H), 5.5 (m, 1H), 6.02 (m, 2H), 6.35(m, 1H), 7.44 (m, 3H), 7.77 (m, 1H), 11.5 (s, 1H); MS, m/e 611.87 (M + 1)+ |
| 33 | 4-Me—Ph | H | H | Me | i-Pr | 1H NMR (DMS)-d₆) δ 1.14-1.27 (m, 12H), 2.17-2.26 (m, 3H), 3.73-3.82 (m, 1H), 3.99-4.02 (m, 1H), 4.23-4.26 (m, 1H), 4.37-4.40 (m, 1H), 4.82-4.88 (m, 1H), 5.52-538 (m, 1H), 5.85-6.07 (m, 3H), 7.01-7.20 (m, 4H), 7.55 (d, J= 16 Hz, 1H), 11.51 (s, 1H); MS, m/e 543.98 (M + 1)+; 1108.86 (2M + 23)+ |
| 34 | 4-F—Ph | H | H | Me | n-Bu | 1H NMR (DMSO-d₆) δ 0.82-0.89 (m, 3H), 1.20-1.31 (m, 8H), 1.48-1.53 (m, 2H), 3.77-3.90 (m, 2H), 3,95-4.10 (m, 3H), 4.21-4.45 (m, 2H), 5.56-5.61 (t, 1H), 5.83-6.20 (m, 3H), 7.18-7.25 (m, 4H), 7.55-7.58 (d, 1H), 11.50 (s, 1H);t MS, m/e 584.1 (M + 23)+ |
| 35 | 3,4-diCl—Ph | H | H | Me | Et | 1H NMR (DMSO-d₆) δ 1.12-1.31 (m, 9H), 3.77-3.92 (m, 2H), 3.95-4.08 (m, 3H), 4.21-4.45 (m, 2H), 5.56-5.62 (t, 1H), 5.80-6.11 (m, 2H), 6.18-6.33 (m, 1H), 7.18-7.25 (m, 1H), 7.49-7.56 (d, 2H), 7.62-7.67 (m,1H), 11.50 (s, 1H); MS, m/e 606.1 (M + 23)+ |
| 36 | 2-Cl—Ph | H | H | Me | i-Pr | 1HNMR (400 MHz, DMSO-d₆) δ = 1.12-1.16 (m, 6H), 1.21-1.27 (m, 6H), 3.79-3.85 (m, 2H), 4.00-4.07 (m, 1H), 4.28-4.32 (m, 1H), 4,38-4.43 (m, 1H), 4.83-4.87 (m,1H), 5.56 (dd, J1 = 16.0 Hz, J2 = 8.0 Hz, 1H), 5.85-6.12 (m, 2H), 6.20-6.33 (m, 1H), 7.19-7.22 (m, 1H), 7.33 (t, J = 16.0 Hz, 1H), 7.48-7.55 (m, 3H), 11.55 (s, 1H) |
| 37 | 4-MeO—Ph | H | H | Me | Bn | 1HNMR (400 MHz, DMSO-d₆); δ = 1.19-1.26 (m, 6H), 3.69-3.70 (s, 3H), 3.87 (m, 2H), 3.99 (m, 1H), 4.20-4.21 (m, 1H), 4.35 (m, 1H), 5.07-5.09 (m, 2H), 5.54 (t, J = 16.0 Hz, 1H), 5.85-5.92 (m, 1H), 6.04-6.10 (m, 2H), 6.86 (d, J = 8.0 Hz, 2H), 7.09 (dd, J1 = 16.0 Hz, J2 = 4.0 Hz, 2H), 7.30-7.34 (m, 5H), 7.53(s, 1H), 11.52 (s, 1H) |
| 38 | Ph | H | H | Me | n-Pen | 1H NMR (DMSO-d₆) δ 0.79-0.81 (m, 3H), 1.17-1.23 (m, 10H), 3.74-3.81 (m, 2H), 3.94-3.96 (m, 3H), 4.19-4.36 (m, 2H), 5.49-5.54 (m, 1H), 5.87-6.08 (m, 3H), 7.14-7.33 (m, 3H), 7.31-7.35 (m, 2H), 7.51 (d, J = 8 Hz, 1H), 11.51 (s, 1H); Ms, m/e 557.9 (M + 1)+; 1136.88 (2M + 23)+ |
| 39 | 4-Cl—Ph | H | H | Me | i-Pr | 1H NMR (DMSO-d₆) δ 1.04-1.19 (m, 12H), 3.76-3.80 (m , 2H), 3.98-4.08 (m, 1H), 4.42-4.42 (m, 2H), 4.82-4.85 (m, 1H), 5.55-5.60 (m, 1H), 5.80-6.20 (m, 3H), 7.20-7.25 (m, 2H), 7.43 (d, J = 8.8 Hz, 1H), 7.54 (d, J = 8 Hz, 1H), 11.51 (s, 1H); MS, m/e 563.88 (M + 1)+; 1148.73 (2M + 23)+ |
| 40 | 4-Cl—Ph | H | H | Me | n-Bu | 1H NMR (DMSO-d₆) δ 0.85 (t, J = 7.2 Hz, 3H), 1.22-1.33 (m, 810,1.45-133 (m. 211). 3.80-3.87 (m. 211), 3.96-4.04 (m. 311). 4,24-4.27 (m, 1H), 435-4.39 (m, 1H), 5.56-5.61 (m, 1H), 5.82-6.11 (m, 2H), 6.15-6.18 (m, 1H), 7.20-7.56 (m, 4H), 7.51-7.57 (m, 1H), 11.54 (s, 1H); MS,m/e 577.95 (M + 1)+ |
| 41 | 4-Cl—Ph | H | H | Me | Et | 1H NMR (DMSO-d₆) δ 1.14 (t, J = 7.0 Hz, 3H), 1.20-1.28 (m, 6H), 3.77-3.88 (m, 2H), 3.99-4.07 (m, 3H), 4.24-4.28 (m, 1H), 4.34-4.43 (m, 1H), 5.56-5.61 (m, 1H), 5.86-6.13 (m, 2H), 6.15-6.24 (m, 1H), 7.20-7.26 (m, 2H), 7.44 (d, J= 7.6 Hz, 2H), 7.55 (d, J = 7.6 Hz, 1H), 11.55 (s, 1H); MS, m/e 549.11 (M + 1)+ |
| 42 | 4-Me—Ph | H | H | Me | n-Bu | 1H NMR (DMS)-d₆) δ 0.79-0.83 (m, 3H), 1.17-1.28 (m, 8H), 1.45-1.47 (m, 2H), 2.22 (d, J = 2.8 Hz, 1H), 3.70-3.90 (m, 2H), 3.95-3.98 (m, 3H), 4.10-4.40 (m, 2H), 5.51 (t, 1H), 5.80-5.90 (m, 1H), 5.95-6.05 (m, 2H), 7.02-7.06 (m, 2H), 7.51 (t, J = 4.2 Hz , 4H), 7.51 (d, 1H), 11.51 (s, 1H); MS, m/e 557.99 (M + 1)+; 1136.84 (2M + 23)+ |
| 43 | 4-Me—Phe | H | H | Me | Bn | 1H NMR (DMSO-d₆) δ 1.16-1.24 (m, 6H), 2,22 (s, 3H), 3.65-4.03 (m, 3H), 4.11-4.38 (m, 2H), 5.04-5.05 (m, 2H), 5.48-5.50 (m, 1H), 5.77-5.87 (m, 1H), 5.90-6.11 (m, 2H), 6.98-7.10 (m, 4H), 7.28-7.32 (m, 5H), 7.50 (t, 1H), 11.48 (s, 1H); MS, m/e 592.00 (M + 1)+. |
| 44 | Ph | H | H | Et | Me | 1H NMR (DMSO-d₆) δ 0.70-0.80 (m, 3H), 1.11-1.26 (m, 3H), 1,42-1.61 (m, 2H), 3.50-3.54 (m, 3H), 3.58-3.80 (m, 2H), 3.91-4.02 (m, 1H), 4.12-4.38 (m, 2H), 5.47-5.52 (m, 1H), 5.90-6.03 (m, 2H), 7.08-7.16 (m, 3H), 7.26-7.35 (m, 2H), 7.48 (t, 1H), 11.45 (s, 1H); MS, m/e 515.95 (M + 1)+; 1052.82 (2M + 23)+ |
| 45 | Ph | H | H | Me | 4-F—Bn | ¹HNMR (400 MHz, DMSO-d₆): δ 1.20-1.26 (m, 6H), 3.80-3.93 (m, 2H), 3.98 (s, 1H), 4.25-4.26 (m, 1H), 4.36-4.37 (m, 1H), 5.07 (s, 2H), 5.52-5.55 (m, 1H), 5.86-5.87(m, 1H), 5.98-6.04 (m, 1H), 6.14-6.17 (m, 1H), 7.15-7.20 (m, 5H), 7.36 (dd, J = 20.0, 8.0 Hz, 4H), 7.54 (s, 1H), 11.55 (s, 1H) |
| 46 | 4-Cl—Ph | H | H | Me | n-Bu | ¹HNMR (400 MHz, DMSO-d₆): δ 1.21-1.28 (m, 6H), 3.71-3.88 (m, 1H), 3.91-3.98 (m, 1H), 4.00-4.01 (m, 1H), 4.23-4.27 (m, 1H), 4.35-4.38 (m, 1H), 5.08 (d, J = 4.0 Hz, 2H), 5.57 (dd, J = 12.0, 8.0 Hz, 1H), 5.91 (d, J = 8.0 Hz, 1H), 6.01 (d, J = 8.0 Hz, 1H), 6.22-6.24 (m, 1H), 7.17-7.23 (m, 2H), 7.31-7.40 (m, 7H), 7.53 (s, 1H), 11.50 (s, 1H) |

-continued

| Ex. | R¹ | R² | R³ᵃ | R³ᵇ | R⁴ | NMR/MS |
|---|---|---|---|---|---|---|
| 47 | Ph | H | H | Me | 3-Me-1-Bu | ¹H NMR (DMSO-d₆) δ 0.80-0.82 (m, 6H), 1.18-1.40 (m, 8H), 1.50-1.58 (m, 1H), 3.71-3.82 (m, 3H), 3.97-3.4.01 (m, 3H), 4.21-4.40 (m, 2H), 5.30 (t, J = 8.6 Hz, 1H), 5.81-6.10 (m, 3H), 7.15-7.20 (m, 3H), 7-32-7.38 (m, 2H), 7.48 (d, J = 8.4 Hz, 1H), 11.38 (s, 1H); MS, m/e 557.98 (M + 1); 1136.88 (2M + 23)⁺ |
| 48 | 3,4-diCl—Ph | H | H | Me | Bn | ¹H NMR (DMSO-d6) δ 1.05-1.37 (m, 6H), 3.71-3.82 (m, 1H), 3.87-4.02 (m, 2H), 4.28-4.29 (m, 1H), 4.36-4.38 (m, 1H), 5.04 (d, J = 5.2 Hz, 2H), 5.55-5.64 (m, 1H), 5.85-5.94 (m, 1H), 6.00-6.05 (m, 1H), 6.29-6.40 (m, 1H), 7.17-7.24 (m, 1H), 7.30-7.41 (m, 5H), 7.45-7.58 (m, 2H), 7.61 (d, J = 4.0 Hz, 1H), 11.53 (s, 1H); MS, m/e 545.80 (M + 1)⁺; |
| 49 | Ph | H | H | Me | c-Hex | ¹H NMR (DMSO-d₆) δ 1.18-1.41 (m, 12H), 1.59-1.67 (m, 4H), 3.74-13.80 (m, 1H), 3.96-4.02 (m, 1H), 4.19-4.26 (m, 1H), 4.31-4.39 (m, 1H), 4.60 (s, 1H), 5.52 (t, J = 7.8 Hz, 1H), 5.80-6.09 (m, 3H), 7.15-7.20 (m, 3H), 7.32-7.36 (m, 2H), 7.52 (d, J = 8 Hz, 1H), 11.50 (s, 1H); MS, m/e 569.98 (M + 1)⁺; 592.14 (M + 23)⁺ |
| 50 | Ph | H | Me | H | n-Bu | 1H NMR (DMSO-d₆) δ 0.76 (t, J = 7.2 Hz, 3H), 1.10-1.22 (m, 8H), 1.38-1.43 (m, 2H), 3.72-3.75 (m, 2H), 3.87-3.93 (m, 3H), 4.14-4.21 (m, 1H), 4.23-4.33 (m, 1H), 5.46-5.54 (m, 1H), 5.84-6.11 (m, 3H), 7.09-7.14 (m, 2H), 7.27-7.32 (m, 2H), 7.34-7.51 (m, 1H), 11.47 (s, 1H); MS, m/e 543.98 (M + 1)+ |
| 51 | Ph | H | Me | H | i-Pr | 1H NMR (DMSO-d₆) δ 1.39 (d, J = 7.2 Hz, 6H), 1.19-1.29 (m, 6H), 3.65-3.75 (m, 2H), 3.95-4.05 (m, 1H), 4.20-4.22 (m, 1H), 4.31-4.33 (m, 1H), 4.79-4.82 (m, 1H), 5.48-5.57 (m, 1H), 5.84-5.91 (m, 1H), 5.96-6.07 (m, 2H), 7.12-7.35 (m, 5H), 7.44-7.54 (m, 1H), 11.49(s, 1H); MS, m/e 529.96 (M + 1)+ |
| 52 | Ph | H | Me | H | Bn | ¹H NMR (DMSO-d₆) δ 1.18-1.28 (m, 6H), 3.70-3.83 (m, 1H), 3.87-3.94 (m, 1H), 3.99-4.01 (m, 1H), 4.23-4.26 (m, 1H), 4.33-4.37 (m, 1H), 5.03-5.12 (m, 2H), 5.51-5.59 (m, 1H), 5.87-5.90 (m, 1H), 5.95-6.07 (m, 1H), 6.10-6.27 (m, 1H), 7.15-7.23 (m, 3H), 7.31-7.38 (m, 7H), 7.47-7.56 (m, 1H), 11.50 (s, 1H); MS, m/e 577.99 (M + 1)+ |
| 53 | 2-Cl—Ph | H | H | Me | n-Bu | ¹HNMR (400 MHz DMSO-d₆): δ 0.81-0.86 (m, 3H), 1,21-1.31 (m, 8H), 1.46-1.52 (m, 2H), 3.84-3.90 (m, 1H), 3.97-4.04 (m, 3H), 4.27-4.41 (m, 2H), 5.53-5.58 (m, 1H), 5.82-5.95 (m, 1H), 5.96-6.10 (m, 1H), 6.27-6.31 (m, 1H), 7.19-7.22 (m, 1H), 7.34 (dd, J = 8,0, 4.0 Hz, 1H), 7.47-7.55 (m, 3H), 11.55 (s, 1H) |
| 54 | 4-Br—Ph | H | H | Me | i-Pr | ¹HNMR (400 MHz, DMSO-d₆): δ 1.10-1.14 (m, 6H), 1.20-1.27(m, 6H), 3.74-3.81 (m, 2H), 3.99-4.01 (m, 1H), 4.21-4.25 (m, 1H), 4.37-4.38 (m, 1H), 4.81-4.85 (m, 1H), 5.58 (dd, J = 8.0, 4.0 Hz, 1H), 5.82-5.95 (m, 1H), 5.96-6.09 (m, 1H), 6.10-6.13 (m, 1H), 7.18 (dd, J = 12.0, 8.0 Hz, 2H), 7.53-7.37 (m,3H), 11.52 (s, 1H) |
| 55 | 4-F—Ph | H | H | Me | c-Hex | ¹H NMR (DMSO-d₆) δ 1.20-1.44 (m, 12H), 1.60-1.71 (m, 4H), 3.75-4.02 (m, 2H), 3.94-4.02 (m, 1H), 4.19-4.26 (m, 2H), 4.59-4.61 (m, 1H), 5.57 (t, J = 8.4 Hz, 1H), 5.85-6.06 (m, 3H), 7.17-7.23 (m, 4H1), 7.54 (d, J = 8.4 Hz, 1H), 11.50 (s, 1H); MS, m/e 587.92 (M + 1)⁺ |
| 56 | 4-Br—Ph | H | H | Me | c-Hex | ¹HNMR (400 MHz, DMSO-d₆): δ = 1.18-1.46 (m, 12H), 1.61-1,69 (m, 4H), 3.75-3.82 (m, 2H), 3.95-4.08 (m, 1H), 4.25-4.28 (m, 1H), 4.38 (s, 1H), 4.60-4.62 (m, 1H), 5.56-5.60 (m, 1H), 5.82.5.95 (m, 1H), 6.02-6.20 (m,7H), 7.09-7.20 (m, 2H), 7.53-7.57 (m, 3H), 11.52(s, 1H) MS, m/e 650.0 (M + 3)⁺ |
| 57 | Ph | H | H | Et | i-Pr | ¹HNMR (400 MHz, DMSO-d₆): δ = 0.75-0.82 (m, 3H), 1.12-1.26 (m, 9H) 1.52-1.59 (m, 2H), 3.55-3.68 (m, 1H), 3.72-3.85 (m, 1H) 3.95-4.08 (m, 1H), 4.18-4.28 (m, 1H), 4.32-4.41 (m, 1H), 4,83-4.86 (m, 1H) 5.55 (m, J = 7.6 Hz, 1H), 5.99-6.04 (m, 2H), 6.05-6.10 (m, 1H), 7.14-7.21 (m, 3H), 7.33-7.37 (m, 2H), 7.52-7.54 (m. 1H), 11.53 (s, 1H); MS, m/e 566.07 (M + 23)⁺ |
| 58 | Ph | H | H | Et | c-Hex | ¹HNMR (400 MHz, DMSO-d₆): δ 0.75-0.88 (m, 3H), 1.26-1.46 (m, 9H), 1.52-1.69 (m, 6H), 3.60-3.63 (m, 1H), 3.72-3.90 (m 1H), 4.02-4.03 (m, 1H), 4.24-4.27 (m, 1H), 4.37-4.38 (m, 1H), 4.63-4.65 (m, 1H), 5.55 (dd, J = 8.0 Hz, 4.4 Hz, 1H), 5.80-5.95 (m, 1H), 6.00-6.07 (m, 2H), 7.15-7.22 (m, 3H), 7.34-7.38 (m, 2H), 7.54 (d, J = 8.0 Hz, 1H), 11.55 (s, 1H): MS, m/e 584.01 (M + 1)⁺. 606.17 (M + 23)⁺ |
| 59 | 4-F—Ph | H | H | Et | c-Hex | ¹H NMR (DMSO-d₆) δ 0.75-0.84 (m, 3H), 1.24 (d, J = 22.8 Hz, 3H), 1.29-1.47 (m, 6H), 1.51-1 70 (m, 6H), 3.59-3.66 (m, 1H), 3.77-3.84 (m, 1H), 3.98-4.04 (m, 1H), 4.21-4.27 (m, 1H), 4.34-4.41 (m, 1H), 4.60-4.65 (m, 1H), 5.56-5.60 (m, 1H), 5.84-5.90 (m, 1H), 6.00-6.08 (m, 2H), 7.20-7.24 (m, 4H), 7.56 (d, J = 8.0 Hz, 1H), 11.49 (s, 1H); MS, m/e 602.00 (M + 1)⁺ |
| 60 | Ph | H | H | Me | F—CH₂—CH₂— | ¹H NMR (DMSO-d₆) δ 1.18-1.25 (m, 6H), 3.71-3.89 (m, 2H), 3.92-3.99 (m, 1H), 4.19-4.27 (m, 4H), 4.48-4.61 (m, 2H), 3.94-3.98 (m, 2H), 4.11-4.23 (m, 4H), 5.47-5.52 (m, 1H), 6.01-6.11 (m, 1H), 5.90-6.14 (m, 2H), 7.15-7.21 (m, 3H), 7.32-7.36 (m, 2H), 7.46-7.57 (m, 1H), 11.49 (s,1H); MS, m/e 533.86 (M + 1)⁺ |
| 61 | Ph | H | H | Me | F₂—CH₂—CH₂— | ¹H NMR (DMSO-d₆) δ 1.17-1.24 (m, 6H), 3.67-3.81 (m, 1H), 3.89-3.98 (m, 2H), 4.21-4.36 (m, 4H), 5.48-5.53 (m, 1H) , 5.82-6.05 (m, 2H), 6.18-6.22 (m, 2H), 7.15-7.20 (m, 3H), 7.32-7.36 (m , 2H), 7.51 (s, 1H),11.50 (s, 1H); MS, m/e 551.92 (M + 1)⁺; |

| Ex. | R¹ | R² | R³ᵃ | R³ᵇ | R⁴ | NMR/MS |
|---|---|---|---|---|---|---|
| 62 | Ph | H | H | Me | (CF₃)₂—CH— | ¹H NMR (DMSO-d₆) δ 1.13-1.29 (m, 6H), 3.67-3.81 (m, 1H), 3.94-4.32 (m, 4H), 5.47 (t, J = 8 Hz 1H), 5.82-6.01 (m, 2H), 6.33-6.36 (m, 1H), 6.70-6.78 (m, 1H), 7.09-7.15 (m, 3H), 7.28-7.32 (m, 2H), 7.43-7.46 (m, 1H), 11.44 (s, 1H); MS, m/e 637.90 (M + 1)⁺ |
| 63 | Ph | H | H | Me | (CH₂F)₂—CH— | ¹H NMR (DMSO-d₆) δ 1.20-1.29 (m, 6H), 3.70-3.90 (m, 1H), 3.91-4.12 (m, 2H), 4.20-4.33 (m, 1H), 4.35-4 48 (m, 1H), 4.52-4.55 (m, 2H), 4.63-4.67 (m, 2H), 5.20-5.35 (m, 1H), 5.56 (t, J = 8.4 Hz, 1H), 5.80-5.95 (m, 1H), 5.95-6.10 (m, 1H), 6.18-6.21 (m, 1H), 7.18-7.23 (m, 3H), 7.35-7.39 (m, 2H), 7.54 (s, 1H), 11.55 (s, 1H); MS. m/e 565.98 (M + 1)⁺ |
| 64 | Ph | H | H | Me | c-Pr—CH₂— | ¹H NMR (DMSO-d₆) δ 0.20-0.24 (m, 2H), 0.47-0.48 (m, 2H), 0.76-0.84 (m, 3H), 1.03-1.05 (m, 1H), 1.23 (dd, J = 22.4 6.8 Hz 3H), 1.55-1.60 (m, 2H), 3.61-3.68 (m, 1H), 3.81-3.89 (m, 3H), 3.98-4.03 (m, 1H), 4.23-4.29 (m, 1H), 4.35-4.41 (m, 1H), 5.56-6.00 (m, 1H), 5.88-5.91 (m, 1H), 6.04-6.10 (m, 2H), 7.20-7.24 (m, 4H), 7.55 (d, J = 7.6 Hz 1H), 11.53 (s, 1H); MS 573.17 (M + 1)⁺ |
| 65 | Ph | H | H | Et | c-Pen | ¹H NMR (DMSO-d₆) δ 0.75-0.83 (m, 3H), 1.20-1.28 (m, 3H), 1.49-1.63 (m, 8H), 1.76-1.80 (m, 2H), 3.58-3.60 (m, 1H), 3.70-3.82 (m, 1H), 3.98-4.05 (m, 1H), 4.24-4.26 (m, 1H), 4.37-4.42 (m, 1H), 5.03 (s, 1H), 5.54-5.57 (m, 1H), 5.90-6.00 (m, 1H), 6.02-6.07 (m, 2H), 7.15-7.22 (m, 3H), 7.35-7.39 (m, 2H) 7.55 (d, J = 8.0 Hz, 1H), 11.55 (s, 1H); MS, m/e 570.03 (M + 1)⁺ |

*R² and R³ᵇ together are —(CH₂)₃— as derived from L-proline

The Purification Procedure by Prep-HPLC:

Crude products were dissolved in methanol. Injection volumes of these solutions were 5 mL.

The preparative HPLC system including 2 sets of Gilson 306 pumps, a Gilson 156 UV/Vis detector, a Gilson 215 injector & fraction collector, with Unipoint control software, AYmc 25×30×2 mm column was used. The mobile phase was HPLC grade water (A), and HPLC grade acetonitrile (B). Fractions were collected into 100*15 mm glass tubes.

HPLC gradient is shown in Table 1. Once the gradient was selected, acetonitrile solution was injected into HPLC system, and then fractions collected according to UV peaks. After the separation, each glass tubes were run MS test to collect the desired compounds. The fractions with target MS were combined in a well-weighted flask. Most of acetonitrile was removed under reduce pressure and the remaining solution was freeze-dried to give desired compound.

TABLE 1

Preparative HPLC gradient

| Time (min) | Flow rate (mL/min) | % A | % B |
|---|---|---|---|
| 0 | 15 | 90 | 10 |
| 30 | 15 | 60 | 40 |

Preparation of Example 66

Scheme

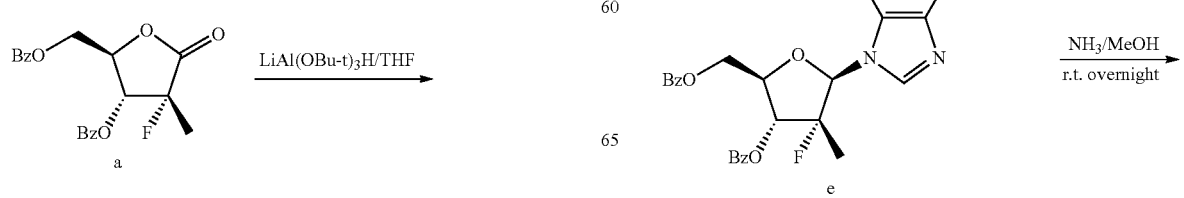

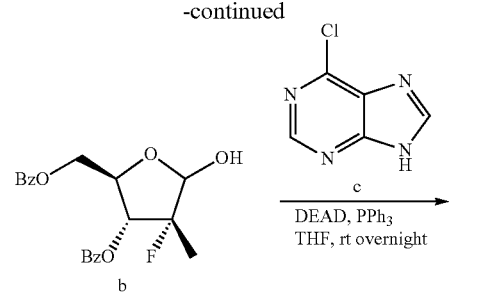

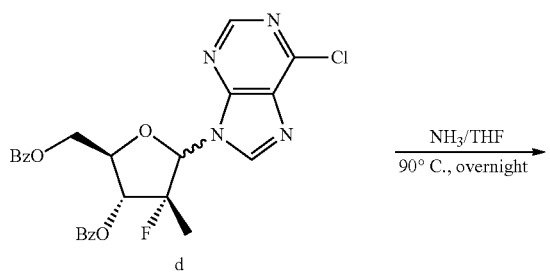

-continued

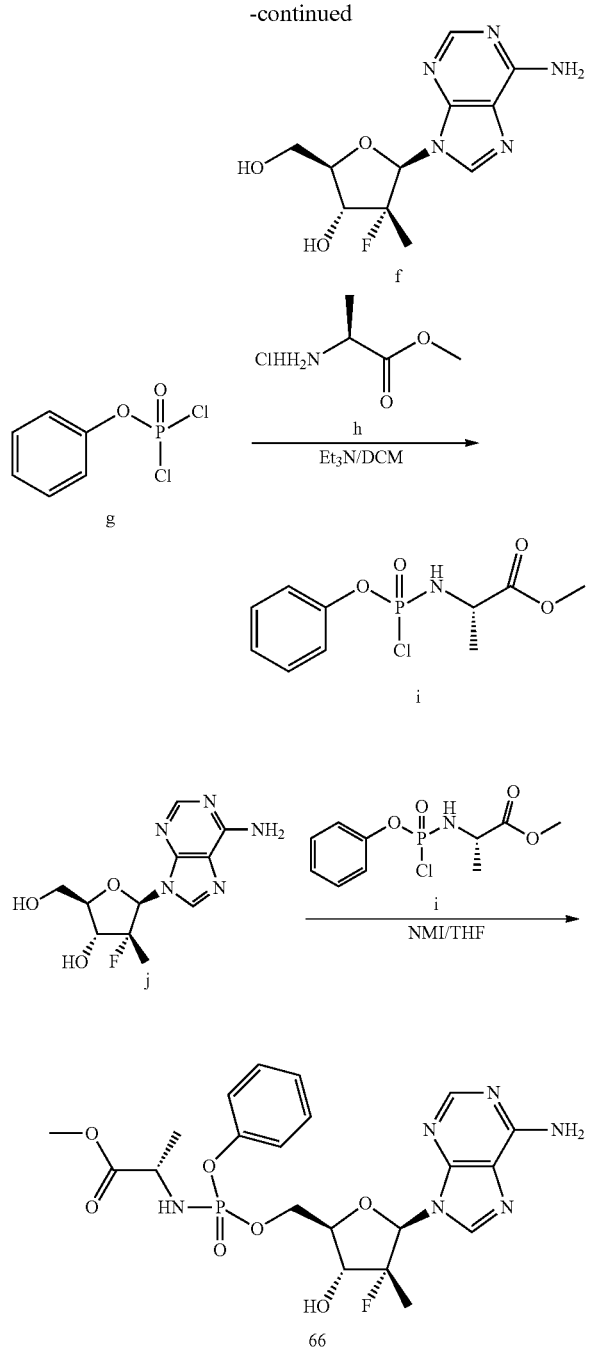

Preparation of Compound (b)

To a solution of compound a (1 g, 2.69 mmol) in anhydrous THF (30 mL) was added dropwise 1 M solution of LiAl(OBu-t)$_3$H in THF (2.69 mL, 2.69 mmol) at −20° C. The reaction mixture was stirred for 2-3 h at the same temperature. EtOAc (100 mL) was added followed by saturated NH$_4$Cl solution (10 mL) and reaction mixture was slowly brought to room temperature. Reaction mixture was extracted with EtOAc and washed with 1N HCl and water. Combined organic phase was evaporated to give 0.8 g of crude compound b as transparent oil, which was used directly for next reaction.

Preparation of Compound (d)

To a solution of compound b (0.8 g, 2.1 mmol), compound c (0.45 g, 2.5 mmol) and Ph$_3$P (0.56 g, 2.1 mmol) in anhydrous THF (20 mL) under nitrogen atmosphere was added DEAD (1.8 mL). The reaction mixture was stirred at room temperature overnight. The reaction solution was concentrated under reduce pressure. The residue was separated by preparative layer chromatography (hexanes:EtOAc=3:1) to give crude compound d (0.8 g). The crude compound d was used to the next step without further purification.

Preparation of Compound (e)

Compound d (0.8 g, 1.57 mmol) was dissolved in THF (2 mL) and THF saturated with ammonia (5 mL) was then added to this solution. The reaction mixture was heated to 90° C. overnight. After 18 hours, the solution was cooled to room temperature by ice water, then the solvent was removed under reduced pressure and the residue was purified by column to give compound e (0.75 g) for the next step.

Preparation of Compound (f)

Compound e (0.5 g, 1.01 mmol) was dissolved in methanol (2 mL) and methanol was saturated with ammonia (5 mL) was then added to this solution. The reaction mixture was stirred at room temperature overnight. After 18 hours, the solvent was removed under reduced pressure and the residue was purified by column to give crude compound f (0.15 g) for the next step.

Preparation of Compound (i)

A solution of triethylamine (1.07 g, 10.6 mmol) in anhydrous dichloromethane (15 mL) was added dropwise to a solution of compound g (1.16 g, 53 mmol) and compound h (1.31 g, 5.3 mmol) in dichloromethane (10 mL) with vigorous stirring at −78° C. over a period of 2 hours. After completion of addition, the reaction temperature was allowed to warm to room temperature gradually and stirred over night. Then the solvent was removed under vacuum and anhydrous ether 20 mL was added and the precipitated salt was filtered and the precipitate was washed with ether. The combined organic phase was concentrated to give the colorless oil of compound i (1.0 g).

Preparation of Compound 66

To a solution of compound j (0.1 g, 0.35 mmol) dissolved in 10 mL of anhydrous THF, stirred and added 0.4 g NMI till the solution became clear, added compound i (0.8 g, 2.89 mmol) in 10 mL TI-IF dropwise, stirred at r.t. overnight. Compound purity and identification was confirmed by LCMS. The solvent was evaporated and purified by Prep-HPLC to afford 66. (25 mg, Yield: 13.6%). $^1$H NMR (DMSO-d$_6$) δ 1.08 (d, J=22.8 Hz, 3H), 1.17-1.24 (m, 3H), 3.50-3.52 (m, 3H), 3.78-3.83 (m, 1H), 4.10-4.13 (m, 1H), 4.24-444 (m, 2H), 5.85-5.92 (m, 1H), 6.01-6.11 (m, 1H), 6.2-6.27 (m, 1H), 7.08-7.1.9 (m, 4H), 7.31-7.38 (m, 3H), 8.15 (s, 1H), 8.26 (s, 1H); MS, m/e 525 (M+1)$^+$.

Example numbers 67-74, identified below, were prepared using similar procedures disclosed for Example 66, above.

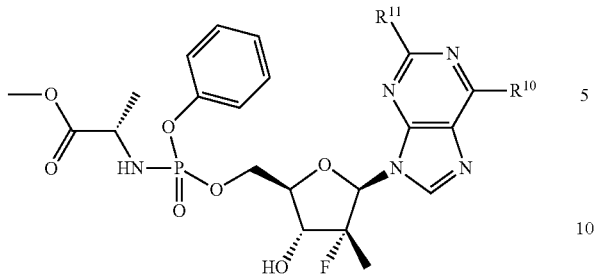

| Example | R[11] | R[10] | NMR/MS |
|---|---|---|---|
| 67 | OH | NH$_2$ | $^1$H NMR (DMSO-d$_6$) δ 1.06-1.13 (m, 3H), 1.20-1.24 (m, 3H), 3.27-3.33 (m, 3H), 3.56 (s, 1H), 3.82-3.88 (m, 1H), 4.07-4.13 (m, 1H), 4.25-4.40 (m, 2H), 5.85-5.87 (m, 1H), 5.98-6.09 (m, 2H), 6.59 (s, 32H), 7.14-7.37 (m, 3H), 7.35-7.37 (m, 2H), 7.79 (d, J = 7.2 Hz, 1H), 10.69 (s, 1H); MS, m/e 541 (M + 1)$^+$; |
| 68 | NH$_2$ | NH$_2$ | $^1$H NMR (DMSO-d$_6$) δ 1.07 (d, J = 22.8 Hz, 3H), 1.19 (d, J = 7.2 Hz, 3H), 3.51 (s, 3H), 3.62 (s, 1H), 3.75-3.81 (m, 1H), 4.05-4.11 (m, 1H), 4.27-4.42 (m, 2H), 5.79-5.83 (m, 1H), 5.92 (s, 2H), 6.00-6.09 (m, 2H), 6.75 (s, 2H), 7.08-7.17 (m, 3H), 7.31-7.35 (m, 2H), 7.78 (s, 1H); MS, m/e 540 (M + 1)$^+$; |
| 69 | NH$_2$ | c-Pentyl-NH— | $^1$H NMR (DMSO-d$_6$) δ 1.05 (d, J = 22.8 Hz, 3H), 1.09-1.19 (m, 3H), 1.48 (s, 4H), 1.66 (s, 1H), 1.86 (m, 3H), 3.54 (d, J = 14 Hz, 3H), 3.65 (s, 1H), 4.25-4.43 (m, 4H), 5.71-5.82 (m, 1H), 5.94-6.04 (m, 4H), 7.11-7.24 (m, 3H), 7.26-7.34 (m, 2H), 7.77 (d, J = 3.6 Hz, 1H): MS, m/e 608 (M + 1)$^+$ |
| 70 | NH$_2$ | —N⬜ (azetidinyl) | $^1$H NMR (DMSO-d$_6$) δ 1.07 (d, J = 22.4 Hz, 3H), 2.35-2.38 (m, 2H), 3.54 (d, J = 9.2 Hz, 3H), 3.59-3.62 (m, 2H), 3.65 (s, 1H), 3.75-3.82 (m, 1H), 4.01-4.13 (m, 2H), 4.22-4.40 (m, 6H), 5.75-5.85 (m, 1H), 6.00-6.07 (m, 4H), 7.15-7.21 (m, 3H), 7.32-7.35 (m, 2H), 7.79 (d, J = 4.0 Hz, 1H); MS, m/e 580 (M + 1)$^+$ |
| 71 | NH$_2$ | Et$_2$N— | $^1$H NMR (DMSO-d$_6$) δ 1.06-1.28 (m, 12H), 3.55 (d, J = 4.8 Hz, 3H), 3.79-3.87 (m, 4H), 4.07-4.12 (m, 2H), 4.29-4.42 (m, 3H), 5.75-5.82 (m, 1H), 5.94 (s, 2H), 6.04-6.10 (m, 2H), 7.14-7.22 (m, 3H), 7.31-7.37 (m, 2H), 7.82 (d, J = 4.4 Hz, 1H); MS, m/e 596 (M + 1)$^+$ |
| 72 | NH$_2$ | n-Propyl-NH— | $^1$H NMR (DMSO-d$_6$) δ 0.84 (t, J = 7.2 Hz, 3H), 1.01-1.01 (m, 3H), 1.09-1.12 (m, 3H), 1.51-1.56 (m, 2H), 3.48 (d, J = 15.2 Hz, 3H), 3.79-3.82 (m, 1H), 4.04-4.05 (m, 1H), 4.27-4.38 (m, 3H), 5.72-5.79 (m, 1H), 5.98-6.04 (m, 4H), 7.13-7.20 (n, 3H), 7.26-7.32 (m, 2H), 7.76 (d, J = 5.2 Hz, 1H); MS, m/e 582 (M + 1)$^+$ |
| 73 | NH$_2$ | c-Butyl-NH— | $^1$H NMR (DMSO-d$_6$) δ 1.02-1.08 (m, 3H), 1.18 (d, J = 4.8 Hz, 3H), 1.44-1.61 (m, 2H), 2.02-2.17 (m, 4H), 3.51 (d, J = 10.8 Hz, 3H), 3.78-3.83 (m, 1H), 4.03-4.06 (m, 1H), 4.27-4.38 (m, 2H), 4.53-4.62 (m, 1H), 5.68-5.79 (m, 1H), 5.95-6.04 (m, 4H), 7.11-7.18 (m, 3H), 7.29-7.35 (m, 2H), 7.51-7.58 (m, 1H), 7.78 (d, J = 5.2 Hz, 1H); MS, m/e 594 (M + 1)$^+$ |
| 74 | NH$_2$ | Me—N⬡N— (4-methylpiperazinyl) | $^1$H NMR (DMSO-d$_6$) δ 0.97-1.20 (m, 6H), 2.18 (s, 3H), 2.19 (s, 4H), 3.43-3.47 (m, 3H), 3.75 (s, 1H), 4.01-4.06 (m, 4H), 4.22.4.35 (m, 3H), 5.69-5.75 (m, 1H), 5.98-6.05 (m, 3H), 7.09-7.15 (m, 3H), 7.25-7.29 (m, 2H), 7.77 (d, J = 3.6 Hz, 1H); MS, m/e 623 (M + 1)$^+$ |

Example numbers 75-80 are prepared using similar procedures disclosed for Example 66, above.

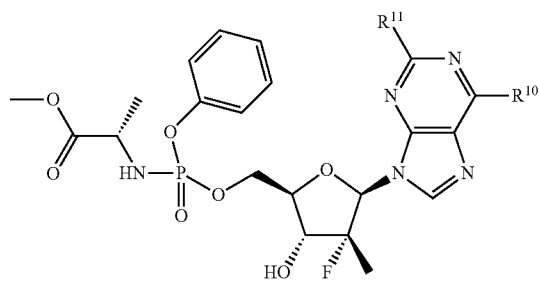

| Example | R[11] | R[10] |
|---|---|---|
| 75 | H | n-propyl-NH— |
| 76 | H | c-Butyl-NH— |
| 77 | H | c-Pentyl-NH— |
| 78 | H | —N⟨ (aziridinyl) |
| 79 | H | —N(piperidinyl) |
| 80 | H | —N(azetidinyl) |

EXAMPLE 81

Certain exemplified compounds were obtained as mixture of diastereomers because of the chirality at phosphorous. The diastereomers were separated on a Chiralpak-AS-H (2×25 cm) column under Supercritical Fluid Chromatography (SFC) conditions using 20% methanol in carbon dioxide as solvent. The absolute stereochemistry of the P-chiral center of the diastereromers were not determined. However, chromatographic resolution of these two diastereomers provides for isomers that are characterized as fast eluting and slow eluting isomers. Some examples are shown below.

| Compound | EC90 (uM) |
|---|---|
| Example 15 (Diastereomeric mixture) | 0.86 |
| Fast Moving isomer of Example 15 | 1.35 |
| Slow Moving isomer of Example 15 | 0.26 |
| Example 39 (Diastereomeric mixture) | 0.47 |
| Fast Moving isomer of Example 39 | 0.78 |
| Slow Moving isomer of Example 39 | 0.02 |
| Example 49 (Diastereomeric mixture) | 0.126 |
| Fast Moving isomer of Example 49 | 0.03 |
| Slow Moving isomer of Example 49 | 5.78 |

EXAMPLE 82

HCV Replicon Assay

HCV replicon RNA-containing Huh7 cells (clone A cells; Apath, LLC, St. Louis, Mo.) were kept at exponential growth in Dulbecco's modified Eagle's medium (high glucose) containing 10% fetal bovine serum, 4 mM L-glutamine and 1 mM sodium pyruvate, 1× nonessential amino acids, and G418 (1,000 μg/ml). Antiviral assays were performed in the same medium without G418. Cells were seeded in a 96-well plate at 1,500 cells per well, and test compounds were added immediately after seeding. Incubation time 4 days. At the end of the incubation step, total cellular RNA was isolated (RNeasy 96 kit; Qiagen). Replicon RNA and an internal control (TaqMan rRNA control reagents; Applied Biosystems) were amplified in a single-step multiplex RT-PCR protocol as recommended by the manufacturer. The HCV primers and probe were designed with Primer Express software (Applied Biosystems) and covered highly conserved 5'-untranslated region (UTR) sequences (sense 5'-AGCCATGGCGTTAGTA(T) GAGTGT-3' (SEQ ID NO: 1), and antisense, 5'-TTCCGCA-GACCACTATGG-3' (SEQ ID NO: 2); probe, 5'-FAM-CCTCCAGGACCCCCCCTCCC-TAMRA-3' (SEQ ID NO: 3)).

To express the antiviral effectiveness of a compound, the threshold RT-PCR cycle of the test compound was subtracted from the average threshold RT-PCR cycle of the no-drug control ($\Delta Ct_{HCV}$). A $\Delta Ct$ of 3.3 equals a 1-log 10 reduction (equal to the 90% effective concentration [$EC_{90}$]) in replicon RNA levels. The cytotoxicity of the test compound could also be expressed by calculating the $\Delta Ct_{rRNA}$ values. The $\Delta\Delta Ct$ specificity parameter could then be introduced ($\Delta Ct_{HCV}-\Delta Ct_{rRNA}$), in which the levels of HCV RNA are normalized for the rRNA levels and calibrated against the no-drug control.

| Ex # | Compound | Log10 Reduction at 50 μm | EC90 (μm) |
|---|---|---|---|
| 5 | (structure shown) | −1.21 | 3.0 |

-continued

| Ex # | Compound | Log10 Reduction at 50 μm | EC90 (μm) |
|---|---|---|---|
| 6 | | −0.45 | ND |
| 7 | | 0.31 | ND |
| 8 | | −1.48 | 2.11 |
| 10 | | −1.25 | 19.15 |
| 11 | | −0.55 | ND |

-continued

| Ex # | Compound | Log10 Reduction at 50 μm | EC90 (μm) |
|---|---|---|---|
| 12 | | 0.31 | ND |
| 15 | | ND | 0.86 |
| 25 | | −2.22 | 0.39 |
| 27 | | −2.25 | 0.66 |
| 28 | | −2.16 | 0.75 |

-continued

| Ex # | Compound | Log10 Reduction at 50 μm | EC90 (μm) |
|---|---|---|---|
| 36 | | −1.64 | 21.9 |
| 39 | | −1.78 | 0.47 |
| 49 | | −2.69 | 0.126 |
| 53 | | −1.33 | <0.3 |

-continued

| Ex # | Compound | Log10 Reduction at 50 μm | EC90 (μm) |
|---|---|---|---|
| 54 | [structure with 4-bromo-phenyl, isopropyl ester, alanine phosphoramidate, 2'-methyl-2'-fluoro uridine] | −1.55 | 0.57 |
| 55 | [structure with 4-fluoro-phenyl, cyclohexyl ester, alanine phosphoramidate, 2'-methyl-2'-fluoro uridine] | −2.38 | <0.3 |
| 69 | [structure with phenyl, methyl ester, alanine phosphoramidate, 2'-methyl-2'-fluoro nucleoside with cyclopentylamino-diaminopurine base] | −2.25 | <0.3 |
| 70 | [structure with phenyl, methyl ester, alanine phosphoramidate, 2'-methyl-2'-fluoro nucleoside with azetidinyl-diaminopurine base] | −2.25 | <0.3 |

[1](4-BrPh): 4-bromo-phenyl.

[1](4-BrPh): 4-bromo-phenyl.

The entire contents of U.S. Provisional Application Nos. 60/909,315, filed Mar. 30, 2007, and 60/982,309, filed Oct. 24, 2007, are hereby incorporated by reference in the present application so far as needed to supplement the present disclosure and/or rectify any errors. Moreover, the patent and non-patent references disclosed herein are incorporated by reference. In the event that the incorporated patent and non-patent reference contains a term that conflicts with a term disclosed in either one of the two Provisional Applications or the present application text, the meaning of the term contained in the present application text and the two Provisional Applications controls provided that the overall meaning of the incorporated subject matter is not lost.

We claim:

1. A compound represented by the following formula:

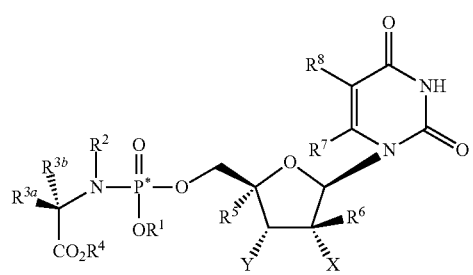

wherein (a) $R^1$ is phenyl;

(b) $R^2$ is hydrogen;

(c) $R^{3a}$ and $R^{3b}$ independently H or $CH_3$;

(d) $R^4$ is $^iPr$, $^nPr$, $^nBu$, 2-butyl, $^tBu$, or benzyl;

(e) $R^5$ is H;

(f) $R^6$ is $CH_3$;

(g) X is Cl;

(h) Y is OH; and (i) $R^7$ and $R^8$ are H.

2. The compound of claim 1, having the following structure:

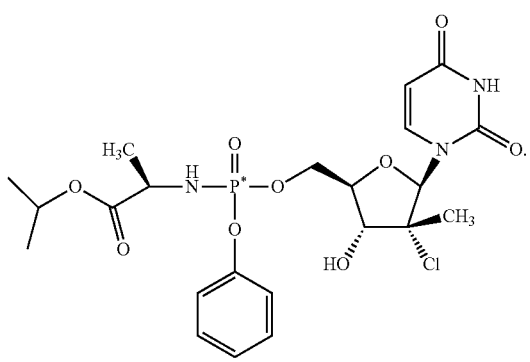

3. The compound of claim 1, having the following structure:

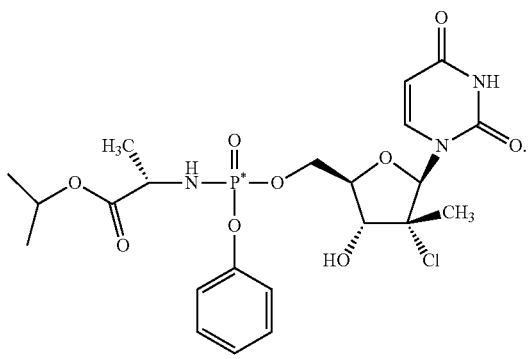

4. The compound of claim 1, having the following structure:

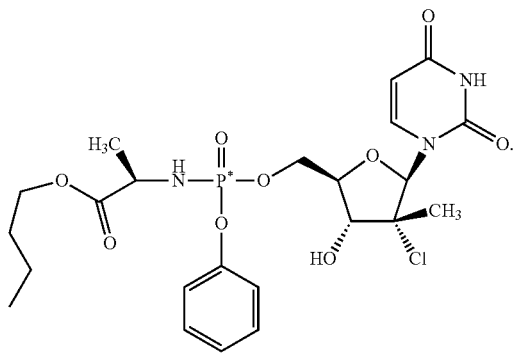

5. The compound of claim 1, having the following structure:

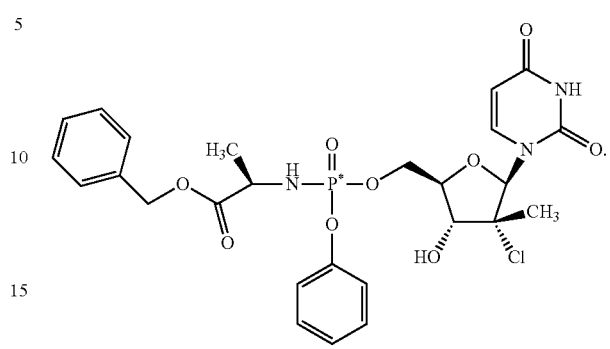

6. A pharmaceutical formulation comprising a compound of claim 1 and a pharmaceutically acceptable excipient.

7. A method of treating HCV comprising administering a therapeutically effective amount of a compound of claim 4 to a human subject in need thereof.

8. The method of claim 7 further comprising administering to the human subject a therapeutically effective amount of another antiviral agent.

9. The methods of claim 8, wherein the another antiviral agent is an NS5A inhibitor.

10. The methods of claim 8, wherein the another antiviral agent is an NS3 inhibitor.

11. The method of claim 10, further comprising administering to the human subject a therapeutically effective amount of an NS5A inhibitor.

* * * * *

UNITED STATES PATENT AND TRADEMARK OFFICE
CERTIFICATE OF CORRECTION

PATENT NO. : 8,906,880 B2  
APPLICATION NO. : 14/255833  
DATED : December 9, 2014  
INVENTOR(S) : Jinfa Du et al.

Page 1 of 3

It is certified that error appears in the above-identified patent and that said Letters Patent is hereby corrected as shown below:

IN THE SPECIFICATION

In Column 3, Line 24, please replace "*Crir. Rev.*" with --*Crit. Rev.*--.

In Column 9, Lines 1-4, please replace

" 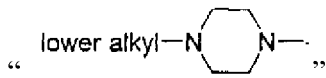 "

with the following:

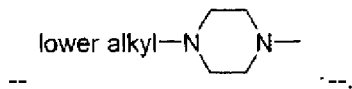

In Column 11, Line 41, please replace "$C^6$-lodo-pyridine" with --$C^6$-iodo-pyridine--.

In Column 615, Line 38, please replace "give 1" with --give I--.

In Column 617, Line 15, please replace "2'-Deoxy-2''-fluoro-2'-C-methyluridine" with --2'-Deoxy-2'-fluoro-2'-C-methyluridine--.

In Column 618, Line 42, please replace "2'Deoxy-2'-fluoro-2'-C-methyluridine" with --2'-Deoxy-2'-fluoro-2'-C-methyluridine--.

IN THE CLAIMS

In Claim 2, Column 648, Lines 54-67, please replace

Signed and Sealed this  
Thirtieth Day of June, 2015

Michelle K. Lee  
*Director of the United States Patent and Trademark Office*

CERTIFICATE OF CORRECTION (continued)
U.S. Pat. No. 8,906,880 B2

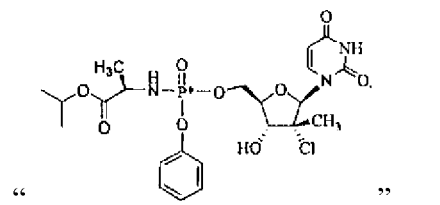

with the following:

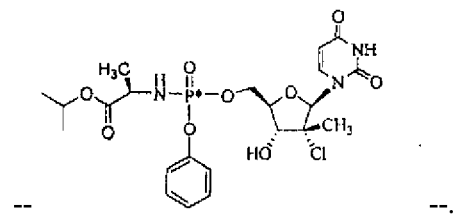

In Claim 3, Column 649, Lines 4-18, please replace

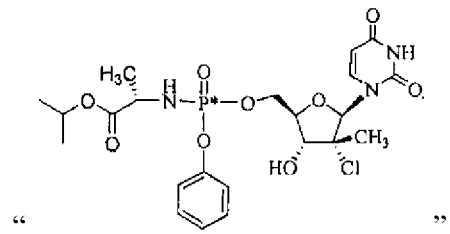

with the following:

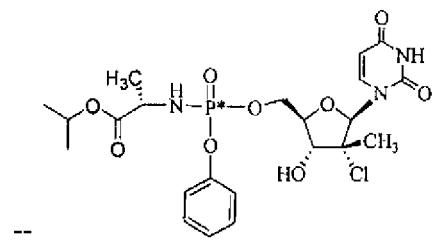

In Claim 4, Column 649, Lines 23-36, please replace

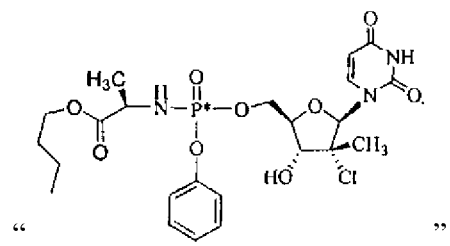

with the following:

CERTIFICATE OF CORRECTION (continued)
U.S. Pat. No. 8,906,880 B2

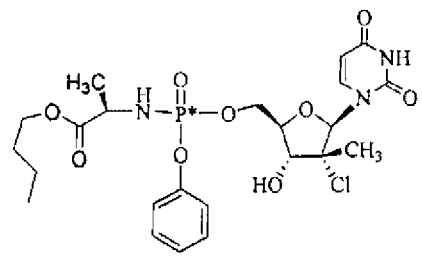

-- --.

In Claim 5, Column 649, Lines 5-18, please replace

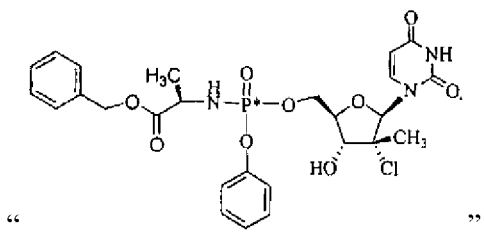

" "

with the following:

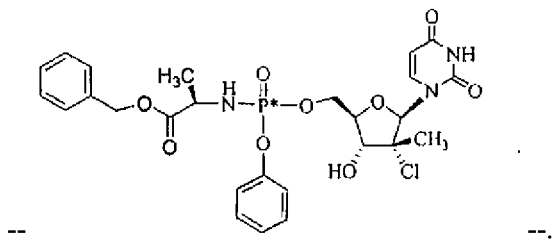

-- --.

In Claim 7, Column 650, Line 23, please replace "claim 4" with --claim 1--.

In Claim 9, Column 650, Line 29, please replace "The methods" with --The method--.

In Claim 10, Column 650, Line 32, please replace "The methods" with --The method--.